(12) United States Patent
Charifson et al.

(10) Patent No.: US 8,829,007 B2
(45) Date of Patent: Sep. 9, 2014

(54) INHIBITORS OF INFLUENZA VIRUSES REPLICATION

(71) Applicant: Vertex Pharmaceuticals Incorporated, Boston, MA (US)

(72) Inventors: Paul S. Charifson, Framingham, MA (US); Michael P. Clark, Concord, MA (US); Upul K. Bandarage, Lexington, MA (US); Randy S. Bethiel, Lexington, MA (US); John J. Court, Littleton, MA (US); Hongbo Deng, Southborough, MA (US); Ioana Davies, Arlington, MA (US); John P. Duffy, Northborough, MA (US); Luc J. Farmer, Montreal (CA); Huai Gao, Arlington, MA (US); Wenxin Gu, Concord, MA (US); Dylan H. Jacobs, South Boston, MA (US); Joseph M. Kennedy, Charlestown, MA (US); Mark W. Ledeboer, Acton, MA (US); Brian Ledford, Norton, MA (US); Francois Maltais, Tewksbury, MA (US); Emanuele Perola, Brookline, MA (US); Tiansheng Wang, Concord, MA (US); M. Woods Wannamaker, Stow, MA (US); Randal Bym, Wayland, MA (US); Yi Zhou, Lexington, MA (US); Chao Lin, Winchester, MA (US); Min Jiang, Lexington, MA (US); Steven Jones, Hyde Park, MA (US); Ursula A. Germann, Newton, MA (US); Francesco G. Salituro, Marlborough, MA (US); Ann Dak-Yee Kwong, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/098,867

(22) Filed: Dec. 6, 2013

(65) Prior Publication Data

US 2014/0142119 A1    May 22, 2014

Related U.S. Application Data

(60) Division of application No. 13/327,206, filed on Dec. 15, 2011, now abandoned, which is a continuation of application No. PCT/US2010/038988, filed on Jun. 17, 2010.

(60) Provisional application No. 61/287,781, filed on Dec. 18, 2009, provisional application No. 61/187,713, filed on Jun. 17, 2009.

(51) Int. Cl.
| | | |
|---|---|---|
| C07D 239/12 | (2006.01) | |
| C07D 401/04 | (2006.01) | |
| C07D 401/10 | (2006.01) | |
| C07D 239/30 | (2006.01) | |

(52) U.S. Cl.
CPC ............ C07D 401/10 (2013.01); *C07D 401/04* (2013.01); *C07D 239/30* (2013.01)
USPC .......................................... 514/256; 544/328

(58) Field of Classification Search
CPC ... C07D 401/10; C07D 401/04; C07D 239/30
USPC .......................................... 544/328; 514/256
See application file for complete search history.

(56) References Cited

U.S. PATENT DOCUMENTS

| | | |
|---|---|---|
| 5,051,412 A | 9/1991 | Macor |
| 5,304,121 A | 4/1994 | Sahatjian |

(Continued)

FOREIGN PATENT DOCUMENTS

| | | |
|---|---|---|
| EP | 0557171 | 8/1993 |
| EP | 1748829 | 7/2007 |

(Continued)

OTHER PUBLICATIONS

U.S. Appl. No. 13/918,048, filed Jun. 14, 2013, Pagano, A.R.

(Continued)

*Primary Examiner* — Shengjun Wang
(74) *Attorney, Agent, or Firm* — Honigman Miller Schwartz and Cohn LLP; Andrew N. Weber; Jonathan P. O'Brien

(57) ABSTRACT

Methods of inhibiting the replication of influenza viruses in a biological sample or patient, of reducing the amount of influenza viruses in a biological sample or patient, and of treating influenza in a patient, comprises administering to said biological sample or patient an effective amount of a compound represented by Structural Formula (I):

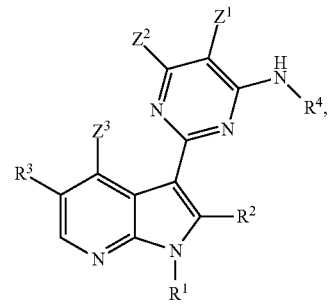

(IA)

or a pharmaceutically acceptable salt thereof, wherein the values of Structural Formula (IA) are as described herein. A compound is represented by Structural Formula (IA) or a pharmaceutically acceptable salt thereof, wherein the values of Structural Formula (IA) are as described herein. A pharmaceutical composition comprises an effective amount of such a compound or pharmaceutically acceptable salt thereof, and a pharmaceutically acceptable carrier, adjuvant or vehicle.

2 Claims, 115 Drawing Sheets

(56) References Cited

U.S. PATENT DOCUMENTS

| | | |
|---|---|---|
| 5,338,849 A | 8/1994 | Festal et al. |
| 5,395,840 A | 3/1995 | Miiller et al. |
| 5,886,026 A | 3/1999 | Hunter et al. |
| 6,099,562 A | 8/2000 | Ding et al. |
| 6,169,181 B1 | 1/2001 | Romines et al. |
| 6,265,403 B1 | 7/2001 | Fraley et al. |
| 6,313,126 B1 | 11/2001 | Mewshaw et al. |
| 6,699,883 B1 | 3/2004 | Doemling et al. |
| 6,825,190 B2 | 11/2004 | Moon et al. |
| 6,900,201 B2 | 5/2005 | Noe et al. |
| 7,041,687 B2 | 5/2006 | Binch et al. |
| 7,135,550 B2 | 11/2006 | Come et al. |
| 7,507,826 B2 | 3/2009 | Salituro et al. |
| 7,514,448 B2 | 4/2009 | Green et al. |
| 7,645,769 B2 | 1/2010 | Khan et al. |
| 7,659,283 B2 | 2/2010 | Collier et al. |
| 7,700,609 B2 | 4/2010 | Jimenez et al. |
| 7,767,816 B2 | 8/2010 | Farmer et al. |
| 7,795,259 B2 | 9/2010 | Binch et al. |
| 7,872,129 B2 | 1/2011 | Forster et al. |
| 8,017,619 B2 | 9/2011 | Jimenez et al. |
| 8,101,770 B2 | 1/2012 | Charrier et al. |
| 8,163,917 B2 | 4/2012 | Farmer et al. |
| 8,173,635 B2 | 5/2012 | Jimenez et al. |
| 8,188,281 B2 | 5/2012 | Salituro et al. |
| 8,247,421 B2 | 8/2012 | Mortimore et al. |
| 8,288,400 B2 | 10/2012 | Jimenez et al. |
| 8,338,597 B2 | 12/2012 | Charrier et al. |
| 8,367,697 B2 | 2/2013 | Jimenez et al. |
| 8,372,835 B2 | 2/2013 | Binch et al. |
| 8,450,489 B2 | 5/2013 | Farmer et al. |
| 8,501,446 B2 | 8/2013 | Salituro et al. |
| 8,513,414 B2 | 8/2013 | Tanoury et al. |
| 8,580,802 B2 | 11/2013 | Salituro et al. |
| 2002/0052386 A1 | 5/2002 | Armistead et al. |
| 2002/0065270 A1 | 5/2002 | Moriarty et al. |
| 2002/0147189 A1 | 10/2002 | Cai et al. |
| 2002/0183329 A1 | 12/2002 | Gross et al. |
| 2002/0183352 A1 | 12/2002 | Stack et al. |
| 2002/0183353 A1 | 12/2002 | Stack et al. |
| 2002/0183354 A1 | 12/2002 | Tran et al. |
| 2002/0193400 A1 | 12/2002 | Husbands et al. |
| 2003/0078268 A1 | 4/2003 | Zhao et al. |
| 2003/0100579 A1 | 5/2003 | Gross et al. |
| 2003/0153560 A1 | 8/2003 | Salituro et al. |
| 2003/0166668 A1 | 9/2003 | Van Zandt et al. |
| 2004/0009968 A1 | 1/2004 | Binch et al. |
| 2004/0009996 A1 | 1/2004 | Moon et al. |
| 2004/0043388 A1 | 3/2004 | Come et al. |
| 2004/0044203 A1 | 3/2004 | Wittman et al. |
| 2004/0236110 A1 | 11/2004 | Ladouceur et al. |
| 2005/0137201 A1 | 6/2005 | Aronov et al. |
| 2005/0148603 A1 | 7/2005 | Jimenez et al. |
| 2005/0208582 A1 | 9/2005 | Ohi et al. |
| 2005/0228005 A1 | 10/2005 | Moon et al. |
| 2005/0288290 A1 | 12/2005 | Borzilleri et al. |
| 2006/0003968 A1 | 1/2006 | Green et al. |
| 2006/0004014 A1 | 1/2006 | Hoffmann et al. |
| 2006/0122185 A1 | 6/2006 | Green et al. |
| 2006/0122213 A1 | 6/2006 | Pierard et al. |
| 2006/0183761 A1 | 8/2006 | Ledeboer et al. |
| 2006/0183911 A1 | 8/2006 | Charrier et al. |
| 2006/0258662 A1 | 11/2006 | Binch et al. |
| 2007/0043063 A1 | 2/2007 | Salituro et al. |
| 2007/0049615 A1 | 3/2007 | Ibrahim et al. |
| 2007/0066641 A1 | 3/2007 | Ibrahim et al. |
| 2007/0072896 A1 | 3/2007 | Khan et al. |
| 2007/0135466 A1 | 6/2007 | Ledeboer et al. |
| 2007/0203142 A1 | 8/2007 | Farmer et al. |
| 2007/0207995 A1 | 9/2007 | Salituro et al. |
| 2007/0213327 A1 | 9/2007 | Collier et al. |
| 2009/0048250 A1 | 2/2009 | Aronov et al. |
| 2009/0088445 A1 | 4/2009 | Ledeboer et al. |
| 2009/0118278 A1 | 5/2009 | Forster et al. |
| 2009/0176763 A1 | 7/2009 | Salituro et al. |
| 2009/0291937 A1 | 11/2009 | Jimenez et al. |
| 2010/0099686 A1 | 4/2010 | Charrier et al. |
| 2010/0120792 A1 | 5/2010 | Ivashchenko et al. |
| 2010/0189773 A1 | 7/2010 | Mortimore et al. |
| 2010/0280026 A1 | 11/2010 | Jimenez et al. |
| 2010/0311743 A1 | 12/2010 | Farmer et al. |
| 2011/0081364 A1 | 4/2011 | Binch et al. |
| 2011/0224197 A1 | 9/2011 | Henkel et al. |
| 2011/0263575 A1 | 10/2011 | Pierard et al. |
| 2012/0010197 A1 | 1/2012 | Charrier et al. |
| 2012/0028966 A1 | 2/2012 | Charrier et al. |
| 2012/0122879 A1 | 5/2012 | Charrier et al. |
| 2012/0149680 A1 | 6/2012 | Jimenez et al. |
| 2012/0165307 A1 | 6/2012 | Farmer et al. |
| 2012/0171245 A1 | 7/2012 | Charifson et al. |
| 2012/0183577 A1 | 7/2012 | Jimenez et al. |
| 2012/0190699 A1 | 7/2012 | Charrier et al. |
| 2012/0258958 A1 | 10/2012 | Salituro et al. |
| 2012/0309963 A1 | 12/2012 | Mortimore et al. |
| 2013/0102782 A1 | 4/2013 | Tanoury et al. |
| 2013/0184259 A1 | 7/2013 | Charrier et al. |
| 2013/0237516 A1 | 9/2013 | Farmer et al. |
| 2013/0303764 A1 | 11/2013 | Tanoury et al. |
| 2013/0345197 A1 | 12/2013 | Salituro et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0018352 A1 | 1/2014 | Pierard et al. |
| 2014/0045812 A1 | 2/2014 | Mortimore et al. |

FOREIGN PATENT DOCUMENTS

| | | |
|---|---|---|
| JP | 2003-519143 | 6/2003 |
| JP | 2003-532635 | 11/2003 |
| JP | 2008-156370 | 7/2008 |
| WO | 88/01997 | 3/1988 |
| WO | 95/33748 | 12/1995 |
| WO | 99/21859 | 5/1999 |
| WO | 00/40554 | 7/2000 |
| WO | 00/40581 | 7/2000 |
| WO | 00/43393 | 7/2000 |
| WO | 00/64898 | 11/2000 |
| WO | 01/01986 | 1/2001 |
| WO | 01/14374 | 3/2001 |
| WO | 01/87887 | 11/2001 |
| WO | 02/14317 | 2/2002 |
| WO | 02/20013 | 3/2002 |
| WO | 02/051837 | 7/2002 |
| WO | 02/072587 | 9/2002 |
| WO | 02/085896 | 10/2002 |
| WO | 02/085911 | 10/2002 |
| WO | 02/088129 | 11/2002 |
| WO | 02/088131 | 11/2002 |
| WO | 02/088135 | 11/2002 |
| WO | 02/088136 | 11/2002 |
| WO | 02/088140 | 11/2002 |
| WO | 02/088144 | 11/2002 |
| WO | 02/088146 | 11/2002 |
| WO | 02/089811 | 11/2002 |
| WO | 02/092602 | 11/2002 |
| WO | 03/000688 | 1/2003 |
| WO | 03/091246 | 11/2003 |
| WO | 03/101968 | 12/2003 |
| WO | 03/101990 | 12/2003 |
| WO | 2004/013140 | 2/2004 |
| WO | 2004/014912 | 2/2004 |
| WO | 2004/016609 | 2/2004 |
| WO | 2004/016610 | 2/2004 |
| WO | 2004/043388 | 5/2004 |
| WO | 2004/076454 | 9/2004 |
| WO | 2004/078756 | 9/2004 |
| WO | 2004/082638 | 9/2004 |
| WO | 2004/089913 | 10/2004 |
| WO | 2004/106298 | 12/2004 |
| WO | 2005/000813 | 1/2005 |
| WO | 2005/028475 | 3/2005 |
| WO | 2005/044181 | 5/2005 |
| WO | 2005/062795 | 7/2005 |
| WO | 2005/085244 | 9/2005 |

(56) References Cited

FOREIGN PATENT DOCUMENTS

| WO | 2005/095400 | 10/2005 |
|---|---|---|
| WO | 2005/105213 | 11/2005 |
| WO | 2005/123736 | 12/2005 |
| WO | 2006/009755 | 1/2006 |
| WO | 2006/015123 | 2/2006 |
| WO | 2006/030031 | 3/2006 |
| WO | 2006/038001 | 4/2006 |
| WO | 2006/041773 | 4/2006 |
| WO | 2006/050076 | 5/2006 |
| WO | 2006052913 | 5/2006 |
| WO | 2006/063167 | 6/2006 |
| WO | 2006069258 | 6/2006 |
| WO | 2006/124863 | 11/2006 |
| WO | 2006/127587 | 11/2006 |
| WO | 2007/002433 | 1/2007 |
| WO | 2007/084557 | 7/2007 |
| WO | 2007/095188 | 8/2007 |
| WO | 2007/107221 | 9/2007 |
| WO | 2007/117494 | 10/2007 |
| WO | 2007129195 | 11/2007 |
| WO | 2007/146057 | 12/2007 |
| WO | 2008/003958 | 1/2008 |
| WO | 2008/005457 | 1/2008 |
| WO | 2008/076392 | 6/2008 |
| WO | 2008/079346 | 7/2008 |
| WO | 2008/112642 | 9/2008 |
| WO | 2008/112646 | 9/2008 |
| WO | 2008/112651 | 9/2008 |
| WO | 2008/113711 | 9/2008 |
| WO | 2008/123800 | 10/2008 |
| WO | 2009/023269 | 2/2009 |
| WO | 2009/040556 | 4/2009 |
| WO | 2009/046983 | 4/2009 |
| WO | 2009/145814 | 12/2009 |
| WO | 2010/008454 | 1/2010 |
| WO | 2010/008459 | 1/2010 |
| WO | 2010011756 | 1/2010 |
| WO | 2010/148197 | 12/2010 |
| WO | 2011000566 | 1/2011 |
| WO | 2011008915 | 1/2011 |
| WO | 2011137022 | 3/2011 |
| WO | 2011/130146 | 10/2011 |
| WO | 2013/006634 | 1/2013 |
| WO | 2013/019828 | 2/2013 |
| WO | 2013/070606 | 5/2013 |
| WO | 2013184985 | 12/2013 |

OTHER PUBLICATIONS

U.S. Appl. No. 13/918,110, filed Jun. 14, 2013, Cornet, J.P.
U.S. Appl. No. 14/099,054, filed Dec. 6, 2013, Calvillo, J. Z. Y.
Schmidtke, M. et al., "A rapid assay for evaluation of antiviral activity against coxsackie virus B3, influenza virus A, and herpes simplex virus type 1", Elsevier, Journal of Virological Methods, vol. 95, 2001, pp. 133-143.
Tobita, K. et al., "Plaque Assay and Primary Isolation of Influenza A Viruses in an Established Line of Canine Kidney Cells (MDCK) in the Presence of Trypsin", Med. Microbiol. Immunol., vol. 162, 1975, pp. 9-14.
Alvarez, Mercedes et al., "Synthesis of 3-Aryl- and 3-Heteroaryl-7-azaindoles", Synthesis, Thieme Stuttgart, New York, No. 4, 1999, pp. 615-620.
Amano, Mutsuki et al., "Formation of Actin Stress Fibers and Focal Adhesions Enhanced by Rho-Kinase", Science, vol. 275, Feb. 28, 1997, pp. 1308-1311.
Amano, Mutsuki et al., "Identification of a Putative Target for Rho as the Serine-Threonine Kinase Protein Kinase N", Science vol. 271, 199602-02, pp. 648-650.
Berge, Stephen M. et al., "Pharmaceutical Salts" Journal of Pharmaceutical Sciences, vol. 66, No. 1, Jan. 1977, pp. 1-19.
Bettayeb, Karima et al., "Meriolins, a New Class of Cell Death-Inducing Kinase Inhibitors with Enhanced Selectivity for Cyclin-Dependent Kinases", Cancer Research, vol. 67, No. 17, Sep. 1, 2007, pp. 8325-8334.
Burns, Timothy F. et al., "Silencing of the Novel p53 Target Gene Snk/Plk2 Leads to Mitotic Catastrophe in Paclitaxel (Taxol)-Exposed Cells", Molecular and cellular Biology, vol. 23, No. 16, Aug. 2003, pp. 5556-5571.
Catlett-Falcone, Robyn et al, "Constitutive Activation of Stat3 Signaling Confers Resistance to Apoptosis in Human U266 Myeloma Cells", Immunity, vol. 10, Jan. 1999, pp. 105-115.
Chelucci, Giorgio et al., "An easy route to optically active 1-substituted-1-pyridyl-methylamines by diastereoselective reduction of enantiopure N-tert-butanesulfinyl ketimines", Tetrahedron: Asymmetry, Elsevier, 2006, vol. 17, No. 22, pp. 3163-3169.
Chiba, Yoshihiko et al., "Augmented acetylcholine-induced translocation of RhoA in bronchial smooth muscle from antigen-induced airway hyperresponsive rats", British Journal of Pharmacology, vol. 133, 2001, pp. 886-890.
Chiba, Yoshihiko et al., "Augmented acetylcholine-induced, Rho-mediated Ca2+ sensitization of bronchial smooth muscle contraction in antigen-induced airway hyperresponsive rats", British Journal of Pharmacology, vol. 127, 1999, pp. 597-600.
Chiba, Yoshihiko et al., "Characteristics of muscarinic cholilnoceptors in airways of antigen-induced airway hyperresponsive rats", Comp. Biochem. Physiol. C Pharmacol. Toxicol. Endocrinol., vol. 111C, No. 3, 1995, pp. 351-335.
Chitaley, Kanchan et al., "Antagonism of Rho-kinase stimulates rat penile erection via a nitric oxide-independent pathway", Nature Medicine, Nature Publishing Group, vol. 7, No. 1, Jan. 2001, pp. 119-122.
Eto, Masato et al., "Thrombin Suppresses Endothelial Nitric Oxide Synthase and Upregulates Endothelin-Converting Enzyme-1 Expression by Distinct Pathways", Circulation Research, vol. 89, 2001, pp. 583-585.
Eto, Yasuhiro et al., "Gene transfer of dominant negative Rho kinase suppresses neointimal formation after balloon injury in pigs", Am. J. Physiol. Heart Circ. Physiol., American Physiological Society, vol. 278, 2000, pp. H1744-H1750.
Fan, Yu et al., "Apoptosis induction with polo-like kinase-1 antisense phosph-orothioate oligodeoxynucleotide of colon cancer cell line SW480", World J. Gastroenterol, vol. 11, No. 29, 2005, pp. 4596-4599.
Fernandez, David et al., "Synthesis of Polyheterocyclic Nitrogen-Containing Marine Natural Products#", Monatshefte Fur Chemie, Chemical Monthly, AU, vol. 135, 2004, pp. 615-627.
Fournier, Alyson E. et al., "Rho Kinase Inhibition Enhances Axonal Regeneration in the Injured CNS", The Journal of Neuroscience, vol. 23, No. 4, Feb. 15, 2003, pp. 1416-1423.
Frank, David A, "STAT Signaling in the Pathogenesis and Treatment of Cancer", Molecular Medicine, vol. 5, Jul. 1999, pp. 432-456.
Fresneda, Pilar M. et al., "Synthesis of the indole alkaloids meridianins from the tunicate Aplidium meridianum", Tetrahedron, Pergamon, vol. 57, No. 12, 2001, pp. 2355-2363.
Fu, Xiahong et al., "The effects of the Rho-kinase inhibitor Y-27632 on arachidonic acid-, GTPgammaS-, and phorbol ester-induced induced Ca2+ -sensitization of smooth muscle", FEBS Letters, vol. 440, 1998, pp. 183-187.
Fukata, Yuko et al., "Rho-Rho-kinase pathway in smooth muscle contraction and cytoskeletal reorganization of non-muscle cells", Trends Pharmacological Sciences, vol. 22, No. 1, Jan. 2001, pp. 32-39.
Galli, Stephan J., MD, "New Concepts About the Mast Cell", New England Journal of Medicine, vol. 328, No. 4, 1993, pp. 257-265.
Garcia-Bustos, Jose F. et al., "PIK1, an essential phosphatidylinositol 4-kinase associated with the yeast nucleus", The EMBO Journal, vol. 13, No. 10, 1994, pp. 2352-2361.
Genda, Takuya et al., "Cell Motility Mediated by Rho and Rho-Associated Protein Kinase Plays a Critical Role in Intrahepatic Metastasis of Human Hepatocellular Carcinoma", Hepatology, vol. 30, No. 4, Oct. 1999, pp. 1027-1036.
Gordon, John R. et al, "Mast cells as a source of both preformed and immunologically inducible TNF-alpha/cachectin", Nature, vol. 346, Jul. 19, 1990, pp. 274-276.
Guan, Ran et al., "Small Interfering RNA-Mediated Polo-Like Kinase 1 Depletion Preferentially Reduces the Survival of p53-De-

(56) References Cited

OTHER PUBLICATIONS fective, Oncogenic Transformed Cells and Inhibits Tumor Growth in Animals", Cancer Res., vol. 65, No. 7, Apr. 1, 2005, pp. 2698-2704.
Ha, Hyung-Ho et al., "Novel heterocycle-substituted pyrimidines as inhibitors of NF-κB transcription regulation related to TNF-alpha cytokine release", Bioorganic & Medicinal Chemistry Letters, Elsevier, vol. 18, 2008, pp. 653-656.
Hamanaka, Ryoji et al., "Polo-like Kinase Is a Cell Cycle-regulated Kinase Activated during Mitosis", Journal of Biological Chemistry, vol. 270, No. 36, Sep. 8, 1995, pp. 21086-21091.
Hanks, Steven K. et al., "Protein kinases 6. The eukaryotic protein kinase superfamily: kinase (catalytic) domain structure and classification", FASEB J., vol. 9, No. 8, 1995, pp. 576-596.
Harrington, Elizabeth A. et al., "VX-680, a potent and selective small-molecule inhibitor of the Aurora kinases, suppresses tumor growth in vivo", Nature Medicine, vol. 10, No. 3, Feb. 22, 2004, pp. 262-267.
Hatanaka, Masashi. et al., "Preparation and antioxidant activity of alpha-pyridoin and its derivatives", Bioorganic & Medicinal Chemistry, Elsevier, 2005, vol. 13, pp. 6763-6770.
Herbert, R. et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.
Hernandez-Perera, Octavio et al., "Involvement of Rho GTPases in the Transcriptional Inhibition of Preproendothelin-1 Gene Expression by Simvastatin in Vascular Endothelial Cells", Circulation Research, vol. 87, 2000, pp. 616-622.
Hiles, Ian D. et al., "Phosphatidylinositol 3-Kinase: Structure and Expression of the 110 kd Catalytic Subunit", Cell, vol. 70, No. 3, Aug. 7, 1992, pp. 419-429.
Hirose, Masaya et al., "Molecular Dissection of the Rho-associated Protein Kinase (p160ROCK)—regulated Neurite Remodeling in Neuroblastoma N1E-115 Cells", Journal of Cell Biology, vol. 141, No. 7, Jun. 29, 1998, pp. 1625-1636.
Honjo, Meguni et al., "Effects of Protein Kinase Inhibitor, HA1077 on Intraocular Pressure and Outflow Facility in Rabbit Eyes", Arch. Ophthalmol, vol. 119, Aug. 2001, pp. 1171-1178.
Hoshijima, Masahiko et al., "The Low Molecular Weight GTPase Rho Regulates Myofibril Formation and Organization in Neonatal Rat Ventricular Myocytes", The Journal of Biological Chemistry, USA, vol. 273, No. 13, Mar. 27, 1998, pp. 7725-7730.
Huang, Shenlin, et al., "Synthesis of 2-amino-4-(7-azaindol-3-yl)pyrimidines as cyclin dependent kinase 1 (CDK1) inhibitors", Bioorganic & Medicinal Chemistry Letters, Elsevier, vol. 16, 2006, pp. 4818-4821.
Hudson, J.W. et al., "Late mitotic failure in mice lacking Sak, a polo-like kinase", Current Biology, vol. 11, No. 6, Mar. 20, 2001, pp. 441-446.
Iizuka, Kunihiko et al., "Evaluation of Y-27632, a Rho-kinase inhibitor, as a bronchodilator in guinea pigs", European Journal of Pharmacology, vol. 406, No. 2, 2000, pp. 273-279.
Ikeda, Fusao et al., "Reduction of Hepatic Ischemia/Reperfusion-Induced Injury by a Specific ROCK/Rho Kinase Inhibitor Y-27632", Journal of Surgical Research, Elsevier Science (USA), vol. 109, 2003, pp. 155-160.
International Search Report issued for PCT Application No. PCT/US2005/010846 Dated Aug. 19, 2005.
International Search Report issued for PCT Application No. PCT/US2007/001225 Dated Jul. 20, 2007.
International Search Report issued for PCT Application No. PCT/US2007/026190 Dated May 20, 2008.
International Search Report issued for PCT Application No. PCT/US2008/009786 Dated Jan. 19, 2009.
International Search Report issued for PCT Application No. PCT/US2009/001534 Dated Apr. 2, 2010.
International Search Report issued for PCT Application No. PCT/US2010/038988 dated Aug. 20, 2010.
International Search Report issued for PCT Application No. PCT/US2012/045431 dated Feb. 5, 2013.
International Search Report issued for PCT Application No. PCT/US2012/049097 Dated Sep. 25, 2012.
International Search Report issued for PCT Application No. PCT/US2012/063712 dated Jan. 8, 2013.
IPRP issued for PCT/US2005/010846 Dated Oct. 4, 2006.
IPRP issued for PCT/US2007/001225 Dated Jul. 22, 2008.
IPRP issued for PCT/US2010/038988 dated Dec. 20, 2011.
Ishibashi, Toshiyuki et al., "Inhibition of Rho/Rho-kinase signaling downregulates plasminogen activator inhibitor-1 synthesis in cultured human monocytes", Biochimica Et Biophysica Acta, Elsevier, vol. 1590, 2002, pp. 123-130.
Ishizaki, Toshimasa et al., "p160ROCK, a Rho-associated coiled-coil forming protein kinase, works downstream of Rho and induces focal adhesions", FEBS Letters, vol. 404, No. 2, 1997, pp. 118-124.
Ishizaki, Toshimasa et al., "The small GTP-binding protein Rho binds to and activates a 160 kDa Ser/Thr protein kinase homologous to myotonic dystrophy kinase", The EMBO Journal, vol. 15, No. 8, 1996, pp. 1885-1893.
Itoh, Kazuyuki et al., "An essential part for Rho-associated kinase in the transcellular invasion of tumor cells", Nature Medicine, vol. 5, No. 2, Feb. 1999, pp. 221-225.
Kandabashi, Tadashi, MD et al., "Inhibition of Myosin Phosphatase by Upregulated Rho-Kinase Plays a Key Role for Coronary Artery Spasm in a Porcine Model with Interleukin-1beta", Circulation, vol. 101, No. 11, Mar. 21, 2000, pp. 1319-1323.
Karpov, Alexei S. et al., "Concise Synthesis of Meridianins by Carbonylative Alkynylation and a Four-Component Pyrimidine Synthesis", Angewandte Chemie., International Edition, Wiley VCH Verlag, Weinheim, DE, vol. 44, 2005, pp. 6951-6956.
Katsumata, Naoki et al., "Enhanced Myosin Light Chain Phosphorylations as a Central Mechanism for Coronary Artery Spasm in a Swine Model With Interleukin-1beta", Circulation, vol. 96, No. 12, 1997, pp. 4357-4363.
Kelly, Terence A. et al., "Novel Non-Nucleoside Inhibitors of Human Immunodeficiency Virus Type 1 Reverse Transcriptase. 6. 2-Indol-3-yl and 2-Azaindol-3-yl-dipyridodiazepinones1", Journal of Medicinal Chemistry, vol. 40, No. 15, 1997, pp. 2430-2433.
Kimura, Kazushi et al., "Regulation of Myosin Phosphatase by Rho and Rho-Associated Kinase (Rho-Kinase)", Science, vol. 273, Jul. 12, 1996, pp. 245-248.
Kirken, R. A., "Targeting Jak3 for Immune Suppression and Allograft Acceptance", Transplantation Proceedings, Elsevier, vol. 33, No. 7-8, 2001, pp. 3268-3270.
Klages, Birgit et al., "Activation of G12/G13 Results in Shape Change and Rho/Rho-Kinase-mediated Myosin Light Chain Phosphorylation in Mouse Platelets", Journal of Cell Biology, vol. 144, No. 4, Feb. 9, 1999, pp. 745-754.
Knighton, Daniel R. et al., "Crystal Structure of the Catalytic Subunit of Cyclic Adenosine Monophosphate-Dependent Protein Kinase", Science, vol. 253, Jul. 26, 1991, pp. 407-414.
Kunz, Jeannette et al., "Target of Rapamycin in Yeast, TOR2, Is an Essential Phosphatidylinositol Kinase Homolog Required for G1 Progression", Cell, vol. 73, No. 3, May 7, 1993, pp. 585-596.
Kupittayanant, S. et al., "The effects of inhibiting Rho-associated kinase with Y-27632 on force and intracellular calcium in human myometrium", Pflugers Arch—Eur J Physiol, vol. 443, 2001, pp. 112-114.
Kuwahara, Koichiro et al., "The effects of the selective ROCK inhibitor, Y27632, on ET-1-induced hypertrophic response in nenatal rat cardiac myocytes—possible involvement of Rho/ROCK pathway in cardiac muscle cell hypertrophy" Federation of European Biochemial Societies Letters, vol. 452, 1999, pp. 314-318.
Lane, Heidi A. et al., "Antibody Microinjection Reveals an Essential Role for Human Polo-like Kinase 1 (Plk1) in the Functional Maturation of Mitotic Centrosomes", Journal of Cell Biology, vol. 135, No. 6-2, Dec. 1996, pp. 1701-1713.
Laufs, Ulrich et al., "Post-transcriptional Regulation of Endothelial Nitric Oxide Synthase mRNA Stability by Rho GTPase*", The Journal of Biological Chemistry, USA, vol. 273, No. 37, Sep. 11, 1998, pp. 24266-24271.

(56) References Cited

OTHER PUBLICATIONS

Leung, Thomas et al., "A Novel Serine/Threonine Kinase Binding the Ras-related RhoA GTPase Which Translocates the Kinase to Peripheral Membranes", Journal of Biological Chemistry, vol. 270, No. 49, Dec. 8, 1995, pp. 29051-29054.

Leung, Thomas et al., "The p160 RhoA-Binding Kinase ROKalpha is a Member of a Kinase Family and is Involved in the Reorganization of the Cytoskeleton", Molecular and Cellular Biology, vol. 16, No. 10, Oct. 1996, pp. 5313-5327.

Li, Jun et. al "SAK, a New Polo-Like Kinase, Is Transcriptionally Repressed by p53 and Induces Apoptosis upon RNAi Silencing", Neoplasia, vol. 7, No. 4, Apr. 2005, pp. 312-323.

Li, Zhongkui et al., "Function of Polo-like Kinase 3 in NF-κB-mediated Proapoptotic Response", Journal of Biological Chemistry, vol. 280, No. 17, Apr. 29, 2005, pp. 16843-16850.

Liu, Xiaoqi et al., "Polo-like kinase (Plk)1 depletion induces apoptosis in cancer cells", Proc. Nat'l. Acad. Sci., USA, vol. 100, No. 10, May 13, 2003, pp. 5789-5794.

Lowery, Drew M. et al., "Structure and function of Polo-like Kinases", Oncogene, Nature Publishing Group, vol. 24, 2005, pp. 248-225.

M.A. Malllkobcknn, "JleKapcTBeHHble cpeAcTBa", 2001, vol. 1, p. 14.

Ma, Sheng et al., "Role of Plk2 (Snk) in Mouse Development and Cell Proliferation", Molecular and Cellular Biology, vol. 23, No. 19, Oct. 2003, pp. 6936-6943.

MacMillan, Jennifer C. et al., "Comparative Expression of the Mitotic Regulators SAK and PLK in Colorectal Cancer", Annals of Surgical Oncology, vol. 8, No. 9, 2001, pp. 729-740.

Madaule, Pascal et al., "A novel partner for the GTP-bound forms of rho and rac", FEBS Letters, vol. 377, No. 2, 1995, pp. 243-248.

Madaule, Pascal et al., "Role of citron kinase as a target of the small GTPase Rho in cytokinesis", Nature, vol. 394, Jul. 30, 1998, pp. 491-494.

Malaviya, Ravi et al., "Genetic and Biochemical Evidence for a Critical Role of Janus Kinase (JAK)-3 in Mast Cell-Mediated Type I Hypersensitivity Reactions", Biochemical and Biophysical Research Communications, vol. 257, No. 3, 1999, pp. 807-813.

Malaviya, Ravi et al., "Targeting Janus Kinase 3 in Mast Cells Prevents Immediate Hypersensitivity Reactions and Anaphylaxis", Journal of Biological Chemistry, vol. 274, No. 38, Sep. 17, 1999, pp. 27028-27038.

Martinez, Ana et al. "Glycogen Synthase Kinase 3 Inhibitors in the Next Horizon for Alzheimer's Disease Treatment", International Journal of Alzheimer's Disease, vol. 2011, 2011 pp. 1-7.

Masumoto, Akihiro et al., "Possible Involvement of Rho-kinase in the Pathogenesis of Hypertension in Humans", Hypertension, vol. 38, No. 6, Dec. 2001, pp. 1307-1310.

Masumoto, Akihiro et al., "Suppression of Coronary Artery Spasm by the Rho-Kinase Inhibitor Fasudil in Patients With *Vasospastic angina*", Circulation, vol. 105, 2002, pp. 1545-1547.

Matsui, Takeshi et al., "Rho-associated kinase, a novel serine/threonine kinase, as a putative target for small GTP binding protein Rho", The EMBO Journal, vol. 15, No. 9, 1996, pp. 2208-2216.

Mills, Thomas M. et al., "Effect of Rho-kinase inhibition on vasoconstriction in the penil circulation", J. Appl. Physiol., vol. 91, 2001, pp. 1269-1273.

Miyagi, Yasushi, M.D., Ph.D. et al., "Upregulation of rho A and rho kinase messenger RNAs in the basilar artery of a rat model of subarachnoid hemorrhage", J. Neurosurg., vol. 93, No. 3, Sep. 2000, pp. 471-476.

Mizunuma, Kazuyuki et al., "Prevention of Ischemia-Reperfusion-Induced Hepatic Microcirculatory Disruption by Inhibiting Stellate Cell Contraction Using Rock Inhibitor1", Transplantation, USA, vol. 75, No. 5, Mar. 15, 2003, pp. 579-586.

Morishige, Kunio et al., "Asenovirus-Mediated Transfer of Dominant-Negative Rho-Kinase Induces a Regression of Coronary Arteriosclerosis in Pigs in Vivo", Arterioscler. Thromb. Vasc. Biol., vol. 21, Apr. 2001, pp. 548-555.

Mukai, Yasushi et al., "Involvement of Rho-kinase in hypertensive vascular disease: a novel therapeutic target in hypertension", The FASEB Journal, vol. 15, No. 6, Apr. 2001, pp. 1062-1064.

Müller-Ladner, Ulf et al., "Activation of the IL-4 STAT Pathway in Rheumatoid Synovium", Journal of Immunology, vol. 164, No. 4, 2000, pp. 3894-3901.

Nakagawa, Osamu et al., "ROCK-I and ROCK-II, two isoforms of Rho-associated coiled-coil forming protein serine/threonine kinase in mice", FEBS Letters, vol. 392, No. 2, 1996, pp. 189-193.

Nielsen, Mette et al., "Constitutive activation of a slowly migrating isoform of Stat3 in mycosis fungoides: Tyrphostin AG490 inhibits Stat3 activation and growth of mycosis fungoides tumor cell lines", Proc. Nat. Acad. Sci., USA, vol. 94, No. 13, Jun. 1997, pp. 6764-6769.

Niggli, Verena, "Rho-kinase in human neutrophils: a role in signalling for myosin light chain phosphorylation and cell migration", FEBS Letters, vol. 445, No. 1, 1999, pp. 69-72.

Niiro, Naohisa et al., "Up-Regulation of rho A and rho-Kinase mRHAs in the Rat Myometrium during Pregnancy", Biochemiacl and Biophysical Research Communications, vol. 230, 1997, pp. 356-359.

Nilius, Bernd et al., "Role of Rho and Rho kinase in the activation of volume-regulated anion channels in bovine endothelial cells", Journal of Physiology, vol. 516, No. 1, 1999, pp. 67-74.

Nobes, Catherine D. et al., "Rho GTPases Control Polarity, Protrusion, and Adhesion during Cell Movement", Journal of Cell Biology, vol. 144, No. 6, Mar. 2, 1999, pp. 1235-1244.

Pungpo, Pornpan et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.

Rao, P. Vasantha et al., "Modulation of Aqueous Humor Outflow Facility by the Rho Kinase-Specific Inhibitor Y-27632", Investigative Ophthalmology & Visual Science, vol. 42, No. 5, Apr. 2001, pp. 1029-1037.

Rees, Rowland W. et al., "Y-27632, a Rho-Kinase Inhibitor, Inhibits Proliferation and Adrenergic Contraction of Prostatic Smooth Muscle Cells", The Journal of Urology, USA, vol. 170, Dec. 2003, pp. 2517-2522.

Retzer, Michaela et al., "Mildly oxidised low density lipoprotein induces platelet shape change via Rho-kinase-dependent phosphorylation of myosin light chain and moesin", Federation of European Biochemial Societies Letters, vol. 466, 2000, pp. 70-74.

Rizki, Aylin et al., "Polo-like Kinase 1 Is Involved in Invasion through Extracellular Matrix", American Association of Cancer Research, vol. 67, No. 23, Dec. 1, 2007, pp. 11106-11110.

Sah, Valerie P. et al., "Rho Is Required for Galphaq and alpha1-Adrenergic Receptor Signaling in Cardiomyocytes", The Journal of Biological Chemistry, USA, vol. 27, No. 49, Dec. 6, 1996, pp. 31185-31190.

Sahai, Erik et al., "Transformation mediated by RhoA requires activity of ROCK kinases", Current Biology, vol. 9, No. 3, 1999, pp. 136-145.

Sanborn, M.D., William J. et al., "Tofacitinib, an Oral Janus Kinase Inhibitor, in Active Ulcerative Colitis", The New England Journal of Medicine, vol. 367, No. 7, Aug. 16, 2012, pp. 616-624.

Sato, Motohiko et al., "Involvement of Rho-Kinase-Mediated Phosphorylation of Myosin Light Chain in Enhancement of Cerebral Vasospasm", Circulation Research, vol. 87, No. 2, Aug. 4, 2000, pp. 195-200.

Satoh, Shin-Ichi et al., "Antiischemic Properties of Fasudil in Experimental Models of Vasospastic Angina", Jpn. J. Pharmacol., vol. 87, 2001, pp. 34-40.

Satoh, Shinji et al., "Augmented Agonist-induced Ca2+-Sensitization of Coronary Artery Contraction in Genetically Hypertensive Rats: Evidence for Altered Signal Transduction in the Coronary Smooth Muscle Cells", J. Clin. Invest., vol. 94, No. 4, Oct. 1994, pp. 1397-1403.

Sawada, Naoki et al., "Inhibition of Rho-Associated Kinase Results in Suppression of Neointimal Formation of Balloon-Injured Arteries", Circulation, vol. 101, May 2, 2000, pp. 2030-2023.

(56) References Cited

OTHER PUBLICATIONS

Schwaller, Juerg et al., "Transformation of hematopoietic cell lines to growth-factor independence and induction of a fatal myelo- and lymphoproliferative disease in mice by retrovirally transduced TEL/JAK2 fusion genes", The EMBO Journal, vol. 17, No. 18, 1998, pp. 5321-5333.
Seasholtz, Tammy M. et al., "Rho and Rho Kinase Mediate Thrombin-Stimulated Vascular Smooth Muscle Cell DNA Synthesis and Migration", Circulation Research, vol. 84, No. 4, 1999, pp. 1186-1193.
Segain, Jean-Pierre et al., "Rho Kinase Blockade Prevents Inflammation via Nuclear Factor κB Inhibition: Evidence in Crohn's Disease and Experimental Colitis", Gastroenterology, vol. 124, No. 5, May 2003, pp. 1180-1187.
Seidel, H. Martin et al., "Pharmaceutical intervention in the JAK/STAT signaling pathway", Oncogene, vol. 19, No. 21, 2000, pp. 2645-2656.
Shibata, Rei et al., Role of Rho-Associated Kinase in Neointima Formation After Vascular Injury, Circulation, vol. 130, Jan. 16, 2001, pp. 284-289.
Shimokawa, Hiroaki et al., "Anti-anginal Effect of Fasudil, a Rho-Kinase Inhibitor, in Patients With Stable Effort Angina: A Multicenter Study", Journal of Cardiovascular Pharmacology, vol. 40, No. 5, 2002, pp. 751-761.
Shimokawa, Hiroaki et al., "Cellular and Molecular Mechanisms of Coronary Artery Spasm: Lessons From Animal Models", Jpn. Cir. J., vol. 64, No. 1, 2000, pp. 1-12.
Shimokawa, Hiroaki et al., "Long-term inhibition of Rho-kinase induces a regression of arteriosclerotic coronary lesions in a percine model in vivo", Cardiovascular Research, Elsevier, vol. 51, 2001, pp. 169-177.
Shimokawa, Hiroaki et al., "Rho-kinase as a Novel Therapeutic Target in Treatment of Cardiovascilar Diseases", Journal of Cardiovascular Pharmacology, vol. 39, No. 3, 2002, pp. 319-327.
Smith, Mark R. et al., "Malignant Transformation of Mammalian Cells Initiated by Constitutive Expression of the Polo-like Kinase1", Biochemical and Biophysical Research Communications, vol. 234, No. 2, 1997, pp. 397-405.
Somlyo, Avril V. et al., Kinase Inhibitor Retards Migration and in Vivo Dissemination of Human Prostate Cancer Cells, Biochemical and Biophysical Research Communications, vol. 269, No. 3, 2000, pp. 652-659.
Strebhardt, Klaus et al., "Targeting polo-like kinase 1 for cancer therapy", Nature Reviews, Cancer, Nature Publishing Group, London, GB, vol. 6, No. 4, Apr. 1, 2006, pp. 321-330.
Stump, Kristine L. et al., "A highly selective, orally active inhibitor of Janus kinase 2, CEP-33779, ablates disease in two mouse models of rheumatoid arthritis", Arthritis Research & Therapy, BioMed Central, London, GB, vol. 13, No. 2, Apr. 21, 2011, p. 1, abstract.
Sudbeck, Elise A. et al., "Structure-based Design of Specific Inhibitors of Janus Kinase 3 as Apoptosis-inducing Antileukemic Agents", Clinical Cancer Research, vol. 5, No. 6, Jun. 1999, pp. 1569-1582.
Suzuki, Kotaro et al., "Role of common cytokine receptor gamma chain (gamma(c))- and Jak3-dependent signaling in the proliferation and survival of murine mast cells", Blood, 2000, 96(6), pp. 2172-2180.
Tachibana, E. et al., "Intra-arterial infusion of fasudil hydrochloride for treating vasospasm following subarachnoid haemorrhage", Acta Neurochir (Wien), 1999, 141(1), pp. 13-19.
Tahara, Masahiro et al., "RhoA/Rho-Kinase Cascade Is Involved in Oxytocin-Induced Rat Uterine Contraction", Endocrinology, vol. 143, No. 3, Mar. 2002, pp. 920-929.
Trieu, Vuong N. et al., "A Specific Inhibitor of Janus Kinase-3 Increases Survival in a Transgenic Mouse Model of Amyotrophic Lateral Sclerosis", Biochemical and Biophysical Research Communications, vol. 267, No. 1, 2000, pp. 22-25.
Uehata, Masayoshi et al., "Calcium sensitization of smooth muscle mediated by a Rho-associated protein kinase in hypertension", Nature, vol. 389, Oct. 30, 1997, pp. 990-994.
Utsunomiya, T. et al., "Antianginal effects of hydroxyfasudil, a Rho-kinase inhibitor, in a canine model of effort angina", British Journal of Pharmacology, vol. 134, No. 8, 2001, pp. 1724-1730 C.
Venkatesh, Srini et al., "Role of the Development Scientist in Compound Lead Selection and Optimization", Journal of Pharmaceutical Sciences, vol. 89, No. 2, Feb. 2000, pp. 145-154.
Wada, Makoto et al "siRNA targeting PLK-1 induces apoptosis of synoviocytes in rheumatoid arthritis", Biochemical and Biophysical Research Communications, vol. 357, No. 2, 2007, pp. 353-359.
Watanabe, Go et al., "Protein Kinase N (PKN) and PKN-Related Protein Rhophilin as Targets of Small GTPase Rho", Science, vol. 271, Feb. 2, 1996, pp. 645-648.
Weichert, Wilko et al., "Polo-like kinase isoform expression is a prognostic factor in ovarian carcinoma", British Journal of Cancer, vol. 90, No. 4, 2004, pp. 815-821.
Weichert, Wilko et al., "Polo-like kinase isoforms in breast cancer: expression patterns and prognostic implications", Virchows Archiv, vol. 446, No. 4, 2005, pp. 442-450.
Written Opinion of the International Searching Authority issued for PCT Application No. PCT/US2005/010846 Dated Aug. 19, 2005.
Written Opinion of the International Searching Authority issued for PCT Application No. PCT/US2007/001225 Dated Jul. 20, 2007.
Written Opinion of the International Searching Authority issued for PCT Application No. PCT/US2007/025688 Dated Apr. 6, 2008.
Written Opinion of the International Searching Authority issued for PCT Application No. PCT/US2007/026190 Dated May 20, 2008.
Written Opinion of the International Searching Authority issued for PCT Application No. PCT/US2008/009786 Dated Jan. 19, 2009.
Written Opinion of the International Searching Authority issued for PCT Application No. PCT/US2009/001534 Dated Apr. 2, 2010.
Written Opinion of the International Searching Authority issued for PCT Application No. PCT/US2009/003716 Dated Nov. 20, 2009.
Written Opinion of the International Searching Authority issued for PCT Application No. PCT/US2009/003723 Dated Nov. 20, 2009.
Yanazume, Tetsuhiko et al., "Rho/ROCK Pathway Contributes to the Activation of Extracellular Signal-regulated Kinase/GTA-4 during Myocardial Cell Hypertrophy", The Journal of Biological Chemistry, USA, vol. 277, No. 10, Mar. 8, 2002, pp. 8618-8625.
Yoshii, Akihiro et al. "Relaxation of Contracted Rabbit Tracheal and Human Bronchial Smooth Muscle by Y-27632 through Inhibition of Ca2+ Sensitization", American Journal of Respiratory Cell and Molecular Biology, vol. 20, No. 6, 1999, pp. 1190-1200.
Yu, Chao-Lan et al., "Constitutive Activation of the Janus Kinase-STAT Pathway in T Lymphoma Overexpressing the Lck protein tyrosine kinase1", Journal of Immunology, vol. 159, No. 11, 1997, pp. 5206-5210.
Zhou, Yan et al., "Nonsteroidal Anti-Inflammatory Drugs Can Lower Amyloidogenic Aβ42 by Inhibiting Rho", Science, vol. 302, No. 14, Nov. 2003, pp. 1215-1218.

INHIBITORS OF INFLUENZA VIRUSES REPLICATION

RELATED APPLICATIONS

This application is a divisional of U.S. application Ser. No. 13/327,206, filed on Dec. 15, 2011, which is a continuation of PCT Application No. PCT/US2010/038988, filed Jun. 17, 2010 which claims priority to U.S. Provisional Application No. 61/187,713, filed on Jun. 17, 2009, and to U.S. Provisional Application No. 61/287,781, filed on Dec. 18, 2009. The entire teachings of these applications are incorporated herein by reference.

BACKGROUND OF THE INVENTION

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant—antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs.

Thus, there is still a need for drugs for treating influenza infections, such as for drugs with expanded treatment window, and/or reduced sensitivity to viral titer.

SUMMARY OF THE INVENTION

The present invention generally relates to methods of treating influenza, to methods of inhibiting the replication of influenza viruses, to methods of reducing the amount of influenza viruses, to compounds and compositions that can be employed for such methods.

In one aspect, the present invention is directed to a method of inhibiting the replication of influenza viruses in a biological sample or in a patient. In one embodiment, the method comprises administering to said biological sample or patient an effective amount of a compound represented by Structural Formula (IA):

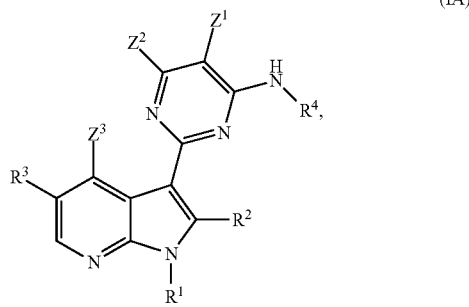

(IA)

or a pharmaceutically acceptable salt thereof, wherein:

$Z^1$ is —$R^*$, —F, —Cl, —CN, —$OR^*$, —$CO_2R^*$, —$NO_2$, or —$CON(R^*)_2$;

$Z^2$ is —$R^*$, —$OR^*$, —$CO_2R^*$, —$NR^*_2$, or —$CON(R^*)_2$;

$Z^3$ is —H, —OH, halogen (e.g., —Cl or —Br), —$NH_2$; —$NH(C_1$-$C_4$ alkyl); —$N(C_1$-$C_4$ alkyl)$_2$, —$O(C_1$-$C_4$ alkyl), or $C_1$-$C_6$ alkyl that is optionally substituted with one or more substituents independently selected from the group consisting of halogen, cyano, hydroxy, and —$O(C_1$-$C_4$ alkyl);

$R^1$ is —H or $C_1$-$C_6$ alkyl;

$R^2$ is —H; —F; —$NH_2$; —$NH(C_1$-$C_4$ alkyl); —$N(C_1$-$C_4$ alkyl)$_2$; —C=N—OH; cyclopropyl that is optionally substituted with one or more substituents independently selected from the group consisting of halogen, cyano, hydroxy, —$OCH_3$, and —$CH_3$; or $C_1$-$C_4$ alkyl that is optionally substituted with one or more substituents independently selected from the group consisting of halogen, cyano, hydroxy, and —$O(C_1$-$C_4$ alkyl); and $R^3$ is —H, —Cl, —F, —OH, —$O(C_1$-$C_4$ alkyl), —$NH_2$, —$NH(C_1$-$C_4$ alkyl), —$N(C_1$-$C_4$ alkyl)$_2$, —Br, —CN, or $C_1$-$C_4$ aliphatic that is optionally substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy;

$R^4$ is:

i) 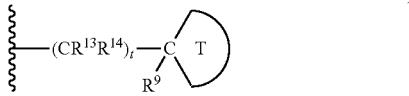

wherein ring T is a $C_3$-$C_{10}$ non-aromatic carbocycle optionally substituted with one or more instances of $J^A$, or a 3-10 membered non-aromatic heterocycle optionally substituted with one or more instances of $J^B$, or ring T and $R^9$ optionally form a non-aromatic $C_5$-$C_{10}$ membered carbocycle optionally substituted with one or more instances of $J^A$ or 5-10 membered non-aromatic heterocycle optionally substituted with one or more instances of $J^B$;

ii) 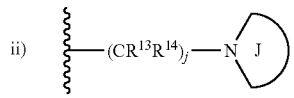

wherein ring J is a 3-10 membered non-aromatic heterocycle optionally substituted with one or more instances of $J^B$; or iii) 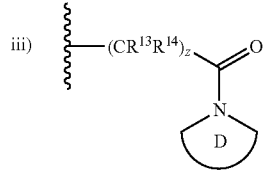

wherein ring D is a 4-10 membered non-aromatic heterocycle optionally substituted with one or more instances of $J^{D1}$; and each of $J^A$ and $J^B$ is independently selected from the group consisting of halogen, cyano, oxo, —NCO, and $Q^1$-$R^5$; or optionally two $J^A$ and two $J^B$, respectively, together with the atom(s) to which they are attached, independently form a 4-8 membered ring (e.g., spiro ring or fused ring) that is optionally substituted with one or more instances of $J^{E1}$;

$Q^1$ is independently a bond, —O—, —S—, —NR'—, —C(O)—, —C(=NR)—, —C(=NR)NR—, —NRC(=NR)NR—, —$CO_2$—, —OC(O)—, —C(O)NR'—, —C(O)NRC(O)O—, —NRC(O)NRC(O)O—, —NRC(O)—, —NRC(O)NR'—, —$NRCO_2$—, —OC(O)NR'—, —S(O)—, —$SO_2$—, —$SO_2NR'$—, —$NRSO_2$—, or —$NRSO_2NR'$—, —P(O)(OR)O—, —OP(O)($OR^a$)O—, —$P(O)_2O$—, —$CO_2SO_2$—, or —$(CR^6R^7)_p$—$Y^1$—;

$Y^1$ is independently a bond, —O—, —S—, —NR'—, —C(O)—, —C(=NR)—, —C(=NR)NR—, —NRC(=NR)NR—, —$CO_2$—, —OC(O)—, —C(O)NR'—, —C(O)NRC(O)O—, —NRC(O)NRC(O)O—, —NRC(O)—, —NRC(O)NR'—, —$NRCO_2$—, —OC(O)NR'—, —S(O)—, —$SO_2$—, —$SO_2NR'$—, —$NRSO_2$—, —$NRSO_2NR'$—, —P(O)(OR)O—, —OP(O)($OR^a$)O—, —$P(O)_2O$—, or —$CO_2SO_2$—;

$R^5$ is: i) —H; ii) a $C_1$-$C_6$ aliphatic group optionally substituted with one or more instances of $J^{C1}$; iii) a $C_3$-$C_{10}$ non-aromatic carbocycle, or a 6-10 membered carbocyclic aryl group, each optionally and independently substituted with one or more instances of $J^{C1}$; or iv) a 4-10 membered non-aromatic heterocycle, or a 5-10 membered heteroaryl group, each optionally and independently substituted with one or more instances of $J^{D1}$; or $R^5$, together with $Q^1$, optionally forms a 4-8 membered, non-aromatic ring optionally substituted with one or more instances of $J^{E1}$; and $R^6$ and $R^7$ are each independently —H or $C_1$-$C_6$ alkyl optionally substituted with one or more substituents selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy, or optionally $R^6$ and $R^7$, together with the carbon atom to which they are attached, form a cyclopropane ring optionally substituted with one or more instances of methyl;

$R^9$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy;

$R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy;

optionally, $R^{13}$ and $R^{14}$, together with the carbon atom to which they are attached, form a cyclopropane ring optionally substituted with one or more instances of methyl;

R and R' are each independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy; or optionally R', together with $R^5$ and the nitrogen atom to which they are attached, forms a 5-7 membered non-aromatic heterocycle optionally substituted with one or more instances of $J^{D1}$;

R* is independently: i) —H; ii) a $C_1$-$C_6$ alkyl group optionally substituted with one or more substituents independently selected from the group consisting of halogen, cyano, hydroxy, oxo, amino, carboxy, $C_3$-$C_8$ non-aromatic carbocycle, 5-6 membered non-aromatic heterocycle, phenyl, 5-6 membered heteroaryl, —O($C_1$-$C_6$ alkyl), and —C(O)($C_1$-$C_6$-alkyl); wherein each of said alkyl groups in —O($C_1$-$C_6$ alkyl), and —C(O)($C_1$-$C_6$-alkyl) is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy; and wherein each of said carbocycle, heterocycle, phenyl, and heteroaryl is independently and optionally substituted with one or more instances of $J^{E1}$; or iii) a $C_3$-$C_8$ non-aromatic carbocycle, or a 4-8 membered non-aromatic heterocycle, each of which is independently and optionally substituted with one or more instances of $J^{E1}$; and each of $J^{C1}$ and $J^{D1}$ is independently selected from the group consisting of halogen, cyano, oxo, $R^a$, —OR$^b$, —SR$^b$, —S(O)R$^a$, —SO$_2$R$^a$, —NR$^b$R$^c$, —C(O)R$^b$, —C(=NR)R$^c$, —C(=NR)NR$^b$R$^c$, —NRC(=NR)NR$^b$R$^c$, —C(O)OR$^b$, —OC(O)R$^b$, —NRC(O)R$^b$, —C(O)NR$^b$R$^c$, —NRC(O)NR$^b$R$^c$, —NRC(O)OR$^b$, —OCONR$^b$R$^c$, —C(O)NRCO$_2$R$^b$, —NRC(O)NRC(O)OR$^b$, —C(O)NR(OR$^b$), —SO$_2$NR$^c$R$^b$, —NRSO$_2$R$^b$, —NRSO$_2$NR$^c$R$^b$, —P(O)(OR$^a$)$_2$, —OP(O)(OR$^a$)$_2$, —P(O)$_2$OR$^a$ and —CO$_2$SO$_2$R$^b$, or optionally, two $J^{C1}$ and two $J^{D1}$, respectively, together with the atom(s) to which they are attached, independently form a 4-8-membered ring that is optionally substituted with one or more instances of $J^{E1}$;

each $J^{E1}$ is independently selected from the group consisting of halogen, cyano, hydroxy, oxo, amino, carboxy, amido, $C_1$-$C_6$ alkyl, —O($C_1$-$C_6$ alkyl), and —C(O)($C_1$-$C_6$-alkyl), wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy; and $R^a$ is independently: i) a $C_1$-$C_6$ aliphatic group optionally substituted with one or more substituents independently selected from the group consisting of halogen, cyano, hydroxy, oxo, amino, carboxy, amido, —O($C_1$-$C_6$ alkyl), —C(O)($C_1$-$C_6$-alkyl), $C_3$-$C_8$ non-aromatic carbocycle, 4-8 membered non-aromatic heterocycle, 5-10 membered heteroaryl group, and 6-10 membered carbocyclic aryl group; wherein each of said alkyl groups for the substituents of the $C_1$-$C_6$ aliphatic group represented by $R^a$ is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy; and wherein each of said carbocycle, heterocycle, heteroaryl and carbocyclic aryl groups for the substituents of the $C_1$-$C_6$ aliphatic group represented by $R^a$ is optionally and independently substituted with one or more instances of $J^{E1}$;

ii) a $C_3$-$C_8$ non-aromatic carbocycle, or a 4-8 membered non-aromatic heterocycle, each of which is optionally and independently substituted with one or more instances of $J^{E1}$; or iii) a 5-10 membered heteroaryl, or 6-10 membered carbocyclic aryl group, each of which is optionally and independently substituted with one or more instances of $J^{E1}$; and $R^b$ and $R^c$ are each independently $R^a$ or —H; or optionally, $R^b$ and $R^c$, together with the nitrogen atom(s) to which they are attached, each independently form a 5-7 membered non-aromatic heterocycle optionally substituted with one or more instances of $J^{E1}$;

p is independently 1, 2, 3 or 4;

t is 0, 1 or 2;

j is 1 or 2; and z is 1 or 2.

In another embodiment, the method comprises administering to said biological sample or patient an effective amount of a compound represented by Structural Formula (I):

(I)

[Structural formula showing a pyrrolopyridine-pyrimidine compound with substituents Z¹, Z², R₁, R₂, R₃, R₄, and NH]

or a pharmaceutically acceptable salt thereof, wherein:

$R^1$ is —H;

$R^2$ is —H, —CH₃, —NH₂, —NH(C₁-C₄ alkyl), or —N(C₁-C₄ alkyl)₂;

$R^4$ is: i) a C₃-C₁₀ non-aromatic carbocycle optionally substituted with one or more instances of $J^A$; ii) a 4-10 membered non-aromatic heterocycle optionally substituted with one or more instances of $J^B$; or iii) a C₁-C₆ aliphatic group optionally substituted with one or more substituents independently selected from the group consisting off; a C₃-C₈ non-aromatic carbocycle, or a 6-10 membered carbocyclic aryl group, each optionally and independently substituted with one or more instances of $J^A$; and a 5-10 membered heteroaryl group, or a 4-10 membered non-aromatic heterocycle, each optionally and independently substituted with one or more instances of $J^B$;

each of $J^A$ and $J^B$ is independently selected from the group consisting of halogen, cyano, oxo, —NCO, and $Q^1$-$R^5$; or optionally two $J^A$ and two $J^B$, respectively, together with the atom(s) to which they are attached, independently form a 5-7 membered ring that is optionally substituted with one or more instanced of $J^{E1}$;

$J^C$ is independently selected from the group consisting of halogen, cyano, oxo, —OR⁵, —SR⁵, —NR'R⁵, —C(O)R⁵, —CO₂R⁵, —OC(O)R⁵, —C(O)NR'R⁵, —C(O)NRC(O)OR⁵, —NRC(O)NRC(O)OR⁵, —NRC(O)R⁵, —NRC(O)NR'R⁵, —NRCO₂R⁵, —OC(O)NR'R⁵, —S(O)R⁵, —SO₂R⁵, —SO₂NR'R⁵, —NRSO₂R⁵, and —NRSO₂NR'R⁵;

$Q^1$ is independently a bond, —O—, —S—, —NR'—, —C(O)—, —C(=NR)—, —CO₂—, —OC(O)—, —C(O) NR'—, —C(O)NRC(O)O—, NRC(O)NRC(O)O—, —NRC(O)—, —NRC(O)NR'—, —NRCO₂—, —OC(O)NR'—, —S(O)—, —SO₂—, —SO₂NR'—, —NRSO₂—, or —NRSO₂NR'—, or —(CR⁶R⁷)ₚ—Y¹—;

$Y^1$ is independently a bond, —O—, —S—, —NR'—, —C(O)—, —C(=NR)—, —CO₂—, —OC(O)—, —C(O) NR'—, —C(O)NRC(O)O—, —NRC(O)NRC(O)O—, —NRC(O)—, —NRC(O)NR'—, —NRCO₂—, —OC(O) NR'—, —S(O)—, —SO₂—, —SO₂NR'—, —NRSO₂—, or —NRSO₂NR'—;

$R^5$ is: i) —H; ii) a C₁-C₆ aliphatic group optionally substituted with one or more instances of $J^{C1}$; iii) a C₃-C₈ non-aromatic carbocycle, or a 6-10 membered carbocyclic aryl group, each optionally and independently substituted with one or more instances of $J^{C1}$; or iv) a 4-8 membered non-aromatic heterocycle, or a 5-10 membered heteroaryl group, each optionally and independently substituted with one or more instances of $J^{D1}$. Optionally, $R^5$, together with $Q^1$, optionally forms a 5-7 membered, non-aromatic ring optionally substituted with one or more instances of $J^{E1}$;

each of $J^{C1}$ and $J^{D1}$ is independently selected from the group consisting of halogen, cyano, oxo, $R^a$, —OR$^b$, —SR$^b$, —S(O)R$^a$, —SO₂R$^a$, —NR$^b$R$^c$, —C(O)R$^b$, —C(O)OR$^b$, —OC(O)R$^b$, —NRC(O)R$^b$, —C(O)NR$^b$R$^c$, —NRC(O) NR$^b$R$^c$, —NRC(O)OR$^b$, —OCONR$^b$R$^c$, —C(O)NRCO₂R$^b$, —NRC(O)NRC(O)OR$^b$, —C(O)NR(OR$^b$), —SO₂NR$^c$R$^b$, —NRSO₂R$^b$, —NRSO₂NR$^c$R$^b$, and —P(O)(OR$^a$)₂—, or optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached; and each of $Z^1$, $Z^2$, $R^3$, $R^6$, $R^7$, R, R', R*, $J^{E1}$, $R^a$, $R^b$, $R^c$ and p is independently as described above for Structural Formula (IA).

In another embodiment, the present invention is directed to a method of reducing the amount of influenza viruses in a biological sample or in a patient. The method comprises administering to said biological sample or patient an effective amount of a compound represented by Structural Formula (I) or Structural Formula (IA), each and independently as described above.

In yet another embodiment, the present invention is directed to a method of treating or preventing influenza in a patient, comprising administering to said patient an effective amount of a compound represented by Structural Formula (I) or Structural Formula (IA), each and independently as described above.

In yet another embodiment, the present invention is directed to a compound represented by Structural Formula (IA) or a pharmaceutically acceptable salt thereof: or a pharmaceutically acceptable salt thereof, wherein:

$R^1$ is —H, C₁-C₆ alkyl, —S(O)₂—R", or —C(O)OR"; or alternatively $R^1$ is —H or C₁-C₆ alkyl;

$R^4$ is:

[Three ring structures labeled A, B, C with substituents R⁸, R⁹, R¹⁰, R¹¹, R¹², R¹³, R¹⁴, Q², Q³, R⁵, and indices n, m, k, x, y]

or

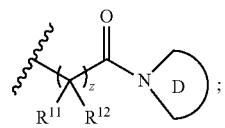

wherein:

ring A is a $C_3$-$C_{10}$ non-aromatic carbocycle optionally further substituted with one or more instances of $J^A$, or heterocyle optionally further substituted with one or more instances of $J^B$;

rings B and C are each independently a 4-10 membered, non-aromatic heterocycle optionally and independently further substituted with one or more instances of $J^B$;

ring D is a 4-10 membered, non-aromatic heterocycle optionally substituted with one or more instances of $J^{D1}$; or ring A and $R^8$ optionally form a non-aromatic, 5-10 membered, bridged carbocycle or heterocycle, or ring A and $R^9$ optionally form a non-aromatic, 5-10 membered, bridged carbocycle or heterocycle, or ring A and $R^{11}$ optionally form a non-aromatic, 5-10 membered, bridged carbocycle or heterocycle, wherein each carbocycle is optionally further substituted with one or more instances of $J^A$, and wherein each heterocycle is optionally further substituted with one or more instances of $J^B$; and $Q^2$ is independently a bond, —O—, —S—, —NR—, —C(O)—, —C(=NR)—, —C(=NR)NR—, —NRC(=NR)NR—, —$CO_2$—, —OC(O)—, —C(O)NR—, —C(O)NRC(O)O—, NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$N(R)—, —$NRSO_2NR$—, —P(O)(OR)O—, —OP(O)($OR^a$)O—, —$P(O)_2O$—, —$CO_2SO_2$—, or —$(CR^6R^7)_p$—$Y^1$—;

$Q^3$ is independently a bond, —C(O)—, —C(=NR)—, —C(=NR)NR—, —NRC(=NR)NR—, —$CO_2$—, —C(O)NR—, —$SO_2$N(R)—, —C(O)NRC(O)O— or —$(CR^6R^7)_p$—$Y^1$—;

R" is independently: i) a $C_1$-$C_6$-alkyl optionally substituted with one or more substituents selected independently from the group consisting of halogen, cyano, hydroxyl, —$NH_2$, —NH($C_1$-$C_6$ alkyl), —N($C_1$-$C_6$ alkyl)$_2$, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or ii) a $C_3$-$C_6$ carbocyclic group, a 5-6 membered heteroaryl group, or a phenyl group, each optionally and independently being substituted with one or more substituents independently selected from the group consisting of halogen, cyano, hydroxy, oxo, nitro, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ cyanoalkyl, $C_1$-$C_6$-hydroxyalkyl, $C_2$-$C_6$-alkoxyalkyl, $C_1$-$C_6$-aminoalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$-hydroxyalkoxy, and $C_2$-$C_6$ alkoxyalkoxy;

each of $Z^1$, $Z^2$, $Z^3$, $Q^1$, $Q^2$, $Q^3$, $Y^1$, $R^2$, $R^3$, $R^5$, $R^6$, $R^7$, $R^8$, $R^9$, $R^{10}$, $R^{11}$, $R^{12}$, $R^{13}$, $R^{14}$, R, R', R*, $J^A$, $J^B$, $J^{C1}$, $J^{D1}$, $J^{E1}$, $R^a$, $R^b$, $R^c$ and p is independently as described above for Structural Formula (IA) for the method of inhibiting the replication of influenza viruses;

n and m are each independently 0 or 1 when rings A and B are 3-6-membered; or n and m are each independently 0, 1 or 2 when rings A and B are 7-10-membered;

k is 0, 1 or 2;

x and y are each independently 0, 1 or 2;

z is 1 or 2; and provided that if $Y^1$ is a bond, then $R^5$ is neither —H nor a $C_1$-$C_6$ aliphatic group; and provided that if each $Q^2$ and $Q^3$ independently is a bond, then $R^5$ is neither —H nor a $C_1$-$C_6$ aliphatic group.

In yet another embodiment, the present invention is directed to a compound represented by Structural Formula (I) or a pharmaceutically acceptable salt thereof, wherein: the values of the variables of Structural Formula (I) are as described below:

$R^1$ is —H, $C_1$-$C_6$ alkyl, —$S(O)_2$—R", or —C(O)OR"; or alternatively $R^1$ is —H or $C_1$-$C_6$ alkyl.

$R^4$ is:

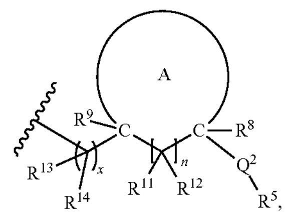

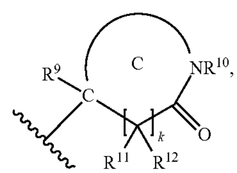

or 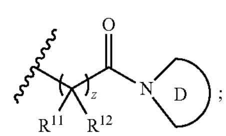 ring A is a $C_3$-$C_8$ non-aromatic carbocycle optionally further substituted with one or more instances of $J^A$, or heterocycle optionally further substituted with one or more instances of $J^B$;

rings B and C are each independently a 4-8 membered, non-aromatic heterocycle optionally and independently further substituted with one or more instances of $J^B$;

ring D is a 4-8 membered, non-aromatic heterocycle optionally substituted with one or more instances of $J^{D1}$;

R" is independently: i) a $C_1$-$C_6$-alkyl optionally substituted with one or more substituents independently selected from the group consisting of halogen, cyano, hydroxyl, —$NH_2$, —NH($C_1$-$C_6$ alkyl), —N($C_1$-$C_6$ alkyl)$_2$, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy; or ii) a $C_3$-$C_6$ carbocyclic group, 5-6 membered heteroaryl group, or phenyl group, each optionally and independently being substituted with one or more substituents independently selected from the group consisting of halogen, cyano, hydroxy, oxo, nitro, —NH₂, —NH(C₁-C₆ alkyl), —N(C₁-C₆ alkyl)₂, C₁-C₆ alkyl, C₁-C₆ haloalkyl, C₁-C₆ cyanoalkyl, C₁-C₆-hydroxyalkyl, C₂-C₆-alkoxyalkyl, C₁-C₆-aminoalkyl, C₁-C₆ alkoxy, C₁-C₆ haloalkoxy, C₁-C₆ aminoalkoxy, C₁-C₆ cyanoalkoxy, C₁-C₆-hydroxyalkoxy, and C₂-C₆ alkoxyalkoxy;

each of $Z^1$, $Z^2$, $Z^3$, $Q^1$, $Q^2$, $Q^3$, $Y^1$, $R^2$, $R^3$, $R^5$, $R^6$, $R^7$, $R^8$, $R^9$, $R^{10}$, $R^{11}$, $R^{12}$, $R^{13}$, $R^{14}$, R, R', R*, $J^{C1}$, $J^{D1}$, $J^{E1}$, $R^a$, $R^b$, $R^c$ and p is independently as described above for Structural Formula (I) for the method of inhibiting the replication of influenza viruses;

n and m are each independently 0 or 1 when rings A and B are 4-6-membered; or n and m are each independently 0, 1 or 2 when rings A and B are 7-8 membered;

k is 0, 1 or 2;

x and y are each independently 0, 1 or 2;

z is 1 or 2;

provided that if $Y^1$ is a bond, then $R^5$ is neither —H nor an unsubstituted C₁-C₆ aliphatic group; and provided that if each $Q^2$ and $Q^3$ independently is a bond, then $R^5$ is neither —H nor a C₁-C₆ aliphatic group.

In yet another embodiment, the present invention is directed to a pharmaceutical composition comprising a compound represented by Structural Formula (I) or Structural Formula (IA), or a pharmaceutically acceptable salt thereof, and a pharmaceutically acceptable carrier, adjuvant or vehicle, wherein the values of the variable of Structural Formulae (I) and (IA) are each and independently as described above for the compounds of the invention.

The present invention also provides use of a compound described herein for inhibiting the replication of influenza viruses in a biological sample or patient, for reducing the amount of influenza viruses in a biological sample or patient, or for treating influenza in a patient.

Also provided herein is use of a compound described herein for the manufacture of a medicament for treating influenza in a patient, for reducing the amount of influenza viruses in a biological sample or in a patient, or for inhibiting the replication of influenza viruses in a biological sample or patient.

DETAILED DESCRIPTION OF THE INVENTION

Uses of Disclosed Compounds

Figures 1, 2:
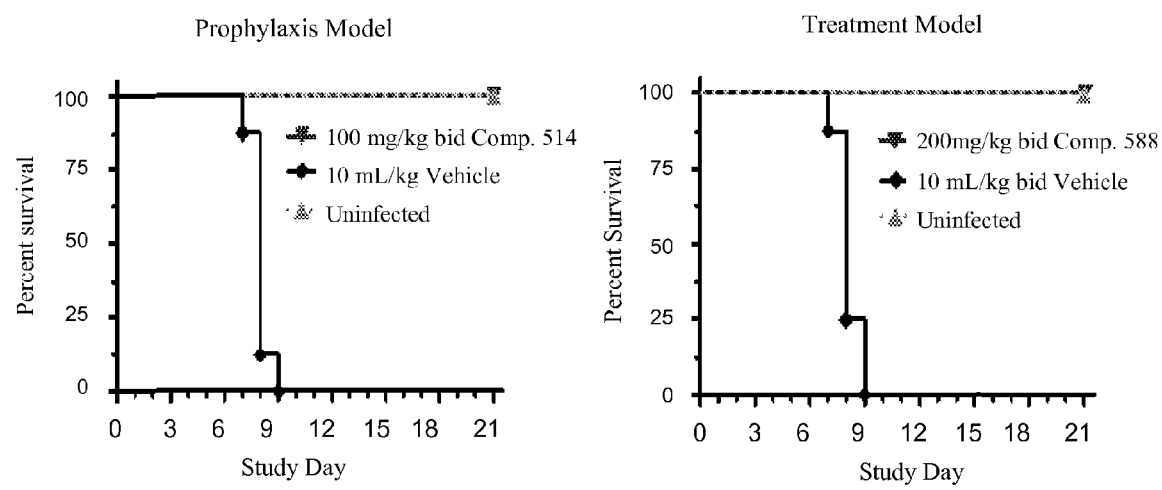
FIG. 1 is a graph showing percentages of survival of Balb/c mice (4-5 weeks of age) over time for a prophylaxis study in which an initial dose of Compound 514 (100 mg/kg) or vehicle only (0.5% Methylcellulose/0.5% Tween 80) were administered 2 hours prior to infection by oral gavage (10 mL/kg) and continued twice daily for 5 days.
FIG. 2 is a graph showing percentages of survival of Balb/c mice (4-5 weeks of age) over time for a therapeutic treatment study in which Compound 588 (200 mg/kg) or vehicle only were administered by oral gavage 24 hours post infection and continued twice daily for 10 days.
Figure 3A:
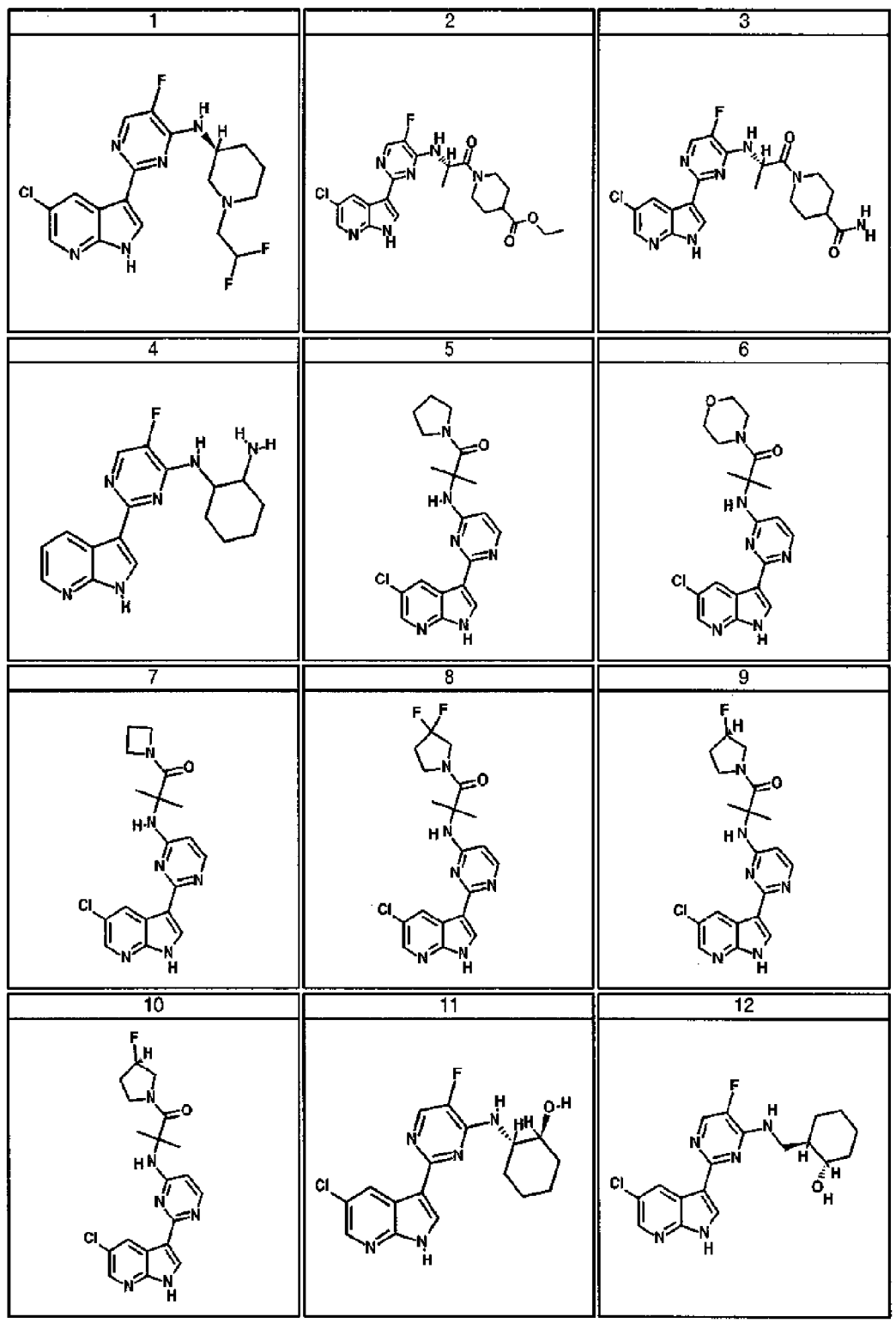
FIGS. 3-8 are tables showing some specific compounds of the invention.
Figure 3B:
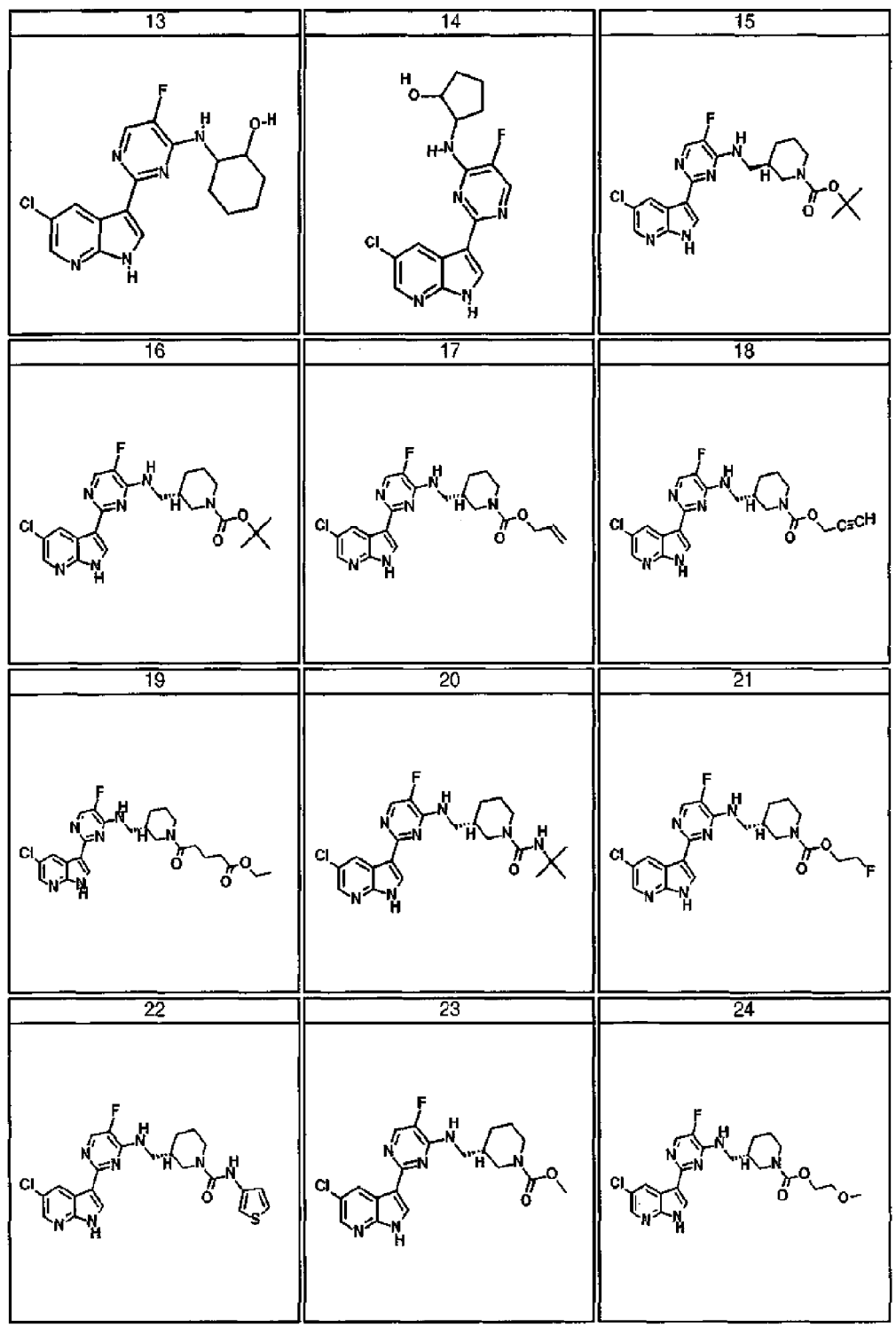
Figure 3C:
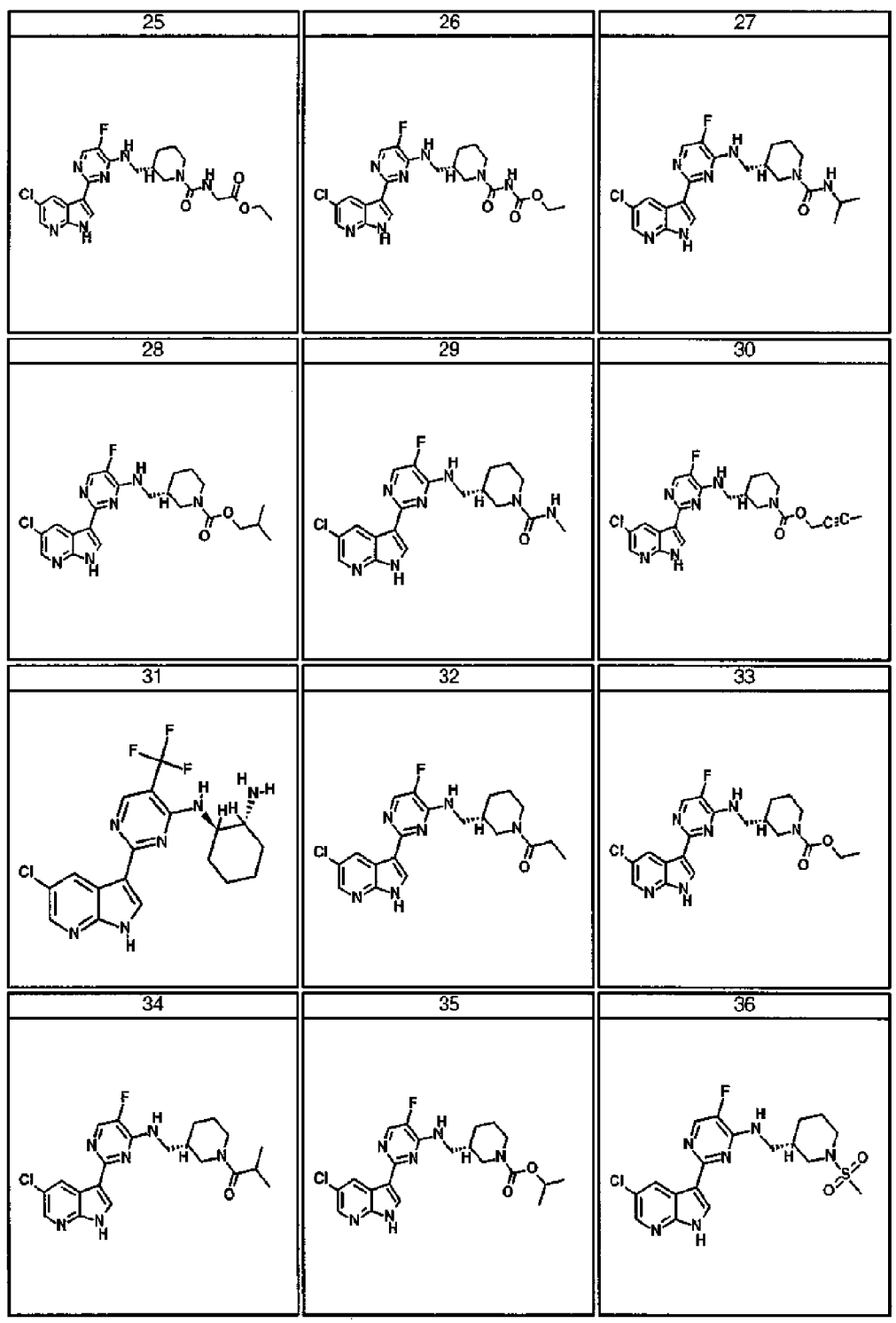
Figure 3D:
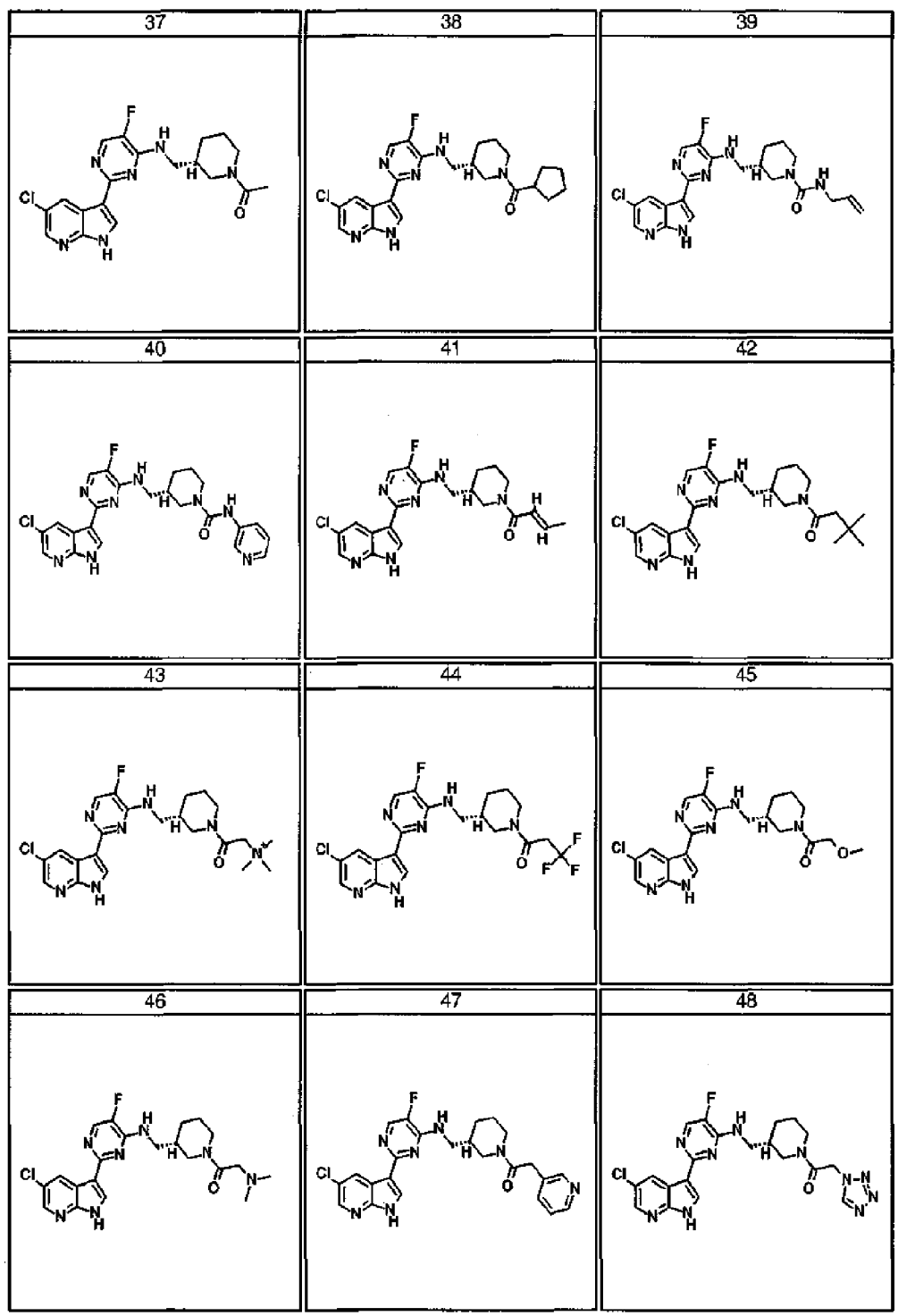
Figure 3E:
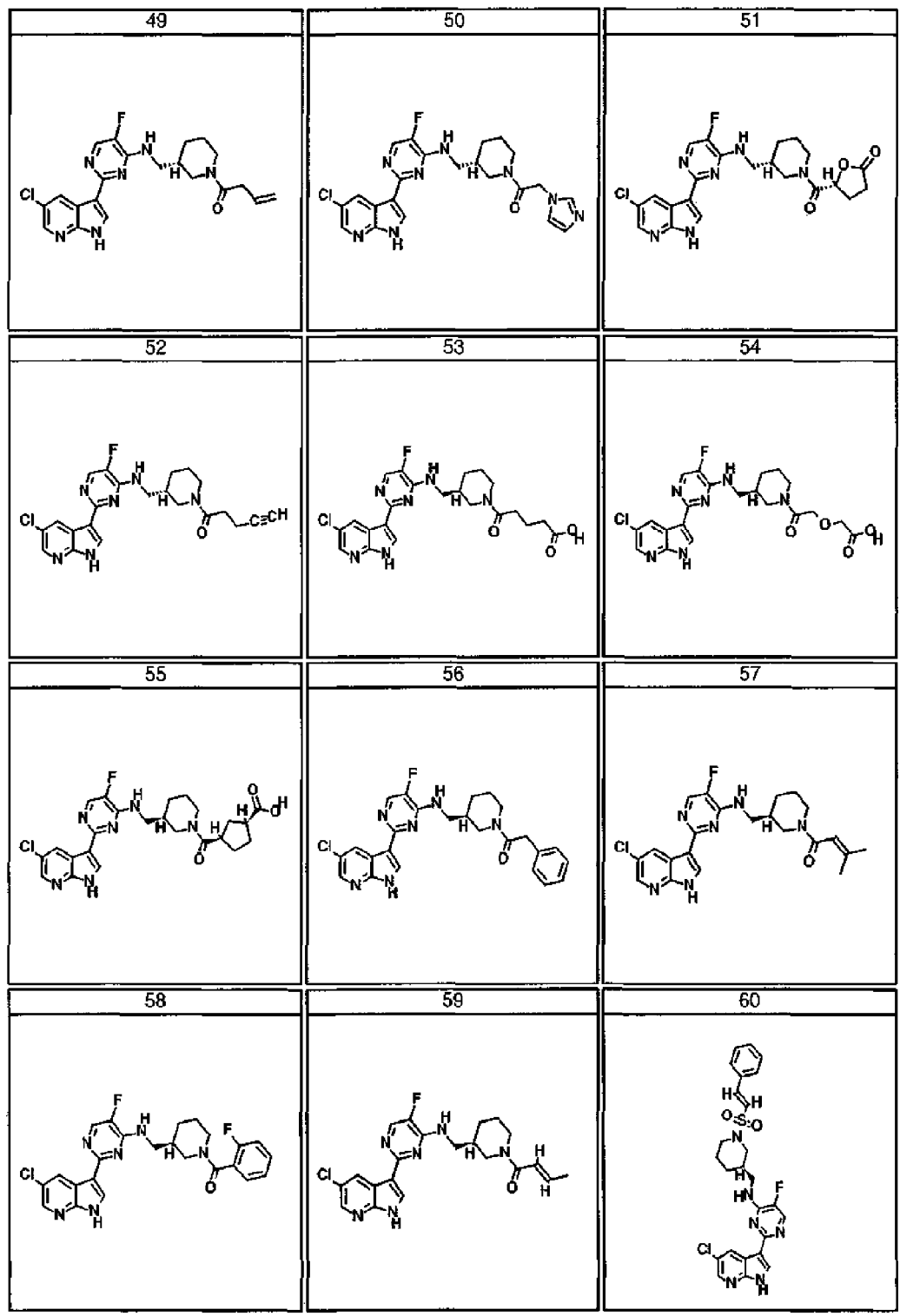
Figure 3F:
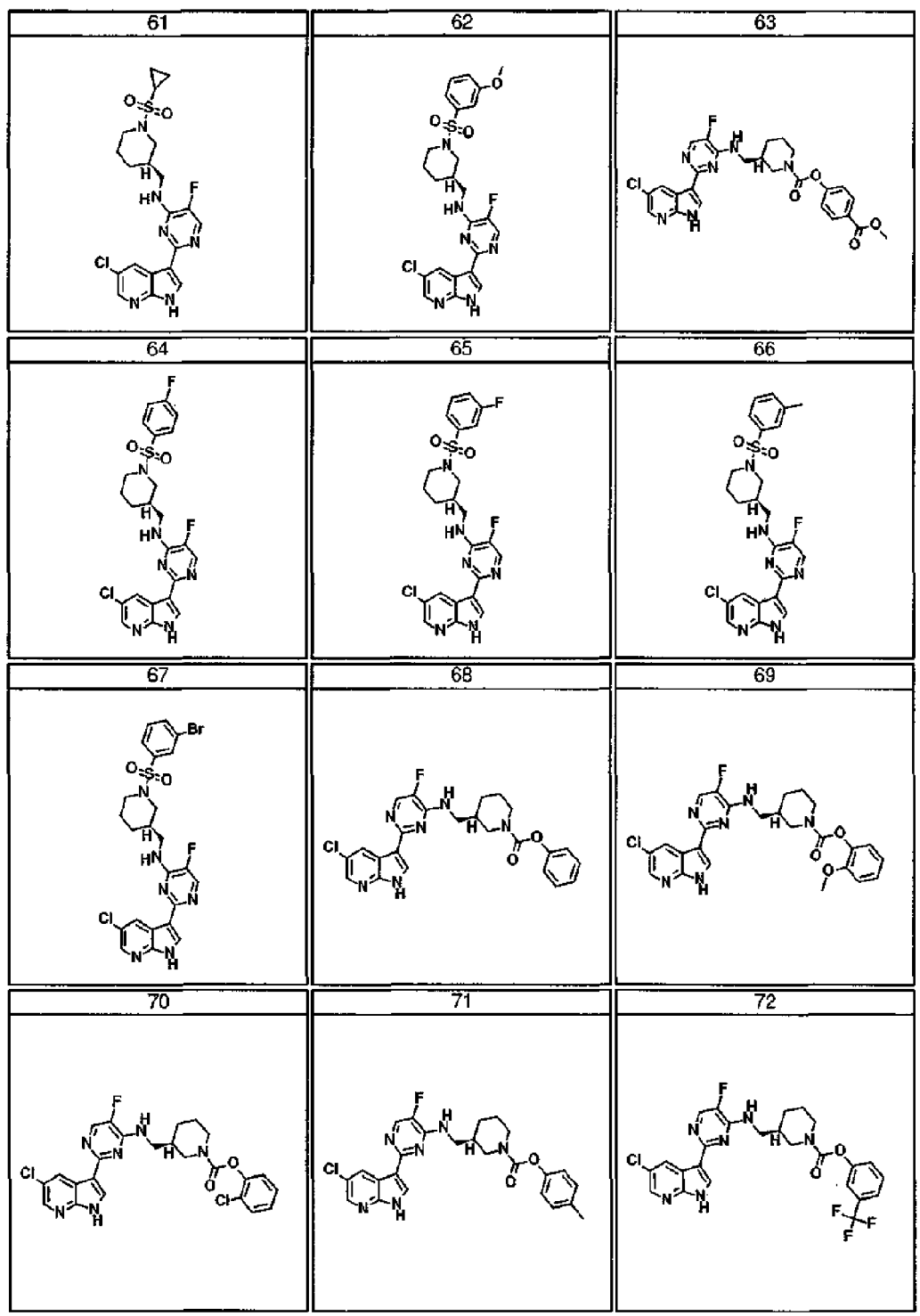
Figure 3G:
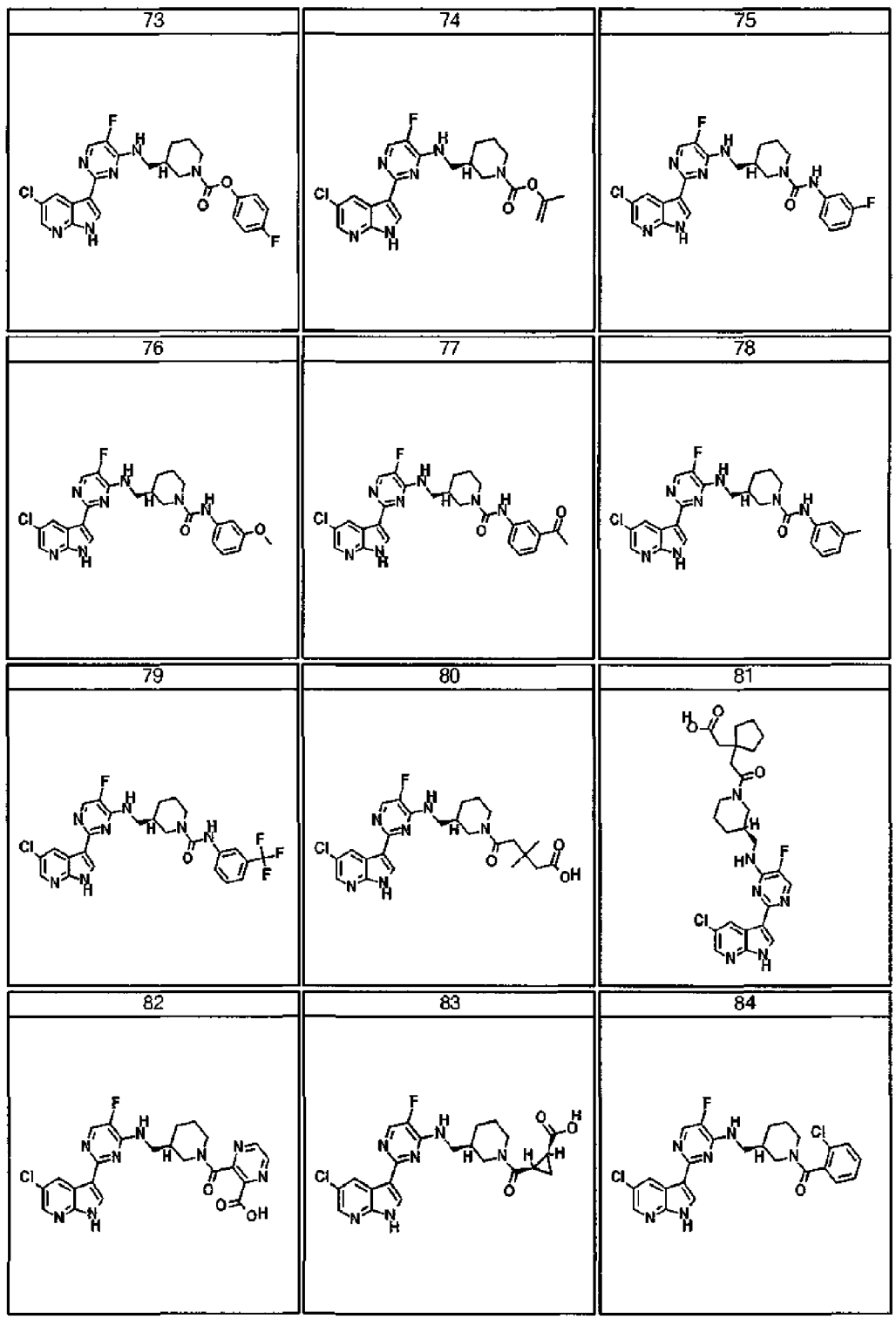
Figure 3H:
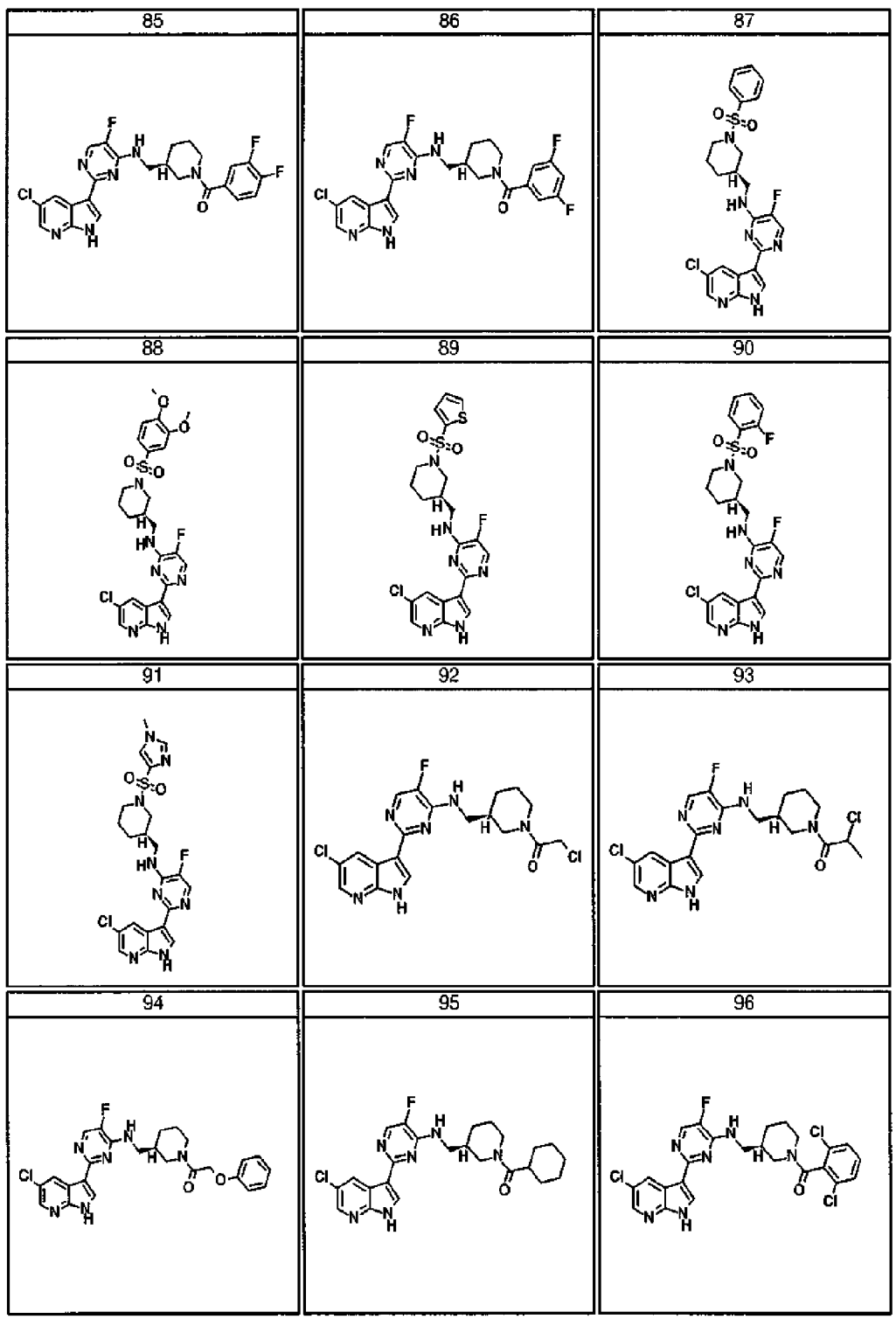
Figure 3I:
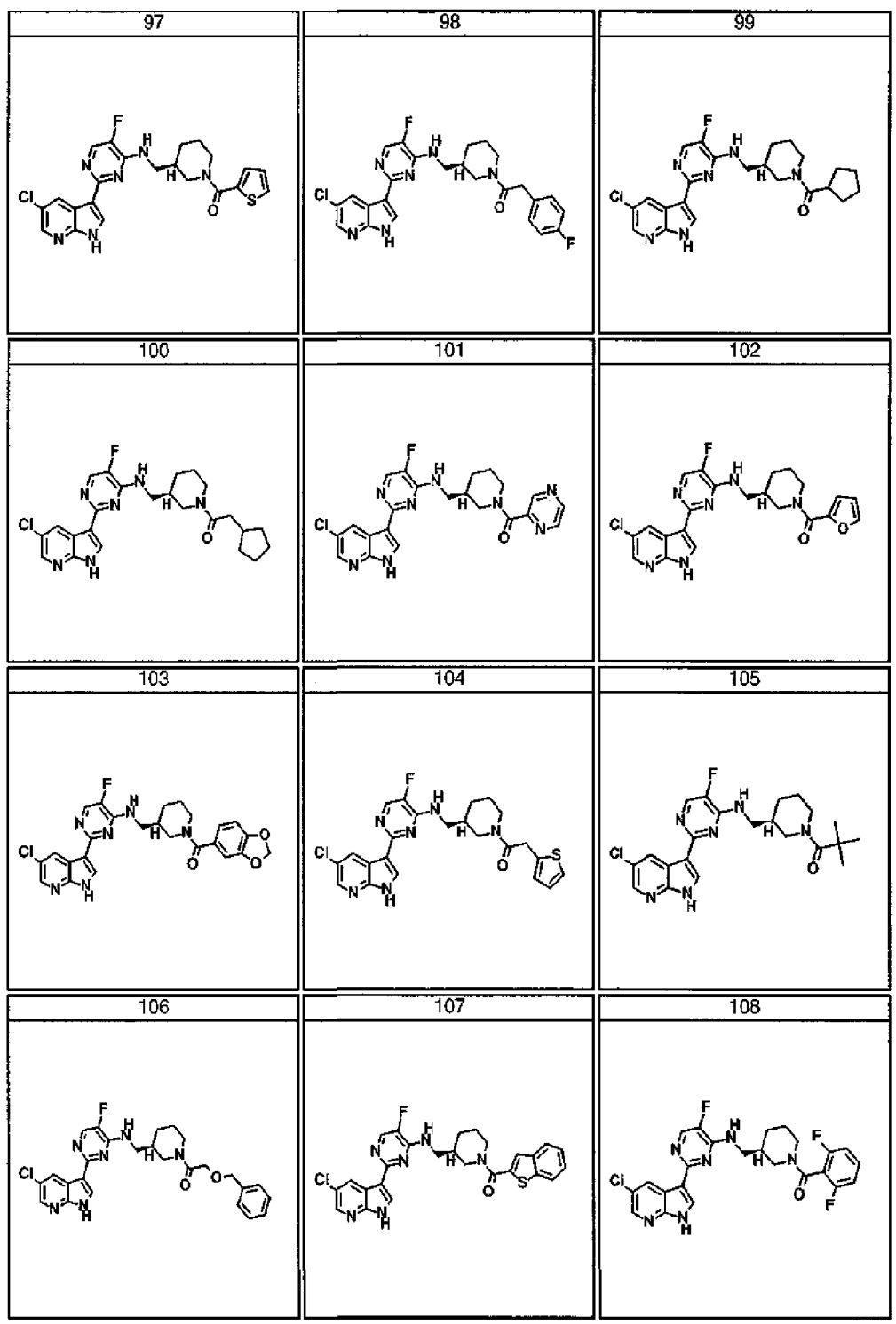
Figure 3J:
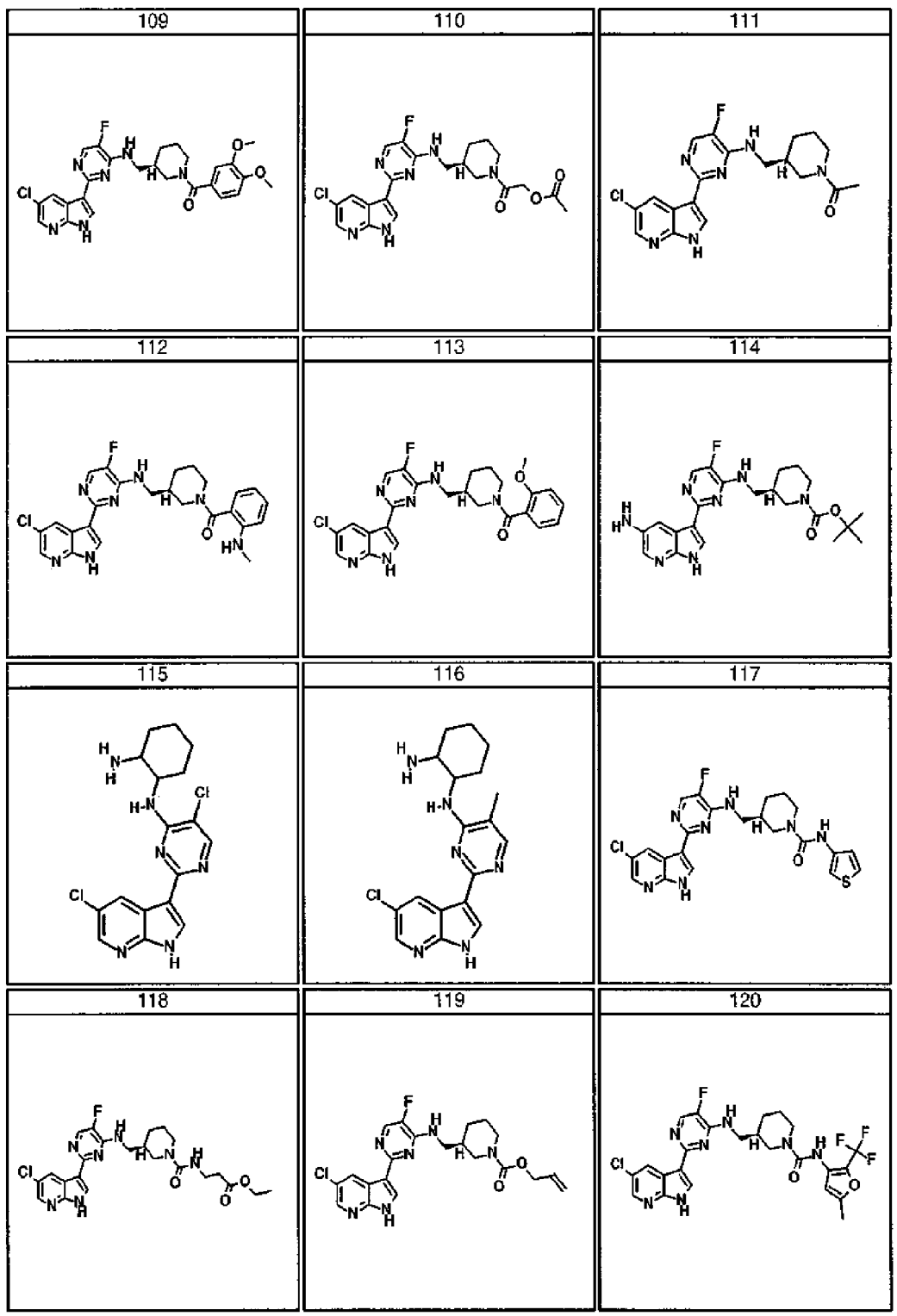
Figure 3K:
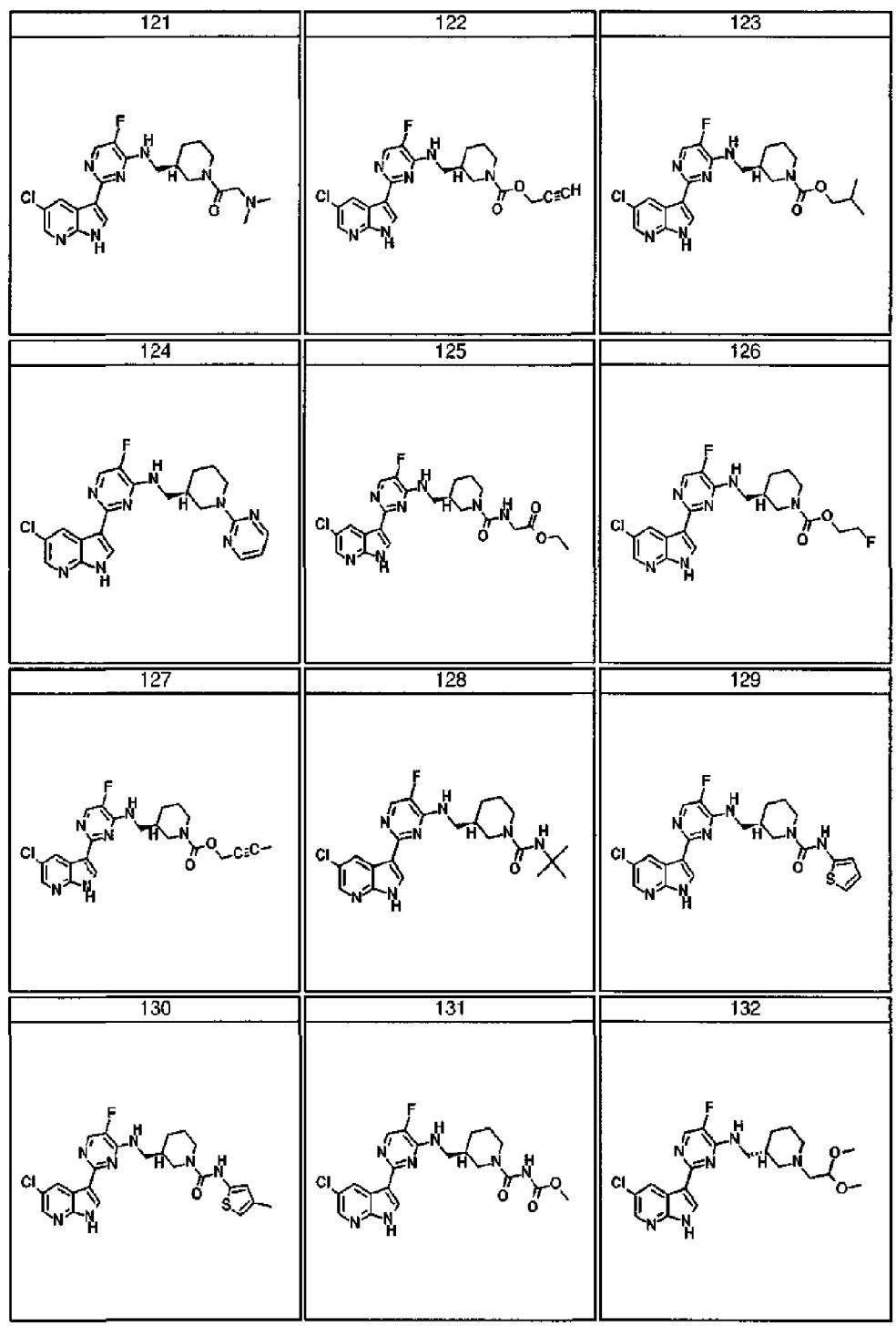
Figure 3L:
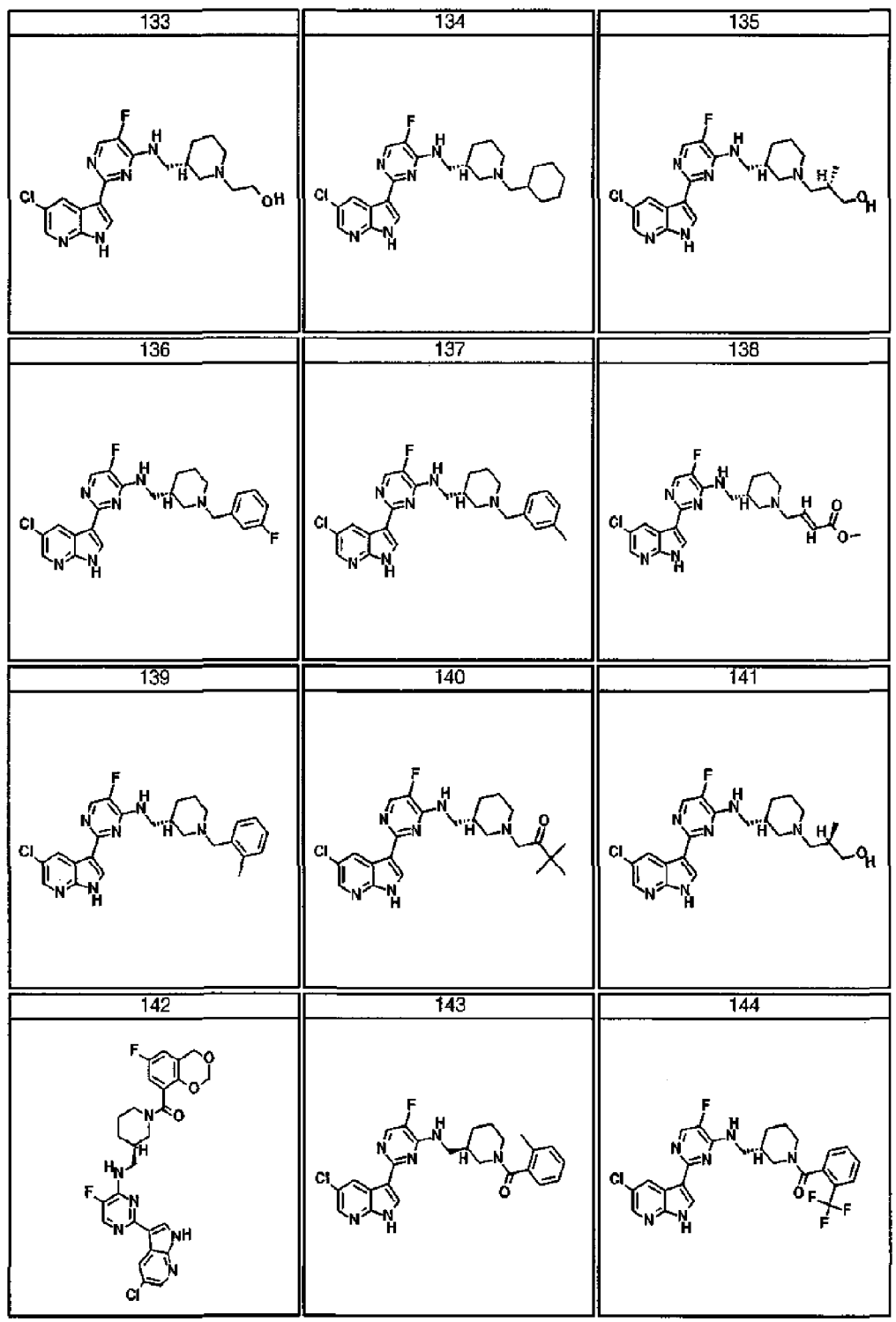
Figure 3M:
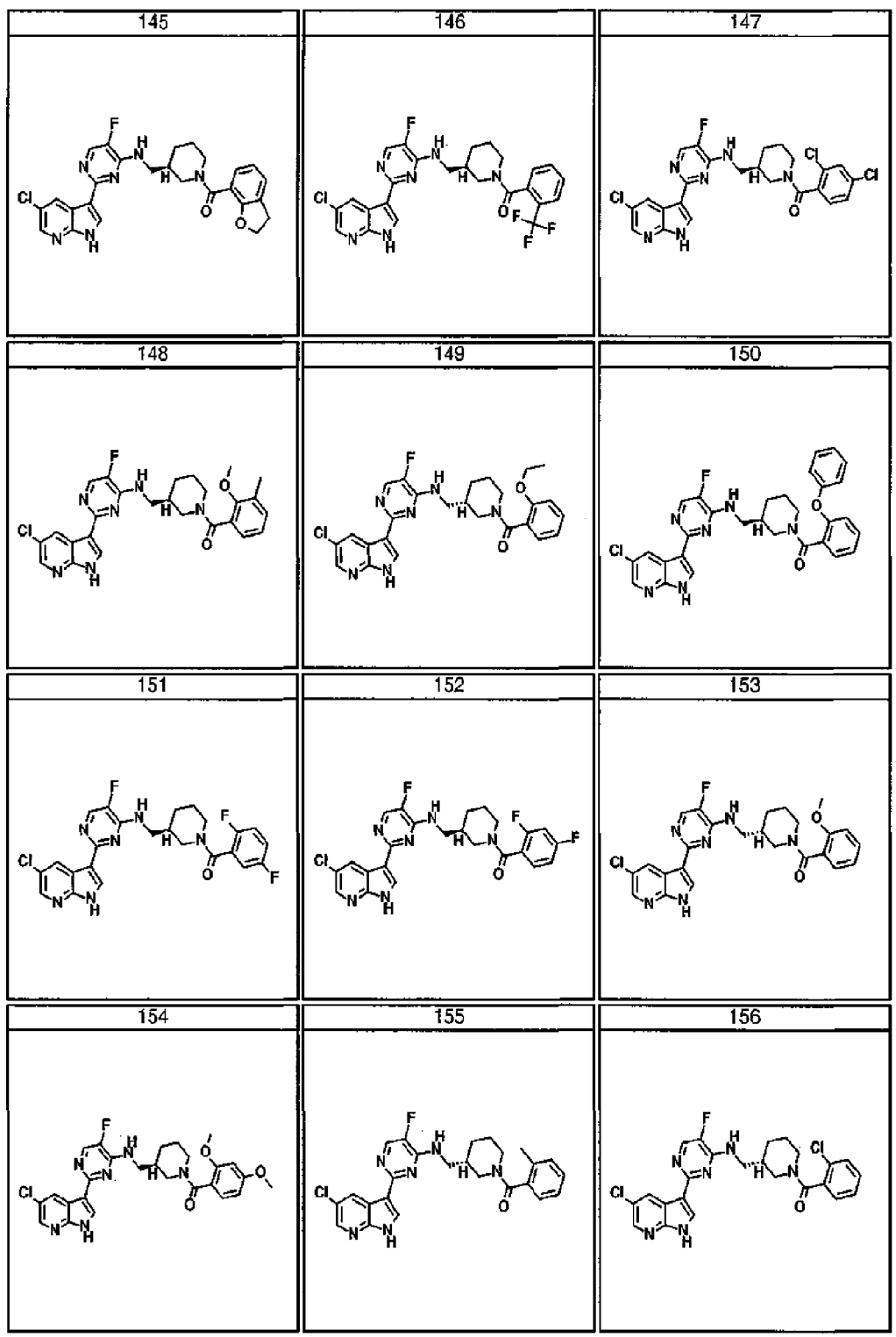
Figure 3N:
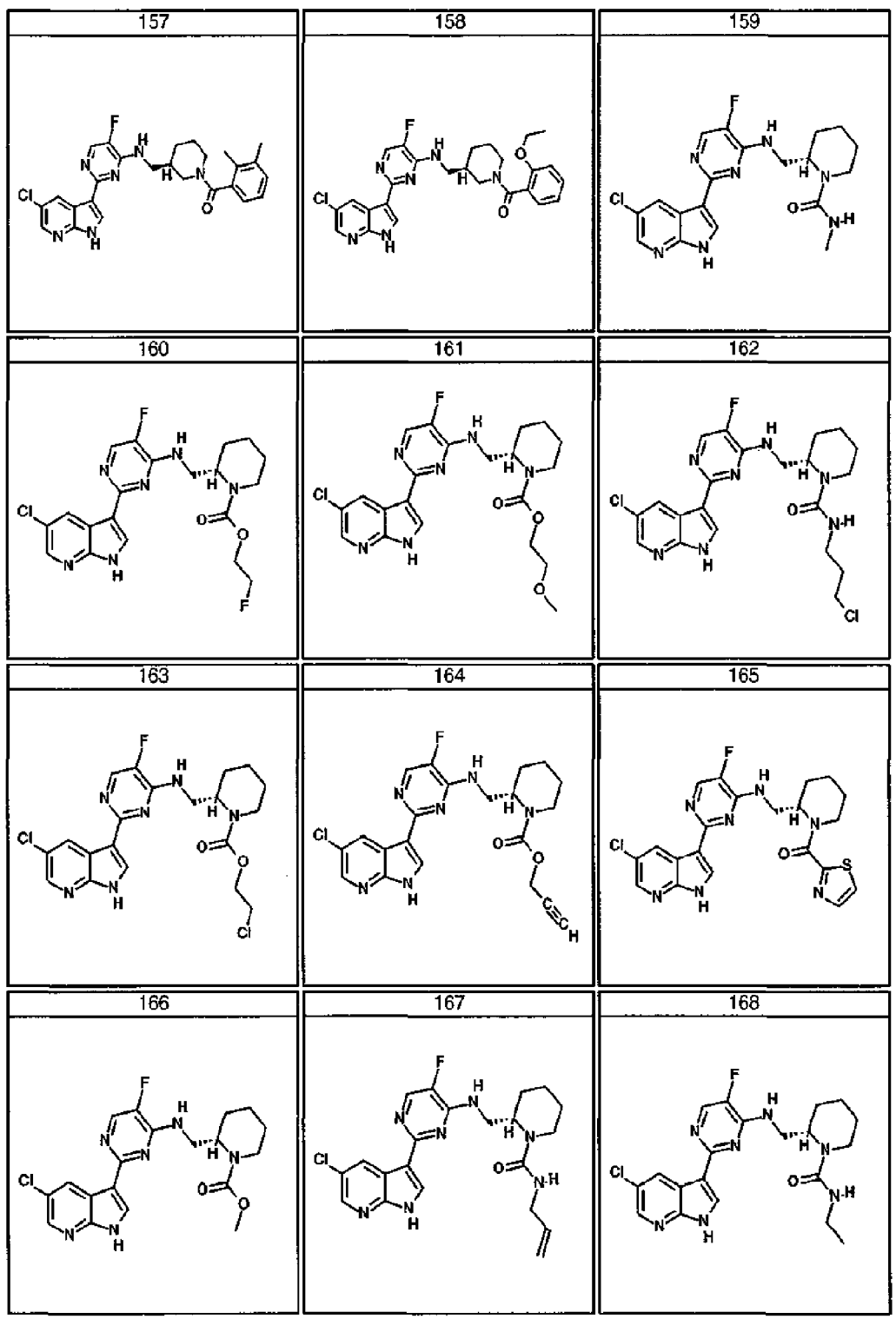
Figure 3O:
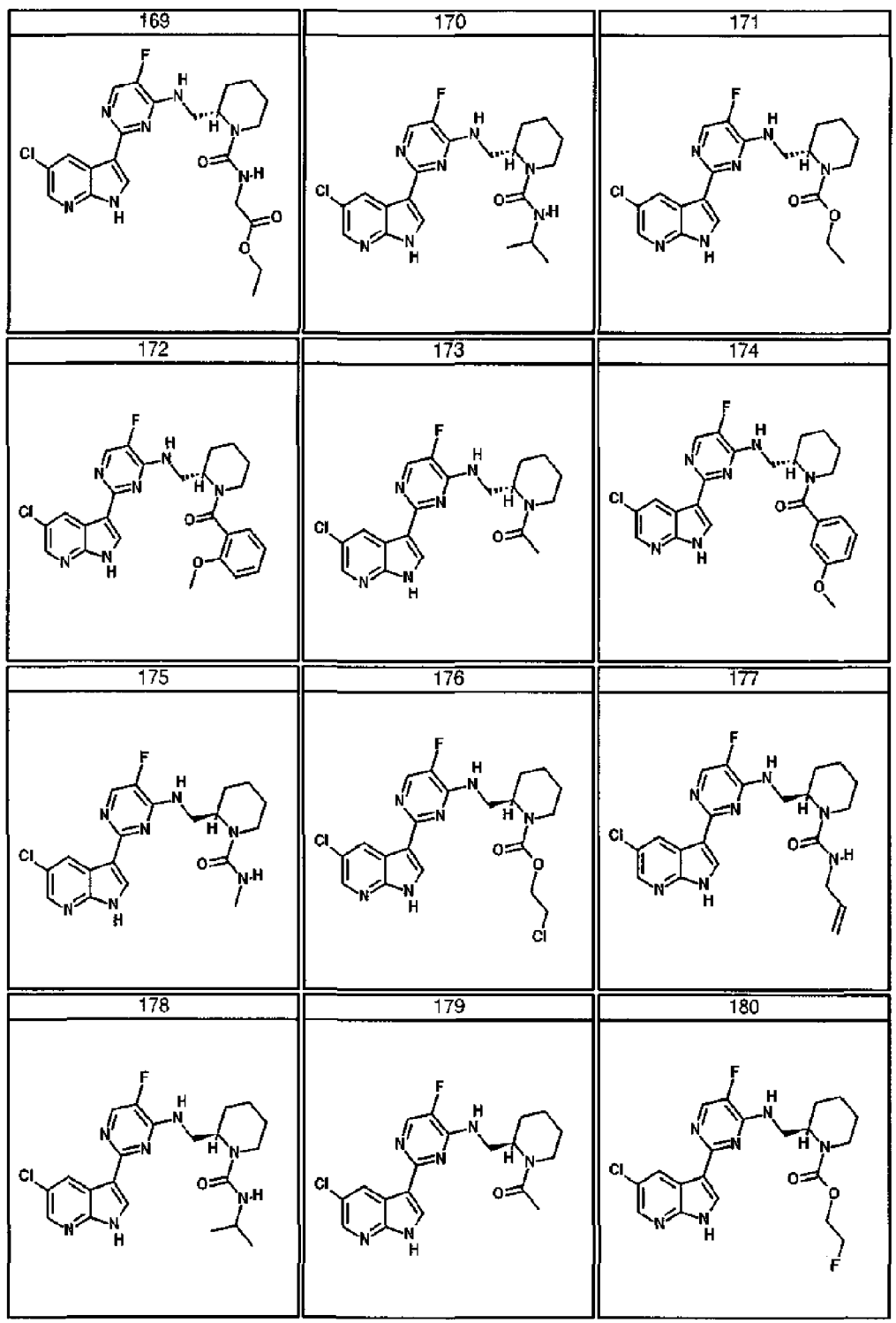
Figure 3P:
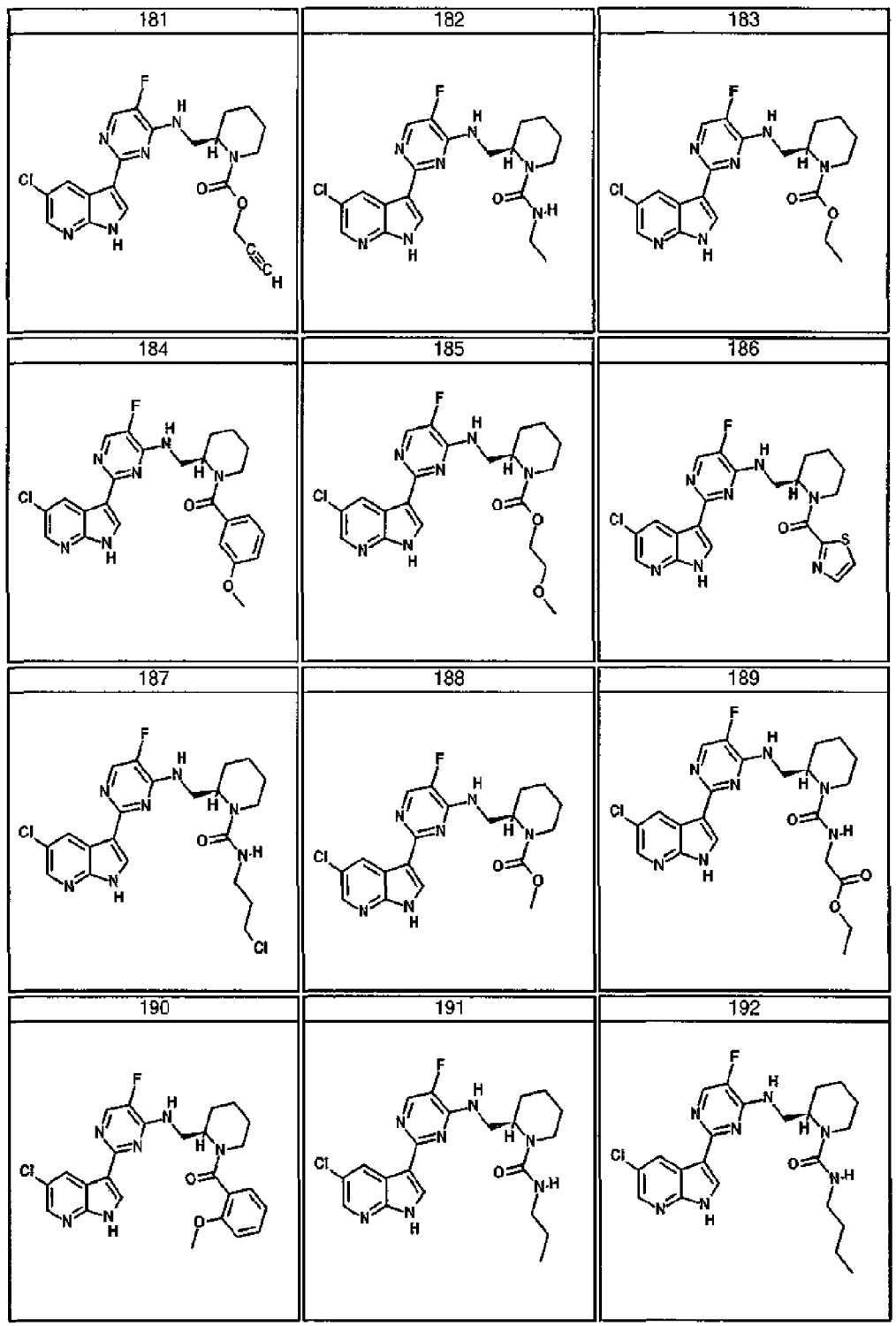
Figure 3Q:
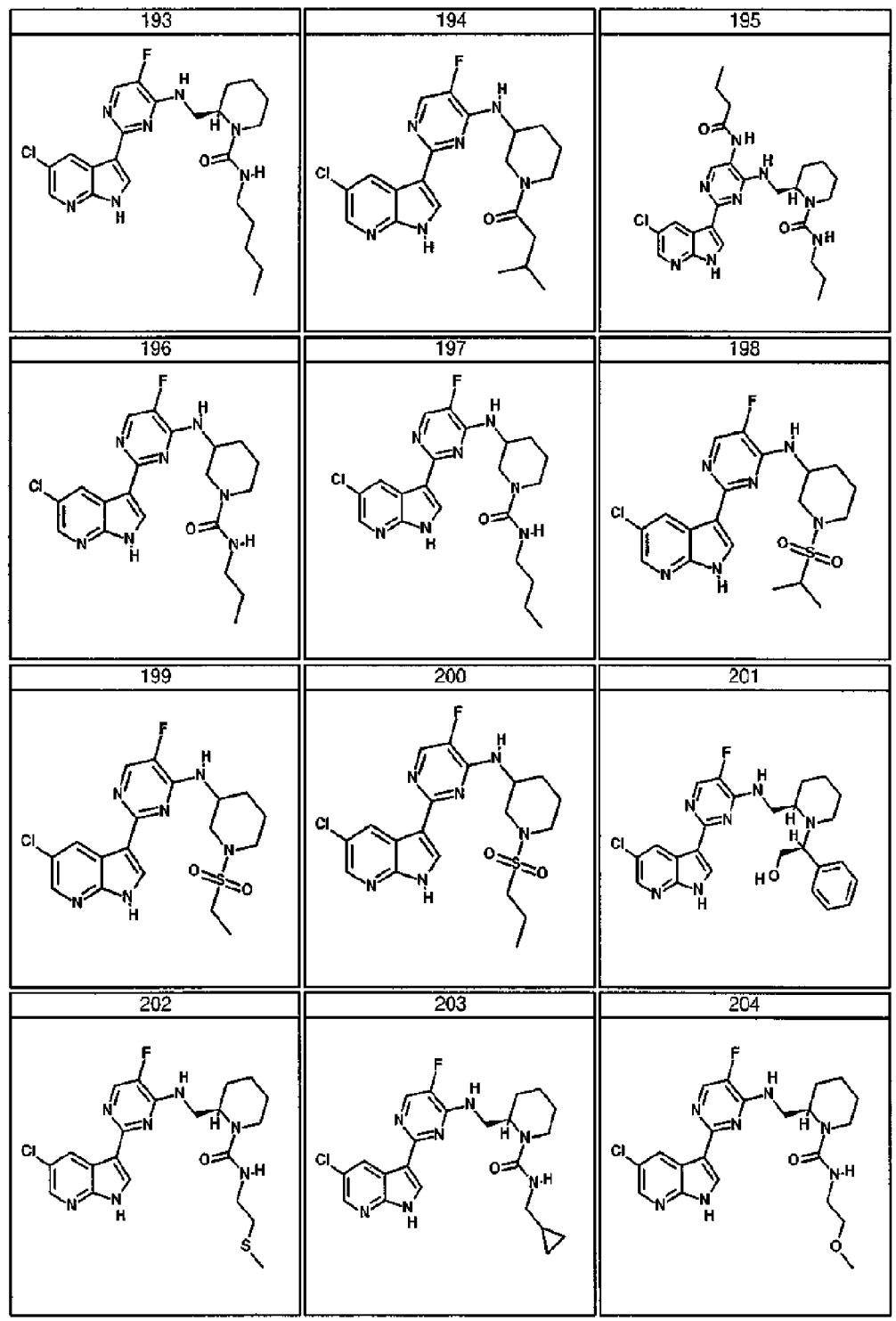
Figure 3R:
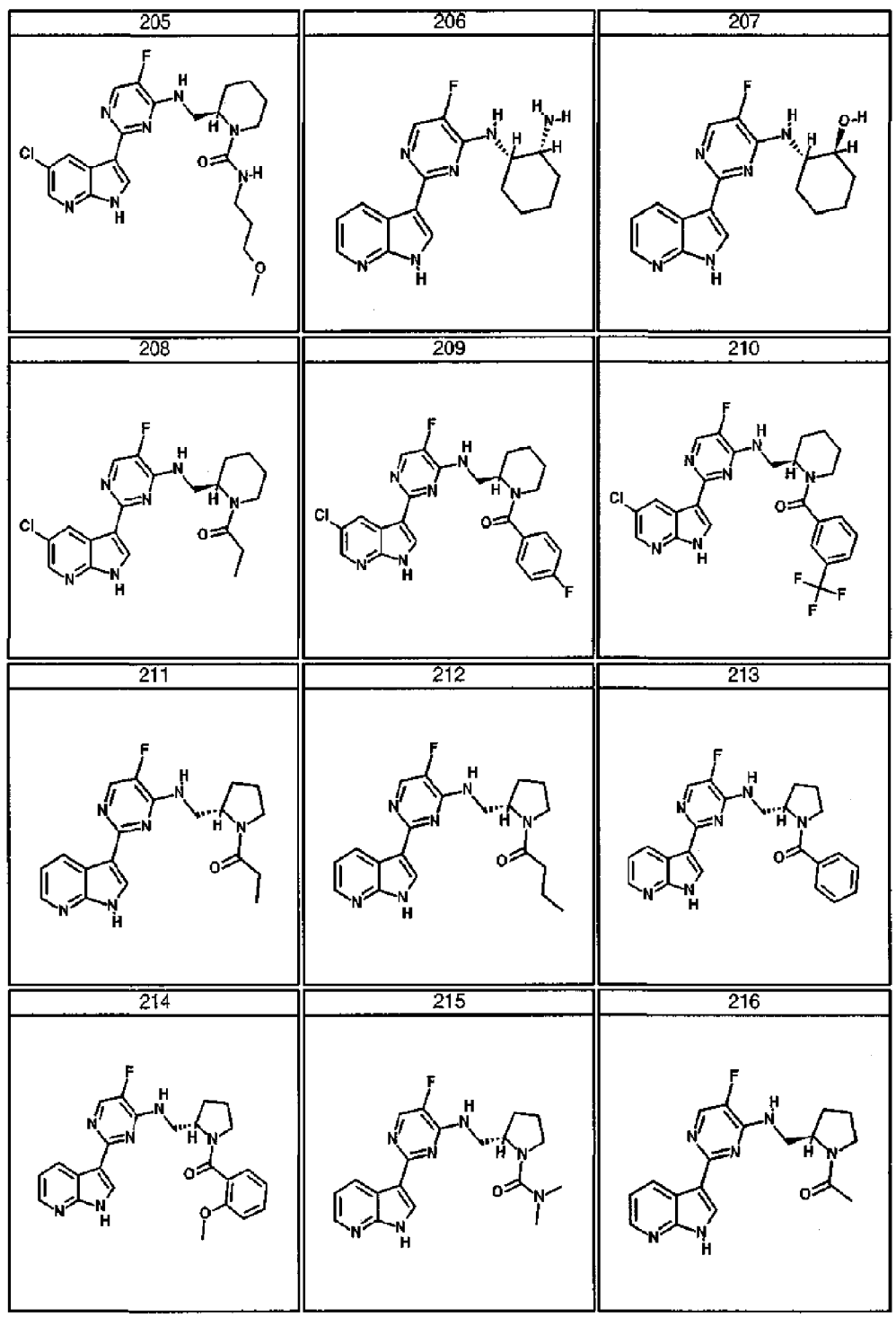
Figure 3S:
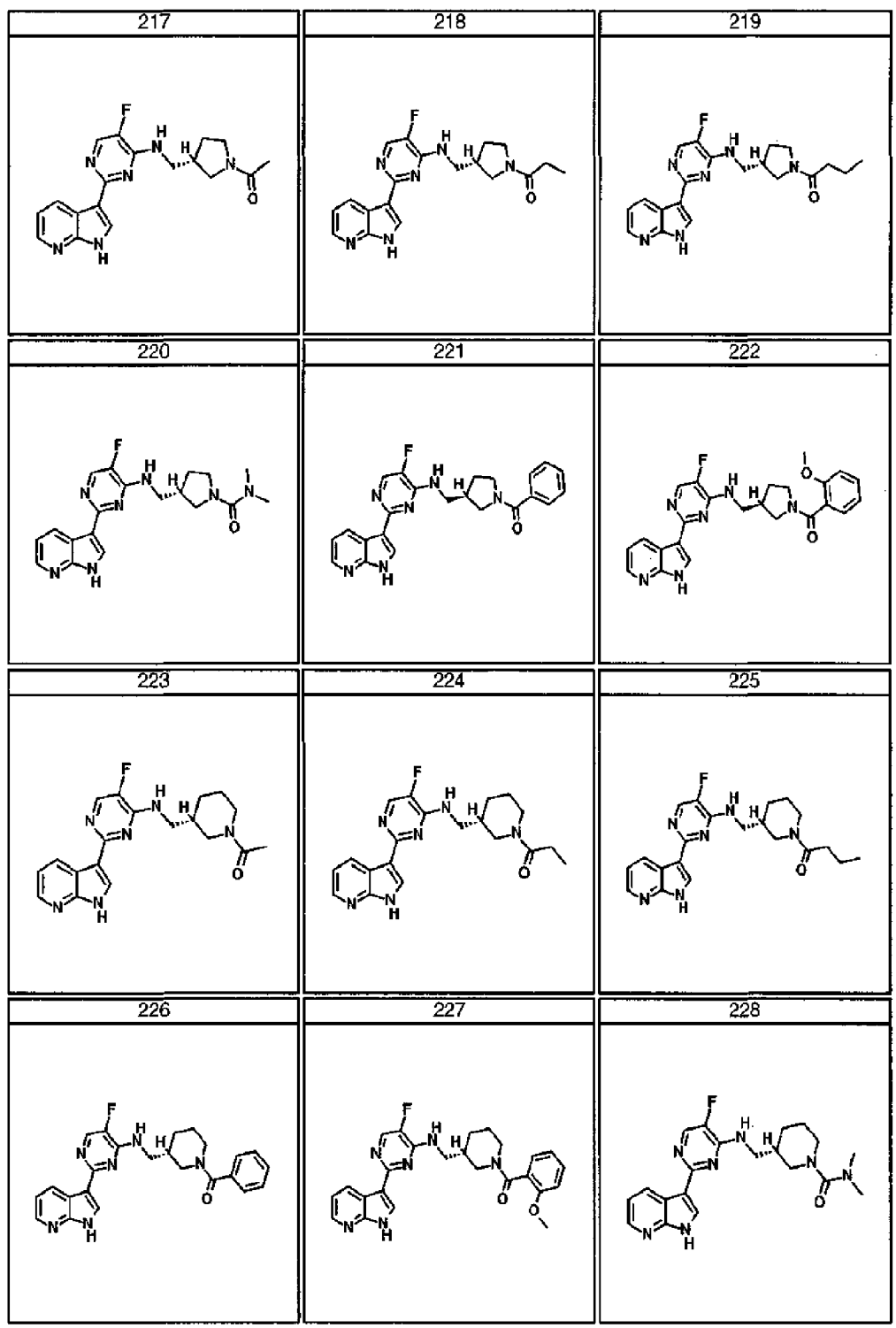
Figure 3T:
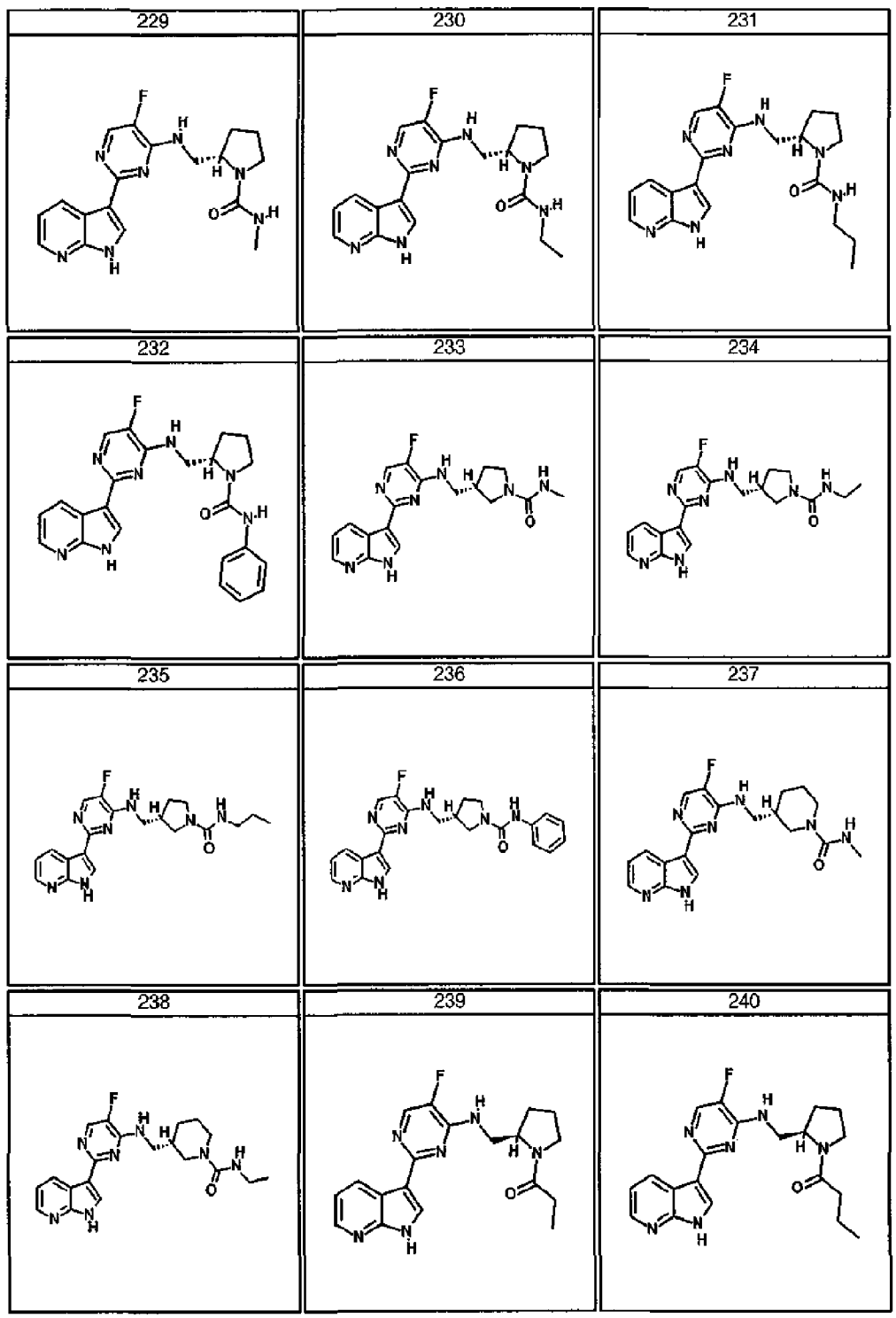
Figure 3U:
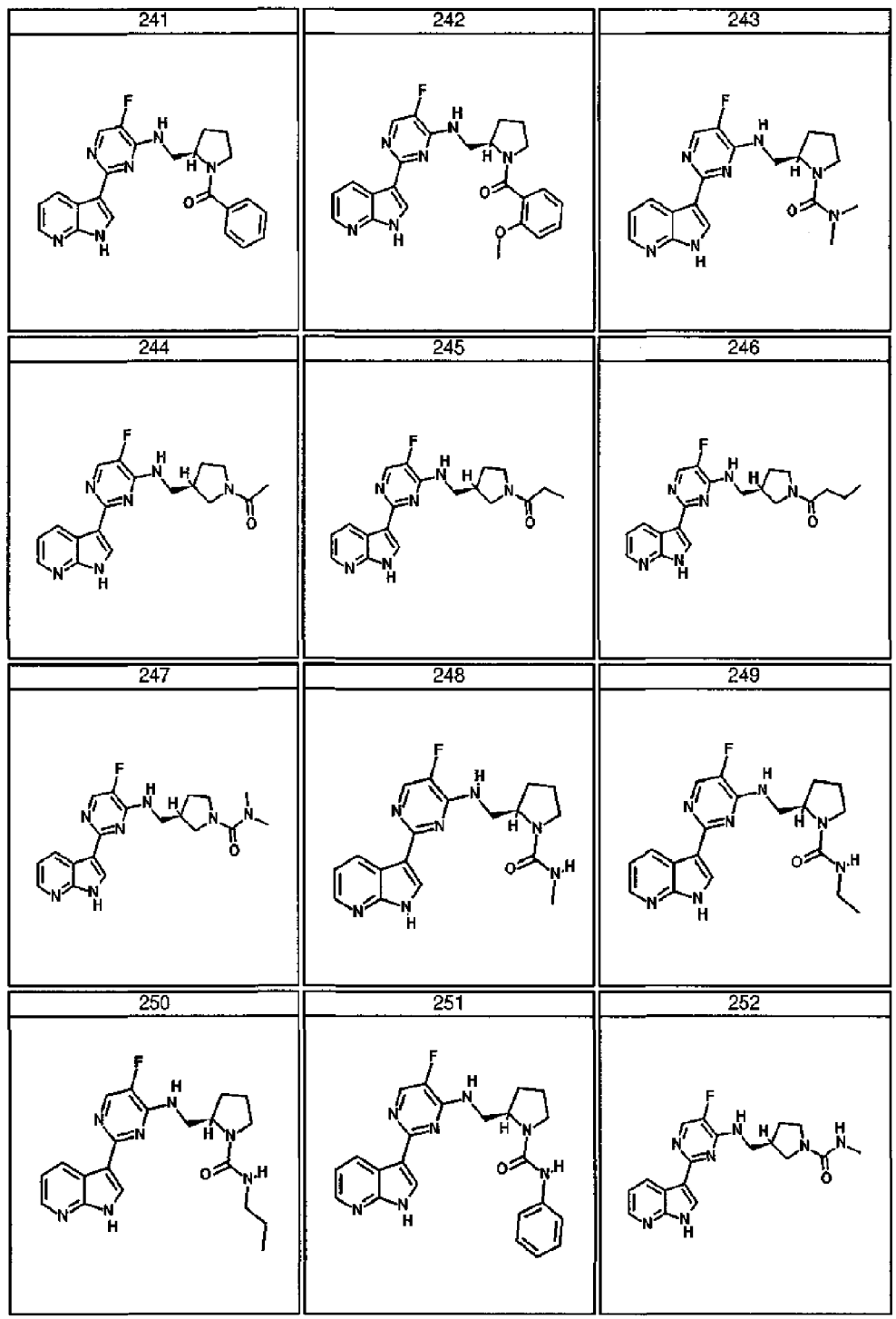
Figure 3V:
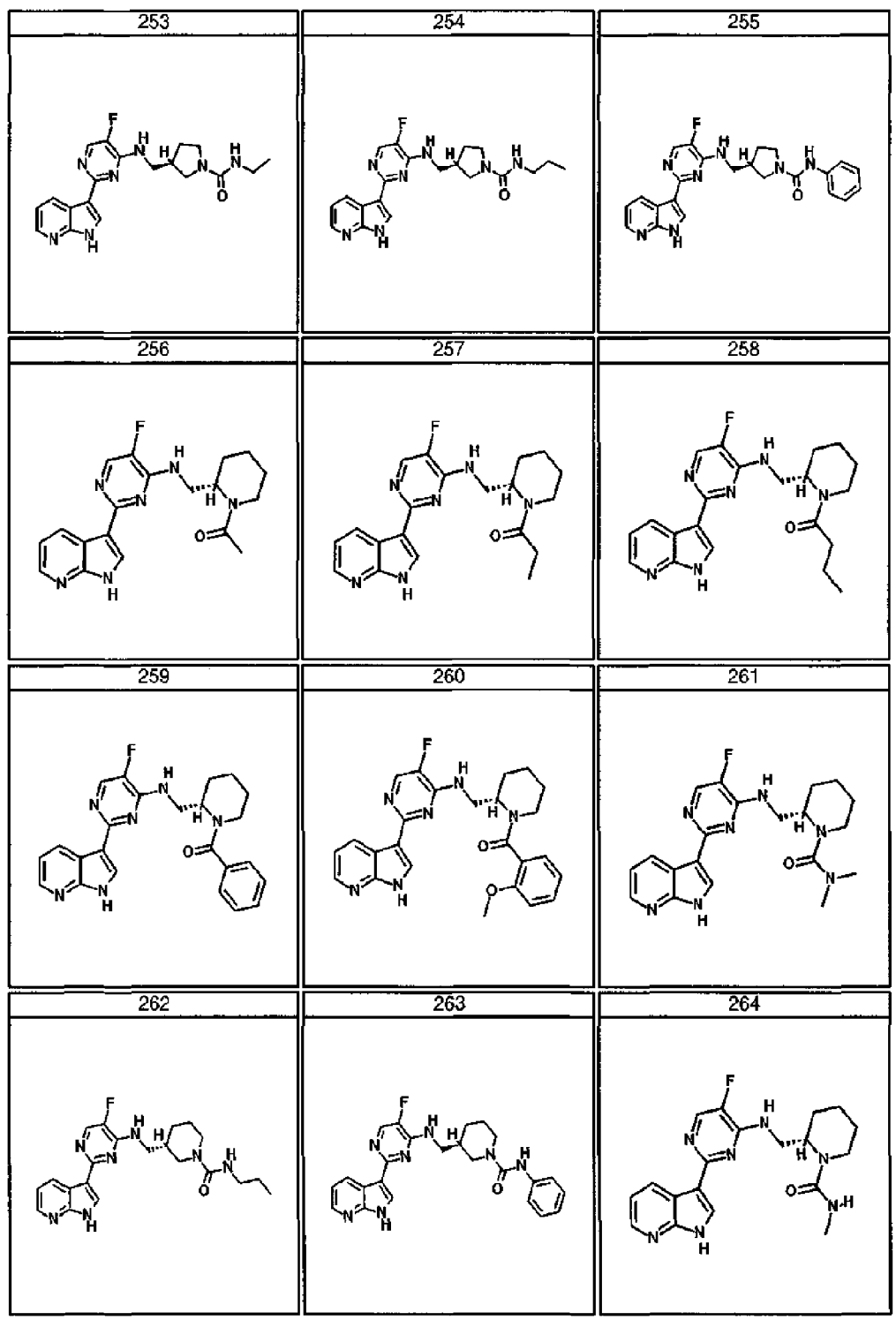
Figure 3W:
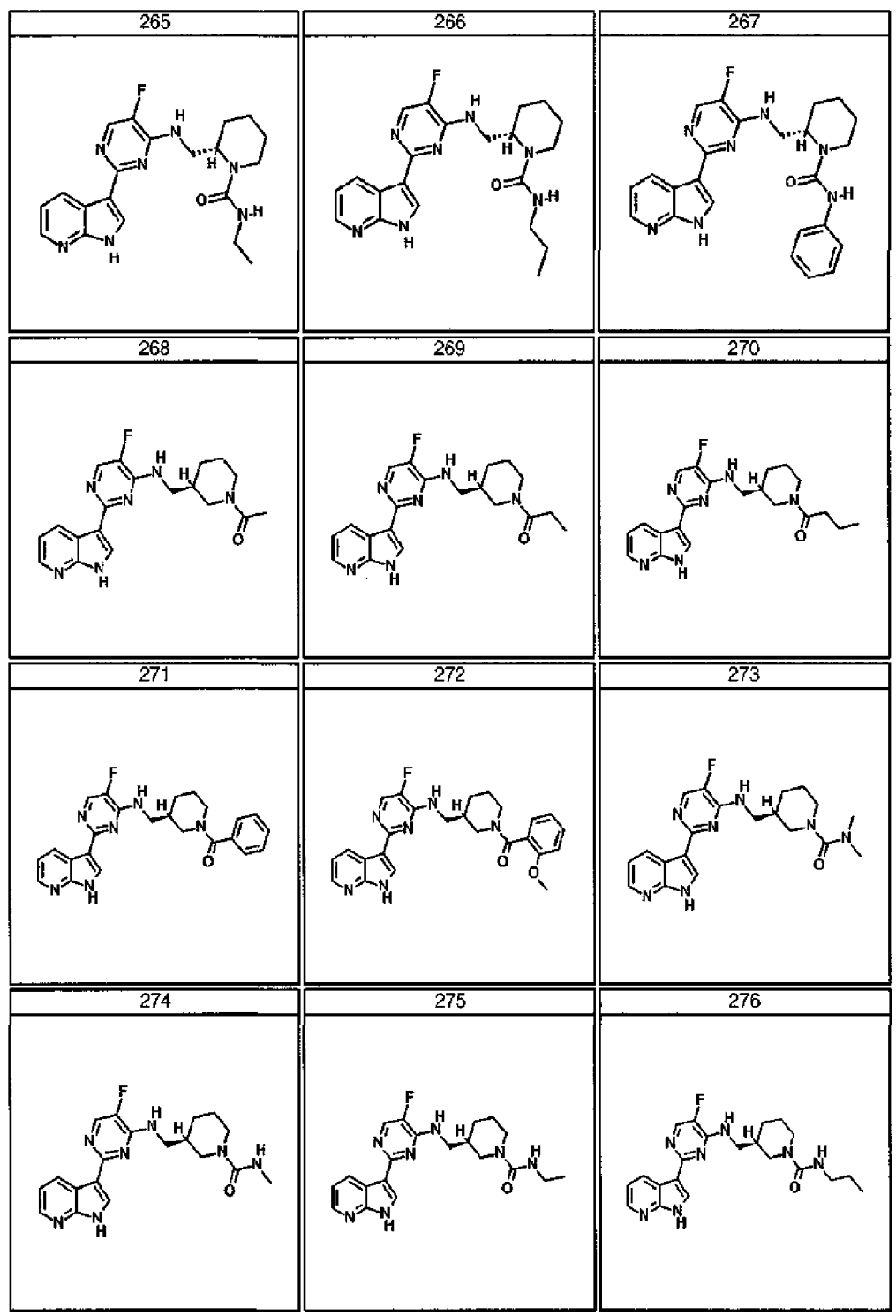
Figure 3X:
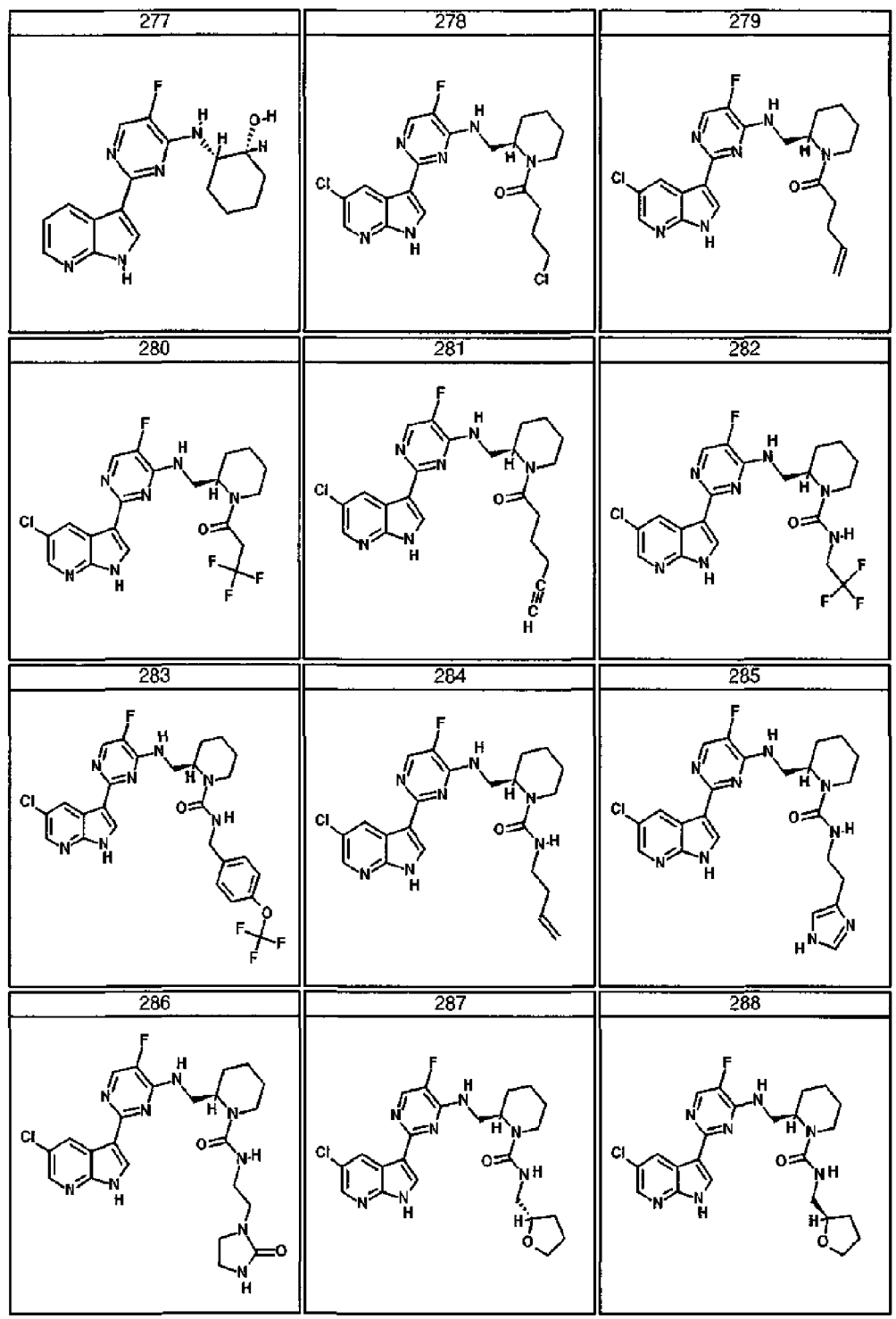
Figure 3Y:
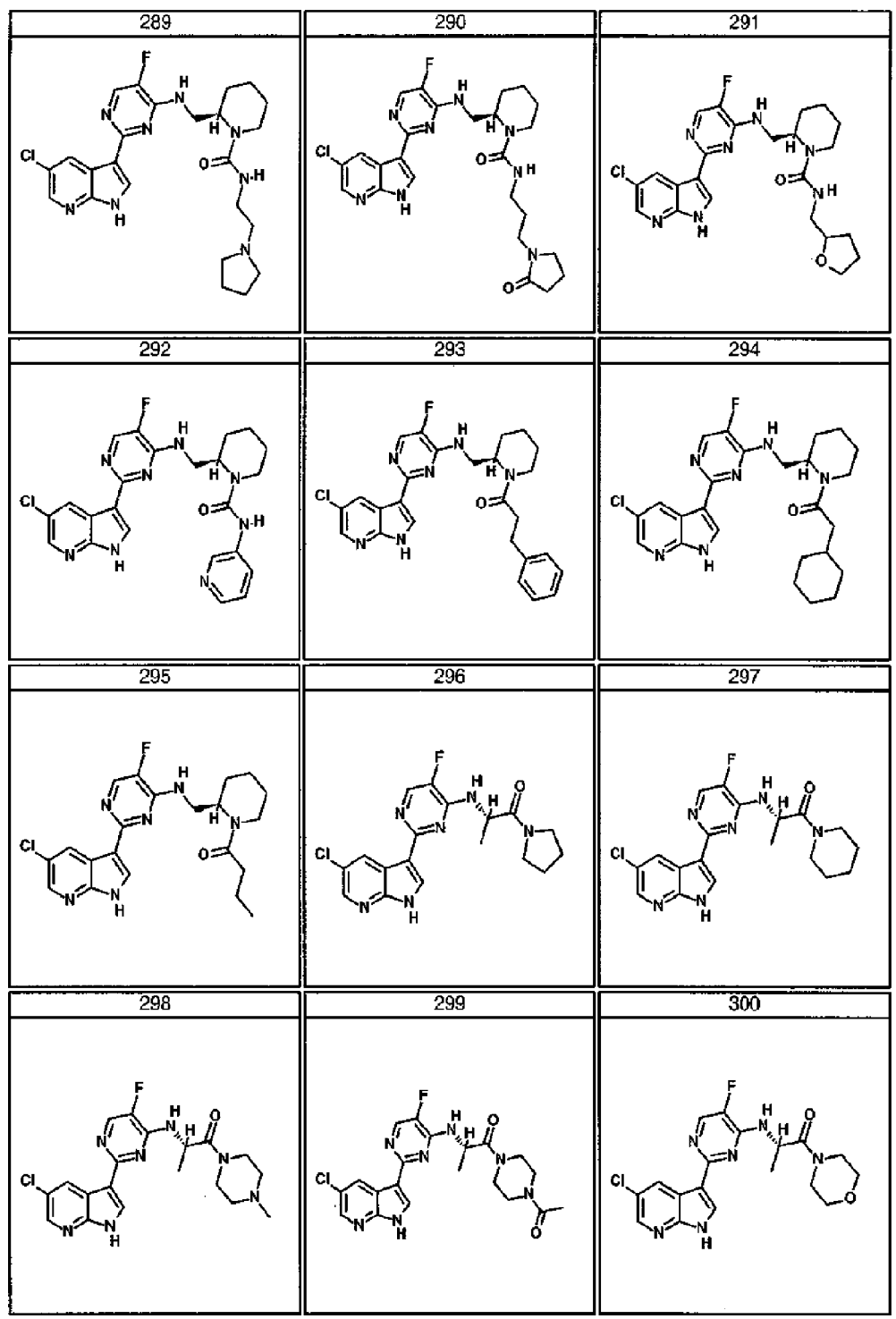
Figure 3Z:
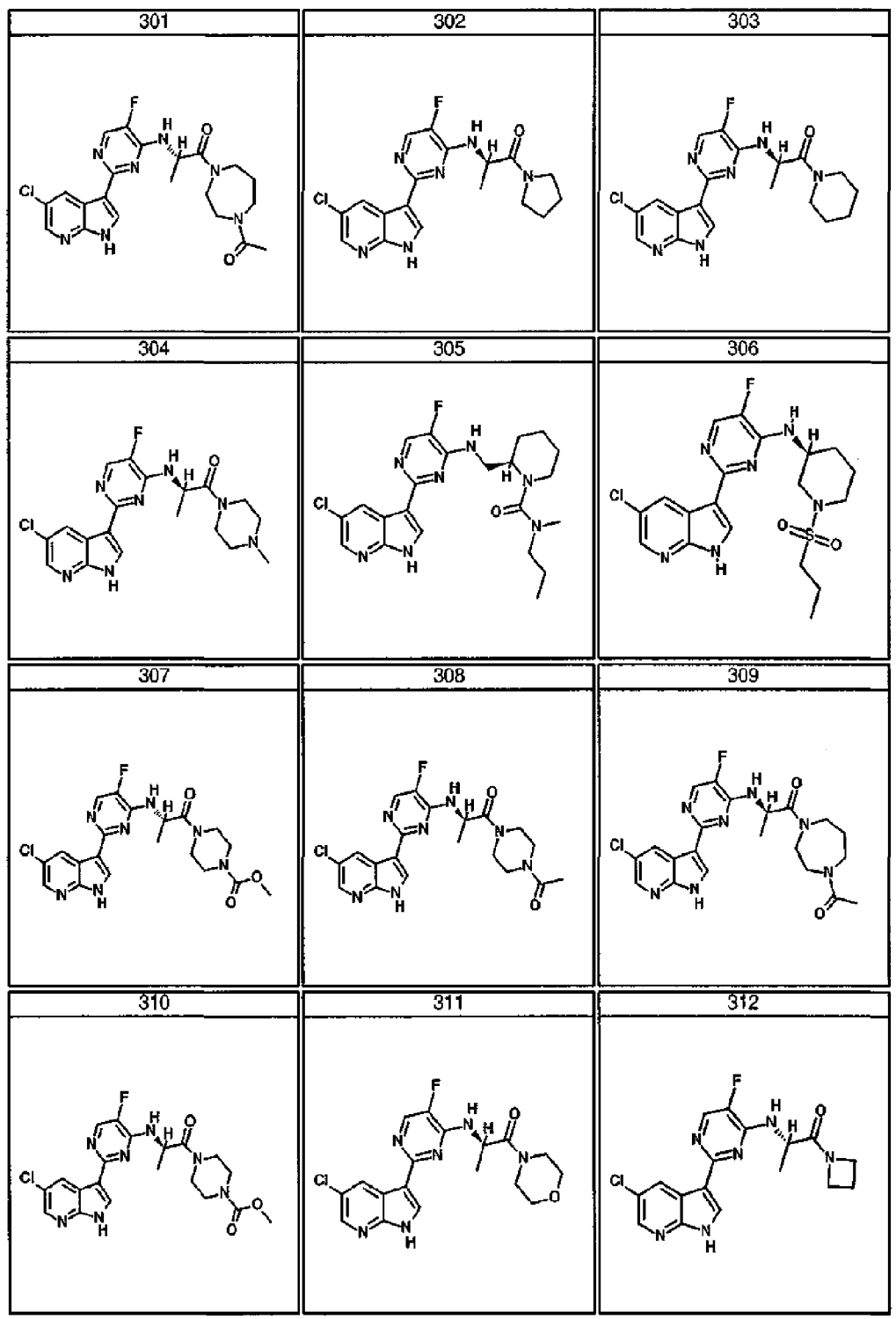
Figure 3A:
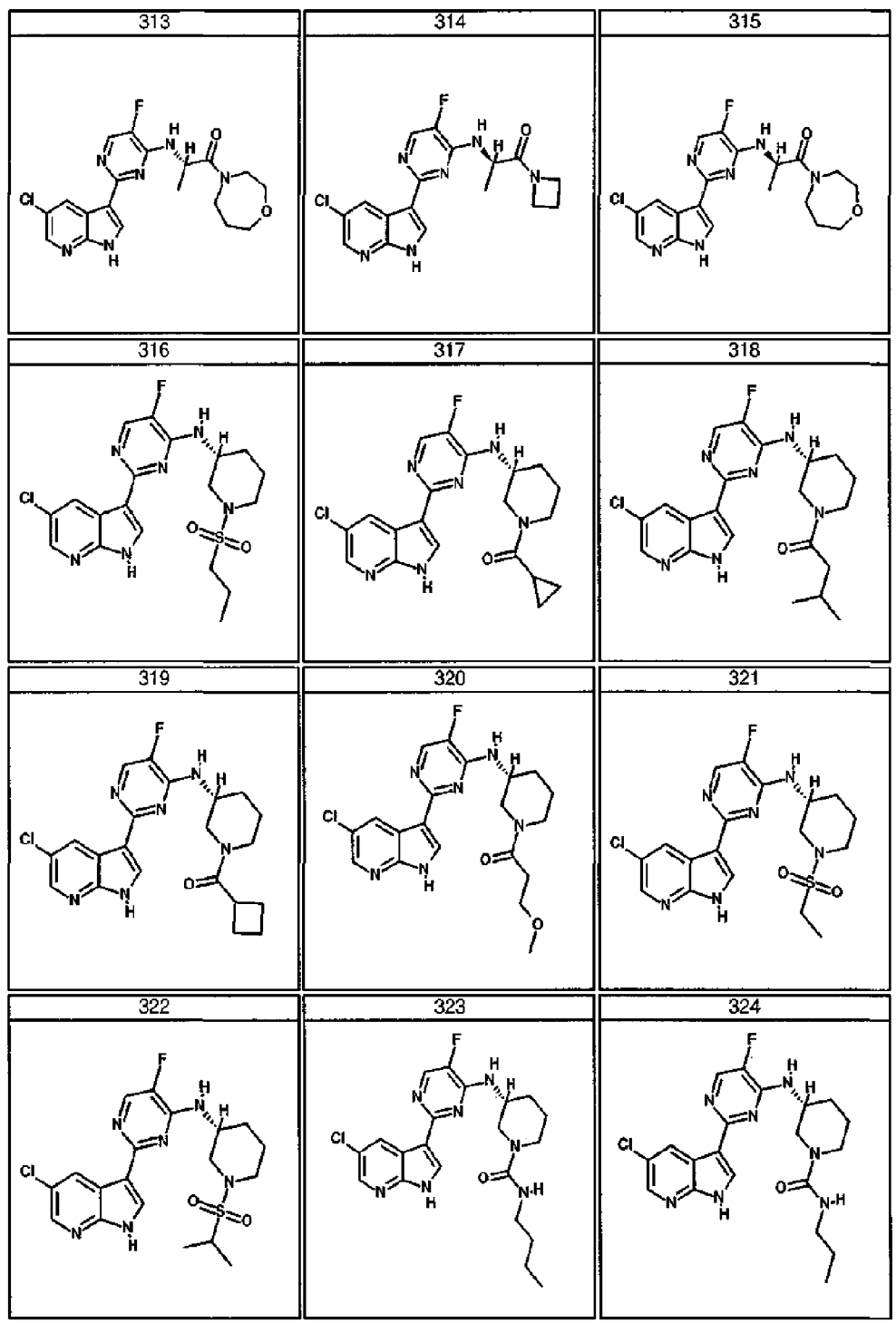
Figure 3A:
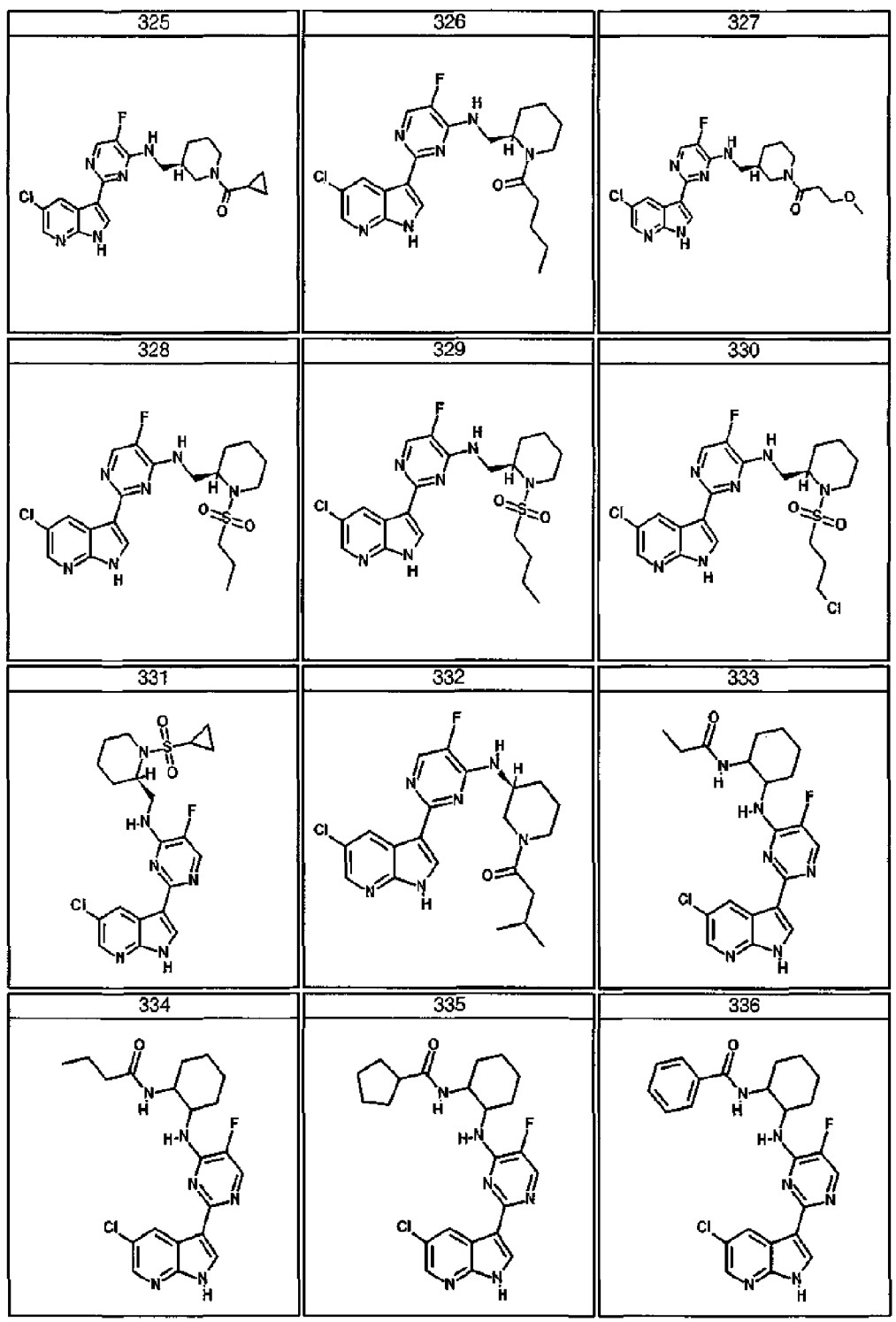
Figure 3A:
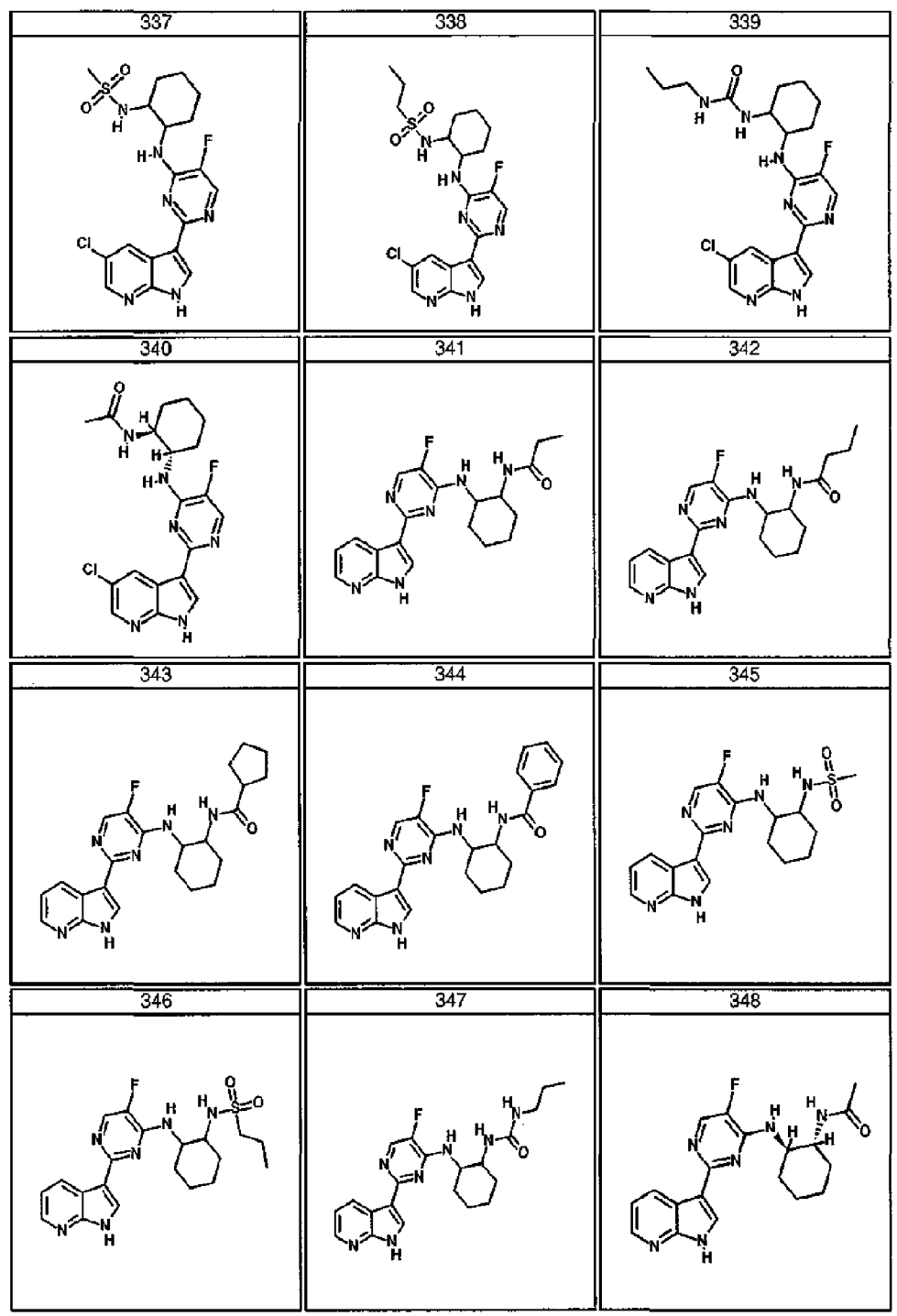
Figure 3A:
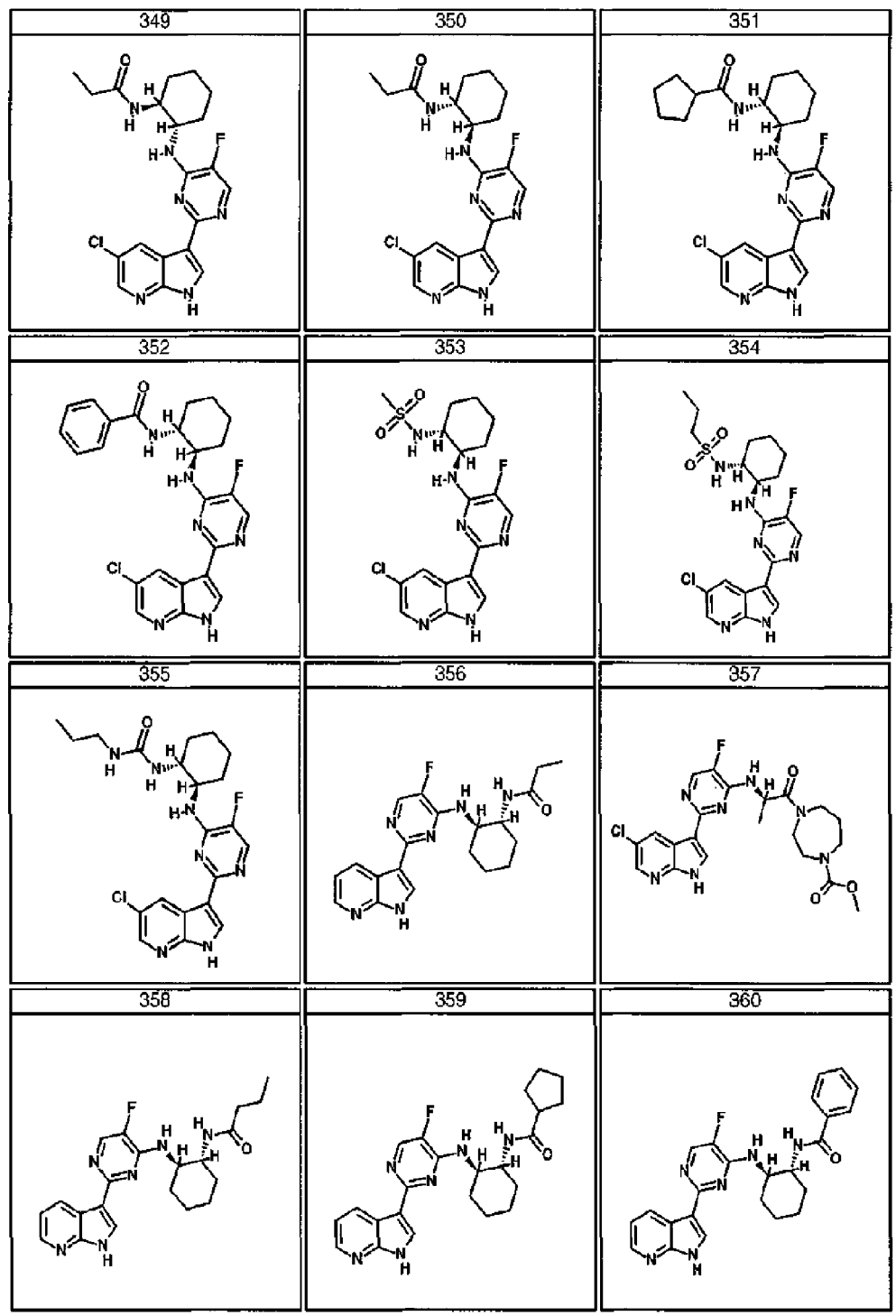
Figure 3A:
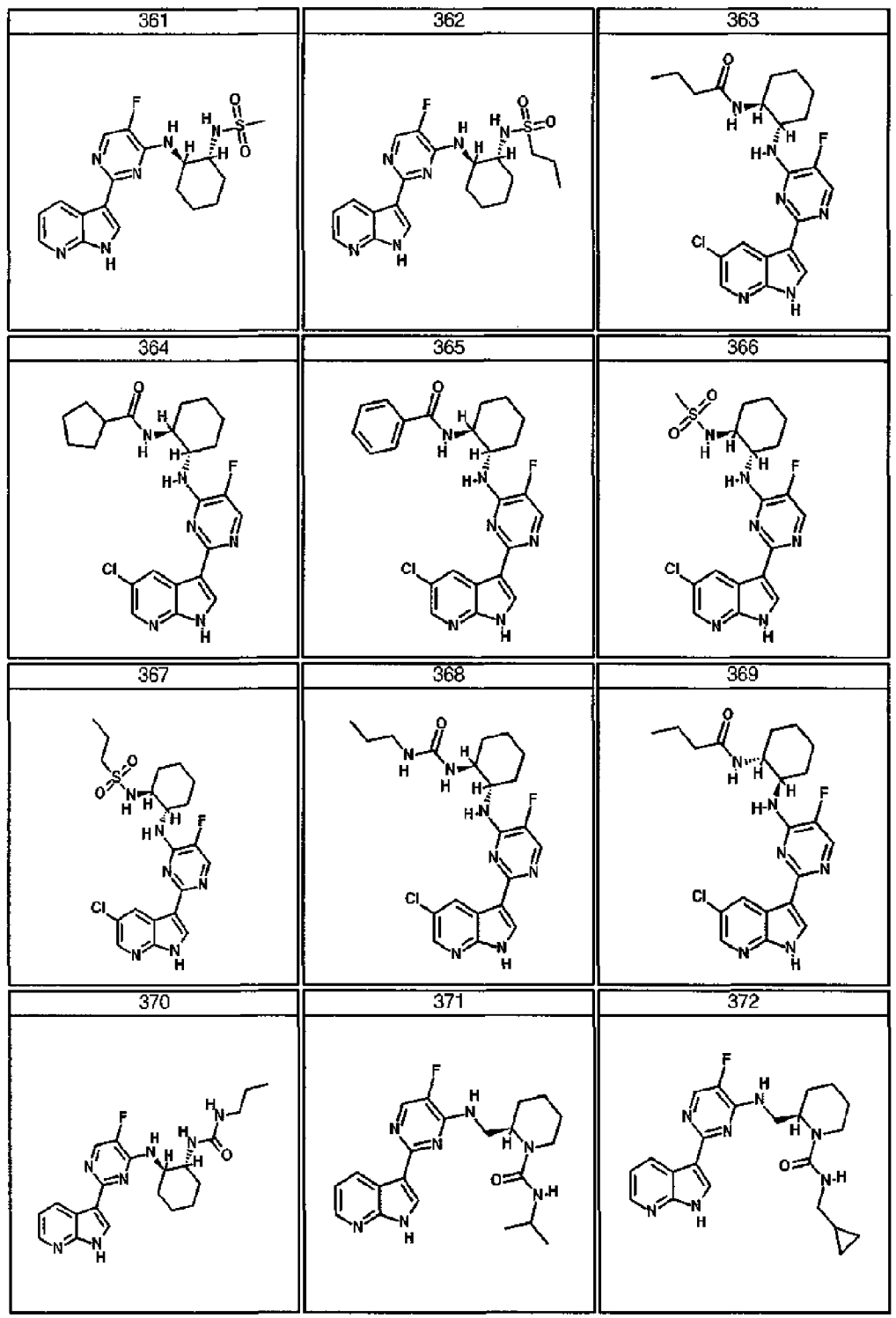
Figure 3A:
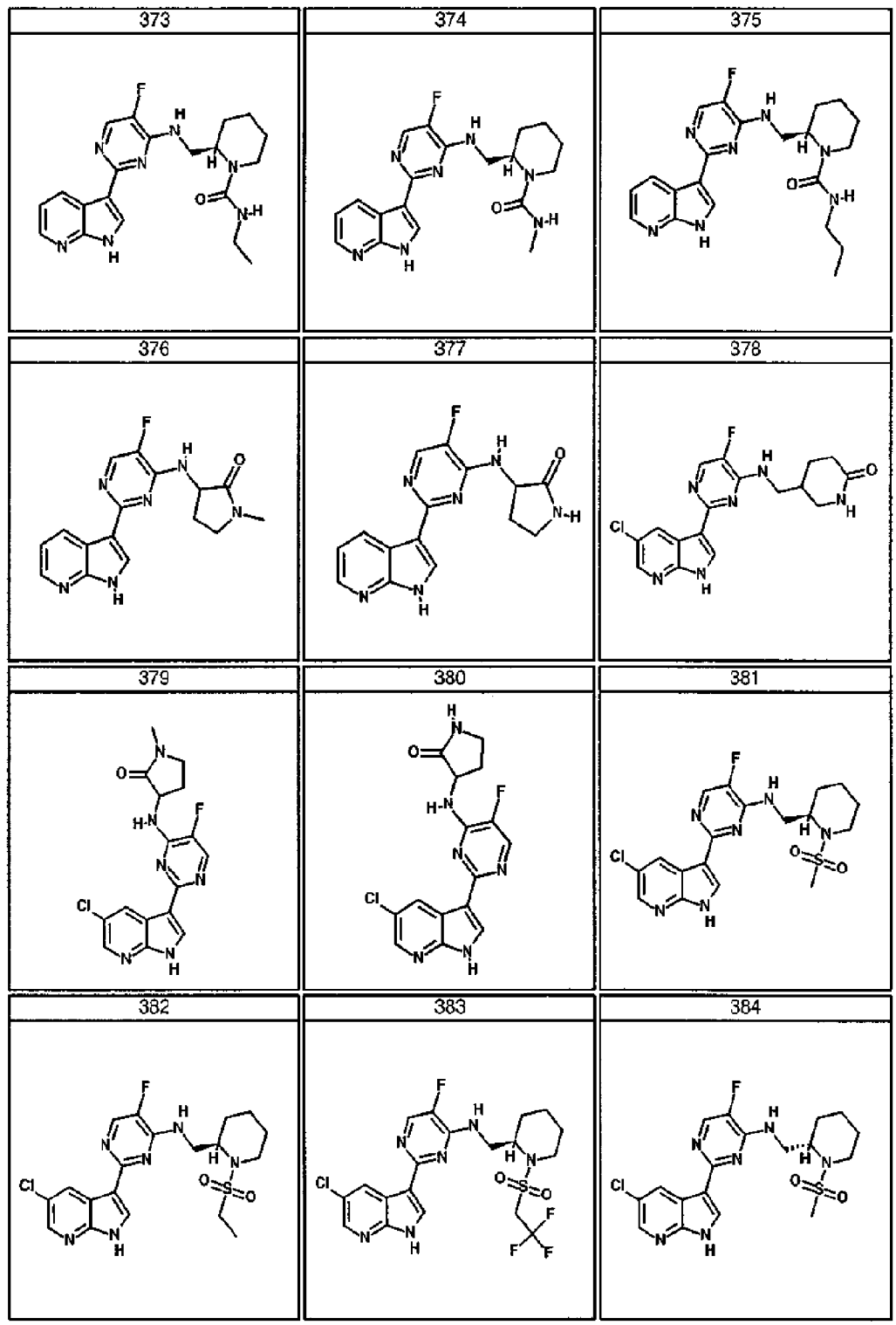
Figure 3A:
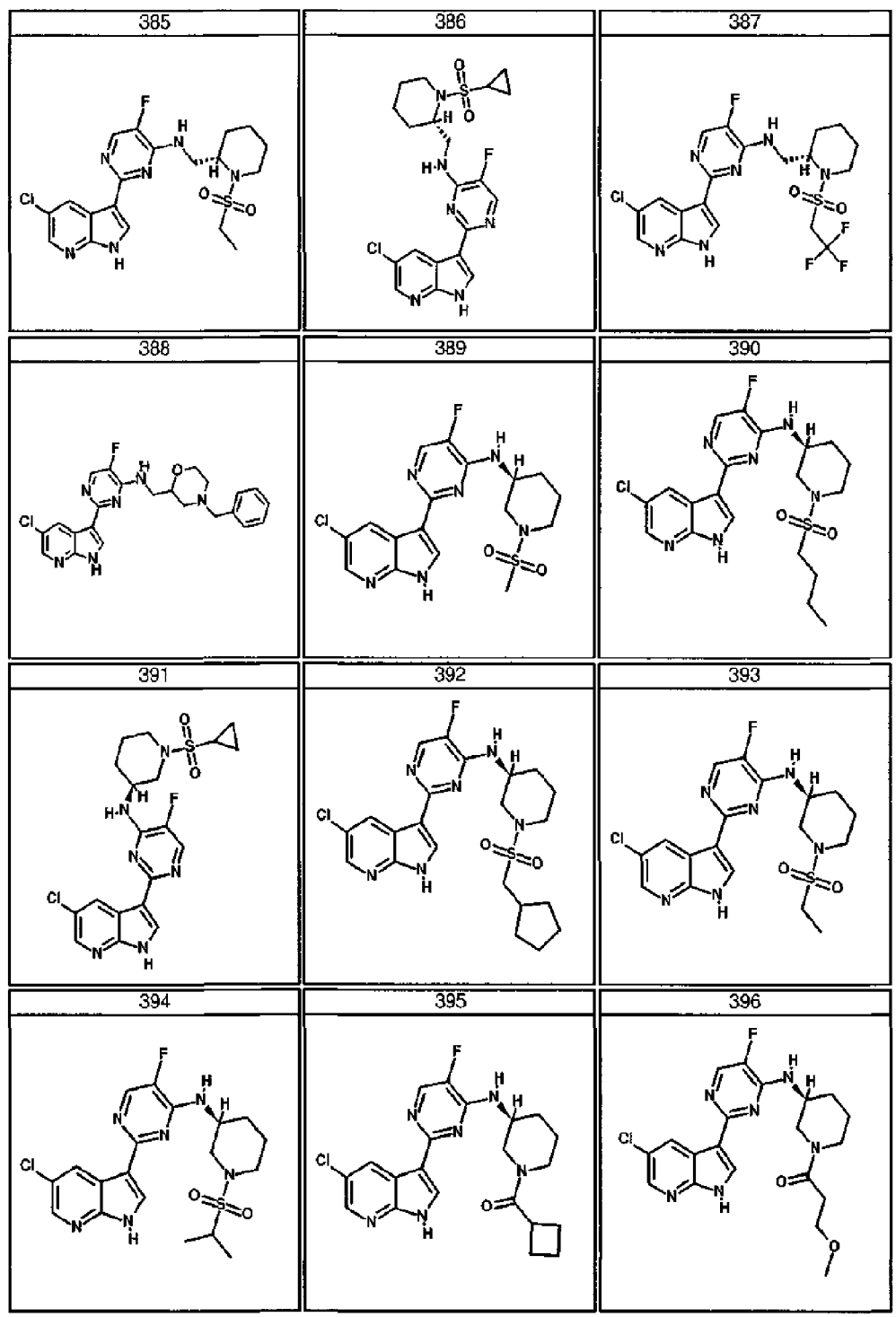
Figure 3A:
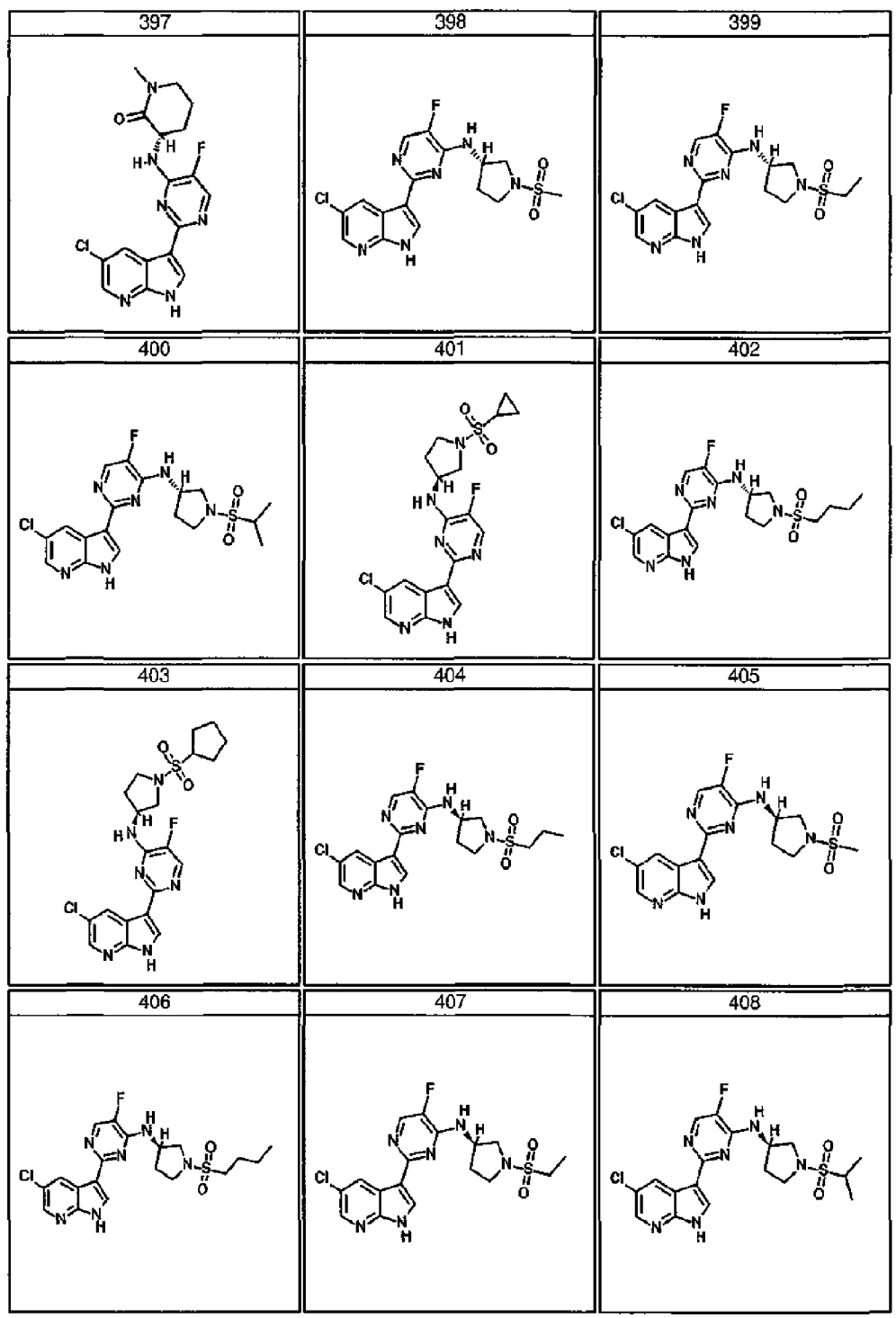
Figure 3A:
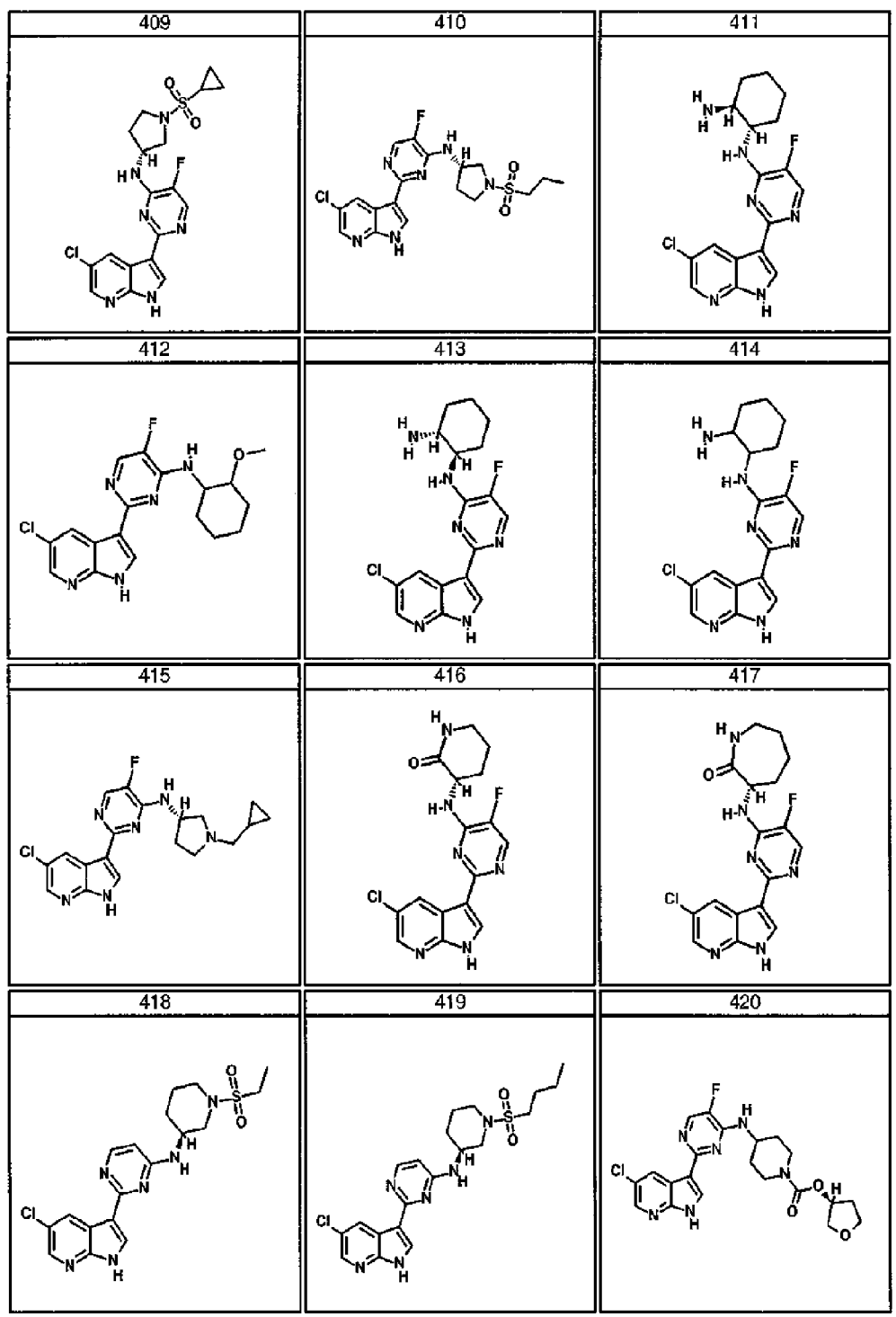
Figure 3A:
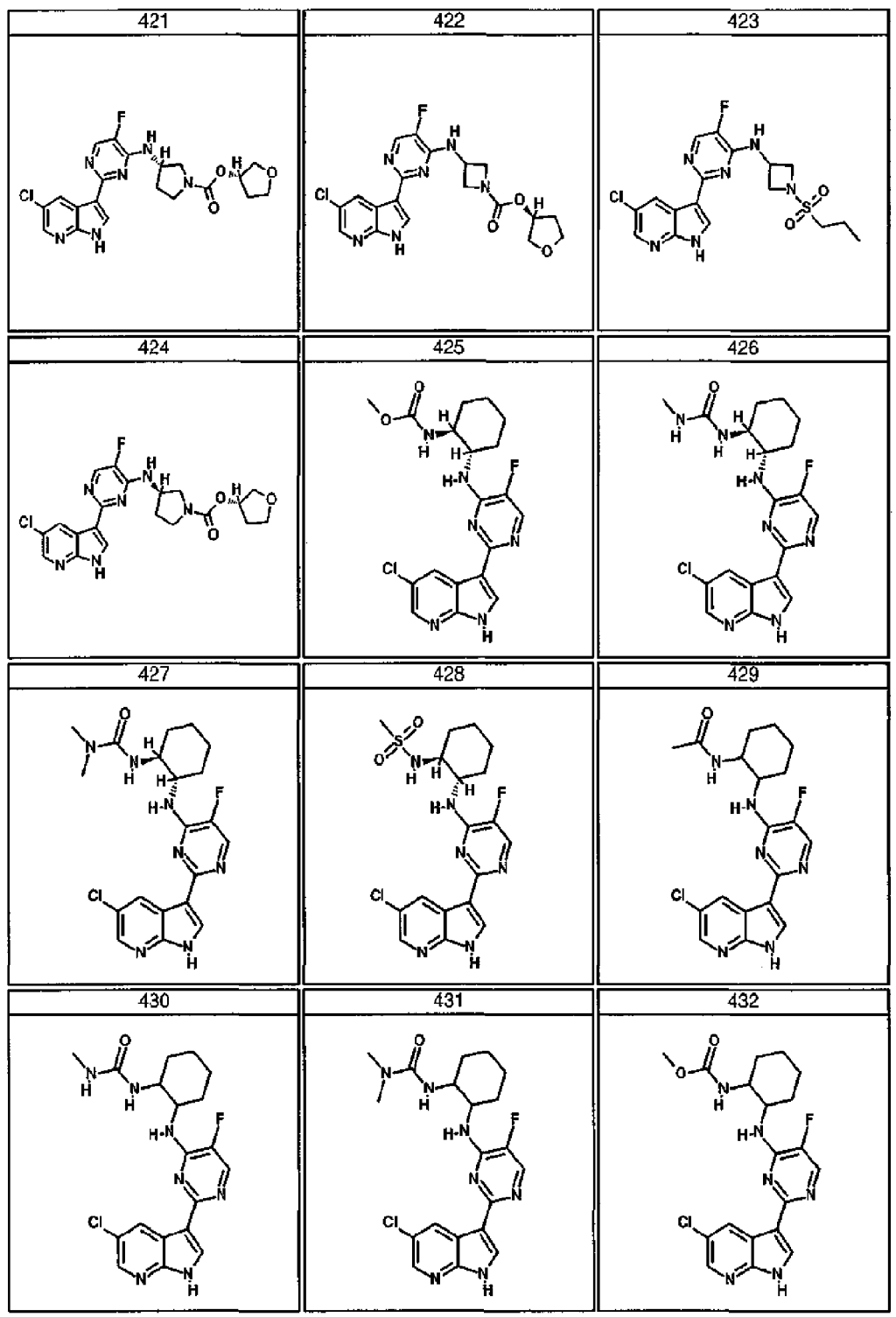
Figure 3A:
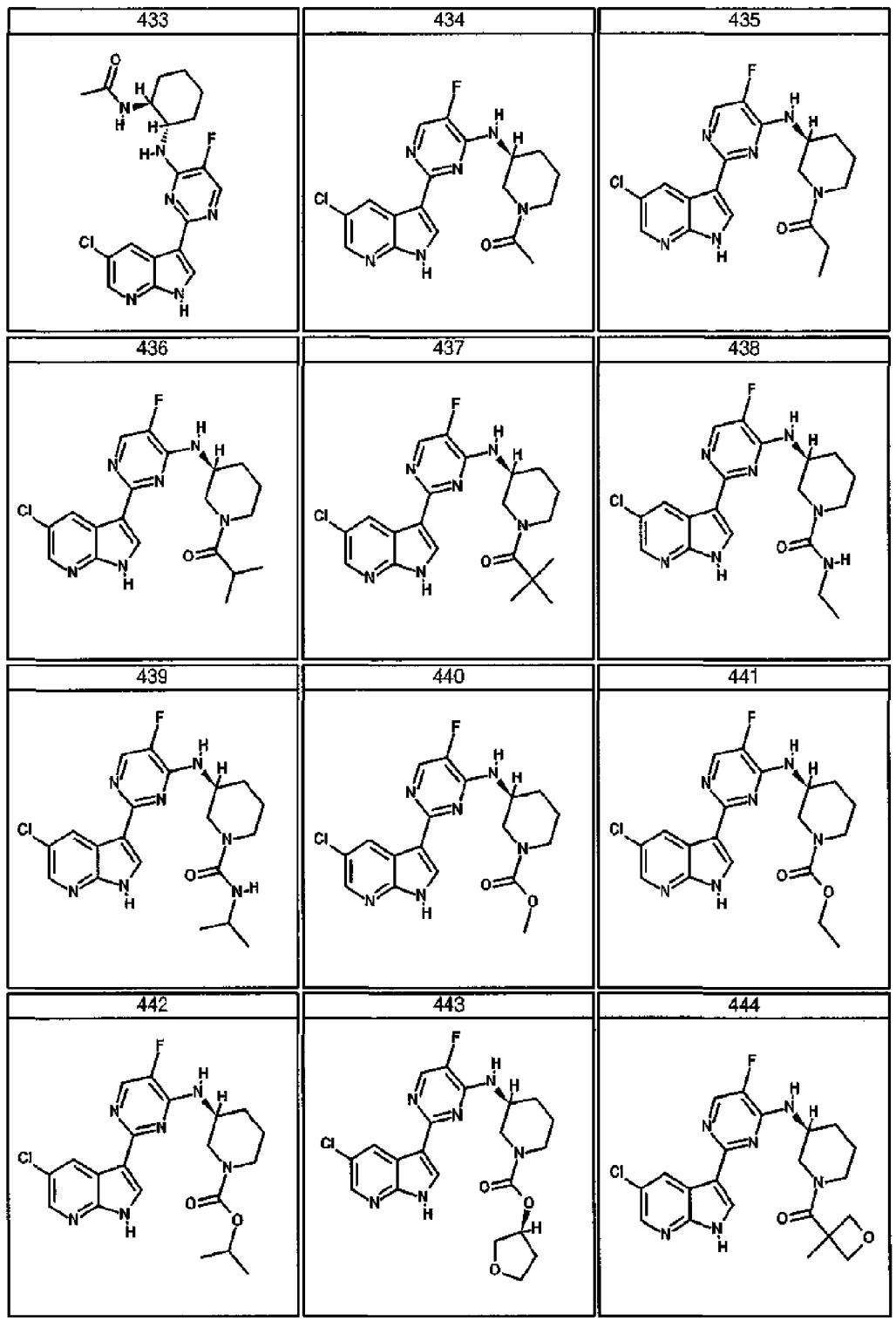
Figure 3A:
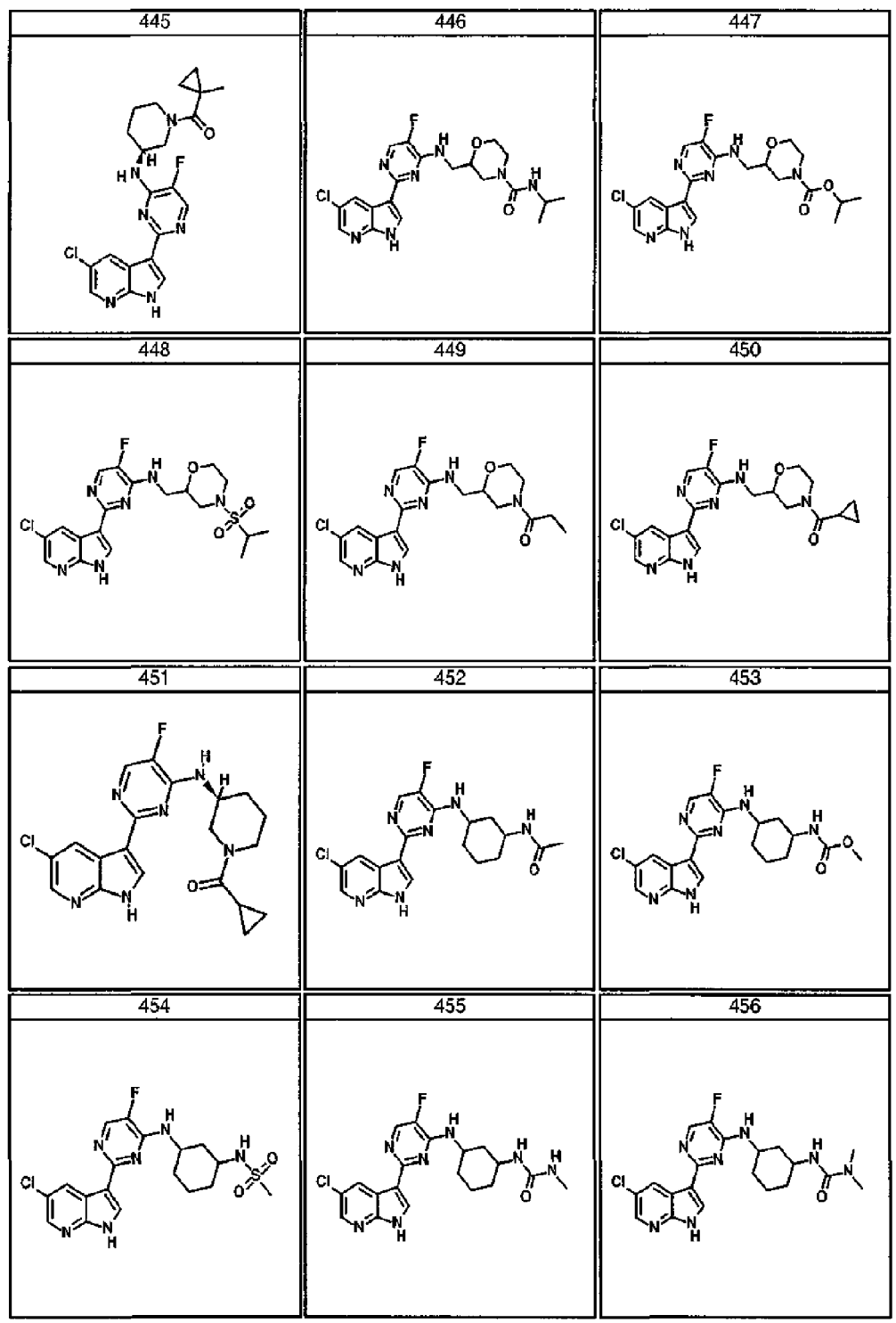
Figure 3A:
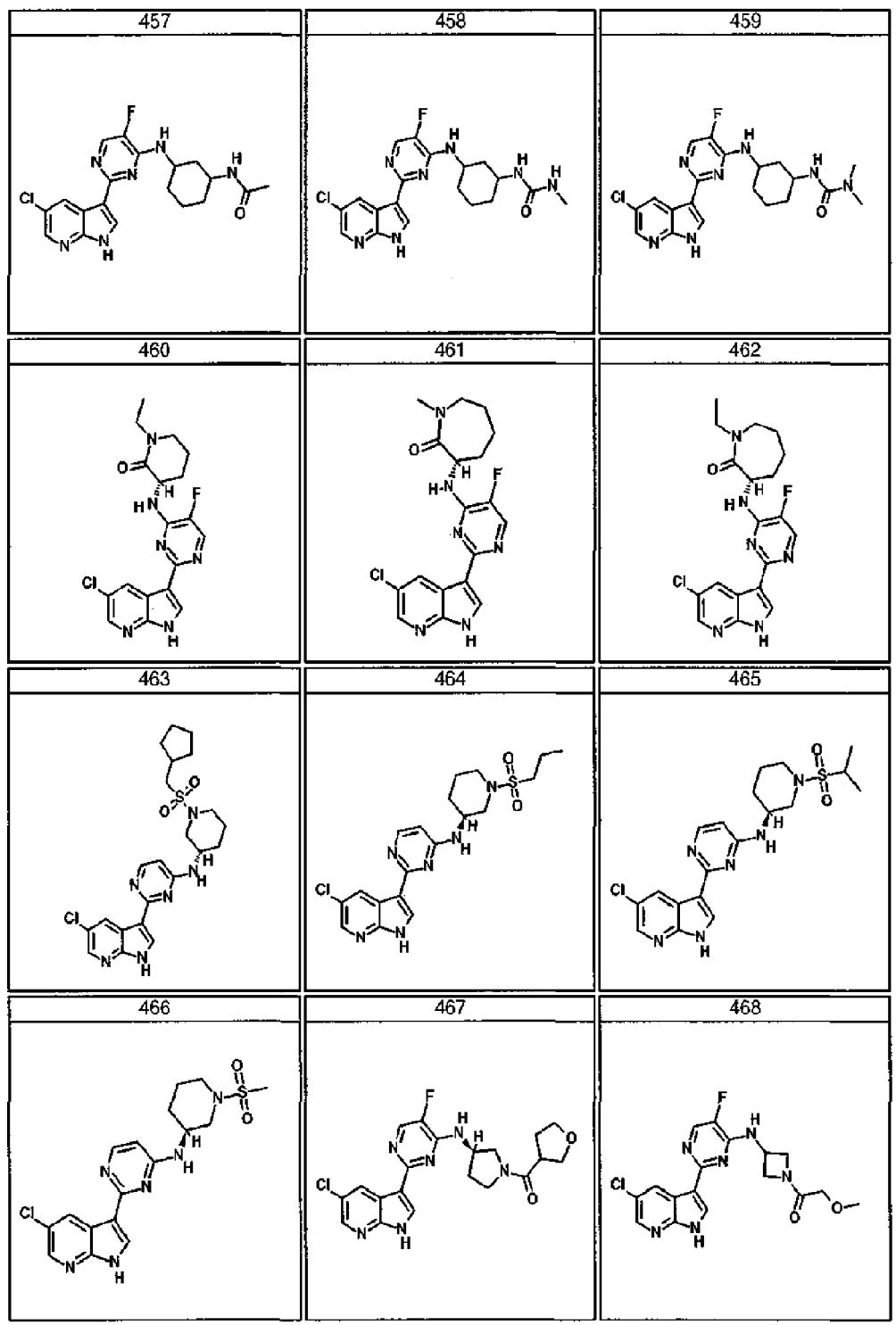
Figure 3A:
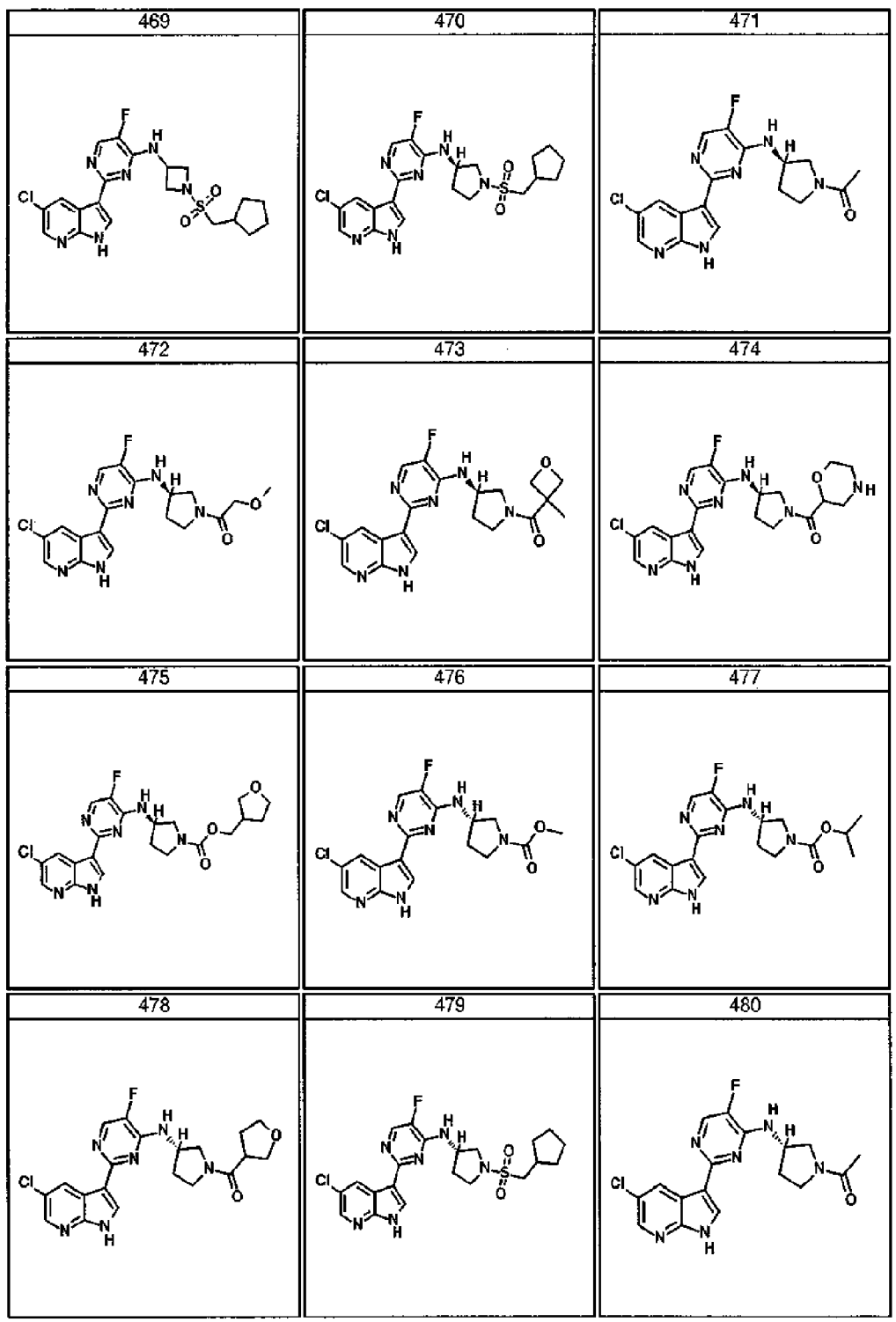
Figure 3A:
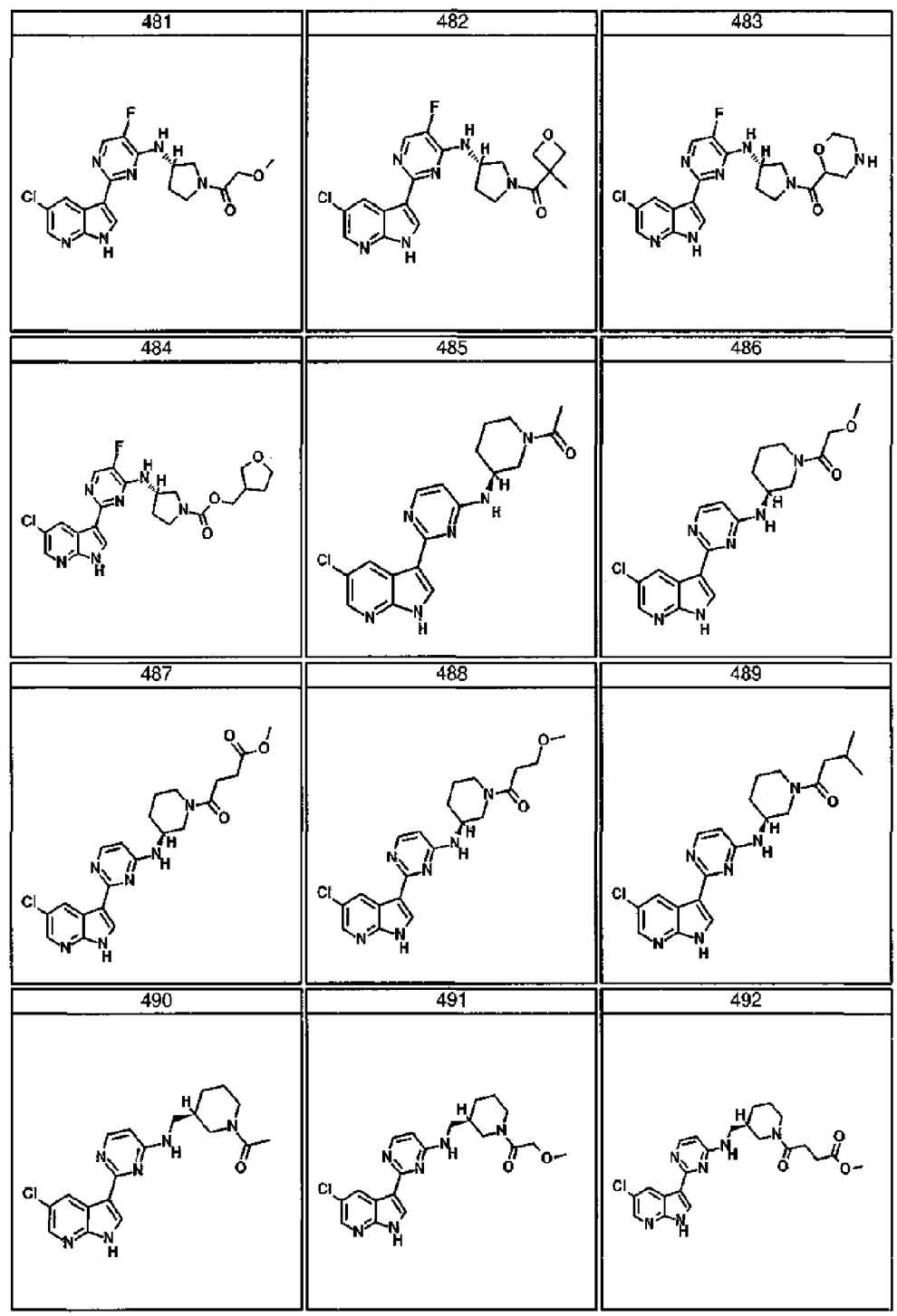
Figure 3A:
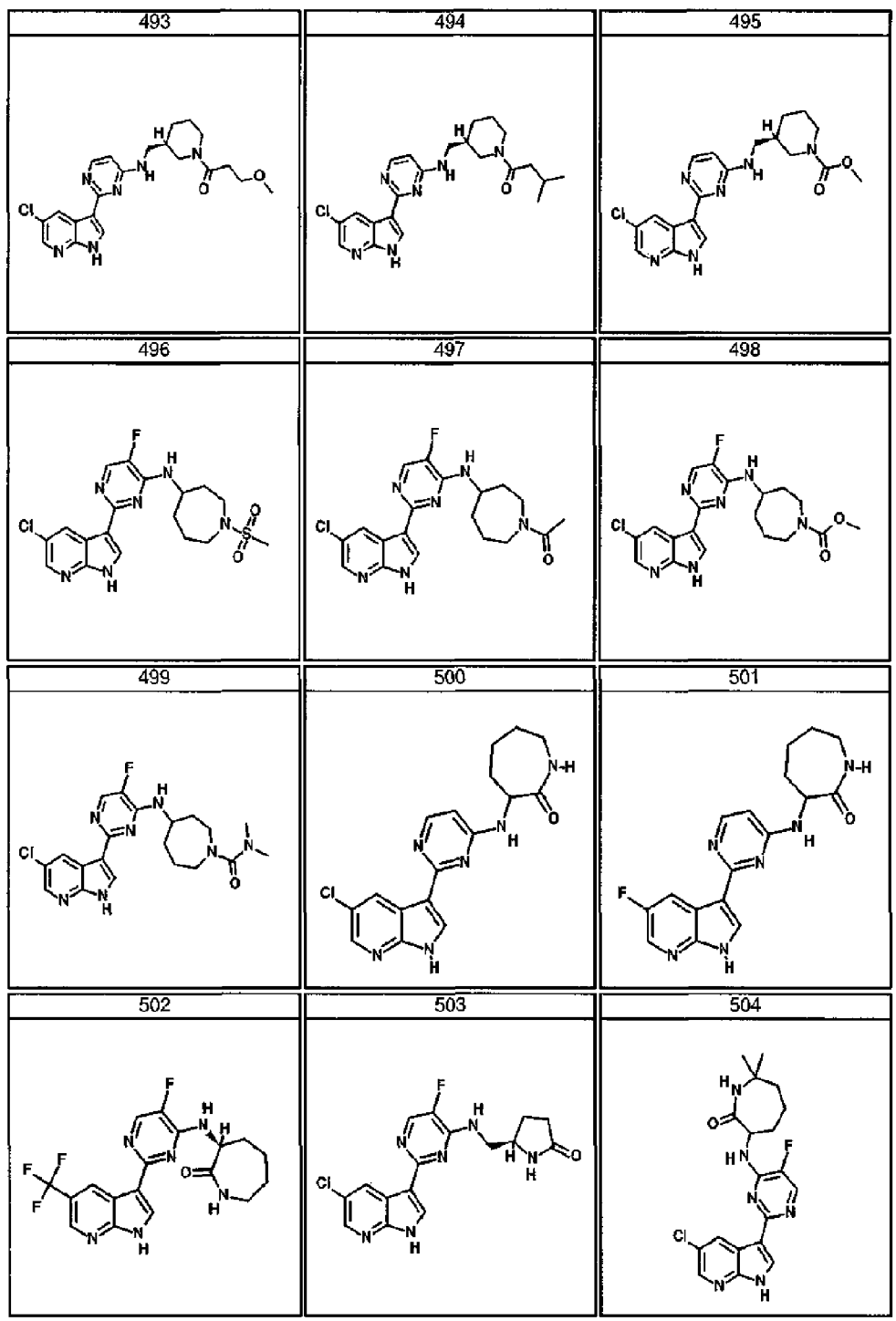
Figure 3A:
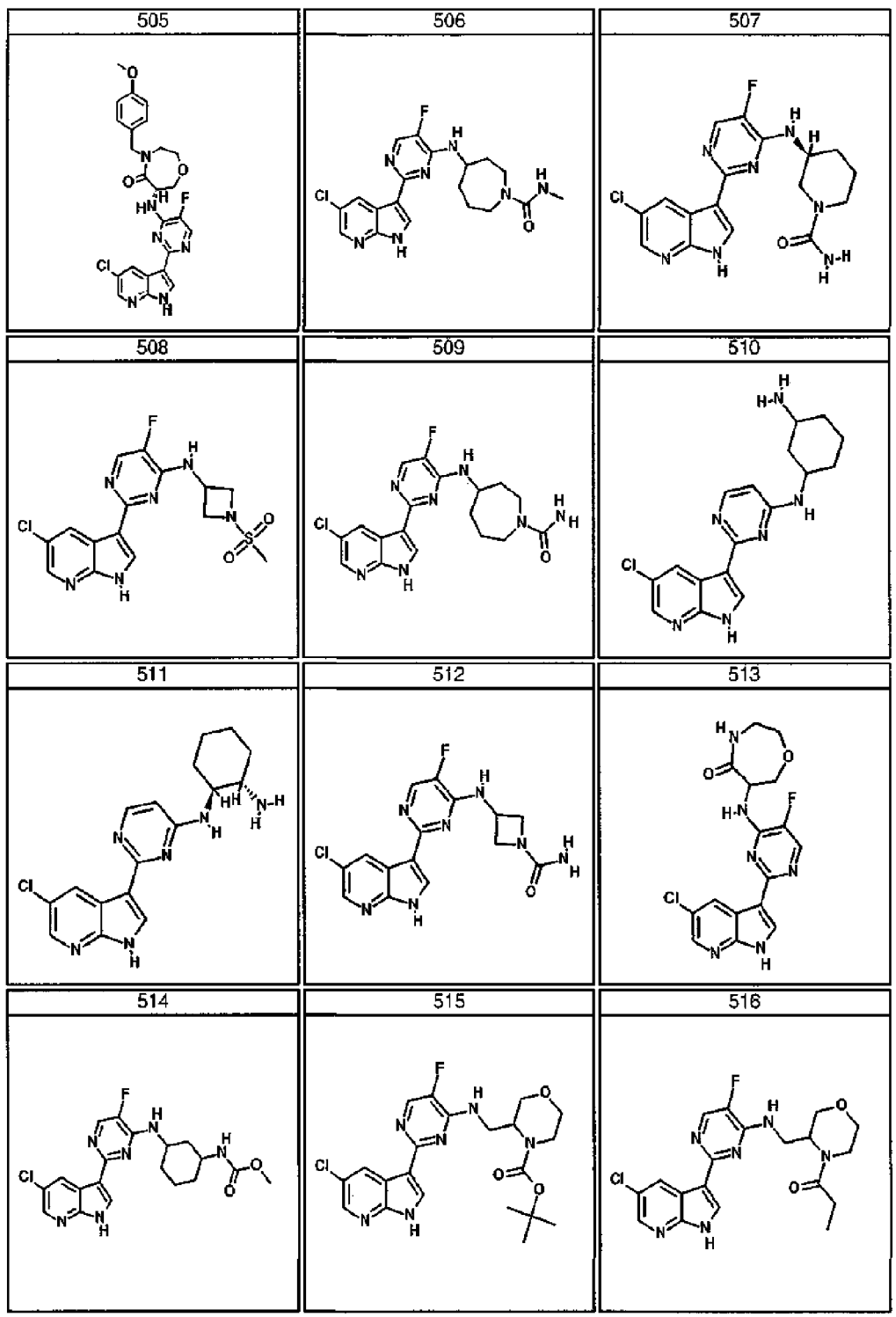
Figure 3A:
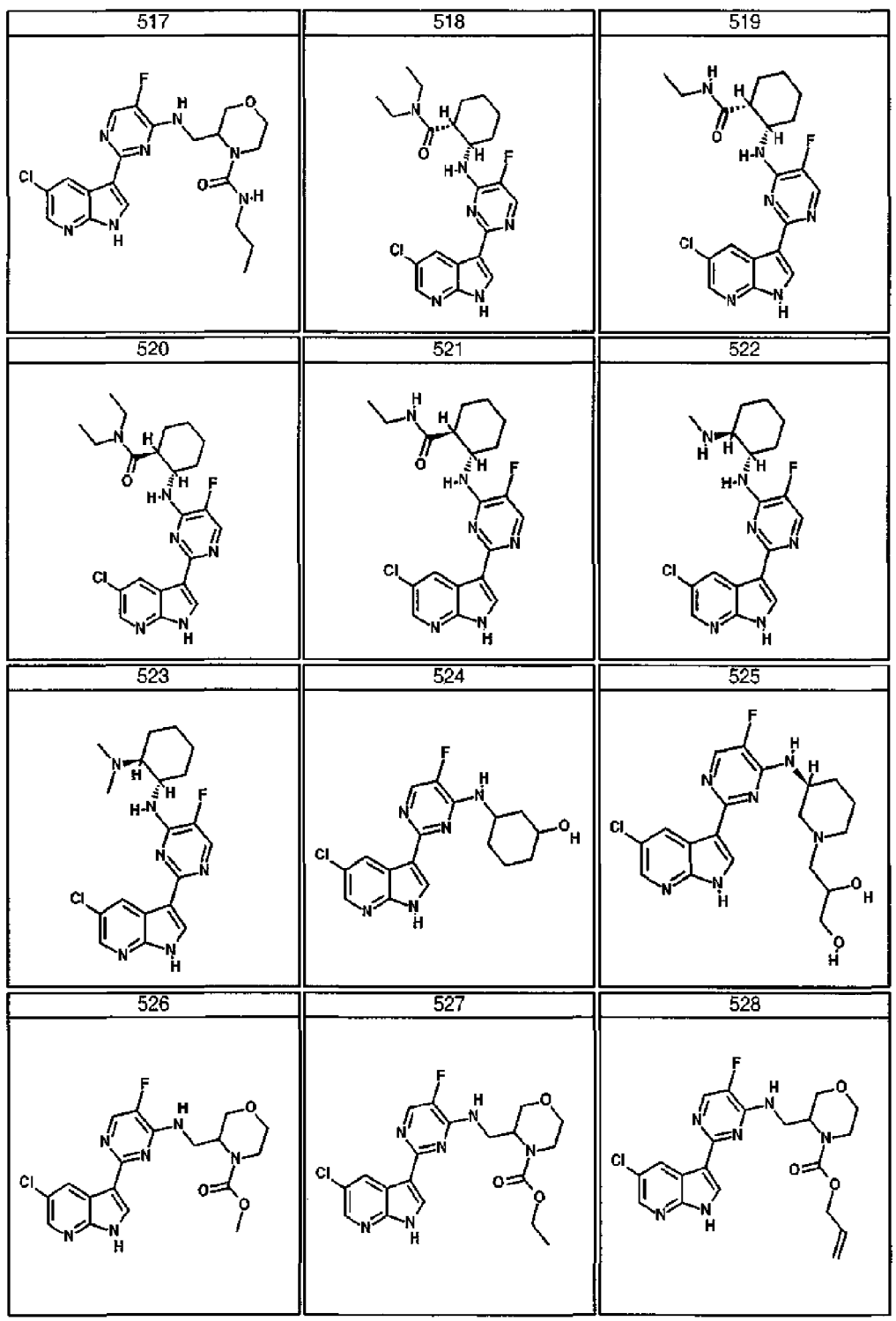
Figure 3A:
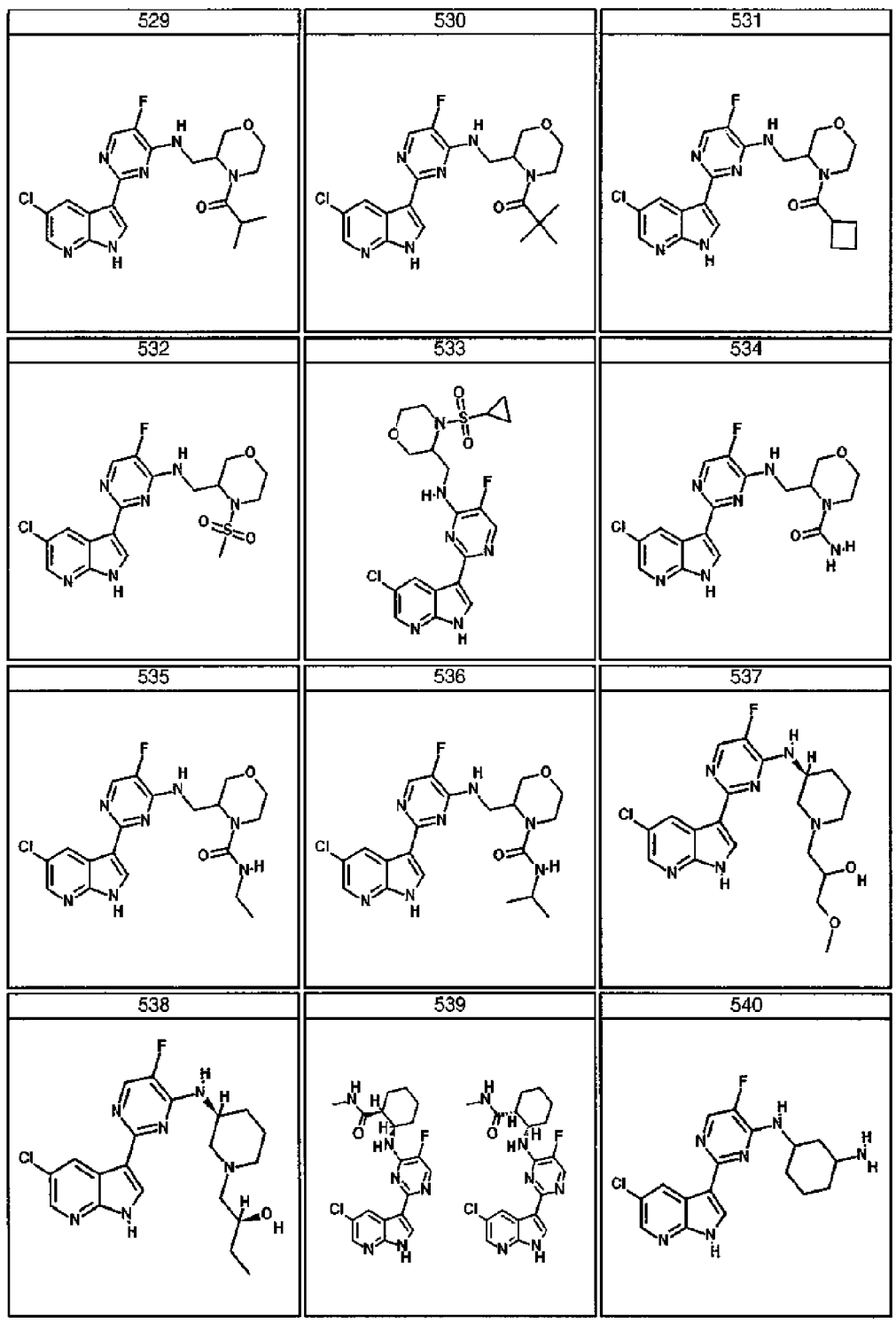
Figure 3A:
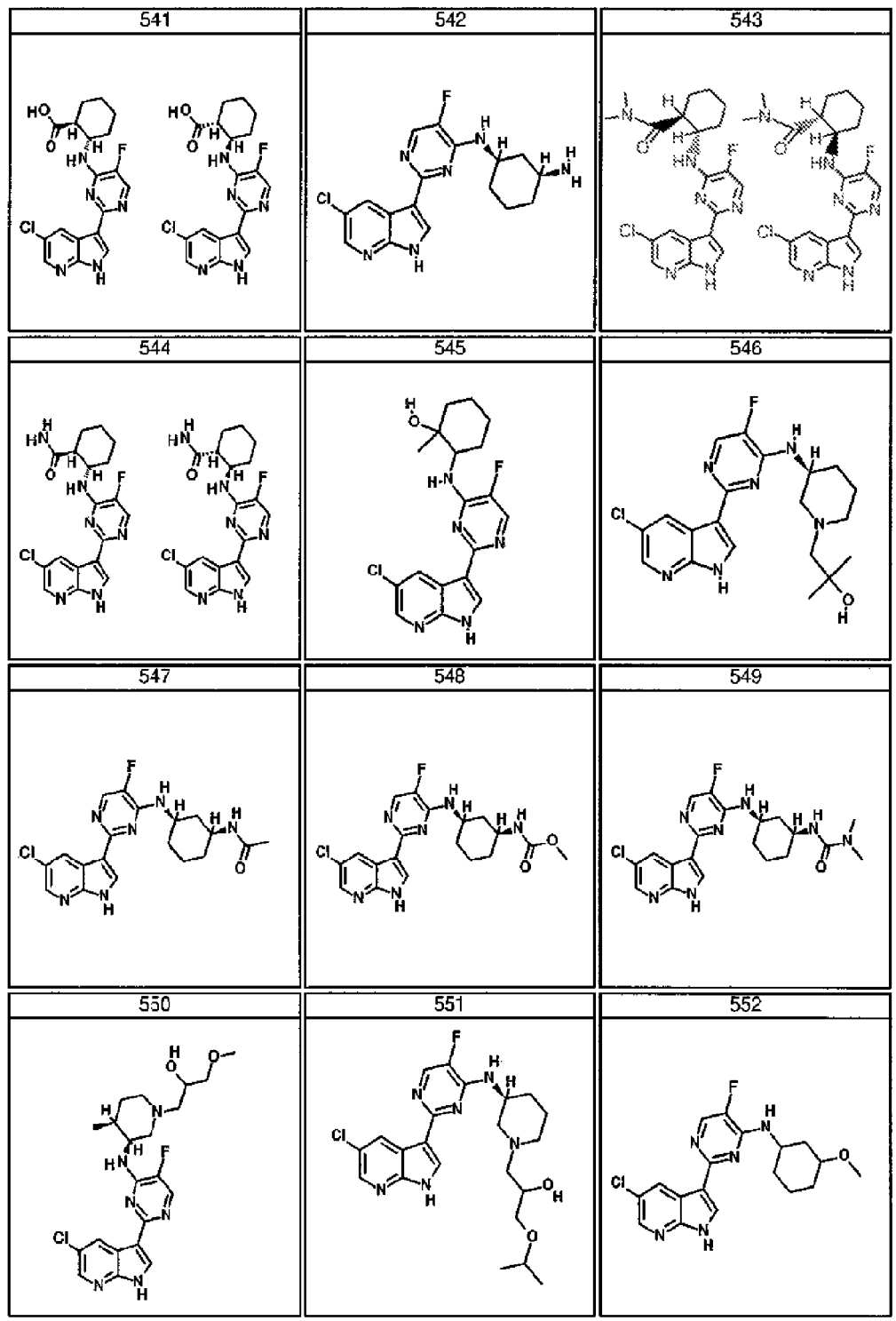
Figure 3A:
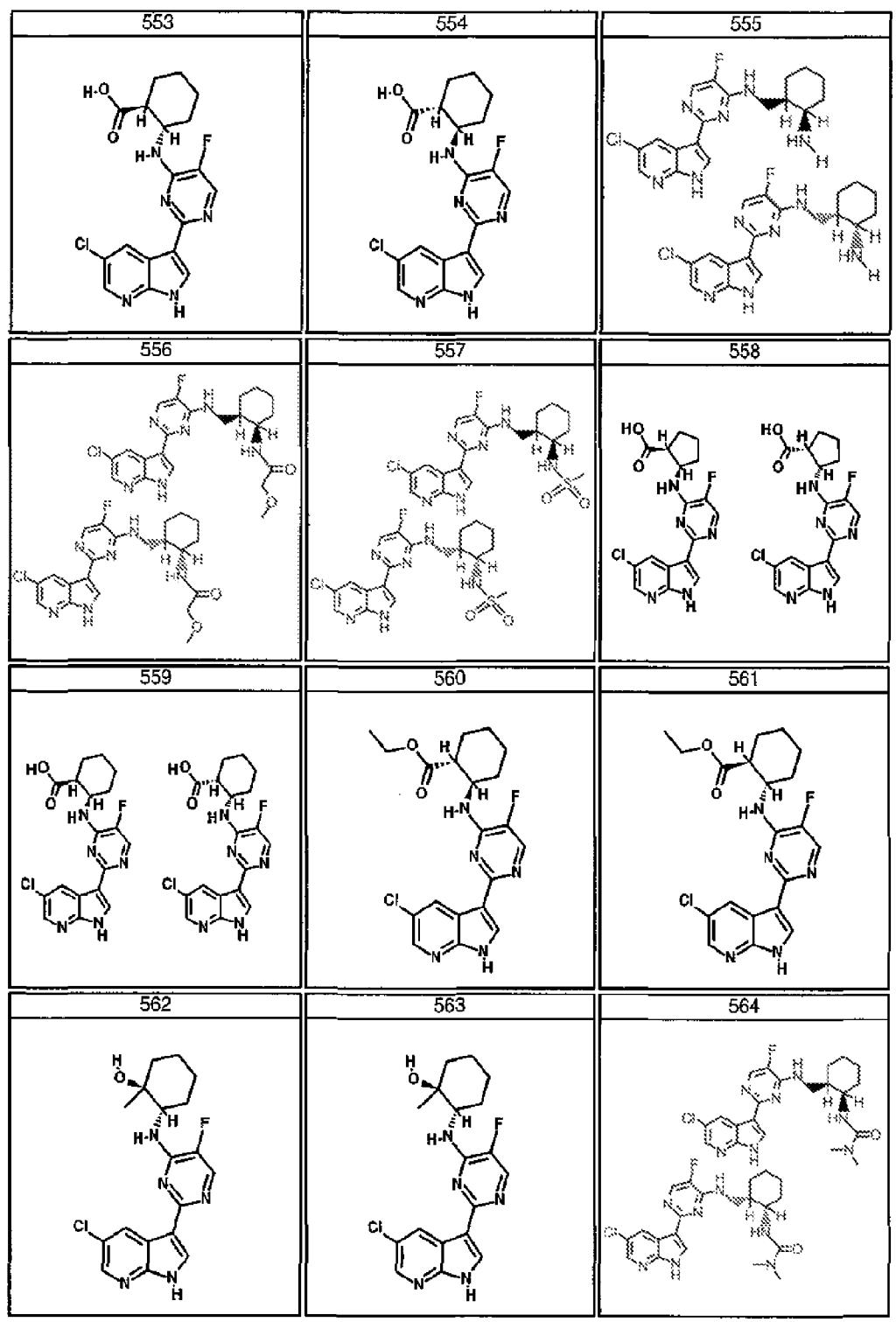
Figure 3A:
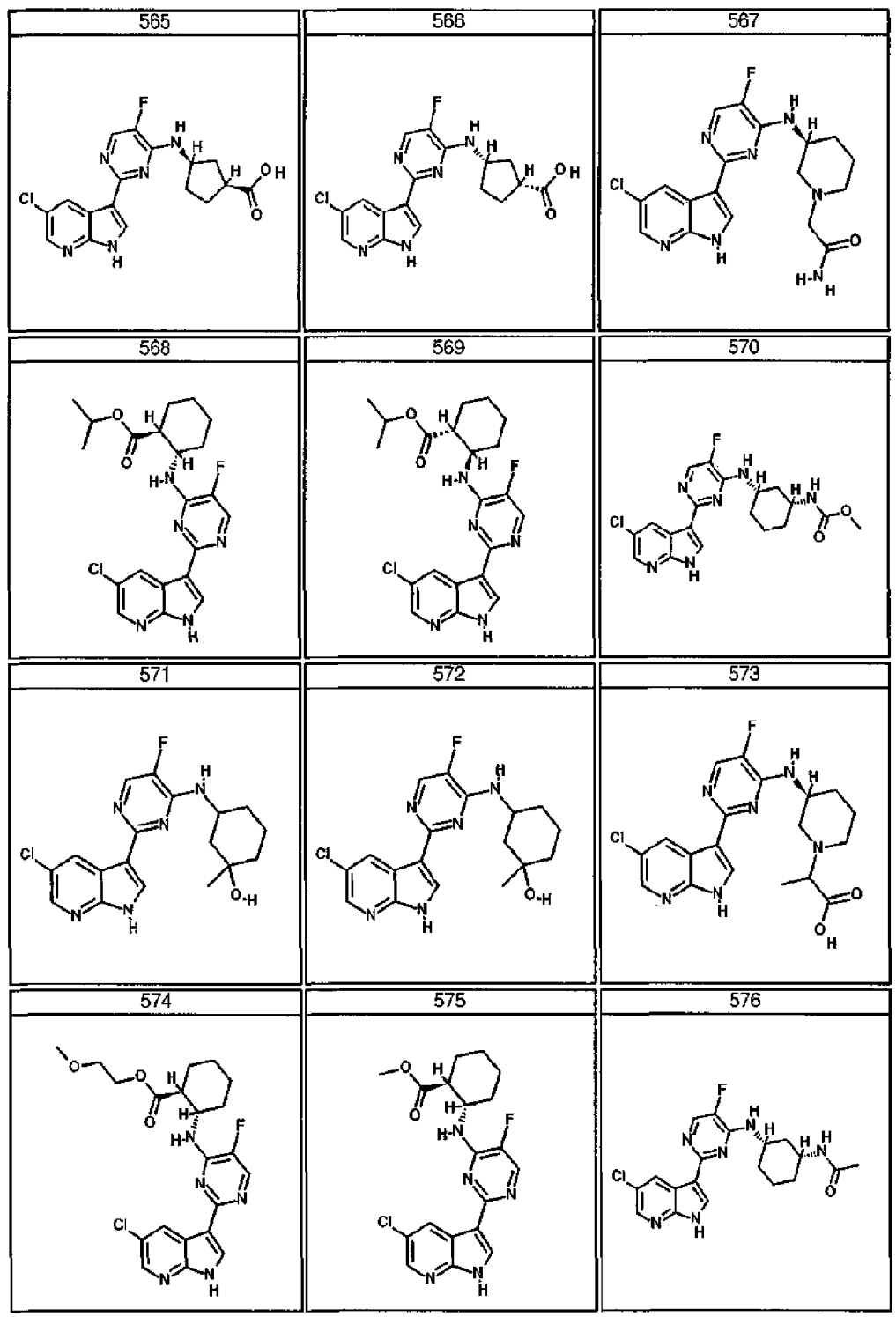
Figure 3A:
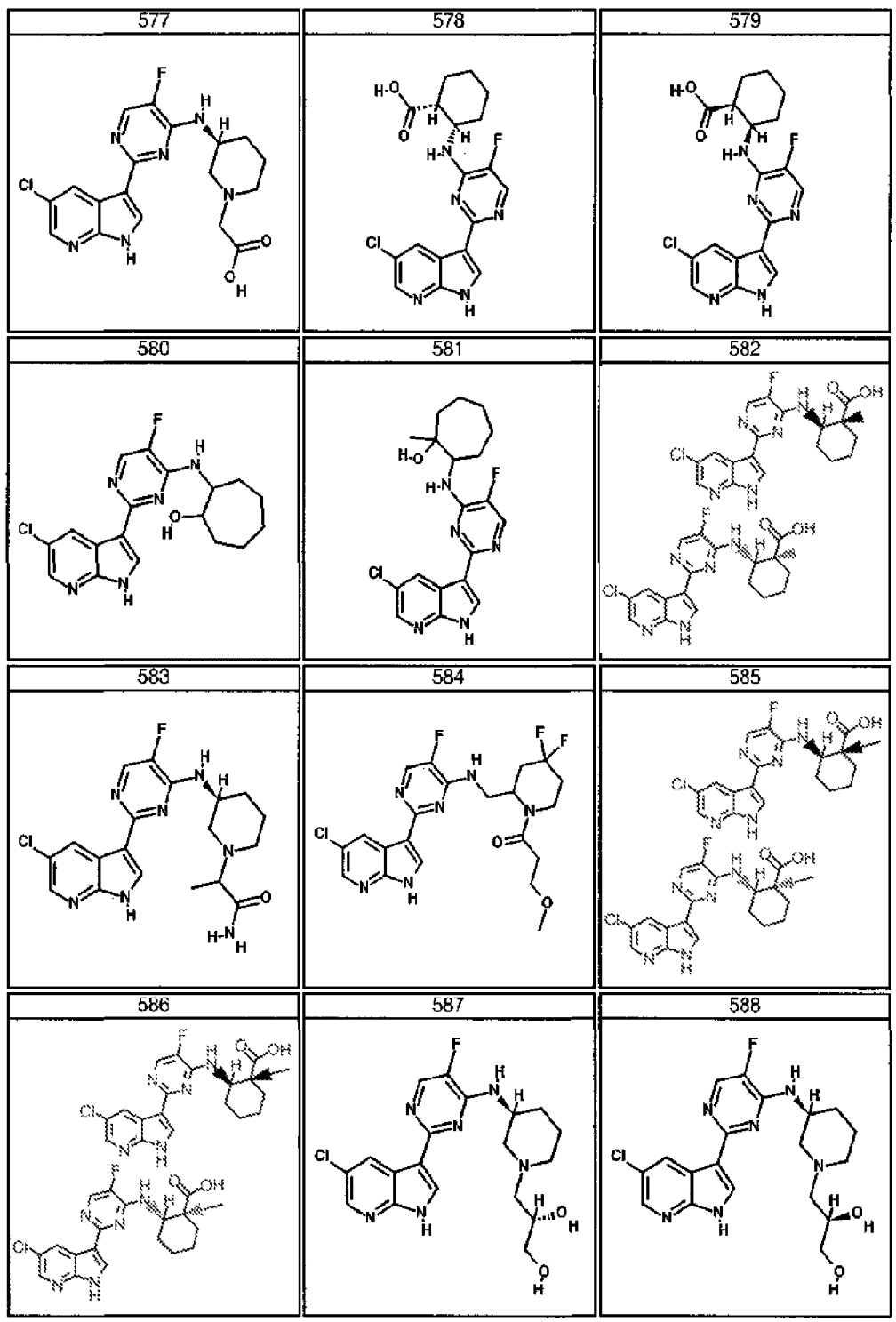
Figure 3A:
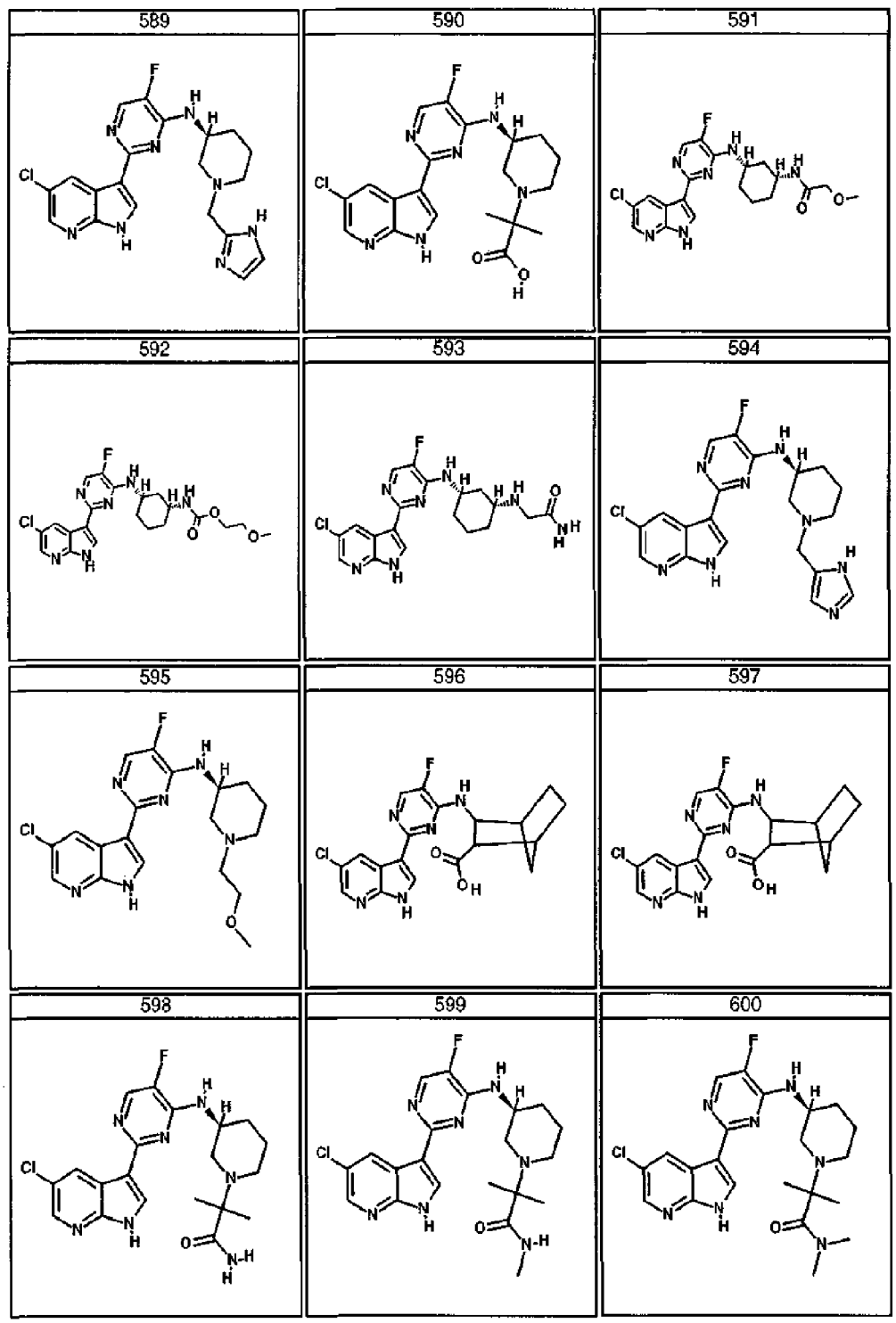
Figure 3A:
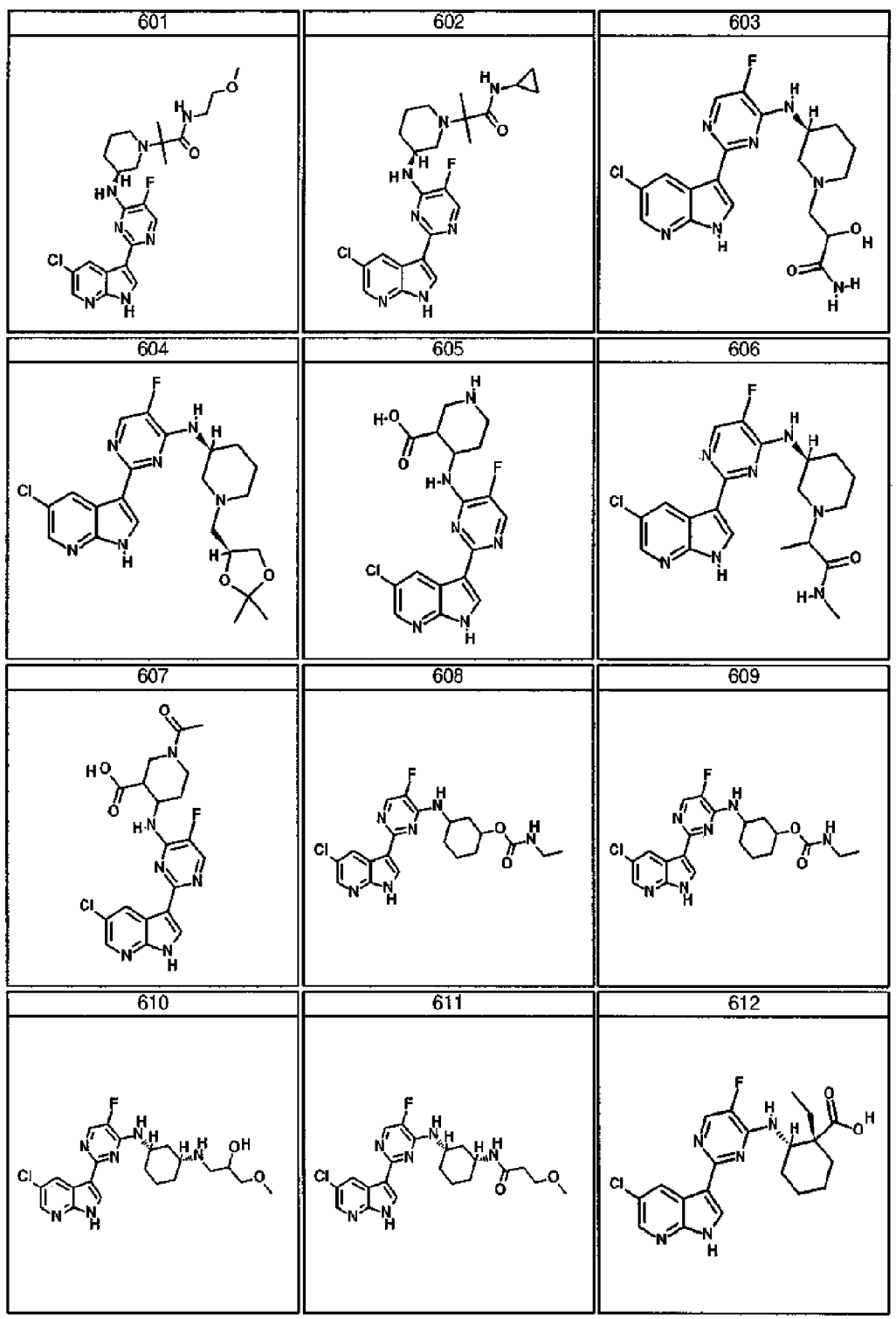
Figure 3A:
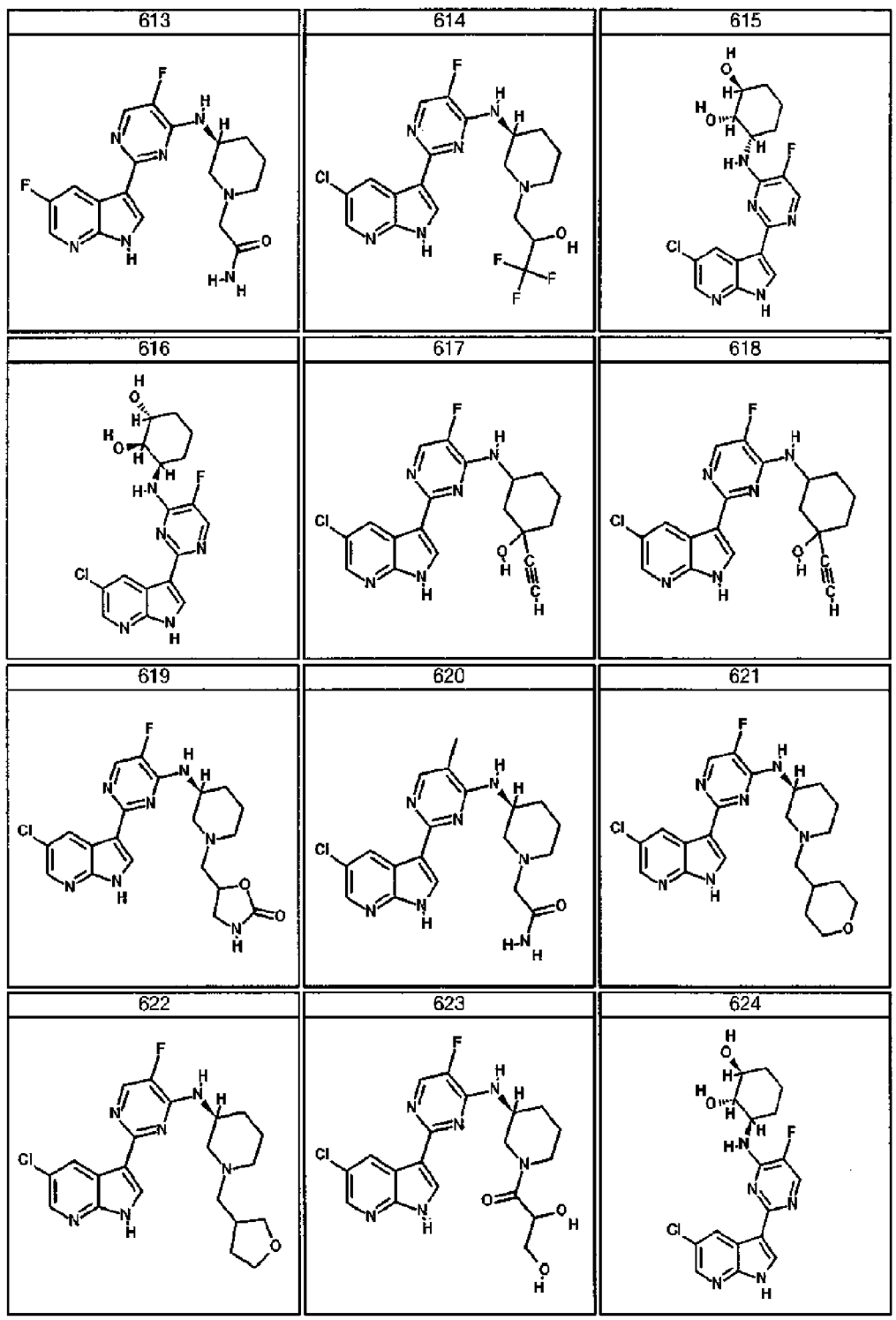
Figure 3B:
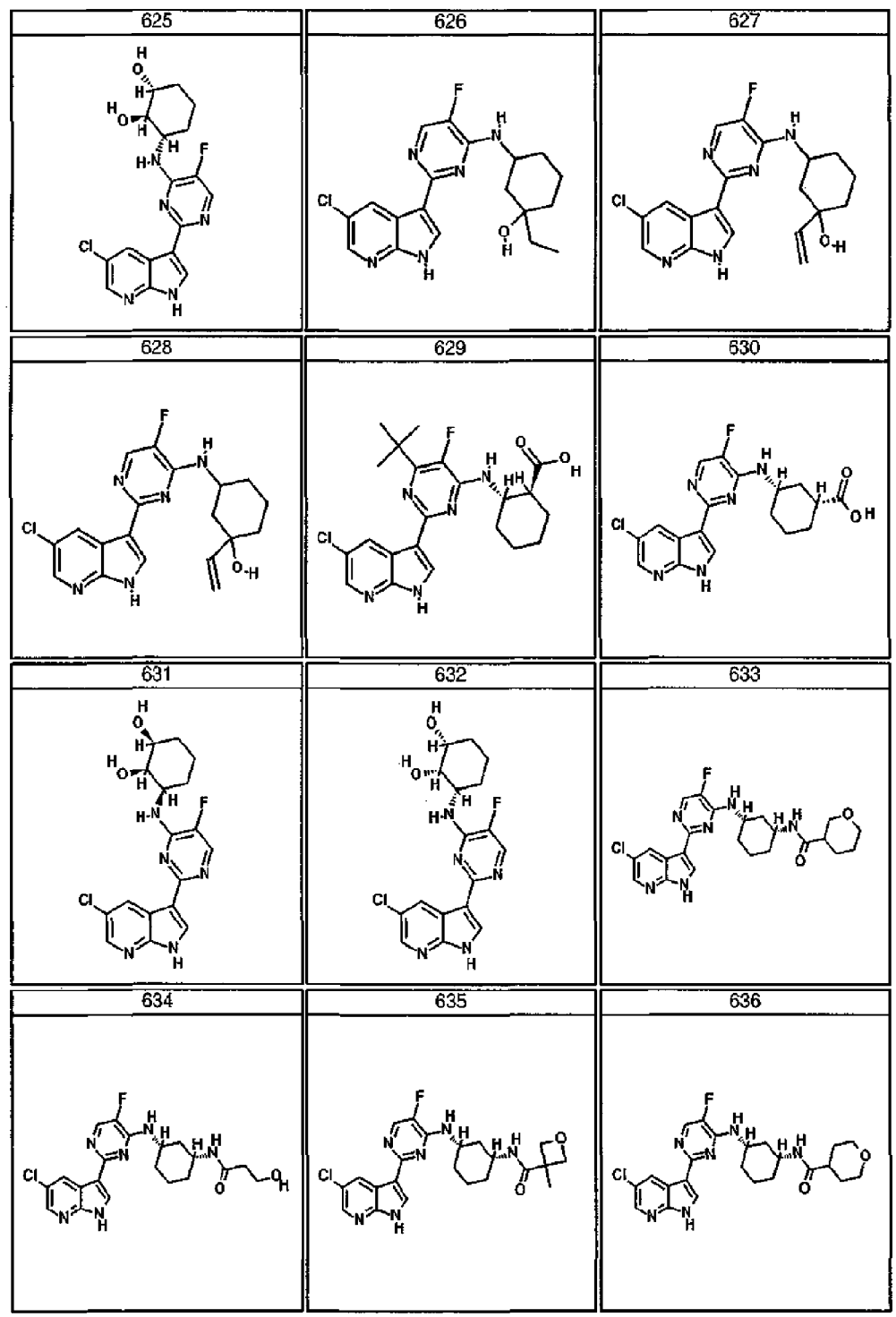
Figure 3B:
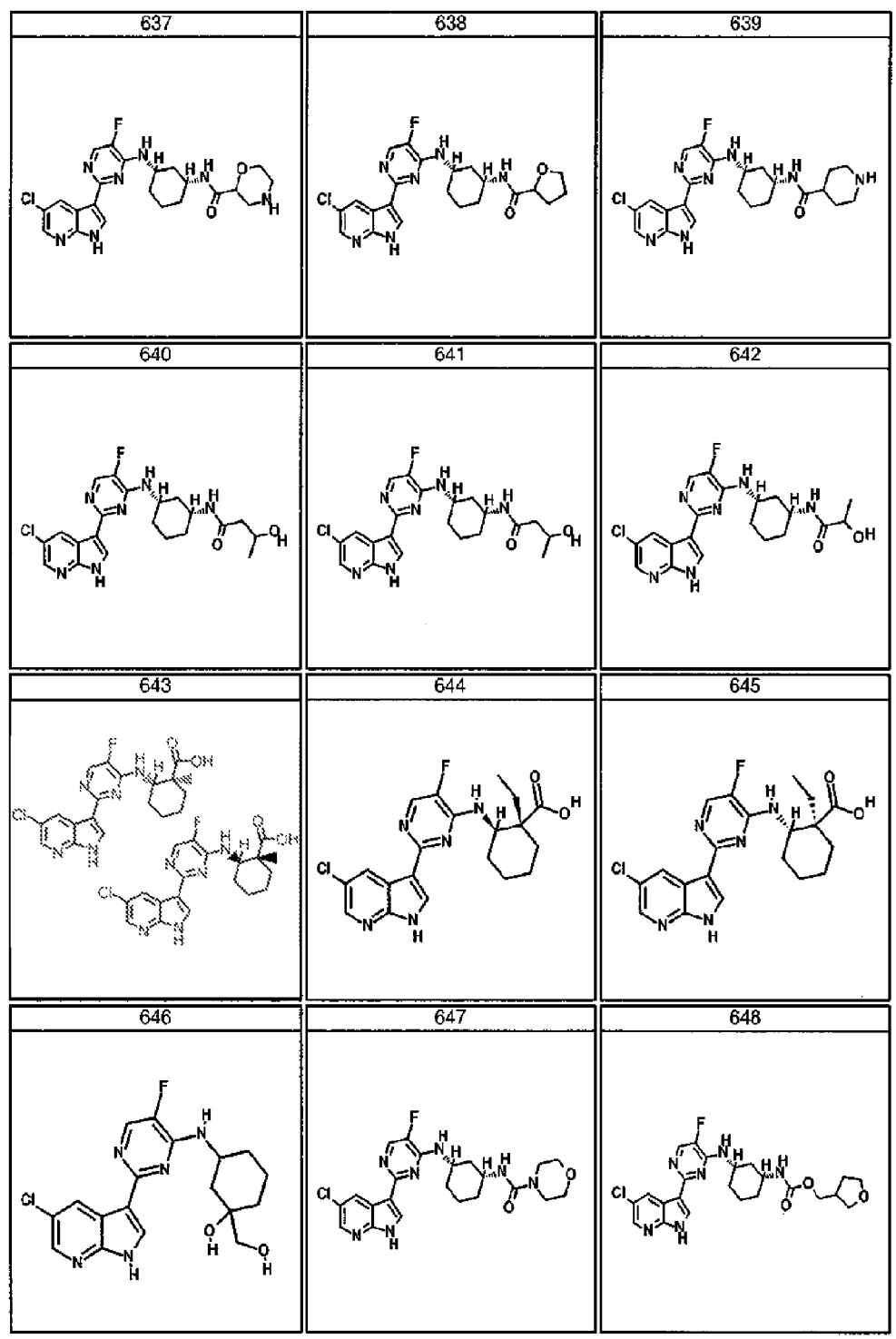
Figure 3B:
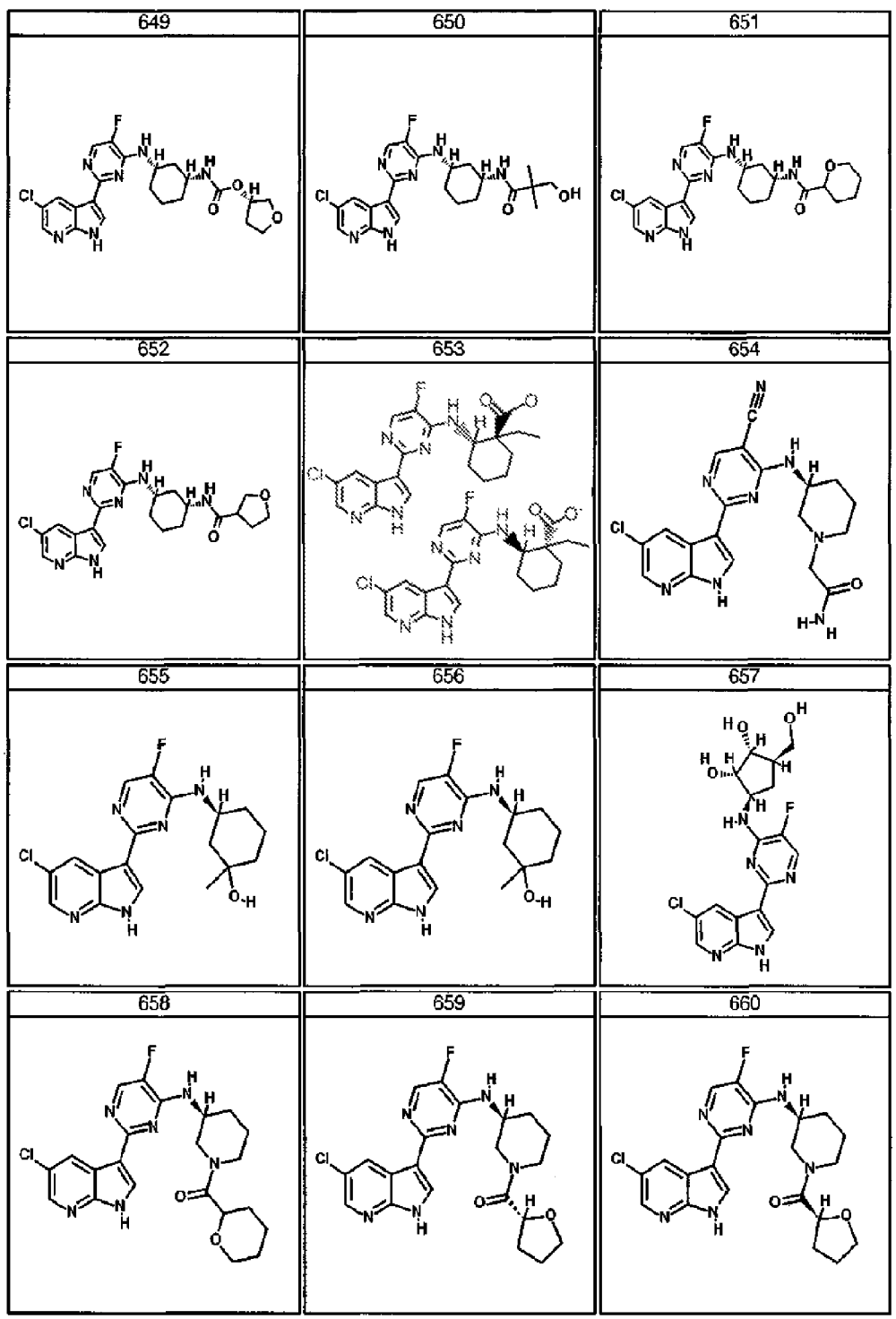
Figure 3B:
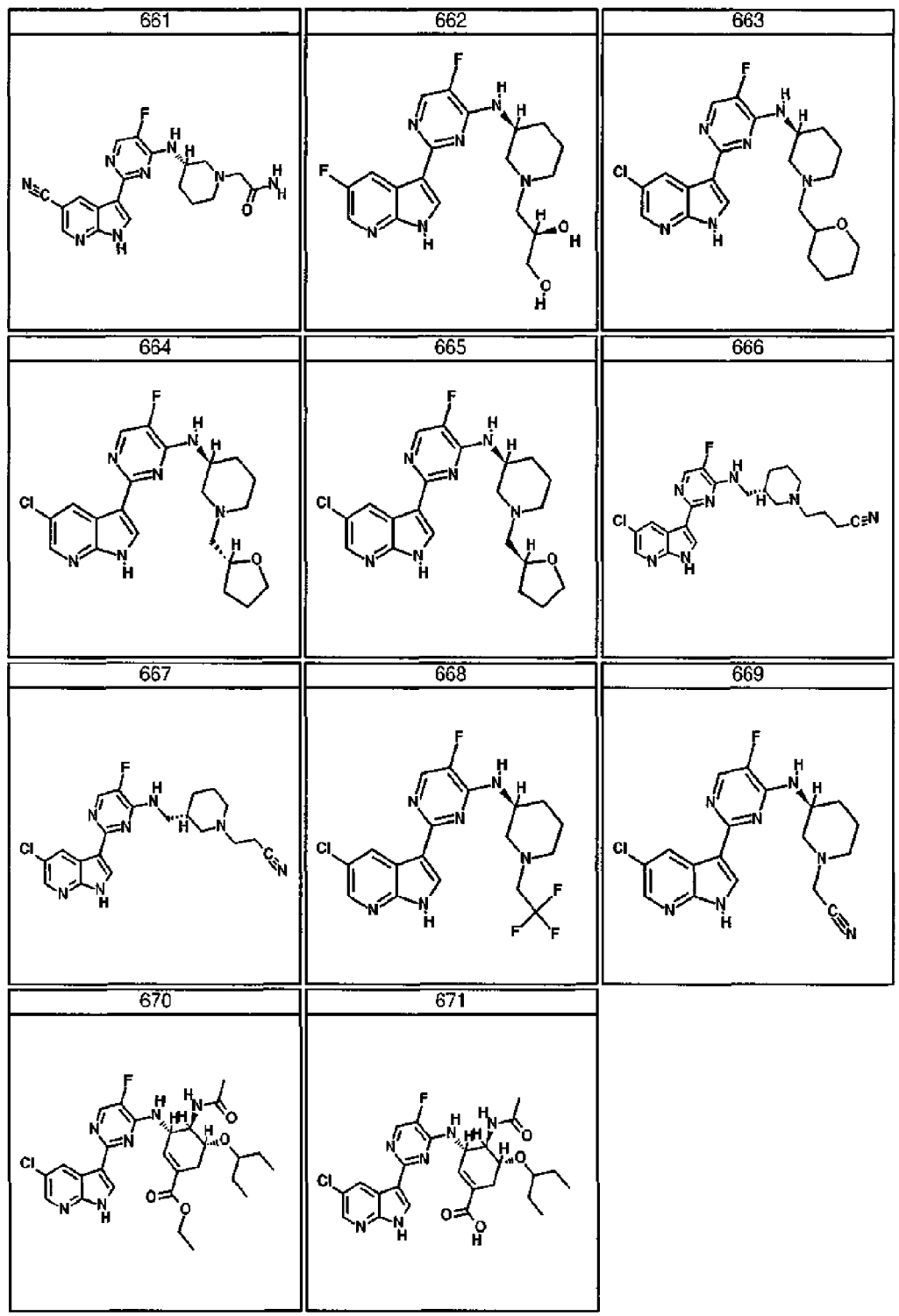
Figure 4A:
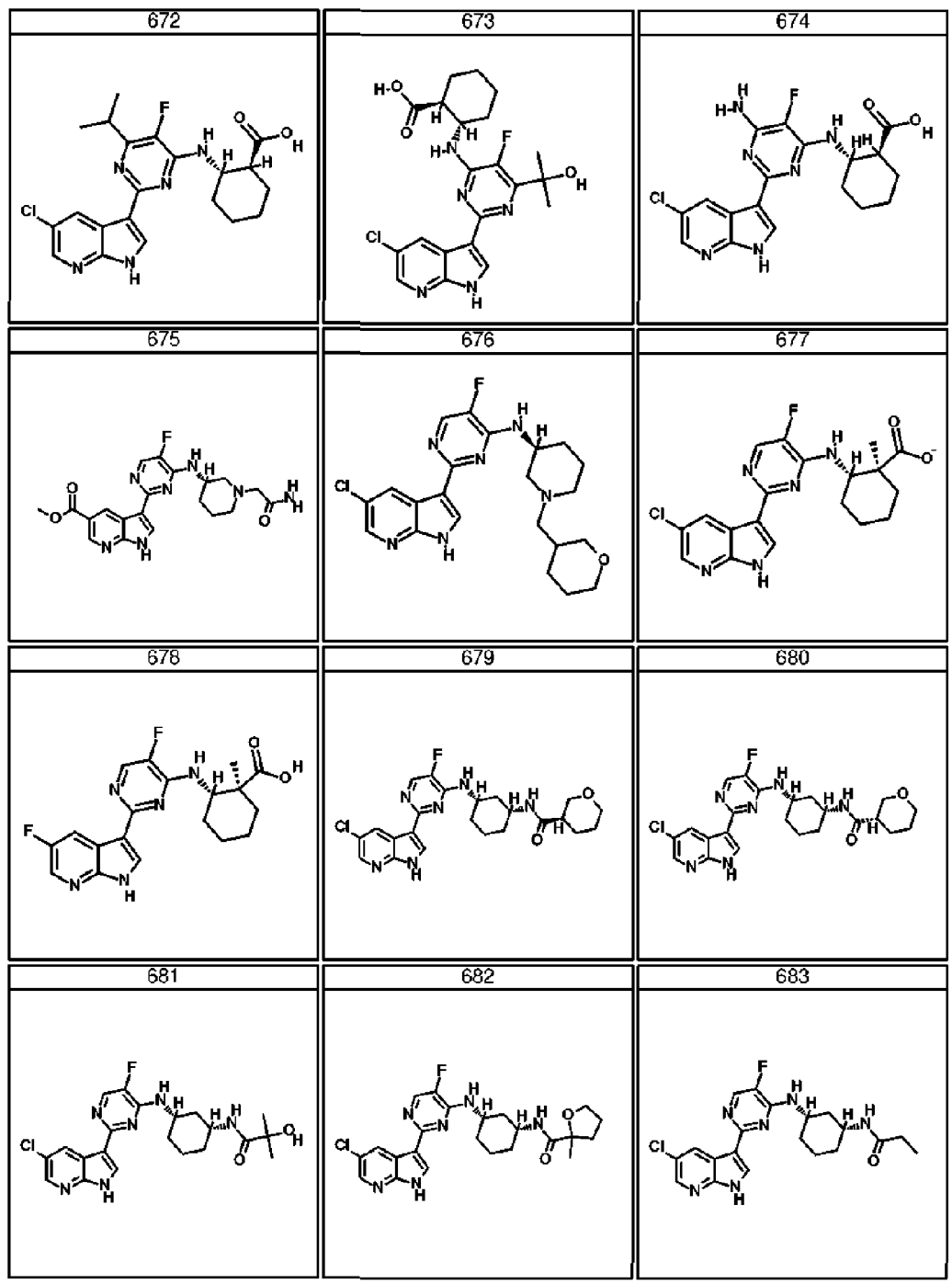
Figure 4B:
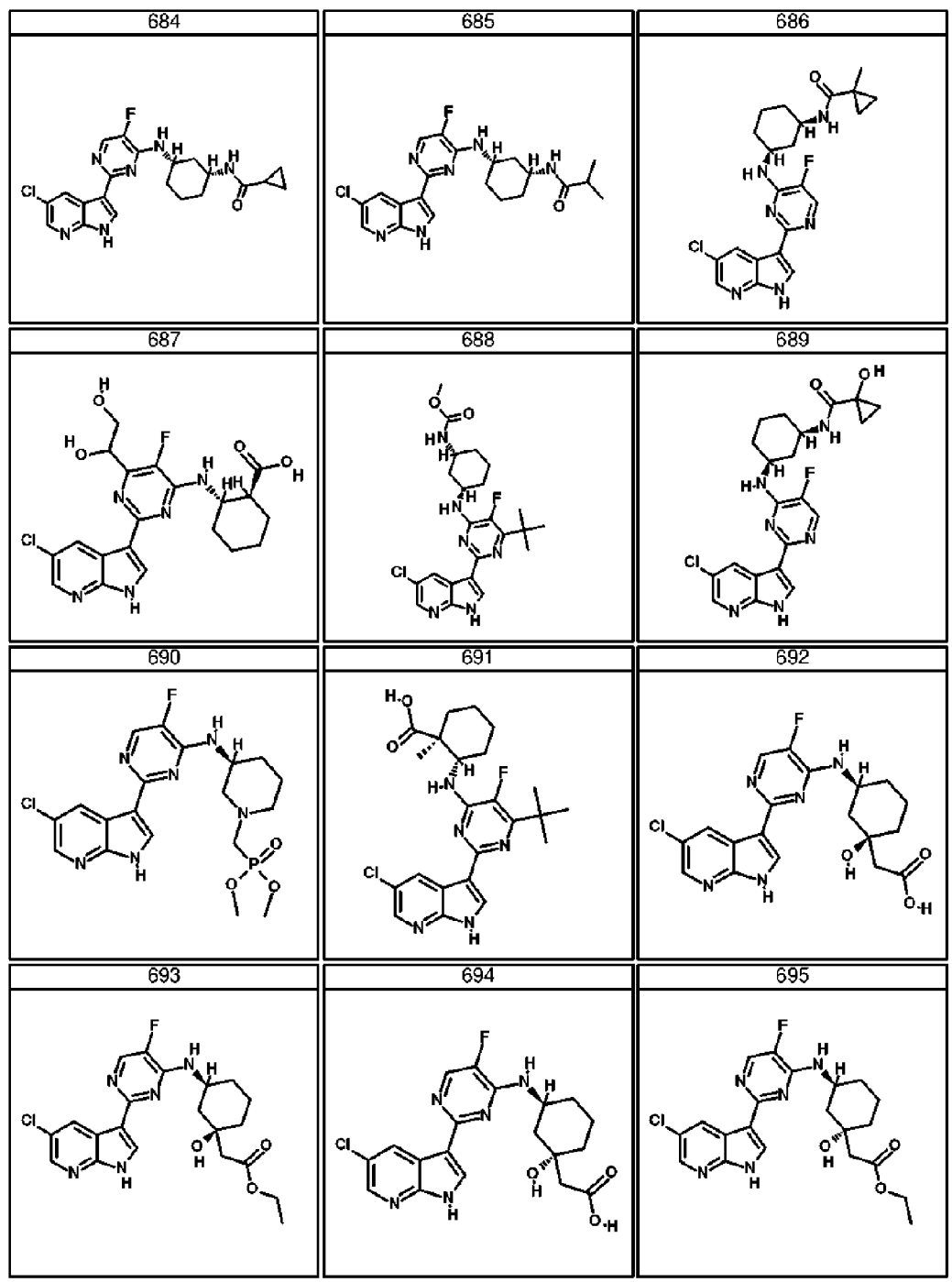
Figure 4C:
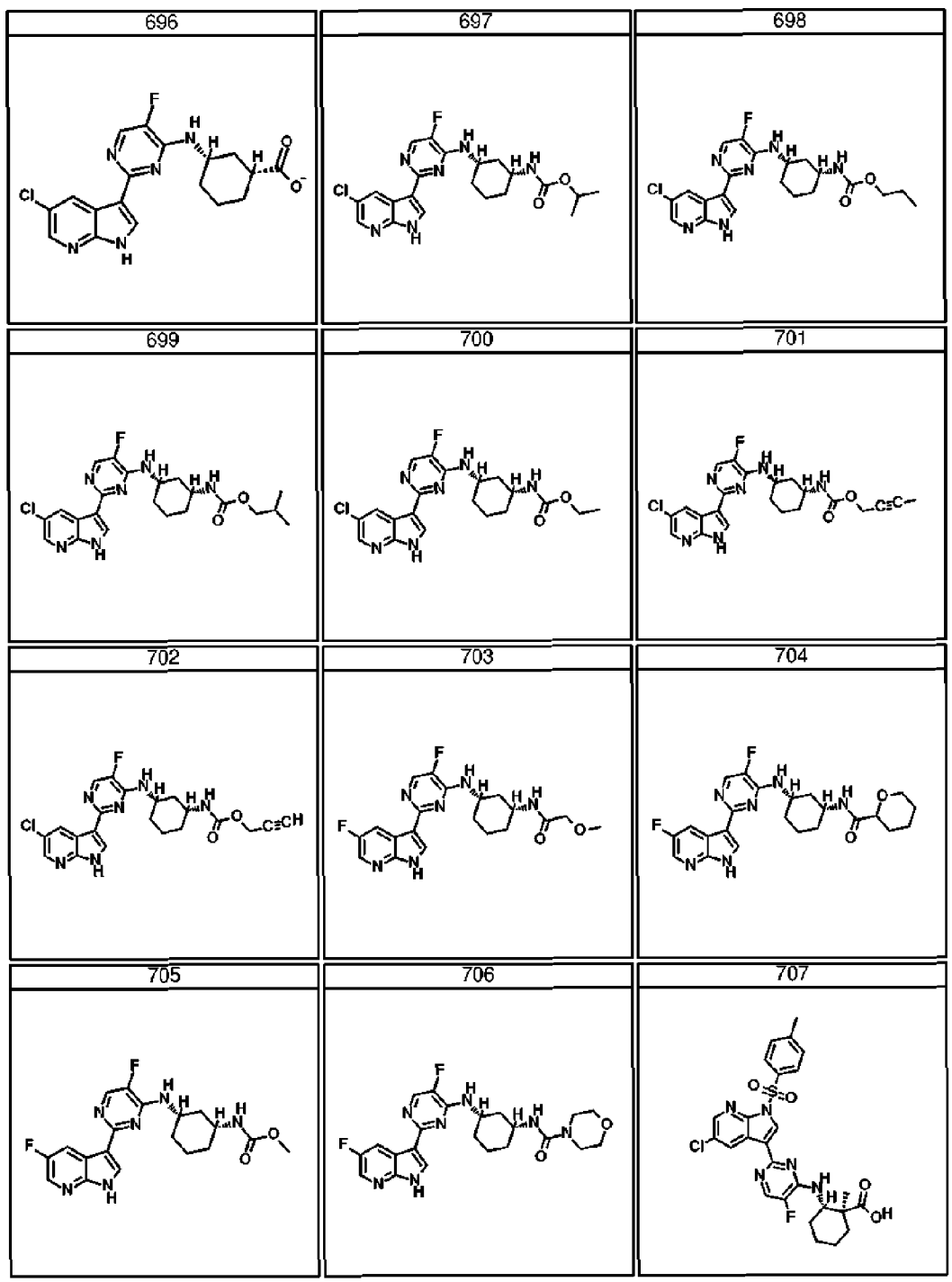
Figure 4D:
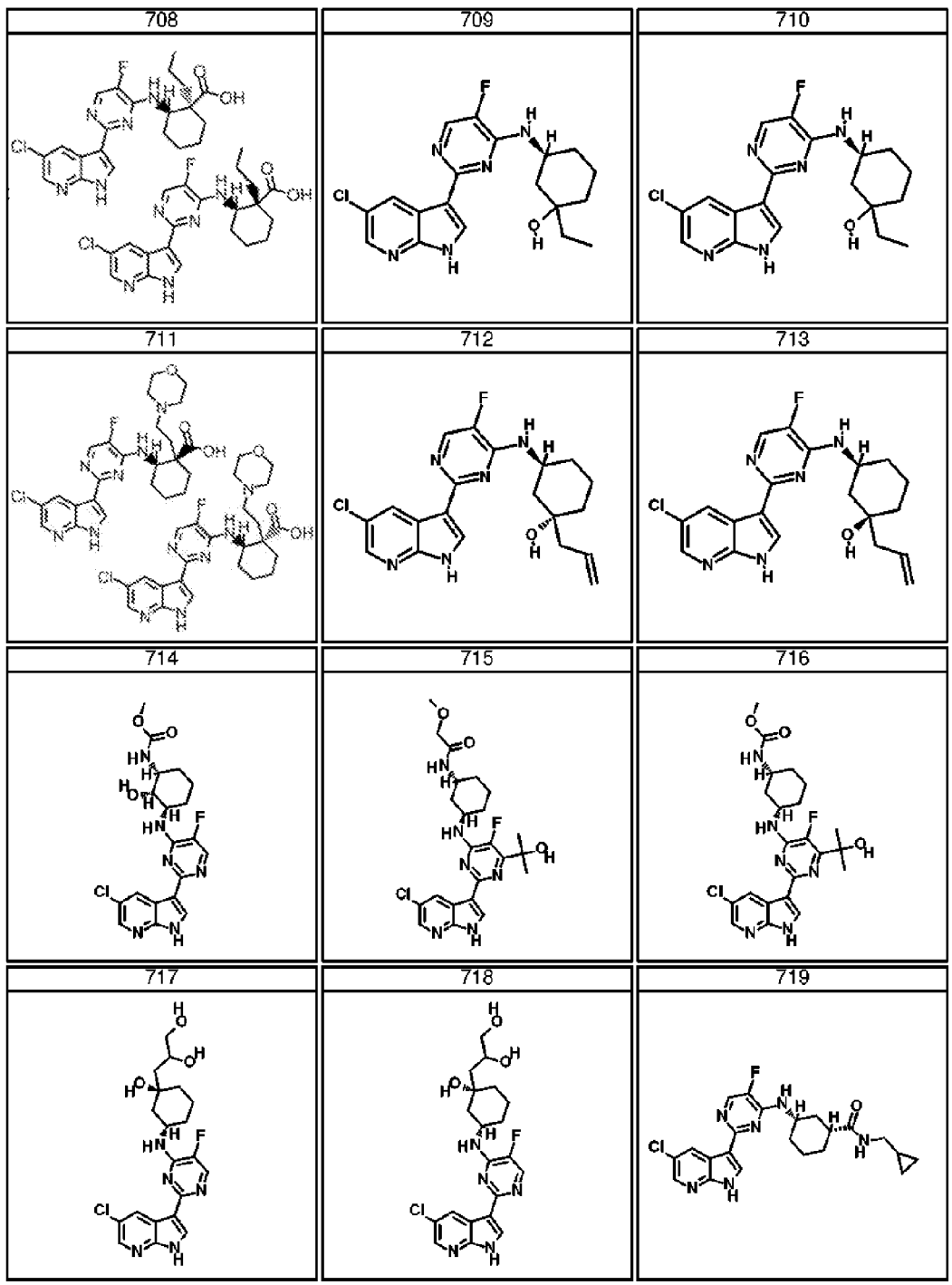
Figure 4E:
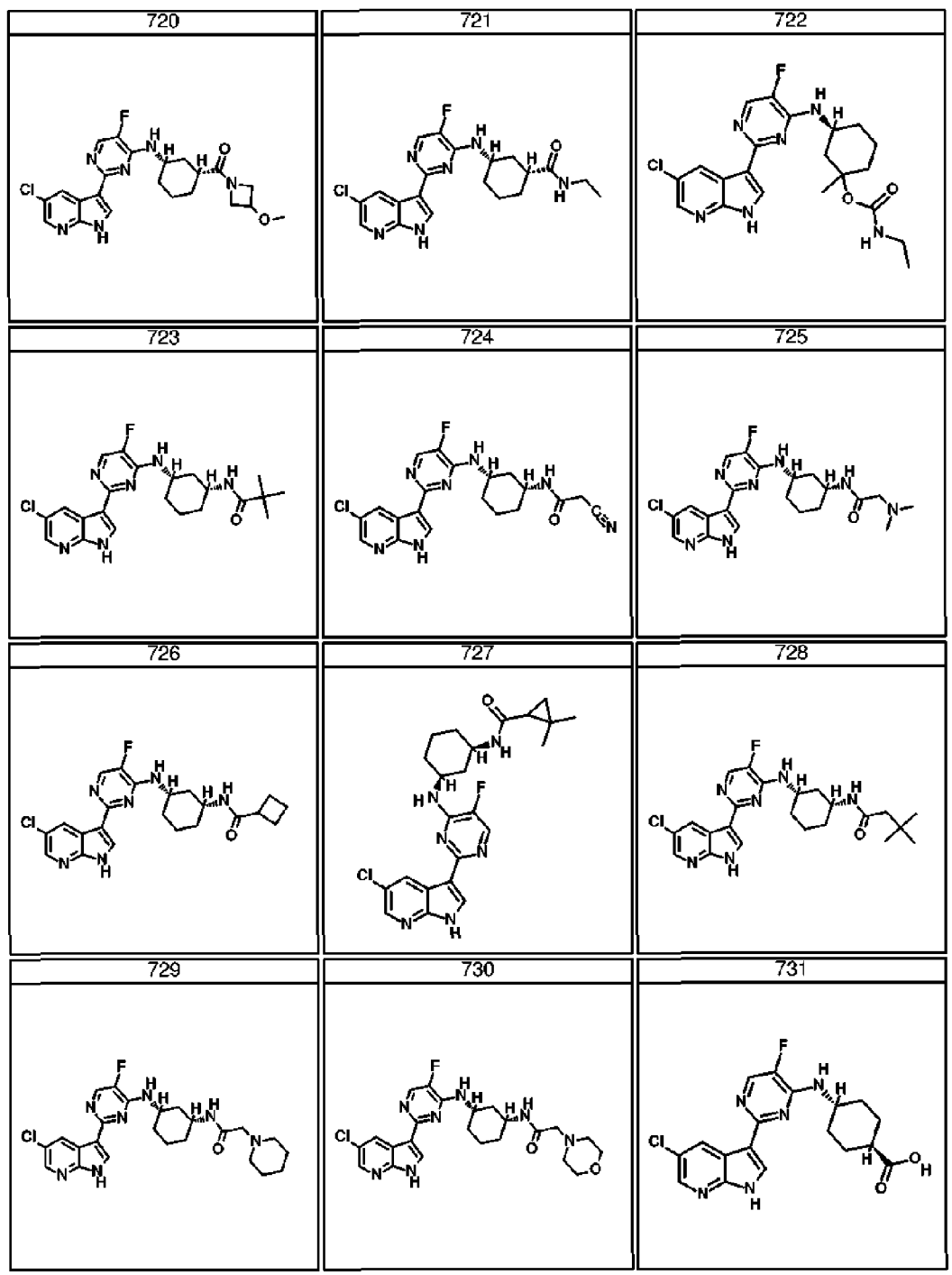
Figure 4F:
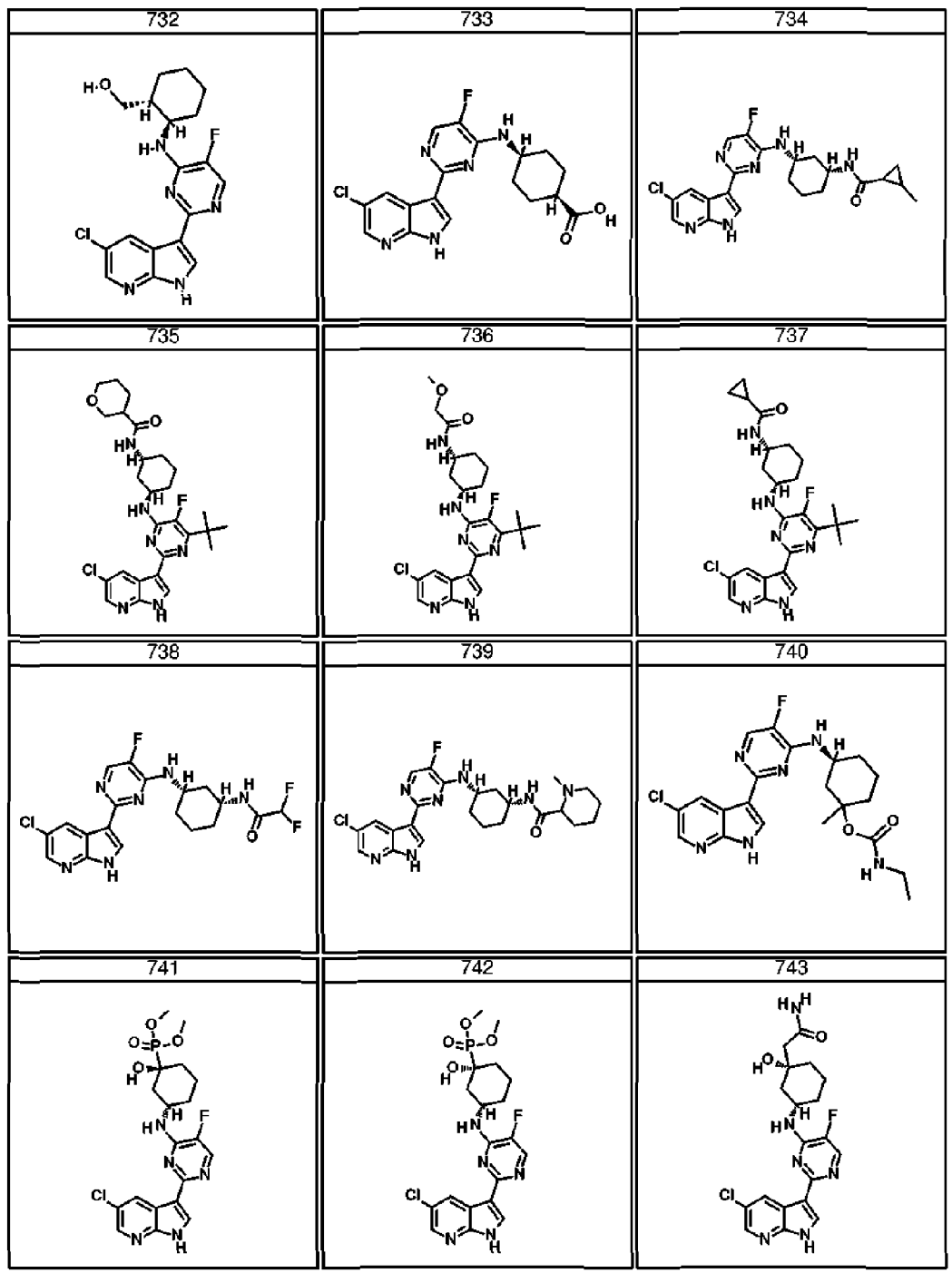
Figure 4G:
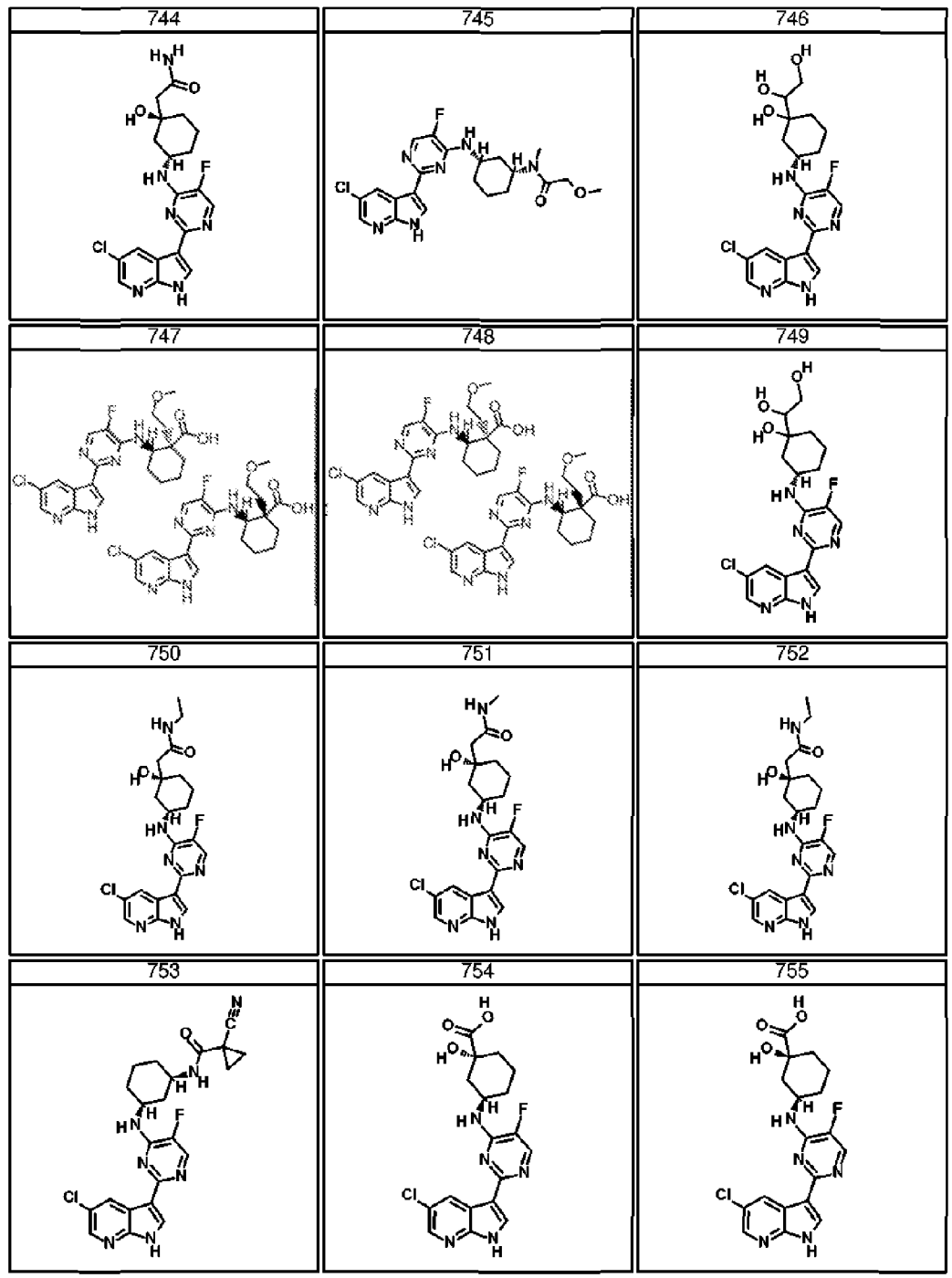
Figure 4H:
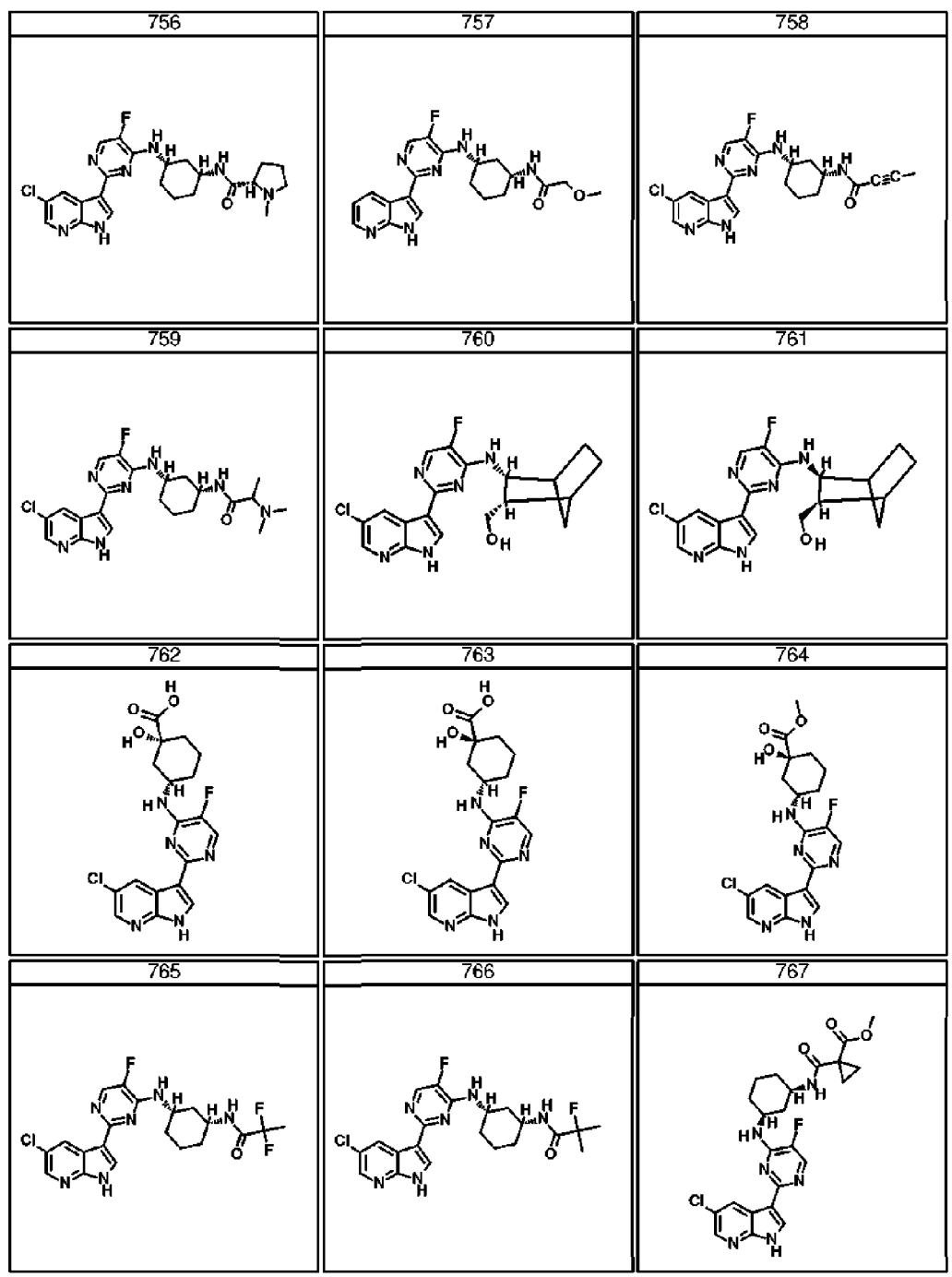
Figure 4I:
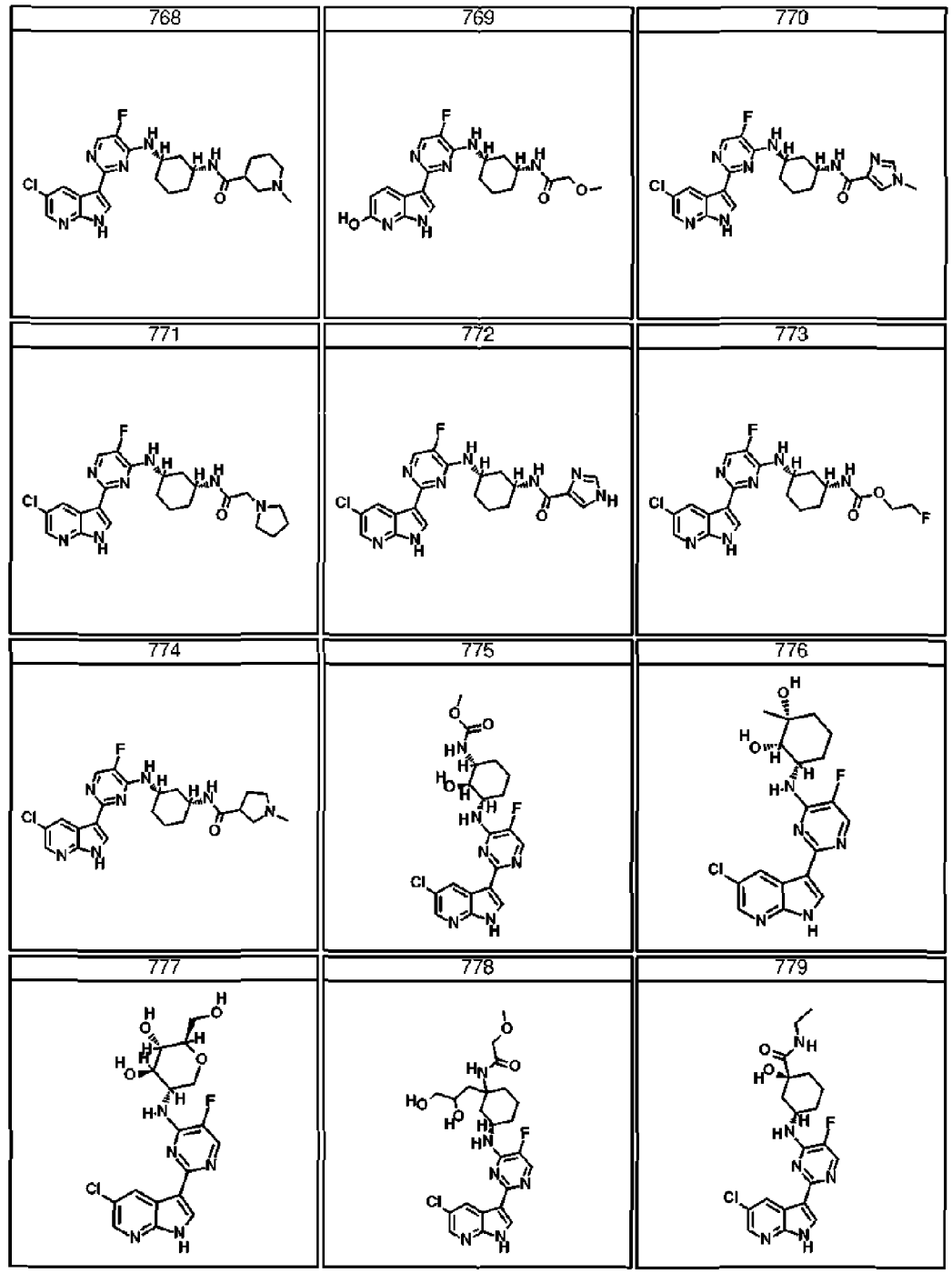
Figure 4J:
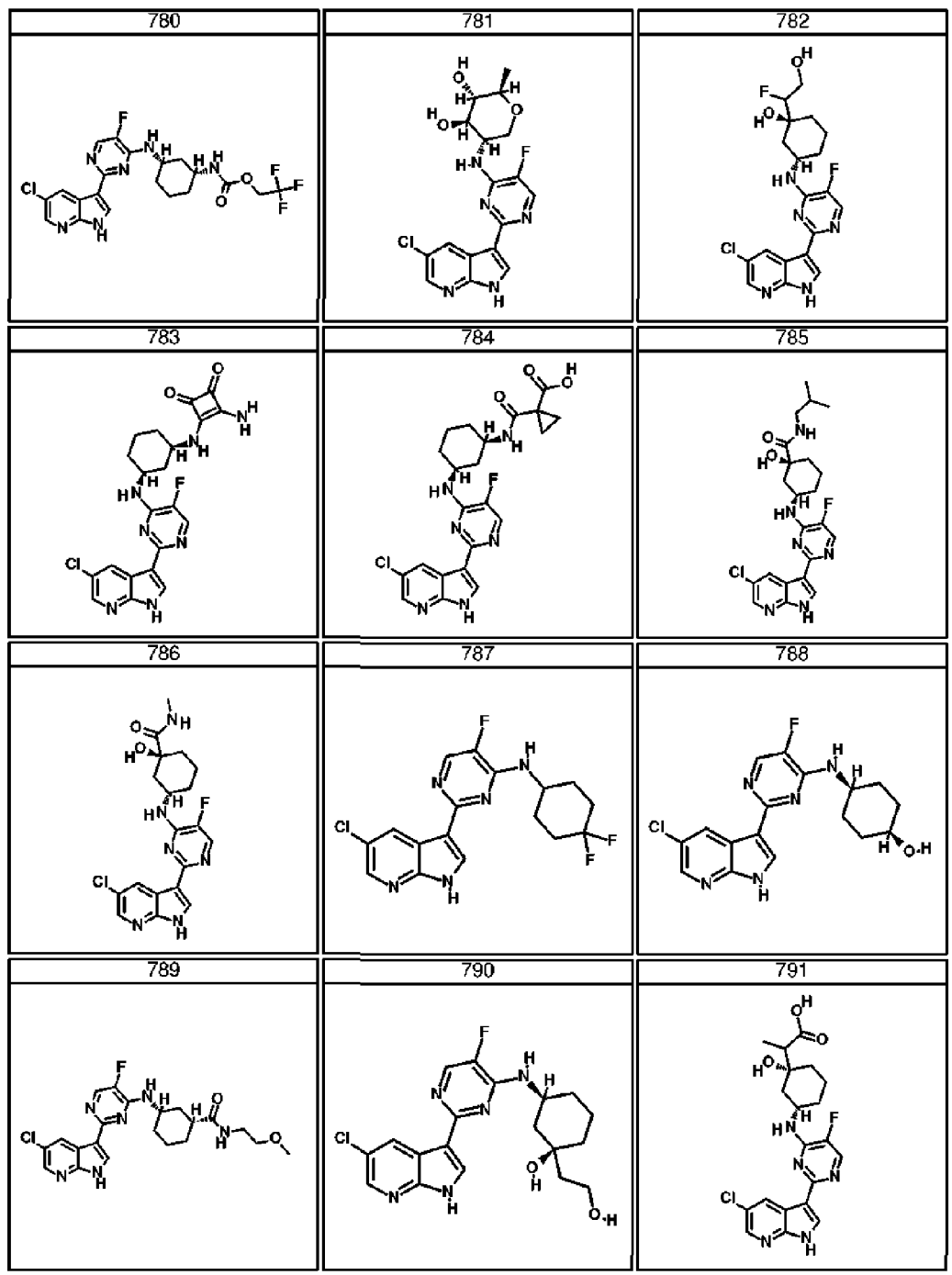
Figure 4K:
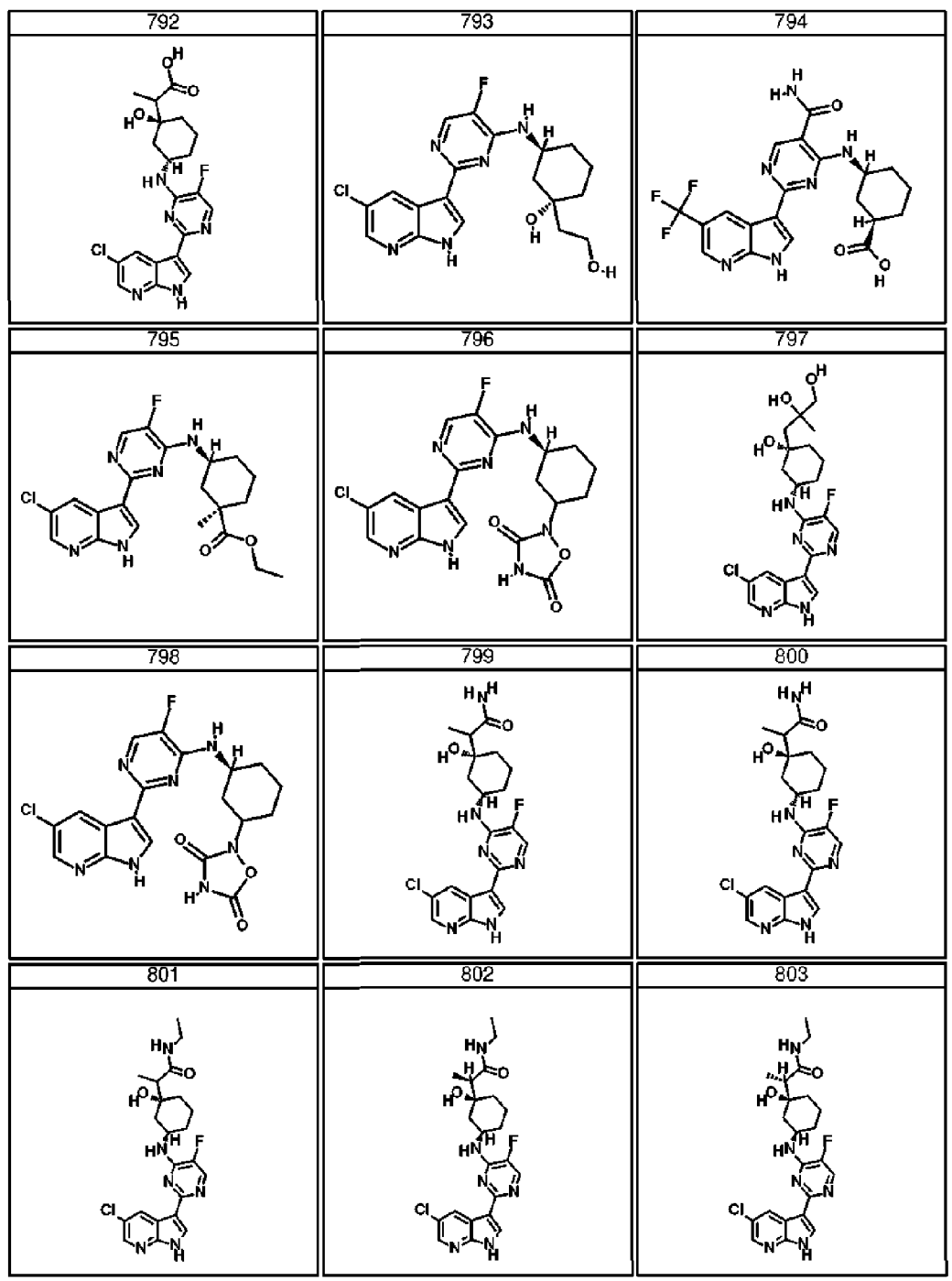
Figure 4L:
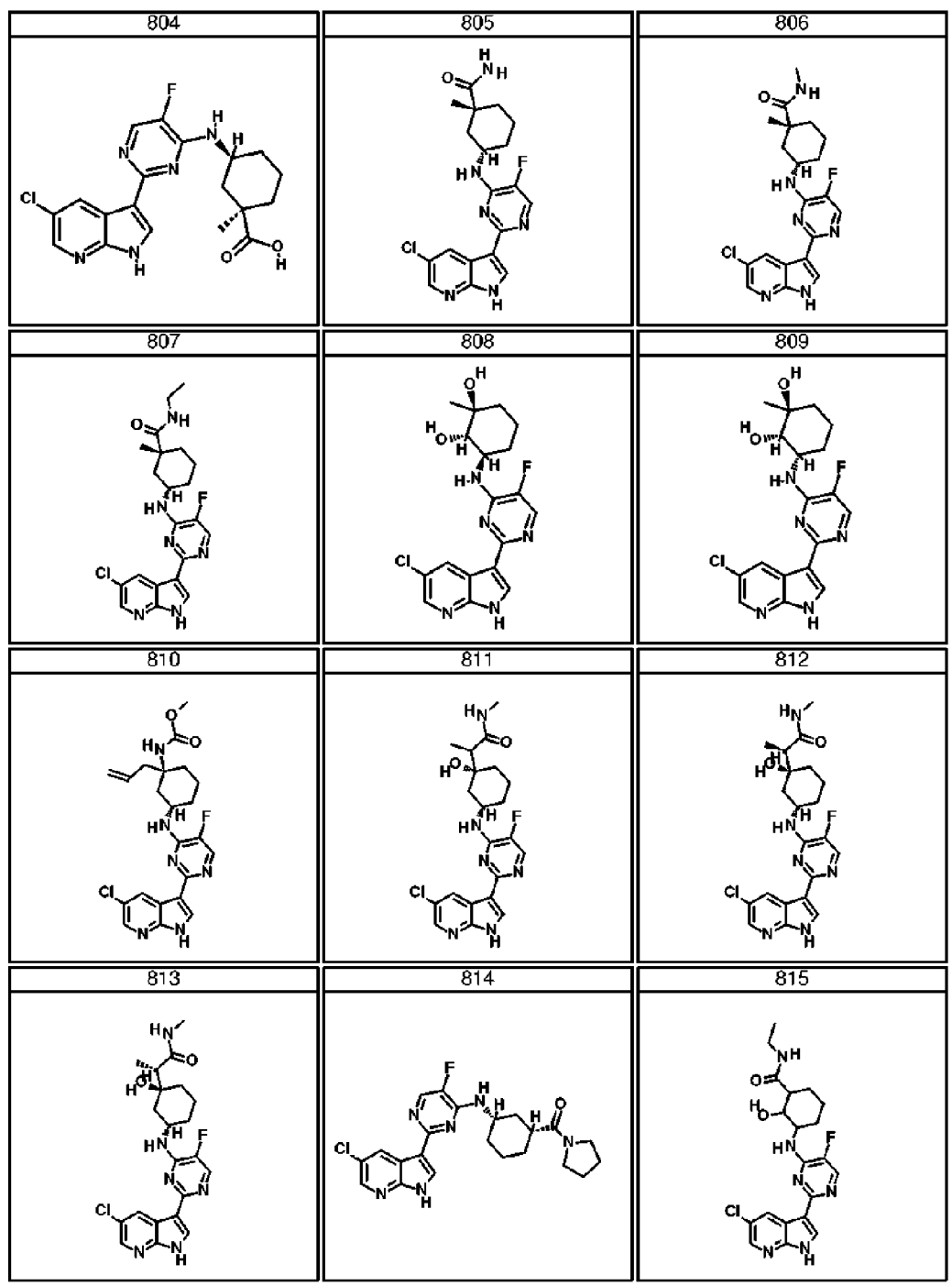
Figure 4M:
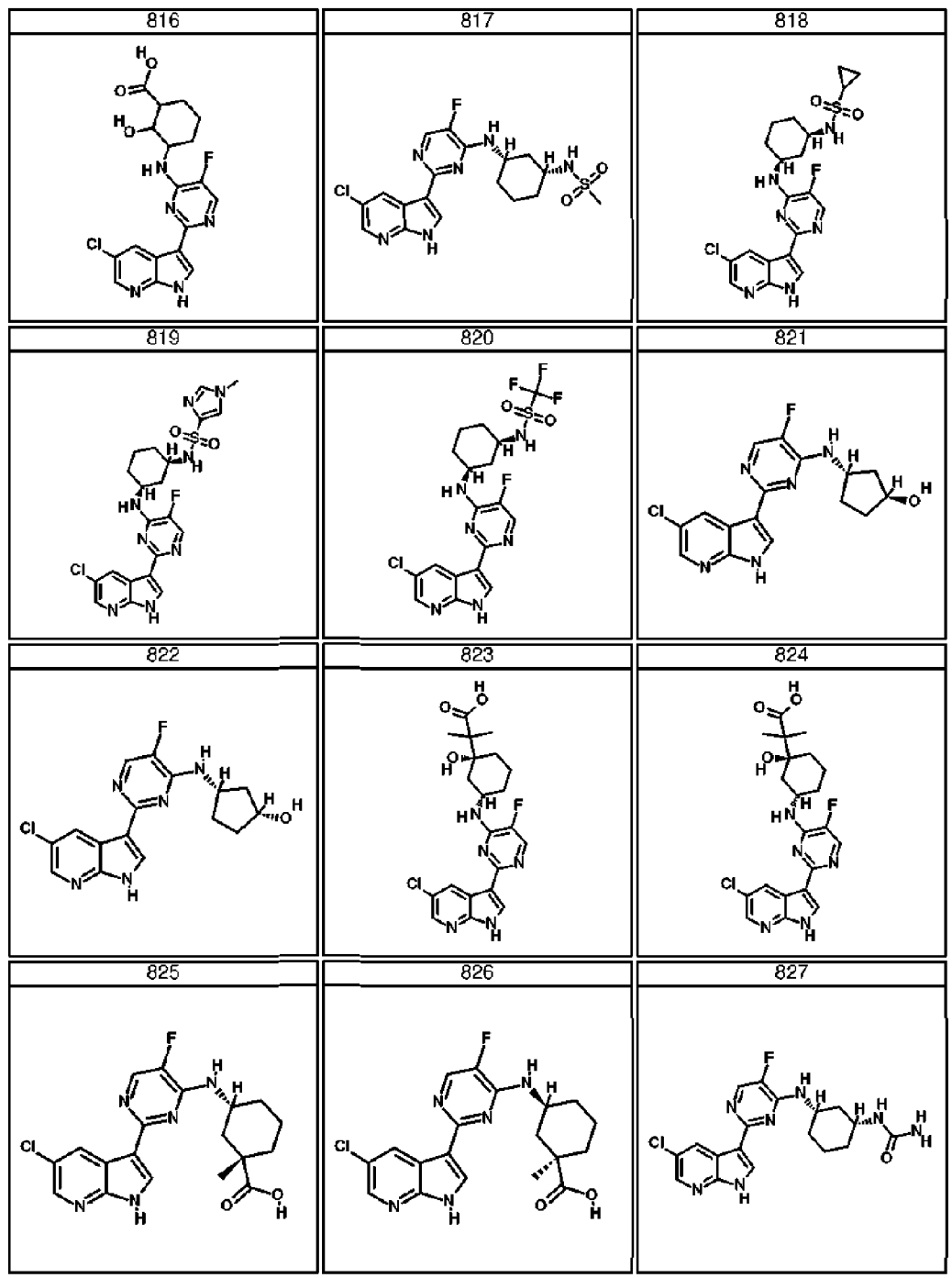
Figure 4N:
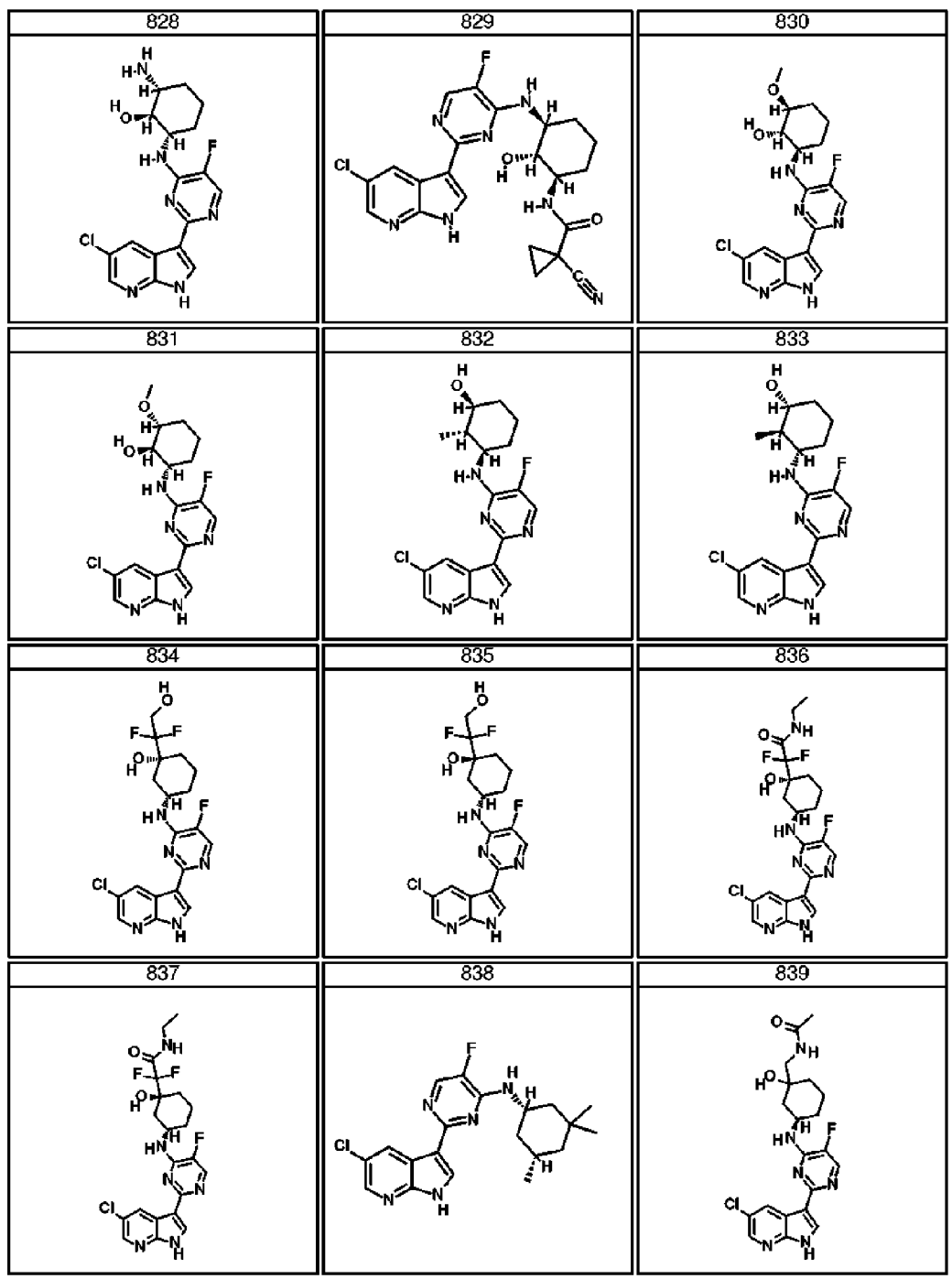
Figure 4O:
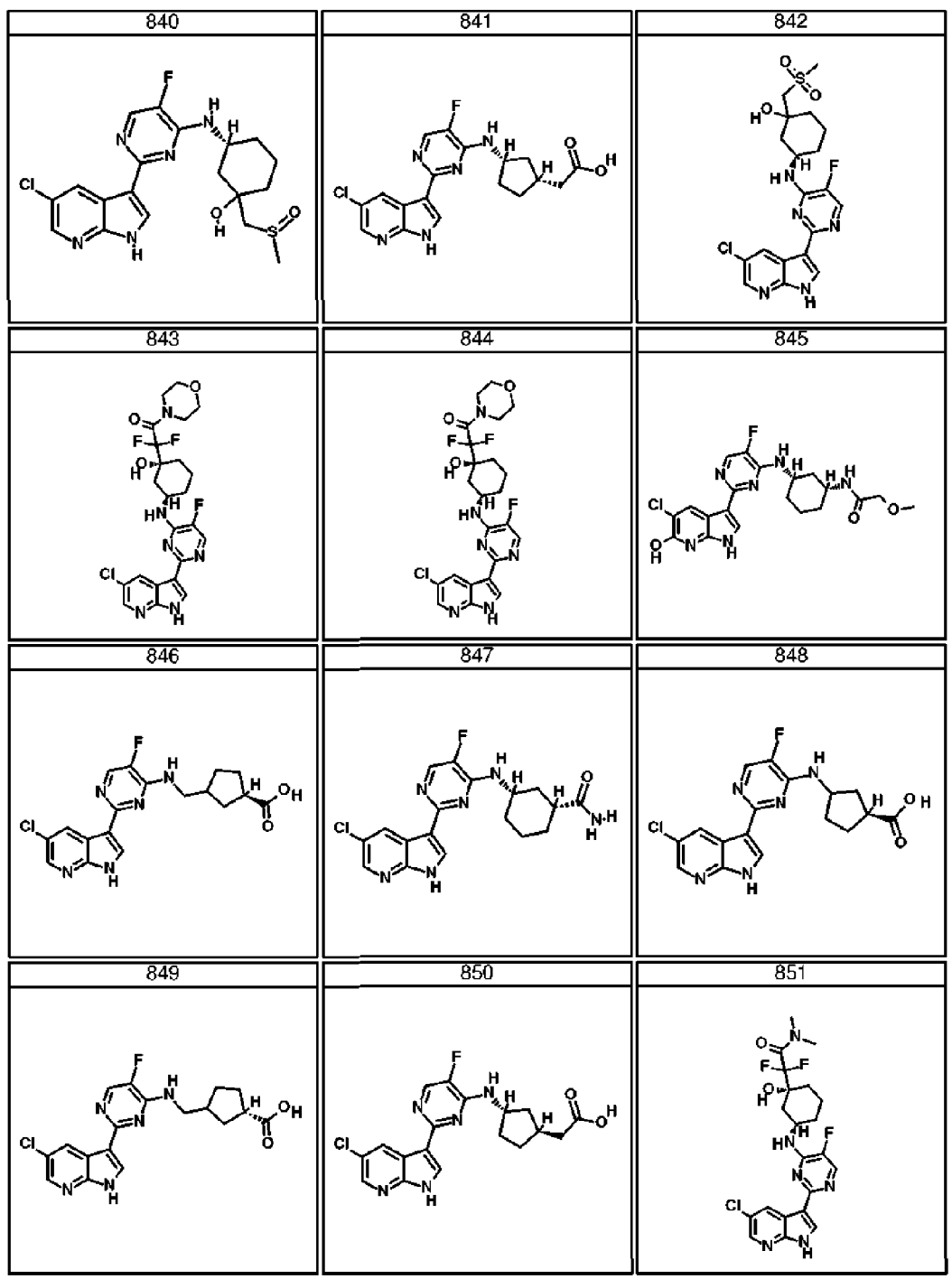
Figure 4P:
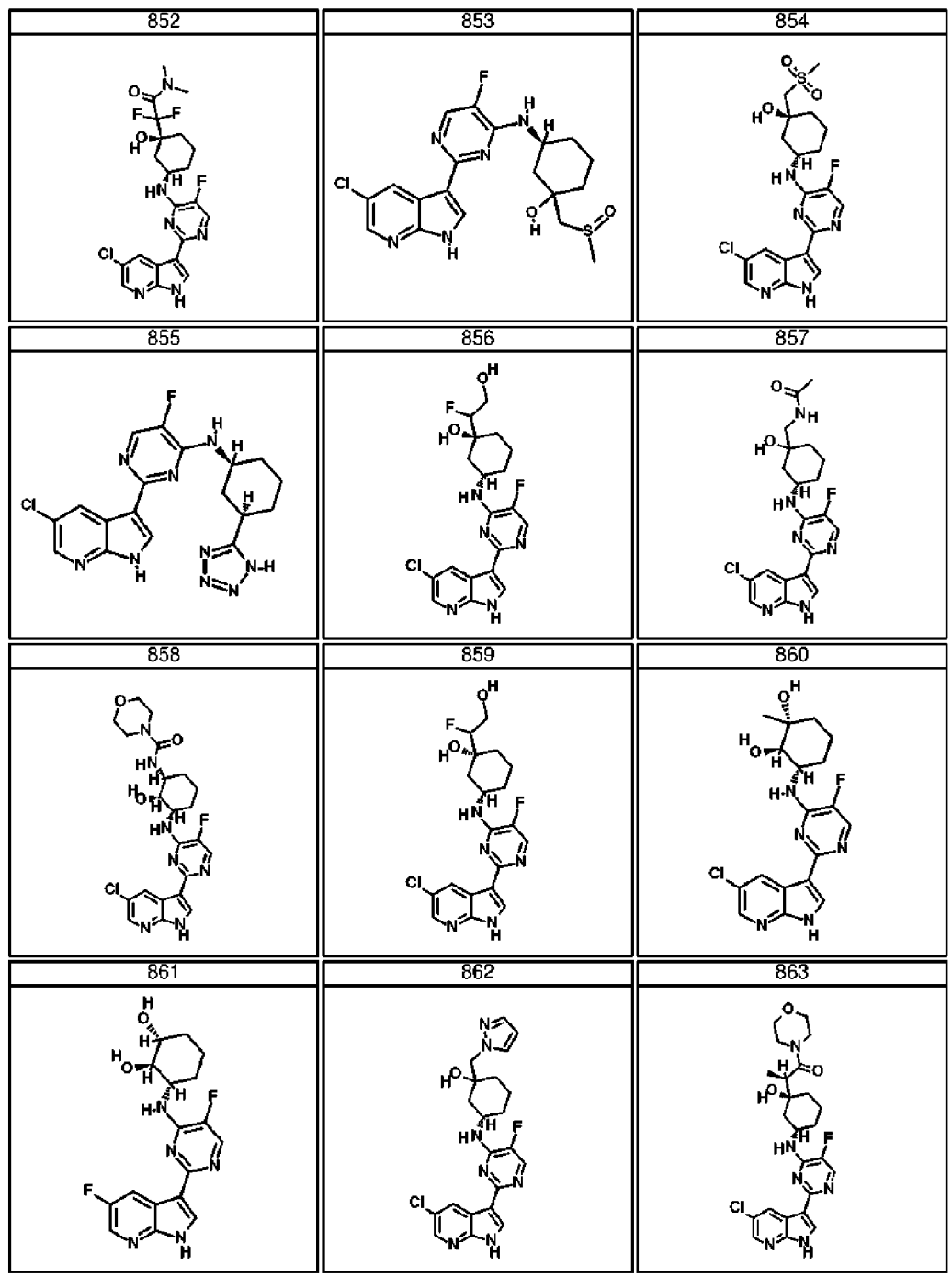
Figure 4Q:
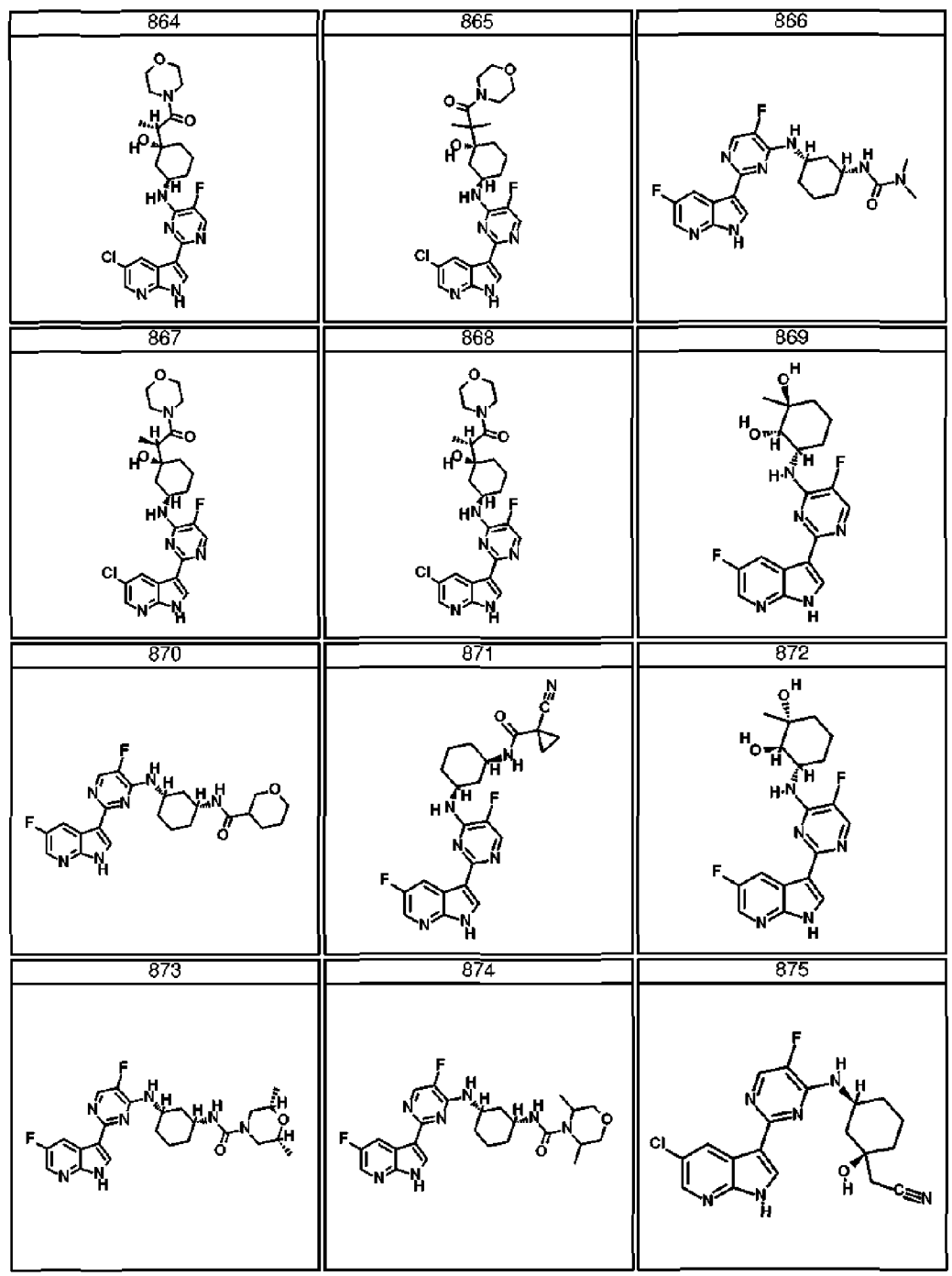
Figure 4R:
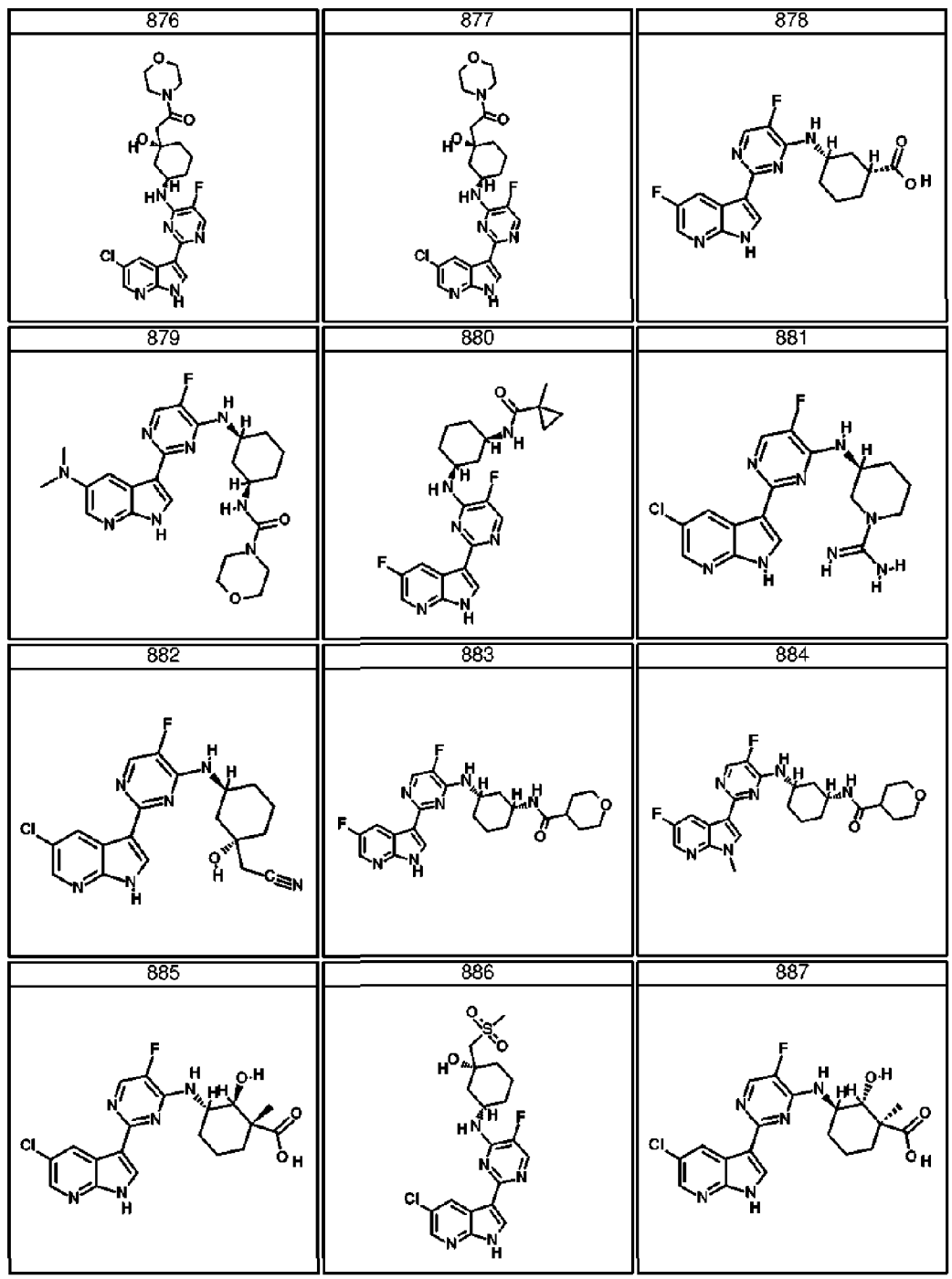
Figure 4S:
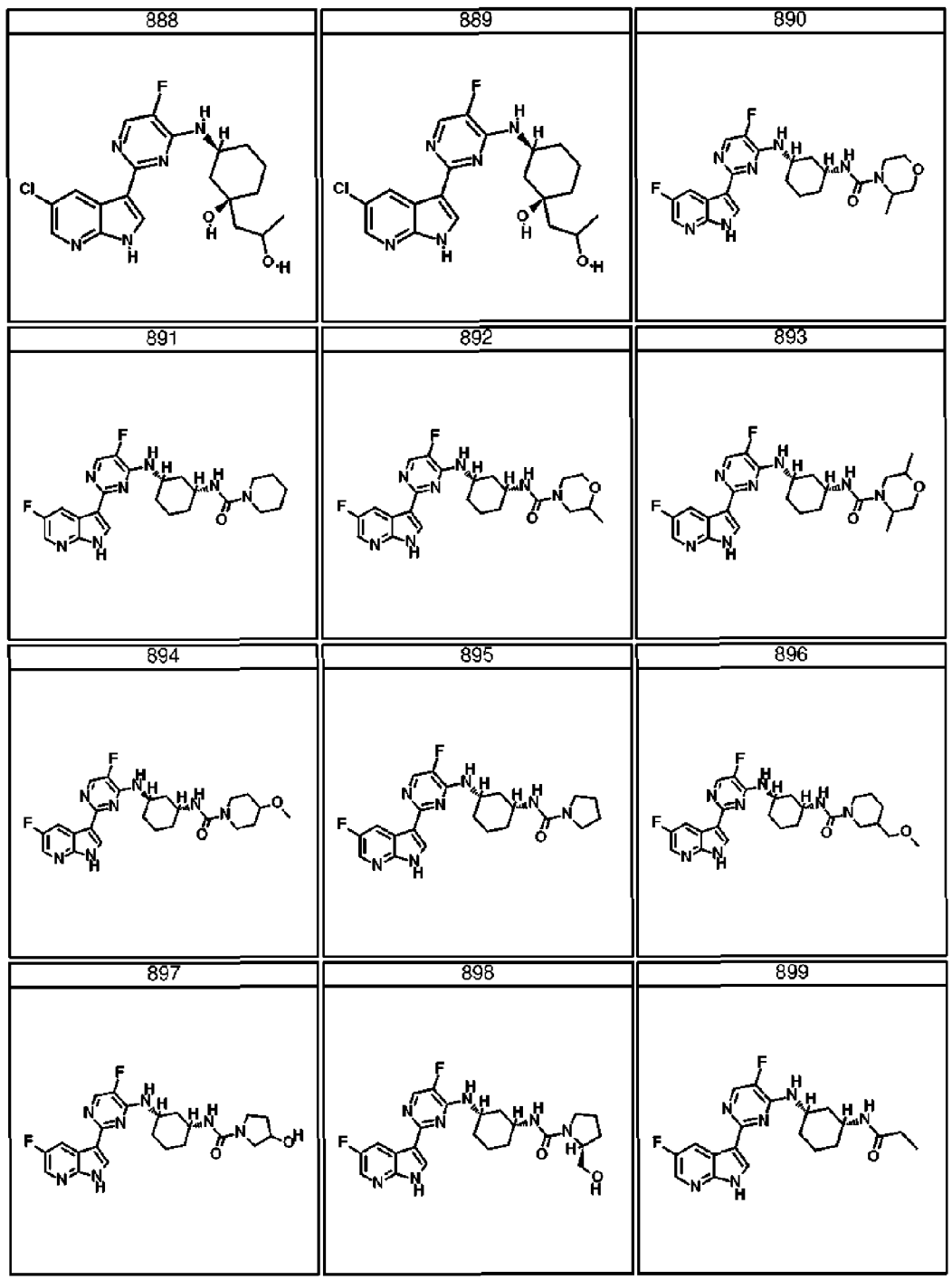
Figure 4T:
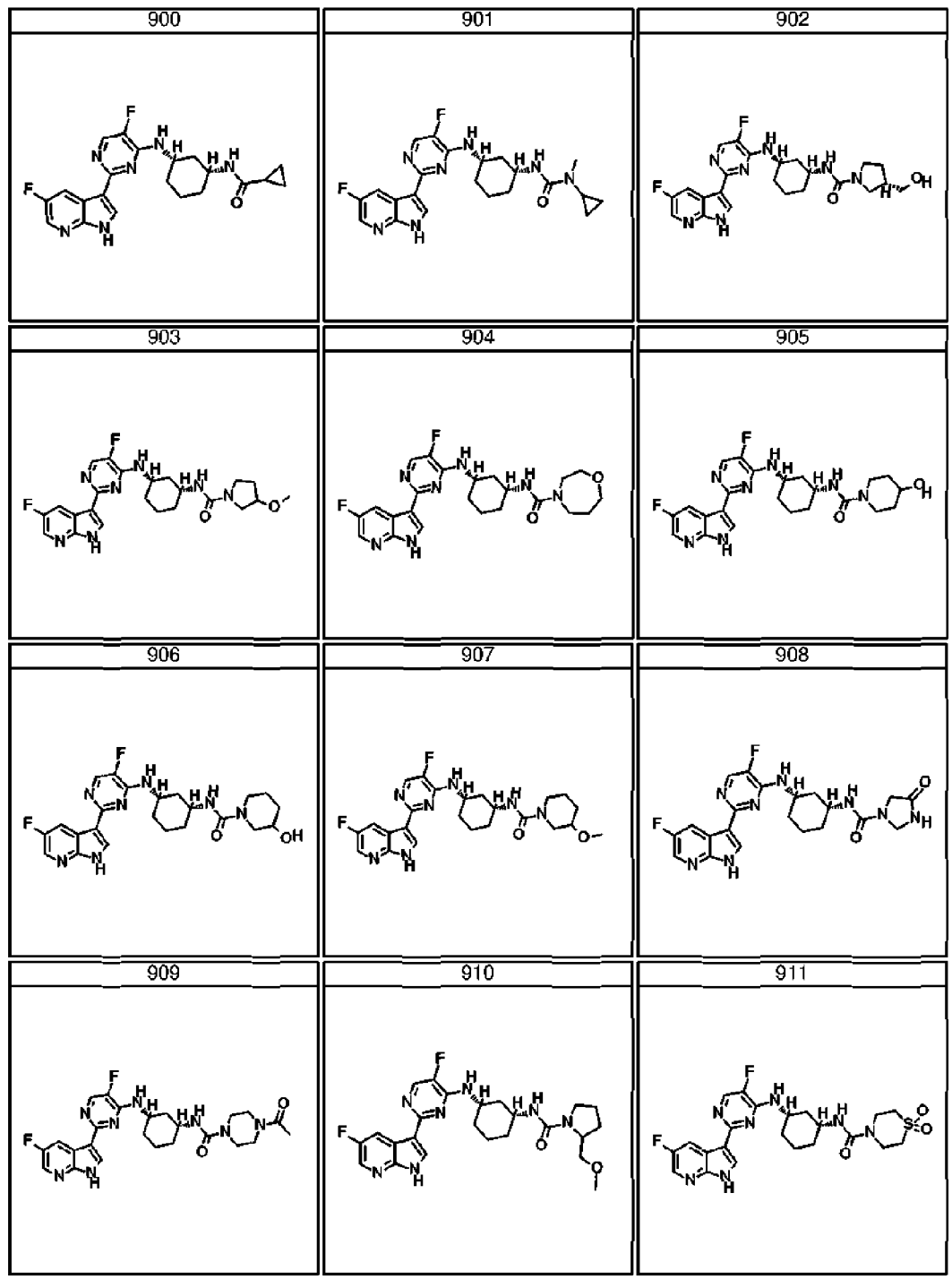
Figure 4U:
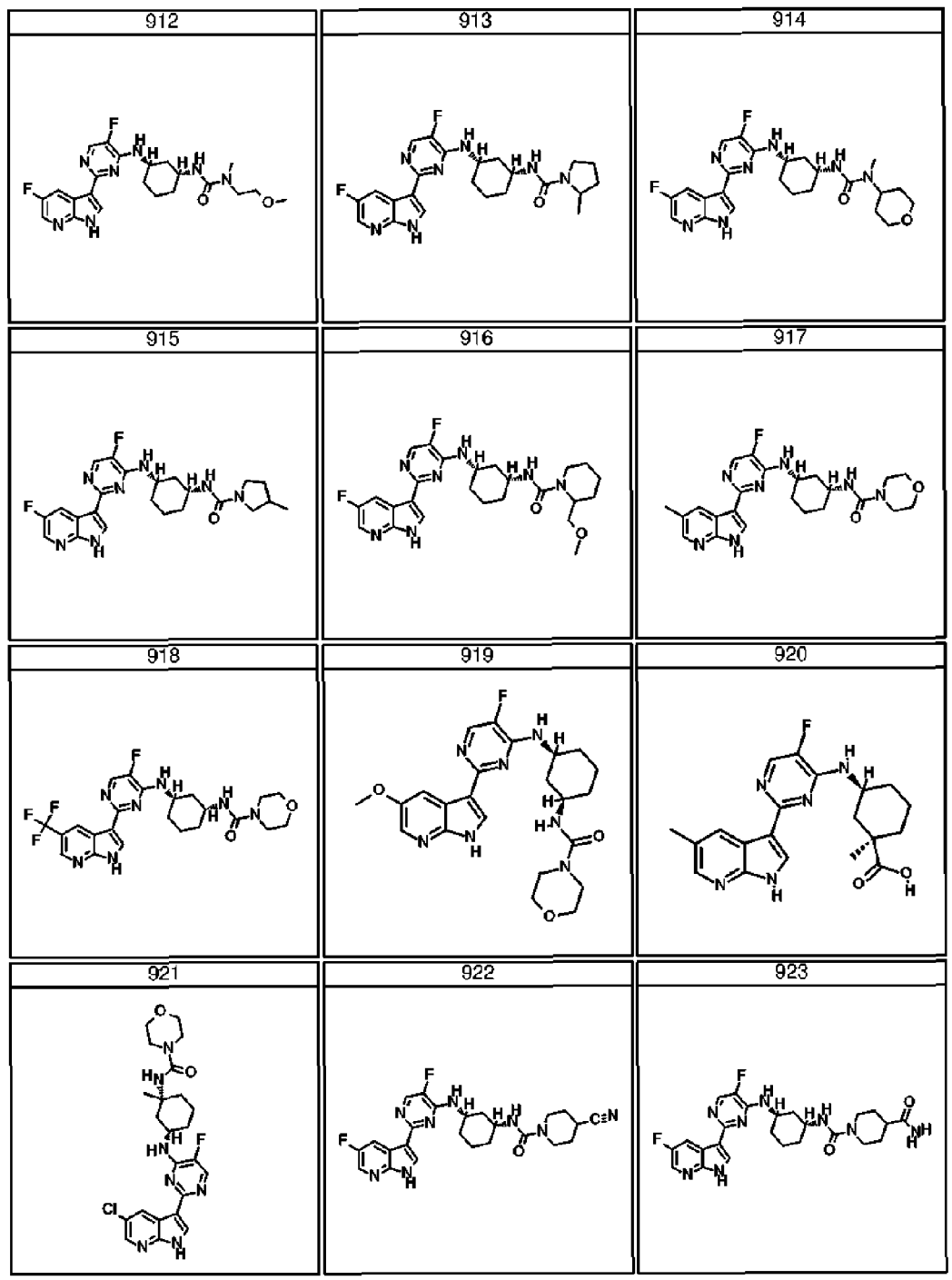
Figure 4V:
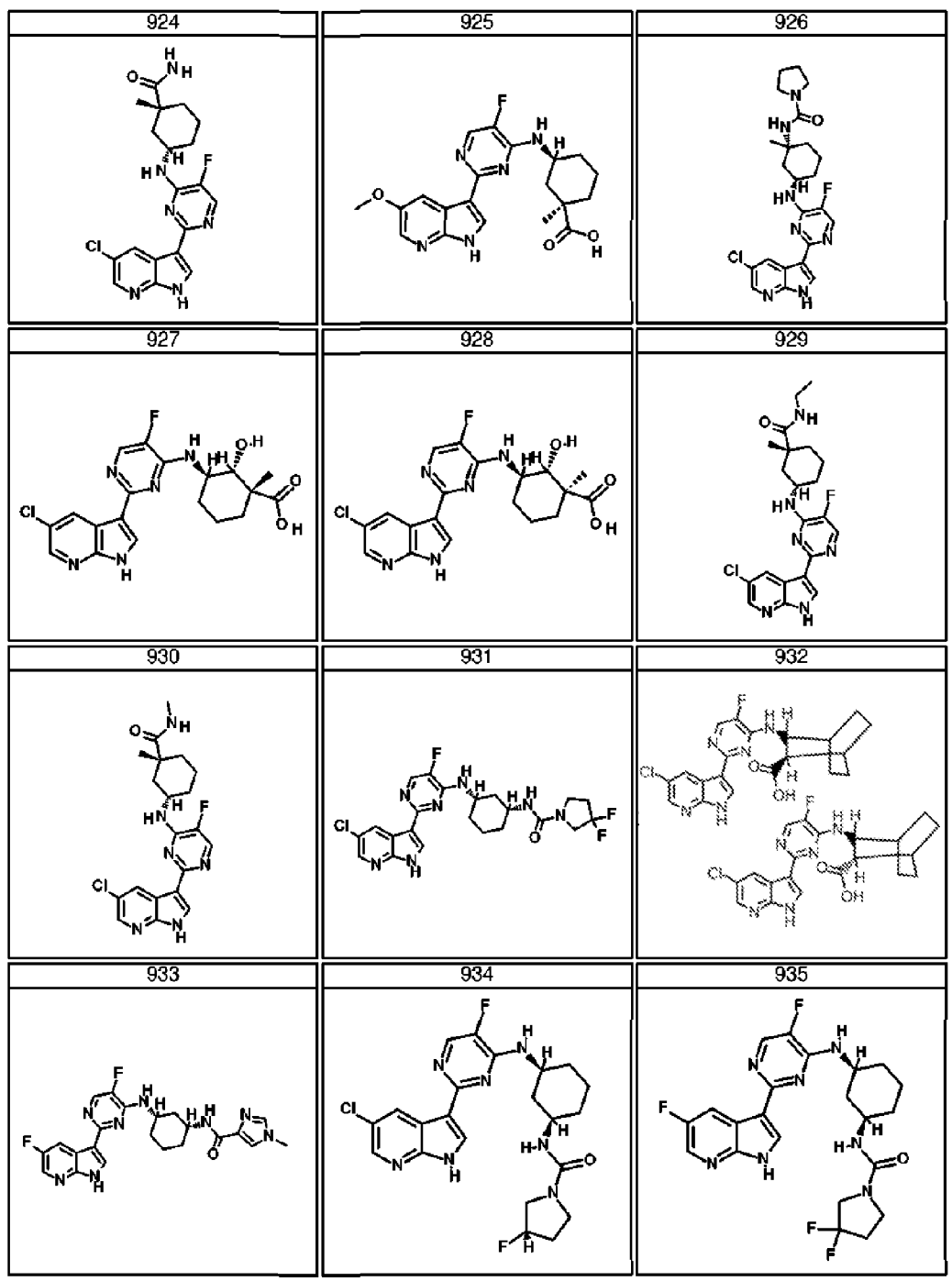
Figure 4W:
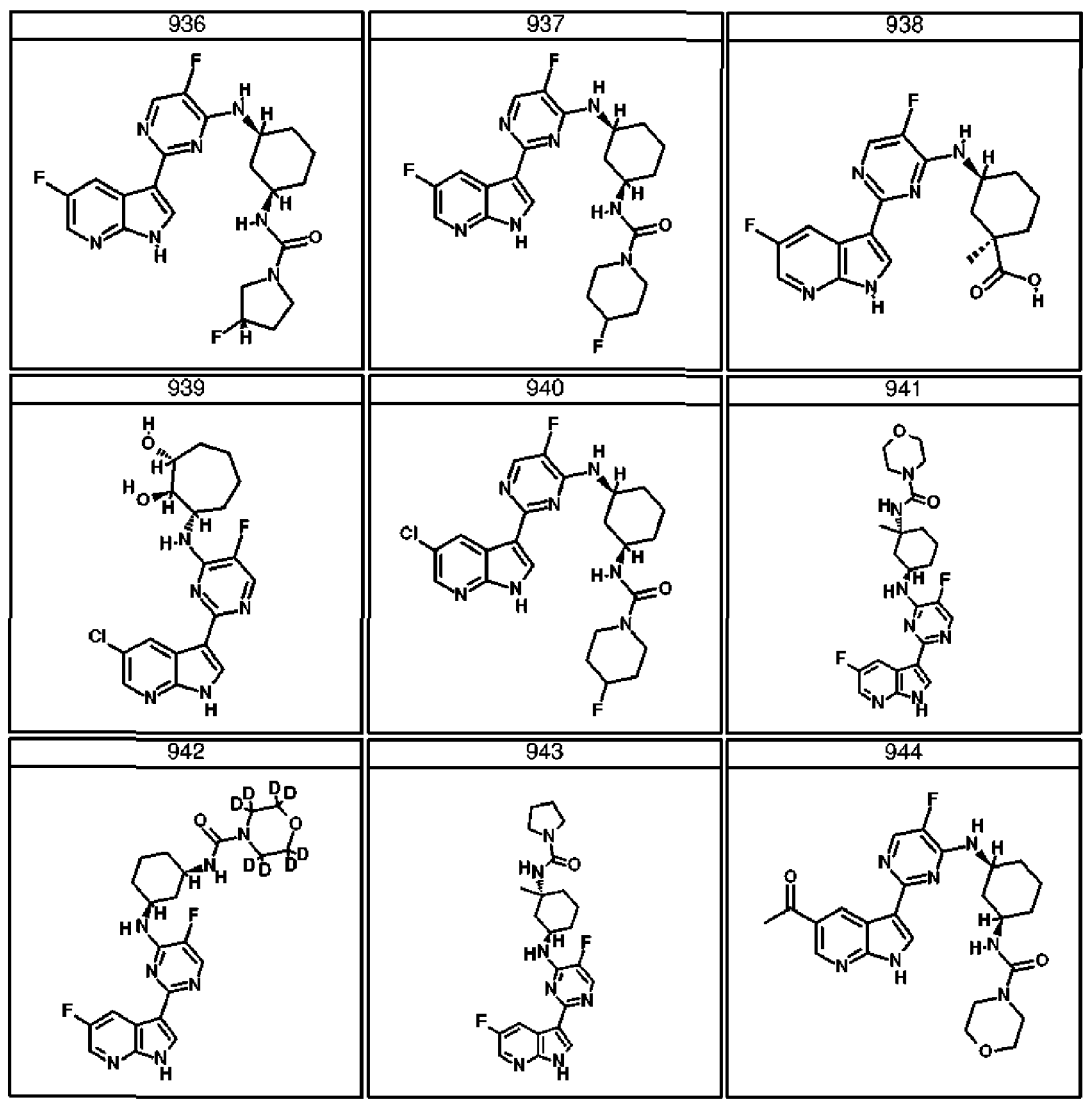

One aspect of the present invention is generally related to the use of the compounds described herein or pharmaceutically acceptable salts, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

In one embodiment, the present invention is generally related to the use of compounds represented by Structural Formula (I) or Structural Formula (IA), or pharmaceutically acceptable salts thereof for any of the uses specified above:

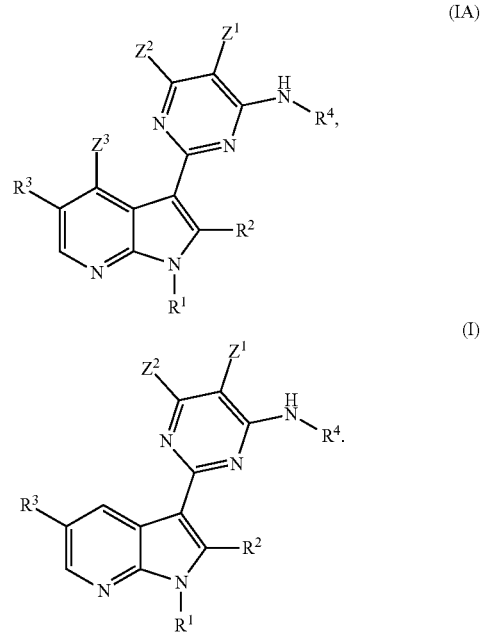

A first set of variables of Structural Formulae (I) and (IA) is independently as follows:

$Z^1$ is —R*, —F, —Cl, —CN, —OR*, —CO₂R*, —NO₂, or —CON(R*)₂. Specifically, $Z^1$ is —H, C₁-C₆ alkyl, —O(C₁-C₆ alkyl), —F, —Cl, —CN, —CO₂H, —CO₂(C₁-C₆ alkyl), —CONH₂, —CONH(C₁-C₆ alkyl), or —CON(C₁-C₆ alkyl)₂, wherein each of said alkyl groups (e.g., represented by C₁-C₆ alkyl, —O(C₁-C₆ alkyl), —CO₂(C₁-C₆ alkyl), —CONH(C₁-C₆ alkyl), and —CON(C₁-C₆ alkyl)₂) is optionally and independently substituted with one or more substituents independently selected from the group consisting of halogen, cyano, hydroxy, oxo, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy. Specifically, $Z^1$ is —H, —F, —C₁, C₁-C₄ haloalkyl (e.g., —CF₃), C₁-C₄ alkyl, —CH₂NH₂, —C(O)NH₂, —C(O)NH (CH₃), —C(O)N(CH₃)₂, —O(C₁-C₄ alkyl), or —CN. Specifically, $Z^1$ is —H, —F, —Cl, —CF₃, C₁-C₄ alkyl, or —CN. Specifically, $Z^1$ is —H, —F, —Cl, —CF₃, —CH₃, or —CN. Specifically, $Z^1$ is —H, —F, or —CN. Specifically, $Z^1$ is —H or —F.

$Z^2$ is —R*, —OR*, —CO₂R*, —NR*₂, or —CON(R*)₂. Specifically, $Z^2$ is —H, C₁-C₆ alkyl, —O(C₁-C₆ alkyl), —NH₂, —NH(C₁-C₆ alkyl), or —N(C₁-C₆ alkyl)₂, wherein each of said alkyl groups (e.g., represented by C₁-C₆ alkyl, —O(C₁-C₆ alkyl), —NH(C₁-C₆ alkyl), and —N(C₁-C₆ alkyl)₂) is optionally and independently substituted with one or more substituents independently selected from the group consisting of halogen, cyano, hydroxy, oxo, —NH₂, —NH (C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy. Specifically, $Z^2$ is —H, C₁-C₆ alkyl, or —O(C₁-C₆ alkyl), wherein each of the alkyl groups is optionally and independently substituted. Specifically, $Z^2$ is —H, or an optionally substituted C₁-C₆ alkyl.

$Z^3$ in Structural Formula (IA) is —H, —OH, halogen, —NH₂; —NH(C₁-C₄ alkyl); —N(C₁-C₄ alkyl)₂, —O(C₁-C₄ alkyl), or C₁-C₆ alkyl that is optionally substituted with one or more substituents independently selected from the group consisting of halogen, cyano, hydroxy, and —O(C₁-C₄ alkyl). Specifically, $Z^3$ is —H, —O(C₁-C₄ alkyl), or C₁-C₆ alkyl that is optionally substituted with one or more substituents independently selected from the group consisting of halogen, cyano, hydroxy, and —O(C₁-C₄ alkyl). Specifically, $Z^3$ is —H or C₁-C₆ alkyl optionally substituted with one or more substituents independently selected from the group consisting of halogen, cyano, hydroxy, and —O(C₁-C₄ alkyl). Specifically, $Z^3$ is —H.

$R^1$ is —H or $C_{1-6}$ alkyl. Specifically, $R^1$ is —H.

$R^2$ is —H; —F; —NH₂; —NH(C₁-C₄ alkyl); —N(C₁-C₄ alkyl)₂; —C≡N—OH; cyclopropyl that is optionally substituted with one or more substituents independently selected from the group consisting of halogen, cyano, hydroxy, —OCH₃, and —CH₃; or C₁-C₄ alkyl that is optionally substituted with one or more substituents independently selected from the group consisting of halogen, cyano, hydroxy, and —O(C₁-C₄ alkyl). Specifically, $R^2$ is —H, —CH₃, —NH₂, —NH(C₁-C₄ alkyl), or —N(C₁-C₄ alkyl)₂. Specifically, $R^2$ is —H, —F, —CH₃, —CH₂OH, or —NH₂. Specifically, $R^2$ is —H or —CH₃.

$R^3$ is —H, —F, —OH, —O(C₁-C₄ alkyl), —NH₂, —NH(C₁-C₄ alkyl), —N(C₁-C₄ alkyl)₂, —Br, —CN, or C₁-C₄ aliphatic that is optionally substituted with one or more substituents independently selected from the group consisting of halogen, cyano, hydroxy, oxo, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy. Specifically, $R^3$ is —H, —Cl, —F, —CF₃, —OCH₃, —NH₂, —NH(C₁-C₄alkyl), —N(C₁-C₄ alkyl)₂, —Br, —O(C₁-C₄ alkyl), —CN, —C₁-C₄ haloalkyl, —OH, or —C₁-C₄ aliphatic. Specifically, $R^3$ is —H, —F, —CF₃, —OCH₃, —NH₂, —NH(C₁-C₄alkyl), —N(C₁-C₄ alkyl)₂, —Br, —O(C₁-C₄ alkyl), —CHCH(CH₃), —CHCH₂, —CN, —CH₂CF₃, —CH₂F, —CHF₂, —OH, or —C₁-C₄ alkyl. Specifically, $R^3$ is —H, —F, —Br, —CN, —CF₃, —O(C₁-C₄ alkyl), —OH, —NH₂, —NH(C₁-C₄ alkyl), or —N(C₁-C₄ alkyl)₂. Specifically, $R^3$ is —H, —F, —Cl, —CF₃, —NH₂, —NH(CH₃), or —N(CH₃)₂. Specifically, $R^3$ is —H, —Cl, or —F. Specifically, $R^3$ is —Cl. Specifically, $R^3$ is —H, —F, —Br, —CN, —CF₃, —CH₃, —C₂H₅, —O(C₁-C₄ alkyl), —OH, —NH₂, —NH(C₁-C₄ alkyl), or —N(C₁-C₄ alkyl)₂. Specifically, $R^3$ is —H, —F, —CF₃, —CH₃, —C₂H₅, —NH₂, —NH(CH₃), or —N(CH₃)₂. Specifically, $R^3$ is —F or —Cl.

$R^4$ is: i) a C₃-C₁₀ non-aromatic carbocycle optionally substituted with one or more instances of $J^A$; ii) a C₁-C₆ aliphatic group (e.g., C₁-C₆ alkyl or C₂-C₆ alkenyl group) optionally substituted with one or more substituents independently selected from the group consisting of $J^C$; a C₃-C₈ non-aromatic carbocycle, or a 6-10 membered carbocyclic aryl group, each optionally and independently substituted with one or more instances of $J^A$; and a 5-10 membered heteroaryl group, or a 4-10 membered non-aromatic heterocycle, each optionally and independently substituted with one or more instances of $J^B$; or iii) a 4-10 membered non-aromatic heterocycle optionally substituted with one or more instances of $J^B$. Specifically, $R^4$ is i) an optionally substituted C₃-C₁₀ carbocyclic ring; ii) a C₁-C₆ aliphatic group (e.g., C₁-C₆ alkyl or C₂-C₆ alkenyl group) that is substituted with one or more substituents independently selected from the group consisting of $J^C$, an optionally substituted C₃-C₈ non-aromatic carbocycle, and an optionally substituted 4-10 membered non-aromatic heterocycle; or iii) an optionally substituted, 4-10 membered non-aromatic heterocycle. Specifically, the C₁-C₆ aliphatic group represented by $R^4$ is substituted with —OR⁵, —SR⁵, —NR'R⁵, —C(O)R⁵, —CO₂R⁵, —OC(O)R⁵, —C(O)NR'R⁵, —C(O)NRC(O)OR⁵, —NRC(O)NRC(O)OR⁵, —NRC(O)R⁵, —NRC(O)NR'R⁵, —NRCO₂R⁵, —OC(O)NR'R⁵, —SOR⁵, —SO₂R⁵, —SO₂NR'R⁵—, N(R)SO₂R⁵, —NRSO₂NR'R⁵, an optionally substituted C₃-C₈ non-aromatic carbocycle, and an optionally substituted 4-10 membered non-aromatic heterocycle. More specifically, $R^4$ is:

i) 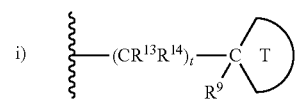

wherein ring T (including rings A, B and C described below) is a C₃-C₁₀ non-aromatic carbocycle optionally substituted with one or more instances of $J^A$, or a 3-10 membered non-aromatic heterocycle optionally substituted with one or more instances of $J^B$, or ring T and $R^9$ optionally form a non-aromatic C₅-C₁₀ membered carbocycle optionally substituted with one or more instances of $J^A$ or 5-10 membered non-aromatic heterocycle optionally substituted with one or more instances of $J^B$;

ii) 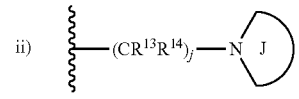

wherein ring J is a 3-10 membered non-aromatic heterocycle optionally substituted with one or more instances of $J^B$; or iii)

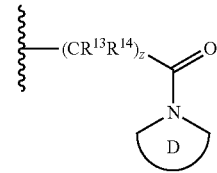

wherein ring D is a 4-10 membered non-aromatic heterocycle optionally substituted with one or more instances of $J^{D1}$. More specifically, $R^4$ is:

(A)

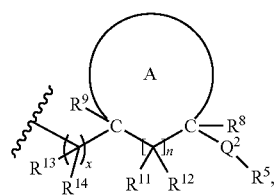

-continued

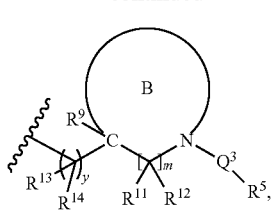

(B)

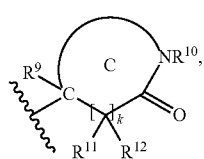

(C)

or

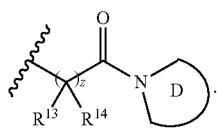

(D)

$R^5$ is: i) —H; ii) a $C_1$-$C_6$ aliphatic group optionally substituted with one or more instances of $J^{C1}$; iii) a $C_3$-$C_{10}$ non-aromatic carbocycle, or a 6-10 membered carbocyclic aryl group, each optionally and independently substituted with one or more instances of $J^{C1}$; or iv) a 4-10 membered non-aromatic heterocycle, or a 5-10 membered heteroaryl group, each optionally and independently substituted with one or more instances of $J^{D1}$. Specifically, $R^5$ is: i) —H; ii) a $C_1$-$C_6$ aliphatic group (e.g., $C_1$-$C_6$ alkyl or $C_2$-$C_6$ alkenyl group) optionally substituted with one or more instances of $J^{C1}$; iii) a $C_3$-$C_8$ non-aromatic carbocycle, or a 6-10 membered carbocyclic aryl group, each optionally and independently substituted with one or more instances of $J^{C1}$; or iv) a 4-8 membered non-aromatic heterocycle, or a 5-10 membered heteroaryl group, each optionally and independently substituted with one or more instances of $J^{D1}$. Optionally, $R^5$, together with each of $Q^1$, $Q^2$ and $Q^3$, optionally and independently forms a 4-8 membered, non-aromatic ring optionally substituted with one or more instances of $J^{E1}$. It is understood that the non-aromatic ring formed with $R^5$ and $Q^1$ can employ a portion of $Q^1$. In some embodiments, $R^5$, together with $Q^2$ and $R^8$, optionally and independently forms a 5-7 membered, non-aromatic ring optionally substituted with one or more instances of $J^{E1}$.

Specifically, $R^5$ is independently i) —H; ii) a $C_1$-$C_6$-alkyl or $C_2$-$C_6$-alkenyl group optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$; or vi) a 5-6 membered heteroaryl ring optionally substituted with one or more instances of $J^{D1}$. Specifically, $R^5$ is independently i) —H; ii) a $C_1$-$C_6$-alkyl or $C_2$-$C_6$-alkenyl group optionally substituted with one or more instances of $J^{C1}$; or iii) a 4-8 membered non-aromatic heterocycle optionally substituted with one or more instances of $J^{D1}$. Specifically, $R^5$ is independently i) —H; or ii) a $C_1$-$C_6$-alkyl or $C_2$-$C_6$-alkenyl group optionally and independently substituted with one or more instances of $J^{C1}$.

$R^6$ and $R^7$ are each independently —H or $C_1$-$C_6$ alkyl optionally substituted with one or more substitutents selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy, or optionally $R^6$ and $R^7$, together with the carbon atom to which they are attached, form a cyclopropane ring optionally substituted with one or more instances of methyl. Alternatively, $R^6$ and $R^7$ are each independently —H or $C_1$-$C_4$ alkyl optionally substituted with one or more substitutents selected from the group consisting of halogen, cyano, hydroxy, oxo, —$NH_2$, —$NH(C_1$-$C_6$ alkyl), —$N(C_1$-$C_6$ alkyl)$_2$, —C(O)OH, —(CO)O($C_1$-$C_6$ alkyl), —OC(O)($C_1$-$C_6$ alkyl), $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy, or optionally $R^6$ and $R^7$, together with the carbon atom to which they are attached, form a cyclopropane ring optionally substituted with one or more instances of methyl. Specifically, $R^6$ and $R^7$ are each independently —H or —$CH_3$, or, together with the carbon atoms to which they are attached, they form a cyclopropane ring.

Each $R^8$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or $R^8$, together with $Q^2$ and $R^5$, optionally and independently forms a 5-7 membered, non-aromatic ring optionally substituted with one or more instances of $J^{E1}$.

Each $R^9$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or $R^8$, together with $Q^2$ and $R^5$, optionally and independently forms a 5-7 membered, non-aromatic ring optionally substituted with one or more instances of $J^{E1}$. Specifically, each $R^9$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or $R^8$, together with $Q^2$ and $R^5$, optionally and independently forms a 5-7 membered, non-aromatic ring optionally substituted with one or more instances of $J^{E1}$.

Optionally, $R^9$ and ring T form a non-aromatic $C_5$-$C_{10}$ membered carbocycle optionally substituted with one or more instances of $J^4$ or 5-10 membered non-aromatic heterocycle optionally substituted with one or more instances of $J^B$.

Specifically, each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$alkyl), —$NH_2$, —$NH(C_1$-$C_4$ alkyl), or —$N(C_1$-$C_4$ alkyl)$_2$; and each $R^9$ is independently —H or $C_1$-$C_4$ alkyl, more specifically, —H, —$CH_3$, or —$CH_2CH_3$.

$R^{10}$ is independently —H; or a $C_1$-$C_6$ alkyl group optionally substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, $C_2$-$C_6$ alkoxyalkoxy, $C_3$-$C_8$ non-aromatic carbocycle, phenyl, a 4-8 membered non-aromatic heterocycle, and a 5-6 membered heteroaryl group; wherein each of said carbocycle, phenyl, heterocycle, and heteroaryl group for the substituents of the $C_1$-$C_6$ alkyl group represented by $R^{10}$ is optionally and independently substituted with one or more substituents independently selected from the group consisting of halogen, cyano, hydroxy, oxo, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy. Specifically, $R^{10}$ is independently —H, $C_1$-$C_6$ alkyl, $C_1$-$C_6$ haloalkyl, $C_2$-$C_6$-alkoxyalkyl, $C_1$-$C_6$ hydroxyalkyl, $C_1$-$C_6$ aminoalkyl, or $C_1$-$C_6$ cyanoalkyl. Specifically, $R^{10}$ is —H or $C_1$-$C_6$-alkyl optionally substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO_2H$, —$CO_2(C_1$-$C_4$ alkyl), and $C_1$-$C_4$ alkoxy. Specifically, $R^{10}$ is —H or $C_1$-$C_6$-alkyl.

$R^{11}$, $R^{12}$, $R^{13}$ and $R^{14}$ are each independently —H, halogen, or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or optionally, $R^{13}$ and $R^{14}$ together with the carbon atom to which they are attached form a cyclopropane ring, optionally substituted with one or more instances of methyl. Specifically, $R^{11}$ and $R^{12}$ are each independently —H or $C_1$-$C_4$ alkyl; and $R^{13}$ and $R^{14}$ are each independently —H or $C_1$-$C_4$ alkyl, or together with the carbon atoms to which they are attached, they form a cyclopropane ring. Specifically, $R^{11}$ and $R^{12}$ are each independently —H or —$CH_3$; and $R^{13}$ and $R^{14}$ are each independently —H, —$CH_3$, or —$CH_2CH_3$, or together with the carbon atoms to which they are attached, they form a cyclopropane ring.

Optionally $R^{11}$ and ring A form a bridged ring optionally further substituted with one or more instances of $J^A$.

Ring A is a $C_3$-$C_{10}$ non-aromatic carbocycle optionally further substituted with one or more instances of $J^A$, or 3-10 membered non-aromatic heterocycle optionally further substituted with one or more instances of $J^B$. Specifically, ring A is an optionally substituted $C_3$-$C_8$ non-aromatic carbocyclic or heterocyclic ring. Specifically, Ring A is a $C_3$-$C_8$ non-aromatic carbocycle optionally further substituted with one or more instances of $J^A$. Specifically, Ring A is a non-aromatic, 4-7 or 5-7 membered, carbocyclic ring optionally further substituted with one or more instances of $J^A$. A specific example of Ring A is an optionally substituted, cyclohexyl or cyclopentyl ring.

Optionally, ring A and $R^8$ form a non-aromatic, 5-10 membered, bridged carbocycle or heterocycle, or ring A and $R^9$ optionally form a non-aromatic, 5-10 membered, bridged carbocycle or heterocycle, ring A and $R^{11}$ optionally form a non-aromatic, 5-10 membered, bridged carbocycle or heterocycle, wherein each carbocycle is optionally further substituted with one or more instances of $J^A$, and wherein each heterocycle is optionally further substituted with one or more instances of $J^B$. In some embodiments, the bridged rings are each independently 6-10 membered. Exemplary bridged rings include:

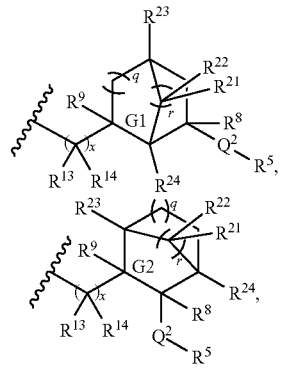

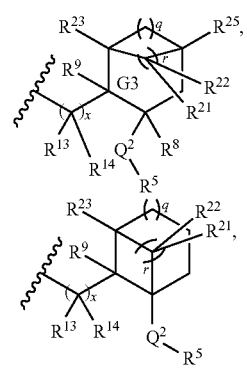

or

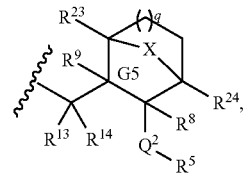

wherein each of rings G1-G4 is independently a 5-10 membered non-aromatic bridged carbocycle optionally further substituted with one or more instances of $J^A$, and ring G5 is a 5-10 membered non-aromatic bridged heterocycle optionally further substituted with one or more instances of $J^B$; $R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; X is —O—, —S—, or —$NR^g$—; $R^g$ is —H or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; q is 0, 1 or 2; x is 0, 1 or 2; r is 1 or 2. An additional example of the bridged rings includes an adamantyl ring.

Ring B is a 4-10 membered, non-aromatic, heterocyclic ring that is optionally further substituted with one or more instances of $J^B$. Specifically, ring B is 4-8 membered. Specifically, ring B is 4-7 or 5-7 membered. Specific examples of Ring B include:

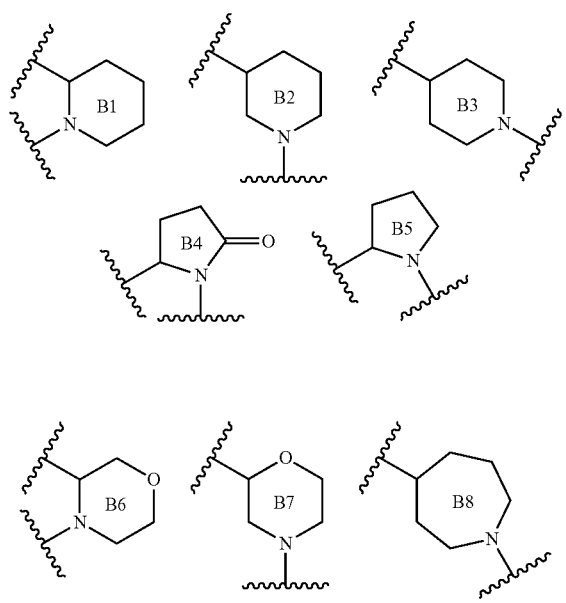

and

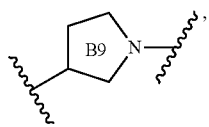

wherein each of rings B1-B9 is optionally substituted.

Ring C is a 4-10 membered, non-aromatic, heterocyclic ring that is optionally further substituted with one or more instances of $J^B$. Specifically, ring C is 4-8 membered. Specifically, ring C is 4-7 or 5-7 membered. Specific examples of Ring C include:

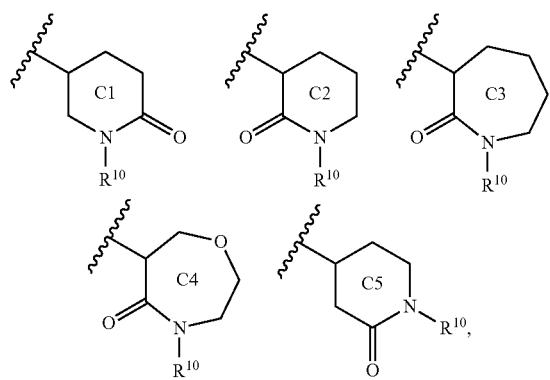

wherein each of rings C1-C5 is optionally and independently substituted.

Ring D is a 4-10 membered, non-aromatic, heterocyclic ring that is optionally substituted with one or more substituents instances of $J^{D1}$. Specifically, ring D is 4-8 membered. Specifically, ring D is 4-7 or 5-7 membered. Specific examples of ring D include:

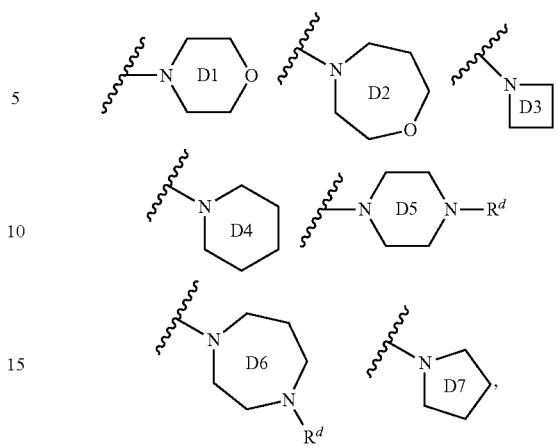

wherein each of rings D1-D7 is optionally substituted.

Specifically, each of Rings A-D is independently and optionally substituted 4-8 or 4-7 membered ring.

Each $Q^1$ is independently a bond, —O—, —S—, —NR'—, C(O)—, —C(=NR)—, —C(=NR)NR—, —NRC(=NR) NR—, —CO$_2$—, —OC(O)—, —C(O)NR'—, —C(O)NRC (O)O—, —NRC(O)NRC(O)O—, —NRC(O)—, —NRC(O) NR'—, —NRCO$_2$—, —OC(O)NR'—, —S(O)—, —SO$_2$—, —SO$_2$NR'—, —NRSO$_2$—, or —NRSO$_2$NR'—, —P(O) (OR)O—, —OP(O)(OR$^a$)O—, —P(O)$_2$O—, —CO$_2$SO$_2$—, or —(CR$^6$R$^7$)$_p$—Y$^1$—. Specifically, each Q' is independently a bond, —O—, —S—, —NR'—, —C(O)—, —C(=NR)—, —CO$_2$—, —OC(O)—, —C(O)NR'—, —C(O)NRC(O)O—, NRC(O)NRC(O)O—, —NRC(O)—, —NRC(O)NR'—, —NRCO$_2$—, —OC(O)NR'—, —S(O)—, —SO$_2$—, —NRSO$_2$—, —SO$_2$NR'—, NRSO$_2$NR'—, or —(CR$^6$R$^7$)$_p$—Y$^1$—. Specifically, each Q$^1$ is independently a bond, —O—, —S—, —NR'—, —C(O)—, —CO$_2$—, —OC(O)—, —C(O) NR'—, —C(O)NHC(O)O—, —C(O)N(CH$_3$)C(O)O, —NHC(O)NHC(O)O—, —N(CH$_3$)C(O)NHC(O)O—, —NHC(O)—, —N(CH$_3$)C(O)—, —NHC(O)NR'—, —N(CH$_3$)C(O)NR'—, —NHCO$_2$—, —N(CH$_3$)CO$_2$—, —OC(O)NR'—, —S(O)—, —SO$_2$—, —NHSO$_2$—, —N(CH$_3$)SO$_2$—, —SO$_2$NR'—, or —(CR$^6$R$^7$)$_p$—Y$^1$—.

Each Q$^2$ is independently a bond, —O—, —S—, —NR—, —C(O)—, —C(=NR)—, —C(=NR)NR—, —NRC (=NR)NR—, —CO$_2$—, —OC(O)—, —C(O)NR—, —C(O)NRC(O)O—, —NRC(O)NRC(O)O—, —NRC (O)—, —NRC(O)NR—, —NRCO$_2$—, —OC(O)NR—, —S(O)—, —SO$_2$—, —N(R)SO$_2$—, —SO$_2$N(R)—, —NRSO$_2$NR—, —P(O)(OR)O—, —OP(O)(OR$^a$)O—, —P(O)$_2$O—, —CO$_2$SO$_2$—, or —(CR$^6$R$^7$)$_p$—Y$^1$—. Specifically each Q$^2$ is independently a bond, —O—, —S—, —NR'—, C(O)—, —C(=NR)—, —CO$_2$—, —OC(O)—, —C(O)NR'—, —C(O)NRC(O)O—, NRC(O)NRC(O)O—, —NRC(O)—, —NRC(O)NR'—, —NRCO$_2$—, —OC(O) NR'—, —S(O)—, —SO$_2$—, —NRSO$_2$—, —SO$_2$NR'—, NRSO$_2$NR'—, or —(CR$^6$R$^7$)$_p$—Y$^1$—. Specifically, each Q$^2$ is independently —O—, —NR'—, —C(O)—, —CO$_2$—, —C(O)NR'—, —NRC(O)—, —NRC(O)NR'—, —NRCO$_2$—, —OC(O)NR'—, —NRSO$_2$—, —SO$_2$NR'—, or —(CR$^6$R$^7$)$_p$—Y$^1$—. Specifically, each Q$^2$ is independently —CO$_2$—, —C(O)NR'—, —NRC(O)—, —NRC(O) NR'—, —NRCO$_2$—, —OC(O)NR'—, —NRSO$_2$—, or —(CR$^6$R$^7$)$_p$—Y$^1$—. Specifically, each Q$^2$ is independently —NR'—, —C(O)NR'—, —NRC(O)—, —SO$_2$NR'—, —NRC(O)NR'—, —NRCO$_2$—, —OCONR'—, or —(CR⁶R⁷)$_p$—Y¹—. Specifically, each Q² is independently —C(O)NR'—, —NRC(O)—, —NRC(O)NR'—, —NRCO₂—, —OCONR'—, or —(CR⁶R⁷)$_p$—Y¹—. Specifically, each Q² is independently —O—, —NR'—, —C(O)—, —CO₂—, —C(O)NR'—, —NHC(O)—, —N(CH₃)C(O)—, —NHC(O)NR'—, —N(CH₃)C(O)NR'—, —NHCO₂—, —N(CH₃)CO₂—, —OC(O)NR'—, —NHSO₂—, —N(CH₃)SO₂—, —SO₂NR'—, or —(CR⁶R⁷)$_p$—Y¹—. Specifically, each Q² is independently —CO₂—, —C(O)NR'—, —NHC(O)—, —N(CH₃)C(O)—, —NHC(O)NR'—, —N(CH₃)C(O)NR'—, —NHCO₂—, —N(CH₃)CO₂—, —OC(O)NR'—, —NHSO₂—, —N(CH₃)SO₂—, —SO₂NH—, —SO₂N(CH₃)—, or —(CR⁶R⁷)$_p$—Y¹—. Specifically, each Q² is independently —NR'—, —C(O)NR'—, —NHC(O)—, —N(CH₃)C(O)—, —NHC(O)NR'—, —N(CH₃)C(O)NR'—, —NHCO₂—, —N(CH₃)CO₂—, —OCONR'—, or —(CR⁶R⁷)$_p$—Y¹—. Specifically, each Q² is independently —C(O)NR'—, —NHC(O)—, —N(CH₃)C(O)—, —NHC(O)NR'—, —N(CH₃)C(O)NR'—, —NHCO₂—, —N(CH₃)CO₂—, —OCONR'—, or —(CR⁶R⁷)$_p$—Y¹—.

Each Q³ is independently a bond, —C(O)—, —C(=NR)—, —C(=NR)NR—, —NRC(=NR)NR—, —CO₂—, —C(O)NR—, —SO₂—, —SO₂N(R)—, —C(O)NRC(O)O— or —(CR⁶R⁷)$_p$—Y¹—. Specifically, each Q³ is independently is a bond, —C(O)—, —C(=NR)—, —CO₂—, —C(O)NR'—, —SO₂—, —SO₂NR'—, —C(O)NRC(O)O—, or —(CR⁶R⁷)$_p$—Y¹—. Specifically, each Q³ is independently —C(O)—, —CO₂—, —C(O)NR'—, —SO₂—, —SO₂NR'—, —C(O)NRC(O)O—, or —(CR⁶R⁷)$_p$—Y¹—. Specifically, each Q³ is independently —C(O)—, —CO₂—, —C(O)NH—, —C(O)N(CH₃)—, —SO₂—, —SO₂NH—, □ —SO₂N(CH₃)—, —C(O)NHC(O)O—, —C(O)N(CH₃)C(O)O—, or —(CR⁶R⁷)$_p$—Y¹—. Specifically, each Q³ is independently —C(O)—, —CO₂—, —C(O)NR'—, —C(O)NHC(O)O—, or —(CR⁶R⁷)$_p$—Y¹—. Specifically, each Q³ is independently —C(O)—, —CO₂—, —C(O)NR'—, or —(CR⁶R⁷)$_p$—Y¹—.

Optionally, Q² and Q³, together with R⁵, each and independently can form a 5-7 membered, non-aromatic ring optionally substituted with one or more instances of J$^{E1}$. It is understood that the non-aromatic ring formed with R⁵ and Q² can employ a portion of Q². It is also understood that the non-aromatic ring formed with R⁵ and Q³ can employ a portion of Q³.

Each Y¹ is independently a bond, —O—, —S—, —NR—, —C(O)—, —C(=NR)—, —C(=NR)NR—, —NRC(=NR)NR—, —CO₂—, —OC(O)—, —C(O)NR—, —C(O)NRC(O)O—, NRC(O)NRC(O)O—, —NRC(O)—, —NRC(O)NR—, —NRCO₂—, —OC(O)NR—, —S(O)—, —SO₂—, —N(R)SO₂—, —SO₂N(R)—, —NRSO₂NR—, —P(O)(OR)O—, —OP(O)(OR$^a$)O—, —P(O)₂O—, or —CO₂SO₂—. Specifically each Y¹ is independently a bond, —O—, —S—, —NR'—, C(O)—, —C(=NR)—, —CO₂—, —OC(O)—, —C(O)NR'—, —NRC(O)—, —NRC(O)NR'—, —NRCO₂—, —OC(O)NR'—, —S(O)—, —SO₂—, —SO₂NR'—, —NRSO₂—, —NRSO₂NR'—, —NRC(O)NRC(O)O—, or —C(O)NRC(O)O—. Specifically, each Y¹ is independently a bond, —O—, —NR'—, —C(O)NR'—, —NRC(O)—, —NRC(O)NR'—, —NRCO₂—, —OC(O)NR'—, —NRC(O)NHC(O)O—, or —C(O)NHC(O)O—. Specifically, each Y¹ is independently a bond, —O—, —S—, —NR'—, —C(O)—, —CO₂—, —OC(O)—, —C(O)NR'—, —NHC(O)—, —N(CH₃)C(O)—, —NHC(O)NR'—, —N(CH₃)C(O)NR'—, —NHCO₂—, —N(CH₃)CO₂—, —OC(O)NR'—, —S(O)—, —SO₂—, —NHSO₂—, —N(CH₃)SO₂—, —SO₂NH—, SO₂N(CH₃)—, —NHSO₂NH—, —N(CH₃)SO₂NH—, —N(CH₃)SO₂N(CH₃)—, —C(O)NHC(O)O—, —C(O)N(CH₃)C(O)O—, □□ —NHC(O)NHC(O)O—, or —N(CH₃)C(O)NHC(O)O—. Specifically, each Y¹ is independently a bond, —O—, —NR'—, —C(O)NR'—, —NHC(O)—, —N(CH₃)C(O)—, —NHC(O)NR'—, —N(CH₃)C(O)NR'—, —NHCO₂—, —N(CH₃)CO₂—, —OC(O)NR'—, —C(O)NHC(O)O—, or —NHC(O)NHC(O)O—.

Each of J$^A$ and J$^B$ is independently selected from the group consisting of halogen, cyano, oxo, —NCO, and Q¹-R⁵; or optionally two J$^A$ and two J$^B$, respectively, together with the atom(s) to which they are attached, independently form a 4-8 membered ring (e.g., spiro ring or fused ring) that is optionally substituted with one or more instances of J$^{E1}$. Specifically each of J$^A$ and J$^B$ is independently selected from the group consisting of halogen, cyano, oxo, —NCO, and Q¹-R⁵; or optionally two J$^A$ and two J$^B$, respectively, together with the atom(s) to which they are attached, independently form a 5-7 membered ring that is optionally substituted with one or more instanced of J$^{E1}$. The 5-7-membered ring formed with J$^A$ or J$^B$ can be aromatic or non-aromatic. The 5-7-membered ring formed with J$^A$ or J$^B$ can optionally be fused to the ring to which they are attached. In some embodiments, the 5-7-membered ring can optionally be a spiro ring formed by two geminal J$^A$ and two geminal J$^B$, respectively.

J$^C$ is independently selected from the group consisting of halogen, cyano, oxo, —OR⁵, —SR⁵, —NR'R⁵, —C(O)R⁵, —CO₂R⁵, —OC(O)R⁵, —C(O)NR'R⁵, —C(O)NRC(O)OR⁵, —NRC(O)NRC(O)OR⁵, —NRC(O)R⁵, —NRC(O)NR'R⁵, —NRCO₂R⁵, —OC(O)NR'R⁵, —S(O)R⁵, —SO₂R⁵, —SO₂NR'R⁵, —NRSO₂R⁵, —NRSO₂NR'R⁵, and —P(O)(OR$^a$)₂—. Specifically, J$^C$ is independently selected from the group consisting of —OR⁵, —SR⁵, —NR'R⁵, —C(O)R⁵, —CO₂R⁵, —OC(O)R⁵, —C(O)NR'R⁵, —C(O)NRC(O)OR⁵, —NRC(O)NRC(O)OR⁵, —NRC(O)R⁵, —NRC(O)NR'R⁵, —NRCO₂R⁵, —OC(O)NR'R⁵, —S(O)R⁵, —SO₂R⁵, —SO₂NR'R⁵, —NRSO₂R⁵, and —NRSO₂NR'R⁵. Specifically, J$^C$ is selected from the group consisting of halogen, cyano, oxo, —OR⁵, —NR'R⁵, —C(O)R⁵, —CO₂R⁵, —OC(O)R⁵, —C(O)NR'R⁵, —C(O)NRC(O)OR⁵, —NRC(O)R⁵, —NRC(O)NR'R⁵, —NRCO₂R⁵, and —OC(O)NR'R⁵. Specifically, J$^C$ is selected from the group consisting of halogen, cyano, oxo, —OR⁵, —NR'R⁵, —C(O)R⁵, —CO₂R⁵, —OC(O)R⁵, —C(O)NR'R⁵, and —NRC(O)R⁵. Specifically, J$^C$ is selected from the group consisting of halogen, cyano, oxo, —OR⁵, —NR'R⁵, —C(O)NR'R⁵, and —NRC(O)R⁵. Specifically, J$^C$ is selected from the group consisting of —OR⁵, —NR'R⁵, —C(O)NR'R⁵, and —NRC(O)R⁵.

Each of J$^{C1}$ and J$^{D1}$ is independently selected from the group consisting of halogen, cyano, oxo, R$^a$, —OR$^b$, —SR$^b$, —S(O)R$^a$, —SO₂R$^a$, —NR$^b$R$^c$, —C(O)R$^b$, —C(=NR)R$^c$, —C(=NR)NR$^b$R$^c$, —NRC(=NR)NR$^b$R$^c$, —C(O)OR$^b$, —OC(O)R$^b$, —NRC(O)R$^b$, —C(O)NR$^b$R$^c$, —NRC(O)NR$^b$R$^c$, —NRC(O)OR$^b$, —OCONR$^b$R$^c$, —C(O)NRCO₂R$^b$, —NRC(O)NRC(O)OR$^b$, —C(O)NR(OR$^b$), —SO₂NR$^c$R$^b$, —NRSO₂R$^b$, —NRSO₂NR$^c$R$^b$, —P(O)(OR$^a$)₂, —OP(O)(OR$^a$)₂, —P(O)₂(OR$^a$), and —CO₂SO₂R$^b$, or optionally, two J$^{C1}$ and two J$^{D1}$, respectively, together with the atom(s) to which they are attached, independently form a 4-8-membered ring that is optionally substituted with one or more instances of J$^{E1}$. Specifically, each of J$^{C1}$ and J$^{D1}$ is independently selected from the group consisting of halogen, cyano, oxo, R$^a$, —OR$^b$, —SR$^b$, —S(O)R$^a$, —SO₂R$^a$, —NR$^b$R$^c$, —C(O)R$^b$, —C(O)OR$^b$, —OC(O)R$^b$, —NRC(O)R$^b$, —C(O)NR$^b$R$^c$, —NRC(O)NR$^b$R$^c$, —NRC(O)OR$^b$, —OCONR$^b$R$^c$, —C(O)NRCO₂R$^b$, —NRC(O)NRC(O)OR$^b$, —C(O)NR(OR$^b$), —SO₂NR$^c$R$^b$, —NRSO₂R$^b$, and —NRSO₂NR$^c$R$^b$.

Optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached. It is understood that selections of values of each $J^{C1}$ and $J^{D1}$ are those that result in the formation of stable or chemically feasible compounds. For example, suitable values of each $J^{C1}$ and $J^{D1}$ on a carbon atom independently include halogen, cyano, oxo, $R^a$, —$OR^b$, —$SR^b$, —$S(O)R^a$, —$SO_2R^a$, —$NR^bR^c$, —$C(O)R^b$, —$C(O)OR^b$, —$OC(O)R^b$, —$NR^bC(O)R^b$, —$C(O)NR^bR^c$, —$NRC(O)NR^bR^c$, —$NRC(O)OR^b$, —$OCONR^bR^c$, —$C(O)NRCO_2R^b$, —$NRC(O)NRC(O)OR^b$, —$C(O)NR(OR^b)$, —$SO_2NR^cR^b$, —$NRSO_2R^b$, and —$NRSO_2NR^cR^b$; and suitable values of $J^{D1}$ on a nitrogen atom include $R^a$, —$SO_2R^a$, —$SO_2N(R)R^b$, —$C(O)R^b$, —$C(O)OR^b$, —$C(O)NR^bR^c$, —$C(O)NRCO_2R^b$, and —$C(O)NR(OR^b)$. Specific examples of each $J^{C1}$ and $J^{D1}$ on a carbon atom independently include halogen, cyano, oxo, $R^a$, —$OR^b$, —$SR^b$, —$S(O)R^a$, —$SO_2R^a$, —$NHR^c$, —$C(O)R^b$, —$C(O)OR^b$, —$OC(O)R^b$, —$NHC(O)R^b$, —$C(O)NHR^c$, —$NHC(O)NHR^c$, —$NHC(O)OR^b$ and —$OCONHR^c$, —$N(CH_3)R^c$, —$N(CH_3)C(O)R^b$, —$C(O)N(CH_3)R^c$, —$N(CH_3)C(O)NHR^c$, —$N(CH_3)C(O)OR^b$, —$OCON(CH_3)R^c$, —$C(O)NHCO_2R^b$, —$C(O)N(CH_3)CO_2R^b$, —$NHC(O)NHC(O)OR^b$, —$N(CH_3)C(O)NHC(O)OR^b$, —$C(O)NH(OR^b)$—, $C(O)N(CH_3)(OR^b)$, —$NHSO_2R^b$, —$SO_2NHR^b$, —$SO_2N(CH_3)R^b$, and —$N(CH_3)SO_2R^b$. Specific examples of each $J^{D1}$ on a nitrogen atom independently include $R^a$, —$SO_2R^a$, —$C(O)R^b$, —$C(O)OR^b$, —$C(O)NHR^c$, —$C(O)N(CH_3)R^c$, —$C(O)NHCO_2R^b$, —$C(O)N(CH_3)CO_2R^b$, —$C(O)NH(OR^b)$—, and —$C(O)N(CH_3)(OR^b)$. More specific examples of each fl and $J^{131}$ on a carbon atom independently include halogen, cyano, hydroxy, oxo, $C_1$-$C_4$ alkyl, —$O(C_1$-$C_4$ alkyl), —$NH_2$, —$NH(C_1$-$C_4$ alkyl), —$N(C_1$-$C_4$ alkyl)$_2$, —$C(O)(C_1$-$C_4$ alkyl), —$OC(O)(C_1$-$C_4$ alkyl), —$C(O)O(C_1$-$C_4$ alkyl), $C_3$-$C_6$ cycloalkyl, and —$CO_2H$, wherein each of said alkyl groups (e.g., represented by $C_1$-$C_4$ alkyl, —$O(C_1$-$C_4$ alkyl), —$NH_2$, —$NH(C_1$-$C_4$ alkyl), —$N(C_1$-$C_4$ alkyl)$_2$, —$C(O)(C_1$-$C_4$ alkyl), —$OC(O)(C_1$-$C_4$ alkyl), —$C(O)O(C_1$-$C_4$ alkyl), and $C_3$-$C_6$ cycloalkyl) is optionally and independently substituted with one or more substituents independently selected from the group consisting of halogen, cyano, hydroxy, oxo, —$NH_2$, —$NH(C_1$-$C_4$ alkyl), —$N(C_1$-$C_4$alkyl)$_2$, —$C(O)(C_1$-$C_4$alkyl), —$OCO(C_1$-$C_4$ alkyl), —$CO_2H$, —$CO_2(C_1$-$C_4$ alkyl), and $C_1$-$C_4$ alkoxy. More specific examples of each $J^{D1}$ on a nitrogen atom independently include halogen, cyano, hydroxy, oxo, $C_1$-$C_4$ alkyl, —$C(O)(C_1$-$C_4$ alkyl), —$C(O)O(C_1$-$C_4$ alkyl), and $C_3$-$C_6$ cyclo(alkyl), wherein each of said alkyl groups is optionally and independently substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$C(O)(C_1$-$C_4$ alkyl), —$OCO(C_1$-$C_4$ alkyl), —$CO_2H$, —$CO_2(C_1$-$C_4$ alkyl), and $C_1$-$C_4$ alkoxy.

Each $J^{E1}$ is independently selected from the group consisting of halogen, cyano, hydroxy, oxo, amino, carboxy, amido, $C_1$-$C_6$ alkyl, —$O(C_1$-$C_6$ alkyl), and —$C(O)(C_1$-$C_6$-alkyl), wherein each of said alkyl groups is optionally and independently substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy. Specifically, each $J^{E1}$ is independently selected from the group consisting of halogen, cyano, hydroxy, oxo, $C_1$-$C_6$ alkyl, —$O(C_1$-$C_6$ alkyl), —$C(O)(C_1$-$C_6$-alkyl), —$NH_2$, —$NH(C_1$-$C_6$ alkyl), —$N(C_1$-$C_6$ alkyl)$_2$, —$C(O)NH_2$, —$C(O)NH(C_1$-$C_6$ alkyl), —$C(O)N(C_1$-$C_6$ alkyl)$_2$, —$C(O)(C_1$-$C_6$-alkyl), —$C(O)O(C_1$-$C_6$ alkyl), —$OC(O)(C_1$-$C_6$ alkyl), —$NHC(O)(C_1$-$C_6$ alkyl), —$N(C_1$-$C_6$ alkyl)$C(O)(C_1$-$C_6$ alkyl), and —$CO_2H$, wherein each of said alkyl groups is optionally and independently substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy. It is understood that selections of suitable $J^{E1}$ are those that result in the formation of stable or chemically feasible compounds. For example, suitable substituents on a carbon atom independently include halogen, cyano, hydroxy, oxo, $C_1$-$C_6$ alkyl, —$O(C_1$-$C_6$ alkyl), —$C(O)(C_1$-$C_6$-alkyl), —$NH_2$, —$NH(C_1$-$C_6$ alkyl), —$N(C_1$-$C_6$ alkyl)$_2$, —$C(O)NH_2$, —$C(O)NH(C_1$-$C_6$ alkyl), —$C(O)N(C_1$-$C_6$ alkyl)$_2$, —$C(O)(C_1$-$C_6$-alkyl), —$C(O)O(C_1$-$C_6$ alkyl), —$OC(O)(C_1$-$C_6$ alkyl), —$NHC(O)(C_1$-$C_6$ alkyl), —$N(C_1$-$C_6$ alkyl)$C(O)(C_1$-$C_6$ alkyl), and —$CO_2H$, wherein each of said alkyl groups is optionally and independently substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy. For example, suitable substituents on a nitrogen atom independently include $C_1$-$C_6$ alkyl, —$C(O)NH(C_1$-$C_6$ alkyl), —$C(O)N(C_1$-$C_6$ alkyl)$_2$, —$C(O)(C_1$-$C_6$-alkyl), and —$C(O)O(C_1$-$C_6$ alkyl), wherein each of said alkyl groups is optionally and independently substituted with one or more substituents independently selected from the group consisting of halogen, cyano, hydroxy, oxo, —$NH_2$, —$NH(C_1$-$C_4$ alkyl), —$N(C_1$-$C_4$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy.

R and R' are each independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy. Specifically, R and R' are each independently —H or $C_1$-$C_6$ alkyl optionally substituted with one or more substituents independently selected from the group consisting of halogen, cyano, hydroxy, oxo, —$NH_2$, —$NH(C_1$-$C_6$ alkyl), —$N(C_1$-$C_6$ alkyl)$_2$, —$C(O)O(C_1$-$C_6$ alkyl), —$OC(O)(C_1$-$C_6$ alkyl), —$CO_2H$, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_1$-$C_6$alkoxyalkoxy. Specifically, R and R' are each independently —H or $C_1$-$C_6$ alkyl optionally substituted with one or more substituents independently selected from the group consisting of halogen, cyano, hydroxy, oxo, —$NH_2$, —$NH(C_1$-$C_6$ alkyl), —$N(C_1$-$C_6$ alkyl)$_2$, and —$O(C_1$-$C_6$ alkyl)). Specifically, R and R' are each independently —H or $C_1$-$C_6$ alkyl (e.g., —$CH_3$ or —$CH_2CH_3$).

Optionally R', together with $R^5$ and the nitrogen atom to which they are attached, forms a 5-7 membered, non-aromatic, heterocyclic ring optionally substituted with one or more instances of $J^{D1}$. Specifically, the non-aromatic heterocycle is optionally substituted with one or more substituents independently selected from the group consisting of halogen, cyano, hydroxy, oxo, $C_1$-$C_6$ alkyl, $C_2$-$C_6$ alkenyl, —$NH_2$, —$NH(C_1$-$C_6$ alkyl), —$N(C_1$-$C_6$ alkyl)$_2$, —$O(C_1$-$C_6$ alkyl), —$C(O)NH_2$, —$C(O)NH(C_1$-$C_6$ alkyl), —$C(O)N(C_1$-$C_6$ alkyl)$_2$, —$C(O)(C_1$-$C_6$-alkyl), —$OC(O)(C_1$-$C_6$ alkyl), —$NHC(O)(C_1$-$C_6$ alkyl), —$N(C_1$-$C_6$ alkyl)$C(O)(C_1$-$C_6$ alkyl), and —$CO_2R^b$; wherein each of said alkyl and alkenyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —C(O)(C$_1$-C$_4$ alkyl), —CO$_2$H, —CO$_2$(C$_1$-C$_4$ alkyl), and C$_1$-C$_4$ alkoxy. Specifically, the non-aromatic heterocycle is optionally substituted with one or more substituents independently selected from the group consisting of halogen, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —OCO(C$_1$-C$_4$ alkyl), —C(O)(C$_1$-C$_4$ alkyl), —CO$_2$H, and —CO$_2$(C$_1$-C$_4$ alkyl), wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO$_2$H, —CO$_2$(C$_1$-C$_4$ alkyl), and C$_1$-C$_4$ alkoxy.

Each R* is independently: i) —H; ii) a C$_1$-C$_6$ alkyl group optionally substituted with one or more substituents independently selected from the group consisting of halogen, cyano, hydroxy, oxo, amino, carboxy, C$_3$-C$_8$ non-aromatic carbocycle, 5-6 membered non-aromatic heterocycle, phenyl, 5-6 membered heteroaryl, —O(C$_1$-C$_6$ alkyl), and —C(O)(C$_1$-C$_6$-alkyl); wherein each of said alkyl groups (e.g., represented by —O(C$_1$-C$_6$ alkyl), and —C(O)(C$_1$-C$_6$-alkyl)) is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said C$_3$-C$_8$ non-aromatic carbocycle, 5-6 membered non-aromatic heterocycle, phenyl, and 5-6 membered heteroaryl is independently and optionally substituted with one or more instances of J$^{E1}$; or iii) a C$_3$-C$_8$ non-aromatic carbocycle, or a 4-8 membered non-aromatic heterocycle, each of which is independently and optionally substituted with one or more instances of J$^{E1}$. Specifically, each R* independently is: i) —H; ii) C$_1$-C$_6$ alkyl optionally substituted with one or more substituents independently selected from the group consisting of halogen, cyano, hydroxy, oxo, amino, carboxy, C$_1$-C$_4$ alkoxy, C$_1$-C$_4$ haloalkoxy, C$_1$-C$_4$ aminoalkoxy, C$_1$-C$_4$ cyanoalkoxy, C$_1$-C$_4$ hydroxyalkoxy, and C$_2$-C$_4$ alkoxyalkoxy; or iii) a 3-7 membered carbocyclic ring optionally substituted with one or more substituents independently selected from the group consisting of halogen, cyano, hydroxy, oxo, amino, carboxy, C$_1$-C$_4$ alkyl, C$_1$-C$_4$ haloalkyl, C$_1$-C$_4$ cyanoalkyl, C$_2$-C$_4$ alkoxyalkyl, C$_1$-C$_4$ aminoalkyl, C$_1$-C$_4$ hydroxyalkyl, C$_1$-C$_4$ alkoxy, C$_1$-C$_4$ haloalkoxy, C$_1$-C$_4$ aminoalkoxy, C$_1$-C$_4$ cyanoalkoxy, C$_1$-C$_4$ hydroxyalkoxy, and C$_2$-C$_4$ alkoxyalkoxy. Specifically, each R* is i) —H, ii) C$_1$-C$_6$ alkyl optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; or iii) a 3-7 membered carbocyclic ring optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkoxy, and C$_1$-C$_6$ alkyl, wherein each alkyl optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Each R$^a$ is independently: i) a C$_1$-C$_6$ aliphatic group optionally substituted with one or more substituents independently selected from the group consisting of halogen, cyano, hydroxy, oxo, amino, carboxy, amido, —O(C$_1$-C$_6$ alkyl), —C(O)(C$_1$-C$_6$-alkyl), C$_3$-C$_8$ non-aromatic carbocycle, 4-8 membered non-aromatic heterocycle, 5-10 membered heteroaryl group, and 6-10 membered carbocyclic aryl group; wherein each of said alkyl groups for the substituents of the C$_1$-C$_6$ aliphatic group represented by R$^a$ is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said carbocycle, heterocycle, heteroaryl and carbocyclic aryl groups for the substituents of the C$_1$-C$_6$ aliphatic group represented by R$^a$ is optionally and independently substituted with one or more instances of J$^{E1}$; ii) a C$_3$-C$_8$ non-aromatic carbocycle, or a 4-8 membered non-aromatic heterocycle, each of which is optionally and independently substituted with one or more instances of J$^{E1}$; iii) a 5-10 membered heteroaryl, or 6-10 membered carbocyclic aryl group, each of which is optionally and independently substituted with one or more instances of J$^{E1}$.

Alternatively, each R$^a$ is independently: i) a C$_1$-C$_6$ aliphatic group optionally substituted with one or more substituents independently selected from the group consisting of halogen, cyano, hydroxy, oxo, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), —C(O)N(C$_1$-C$_6$ alkyl)$_2$, —NHC(O)(C$_1$-C$_6$ alkyl), —N(C$_1$-C$_6$ alkyl)C(O)(C$_1$-C$_6$ alkyl), —O(C$_1$-C$_6$ alkyl), —C(O)(C$_1$-C$_6$-alkyl), C$_3$-C$_8$ non-aromatic carbocycle, 6-10 membered carbocyclic aryl, 4-8 membered non-aromatic heterocycle, and 5-10 membered heteroaryl; wherein each of said alkyl groups for the substituents of the C$_1$-C$_6$ aliphatic group represented by R$^a$ is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said carbocycle, phenyl, non-aromatic heterocycle, and heteroaryl groups for the substituents of the C$_1$-C$_6$ aliphatic group represented by R$^a$ is optionally and independently substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), —C(O)N(C$_1$-C$_6$ alkyl)$_2$, —NHC(O)(C$_1$-C$_6$ alkyl), —N(C$_1$-C$_6$ alkyl)C(O)(C$_1$-C$_6$ alkyl), —O(C$_1$-C$_6$ alkyl), and —C(O)(C$_1$-C$_6$-alkyl), each said alkyl groups being optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_r$-C$_4$ alkoxy; ii) a C$_3$-C$_8$ non-aromatic carbocyclic group, or a 4-8 membered, non-aromatic heterocyclic group, each of which is optionally and independently substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), —C(O)N(C$_1$-C$_6$ alkyl)$_2$, —NHC(O)(C$_1$-C$_6$ alkyl), —N(C$_1$-C$_6$ alkyl)C(O)(C$_1$-C$_6$ alkyl), —O(C$_1$-C$_6$ alkyl), and —C(O)(C$_1$-C$_6$-alkyl), wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; or iii) a 5-10 membered heteroaryl group or a 6-10 membered carbocyclic aryl group, each of which is optionally and independently substituted with one or more instances of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), —C(O)N(C$_1$-C$_6$ alkyl)$_2$, —NHC(O)(C$_1$-C$_6$ alkyl), —N(C$_1$-C$_6$ alkyl)C(O)(C$_1$-C$_6$ alkyl), —O(C$_1$-C$_6$ alkyl), and —C(O)(C$_1$-C$_6$-alkyl), wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Specifically, R$^a$ is independently: i) a C$_1$-C$_6$ aliphatic group optionally substituted with one or more substituents independently selected from the group consisting of halogen; cyano; hydroxy; oxo; —NH$_2$; —NH(C$_1$-C$_6$ alkyl); —N(C$_1$-C$_6$ alkyl)$_2$; —C(O)O(C$_1$-C$_6$-alkyl); —OC(O)(C$_1$-C$_6$-alkyl); —CO$_2$H; —O(C$_1$-C$_6$ alkyl); —C(O)(C$_1$-C$_6$-alkyl); and a C$_3$-C$_7$ non-aromatic carbocyclic group, phenyl group, 4-7 membered non-aromatic heterocyclic group, or 5-6 membered heteroaryl group, each of which is optionally and independently substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —O(C$_1$-C$_6$ alkyl), and —C(O)(C$_1$-C$_6$-alkyl); ii) a C$_3$-C$_7$ non-aromatic carbocyclic group optionally substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —O(C$_1$-C$_6$ alkyl), and —C(O)(C$_1$-C$_6$-alkyl); iii) a 4-7 membered, non-aromatic heterocyclic group optionally substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —O(C$_1$-C$_6$ alkyl), and —C(O)(C$_1$-C$_6$-alkyl); iv) a 5-6 membered heteroaryl group or a phenyl group, each of which is optionally and independently substituted with one or more substituents independently selected from the group consisting of halogen, cyano, hydroxy, oxo, C$_1$-C$_6$ alkyl, —NH$_2$, —NH(C$_1$-C$_6$ alkyl), —N(C$_1$-C$_6$ alkyl)$_2$, —C(O)O(C$_1$-C$_6$-alkyl), —OC(O)(C$_1$-C$_6$-alkyl), —CO$_2$H, —O(C$_1$-C$_6$ alkyl), and —C(O)(C$_1$-C$_6$-alkyl). Each of the alkyl groups referred to in the values of R$^a$, including substituents thereof, independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Specifically, the optionally substituted C$_1$-C$_6$ aliphatic group represented by R$^a$ is an optionally substituted C$_1$-C$_6$ alkyl group.

R$^b$ and R$^c$ are each independently R$^a$ or —H; or optionally, R$^b$ and R$^c$, together with the nitrogen atom(s) to which they are attached (e.g., represented by —NR$^b$R$^c$, —C(O)NR$^b$R$^c$, —NRC(O)NR$^b$R$^c$, or —OCONR$^b$R$^c$), each independently form a non-aromatic, 5-7 membered, heterocyclic ring that is optionally substituted with one or more instances of J$^{E1}$. Suitable specific substituents for the heterocyclic ring formed with R$^b$ and R$^c$ independently include halogen, cyano, hydroxy, oxo, amino, carboxy, amido, C$_1$-C$_6$ alkyl, C$_1$-C$_6$ haloalkyl, C$_1$-C$_6$ cyanoalkyl, C$_2$-C$_6$-alkoxyalkyl, C$_1$-C$_6$ aminoalkyl, C$_1$-C$_6$ hydroxyalkyl, C$_1$-C$_6$ alkoxy, C$_1$-C$_6$ haloalkoxy, C$_1$-C$_6$ aminoalkoxy, C$_1$-C$_6$ cyanoalkoxy, C$_1$-C$_6$ hydroxyalkoxy, C$_2$-C$_6$ alkoxyalkoxy, and —C(O)(C$_1$-C$_6$-alkyl). Specific suitable substituents for the heterocyclic ring formed with R$^b$ and R$^c$ independently include halogen, cyano, hydroxy, oxo, —NH$_2$, —NH(C$_1$-C$_4$ alkyl), —N(C$_1$-C$_4$ alkyl)$_2$, C$_1$-C$_4$ alkyl, C$_1$-C$_4$ haloalkyl, C$_1$-C$_4$ hydroxyalkyl, C$_2$-C$_4$ alkoxyalkyl, C$_1$-C$_4$ alkoxy, C$_1$-C$_4$ haloalkoxy, C$_1$-C$_4$ hydroxyalkoxy, C$_2$-C$_4$ alkoxyalkoxy, —CO$_2$(C$_1$-C$_4$ alkyl), —OC(O)(C$_1$-C$_4$ alkyl), and —CO$_2$H.

It is understood that selections of suitable substituents for the heterocyclic ring formed with R$^b$ and R$^c$ are those that result in the formation of stable or chemically feasible compounds. For example, suitable substituents on a carbon atom independently include halogen, cyano, hydroxy, oxo, —NH$_2$, —NH(C$_1$-C$_6$ alkyl), —N(C$_1$-C$_6$ alkyl)$_2$, C$_1$-C$_6$ alkyl, C$_1$-C$_6$ haloalkyl, C$_1$-C$_6$ hydroxyalkyl, C$_2$-C$_6$ alkoxyalkyl, C$_1$-C$_6$ aminoalkyl, C$_1$-C$_6$ cyanoalkyl, C$_1$-C$_6$ alkoxy, C$_1$-C$_6$ haloalkoxy, C$_1$-C$_6$-aminoalkoxy, C$_1$-C$_6$-cyanoalkoxy, C$_1$-C$_6$-hydroxyalkoxy, C$_2$-C$_6$-alkoxyalkoxy, —C(O)(C$_1$-C$_6$-alkyl), —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), —C(O)N(C$_1$-C$_6$ alkyl)$_2$, —NHC(O)(C$_1$-C$_6$ alkyl), and —N(C$_1$-C$_6$ alkyl)C(O)(C$_1$-C$_6$ alkyl). In another example, suitable substituents on a carbon atom independently include halogen, cyano, hydroxy, oxo, —NH$_2$, —NH(C$_1$-C$_4$ alkyl), —N(C$_1$-C$_4$ alkyl)$_2$, C$_1$-C$_4$ alkyl, C$_1$-C$_4$ haloalkyl, C$_1$-C$_4$ hydroxyalkyl, C$_2$-C$_4$ alkoxyalkyl, C$_1$-C$_4$ alkoxy, C$_1$-C$_4$ haloalkoxy, C$_2$-C$_4$ hydroxyalkoxy, C$_2$-C$_4$ alkoxyalkoxy, —CO(C$_1$-C$_4$ alkyl), —CO$_2$(C$_1$-C$_4$ alkyl), and —CO$_2$H. For example, suitable substituents on a nitrogen atom independently include C$_1$-C$_6$ alkyl, C$_1$-C$_6$ haloalkyl, C$_1$-C$_6$ hydroxyalkyl, C$_2$-C$_6$ alkoxyalkyl, C$_1$-C$_6$ aminoalkyl, C$_1$-C$_6$ cyanoalkyl, —C(O)(C$_1$-C$_6$-alkyl), —C(O)O(C$_1$-C$_6$-alkyl), —OC(O)(C$_1$-C$_6$-alkyl), —CO$_2$H, —C(O)NH$_2$, —C(O)NH(C$_1$-C$_6$ alkyl), and —C(O)N(C$_1$-C$_6$ alkyl)$_2$. In another example, suitable substituents on a nitrogen atom independently include C$_1$-C$_4$ alkyl, C$_1$-C$_4$ haloalkyl, C$_1$-C$_4$ hydroxyalkyl, C$_2$-C$_4$ alkoxyalkyl, C$_1$-C$_4$ alkoxy, C$_1$-C$_4$ haloalkoxy, C$_2$-C$_4$ hydroxyalkoxy, —CO(C$_1$-C$_4$ alkyl), —CO$_2$(C$_1$-C$_4$ alkyl), and —CO$_2$H.

Each R$^d$ is independently —H, C$_1$-C$_6$ alkyl or —C(O)(C$_1$-C$_6$ alkyl), wherein each of said alkyl moiety is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, each R$^d$ is independently —H, or C$_1$-C$_6$ alkyl optionally substituted with one or more groups selected from halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

p is independently 1, 2, 3 or 4. Specifically, p is independently 1 or 2.

k, n and m are each independently 0, 1 or 2. Alternatively, when rings A and B are 3-6-membered, n and m are each independently 0 or 1; and k is independently 0, 1 or 2; and when rings A and B are 7-8-membered, n and m, are each independently 0, 1 or 2; and k is independently 0, 1 or 2.

x and y are each independently 0, 1 or 2.

z is 1 or 2.

A second set of variables of Structural Formulae (I) and (IA) is as follows:

$R^2$ is —H or —$CH_3$.

$R^3$ is —H, —Cl, —F, —Br, —CN, —$CF_3$, —O($C_1$-$C_4$ alkyl), —OH, —$NH_2$, —NH($C_1$-$C_4$ alkyl), or —N($C_1$-$C_4$ alkyl)$_2$.

Values of the remaining variables of Structural Formulae (I) and (IA), including specific values, and provisos are each and independently as described above for the first set of variables of Structural Formulae (I) and (IA).

A third set of variables of Structural Formulae (I) and (IA) is as follows:

$R^2$ is —H or —$CH_3$.

$R^4$ is i) an optionally substituted $C_3$-$C_{10}$ carbocyclic ring; ii) a $C_1$-$C_6$ aliphatic group (e.g., $C_1$-$C_6$ alkyl or $C_2$-$C_6$ alkenyl group) that is substituted with one or more substituents independently selected from the group consisting of $J^C$, an optionally substituted, $C_3$-$C_8$ non-aromatic carbocycle, and an optionally substituted, 4-10 membered non-aromatic heterocycle; or iii) an optionally substituted, 4-10 membered non-aromatic heterocycle.

Values of the remaining variables of Structural Formulae (I) and (IA), including specific values, and provisos are each and independently as described above for the first set of variables of Structural Formulae (I) and (IA).

A fourth set of variables of Structural Formulae (I) and (IA) is as follows:

$R^2$ is —H or —$CH_3$.

$R^3$ is —H, —Cl, —F, —Br, —CN, —$CF_3$, —O($C_1$-$C_4$ alkyl), —OH, —$NH_2$, —NH($C_1$-$C_4$ alkyl), or —N($C_1$-$C_4$ alkyl)$_2$.

$R^4$ is selected from formulae A-D depicted above.

The remaining variables of Structural Formulae (I) and (IA), including specific values, are each and independently as described above for the first set of variables of Structural Formulae (I) and (IA).

A fifth set of variables of Structural Formulae (I) and (IA) is as follows:

$R^2$ is —H or —$CH_3$.

$R^3$ is —H, —F, —$CF_3$, —$NH_2$, —NHMe or —$NMe_2$.

$R^4$ is i) an optionally substituted $C_3$-$C_{10}$ carbocyclic ring; ii) a $C_1$-$C_6$ aliphatic group (e.g., O—$C_6$ alkyl or $C_2$-$C_6$ alkenyl group) that is substituted with one or more substituents independently selected from the group consisting off, an optionally substituted, $C_3$-$C_8$ non-aromatic carbocycle, and an optionally substituted, 4-10 membered non-aromatic heterocycle; or iii) an optionally substituted, 4-10 membered non-aromatic heterocycle.

Values of the remaining variables of Structural Formulae (I) and (IA), including specific values, and provisos are each and independently as described above for the first set of variables of Structural Formulae (I) and (IA).

A sixth set of variables of Structural Formulae (I) and (IA) is as follows:

$R^2$ is —H or —$CH_3$.

$R^3$ is —H, —F, —$CF_3$, —$NH_2$, —NH($CH_3$), or —N($CH_3$)$_2$.

$R^4$ is selected from formulae A-D depicted above.

Values of the remaining variables of Structural Formulae (I) and (IA), including specific values, are each and independently as each and independently as described above for the first set of variables of Structural Formulae (I) and (IA).

A seventh set of variables of Structural Formulae (I) and (IA) is as follows:

$R^2$ is —H or —$CH_3$.

$R^3$ is —H, —F, or —Cl.

$R^4$ is i) an optionally substituted $C_3$-$C_{10}$ carbocyclic ring; ii) a $C_1$-$C_6$ aliphatic group (e.g., $C_1$-$C_6$ alkyl or $C_2$-$C_6$ alkenyl group) that is substituted with one or more substituents independently selected from the group consisting of $J^C$, an optionally substituted, $C_3$-$C_8$ non-aromatic carbocycle, and an optionally substituted, 4-10 membered non-aromatic heterocycle; or iii) an optionally substituted, 4-10 membered non-aromatic heterocycle.

Values of the remaining variables of Structural Formulae (I) and (IA), including specific values, and provisos are each and independently as each and independently as described above for the first set of variables of Structural Formulae (I) and (IA).

An eighth set of variables of Structural Formula I is as follows:

$R^2$ is —H or —$CH_3$.

$R^3$ is —H, —F, or —Cl.

$R^4$ is selected from formulae A-D depicted above.

Values of the remaining variables of Structural Formulae (I) and (IA), including specific values, and provisos are each and independently as each and independently as described above for the first set of variables of Structural Formulae (I) and (IA).

A ninth set of variables of Structural Formulae (I) and (IA) is as follows:

$R^2$ is —H.

$R^3$ is —H or —Cl.

$R^4$ is i) an optionally substituted $C_3$-$C_{10}$ carbocyclic ring; ii) a $C_1$-$C_6$ aliphatic group (e.g., $C_1$-$C_6$ alkyl or $C_2$-$C_6$ alkenyl group) that is substituted with one or more substituents independently selected from the group consisting of $J^C$, an optionally substituted, $C_3$-$C_8$ non-aromatic carbocycle, and an optionally substituted, 4-10 membered non-aromatic heterocycle; or iii) an optionally substituted, 4-10 membered non-aromatic heterocycle.

Values of the remaining variables of Structural Formulae (I) and (IA), including specific values, and provisos are each and independently as each and independently as described above for the first set of variables of Structural Formulae (I) and (IA).

A tenth set of variables of Structural Formulae (I) and (IA) is as follows:

$R^2$ is —H.

$R^3$ is —H or —Cl.

$R^4$ is selected from formulae A-D depicted above.

Values of the remaining variables of Structural Formulae (I) and (IA), including specific values, and provisos are each and independently as each and independently as described above for the first set of variables of Structural Formulae (I) and (IA).

An eleventh set of variables of Structural Formulae (I) and (IA) is as follows:

Each of $R^2$, $R^3$ and $R^4$ is independently as described in the first, second, third, fourth, fifth, sixth, seventh, eighth, ninth, or tenth set of variables of Structural Formulae (I) and (IA).

$Z^1$ is —H, $C_1$-$C_6$ alkyl, —O($C_1$-$C_6$ alkyl), —F, —Cl, —CN, —$CO_2H$, —$CO_2$($C_1$-$C_6$ alkyl), —$CONH_2$, —CONH($C_1$-$C_6$ alkyl), or —CON($C_1$-$C_6$ alkyl)$_2$; and $Z^2$ is —H, $C_1$-$C_6$ alkyl, —O($C_1$-$C_6$ alkyl), —$NH_2$, —NH($C_1$-$C_6$ alkyl), or —N($C_1$-$C_6$ alkyl)$_2$; wherein each of said alkyl groups (e.g., represented by $C_1$-$C_6$ alkyl, —O($C_1$-$C_6$ alkyl), —$CO_2$($C_1$-$C_6$ alkyl), —NH($C_1$-$C_6$ alkyl), and —N($C_1$-$C_6$ alkyl)$_2$) is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Values of the remaining variables of Structural Formulae (I) and (IA), including specific values, and provisos are each and independently as described above for the first set of variables of Structural Formulae (I) and (IA).

A twelfth set of variables of Structural Formulae (I) and (IA) is as follows:

Each of $R^2$, $R^3$ and $R^4$ is independently as described in the first, second, third, fourth, fifth, sixth, seventh, eighth, ninth, or tenth set of variables of Structural Formulae (I) and (IA).

$Z^1$ is —H, —F, —$C_1$, $C_1$-$C_4$ haloalkyl (e.g, —$CF_3$), $C_1$-$C_4$ alkyl, —O($C_1$-$C_4$ alkyl), or —CN.

$Z^2$ is —H, $C_1$-$C_6$ alkyl, —O($C_1$-$C_6$ alkyl), —$NH_2$, —NH($C_1$-$C_6$ alkyl), or —N($C_1$-$C_6$ alkyl)$_2$; wherein each of said alkyl groups (e.g., represented by $C_1$-$C_6$ alkyl, —O($C_1$-$C_6$ alkyl), —NH($C_1$-$C_6$ alkyl), and —N($C_1$-$C_6$ alkyl)$_2$) is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (I) and (IA), including specific values, and provisos are each and independently as described above for the first set of variables of Structural Formulae (I) and (IA).

A thirteenth set of variables of Structural Formulae (I) and (IA) is as follows:

Each of $R^2$, $R^3$ and $R^4$ is independently as described in the first set, second set, third set, fourth set, fifth set, sixth set, seventh set, eighth set, ninth set, or tenth set, of variables of Structural Formulae (I) and (IA).

$Z^1$ is —H, —F, —$C_1$, $C_1$-$C_4$ haloalkyl (e.g, —$CF_3$), $C_1$-$C_4$ alkyl, —O($C_1$-$C_4$ alkyl), or —CN.

$Z^2$ is —H or a $C_1$-$C_6$ alkyl optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (I) and (IA), including specific values, and provisos are each and independently as described above for the first set of variables of Structural Formulae (I) and (IA).

A fourteenth set of variables of Structural Formulae (I) and (IA) is as follows:

Each of $R^2$, $R^3$ and $R^4$ is independently as described in the first, second, third, fourth, fifth, sixth, seventh, eighth, ninth, or tenth set of variables of Structural Formulae (I) and (IA).

$Z^1$ is —H, —F, —Cl, —$CF_3$, —$CH_3$, or —CN.

$Z^2$ is —H or a $C_1$-$C_6$ alkyl optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (I) and (IA), including specific values, and provisos are each and independently as described above for the first set of variables of Structural Formulae (I) and (IA).

In a fifteenth set of variables of Structural Formulae (I) and (IA), values of the variables, except R*, R and R', of Structural Formulae (I) and (IA), including specific values, and provisos are each and independently as described above in the first, second, third, fourth, fifth, sixth, seventh, eighth, ninth, tenth, eleventh, twelfth, thirteenth, or fourteenth set of variables of Structural Formulae (I) and (IA); and, where applicable:

each R* independently is: i) —H; ii) $C_1$-$C_6$ alkyl optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy; or iii) a 3-7 membered carbocyclic ring optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkoxy, and $C_1$-$C_6$ alkyl, wherein each alkyl is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy; and R and R' are each independently —H or $C_1$-$C_6$ alkyl optionally substituted with one or more substituents independently selected from the group consisting of halogen, cyano, hydroxy, oxo, —$NH_2$, —NH($C_1$-$C_6$ alkyl), —N($C_1$-$C_6$ alkyl)$_2$, and —O($C_1$-$C_6$ alkyl); or optionally R', together with $R^5$ and the nitrogen atom to which they are attached, forms a 5-7 membered, non-aromatic, heterocyclic ring optionally substituted with one or more instances of $J^{D1}$.

A sixteenth set of variables of Structural Formulae (I) and (IA) is as follows:

Each of $J^A$ and $J^B$ is independently selected from the group consisting of halogen, cyano, oxo, and $Q^1$-$R^5$; or optionally two $J^A$ and two $J^B$, respectively, together with the atom(s) to which they are attached, independently form a 5-7 membered ring that is optionally substituted with one or more instances of $J^{E1}$, and fused to the ring to which they are attached.

$Q^1$ is independently a bond, —O—, —S—, —NR'—, —C(O)—, —$CO_2$—, —OC(O)—, —C(O)NR'—, —C(O)NRC(O)O—, NRC(O)NRC(O)O—, —NRC(O)—, —NRC(O)NR'—, —$NRCO_2$—, —OC(O)NR'—, —S(O)—, —$SO_2$—, —$SO_2$NR'—, —$NRSO_2$—, or —$NRSO_2$NR'—, or —$(CR^6R^7)_p$—$Y^1$—.

Each of $J^{C1}$ and $J^{D1}$ is independently selected from the group consisting of halogen, cyano, oxo, $R^a$, —$OR^b$, —$SR^b$, —S(O)$R^a$, —$SO_2R^a$, —$NR^bR^c$, —C(O)$R^b$, —C(O)$OR^b$, —OC(O)$R^b$, —NRC(O)$R^b$, —C(O)$NR^bR^c$, —NRC(O)$NR^bR^c$, —NRC(O)$OR^b$, —$OCONR^bR^c$, —C(O)$NRCO_2R^b$, —NRC(O)NRC(O)$OR^b$, —C(O)NR(OR$^b$), —$SO_2NR^cR^b$, —$NRSO_2R^b$, and —$NRSO_2NR^cR^b$, or optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

Values of the remaining variables of Structural Formulae (I) and (IA), including specific values, and provisos are each and independently as described above for the first, second, third, fourth, fifth, sixth, seventh, eighth, ninth, tenth, eleventh, twelfth, thirteenth, or fourteenth set of variables of Structural Formulae (I) and (IA).

A seventeenth set of variables of Structural Formulae (I) and (IA) is as follows:

$R^1$ is —H.

$R^2$ is —H, —$CH_3$, —$CH_2OH$, or —$NH_2$. Alternatively $R^2$ is —H or —$CH_2OH$.

$R^3$ is —H, —F, —$C_1$, $C_{1-4}$ alkyl, or $C_{1-4}$ haloalkyl. Alternatively, $R^3$ is —H, —F, or —Cl.

$Z^1$ is —H, —F, or —Cl.

$Z^2$ is —H or $C_1$-$C_6$ alkyl optionally substituted with one or more substituents independently selected from the group consisting of halogen, cyano, hydroxy, and —O($C_1$-$C_4$ alkyl).

$Z^3$ is —H or $C_1$-$C_6$ alkyl optionally substituted with one or more substituents independently selected from the group consisting of halogen, cyano, hydroxy, and —O($C_1$-$C_4$ alkyl).

The remaining variables are as described above in any set of variables for Structural Formulae (IA) and (I) as applicable.

An eighteenth set of variables of Structural Formulae (I) and (IA) is as follows:

$R^1$ is —H.

$R^2$ is —H or —CH$_2$OH.

$R^3$ is —H, —F, or —Cl. Alternatively $R^3$ is —F or —Cl.

$Z^1$ is —H, —F, or —Cl.

$Z^2$ and $Z^3$ are —H.

The remaining variables are each and independently as described above in any set of variables for Structural Formulae (IA) and (I).

A nineteenth set of variables of Structural Formulae (I) and (IA) is as follows:

$R^5$ is: i) —H; ii) an optionally substituted $C_1$-$C_6$ alkyl group; iii) an optionally substituted, $C_3$-$C_7$ non-aromatic carbocycle; iv) an optionally substituted, 4-7 membered non-aromatic heterocycle; v) an optionally substituted phenyl group; vi) an optionally substituted 5-6 membered heteroaryl ring; or optionally, together with R and the nitrogen atom to which it is attached, form a 5-7 membered, optionally substituted non-aromatic heterocycle; and said alkyl group represented by $R^5$ is optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, —NRCO($C_1$-$C_4$ alkyl), —CONR($C_1$-$C_4$ alkyl), —NRCO$_2$($C_1$-$C_4$ alkyl), a $C_3$-$C_7$ non-aromatic carbocycle optionally substituted with one or more instances of $J^{E1}$, a 4-7 membered non-aromatic heterocycle optionally substituted with one or more instances of $J^{E1}$; and a phenyl optionally substituted with one or more instances of $J^{E1}$; and wherein each of said carbocycle, heterocycle, phenyl and heteroaryl represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —CO$_2$H, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

$R^1$, $R^2$, $R^3$, $Z^1$, $Z^2$, and $Z^3$ are each independently as described in the seventeenth or eighteenth set of variables above.

The remaining variables are each and independently as described above in any set of variables for Structural Formulae (IA) and (I).

In some embodiments, the variables of Structural Formulae (IA) and (I) are each and independently as described above in any set of variables, provided that: $R^4$ is:

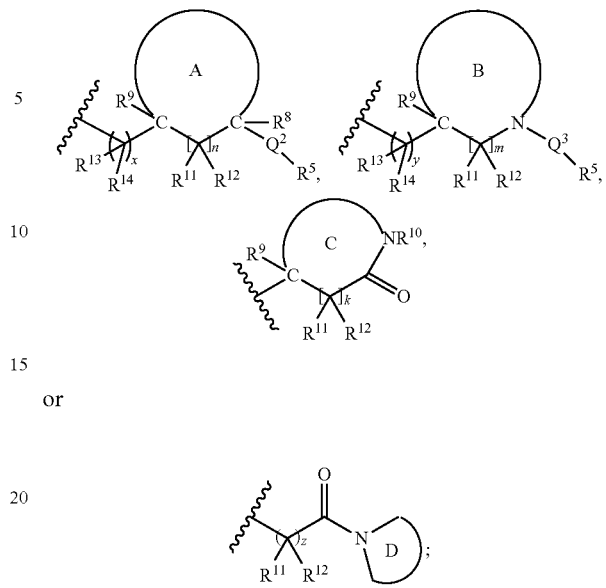

or

n and m are each independently 0 or 1 when rings A and B are 3-6-membered; or n and m are each independently 0, 1 or 2 when rings A and B are 7-10-membered; and provided that if $Y^1$ is a bond, then $R^5$ is neither —H nor a $C_1$-$C_6$ aliphatic group; and provided that if each $Q^2$ and $Q^3$ independently is a bond, then $R^5$ is neither —H nor a $C_1$-$C_6$ aliphatic group.

In another embodiment, the present invention is directed to the use of compounds represented by any one of the Structural Formulae II, III, IV, and V, depicted below, or pharmaceutically acceptable salts thereof, for any of the uses described above:

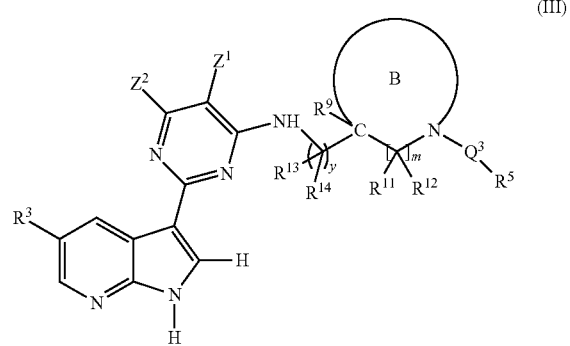

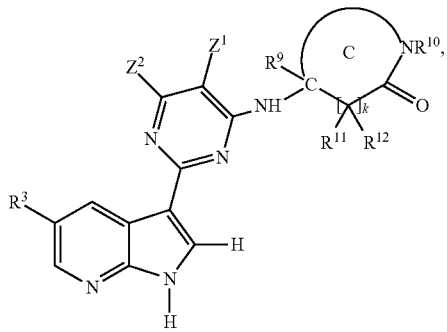

(IV)

and

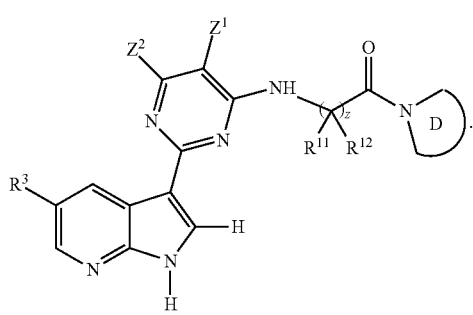

(V)

The first set of variables of Structural Formulae II-V is as follows:

$Z^1$ is —H, —F, —Cl, $C_1$-$C_4$ haloalkyl (e.g, —CF$_3$), $C_1$-$C_4$ alkyl, —O($C_1$-$C_4$ alkyl), or —CN.

$Z^2$ is —H, $C_1$-$C_6$ alkyl, —O($C_1$-$C_6$ alkyl), —NH$_2$, —NH($C_1$-$C_6$ alkyl), or —N($C_1$-$C_6$ alkyl)$_2$, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

$R^3$ is —H, —Cl, —F, —Br, —CN, —CF$_3$, —O($C_1$-$C_4$ alkyl), —OH, —NH$_2$, —NH($C_1$-$C_4$ alkyl), o' r —N($C_1$-$C_4$ alkyl)$_2$. Specifically, $R^3$ is —H, —F, —Cl, —CF$_3$, —NH$_2$, —NH(CH$_3$), or —N(CH$_3$)$_2$. Specifically, $R^3$ is —H, —Cl, or —F. Specifically, $R^3$ is —Cl.

Each R and R' are independently —H or $C_1$-$C_6$alkyl.

Definitions of rings A-D of formulae II-V, including specific variables, are each and independently as described above for the first set of variables of Structural Formulae (I) and (IA), wherein each of rings A-D is independently an optionally substituted, 4-7 membered ring.

Values of the remaining variables of Structural Formulae II-V, including specific values, and provisos are each and independently as described above for the first set of variables of Structural Formulae (I) and (IA).

A second set of variables of Structural Formulae II, III, IV and V is as follows:

$Z^1$ is —H, —F, —Cl, —CF$_3$, —CH$_3$, or —CN.

$Z^2$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

Values of the remaining variables of Structural Formulae II-V, including specific values, and provisos are each and independently as described above for the first set of variables of Structural Formulae II-V.

A third set of variables of Structural Formulae II, III, IV and V is as follows:

$Z^1$ is —H, —F or —CN.

$Z^2$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$" $C_4$ alkyl), and $C_1$-$C_4$ alkoxy.

Values of the remaining variables of Structural Formulae II-V, including specific values, and provisos are each and independently as described above for the first set of variables of Structural Formulae II-V.

A fourth set of variables of Structural Formulae II, III, IV and V is as follows:

$Z^1$ is —H, —F or —CN.

$Z^2$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

$R^3$ is —H, —Cl or —F.

Values of the remaining variables of Structural Formulae II-V, including specific values, and provisos are each and independently as described above for the first set of variables of Structural Formulae II-V.

A fifth set of variables of Structural Formulae II, III, IV and V is as follows:

$Z^1$ is —H, —F or —CN.

$Z^2$ is —H or $C_1$-$C_6$ alkyl optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

$R^3$ is —H, —Cl, —F, —CF$_3$, —NH$_2$, —NH(CH$_3$), or —N(CH$_3$)$_2$.

$R^6$ and $R^7$ are each independently —H or —CH$_3$, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

Each $R^9$ is independently —H or —CH$_3$.

$R^{11}$ and $R^{12}$ are each independently —H or —CH$_3$.

$R^{13}$ and $R^{14}$ are each independently —H or —CH$_3$, or together with the carbon atoms to which they are attached they form a cyclopropane ring.

Values of the remaining variables of Structural Formulae II-V, including specific values, and provisos are each and independently as described above for the first set of variables of Structural Formulae II-V.

A sixth set of variables of Structural Formulae II, III, IV and V is as follows:

$Z^1$ is —H, —F or —CN.

$Z^2$ is —H or an optionally substituted $C_1$-$C_6$ alkyl.

$R^3$ is —H, —Cl or —F.

$R^6$ and $R^7$ are each independently —H or —$CH_3$, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —$NH_2$, —NH($C_1$-$C_4$ alkyl) or —N($C_1$-$C_4$ alkyl)$_2$.

Each $R^9$ is independently —H or —$CH_3$.

$R^{11}$ and $R^{12}$ are each independently —H or —$CH_3$.

$R^{13}$ and $R^{14}$ are each independently —H or —$CH_3$, or together with the carbon atoms to which they are attached they form a cyclopropane ring.

Values of the remaining variables of Structural Formulae II-V, including specific values, and provisos are each and independently as described above for the first set of variables of Structural Formulae II-V.

In a seventh set of variables of Structural Formulae II-V, values for variables, except $R^6$, $R^7$, $R^8$, $R^9$, $R^{11}$, $R^{12}$, $R^{13}$, and $R^{14}$, of Structural Formulae II-V, including specific values, are each and independently as described above for the first, second, third, or fourth set of variables of Structural Formulae II-V; and $R^6$ and $R^7$ are each independently —H or —$C_1$-$C_4$ alkyl, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —$NH_2$, —NH($C_1$-$C_4$ alkyl) or —N($C_1$-$C_4$ alkyl)$_2$.

Each $R^9$ is independently —H or —$C_1$-$C_4$ alkyl.

$R^{11}$ and $R^{12}$ are each independently —H or —$C_1$-$C_4$ alkyl.

$R^{13}$ and $R^{14}$ are each independently —H or —$C_1$-$C_4$ alkyl, or together with the carbon atoms to which they are attached they form a cyclopropane ring.

In an eighth set of variables of Structural Formulae II-V, values for variables of Structural Formulae II-V, including specific values, are each and independently as described above for the first set of variables of Structural Formulae II-V.

It is provided that when $Q^2$-$R^5$ is —$OR^5$ or —NR'$R^5$, ring A is further substituted with one or more instances of $J^A$ other than —H.

It is provided that if $Q^3$ is —C(O)—, then $R^5$ is a substituted $C_1$-$C_6$ aliphatic group (e.g., $C_1$-$C_6$ alkyl group or $C_2$-$C_6$ alkenyl group); an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroaryl group. In one embodiment, the $C_1$-$C_6$ aliphatic group is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —S(O)$R^a$; —$SO_2R^a$; —$NR^bR^c$; —C(O)$R^b$; —C(O)$OR^b$; —OC(O)$R^b$; —NRC(O)$R^b$; —C(O)$NR^bR^c$; —NRC(O)$NR^bR^c$; —NRC(O)$OR^b$; —OCONR$^bR^c$; —C(O)$NRCO_2R^b$; —NRC(O)$NRCO_2R^b$; —C(O)NR(OR$^b$); —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In a ninth set of variables of Structural Formulae II-V, values for variables of Structural Formulae II-V, including specific values, and provisos are each and independently as described above in the first set of variables of Structural Formulae (I) and (IA).

A tenth set of variables of Structural Formulae II-V is as follows:

Each of $J^A$ and $J^B$ is independently selected from the group consisting of halogen, cyano, oxo, and $Q^1$-$R^5$; or optionally two $J^A$ and two $J^B$, respectively, together with the atom(s) to which they are attached, independently form a 5-7 membered ring that is optionally substituted with one or more instances of $J^{E1}$, and fused to the ring to which they are attached.

$Q^1$ is independently a bond, —O—, —S—, —NR—, —C(O)—, —$CO_2$—, —OC(O)—, —C(O)NR—, —C(O)NRC(O)O—, NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$N(R)—, —$NRSO_2NR$—, or —(C$R^6R^7)_p$—$Y^1$—.

$Q^2$ is independently a bond, —O—, —S—, —NR—, —C(O)—, —$CO_2$—, —OC(O)—, —C(O)NR—, —C(O)NRC(O)O—, NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$N(R)—, —$NRSO_2NR$—, or —(C$R^6R^7)_p$—$Y^1$—.

$Q^3$ is independently a bond, —C(O)—, —$CO_2$—, —C(O)NR—, —$SO_2$—, —$SO_2$N(R)—, —C(O)NRC(O)O— or —(C$R^6R^7)_p$—$Y^1$—.

$R^5$ is: i) —H; ii) a $C_1$-$C_6$ aliphatic group optionally substituted with one or more instances of $J^{C1}$; iii) a $C_3$-$C_8$ non-aromatic carbocycle, or 6-10 membered carbocyclic aryl group, each optionally and independently substituted with one or more instances of $J^{C1}$; or iv) a 4-8 membered non-aromatic heterocycle, or a 5-10 membered heteroaryl group, each optionally and independently substituted with one or more instances of $J^{D1}$.

Each of $J^{C1}$ and $J^{D1}$ is independently selected from the group consisting of halogen, cyano, oxo, $R^a$, —$OR^b$, —$SR^b$, —S(O)$R^a$, —$SO_2R^a$, —$NR^bR^c$, —C(O)$R^b$, —C(O)$OR^b$, —OC(O)$R^b$, —NRC(O)$R^b$, —C(O)$NR^bR^c$, —NRC(O)$NR^bR^c$, —NRC(O)$OR^b$, —OCONR$^bR^c$, —C(O)$NRCO_2R^b$, —NRC(O)$NRC(O)OR^b$, —C(O)NR(OR$^b$), —$SO_2NR^cR^b$, —$NRSO_2R^b$, and —$NRSO_2NR^cR^b$, or optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

Ring A is a $C_3$-$C_8$ non-aromatic carbocycle optionally and independently further substituted with one or more instances of $J^A$.

Values of the remaining variables of Structural Formulae II-V, including specific values, and provisos are each and independently as described above for the first, second, third, fourth, fifth, sixth, seventh, eighth, or ninth set of variables of Structural Formulae II-V.

In another embodiment, the present invention is directed to the use of compounds represented by the Structural Formula below XI(A) or XI(B), or a pharmaceutically acceptable salt thereof, for any of the uses described above.

XI(A)

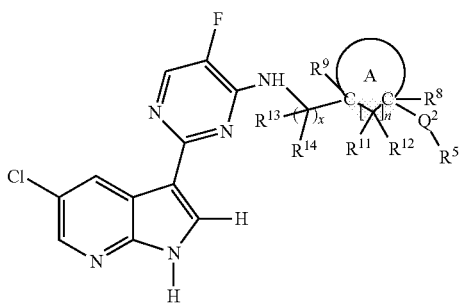

or

XI(B)

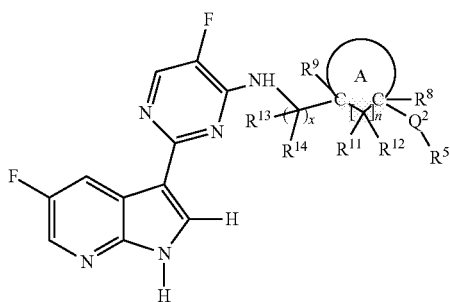

A first set of variables of Structural formulae XI(A) and XI(B) is as follows:

Ring A is a 5-7 membered, non-aromatic carbocyclic ring optionally further substituted with one or more substituents independently selected from the group consisting of halogen, cyano, hydroxy, oxo, $C_1$-$C_6$ alkyl, $C_2$-$C_6$ alkenyl, —$NH_2$, —NH($C_1$-$C_6$ alkyl), —N($C_1$-$C_6$ alkyl)$_2$, —O($C_1$-$C_6$ alkyl), —C(O)$NH_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —$CO_2R^b$; wherein each of said alkyl and alkenyl groups is optionally and independently substituted with one or more substituents independently selected from the group consisting of halogen, cyano, hydroxy, oxo, —$NH_2$, —NH ($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, ring A is a 5-7 membered, non-aromatic carbocyclic ring optionally further substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —$CO_2H$, and —$CO_2$($C_1$-$C_4$ alkyl), wherein each of said alkyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, ring A is a 5-7 membered carbocyclic ring optionally further substituted with one or more substituents independently selected from the group consisting of halogen, cyano, hydroxy, oxo, —$NH_2$, —NH ($C_1$-$C_2$ alkyl), —NH($C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —$CO_2H$, and —$CO_2$($C_1$-$C_4$ alkyl).

$R^6$ and $R^7$ are each independently —H or —$CH_3$, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —$NH_2$, —NH($C_1$-$C_4$ alkyl), or —N($C_1$-$C_4$ alkyl)$_2$.

Each $R^9$ is independently —H or —$CH_3$.

$R^{11}$ and $R^{12}$ are each independently —H or —$CH_3$.

$R^{13}$ and $R^{14}$ are each independently —H or —$CH_3$, or together with the carbon atoms to which they are attached they form a cyclopropane ring.

Each R and R' are independently —H or $C_1$-$C_6$ alkyl.

Values of the remaining variables of Structural formulae XI(A) and XI(B), including specific values, and provisos are each and independently as described above in the first set of variables of Structural Formulae (I) and (IA).

A second set of variables for Structural formulae XI(A) and XI(B) is as follows:

Values of Ring A, R, R', $R^6$, $R^7$, $R^8$, $R^9$, $R^{11}$, $R^{12}$, $R^{13}$ and $R^{14}$, including specific values, are each and independently as described above in the first set of variables of Structural formulae XI(A) and XI(B).

Variable x is 0 or 1 and variable n is 0 or 1.

Values of the remaining other variables of Structural formulae XI(A) and XI(B), including specific values, and provisos are each and independently as described above in the first set of variables of Structural Formulae (I) and (IA).

A third set of variables for Structural formulae XI(A) and XI(B) is as follows:

Values of Ring A, R, R', $R^6$, $R^7$, $R^8$, $R^9$, $R^{11}$, $R^{12}$, $R^{13}$, $R^{14}$, x and n, including specific values, are each and independently as described above in the second set of variables of Structural formulae XI(A) and XI(B).

$Q^2$ is —O—, —NR'—, —CO—, —$CO_2$—, —C(O)NR'—, —NRC(O)—, —NRC(O)NR—, —$NRCO_2$—, —OCONR'—, —$NRSO_2$—, —$SO_2NR'$—, or —$(CR^6R^7)_p$—$Y^1$—. Specifically, $Q^2$ is —O—, —NH—, —N($CH_3$)—, —C(O)—, —$CO_2$—, —C(O)NH—, —C(O)N($CH_3$)—, —NHC(O)—, —N($CH_3$)C(O)—, —NHC(O)NR'—, —N($CH_3$)C(O)NR'—, —$NHCO_2$—, —N($CH_3$)$CO_2$—, —OC(O)NR'—, —$NHSO_2$—, —N($CH_3$)$SO_2$—, —$SO_2NH$—, —$SO_2N(CH_3)$—, or —$(CR^6R^7)_p$—$Y^1$—.

Values of the remaining variables of Structural formulae XI(A) and XI(B), including specific values, and provisos are each and independently as described above in the first set of variables of Structural Formulae (I) and (IA).

A fourth set of variables for Structural formulae XI(A) and XI(B) is as follows:

Values of Ring A, $Q^2$, R, R', $R^6$, $R^7$, $R^8$, $R^9$, $R^{11}$, $R^{12}$, $R^{13}$, $R^{14}$, x and n, including specific values, are each and independently as described above in the third set of variables of Structural formulae XI(A) and XI(B).

$R^5$ is independently —H; ii) a $C_1$-$C_6$-aliphatic group (e.g., $C_1$-$C_6$-alkyl or $C_2$-$C_6$-alkenyl group) optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$.

Each of $J^{C1}$ and $J^{D1}$ is independently selected from the group consisting of halogen, cyano, oxo, $R^a$, —$OR^b$, —S(O)$R^a$—, —$SO_2R^a$, —$NHR^a$, —C(O)$R^b$, —C(O)$OR^b$, —OC(O)

$R^b$, —NHC(O)$R^b$, —C(O)NH$R^c$, —NHC(O)NH$R^c$, —NHC(O)O$R^b$, —OCONH$R^c$, —NHC(O)NHC(O)O$R^b$, —N(CH$_3$)$R^c$, —N(CH$_3$)C(O)$R^b$, —C(O)N(CH$_3$)$R^c$, —N(CH$_3$)C(O)NH$R^c$, —N(CH$_3$)C(O)O$R^b$, —OCON(CH$_3$)$R^c$, —C(O)NHCO$_2R^b$, —C(O)N(CH$_3$)CO$_2R^b$, —N(CH$_3$)C(O)NHC(O)O$R^b$, —NHSO$_2R^b$, —SO$_2$NH$R^b$, —SO$_2$N(CH$_3$)$R^b$, and —N(CH$_3$)SO$_2R^b$.

Values of the remaining variables of Structural formulae XI(A) and XI(B), including specific values, and provisos are each and independently as described above in the first set of variables of Structural Formulae (I) and (IA).

A fifth set of variables for structure Structural formulae XI(A) and XI(B) is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, are each and independently as described above in the fourth set of variables of Structural formulae XI(A) and XI(B).

Ring A is optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H, and —CO$_2$(C$_1$-C$_4$ alkyl), wherein each of said alkyl groups is optionally and independently substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural formulae XI(A) and XI(B), including specific values, and provisos are each and independently as described above in the first set of variables of Structural Formulae (I) and (IA).

A sixth set of variables for Structural formulae XI(A) and XI(B) is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, are each and independently as described above in the fifth set of variables of Structural formulae XI(A) and XI(B).

The group —[(C)$_{0-1}R^{13}R^{14}$]-ring A-Q$^2$-$R^5$ is independently selected from one of the depicted below:

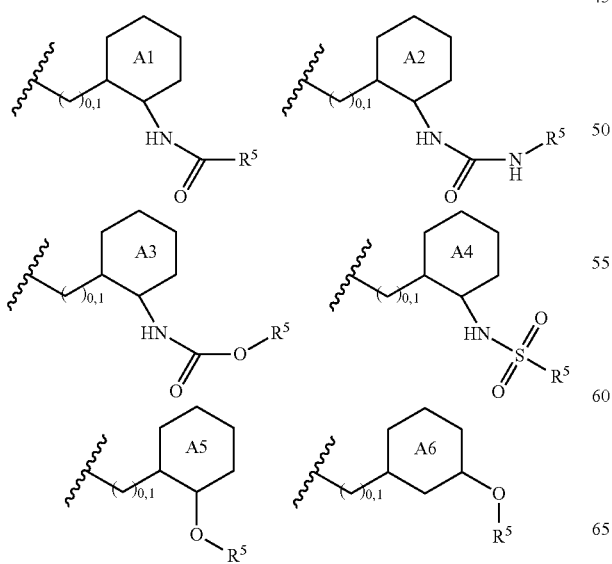

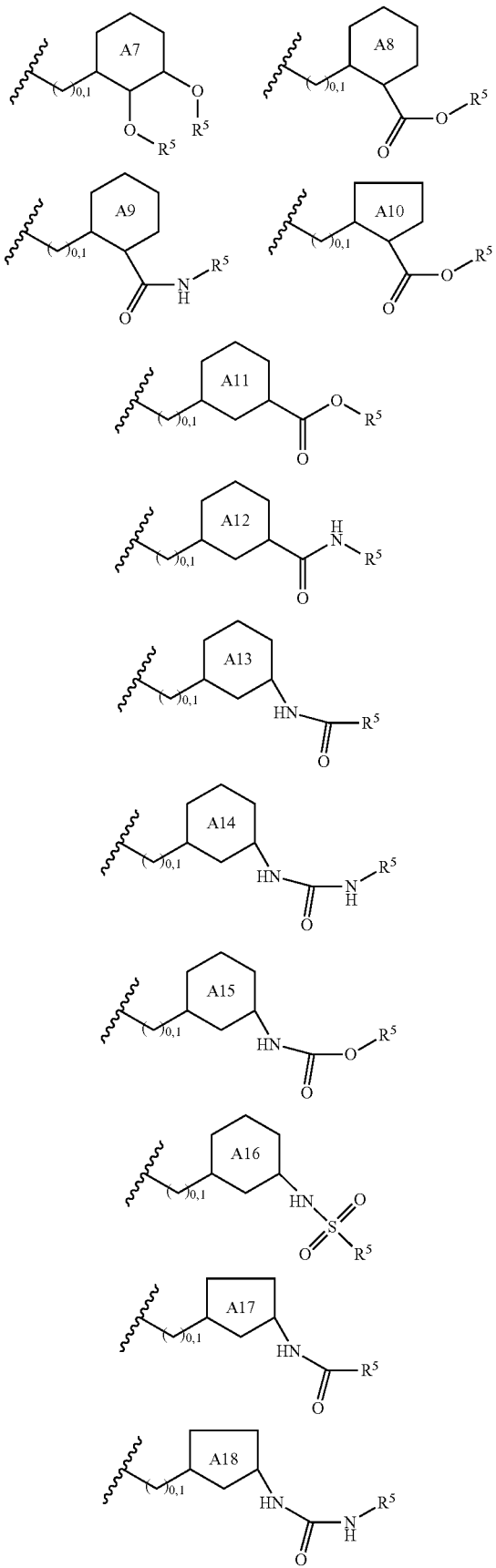

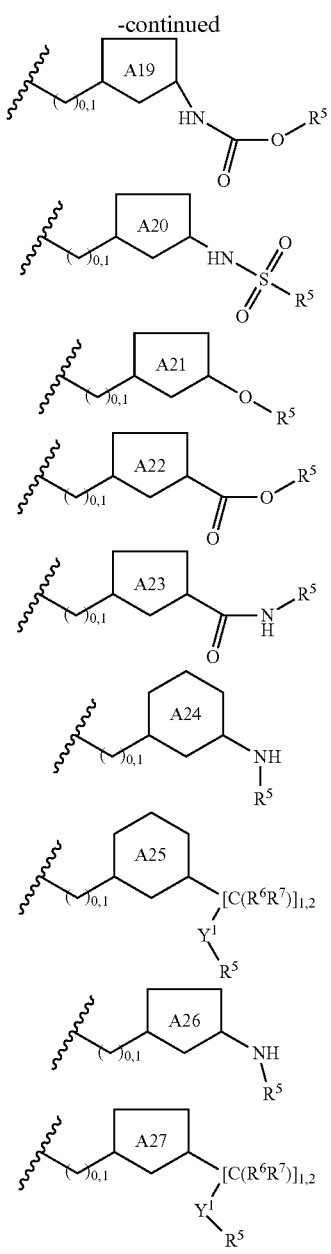

—NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), —CO$_2$H, C$_3$-C$_8$ non-aromatic carbocycle, phenyl, 4-8 membered non-aromatic heterocycle, and 5-6 membered heteroaryl; or iii) a C$_3$-C$_7$ non-aromatic carbocycle, a 4-7 membered non-aromatic heterocycle, a phenyl group, or a 5-6 membered heteroaryl ring, each of which is optionally and independently substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), and —CO$_2$H; wherein each of said alkyl groups for the substituents of the aliphatic group, carbocycle, heterocycle, phenyl and heteroaryl group represented by R$^5$ is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said carbocycle, phenyl, heterocycle, and heteroaryl for the substituents of the C$_1$-C$_6$-aliphatic group represented by R$^5$ is independently and optionally substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural formulae XI(A) and XI(B), including specific values, and provisos are each and independently as described above in the first set of variables of Structural Formulae (I) and (IA).

An eighth set of variables of Structural formulae XI(A) and XI(B) is as follows:

Values of Q$^2$, R, R', R$^5$, R$^6$, R$^7$, R$^8$, R$^9$, R$^{11}$, R$^{12}$, R$^{13}$, R$^{14}$, x and a including specific values, are each and independently as described above in the seventh set of variables of Structural formulae XI(A) and XI(B).

The group —[(C)$_{0-1}$R$^{13}$R$^{14}$]-ring A-Q$^2$-R$^5$ is independently selected from one of the depicted below

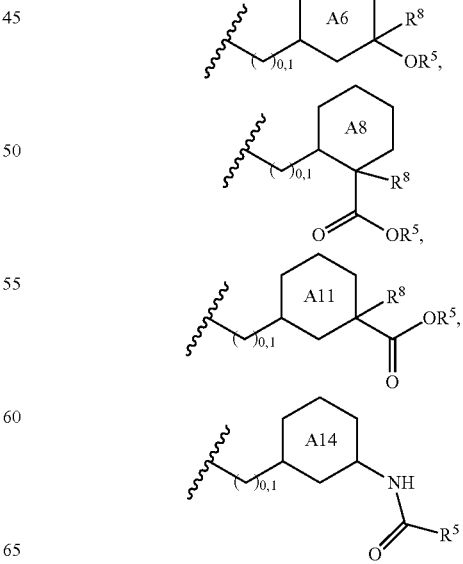

wherein each of rings A1-A27 is independently and optionally further substituted with one or more substituents. Suitable substituents are as described above for ring A in the first set of variables of Structural formulae XI(A) and XI(B).

Values of the remaining variables of Structural formulae XI(A) and XI(B), including specific values, and provisos are each and independently as described above in the first set of variables of Structural Formulae (I) and (IA).

A seventh set of variables of Structural formulae XI(A) and XI(B) is as follows:

Values of the group —[CR$^{13}$R$^{14}$]$_x$-ring A-Q$^2$-R$^5$, Q$^2$, R, R', R$^6$, R$^7$, R$^8$, R$^9$, R$^{11}$, R$^{12}$, R$^{13}$, R$^{14}$, x and n, including specific values, are each and independently as described above in the sixth set of variables of Structural formulae XI(A) and XI(B).

Each R$^5$ is independently: i) —H; ii) a C$_1$-C$_6$-aliphatic group optionally substituted with one or more substituents independently selected from the group consisting of halogen, cyano, hydroxy, oxo, C$_1$-C$_4$ alkyl, —O(C$_1$-C$_4$ alkyl), —NH$_2$,

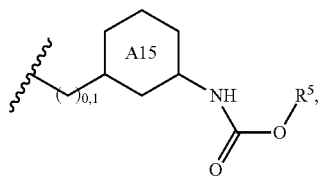

wherein each of rings A6, A8, A11, A14 and A15 is optionally and independently further substituted.

$R^8$ independently is halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

Values of the remaining variables of Structural formulae XI(A) and XI(B), including specific values, and provisos are each and independently as described above in the first set of variables of Structural Formulae (I) and (IA).

A ninth set of variables of Structural formulae XI(A) and XI(B) is as follows:

Values of the group —[$CR^{13}R^{14}$]$_x$-ring A-$Q^2$-$R^5$, $Q^2$, R, R', $R^6$, $R^7$, $R^8$, $R^9$, $R^{11}$, $R^{12}$, $R^{13}$, $R^{14}$, x and n, including specific values, are each and independently as described above in the eighth set of variables of Structural formulae XI(A) and XI(B).

$R^5$ is: i) —H; ii) an optionally substituted $C_1$-$C_6$ alkyl group; iii) an optionally substituted, $C_3$-$C_7$ non-aromatic carbocycle; or iv) an optionally substituted, 4-7 membered non-aromatic heterocycle. Each of said alkyl group represented by $R^5$ is optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, optionally substituted, $C_3$-$C_7$ non-aromatic carbocycle, and optionally substituted, 4-7 membered non-aromatic heterocycle. Each of said carbocycles and heterocycles represented by $R^5$, and referred to for the substituents of the $C_1$-$C_6$ alkyl group represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), and —CO$_2$H, wherein each of said alkyl groups (e.g., represented by $C_1$-$C_4$ alkyl, —O($C_1$-$C_4$ alkyl), —NH($C_1$-$C_4$ alkyl), —N($C_1$-$C_4$ alkyl)$_2$, —C(O)($C_1$-$C_4$ alkyl), —OC(O)($C_1$-$C_4$ alkyl), and —C(O)O($C_1$-$C_4$ alkyl)) is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

Values of the remaining variables of Structural formulae XI(A) and XI(B), including specific values, and provisos are each and independently as described above in the first set of variables of Structural Formulae (I) and (IA).

A tenth set of variables of Structural formulae XI(A) and XI(B) is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, are each and independently as described above in the seventh set of variables of Structural formulae XI(A) and XI(B).

The group —[(C)$_{0-1}R^{13}R^{14}$]-ring A-$Q^2$-$R^5$ is independently selected from one of the depicted below:

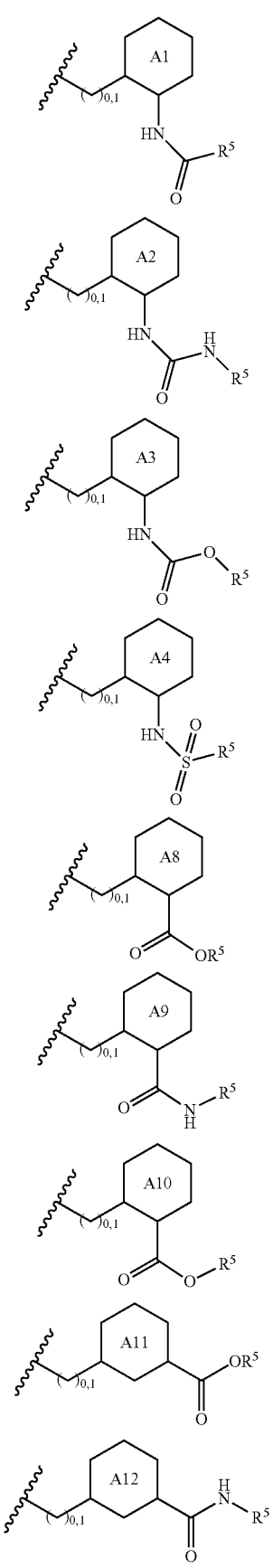

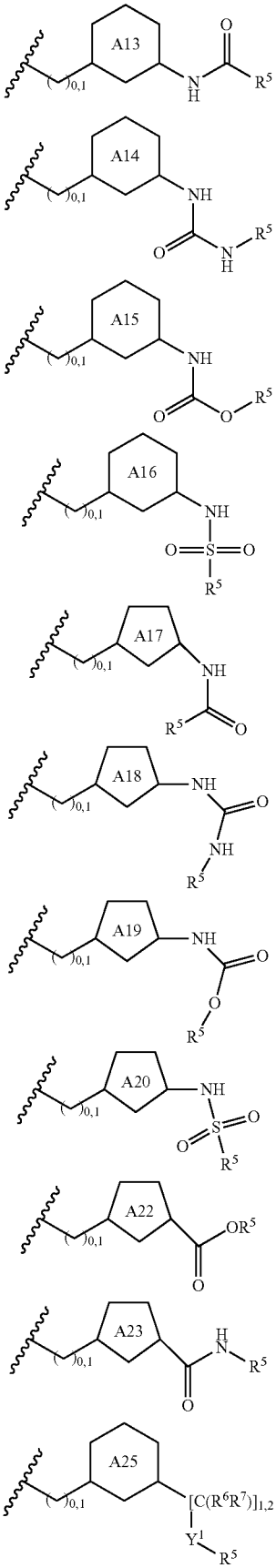

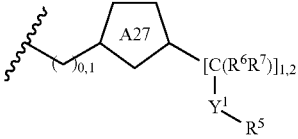

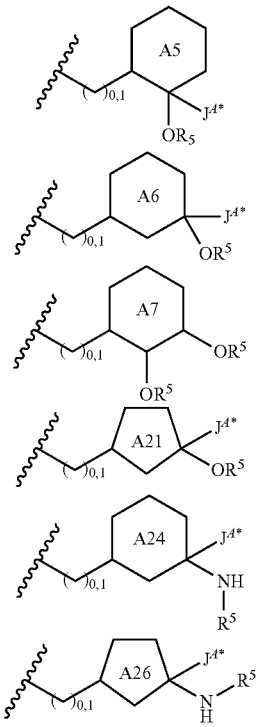

wherein each of rings A1-A4, A7-A20, A22, A23, A25 and A27 is independently and optionally further substituted. Suitable substituents are as described above for ring A in the first set of variables of Structural formulae XI(A) and XI(B).

Values of the remaining variables of Structural formulae XI(A) and XI(B), including specific values, and provisos are each and independently as described above in the first set of variables of Structural Formulae (I) and (IA).

An eleventh set of variables of Structural formulae XI(A) and XI(B) is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, are each and independently as described above in the seventh set of variables of Structural formulae XI(A) and XI(B).

The group —$[(C)_{0-1}R^{13}R^{14}]$-ring A-$Q^2$-$R^5$ is independently selected from one of the depicted below:

wherein each of rings A5-A7, A21, A24 and A26 is independently and optionally further substituted. Suitable substituents are as described above for ring A in the first set of variables of Structure Formulae XI(A) and XI(B).

Values of the remaining variables of Structural formulae XI(A) and XI(B), including specific values, and provisos are each and independently as described above in the first set of variables of Structural Formulae (I) and (IA).

In a twelfth set of variables of Structural formulae XI(A) and XI(B), values of the variables for Structural formulae XI(A) and XI(B), including specific values, and provisos are each and independently as described above in the first set of variables of Structural Formulae (I) and (IA).

In a thirteenth set of variables of Structural Formulae XI(A) and XI(B), values of the variables for Structural Formulae XI(A) and XI(B), including specific values, are each and independently as described above in the sixteenth set of variables of Structural Formulae (I) and (IA), or in the tenth set of variables of Structural Formulae II-V.

In another embodiment, the present invention is directed to the use of compounds represented by Structural Formula below XII(A) or XII(B), or a pharmaceutically acceptable salt thereof, for any of the uses described above:

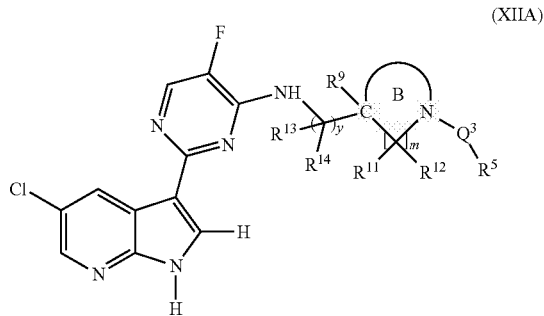

(XIIA)

or

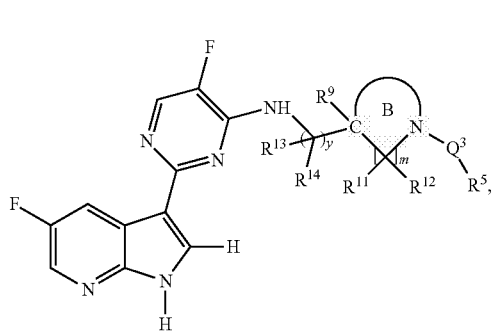

(XIIB)

A first set of variables of Structural Formulae XII(A) and XII(B) is as follows:

Ring B is a 4-7 membered, non-aromatic, heterocyclic ring optionally further substituted with one or more substituents independently selected from the group consisting of halogen, cyano, hydroxy, oxo, $C_1$-$C_6$ alkyl, $C_2$-$C_6$ alkenyl, —$NH_2$, —NH($C_1$-$C_6$ alkyl), —N($C_1$-$C_6$ alkyl)$_2$, —O($C_1$-$C_6$ alkyl), —C(O)$NH_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —$CO_2R^b$; wherein each of said alkyl and alkenyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, Ring B is optionally further substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —$CO_2H$, and —$CO_2$($C_1$-$C_4$ alkyl), wherein each of said alkyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, Ring B is optionally further substituted with one or more substituents independently selected from the group consisting of halogen, cyano, hydroxy, oxo, —$NH_2$, —NH($C_1$-$C_2$ alkyl), —NH($C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —$CO_2H$, and —$CO_2$($C_1$-$C_4$ alkyl).

$R^6$ and $R^7$ are each independently —H or —$CH_3$, or together with the carbon atoms to which they are attached they form a cyclopropane ring.

$R^9$ is —H or —$CH_3$.

$R^{11}$ and $R^{12}$ are each independently —H or —$CH_3$.

$R^{13}$ and $R^{14}$ are each independently —H or —$CH_3$, or together with the carbon atoms to which they are attached they form a cyclopropane ring.

Each R and R' are independently —H or $C_1$-$C_6$ alkyl.

Values of the remaining variables of Structural Formulae XII(A) and XII(B), including specific values, and provisos are each and independently as described above in the first set of variables of Structural Formulae (I) and (IA).

A second set of variables of Structural Formulae XII(A) and XII(B) is as follows:

Values of Ring B, R, R', $R^6$, $R^7$, $R^9$, $R^{11}$, $R^{12}$, $R^{13}$ and $R^{14}$, including specific values, are each and independently as described above in the first set of variables of Structural Formulae XII(A) and XII(B).

Variable y=0 or 1.

Values of the remaining variables of Structural Formulae XII(A) and XII(B), including specific values, and provisos are each and independently as described above in the first set of variables of Structural Formulae (I) and (IA).

A third set of variables of Structural Formulae XII(A) and XII(B) is as follows:

Values of Ring B, R, R', $R^6$, $R^7$, $R^9$, $R^{11}$, $R^{12}$, $R^{13}$ and $R^{14}$ and y, including specific values, are each and independently as described above in the second set of variables of Structural Formulae XII(A) and XII(B).

$Q^3$ is independently —C(O)—, —$CO_2$—, —C(O)NH—, —C(O)N($CH_3$)—, —C(O)NHC(O)O—, —C(O)N($CH_3$)C(O)O—, —$SO_2$—, —$SO_2$NH—, —$SO_2$N($CH_3$)—, or —($CR^6R^7$)$_p$—$Y^1$—.

Values of the remaining variables of Structural Formulae XII(A) and XII(B), including specific values, and provisos are each and independently as described above in the first set of variables of Structural Formulae (I) and (IA).

A fourth set of variables of Structural Formulae XII(A) and XII(B) is as follows:

Values of Ring B, $Q^3$, R, R', $R^6$, $R^7$, $R^9$, $R^{11}$, $R^{12}$, $R^{13}$ and $R^{14}$ and y a including specific values, are each and independently as described above in the third set of variables of Structural Formulae XII(A) and XII(B).

$R^5$ is independently i) —H; ii) $C_1$-$C_6$-aliphatic group (e.g., $C_1$-$C_6$-alkyl or $C_2$-$C_6$-alkenyl group) optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$.

Each of $J^{C1}$ and $J^{D1}$ is independently selected from the group consisting of halogen, cyano, oxo, $R^a$, —$OR^b$, —$SR^b$, —$SOR^a$, —$SO_2R^a$, —$NHR^c$, —C(O)$R^b$, —C(O)O$R^b$, —OC(O)$R^b$, —NHC(O)$R^b$, —C(O)NH$R^c$, —NHC(O)NH$R^c$, —NHC(O)OR$^b$, —OCONHR$^c$, —NHC(O)NHC(O)OR$^b$, —N(CH$_3$)R$^c$, —N(CH$_3$)C(O)R$^b$, —C(O)N(CH$_3$)R$^a$, —N(CH$_3$)C(O)NHR$^c$, —N(CH$_3$)C(O)OR$^b$, —OCON(CH$_3$)R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N(CH$_3$)R$^b$, and —N(CH$_3$)SO$_2$R$^b$.

Values of the remaining variables of Structural Formulae XII(A) and XII(B), including specific values, and provisos are each and independently as described above in the first set of variables of Structural Formulae (I) and (IA).

A fifth set of variables of Structural Formulae XII(A) and XII(B) is as follows:

Values of Ring B, Q$^3$, R, R', R$^5$, R$^6$, R$^7$, R$^9$, R$^{11}$, R$^{12}$, R$^{13}$ and R$^{14}$ and y a including specific specific values, are each and independently as described above in the fourth set of variables of Structural Formulae XII(A) and XII(B).

Ring B is optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H, and —CO$_2$(C$_1$-C$_4$ alkyl), wherein each of said alkyl groups is optionally and independently substituted with one or more substituents independently selected from the group consisting of halogen, cyano, hydroxy, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae XII(A) and XII(B), including specific values, and provisos are each and independently as described above in the first set of variables of Structural Formulae (I) and (IA).

A sixth set of variables of Structural Formulae XII(A) and XII(B) is as follows:

Values of Ring B, Q$^3$, R, R', R$^5$, R$^6$, R$^7$, R$^9$, R$^{11}$, R$^{12}$, R$^{13}$ and R$^{14}$ and y a including specific and y, including specific values, are each and independently as described above in the fifth set of variables of Structural Formulae XII(A) and XII(B).

Ring B is independently selected from one of the structures depicted below:

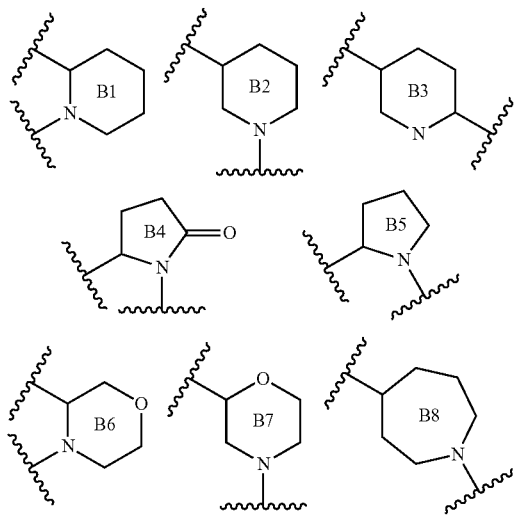

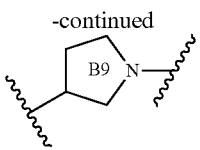

wherein each of rings B1-B9 is optionally and independently substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H and —CO$_2$(C$_1$-C$_4$ alkyl), wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, each of rings B1 to B9 is optionally and independently substituted with one or more substituents independently selected from the group consisting of halogen, cyano, hydroxy, oxo, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

Values of the remaining variables of Structural Formulae XII(A) and XII(B), including specific values, and provisos are each and independently as described above in the first set of variables of Structural Formulae (I) and (IA).

A seventh set of variables of Structural Formulae XII(A) and XII(B) is as follows:

Values of Ring B, Q$^3$, R, R', R$^5$, R$^6$, R$^7$, R$^9$, R$^{11}$, R$^{12}$, R$^{13}$ and R$^{14}$ and y a including specific values, are each and independently as described above in the sixth set of variables of Structural Formulae XII(A) and XII(B).

Each R$^5$ is independently: i) —H; ii) a C$_1$-C$_6$-aliphatic group optionally substituted with one or more substituents independently selected from the group consisting of halogen, cyano, hydroxy, oxo, C$_1$-C$_4$ alkyl, —O(C$_1$-C$_4$alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), —CO$_2$H, C$_3$-C$_8$ non-aromatic carbocycle, phenyl, 4-8 membered non-aromatic heterocycle, and 5-6 membered heteroaryl; or iii) a C$_3$-C$_7$ non-aromatic carbocycle, a 4-7 membered non-aromatic heterocycle, a phenyl group, or a 5-6 membered heteroaryl ring, each of which is optionally and independently substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), and —CO$_2$H; wherein each of said alkyl groups for the substituents of the aliphatic group, carbocycle, heterocycle, phenyl and heteroaryl group represented by R$^5$ is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said carbocycle, phenyl, heterocycle, and heteroaryl for the substituents of the C$_1$-C$_6$-aliphatic group represented by R$^5$ is independently and optionally substituted with one or more substituents independently selected from the group consisting of halogen, cyano, hydroxy, oxo, C$_1$-C$_4$ alkyl, —NH$_2$, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy.

Values of the remaining variables of Structural Formulae XII(A) and XII(B), including specific values, and provisos are each and independently as described above in the first set of variables of Structural Formulae (I) and (IA).

An eighth set of variables of Structural Formulae XII(A) and XII(B) is as follows:

Values of Q³, R, R', R⁵, R⁶, R⁷, R⁹, R¹¹, R¹², R¹³ and R¹⁴ and y a including specific values, are each and independently as described above in the seventh set of variables of Structural Formulae XII(A) and XII(B).

The group (ring B)-Q³-R⁵ is

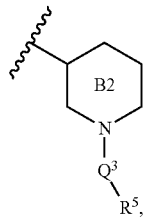

wherein ring B2 is optionally and independently further substituted with one or more substituents independently selected from the group consisting of halogen, cyano, hydroxy, oxo, —NH₂, —NH(C₁-C₂ alkyl), —NH(C₁-C₂ alkyl)₂, C₁-C₂ alkyl, C₁-C₂ haloalkyl, C₁-C₂ hydroxyalkyl, C₂-C₄ alkoxyalkyl, C₁-C₂ alkoxy, C₁-C₂ hydroxyalkoxy, C₁-C₂ haloalkoxy, C₂-C₄ alkoxyalkoxy, —CO₂H, and —CO₂(C₁-C₄ alkyl).

Values of the remaining variables of Structural Formulae XII(A) and XII(B), including specific values, and provisos are each and independently as described above in the first set of variables of Structural Formulae (I) and (IA).

A ninth set of variables of Structural Formulae XII(A) and XII(B) is as follows:

Values of the group (ring B)-Q³-R⁵, Q³, R, R', R⁶, R⁷, R⁹, R¹¹, R¹², R¹³ and R¹⁴ and y, including specific values, are each and independently as described above in the eighth set of variables of Structural Formulae XII(A) and XII(B).

R⁵ is: i) —H; ii) an optionally substituted C₁-C₆ alkyl group; iii) an optionally substituted, C₃-C₇ non-aromatic carbocycle; or iv) an optionally substituted, 4-7 membered non-aromatic heterocycle, wherein said alkyl group represented by R⁵ is optionally substituted with one or more substituents independently selected from the group consisting of halogen, cyano, hydroxy, oxo, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), C₁-C₄ alkoxy, optionally substituted, C₃-C₇ non-aromatic carbocycle, and optionally substituted, 4-7 membered non-aromatic heterocycle. Each of said carbocycles and heterocycles represented by R⁵, and referred to for the substituents of the C₁-C₆ alkyl group represented by R⁵ is independently and optionally substituted with one or more substituents independently selected from the group consisting of halogen, cyano, hydroxy, oxo, C₁-C₄ alkyl, —O(C₁-C₄alkyl), —NH₂, —NH(C₁-C₄ alkyl), —N(C₁-C₄ alkyl)₂, —C(O)(C₁-C₄ alkyl), —OC(O)(C₁-C₄ alkyl), —C(O)O(C₁-C₄ alkyl) and —CO₂H, wherein each of said alkyl groups is optionally and independently substituted with one or more substituents independently selected from the group consisting of halogen, cyano, hydroxy, oxo, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy.

Values of the remaining variables of Structural Formulae XII(A) and XII(B), including specific values, and provisos are each and independently as described above in the first set of variables of Structural Formulae (I) and (IA).

In a tenth set of variables of Structural Formulae XII(A) and XII(B), values of the variables for Structural Formulae XII(A) and XII(B), including specific values, are each and independently as described above in the first set of variables of Structural Formulae (I) and (IA).

In an eleventh set of variables of Structural Formulae XII (A) and XII(B), values of the variables for Structural Formulae XII(A) and XII(B), including specific values, are each and independently as described above in the sixteenth set of variables of Structural Formulae (I) and (IA), or in the tenth set of variables of Structural Formulae II-V.

In another embodiment, the present invention is generally directed to the use of compounds represented by Structural Formula below XIII, or a pharmaceutically acceptable salt thereof, for any of the uses described above.

(XIII)

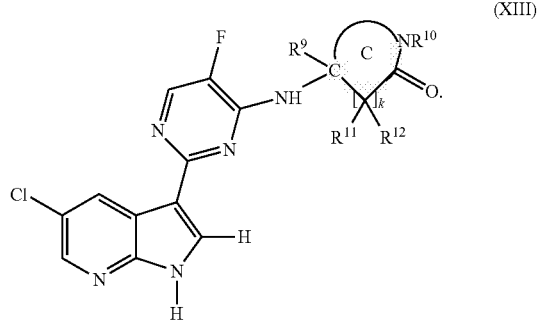

A first set of variables of Structural Formula XIII is as follows:

Ring C is a 5-7 membered, non-aromatic, heterocyclic ring optionally further substituted with one or more substituents independently selected from the group consisting of halogen, cyano, hydroxy, C₁-C₆ alkyl, C₂-C₆ alkenyl, —NH₂, —NH (C₁-C₆ alkyl), —N(C₁-C₆ alkyl)₂, —O(C₁-C₆ alkyl), —C(O) NH₂, —C(O)NH(C₁-C₆ alkyl), —C(O)N(C₁-C₆ alkyl)₂, —C(O)(C₁-C₆-alkyl), —OC(O)(C₁-C₆ alkyl), —NHC(O) (C₁-C₆ alkyl), —N(C₁-C₆ alkyl)C(O)(C₁-C₆ alkyl), and —CO₂Rᵇ; wherein each of said alkyl and alkenyl groups is optionally and independently substituted with one or more substituents independently selected from the group consisting of halogen, cyano, hydroxy, oxo, C₁-C₄ alkyl, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy. Specifically, ring C is optionally further substituted with one or more substituents independently selected from the group consisting of halogen, cyano, hydroxy, C₁-C₄ alkyl, —O(C₁-C₄ alkyl), —NH₂, —NH(C₁-C₄ alkyl), —N(C₁-C₄ alkyl)₂, —C(O)(C₁-C₄ alkyl), —CO₂H, and —CO₂(C₁-C₄ alkyl), wherein each of said alkyl groups is optionally and independently substituted with one or more substituents independently selected from the group consisting of halogen, cyano, hydroxy, oxo, C₁-C₄ alkyl, —NH₂, —NH(C₁-C₄ alkyl), —N(C₁-C₄ alkyl)₂, —OCO(C₁-C₄ alkyl), —CO(C₁-C₄ alkyl), —CO₂H, —CO₂(C₁-C₄ alkyl), and C₁-C₄ alkoxy. Specifically, ring C is optionally further substituted with one or more substituents independently selected from the group consisting of halogen, cyano, hydroxy, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

R$^6$ and R$^7$ are each independently —H or —CH$_3$, or together with the carbon atoms to which they are attached they form a cyclopropane ring.

R$^9$ is —H or —CH$_3$.

R$^{11}$ and R$^{12}$ are each independently —H or —CH$_3$.

Each R and R' are independently —H or C$_1$-C$_6$ alkyl.

Values of the remaining variables of Structural Formula XIII, including specific values, and provisos are each and independently as described above in the first set of variables of Structural Formulae (I) and (IA).

A second set of variables of Structural Formula XIII is as follows:

Values of Ring C, R, R', R$^6$, R$^7$, R$^9$, R$^{11}$ and R$^{12}$, including specific values, are each and independently as described above in the first set of variables of Structural Formula XIII.

R$^{10}$ is —H or C$_1$-C$_6$-alkyl.

Values of the remaining variables of Structural Formula XIII, including specific values, and provisos are each and independently as described above in the first set of variables of Structural Formulae (I) and (IA).

A third set of variables of Structural Formula XIII is as follows:

Values of Ring C, R, R', R$^6$, R$^7$, R$^9$, R$^{11}$ and R$^{12}$, including specific values, are each and independently as described above in the first set of variables of Structure Formula XIII.

Ring C is a 5-7 membered, non-aromatic, heterocyclic group optionally further substituted with one or more substituents independently selected from the group consisting of halogen, cyano, hydroxy, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H and —CO$_2$(C$_1$-C$_4$ alkyl), wherein each of said alkyl groups is optionally and independently substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formula XIII, including specific values, and provisos are each and independently as described above in the first set of variables of Structural Formulae (I) and (IA).

A fourth set of variables of Structural Formula XIII is as follows:

Values of Ring C, R, R', R$^6$, R$^7$, R$^9$, R$^{11}$ and R$^{12}$, including specific values, are each and independently as described above in the second set of variables of Structure Formula XIII.

Ring C is independently selected from:

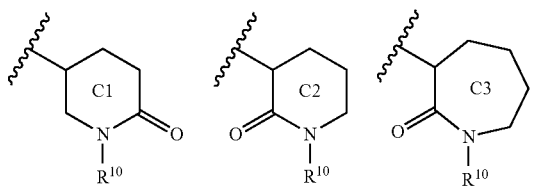

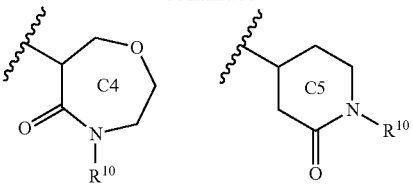

wherein each of rings C1-C5 is optionally and independently substituted. Suitable substituents are as described above for ring C in the first set of variables of Structural Formula XIV.

Values of the remaining variables of Structural Formula XIII, including specific values, and provisos are each and independently as described above in the first set of variables of Structural Formulae (I) and (IA).

In a fifth set of variables of Structural Formula XIII, values of the variables for Structural Formula XIII, including specific values, and provisos are each and independently as described above in the first set of variables of Structural Formulae (I) and (IA).

In another embodiment, the present invention is generally directed to the use of compounds represented by Structural Formula below XIV, or a pharmaceutically acceptable salt thereof for any of the uses described above.

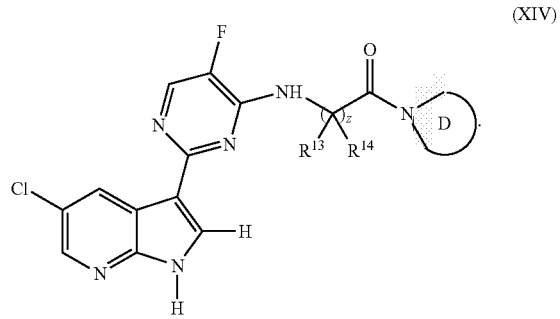

(XIV)

A first set of variables of Structural Formula XIV is as follows:

Ring D is 4-7 membered, non-aromatic, heterocyclic ring optionally substituted with one or more substituents independently selected from the group consisting of halogen, cyano, hydroxy, oxo, C$_1$-C$_6$ alkyl, C$_2$-C$_6$ alkenyl, —NH$_2$, —NH(C$_1$-C$_6$ alkyl), —N(C$_1$-C$_6$ alkyl)$_2$, —O(C$_1$-C$_6$ alkyl), —C(O)NH$_2$, —C(O)NH(C$_1$-C$_6$ alkyl), —C(O)N(C$_1$-C$_6$ alkyl)$_2$, —C(O)(C$_1$-C$_6$-alkyl), —OC(O)(C$_1$-C$_6$ alkyl), —NHC(O)(C$_1$-C$_6$ alkyl), —N(C$_1$-C$_6$ alkyl)C(O)(C$_1$-C$_6$ alkyl), and —CO$_2$R$^b$; wherein each of said alkyl and alkenyl groups is optionally and independently substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, ring D is optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H and —CO$_2$(C$_1$-C$_4$ alkyl), wherein each of said alkyl groups is optionally and independently substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-

$C_4$ alkyl), —CO($C_1$-$C_4$ alkyl), —$CO_2H$, —$CO_2$($C_1$-$C_4$ alkyl), and $C_1$-$C_4$ alkoxy. Specifically, ring D is optionally further substituted with one or more substituents independently selected from the group consisting of halogen, cyano, hydroxy, oxo, —$NH_2$, —NH($C_1$-$C_2$ alkyl), —N($C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —$CO_2H$, and —$CO_2$($C_1$-$C_4$ alkyl).

$R^6$ and $R^7$ are each independently —H or —$CH_3$, or together with the carbon atoms to which they are attached they form a cyclopropane ring.

$R^{13}$ and $R^{14}$ are each independently —H or —$CH_3$, or together with the carbon atoms to which they are attached they form a cyclopropane ring.

Each of R and R' are independently —H or $C_1$-$C_6$ alkyl.

Values of the remaining variables of Structural Formula XIV, including specific values, and provisos are each and independently as described above in the first set of variables of Structural Formulae (I) and (IA).

A second set of variables of Structural Formula XIV is as follows:

Values for Ring D, R, R', $R^6$, $R^7$, $R^{13}$ and $R^{14}$, including specific values, are each and independently as described above in the first set of variables of Structural Formula XIV.

Value z is 1.

Values of the remaining variables of Structural Formula XIV, including specific values, and provisos are each and independently as described above for the first set of variables of Structural Formulae (I) and (IA).

A third set of variables of Structural Formula IV is as follows:

Values for z, R, R', $R^6$, $R^7$, $R^{13}$ and $R^{14}$, including specific values, are each and independently as described above in the second set of variables of Structural Formula XIV.

Ring D is independently selected from the group consisting of

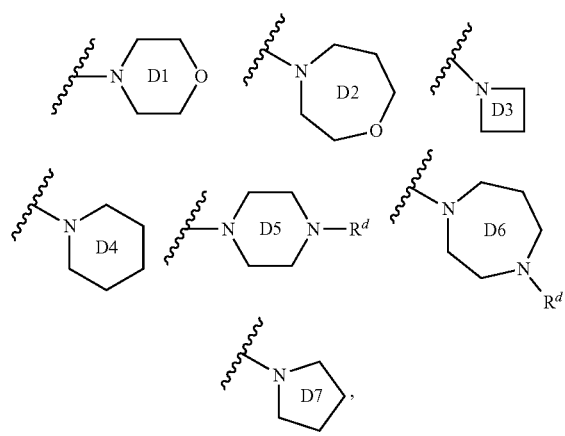

wherein each of rings D1-D7 is optionally and independently substituted. Suitable substituents are as described above for ring D in the first set of variables of Structural Formula XIV.

Each $R^d$ is independently —H, $C_1$-$C_6$ alkyl or —C(O)($C_1$-$C_6$ alkyl), wherein each of said alkyl moiety is optionally and independently substituted with one or more groups selected from halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, each $R^d$ is independently —H or $C_1$-$C_6$ alkyl optionally and independently substituted with one or more groups selected from halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Values of the remaining variables of Structural Formula XIV, including specific values, and provisos are each and independently as described above for the first set of variables of Structural Formulae (I) and (IA).

In a fourth set of variables of Structural Formula XIV, values of the variables for Structural Formula XIV, including specific values, and provisos are each and independently as described above in the first set of variables of Structural Formulae (I) and (IA).

In another embodiment, the compounds of Structural Formulae I-IV and XI-XIV, and pharmaceutically acceptable salts thereof, are independently as described above; and provided that, where applicable, if $Y^1$ is a bond, then $R^5$ is neither —H, nor an unsubstituted $C_1$-$C_6$ aliphatic group. Specifically, if $Y^1$ is a bond, then $R^5$ is a substituted $C_1$-$C_6$ aliphatic group; an optionally substituted $C_3$-$C_8$ non-aromatic carbocycle; an optionally substituted, 6-10-membered carbocyclic aryl group; an optionally substituted, 4-8 membered non-aromatic heterocycle; and an optionally substituted, 5-10 membered heteroary group. Specifically, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR); —$SR^b$; —S(O)$R^a$; —$SO_2R^a$; —$NR^bR^c$; —C(O)$R^b$; —C(O)$OR^b$; —OC(O)$R^b$; —NRC(O)$R^b$; —C(O)$NR^bR^c$; —NRC(O)$NR^bR^c$; —NRC(O)$OR^b$; —OCONR$^b$R$^c$; —C(O)$NRCO_2R^b$; —NRC(O)$NRCO_2R^b$; —C(O)NR(O$R^b$); —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In yet another embodiment, the compounds of Structural Formulae IA-IV and XI-XIV, and pharmaceutically acceptable salts thereof, are independently as described above; and provided that, where applicable, if $Q^2$ is a bond, then $R^5$ is neither —H nor a $C_1$-$C_6$ aliphatic group; and provided that if $Q^3$ is a bond, then $R^5$ is neither —H nor a $C_1$-$C_6$ aliphatic group. Specifically, if $Q^2$ and $Q^3$ are each and independently a bond, then $R^5$ is an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group. Specifically, if $Q^2$ and $Q^3$ are each and independently a bond, then $R^5$ is an optionally substituted $C_3$-$C_8$ non-aromatic carbocycle; or an optionally substituted, 4-8 membered non-aromatic heterocycle.

In yet another embodiment, the compounds are represented by Structural Formula (I), or pharmaceutically acceptable salts thereof, wherein each variables of the formulae are independently as described above; and wherein:

$R^4$ is:

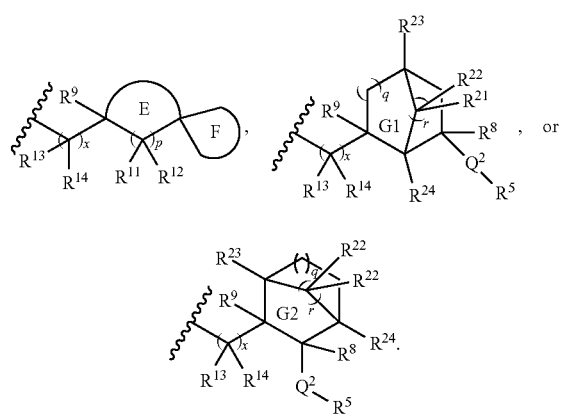

Ring E is a $C_4$-$C_8$ non-aromatic carbocycle optionally further substituted with one or more instances of $J^4$.

Rings F is a 4-8 membered non-aromatic heterocycle optionally substituted with one or more instances of $J^{E1}$.

Each of rings G1 and G2 is independently a 5-10 membered non-aromatic bridged carbocycle optionally substituted with one or more instances of $J^4$.

$Q^2$ is independently bond, —O—, —S—, —NR—, —C(O)—, —C(=NR)—, —$CO_2$—, —OC(O)—, —C(O)NR—, —C(O)NRC(O)O—, NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$NR'—, —$NRSO_2$NR'—, or —$(CR^6R^7)_p$—$Y^1$—.

$R^5$ is: i) —H; ii) an optionally substituted $C_1$-$C_6$ alkyl group; iii) an optionally substituted, $C_3$-$C_7$ non-aromatic carbocycle; or iv) an optionally substituted, 4-7 membered non-aromatic heterocycle; or optionally, together with R and the nitrogen atom to which it is attached, form a 5-7 membered, optionally substituted non-aromatic heterocycle. The alkyl group represented by $R^5$ is optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkoxy, an optionally substituted, $C_3$-$C_7$ non-aromatic carbocycle, and an optionally substituted, 4-7 membered non-aromatic heterocycle; wherein each of said carbocycles and heterocycles represented by $R^5$, and referred to for the substituents of the $C_1$-$C_6$ alkyl group represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —$CO_2$H, wherein each of said alkyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Each of $R^8$ and $R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —$NH_2$, —NH($C_1$-$C_4$ alkyl), or —N($C_1$-$C_4$ alkyl)$_2$.

$R^{11}$, $R^{12}$, $R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or optionally, $R^{13}$ and $R^{14}$, together with the carbon atom to which they are attached, form a cyclopropane ring, optionally substituted with one or more instances of methyl.

$R^{21}$, $R^{22}$, $R^{23}$ and $R^{24}$ are each independently —H, halogen, —OH, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

p and q are each independently 0, 1 or 2.

x is 0, 1 or 2.

r is 1 or 2.

Values of the remaining variables of Structural formula I, including specific values, and provisos are each and independently as described above in any one of the first through fifteenth sets of variables of Structural Formula I.

In yet another embodiment, the compounds represented by Structural Formula (I) or pharmaceutically acceptable salts thereof are independently as described above in the preceding paragraph; and ring F is selected from any one of rings F1-F6:

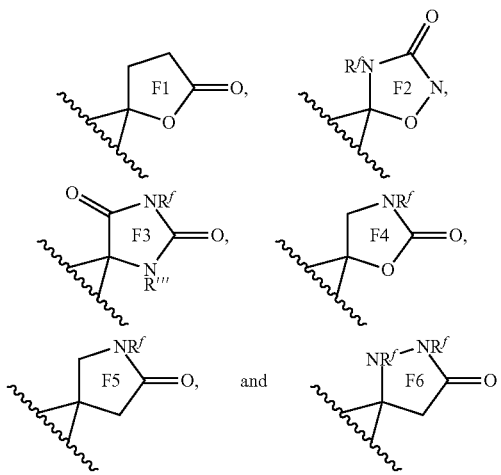

each of rings F1-F6 optionally and independently substituted; and each $R^f$ is independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy.

In yet another embodiment, the compounds represented by Structural Formula (XIA) or (XIB), or pharmaceutically acceptable salts thereof are as described above; and the group —$[C(R^{13}R^{14})]_x$-ring A-$Q^2$-$R^5$ is independently:

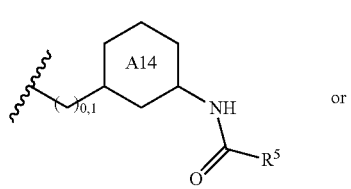

or

-continued

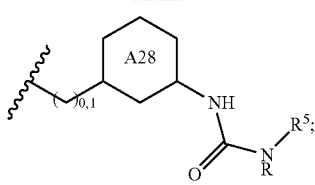

wherein:
each of rings A14 and A28 is optionally and independently further substituted; and
values of the remaining variables of Structural Formulae (XIA) and (XIB), including specific values, and provisos are each and independently as described above in any one of the first through eleventh sets of variables of Structural Formulae (XIA) and (XIB).

In yet another embodiment, the compounds represented by Structural Formula (XIA) or (XIB), or pharmaceutically acceptable salts thereof are independently as described above in the preceding paragraph; and $R^5$ is an optionally substituted $C_1$-$C_6$ alkyl group; an optionally substituted, $C_3$-$C_7$ non-aromatic carbocycle; or an optionally substituted, 4-7 membered non-aromatic heterocycle; or optionally, together with R and the nitrogen atom to which it is attached, form a 5-7 membered, optionally substituted non-aromatic heterocycle. Specifically, $R^5$ is an optionally substituted, 4-7 membered non-aromatic heterocycle; or optionally, together with R and the nitrogen atom to which it is attached, form a 5-7 membered, optionally substituted non-aromatic heterocycle.

In yet another embodiment, the compounds are represented by Structural Formula (IA) or (I), or pharmaceutically acceptable salts, wherein:
$R^4$ is:

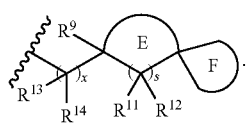

Ring E is a $C_4$-$C_{10}$ non-aromatic carbocycle optionally further substituted with one or more instances of $J^4$.

Rings F is a 4-8 membered non-aromatic heterocycle optionally substituted with one or more instances of $J^{E1}$. Specific examples of ring F includes:

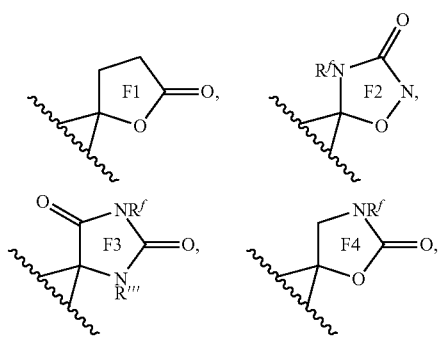

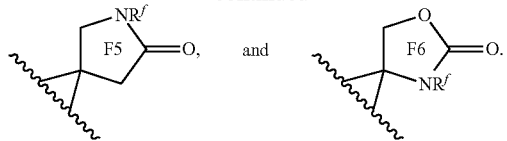

Additional example includes

Each of rings F1-F7 optionally and independently substituted. Exemplary substituents for ring F (including rings F1-F7) include halogen, cyano, hydroxy, $C_1$-$C_4$ alkoxy, and $C_1$-$C_4$ alkyl optionally substituted with one or more substituents selected from the group consisting of halogen, cyano, hydroxy, and —O($C_1$-$C_4$ alkyl).

$R^f$ is independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy.

$R^9$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, or $C_2$-$C_6$ alkoxyalkoxy.

$R^{11}$, $R^{12}$, $R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

Optionally, $R^{13}$ and $R^{14}$, together with the carbon atom to which they are attached, form a cyclopropane ring, optionally substituted with one or more instances of methyl.
s is 0, 1 or 2.
x is 0, 1 or 2.

The remaining variables are each and independently as described above in any one of the sets of variables for Structural Formulae (IA) and (I).

In yet another embodiment, the compounds are represented by Structural Formula (I) or (IA), or pharmaceutically acceptable salts thereof; wherein:
Ring E is a $C_4$-$C_8$ non-aromatic carbocycle optionally further substituted with one or more instances of $J^4$.
$R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

The other variables are each and independently as described in the preceeding paragraph.

In yet another embodiment, the compounds are represented by Structural Formula (IA) or (I), or pharmaceutically acceptable salts, wherein:

$R^4$ is:

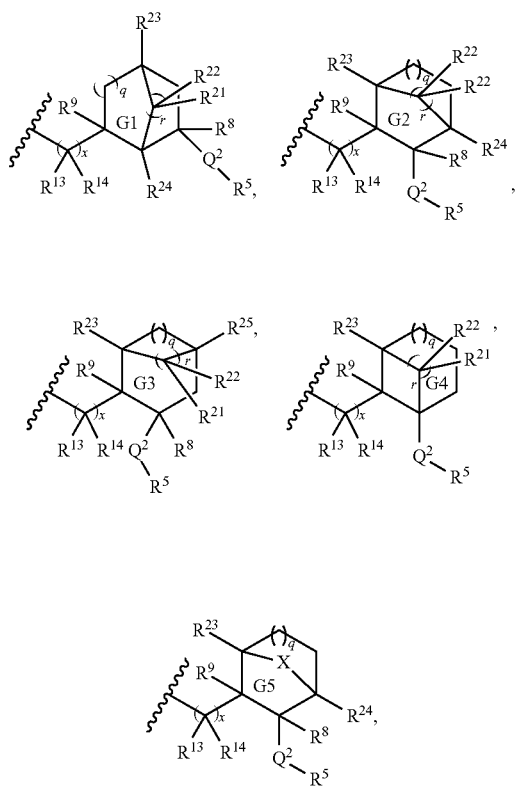

or

Each of rings G1-G4 is independently a 5-10 membered non-aromatic bridged ring optionally further substituted with one or more instances of $J^4$.

Ring G5 is a 5-10 membered non-aromatic bridged ring optionally further substituted with one or more instances of $J^{13}$.

X is —O—, —S—, or —NR$^g$—.

$R^8$ and $R^9$ are each independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, or $C_2$-$C_6$ alkoxyalkoxy.

$R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

Optionally, $R^{13}$ and $R^{14}$, together with the carbon atom to which they are attached, form a cyclopropane ring, optionally substituted with one or more instances of methyl.

$R^{21}$, $R^{22}$, $R^{23}$, $R^{24}$, and $R^{25}$ are each —H, halogen, —OH, $C_1$-$C_6$ alkoxy, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy. Specifically, $R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl).

$R^g$ is —H or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

q is 0, 1 or 2; x is 0, 1 or 2; and r is 1 or 2.

The remaining variables are each and independently as described above in any set of variables for Structural Formulae (IA) and (I).

In yet another embodiment, the compounds are represented by Structural Formula (IA) or (I), pharmaceutically acceptable salts thereof, wherein:
$R^4$ is:

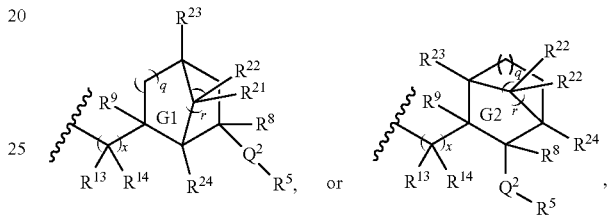

wherein rings G1 and G2 are each and independently a 5-10 membered non-aromatic bridged ring optionally further substituted with one or more instances of $J^4$.

Each of $R^8$ and $R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

$R^{21}$, $R^{22}$, $R^{23}$, and $R^{24}$ are each independently —H, halogen, —OH, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

$Q^2$ is independently a bond, —O—, —S—, —NR—, —C(O)—, —C(=NR)—, —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—. Alternatively $Q^2$ is independently —O—, —CO$_2$—, —OC(O)—, —C(O)NR—, —NRC(O)—, —NRC(O)NR—, —NRCO$_2$—, —OC(O)NR—, —CO$_2$SO$_2$—, —P(O)$_2$O—, or —(CR$^6$R$^7$)$_p$—Y$^1$—. Alternatively $Q^2$ is independently —O— or —CO$_2$—.

In some embodiments, rings E and G (including G1-G5) are optionally and independently further substituted with one or more instances of $J^A$ (for carbocycle) or $J^B$ (for heterocycle), wherein each of $J^A$ and $J^B$ is independently selected from the group consisting of halogen, cyano, oxo, —NCO, and Q$^1$-R$^5$, and wherein:

$Q^1$ is independently a bond, —O—, —S—, —NR—, C(O)—, —C(=NR)—, —CO$_2$—, —OC(O)—, —C(O) NR—, —C(O)NRC(O)O—, —NRC(O)NRC(O)O—, —NRC(O)—, —NRC(O)NR—, —NRCO$_2$—, —OC(O) NR—, —S(O)—, —SO$_2$—, —N(R)SO$_2$—, —SO$_2$NR'—, —NRSO$_2$NR'—, or —(CR$^6$R$^7$)$_p$—Y$^1$—; and Y$^1$ is independently a bond, —O—, —S—, —NR', C(O)—, —C(=NR)—, —CO$_2$—, —OC(O)—, —C(O)NR'—, —C(O)NRC(O)O—, —NRC(O)NRC(O)O—, —NRC (O)—, —NRC(O)NR'—, —NRCO$_2$—, —OC(O)NR'—, —S(O)—, —SO$_2$—, —SO$_2$NR'—, —NRSO$_2$—, or —NRSO$_2$NR'—.

Alternatively: $Q^1$ is independently a bond, —O—, —S—, —NR—, —C(O)—, —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—; and Y$^1$ is independently —O—, —CO$_2$—, —OC(O)—, —C(O)NR—, —NRC(O)—, —NRC(O)NR—, —NRCO$_2$—, or —OC(O)NR—.

In yet another embodiment, $Q^1$ and $Y^1$ are each independently as described above in the preceeding paragraph, and:

$R^5$ is independently i) —H; ii) a $C_1$-$C_6$-aliphatic group optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$; and each of $J^{C1}$ and $J^{D1}$ is independently selected from the group consisting of halogen, cyano, oxo, $R^a$, —OR$^b$, —SR$^b$, —S(O)R$^a$, —SO$_2$R$^a$, —NHR$^c$, —C(O)R$^b$, —C(O)OR$^b$, —OC(O)R$^b$, —NHC(O)R$^b$, —C(O)NHR$^a$, —NHC(O)NHR$^a$, —NHC(O)OR$^b$, —OCONHR$^a$, —NHC(O)NHC(O)OR$^b$, —N(CH$_3$)R', —N(CH$_3$)C(O)R$^b$, —C(O)N(CH$_3$)R$^a$, —N(CH$_3$)C(O)NHR$^a$, —N(CH$_3$)C(O)OR$^b$, —OCON(CH$_3$)R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N(CH$_3$)R$^b$, and —N(CH$_3$)SO$_2$R$^b$.

In some specific embodiments, the compounds are represented by Structural Formula (IA) or (I), wherein:

$R^1$ is —H.

$R^2$ is —H, —CH$_3$, —CH$_2$OH, or —NH$_2$. Specifically, $R^2$ is —H, or —CH$_2$OH.

$R^3$ is —H, —F, —Cl, $C_{1-4}$ alkyl, or $C_{1-4}$ haloalkyl. Alternatively, $R^3$ is —H, —F, or —Cl.

$Z^1$ is —H, —F, or —Cl.

$Z^2$ is —H or $C_1$-$C_6$ alkyl optionally substituted with one or more substituents independently selected from the group consisting of halogen, cyano, hydroxy, and —O($C_1$-$C_4$ alkyl).

$Z^3$ is —H or $C_1$-$C_6$ alkyl optionally substituted with one or more substituents independently selected from the group consisting of halogen, cyano, hydroxy, and —O($C_1$-$C_4$ alkyl).

$R^5$ is: i) —H; ii) an optionally substituted $C_1$-$C_6$ alkyl group; iii) an optionally substituted, $C_3$-$C_7$ non-aromatic carbocycle; iv) an optionally substituted, 4-7 membered non-aromatic heterocycle; v)) an optionally substituted phenyl group; vi) an optionally substituted 5-6 membered heteroaryl ring; or optionally, together with R and the nitrogen atom to which it is attached, form a 5-7 membered, optionally substituted non-aromatic heterocycle; and said alkyl group represented by $R^5$ is optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, —NRCO($C_1$-$C_4$ alkyl), —CONR($C_1$-$C_4$ alkyl), —NRCO$_2$($C_1$-$C_4$ alkyl), a $C_3$-$C_7$ non-aromatic carbocycle optionally substituted with one or more instances of $J^{E1}$, a 4-7 membered non-aromatic heterocycle optionally substituted with one or more instances of $J^{E1}$; and a phenyl optionally substituted with one or more instances of $J^{E1}$; and wherein each of said carbocycle, heterocycle, phenyl and heteroary represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —CO$_2$H, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

The remaining variables, including $R^4$ that includes a spiro ring represented by rings E and F, or a bridged ring represented by rings G1-G5, are each and independently as described in any one of the preceeding four embodiments.

In yet another embodiment, the compounds are presented by Structural Formula (IA) or (I), wherein values of the variables are each and independently as described in the preceeding embodiment, except:

$Z^2$ is —H;

$Z^3$ is —H;

$R^5$ is independently: i) —H or ii) a $C_1$-$C_6$-alkyl group optionally substituted with one or more substituents independently selected from the group consisting of halogen, cyano, hydroxy, oxo, $C_1$-$C_4$ alkyl, —O($C_1$-$C_4$alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), —CO$_2$H, $C_3$-$C_8$ non-aromatic carbocycle, 4-8 membered non-aromatic heterocycle, phenyl, and 5-6 membered heteroaryl;

wherein each of said alkyl groups referred to in the substituents of the $C_1$-$C_6$-alkyl group represented by $R^5$ is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy; and wherein each of said carbocycle, phenyl, heterocycle, and heteroaryl referred to in the substituents of the $C_1$-$C_6$-alkyl group represented by $R^5$ is independently and optionally substituted with one or more substituents independently selected from the group consisting of halogen, cyano, hydroxy, oxo, $C_1$-$C_4$ alkyl, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

In yet another embodiment, each of rings E, G1-G5 is independently and optionally substituted with one or more substituents selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —CO$_2$R$^b$; wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy. Specifically, each of rings E, G1-G5 is independently and optionally substituted with one or more substituents selected from the group consisting of halogen, cyano, hydroxy, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, and $C_1$-$C_4$ alkyl optionally substituted with one or more substituents selected from the group consisting of halogen, cyano, hydroxy, and —O($C_1$-$C_4$ alkyl).

In yet another embodiment, the compounds are represented by Structural Formula (IA) or (I), or pharmaceutically acceptable salts thereof, wherein:

$R^4$ is:

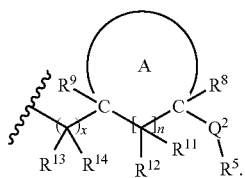

Ring A is a non-aromatic, 5-10 membered, bridged carbocycle or heterocycle, or ring A and $R^8$ optionally form a non-aromatic, 5-10 membered, bridged carbocycle or heterocycle, or ring A and $R^9$ optionally form a non-aromatic, 5-10 membered, bridged carbocycle or heterocycle, or ring A and $R^{11}$ optionally form a non-aromatic, 5-10 membered, bridged carbocycle or heterocycle, wherein each of said carbocycle is independently and optionally substituted with one or more instances of $J^A$ and wherein each carbocycle is independently and optionally substituted with one or more instances of $J^B$.

$R^1$ is —H.

$R^2$ is —H, —$CH_3$, —$CH_2OH$, or —$NH_2$. Specifically, $R^2$ is —H, or —$CH_2OH$.

$R^3$ is —H, —F, —$C_1$, $C_{1-4}$ alkyl (e.g., —$CH_3$ or —$C_2H_5$), or $C_{1-4}$ haloalkyl (e.g., —$CF_3$). Alternatively, $R^3$ is —H, —F, or —Cl.

$Z^1$ is —H, —F, or —Cl.

$Z^2$ is —H or $C_1$-$C_6$ alkyl optionally substituted with one or more substituents independently selected from the group consisting of halogen, cyano, hydroxy, and —O($C_1$-$C_4$ alkyl).

$Z^3$ is —H or $C_1$-$C_6$ alkyl optionally substituted with one or more substituents independently selected from the group consisting of halogen, cyano, hydroxy, and —O($C_1$-$C_4$ alkyl).

$Q^2$ is independently —O—, —$CO_2$—, —OC(O)—, —C(O)NR'—, —C(O)NRC(O)O—, —NRC(O)—, —NRC(O)NR'—, —$NRCO_2$—, —OC(O)NR'—, —P(O)(OR)O—, —OP(O)($OR^a$)O—, —$P(O)_2O$—, —$CO_2SO_2$—, or —$(CR^6R^7)_p$—$Y^1$—.

$Y^1$ is —O—, —$CO_2$—, —OC(O)—, —C(O)NR'—, —C(O)NRC(O)O—, —NRC(O)—, —NRC(O)NR'—, —$NRCO_2$—, —OC(O)NR'—, —P(O)(OR)O—, —OP(O)($OR^a$)O—, —$P(O)_2O$—, or —$CO_2SO_2$—.

$R^5$ is: i) —H; ii) an optionally substituted $C_1$-$C_6$ alkyl group; iii) an optionally substituted, $C_3$-$C_7$ non-aromatic carbocycle; iv) an optionally substituted, 4-7 membered non-aromatic heterocycle; v)) an optionally substituted phenyl group; vi) an optionally substituted 5-6 membered heteroaryl ring; or optionally, together with R and the nitrogen atom to which it is attached, form a 5-7 membered, optionally substituted non-aromatic heterocycle; and said alkyl group represented by $R^5$ is optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), $C_1$-$C_4$ alkoxy, —NRCO($C_1$-$C_4$ alkyl), —CONR($C_1$-$C_4$ alkyl), —$NRCO_2$($C_1$-$C_4$ alkyl), a $C_3$-$C_7$ non-aromatic carbocycle optionally substituted with one or more instances of $J^{E1}$, a 4-7 membered non-aromatic heterocycle optionally substituted with one or more instances of $J^{E1}$; and a phenyl optionally substituted with one or more instances of $J^{E1}$;

wherein each of said carbocycle, heterocycle, phenyl and heteroary represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —$CO_2H$, wherein each of said alkyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Each of $R^8$ and $R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$alkyl), —$NH_2$, —NH($C_1$-$C_4$ alkyl), or —N($C_1$-$C_4$ alkyl)$_2$.

$R^{11}$, $R^{12}$, $R^{13}$, and $R^{14}$ are each independently —H, halogen, or $C_1$-$C_6$ alkyl optionally substituted with one or more substituents independently selected from the group consisting of halogen, hydroxy, and $C_1$-$C_6$ alkoxy.

Each of $J^A$ and $J^B$ is independently selected from the group consisting of halogen, cyano, hydroxy, $C_1$-$C_6$ alkyl, —$NH_2$, —NH($C_1$-$C_6$ alkyl), —N($C_1$-$C_6$ alkyl)$_2$, —O($C_1$-$C_6$ alkyl), —C(O)$NH_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —$CO_2R^b$; wherein each of said alkyl groups is optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

n is 0 or 1.

x is 0 or 1.

The remaining variables are each and independently as described above in any set of variables for Structural Formulae (IA) and (I).

In yet another embodiment, the compounds are represented by Structural Formula (IA) or (I), or pharmaceutically acceptable salts, wherein:

$R^4$ is:

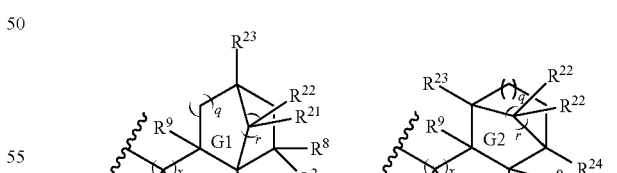

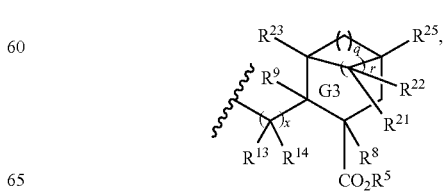

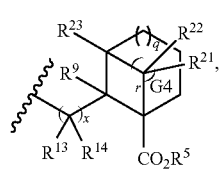

or

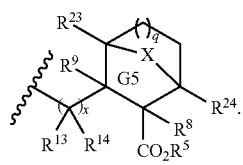

Each of rings G1-G4 is independently a 5-10 membered non-aromatic bridged carbocycle optionally further substituted with one or more instances of $J^A$, and ring G5 is a 5-10 membered non-aromatic bridged heterocycle optionally further substituted with one or more instances of $J^B$.

X is —O—, —S—, or —NR$^g$—.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl).

$R^g$ is —H or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

q is 0, 1 or 2.

r is 1 or 2.

The remaining variables are each and independently as described above in the preceeding paragraph.

In yet another embodiment, the compounds are represented by Structural Formula (IA) or (I), or pharmaceutically acceptable salts thereof, wherein the variables are each and independently as described above in the preceeding paragraph except those described below:

$R^1$ is —H.

$R^2$ is —H.

$R^3$ is —H, —F, —$C_1$, $C_{1-4}$ alkyl, or $C_{1-4}$ haloalkyl. Alternatively, $R^3$ is —H, —F, or —Cl.

$Z^1$ is —H, —F, or —Cl.

$Z^2$ is —H.

$Z^3$ is —H.

X is —O—, $R^5$ is —H, an optionally substituted $C_1$-$C_6$ alkyl, or optionally substituted phenyl.

Each $R^8$ is independently —H, halogen, hydroxy, $C_1$-$C_4$ alkyl, $C_1$-$C_4$ haloalkyl, $C_1$-$C_4$ hydroxyalkyl, $C_2$-$C_4$ alkoxyalkyl, or —O($C_1$-$C_4$ alkyl).

Each of $R^9$, $R^{13}$, and $R^{14}$ is independently —H or $C_1$-$C_4$ alkyl.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, hydroxy, $C_1$-$C_6$ alkyl, and —O($C_1$-$C_6$ alkyl). Specifically $R^{21}$, $R^{22}$, $R^{23}$, $R^{24}$, and $R^{25}$ are each independently —H, $C_{1-6}$ alkyl, or $C_{1-6}$ haloalkyl.

Each rings G1-G5 are independently and optionally substituted with one or more substituents selected from the group consisting of halogen, cyano, hydroxy, —NH$_2$, —NH($C_1$-$C_6$ alkyl), —N($C_1$-$C_6$ alkyl)$_2$, —O($C_1$-$C_6$ alkyl), $C_1$-$C_4$ alkyl that is optionally substituted with one or more substituents selected from the group consisting of halogen, hydroxy, and $C_1$-$C_4$ alkoxy.

In yet another embodiment, the compounds are represented by any one of Structural Formulae I-V (hereinafter reference to Structural Formulae I-IV includes Structural Formulae I, IA, II, III, IV, V, and VI) and XI(A)-XIV (hereinafter reference to Structural Formulae XI(A)-XIV includes Structural Formulae XIA, XIB, XIIA, XIIB, XIII, and XIV), wherein values of the variables therein are independently as described above in any embodiments except that $R^3$ is $C_{1-6}$ alkyl, such as methyl or ethyl.

In yet another embodiment, the compounds are represented by any one of Structural Formulae I-V and XI(A)-XIV, wherein values of the variables therein are independently as described above in any embodiments described above, except that x is 0.

In yet another embodiment, the compounds are represented by any one of Structural Formulae I, IA, II, VI, XI(A), and XI(B), wherein values of the variables therein are independently as described above in any embodiments described above, except that ring A is bridged.

In yet another embodiment, the compounds are represented by any one of Structural Formulae I, IA, II, VI, XI(A), and XI(B), wherein values of the variables therein are independently as described above in any embodiments described above, except that $Q^2$ is independently —C(=NR)—, —C(=NR)NR—, —NRC(=NR)NR—, —CO$_2$—, —OC(O)—, —C(O)NR—, —C(O)NRC(O)O—, NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$N(R)—, —NRSO$_2$NR—, —P(O)(OR)O—, —OP(O)(OR$^a$)O—, —P(O)$_2$O—, —CO$_2$SO$_2$—, or —(CR$^6$R$^7$)$_p$—Y$^1$—; or alternatively, $Q^2$ is independently —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$N(R)—, —NRSO$_2$NR—, —P(O)(OR)O—, —OP(O)(OR$^a$)O—, —P(O)$_2$O—, —CO$_2$SO$_2$—, or —(CR$^6$R$^7$)$_p$—Y$^1$—.

In yet another embodiment, the compounds are represented by any one of Structural Formulae I-V and XI(A)-XIV, wherein values of the variables therein are independently as described above in any embodiments described above, provided that when $Q^2$ is —O— or —NR—, then ring A is further substituted with $J^A$ other than —H; and provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group. In a specific embodiment, when $Q^2$ is —O— or —NR—, then ring A is further substituted with $J^A$ other than —H at the geminal position to -Q$^2$R$^5$.

In yet another embodiment, the present invention is directed to the use of any compound selected from the compounds depicted in FIGS. 3, 4, 5, 6, 7, and 8, or a pharmaceutically acceptable salt thereof, for any of the uses described above.

In some embodiments, the compounds are represented by any one of Structural Formulae I-V and XI(A)-XIV, and the variables are each independently as depicted in the compounds of FIGS. 1-8.

In yet another embodiment, the present invention is directed to the use of a compound described in any one of the embodiments, including various sets of variables, for Structural Formulae I-V and XI(A)-XIV described above, or a pharmaceutically acceptable salt thereof, for any of the uses described above, provided that when $R^3$ is —Cl, $Z^1$ is —F, and $Z^2$ is —H, then $R^4$ is not 2-$NH_2$-cyclohexyl.

In yet another embodiment, the compounds described herein or pharmaceutically acceptable salts thereof can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenzavirus A, Influenzavirus B, Influenzavirus C, Isavirus and Thogotovirus. Influenzavirus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Influenzavirus B genus has one species, influenza B virus. Influenza B almost exclusively infects humans and is less common than influenza A. Influenzavirus C genus has one species, Influenzavirus C virus, which infects humans and pigs and can cause severe illness and local epidemics. However, Influenzavirus C is less common than the other types and usually seems to cause mild disease in children.

In some embodiments of the invention, influenza or influenza viruses are associated with Influenzavirus A or B. In some embodiments of the invention, influenza or influenza viruses are associated with Influenzavirus A. In some specific embodiments of the invention, Influenzavirus A is H1N1, H2N2, H3N2 or H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, . . . , $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc).

According to the US CDC, an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc) over the normal background rate or when any subject in the population being analyzed tests positive for influenza. One case of confirmed influenza by any testing method is considered an outbreak.

A "cluster" is defined as a group of three or more cases of AFR1 occurring within a 48 to 72 hour period, in a group of people who are in close proximity to each other (e.g. in the same area of an assisted living facility, in the same household, etc).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In one embodiment, the methods of the invention are a preventative or "pre-emptive" measure to a patient, specifically a human, having a predisposition to complications resulting from infection by an influenza virus. The term "pre-emptive" as used herein as for example in pre-emptive use, "pre-emptively", etc, is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), tree times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Various types of administration methods can be employed in the invention, and are described in detail below under the section entitled "Administration Methods."

Combination Therapy

An effective amount can be achieved in the method or pharmaceutical composition of the invention employing a compound of any one of Structural Formulae I-V (e.g., Structural Formulae I, IA, II, III, IV and V) and XI(A)-XIV (e.g., Structural Formulae XIA, XIB, XIIA, XIIB, XIII, and XIV) or a pharmaceutically acceptable salt or solvate (e.g., hydrate) thereof alone or in combination with an additional suitable therapeutic agent, for example, an antiviral agent or a vaccine. When "combination therapy" is employed, an effective amount can be achieved using a first amount of a compound of any one of Structural Formulae I-V and XI(A)-XIV, or a pharmaceutically acceptable salt or solvate (e.g., hydrate) thereof, and a second amount of an additional suitable therapeutic agent (e.g. an antiviral agent or vaccine).

In another embodiment of this invention, the compound of any one of Structural Formulae I-V and XI(A)-XIV, and the additional therapeutic agent, are each administered in an effective amount (i.e., each in an amount which would be therapeutically effective if administered alone). In another embodiment, the compound of any one of Structural Formulae I-V and XI(A)-XIV, and the additional therapeutic agent, are each administered in an amount which alone does not provide a therapeutic effect (a sub-therapeutic dose). In yet another embodiment, the compound of any one of Structural Formulae I-V and XI(A)-XIV can be administered in an effective amount, while the additional therapeutic agent is administered in a sub-therapeutic dose. In still another embodiment, the compound of any one of Structural Formulae I-V and XI(A)-XIV can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In one embodiment, the present invention is directed to methods of combination therapy for inhibiting Flu viruses replication in biological samples or patients, or for treating or preventing Influenza virus infections in patients using the compounds or pharmaceutical compositions of the invention of any one of Structural Formulae I-V and XI(A)-XIV. Accordingly, pharmaceutical compositions of the invention also include those comprising an inhibitor of Flu virus replication of this invention in combination with an anti-viral compound exhibiting anti-Influenza virus activity.

Methods of use of the compounds and compositions of the invention also include combination of chemotherapy with a compound or composition of any one of Structural Formulae I-V and XI(A)-XIV or with a combination of a compound or composition of this invention with another anti-viral agent and vaccination with a Flu vaccine.

When co-administration involves the separate administration of the first amount of a compound of any of Structural Formulae I-V and XI(A)-XIV and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of any one of Structural Formulae I-V and XI(A)-XIV and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of any one of Structural Formulae I-V and XI(A)-XIV and a second amount of an additional therapeutic agent can result in an enhanced or synergistic therapeutic effect, wherein the combined effect is greater than the additive effect that would result from separate administration of the first amount of the compound of any one of Structural Formulae I-V and XI(A)-XIV and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using compounds of the present invention of any one of Structural Formulae I-V and XI(A)-XIV is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N.H.G. and Scheiner, L.B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Research, 82: 95-102 (2009), "T-705 (flavipiravir) and related compounds: Novel broad-spectrum inhibitors of RNA viral infections.") In some embodiments, the compounds described herein can be co-administered with a traditional influenza vaccine.

Compounds of the Invention

Another aspect of the present invention is generally related to compounds. In one embodiment, the present invention is generally related to compounds represented by Structural Formula (IA) or (I), or pharmaceutically acceptable salts thereof:

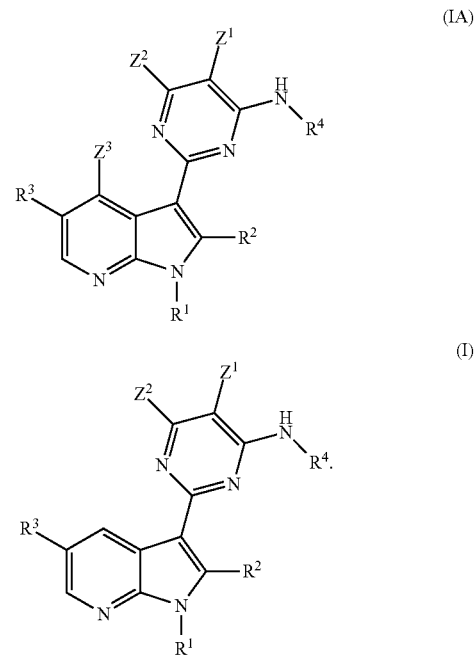

A first subset of variables of Structural Formulae (I) and (IA) for the compounds of the invention is as follows:

$R^1$ is —H, $C_1$-$C_6$ alkyl, —S(O)$_2$—R" or —C(O)OR". Specifically, $R^1$ is —H or S(O)$_2$—R". Specifically, $R^1$ is —H or —S(O)$_2$-(phenyl), wherein the phenyl is optionally substituted with one or more selected from the group consisting of $C_1$-$C_6$ alkyl and $C_1$-$C_6$ haloalkyl. More specifically, the phenyl is optionally substituted with one or more selected from the group consisting of —CH$_3$ and —CF$_3$ (e.g., at its para position). Specifically, $R^1$ is —H or $C_{1-6}$ alkyl. Specifically, $R^1$ is —H.

$R^4$ is:

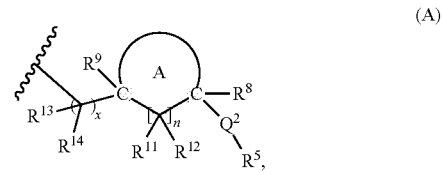

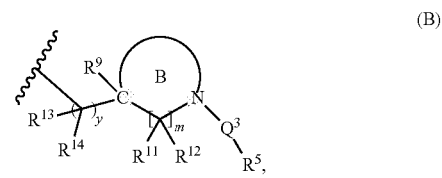

(C)

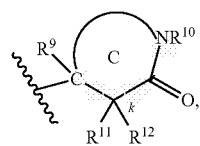

or (D)

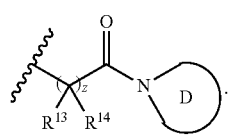

R" is independently: i) a $C_1$-$C_6$-alkyl optionally substituted with one or more substituents independently selected from the group consisting of halogen, cyano, hydroxyl, —$NH_2$, —NH($C_1$-$C_6$ alkyl), —N($C_1$-$C_6$ alkyl)$_2$, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy; or ii) a $C_3$-$C_6$ carbocyclic group, a 5-6 membered heteroaryl group, or a phenyl group, each optionally and independently being substituted with one or more substituents independently selected from the group consisting of halogen, cyano, hydroxy, oxo, nitro, —$NH_2$, —NH($C_1$-$C_6$ alkyl), —N($C_1$-$C_6$ alkyl)$_2$, $C_1$-$C_6$ alkyl, $C_1$-$C_6$ haloalkyl, $C_1$-$C_6$ cyanoalkyl, $C_1$-$C_6$ hydroxyalkyl, $C_2$-$C_6$ alkoxyalkyl, $C_1$-$C_6$ aminoalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy. Specifically, R" is independently an optionally substituted, 5-6 membered heteroaryl group, or an optionally substituted phenyl group. Specifically, R" is independently a phenyl group optionally substituted with one or more substituents independently selected from the group consisting of $C_1$-$C_6$ alkyl and $C_1$-$C_6$ haloalkyl.

Values of $Z^1$, $Z^2$, $Z^3$, $Q^1$, $Q^2$, $Q^3$, $Y^1$, rings A-D, R*, R, R', $R^2$, $R^3$, $R^5$, $R^6$, $R^7$, $R^8$, $R^9$, $R^{10}$, $R^{11}$, $R^{12}$, $R^{13}$, $R^{14}$, $R^a$, $R^b$, $R^c$, $R^d$, $J^A$, $J^B$, $J^{C1}$, $J^{D1}$ and $J^{E1}$, including specific values and substituents therefor, are each and independently as described above in the first set of variables of Structural Formulae (IA) and (I) for the methods of the invention.

Value p is independently 1, 2, 3 or 4. Specifically, p is independently 1 or 2.

When rings A and B are 3-6-membered, n and m are each independently 0 or 1; and k is independently 0, 1 or 2. Alternatively, when rings A and B are 7-10-membered, n and m, are each independently 0, 1 or 2; and k is independently 0, 1 or 2.

Values x and y are each independently 0, 1 or 2.

Value z is 1 or 2.

It is provided that if $Y^1$ is a bond, then $R^5$ is neither —H, nor an unsubstituted $C_1$-$C_6$ aliphatic group. Specifically, if $Y^1$ is a bond, then $R^5$ is a substituted $C_1$-$C_6$ aliphatic group; an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group. Specifically, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —S(O)$R^a$; —$SO_2R^a$; —$NR^bR^c$; —C(O)$R^b$; —C(O)O$R^b$; —OC(O)$R^b$; —NRC(O)$R^b$; —C(O)N$R^bR^c$; —NRC(O)N$R^bR^c$; —NRC(O)O$R^b$; —OCON$R^bR^c$; —C(O)NRCO$_2R^b$; —NRC(O)NRCO$_2R^b$; —C(O)NR(O$R^b$); —SO$_2$N(R)$R^b$; —NRSO$_2R^b$; and —NRSO$_2$NR$R^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

It is provided that if $Q^2$ and $Q^3$ are each and independently a bond, then $R^5$ is an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group. Specifically, if $Q^2$ and $Q^3$ are each and independently a bond, then $R^5$ is an optionally substituted $C_3$-$C_8$ non-aromatic carbocycle; or an optionally substituted, 4-8 membered non-aromatic heterocycle.

Alternatively, it is provided that if rings A and B each and independently 5- or 6-membered, $R^1$ and $R^2$ are both —H, $R^3$ is —$C^1$, $Z^2$ is —H, and $Z^1$ is —F, then $Q^2$-$R^5$ and $Q^3$-$R^5$, respectively, are not —H; and it is provided that the ring B-$Q^3$-$R^5$ moiety is not N-methyl-3-pyrrolidinyl ( 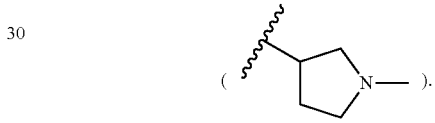 ).

A second subset of variables of Structural Formulae (IA) and (I) for the compounds of the invention is as follows:

$R^2$ is —H or —$CH_3$.

$R^3$ is —H, —Cl, —F, —Br, —CN, —$CF_3$, —O($C_1$-$C_4$ alkyl), —OH, —$NH_2$, —NH($C_1$-$C_4$ alkyl), or —N($C_1$-$C_4$ alkyl)$_2$.

$R^4$ is selected from formulae A-D depicted above.

Values of the remaining variables of Structural Formulae (IA) and (I), including specific values, and provisos are each and independently as described above for the first subset of variables of Structural Formulae (IA) and (I).

A third subset of variables of Structural Formula I for the compounds of the invention is as follows:

$R^2$ is —H or —$CH_3$.

$R^3$ is —H, —F, —Cl, —$CF_3$, —$NH_2$, —NH($CH_3$), or —N($CH_3$)$_2$.

$R^4$ is selected from formulae A-D depicted above.

Values of the remaining variables of Structural Formulae (IA) and (I), including specific values, and provisos are each and independently as described above for the first subset of variables of Structural Formulae (IA) and (I).

A fourth subset of variables of Structural Formulae (IA) and (I) for the compounds of the invention is as follows:

$R^2$ is —H or —$CH_3$.

$R^3$ is —H, —F, or —Cl.

$R^4$ is selected from formulae A-D depicted above.

Values of the remaining variables of Structural Formulae (IA) and (I), including specific values, are each and independently as described above for the first subset of variables of Structural Formulae (IA) and (I).

A fifth subset of variables of Structural Formulae (IA) and (I) for the compounds of the invention is as follows:

$R^2$ is —H.

$R^3$ is —H or —Cl.

$R^4$ is selected from formulae A-D depicted above.

Values of the remaining variables of Structural Formulae (IA) and (I), including specific values, and provisos are each and independently as described above for the first subset of variables of Structural Formulae (IA) and (I).

A sixth subset of variables of Structural Formulae (IA) and (I) for the compounds of the invention is as follows:

Each of $R^2$, $R^3$ and $R^4$ is independently as described in the first subset, second subset, third subset, fourth subset, or fifth subset, of variables of Structural Formulae (IA) and (I).

$Z^1$ is —H, $C_1$-$C_6$ alkyl, —O($C_1$-$C_6$ alkyl), —F, —Cl, —CN, —$CO_2$H, —$CO_2$($C_1$-$C_6$ alkyl), —$CONH_2$, —CONH($C_1$-$C_6$ alkyl), or —CON($C_1$-$C_6$ alkyl)$_2$; and $Z^2$ is —H, $C_1$-$C_6$ alkyl, —O($C_1$-$C_6$ alkyl), —$NH_2$, —NH($C_1$-$C_6$ alkyl), or —N($C_1$-$C_6$ alkyl)$_2$; wherein each of said alkyl groups (e.g., represented by $C_1$-$C_6$ alkyl, —O($C_1$-$C_6$ alkyl), —$CO_2$($C_1$-$C_6$ alkyl), —NH($C_1$-$C_6$ alkyl), and —N($C_1$-$C_6$ alkyl)$_2$) is optionally and independently substituted with one or more substituents independently selected from the group consisting of halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (IA) and (I), including specific values, and provisos are each and independently as described above for the first subset of variables of Structural Formulae (IA) and (I).

A seventh subset of variables of Structural Formulae (IA) and (I) for the compounds of the invention is as follows:

Each of $R^2$, $R^3$ and $R^4$ is independently as described in the first subset, second subset, third subset, fourth subset, or fifth subset, of variables of Structural Formulae (IA) and (I).

$Z^1$ is —H, —F, —Cl, —$CF_3$, $C_1$-$C_4$ alkyl, —O($C_1$-$C_4$ alkyl), or —CN; and $Z^2$ is —H, $C_1$-$C_6$ alkyl, —O($C_1$-$C_6$ alkyl), —$NH_2$, —NH($C_1$-$C_6$ alkyl), or —N($C_1$-$C_6$ alkyl)$_2$, wherein each of said alkyl groups (e.g., represented by $C_1$-$C_6$ alkyl, —O($C_1$-$C_6$ alkyl), —NH($C_1$-$C_6$ alkyl), and —N($C_1$-$C_6$ alkyl)$_2$) is optionally and independently substituted with one or more substituents independently selected from the group consisting of halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (IA) and (I), including specific values, and provisos are each and independently as described above for the first subset of variables.

An eighth subset of variables of Structural Formulae (IA) and (I) for the compounds of the invention is as follows:

Each of $R^2$, $R^3$ and $R^4$ is independently as described in the first subset, second subset, third subset, fourth subset, or fifth subset, of variables of Structural Formulae (IA) and (I).

$Z^1$ is —H, —F, —$C_1$, $C_1$-$C_4$ haloalkyl (e.g, —$CF_3$), $C_1$-$C_4$ alkyl, —O($C_1$-$C_4$ alkyl), or —CN.

$Z^2$ is —H or a $C_1$-$C_6$ alkyl optionally substituted with one or more substituents independently selected from the group consisting of halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (IA) and (I), including specific values, and provisos are each and independently as described above for the first subset of variables.

A ninth subset of variables of Structural Formulae (IA) and (I) for the compounds of the invention is as follows:

Each of $R^2$, $R^3$ and $R^4$ is independently as described in the first subset, second subset, third subset, fourth subset, or fifth subset, of variables of Structural Formulae (IA) and (I).

$Z^1$ is —H, —F, —Cl, —$CF_3$, —$CH_3$, or —CN.

$Z^2$ is —H or a $C_1$-$C_6$ alkyl optionally substituted with one or more substituents independently selected from the group consisting of halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy.

Values of the remaining variables of Structural Formulae (IA) and (I), including specific values, and provisos are each and independently as described above for the first subset of variables of Structural Formulae (IA) and (I).

In a tenth subset of variables of Structural Formulae (IA) and (I) for the compounds of the invention, the variables of Structural Formulae (IA) and (I), including specific values, are each and independently as described above for the first, second, third, fourth, fifth, sixth, seventh, eighth, or ninth subset of variables of Structural Formulae (IA) and (I); and where applicable:

each R* independently is: i) —H; ii) $C_1$-$C_6$ alkyl optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy; or iii) a 3-7 membered carbocyclic ring optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), $C_1$-$C_4$ alkoxy, and $C_1$-$C_6$ alkyl, wherein each alkyl is independently and optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2$H, —$CO_2$($C_1$-$C_4$ alkyl), and $C_1$-$C_4$ alkoxy; and R and R' are each independently —H or $C_1$-$C_6$ alkyl optionally substituted with one or more substituents independently selected from the group consisting of halogen, cyano, hydroxy, oxo, —$NH_2$, —NH($C_1$-$C_6$ alkyl), —N($C_1$-$C_6$ alkyl)$_2$, and —O($C_1$-$C_6$ alkyl); or optionally R', together with $R^5$ and the nitrogen atom to which they are attached, forms a 5-7 membered, non-aromatic, heterocyclic ring optionally substituted with one or more instances of $J^{D1}$; and R" is independently a phenyl group optionally substituted with one or more substituents independently selected from the group consisting of $C_1$-$C_6$ alkyl and $C_1$-$C_6$ haloalkyl.

In an eleventh subset of variables of Structural Formulae (IA) and (I) for the compounds of the invention, the variables of Structural Formulae (IA) and (I), including specific values, are each and independently as described above for the first, second, third, fourth, fifth, sixth, seventh, eighth, ninth, or tenth subset of variables of Structural Formulae (IA) and (I); and where applicable:

provided that if $Y^1$ is a bond, then $R^5$ is a substituted $C_1$-$C_6$ aliphatic group; an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group; and provided that if $Q^2$ and $Q^3$ are each and independently a bond, then $R^5$ is an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group.

In a twelfth subset of variables of Structural Formulae (IA) and (I) for the compounds of the invention, the variables of Structural Formulae (IA) and (I), including specific values, are each and independently as described above for the eleventh subset of variables of Structural Formulae (IA) and (I); and the $C_1$-$C_6$ aliphatic group represented by $R^5$, when $Y^1$ is a bond, is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —$S(O)R^a$; —$SO_2R^a$; —$NR^bR^c$; —$C(O)R^b$; —$C(O)OR^b$; —$OC(O)R^b$; —$NRC(O)R^b$; —$C(O)NR^bR^c$; —$NRC(O)NR^bR^c$; —$NRC(O)OR^b$; —$OCONR^bR^c$; —$C(O)NRCO_2R^b$; —$NRC(O)NRCO_2R^b$; —$C(O)NR(OR^b)$; —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

A thirteenth subset of variables of Structural Formulae (IA) and (I) is as follows:

Each of $J^A$ and $J^B$ is independently selected from the group consisting of halogen, cyano, oxo, and $Q^1$-$R^5$; or optionally two $J^A$ and two $J^B$, respectively, together with the atom(s) to which they are attached, independently form a 5-7 membered ring that is optionally substituted with one or more instances of $J^{E1}$, and fused to the ring to which they are attached.

$Q^1$ is independently a bond, —O—, —S—, —NR'—, —C(O)—, —CO_2—, —OC(O)—, —C(O)NR'—, —C(O)NRC(O)O—, NRC(O)NRC(O)O—, —NRC(O)—, —NRC(O)NR'—, —NRCO_2—, —OC(O)NR'—, —S(O)—, —SO_2—, —SO_2NR'—, —NRSO_2—, or —NRSO_2NR'—, or —$(CR^6R^7)_p$—$Y^1$—.

Each of $J^{C1}$ and $J^{D1}$ is independently selected from the group consisting of halogen, cyano, oxo, $R^a$, —$OR^b$, —$SR^b$, —$S(O)R^a$, —$SO_2R^a$, —$NR^bR^c$, —$C(O)R^b$, —$C(O)OR^b$, —$OC(O)R^b$, —$NRC(O)R^b$, —$C(O)NR^bR^c$, —$NRC(O)NR^bR^c$, —$NRC(O)OR^b$, —$OCONR^bR^c$, —$C(O)NRCO_2R^b$, —$NRC(O)NRC(O)OR^b$, —$C(O)NR(OR^b)$, —$SO_2NR^cR^b$, —$NRSO_2R^b$, and —$NRSO_2NR^cR^b$, or optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

Values of the remaining variables of Structural Formulae (IA) and (I), including specific values, and provisos are each and independently as described above for the first, second, third, fourth, fifth, sixth, seventh, eighth, ninth, tenth, eleventh, or twelfth subset of variables of Structural Formulae (IA) and (I).

In a fourteenth subset of variables of Structural Formulae (IA) and (I), values of the variables are independently as described above in the seventeenth set of variables of Structural Formulae (IA) and (I).

In a fifteenth subset of variables of Structural Formulae (IA) and (I), values of the variables are independently as described above in the eighteenth set of variables of Structural Formulae (IA) and (I).

In a sixteenth subset of variables of Structural Formulae (IA) and (I), values of the variables are independently as described above in the nineteenth set of variables of Structural Formulae (IA) and (I).

In some embodiments, the compounds are represented by Structural Formula (IA) or (I), or pharmaceutically acceptable salts thereof, wherein $R^1$ is —H or $C_{1-6}$ alkyl, and wherein values of the remaining variables are independently as described above in any one of the subsets of variables of Structural Formulae (IA) and (I).

In another embodiment, the present invention is generally related to compounds represented by Structural Formula VI, or pharmaceutically acceptable salts thereof.

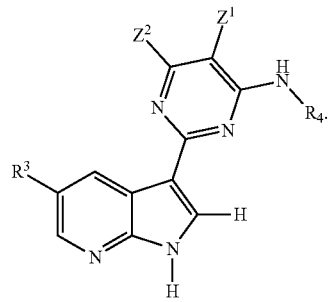

(VI)

A first subset of variables of Structural Formula VI for the compounds of this invention is as follows:

$Z^1$ is —H, $C_1$-$C_6$ alkyl, —O($C_1$-$C_6$ alkyl), —F, —Cl, —CN, —$CO_2H$, —$CO_2(C_1$-$C_6$ alkyl), —$CONH_2$, —CONH($C_1$-$C_6$ alkyl), or —CON($C_1$-$C_6$ alkyl)$_2$, wherein each of said alkyl groups (e.g., represented by $C_1$-$C_6$ alkyl, —O($C_1$-$C_6$ alkyl), —$CO_2(C_1$-$C_6$ alkyl), —CONH($C_1$-$C_6$ alkyl), and —CON($C_1$-$C_6$ alkyl)$_2$) is optionally and independently substituted with one or more substituents independently selected from the group consisting of halogen, cyano, hydroxy, oxo, $C_1$-$C_4$ alkyl, —$NH_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2$ ($C_1$-$C_4$ alkyl), and $C_1$-$C_4$ alkoxy.

$Z^2$ is —H, $C_1$-$C_6$ alkyl, —O($C_1$-$C_6$ alkyl), —$NH_2$, —NH($C_1$-$C_6$ alkyl), or —N($C_1$-$C_6$ alkyl)$_2$, wherein each of said alkyl groups (e.g., represented by $C_1$-$C_6$ alkyl, —O($C_1$-$C_6$ alkyl), —NH($C_1$-$C_6$ alkyl), and —N($C_1$-$C_6$ alkyl)$_2$) is optionally and independently substituted with one or more substituents independently selected from the group consisting of halogen, cyano, hydroxy, oxo, $C_1$-$C_4$ alkyl, —$NH_2$, —NH ($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2(C_1$-$C_4$ alkyl), and $C_1$-$C_4$ alkoxy.

Values of the remaining variables of Structural Formula VI, including specific values, and provisos are each and independently as described above for the first subset of variables of Structural Formulae (IA) and (I).

A second subset of variables of Structural Formula VI for the compounds of this invention is as follows:

$Z^1$ is —H, $C_1$-$C_6$ alkyl, —O($C_1$-$C_6$ alkyl), —F, —Cl, —CN, —$CO_2H$, —$CO_2(C_1$-$C_6$ alkyl), —$CONH_2$, —CONH($C_1$-$C_6$ alkyl), or —CON($C_1$-$C_6$ alkyl)$_2$, wherein each of said alkyl groups is optionally and independently substituted with one or more substituents independently selected from the group consisting of halogen, cyano, hydroxy, oxo, $C_1$-$C_4$ alkyl, —$NH_2$, —$NH(C_1$-$C_6$ alkyl), —$N(C_1$-$C_6$ alkyl)$_2$, —$OCO(C_1$-$C_4$ alkyl), —$CO(C_1$-$C_4$ alkyl), —$CO_2H$, —$CO_2$ ($C_1$-$C_4$ alkyl), and $C_1$-$C_4$ alkoxy.

$Z^2$ is —H, $C_1$-$C_6$ alkyl, —$O(C_1$-$C_6$ alkyl), —$NH_2$, —NH ($C_1$-$C_6$ alkyl), or —$N(C_1$-$C_6$ alkyl)$_2$; wherein each of said alkyl groups is optionally and independently substituted with one or more substituents independently selected from the group consisting of halogen, cyano, hydroxy, oxo, $C_1$-$C_4$ alkyl, —$NH_2$, —$NH(C_1$-$C_6$ alkyl), —$N(C_1$-$C_6$ alkyl)$_2$, —$OCO(C_1$-$C_4$ alkyl), —$CO(C_1$-$C_4$ alkyl), —$CO_2H$, —$CO_2$ ($C_1$-$C_4$ alkyl), and $C_1$-$C_4$ alkoxy.

$R^3$ is —H, —Cl, —F, —Br, —CN, —$CF_3$, —$O(C_1$-$C_4$ alkyl), —OH, —$NH_2$, —$NH(C_1$-$C_4$ alkyl), or —$N(C_1$-$C_4$ alkyl)$_2$.

Values of the remaining variables of Structural Formula VI, including specific values, and provisos are each and independently as described above for the first subset of variables of Structural Formulae (IA) and (I).

A third subset of variables of Structural Formula VI for the compounds of this invention is as follows:

$Z^1$ is —H, $C_1$-$C_6$ alkyl, —$O(C_1$-$C_6$ alkyl), —F, —Cl, —CN, —$CO_2H$, —$CO_2(C_1$-$C_6$ alkyl), —$CONH_2$, —CONH ($C_1$-$C_6$ alkyl), or —$CON(C_1$-$C_6$ alkyl)$_2$, wherein each of said alkyl groups is optionally and independently substituted with one or more substituents independently selected from the group consisting of halogen, cyano, hydroxy, oxo, $C_1$-$C_4$ alkyl, —$NH_2$, —$NH(C_1$-$C_6$ alkyl), —$N(C_1$-$C_6$ alkyl)$_2$, —$OCO(C_1$-$C_4$ alkyl), —$CO(C_1$-$C_4$ alkyl), —$CO_2H$, —$CO_2$ ($C_1$-$C_4$ alkyl), and $C_1$-$C_4$ alkoxy.

$Z^2$ is —H, $C_1$-$C_6$ alkyl, —$O(C_1$-$C_6$ alkyl), —$NH_2$, —NH ($C_1$-$C_6$ alkyl), or —$N(C_1$-$C_6$ alkyl)$_2$; wherein each of said alkyl groups is optionally and independently substituted with one or more substituents independently selected from the group consisting of halogen, cyano, hydroxy, oxo, $C_1$-$C_4$ alkyl, —$NH_2$, —$NH(C_1$-$C_6$ alkyl), —$N(C_1$-$C_6$ alkyl)$_2$, —$OCO(C_1$-$C_4$ alkyl), —$CO(C_1$-$C_4$ alkyl), —$CO_2H$, —$CO_2$ ($C_1$-$C_4$ alkyl), and $C_1$-$C_4$ alkoxy.

$R^3$ is —H, —F, —Cl, —$CF_3$, —$NH_2$, —$NH(CH_3)$, or —$N(CH_3)_2$. Specifically, $R^3$ is —H, —Cl, or —F. Specifically, $R^3$ is Cl.

Values of the remaining variables of Structural Formula VI, including specific values, and provisos are each and independently as described above for the first subset of variables of Structural Formulae (IA) and (I).

In a fourth subset of variables of Structural Formula VI for the compounds of this invention, values of the variables for Structural Formula VI, including specific values, and provisos are each and independently as described above in the first subset of variables of Structural Formulae (IA) and (I).

In a fifth subset of variables of Structural Formula VI for the compounds of this invention, values of the variables for Structural Formula VI, including specific values, and provisos are each and independently as described above in the first, second, third, or fourth subset of variables of Structural Formulae (IA) and (I); and where applicable:

provided that if $Q^2$-$R^5$ is —$OR^5$ or —$NR'R^5$, then ring A is further substituted with one or more instances of $J^4$ other than —H; and provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group.

In a sixth subset of variables of Structural Formula VI for the compounds of this invention, values of the variables for Structural Formula VI, including specific values, and provisos are each and independently as described above in the fifth subset; and the $C_1$-$C_6$ aliphatic group represented by $R^5$, when $Q^3$ is —C(O)—, is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —$S(O)R^a$; —$SO_2R^a$; —$NR^bR^c$; —$C(O)R^b$; —$C(O)OR^b$; —$OC(O)R^b$; —NRC(O)$R^b$; —$C(O)NR^bR^c$; —$NRC(O)NR^bR^c$; —$NRC(O)OR^b$; —$OCONR^bR^c$; —$C(O)NRCO_2R^b$; —$NRC(O)NRCO_2R^b$; —$C(O)NR(OR^b)$; —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In a seventh subset of variables of Structural Formula VI for the compounds of this invention, values of the variables for Structural Formula VI, including specific values, and provisos are each and independently as described above in the first, second, third, or fourth subset of variables of Structural Formulae (IA) and (I); and where applicable:

provided that if $Y^1$ is a bond, then $R^5$ is a substituted $C_1$-$C_6$ aliphatic group; an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group; and provided that if $Q^2$ and $Q^3$ are each and independently a bond, then $R^5$ is an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group.

In an eighth subset of variables of Structural Formula VI for the compounds of this invention, values of the variables for Structural Formula VI, including specific values, and provisos are each and independently as described above in the seventh subset of variables of Structural Formulae (IA) and (I); and the $C_1$-$C_6$ aliphatic group represented by $R^5$, when $Y^1$ is a bond, is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —$S(O)R^a$; —$SO_2R^a$; —$NR^bR^c$; —$C(O)R^b$; —$C(O)OR^b$; —$OC(O)R^b$; —$NRC(O)R^b$; —$C(O)NR^bR^c$; —$NRC(O)NR^bR^c$; —$NRC(O)OR^b$; —$OCONR^bR^c$; —$C(O)NRCO_2R^b$; —$NRC(O)NRCO_2R^b$; —$C(O)NR(OR^b)$; —$SO_2NR^cR^b$; —$NRSO_2R^b$; and —$NRSO_2NR^cR^b$; or optionally two $J^{C1}$ and two $J^{D%}$ respectively, together with the atoms to which they are attached, independently form a 5-7-membered ring that is optionally substituted with one or more instances of $J^{E1}$, and fused to the respective ring to which they are attached.

In a ninth subset of variables of Structural Formula VI for the compounds of this invention, values of the variables for Structural Formula VI, including specific values, and provisos are each and independently as described above in the first, second, third, or fourth subset of variables of Structural Formulae (IA) and (I); and where applicable:

provided that if $Q^2$-$R^5$ is —$OR^5$ or —$NR'R^5$, then ring A is further substituted with one or more instances of $J^A$ other than —H;

provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group;

provided that if $Y^1$ is a bond, then $R^5$ is a substituted $C_1$-$C_6$ aliphatic group; an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group; and provided that if $Q^2$ and $Q^3$ are each and independently a bond, then $R^5$ is an optionally substituted $C_3$-$C_8$ non-aromatic carbocycle; an optionally substituted 6-10-membered carbocyclic aryl group; an optionally substituted, 4-8 membered non-aromatic heterocycle; or an optionally substituted, 5-10 membered heteroary group.

In a tenth subset of variables of Structural Formula VI for the compounds of this invention, values of the variables for Structural Formula VI, including specific values, and provisos are each and independently as described above in the ninth subset of variables of Structural Formulae (IA) and (I); and when $Q^3$ is —C(O)—, or $Y^1$ is a bond, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —$S(O)R^a$; —$SO_2R^a$; —$NR^bR^c$; —$C(O)R^b$; —$C(O)OR^b$; —$OC(O)R^b$; —NRC(O)$R^b$; —$C(O)NR^bR^c$; —$NRC(O)NR^bR^c$; —$NRC(O)OR^b$; —$OCONR^bR^c$; —$C(O)NRCO_2R^b$; —$NRC(O)NRCO_2R^b$; —$C(O)NR(OR^b)$; —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In an eleventh subset of variables of Structural Formula VI, values of the variables for Structural Formula VI, including specific values, are each and independently as described above in the thirteenth subset of variables of Structural Formulae (IA) and (I).

In another embodiment, the present invention is generally related to compounds represented by any one of Structural Formulae II, III, IV and V, or pharmaceutically acceptable salts thereof:

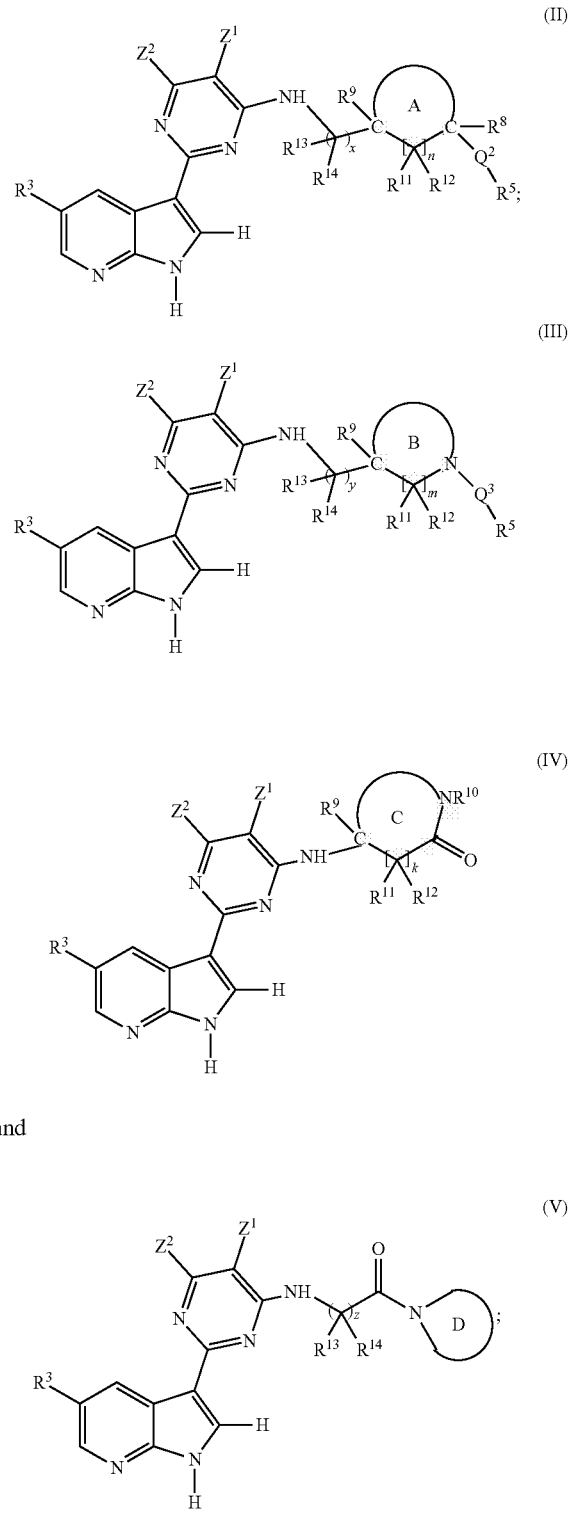

A first subset of variables of Structural Formulae II, III, IV and V for the compounds of the invention is as follows:

Each $Q^2$ is independently —O—, —S—, —NR'—, —C(O)—, —$CO_2$—, —OC(O)—, —C(O)NR'—, —C(O)NRC(O)O—, —NRC(O)NRC(O)O—, —NRC(O)—, —NRC(O)NR'—, —$NRCO_2$—, —OC(O)NR'—, —S(O)—, —$SO_2$—, —$N(R)SO_2$—, —$SO_2NR'$—, —$NRSO_2NR'$—, or —$(CR^6R^7)_p$—$Y^1$—.

Each $Q^3$ is independently —C(O)—, —CO$_2$—, —C(O)NR'—, —SO$_2$—, —SO$_2$NR'—, —C(O)NRC(O)O—, or —(CR$^6$R$^7$)$_p$—Y$^1$—.

$Z^1$ is —H, —F, —Cl, C$_1$-C$_4$ haloalkyl (e.g., —CF$_3$), C$_1$-C$_4$ alkyl, —O(C$_1$-C$_4$ alkyl), or —CN.

$Z^2$ is —H, C$_1$-C$_6$ alkyl, —O(C$_1$-C$_6$ alkyl), —NH$_2$, —NH(C$_1$-C$_6$ alkyl), or —N(C$_1$-C$_6$ alkyl)$_2$, wherein each of said alkyl groups is optionally and independently substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

$R^3$ is —H, —Cl, —F, —Br, —CN, —CF$_3$, —O(C$_1$-C$_4$ alkyl), —OH, —NH$_2$, —NH(C$_1$-C$_4$ alkyl) or —N(C$_1$-C$_4$ alkyl)$_2$. Specifically, $R^3$ is —H, —F, —Cl, —CF$_3$, —NH$_2$, —NH(CH$_3$), or —N(CH$_3$)$_2$. Specifically, $R^3$ is —H, —Cl, or —F. Specifically, $R^3$ is —Cl.

Each R and R' is independently —H or C$_1$-C$_6$alkyl.

Definitions of rings A-D of formulae II-V, including specific variables, are each and independently as described above for the first set of variables of Structural Formulae (IA) and (I), wherein each of rings A-D is independently an optionally substituted, 4-7 membered ring.

Values of the remaining variables of Structural Formulae II-V, including specific values, and provisos are each and independently as described above for the first subset of variables of Structural Formulae (IA) and (I).

A second subset of variables of Structural Formulae II, III, IV and V for the compounds of the invention is as follows:

$Z^1$ is —H, —F, —Cl, —CF$_3$, —CH$_3$, or —CN.

$Z^2$ is —H or C$_1$-C$_6$ alkyl optionally substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae II-V, including specific values and provisos are each and independently as described above for the first subset of variables of Structural Formulae II-V.

A third subset of variables of Structural Formulae II, III, IV and V for the compounds of the invention is as follows:

$Z^1$ is —H, —F, or —CN.

$Z^2$ is —H or C$_1$-C$_6$ alkyl optionally substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae II-V, including specific values, and provisos are each and independently as described above for the first subset of variables of Structural Formulae II-V.

A fourth subset of variables of Structural Formulae II, III, IV and V for the compounds of the invention is as follows:

$Z^1$ is —H, —F, or —CN.

$Z^2$ is —H or C$_1$-C$_6$ alkyl optionally substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CNC$_1$-C$_4$ alkyl), and C$_1$-C$_4$ alkoxy.

$R^3$ is —H, —Cl or —F.

Values of the remaining variables of Structural Formulae II-V, including specific values, and provisos are each and independently as described above for the first subset of variables of Structural Formulae II-V.

A fifth subset of variables of Structural Formulae II, III, IV and V for the compounds of the invention is as follows:

$Z^1$ is —H, —F or —CN.

$Z^2$ is —H or C$_1$-C$_6$ alkyl optionally substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

$R^3$ is —H, —Cl, —F, —CF$_3$, —NH$_2$, —NH(CH$_3$), —N(CH$_3$)$_2$.

$R^6$ and $R^7$ are each independently —H or —CH$_3$, or together with the carbon atoms to which they are attached they form a cyclopropane ring.

Each $R^8$ is independently —H, halogen, cyano, hydroxy, C$_1$-C$_4$ alkyl, C$_1$-C$_4$ haloalkyl, C$_1$-C$_4$ hydroxyalkyl, C$_2$-C$_4$ alkoxyalkyl, —O(C$_1$-C$_4$ alkyl), —NH$_2$, —NH(C$_1$-C$_4$ alkyl) or —N(C$_1$-C$_4$ alkyl)$_2$.

Each $R^9$ is independently —H or —CH$_3$.

$R^{11}$ and $R^{12}$ are each independently —H or —CH$_3$.

$R^{13}$ and $R^{14}$ are each independently —H or —CH$_3$, or together with the carbon atoms to which they are attached they form a cyclopropane ring.

Values of the remaining variables of Structural Formulae II-V, including specific values, and provisos are each and independently as described above for the first subset of variables of Structural Formulae II-V.

A sixth subset of variables of Structural Formulae II, III, IV and V for the compounds of the invention is as follows:

$Z^1$ is —H, —F or —CN.

$Z^2$ is —H or C$_1$-C$_6$ alkyl optionally substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

$R^3$ is —H, —Cl or —F.

$R^6$ and $R^7$ are each independently —H or —CH$_3$, or together with the carbon atoms to which they are attached they form a cyclopropane ring.

Each $R^8$ is independently —H, halogen, cyano, hydroxy, C$_1$-C$_4$ alkyl, C$_1$-C$_4$ haloalkyl, C$_1$-C$_4$ hydroxyalkyl, C$_2$-C$_4$ alkoxyalkyl, —O(C$_1$-C$_4$ alkyl), —NH$_2$, —NH(C$_1$-C$_4$ alkyl), or —N(C$_1$-C$_4$ alkyl)$_2$.

Each $R^9$ is independently —H or —CH$_3$.

$R^{11}$ and $R^{12}$ are each independently —H or —CH$_3$.

$R^{13}$ and $R^{14}$ are each independently —H or —CH$_3$, or together with the carbon atoms to which they are attached they form a cyclopropane ring.

Values of the remaining variables of Structural Formulae II-V, including specific values, and provisos are each and independently as described above for the first subset of variables of Structural Formulae II-V.

In a seventh subset of variables of Structural Formulae II-V for the compounds of the invention, values for variables, except for $R^6$, $R^7$, $R^8$, $R^9$, $R^{11}$, $R^{12}$, $R^{13}$ and $R^{14}$, of Structural Formulae II-V, including specific values, and provisos are each and independently as described above in the first, second, third, or fourth subset of variables of Structural Formulae (IA) and (I).

$R^6$ and $R^7$ are each independently —H or —C$_1$-C$_4$ alkyl, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl) or —N($C_1$-$C_4$ alkyl)$_2$.

Each $R^9$ is independently —H or —$C_1$-$C_4$ alkyl.

$R^{11}$ and $R^{12}$ are each independently —H or —$C_1$-$C_4$ alkyl.

$R^{13}$ and $R^{14}$ are each independently —H or —$C_1$-$C_4$ alkyl, or together with the carbon atoms to which they are attached they form a cyclopropane ring In an eighth subset of variables of Structural Formulae II-V for the compounds of the invention, values for variables of Structural Formulae II-V, including specific values, and provisos are each and independently as described above in the first subset of variables of Structural Formulae (IA) and (I).

In a ninth subset of variables of Structural Formulae II-V for the compounds of the invention, values for variables of Structural Formulae II-V, including specific values, are each and independently as described above for the first, second, third, fourth, fifth, sixth, seventh, or eighth subset of variables of Structural Formulae II-V; and where applicable:

provided that if $Q^2$-$R^5$ is —OR$^5$ or —NR'R$^5$, then ring A is further substituted with one or more instances of $J^4$ other than —H; and provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group.

In a tenth subset of variables of Structural Formulae II-V for the compounds of the invention, values for variables of Structural Formulae II-V, including specific values, are each and independently as described above for the ninth subset of variables of Structural Formulae II-V; and where applicable:

when $Q^3$ is —C(O)—, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR$^b$; —SR$^b$; —S(O)R$^a$; —SO$_2$R$^a$; —NR$^b$R$^c$; —C(O)R$^b$; —C(O)OR$^b$; —OC(O)R$^b$; —NRC(O)R$^b$; —C(O)NR$^b$R$^c$; —NRC(O)NR$^b$R$^c$; —NRC(O)OR$^b$; —OCONR$^b$R$^c$; —C(O)NRCO$_2$R$^b$; —NRC(O)NRCO$_2$R$^b$; —C(O)NR(OR$^b$); —SO$_2$NR$^c$R$^b$; —NRSO$_2$R$^b$; and —NRSO$_2$NR$^c$R$^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In an eleventh subset of variables of Structural Formulae II-V for the compounds of the invention, values for variables of Structural Formulae II-V, including specific values, are each and independently as described above for the first, second, third, fourth, fifth, sixth, seventh, or eighth subset of variables of Structural Formulae II-V; and where applicable:

provided that if $Y^1$ is a bond, then $R^5$ is a substituted $C_1$-$C_6$ aliphatic group; an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group; and provided that if $Q^2$ and $Q^3$ are each and independently a bond, then $R^5$ is an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group.

In a twelfth subset of variables of Structural Formulae II-V for the compounds of the invention, values for variables of Structural Formulae II-V, including specific values, are each and independently as described above for the eleventh subset of variables of Structural Formulae II-V; and where applicable:

when $Y^1$ is a bond, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR$^b$; —SR$^b$; —S(O)$_2$R$^a$; —SO$_2$R$^a$; —NR$^b$R$^c$; —C(O)R$^b$; —C(O)OR$^b$; —OC(O)R$^b$; —NRC(O)R$^b$; —C(O)NR$^b$R$^c$; —NRC(O)NR$^b$R$^c$; —NRC(O)OR$^b$; —OCONR$^b$R$^c$; —C(O)NRCO$_2$R$^b$; —NRC(O)NRCO$_2$R$^b$; —C(O)NR(OR$^b$); —SO$_2$NR$^c$R$^b$; —NRSO$_2$R$^b$; and —NRSO$_2$NR$^c$R$^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In a thirteenth subset of variables of Structural Formulae II-V for the compounds of the invention, values for variables of Structural Formulae II-V, including specific values, are each and independently as described above for the first, second, third, fourth, fifth, sixth, seventh, or eighth subset of variables of Structural Formulae II-V; and where applicable:

provided that if $Q^2$-$R^5$ is —OR$^5$ or —NR'R$^5$, then ring A is further substituted with one or more instances of $J^4$ other than —H;

provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group.

provided that if $Y^1$ is a bond, then $R^5$ is a substituted $C_1$-$C_6$ aliphatic group; an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group; and provided that if $Q^2$ and $Q^3$ are each and independently a bond, then $R^5$ is an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group.

In a fourteenth subset of variables of Structural Formulae II-V for the compounds of the invention, values for variables of Structural Formulae II-V, including specific values, are each and independently as described above for the thirteenth subset of variables of Structural Formulae II-V; and where applicable:

when $Q^3$ is —C(O)—, or $Y^1$ is a bond, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR$^b$; —SR$^b$; —S(O)R$^a$; —SO$_2$R$^a$; —NR$^b$R$^c$; —C(O)R$^b$; —C(O)OR$^b$; —OC(O)R$^b$; —NRC(O)R$^b$; —C(O)NR$^b$R$^c$; —NRC(O)NR$^b$R$^c$; —NRC(O)OR$^b$; —OCONR$^b$R$^c$; —C(O)NRCO$_2$R$^b$; —NRC(O)NRCO$_2$R$^b$; —C(O)NR(OR$^b$); —SO$_2$NR$^c$R$^b$; —NRSO$_2$R$^b$; and —NRSO$_2$NR$^c$R$^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

A fifteenth subset of variables of Structural Formulae II-V is as follows:

Each of $J^A$ and $J^B$ is independently selected from the group consisting of halogen, cyano, oxo, and Q'—R$^5$; or optionally two $J^A$ and two $J^B$, respectively, together with the atom(s) to which they are attached, independently form a 5-7 membered ring that is optionally substituted with one or more instances of $J^{E1}$, and fused to the ring to which they are attached.

$Q^1$ is independently a bond, —O—, —S—, —NR—, —C(O)—, —CO$_2$—, —OC(O)—, —C(O)NR—, —C(O)NRC(O)O—, NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$N(R)—, —NRSO$_2$NR—, or —(CR$^6$R$^7$)$_p$—Y$^1$—.

$Q^2$ is independently a bond, —O—, —S—, —NR—, —C(O)—, —CO$_2$—, —OC(O)—, —C(O)NR—, —C(O)NRC(O)O—, NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$N(R)—, —NRSO$_2$NR—, or —(CR$^6$R$^7$)$_p$—Y$^1$—.

$Q^3$ is independently a bond, —C(O)—, —CO$_2$—, —C(O)NR—, —SO$_2$—, —SO$_2$N(R)—, —C(O)NRC(O)O— or —(CR$^6$R$^7$)$_p$—Y$^1$—.

R$^5$ is: i) —H; ii) a C$_1$-C$_6$ aliphatic group optionally substituted with one or more instances of $J^{C1}$; iii) a C$_3$-C$_8$ non-aromatic carbocycle, or 6-10 membered carbocyclic aryl group, each optionally and independently substituted with one or more instances of $J^{C1}$; or iv) a 4-8 membered non-aromatic heterocycle, or a 5-10 membered heteroaryl group, each optionally and independently substituted with one or more instances of $J^{D1}$.

Each of $J^{C1}$ and $J^{D1}$ is independently selected from the group consisting of halogen, cyano, oxo, R$^a$, —OR$^b$, —SR$^b$, —S(O)R$^a$, —SO$_2$R$^a$, —NR$^b$R$^c$, —C(O)R$^b$, —C(O)OR$^b$, —OC(O)R$^b$, —NRC(O)R$^b$, —C(O)NR$^b$R$^c$, —NRC(O)NR$^b$R$^c$, —NRC(O)OR$^b$, —OCONR$^b$R$^c$, —C(O)NRCO$_2$R$^b$, —NRC(O)NRC(O)OR$^b$, —C(O)NR(OR$^b$), —SO$_2$NR$^c$R$^b$, —NRSO$_2$R$^b$, and —NRSO$_2$NR$^c$R$^b$, or optionally, two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

Ring A is a C$_3$-C$_8$ non-aromatic carbocycle optionally and independently further substituted with one or more instances of $J^A$.

Values of the remaining variables of Structural Formulae II-V, including specific values, and provisos are each and independently as described above for the first, second, third, fourth, fifth, sixth, seventh, eighth, ninth, tenth, eleventh, twelfth, thirteenth, or fourteenth subset of variables of Structural Formulae II-V.

In another embodiment, the present invention is generally related to compounds of Structural Formula XI(A) or XI(B), or pharmaceutically acceptable salts thereof.

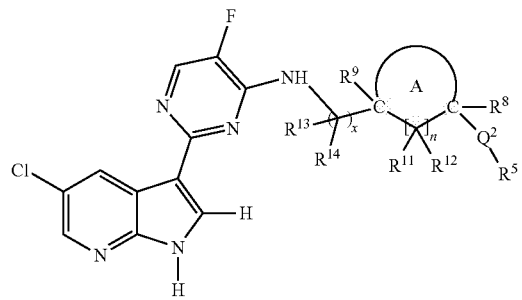

(XIA)

or

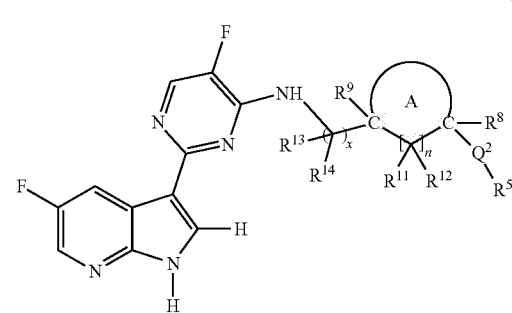

(XIB)

A first subset of variables of Structural Formulae XI(A) and XI(B) for the compounds of the invention is as follows:

Each Q$^2$ is independently —O—, —S—, —NR'—, —C(O)—, —CO$_2$—, —OC(O)—, —C(O)NR'—, —C(O)NRC(O)O—, —NRC(O)NRC(O)O—, —NRC(O)—, —NRC(O)NR'—, —NRCO$_2$—, —OC(O)NR'—, —SO$_2$—, —N(R)SO$_2$—, —SO$_2$NR'—, or —(CR$^6$R$^7$)$_p$—Y$^1$—.

Ring A is a 5-7 membered, non-aromatic carbocyclic ring optionally further substituted with one or more substituents independently selected from the group consisting of halogen, cyano, hydroxy, oxo, C$_1$-C$_6$ alkyl, C$_2$-C$_6$ alkenyl, —NH$_2$, —NH(C$_1$-C$_6$ alkyl), —N(C$_1$-C$_6$ alkyl)$_2$, —O(C$_1$-C$_6$ alkyl), —C(O)NH$_2$, —C(O)NH(C$_1$-C$_6$ alkyl), —C(O)N(C$_1$-C$_6$ alkyl)$_2$, —C(O)(C$_1$-C$_6$-alkyl), —OC(O)(C$_1$-C$_6$ alkyl), —NHC(O)(C$_1$-C$_6$ alkyl), —N(C$_1$-C$_6$ alkyl)C(O)(C$_1$-C$_6$ alkyl), and —CO$_2$R$^b$; wherein each of said alkyl and alkenyl groups is optionally and independently substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, ring A is a 5-7 membered, non-aromatic carbocyclic ring optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H, and —CO$_2$(C$_1$-C$_4$ alkyl), wherein each of said alkyl groups is optionally and independently substituted with one or more substituents independently selected from the group consisting of halogen, cyano, hydroxy, oxo, C$_1$-C$_4$ alkyl, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, ring A is a 5-7 membered carbocyclic ring optionally further substituted with one or more substituents independently selected from the group consisting of halogen, cyano, hydroxy, oxo, —$NH_2$, —$NH(C_1$-$C_2$ alkyl), —$NH(C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —$CO_2H$, and —$CO_2(C_1$-$C_4$ alkyl).

$R^6$ and $R^7$ are each independently —H or —$CH_3$, or together with the carbon atoms to which they are attached they form a cyclopropane ring.

Each $R^8$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —$O(C_1$-$C_4$ alkyl), —$NH_2$, —$NH(C_1$-$C_4$ alkyl), or —$N(C_1$-$C_4$ alkyl)$_2$.

Each $R^9$ is independently —H or —$CH_3$.

$R^{11}$ and $R^{12}$ are each independently —H or —$CH_3$.

$R^{13}$ and $R^{14}$ are each independently —H or —$CH_3$, or together with the carbon atoms to which they are attached they form a cyclopropane ring.

Each R and R' is independently —H or $C_1$-$C_6$ alkyl.

Provided that if $Q^2$-$R^5$ is —$OR^5$ or —$NR'R^5$, then ring A is further substituted with one or more instances of $J^A$ other than —H.

Values of the remaining variables of Structural Formulae XI(A) and XI(B), including specific values, and provisos are each and independently as described above in the first subset of variables of Structural Formulae (IA) and (I).

A second subset of variables of Structural Formulae XI(A) and XI(B) for the compounds of the invention is as follows:

Values of Ring A, $Q^2$, R, R', $R^5$, $R^6$, $R^7$, $R^8$, $R^9$, $R^{10}$, $R^{11}$, $R^{12}$, $R^{13}$, $R^{14}$, including specific values, and provisos are each and independently as described above in the first subset of variables of Structural Formulae XI(A) and XI(B).

Variable x is 0 or 1 and variable n is 0 or 1.

Values of the remaining variables of Structural Formulae XI(A) or XI(B), including specific values, and provisos are each and independently as described above in the first subset of variables of Structural Formulae XI(A) and XI(B).

A third subset of variables of Structural Formulae XI(A) and XI(B) for the compounds of the invention is as follows:

Values of Ring A, R, R', $R^6$, $R^7$, $R^8$, $R^9$, $R^{11}$, $R^{12}$, $R^{13}$, $R^{14}$, x and n, including specific values, and provisos are each and independently as described above in the second subset of variables of Structural Formulae XI(A) and XI(B).

$Q^2$ is —O—, —NR'—, —CO—, —$CO_2$—, —C(O)NR'—, —NRC(O)—, —NRC(O)NR—, —$NRCO_2$—, —OCONR'—, —$NRSO_2$—, —$SO_2NR'$—, or —$(CR^6R^7)_p$—$Y^1$—. Specifically, $Q^2$ is —O—, —NH—, —$N(CH_3)$—, —C(O)—, —$CO_2$—, —C(O)NH—, —C(O)N($CH_3$)—, —NHC(O)—, —N($CH_3$)C(O)—, —NHC(O)NR'—, —N($CH_3$)C(O)NR'—, —$NHCO_2$—, —N($CH_3$)$CO_2$—, —OC(O)NR'—, —$NHSO_2$—, —N($CH_3$)$SO_2$—, —$SO_2NH$—, —$SO_2N(CH_3)$—, or —$(CR^6R^7)_p$—$Y^1$—.

Values of the remaining variables of Structural Formulae XI(A) and XI(B), including specific values, and provisos are each and independently as described above in the first subset of variables of Structural Formulae (IA) and (I).

A fourth subset of variables of Structural Formulae XI(A) and XI(B) for the compounds of the invention is as follows:

Values of Ring A, $Q^2$, R, R', $R^6$, $R^7$, $R^8$, $R^9$, $R^{11}$, $R^{12}$, $R^{13}$, $R^{14}$, X and n, including specific values, and provisos are each and independently as described above in the third subset of variables of Structural Formulae XI(A) and XI(B)

$R^5$ is independently i) —H; ii) a $C_1$-$C_6$ aliphatic group (e.g., $C_1$-$C_6$-alkyl or $C_2$-$C_6$ alkenyl group) optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$.

Each $J^{C1}$ and $J^{D1}$ is independently selected from the group consisting of halogen, cyano, oxo, $R^a$, —$OR^b$, —$SR^b$, —$S(O)R^a$—, —$SO_2R^a$, —$NHR^c$, —$C(O)R^b$, —$C(O)OR^b$, —$OC(O)R^b$, —$NHC(O)R^b$, —$C(O)NHR^a$, —$NHC(O)NHR^a$, —$NHC(O)OR^b$, —$OCONHR^c$, —$NHC(O)NHC(O)OR^b$, —$N(CH_3)R^a$, —$N(CH_3)C(O)R^b$, —$C(O)N(CH_3)R^c$, —$N(CH_3)C(O)NHR^c$, —$N(CH_3)C(O)OR^b$, —$OCON(CH_3)R^a$, —$C(O)NHCO_2R^b$, —$C(O)N(CH_3)CO_2R^b$, —$N(CH_3)C(O)NHC(O)OR^b$, —$NHSO_2R^b$, —$SO_2NHR^b$, —$SO_2N(CH_3)R^b$, and —$N(CH_3)SO_2R^b$.

Values of the remaining variables of Structural Formulae XI(A) and XI(B), including specific values, and provisos are each and independently as described above in the first subset of variables of Structural Formulae (IA) and (I).

A fifth subset of variables of Structural Formulae XI(A) and XI(B) for the compounds of the invention is as follows:

Values of $Q^2$, R, R'$R^6$, $R^7$, $R^8$, $R^9$, $R^{11}$, $R^{12}$, $R^{13}$, $R^{14}$, x and n, including specific values, and provisos are each and independently as described above in the fourth subset of variables of Structural Formulae XI(A) and XI(B).

Ring A is optionally further substituted with one or more substituents independently selected from the group consisting of halogen, cyano, hydroxy, oxo, $C_1$-$C_4$ alkyl, —$O(C_1$-$C_4$ alkyl), —$NH_2$, —$NH(C_1$-$C_4$ alkyl), —$N(C_1$-$C_4$ alkyl)$_2$, —$C(O)(C_1$-$C_4$ alkyl), —$CO_2H$, and —$CO_2(C_1$-$C_4$ alkyl), wherein each of said alkyl groups is optionally and independently substituted with one or more substituents independently selected from the group consisting of h halogen, cyano, hydroxy, oxo, $C_1$-$C_4$ alkyl, —$NH_2$, —$NH(C_1$-$C_6$ alkyl), —$N(C_1$-$C_6$ alkyl)$_2$, —$OCO(C_1$-$C_4$ alkyl), —$CO(C_1$-$C_4$ alkyl), —$CO_2H$, —$CO_2(C_1$-$C_4$ alkyl), and $C_1$-$C_4$ alkoxy.

It is provided that if $Q^2$-$R^5$ is —$OR^5$ or —$NR'R^5$, then ring A is further substituted with one or more instances of $J^A$ other than —H.

Values of the remaining variables of Structural Formulae XI(A) and XI(B), including specific values, and provisos are each and independently as described above in the first subset of variables of Structural Formulae (IA) and (I).

A sixth subset of variables of Structural Formulae XI(A) and XI(B) for the compounds of the invention is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, and provisos are each and independently as described above in the fifth subset of variables of Structural Formulae XI(A) and XI(B).

The group —[(C)$_{0-1}R^{13}R^{14}$]-ring A-$Q^2$-$R^5$ is independently selected from one of the depicted below

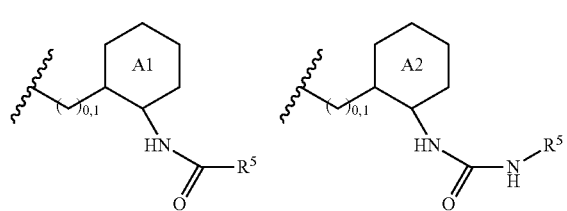

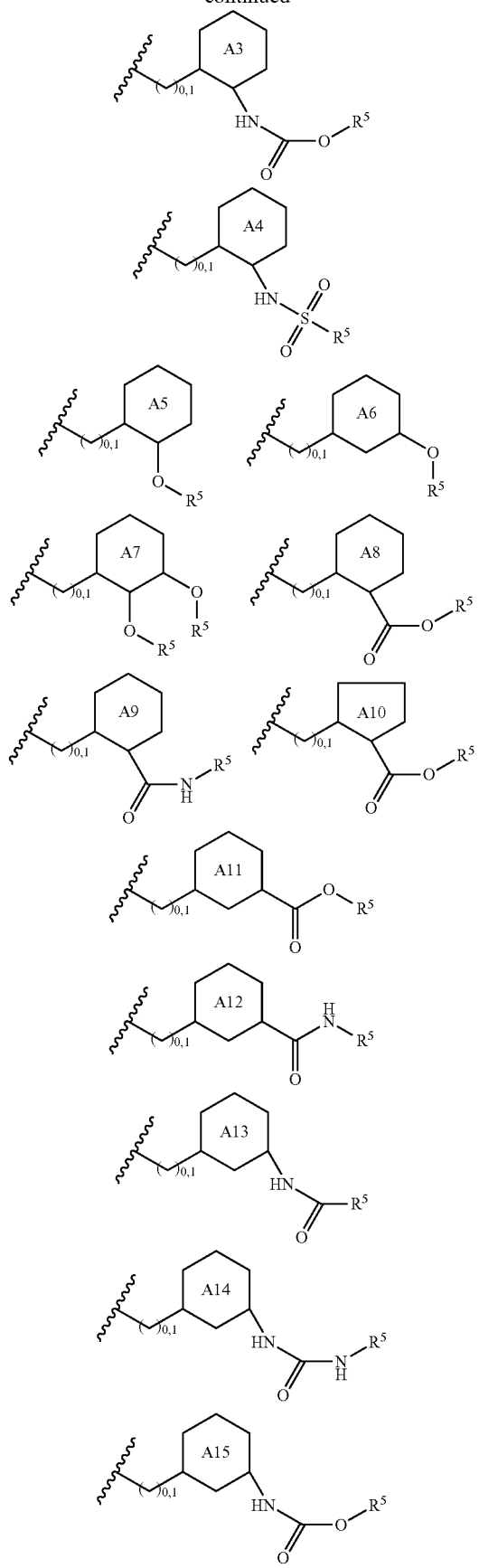
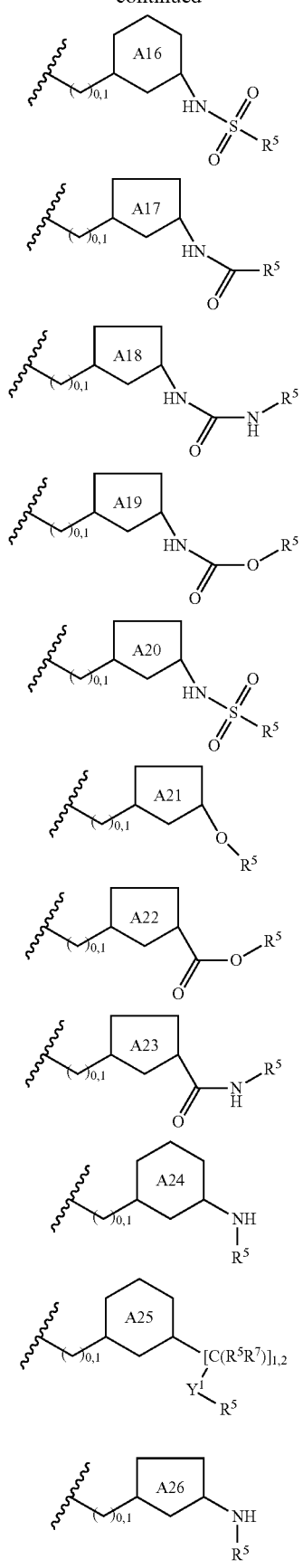

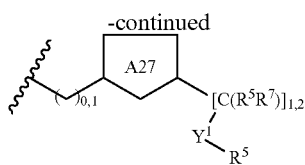

wherein each of rings A1-A27 is independently and optionally further substituted with one or more substituents. Specifically, rings A5, A6, A21, A24, and A26 are each independently further substituted with one or more instances of substituents other than —H. Suitable substituents are as described above for ring A in the first subset of variables of Structural Formulae XI(A) and XI(B).

Values of the remaining variables of Structural Formulae XI(A) and XI(B), including specific values, and provisos are each and independently as described above in the first subset of variables of Structural Formulae (IA) and (I).

A seventh subset of variables of Structural Formulae XI(A) and XI(B) for the compounds of the invention is as follows:

Values of the group —[$CR^{13}R^{14}$]$_x$-ring A-$Q^2$-$R^5$, ring A, $Q^2$, R, R', $R^6$, $R^7$, $R^8$, $R^9$, $R^{11}$, $R^{12}$, $R^{13}$, $R^{14}$, x and n, including specific values, and provisos are each and independently as described above in the sixth subset of variables of Structural Formulae XI(A) and XI(B).

Each $R^5$ is independently: i) —H; ii) a $C_1$-$C_6$-aliphatic group optionally substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), —$CO_2H$, $C_3$-$C_8$ non-aromatic carbocycle, phenyl, 4-8 membered non-aromatic heterocycle, and 5-6 membered heteroaryl; or iii) a $C_3$-$C_7$ non-aromatic carbocycle, a 4-7 membered non-aromatic heterocycle, a phenyl group, or a 5-6 membered heteroaryl ring, each of which is optionally and independently substituted with one or more substituents independently selected from the group consisting of halogen, cyano, hydroxy, oxo, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), and —$CO_2H$; wherein each of said alkyl groups for the substituents of the aliphatic group, carbocycle, heterocycle, phenyl and heteroaryl group represented by $R^5$ is independently and optionally substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; and wherein each of said carbocycle, phenyl, heterocycle, and heteroaryl for the substituents of the $C_1$-$C_6$-aliphatic group represented by $R^5$ is independently and optionally substituted with one or more substituents independently selected from the group consisting of halogen, cyano, hydroxy, oxo, $C_1$-$C_4$ alkyl, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Values of the remaining variables of Structural Formulae XI(A) and XI(B), including specific values, and provisos are each and independently as described above in the first subset of variables of Structural Formulae (IA) and (I).

An eighth subset of variables of Structural Formulae XI(A) and XI(B) for the compounds of the invention is as follows:

Values of $Q^2$, R, R', $R^5$, $R^6$, $R^7$, $R^8$, $R^9$, $R^{11}$, $R^{12}$, $R^{13}$, $R^{14}$, x and n including specific values, and provisos are each and independently as described above in the seventh subset of variables of Structural Formulae XI(A) and XI(B).

The group —[(C)$_{0-1}R^{13}R^{14}$]-ring A-$Q^2$-$R^5$ is independently selected from one of the depicted below

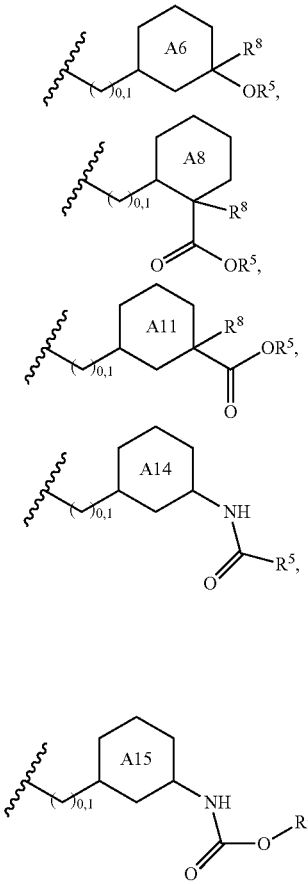

or wherein each of rings A6, A8, A11, A14 and A15 is optionally and independently further substituted. Suitable substituents are as described above for ring A in the first subset of variables of Structural Formulae XI(A) and XI(B).

Each $R^8$ independently is halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —$NH_2$, —NH($C_1$-$C_4$ alkyl) or —N($C_1$-$C_4$ alkyl)$_2$.

Values of the remaining variables of Structural Formulae XI(A) and XI(B), including specific values, and provisos are each and independently as described above in the first subset of variables of Structural Formulae (IA) and (I).

A ninth subset of variables of Structural Formulae XI(A) and XI(B) for the compounds of the invention is as follows:

Values of the group —[$CR^{13}R^{14}$]$_x$-ring A-$Q^2$-$R^5$, ring A, $Q^2$, R, R', $R^6$, $R^7$, $R^8$, $R^9$, $R^{11}$, $R^{12}$, $R^{13}$, $R^{14}$, x and n, including specific values, and provisos are each and independently as described above in the eighth subset of variables of Structural Formulae XI(A) and XI(B).

Each $R^5$ is independently: i) —H; ii) an optionally substituted $C_1$-$C_6$ alkyl group; iii) an optionally substituted, $C_3$-$C_7$ non-aromatic carbocycle; or iv) an optionally substituted, 4-7 membered non-aromatic heterocycle, wherein said alkyl group represented by $R^5$ is optionally substituted with one or more substituents independently selected from the group consisting of halogen, cyano, hydroxy, oxo, —$NH_2$, —NH($C_1$-

$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, optionally substituted, $C_3$-$C_7$ non-aromatic carbocycle, and optionally substituted, 4-7 membered non-aromatic heterocycle. Each of said carbocycles and heterocycles represented by $R^5$, and referred to for the substituents of the $C_1$-$C_6$ alkyl group represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —CO$_2$H, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

Values of the remaining variables of Structural Formulae XI(A) and XI(B), including specific values, and provisos are each and independently as described above in the first subset of variables of Structural Formulae (IA) and (I).

A tenth subset of variables of Structural Formulae XI(A) and XI(B) for the compounds of the invention is as follows:

Values of $Q^2$, R, R', $R^5$, $R^6$, $R^7$, $R^8$, $R^9$, $R^{11}$, $R^{12}$, $R^{13}$, $R^{14}$, x and n, including specific values, and provisos are each and independently as described above in the seventh subset of variables of Structural Formulae XI(A) and XI(B).

The group —[(C)$_{0-1}$R$^{13}$R$^{14}$]-ring A-Q$^2$-R$^5$ is independently selected from one of the depicted below:

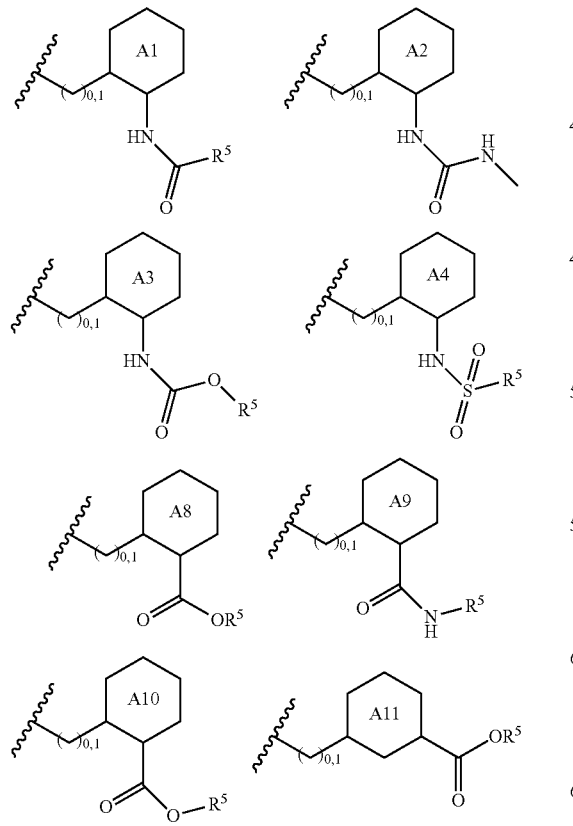

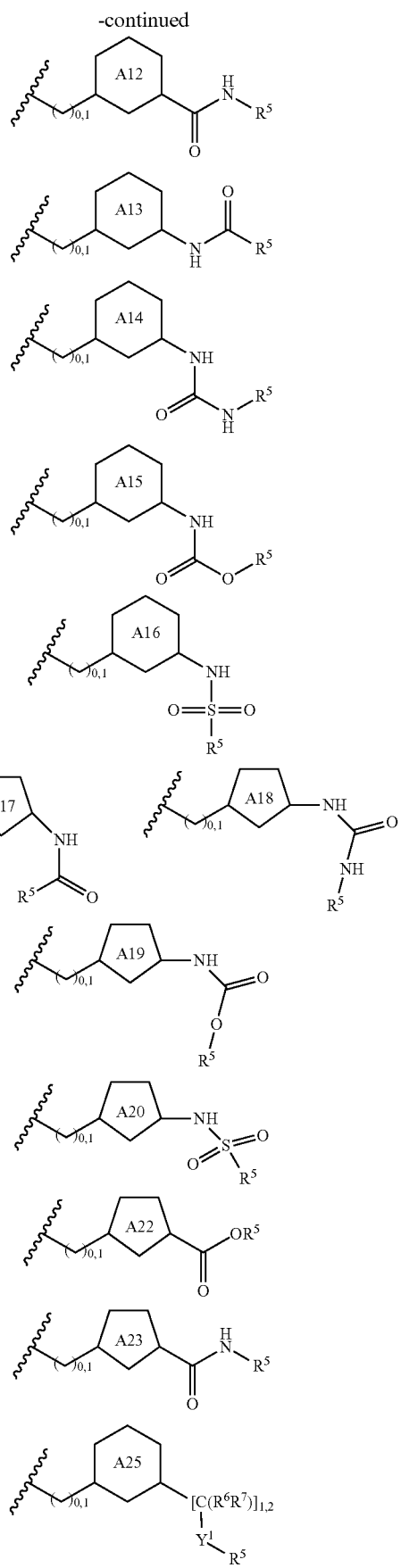

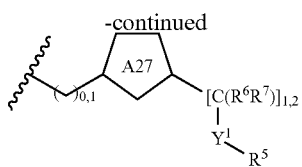

wherein each of rings A1-A4, A7-A20, A22, A23, A25 and A27 is independently and optionally further substituted. Suitable substituents are as described above for ring A in the first subset of variables of Structural Formulae XI(A) and XI(B).

Values of the remaining variables of Structural Formulae XI(A) and XI(B), including specific values, and provisos are each and independently as described above in the first subset of variables of Structural Formulae (IA) and (I).

An eleventh subset of variables of Structural Formulae XI(A) and XI(B) for the compounds of the invention is as follows:

Values of $Q^2$, R, R', $R^5$, $R^6$, $R^7$, $R^8$, $R^9$, $R^{11}$, $R^{12}$, $R^{13}$, $R^{14}$, x, and n, including specific values, and provisos are each and independently as described above in the seventh subset of variables of Structural Formulae XI(A) and XI(B).

The group $—[(C)_{0-1}R^{13}R^{14}]$-ring A-$Q^2$-$R^5$ is independently selected from one of the depicted below:

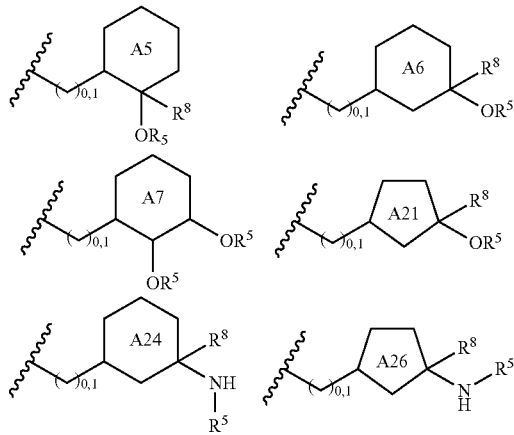

wherein each of rings A5-A7, A21, A24 and A26 is independently and optionally further substituted. Suitable substituents are as described above for ring A in the first subset of variables of Structural Formulae XI(A) and XI(B).

Each $R^8$ independently is halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$alkyl), —$NH_2$, —NH($C_1$-$C_4$ alkyl), or —N($C_1$-$C_4$ alkyl)$_2$.

Values of the remaining variables of Structural Formulae XI(A) and XI(B), including specific values, and provisos are each and independently as described above in the first subset of variables of Structural Formulae (IA) and (I).

In a twelfth subset of variables of Structural Formulae XI(A) and XI(B) for the compounds of the invention, values of the variables for Structural Formulae XI(A) and XI(B), including specific values, and provisos are each and independently as described above in the first subset of variables of Structural Formulae (IA) and (I).

In a thirteenth subset of variables of Structural Formulae XI(A) and XI(B) for the compounds of the invention, values of the variables for Structural Formulae XI(A) and XI(B), including specific values, and provisos are each and independently as described above in the first, second, third, fourth, fifth, sixth, seventh, eighth, ninth, tenth, or eleventh subset of variables of Structural Formulae XI(A) and XI(B); and where applicable:

provided that if $Y^1$ is a bond, then $R^5$ is a substituted $C_1$-$C_6$ aliphatic group; an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group; and provided that if $Q^2$ is a bond, then $R^5$ is an optionally substituted $C_3$-$C_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group.

In a fourteenth subset of variables of Structural Formulae XI(A) and XI(B) for the compounds of the invention, values of the variables for Structural Formulae XI(A) and XI(B), including specific values, and provisos are each and independently as described above in the thirteenth subset of variables of Structural Formulae XI(A) and XI(B); and where applicable:

when $Y^1$ is a bond, the $C_1$-$C_6$ aliphatic group represented by $R^5$ is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —$OR^b$; —$SR^b$; —S(O)$R^a$; —$SO_2R^a$; —$NR^bR^c$; —C(O)$R^b$; —C(O)O$R^b$; —OC(O)$R^b$; —NRC(O)$R^b$; —C(O)$NR^bR^c$; —NRC(O)$NR^bR^c$; —NRC(O)O$R^b$; —OCON$R^bR^c$; —C(O)NRCO$_2R^6$; —NRC(O)NRCO$_2R^6$; —C(O)NR(O$R^b$); —$SO_2NR^cR^b$; —$NRSO_2R^b$; and —$NRSO_2NR^cR^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

In a fifteenth subset of variables of Structural Formulae XI(A) and XI(B), values of the variables for Structural Formulae XI(A) and XI(B), including specific values, are each and independently as described above in the thirteenth subset of variables of Structural Formulae (IA) and (I), in the eleventh subset of variables of Structural Formula (VI), or in the fifteenth subset of variables of Structural Formulae (II)-(V).

In another embodiment, the present invention generally relates to compounds of Structural Formula XII(A) or XII(B), or pharmaceutically acceptable salts thereof.

(XIIA)

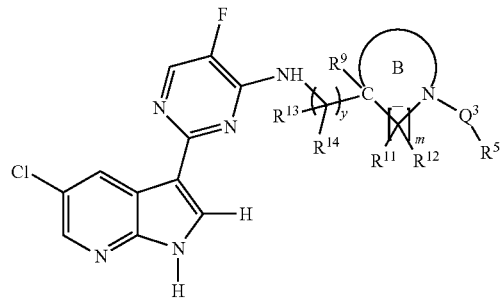

or

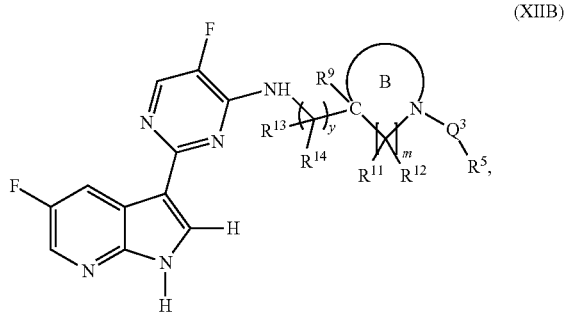

(XIIB)

A first subset of variables of Structural Formulae XII(A) and XII(B) for the compounds of the invention is as follows:

Each $Q^3$ is independently —C(O)—, —CO$_2$—, —C(O)NR'—, —SO$_2$—, —SO$_2$NR'—, —C(O)NRC(O)O—, or —(CR$^6$R$^7$)$_p$—Y$^1$—.

Ring B is a 4-7 membered, non-aromatic, heterocyclic ring optionally further substituted with one or more substituents independently selected from the group consisting of halogen, cyano, hydroxy, oxo, $C_1$-$C_6$ alkyl, $C_2$-$C_6$ alkenyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —CO$_2$R$^b$; wherein each of said alkyl and alkenyl groups is optionally and independently substituted with one or more substituents independently selected from the group consisting of halogen, cyano, hydroxy, oxo, $C_1$-$C_4$ alkyl, —NH$_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy. Specifically, Ring B is optionally further substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —CO$_2$H, and —CO$_2$($C_1$-$C_4$ alkyl), wherein each of said alkyl groups is optionally and independently substituted with one or more substituents independently selected from the group consisting of halogen, cyano, hydroxy, oxo, $C_1$-$C_4$ alkyl, —NH$_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy. Specifically, Ring B is optionally further substituted with one or more substituents independently selected from the group consisting of halogen, cyano, hydroxy, oxo, —NH$_2$, —NH($C_1$-$C_2$ alkyl), —NH($C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —CO$_2$H, and —CO$_2$($C_1$-$C_4$ alkyl).

$R^6$ and $R^7$ are each independently —H or —CH$_3$, or together with the carbon atoms to which they are attached they form a cyclopropane ring.

$R^9$ is —H or —CH$_3$.

$R^{11}$ and $R^{12}$ are each independently —H or —CH$_3$.

$R^{13}$ and $R^{14}$ are each independently —H or —CH$_3$, or together with the carbon atoms to which they are attached they form a cyclopropane ring.

Each R and R' is independently —H or $C_1$-$C_6$ alkyl.

Provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group. Specifically, the $C_1$-$C_6$ aliphatic group is substituted with one or more instances of $J^{C1}$, wherein $J^{C1}$ is independently selected from: an optionally substituted, $C_3$-$C_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR$^b$; —SR$^b$; —S(O)R$^a$; —SO$_2$R$^a$; —NR$^b$R$^c$; —C(O)R$^b$; —C(O)OR$^b$; —OC(O)R$^b$; —NRC(O)R$^b$; —C(O)NR$^b$R$^c$; —NRC(O)NR$^b$R$^c$; —NRC(O)OR$^b$; —OCONR$^b$R$^c$; —C(O)NRCO$_2$R$^b$; —NRC(O)NRCO$_2$R$^b$; —C(O)NR(OR$^b$); —SO$_2$NR$^c$R$^b$; —NRSO$_2$R$^b$; and —NRSO$_2$NR$^c$R$^b$; or optionally two $J^{C1}$ and two $J^{D1}$, respectively, together with the atoms to which they are attached, independently form a 5-7-membered ring that is optionally substituted with one or more instances of $J^{E1}$, and fused to the respective ring to which they are attached.

Values of the remaining variables of Structural Formulae XII(A) and XII(B), including specific values, and provisos are each and independently as described above in the first subset of variables of Structural Formulae (IA) and (I).

A second subset of variables of Structural Formulae XII(A) and XII(B) for the compounds of the invention is as follows:

Values of Ring B, $Q^3$, R, R', $R^6$, $R^7$, $R^9$, $R^{11}$, $R^{12}$, $R^{13}$, and $R^{14}$, including specific values, and provisos are each and independently as described above in the first subset of variables of Structural Formulae XII(A) and XII(B).

Variable y=0 or 1.

Values of the remaining variables of Structural Formulae XII(A) and XII(B), including specific values, and provisos are each and independently as described above in the first subset of variables of Structural Formulae (IA) and (I).

A third subset of variables of Structural Formulae XII(A) and XII(B) is as follows:

Values of Ring B, $Q^3$, R, R', $R^6$, $R^7$, $R^9$, $R^{11}$, $R^{12}$, $R^{13}$ and $R^{14}$ and y, including specific values, and provisos are each and independently as described above in the second subset of variables of Structural Formulae XII(A) and XII(B).

$Q^3$ is independently —C(O)—, —CO$_2$—, —C(O)NH—, —C(O)N(CH$_3$)—, —C(O)NHC(O)O—, —C(O)N(CH$_3$)C(O)O—, —SO$_2$—, —SO$_2$NH—, —SO$_2$N(CH$_3$)—, or —(CR$^6$R$^7$)$_p$—Y$^1$—.

Values of the remaining variables of Structural Formulae XII(A) and XII(B), including specific values, and provisos are each and independently as described above in the first subset of variables of Structural Formulae (IA) and (I).

A fourth subset of variables of Structural Formulae XII(A) and XII(B) for the compounds of the invention is as follows:

Values of Ring B, $Q^3$, R, R', $R^6$, $R^7$, $R^9$, $R^{11}$, $R^{12}$, $R^{13}$, $R^{14}$, and y, including specific values, and provisos are each and independently as described above in the third subset of variables of Structural Formulae XII(A) and XII(B).

$R^5$ is independently i) —H; ii) a $C_1$-$C_6$ aliphatic group (e.g., $C_1$-$C_6$-alkyl or $C_2$-$C_6$-alkenyl group) optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$.

Each of $J^{C1}$ and $J^{D1}$ is independently selected from the group consisting of halogen, cyano, oxo, R$^a$, —OR$^b$, —SR$^b$, —S(O)R$^a$, —SO$_2$R$^a$, —NHR$^c$, —C(O)R$^b$, —C(O)OR$^b$, —OC(O)R$^b$, —NHC(O)R$^b$, —C(O)NHR$^c$, —NHC(O)

NHR$^c$, —NHC(O)OR$^b$, —OCONHR$^c$, —NHC(O)NHC(O)OR$^b$, —N(CH$_3$)R$^c$, —N(CH$_3$)C(O)R$^b$, —C(O)N(CH$_3$)R$^c$, N(CH$_3$)C(O)NHR$^c$, —N(CH$_3$)C(O)OR$^b$, —OCON(CH$_3$) R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N (CH$_3$)R$^b$, and —N(CH$_3$)SO$_2$R$^b$.

Values of the remaining variables of Structural Formulae XII(A) and XII(B), including specific values, and provisos are each and independently as described above in the first subset of variables of Structural Formulae (IA) and (I).

A fifth subset of variables of Structural Formulae XII(A) and XII(B) for the compounds of the invention is as follows:

Values of Q$^3$, R, R', R$^5$, R$^6$, R$^7$, R$^9$, R$^{11}$, R$^{12}$, R$^{13}$, R$^{14}$, and y, including specific values, and provisos are each and independently as described above in the fourth subset of variables of Structural Formulae XII(A) and XII(B).

Ring B is optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H, and —CO$_2$(C$_1$-C$_4$ alkyl), wherein each of said alkyl groups is optionally and independently substituted with one or more substituents independently selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae XII(A) and XII(B), including specific values, and provisos are each and independently as described above in the first subset of variables of Structural Formulae (IA) and (I).

A sixth subset of variables of Structural Formulae XII(A) and XII(B) for the compounds of the invention is as follows:

Values of Q$^3$, R, R', R$^5$, R$^6$, R$^7$, R$^9$, R$^{11}$, R$^{12}$, R$^{13}$, R$^{14}$, and y, including specific values, and provisos are each and independently as described above in the fifth subset of variables of Structural Formulae XII(A) and XII(B).

Ring B is independently selected from one of the structures depicted below:

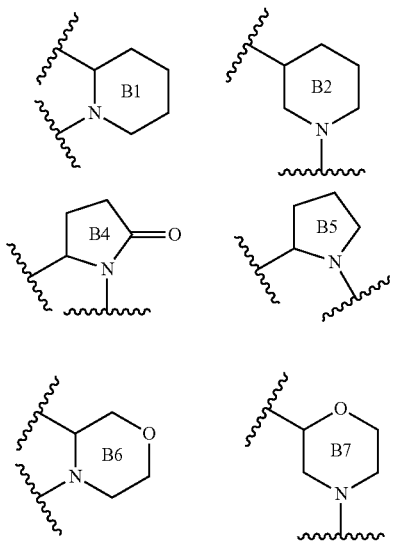

-continued

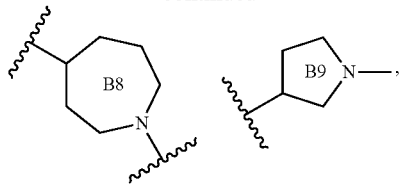

wherein each of rings B1, B2 and B4-B9 is optionally and independently substituted. Suitable substituents are independently as described above for ring B in the first subset of variables of Structural Formulae (IA) and (I).

Values of the remaining variables of Structural Formulae XII(A) and XII(B), including specific values, and provisos are each and independently as described above in the first subset of variables of Structural Formulae (IA) and (I).

A seventh subset of variables of Structural Formulae XII (A) and XII(B) for the compounds of the invention is as follows:

Values of Ring B, Q$^3$, R, R', R$^6$, R$^7$, R$^9$, R$^{11}$, R$^{12}$, R$^{13}$, R$^{14}$, and y, including specific values, and provisos are each and independently as described above in the sixth subset of variables of Structural Formulae XII(A) and XII(B).

Each R$^5$ is independently: i) —H; ii) a C$_1$-C$_6$-aliphatic group optionally substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), —CO$_2$H, C$_3$-C$_8$ non-aromatic carbocycle, phenyl, 4-8 membered non-aromatic heterocycle, and 5-6 membered heteroaryl; or iii) a C$_3$-C$_7$ non-aromatic carbocycle, a 4-7 membered non-aromatic heterocycle, a phenyl group, or a 5-6 membered heteroaryl ring, each of which is optionally and independently substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl), and —CO$_2$H; wherein each of said alkyl groups for the substituents of the aliphatic group, carbocycle, heterocycle, phenyl and heteroaryl group represented by R$^5$ is independently and optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy; and wherein each of said carbocycle, phenyl, heterocycle, and heteroaryl for the substituents of the C$_1$-C$_6$-aliphatic group represented by R$^5$ is independently and optionally substituted with one or more substituents independently selected from the group consisting of halogen, cyano, hydroxy, oxo, C$_1$-C$_4$ alkyl, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae XII(A) and XII(B), including specific values, and provisos are each and independently as described above in the first subset of variables of Structural Formulae (IA) and (I).

An eighth subset of variables of Structural Formulae XII (A) and XII(B) for the compounds of the invention is as follows:

Values of Q$^3$, R, R', R$^5$, R$^6$, R$^7$, R$^9$, R$^{11}$, R$^{12}$, R$^{13}$, R$^{14}$, and y, including specific values, and provisos are each and independently as described above in the seventh subset of variables of Structural Formulae XII(A) and XII(B).

The group —[C(R$^{13}$R$^{14}$)]$_x$-ring B-Q$^2$-R$^5$:

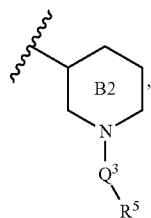

wherein ring B2 is optionally and independently further substituted with one or more substituents independently selected from the group consisting of with one or more substituents independently selected from the group consisting of halogen, cyano, hydroxy, oxo, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

Values of the remaining variables of Structural Formulae XII(A) and XII(B), including specific values, and provisos are each and independently as described above in the first subset of variables of Structural Formulae (IA) and (I).

A ninth subset of variables of Structural Formulae XII(A) and XII(B) for the compounds of the invention is as follows:

Values of ring B, Q$^3$, R, R', R$^5$, R$^6$, R$^7$, R$^9$, R$^{11}$, R$^{12}$, R$^{13}$, R$^{14}$, and y, including specific values, and provisos are each and independently as described above in the eighth subset of variables of Structural Formulae XII(A) and XII(B).

Each R$^5$ is independently: i) —H; ii) an optionally substituted C$_1$-C$_6$ alkyl group; iii) an optionally substituted, C$_3$-C$_7$ non-aromatic carbocycle; or iv) an optionally substituted, 4-7 membered non-aromatic heterocycle, wherein said alkyl group represented by R$^5$ is optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkoxy, optionally substituted, C$_3$-C$_7$ non-aromatic carbocycle, and optionally substituted, 4-7 membered non-aromatic heterocycle. Each of said carbocycles and heterocycles represented by R$^5$, and referred to for the substituents of the C$_1$-C$_6$ alkyl group represented by R$^5$ is independently and optionally substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl) and —CO$_2$H, wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formulae XII(A) and XII(B), including specific values, and provisos are each and independently as described above in the first subset of variables of Structural Formulae (IA) and (I).

In a tenth set of variables of Structural Formulae XII(A) and XII(B) for the compounds of the invention, values of the variables for Structural Formulae XII(A) and XII(B), including specific values, and provisos are each and independently as described above in the first subset of variables of Structural Formulae (IA) and (I).

In an eleventh subset of variables of Structural Formulae XII(A) and XII(B) for the compounds of the invention, values of the variables for Structural Formulae XII(A) and XII(B), including specific values, and provisos are each and independently as described above in the first, second, third, fourth, fifth, sixth, seventh, eighth, ninth, tenth, or eleventh subset of variables of Structural Formulae XII(A) and XII(B); and where applicable:

provided that if Y$^1$ is a bond, then R$^5$ is a substituted C$_1$-C$_6$ aliphatic group; an optionally substituted C$_3$-C$_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group; and provided that if Q$^3$ is a bond, then R$^5$ is an optionally substituted C$_3$-C$_8$ non-aromatic carbocycle; an optionally substituted, 6-10-membered carbocyclic aryl group; an optionally substituted, 4-8 membered non-aromatic heterocycle; or an optionally substituted, 5-10 membered heteroary group.

In a twelfth subset of variables of Structural Formulae XII(A) and XII(B) for the compounds of the invention, values of the variables for Structural Formulae XII(A) and XII(B), including specific values, and provisos are each and independently as described above in the eleventh subset of variables of Structural Formulae XII(A) and XII(B); and where applicable:

when Y$^1$ is a bond, the C$_1$-C$_6$ aliphatic group represented by R$^5$ is substituted with one or more instances of J$^{C1}$, wherein J$^{C1}$ is independently selected from: an optionally substituted, C$_3$-C$_8$ non-aromatic carbocycle; an optionally substituted, 6-10-membered carbocyclic aryl group; an optionally substituted, 4-8 membered non-aromatic heterocycle; an optionally substituted, 5-10 membered heteroaryl group; —OR$^b$; —SR$^b$; —S(O)R$^a$; —SO$_2$R$^a$; —NR$^b$R$^c$; —C(O)R$^b$; —C(O)OR$^b$; —OC(O)R$^b$; —NRC(O)R$^b$; —C(O)NR$^b$R$^c$; —NRC(O)NR$^b$R$^c$; —NRC(O)OR$^b$; —OCONR$^b$R$^c$; —C(O)NRCO$_2$R$^b$; —NRC(O)NRCO$_2$R$^b$; —C(O)NR(OR$^b$); —SO$_2$NR$^c$R$^b$; —NRSO$_2$R$^b$; and —NRSO$_2$NR$^c$R$^b$; or optionally two J$^{C1}$ and two J$^{D1}$, respectively, together with the atoms to which they are attached, independently form a 5-7-membered ring that is optionally substituted with one or more instances of J$^{E1}$, and fused to the respective ring to which they are attached.

In a thirteenth subset of variables of Structural Formulae XII(A) and XII(B), values of the variables for Structural Formulae XII(A) and XII(B), including specific values, are each and independently as described above in the thirteenth subset of variables of Structural Formulae (IA) and (I), in the eleventh subset of variables of Structural Formula VI, or in the fifteenth subset of variables of Structural Formulae II-V.

In another embodiment, the present invention generally relates to compounds of Structural Formula XIII, or pharmaceutically acceptable salts thereof:

(XIII)

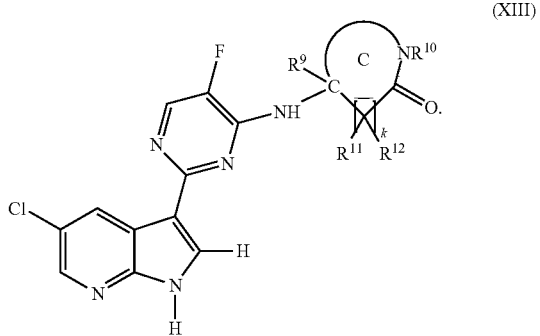

A first subset of variables of Structural Formula XIII for the compounds of the invention is as follows:

Ring C is a 5-7 membered, non-aromatic, heterocyclic ring optionally further substituted with one or more substituents independently selected from the group consisting of halogen, cyano, hydroxy, $C_1$-$C_6$ alkyl, $C_2$-$C_6$ alkenyl, —$NH_2$, —NH($C_1$-$C_6$ alkyl), —N($C_1$-$C_6$ alkyl)$_2$, —O($C_1$-$C_6$ alkyl), —C(O)$NH_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —$CO_2R^b$; wherein each of said alkyl and alkenyl groups is optionally and independently substituted with one or more substituents independently selected from the group consisting of halogen, cyano, hydroxy, oxo, —$NH_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, ring C is optionally further substituted with one or more substituents independently selected from the group consisting of halogen, cyano, hydroxy, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —$CO_2H$ and —$CO_2$($C_1$-$C_4$ alkyl), wherein each of said alkyl groups is optionally and independently substituted with one or more substituents independently selected from the group consisting of halogen, cyano, hydroxy, oxo, —$NH_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy. Specifically, ring C is optionally further substituted with one or more substituents independently selected from the group consisting of halogen, cyano, hydroxy, —$NH_2$, —NH($C_1$-$C_2$ alkyl), —NH($C_1$-$C_2$ alkyl)$_2$, $C_1$-$C_2$ alkyl, $C_1$-$C_2$ haloalkyl, $C_1$-$C_2$ hydroxyalkyl, $C_2$-$C_4$ alkoxyalkyl, $C_1$-$C_2$ alkoxy, $C_1$-$C_2$ hydroxyalkoxy, $C_1$-$C_2$ haloalkoxy, $C_2$-$C_4$ alkoxyalkoxy, —$CO_2H$, and —$CO_2$($C_1$-$C_4$ alkyl).

$R^6$ and $R^7$ are each independently —H or —$CH_3$, or together with the carbon atoms to which they are attached they form a cyclopropane ring.

$R^9$ is —H or —$CH_3$.

$R^{11}$ and $R^{12}$ are each independently —H or —$CH_3$.

Each R and R' is independently —H or $C_1$-$C_6$ alkyl.

Values of the remaining variables of Structural Formula XIII, including specific values, and provisos are each and independently as described above in the first subset of variables of Structural Formulae (IA) and (I).

A second subset of variables of Structural Formula XIII for the compounds of the invention is as follows:

Values of Ring C, R, R', $R^6$, $R^7$, $R^9$, $R^{11}$, and $R^{12}$, including specific values, are each and independently as described above in the first subset of variables of Structural Formula XIII.

$R^{10}$ is —H or $C_1$-$C_6$-alkyl.

Values of the remaining variables of Structural Formula XIII, including specific values, and provisos are each and independently as described above in the first subset of variables of Structural Formulae (IA) and (I).

A third subset of variables of Structural Formula XIII for the compounds of the invention is as follows:

Values of R, R', $R^6$, $R^7$, $R^9$, $R^{11}$, and $R^{12}$, including specific values, are each and independently as described above in the second subset of variables of Structure Formula XIII.

Ring C is a 5-7 membered, non-aromatic, heterocyclic group optionally further substituted with one or more substituents independently selected from the group consisting of halogen, hydroxy, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —$CO_2H$, and —$CO_2$($C_1$-$C_4$ alkyl), wherein each of said alkyl groups is optionally and independently substituted with one or more substituents independently selected from the group consisting of halogen, cyano, hydroxy, oxo, —$NH_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Values of the remaining variables of Structural Formula XIII, including specific values, and provisos are each and independently as described above in the first subset of variables of Structural Formulae (IA) and (I).

A fourth subset of variables of Structural Formula XIII for the compounds of the invention is as follows:

Values of R, R', $R^6$, $R^7$, $R^9$, $R^{11}$, and $R^{12}$, including specific values, are each and independently as described above in the third subset of variables of Structure Formula XIII.

Ring C is independently selected from:

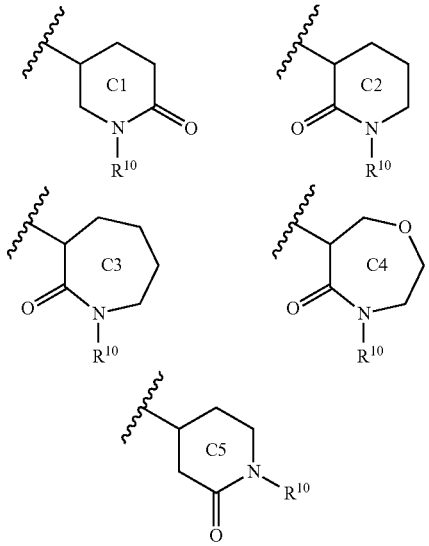

wherein each of rings C1-C5 is optionally and independently substituted with one or more substituents independently selected from the group consisting of halogen, cyano, hydroxy, $C_1$-$C_4$ alkyl, —O($C_1$-$C_4$ alkyl), —$NH_2$, —NH($C_1$-$C_4$ alkyl), —N($C_1$-$C_4$ alkyl)$_2$, —C(O)($C_1$-$C_4$ alkyl), —$CO_2H$, and —$CO_2$($C_1$-$C_4$ alkyl), wherein each of said alkyl groups is optionally and independently substituted with one or more independently substituents independently selected from the group consisting of halogen, cyano, hydroxy, oxo, —$NH_2$, —NH($C_1$-$C_6$ alkyl), —N($C_1$-$C_6$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy.

Specifically, each of rings C1-C5 is optionally and independently further substituted with one or more substituents independently selected from the group consisting of halogen, cyano, hydroxy, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

Values of the remaining variables of Structural Formula XIII, including specific values, and provisos are each and independently as described above in the first subset of variables of Structural Formulae (IA) and (I).

In a fifth set of variables of Structural Formula XIII for the compounds of the invention, values of the variables for Structural Formula XIII, including specific values, are each and independently as described above in the first subset of variables of Structural Formulae (IA) and (I).

In another embodiment, the present invention generally relates to compounds represented by Structural Formula below XIV, or a pharmaceutically acceptable salt thereof:

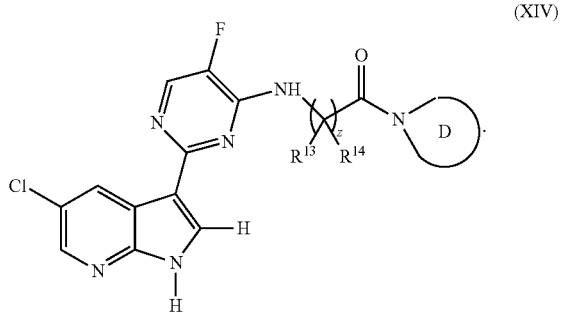

(XIV)

A first subset of variables of Structural Formula XIV for the compounds of the invention is as follows:

Ring D is 4-7 membered, non-aromatic, heterocyclic ring optionally substituted with one or more substituents independently selected from the group consisting of halogen, cyano, hydroxy, oxo, C$_1$-C$_6$ alkyl, C$_2$-C$_6$ alkenyl, —NH$_2$, —NH(C$_1$-C$_6$ alkyl), —N(C$_1$-C$_6$ alkyl)$_2$, —O(C$_1$-C$_6$ alkyl), —C(O)NH$_2$, —C(O)NH(C$_1$-C$_6$ alkyl), —C(O)N(C$_1$-C$_6$ alkyl)$_2$, —C(O)(C$_1$-C$_6$-alkyl), —OC(O)(C$_1$-C$_6$ alkyl), —NHC(O)(C$_1$-C$_6$ alkyl), —N(C$_1$-C$_6$ alkyl)C(O)(C$_1$-C$_6$ alkyl), and —CO$_2$R$^b$; wherein each of said alkyl and alkenyl groups is optionally and independently substituted with one or more substituents independently selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, ring D is optionally further substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H and —CO$_2$(C$_1$-C$_4$ alkyl), wherein each of said alkyl groups is optionally and independently substituted with one or more substituents independently selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, ring D is optionally further substituted with one or more substituents independently selected from the group consisting of halogen, cyano, hydroxy, oxo, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

R$^6$ and R$^7$ are each independently —H or —CH$_3$, or together with the carbon atoms to which they are attached they form a cyclopropane ring.

R$^{13}$ and R$^{14}$ are each independently —H or —CH$_3$, or together with the carbon atoms to which they are attached they form a cyclopropane ring.

Each of R and R' is independently —H or C$_1$-C$_6$ alkyl.

Values of the remaining variables of Structural Formula XIV, including specific values, and provisos are each and independently as described above in the first subset of variables of Structural Formulae (IA) and (I).

A second subset of variables of Structural Formula XIV for the compounds of the invention is as follows:

Values for Ring D, R, R', R$^6$, R$^7$, R$^{13}$, and R$^{14}$, including specific values, are each and independently as described above in the first subset of variables of Structural Formula XIV.

Variable z is 1.

All other variables of Structural Formula XIV, including specific values, and provisos are each and independently as described above for the first subset of variables of Structural Formulae (IA) and (I).

A third subset of variables of Structural Formula IV for the compounds of the invention is as follows:

Values for z, R, R', R$^6$, R$^7$, R$^{13}$, and R$^{14}$, including specific values, are each and independently as described above in the second subset of variables of Structural Formula XIV.

Ring D is independently selected from the group consisting of

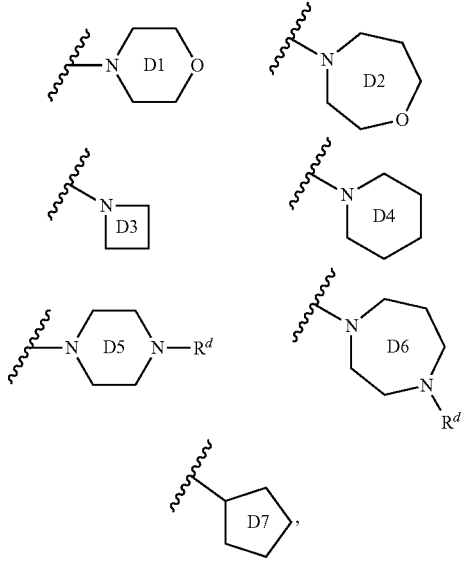

wherein each of rings D1-D7 is optionally and independently substituted one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —CO$_2$H and —CO$_2$(C$_1$-C$_4$ alkyl), wherein each of said alkyl groups is optionally and independently substituted with one or more substituents independently selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Specifically, each of rings D1-D7 is optionally and independently further substituted with one or more substituents independently selected from the group consisting of halogen, cyano, hydroxy, oxo, —NH$_2$, —NH(C$_1$-C$_2$ alkyl), —NH(C$_1$-C$_2$ alkyl)$_2$, C$_1$-C$_2$ alkyl, C$_1$-C$_2$ haloalkyl, C$_1$-C$_2$ hydroxyalkyl, C$_2$-C$_4$ alkoxyalkyl, C$_1$-C$_2$ alkoxy, C$_1$-C$_2$ hydroxyalkoxy, C$_1$-C$_2$ haloalkoxy, C$_2$-C$_4$ alkoxyalkoxy, —CO$_2$H, and —CO$_2$(C$_1$-C$_4$ alkyl).

Each R$^d$ is independently —H, C$_1$-C$_6$ alkyl or —C(O)(C$_1$-C$_6$ alkyl), wherein each of said alkyl moiety is optionally and independently substituted with one or more groups selected from halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Specifically, each R$^d$ is independently —H or C$_1$-C$_6$ alkyl optionally and independently substituted with one or more groups selected from halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

Values of the remaining variables of Structural Formula XIV, including specific values, and provisos are each and independently as described above for the first subset of variables of Structural Formulae (IA) and (I).

In a fourth subset of variables of Structural Formula XIV for the compounds of the invention, values of the variables for Structural Formula XIV, including specific values and provisos, are each and independently as described above in the first subset of variables of Structural Formulae (IA) and (I).

In yet another embodiment, the compounds are represented by Structural Formula (I), or pharmaceutically acceptable salts thereof, wherein each variables of the formulae are independently as described above; and wherein:
R$^4$ is:

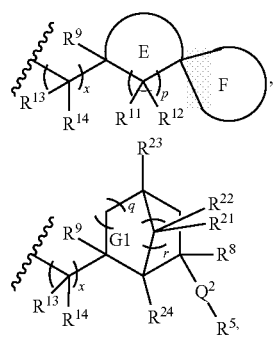

or

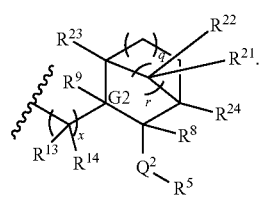

Ring E is a C$_4$-C$_8$ non-aromatic carbocycle optionally further substituted with one or more instances of J$^A$.

Rings F is a 4-8 membered non-aromatic heterocycle optionally substituted with one or more instances of J$^{E1}$.

Each of rings G1 and G2 is independently a 5-10 membered non-aromatic bridged carbocycle optionally substituted with one or more instances of J$^A$.

Q$^2$ is independently bond, —O—, —S—, —NR—, —C(O)—, —C(=NR)—, —CO$_2$—, —OC(O)—, —C(O)NR—, —C(O)NRC(O)O—, NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—.

R$^5$ is: i) —H; ii) an optionally substituted C$_1$-C$_6$ alkyl group; iii) an optionally substituted, C$_3$-C$_7$ non-aromatic carbocycle; or iv) an optionally substituted, 4-7 membered non-aromatic heterocycle; or optionally, together with R and the nitrogen atom to which it is attached, form a 5-7 membered, optionally substituted non-aromatic heterocycle. The alkyl group represented by R$^5$ is optionally substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), C$_1$-C$_4$ alkoxy, an optionally substituted, C$_3$-C$_7$ non-aromatic carbocycle, and an optionally substituted, 4-7 membered non-aromatic heterocycle; wherein each of said carbocycles and heterocycles represented by R$^5$, and referred to for the substituents of the C$_1$-C$_6$ alkyl group represented by R$^5$ is independently and optionally substituted with one or more substituents independently selected from the group consisting of halogen, cyano, hydroxy, oxo, C$_1$-C$_4$ alkyl, —O(C$_1$-C$_4$ alkyl), —NH$_2$, —NH(C$_1$-C$_4$ alkyl), —N(C$_1$-C$_4$ alkyl)$_2$, —C(O)(C$_1$-C$_4$ alkyl), —OC(O)(C$_1$-C$_4$ alkyl), —C(O)O(C$_1$-C$_4$ alkyl) and —CO$_2$H, wherein each of said alkyl groups is optionally and independently substituted with one or more substituents independently selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_r$-C$_4$ alkoxy.

Each of R$^8$ and R$^9$ is independently —H, halogen, cyano, hydroxy, C$_1$-C$_4$ alkyl, C$_1$-C$_4$ haloalkyl, C$_1$-C$_4$ hydroxyalkyl, C$_2$-C$_4$ alkoxyalkyl, —O(C$_1$-C$_4$ alkyl), —NH$_2$, —NH(C$_1$-C$_4$ alkyl), or —N(C$_1$-C$_4$ alkyl)$_2$.

R$^{11}$, R$^{12}$, R$^{13}$ and R$^{14}$ are each independently —H, halogen, or C$_1$-C$_6$ alkyl optionally substituted with one or more substituents independently selected from the group consisting of halogen, cyano, oxo, hydroxy, oxo, amino, carboxy, C$_1$-C$_6$ alkoxy, C$_1$-C$_6$ haloalkoxy, C$_1$-C$_6$ aminoalkoxy, C$_1$-C$_6$ cyanoalkoxy, C$_1$-C$_6$ hydroxyalkoxy, and C$_2$-C$_6$ alkoxyalkoxy; or optionally, R$^{13}$ and R$^{14}$, together with the carbon atom to which they are attached, form a cyclopropane ring, optionally substituted with one or more instances of methyl.

R$^{21}$, R$^{22}$, R$^{23}$ and R$^{24}$ are each independently —H, halogen, —OH, or C$_1$-C$_6$ alkyl optionally substituted with one or more substituents independently selected from the group consisting of halogen, cyano, oxo, hydroxy, oxo, amino, carboxy, C$_1$-C$_6$ alkoxy, C$_1$-C$_6$ haloalkoxy, C$_1$-C$_6$ aminoalkoxy, C$_1$-C$_6$ cyanoalkoxy, C$_1$-C$_6$ hydroxyalkoxy, and C$_2$-C$_6$ alkoxyalkoxy.

p and q are each independently 0, 1 or 2.
x is 0, 1 or 2.
r is 1 or 2.

Values of the remaining variables of Structural formula I, including specific values, and provisos are each and independently as described above in any one of the first through fifteenth sets of variables of Structural Formula I.

In yet another embodiment, the compounds represented by Structural Formula (I) or pharmaceutically acceptable salts thereof are independently as described above in the preceding paragraph; and ring F is selected from any one of rings F1-F6:

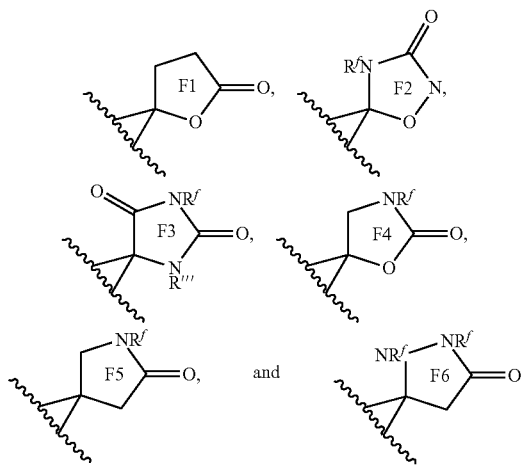

; each of rings F1-F6 optionally and independently substituted; and each $R^f$ is independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy.

In yet another embodiment, the compounds represented by Structural Formula (XIA) or (XIB), or pharmaceutically acceptable salts thereof are as described above; and the group —[C($R^{13}R^{14}$)]$_x$-ring A-$Q^2$-$R^5$ is independently:

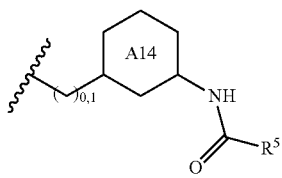

or

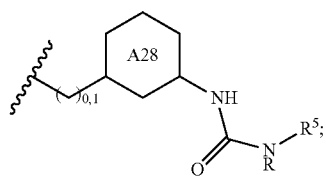

each of rings A14 and A28 is optionally and independently further substituted; and values of the remaining variables of Structural Formulae (XIA) and (XIB), including specific values, and provisos are each and independently as described above in any one of the first through eleventh sets of variables of Structural Formulae (XIA) and (XIB).

In yet another embodiment, the compounds represented by Structural Formula (XIA) or (XIB), or pharmaceutically acceptable salts thereof are independently as described above in the preceding paragraph; and $R^5$ is an optionally substituted $C_1$-$C_6$ alkyl group; an optionally substituted, $C_3$-$C_7$ non-aromatic carbocycle; or an optionally substituted, 4-7 membered non-aromatic heterocycle; or optionally, together with R and the nitrogen atom to which it is attached, form a 5-7 membered, optionally substituted non-aromatic heterocycle. Specifically, $R^5$ is an optionally substituted, 4-7 membered non-aromatic heterocycle; or optionally, together with R and the nitrogen atom to which it is attached, form a 5-7 membered, optionally substituted non-aromatic heterocycle.

In yet another embodiment, the compounds are represented by Structural Formula (IA) or (I), or pharmaceutically acceptable salts, wherein:

$R^4$ is:

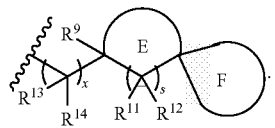

Ring E is a $C_4$-$C_{10}$ non-aromatic carbocycle optionally further substituted with one or more instances of $J^4$.

Rings F is a 4-8 membered non-aromatic heterocycle optionally substituted with one or more instances of $J^{E1}$. Specific examples of ring F includes:

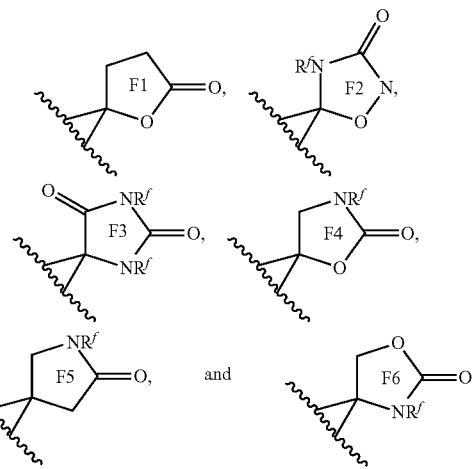

Additional example includes

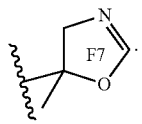

Each of rings F1-F7 optionally and independently substituted. Exemplary substituents for ring F (including rings F1-F7) include halogen, cyano, hydroxy, $C_1$-$C_4$ alkoxy, and $C_1$-$C_4$ alkyl optionally substituted with one or more substituents selected from the group consisting of halogen, cyano, hydroxy, and —O($C_1$-$C_4$ alkyl).

$R^f$ is independently —H or $C_1$-$C_6$ alkyl optionally and independently substituted with one or more substituents independently selected from the group consisting of halogen, cyano, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy and $C_2$-$C_6$ alkoxyalkoxy.

$R^9$ is independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, or $C_2$-$C_6$ alkoxyalkoxy.

$R^{11}$, $R^{12}$, $R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

Optionally, $R^{13}$ and $R^{14}$, together with the carbon atom to which they are attached, form a cyclopropane ring, optionally substituted with one or more instances of methyl.

s is 0, 1 or 2.

x is 0, 1 or 2.

The remaining variables are each and independently as described above in any one of the sets of variables for Structural Formulae (IA) and (I).

In yet another embodiment, the compounds are represented by Structural Formula (I) or (IA), or pharmaceutically acceptable salts thereof, wherein:

Ring E is a $C_4$-$C_8$ non-aromatic carbocycle optionally further substituted with one or more instances of $J^4$.

$R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

The other variables are each and independently as described in the preceeding paragraph.

In yet another embodiment, the compounds are represented by Structural Formula (IA) or (I), or pharmaceutically acceptable salts, wherein:

$R^4$ is:

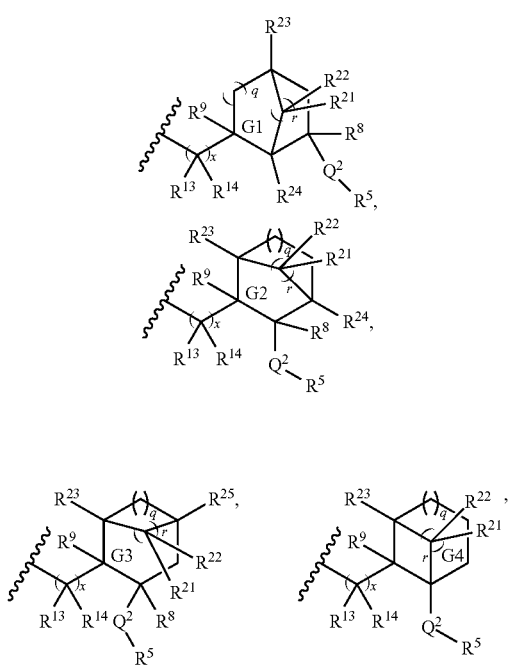

or

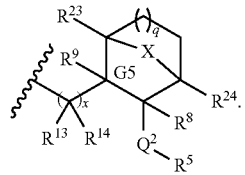

Each of rings G1-G4 is independently a 5-10 membered non-aromatic bridged ring optionally further substituted with one or more instances of $J^4$.

Ring G5 is a 5-10 membered non-aromatic bridged ring optionally further substituted with one or more instances of $J^B$.

X is —O—, —S—, or —NR$^g$—.

$R^8$ and $R^9$ are each independently —H, halogen, cyano, hydroxy, amino, carboxy, $C_1$-$C_6$ alkyl, $C_1$-$C_6$ haloalkyl, $C_1$-$C_6$ cyanoalkyl, $C_2$-$C_6$ alkoxyalkyl, $C_1$-$C_6$ aminoalkyl, $C_1$-$C_6$ hydroxyalkyl, $C_1$-$C_6$ carboxyalkyl, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, or $C_2$-$C_6$ alkoxyalkoxy.

$R^{13}$ and $R^{14}$ are each independently —H, halogen, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

Optionally, $R^{13}$ and $R^{14}$, together with the carbon atom to which they are attached, form a cyclopropane ring, optionally substituted with one or more instances of methyl.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy. Specifically, $R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl).

$R^g$ is —H or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

q is 0, 1 or 2; x is 0, 1 or 2; and r is 1 or 2.

The remaining variables are each and independently as described above in any set of variables for Structural Formulae (IA) and (I).

In yet another embodiment, the compounds are represented by Structural Formula (IA) or (I), pharmaceutically acceptable salts thereof, wherein:

$R^4$ is:

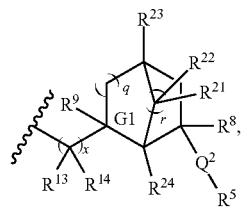

or

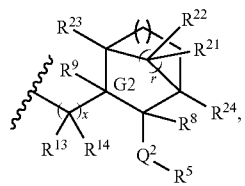

wherein rings G1 and G2 are each and independently a 5-10 membered non-aromatic bridged ring optionally further substituted with one or more instances of $J^A$.

Each of $R^8$ and $R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

$R^{21}$, $R^{22}$, $R^{23}$, and $R^{24}$ are each independently —H, halogen, —OH, or $C_1$-$C_6$ alkyl optionally substituted with one or more substituents independently selected from the group consisting of halogen, cyano, oxo, hydroxy, oxo, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

$Q^2$ is independently a bond, —O—, —S—, —NR—, —C(O)—, —C(=NR)—, —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—. Alternatively $Q^2$ is independently —O—, —CO$_2$—, —OC(O)—, —C(O)NR—, —NRC(O)—, —NRC(O)NR—, —NRCO$_2$—, —OC(O)NR—, —CO$_2$SO$_2$—, —P(O)$_2$O—, or —(CR$^6$R$^7$)$_p$—Y$^1$—. Alternatively $Q^2$ is independently —O— or —CO$_2$—.

In some embodiments, rings E and G (including G1-G5) are optionally and independently further substituted with one or more instances of $J^A$ (for carbocycle) or $J^B$ (for heterocycle), wherein each of $J^A$ and $J^B$ is independently selected from the group consisting of halogen, cyano, oxo, —NCO, and $Q^1$-$R^5$, and wherein:

$Q^1$ is independently a bond, —O—, —S—, —NR, C(O)—, —C(=NR)—, —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—; and Y$^1$ is independently a bond, —O—, —S—, —NR'—, —C(O)—, —C(=NR)—, —CO$_2$—, —OC(O)—, —C(O)NR'—, —C(O)NRC(O)O—, —NRC(O)NRC(O)O—, —NRC(O)—, —NRC(O)NR'—, —NRCO$_2$—, —OC(O)NR'—, —S(O)—, —SO$_2$—, —SO$_2$NR'—, —NRSO$_2$—, or —NRSO$_2$NR'—.

Alternatively: $Q^1$ is independently a bond, —O—, —S—, —NR—, —C(O)—, —CO$_2$—, —OC(O)—, —C(O)NR—, —C(O)NRC(O)O—, —NRC(O)NRC(O)O—, —NRC(O)—, —NRC(O)NR—, —NRCO$_2$—, —OC(O)NR—, —S(O)—, —SO$_2$—, —N(R)SO$_2$—, —SO$_2$NR'—, —NRSO$_2$NR'—, or —(CR$^6$R$^7$)$_p$—Y$^1$—; and Y$^1$ is independently —O—, —CO$_2$—, —OC(O)—, —C(O)NR—, —NRC(O)—, —NRC(O)NR—, —NRCO$_2$—, or —OC(O)NR—.

In yet another embodiment, $Q^1$ and Y$^1$ are each independently as described above in the preceeding paragraph, and:

$R^5$ is independently i) —H; ii) a $C_1$-$C_6$-aliphatic group optionally substituted with one or more instances of $J^{C1}$; iii) a $C_3$-$C_8$ non-aromatic carbocycle optionally substituted with one or more instances of $J^{C1}$; iv) a phenyl group optionally substituted with one or more instances of $J^{C1}$; v) a 4-8 membered non-aromatic heterocycle optionally substituted with one or more instances of $J^{D1}$ or vi) a 5-6 membered heteroaryl ring optionally substituted with one or more instances of $J^{D1}$; and each of $J^{C1}$ and $J^{D1}$ is independently selected from the group consisting of halogen, cyano, oxo, R$^a$, —OR$^b$, —SR$^b$, —S(O)R$^a$, —SO$_2$R$^a$, —NHR$^c$, —C(O)R$^b$, —C(O)OR$^b$, —OC(O)R$^b$, —NHC(O)R$^b$, —C(O)NHR$^c$, —NHC(O)NHR$^c$, —NHC(O)OR$^b$, —OCONHR$^c$, —NHC(O)NHC(O)OR$^b$, —N(CH$_3$)R$^c$, —N(CH$_3$)C(O)R$^b$, —C(O)N(CH$_3$)R$^c$, —N(CH$_3$)C(O)NHR$^c$, —N(CH$_3$)C(O)OR$^b$, —OCON(CH$_3$)R$^c$, —C(O)NHCO$_2$R$^b$, —C(O)N(CH$_3$)CO$_2$R$^b$, —N(CH$_3$)C(O)NHC(O)OR$^b$, —NHSO$_2$R$^b$, —SO$_2$NHR$^b$, —SO$_2$N(CH$_3$)R$^b$, and —N(CH$_3$)SO$_2$R$^b$.

In some specific embodiments, the compounds are represented by Structural Formula (IA) or (I), wherein:

$R^1$ is —H.

$R^2$ is —H, —CH$_3$, —CH$_2$OH, or —NH$_2$. Specifically, $R^2$ is —H, or —CH$_2$OH.

$R^3$ is —H, —F, —C$_1$, $C_{1-4}$ alkyl, or $C_{1-4}$ haloalkyl. Alternatively, $R^3$ is —H, —F, or —Cl.

$Z^1$ is —H, —F, or —Cl.

$Z^2$ is —H or $C_1$-$C_6$ alkyl optionally substituted with one or more substituents independently selected from the group consisting of halogen, cyano, hydroxy, and —O($C_1$-$C_4$ alkyl).

$Z^3$ is —H or $C_1$-$C_6$ alkyl optionally substituted with one or more substituents independently selected from the group consisting of halogen, cyano, hydroxy, and —O($C_1$-$C_4$ alkyl).

$R^5$ is: i) —H; ii) an optionally substituted $C_1$-$C_6$ alkyl group; iii) an optionally substituted, $C_3$-$C_7$ non-aromatic carbocycle; iv) an optionally substituted, 4-7 membered non-aromatic heterocycle; v)) an optionally substituted phenyl group; vi) an optionally substituted 5-6 membered heteroaryl ring; or optionally, together with R and the nitrogen atom to which it is attached, form a 5-7 membered, optionally substituted non-aromatic heterocycle; and said alkyl group represented by $R^5$ is optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, —NRCO($C_1$-$C_4$ alkyl), —CONR($C_1$-$C_4$ alkyl), —NRCO$_2$($C_1$-$C_4$ alkyl), a $C_3$-$C_7$ non-aromatic carbocycle optionally substituted with one or more instances of $J^{E1}$, a 4-7 membered non-aromatic heterocycle optionally substituted with one or more instances of $J^{E1}$; and a phenyl optionally substituted with one or more instances of $J^{E1}$; and wherein each of said carbocycle, heterocycle, phenyl and heteroaryl represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —CO$_2$H, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

The remaining variables, including $R^4$ that includes a spiro ring represented by rings E and F, or a bridged ring represented by rings G1-G5, are each and independently as described in any one of the preceeding four embodiments.

In yet another embodiment, the compounds are presented by Structural Formula (IA) or (I), wherein values of the variables are each and independently as described in the preceeding embodiment, except:

$Z^2$ is —H;
$Z^3$ is —H;
$R^5$ is independently: i) —H or ii) a $C_1$-$C_6$-alkyl group optionally substituted with one or more substituents independently selected from the group consisting of halogen, cyano, hydroxy, oxo, $C_1$-$C_4$ alkyl, —O($C_1$-$C_4$alkyl), —NH$_2$, —NH($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl), —CO$_2$H, $C_3$-$C_8$ non-aromatic carbocycle, 4-8 membered non-aromatic heterocycle, phenyl, and 5-6 membered heteroaryl;

wherein each of said alkyl groups referred to in the substituents of the $C_1$-$C_6$-alkyl group represented by $R^5$ is independently and optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy; and wherein each of said carbocycle, phenyl, heterocycle, and heteroaryl referred to in the substituents of the $C_1$-$C_6$-alkyl group represented by $R^5$ is independently and optionally substituted with one or more substituents independently selected from the group consisting of halogen, cyano, hydroxy, oxo, $C_1$-$C_4$ alkyl, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

In yet another embodiment, each of rings E, G1-G5 is independently and optionally substituted with one or more substituents selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —CO$_2$$R^b$; wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy. Specifically, each of rings E, G1-G5 is independently and optionally substituted with one or more substituents selected from the group consisting of halogen, cyano, hydroxy, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, and $C_1$-$C_4$ alkyl optionally substituted with one or more substituents selected from the group consisting of halogen, cyano, hydroxy, and —O($C_1$-$C_4$ alkyl).

In yet another embodiment, the compounds are represented by Structural Formula (IA) or (I), or pharmaceutically acceptable salts thereof, wherein:

$R^4$ is:

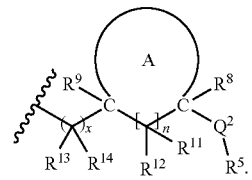

Ring A is a non-aromatic, 5-10 membered, bridged carbocycle or heterocycle, or ring A and $R^8$ optionally form a non-aromatic, 5-10 membered, bridged carbocycle or heterocycle, or ring A and $R^9$ optionally form a non-aromatic, 5-10 membered, bridged carbocycle or heterocycle, or ring A and $R^{11}$ optionally form a non-aromatic, 5-10 membered, bridged carbocycle or heterocycle, wherein each of said carbocycle is independently and optionally substituted with one or more instances of $J^A$ and wherein each carbocycle is independently and optionally substituted with one or more instances of $J^B$.

$R^1$ is —H.
$R^2$ is —H, —CH$_3$, —CH$_2$OH, or —NH$_2$. Specifically, $R^2$ is —H, or —CH$_2$OH.
$R^3$ is —H, —F, —Cl, $C_{1-4}$ alkyl (e.g., —CH$_3$ or —C$_2$H$_5$), or $C_{1-4}$ haloalkyl (e.g., —CF$_3$). Alternatively, $R^3$ is —H, —F, or —Cl.
$Z^1$ is —H, —F, or —Cl.
$Z^2$ is —H or $C_1$-$C_6$ alkyl optionally substituted with one or more substituents independently selected from the group consisting of halogen, cyano, hydroxy, and —O($C_1$-$C_4$ alkyl).
$Z^3$ is —H or $C_1$-$C_6$ alkyl optionally substituted with one or more substituents independently selected from the group consisting of halogen, cyano, hydroxy, and —O($C_1$-$C_4$ alkyl).
$Q^2$ is independently —O—, —CO$_2$—, —OC(O)—, —C(O)NR'—, —C(O)NRC(O)O—, —NRC(O)—, —NRC(O)NR'—, —NRCO$_2$—, —OC(O)NR'—, —P(O)(OR)O—, —OP(O)(OR$^a$)O—, —P(O)$_2$O—, —CO$_2$SO$_2$—, or —(CR$^6$R$^7$)$_p$—Y$^1$—.
$Y^1$ is —O—, —CO$_2$—, —OC(O)—, —C(O)NR'—, —C(O)NRC(O)O—, —NRC(O)—, —NRC(O)NR'—, —NRCO$_2$—, —OC(O)NR'—, —P(O)(OR)O—, —OP(O)(OR$^a$)O—, —P(O)$_2$O—, or —CO$_2$SO$_2$—.
$R^5$ is: i) —H; ii) an optionally substituted $C_1$-$C_6$ alkyl group; iii) an optionally substituted, $C_3$-$C_7$ non-aromatic carbocycle; iv) an optionally substituted, 4-7 membered non-aromatic heterocycle; v)) an optionally substituted phenyl group; vi) an optionally substituted 5-6 membered heteroaryl ring; or optionally, together with R and the nitrogen atom to which it is attached, form a 5-7 membered, optionally substituted non-aromatic heterocycle; and said alkyl group represented by $R^5$ is optionally substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), $C_1$-$C_4$ alkoxy, —NRCO($C_1$-$C_4$ alkyl), —CONR($C_1$-$C_4$ alkyl), —NRCO$_2$($C_1$-$C_4$ alkyl), a $C_3$-$C_7$ non-aromatic carbocycle optionally substituted with one or more instances of $J^{E1}$, a 4-7 membered non-aromatic heterocycle optionally substituted with one or more instances of $J^{E1}$; and a phenyl optionally substituted with one or more instances of $J^{E1}$;

wherein each of said carbocycle, heterocycle, phenyl and heteroary represented by $R^5$ is independently and optionally substituted with one or more substituents independently selected from the group consisting of halogen, cyano, hydroxy, oxo, $C_1$-$C_4$ alkyl, —O($C_1$-$C_4$ alkyl), —NH$_2$, —NH ($C_1$-$C_4$ alkyl), —N($C_1$-$C_4$ alkyl)$_2$, —C(O)($C_1$-$C_4$ alkyl), —OC(O)($C_1$-$C_4$ alkyl), —C(O)O($C_1$-$C_4$ alkyl) and —CO$_2$H, wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

Each of $R^8$ and $R^9$ is independently —H, halogen, cyano, hydroxy, $C_1$-$C_4$ alkyl, $C_1$-$C_4$ haloalkyl, $C_1$-$C_4$ hydroxyalkyl, $C_2$-$C_4$ alkoxyalkyl, —O($C_1$-$C_4$ alkyl), —NH$_2$, —NH($C_1$-$C_4$ alkyl), or —N($C_1$-$C_4$ alkyl)$_2$.

$R^{11}$, $R^{12}$, $R^{13}$, and $R^{14}$ are each independently —H, halogen, or $C_1$-$C_6$ alkyl optionally substituted with one or more substituents independently selected from the group consisting of halogen, hydroxy, and $C_1$-$C_6$ alkoxy.

Each of $J^A$ and $J^B$ is independently selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O)($C_1$-$C_6$ alkyl), —NHC(O)($C_1$-$C_6$ alkyl), —N($C_1$-$C_6$ alkyl)C(O)($C_1$-$C_6$ alkyl), and —CO$_2$R$^b$; wherein each of said alkyl groups is optionally and independently substituted with one or more substituents independently selected from the group consisting of halogen, cyano, hydroxy, oxo, —NH$_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —CO$_2$H, —CO$_2$($C_1$-$C_4$ alkyl), and $C_1$-$C_4$ alkoxy.

n is 0 or 1.

x is 0 or 1.

The remaining variables are each and independently as described above in any set of variables for Structural Formulae (IA) and (I).

In yet another embodiment, the compounds are represented by Structural Formula (IA) or (I), or pharmaceutically acceptable salts, wherein:

$R^4$ is:

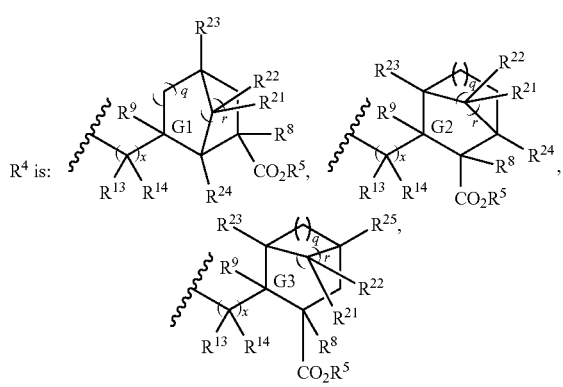

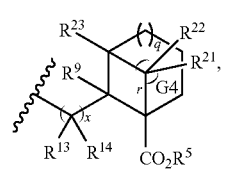

or

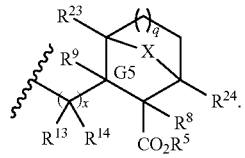

Each of rings G1-G4 is independently a 5-10 membered non-aromatic bridged carbocycle optionally further substituted with one or more instances of $J^A$, and ring G5 is a 5-10 membered non-aromatic bridged heterocycle optionally further substituted with one or more instances of $J^B$.

X is —O—, —S—, or —NR$^g$—.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, cyano, hydroxy, $C_1$-$C_6$ alkyl, —NH$_2$, —NH($C_1$-$C_6$ alkyl), —N($C_1$-$C_6$ alkyl)$_2$, —O($C_1$-$C_6$ alkyl), —C(O)NH$_2$, —C(O)NH($C_1$-$C_6$ alkyl), —C(O)N($C_1$-$C_6$ alkyl)$_2$, —C(O)($C_1$-$C_6$-alkyl), —OC(O) ($C_1$-$C_6$ alkyl), —NHC(O)($C_1$-$C_6$ alkyl), —N($C_1$-$C_6$ alkyl)C(O)($C_1$-$C_6$ alkyl).

R$^g$ is —H or $C_1$-$C_6$ alkyl optionally substituted with one or more substituents independently selected from the group consisting of halogen, cyano, oxo, hydroxy, amino, carboxy, $C_1$-$C_6$ alkoxy, $C_1$-$C_6$ haloalkoxy, $C_1$-$C_6$ aminoalkoxy, $C_1$-$C_6$ cyanoalkoxy, $C_1$-$C_6$ hydroxyalkoxy, and $C_2$-$C_6$ alkoxyalkoxy.

q is 0, 1 or 2.

r is 1 or 2.

The remaining variables are each and independently as described above in the preceeding paragraph.

In yet another embodiment, the compounds are represented by Structural Formula (IA) or (I), or pharmaceutically acceptable salts thereof, wherein the variables are each and independently as described above in the preceeding paragraph except those described below:

$R^1$ is —H.

$R^2$ is —H.

$R^3$ is —H, —F, —C$_1$, $C_{1-4}$ alkyl, or $C_{1-4}$ haloalkyl. Alternatively, $R^3$ is —H, —F, or —Cl.

$Z^1$ is —H, —F, or —Cl.

$Z^2$ is —H.

$Z^3$ is —H.

X is —O—.

$R^5$ is —H, an optionally substituted $C_1$-$C_6$ alkyl, or optionally substituted phenyl.

Each $R^8$ is independently —H, halogen, hydroxy, $C_1$-$C_4$ alkyl, $C_1$-$C_4$ haloalkyl, $C_1$-$C_4$ hydroxyalkyl, $C_2$-$C_4$ alkoxyalkyl, or —O($C_1$-$C_4$ alkyl).

Each of $R^9$, $R^{13}$, and $R^{14}$ is independently —H or $C_1$-$C_4$ alkyl.

$R^{21}$, $R^{22}$, $R^{23}$, $R^{24}$, and $R^{25}$ are each independently —H, halogen, —OH, $C_1$-$C_6$ alkoxy, or $C_1$-$C_6$ alkyl optionally substituted with one or more substituents independently selected from the group consisting of halogen, hydroxy, $C_1$-$C_6$ alkyl, and —O($C_1$-$C_6$ alkyl). Specifically $R^{21}$, $R^{22}$, $R^{23}$, $R^{24}$, and $R^{25}$ are each independently —H, $C_{1-6}$ alkyl, or $C_{1-6}$ haloalkyl.

Each rings G1-G5 are independently and optionally substituted with one or more substituents selected from the group consisting of halogen, cyano, hydroxy, —NH$_2$, —NH($C_1$-$C_6$ alkyl), —N($C_1$-$C_6$ alkyl)$_2$, —O($C_1$-$C_6$ alkyl), $C_1$-$C_4$ alkyl that is optionally substituted with one or more substituents selected from the group consisting of halogen, hydroxy, and $C_1$-$C_4$ alkoxy.

In yet another embodiment, the compounds are represented by any one of Structural Formulae I-VI (hereinafter reference to Structural Formulae I-VI includes Structural Formulae I, IA, II, III, IV, V, VI) and XI(A)-XIV (hereinafter reference to Structural Formulae XI(A)-XIV includes Structural Formulae XIA, XIB, XIIA, XIIB, XIII, and XIV), wherein values of the variables therein are independently as described above in any embodiments for the compounds of the invention, except that $R^3$ is $C_{1-6}$ alkyl, such as methyl or ethyl.

In yet another embodiment, the compounds are represented by any one of Structural Formulae I-VI and XI(A)-XIV, wherein values of the variables therein are independently as described above in any embodiments for the compounds of the invention, except that x is 0.

In yet another embodiment, the compounds are represented by any one of Structural Formulae I, IA, II, VI, XI(A), and XI(B), wherein values of the variables therein are independently as described above in any embodiments for the compounds of the invention, except that ring A is bridged.

In yet another embodiment, the compounds are represented by any one of Structural Formulae I, IA, II, VI, XI(A), and XI(B), wherein values of the variables therein are independently as described above in any embodiments for the compounds of the invention, except that $Q^2$ is independently —C(═NR)—, —C(═NR)NR—, —NRC(═NR)NR—, —$CO_2$—, —OC(O)—, —C(O)NR—, —C(O)NRC(O)O—, NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$N(R)—, —$NRSO_2$NR—, —P(O)(OR)O—, —OP(O)($OR^a$)O—, —$P(O)_2O$—, —$CO_2SO_2$—, or —$(CR^6R^7)_p$—$Y^1$—; or alternatively, $Q^2$ is independently —$CO_2$—, —OC(O)—, —C(O)NR—, —C(O)NRC(O)O—, —NRC(O)NRC(O)O—, —NRC(O)—, —NRC(O)NR—, —$NRCO_2$—, —OC(O)NR—, —S(O)—, —$SO_2$—, —N(R)$SO_2$—, —$SO_2$N(R)—, —$NRSO_2$NR—, —P(O)(OR)O—, —OP(O)($OR^a$)O—, —$P(O)_2O$—, —$CO_2SO_2$—, or —$(CR^6R^7)_p$—$Y^1$—.

In yet another embodiment, the compounds are represented by any one of Structural Formulae I-VI and XI(A)-XIV, wherein values of the variables therein are independently as described above in any embodiments for the compounds of the invention, provided that when $Q^2$ is —O— or —NR—, then ring A is further substituted with $J^A$ other than —H; and provided that if $Q^3$ is —C(O)—, then $R^5$ is a substituted $C_1$-$C_6$ aliphatic group; an optionally substituted $C_3$-$C_8$ non-aromatic carbocycle; an optionally substituted, 6-10-membered carbocyclic aryl group; optionally substituted, 4-8 membered non-aromatic heterocycle; or an optionally substituted 5-10 membered heteroaryl group. In a specific embodiment, when $Q^2$ is —O— or —NR—, then ring A is further substituted with $J^A$ other than —H at the geminal position to -$Q^2R^5$.

Figure 5A:
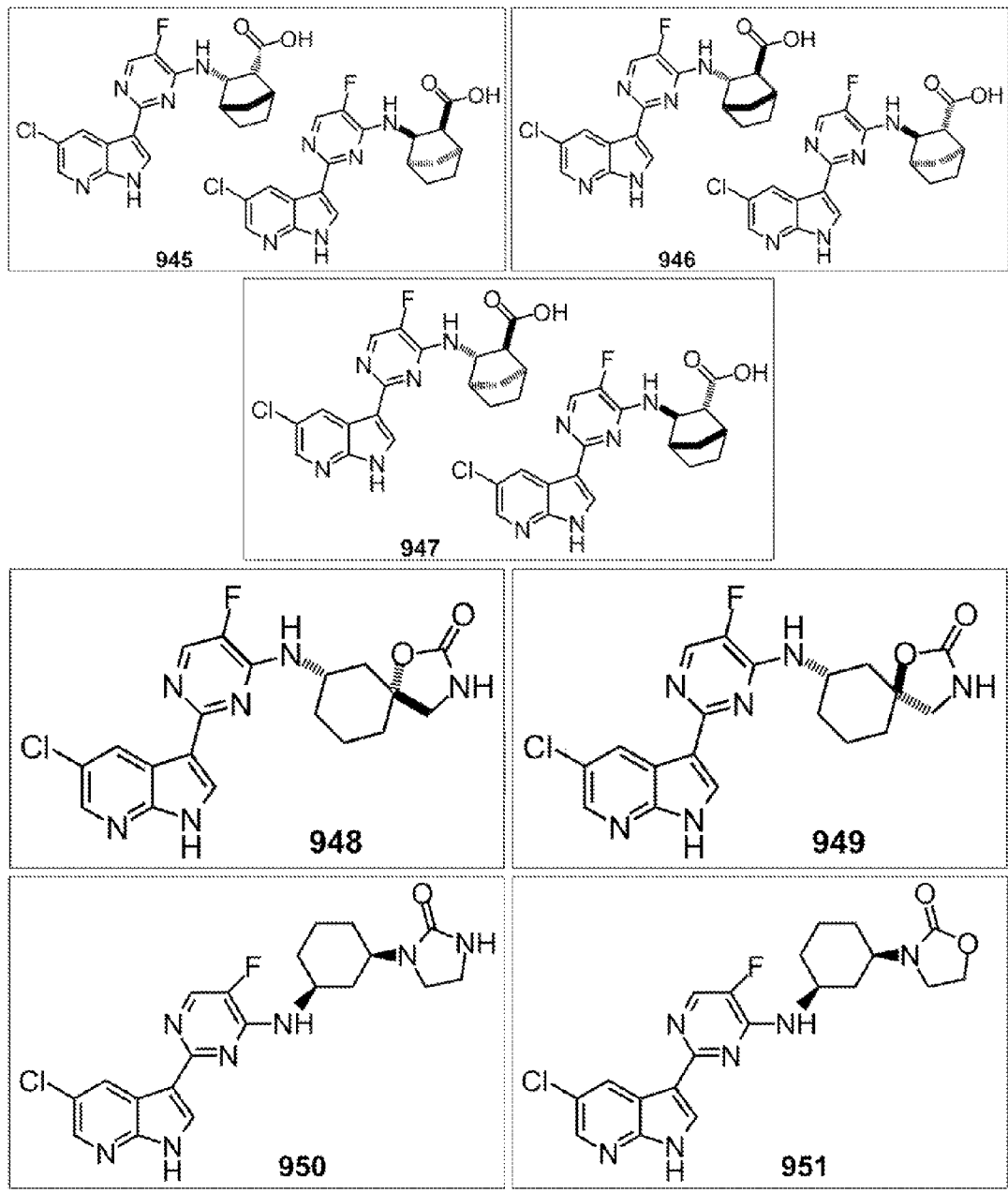
Figure 5B:
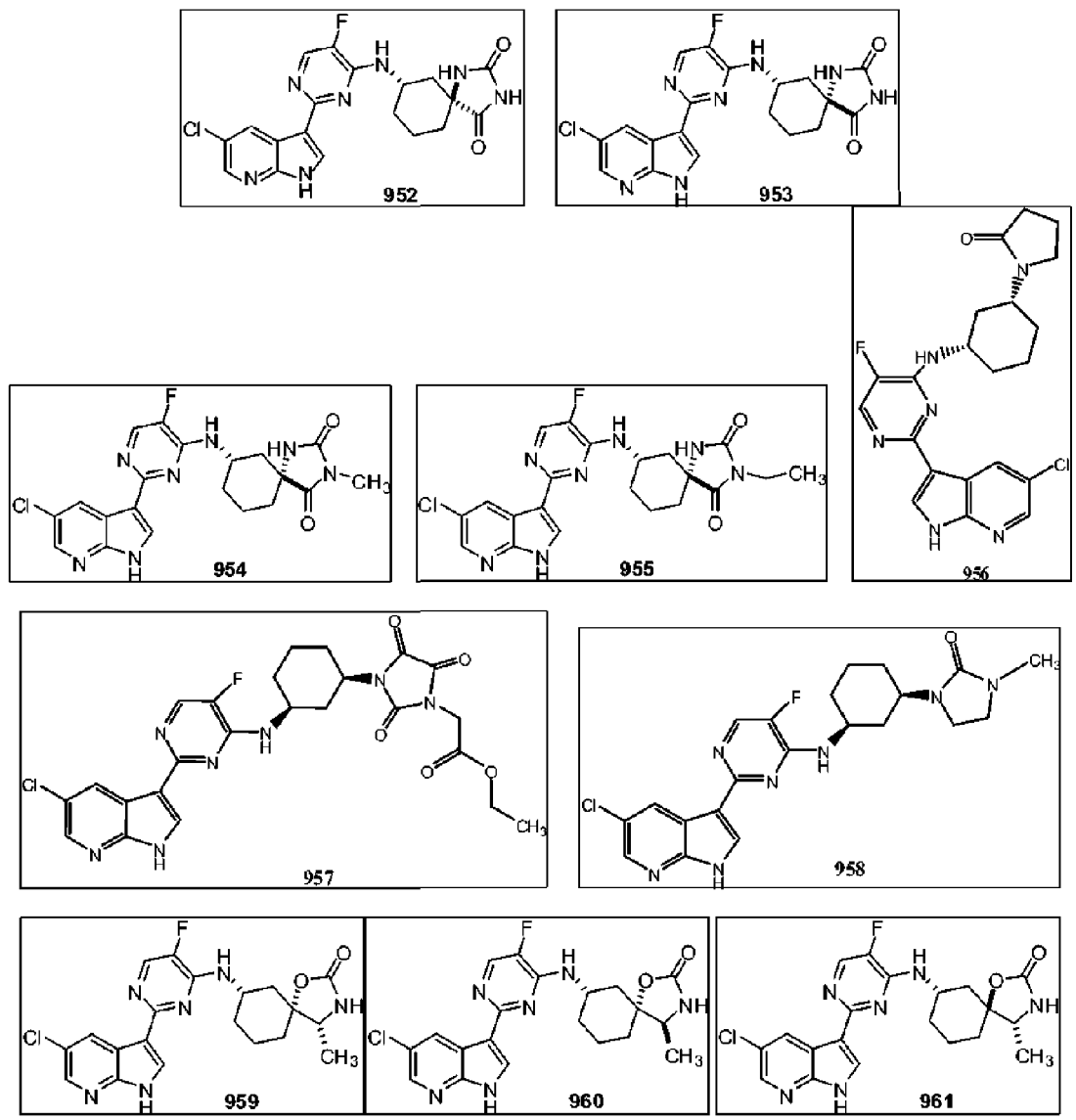
Figure 5C:
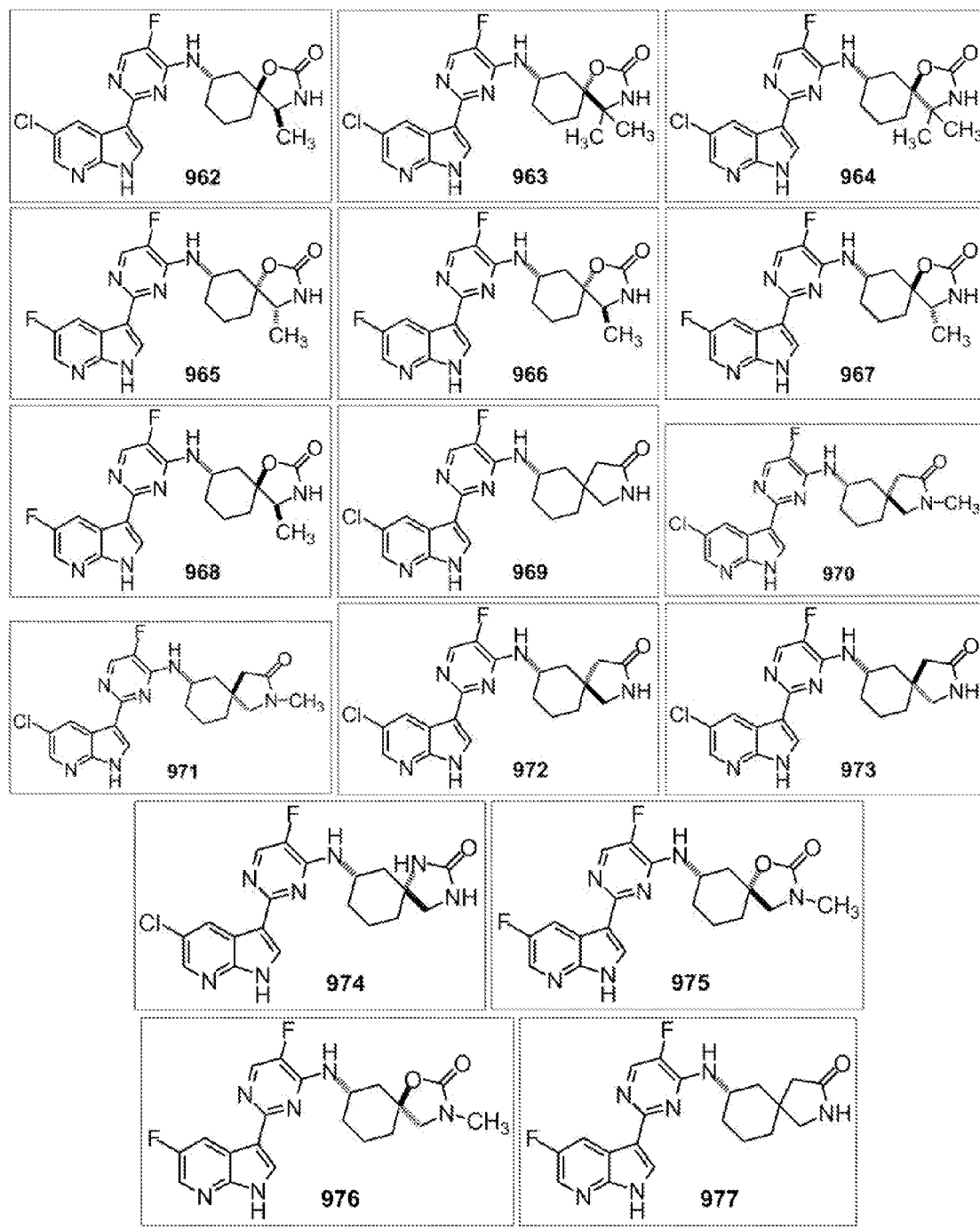
Figure 6A:
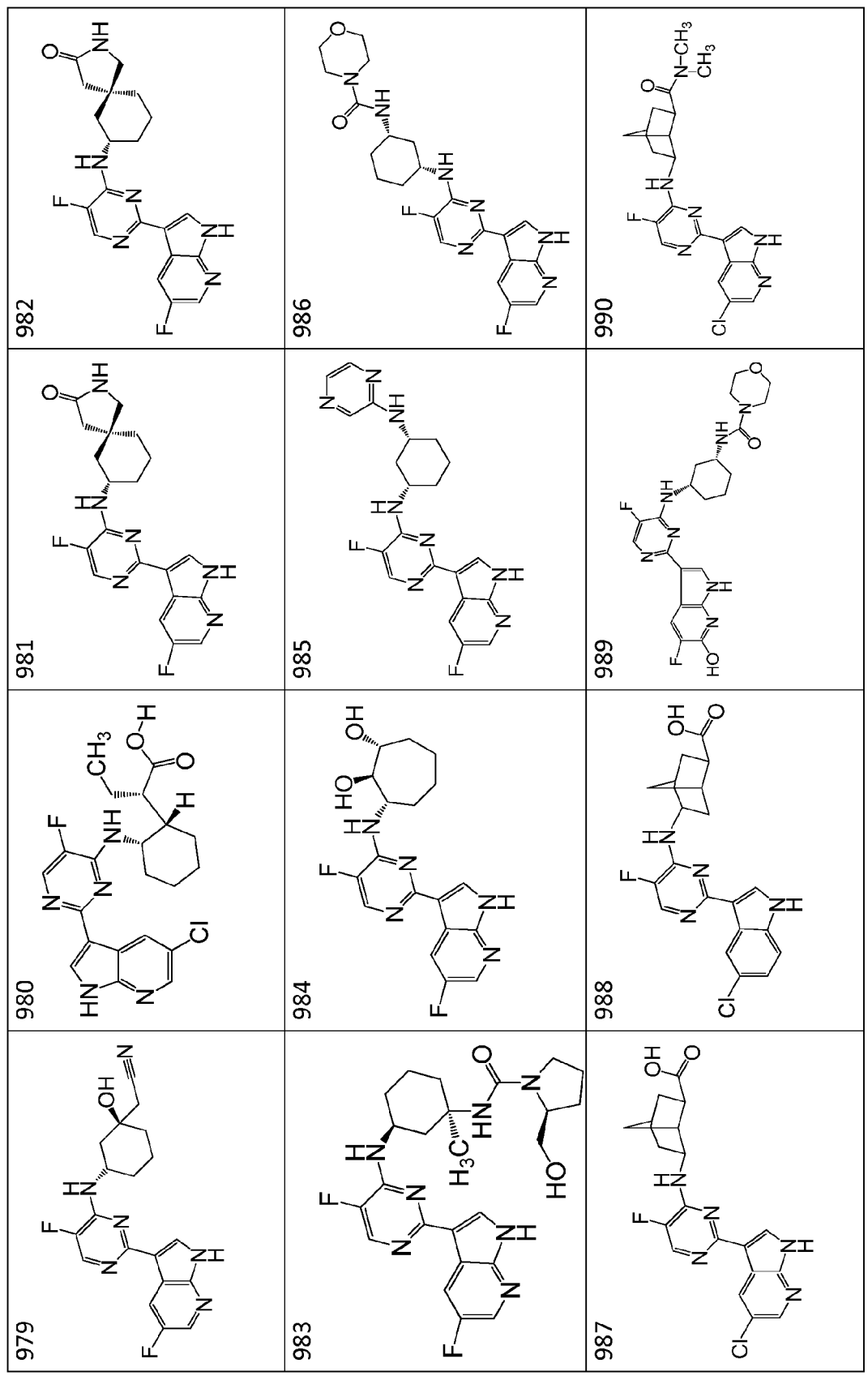
Figure 6B:
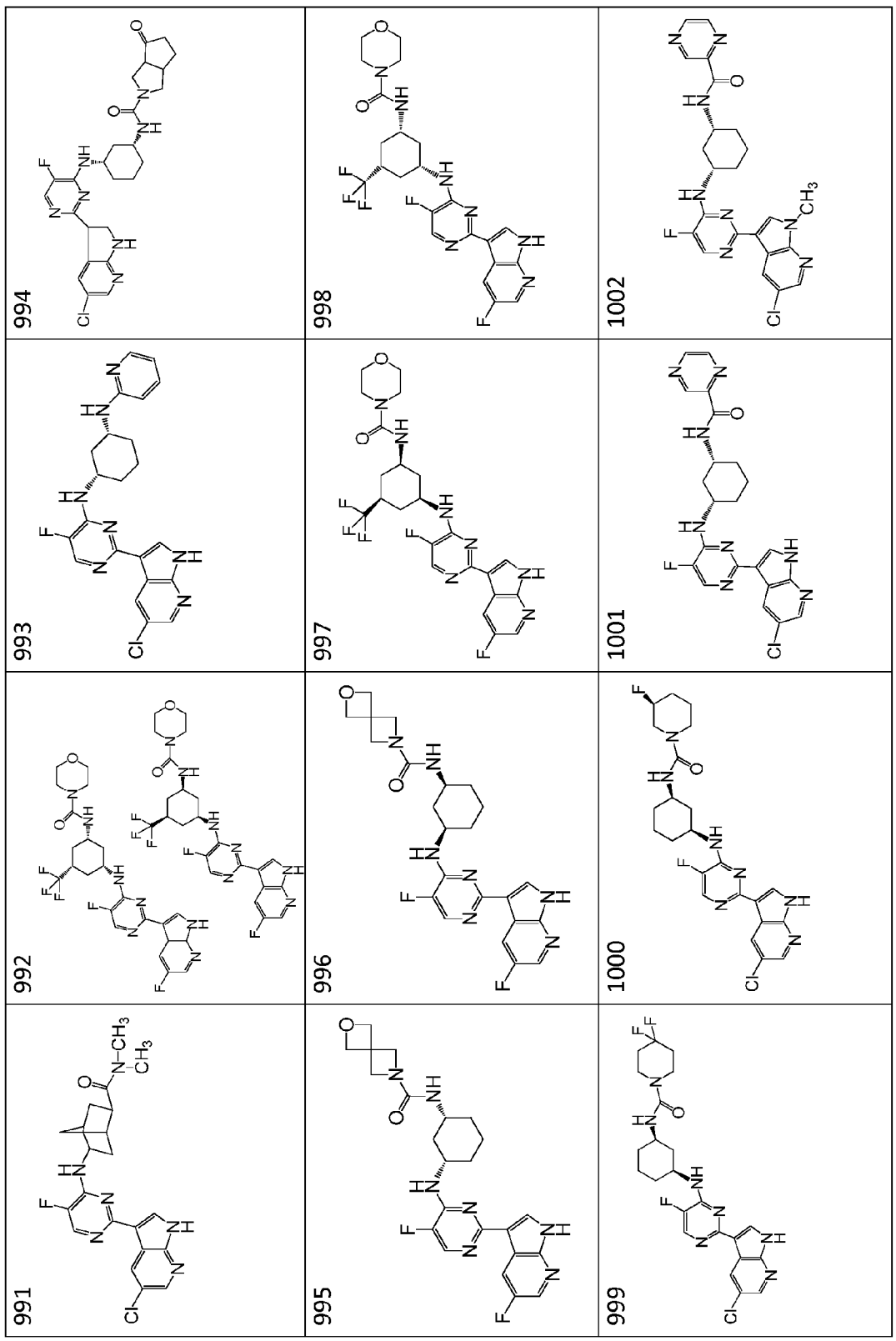
Figure 6C:
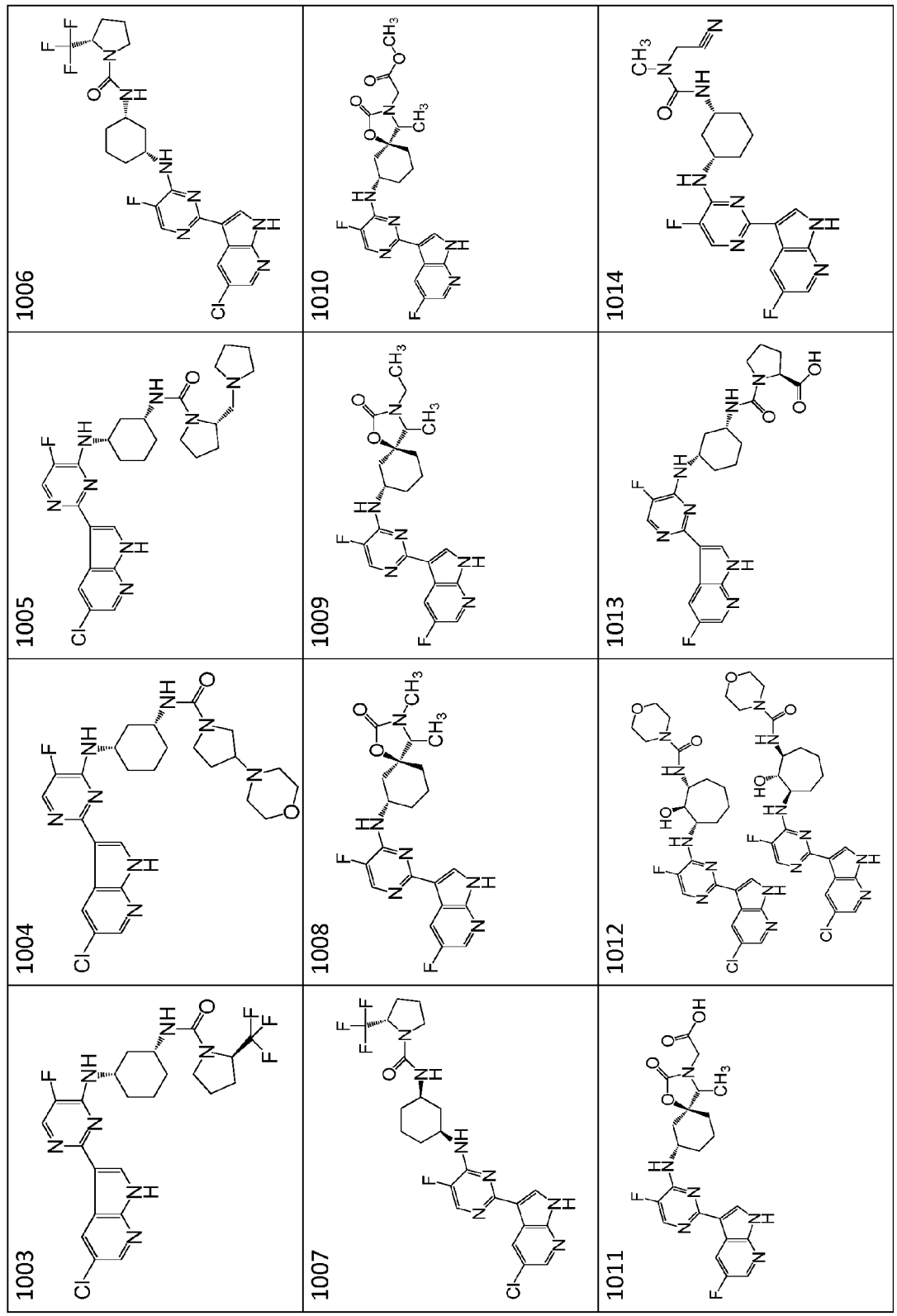
Figure 6D:
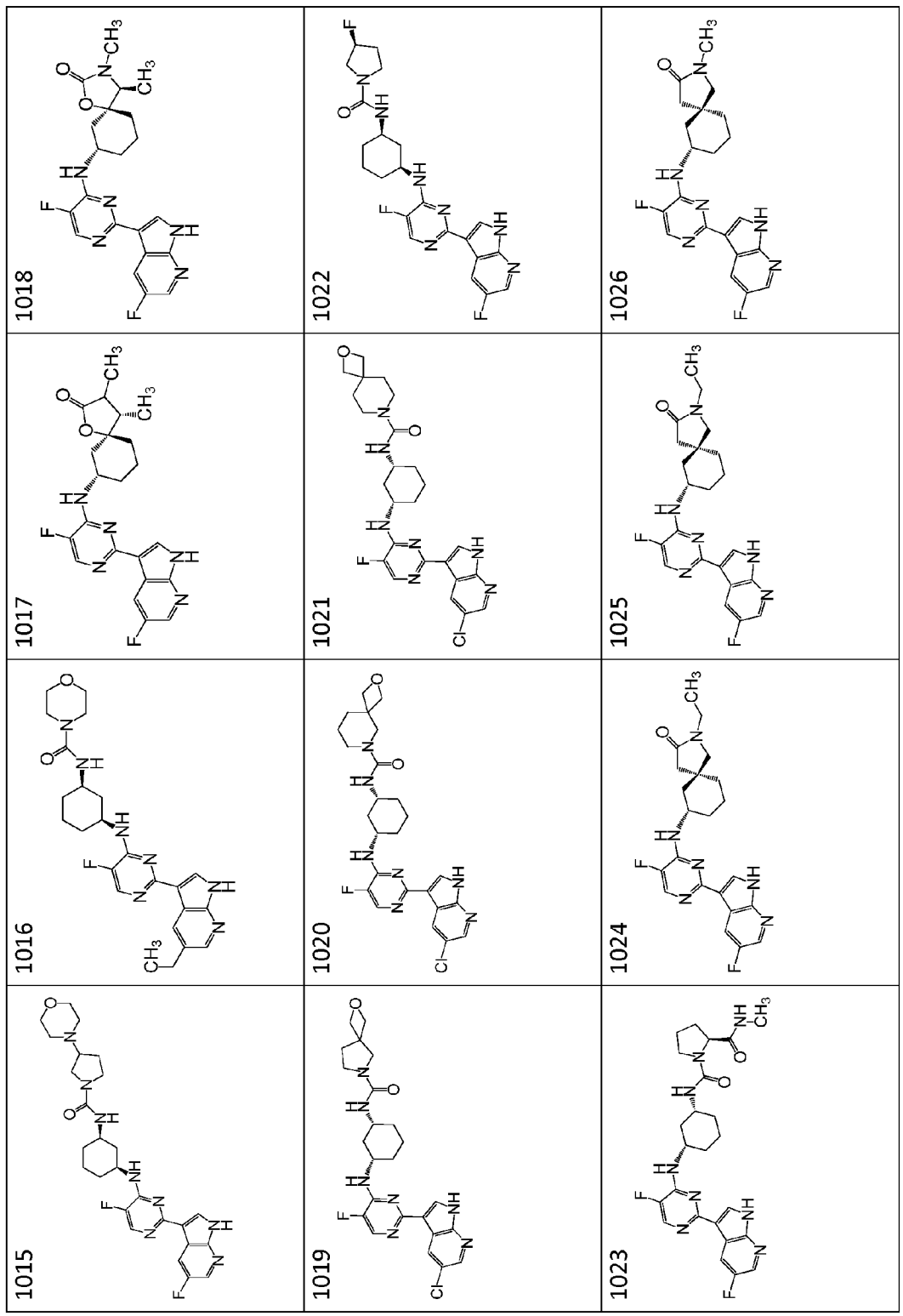
Figure 6E:
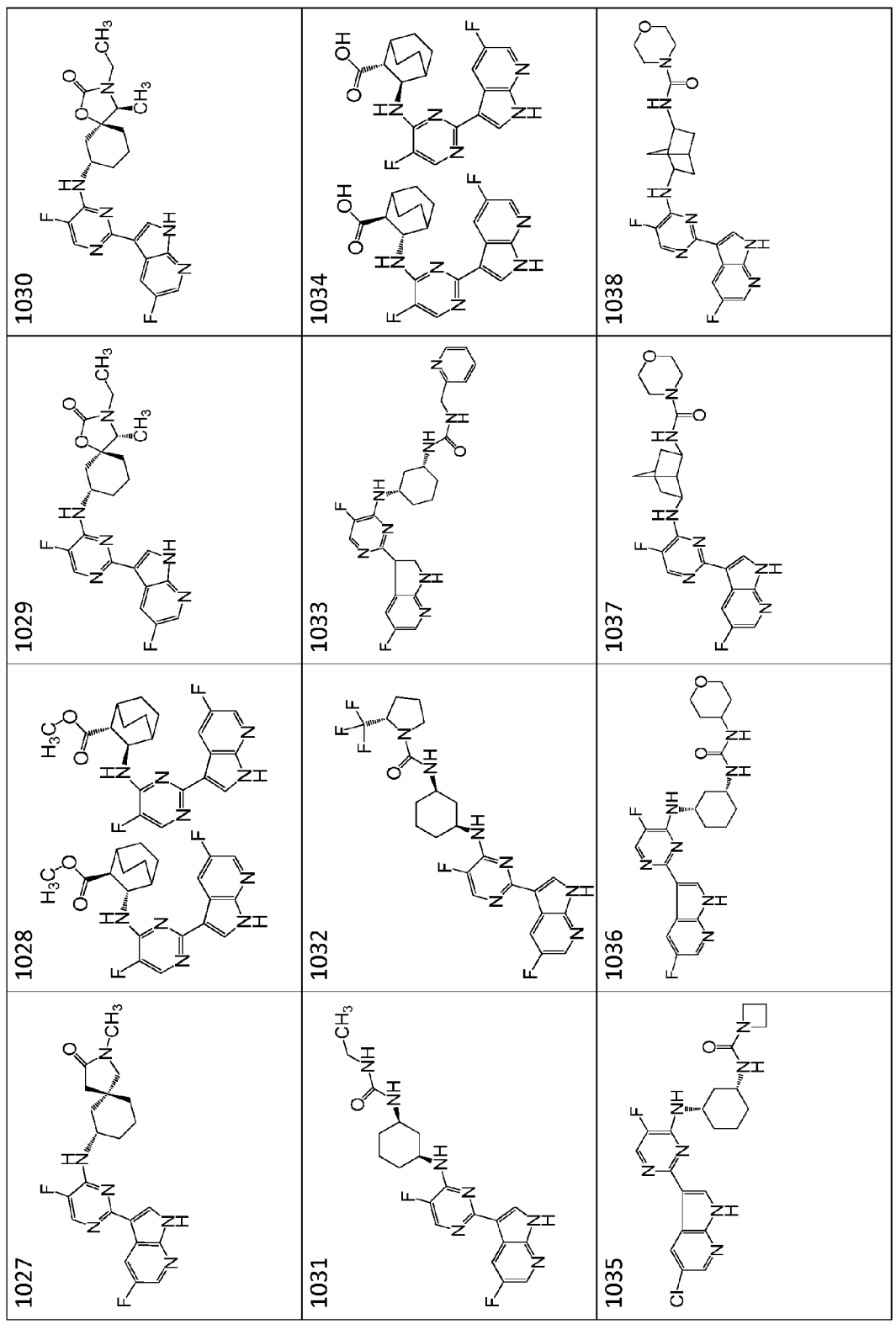
Figure 6F:
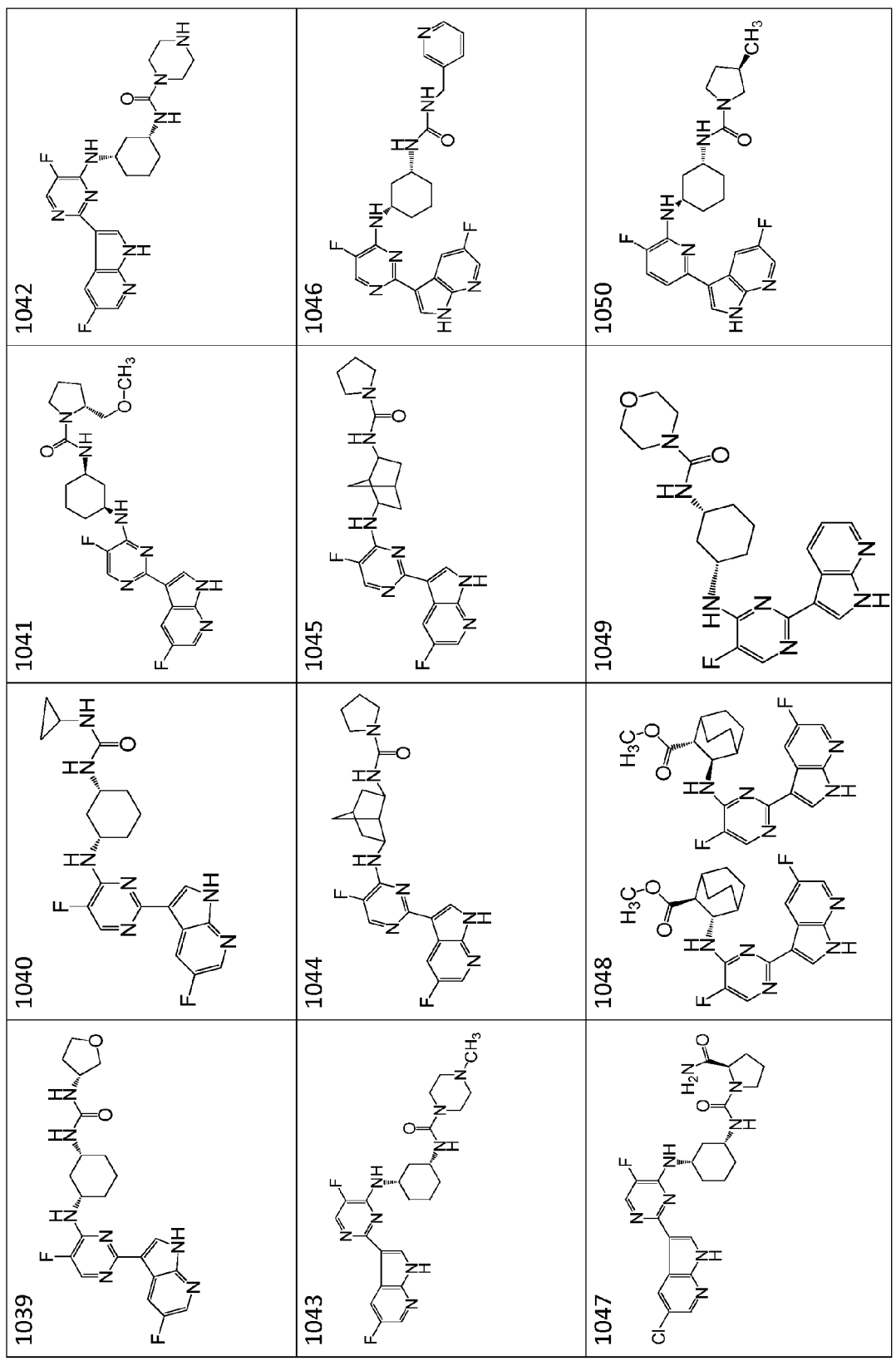
Figure 6G:
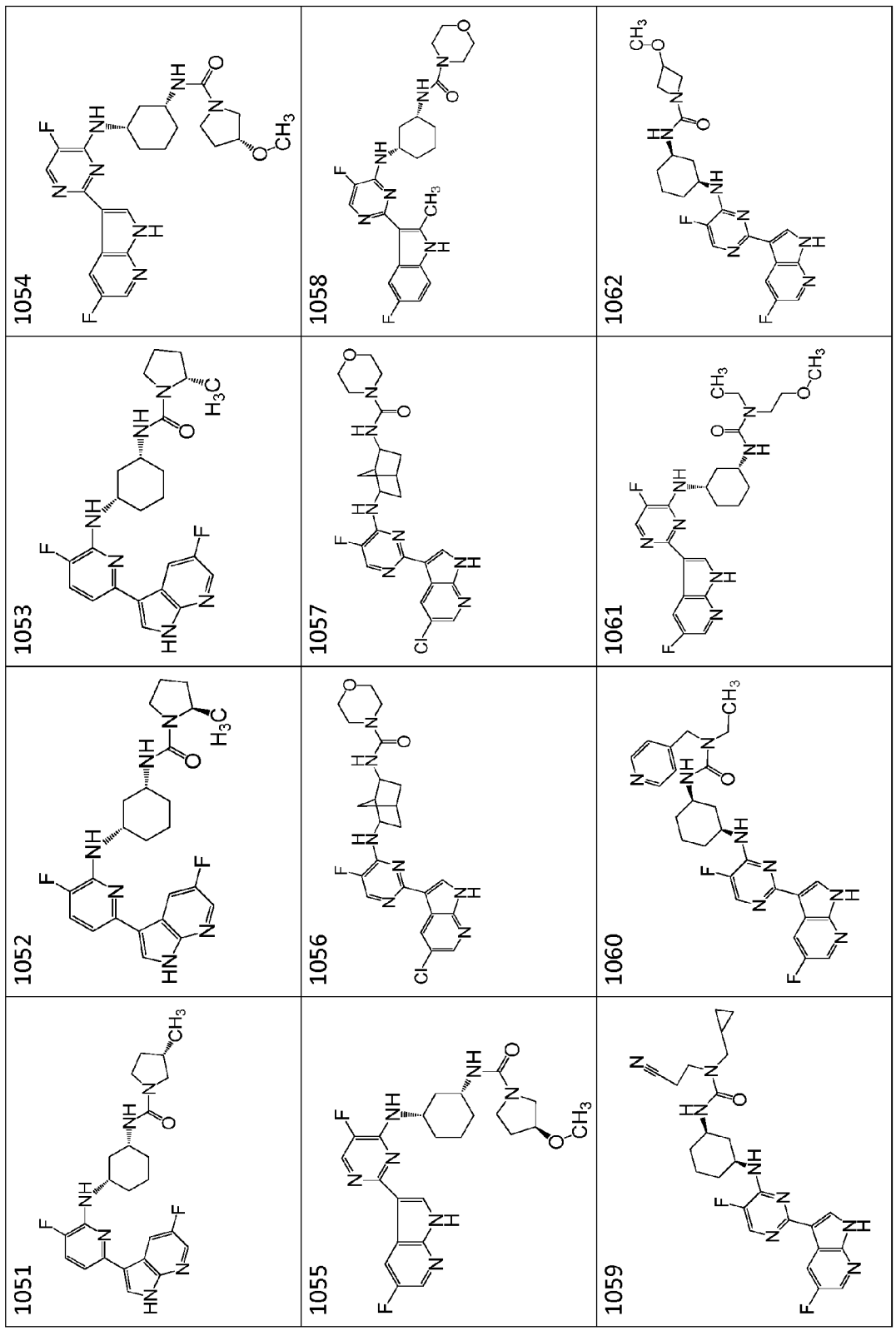
Figure 6H:
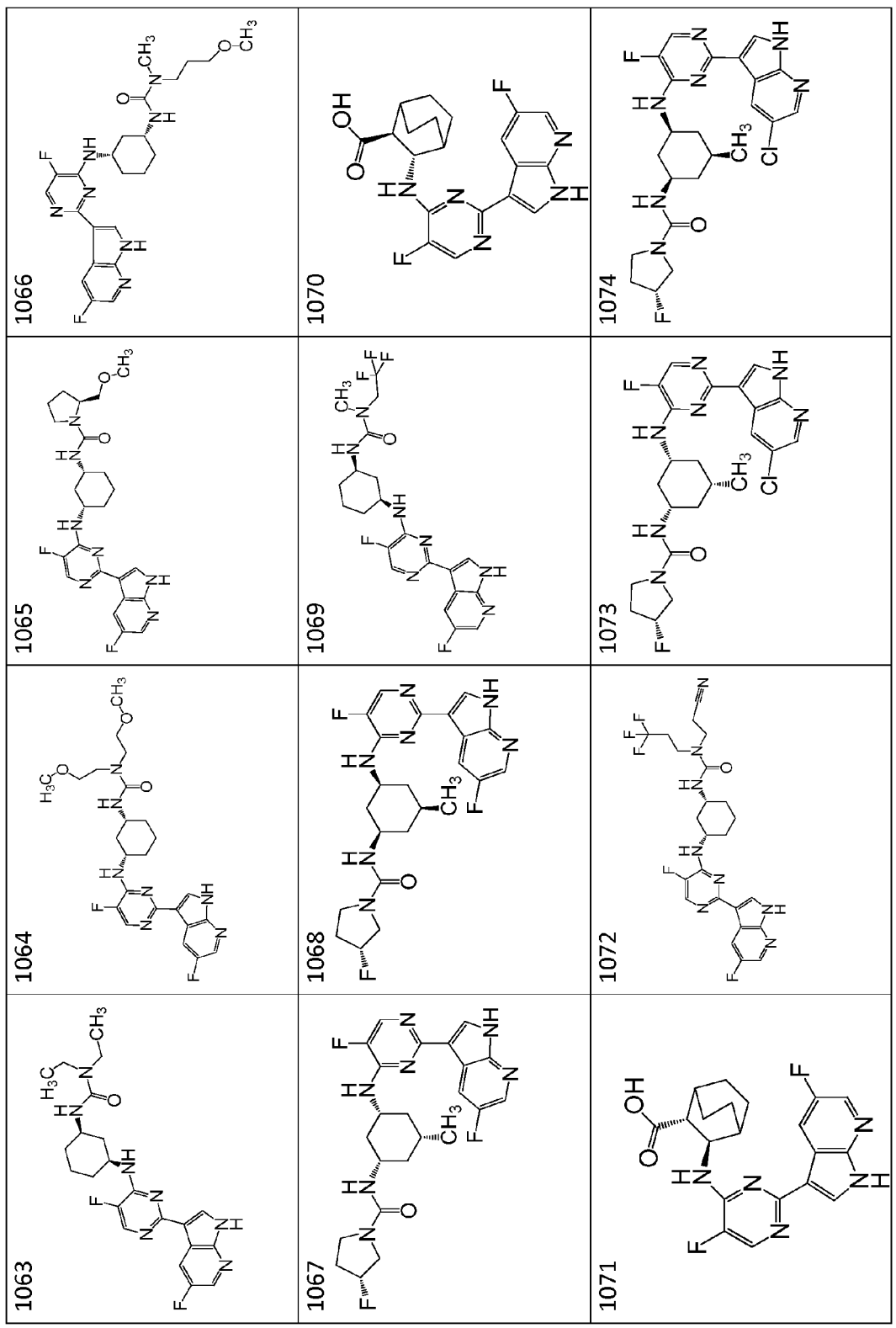
Figure 6I:
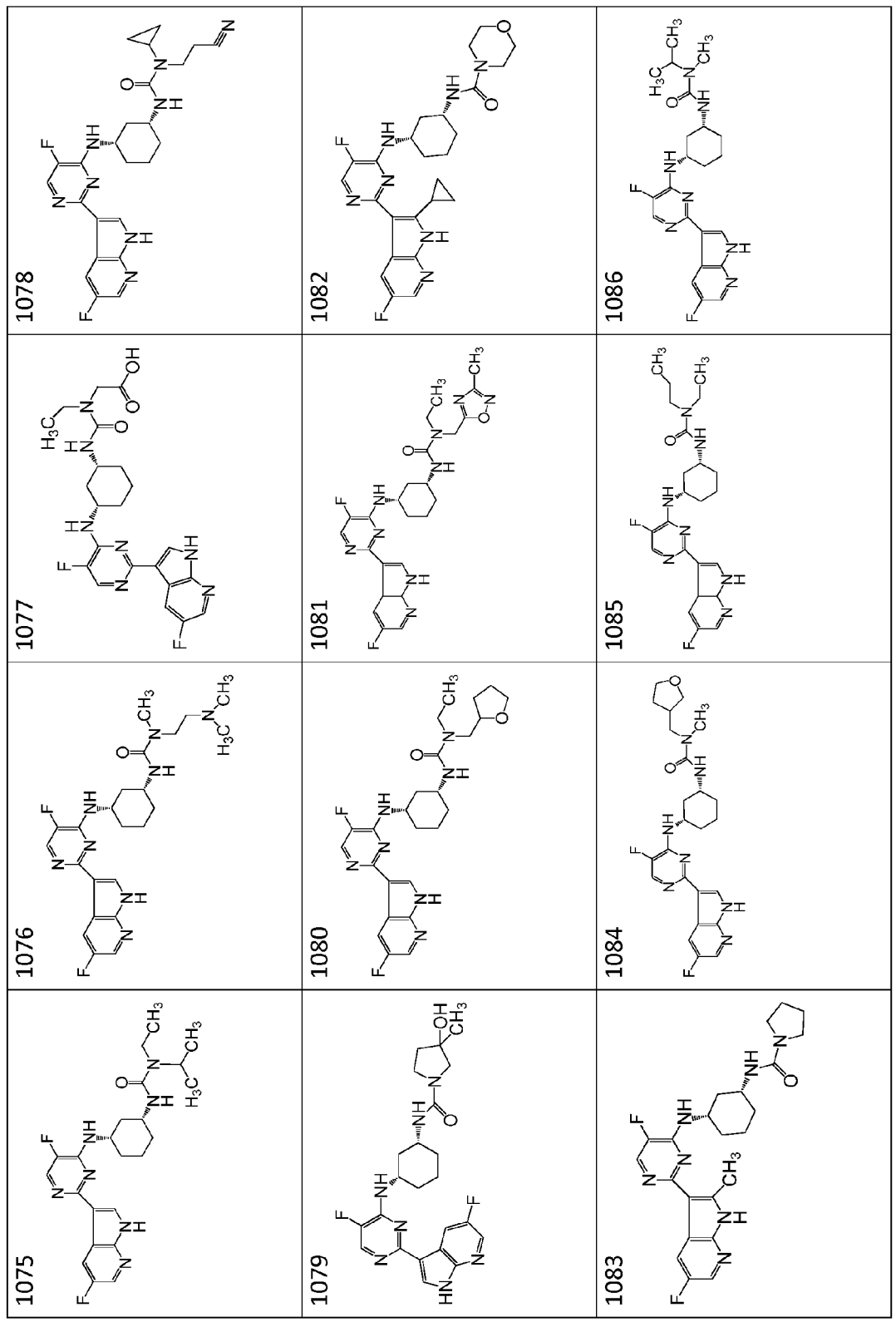
Figure 6J:
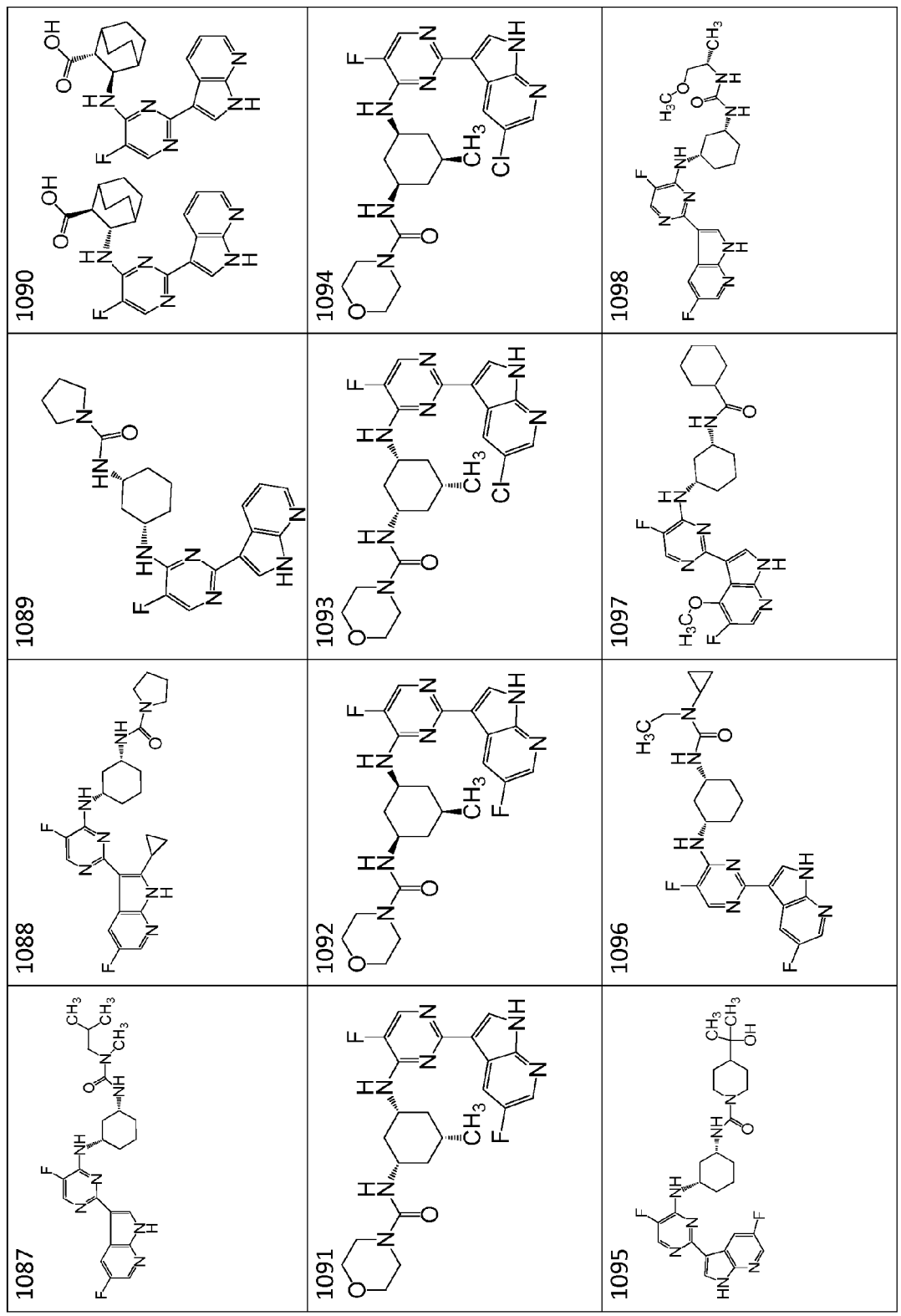
Figure 6K:
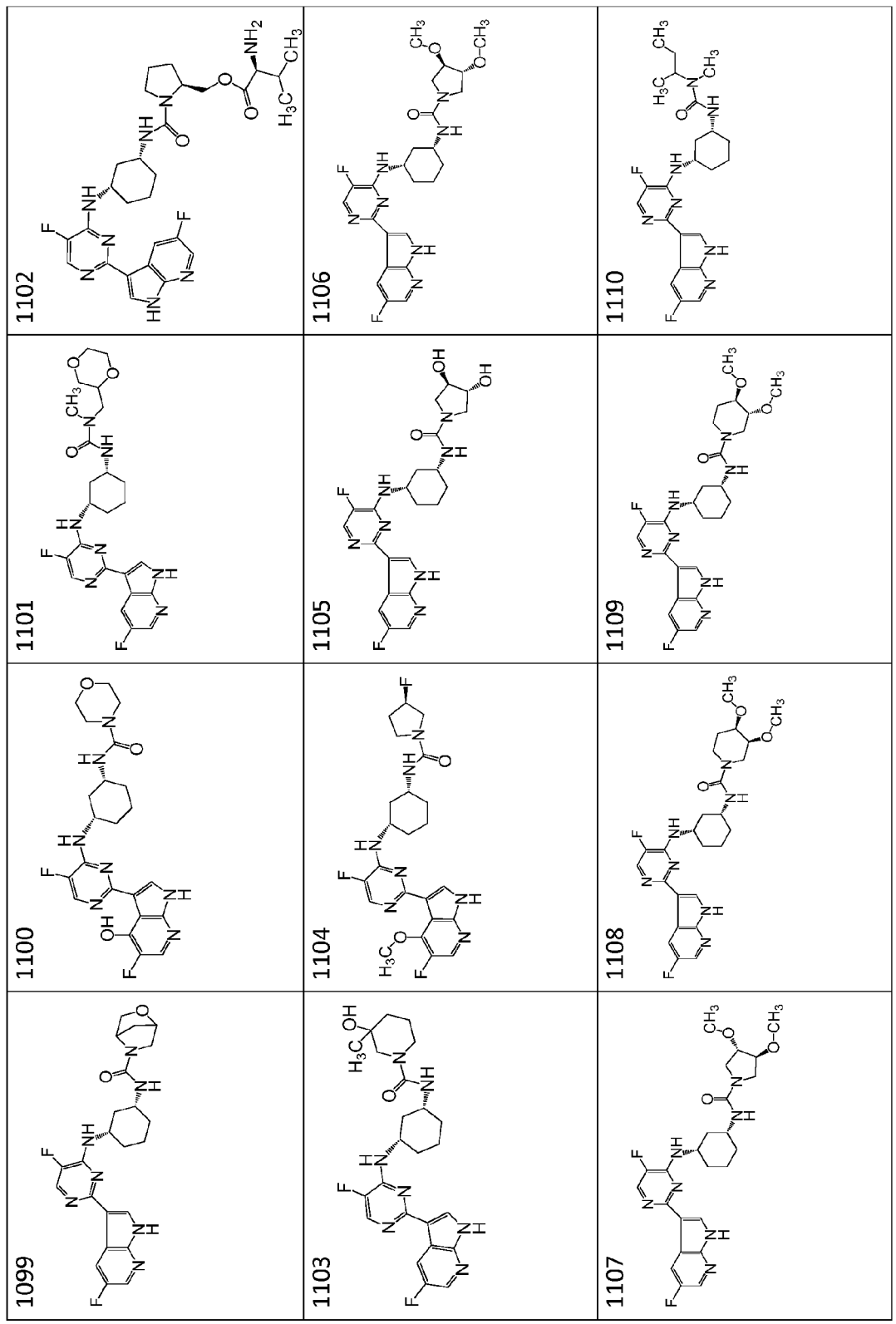
Figure 6L:
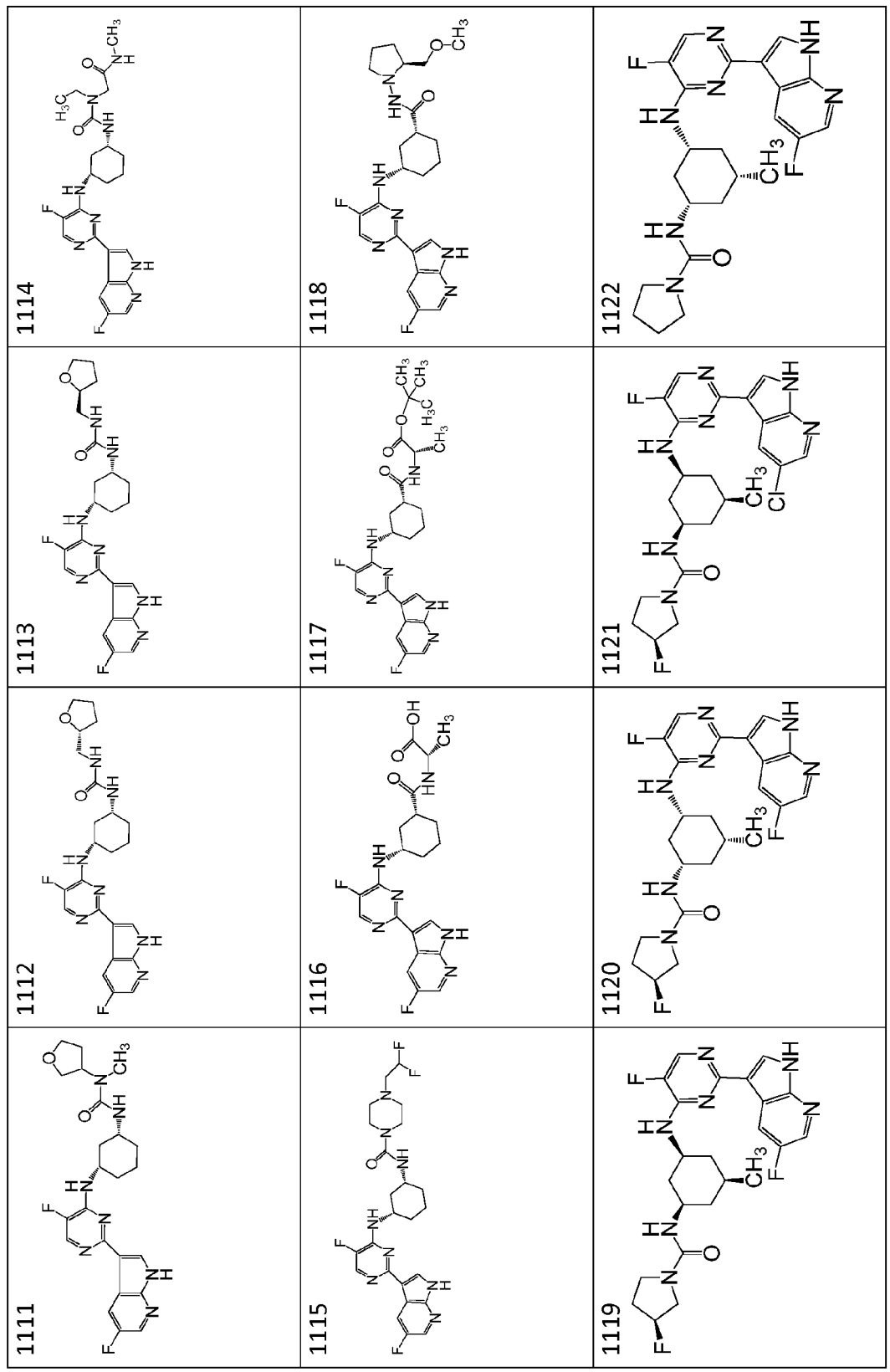
Figure 6M:
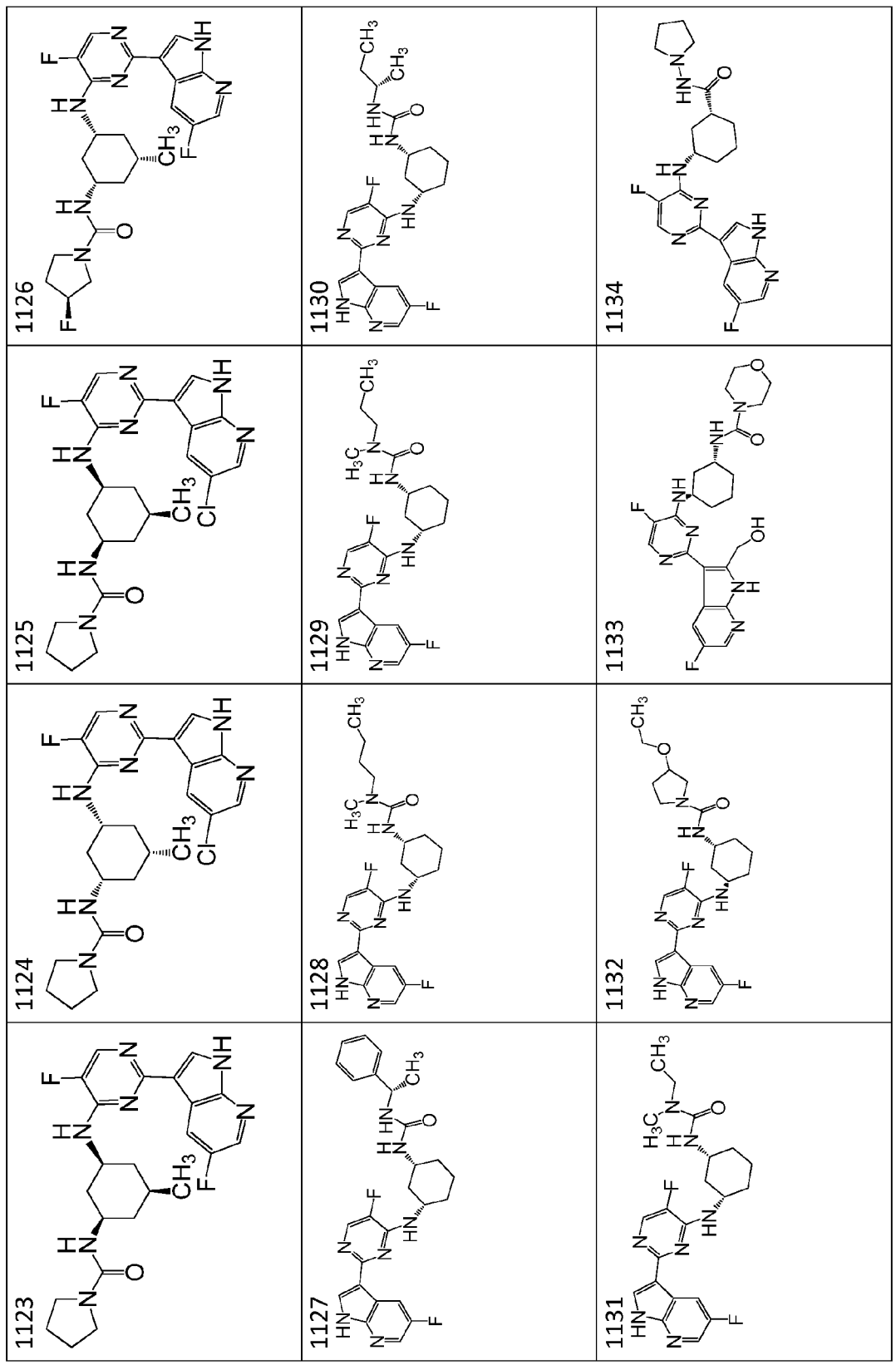
Figure 6N:
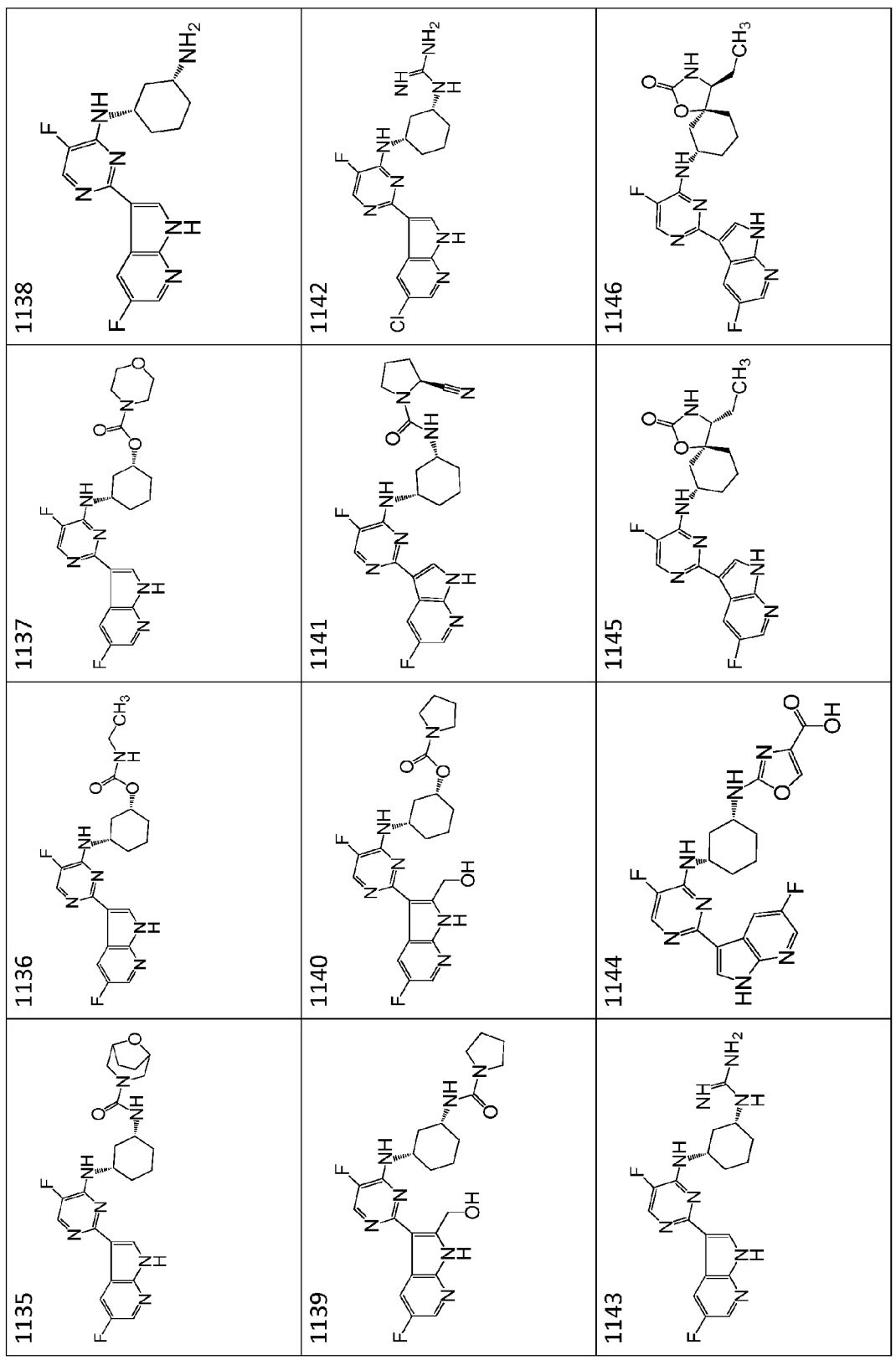
Figure 6O:
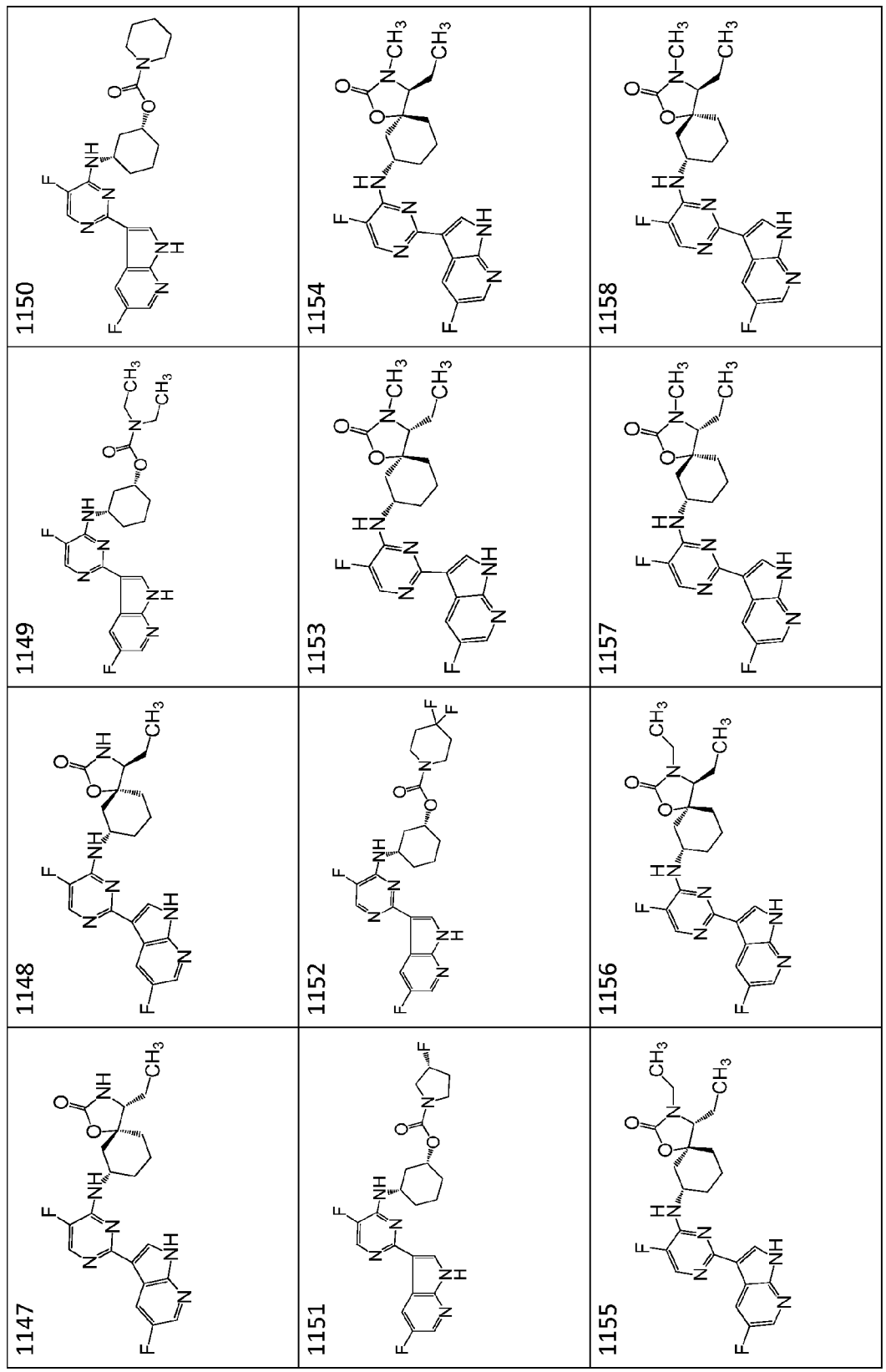
Figure 6P:
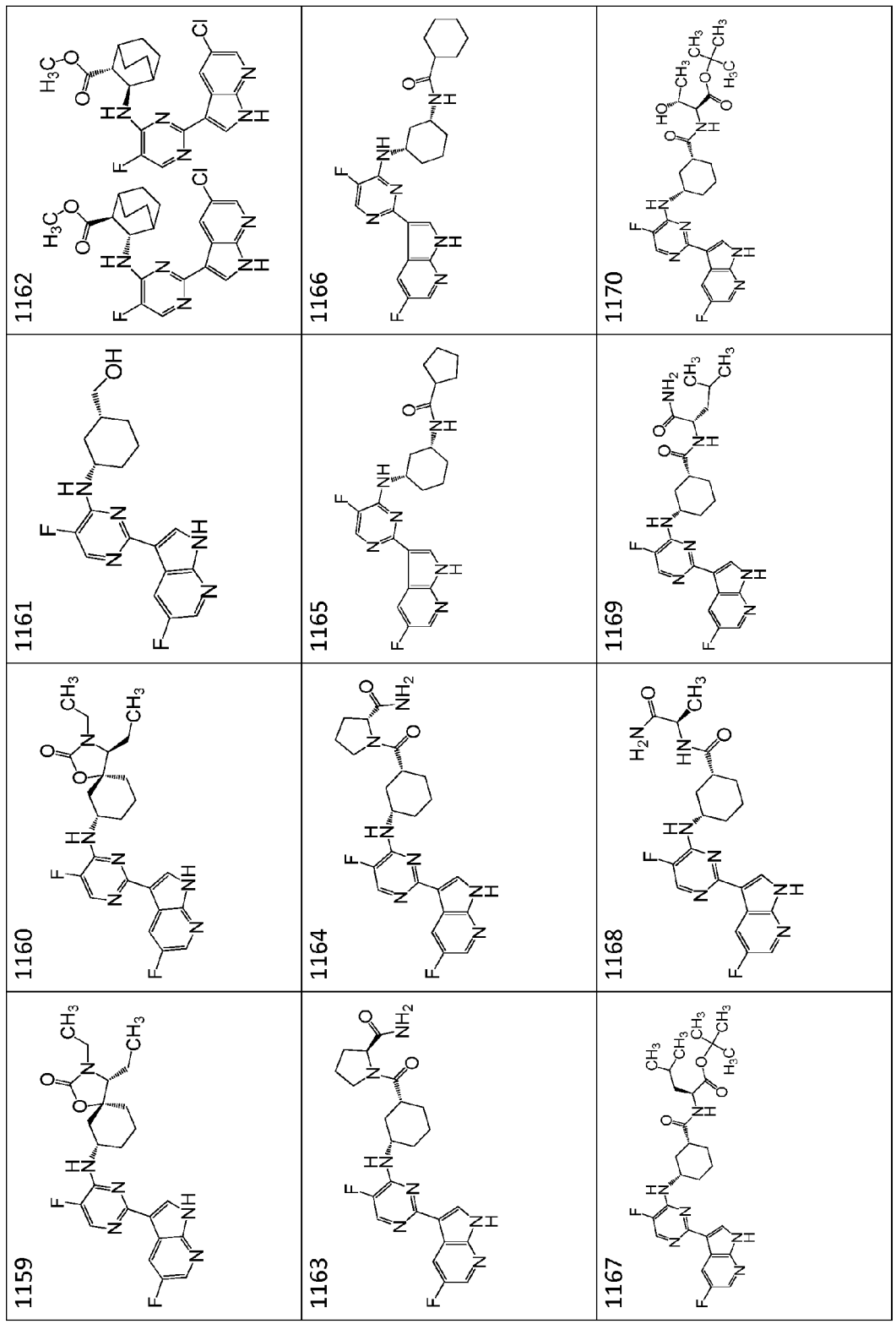
Figure 6Q:
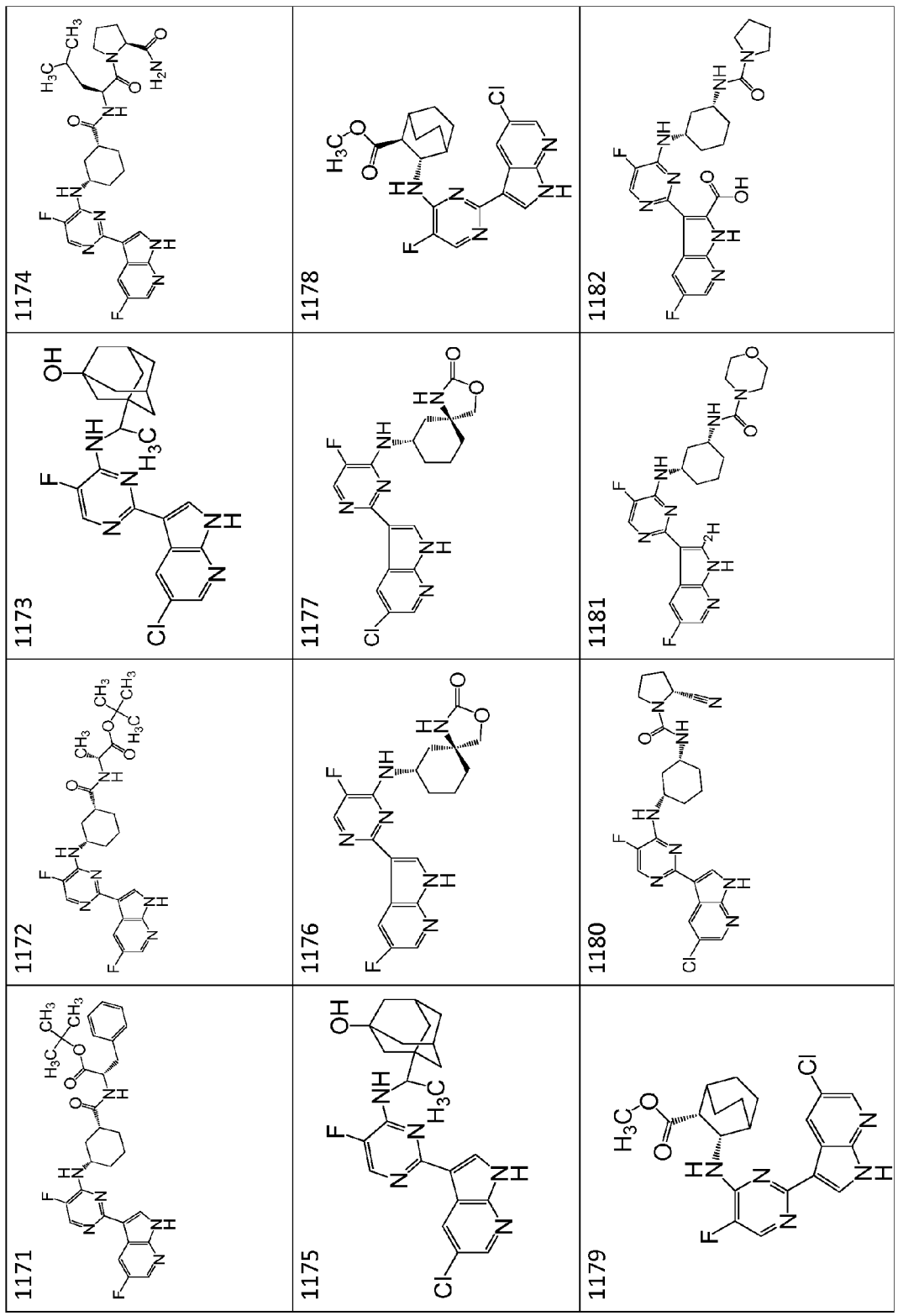
Figure 6R:
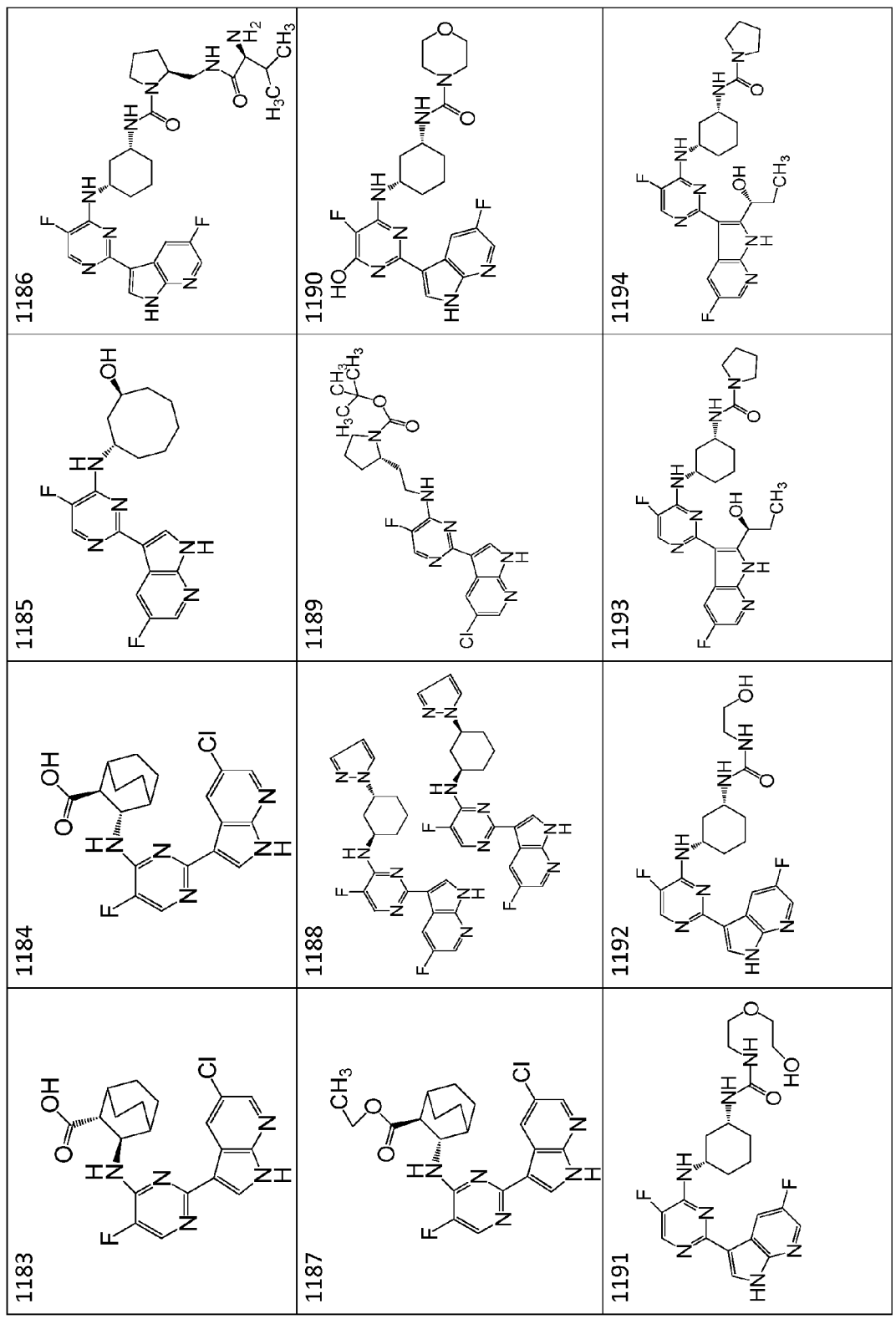
Figure 6S:
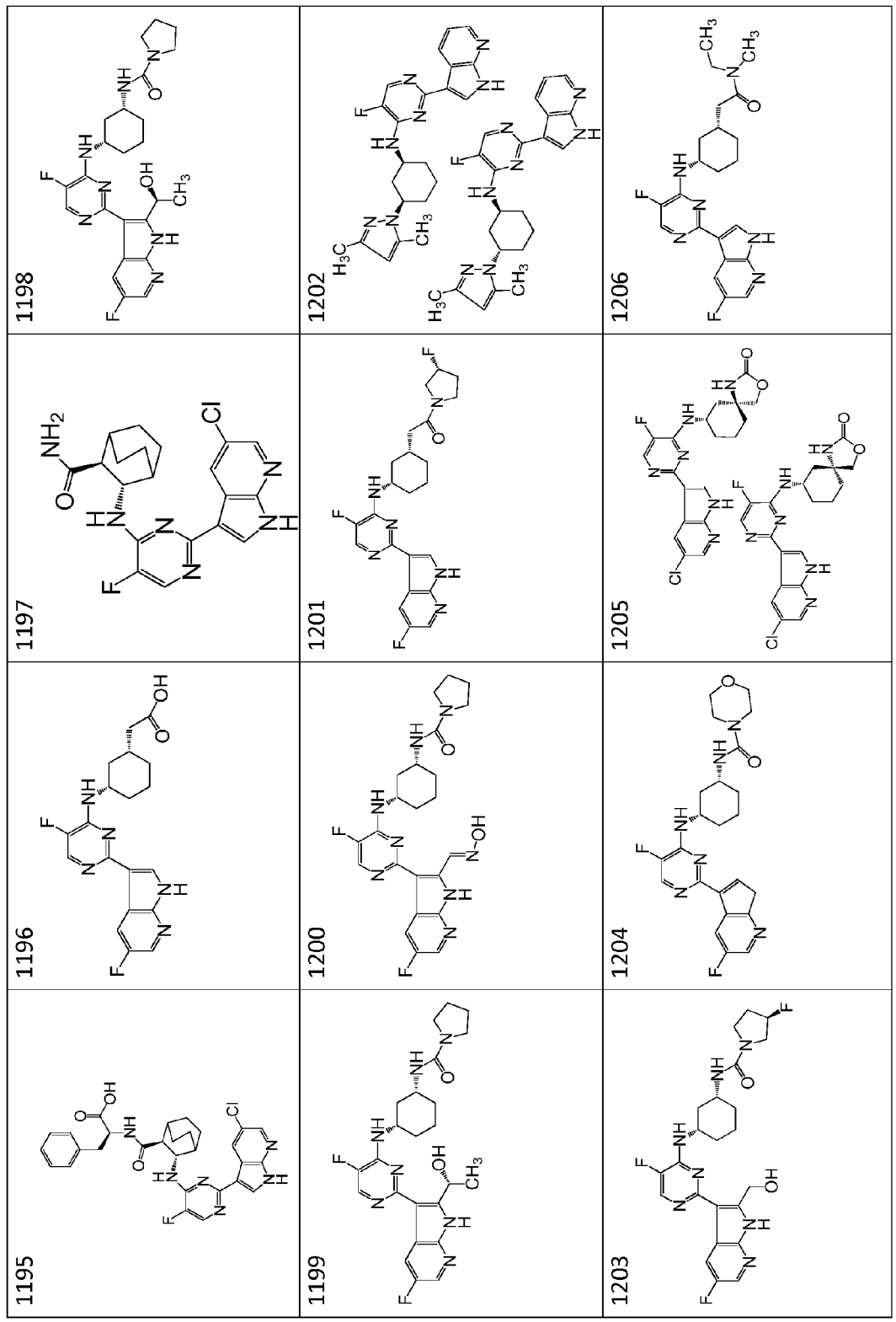
Figure 6T:
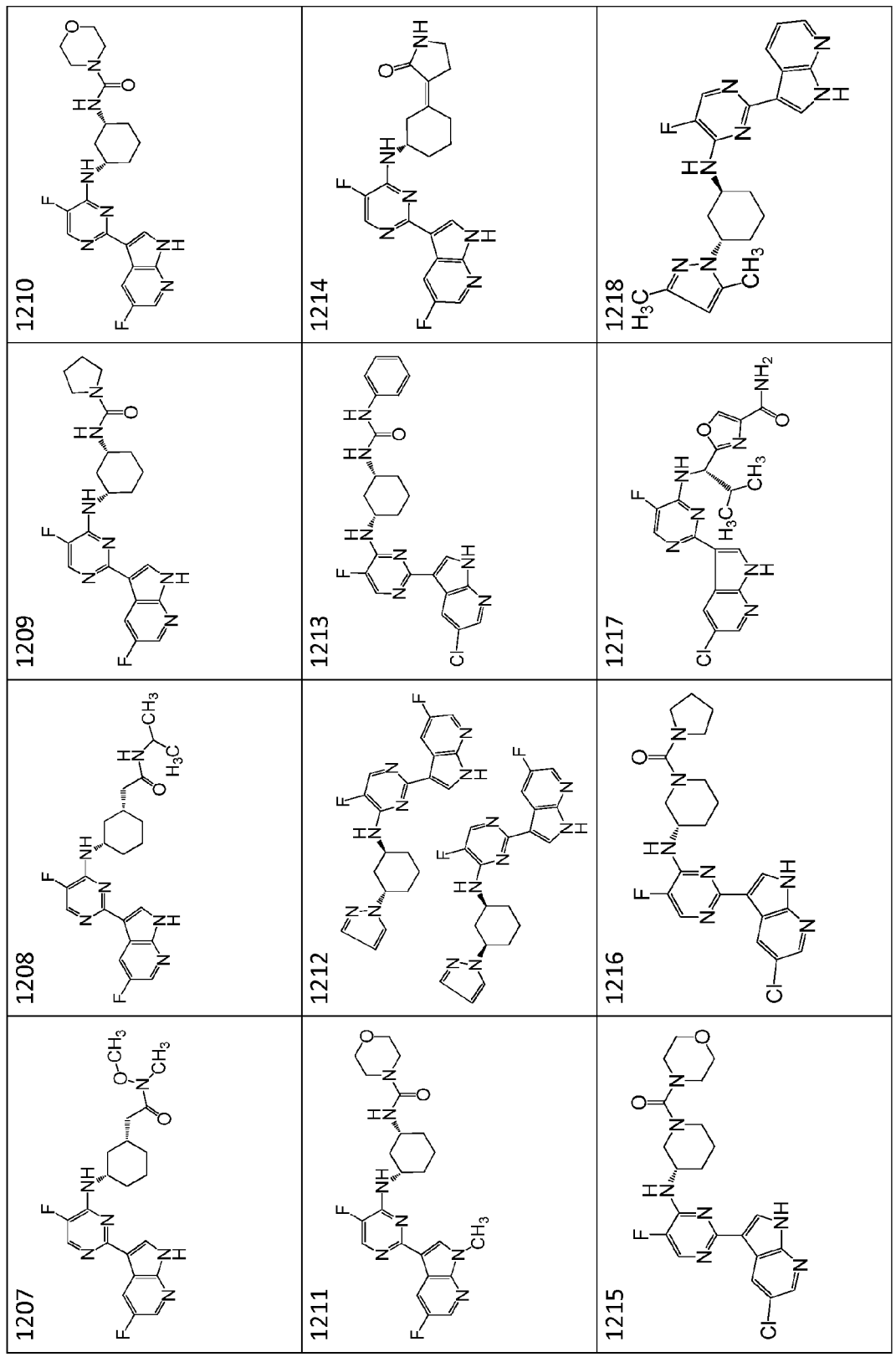
Figure 6U:
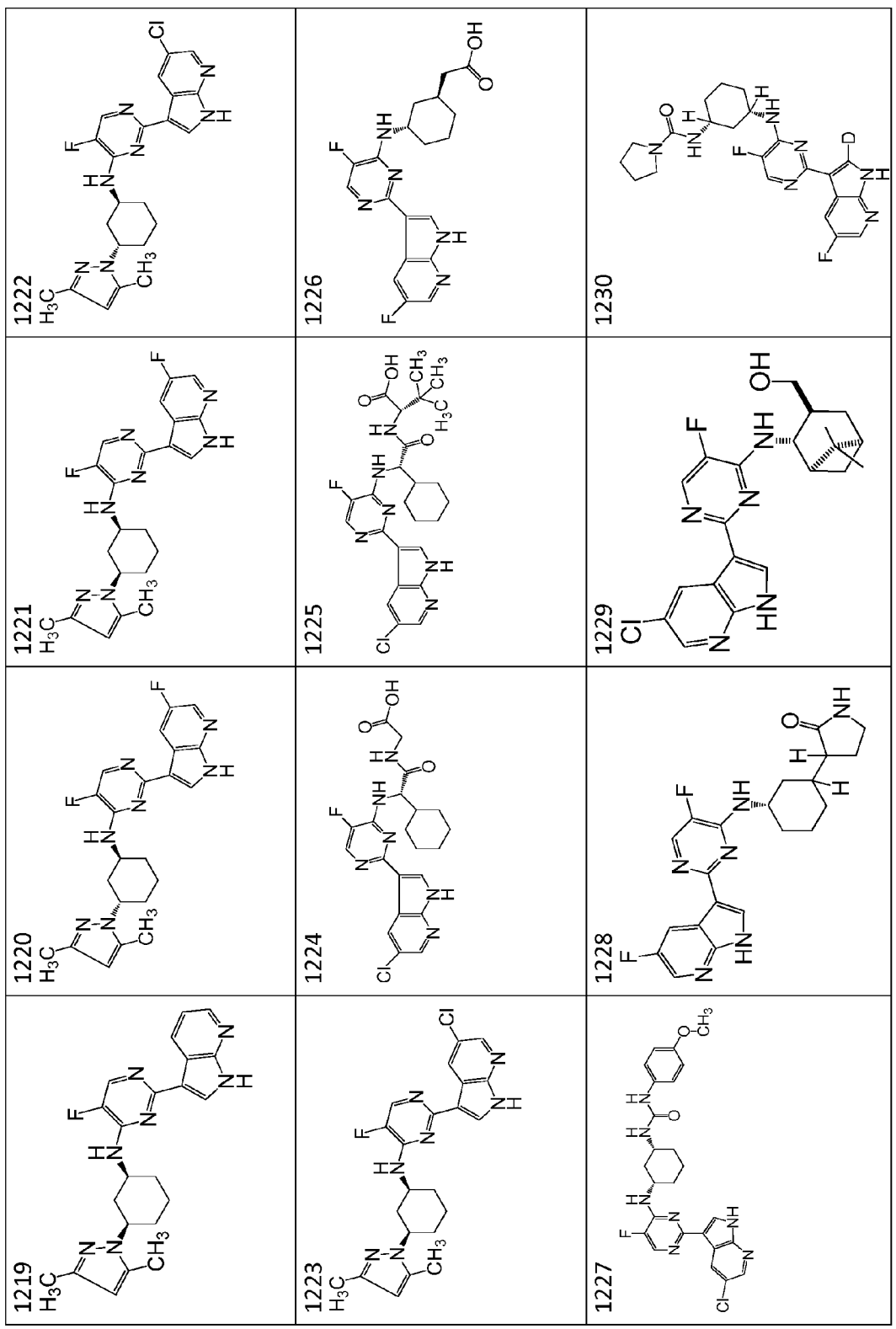
Figure 6V:
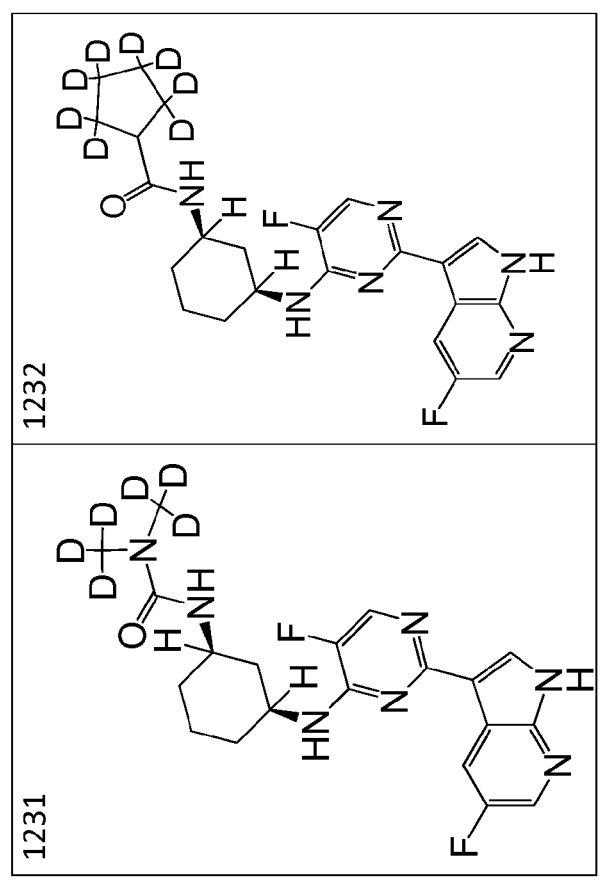
Figure 7A:
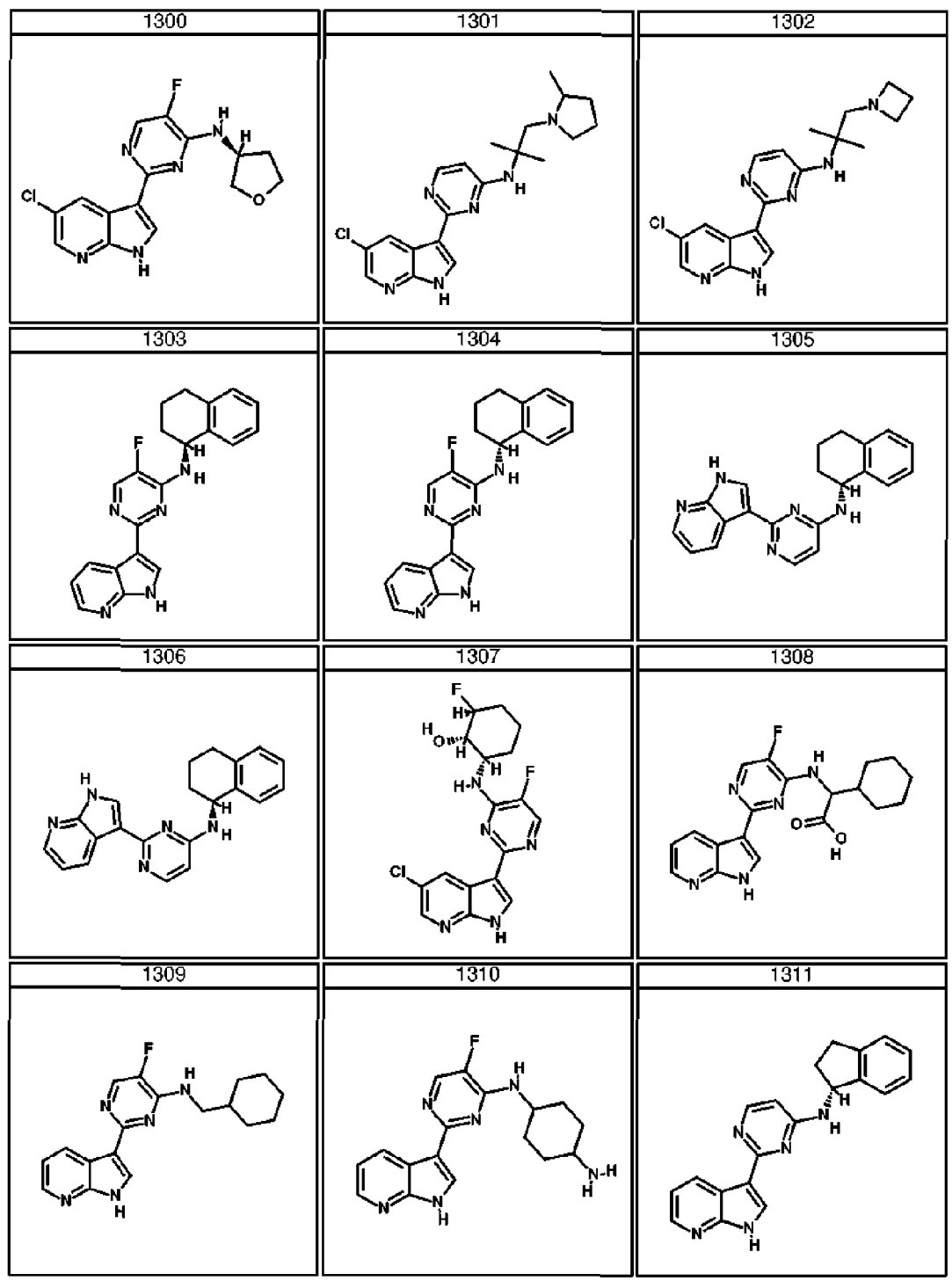
Figure 7B:
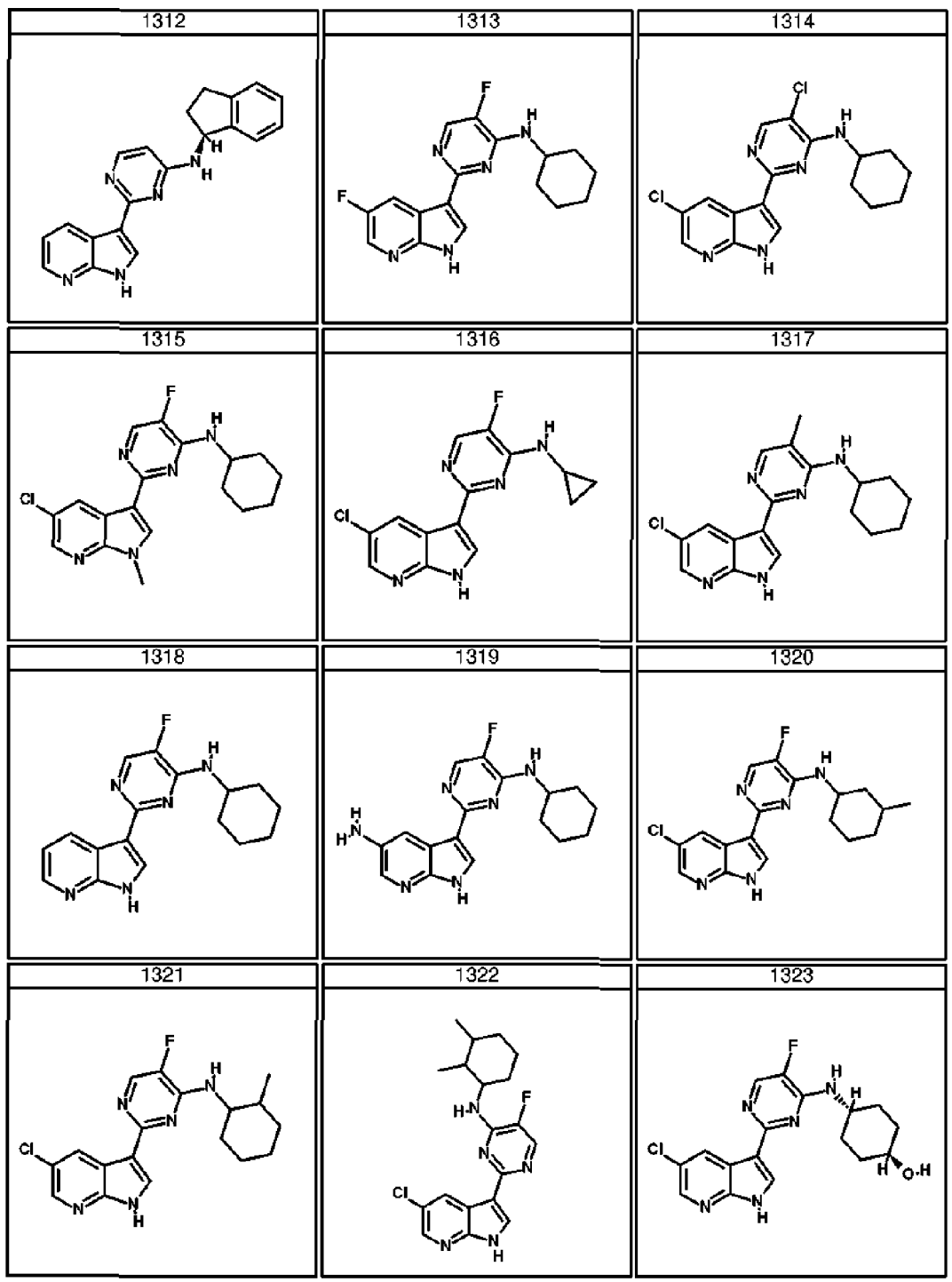
Figure 7C:
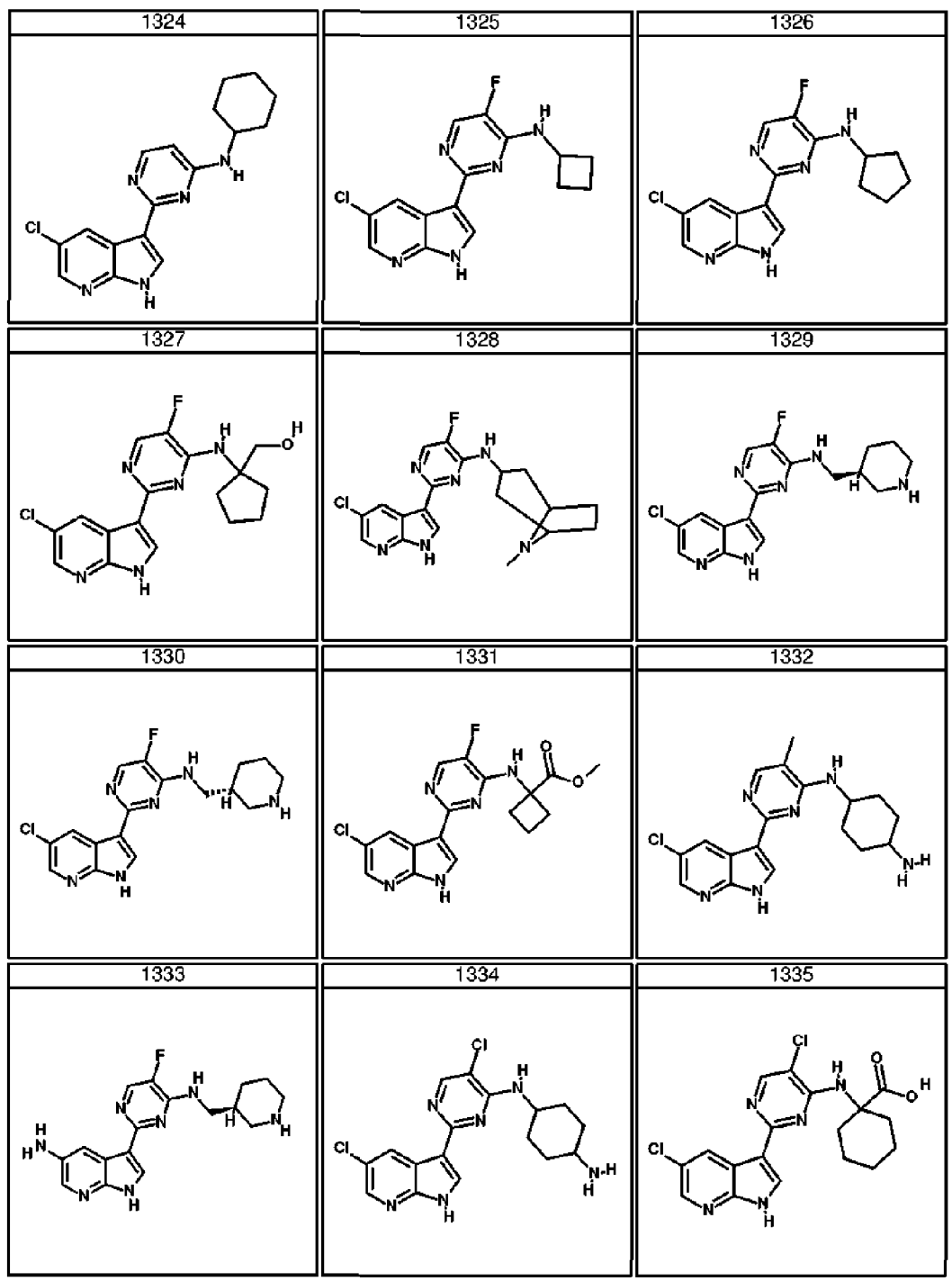
Figure 7D:
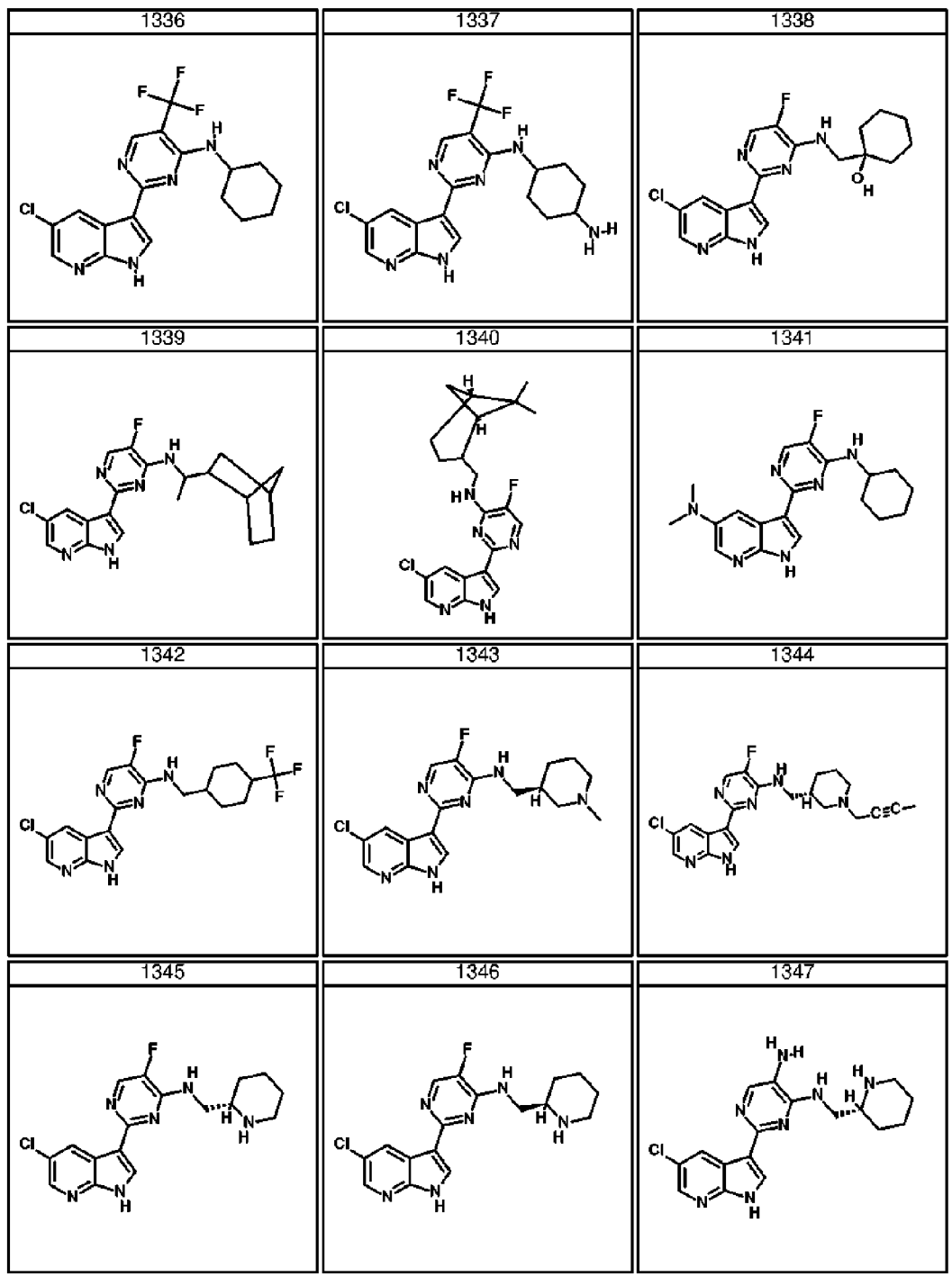
Figure 7E:
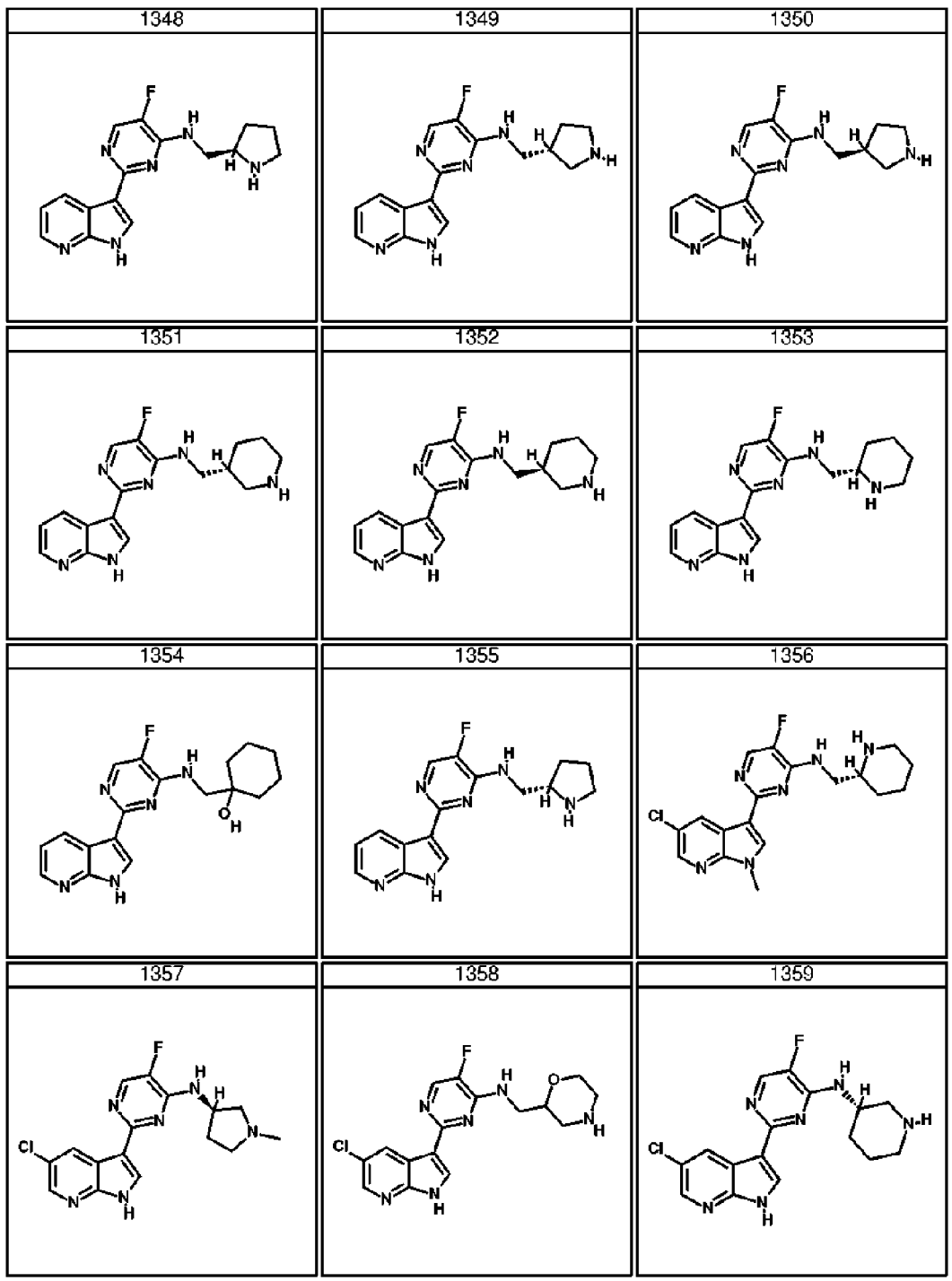
Figure 7F:
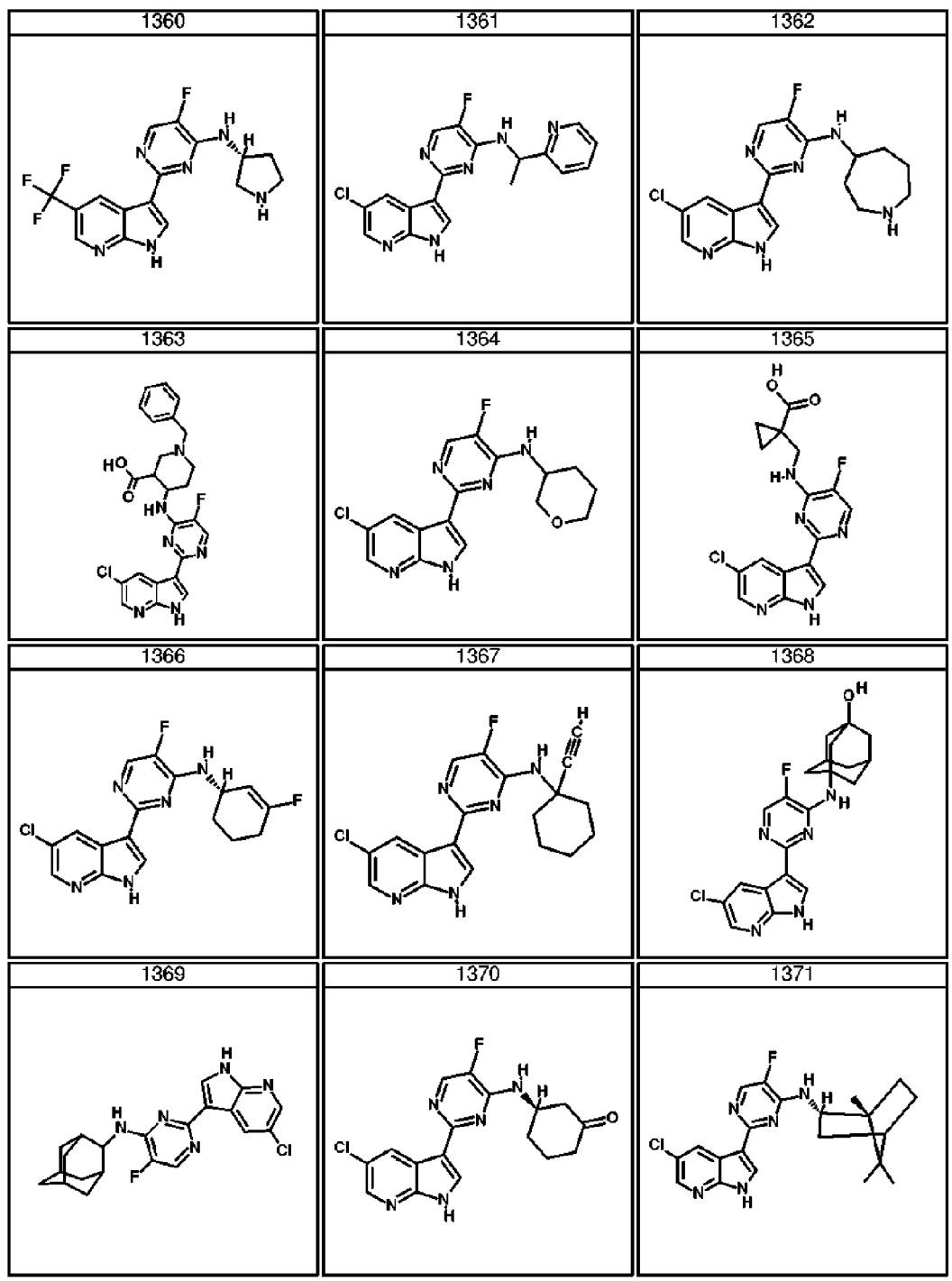
Figure 7G:
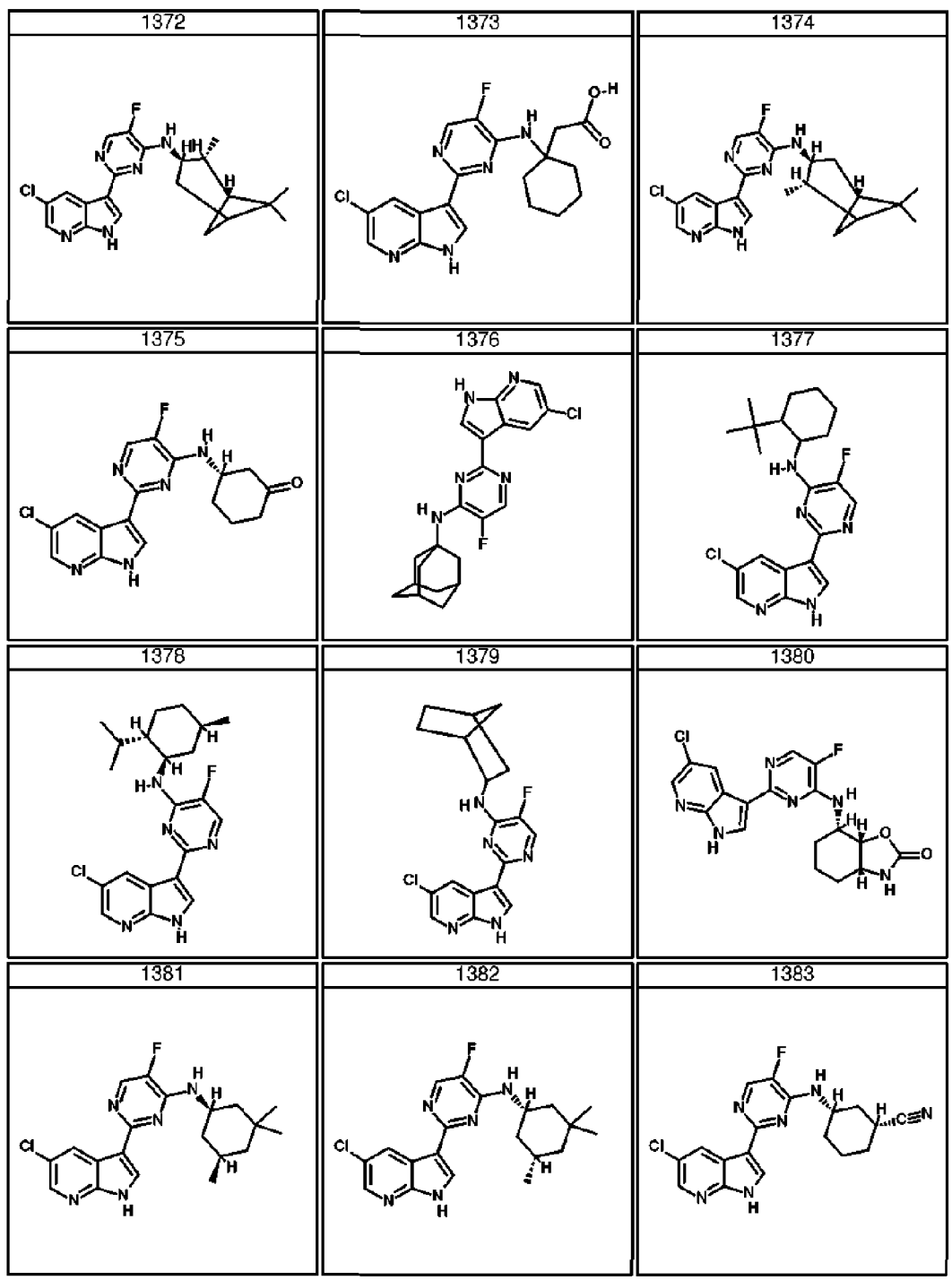
Figure 7H:
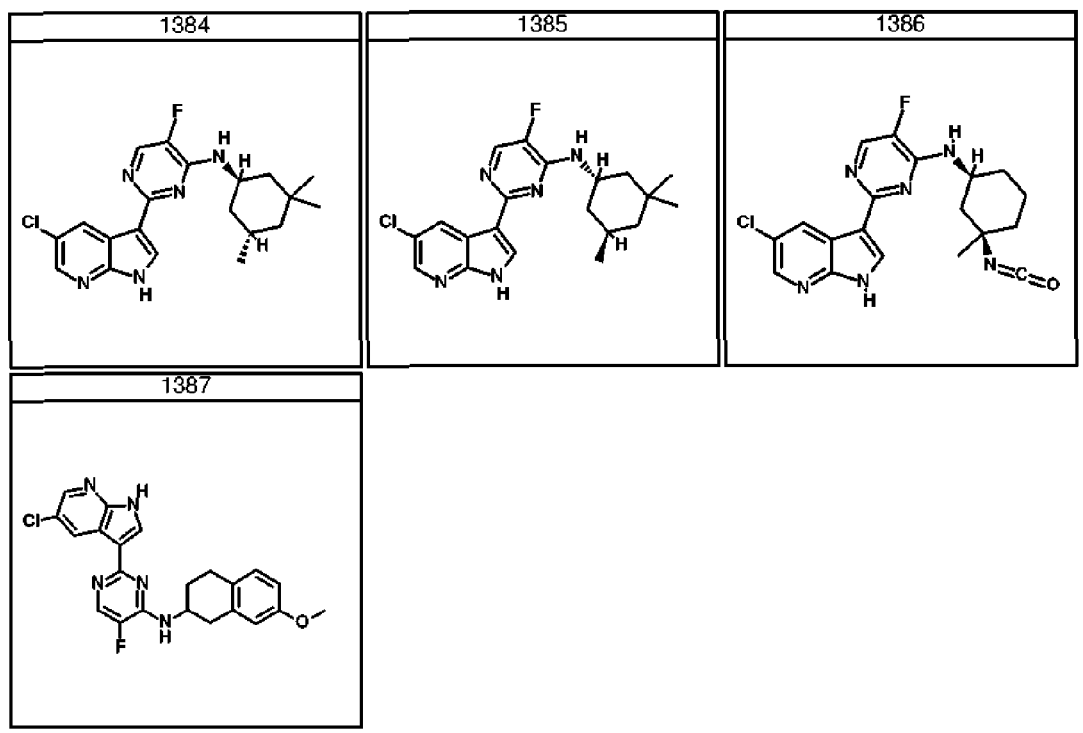

In yet another embodiment, the present invention is directed to any one of the compounds depicted in FIGS. 3-5, or pharmaceutically acceptable salts thereof.

In yet another embodiment, the present invention is directed to any one of the compounds depicted in FIG. 6, or pharmaceutically acceptable salts thereof. In yet another embodiment, the present invention is directed to any one of the compounds depicted in FIG. 7, or pharmaceutically acceptable salts thereof. In yet another embodiment, the present invention is directed to any one of the compounds depicted in FIG. 8, or pharmaceutically acceptable salts thereof.

In some embodiments, the variables of Structural Formulae I-VI and XI(A)-XIV are each and independently as depicted in the compounds of FIGS. 3-8.

Each and independently as described above for the methods of the invention, the aforementioned compounds of the invention can be useful as inhibitors of influenza virus replication in biological samples or in a patient. These compounds can also be useful in reducing the amount of influenza viruses (viral titer) in a biological sample or in a patient. They can also be useful for therapeutic and prophylactic treatment of infections caused by the influenza viruses in a biological sample or in a patient.

The present invention also provides methods of preparing a compound of the invention. In one embodiment, the methods are directed to prepare compounds represented by Structural Formula (IA) or pharmaceutically acceptable salts thereof. The methods comprise a step of reacting compound A:

(A)

with compound B:

(B)

to form a compound represented by Structural Formula (XX), as shown in Scheme A below:

Scheme A (A)

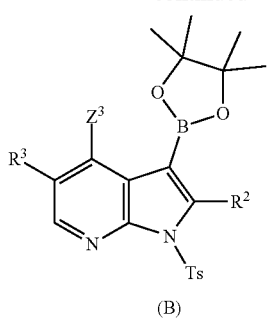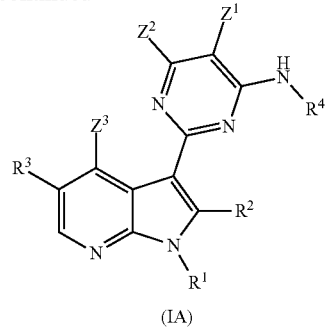

(B)

(IA)

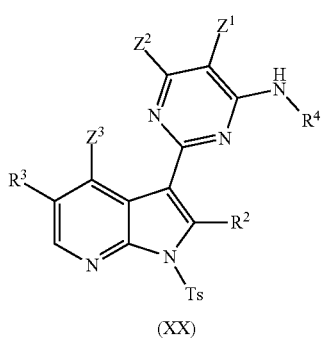

(XX)

The variables of Structural Formulae (IA) and (XX), and compounds (A) and (B) are independently as defined in any one of the embodiments described above. Ts is tosyl. Any suitable reaction condition known in the art, for example, in WO 2005/095400 and WO 2007/084557 for the coupling of a dioxaboraolan with a chloro-pyrimidine can be employed for the reaction between compound (A) and (B). For example, the reaction between compound (A) and (B) can be performed in the presence of $Pd(PPh_3)_4$. Specific exemplary conditions are described in the Exemplification below (e.g., General Schemes 5A, 6A, 7, 11, 14, 16, 31, 32, 33, 40, 44, 49, 51, 52, 58, 60, 61, 62, 63, 64, 66, 67, 68, 69, 70, 76).

In another embodiment, the methods comprise a step of reacting compound C1 or C2 with $NH_2R^4$ to form a compound represented by Structural Formula (XX), as shown in Scheme B below:

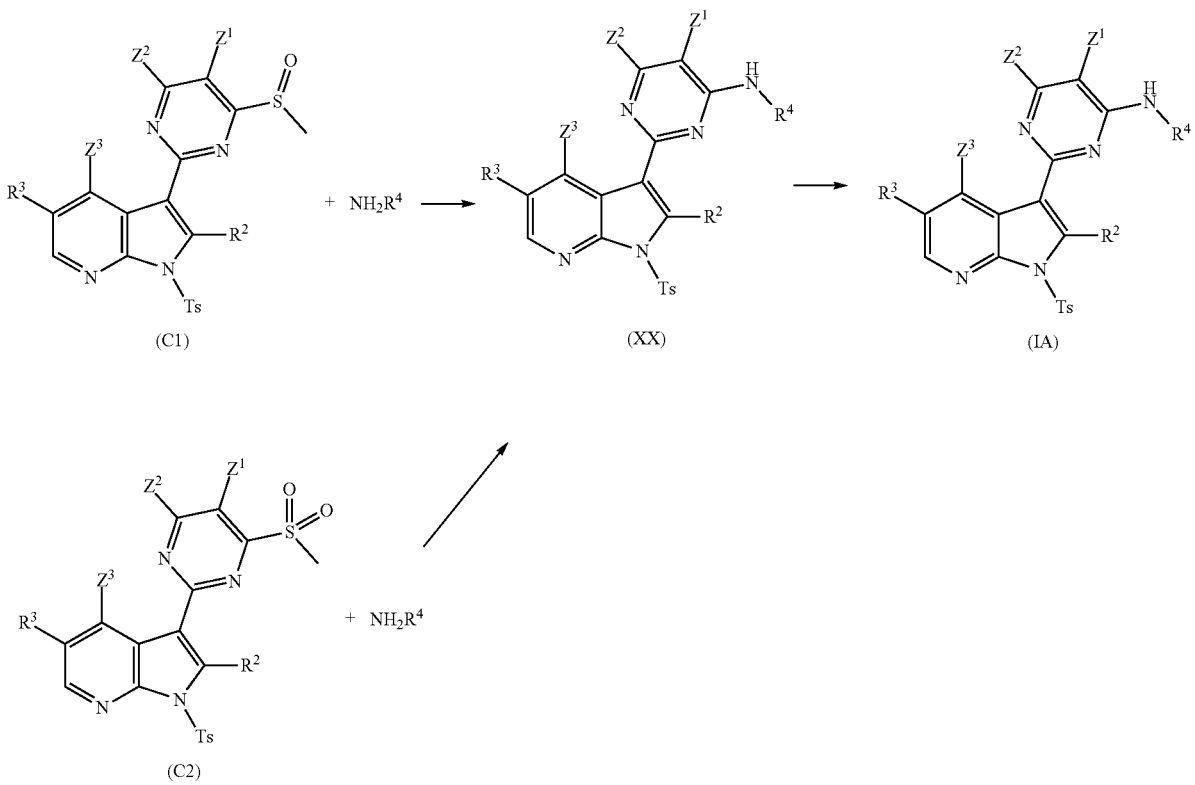

The variables of Structural Formulae (IA) and (XX), compounds (C1) and (C2), and $R^4$ of $NH_2R^4$ are independently as defined in any one of the embodiments described above. Ts is tosyl. Any suitable reaction condition known in the art, for example, in WO 2005/095400 and WO 2007/084557 for the coupling of an amine with a sulfinyl group can be employed for the reaction of compounds (C1) and (C2) with $NH_2R^4$. Specific exemplary conditions are described in the Exemplification below (e.g., General Schemes 13, 15, 19, 20, 23, 30, 39, 41, 42, 44, 45, 50, 53, 54, 65, 72, 73, 74, and 77).

The methods described above with reference to Schemes A and B optionally and independently further comprises deprotecting the Ts group of the compound of Structural Formula (XX) to form the compound of Structural Formula (IA). Any suitable condition for deprotecting a Ts group known in the art can be employed in the invention. Specific exemplary conditions are described in the Exemplification below. The de-tosylation can generate the compounds of Structural Formula (IA) where $R^1$ is —H. If desired, the $R^1$ position can be alkylated by any suitable method known in the art to from the compounds of Structural Formula (IA) where $R^1$ is $C_{1-6}$ alkyl.

Compounds (A), (B), (C1), (C2), and $NH_2R^4$ can be prepared by any suitable method known in the art. Specific exemplary synthetic methods are described below in the Exemplification below. For example, compound (C1) can be prepared as described in Scheme C: reaction between compounds (D) and (E), for example, in the presence of $Pd(PPh_3)_4$ can produce compound (F). Compound (F) can then be oxidated under suitable conditions, for example, by treatment with meta-chloroperbenzoic acid to form compound (C). (See, for example, detailed experimental details described in the Exemplification for General Scheme 44.)

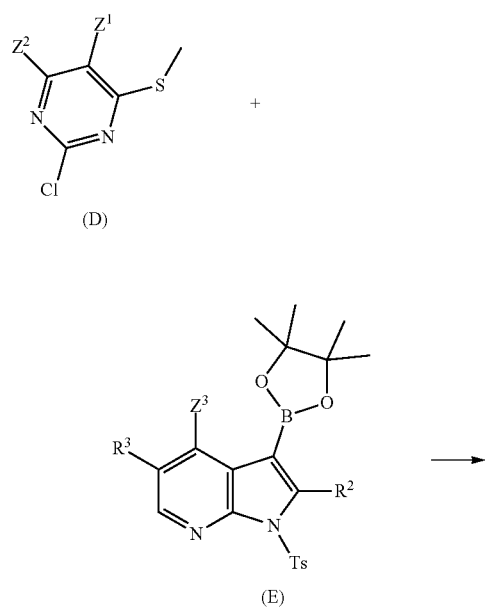

Scheme C

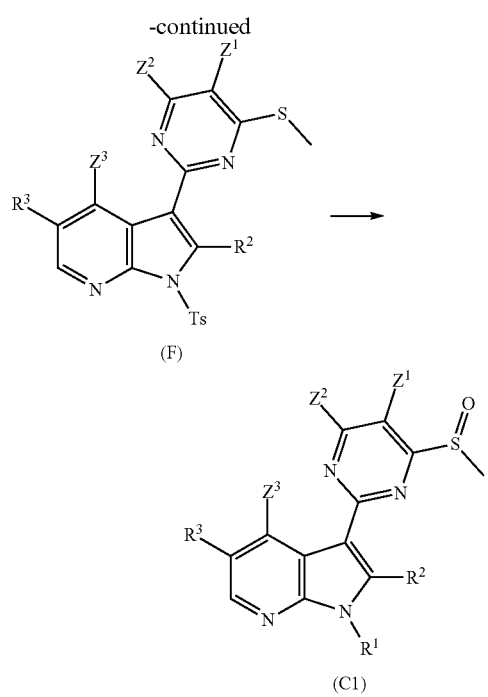

Definitions and General Terminology

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as illustrated generally below, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$-$C_3$alkyl or phenyl; X may be either optionally substituted $C_1$-$C_3$ alkyl or optionally substituted phenyl. Likewise, if the term "optionally substituted" follows a list, said term also refers to all of the substitutable groups in the prior list unless otherwise indicated. For example: if X is $C_1$-$C_3$alkyl or phenyl wherein X is optionally and independently substituted by $J^X$, then both $C_1$-$C_3$alkyl and phenyl may be optionally substituted by $J^X$. As is apparent to one having ordinary skill in the art, groups such as H, halogen, $NO_2$, CN, $NH_2$, OH, or $OCF_3$ would not be substitutable groups.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$-$C_6$ alkyl or $C_1$-$C_4$ alkyl. In some embodiments, the "alkenyl" is $C_2$-$C_6$ alkenyl or $C_2$-$C_4$ alkenyl. In some embodiments, the "alkynyl" is $C_2$-$C_6$ alkynyl or $C_2$-$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to both carbocyclic or heterocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6.5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl) carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above, for example, in the definitions of $J^A$, $J^B$, $J^{C1}$, $J^{D1}$, and $J^{E1}$. Other suitable substitutents include those listed as suitable for the unsaturated carbon of a carbocyclic aryl or heteroaryl group and additionally include the following: =O, =S, =NNHR*, =NN(R*)$_2$, =NNHC(O)R*, =NNHCO$_2$ (alkyl), =NNHSO$_2$(alkyl), or =NR*, wherein each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include those used above, for example, in the definitions of $J^B$, $J^{D1}$ and $J^{E1}$. Other suitable substituents include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR+SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R⁺ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄ aliphatic groups of R⁺ is unsubstituted.

In some embodiments, a carbocyclic aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of a carbocyclic aryl or heteroaryl group are selected from those listed above, for example, in the definitions of J^A, J^B, J^C1, J^D1 and J^E1. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —(CH₂)₁₋₂(Ph), optionally substituted with R°; —CH=CH(Ph), optionally substituted with R°; —NO₂; —CN; —N(R°)₂; —NR°C(O)R°; —NR°C(S)R°)₂; —NR°C(O)N(R°)₂; —NR°C(S)N(R°)₂; —NR°CO₂R°; —NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; or —(CH₂)₀₋₂NHC(O)R°; wherein each independent occurrence of R° is selected from hydrogen, optionally substituted C₁₋₆ aliphatic, an unsubstituted 5-6 membered heteroaryl or heterocyclic ring, phenyl, —O(Ph), or —CH₂(Ph), or, two independent occurrences of R°, on the same substituent or different substituents, taken together with the atom(s) to which each R° group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), O(haloC₁₋₄ aliphatic), or haloC₁₋₄aliphatic, CHO, N(CO)(C₁₋₄ aliphatic), C(O)N(C₁₋₄ aliphatic), wherein each of the foregoing C₁₋₄aliphatic groups of R° is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation.

As detailed above, in some embodiments, two independent occurrences of R° (or R⁺, or any other variable similarly defined herein), may be taken together with the atom(s) to which each variable is bound to form a 5-8-membered heterocyclyl, carbocyclic aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

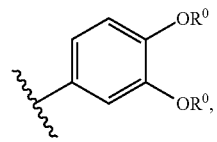

these two occurrences of R° are taken together with the oxygen atoms to which they are bound to form a fused 6-membered oxygen containing ring:

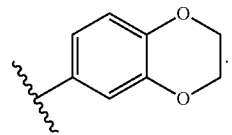 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to those listed in the definitions of Q¹, Y¹, Q² and Q³. Further examples include —NR—, —O—, —S—, —CO₂—, —OC(O)—, —C(O)CO—, —C(O)—, —C(O)NR—, —C(=N—CN)—, —NRCO—, —NRC(O)O—, —SO₂NR—, —NRSO₂—, —NRC(O)NR—, —OC(O)NR—, —NRSO₂NR—, —SO—, or —SO₂—, wherein R is as defined above.

As used herein, an "amino" group refers to —NR^X R^Y wherein each of R^X and R^Y is independently —H, C₁-C₆ aliphatic, a C₃₋₇ non-aromatic carbocycle, a 5-6 membered carbocyclic aryl or heteroaryl, or a 4-7 membered non-aromatic heterocycle, each of which independently being defined herein and being optionally substituted. Suitable substituents for the carbocycle, carbocyclic aryl, heteroaryl, and heterocycl are each independently include halogen, cyano, hydroxy, oxo, —NH₂, —NH(C₁-C₆ alkyl), —N(C₁-C₆ alkyl)₂, C₁-C₆ alkyl, —O(C₁-C₆ alkyl), —C(O)OH, —C(O)O(C₁-C₆ alkyl), —OC(O)(C₁-C₆ alkyl), —NHC(O)(C₁-C₆ alkyl), —NHC(O)O(C₁-C₆ alkyl), —C(O)NH(C₁-C₆ alkyl), and —C(O)N(C₁-C₆ alkyl)₂, wherein each of said alkyl groups is optionally and independently substituted with one or more substituents selected from the group consisting of halogen, cyano, hydroxy, oxo, —NH$_2$, —NH(C$_1$-C$_4$ alkyl), and —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Suitable substituents for the C$_1$-C$_6$ aliphatic (including C$_1$-C$_6$ alkyl) include halogen, cyano, hydroxy, oxo, —NH$_2$, —NH(C$_1$-C$_6$ alkyl), —N(C$_1$-C$_6$ alkyl)$_2$, —O(C$_1$-C$_6$ alkyl), —C(O)OH, —C(O)O(C$_1$-C$_6$ alkyl), —OC(O)(C$_1$-C$_6$ alkyl), —NHC(O)(C$_1$-C$_6$ alkyl), —NHC(O)O(C$_1$-C$_6$ alkyl), —C(O)NH(C$_1$-C$_6$ alkyl), —C(O)N(C$_1$-C$_6$ alkyl)$_2$, phenyl, a 5-6 membered heteroaryl, a 5-6 membered non-aromatic heterocycle, and a C$_3$-C$_7$ carbocycle, wherein each of said alkyl groups is optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy, and wherein each of said phenyl, heteroaryl, heterocycle and carbocycle is optionally and independently substituted with one or more substituents described above for the carbocycle, carbocyclic aryl, heteroaryl, and heterocycle represented by R$^X$ and R$^Y$. In some embodiments, each of R$^X$ and R$^Y$ is independently —H, an optionally substituted C$_{1-6}$ aliphatic group, or an optionally substituted C$_{3-8}$ non-aromatic carbocycle. In some embodiments, each of R$^X$ and R$^Y$ is independently —H or an optionally substituted C$_{1-6}$ aliphatic group. In some embodiments, each of R$^X$ and R$^Y$ is independently —H or C$_{1-6}$ alkyl optionally substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. Examples of amino groups include —NH$_2$, aliphatic amino, alkylamino, dialkylamino, or arylamino. As used herein, an "aliphatic amino" group refers to —NR$^X$R$^Y$ wherein R$^X$ is a C$_{1-6}$ aliphatic group optionally substituted as described above; and R$^Y$ is —H or a C$_{1-6}$ aliphatic group optionally substituted as described above. As used herein, an "alkylamino" group refers to —NHR$^X$ wherein R$^X$ is a C$_{1-6}$ alkyl group optionally substituted as described above. As used herein, a "dialkylamino" group refers to —NR$^X$R$^Y$ wherein each of R$^X$ and R$^Y$ is independently a C$_{1-6}$ alkyl group optionally substituted as described above. As used herein, an "arylamino" group refers to —NR$^X$R$^Y$ wherein R$^X$ is 5-6 membered, carbocyclic aryl or heteroaryl, and R$^Y$ is —H or 5-6 membered, carbocyclic aryl or heteroaryl, wherein each of said carbocyclic aryl and heteroaryl groups is independently and optionally substituted as described above. When the term "amino" is not the terminal group (e.g., alkylcarbonylamino), it is represented by —NR$^X$—. R$^X$ has the same meaning as defined above. In one embodiment, the amino group is —NH$_2$ or an aliphatic amino. In another embodiment, the amino group is —NH$_2$, alkylamino or dialkylamino. In yet another embodiment, the amino group is —NH$_2$ or an arylamino. In yet another embodiment, the amino group is —NH$_2$, —NH(C$_1$-C$_6$ alkyl) or —N(C$_1$-C$_6$ alkyl)$_2$, wherein each of the alkyl groups is optionally and independently substituted with one or more substituents selected from the group consisting of halogen, cyano, hydroxy, oxo, —NH$_2$, —NH(C$_1$-C$_4$ alkyl), —N(C$_1$-C$_4$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

As used herein, an "amido" encompasses both "aminocarbonyl" and "carbonylamino". These terms when used alone or in connection with another group refer to an amido group such as N(R$^X$R$^Y$)—C(O)— or R$^Y$C(O)—N(R$^X$)— when used terminally and —C(O)—N(R$^X$)— or —N(R$^x$)—C(O)— when used internally, wherein R$^X$ and R$^Y$ are defined above. Examples of amido groups include alkylamido (such as alkylcarbonylamino or alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido. In some embodiments, the amido group is —NHC(O)(C$_1$-C$_6$ alkyl), —N(C$_1$-C$_6$ alkyl)C(O)(C$_1$-C$_6$ alkyl), —C(O)NH$_2$, —C(O)NH(C$_1$-C$_6$ alkyl), or —C(O)NH(C$_1$-C$_6$ alkyl)$_2$, wherein each of said alkyl is optionally and independently substituted with one or more substituents selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy. In some embodiments, the amido group is —NHC(O)(C$_1$-C$_6$ alkyl), —N(C$_1$-C$_6$ alkyl)C(O)(C$_1$-C$_6$ alkyl), —C(O)NH$_2$, —C(O)NH(C$_1$-C$_6$ alkyl), or —C(O)NH(C$_1$-C$_6$ alkyl)$_2$, wherein each of the alkyl groups is optionally and independently substituted with one or more substituents selected from the group consisting of halogen, cyano, hydroxy, oxo, —NH$_2$, —NH(C$_1$-C$_6$ alkyl), —N(C$_1$-C$_6$ alkyl)$_2$, —OCO(C$_1$-C$_4$ alkyl), —CO(C$_1$-C$_4$ alkyl), —CO$_2$H, —CO$_2$(C$_1$-C$_4$ alkyl), and C$_1$-C$_4$ alkoxy.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ are each independently as defined above.

As used herein, an "acyl" group refers to a formyl group or R$^X$—C(O)— (such as -alkyl-C(O)—, also referred to as "alkylcarbonyl") where R$^X$ and "alkyl" have been defined previously. Acetyl and pivaloyl are examples of acyl groups.

As used herein, a "carboxy" group refers to —COOH, —COOR$^X$, —OC(O)H, —OC(O)R$^X$ when used as a terminal group; or —OC(O)— or —C(O)O— when used as an internal group, wherein R$^X$ is as defined above.

The term "hydroxyl" or "hydroxy" or "alcohol moiety" refers to —OH.

As used herein, an "alkoxycarbonyl," which is encompassed by the term carboxy, used alone or in connection with another group refers to a group such as (alkyl-O)—C(O)—.

As used herein, a "carbonyl" refers to —C(O)—.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O-alkyl) or sulfur ("alkylthio" e.g., —S-alkyl) atom.

As used herein, the terms "halogen", "halo", and "hal" mean F, Cl, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF$_3$ and —CF$_2$CF$_3$.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (NC)-alkyl-.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above. In some embodiments, the aminoaliphatic is a $C_1$-$C_6$ aliphatic group substituted with one or more —$NH_2$ groups. In some embodiments, the aminoalkyl refers to the structure ($R^X R^Y$)N-alkyl-, wherein each of $R^X$ and $R^Y$ independently is as defined above. In some specific embodiments, the aminoalkyl is $C_1$-$C_6$ alkyl substituted with one or more —$NH_2$ groups. In some specific embodiments, the aminoalkenyl is C1-C6 alkenyl substituted with one or more —$NH_2$ groups. In some embodiments, the aminoalkoxy is —O($C_1$-$C_6$ alkyl) wherein the alkyl group is substituted with one or more —$NH_2$ groups.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)-alkyl-, wherein alkyl is as defined above.

The term "carboxyalkyl" means alkyl substituted with one or more carboxy groups, wherein alkyl and carboxy are as defined above.

In some embodiments, each of the amino groups referred to in the descriptions for the variables of Structural Formulae I-VI and XI(A)-XIV (e.g., $R^6$, $R^7$, $J^{E1}$, R, R', R", R*, $R^a$, $R^b$ and $R^c$) above is independently —$NH_2$, —NH($C_1$-$C_6$ alkyl), —NH($C_3$-$C_6$ carbocycle), —N($C_1$-$C_6$ alkyl)$_2$, or —N($C_1$-$C_6$ alkyl)($C_3$-$C_6$ carbocycle), wherein said alkyl and carbocycle groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the carboxy groups referred to in the descriptions for the variables of Structural Formulae I-VI and XI(A)-XIV (e.g., $R^6$, $R^7$, $J^{E1}$, R, R', R", R*, $R^a$, $R^b$ and $R^c$) above is independently —C(O)O($C_1$-$C_6$ alkyl), —OC(O)($C_1$-$C_6$ alkyl), —C(O)O($C_3$-$C_6$ carbocycle), —OC(O)($C_3$-$C_6$ carbocycle), or —$CO_2H$, wherein said alkyl and carbocylce groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the amido groups referred to in the descriptions for the variables of Structural Formulae I-VI and XI(A)-XIV (e.g., $R^6$, $R^7$, $J^{E1}$, R, R', R", R*, $R^a$, $R^b$ and $R^c$) above is independently —NHC(O)($C_1$-$C_6$ alkyl), —N($C_1$-$C_6$ alkyl)C(O)($C_1$-$C_6$ alkyl), —C(O)NH($C_1$-$C_6$ alkyl), —C(O)N($C_1$-$C_6$ alkyl)$_2$, —NHC(O)($C_3$-$C_6$ carbocycle), —N($C_1$-$C_6$ alkyl)C(O)($C_3$-$C_6$ carbocycle), —C(O)NH($C_3$-$C_6$ carbocycle), —C(O)N($C_1$-$C_6$ alkyl)($C_3$-$C_6$ carbocycle), or —C(O)$NH_2$, wherein said alkyl and carbocycle groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the aminoalkyl groups referred to in the descriptions for the variables of Structural Formulae I-VI and XI(A)-XIV (e.g., $R^8$, $R^9$, and R") above is independently a C1-C6 alkyl group substituted with one or more amino groups independently selected from the group consisting of —$NH_2$, —NH($C_1$-$C_4$ alkyl), and —N($C_1$-$C_4$ alkyl)$_2$; and each of the aminoalkoxy groups referred to in the descriptions for the variables of Structural Formulae I-VI and XI(A)-XIV (e.g., $R^6$, $R^7$, $R^8$, $R^9$, $R^{10}$, $R^{11}$, $R^{12}$, $R^{13}$, $R^{14}$, R, R', and R") above is independently is a —O(C1-C6 alkyl) group wherein the alkyl group is substituted with one or more one or more amino groups independently selected from the group consisting of —$NH_2$, —NH($C_1$-$C_4$ alkyl), and —N($C_1$-$C_4$ alkyl)$_2$.

In some embodiments, each of the amino groups referred to in the descriptions for the variables of Structural Formulae I-VI and XI(A)-XIV (e.g., $R^6$, $R^7$, $J^{E1}$, R, R', R", R*, $R^a$, $R^b$ and $R^c$) above is independently —$NH_2$, —NH($C_1$-$C_6$ alkyl), or —N($C_1$-$C_6$ alkyl)$_2$, wherein said alkyl groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the carboxy groups referred to in the descriptions for the variables of Structural Formulae I-VI and XI(A)-XIV (e.g., $R^6$, $R^7$, $J^{E1}$, R, R', R", $R^a$, $R^b$ and $R^c$) above is independently —C(O)O($C_1$-$C_6$ alkyl), —OC(O)($C_1$-$C_6$ alkyl), or —$CO_2H$, wherein said alkyl groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the amido groups referred to in the descriptions for the variables of Structural Formulae I-VI and XI(A)-XIV (e.g., $R^6$, $R^7$, $J^{E1}$, R, R', R", R*, $R^a$, $R^b$ and $R^c$) above is independently —NHC(O)($C_1$-$C_6$ alkyl), —N($C_1$-$C_6$ alkyl)C(O)($C_1$-$C_6$ alkyl), —C(O)NH($C_1$-$C_6$ alkyl), —C(O)N($C_1$-$C_6$ alkyl)$_2$, or —C(O)$NH_2$, wherein said alkyl groups are each optionally and independently substituted with one or more substituents independently selected from the group consisting of halogen, cyano, hydroxy, oxo, —$NH_2$, —NH($C_1$-$C_4$ alkyl), —N($C_1$-$C_4$ alkyl)$_2$, —OCO($C_1$-$C_4$ alkyl), —CO($C_1$-$C_4$ alkyl), —$CO_2H$, —$CO_2$($C_1$-$C_4$ alkyl), and $C_1$-$C_4$ alkoxy; each of the aminoalkyl groups referred to in the descriptions for the variables of Structural Formulae I-VI and XI(A)-XIV (e.g., $R^8$, $R^9$, and R") above is independently a C1-C6 alkyl group substituted with one or more amino groups independently selected from the group consisting of —$NH_2$, —NH($C_1$-$C_4$ alkyl), and —N($C_1$-$C_4$ alkyl)$_2$; and each of the aminoalkoxy groups referred to in the descriptions for the variables of Structural Formulae I-VI and XI(A)-XIV (e.g., $R^6$, $R^7$, $R^8$, $R^9$, $R^{10}$, $R^{11}$, $R^{12}$, $R^{13}$, $R^{14}$, R, R', and R") above is independently is a —O(C1-C6 alkyl) group wherein the alkyl group is substituted with one or more one or more amino groups independently selected from the group consisting of —$NH_2$, —NH($C_1$-$C_4$ alkyl), and —N($C_1$-$C_4$ alkyl)$_2$.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

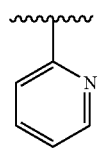

also represents

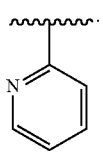

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. For example, compounds of Structural Formulae I-VI (e.g., Structural Formulae I, IA, II, III, IV, V, and VI) and XI(A)-XIV (e.g., Structural Formulae XIA, XIB, XIIA, XIIB, XIII, and XIV) that have -D at the position corresponding to $R^2$ are also within the scope of this invention. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, he term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

Pharmaceutically acceptable prodrugs of the compounds described herein include, without limitation, esters, amino acid esters, phosphate esters, metal salts and sulfonate esters.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

EXEMPLIFICATION

Preparation of Compounds

The compounds disclosed herein, including those of Structural Formulae I-VI (e.g., Structural Formulae I, IA, II, III, IV, V, and VI) and XI(A)-XIV (e.g., Structural Formulae XIA, XIB, XIIA, XIIB, XIII, and XIV) can be prepared by any suitable method known in the art, for example, WO 2005/095400 and WO 2007/084557. For example, the compounds depicted in FIGS. 3-8 can be prepared by any suitable method known in the art, for example, WO 2005/095400 and WO 2007/084557, and by the exemplary syntheses described below. In particular, the compounds depicted in FIG. 8 can be prepared as described in WO 2005/095400 and WO 2007/084557. Syntheses of certain exemplary compounds of Structural Formulae I-VI and XI(A)-XIV are described below. Generally, the compounds of Structural Formulae I-VI and XI(A)-XIV can be prepared as shown in those syntheses optionally with any desired appropriate modification.

General Analytical Methods

As used herein the term RT (min) refers to the LCMS retention time, in minutes, associated with the compound. Unless otherwise indicated, the method employed to obtain the reported retention times is as follows:

Column: YMC-Pack Pro Cig, 50 mm×4.6 mm id

Gradient: 10-95% methanol/$H_2O$. Flow rate: 1.5 ml/min. UV-vis detection.

Methodology for Synthesis and Characterization of Compounds

Syntheses of certain exemplary compounds of Structural Formulae I-VI (e.g., Structural Formulae I, IA, II, III, IV, V, and VI) and XI(A)-XIV (e.g., Structural Formulae XIA, XIB, XIIA, XIIB, XIII, and XIV) are described below. NMR and Mass Spectroscopy data of certain specific compounds are summarized in Tables 1-5.

General Scheme 1:

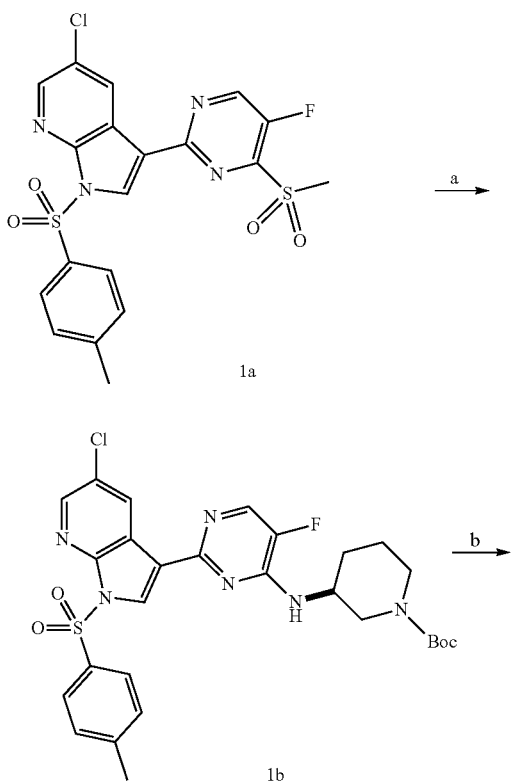

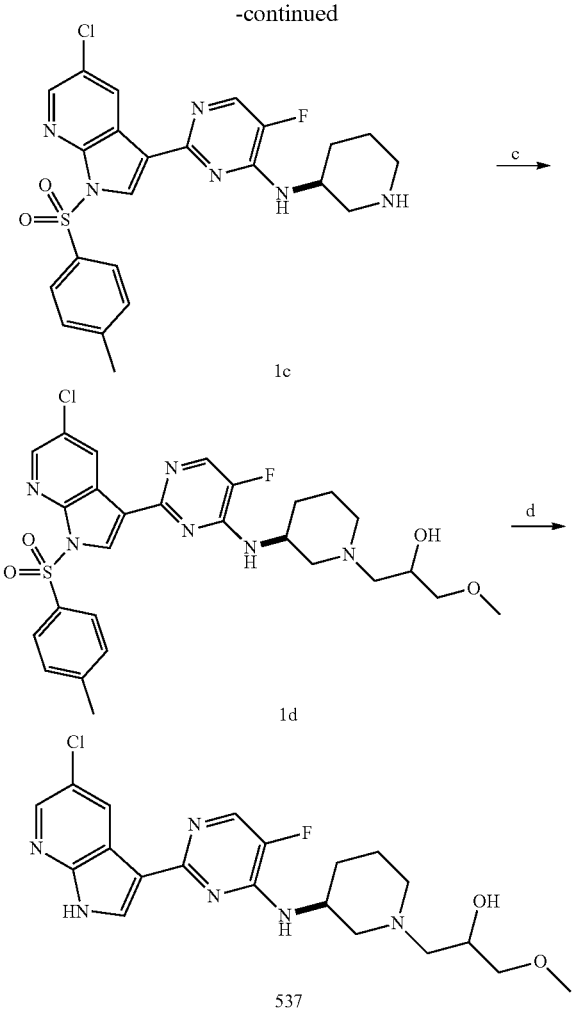

(a) (S)-1-Boc-3-aminopiperidine, $^i$Pr$_2$NEt, DMF, 90° C.; (b) TFA, CH$_2$Cl$_2$; (c) 2-(methoxymethyl)oxirane, EtOH, microwave, 140° C.; (d) 1N LiOH, THF, microwave, 120° C.

Formation of (S)-tert-butyl 3-((2-(5-chloro-1-tosyl-1H-pyrrolo[2,3-b]pyridin-3-yl)-5-fluoropyrimidin-4-ylamino)piperidine-1-carboxylate (1b)

To a solution of 5-chloro-3-(5-fluoro-4-methylsulfonyl-pyrimidin-2-yl)-1-(p-tolylsulfonyl)pyrrolo[2,3-b]pyridine, 1a, (3.5 g, 7.5 mmol) and tert-butyl (3S)-3-aminopiperidine-1-carboxylate (1.8 g, 9.0 mmol) in DMF (32 mL) was added diisopropylethylamine (2.6 mL, 15.1 mmol). The reaction mixture was heated at 90° C. for 75 minutes. The mixture was cooled to room temp and diluted into aqueous saturated NH$_4$Cl solution and extracted with EtOAc. The organic phase was washed with brine (3 times), dried (MgSO$_4$), filtered and concentrated under vacuo. The resulting residue was purified via silica gel chromatography (0%-10% MeOH/CH$_2$Cl$_2$) to afford the desired product 1b as a white solid.
LCMS RT=4.6 (M+1) 601.5, (M−1) 599.6.

Formation of (S)-2-(5-chloro-1-tosyl-1H-pyrrolo[2,3-b]pyridin-3-yl)-5-fluoro-N-(piperidin-3-yl)pyrimidin-4-amine (1c)

To a solution of tert-butyl (3S)-3-[[2-[5-chloro-1-(p-tolyl-sulfonyl)pyrrolo[5,4-b]pyridin-3-yl]-5-fluoro-pyrimidin-4-yl]amino]piperidine-1-carboxylate, 1b, (2.1 g, 3.5 mmol) in CH$_2$Cl$_2$ (30 mL) was added trifluoroacetic acid (20 mL). After stirring the reaction mixture at room temperature for 75 min, the mixture was concentrated under vacuo. The crude residue was diluted with EtOAc and neutralized with 1N sodium hydroxide solution. The aqueous phase was separated and extracted again with EtOAc. The combined organic phases were dried (MgSO$_4$), filtered and concentrated under vacuo to afford the desired product (1c) as a light yellow solid.

$^1$H NMR (300 MHz, d6-DMSO) δ 8.76 (d, J=2.5, Hz, 1H), 8.50 (d, J=2.5 Hz, 1H), 8.44 (s, 1H), 8.27 (d, J=4.0 Hz, 1H), 8.06 (d, J=8.5 Hz, 2H), 7.66 (d, J=6.9 Hz, 1H), 7.45 (d, J=8.2 Hz, 2H), 4.17 (m, 1H), 3.17 (dd, J=3.1, 11.8 Hz, 1H), 2.99-2.94 (m, 1H), 2.67-2.60 (m, 1H), 2.38-2.34 (m, 1H), 2.06-2.02 (m, 1H), 1.77-1.73 (m, 1H) and 1.63-1.50 (m, 2H) ppm. LCMS RT=2.1 (M+1) 501.5, (M−1) 499.5.

Formation of 1-((S)-3-((2-(5-chloro-1-tosyl-1H-pyrrolo[2,3-b]pyridin-3-yl)-5-fluoropyrimidin-4-ylamino)piperidin-1-yl)-3-methoxypropan-2-ol (1d)

To a solution of 2-[5-chloro-1-(p-tolylsulfonyl)pyrrolo[5,4-b]pyridin-3-yl]-5-fluoro-N-[(3S)-3-piperidyl]pyrimidin-4-amine, 1c, (0.20 g, 0.40 mmol) in ethanol was added 2-(methoxymethyl)oxirane (0.04 mL, 0.40 mmol). The reaction mixture was heated in a microwave reactor at 140° C. for 5 minutes. The reaction was evaporated to dryness and the resulting residue was purified via silica gel chromatography (0-10% MeOH: CH$_2$Cl$_2$) to afford the desired product (1d).

$^1$H NMR (300 MHz, d6-DMSO) δ 8.78 (d, J=2.5 Hz, 1H), 8.49 (d, J=2.4 Hz, 1H), 8.43 (d, J=1.2 Hz, 1H), 8.26 (d, J=3.9 Hz, 1H), 8.07 (d, J=8.4 Hz, 2H), 7.60 (d, J=7.5 Hz, 1H), 7.45 (d, J=8.2 Hz, 2H), 4.54-4.50 (m, 1H), 4.20 (m, 1H), 3.35-3.17 (m, 1H), 3.33 (s, 3H), 3.25 (m, 1H), 3.19 (d, 2H), 3.00 (m, 1H), 2.75 (d, J=11.8 Hz, 1H), 2.44-2.26 (m, 4H), 1.93 (m, 1H), 1.73 (m, 2H), 1.63 (m, 1H) and 1.23 (m, 1H) ppm.
LCMS RT=2.4 (M+1) 589.6.

Formation of 1-((S)-3-((2-(5-chloro-1H-pyrrolo[2,3-b]pyridin-3-yl)-5-fluoropyrimidin-4-ylamino)piperidin-1-yl)-3-methoxypropan-2-ol (537)

To a solution of 1-[(3S)-3-[[2-[5-chloro-1-(p-tolylsulfonyl)pyrrolo[2,3-b]pyridin-3-yl]-5-fluoro-pyrimidin-4-yl]amino]-1-piperidyl]-3-methoxy-propan-2-ol, 1d, (0.15 g, 0.24 mmol) in THF was added 1N LiOH solution. The reaction mixture was heated in a microwave reactor at 120° C. for 5 minutes. The reaction mixture was diluted with water and the aqueous phase was extracted with EtOAc (twice). The combined organic phases were dried (MgSO$_4$), filtered and concentrated under vacuo. The resulting solid was purified by silica gel chromatography (5-20% MeOH: CH$_2$Cl$_2$) to afford the desired product (537) as a white solid.

$^1$H NMR (300 MHz, d6-DMSO DMSO) δ 12.35 (s, 1H), 8.73 (d, J=2.4 Hz, 1H), 8.29 (d, J=2.4 Hz, 1H), 8.19-8.09 (m, 2H), 7.36 (d, J=7.5 Hz, 1H), 4.53 (dd, J=4.5, 8.0 Hz, 1H), 4.27 (s, 1H), 3.77-3.72 (m, 1H), 3.36-3.20 (m, 3H), 3.22 (s, 3H), 3.03-2.97 (m, 1H), 2.76 (d, J=10.6 Hz, 1H), 2.44-2.14 (m, 2H), 2.08 (m, 2H), 1.99-1.94 (m, 1H), 1.71-1.63 (m, 2H), 1.44 (m, 1H) and 1.23-1.15 (m, 1H) ppm.

LCMS RT=1.6 (M+1) 435.5.

Other analogs that can be prepared in the same manner as 537 are described below:

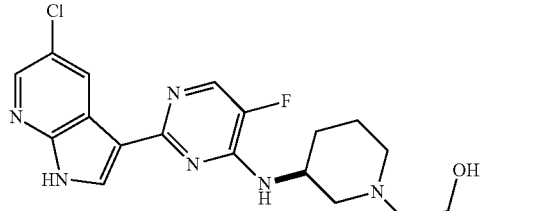

525

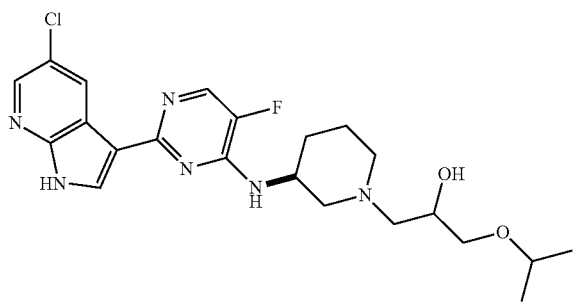

551

3-((S)-3-((2-(5-chloro-1H-pyrrolo[2,3-b]pyridin-3-yl)-5-fluoropyrimidin-4-ylamino)piperidin-1-yl)propane-1,2-diol (525)

$^1$H NMR (300 MHz, d6-DMSO) δ 12.31 (s, 1H), 8.72 (d, J=2.4 Hz, 1H), 8.28 (d, J=2.4 Hz, 1H), 8.20 (s, 1H), 8.17 (d, J=4.0 Hz, 1H), 7.33 (d, J=7.6 Hz, 1H), 4.51 (m, 1H), 4.37 (s, 1H), 4.25 (m, 1H), 3.64 (m, 1H), 3.35 (s, 2H), 3.08-2.95 (m, 1H), 2.80-2.70 (m, 1H), 2.47-2.25 (m, 2H), 2.22-2.12 (m, 2H), 1.99-1.90 (m, 1H), 1.70-1.60 (m, 2H) and 1.45 (m, 1H) ppm.
LCMS RT=1.5 (M+1) 421.5.

1-((S)-3-((2-(5-chloro-1H-pyrrolo[2,3-b]pyridin-3-yl)-5-fluoropyrimidin-4-ylamino)piperidin-1-yl)-3-isopropoxypropan-2-ol (551)

$^1$H NMR (300 MHz, d6-DMSO) δ 12.32 (s, 1H), 8.72 (d, J=2.4 Hz, 1H), 8.28 (d, J=2.4 Hz, 1H), 8.19-8.16 (m, 2H), 7.32 (d, J=8.0 Hz, 1H), 4.42-4.37 (m, 2H), 3.70 (s, 1H), 3.52-3.42 (m, 1H), 3.35-3.25 (m, 1H), 2.99 (m, 1H), 2.73 (m, 1H), 2.43-2.11 (m, 4H), 1.94 (m, 1H), 1.75-1.60 (m, 2H), 1.52-1.40 (M, 1H) and 1.10-0.99 (m, 6H).
LCMS RT=1.7 (M+1) 463.4, (M−1) 461.5.

538

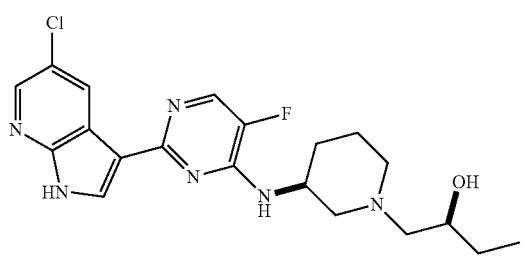

546

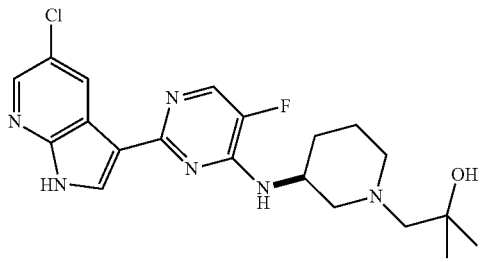

(S)-1-((S)-3-((2-(5-chloro-1H-pyrrolo[2,3-b]pyridin-3-yl)-5-fluoropyrimidin-4-ylamino)piperidin-1-yl)butan-2-ol (538)

$^1$H NMR (300 MHz, d6-DMSO) δ 12.53 (s, 1H), 10.32 (s, 1H), 8.69 (dd, J=2.5, 5.2 Hz, 1H), 8.56 (d, J=2.4 Hz, 1H), 8.31 (m, 2H), 7.97 (s, 1H), 4.76 (m, 1H), 3.92 (m, 2H), 3.84-3.55 (m, 2H), 3.40-2.80 (m, 3H), 2.14-1.90 (m, 3H), 1.80-1.74 (m, 2H), 1.65 (m, 1H), 1.43-1.23 (m, 2H) and 0.96-0.85 (m, 3H) ppm.
LCMS RT=1.6 (M+1) 419.6.

(S)-1-(3-((2-(5-chloro-1H-pyrrolo[2,3-b]pyridin-3-yl)-5-fluoropyrimidin-4-ylamino)piperidin-1-yl)-2-methylpropan-2-ol (546)

$^1$H NMR (300 MHz, CDCl$_3$) δ 9.60 (s, 1H), 8.87 (d, J=2.3 Hz, 1H), 8.33 (d, J=2.3 Hz, 1H), 8.17 (d, J=2.7 Hz, 1H), 8.09 (d, J=3.3 Hz, 1H), 5.34 (d, J=11.5 Hz, 1H), 4.45-4.42 (m, 1H), 3.09 (d, J=11.3 Hz, 1H), 2.75-2.59 (m, 4H), 2.40 (s, 2H), 1.94-1.70 (m, 4H) and 1.27 (s, 6H) ppm.
LCMS RT=1.6 (M+1) 419.5.

588

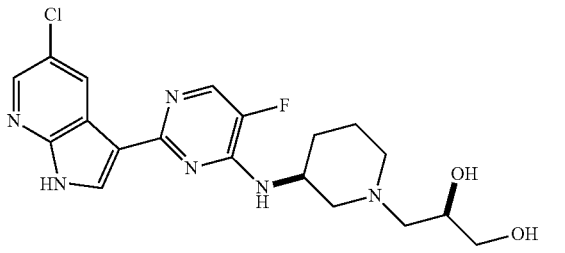

587

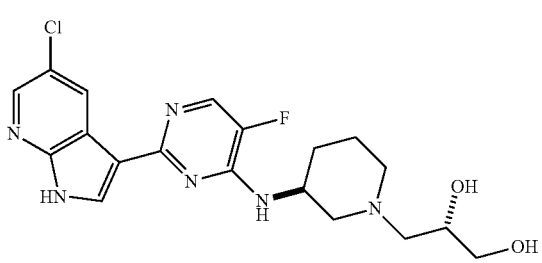

(R)-3-((S)-3-((2-(5-chloro-1H-pyrrolo[2,3-b]pyridin-3-yl)-5-fluoropyrimidin-4-ylamino)piperidin-1-yl)propane-1,2-diol (588)

$^1$H NMR (300 MHz, DMSO) δ 12.31 (s, 1H), 8.72 (d, J=2.4 Hz, 1H), 8.27 (d, J=2.4 Hz, 1H), 8.19 (s, 1H), 8.16 (d, J=4.0

Hz, 1H), 7.33 (d, J=7.8 Hz, 1H), 4.47-4.44 (m, 1H), 4.35 (d, J=4.0 Hz, 1H), 4.28-4.17 (m, 1H), 3.64-3.62 (m, 1H), 3.17 (d, J=5.2 Hz, 1H), 3.02-2.98 (m, 1H), 2.78-2.73 (m, 1H), 2.37 (ddd, J=12.8, 5.2, 5.2 Hz, 2H), 2.22-2.10 (m, 2H), 1.99-1.89 (m, 1H), 1.73-1.63 (m, 2H) and 1.46-1.43 (m, 1H) ppm.
LCMS RT=1.5 (M+1) 421.4.
LCMS RT=1.6 (M+1) 419.3.

(S)-3-((S)-3-((2-(5-chloro-1H-pyrrolo[2,3-b]pyridin-3-yl)-5-fluoropyrimidin-4-ylamino)piperidin-1-yl)propane-1,2-diol (587)

¹H NMR (300 MHz, DMSO) δ 12.31 (s, 1H), 8.72 (d, J=2.4 Hz, 1H), 8.28 (d, J=2.4 Hz, 1H), 8.20 (s, 1H), 8.16 (d, J=4.0 Hz, 1H), 7.33 (d, J=7.5 Hz, 1H), 4.34 (s, 1H), 4.27-4.23 (m, 1H), 3.62 (s, 1H), 3.35 (d, J=5.5 Hz, 1H), 3.06-3.03 (m, 1H), 2.78-2.74 (m, 1H), 2.44 (d, J=5.0 Hz, 1H), 2.27 (dd, J=12.9, 6.9 Hz, 1H), 2.20-2.07 (m, 2H), 2.05-1.90 (m, 1H), 1.75-1.59 (m, 2H) and 1.49-1.39 (m, 1H) ppm.

550

1-((3S,4S)-3-((2-(5-chloro-1H-pyrrolo[2,3-b]pyridin-3-yl)-5-fluoropyrimidin-4-ylamino)-4-methylpiperidin-1-yl)-3-methoxypropan-2-ol (550)

¹H NMR (300 MHz, d6-DMSO) δ 12.33 (s, 1H), 8.72 (d, J=2.5 Hz, 1H), 8.28 (d, J=2.4 Hz, 1H), 8.22-8.20 (m, 2H), 6.72-6.62 (m, 1H), 4.61 (dd, J=4.2, 10.0 Hz, 1H), 4.54 (m, 1H), 3.75-3.71 (m, 1H), 3.34-3.22 (m, 1H), 3.22 (d, 3H), 2.88-2.42 (m, 4H), 2.41-2.25 (m, 4H), 1.93 (m, 1H), 1.56 (m, 2H) and 0.90 (d, J=6.7 Hz, 3H). LCMS RT=1.6 (M+1) 449.5.

3-((S)-3-((2-(5-chloro-1H-pyrrolo[2,3-b]pyridin-3-yl)-5-fluoropyrimidin-4-ylamino)piperidin-1-yl)-2-hydroxypropanamide (603)

¹H NMR (300 MHz, DMSO) δ 12.31 (s, 1H), 8.71 (d, J=2.4 Hz, 1H), 8.28-8.25 (m, 1H), 8.19-8.16 (m, 2H), 7.34-7.30 (m, 1H), 7.19 (s, 1H), 7.11 (s, 1H), 4.24 (s, 1H), 3.99 (dd, J=3.5, 7.6 Hz, 1H), 3.01 (d, J=10.3 Hz, 1H), 2.81-2.63 (m, 2H), 2.36-2.29 (m, 2H), 1.71 (s, 3H) and 1.51-1.44 (m, 2H) ppm.

General Scheme 2:

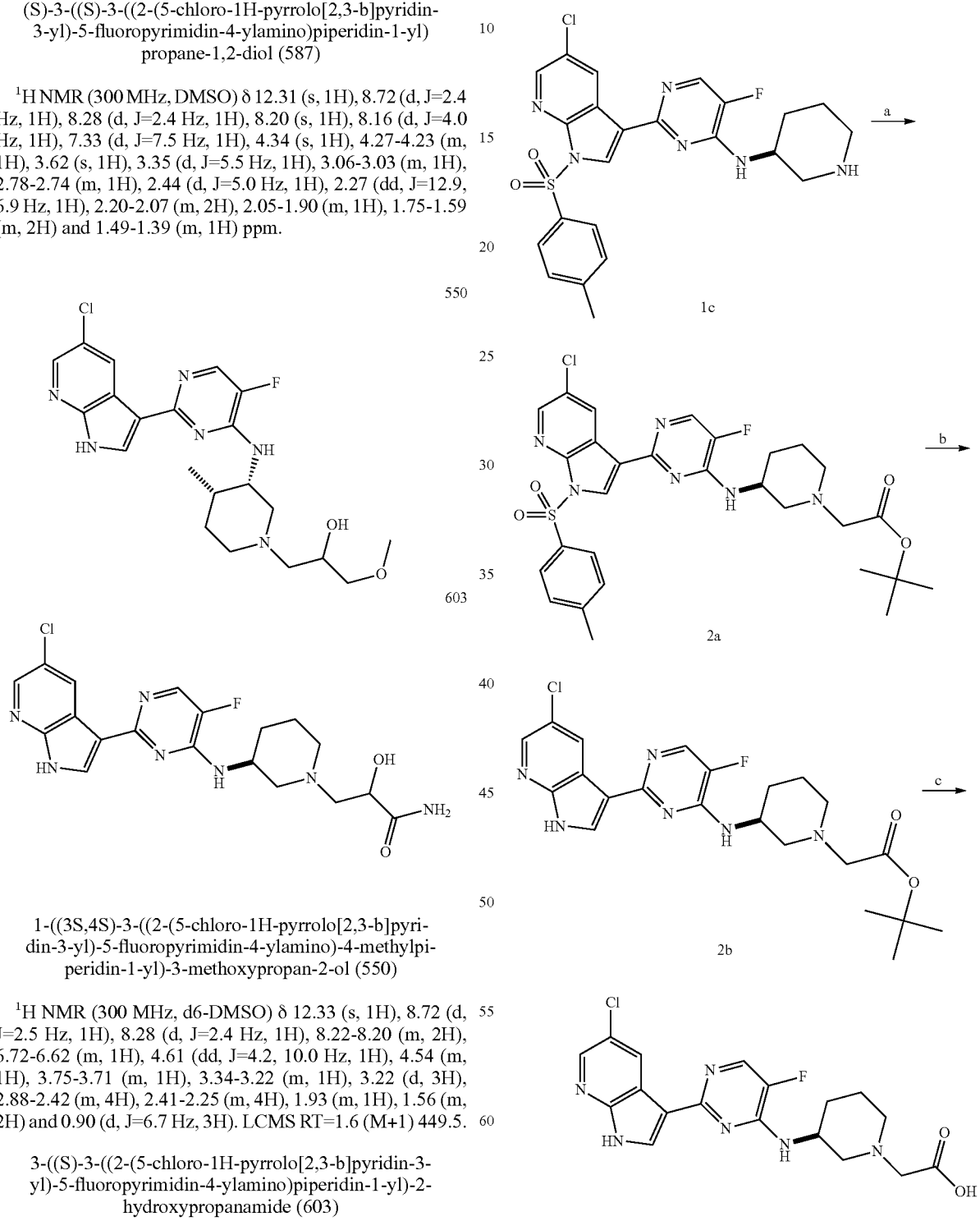

(a) tert-butylbromoacetate, Na₂CO₃, DMF; (b) 1N LiOH, THF, microwave, 120° C., 10 min;
(c) TFA, CH₂Cl₂

Formation of (S)-tert-butyl 3-((2-(5-chloro-1-tosyl-1H-pyrrolo[2,3-b]pyridin-3-yl)-5-fluoropyrimidin-4-ylamino)piperidine-1-carboxylate (2a)

To a solution of 2-[5-chloro-1-(p-tolylsulfonyl)pyrrolo[5,4-b]pyridin-3-yl]-5-fluoro-N-[(3S)-3-piperidyl]pyrimidin-4-amine, 1c, (0.25 g, 0.50 mmol) in DMF was added tert-butylbromoacetate (0.08 mL, 0.55 mmol) and Na₂CO₃ (0.11 g, 0.99 mmol). The reaction mixture was stirred at room temperature for 6 h. The resulting thick white precipitate was diluted with aqueous saturated NaCl solution and washed with water. The white solid was dissolved in CH₂Cl₂ and the solution was dried (MgSO₄), filtered and concentrated in vacuo. The crude was purified via silica gel chromatography (0%-5% MeOH/CH₂Cl₂) to afford the desired product, 2a, as a white solid.

¹H NMR (300 MHz, d6-DMSO) δ 8.76 (d, J=2.4 Hz, 1H), 8.48 (d, J=3.6 Hz, 1H), 8.44 (s, 1H), 8.26 (d, J=3.9 Hz, 2H), 8.07 (d, J=8.4 Hz, 2H), 7.59 (d, J=8.2 Hz, 1H), 7.44 (d, J=8.1 Hz, 2H), 4.18 (m, 1H), 3.19 (s, 2H), 3.03-2.99 (m, 1H), 2.78-2.73 (m, 1H), 2.45-2.30 (m, 2H), 2.37 (s, 3H), 1.99-1.93 (m, 1H), 1.80-1.60 (m, 2H), 1.46-1.40 (m, 1H) and 1.36 (s, 9H) ppm.

LCMS RT=2.8 (M+1) 615.6, (M−1) 613.6.

Formation of (S)-tert-butyl 2-(3-((2-(5-chloro-1H-pyrrolo[2,3-b]pyridin-3-yl)-5-fluoropyrimidin-4-ylamino)piperidin-1-yl)ethanoate (2b)

To a solution of tert-butyl 2-[(3S)-3-[[2-[5-chloro-1-(p-tolylsulfonyl)pyrrolo[2,3-b]pyridin-3-yl]-5-fluoro-pyrimidin-4-yl]amino]-1-piperidyl]acetate, 2a, (0.27 g, 0.44 mmol) in THF was added 1N LiOH solution. The reaction mixture was heated in microwave at 120 degrees for 10 minutes. The reaction mixture diluted with brine, extracted with EtOAc, then with 20% isopropanol/CH₂Cl₂. The combined organic phases were dried (MgSO₄), filtered and concentrated in vacuo. The resulting product, 2b, was used without further purification.

LCMS RT=2.0 (M+1) 461.5.

Formation of (S)-2-(3-((2-(5-chloro-1H-pyrrolo[2,3-b]pyridin-3-yl)-5-fluoropyrimidin-4-ylamino)piperidin-1-yl)ethanoic acid (577)

To a solution tert-butyl 2-[(3S)-3-[[2-(5-chloro-1H-pyrrolo[2,3-b]pyridin-3-yl)-5-fluoro-pyrimidin-4-yl]amino]-1-piperidyl]acetate, 2b, (0.12 g, 0.26 mmol) in CH₂Cl₂ (4 mL) was added trifluoroacetic acid (4 mL). The reaction mixture was stirred at room temperature for 18 h and concentrated in vacuo. The crude residue was diluted with 5% MeOH/CH₂Cl₂ and the resulting white precipitate was filtered and washed with CH₂Cl₂ to afford the desired product, 577, as trifluoroacetic acid salt.

¹H NMR (300 MHz, d6-DMSO) δ 12.46 (s, 1H), 8.70 (d, J=2.4 Hz, 1H), 8.36 (d, J=2.3 Hz, 1H), 8.31 (d, J=2.4 Hz, 1H), 8.29 (d, J=3.9 Hz, 1H), 7.79 (d, J=7.0 Hz, 1H), 4.70-4.50 (m, 1H), 4.21 (s, 2H), 3.80-3.70 (m, 1H), 3.55-3.47 (m, 1H), 3.20-2.90 (m, 2H), 2.10-1.95 (m, 3H) and 1.69-1.60 (m, 1H) ppm. LCMS RT=1.9 (M+1) 405.4.

Other analogs that can be prepared in the same manner as 577:

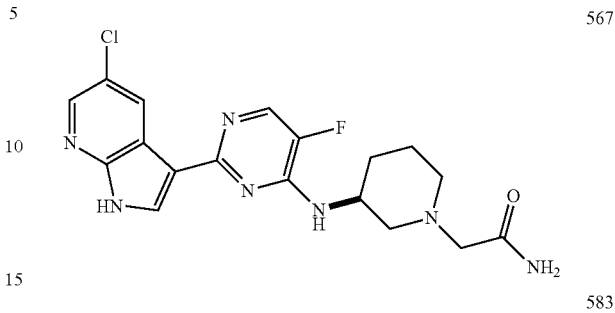

567

(S)-2-(3-((2-(5-chloro-1H-pyrrolo[2,3-b]pyridin-3-yl)-5-fluoropyrimidin-4-ylamino)piperidin-1-yl)ethanamide (567)

¹H NMR (300 MHz, d6-DMSO) δ 12.29 (s, 1H), 8.72 (d, J=2.4 Hz, 1H), 8.28 (d, J=2.4 Hz, 1H), 8.21 (s, 1H), 8.17 (d, J=4.0 Hz, 1H), 7.41 (d, J=7.7 Hz, 1H), 7.29 (s, 1H), 7.10 (s, 1H), 4.35-4.29 (m, 1H), 2.98-2.75 (m, 1H), 2.92 (d, J=6.8 Hz, 2H), 2.68 (d, J=10.8 Hz, 1H), 2.29-2.19 (m, 2H), 1.96-1.92 (m, 1H), 1.80-1.65 (m, 2H) and 1.53-1.42 (m, 1H) ppm.

LCMS RT=2.1 (M+1) 404.4, (M−1) 402.5.

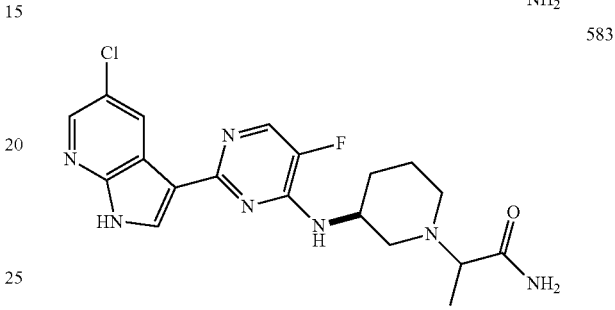

583

2-((S)-3-((2-(5-chloro-1H-pyrrolo[2,3-b]pyridin-3-yl)-5-fluoropyrimidin-4-ylamino)piperidin-1-yl)propanamide (583)

¹H NMR (300 MHz, d6-DMSO) δ 8.70 (d, J=2.3 Hz, 1H), 8.52 (d, J=8.7 Hz, 1H), 8.35 (dd, J=5.0, 6.5 Hz, 2H), 4.10 (dd, J=2.7, 7.0 Hz, 1H), 3.80-3.90 (m, 1H), 3.60-3.80 (m, 1H), 2.35-2.45 (m, 1H), 2.15-2.35 (m, 1H), 1.80-1.95 (m, 1H), and 1.60-1.65 (m, 3H) ppm.

LCMS (M+1) 418.4.

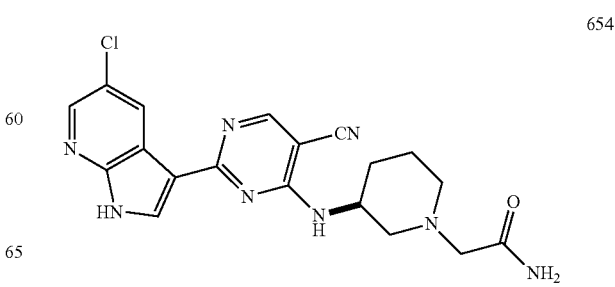

654

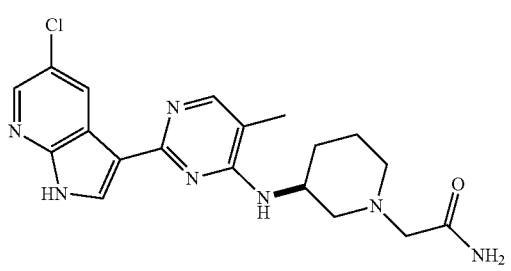

(S)-2-(3-((2-(5-chloro-1H-pyrrolo[2,3-b]pyridin-3-yl)-5-cyanopyrimidin-4-ylamino)piperidin-1-yl)ethanamide (654)

LCMS RT=2.9 (M+1) 411.4, (M−1) 409.4.

(S)-2-(3-((2-(5-chloro-1H-pyrrolo[2,3-b]pyridin-3-yl)-5-methylpyrimidin-4-ylamino)piperidin-1-yl)ethanamide (620)

LCMS RT=1.9 (M+1) 400.4, (M−1) 398.3.

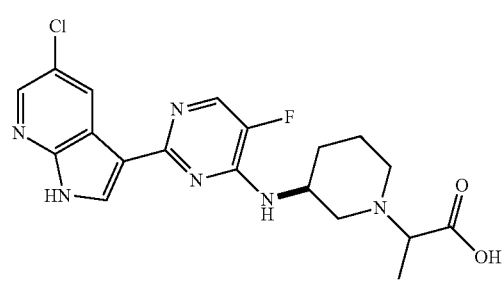

2-((S)-3-((2-(5-chloro-1H-pyrrolo[2,3-b]pyridin-3-yl)-5-fluoropyrimidin-4-ylamino)piperidin-1-yl)propanoic acid (573)

$^1$H NMR (300 MHz, d6-DMSO) δ 12.51 (s, 1H), 10.28-10.00 (m, 1H), 8.70 (s, 1H), 8.38 (s, 1H), 8.31 (d, J=2.4 Hz, 1H), 8.30 (d, J=4.2 Hz, 1H), 7.89-7.75 (m, 1H), 4.70-4.50 (m, 1H), 4.33-4.29 (m, 1H), 3.79-3.45 (m, 2H), 3.20-2.80 (m, 2H), 2.12-1.95 (m, 3H), 1.72-1.60 (m, 1H) and 1.52 (d, J=5.5 Hz, 3H) ppm.

2-((S)-3-((2-(5-chloro-1H-pyrrolo[2,3-b]pyridin-3-yl)-5-fluoropyrimidin-4-ylamino)piperidin-1-yl)-N-methylpropanamide (606)

$^1$H NMR (300 MHz, d6-DMSO) δ 8.69 (d, J=12.7 Hz, 1H), 8.54-8.49 (m, 1H), 8.32 (dd, J=4.8, 7.2 Hz, 2H), 4.83-4.76 (m, 1H), 4.02 (m, 1H), 3.95-3.71 (m, 2H), 3.31-3.10 (m, 1H), 2.86 (s, 3H), 2.33 (d, J=9.9 Hz, 1H), 2.40-2.14 (m, 3H), 1.94 (s, 1H), 1.66-1.58 (m, 3H) and 1.10 (d, J=6.5 Hz, 3H) ppm.

LCMS (M+1) 432.2.

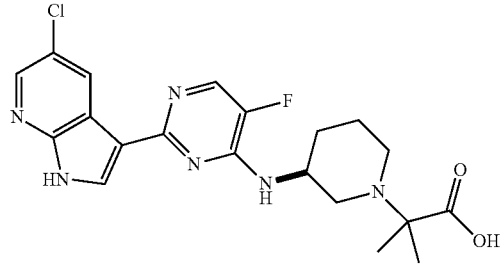

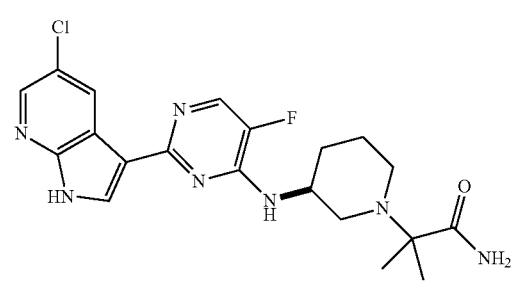

(S)-2-(3-((2-(5-chloro-1H-pyrrolo[2,3-b]pyridin-3-yl)-5-fluoropyrimidin-4-ylamino)piperidin-1-yl)-2-methylpropanoic acid (590)

$^1$H NMR (300 MHz, MeOD) δ 8.81 (d, J=2.3 Hz, 1H), 8.19 (t, J=2.5 Hz, 2H), 7.98 (d, J=4.2 Hz, 1H), 4.48 (s, 1H), 2.90 (d, J=10.1 Hz, 1H), 2.74-2.66 (m, 2H), 2.60 (d, J=5.7 Hz, 1H), 1.89-1.83 (m, 2H), 1.67 (s, 1H), 1.25 (d, J=4.9 Hz, 6H) ppm.
LCMS (M+1) 433.4.

(S)-2-(3-((2-(5-chloro-1H-pyrrolo[2,3-b]pyridin-3-yl)-5-fluoropyrimidin-4-ylamino)piperidin-1-yl)-2-methylpropanamide (598)

LCMS RT=1.8 (M+1) 432.4.

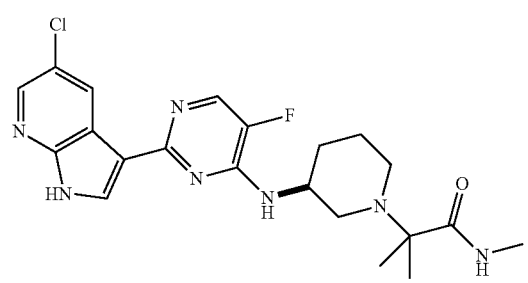

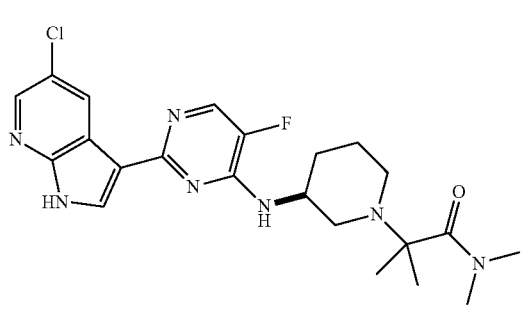

(S)-2-(3-((2-(5-chloro-1H-pyrrolo[2,3-b]pyridin-3-yl)-5-fluoropyrimidin-4-ylamino)piperidin-1-yl)-N,2-dimethylpropanamide (599)

¹H NMR (300 MHz, MeOD) δ 8.86 (d, J=2.4 Hz, 1H), 8.23 (d, J=2.3 Hz, 1H), 8.17 (s, 1H), 8.03 (d, J=4.1 Hz, 1H), 4.46 (dd, J=4.7, 8.8 Hz, 1H), 4.10 (q, J=7.2 Hz, 1H), 3.05 (d, J=12.8 Hz, 1H), 2.66 (s, 3H), 2.34 (dd, J=11.3, 20.6 Hz, 2H), 2.08 (d, J=12.3 Hz, 1H), 1.89-1.71 (m, 2H), 1.66-1.54 (m, 1H) and 1.19 (s, 6H) ppm.

LCMS (M+1) 433.4.

(S)-2-(3-((2-(5-chloro-1H-pyrrolo[2,3-b]pyridin-3-yl)-5-fluoropyrimidin-4-ylamino)piperidin-1-yl)-N,N,2-trimethylpropanamide (600)

¹H NMR (300 MHz, MeOD) δ 8.81 (d, J=2.4 Hz, 1H), 8.22 (d, J=2.4 Hz, 1H), 8.14 (s, 1H), 8.02 (d, J=4.0 Hz, 1H), 4.45-4.37 (m, 1H), 3.61 (s, 3H), 2.97 (d, J=8.8 Hz, 1H), 2.80 (s, 3H), 2.72 (s, 1H), 2.39 (t, J=10.0 Hz, 2H), 2.15 (dd, J=3.6, 12.7 Hz, 1H), 1.91-1.79 (m, 2H), 1.53-1.47 (m, 1H) and 1.28 (s, 6H) ppm.

LCMS (M+1) 460.5.

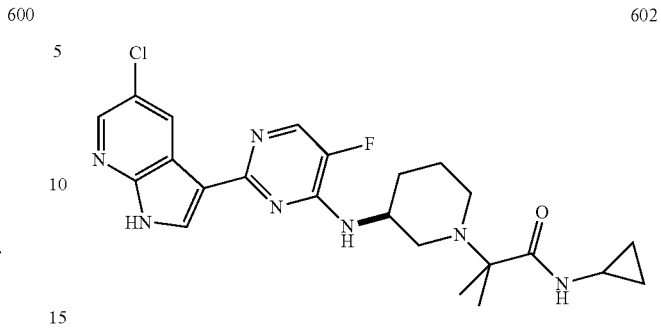

(S)-2-(3-((2-(5-chloro-1H-pyrrolo[2,3-b]pyridin-3-yl)-5-fluoropyrimidin-4-ylamino)piperidin-1-yl)-N-(2-methoxyethyl)-2-methylpropanamide (601)

¹H NMR (300 MHz, MeOD) δ 8.88 (d, J=2.3 Hz, 1H), 8.23 (d, J=2.3 Hz, 1H), 8.17 (s, 1H), 8.02 (d, J=4.1 Hz, 1H), 4.47-4.41 (m, 1H), 3.38 (dd, J=1.6, 4.8 Hz, 4H), 3.12-3.07 (m, 1H), 2.73 (d, J=10.8 Hz, 1H), 2.35-2.29 (m, 2H), 2.19-2.15 (m, 1H), 1.91-1.80 (m, 2H), 1.55 (s, 1H), 1.37 (s, 1H) and 1.20 (s, 6H) ppm.

(S)-2-(3-((2-(5-chloro-1H-pyrrolo[2,3-b]pyridin-3-yl)-5-fluoropyrimidin-4-ylamino)piperidin-1-yl)-N-cyclopropyl-2-methylpropanamide (602)

¹H NMR (300 MHz, MeOD) δ 8.82 (d, J=2.3 Hz, 1H), 8.23 (d, J=2.3 Hz, 1H), 8.15 (s, 1H), 8.01 (d, J=4.0 Hz, 1H), 4.41 (m, 1H), 3.02 (d, J=10.0 Hz, 1H), 2.59-2.47 (m, 1H), 2.40-2.30 (m, 2H), 2.09-2.01 (m, 1H), 1.89-1.85 (m, 1H), 1.78-1.66 (m, 1H), 1.61-1.55 (m, 1H), 1.26-1.16 (m, 1H), 1.10 (d, J=6.6 Hz, 6H), 0.68-0.63 (m, 2H) and 0.44-0.40 (m, 2H) ppm.

LCMS (M+1) 472.4.

General Scheme 3:

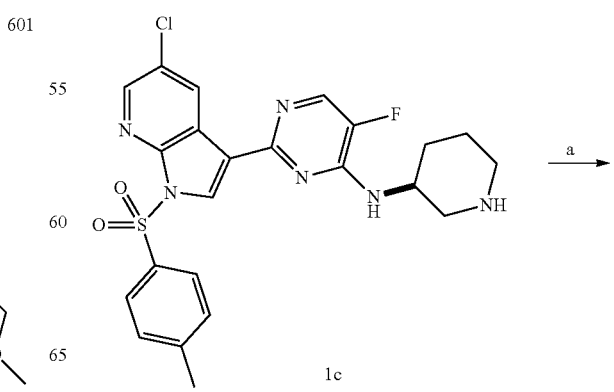

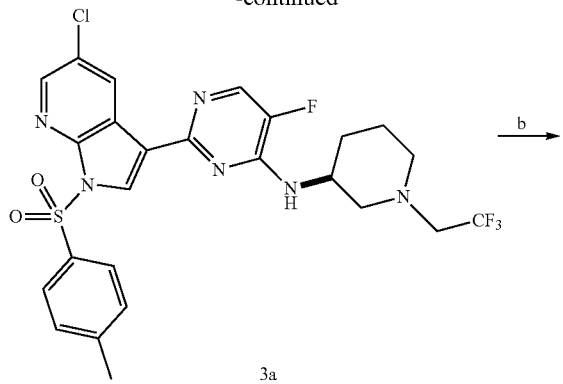

3a

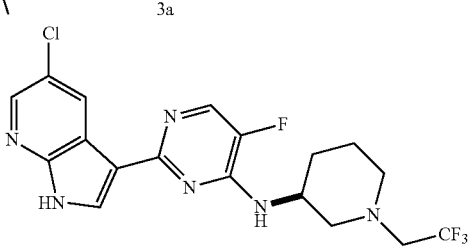

668

(a) CF$_3$CH$_2$SO$_2$CCl$_3$, $^i$Pr$_2$NEt, DMF; (b) 1N LiOH, THF, microwave, 120° C., 10 min.

Formation of (S)-2-(5-chloro-1-tosyl-1H-pyrrolo[2,3-b]pyridin-3-yl)-5-fluoro-N-(1-(2,2,2-trifluoroethyl) piperidin-3-yl)pyrimidin-4-amine (3a)

To a solution of 2-[5-chloro-1-(p-tolylsulfonyl)pyrrolo[5,4-b]pyridin-3-yl]-5-fluoro-N-[(3S)-3-piperidyl]pyrimidin-4-amine, 1c, (0.17 g, 0.34 mmol) in DMF (1.5 mL) was added 2,2,2-trifluoroethyl trichloromethanesulfonate (0.19 g, 0.68 mmol), followed by $^i$Pr$_2$NEt (0.24 mL, 1.36 mmol). The reaction mixture was stirred at room temperature for 18 h. The mixture was poured into brine and extracted twice with EtOAc. The combined organic phases were washed twice with brine, dried (MgSO$_4$), filtered, and concentrated in vacuo. The crude residue was purified by silica gel chromatography (0-10% MeOH/CH$_2$Cl$_2$) afforded the desired product, 3a, as a white solid.

$^1$H NMR (300 MHz, d6-DMSO) δ 8.77 (d, J=2.4 Hz, 1H), 8.48 (d, J=2.4 Hz, 1H), 8.42 (s, 1H), 8.27 (d, J=3.9 Hz, 1H), 8.05 (d, J=8.4 Hz, 2H), 7.62 (d, J=7.5 Hz, 1H), 7.44 (d, J=8.2 Hz, 2H), 4.17 (m, 1H), 3.30-3.18 (m, 3H), 2.90 (m, 1H), 2.44-2.32 (m, 2H), 2.35 (s, 3H), 1.95 (m, 1H), 1.72-1.57 (m, 2H) and 1.51-1.40 (m, 1H) ppm.

LCMS RT=4.6 (M+1) 583.4, (M−1) 581.4.

Formation of (S)-2-(5-chloro-1H-pyrrolo[2,3-b]pyridin-3-yl)-5-fluoro-N-(1-(2,2,2-trifluoroethyl)piperidin-3-yl)pyrimidin-4-amine (668)

To a solution of 2-[5-chloro-1-(p-tolylsulfonyl)pyrrolo[2,3-b]pyridin-3-yl]-5-fluoro-N-[(3S)-1-(2,2,2-trifluoroethyl)-3-piperidyl]pyrimidin-4-amine, 3a, (0.10 g, 0.18 mmol) in THF was added 1M LiOH (0.90 mL, 0.90 mmol) solution. The reaction mixture was heated in microwave at 120° C. for 10 minutes. The reaction mixture was diluted with brine, extracted with EtOAc, then with 20% isopropanol/CH$_2$Cl$_2$. The combined organic phases were dried (MgSO$_4$), filtered and concentrated in vacuo. The resulting residue was purified via silica gel chromatography (0-10% MeOH:CH$_2$Cl$_2$) to afford the desired product, 1339, as a white solid.

$^1$H NMR (300 MHz, d6-DMSO) δ 12.32 (s, 1H), 8.71 (d, J=2.4 Hz, 1H), 8.28 (d, J=2.4 Hz, 1H), 8.18-8.16 (m, 2H), 7.38 (d, J=7.7 Hz, 1H), 4.22-4.17 (m, 1H), 3.31-3.16 (m, 3H), 2.90 (m, 1H), 2.40 (t, J=10.2 Hz, 2H), 2.00-1.95 (m, 1H), 1.77-1.60 (m, 2H) and 1.50-1.38 (m, 1H) ppm.

LCMS RT=3.5 (M+1) 429.4, (M−1) 427.4.

Other analogs that can be prepared in the same manner as 668:

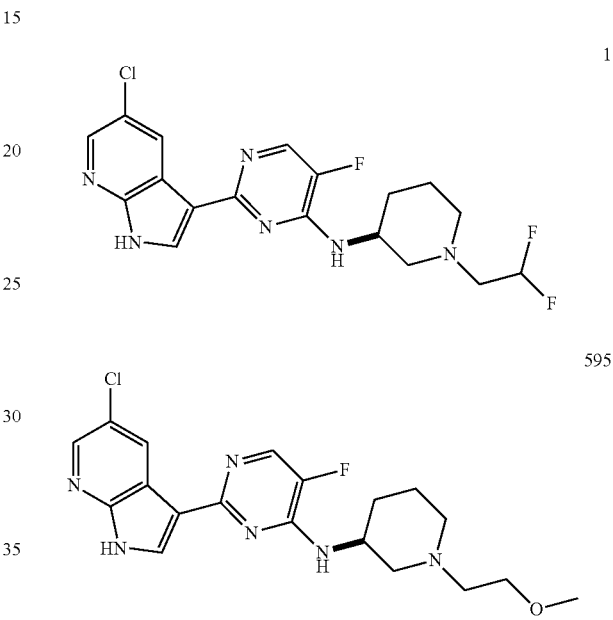

Synthesis of (S)-2-(5-chloro-1H-pyrrolo[2,3-b]pyridin-3-yl)-N-(1-(2,2-difluoroethyl)piperidin-3-yl)-5-fluoropyrimidin-4-amine (1)

$^1$H NMR (300 MHz, d6-DMSO) δ 12.31 (s, 1H), 8.72 (d, J=2.4 Hz, 1H), 8.28 (d, J=2.4 Hz, 1H), 8.20 (s, 1H), 8.17 (d, J=4.0 Hz, 1H), 7.33 (d, J=7.6 Hz, 1H), 4.51 (m, 1H), 4.37 (s, 1H), 4.25 (m, 1H), 3.64 (m, 1H), 3.35 (s, 2H), 3.08-2.95 (m, 1H), 2.80-2.70 (m, 1H), 2.47-2.25 (m, 2H), 2.22-2.12 (m, 2H), 1.99-1.90 (m, 1H), 1.70-1.60 (m, 2H) and 1.45 (m, 1H) ppm.

LCMS RT=2.7 (M+1) 411.4, (M−1) 409.4.

(S)-2-(5-chloro-1H-pyrrolo[2,3-b]pyridin-3-yl)-N-(1-(2,2-difluoroethyl)piperidin-3-yl)-5-fluoropyrimidin-4-amine (595)

$^1$H NMR (300 MHz, d6-DMSO) δ 12.32 (s, 1H), 8.71 (d, J=2.4 Hz, 1H), 8.28 (d, J=2.4 Hz, 1H), 8.18-8.15 (m, 2H), 7.32 (d, J=7.1 Hz, 1H), 4.20 (d, J=7.1 Hz, 1H), 3.46 (t, J=5.8 Hz, 2H), 3.19 (s, 3H), 3.10-3.06 (m, 1H), 2.82-2.78 (m, 1H), 2.57-2.50 (m, 2H), 2.11-1.95 (m, 3H), 1.71-1.63 (m, 2H) and 1.48-1.35 (m, 1H) ppm.

LCMS RT=1.7 (M+1) 405.4, (M−1) 403.4.

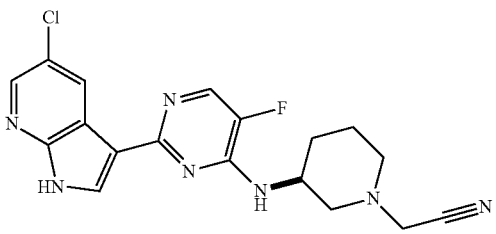

(S)-2-(3-((2-(5-chloro-1H-pyrrolo[2,3-b]pyridin-3-yl)-5-fluoropyrimidin-4-ylamino)piperidin-1-yl)ethanenitrile (669)

$^1$H NMR (300 MHz, d6-DMSO) δ 12.31 (s, 1H), 8.69 (d, J=2.4 Hz, 1H), 8.28 (d, J=2.4 Hz, 1H), 8.19-8.17 (m, 2H), 7.47 (d, J=7.7 Hz, 1H), 4.30-4.20 (m, 1H), 3.80 (s, 2H), 3.07-3.03 (m, 1H), 2.82-2.73 (m, 1H), 2.29-2.10 (m, 2H), 2.05-1.96 (m, 1H), 1.87-1.65 (m, 2H) and 1.49-1.40 (m, 1H) ppm.; LCMS RT=2.3 (M+1) 386.1, (M−1) 384.2.

General Scheme 4:

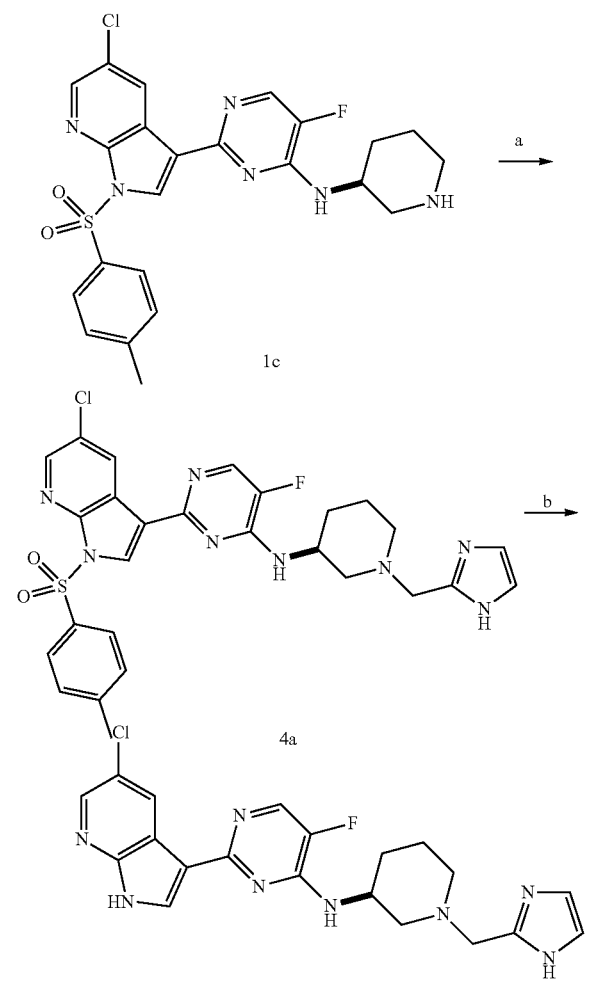

(a) 1H-imidazole-2-carbaldehyde, Na(OAc)$_3$BH, HOAc, 1,2-dichloroethane, 60° C.; (b) 1N LiOH, THF, microwave, 120° C., 10 min.

Formation of (S)—N-(1-((1H-imidazol-2-yl)methyl)piperidin-3-yl)-2-(5-chloro-1-tosyl-1H-pyrrolo[2,3-b]pyridin-3-yl)-5-fluoropyrimidin-4-amine (4a)

To a solution of 2-[5-chloro-1-(p-tolylsulfonyl)pyrrolo[5,4-b]pyridin-3-yl]-5-fluoro-N-[(3S)-3-piperidyl]pyrimidin-4-amine, 1c, (0.16 g, 0.32 mmol) in 1,2-dichloroethane (2 mL) was added 1H-imidazole-2-carbaldehyde (0.03 g, 0.36 mmol) followed by 2 drops of acetic acid and Na(OAc)$_3$BH (0.10 g, 0.49 mmol). The reaction mixture was heated at 60° C. for 18 h. The mixture was cooled to room temperature and diluted with aqueous saturated NaHCO$_3$ solution. The aqueous phase was extracted twice with EtOAc. The combined organic phases were dried (MgSO$_4$), filtered and concentrated in vacuo. The crude residue was purified via silica gel chromatography (0-20% MeOH/CH$_2$Cl$_2$) to afford the product, 4a.

$^1$H NMR (300 MHz, d6-DMSO) δ 11.83 (s, 1H), 8.75 (d, J=2.4 Hz, 1H), 8.48 (d, J=2.4 Hz, 1H), 8.41 (s, 1H), 8.25 (d, J=3.8 Hz, 1H), 8.07 (d, J=8.3 Hz, 2H), 7.56 (d, J=8.2 Hz, 1H), 7.44 (d, J=8.2 Hz, 2H), 7.00-6.80 (m, 2H), 4.22 (m, 1H), 3.58 (dd, J=18.9, 13.8 Hz, 2H), 2.95 (m, 1H), 2.75-2.72 (m, 1H), 2.36 (s, 3H), 2.16-2.04 (m, 2H), 1.99-1.93 (m, 1H), 1.78-1.55 (m, 2H) and 1.45-1.30 (m, 1H) ppm.

Formation of (S)—N-(1-((1H-imidazol-2-yl)methyl)piperidin-3-yl)-2-(5-chloro-1H-pyrrolo[2,3-b]pyridin-3-yl)-5-fluoropyrimidin-4-amine (589)

To a solution of 2-[5-chloro-1-(p-tolylsulfonyl)pyrrolo[2,3-b]pyridin-3-yl]-5-fluoro-N-[(3S)-1-(1H-imidazol-2-ylmethyl)-3-piperidyl]pyrimidin-4-amine, 4a, (0.08 g, 0.13 mmol) in THF (2.5 mL) was added 1M LiOH (0.67 mL, 0.65 mmol) solution. The reaction mixture was heated in microwave at 120° C. for 10 minutes. The mixture was cooled to room temperature and diluted with brine. The aqueous phase was extracted with CH$_2$Cl$_2$, then twice with 20% isopropanol/CH$_2$Cl$_2$. The combined organic phases were dried (MgSO$_4$), filtered and concentrated in vacuo to afford the desired product, 589, as a white solid.

$^1$H NMR (300 MHz, d6-DMSO) δ 8.77 (d, J=2.4 Hz, 1H), 8.48 (d, J=2.4 Hz, 1H), 8.42 (s, 1H), 8.27 (d, J=3.9 Hz, 1H), 8.05 (d, J=8.4 Hz, 2H), 7.62 (d, J=7.5 Hz, 1H), 7.44 (d, J=8.2 Hz, 2H), 4.17 (m, 1H), 3.30-3.18 (m, 3H), 2.90 (m, 1H), 2.44-2.32 (m, 2H), 2.35 (s, 3H), 1.95 (m, 1H), 1.72-1.57 (m, 2H) and 1.51-1.40 (m, 1H) ppm.

LCMS RT=1.6 (M+1) 427.4.

Other analogs which can be prepared in the same manner as 589:

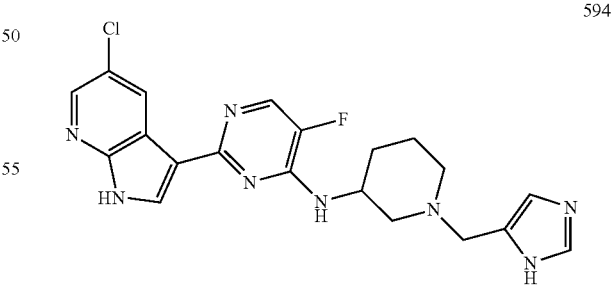

N-(1-((1H-imidazol-5-yl)methyl)piperidin-3-yl)-2-(5-chloro-1H-pyrrolo[2,3-b]pyridin-3-yl)-5-fluoropyrimidin-4-amine (594)

$^1$H NMR (300 MHz, d6-DMSO) δ 12.31 (s, 1H), 11.86-11.77 (m, 1H), 8.70 (d, J=2.2 Hz, 1H), 8.28 (d, J=2.4 Hz, 1H), 8.15 (d, J=3.9 Hz, 1H), 8.10 (d, J=2.5 Hz, 1H), 7.54 (s, 1H), 7.31 (d, J=7.6 Hz, 1H), 6.87 (s, 1H), 4.19 (m, 1H), 3.57 (d, J=13.8 Hz, 1H), 3.48 (d, J=13.8 Hz, 1H), 3.04 (d, J=8.3 Hz, 1H), 2.80 (d, J=10.4 Hz, 1H), 2.10-1.90 (m, 3H), 1.72-1.62 (m, 2H) and 1.51-1.35 (m, 1H) ppm; LCMS RT=1.6 (M+1) 427.4, (M−1) 425.4.

General Scheme 5A:

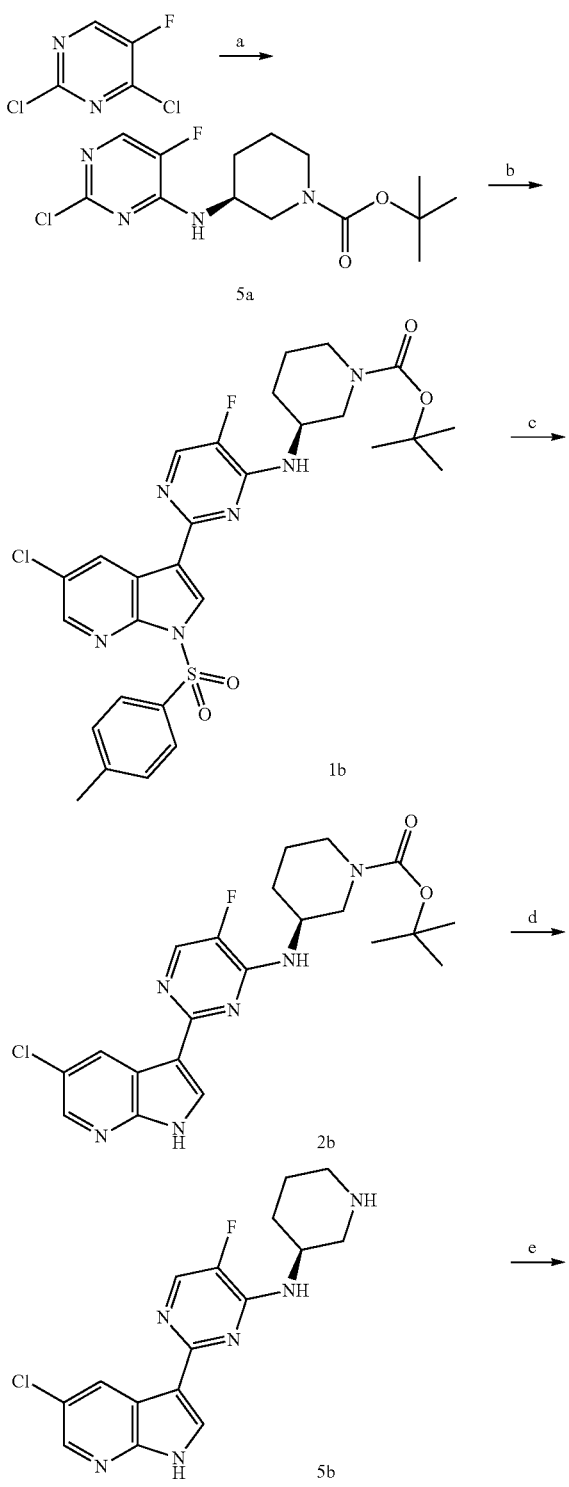

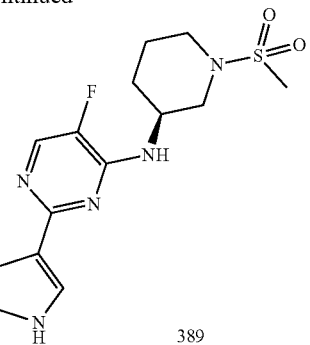

(a) tert-butyl (3S)-3-aminopiperidine-1-carboxylate, $^i$Pr$_2$NEt base, 2-propanol, 80° C.; (b) 5-chloro-1-(p-tolylsulfonyl)-3-(4,4,5,5-tetramethyl-1,3,2-dioxaborolan-2-yl)pyrrolo[2,3-b]pyridine, DME/H$_2$O, K$_2$CO$_3$, tetrakis triphenylphosphine-palladium(0), 90° C.; (c) NaOMe/MeOH; (d) isopropanol/HCl; (e) methanesulfonyl chloride, $^i$Pr$_2$NEt, CH$_2$Cl$_2$/DMF.

Formation of tert-butyl (3S)-3-[(2-chloro-5-fluoro-pyrimidin-4-yl)amino]piperidine-1-carboxylate (5a)

To a solution of tert-butyl (3S)-3-aminopiperidine-1-carboxylate (8.1 g, 40.4 mmol) and 2,4-dichloro-5-fluoro-pyrimidine (6.6 g, 39.8 mmol) in isopropanol (80 mL) was added N,N-diisopropyl-N-ethylamine (9.0 mL, 51.7 mmol). The reaction mixture was warmed to 80° C. and stirred for 17 hours. All volatiles were removed at reduced pressure and the residue was dissolved in EtOAc. The organic layer was partitioned with water and the layers were separated. The organic phase was washed with brine, dried (MgSO$_4$), filtered and concentrated in vacuo. The resulting residue was dissolved in CH$_2$Cl$_2$ and purified by silica gel chromatography (0-50% EtOAc/Hexanes) to afford the desired product, 5a.
LCMS RT=3.3 (M+1) 331.1.

Formation of tert-butyl (3S)-3-[[2-[5-chloro-1-(p-tolylsulfonyl)pyrrolo[5,4-b]pyridin-3-yl]-5-fluoro-pyrimidin-4-yl]amino]piperidine-1-carboxylate (1b)

To a solution of 5-chloro-1-(p-tolylsulfonyl)-3-(4,4,5,5-tetramethyl-1,3,2-dioxaborolan-2-yl)pyrrolo[2,3-b]pyridine (1.8 g, 4.2 mmol) and tert-butyl (3S)-3-[(2-chloro-5-fluoro-pyrimidin-4-yl)amino]piperidine-1-carboxylate, 5a, (1.2 g, 3.7 mmol) in DME (15 mL) and H$_2$O (5 mL) was added K$_2$CO$_3$ (1.7 g, 12.1 mmol). The mixture was purged with nitrogen for 15 min. To the mixture was added tetrakis triphenylphosphine palladium(0) (0.2 g, 0.2 mmol) and the reaction mixture was heated at 90° C. for 3 days. The reaction was cooled down to room temperature and then diluted with EtOAc/H$_2$O. The layers were separated and the organic phase was washed with brine, dried (MgSO$_4$), filtered and evaporated to dryness. The resulting residue was dissolved in CH$_2$Cl$_2$ and purified by silica gel chromatography (0-100% EtOAc/Hexanes) to afford the desired product, 1b.
LCMS RT=4.6 (M+1) 601.2.

Formation of tert-butyl (3S)-3-[[2-(5-chloro-1H-pyrrolo[5,4-b]pyridin-3-yl)-5-fluoro-pyrimidin-4-yl]amino]piperidine-1-carboxylate (2b)

To a solution of tert-butyl (3S)-3-[[2-[5-chloro-1-(p-tolyl-sulfonyl)pyrrolo[5,4-b]pyridin-3-yl]-5-fluoro-pyrimidin-4- yl]amino]piperidine-1-carboxylate, 1b, (0.93 g, 1.55 mmol) in methanol (10 mL) was added sodium methoxide (10 mL of 1M solution). The reaction mixture was warmed to 45° C. After stirring for 30 minutes the reaction was to cooled to room temperature and quenched by addition into water. The mixture was diluted with EtOAc and the layers were separated. The organic phase was washed with brine, dried (MgSO₄), filtered and concentrated in vacuo. The resulting residue was purified by silica gel chromatography (0-100% EtOAc/Hexanes) to afford the desired product, 2b.

LCMS RT=2.8 (M+1) 447.2.

Formation of (S)-2-(5-chloro-1H-pyrrolo[2,3-b]pyridin-3-yl)-5-fluoro-N-(piperidin-3-yl)pyrimidin-4-amine (5b)

To a suspension of tert-butyl (3S)-3-[[2-(5-chloro-1H-pyrrolo[5,4-b]pyridin-3-yl)-5-fluoro-pyrimidin-4-yl]amino]piperidine-1-carboxylate, 2b, (0.45 g, 1.01 mmol) in isopropanol (3 mL) was added propan-2-ol hydrochloride (1.5 mL of 5M solution, 7.500 mmol). The reaction mixture was warmed to 80° C. and stirred for 3 hours. The mixture was cooled to room temperature and all volatiles were removed at reduced pressure. The resulting crude product, 5b, was used without further purification.

LCMS RT=1.5 (M+1) 347.1.

Formation of (S)-2-(5-chloro-1H-pyrrolo[2,3-b]pyridin-3-yl)-5-fluoro-N-(1-(methylsulfonyl)piperidin-3-yl)pyrimidin-4-amine (389)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.04 g, 0.11 mmol) in CH₂Cl₂ (1.4 mL) and DMF (0.30 mL) was added N,N-diisopropyl-N-ethylamine (0.30 mL, 1.70 mmol) followed by methanesulfonyl chloride (0.02 g. 0.20 mmol). The reaction mixture was allowed to stir at room temperature for 17 hours. The mixture was concentrated in vacuo, dissolved in 1 mL of DMSO and purified by preparatory HPLC (0.1% ammonium formate-H₂O/acetonitrile) to afford the desired product, 389.

LCMS RT=1.8 (M+1) 425.3.

Other analogs that can be prepared in the same manner as 389:

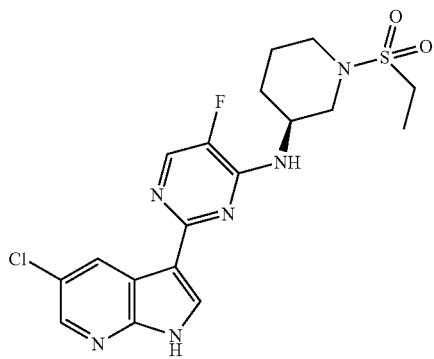

393

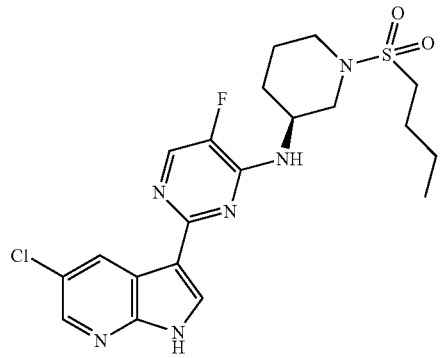

390

(S)-2-(5-chloro-1H-pyrrolo[2,3-b]pyridin-3-yl)-N-(1-(ethylsulfonyl)piperidin-3-yl)-5-fluoropyrimidin-4-amine (393)

LCMS RT=1.8 (M+1) 439.3.

(S)—N-(1-(butylsulfonyl)piperidin-3-yl)-2-(5-chloro-1H-pyrrolo[2,3-b]pyridin-3-yl)-5-fluoropyrimidin-4-amine (390)

LCMS RT=2.1 (M+1) 467.3.

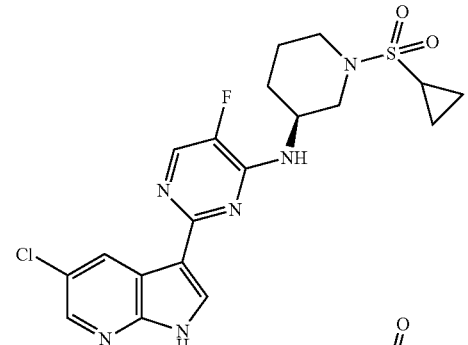

391

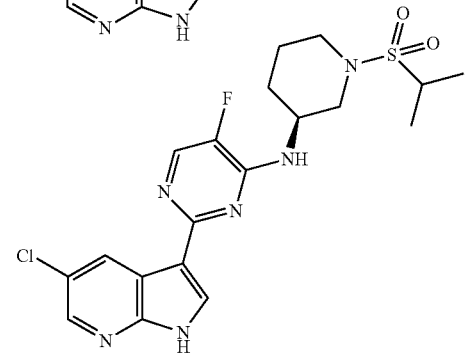

394

(S)-2-(5-chloro-1H-pyrrolo[2,3-b]pyridin-3-yl)-N-(1-(cyclopropylsulfonyl)piperidin-3-yl)-5-fluoropyrimidin-4-amine (391)

LCMS RT=1.9 (M+1) 451.3.

(S)-2-(5-chloro-1H-pyrrolo[2,3-b]pyridin-3-yl)-5-fluoro-N-(1-(isopropylsulfonyl)-piperidin-3-yl)pyrimidin-4-amine (394)

LCMS RT=1.9 (M+1) 453.3.

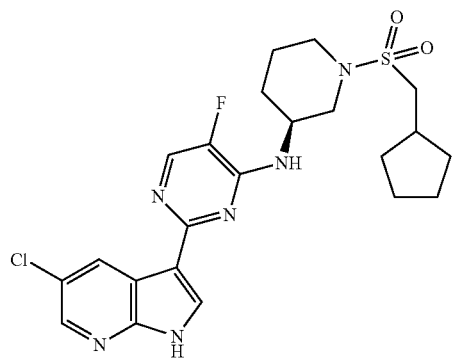

(S)-2-(5-chloro-1H-pyrrolo[2,3-b]pyridin-3-yl)-N-(1-(cyclopentylmethylsulfonyl)piperidin-3-yl)-5-fluoropyrimidin-4-amine (392)

LCMS RT=2.3 (M+1) 493.5.

General Scheme 5B:

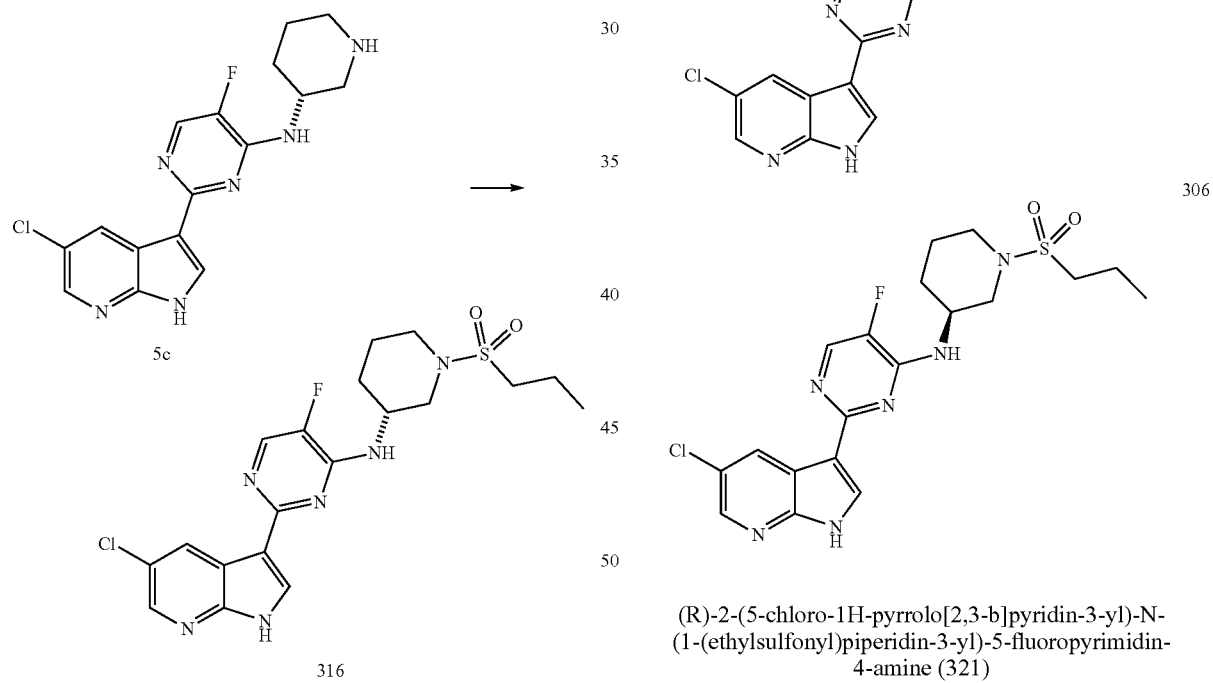

316

Formation of (R)-2-(5-chloro-1H-pyrrolo[2,3-b]pyridin-3-yl)-5-fluoro-N-(1-(propylsulfonyl)piperidin-3-yl)pyrimidin-4-amine (316)

To a solution of 2-(5-chloro-1H-pyrrolo[2,3-b]pyridin-3-yl)-5-fluoro-N-(piperidin-3-yl)pyrimidin-4-amine, 5c, (0.40 g, 1.15 mmol) in 10:1 mixture of CH₂Cl₂/DMF (8 mL) was added $^{i}Pr_2NEt$ (0.60 mL, 3.46 mmol) followed by 1-propanesulfonyl chloride (0.13 mL, 1.15 mmol). The reaction mixture was stirred at room temperature for 5 hours. The resulting residue was purified by preparatory HPLC (0.1% TFA-H₂O/acetonitrile) to afford the desired product, 316.

LCMS RT=2.5 (M+1) 453.3.

Other analogs that can be prepared in the same manner as 316:

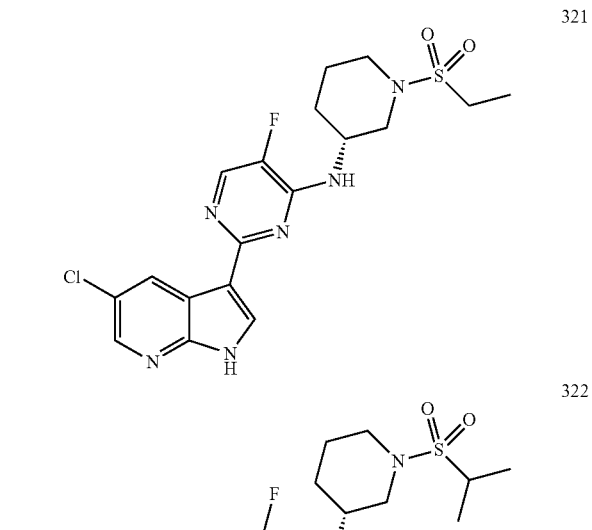

(R)-2-(5-chloro-1H-pyrrolo[2,3-b]pyridin-3-yl)-N-(1-(ethylsulfonyl)piperidin-3-yl)-5-fluoropyrimidin-4-amine (321)

LCMS RT=2.7 (M+1) 439.1.

(R)-2-(5-chloro-1H-pyrrolo[2,3-b]pyridin-3-yl)-5-fluoro-N-(1-(isopropylsulfonyl)-piperidin-3-yl)pyrimidin-4-amine (322)

LCMS RT=2.9 (M+1) 453.1.

(S)-2-(5-chloro-1H-pyrrolo[2,3-b]pyridin-3-yl)-5-fluoro-N-(1-(propylsulfonyl)-piperidin-3-yl)pyrimidin-4-amine (306)

LCMS RT=2.9 (M+1) 453.2.

General Scheme 5C:

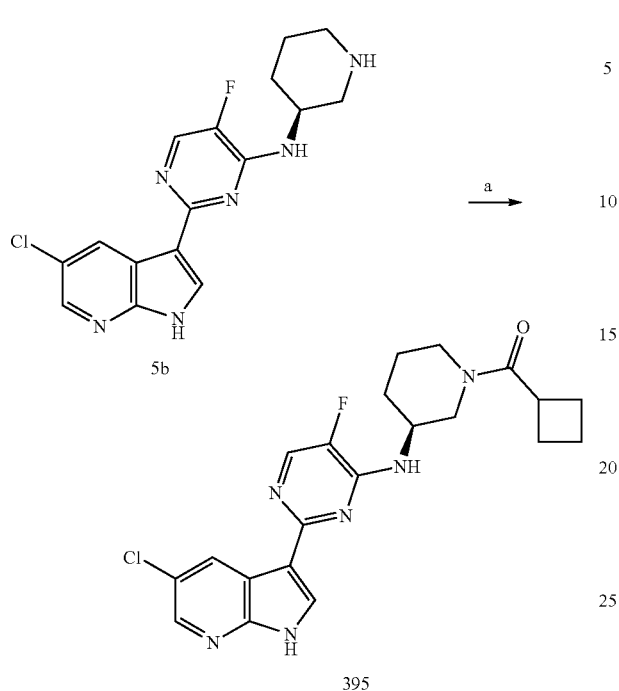

(a) cyclobutanecarbonyl chloride, $^i$Pr$_2$NEt, CH$_2$Cl$_2$/DMF.

Formation of (S)-(3-((2-(5-chloro-1H-pyrrolo[2,3-b]pyridin-3-yl)-5-fluoropyrimidin-4-ylamino)piperidin-1-yl)(cyclobutyl)methanone (395)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.04 g, 0.11 mmol) in CH$_2$Cl$_2$ (1.40 mL) and DMF (300 g was added N,N-diisopropyl-N-ethylamine (0.30 mL, 1.70 mmol) followed by cyclobutanecarbonyl chloride (0.01 g, 0.12 mmol). The reaction mixture was allowed to stir at room temperature for 17 hours. The mixture was concentrated in vacuo, dissolved in 1 mL of DMSO and purified by preparatory HPLC (0.1% ammonium formate-H$_2$O/acetonitrile) to afford the desired product, 395.

LCMS RT=1.9 (M+1) 429.3.

Other analogs that can be prepared in the same manner as 395:

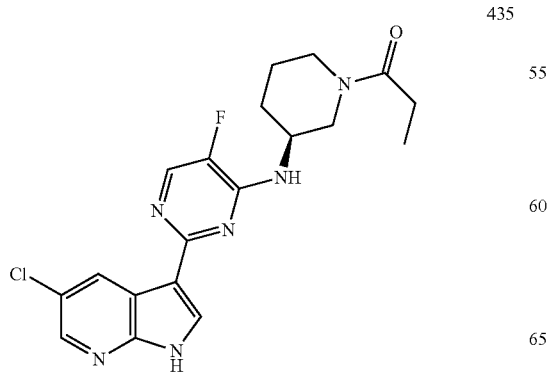

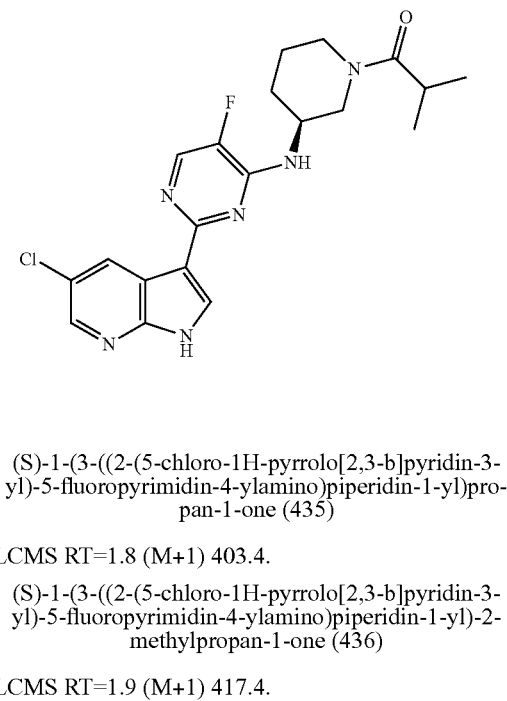

(S)-1-(3-((2-(5-chloro-1H-pyrrolo[2,3-b]pyridin-3-yl)-5-fluoropyrimidin-4-ylamino)piperidin-1-yl)propan-1-one (435)

LCMS RT=1.8 (M+1) 403.4.

(S)-1-(3-((2-(5-chloro-1H-pyrrolo[2,3-b]pyridin-3-yl)-5-fluoropyrimidin-4-ylamino)piperidin-1-yl)-2-methylpropan-1-one (436)

LCMS RT=1.9 (M+1) 417.4.

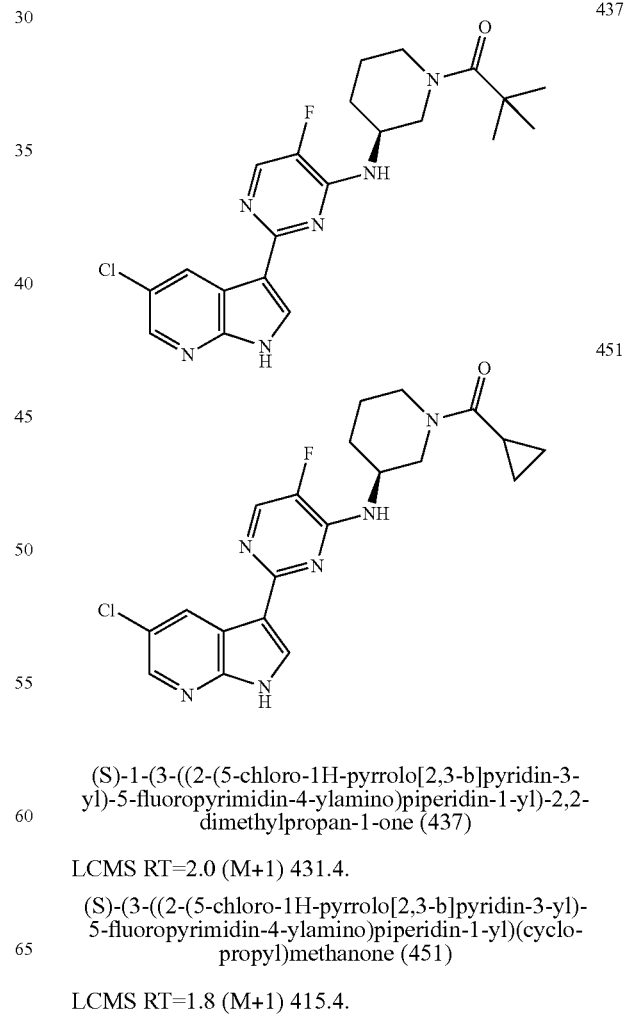

(S)-1-(3-((2-(5-chloro-1H-pyrrolo[2,3-b]pyridin-3-yl)-5-fluoropyrimidin-4-ylamino)piperidin-1-yl)-2,2-dimethylpropan-1-one (437)

LCMS RT=2.0 (M+1) 431.4.

(S)-(3-((2-(5-chloro-1H-pyrrolo[2,3-b]pyridin-3-yl)-5-fluoropyrimidin-4-ylamino)piperidin-1-yl)(cyclopropyl)methanone (451)

LCMS RT=1.8 (M+1) 415.4.

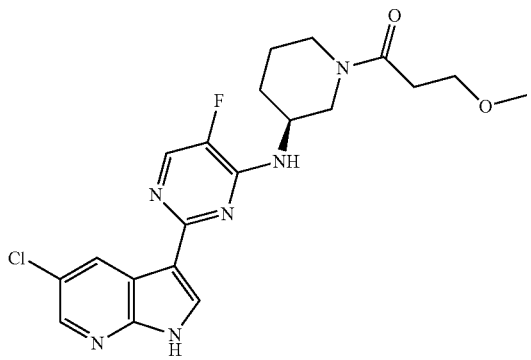

396

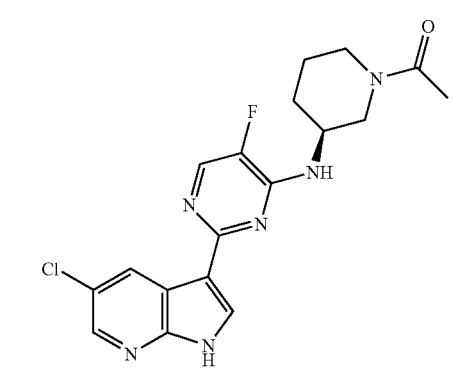

434

(S)-1-(3-((2-(5-chloro-1H-pyrrolo[2,3-b]pyridin-3-yl)-5-fluoropyrimidin-4-ylamino)piperidin-1-yl)-3-methoxypropan-1-one (396)

LCMS RT=1.7 (M+1) 433.3.

(S)-1-(3-((2-(5-chloro-1H-pyrrolo[2,3-b]pyridin-3-yl)-5-fluoropyrimidin-4-ylamino)piperidin-1-yl)ethanone (434)

LCMS RT=1.6 (M+1) 389.4.

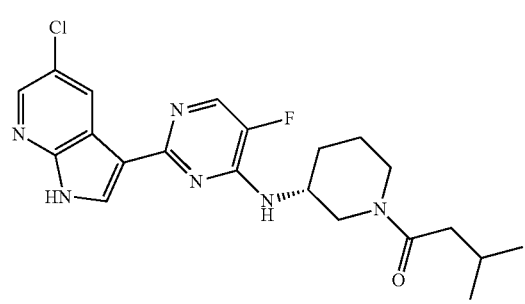

318

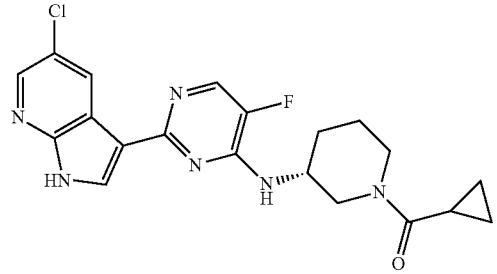

317

(R)-1-(3-((2-(5-chloro-1H-pyrrolo[2,3-b]pyridin-3-yl)-5-fluoropyrimidin-4-ylamino)piperidin-1-yl)-3-methylbutan-1-one (318)

LCMS RT=2.9 (M+1) 431.1.

(R)-(3-((2-(5-chloro-1H-pyrrolo[2,3-b]pyridin-3-yl)-5-fluoropyrimidin-4-ylamino)piperidin-1-yl)(cyclopropyl)methanone (317)

LCMS RT=2.7 (M+1) 415.1.

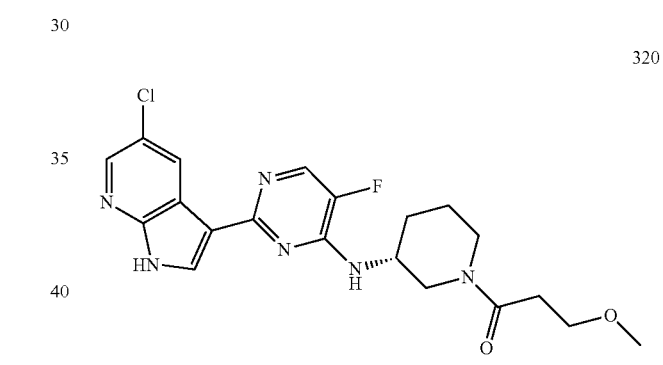

320

319

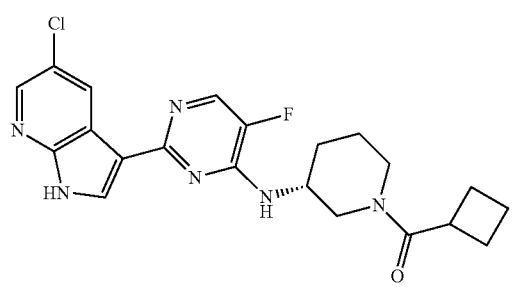

(R)-1-(3-((2-(5-chloro-1H-pyrrolo[2,3-b]pyridin-3-yl)-5-fluoropyrimidin-4-ylamino)piperidin-1-yl)-3-methoxypropan-1-one (320)

LCMS RT=2.5 (M+1) 433.1.

(R)-(3-((2-(5-chloro-1H-pyrrolo[2,3-b]pyridin-3-yl)-5-fluoropyrimidin-4-ylamino)piperidin-1-yl)(cyclobutyl)methanone (319)

LCMS RT=2.8 (M+1) 429.1.

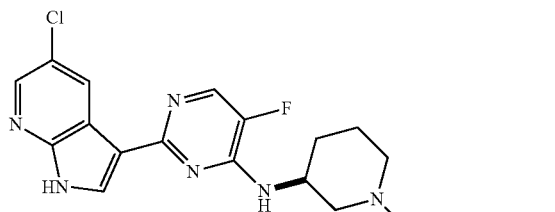

332

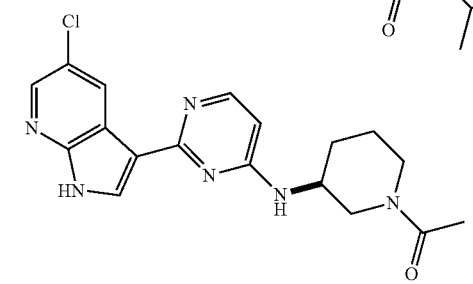

(S)-1-(3-((2-(5-chloro-1H-pyrrolo[2,3-b]pyridin-3-yl)-5-fluoropyrimidin-4-ylamino)piperidin-1-yl)-3-methylbutan-1-one (332)

LCMS RT=2.0 (M+1) 431.2.

(S)-1-(3-((2-(5-chloro-1H-pyrrolo[2,3-b]pyridin-3-yl)pyrimidin-4-ylamino)piperidin-1-yl)ethanone (485)

LCMS RT=1.9 (M+1) 371.5.

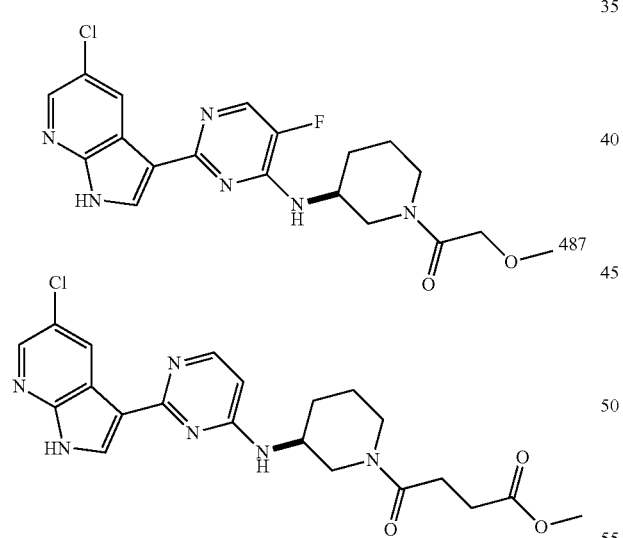

486

487

(S)-1-(3-((2-(5-chloro-1H-pyrrolo[2,3-b]pyridin-3-yl)-5-fluoropyrimidin-4-ylamino)piperidin-1-yl)-2-methoxyethanone (486)

LCMS RT=1.9 (M+1) 401.5.

(S)-methyl 4-(3-((2-(5-chloro-1H-pyrrolo[2,3-b]pyridin-3-yl)pyrimidin-4-ylamino)piperidin-1-yl)-4-oxobutanoate (487)

LCMS RT=2.0 (M+1) 443.9.

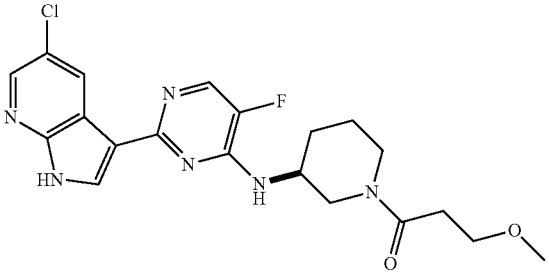

488

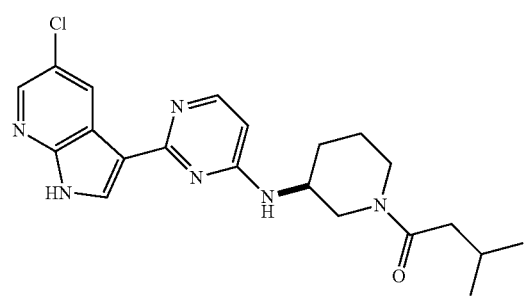

489

(S)-1-(3-((2-(5-chloro-1H-pyrrolo[2,3-b]pyridin-3-yl)-5-fluoropyrimidin-4-ylamino)piperidin-1-yl)-3-methoxypropan-1-one (488)

LCMS RT=1.9 (M+1) 415.5.

(S)-1-(3-((2-(5-chloro-1H-pyrrolo[2,3-b]pyridin-3-yl)pyrimidin-4-ylamino)piperidin-1-yl)-3-methylbutan-1-one (489)

LCMS RT=2.1 (M+1) 413.5.

General Scheme 5D:

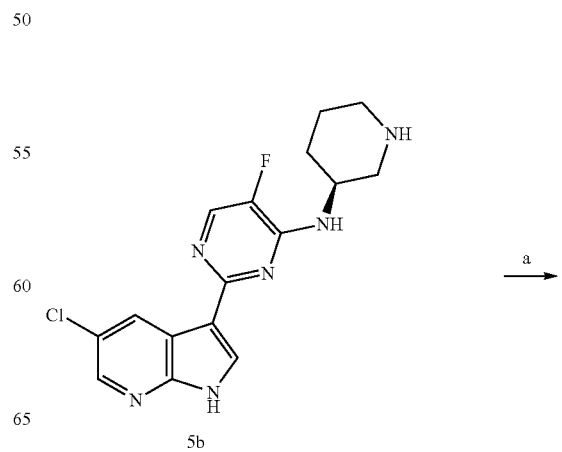

5b

181

-continued

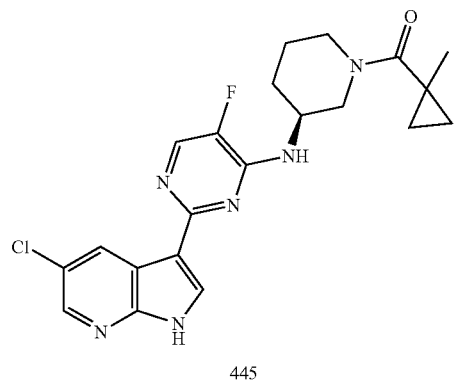

445

(a) 1-methylcyclopropane-1-carboxylic acid, EDAC-HCl, HOBt, $^i$Pr$_2$NEt, CH$_2$Cl$_2$/DMF.

Formation of (S)-(3-((2-(5-chloro-1H-pyrrolo[2,3-b]pyridin-3-yl)-5-fluoropyrimidin-4-ylamino)piperidin-1-yl)(1-methylcyclopropyl)methanone (445)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.04 g, 0.10 mmol) in CH$_2$Cl$_2$ (1.4 mL) and DMF (0.3 mL) was added N,N-diisopropyl-N-ethylamine (0.3 mL, 1.72 mmol), followed by 3-(ethyliminomethyleneamino)-N,N-dimethyl-propan-1-amine hydrochloride (0.02 g, 0.12 mmol), 1-hydroxybenzotriazole hydrate (0.02 g, 0.12 mmol) and 1-methylcyclopropane-1-carboxylic acid (0.01 g, 0.12 mmol). The mixture was concentrated in vacuo, dissolved in 1 mL of DMSO and purified by preparatory HPLC (0.1% ammonium formate-H$_2$O/acetonitrile) to afford the desired product, 445.

LCMS RT=2.1 (M+1) 429.5.

Analogs that can be prepared in the same manner as 445:

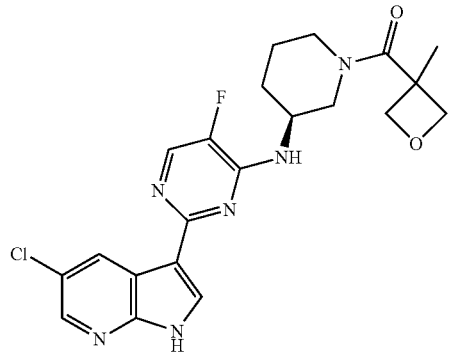

444

(S)-(3-((2-(5-chloro-1H-pyrrolo[2,3-b]pyridin-3-yl)-5-fluoropyrimidin-4-ylamino)piperidin-1-yl)(3-methyloxetan-3-yl)methanone (444)

LCMS RT=1.7 (M+1) 445.4.

182

General Scheme 5E:

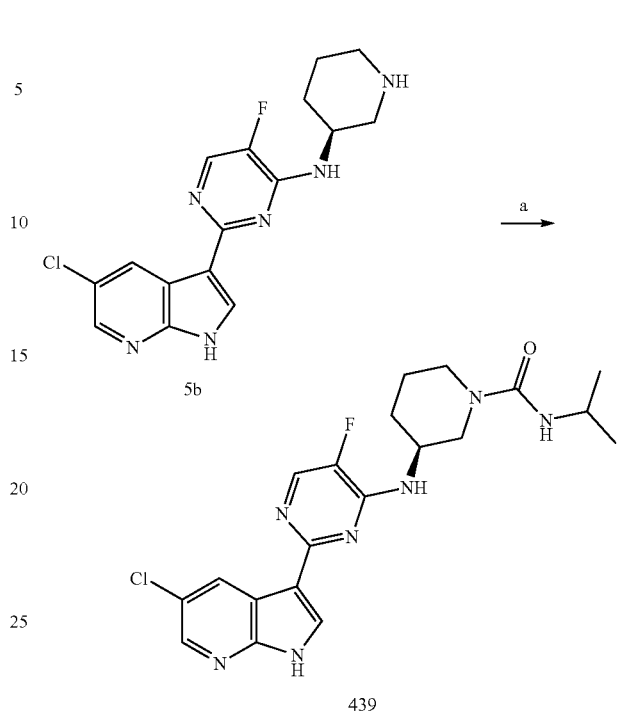

(a) isocyanatopropane, $^i$Pr$_2$NEt, CH$_2$Cl$_2$/DMF.

Formation of (S)-3-((2-(5-chloro-1H-pyrrolo[2,3-b]pyridin-3-yl)-5-fluoropyrimidin-4-ylamino)-N-isopropylpiperidine-1-carboxamide (439)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.042 g, 0.100 mmol) in CH$_2$Cl$_2$ (1.4 mL) and DMF (0.3 mL) was added N,N-diisopropyl-N-ethylamine (0.300 mL, 1.720 mmol) followed by isocyanatopropane (0.120 mmol). The reaction mixture was stirred at room temperature for 17 hours. The mixture was concentrated in vacuo, dissolved in 1 mL of DMSO and purified by preparatory HPLC (0.1% ammonium formate-H$_2$O/acetonitrile) to afford the desired product, 439.

LCMS RT=1.8 (M+1) 432.4.

Other analogs that can be prepared in the same manner as 439:

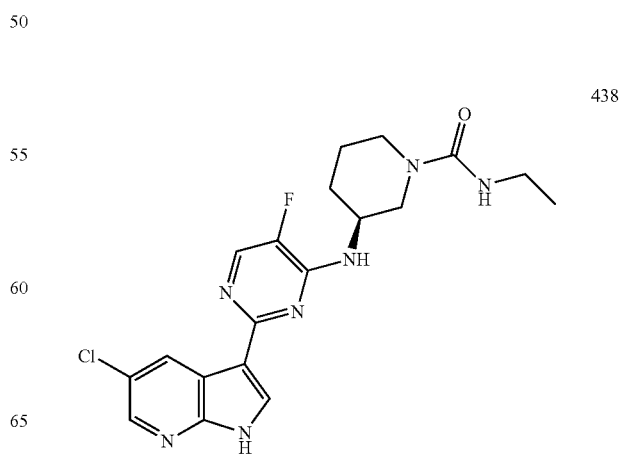

438

183

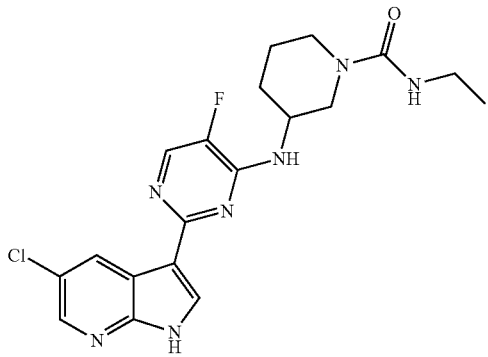

196

(S)-3-((2-(5-chloro-1H-pyrrolo[2,3-b]pyridin-3-yl)-5-fluoropyrimidin-4-ylamino)-N-ethylpiperidine-1-carboxamide (438)

LCMS RT=1.7 (M+1) 418.4.

Formation of 3-((2-(5-chloro-1H-pyrrolo[2,3-b]pyridin-3-yl)-5-fluoropyrimidin-4-ylamino)-N-propylpiperidine-1-carboxamide (196)

To a solution of 2-(5-chloro-1H-pyrrolo[2,3-b]pyridin-3-yl)-5-fluoro-N-(piperidin-3-yl)pyrimidin-4-amine, 5b, (0.020 g, 0.058 mmol) in 1:1 mixture of $CH_2Cl_2$/pyridine (2 mL) was added propylisocyanate (0.005 mL, 0.058 mmol). The reaction mixture was stirred at room temperature for 12 hours. The resulting residue was purified by preparatory HPLC (0.1% TFA-$H_2O$/acetonitrile) to afford the desired product, 196.
LCMS RT=2.6 (M+1) 432.1, (M−1) 430.1.

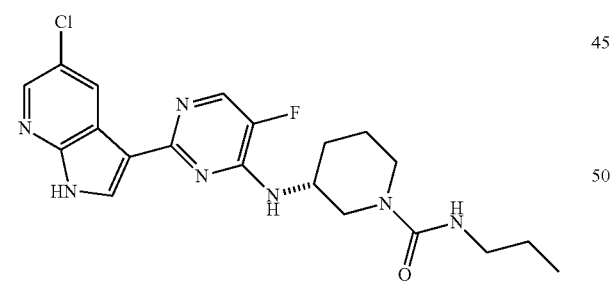

184

(S)-3-((2-(5-chloro-1H-pyrrolo[2,3-b]pyridin-3-yl)-5-fluoropyrimidin-4-ylamino)-N-propylpiperidine-1-carboxamide (324)

LCMS RT=2.6 (M+1) 432.2.

(S)—N-butyl-3-((2-(5-chloro-1H-pyrrolo[2,3-b]pyridin-3-yl)-5-fluoropyrimidin-4-ylamino)piperidine-1-carboxamide (323)

LCMS RT=2.7 (M+1) 446.2.

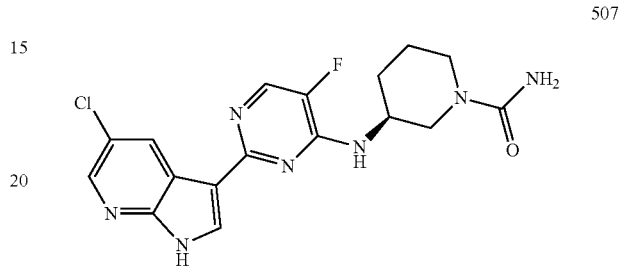

507

(S)-3-((2-(5-chloro-1H-pyrrolo[2,3-b]pyridin-3-yl)-5-fluoro pyrimidin-4-ylamino)piperidine-1-carboxamide (507)

LCMS (TFA buffer): Rt 1.69 min, ES⁺ 390.

General Scheme 5F:

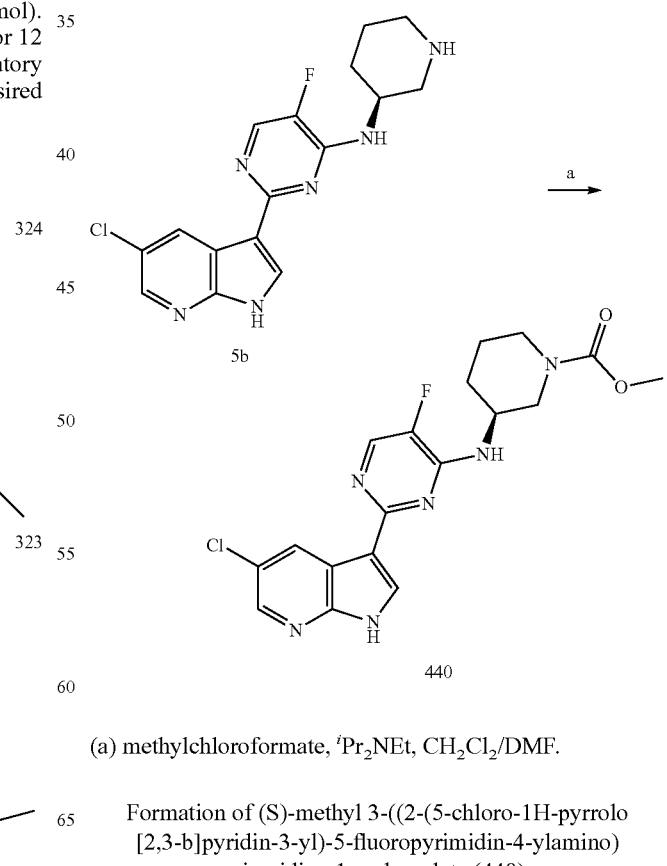

(a) methylchloroformate, $^iPr_2NEt$, $CH_2Cl_2$/DMF.

Formation of (S)-methyl 3-((2-(5-chloro-1H-pyrrolo[2,3-b]pyridin-3-yl)-5-fluoropyrimidin-4-ylamino)piperidine-1-carboxylate (440)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.042 g, 0.100 mmol) in CH₂Cl₂ (1.4 mL) and DMF (0.3 mL) was added N,N-diisopropyl-N-ethylamine (0.300 mL, 1.720 mmol) followed by methyl chloroformate (0.009 g, 0.120 mmol). The reaction mixture was stirred at room temperature for 17 hours. The mixture was concentrated in vacuo, dissolved in 1 mL of DMSO and purified by preparatory HPLC (0.1% ammonium formate-H₂O/acetonitrile) to afford the desired product, 440.

LCMS RT=1.8 (M+1) 405.4.

Analogs that can be prepared in the same manner as 440:

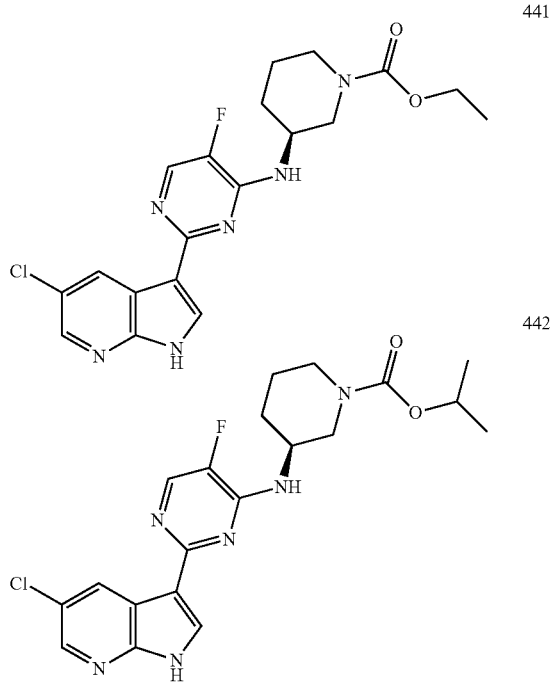

(S)-ethyl 3-((2-(5-chloro-1H-pyrrolo[2,3-b]pyridin-3-yl)-5-fluoropyrimidin-4-ylamino)piperidine-1-carboxylate (441)

LCMS RT=1.9 (M+1) 419.4.

(S)-isopropyl 3-((2-(5-chloro-1H-pyrrolo[2,3-b]pyridin-3-yl)-5-fluoropyrimidin-4-ylamino)piperidine-1-carboxylate (442)

LCMS RT=2.1 (M+1) 433.4.

General Scheme 5G:

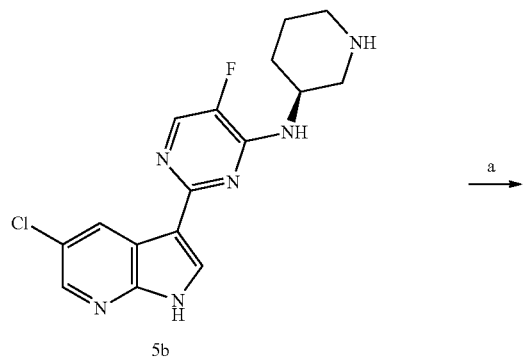

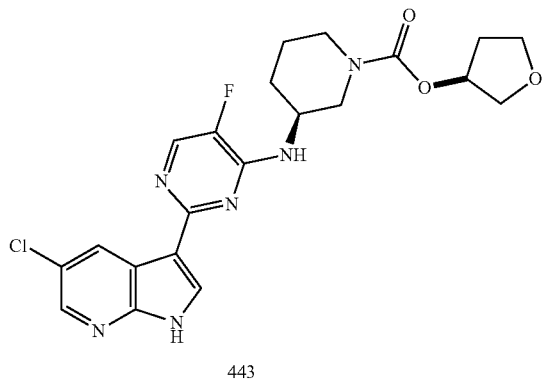

443

(a) (2,5-dioxopyrrolidin-1-yl) [(3S)-tetrahydrofuran-3-yl] carbonate, ⁱPr₂NEt, CH₂Cl₂/DMF.

Formation of (S)-((S)-tetrahydrofuran-3-yl) 3-((2-(5-chloro-1H-pyrrolo[2,3-b]pyridin-3-yl)-5-fluoropyrimidin-4-ylamino)piperidine-1-carboxylate (443)

To a solution of (S)-2-(5-chloro-1H-pyrrolo[2,3-b]pyridin-3-yl)-5-fluoro-N-(piperidin-3-yl)pyrimidin-4-amine hydrochloride, 5b, (0.042 g, 0.100 mmol) in CH₂Cl₂ (1.4 mL) and DMF (0.3 mL) was added N,N-diisopropyl-N-ethylamine (0.300 mL, 1.720 mmol) followed by (2,5-dioxopyrrolidin-1-yl) [(3S)-tetrahydrofuran-3-yl]carbonate (0.028 g, 0.120 mmol). The reaction mixture was stirred at room temperature for 17 hours. The mixture was concentrated in vacuo, dissolved in 1 mL of DMSO and purified by preparatory HPLC (0.1% ammonium formate-H₂O/acetonitrile) to afford the desired product, 443.

LCMS RT=1.8 (M+1) 463.3.

General Scheme 6A:

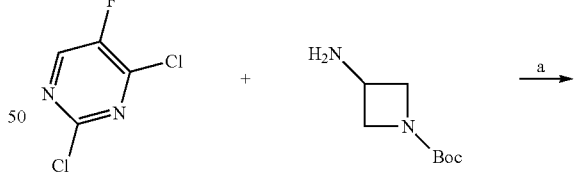

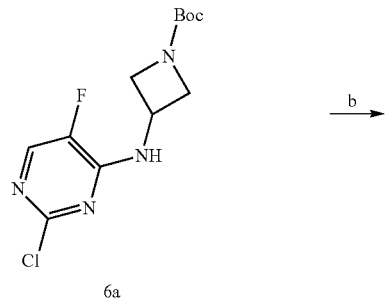

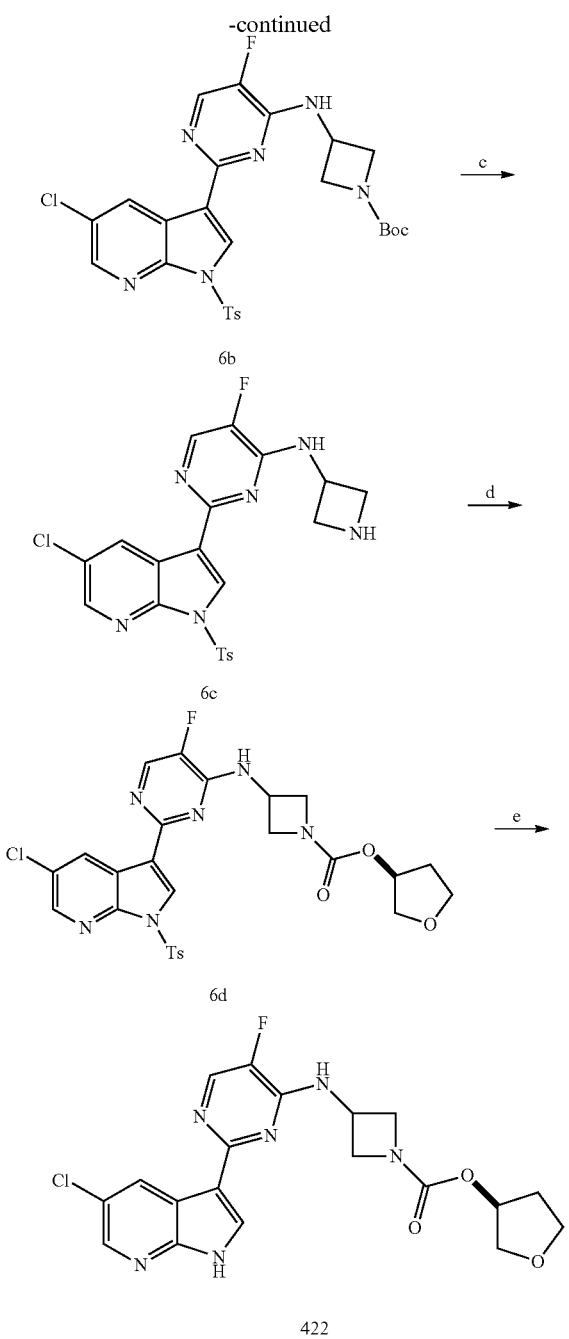

(a) $^i$Pr$_2$NEt, THF; (b) Pd(PPh$_3$)$_4$, 2M Na$_2$CO$_3$ 80° C.; (c) 4N HCl/dioxane, MeOH, 80° C.; (d) (s)-2,5-dioxopyrrolidin-1-yl tetrahydrofuran-3-yl carbonate, $^i$Pr$_2$NEt, THF; (e) 25% NaOMe/MeOH or 1M LiOH, 150° C., microwave, 10 min.

Formation of tert-butyl 3-(2-chloro-5-fluoropyrimidin-4-ylamino)-cyclobutylcarbamate (6a)

A mixture of 2,4-dichloro-5-fluoro-pyrimidine (0.97 g, 5.81 mmol) and $^i$Pr$_2$NEt (2.53 mL, 14.50 mmol) in THF (50 mL) was treated with tert-butyl 3-aminoazetidine-1-carboxylate (1.00 g, 5.81 mmol) and stirred at room temperature until complete by LCMS. The mixture was concentrated to dryness then diluted with water and extracted with dichloromethane. The combined organic layers were dried over Na$_2$SO$_4$ and concentrated in vacuo to afford an oil that was purified by silica gel chromatography (0-100% petroleum ether/EtOAc gradient). Removal of the solvent under reduced pressure afforded 3.36 g (89% yield) of a white solid after vacuum drying.

LCMS: RT=3.2 min, ES$^+$ 303.

Formation of tert-butyl 3-((2-(5-chloro-1-tosyl-1H-pyrrolo[2,3-b]pyridin-3-yl)-5-fluoropyrimidin-4-ylamino)azetidine-1-carboxylate (6b)

A solution of tert-butyl 3-(2-chloro-5-fluoropyrimidin-4-ylamino)-cyclobutylcarbamate, 6a, (0.39 g, 1.28 mmol) and 5-chloro-3-(4,4,5,5-tetramethyl-1,3,2-dioxaborolan-2-yl)-1-tosyl-1H-pyrrolo[2,3-b]pyridine (0.60 g, 1.39 mmol) in DME (10 mL) and 2M Na$_2$CO$_3$ (5 mL) was degassed with argon (3× vacuum and back fill) then treated with catalytic Pd(PPh$_3$)$_4$ and the mixture heated at 80° C. under argon. After 3 h the solvent was concentrated to a reduced volume then diluted with EtOAc and filtered through florisil (40 mL pad) and washed with EtOAc. The solvent was concentrated in vacuo and the resulting dark residue purified with silica-gel chromatography (0-100% petroleum ether/EtOAc gradient) to afford 230 mg (32% yield) of 6b, as white-pink solid.

LCMS: RT=4.7 min, ES$^+$ 573.

Formation of N-(azetidin-3-yl)-2-(5-chloro-1-tosyl-1H-pyrrolo[2,3-b]pyridin-3-yl)-5-fluoropyrimidin-4-amine hydrochloride (6c)

A suspension of tert-butyl 3-((2-(5-chloro-1-tosyl-1H-pyrrolo[2,3-b]pyridin-3-yl)-5-fluoropyrimidin-4-ylamino)azetidine-1-carboxylate, 6b, (0.23 g, 0.40 mmol) in methanol (10 mL) was treated with 4N HCl/dioxane (5 mL, 20 mmol) then heated at 80° C. for 30 minutes. The solvent was removed and the residue dried under vacuum to afford 240 mg of a solid that was used without purification.

LCMS RT=2.4 min, ES$^+$ 473.

Formation of (S)-tetrahydrofuran-3-yl 3-((2-(5-chloro-1H-pyrrolo[2,3-b]pyridin-3-yl)-5-fluoropyrimidin-4-ylamino)azetidine-1-carboxylate (422)

A suspension of N-(azetidin-3-yl)-2-(5-chloro-1-tosyl-1H-pyrrolo[2,3-b]pyridin-3-yl)-5-fluoropyrimidin-4-amine hydrochloride, 6c, (0.06 g, 0.11 mmol) in THF (1 mL) was treated with $^i$Pr$_2$NEt (0.30 mL, 1.70 mmol) then solid (S)-2,5-dioxopyrrolidin-1-yl tetrahydrofuran-3-yl carbonate (0.03 g, 0.11 mmol) was added. The resulting mixture was stirred for 2 hours at room temperature and then quenched with 200 µL of morpholine and evaporated to dryness to afford (S)-tetrahydrofuran-3-yl 3-((2-(5-chloro-1-tosyl-1H-pyrrolo[2,3-b]pyridin-3-yl)-5-fluoropyrimidin-4-ylamino)azetidine-1-carboxylate, 6d, which was used without purification.

LCMS RT=3.8 min, ES$^+$ 588.

(S)-tetrahydrofuran-3-yl 3-((2-(5-chloro-1-tosyl-1H-pyrrolo[2,3-b]pyridin-3-yl)-5-fluoropyrimidin-4-ylamino)azetidine-1-carboxylate, 6d, was dissolved in methanol (2 mL) and then treated with of 25% sodium methoxide/methanol (0.5 mL) and heated at 60° C. in sealed tube. LCMS showed complete reaction after 10 minutes. The resulting solution was quenched with aqueous saturated NH$_4$Cl solution (0.5 mL) then evaporated to dryness and the residue dissolved in DMSO and purified by reverse phase HPLC (ammonium formate buffer) to afford 25.9 mg (55% yield) of the desired product, 422, as a solid.

LCMS RT=1.8 min, ES⁺ 433.

General Scheme 6B:

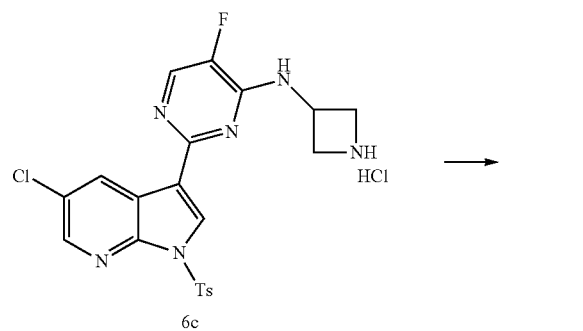

6c

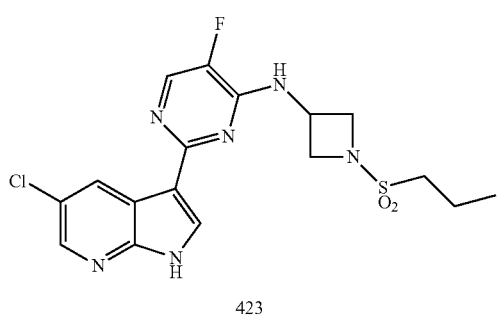

423

Formation of 2-(5-chloro-1-tosyl-1H-pyrrolo[2,3-b]pyridin-3-yl)-5-fluoro-N-(1-(propylsulfonyl)azetidin-3-yl)pyrimidin-4-amine (423)

To a stirred suspension of N-(azetidin-3-yl)-2-(5-chloro-1-tosyl-1H-pyrrolo[2,3-b]pyridin-3-yl)-5-fluoropyrimidin-4-amine hydrochloride, 6c, (0.055 g, 0.110 mmol) in THF (1 mL) was added $^i$Pr$_2$NEt (0.300 mL, 1.720 mmol) followed by propane-1-sulfonyl chloride (0.012 mL, 0.108 mmol). The resulting homogenous light yellow solution mixture was heated at 50° C. for one hour at which time LCMS showed complete reaction. Morpholine (0.20 mL) was added and the solution evaporated to dryness. The resulting residue was dissolved in methanol (2 mL) then treated with 25% sodium methoxide/methanol (0.5 mL) and heated at 60° C. in sealed tube for 10 minutes. The resulting solution was quenched with aqueous saturated NH$_4$Cl solution (0.5 mL) then evaporated to dryness. The resulting residue was dissolved in DMSO and purified by reverse phase HPLC (ammonium formate buffer) to afford 19.8 mg (43% yield) of the desired product, 423, as a solid.

LCMS RT=2.6 min, ES⁺ 425.

Other analogs that can be prepared in a manner similar to 423:

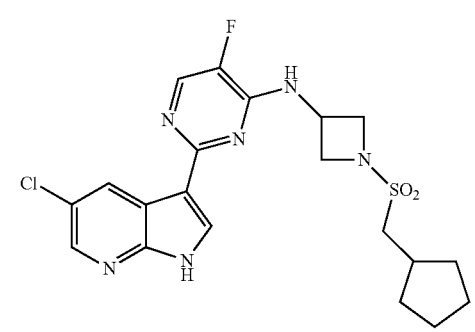

469

Formation of 2-(5-chloro-1H-pyrrolo[2,3-b]pyridin-3-yl)-N-(1-(cyclopentyl-methylsulfonyl)azetidin-3-yl)-5-fluoropyrimidin-4-amine (469)

To a stirred solution of N-(azetidin-3-yl)-2-(5-chloro-1-tosyl-1H-pyrrolo[2,3-b]pyridin-3-yl)-5-fluoropyrimidin-4-amine hydrochloride, 6c, (0.03 g, 0.06 mmol) in dichloromethane (1 mL) was added $^i$Pr$_2$NEt (0.33 μL, 1.90 mmol) followed by cyclopentylmethanesulfonyl chloride (0.01 g, 0.06 mmol). The resulting mixture was stirred 30 minutes at room temperature at which time LCMS showed complete reaction. Morpholine (0.20 mL) was added and the solution evaporated to dryness. The resulting residue was dissolved in methanol (2 mL) then treated with 25% sodium methoxide/methanol (0.5 mL) and heated at 60° C. in sealed tube for 10 minutes. The solution was quenched with aqueous saturated NH$_4$Cl solution (0.5 mL) then evaporated to dryness. The resulting residue was dissolved in DMSO and purified by reverse phase HPLC (ammonium formate buffer) to afford 27.4 mg (88% yield) of the desired product, 469, as a solid. LCMS RT=3.1 min, ES⁺465.

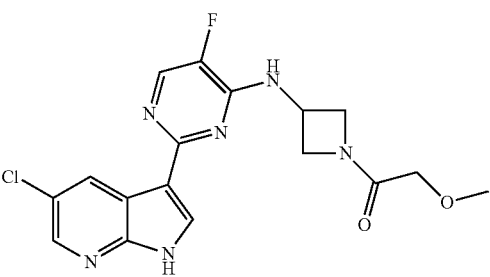

468

Formation of 1-(3-((2-(5-chloro-1H-pyrrolo[2,3-b]pyridin-3-yl)-5-fluoropyrimidin-4-ylamino)azetidin-1-yl)-2-methoxyethanone (468)

According to the procedure for compound 469 using methoxyacetyl chloride afforded 11.7 mg (51% yield) of 468, as a white solid.

LCMS RT=1.6 min, ES+ 390.

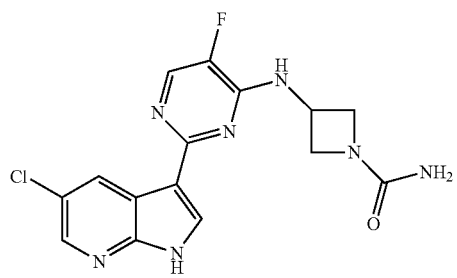

512

Formation of 3-((2-(5-chloro-1H-pyrrolo[2,3-b]pyridin-3-yl)-5-fluoropyrimidin-4-ylamino)azetidine-1-carboxamide (512)

According to the procedure for compound 469 using 61 mg (0.11 mmol) of 6c and isocyanatotrimethylsilane (15.14 µL, 0.11 mmol) afforded 87 mg (79% yield) of 512, as a white solid:

LCMS RT=2.4 min, ES+ 362.

General Scheme 7:

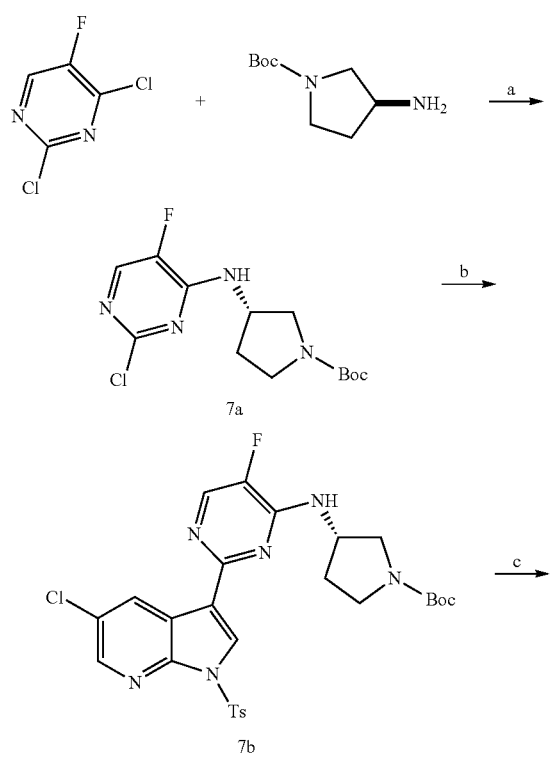

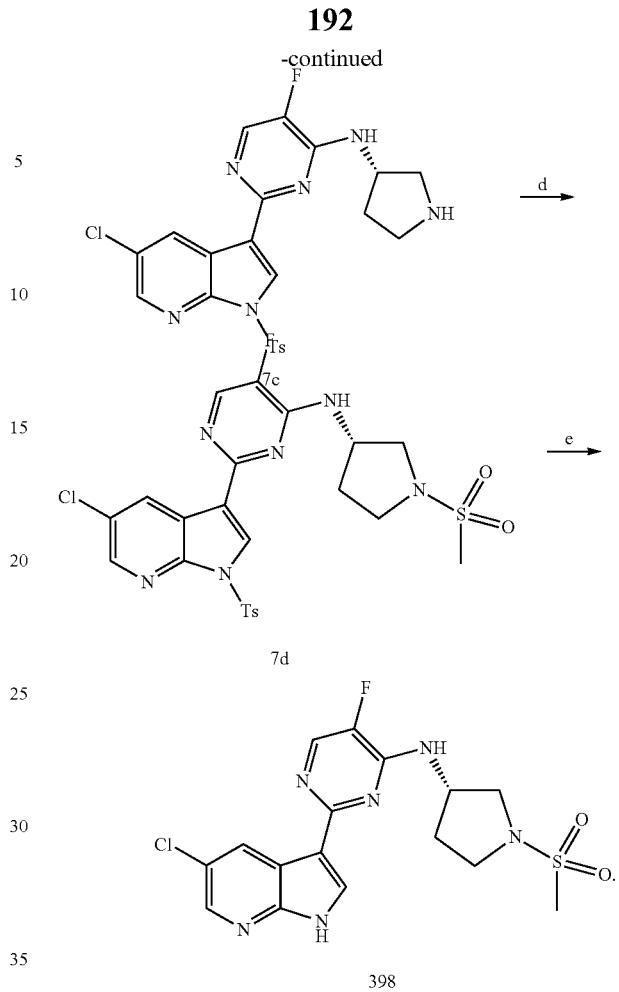

(a) 2,4-dichloro-5-fluoropyrimidine, $^i$Pr$_2$NEt, THF; (b) 5-chloro-3-(4,4,5,5-tetramethyl-1,3,2-dioxaborolan-2-yl)-1-tosyl-1H-pyrrolo[2,3-b]pyridine, Pd(PPh$_3$)$_4$, 2M Na$_2$CO$_3$ 90° C.; (c) 4N HCl/dioxane, MeOH, 80° C.; (d) methanesulfonyl chloride, $^i$Pr$_2$NEt, THF, RT; (e) 25% NaOMe/MeOH or 1M LiOH, 150° C., microwave, 10 min.

Formation of (S)-tert-butyl 3-(2-chloro-5-fluoropyrimidin-4-ylamino)pyrrolidine-1-carboxylate (7a)

To a mixture of 2,4-dichloro-5-fluoro-pyrimidine (1.75 g, 10.48 mmol) and $^i$Pr$_2$NEt (3.27 mL, 18.78 mmol) in THF (50 mL) was added tert-butyl (3S)-3-aminopyrrolidine-1-carboxylate (1.83 mL, 10.48 mmol) in THF (2 mL). The resulting solution was allowed to stir at room temperature for 2 hours. The mixture was concentrated to dryness, diluted with dichloromethane and washed with water. The organic layer was dried over Na$_2$SO$_4$ and concentrated in vacuo to afford 3.41 g of 7a, as a white foamy solid.

LCMS RT=3.0 min. ES+ 317.

Formation of (S)-tert-butyl 3-((2-(5-chloro-1-tosyl-1H-pyrrolo[2,3-b]pyridin-3-yl)-5-fluoropyrimidin-4-ylamino)pyrrolidine-1-carboxylate (7b)

A solution of 5-chloro-1-(p-tolylsulfonyl)-3-(4,4,5,5-tetramethyl-1,3,2-dioxaborolan-2-yl)pyrrolo[2,3-b]pyridine (2.41 g, 5.60 mmol) and tert-butyl (3S)-3-[(2-chloro-5-fluoro-pyrimidin-4-yl)amino]pyrrolidine-1-carboxylate, 7a, (1.69 g, 5.30 mmol) in DME (34 mL) and 2M Na$_2$CO$_3$ (8.5 mL) was degassed with nitrogen (5 min) then treated with Pd(PPh$_3$)$_4$ (0.31 g, 0.27 mmol) then heated at 90° C. overnight. The resulting dark solution was filtered through florisil, washed with EtOAc then concentrated in vacuo. The resulting residue was purified by silica-gel chromatography (0-100%) petroleum ether: EtOAc gradient. Removal of the solvent under reduced pressure afforded 1.33 g (42% yield) of a white solid after vacuum drying.

LCMS RT=4.4 min. ES$^+$ 588.

Formation of 2-[5-chloro-1-(p-tolylsulfonyl)pyrrolo[2,3-b]pyridin-3-yl]-5-fluoro-N-[(3S)-pyrrolidin-3-yl]pyrimidin-4-amine (7c)

A solution of tert-butyl (3S)-3-[[2-[5-chloro-1-(p-tolylsulfonyl)pyrrolo[5,4-b]pyridin-3-yl]-5-fluoro-pyrimidin-4-yl]amino]pyrrolidine-1-carboxylate, 7b, (1.33 g, 2.27 mmol) in THF (25 mL) was treated with hydrogen chloride (12 mL of 4M solution in dioxane, 48.00 mmol) at room temperature. The reaction was then heated at 90° C. until LCMS showed reaction was complete. The mixture was concentrated to dryness then dried under vacuum to afford 1.04 g (88% yield) of 7c, as a tan solid.

LCMS RT=2.3 min. ES$^+$ 487.

Formation of (S)-2-(5-chloro-1H-pyrrolo[2,3-b]pyridin-3-yl)-5-fluoro-N-(1-(methylsulfonyl)pyrrolidin-3-yl)pyrimidin-4-amine (398)

To a stirred suspension of 2-[5-chloro-1-(p-tolylsulfonyl)pyrrolo[2,3-b]pyridin-3-yl]-5-fluoro-N-[(3S)-pyrrolidin-3-yl]pyrimidin-4-amine hydrochloride, 7c, (0.05 g, 0.10 mmol) in THF (1 mL) was added $^i$Pr$_2$NEt (0.10 mL, 0.57 mmol) followed by methanesulfonyl chloride (0.04 mL, 0.57 mmol). The resulting homogenous light yellow mixture was heated at 50° C. for one hour at which time LCMS showed complete reaction. Morpholine (0.20 mL) was added and the solution evaporated to dryness. The resulting residue was dissolved in methanol (2 mL) then treated with 25% sodium methoxide/methanol (0.5 mL) and heated at 60° C. in sealed tube until LCMS showed reaction was complete. The resulting solution was quenched with aqueous saturated NH$_4$Cl (0.5 mL) then evaporated to dryness. The residue was dissolved in DMSO and purified by reverse phase HPLC (ammonium formate buffer) to afford 15.8 mg (37% yield) of 398, as a solid.

LCMS RT=1.7 min. ES$^+$ 411.

Other analogs that can be prepared in a manner similar to 398:

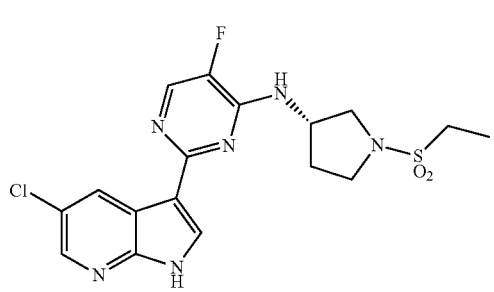

Formation of (S)-2-(5-chloro-1H-pyrrolo[2,3-b]pyridin-3-yl)-N-(1-(ethylsulfonyl)pyrrolidin-3-yl)-5-fluoropyrimidin-4-amine (399)

According to the procedure for compound 398 using 50 mg (0.10 mmol) of 7c and ethanesulfonyl chloride (54 µl, 0.57 mmol) afforded 21.7 mg (49% yield) of 399, as a solid.

LCMS RT=1.8 min. ES$^+$ 425.

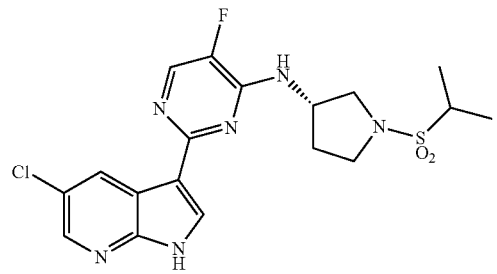

Formation of (S)-2-(5-chloro-1H-pyrrolo[2,3-b]pyridin-3-yl)-5-fluoro-N-(1-(isopropylsulfonyl)pyrrolidin-3-yl)pyrimidin-4-amine (400)

According to the procedure for compound 398 using 2-propanesulfonyl chloride (82 mg, 0.57 mmol) afforded 17.9 mg (39% yield) of 400, as a solid.

LCMS RT=1.9 min. ES$^+$ 439.

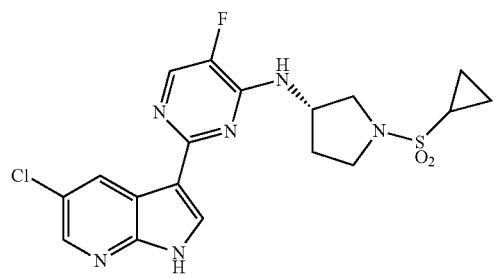

Formation of (S)-2-(5-chloro-1H-pyrrolo[2,3-b]pyridin-3-yl)-N-(1-(cyclopropylsulfonyl)pyrrolidin-3-yl)-5-fluoropyrimidin-4-amine (401)

According to the procedure for compound 398 using cyclopropanesulfonyl chloride (81 mg, 0.57 mmol) afforded 17.1 mg (37% yield) of 401, as a solid.

LCMS RT=1.9 min. ES$^+$ 437.

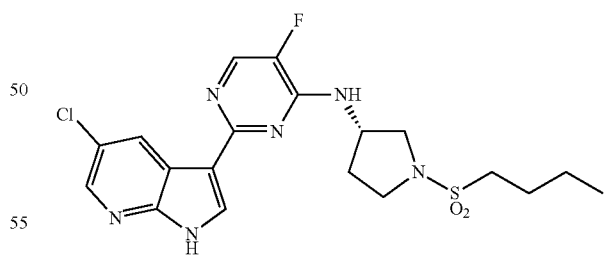

Formation of (S)—N-(1-(butylsulfonyl)pyrrolidin-3-yl)-2-(5-chloro-1H-pyrrolo[2,3-b]pyridin-3-yl)-5-fluoropyrimidin-4-amine (402)

According to the procedure for compound 398 using 1-butanesulfonyl chloride (90 mg, 0.57 mmol) afforded 21 mg (45% yield) of 402, as a solid.

LCMS RT=2.1 min. ES$^+$ 453.

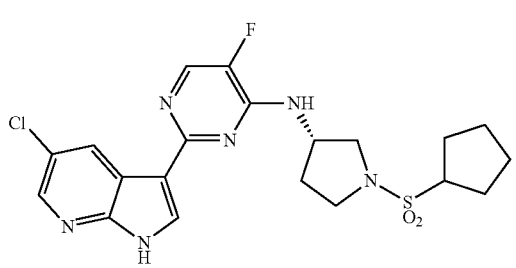

403

Formation of (S)-2-(5-chloro-1H-pyrrolo[2,3-b]pyridin-3-yl)-N-(1-(cyclopentylsulfonyl)pyrrolidin-3-yl)-5-fluoropyrimidin-4-amine (403)

According to the procedure for compound 398 using cyclopentanesulfonyl chloride (97 mg, 0.57 mmol) afforded 9.7 mg (20% yield) of 403, as a solid.
LCMS RT=2.1 min. ES+ 465.

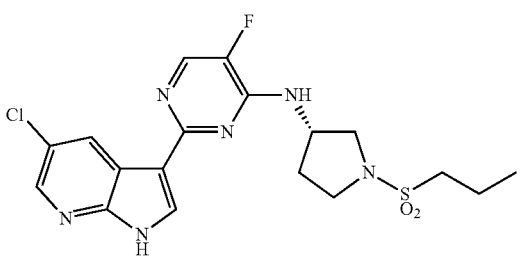

410

Formation of (S)-2-(5-chloro-1H-pyrrolo[2,3-b]pyridin-3-yl)-5-fluoro-N-(1-(propylsulfonyl)pyrrolidin-3-yl)pyrimidin-4-amine (410)

According to the procedure for compound 398 using propylsulfonyl chloride (20 mg, 0.14 mmol) afforded 15.5 mg (36% yield) of 410, as a solid.
LCMS RT=2.0 min. ES+ 439.

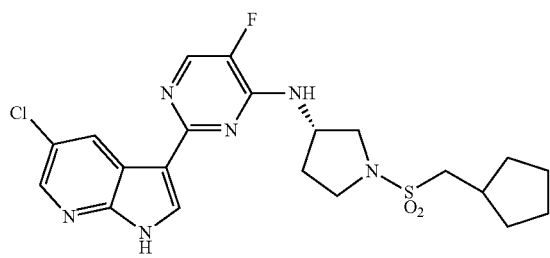

479

Formation of (S)-2-(5-chloro-1H-pyrrolo[2,3-b]pyridin-3-yl)-N-(1-(cyclopentylmethylsulfonyl)pyrrolidin-3-yl)-5-fluoropyrimidin-4-amine (479)

According to the procedure for compound 398 using cyclopentylmethyl sulfonyl chloride (30 mg, 0.16 mmol) afforded 26.7 mg (58% yield) of 479, as a solid.
LCMS RT=2.3 min. ES+ 479.

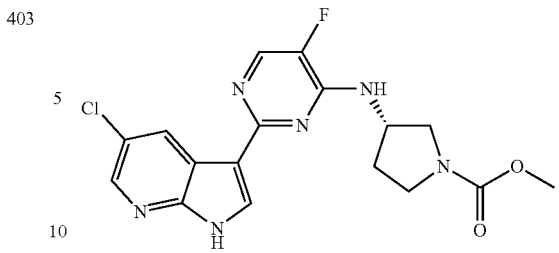

Formation of (S)-methyl 3-((2-(5-chloro-1H-pyrrolo[2,3-b]pyridin-3-yl)-5-fluoropyrimidin-4-ylamino)pyrrolidine-1-carboxylate (476)

According to the procedure for compound 398 using methylchloroformate (20 mg, 0.21 mmol) afforded 13.6 mg (52% yield) of 476, as a trifluoroacetic acid salt after preparatory HPLC purification.
LCMS (ammonium formate buffer) RT=2.6 min. ES+ 391.

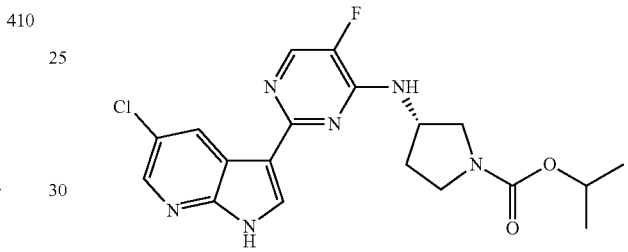

477

Formation of (S)-isopropyl 3-((2-(5-chloro-1H-pyrrolo[2,3-b]pyridin-3-yl)-5-fluoropyrimidin-4-ylamino)pyrrolidine-1-carboxylate (477)

According to the procedure for compound 476 using isopropyl chloroformate (20 mg, 0.21 mmol) afforded 11.3 mg (42% yield) of 477, as a trifluoroacetic acid salt after preparatory HPLC purification.
LCMS (ammonium formate buffer) RT=2.0 min. ES+ 419.

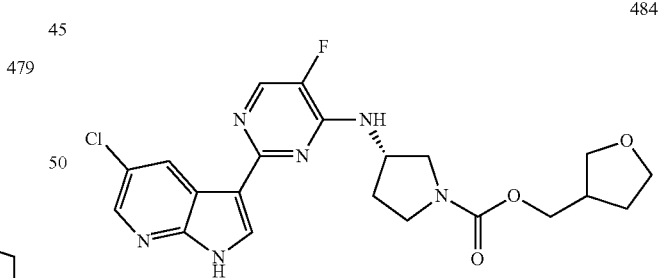

484

Formation of (3S)-(tetrahydrofuran-3-yl)methyl 3-((2-(5-chloro-1H-pyrrolo[2,3-b]pyridin-3-yl)-5-fluoropyrimidin-4-ylamino)pyrrolidine-1-carboxylate (484)

According to the procedure for compound 398 using 2,5-dioxopyrrolidin-1-yl (tetrahydrofuran-3-yl)methyl carbonate (0.023 g, 0.096 mmol) afforded 5.7 mg (10% yield) of 484, as a trifluoroacetic acid salt after preparatory HPLC purification.
LCMS (ammonium formate buffer) RT=2.6 min. ES+ 461.

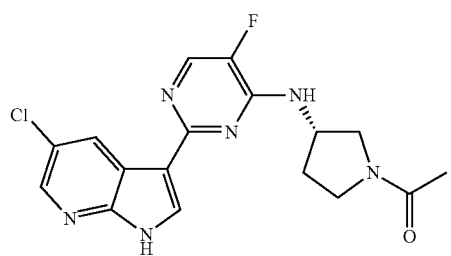

480

Formation of ((S)-3-((2-(5-chloro-1H-pyrrolo[2,3-b]pyridin-3-yl)-5-fluoropyrimidin-4-ylamino)pyrrolidin-1-yl)(tetrahydrofuran-3-3-yl)methanone (478)

According to the procedure for compound 398 using tetrahydrofuran-3-carboxylic acid (35 mg, 0.30 mmol) afforded 22.2 mg (52% yield) of 478, as a solid.
LCMS (TFA buffer) RT=1.6 min. ES+ 431.

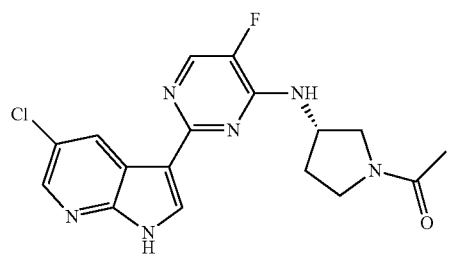

480

Formation of (S)-1-(3-((2-(5-chloro-1H-pyrrolo[2,3-b]pyridin-3-yl)-5-fluoropyrimidin-4-ylamino)pyrrolidin-1-yl)ethanone (480)

According to the procedure for compound 398 using acetyl chloride (45 uL, 0.64 mmol) afforded 4.2 mg (18% yield) of 480, as a solid.
LCMS (TFA buffer) RT=1.6 min, ES+ 375.

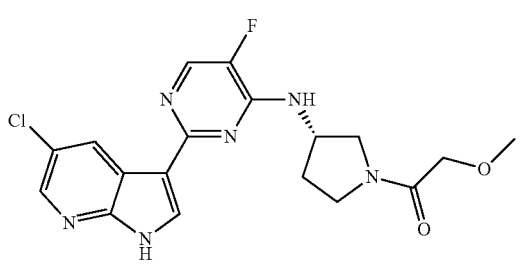

481

Formation of (S)-1-(3-((2-(5-chloro-1H-pyrrolo[2,3-b]pyridin-3-yl)-5-fluoropyrimidin-4-ylamino)pyrrolidin-1-yl)-2-methoxyethanone (481)

According to the procedure for compound 398 using methoxyacetyl chloride (50 mg, 0.46 mmol) afforded 8.6 mg (33% yield) of 481, as a solid.
LCMS (TFA buffer) RT=1.6 min, ES+ 405.

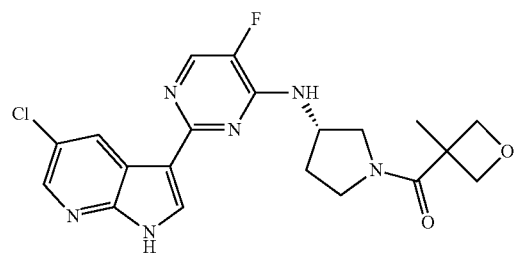

482

Formation of (S)-(3-((2-(5-chloro-1H-pyrrolo[2,3-b]pyridin-3-yl)-5-fluoropyrimidin-4-ylamino)pyrrolidin-1-yl)(3-methyloxetan-3-yl)methanone (482)

According to the procedure for compound 398 using 3-methyloxetane-3-carboxylic acid (15 mg, 0.13 mmol) afforded 17.7 mg (42% yield) of 482, as a solid.
LCMS (TFA buffer) RT=1.6 min, ES+ 431.

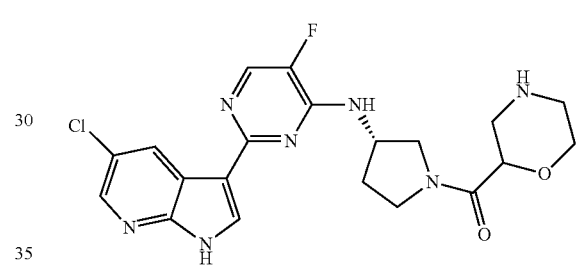

483

Formation of ((S)-3-((2-(5-chloro-1H-pyrrolo[2,3-b]pyridin-3-yl)-5-fluoropyrimidin-4-ylamino)pyrrolidin-1-yl)(morpholin-2-yl)methanone (483)

According to the procedure for compound 398 using morpholine 2-carboxylic acid (25 mg, 0.11 mmol) afforded 3.6 mg (8% yield) of 483 as a solid.
LCMS (TFA buffer): Rt 1.4 min, ES+ 446.

Using a procedure equivalent to that for the preparation of 7c, the other enantiomer (8a) can be obtained.

Analogs that can be prepared from compound 8a.

General Scheme 8:

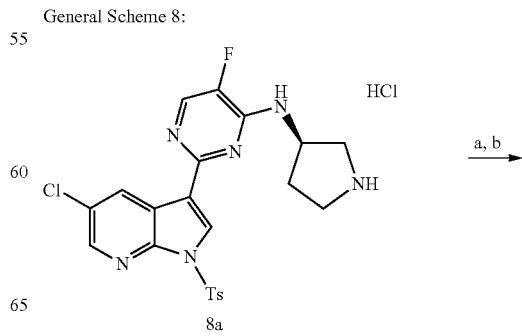

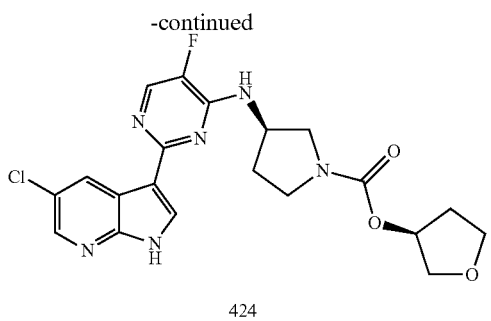

424

(a) (S)-2,5-dioxopyrrolidin-1-yltetrahydrofuran-3-yl carbonate, ⁱPr₂NEt, THF, RT; (b) 25% NaOMe/MeOH or 1M LiOH, 150° C., microwave, 10 min.

Formation of (R)—((S)-tetrahydrofuran-3-yl) 3-((2-(5-chloro-1H-pyrrolo[2,3-b]pyridin-3-yl)-5-fluoropyrimidin-4-ylamino)pyrrolidine-1-carboxylate (424)

According to the procedure for compound 398 using (R)-tert-butyl 3-aminopyrrolidine-1-carboxylate and (S)-2,5-dioxopyrrolidin-1-yl tetrahydrofuran-3-yl carbonate afforded 19.8 mg (47% yield) of 424 as a solid.
LCMS (TFA buffer) RT=1.8 min, ES⁺ 447.

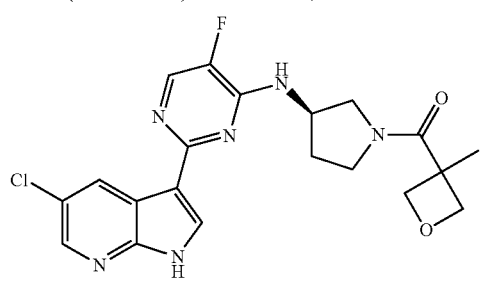

473

Formation of (R)-(3-((2-(5-chloro-1H-pyrrolo[2,3-b]pyridin-3-yl)-5-fluoropyrimidin-4-ylamino)pyrrolidin-1-yl)(3-methyloxetan-3-yl)methanone (473)

According to the procedure for compound 482 using (R)-2-(5-chloro-1-tosyl-1H-pyrrolo[2,3-b]pyridin-3-yl)-5-fluoro-N-(pyrrolidin-3-yl)pyrimidin-4-amine hydrochloride, 8a, and 3-methyloxetane-3-carboxylic acid (50 mg, 0.46 mmol) afforded 18.6 mg (44% yield) of 473, as a solid.
LCMS (TFA buffer) RT=1.6 min, ES⁺ 431.

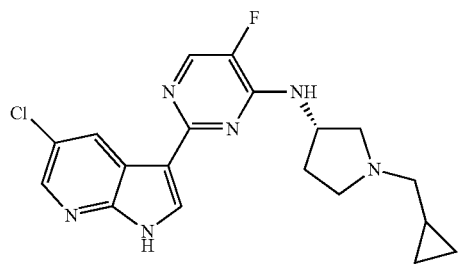

415

Formation of (S)-2-(5-chloro-1H-pyrrolo[2,3-b]pyridin-3-yl)-N-(1-(cyclopropylmethyl)pyrrolidin-3-yl)-5-fluoropyrimidin-4-amine (415)

A solution of (S)-2-(5-chloro-1-tosyl-1H-pyrrolo[2,3-b]pyridin-3-yl)-5-fluoro-N-(pyrrolidin-3-yl)pyrimidin-4-amine hydrochloride, 7c, (0.05 g, 0.10 mmol) in methanol (3 mL) was treated with cyclopropane carboxaldehyde (0.30 mmol), sodium cyanoborohydride (0.30 mmol) and potassium acetate (0.04 g, 0.30 mmol) then stirred at 60° C. until the reaction was complete. Aqueous workup afforded an oil that was dissolved in methanol (2 mL) then treated with of 25% sodium methoxide/methanol (0.5 mL) and heated at 60° C. in sealed tube. LCMS showed complete reaction. The resulting solution was quenched with aqueous saturated NH₄Cl solution (0.5 mL) then evaporated to dryness and the residue dissolved in DMSO and purified by reverse phase HPLC (ammonium formate buffer) to afford 6.2 mg (17% yield) of 415 as a solid.
LCMS RT=1.5 min, ES⁺ 387.

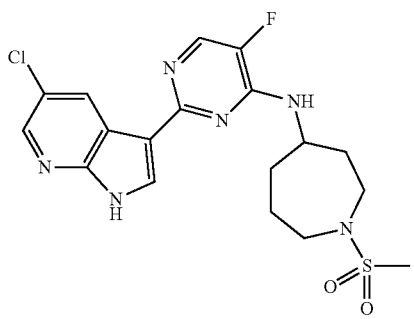

496

Formation of N-(2-(5-chloro-1H-pyrrolo[2,3-b]pyridin-3-yl)-5-fluoropyrimidin-4-yl)-1-(methylsulfonyl)azepan-4-amine (496)

According to the procedure for compound 398 using methanesulfonyl chloride afforded the desired product, 496, as a solid.
LCMS RT=1.8 min, ES⁺ 439.

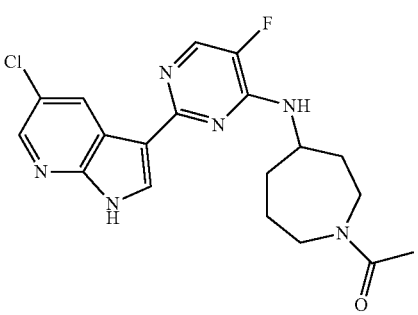

497

Formation of 1-(4-(2-(5-chloro-1H-pyrrolo[2,3-b]pyridin-3-yl)-5-fluoropyrimidin-4-ylamino)azepan-1-yl)ethanone (497)

According to the procedure for compound 398 using acetyl chloride afforded the desired product, 497, as a solid.
LCMS RT=1.7 min, ES⁺ 403.

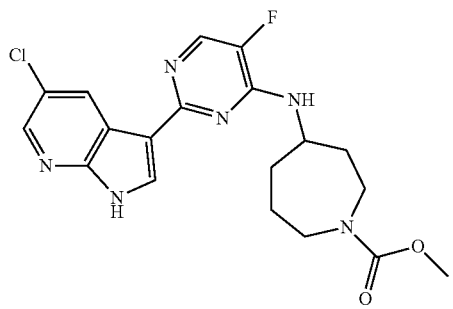

Formation of methyl 4-(2-(5-chloro-1H-pyrrolo[2,3-b]pyridin-3-yl)-5-fluoropyrimidin-4-ylamino)azepane-1-carboxylate (498)

According to the procedure for compound 398 using methyl chloroformate afforded the desired product, 498, as a solid.
LCMS RT=1.9 min, ES+ 419.

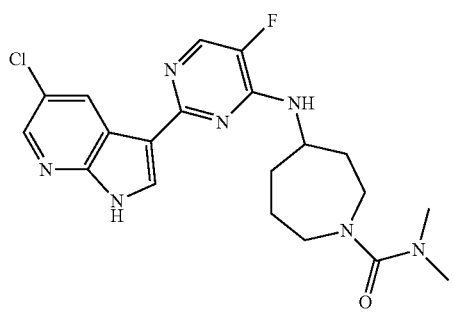

Formation of 4-(2-(5-chloro-1H-pyrrolo[2,3-b]pyridin-3-yl)-5-fluoropyrimidin-4-ylamino)-N,N-dimethylazepane-1-carboxamide (499)

According to the procedure for compound 398 using dimethyl carbamoyl chloride afforded desired product, 499, as a solid.
LCMS RT=1.8 min, ES+ 432.

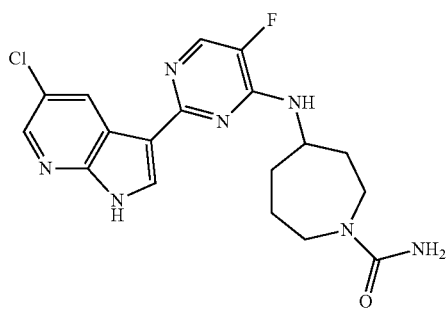 [SMILES: NC(=O)N1CCCC(Nc2nc(-c3c[nH]c4ncc(Cl)cc34)ncc2F)CC1]

Formation of 4-(2-(5-chloro-1H-pyrrolo[2,3-b]pyridin-3-yl)-5-fluoropyrimidin-4-ylamino)azepane-1-carboxamide (509)

According to the procedure for compound 398 using trimethylsilylisocyanate afforded desired product, 509, as a solid.
LCMS RT=1.6 min, ES+ 404.

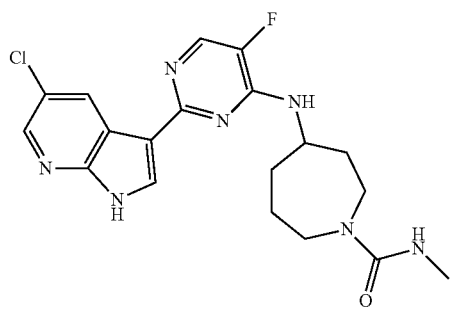

Formation of 4-(2-(5-chloro-1H-pyrrolo[2,3-b]pyridin-3-yl)-5-fluoropyrimidin-4-ylamino)-N-methylazepane-1-carboxamide (506)

According to the procedure for compound 398 using methyl isocyanate afforded the desired product, 506, as a hydrochloride salt after treating with HCl/dioxane.
LCMS RT=2.1 min, ES+ 418.

General Scheme 11:

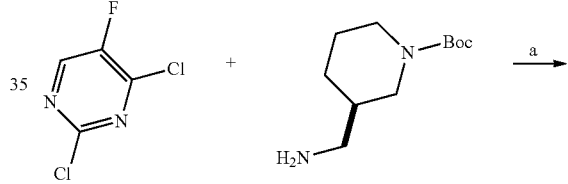

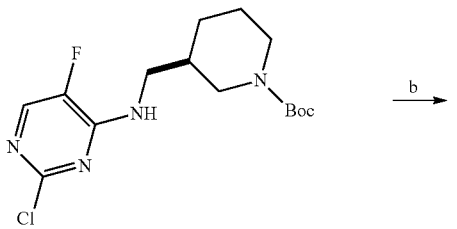

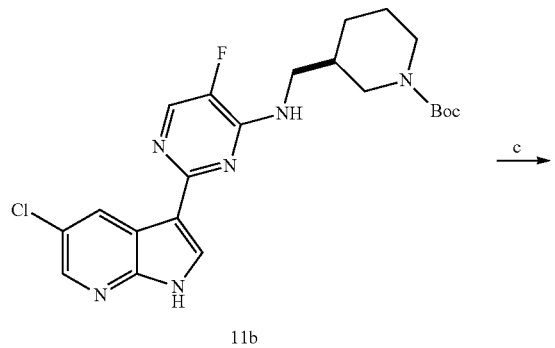

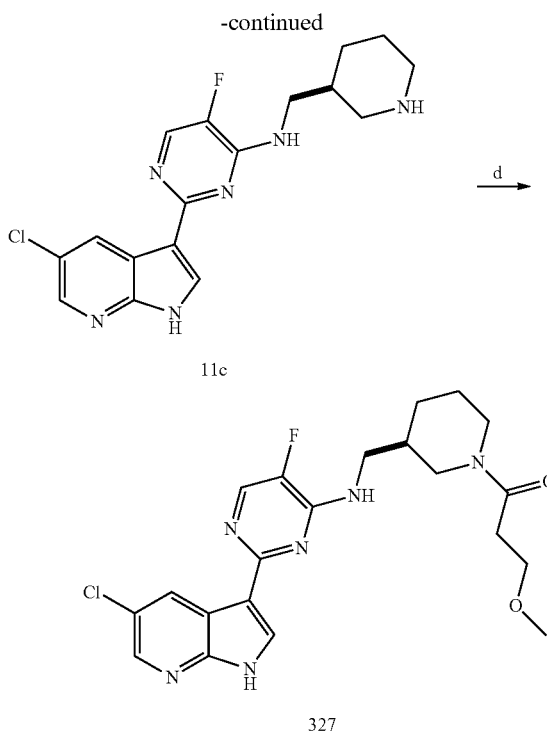

(a) $^iPr_2NEt$, THF; (b) 5-chloro-1-(p-tolylsulfonyl)-3-(4,4,5,5-tetramethyl-1,3,2-dioxaborolan-2-yl)pyrrolo[2,3-b]pyridine, Pd(Ph$_3$P)$_4$, Na$_2$CO$_3$, DME, 130° C.; (c) HCl/dioxane, CH$_2$Cl$_2$; (d) 3-methoxypropanoyl chloride, $^iPr_2NEt$, CH$_2$Cl$_2$/DMF.

Formation of (R)-tert-butyl 3-((2-chloro-5-fluoropyrimidin-4-ylamino)methyl)-piperidine-1-carboxylate (11a)

To a solution of 2,4-dichloro-5-fluoropyrimidine (0.43 g, 2.59 mmol) and (R)-tert-butyl 3-(aminomethyl)piperidine-1-carboxylate (0.56 g, 2.59 mmol) in THF (50 mL) was added $^iPr_2NEt$ (0.45 mL, 2.59 mmol). The reaction mixture was heated at 80° C. at for 8 h. The solvent was concentrated under reduced pressure and the resulting residue was purified by silica gel chromatography (5-30% EtOAc/hexanes) to afford the desired product, 11a.

LCMS (M+1) 345.1.

Formation of (R)-tert-butyl 3-((2-(5-chloro-1H-pyrrolo[2,3-b]pyridin-3-yl)-5-fluoropyrimidin-4-ylamino)methyl)piperidine-1-carboxylate (11b)

To a degassed solution of 5-chloro-1-(p-tolylsulfonyl)-3-(4,4,5,5-tetramethyl-1,3,2-dioxaborolan-2-yl)pyrrolo[2,3-b]pyridine (0.71 g, 1.65 mmol), (R)-tert-butyl 3-((2-chloro-5-fluoropyrimidin-4-ylamino)methyl)-piperidine-1-carboxylate, 11a, (1.19 g, 3.60 mmol) and aqueous K$_2$CO$_3$ (2.48 mL of 2 M solution, 4.97 mmol) in THF (30 mL) was added bis(tri-tert-butylphosphine)palladium(0) (0.17 g, 0.33 mmol). The reaction mixture was degassed for an additional 15 min. The mixture was stirred at room temperature for 4 hours, concentrated in vacuo, and the resulting crude residue was purified by silica gel chromatography (10%-80% EtOAc/hexanes) to afford the desired product, 11b.

LCMS (M+1) 461.4, (M−1) 460.7.

Formation of 2-(5-chloro-1-tosyl-1H-pyrrolo[2,3-b]pyridin-3-yl)-5-fluoro-N-(piperidin-3-ylmethyl)pyrimidin-4-amine (11c)

To a solution of (R)-tert-butyl 3-((2-(5-chloro-1H-pyrrolo[2,3-b]pyridin-3-yl)-5-fluoropyrimidin-4-ylamino)methyl)piperidine-1-carboxylate, 11b, (0.13 g, 2.8 mmol) in 5% MeOH/CH$_2$Cl$_2$ was added 0.7 ml 4N solution of HCl/dioxane. The reaction mixture was stirred at room temperature for 12 hours. The resulting precipitate was filtered and used without further purification.

LCMS (M+1) 361.1.

Formation of (R)-1-(3-((2-(5-chloro-1H-pyrrolo[2,3-b]pyridin-3-yl)-5-fluoropyrimidin-4-ylamino)methyl)piperidin-1-yl)-3-methoxypropan-1-one (327)

To a solution of 2-(5-chloro-1-tosyl-1H-pyrrolo[2,3-b]pyridin-3-yl)-5-fluoro-N-(piperidin-3-ylmethyl)pyrimidin-4-amine, 11c, (0.04 g, 0.11 mmol) in a 10:1 mixture of CH$_2$Cl$_2$/DMF (1 mL) was added $^iPr_2NEt$ (0.058 mL, 0.33 mmol) and 3-methoxypropanoyl chloride (0.02 g, 0.17 mmol). After 12 hours, the solvent was concentrated in vacuo and the resulting crude was and the crude was purified by preparatory HPLC (0.1% TFA-H$_2$O/acetonitrile) to afford the desired product, 327.

LCMS (M+1) 447.3.

Other analogs that can be prepared in the same manner as 327:

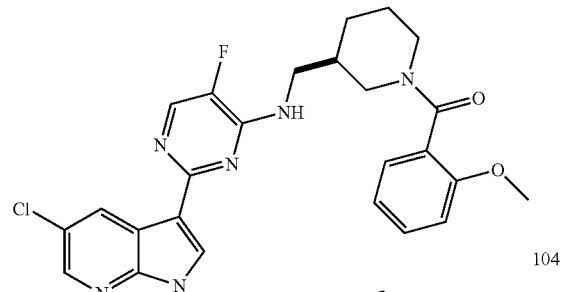

(R)-(3-((2-(5-chloro-1H-pyrrolo[2,3-b]pyridin-3-yl)-5-fluoropyrimidin-4-ylamino)methyl)piperidin-1-yl)(2-methoxyphenyl)methanone (113)

LCMS RT=2.9 (M+1) 479.4, (M−1) 477.6.

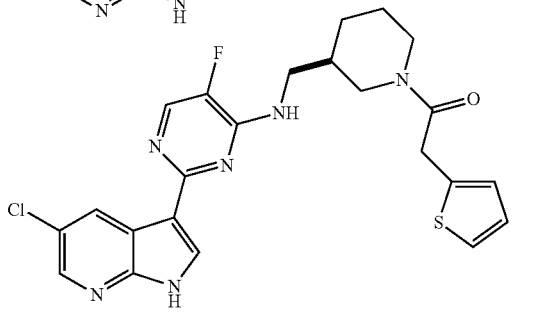

(R)-1-(3-((2-(5-chloro-1H-pyrrolo[2,3-b]pyridin-3-yl)-5-fluoropyrimidin-4-ylamino)methyl)piperidin-1-yl)-2-(thiophen-2-yl)ethanone (104)

LCMS RT=2.8 (M+1) 485.3, (M−1) 483.4.

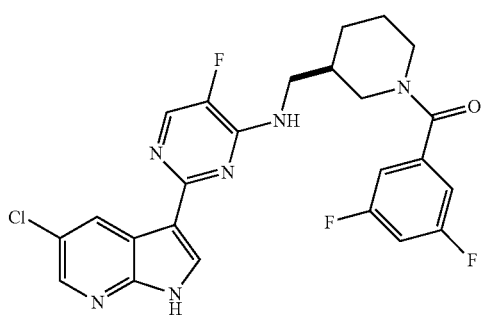

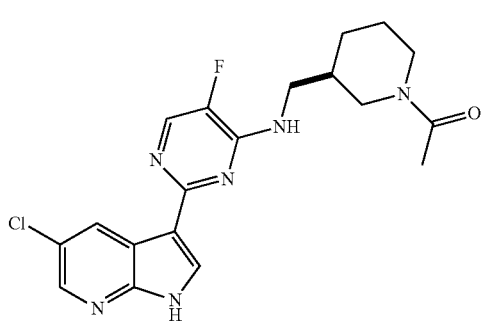

(R)-(3-((2-(5-chloro-1H-pyrrolo[2,3-b]pyridin-3-yl)-5-fluoropyrimidin-4-ylamino)methyl)piperidin-1-yl)(3,5-difluorophenyl)methanone (108)

LCMS RT=2.1 (M+1) 501.3.

(R)-1-(3-((2-(5-chloro-1H-pyrrolo[2,3-b]pyridin-3-yl)-5-fluoropyrimidin-4-ylamino)methyl)piperidin-1-yl)ethanone (111)

LCMS RT=2.5 (M+1) 403.4.

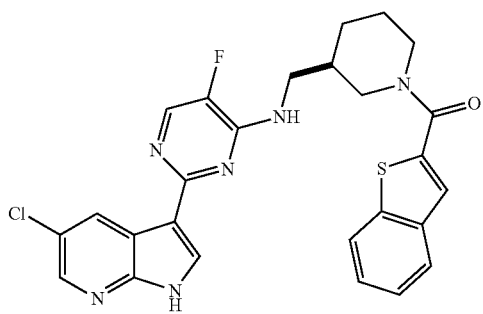

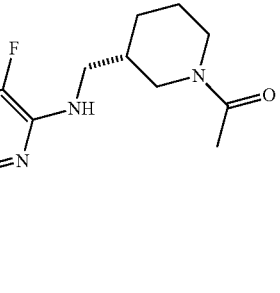

(R)-benzo[b]thiophen-2-yl(3-((2-(5-chloro-1H-pyrrolo[2,3-b]pyridin-3-yl)-5-fluoropyrimidin-4-ylamino)methyl)piperidin-1-yl)methanone (107)

LCMS RT=3.2 (M+1) 521.3.

(S)-1-(3-((2-(5-chloro-1H-pyrrolo[2,3-b]pyridin-3-yl)-5-fluoropyrimidin-4-ylamino)methyl)piperidin-1-yl)ethanone (37)

LCMS RT=2.5 (M+1) 403.3.

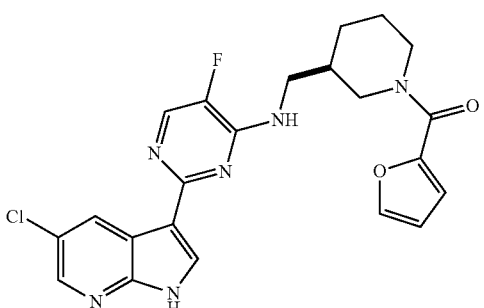

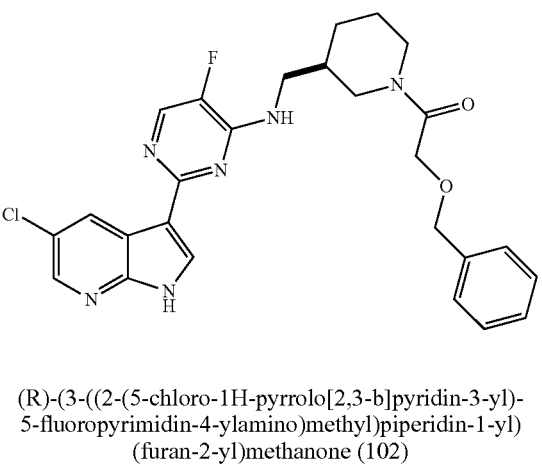

(R)-(3-((2-(5-chloro-1H-pyrrolo[2,3-b]pyridin-3-yl)-5-fluoropyrimidin-4-ylamino)methyl)piperidin-1-yl)(furan-2-yl)methanone (102)

LCMS RT=2.7 (M+1) 455.3, (M−1) 453.3.

(R)-2-(benzyloxy)-1-(3-((2-(5-chloro-1H-pyrrolo[2,3-b]pyridin-3-yl)-5-fluoropyrimidin-4-ylamino)methyl)piperidin-1-yl)ethanone (106)

LCMS RT=3.0 (M+1) 509.3, (M−1) 507.5.

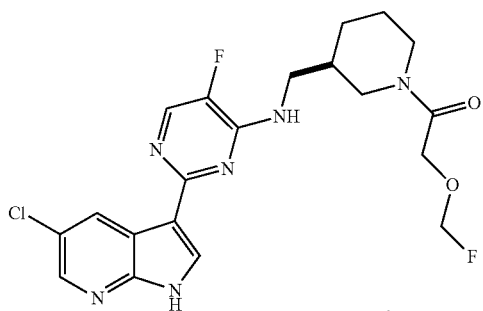

126

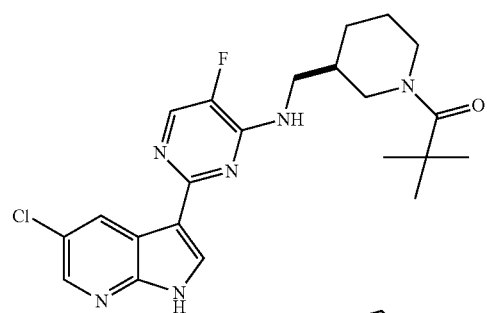

97

(R)-2-fluoroethyl 3-((2-(5-chloro-1H-pyrrolo[2,3-b]pyridin-3-yl)-5-fluoropyrimidin-4-ylamino)methyl)piperidine-1-carboxylate (126)

LCMS RT=2.1 (M+1) 451.4.

(R)-(3-((2-(5-chloro-1H-pyrrolo[2,3-b]pyridin-3-yl)-5-fluoropyrimidin-4-ylamino)methyl)piperidin-1-yl)(thiophen-2-yl)methanone (97)

LCMS RT=2.9 (M+1) 471.2, (M−1) 469.6.

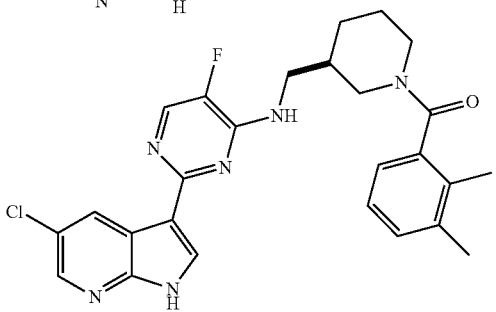

105

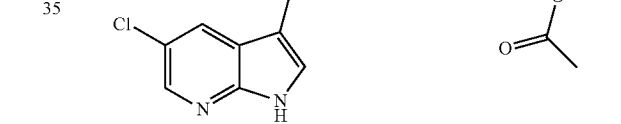

157

(R)-1-(3-((2-(5-chloro-1H-pyrrolo[2,3-b]pyridin-3-yl)-5-fluoropyrimidin-4-ylamino)methyl)piperidin-1-yl)-2,2-dimethylpropan-1-one (105)

LCMS RT=3.0 (M+1) 445.3, (M−1) 443.4.

(R)-(3-((2-(5-chloro-1H-pyrrolo[2,3-b]pyridin-3-yl)-5-fluoropyrimidin-4-ylamino)methyl)piperidin-1-yl)(2,3-dimethylphenyl)methanone (157)

LCMS RT=2.0 (M+1) 493.1.

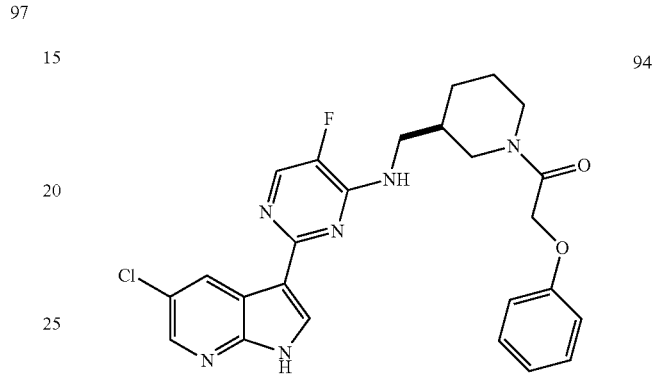

94

110

(R)-1-(3-((2-(5-chloro-1H-pyrrolo[2,3-b]pyridin-3-yl)-5-fluoropyrimidin-4-ylamino)methyl)piperidin-1-yl)-2-phenoxyethanone (94)

LCMS RT=2.9 (M+1) 495.3, (M−1) 493.5.

(R)-2-(3-((2-(5-chloro-1H-pyrrolo[2,3-b]pyridin-3-yl)-5-fluoropyrimidin-4-ylamino)methyl)piperidin-1-yl)-2-oxoethyl ethanoate (110)

LCMS RT=2.5 (M+1) 461.3, (M−1) 459.4.

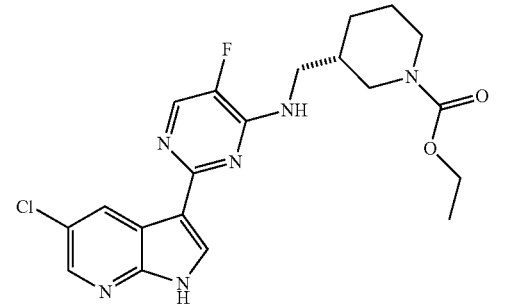

33

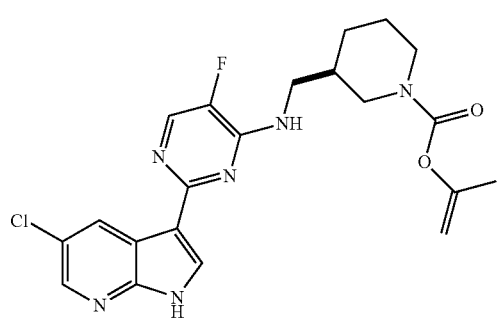

(S)-ethyl 3-((2-(5-chloro-1H-pyrrolo[2,3-b]pyridin-3-yl)-5-fluoropyrimidin-4-ylamino)methyl)piperidine-1-carboxylate (33)

LCMS RT=3.0 (M+1) 433.3, (M−1) 431.4.

(R)-prop-1-en-2-yl 3-((2-(5-chloro-1H-pyrrolo[2,3-b]pyridin-3-yl)-5-fluoropyrimidin-4-ylamino)methyl)piperidine-1-carboxylate (74)

LCMS RT=3.1 (M+1) 445.2, (M−1) 443.4.

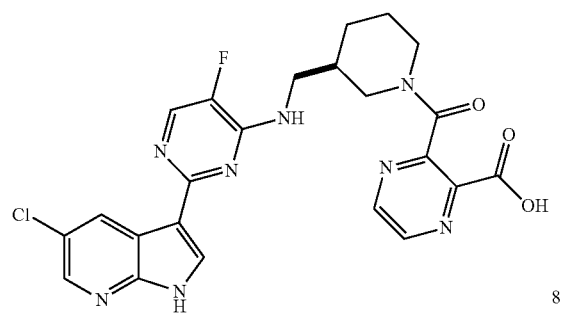

(R)-3-(3-((2-(5-chloro-1H-pyrrolo[2,3-b]pyridin-3-yl)-5-fluoropyrimidin-4-ylamino)methyl)piperidine-1-carbonyl)pyrazine-2-carboxylic acid (82)

LCMS RT=1.6 (M+1) 511.3.

(1S,2R)-2-((R)-3-((2-(5-chloro-1H-pyrrolo[2,3-b]pyridin-3-yl)-5-fluoropyrimidin-4-ylamino)methyl)piperidine-1-carbonyl)cyclopropanecarboxylic acid (83)

LCMS RT=1.6 (M+1) 473.4.

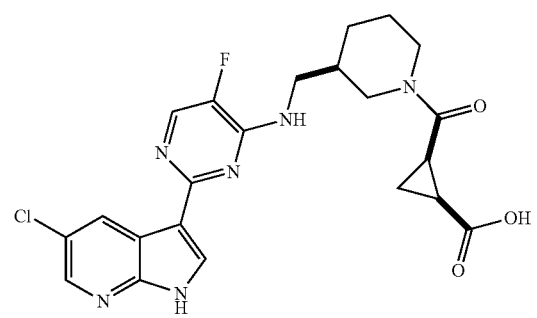

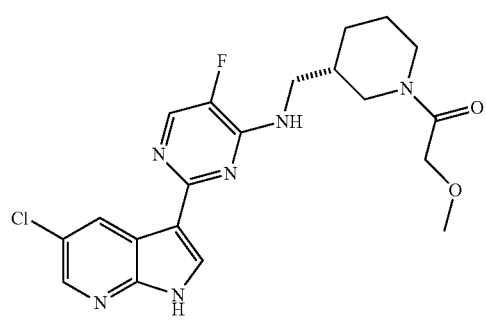

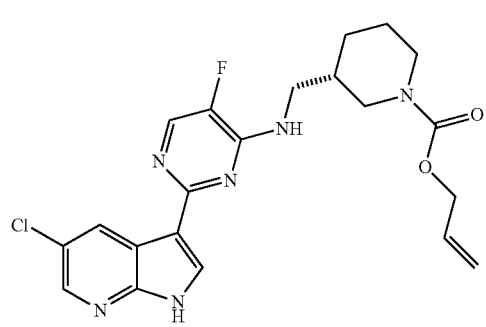

(S)-1-(3-((2-(5-chloro-1H-pyrrolo[2,3-b]pyridin-3-yl)-5-fluoropyrimidin-4-ylamino)methyl)piperidin-1-yl)-2-methoxyethanone (45)

LCMS RT=2.4 (M+1) 433.3, (M−1) 431.4.

(S)-allyl 3-((2-(5-chloro-1H-pyrrolo[2,3-b]pyridin-3-yl)-5-fluoropyrimidin-4-ylamino)methyl)piperidine-1-carboxylate (17)

LCMS RT=3.1 (M+1) 445.3, (M−1) 443.4.

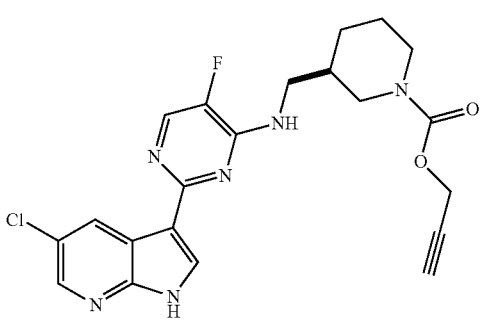

-continued

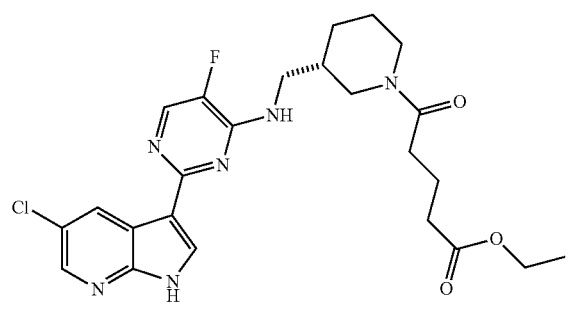

(R)-prop-2-ynyl 3-((2-(5-chloro-1H-pyrrolo[2,3-b]pyridin-3-yl)-5-fluoropyrimidin-4-ylamino)methyl)piperidine-1-carboxylate (122)

LCMS RT=2.9 (M+1) 443.3, (M−1) 441.5.

(S)-ethyl 5-(3-((2-(5-chloro-1H-pyrrolo[2,3-b]pyridin-3-yl)-5-fluoropyrimidin-4-ylamino)methyl)piperidin-1-yl)-5-oxopentanoate (19)

LCMS RT=2.8 (M+1) 503.4, (M−1) 501.5.

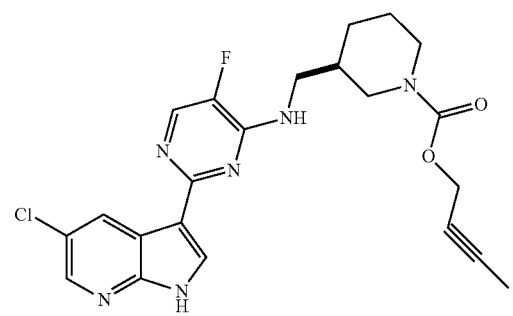

(R)-but-2-ynyl 3-((2-(5-chloro-1H-pyrrolo[2,3-b]pyridin-3-yl)-5-fluoropyrimidin-4-ylamino)methyl)piperidine-1-carboxylate (127)

LCMS RT=3.1 (M+1) 457.3, (M−1) 455.6.

(S)-methyl 3-((2-(5-chloro-1H-pyrrolo[2,3-b]pyridin-3-yl)-5-fluoropyrimidin-4-ylamino)methyl)piperidine-1-carboxylate (23)

LCMS RT=2.8 (M+1) 419.3, (M−1) 417.3.

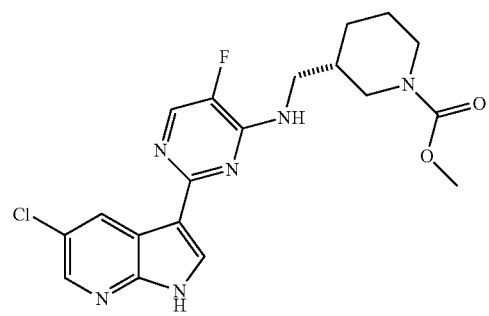

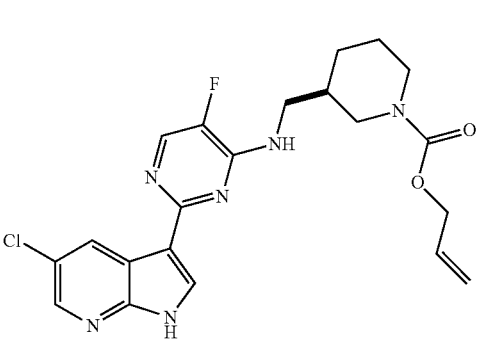

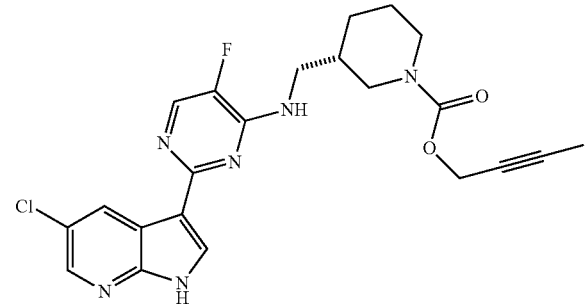

(R)-allyl 3-((2-(5-chloro-1H-pyrrolo[2,3-b]pyridin-3-yl)-5-fluoropyrimidin-4-ylamino)methyl)piperidine-1-carboxylate (119)

LCMS RT=3.1 (M+1) 445.4, (M−1) 443.5.

(S)-but-2-ynyl 3-((2-(5-chloro-1H-pyrrolo[2,3-b]pyridin-3-yl)-5-fluoropyrimidin-4-ylamino)methyl)piperidine-1-carboxylate (30)

LCMS RT=3.1 (M+1) 457.3, (M−1) 455.6.

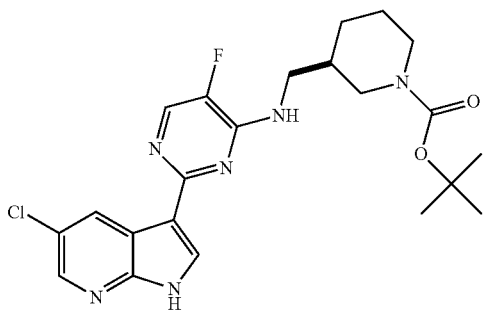

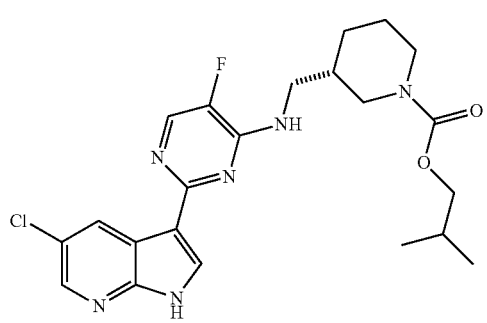

(R)-tert-butyl 3-((2-(5-chloro-1H-pyrrolo[2,3-b]pyridin-3-yl)-5-fluoropyrimidin-4-ylamino)methyl)piperidine-1-carboxylate (15)

LCMS RT=2.7 (M+1) 461.3.

(S)-isobutyl 3-((2-(5-chloro-1H-pyrrolo[2,3-b]pyridin-3-yl)-5-fluoropyrimidin-4-ylamino)methyl)piperidine-1-carboxylate (28)

LCMS RT=3.3 (M+1) 461.4.

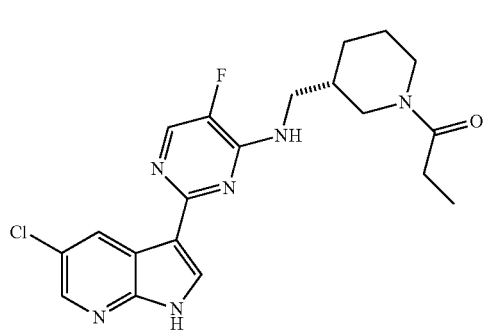

(S)-1-(3-((2-(5-chloro-1H-pyrrolo[2,3-b]pyridin-3-yl)-5-fluoropyrimidin-4-ylamino)methyl)piperidin-1-yl)propan-1-one (32)

LCMS RT=1.9 (M+1) 417.2.

(S)-1-(3-((2-(5-chloro-1H-pyrrolo[2,3-b]pyridin-3-yl)-5-fluoropyrimidin-4-ylamino)methyl)piperidin-1-yl)-2-methylpropan-1-one (34)

LCMS RT=3.2 (M+1) 447.4, (M−1) 445.5.

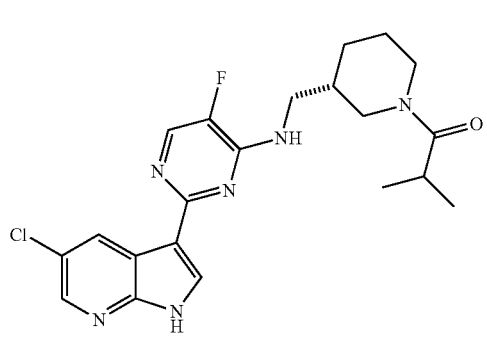

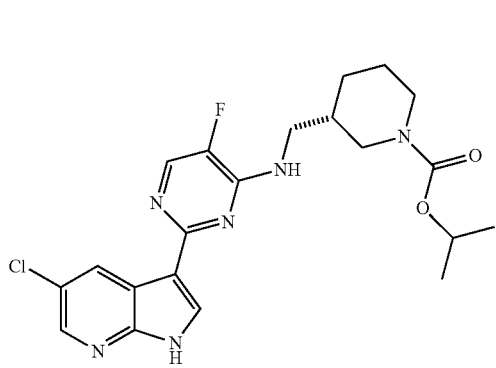

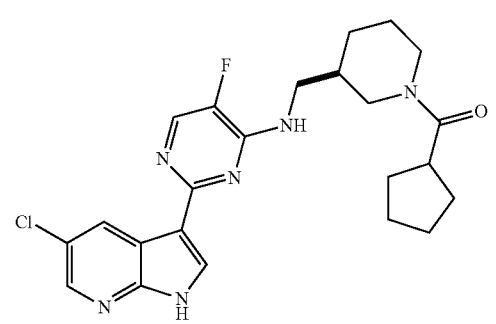

(S)-isopropyl 3-((2-(5-chloro-1H-pyrrolo[2,3-b]pyridin-3-yl)-5-fluoropyrimidin-4-ylamino)methyl)piperidine-1-carboxylate (3S)

LCMS RT=3.0 (M+1) 447.3, (M−1) 445.4.

(R)-(3-((2-(5-chloro-1H-pyrrolo[2,3-b]pyridin-3-yl)-5-fluoropyrimidin-4-ylamino)methyl)piperidin-1-yl)(cyclopentyl)methanone (99)

LCMS RT=3.1 (M+1) 457.3, (M−1) 455.4.\

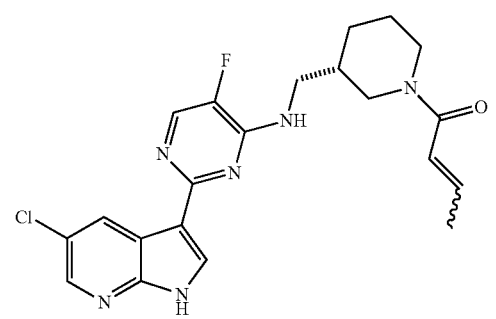

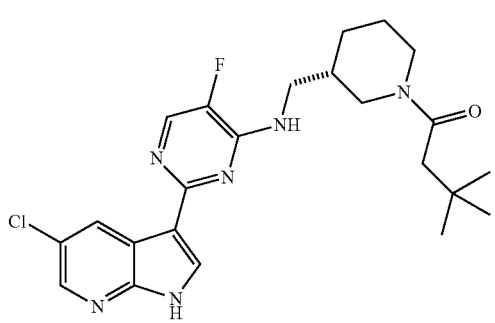

42

(S)-1-(3-((2-(5-chloro-1H-pyrrolo[2,3-b]pyridin-3-yl)-5-fluoropyrimidin-4-ylamino)methyl)piperidin-1-yl)but-2-en-1-one (41)

LCMS RT=2.7 (M+1) 429.3, (M−1) 427.4.

(S)-1-(3-((2-(5-chloro-1H-pyrrolo[2,3-b]pyridin-3-yl)-5-fluoropyrimidin-4-ylamino)methyl)piperidin-1-yl)-3,3-dimethylbutan-1-one (42)

LCMS RT=3.1 (M+1) 459.3, (M−1) 457.4.

44

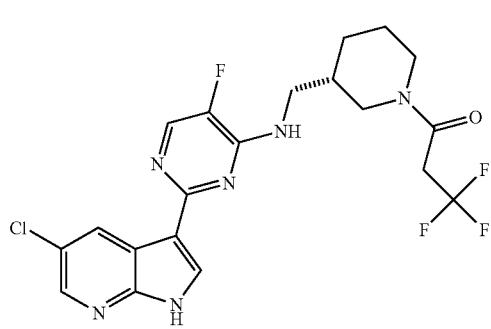

(S)-1-(3-((2-(5-chloro-1H-pyrrolo[2,3-b]pyridin-3-yl)-5-fluoropyrimidin-4-ylamino)methyl)piperidin-1-yl)-3,3,3-trifluoropropan-1-one (44)

LCMS RT=2.8 (M+1) 471.3, (M−1) 469.4.

(S)-2-(3-((2-(5-chloro-1H-pyrrolo[2,3-b]pyridin-3-yl)-5-fluoropyrimidin-4-ylamino)methyl)piperidin-1-yl)-N,N,N-trimethyl-2-oxoethanaminium (43)

LCMS RT=2.4 (M+1) 460.3, (M−1) 458.5.

46

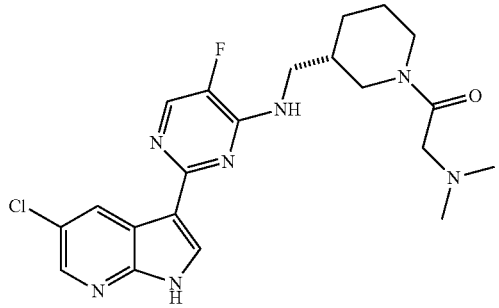

47

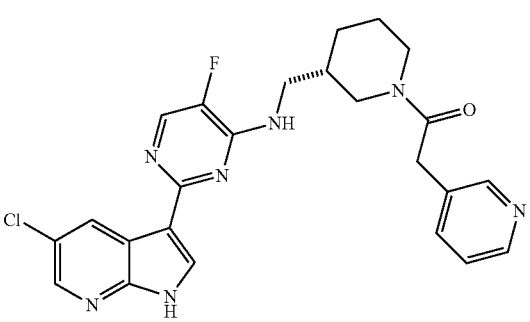

(S)-1-(3-((2-(5-chloro-1H-pyrrolo[2,3-b]pyridin-3-yl)-5-fluoropyrimidin-4-ylamino)methyl)piperidin-1-yl)-2-(dimethylamino)ethanone (46)

LCMS RT=2.2 (M+1) 446.4, (M−1) 444.5.

(S)-1-(3-((2-(5-chloro-1H-pyrrolo[2,3-b]pyridin-3-yl)-5-fluoropyrimidin-4-ylamino)methyl)piperidin-1-yl)-2-(pyridin-3-yl)ethanone (47)

LCMS RT=2.4 (M+1) 480.3, (M−1) 478.6.

49

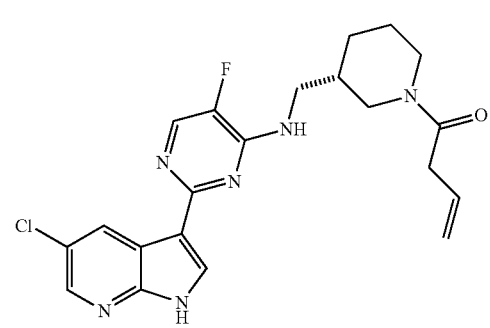

48

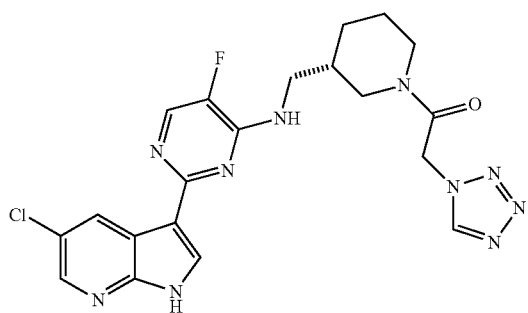

(S)-1-(3-((2-(5-chloro-1H-pyrrolo[2,3-b]pyridin-3-yl)-5-fluoropyrimidin-4-ylamino)methyl)piperidin-1-yl)but-3-en-1-one (49)

LCMS RT=2.7 (M+1) 429.3, (M−1) 427.4.

(S)-1-(3-((2-(5-chloro-1H-pyrrolo[2,3-b]pyridin-3-yl)-5-fluoropyrimidin-4-ylamino)methyl)piperidin-1-yl)-2-(1H-tetrazol-1-yl)ethanone (48)

LCMS RT=2.4 (M+1) 471.3, (M−1) 469.4.

51

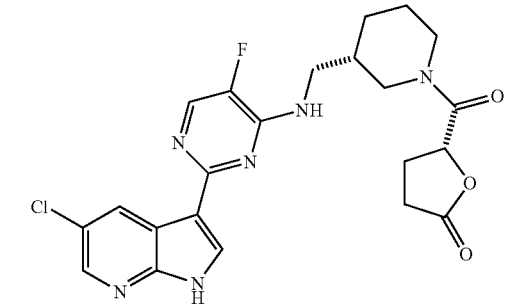

50

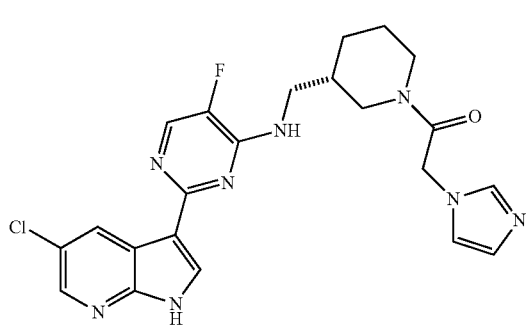

(R)-5-((S)-3-((2-(5-chloro-1H-pyrrolo[2,3-b]pyridin-3-yl)-5-fluoropyrimidin-4-ylamino)methyl)piperidine-1-carbonyl)dihydrofuran-2(3H)-one (51)

LCMS RT=1.7 (M+1) 472.9.

(S)-1-(3-((2-(5-chloro-1H-pyrrolo[2,3-b]pyridin-3-yl)-5-fluoropyrimidin-4-ylamino)methyl)piperidin-1-yl)-2-(1H-imidazol-1-yl)ethanone (50)

LCMS RT=2.3 (M+1) 469.3, (M−1) 467.4.

52

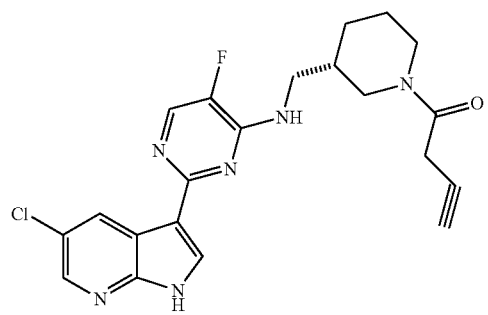

53

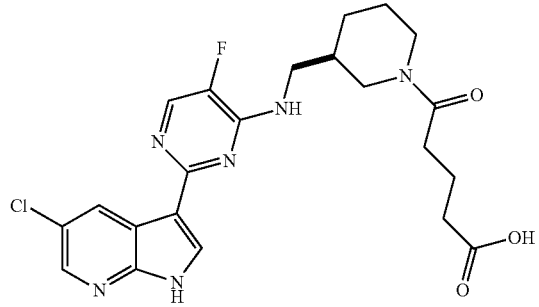

(S)-1-(3-((2-(5-chloro-1H-pyrrolo[2,3-b]pyridin-3-yl)-5-fluoropyrimidin-4-ylamino)methyl)piperidin-1-yl)pent-4-yn-1-one (52)

LCMS RT=1.9 (M+1) 441.3.

(R)-5-(3-((2-(5-chloro-1H-pyrrolo[2,3-b]pyridin-3-yl)-5-fluoropyrimidin-4-ylamino)methyl)piperidin-1-yl)-5-oxopentanoic acid (53)

LCMS RT=1.8 (M+1) 475.3, (M−1) 473.4.

54

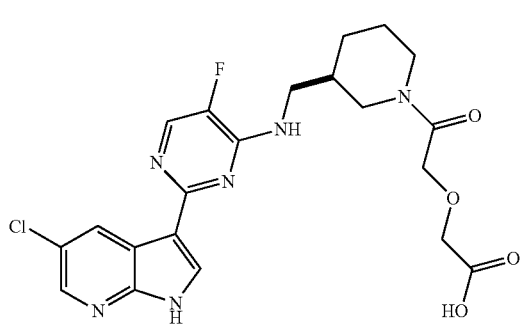

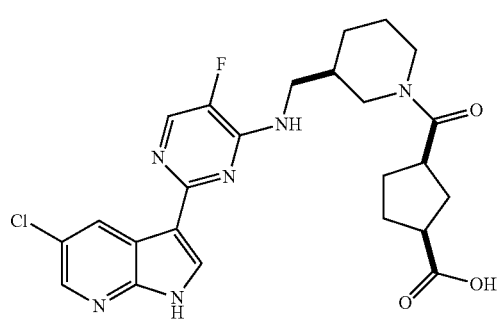

(R)-2-(2-(3-((2-(5-chloro-1H-pyrrolo[2,3-b]pyridin-3-yl)-5-fluoropyrimidin-4-ylamino)methyl)piperidin-1-yl)-2-oxoethoxy)ethanoic acid (54)

LCMS RT=1.7 (M+1) 477.3, (M−1) 475.4.

(1S,3R)-3-((R)-3-((2-(5-chloro-1H-pyrrolo[2,3-b]pyridin-3-yl)-5-fluoropyrimidin-4-ylamino)methyl)piperidine-1-carbonyl)cyclopentanecarboxylic acid (55)

LCMS RT=2.5 (M+1) 501.3, (M−1) 499.6.

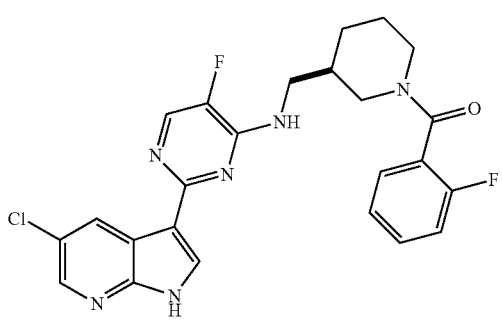

(R)-(3-((2-(5-chloro-1H-pyrrolo[2,3-b]pyridin-3-yl)-5-fluoropyrimidin-4-ylamino)methyl)piperidin-1-yl)(2-fluorophenyl)methanone (58)

LCMS RT=2.9 (M+1) 483.3, (M−1) 481.5

(R)-5-(3-((2-(5-chloro-1H-pyrrolo[2,3-b]pyridin-3-yl)-5-fluoropyrimidin-4-ylamino)methyl)piperidin-1-yl)-3,3-dimethyl-5-oxopentanoic acid (80)

LCMS RT=1.9 (M+1) 503.3..

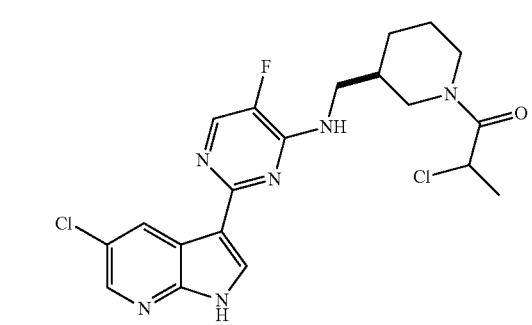

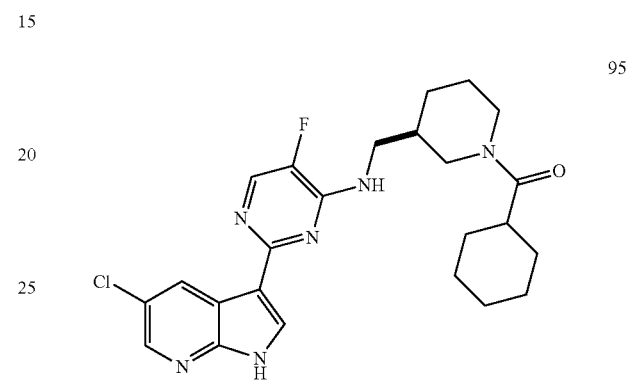

2-chloro-1-((R)-3-((2-(5-chloro-1H-pyrrolo[2,3-b]pyridin-3-yl)-5-fluoropyrimidin-4-ylamino)methyl)piperidin-1-yl)propan-1-one (93)

LCMS RT=2.9 (M+1) 451.2, (M−1) 449.4.

(R)-(3-((2-(5-chloro-1H-pyrrolo[2,3-b]pyridin-3-yl)-5-fluoropyrimidin-4-ylamino)methyl)piperidin-1-yl)(cyclohexyl)methanone (95)

LCMS RT=3.2 (M+1) 471.3, (M−1) 449.4.

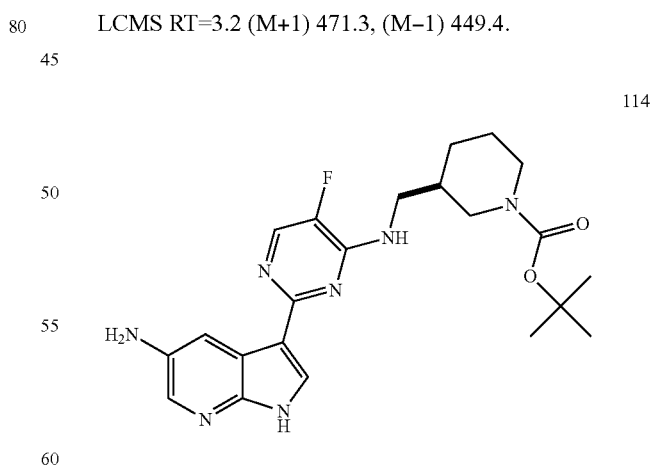

(R)-tert-butyl 3-((2-(5-amino-1H-pyrrolo[2,3-b]pyridin-3-yl)-5-fluoropyrimidin-4-ylamino)methyl)piperidine-1-carboxylate (114)

LCMS RT=2.7 (M+1) 461.3.

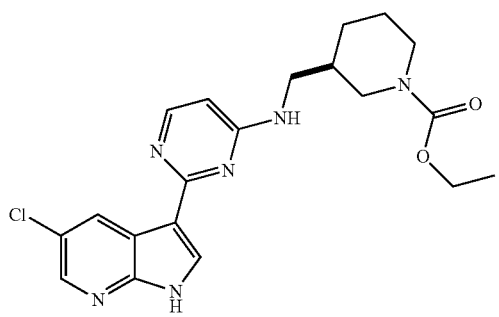

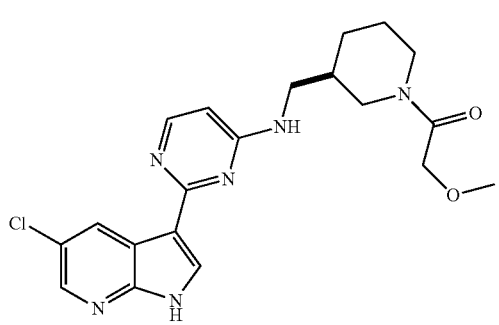

(R)-ethyl 3-((2-(5-chloro-1H-pyrrolo[2,3-b]pyridin-3-yl)pyrimidin-4-ylamino)methyl)piperidine-1-carboxylate (495)

LCMS RT=1.7 (M+1) 385.4.

(R)-1-(3-((2-(5-chloro-1H-pyrrolo[2,3-b]pyridin-3-yl)pyrimidin-4-ylamino)methyl)piperidin-1-yl)-2-methoxyethanone (491)

LCMS RT=1.7 (M+1) 415.4.

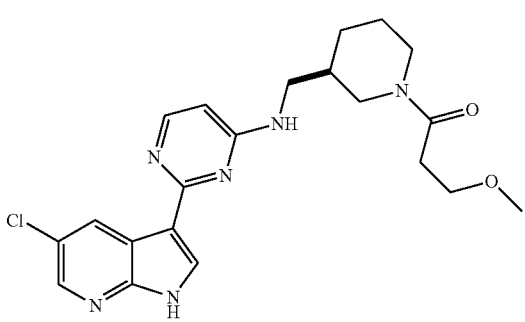

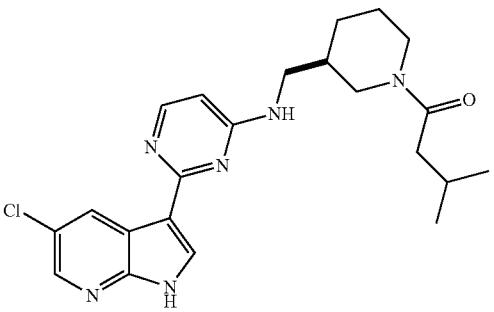

(R)-1-(3-((2-(5-chloro-1H-pyrrolo[2,3-b]pyridin-3-yl)pyrimidin-4-ylamino)methyl)piperidin-1-yl)-3-methoxypropan-1-one (493)

LCMS RT=1.7 (M+1) 429.5.

(R)-1-(3-((2-(5-chloro-1H-pyrrolo[2,3-b]pyridin-3-yl)pyrimidin-4-ylamino)methyl)piperidin-1-yl)-3-methylbutan-1-one (494)

LCMS RT=1.9 (M+1) 427.5.

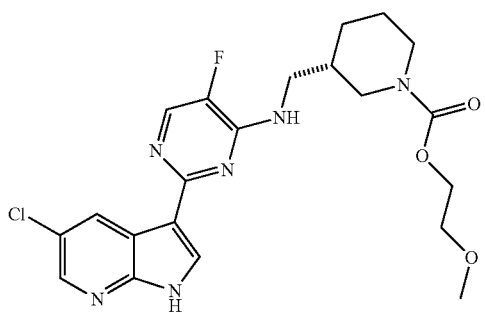

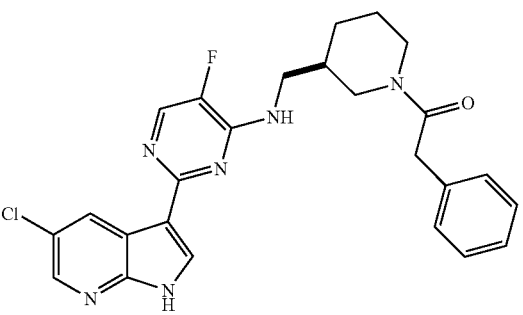

(S)-2-methoxyethyl 3-((2-(5-chloro-1H-pyrrolo[2,3-b]pyridin-3-yl)-5-fluoropyrimidin-4-ylamino)methyl)piperidine-1-carboxylate (24)

LCMS RT=2.8 (M+1) 463.2, (M−1) 461.3.

(R)-1-(3-((2-(5-chloro-1H-pyrrolo[2,3-b]pyridin-3-yl)-5-fluoropyrimidin-4-ylamino)methyl)piperidin-1-yl)-2-phenylethanone (56)

LCMS RT=2.9 (M+1) 479.3, (M−1) 477.4.

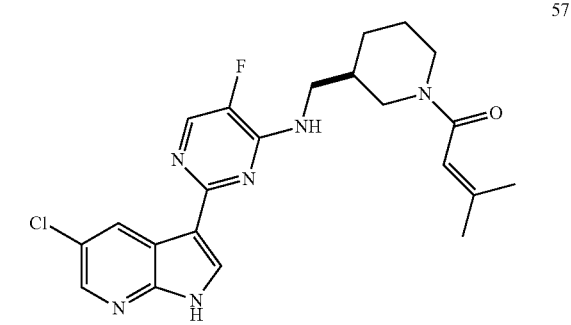

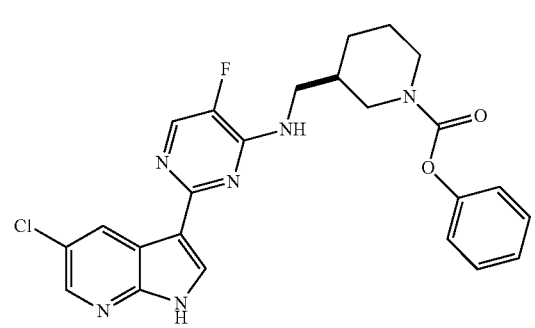

(R)-1-(3-((2-(5-chloro-1H-pyrrolo[2,3-b]pyridin-3-yl)-5-fluoropyrimidin-4-ylamino)methyl)piperidin-1-yl)-3-methylbut-2-en-1-one (57)

LCMS RT=2.8 (M+1) 443.3, (M−1) 441.4.

(R)-4-(methoxycarbonyl)phenyl 3-((2-(5-chloro-1H-pyrrolo[2,3-b]pyridin-3-yl)-5-fluoropyrimidin-4-ylamino)methyl)piperidine-1-carboxylate (63)

LCMS RT=3.2 (M+1) 539.3, (M−1) 537.4.

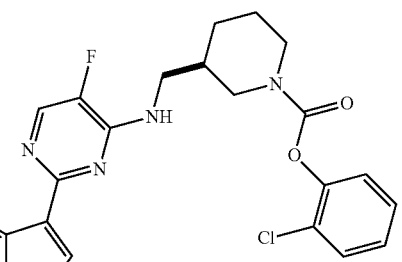

(R)-phenyl 3-((2-(5-chloro-1H-pyrrolo[2,3-b]pyridin-3-yl)-5-fluoropyrimidin-4-ylamino)methyl)piperidine-1-carboxylate (68)

LCMS RT=3.2 (M+1) 481.4, (M−1) 479.4.

(R)-2-chlorophenyl 3-((2-(5-chloro-1H-pyrrolo[2,3-b]pyridin-3-yl)-5-fluoropyrimidin-4-ylamino)methyl)piperidine-1-carboxylate (70)

LCMS RT=3.3 (M+1) 515.3, (M−1) 513.3.

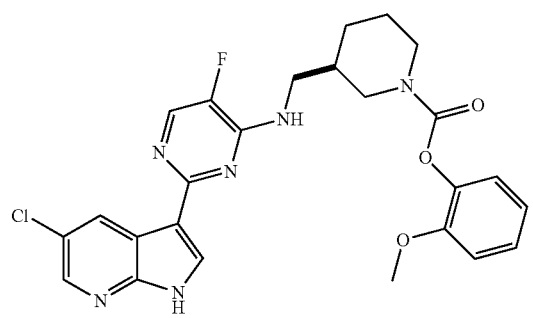

(R)-2-methoxyphenyl 3-((2-(5-chloro-1H-pyrrolo[2,3-b]pyridin-3-yl)-5-fluoropyrimidin-4-ylamino)methyl)piperidine-1-carboxylate (69)

LCMS RT=3.2 (M+1) 511.3.

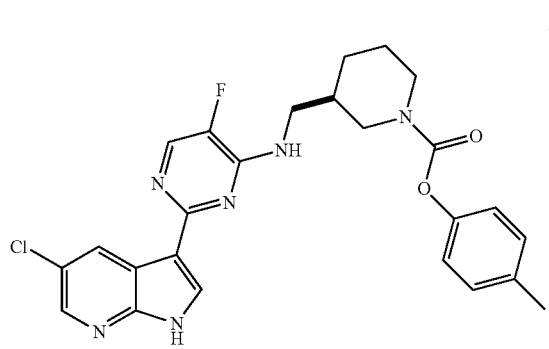

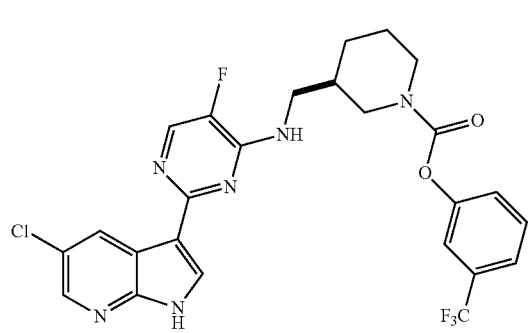

(R)-p-tolyl 3-((2-(5-chloro-1H-pyrrolo[2,3-b]pyridin-3-yl)-5-fluoropyrimidin-4-ylamino)methyl)piperidine-1-carboxylate (71)

LCMS RT=3.4 (M+1) 495.3, (M−1) 493.4.

(R)-3-(trifluoromethyl)phenyl 3-((2-(5-chloro-1H-pyrrolo[2,3-b]pyridin-3-yl)-5-fluoropyrimidin-4-ylamino)methyl)piperidine-1-carboxylate (72)

LCMS RT=3.5 (M+1) 549.3, (M−1) 547.4.

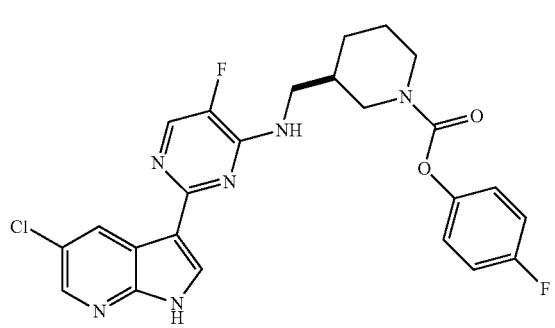

(R)-4-fluorophenyl 3-((2-(5-chloro-1H-pyrrolo[2,3-b]pyridin-3-yl)-5-fluoropyrimidin-4-ylamino)methyl)piperidine-1-carboxylate (73)

LCMS RT=3.3 (M+1) 499.3, (M−1) 497.4.

(R)-2-(1-(2-(3-((2-(5-chloro-1H-pyrrolo[2,3-b]pyridin-3-yl)-5-fluoropyrimidin-4-ylamino)methyl)piperidin-1-yl)-2-oxoethyl)cyclopentyl)ethanoic acid (81)

LCMS RT=2.0 (M+1) 529.3.

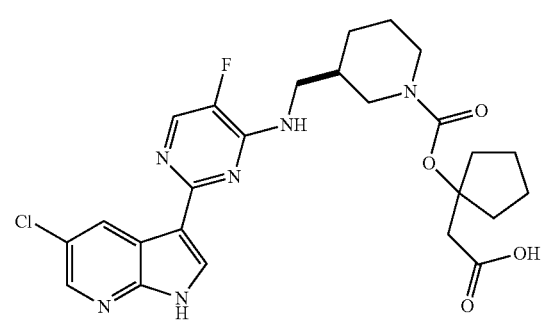
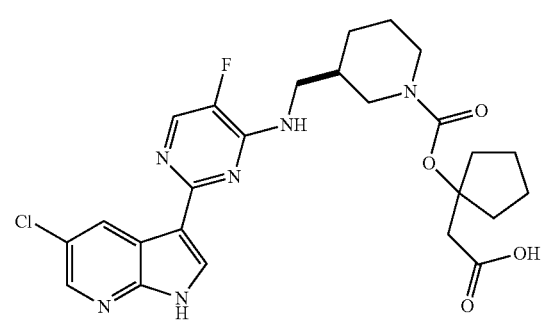

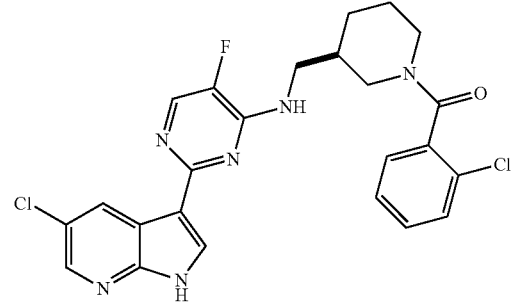

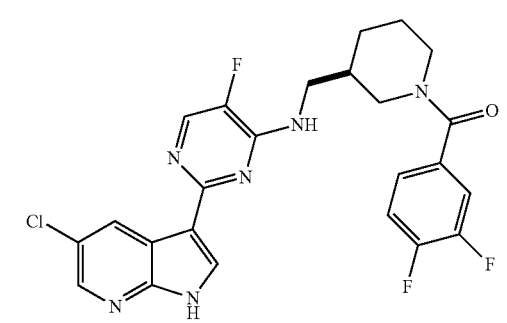

(R)-(3-((2-(5-chloro-1H-pyrrolo[2,3-b]pyridin-3-yl)-5-fluoropyrimidin-4-ylamino)methyl)piperidin-1-yl)(2-chlorophenyl)methanone (84)

LCMS RT=2.0 (M+1) 499.4.

(R)-(3-((2-(5-chloro-1H-pyrrolo[2,3-b]pyridin-3-yl)-5-fluoropyrimidin-4-ylamino)methyl)piperidin-1-yl)(3,4-difluorophenyl)methanone (85)

LCMS RT=2.1 (M+1) 501.3.

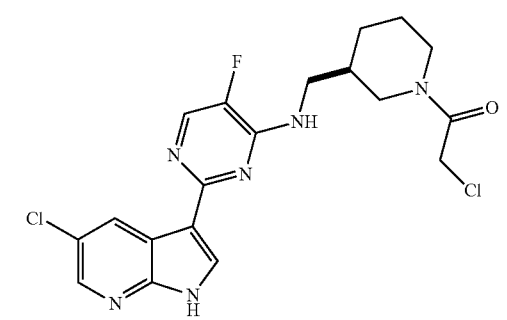

96

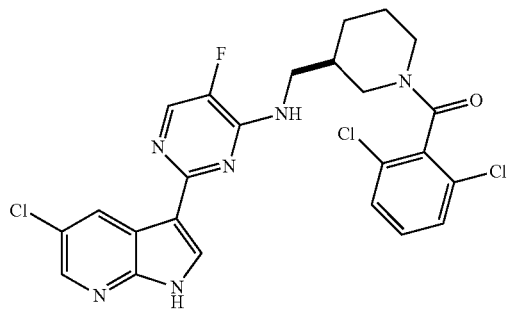

(R)-2-chloro-1-(3-((2-(5-chloro-1H-pyrrolo[2,3-b]pyridin-3-yl)-5-fluoropyrimidin-4-ylamino)methyl)piperidin-1-yl)ethanone (92)

LCMS RT=2.7 (M+1) 437.2, (M−1) 435.3.

(R)-(3-((2-(5-chloro-1H-pyrrolo[2,3-b]pyridin-3-yl)-5-fluoropyrimidin-4-ylamino)methyl)piperidin-1-yl)(2,6-dichlorophenyl)methanone (96)

LCMS RT=2.9 (M+1) 535.2, (M−1) 533.2.

98

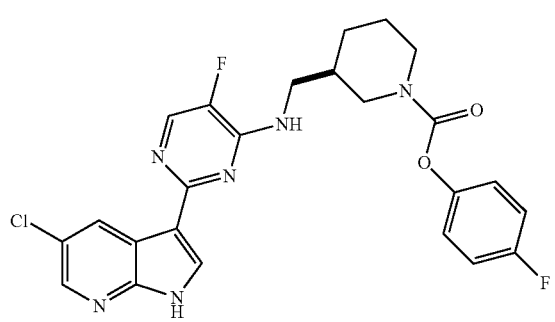

100

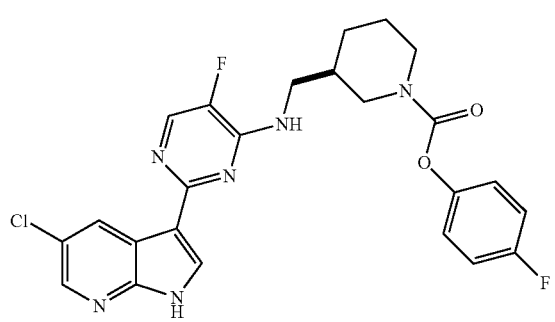

(R)-1-(3-((2-(5-chloro-1H-pyrrolo[2,3-b]pyridin-3-yl)-5-fluoropyrimidin-4-ylamino)methyl)piperidin-1-yl)-2-(4-fluorophenyl)ethanone (98)

LCMS RT=2.9 (M+1) 497.3, (M−1) 495.4.

(R)-1-(3-((2-(5-chloro-1H-pyrrolo[2,3-b]pyridin-3-yl)-5-fluoropyrimidin-4-ylamino)methyl)piperidin-1-yl)-2-cyclopentylethanone (100)

LCMS RT=3.1 (M+1) 471.3, (M−1) 469.5.

111

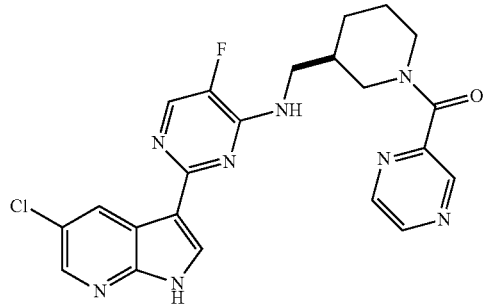

186

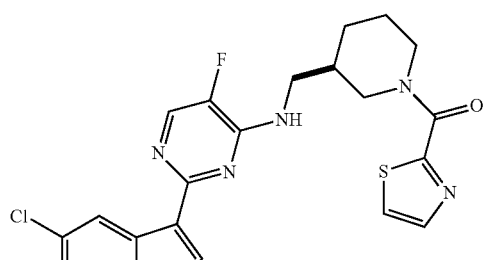

(R)-(3-((2-(5-chloro-1H-pyrrolo[2,3-b]pyridin-3-yl)-5-fluoropyrimidin-4-ylamino)methyl)piperidin-1-yl)(pyrazin-2-yl)methanone (111)

LCMS RT=2.5 (M+1) 467.2, (M−1) 465.4.

(R)-(3-((2-(5-chloro-1H-pyrrolo[2,3-b]pyridin-3-yl)-5-fluoropyrimidin-4-ylamino)methyl)piperidin-1-yl)(furan-2-yl)methanone (186)

LCMS RT=2.7 (M+1) 455.3, (M−1) 453.3.

103

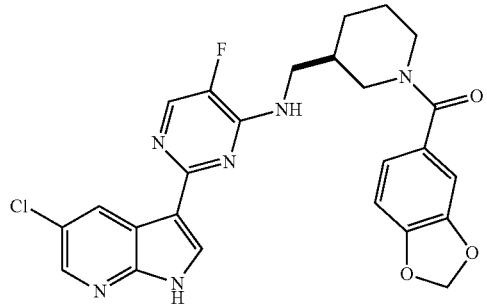

152

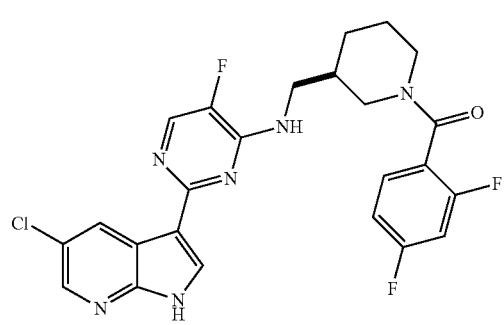

(R)-benzo[d][1,3]dioxol-5-yl(3-((2-(5-chloro-1H-pyrrolo[2,3-b]pyridin-3-yl)-5-fluoropyrimidin-4-ylamino)methyl)piperidin-1-yl)methanone (103)

LCMS RT=2.8 (M+1) 509.3, (M−1) 507.5.

(R)-(3-((2-(5-chloro-1H-pyrrolo[2,3-b]pyridin-3-yl)-5-fluoropyrimidin-4-ylamino)methyl)piperidin-1-yl)(2,4-difluorophenyl)methanone (152)

LCMS RT=2.8 (M+1) 501.3, (M−1) 499.4.

112

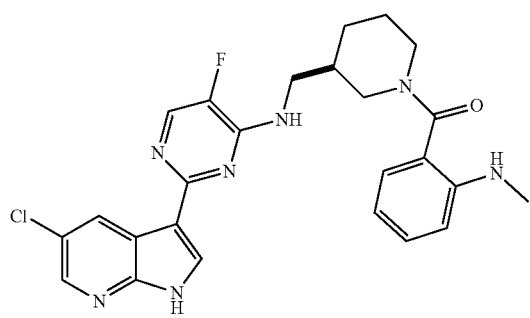

109

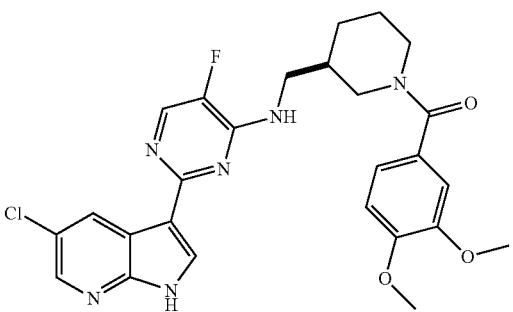

(R)-(3-((2-(5-chloro-1H-pyrrolo[2,3-b]pyridin-3-yl)-5-fluoropyrimidin-4-ylamino)methyl)piperidin-1-yl)(2-(methylamino)phenyl)methanone (112)

LCMS RT=3.0 (M+1) 494.3, (M−1) 492.5.

(R)-(3-((2-(5-chloro-1H-pyrrolo[2,3-b]pyridin-3-yl)-5-fluoropyrimidin-4-ylamino)methyl)piperidin-1-yl)(3,4-dimethoxyphenyl)methanone (109)

LCMS RT=2.7 (M+1) 525.3, (M−1) 523.4.

86

142

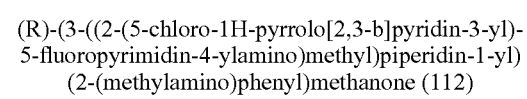

(R)-(3-((2-(5-chloro-1H-pyrrolo[2,3-b]pyridin-3-yl)-5-fluoropyrimidin-4-ylamino)methyl)piperidin-1-yl)(3,5-difluorophenyl)methanone (86)

LCMS RT=2.8 (M+1) 501, (M−1) 499.

(R)-(3-((2-(5-chloro-1H-pyrrolo[2,3-b]pyridin-3-yl)-5-fluoropyrimidin-4-ylamino)methyl)piperidin-1-yl)(6-fluoro-4H-benzo[d][1,3]dioxin-8-yl)methanone (142)

LCMS RT=2.8 (M+1) 541.5.

143

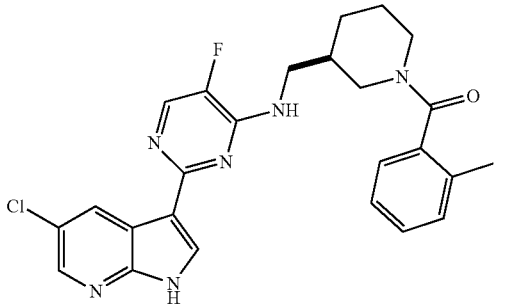

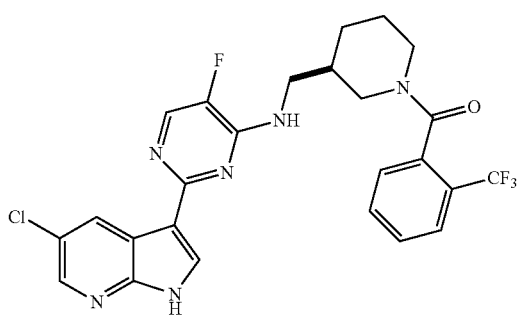

(R)-(3-((2-(5-chloro-1H-pyrrolo[2,3-b]pyridin-3-yl)-5-fluoropyrimidin-4-ylamino)methyl)piperidin-1-yl)(o-tolyl)methanone (143)

LCMS RT=2.9 (M+1) 479.4, (M−1) 477.6.

(R)-(3-((2-(5-chloro-1H-pyrrolo[2,3-b]pyridin-3-yl)-5-fluoropyrimidin-4-ylamino)methyl)piperidin-1-yl)(2-(trifluoromethyl)phenyl)methanone (146)

LCMS RT=3.0 (M+1) 533.3, (M−1) 531.5.

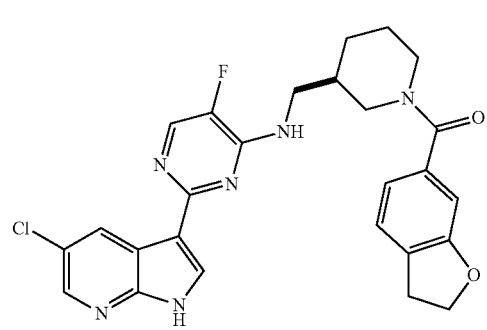

(R)-(3-((2-(5-chloro-1H-pyrrolo[2,3-b]pyridin-3-yl)-5-fluoropyrimidin-4-ylamino)methyl)piperidin-1-yl)(2,3-dihydrobenzofuran-6-yl)methanone (145)

LCMS RT=2.9 (M+1) 507.3, (M−1) 505.5.

(R)-(3-((2-(5-chloro-1H-pyrrolo[2,3-b]pyridin-3-yl)-5-fluoropyrimidin-4-ylamino)methyl)piperidin-1-yl)(2,4-dichlorophenyl)methanone (147)

LCMS RT=3.2 (M+1) 533.3, (M−1) 531.4.

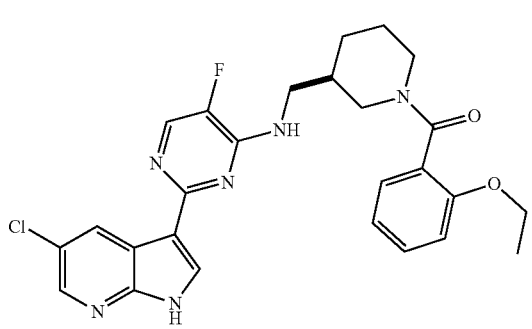

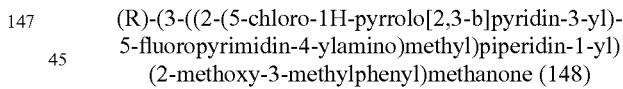

(R)-(3-((2-(5-chloro-1H-pyrrolo[2,3-b]pyridin-3-yl)-5-fluoropyrimidin-4-ylamino)methyl)piperidin-1-yl)(2-ethoxyphenyl)methanone (158)

LCMS RT=3.0 (M+1) 509.4, (M−1) 507.5.

(R)-(3-((2-(5-chloro-1H-pyrrolo[2,3-b]pyridin-3-yl)-5-fluoropyrimidin-4-ylamino)methyl)piperidin-1-yl)(2-methoxy-3-methylphenyl)methanone (148)

LCMS RT=3.0 (M+1) 509.3, (M−1) 507.5.

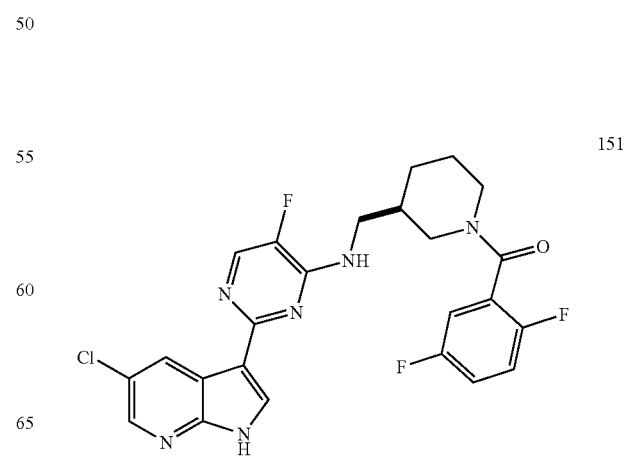

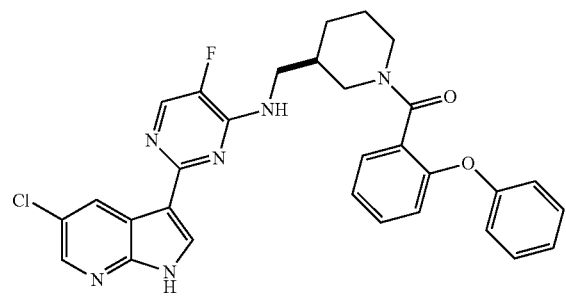

(R)-(3-((2-(5-chloro-1H-pyrrolo[2,3-b]pyridin-3-yl)-
5-fluoropyrimidin-4-ylamino)methyl)piperidin-1-yl)
(2,5-difluorophenyl)methanone (151)

LCMS RT=2.9 (M+1) 501.2, (M−1) 499.5.

(R)-(3-((2-(5-chloro-1H-pyrrolo[2,3-b]pyridin-3-yl)-
5-fluoropyrimidin-4-ylamino)methyl)piperidin-1-yl)
(2-phenoxyphenyl)methanone (150)

LCMS RT=3.2 (M+1) 557.3, (M−1) 555.6.

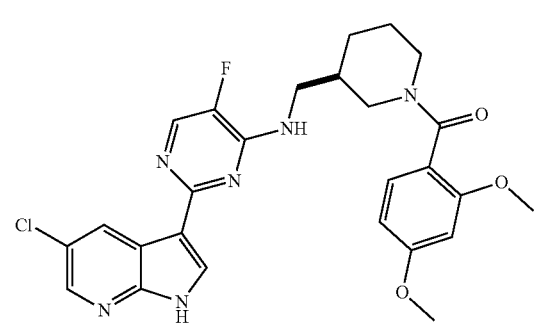

(R)-(3-((2-(5-chloro-1H-pyrrolo[2,3-b]pyridin-3-yl)-
5-fluoropyrimidin-4-ylamino)methyl)piperidin-1-yl)
(2,4-dimethoxyphenyl)methanone (154)

LCMS RT=2.3 (M+1) 525.3, (M−1) 523.2.

(R)-(3-((2-(5-chloro-1H-pyrrolo[2,3-b]pyridin-3-yl)-
5-fluoropyrimidin-4-ylamino)methyl)piperidin-1-yl)
(cyclopropyl)methanone (325)

LCMS RT=2.7 (M+1) 429.2.

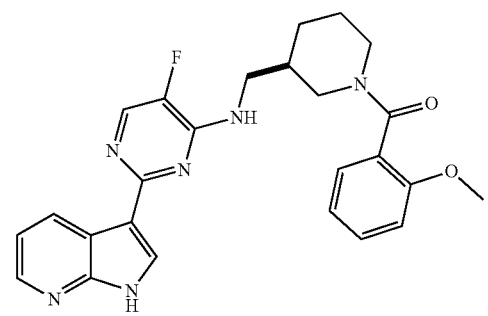

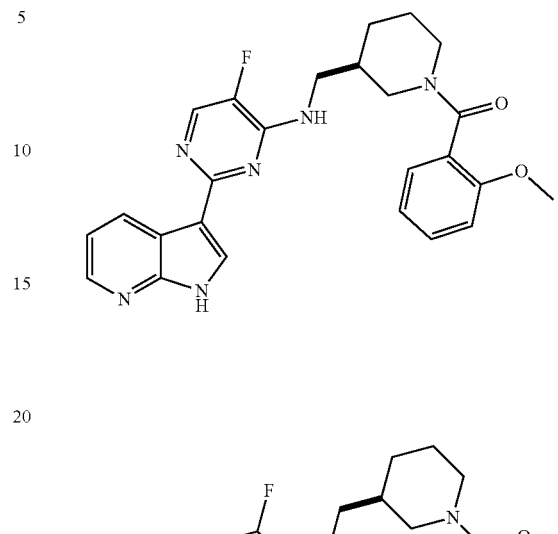

(R)-(3-((5-fluoro-2-(1H-pyrrolo[2,3-b]pyridin-3-yl)
pyrimidin-4-ylamino)methyl)piperidin-1-yl)(2-meth-
oxyphenyl)methanone (272)

LCMS RT=2.5 (M+1) 461.3.

(R)-1-(3-((5-fluoro-2-(1H-pyrrolo[2,3-b]pyridin-3-
yl)pyrimidin-4-ylamino)methyl)piperidin-1-yl)etha-
none (268)

LCMS RT=2.1 (M+1) 369.3.

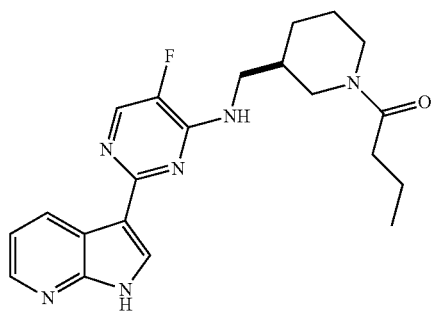

(R)-(3-((5-fluoro-2-(1H-pyrrolo[2,3-b]pyridin-3-yl)
pyrimidin-4-ylamino)methyl)piperidin-1-yl)(phenyl)
methanone (271)

LCMS RT=2.5 (M+1) 431.4.

(R)-1-(3-((5-fluoro-2-(1H-pyrrolo[2,3-b]pyridin-3-
yl)pyrimidin-4-ylamino)methyl)piperidin-1-yl)bu-
tan-1-one (270)

LCMS RT=2.4 (M+1) 397.3.

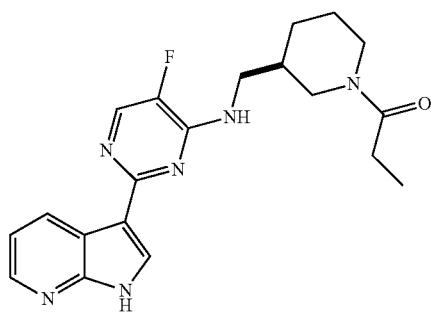

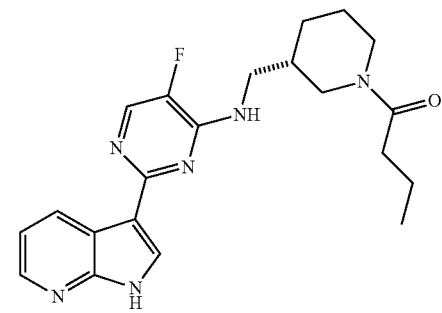

(R)-(3-((5-fluoro-2-(1H-pyrrolo[2,3-b]pyridin-3-yl)
pyrimidin-4-ylamino)methyl)piperidin-1-yl)(phenyl)
propan-1-one (269)

LCMS RT=2.3 (M+1) 383.3.

(S)-1-(3-((5-fluoro-2-(1H-pyrrolo[2,3-b]pyridin-3-
yl)pyrimidin-4-ylamino)methyl)piperidin-1-yl)bu-
tan-1-one (225)

LCMS RT=2.4 (M+1) 397.4.

In a manner analogous to that of the preparation of compound 327, compounds with the opposite absolute stereochemistry, were prepared as follows:

General Scheme 12A:

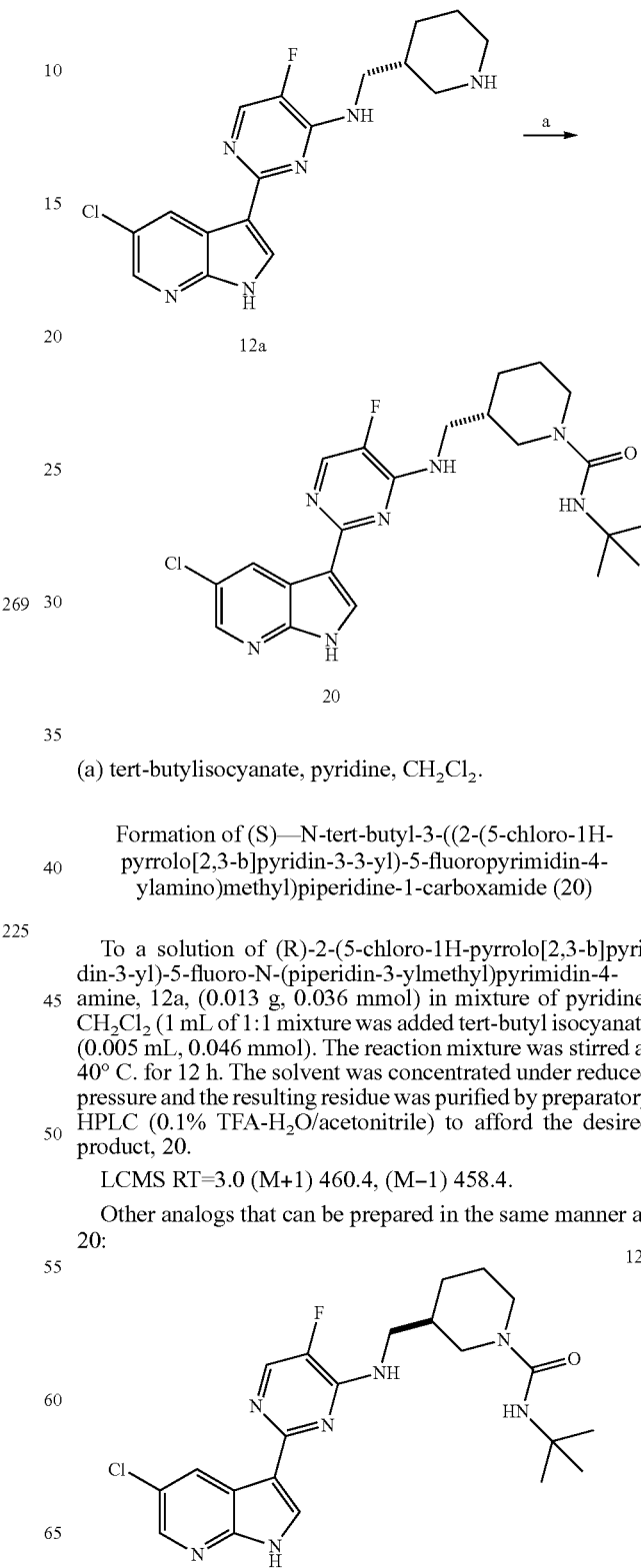

(a) tert-butylisocyanate, pyridine, CH$_2$Cl$_2$.

Formation of (S)—N-tert-butyl-3-((2-(5-chloro-1H-
pyrrolo[2,3-b]pyridin-3-3-yl)-5-fluoropyrimidin-4-
ylamino)methyl)piperidine-1-carboxamide (20)

To a solution of (R)-2-(5-chloro-1H-pyrrolo[2,3-b]pyridin-3-yl)-5-fluoro-N-(piperidin-3-ylmethyl)pyrimidin-4-amine, 12a, (0.013 g, 0.036 mmol) in mixture of pyridine/CH$_2$Cl$_2$ (1 mL of 1:1 mixture was added tert-butyl isocyanate (0.005 mL, 0.046 mmol). The reaction mixture was stirred at 40° C. for 12 h. The solvent was concentrated under reduced pressure and the resulting residue was purified by preparatory HPLC (0.1% TFA-H$_2$O/acetonitrile) to afford the desired product, 20.

LCMS RT=3.0 (M+1) 460.4, (M−1) 458.4.

Other analogs that can be prepared in the same manner as 20:

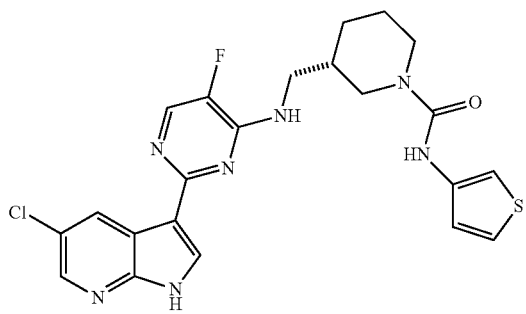

(R)—N-tert-butyl-3-((2-(5-chloro-1H-pyrrolo[2,3-b]pyridin-3-yl)-5-fluoropyrimidin-4-ylamino)methyl)piperidine-1-carboxamide (128)

LCMS RT=3.0 (M+1) 460.4, (M−1) 458.4.

(S)-3-((2-(5-chloro-1H-pyrrolo[2,3-b]pyridin-3-yl)-5-fluoropyrimidin-4-ylamino)methyl)-N-(thiophen-3-yl)piperidine-1-carboxamide (22)

LCMS RT=2.9 (M+1) 486.3, (M−1) 484.6.

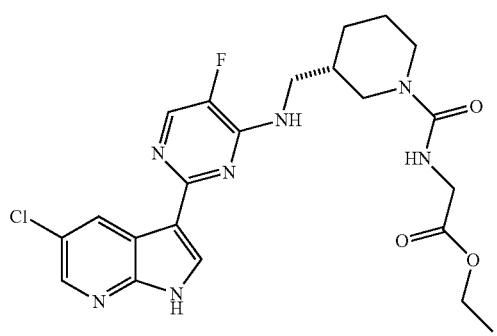

(S)-ethyl 2-(3-((2-(5-chloro-1H-pyrrolo[2,3-b]pyridin-3-yl)-5-fluoropyrimidin-4-ylamino)methyl)piperidine-1-carboxamido)ethanoate (25)

LCMS RT=2.6 (M+1) 490.3, (M−1) 488.4.

(S)-ethyl 3-((2-(5-chloro-1H-pyrrolo[2,3-b]pyridin-3-yl)-5-fluoropyrimidin-4-ylamino)methyl)piperidine-1-carbonylcarbamate (26)

LCMS RT=2.5 (M+1) 476.3, (M−1) 474.5.

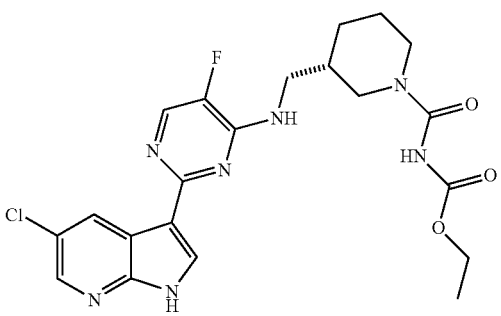

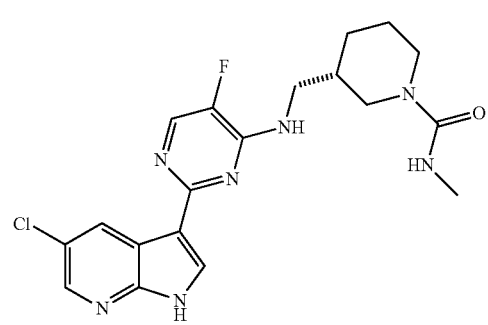

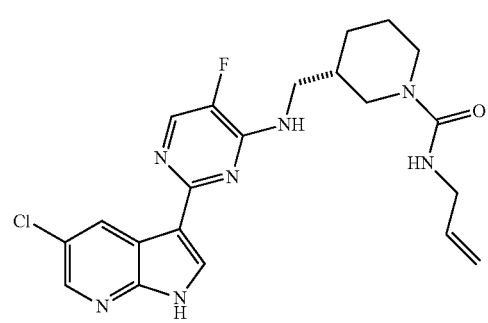

(S)-3-((2-(5-chloro-1H-pyrrolo[2,3-b]pyridin-3-yl)-5-fluoropyrimidin-4-ylamino)methyl)-N-isopropylpiperidine-1-carboxamide (27)

LCMS RT=2.7 (M+1) 446.4, (M−1) 444.5.

(S)-3-((2-(5-chloro-1H-pyrrolo[2,3-b]pyridin-3-yl)-5-fluoropyrimidin-4-ylamino)methyl)-N-methylpiperidine-1-carboxamide (29)

LCMS RT=2.4 (M+1) 418.3, (M−1) 416.1.

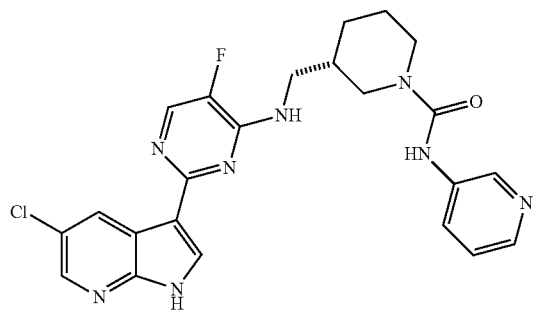

(S)—N-allyl-3-((2-(5-chloro-1H-pyrrolo[2,3-b]pyridin-3-yl)-5-fluoropyrimidin-4-ylamino)methyl)piperidine-1-carboxamide (39)

LCMS RT=2.6 (M+1) 444.4, (M−1) 442.4.

(S)-3-((2-(5-chloro-1H-pyrrolo[2,3-b]pyridin-3-yl)-5-fluoropyrimidin-4-ylamino)methyl)-N-(pyridin-3-yl)piperidine-1-carboxamide (40)

LCMS RT=2.5 (M+1) 481.3, (M−1) 479.4.

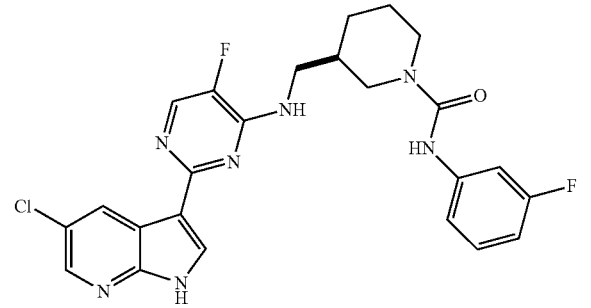

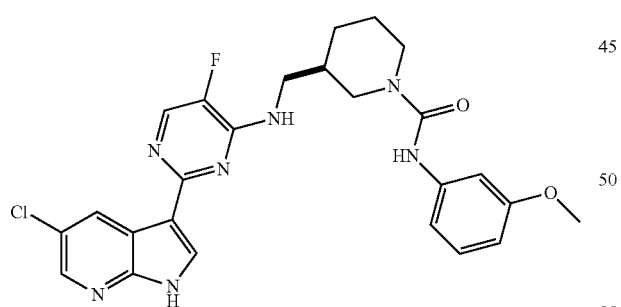

(R)-3-((2-(5-chloro-1H-pyrrolo[2,3-b]pyridin-3-yl)-5-fluoropyrimidin-4-ylamino)methyl)-N-(3-fluorophenyl)piperidine-1-carboxamide (75)

LCMS RT=3.0 (M+1) 498.3, (M−1) 496.5.

(R)-3-((2-(5-chloro-1H-pyrrolo[2,3-b]pyridin-3-yl)-5-fluoropyrimidin-4-ylamino)methyl)-N-(3-methoxyphenyl)piperidine-1-carboxamide (76)

LCMS RT=2.9 (M+1) 510.3, (M−1) 508.5.

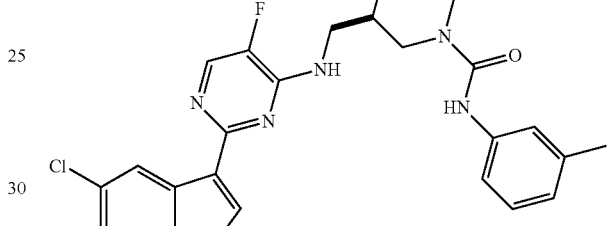

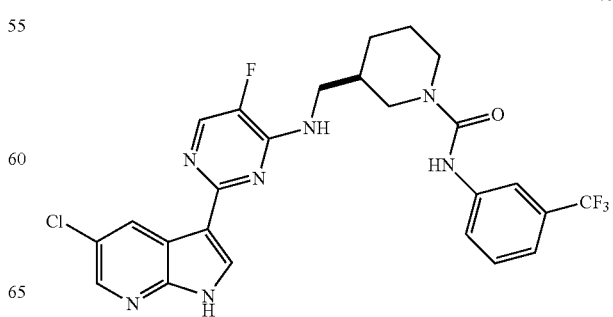

(R)-3-((2-(5-chloro-1H-pyrrolo[2,3-b]pyridin-3-yl)-5-fluoropyrimidin-4-ylamino)methyl)-N-(3-ethanoylphenyl)piperidine-1-carboxamide (77)

LCMS RT=2.8 (M+1) 522.3, (M−1) 520.4.

(R)-3-((2-(5-chloro-1H-pyrrolo[2,3-b]pyridin-3-yl)-5-fluoropyrimidin-4-ylamino)methyl)-N-m-tolylpiperidine-1-carboxamide (78)

LCMS RT=3.0 (M+1) 494.3, (M−1) 492.4.

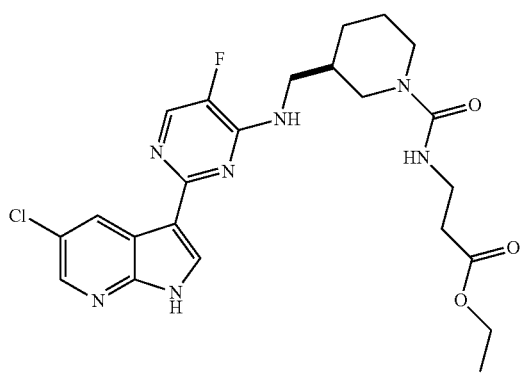

(R)-3-((2-(5-chloro-1H-pyrrolo[2,3-b]pyridin-3-yl)-5-fluoropyrimidin-4-ylamino)methyl)-N-(3-(trifluoromethyl)phenyl)piperidine-1-carboxamide (79)

LCMS RT=3.3 (M+1) 548.3, (M−1) 546.4.

(R)-ethyl 3-(3-((2-(5-chloro-1H-pyrrolo[2,3-b]pyridin-3-yl)-5-fluoropyrimidin-4-ylamino)methyl)piperidine-1-carboxamido)propanoate (118)

LCMS RT=2.6 (M+1) 504.2, (M−1) 502.5.

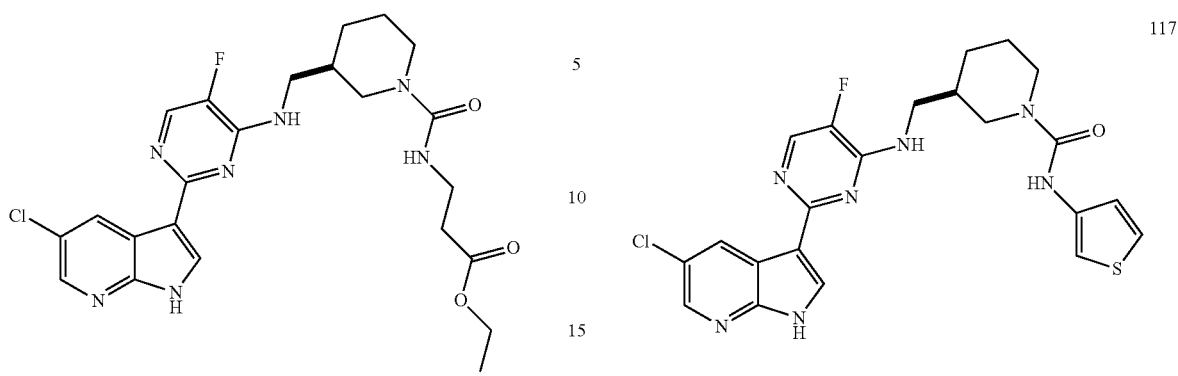

(R)-3-((2-(5-chloro-1H-pyrrolo[2,3-b]pyridin-3-yl)-5-fluoropyrimidin-4-ylamino)methyl)-N-(5-methyl-2-(trifluoromethyl)furan-3-yl)piperidine-1-carboxamide (120)

LCMS RT=3.2 (M+1) 552.4, (M−1) 550.5.

(R)-methyl 2-(3-((2-(5-chloro-1H-pyrrolo[2,3-b]pyridin-3-yl)-5-fluoropyrimidin-4-ylamino)methyl)piperidine-1-carboxamido)ethanoate (125)

LCMS RT=2.6 (M+1) 490.4, (M−1) 488.6.

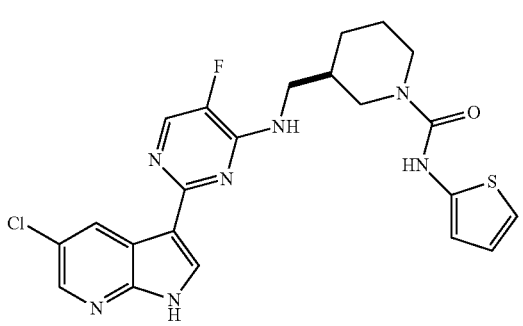

(R)—N-tert-butyl-3-((2-(5-chloro-1H-pyrrolo[2,3-b]pyridin-3-yl)-5-fluoropyrimidin-4-ylamino)methyl)piperidine-1-carboxamide (117)

LCMS RT=2.8 (M+1) 486.3, (M−1) 484.5.

(R)-3-((2-(5-chloro-1H-pyrrolo[2,3-b]pyridin-3-yl)-5-fluoropyrimidin-4-ylamino)methyl)-N-(thiophen-2-yl)piperidine-1-carboxamide (129)

LCMS RT=2.8 (M+1) 486.3, (M−1) 484.5.

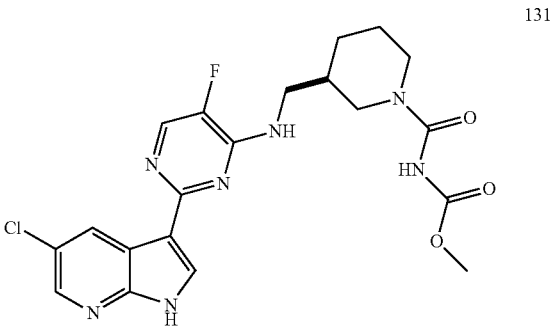

-continued

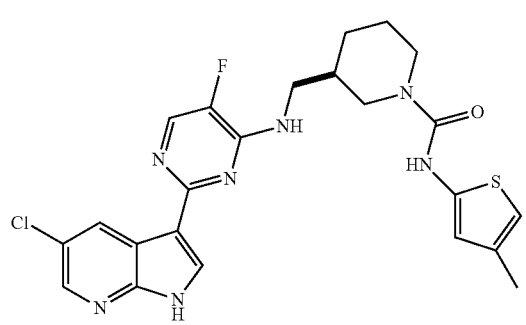
130

(R)-methyl 3-((2-(5-chloro-1H-pyrrolo[2,3-b]pyridin-3-yl)-5-fluoropyrimidin-4-ylamino)methyl)piperidine-1-carbonylcarbamate (131)

LCMS RT=1.6 (M+1) 462.7.

(R)-3-((2-(5-chloro-1H-pyrrolo[2,3-b]pyridin-3-yl)-5-fluoropyrimidin-4-ylamino)methyl)-N-(4-methylthiophen-2-yl)piperidine-1-carboxamide (130)

LCMS RT=2.0 (M+1) 500.6.

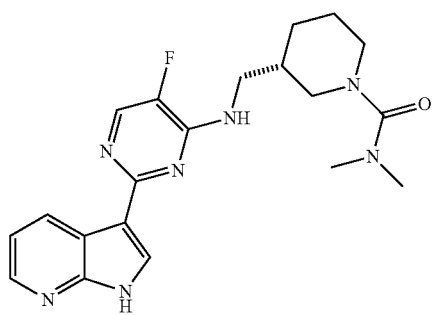
228

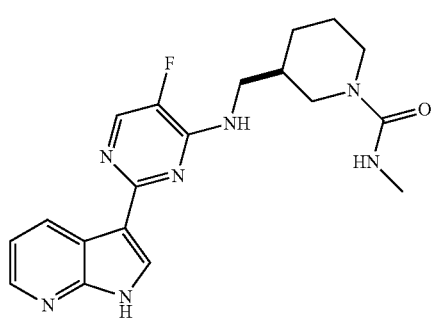
274

(S)-3-((5-fluoro-2-(1H-pyrrolo[2,3-b]pyridin-3-yl)pyrimidin-4-ylamino)methyl)-N,N-dimethylpiperidine-1-carboxamide (228)

LCMS RT=2.3 (M+1) 398.3.

(R)-3-(5-fluoro-2-(1H-pyrrolo[2,3-b]pyridin-3-yl)pyrimidin-4-ylamino)methyl)-N-methylpiperidine-1-carboxamide (274)

LCMS RT=2.1 (M+1) 384.3.

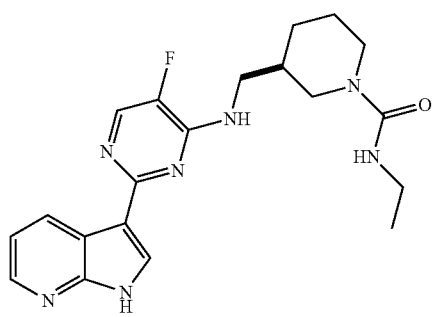
275

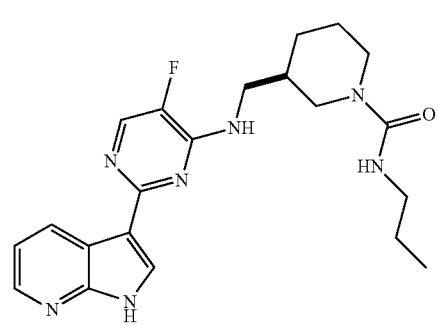
276

(R)—N-ethyl-3-((5-fluoro-2-(1H-pyrrolo[2,3-b]pyridin-3-yl)pyrimidin-4-ylamino)methyl)piperidine-1-carboxamide (275)

LCMS RT=2.2 (M+1) 398.4.

(R)-3-(5-fluoro-2-(1H-pyrrolo[2,3-b]pyridin-3-yl)pyrimidin-4-ylamino)methyl)-N-propylpiperidine-1-carboxamide (276)

LCMS RT=2.3 (M+1) 412.4.

General Scheme 12B:

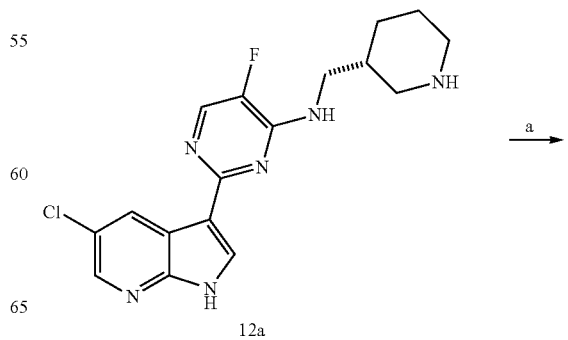
12a

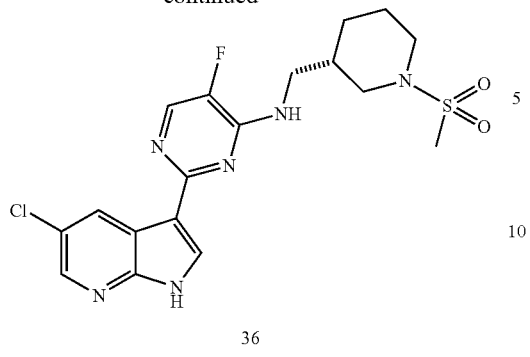

36

(a) propylisocyanate, $^i$Pr$_2$NEt, pyridine, CH$_2$Cl$_2$.

(S)-2-(5-chloro-1H-pyrrolo[2,3-b]pyridin-3-yl)-5-fluoro-N-((1-(methylsulfonyl)-piperidin-3-yl)methyl)pyrimidin-4-amine (36)

To a solution of (R)-2-(5-chloro-1H-pyrrolo[2,3-b]pyridin-3-yl)-5-fluoro-N-(piperidin-3-ylmethyl)pyrimidin-4-amine, 12a, (0.018 g, 0.050 mmol) and pyridine (0.7 mL) in CH$_2$Cl$_2$ (0.7 mL) was added methanesulfonyl chloride (0.004 mL, 0.050 mmol). The reaction mixture was stirred at room temperature for 24 hours. The solvent was concentrated under reduced pressure and the resulting residue was purified by preparatory HPLC (0.1% TFA-H$_2$O/acetonitrile) to afford the desired product, 36.

LCMS RT=2.7 (M+1) 439.3, (M−1) 437.3.

Other analogs that can be prepared in the same manner as 36:

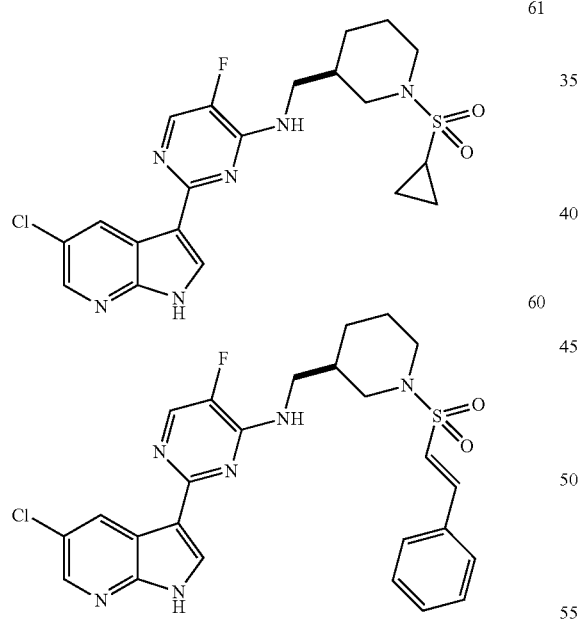

(R)-2-(5-chloro-1H-pyrrolo[2,3-b]pyridin-3-yl)-N-((1-(cyclopropylsulfonyl)piperidin-3-yl)methyl)-5-fluoropyrimidin-4-amine (61)

LCMS RT=2.8 (M+1) 465.3, (M−1) 463.3.

(R,E)-2-(5-chloro-1H-pyrrolo[2,3-b]pyridin-3-yl)-5-fluoro-N-((1-(styrylsulfonyl)piperidin-3-yl)methyl)pyrimidin-4-amine (60)

LCMS RT=3.2 (M+1) 525.3.

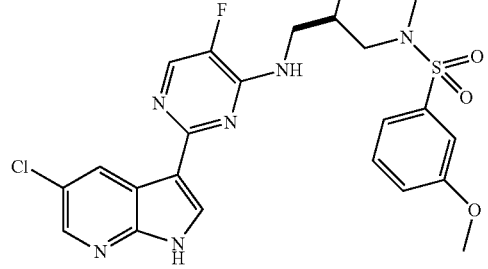

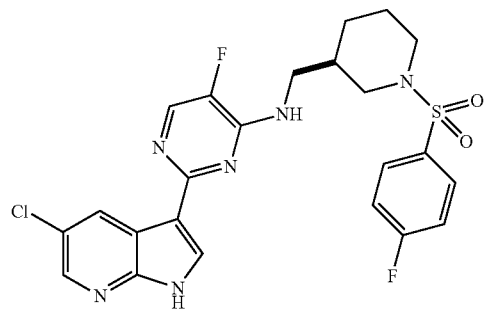

(R)-2-(5-chloro-1H-pyrrolo[2,3-b]pyridin-3-yl)-5-fluoro-N-((1-(3-methoxyphenylsulfonyl)piperidin-3-yl)methyl)pyrimidin-4-amine (62)

LCMS RT=3.1 (M+1) 531.3, (M−1) 529.4.

(R)-2-(5-chloro-1H-pyrrolo[2,3-b]pyridin-3-yl)-5-fluoro-N-((1-(4-fluorophenylsulfonyl)piperidin-3-yl)methyl)pyrimidin-4-amine (64)

LCMS RT=3.1 (M+1) 519.3, (M−1) 517.4

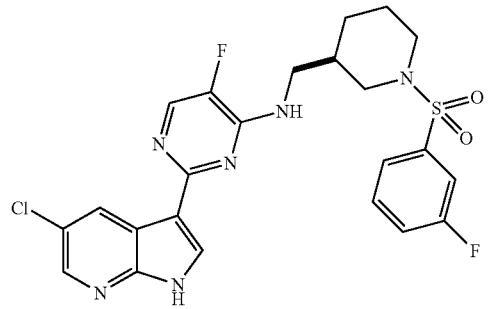

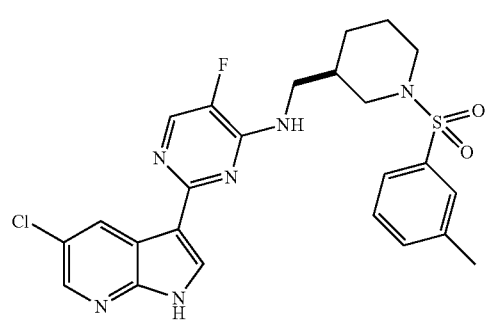

(R)-2-(5-chloro-1H-pyrrolo[2,3-b]pyridin-3-yl)-5-fluoro-N-((1-(3-fluorophenylsulfonyl)piperidin-3-yl)methyl)pyrimidin-4-amine (65)

LCMS RT=3.1 (M+1) 519.2, (M−1) 517.4.

(R)-2-(5-chloro-1H-pyrrolo[2,3-b]pyridin-3-yl)-5-fluoro-N-((1-(m-tolylsulfonyl)piperidin-3-yl)methyl)pyrimidin-4-amine (66)

LCMS RT=3.2 (M+1) 515.3, (M−1) 513.4

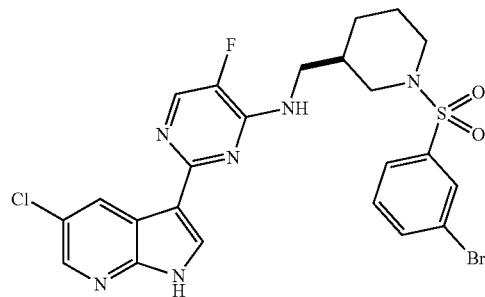

(R)—N-((1-(3-bromophenylsulfonyl)piperidin-3-yl)methyl)-2-(5-chloro-1H-pyrrolo[2,3-b]pyridin-3-yl)-5-fluoropyrimidin-4-amine (67)

LCMS RT=3.3 (M+1) 579.2, (M−1) 577.2.

(R)-2-(5-chloro-1H-pyrrolo[2,3-b]pyridin-3-yl)-5-fluoro-N-((1-(phenylsulfonyl)piperidin-3-yl)methyl)pyrimidin-4-amine (87)

LCMS RT=2.1 (M+1) 501.3.

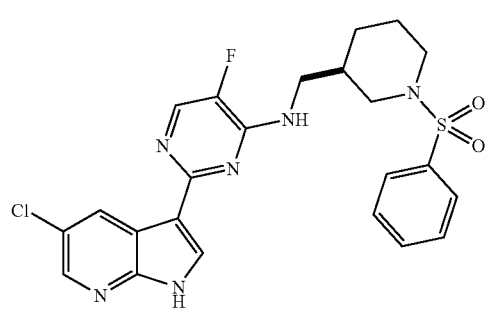

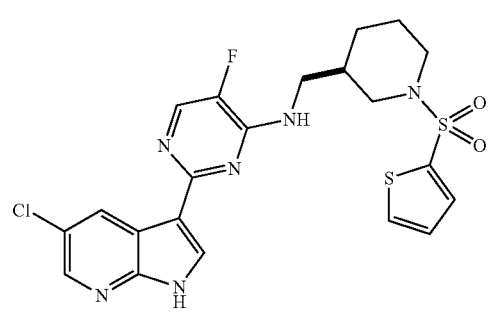

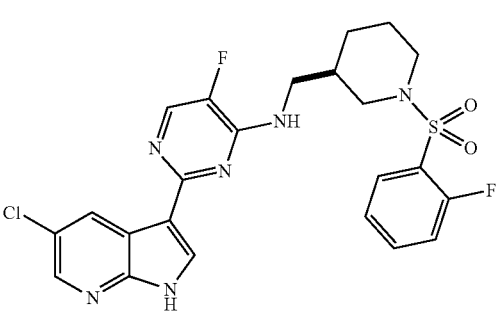

(R)—N-((1-(3-bromophenylsulfonyl)piperidin-3-yl)methyl)-2-(5-chloro-1H-pyrrolo[2,3-b]pyridin-3-yl)-5-fluoropyrimidin-4-amine (88)

LCMS RT=2.0 (M+1) 561.3.

(R)-2-(5-chloro-1H-pyrrolo[2,3-b]pyridin-3-yl)-5-fluoro-N-((1-(phenylsulfonyl)piperidin-3-yl)methyl)pyrimidin-4-amine (89)

LCMS RT=2.1 (M+1) 507.2.

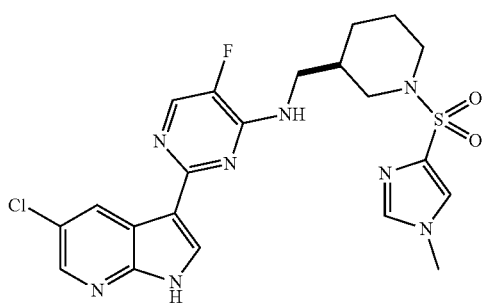

(R)-2-(5-chloro-1H-pyrrolo[2,3-b]pyridin-3-yl)-5-fluoro-N-((1-(2-fluorophenylsulfonyl)piperidin-3-yl)methyl)pyrimidin-4-amine (90)

LCMS RT=2.1 (M+1) 519.2.

(R)-2-(5-chloro-1H-pyrrolo[2,3-b]pyridin-3-yl)-5-fluoro-N-((1-(1-methyl-1H-imidazol-4-ylsulfonyl)piperidin-3-yl)methyl)pyrimidin-4-amine (91)

LCMS RT=1.8 (M+1) 505.3.

General Scheme 12C:

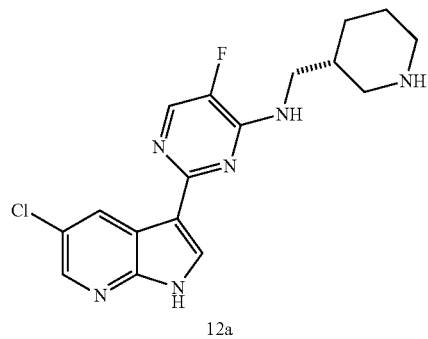

12a

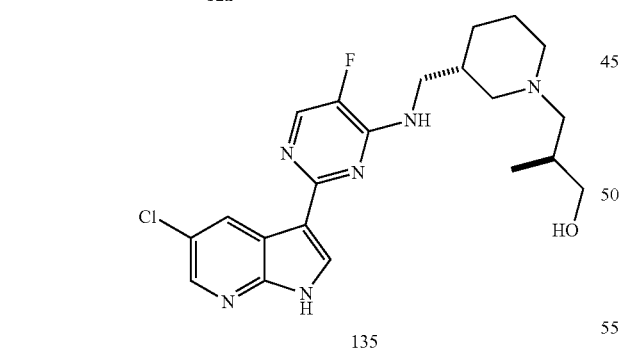

135

(a) (R)-3-bromo-2-methylpropan-1-ol, $^{i}$Pr$_2$NEt, THF.

Formation of (S)-3-(S)-3-((2-(5-chloro-1H-pyrrolo[2,3-b]pyridin-3-yl)-5-fluoropyrimidin-4-ylamino)methyl)piperidin-1-yl)-2-methylpropan-1-ol (135)

To a solution of (R)-3-bromo-2-methylpropan-1-ol (0.006 mL, 0.055 mmol) and (R)-2-(5-chloro-1H-pyrrolo[2,3-b]pyridin-3-yl)-5-fluoro-N-(piperidin-3-ylmethyl)-pyrimidin-4-amine, 12a, (0.020 g, 0.055 mmol) in CH$_3$CN (2 mL) was added K$_2$CO$_3$ (0.023 g, 0.165 mmol). The reaction mixture was heated at 80° C. at for 24 h. The solvent was concentrated under reduced pressure and the resulting residue was purified by preparatory HPLC (0.1% TFA-H$_2$O/acetonitrile) to afford the desired product, 135.

LCMS RT=2.5 (M+1) 433.4, (M−1) 431.6.

Other analogs that can be prepared in the same manner as 135:

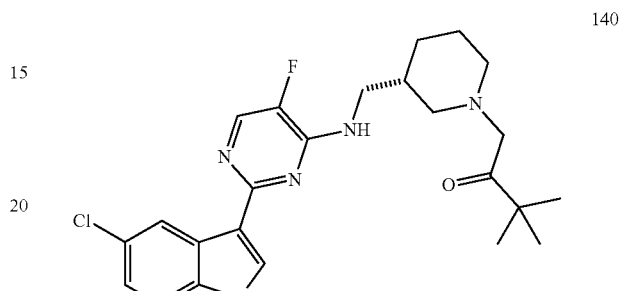

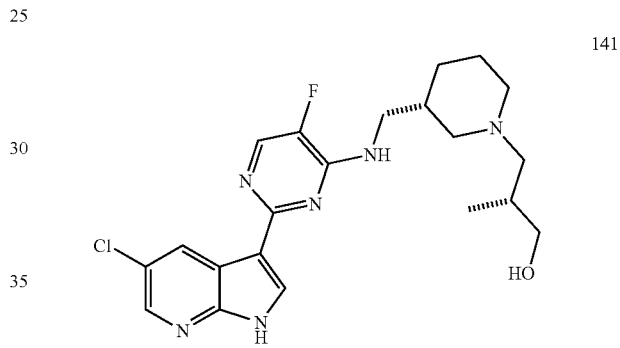

(S)-1-(3-((2-(5-chloro-1H-pyrrolo[2,3-b]pyridin-3-yl)-5-fluoropyrimidin-4-ylamino)methyl)piperidin-1-yl)-3,3-dimethylbutan-2-one (140)

LCMS RT=2.9 (M+1) 459.3, (M−1) 457.5.

(R)-3-((S)-3-((2-(5-chloro-1H-pyrrolo[2,3-b]pyridin-3-yl)-5-fluoropyrimidin-4-ylamino)methyl)piperidin-1-yl)-2-methylpropan-1-ol (141)

LCMS RT=1.4 (M+1) 433.5.

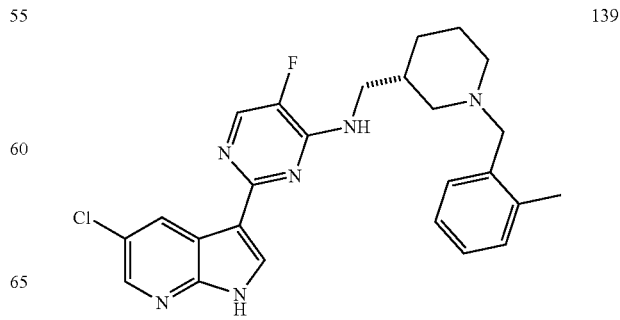

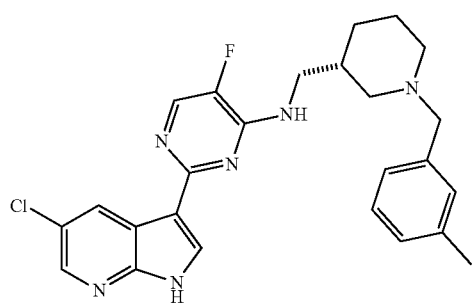

(S)-2-(5-chloro-1H-pyrrolo[2,3-b]pyridin-3-yl)-5-fluoro-N-((1-(2-methylbenzyl)piperidin-3-yl)methyl)pyrimidin-4-amine (139)

LCMS RT=3.2 (M+1) 465.3, (M−1) 463.4.

(S)-2-(5-chloro-1H-pyrrolo[2,3-b]pyridin-3-yl)-5-fluoro-N-((1-(3-methylbenzyl)piperidin-3-yl)methyl)pyrimidin-4-amine (137)

LCMS RT=3.1 (M+1) 465.4, (M−1) 463.6.

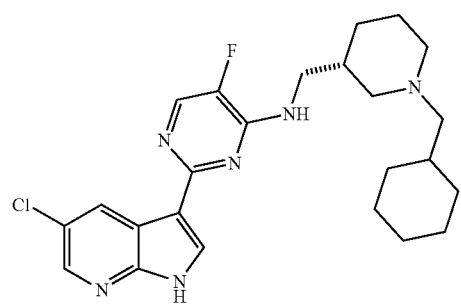

(S)-2-(5-chloro-1H-pyrrolo[2,3-b]pyridin-3-yl)-N-((1-(cyclohexylmethyl)piperidin-3-yl)methyl)-5-fluoropyrimidin-4-amine (134)

LCMS RT=3.1 (M+1) 457.3, (M−1) 455.5.

(S)-2-(3-((2-(5-chloro-1H-pyrrolo[2,3-b]pyridin-3-yl)-5-fluoropyrimidin-4-ylamino)methyl)piperidin-1-yl)ethanol (133)

LCMS RT=2.3 (M+1) 405.3, (M−1) 403.6.

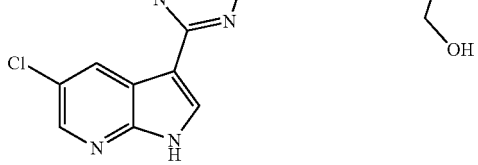

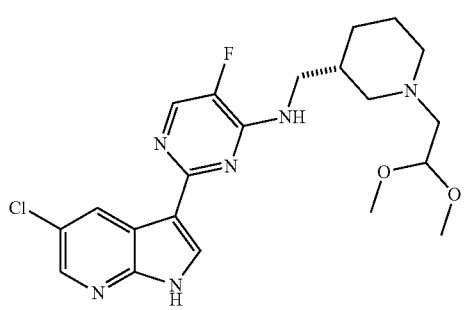

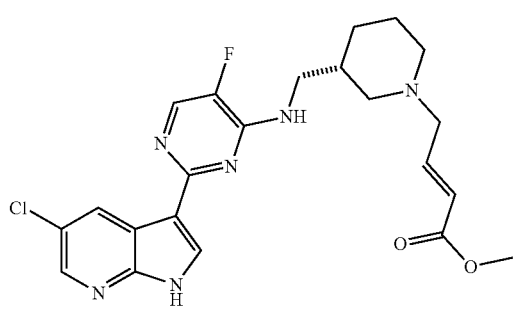

(S)-2-(5-chloro-1H-pyrrolo[2,3-b]pyridin-3-yl)-N-((1-(2,2-dimethoxyethyl)piperidin-3-yl)methyl)-5-fluoropyrimidin-4-amine (132)

LCMS RT=2.2 (M+1) 449.7.

(S,E)-methyl 4-(3-((2-(5-chloro-1H-pyrrolo[2,3-b]pyridin-3-yl)-5-fluoropyrimidin-4-ylamino)methyl)piperidin-1-yl)but-2-enoate (138)

LCMS RT=2.8 (M+1) 459.3, (M−1) 457.7.

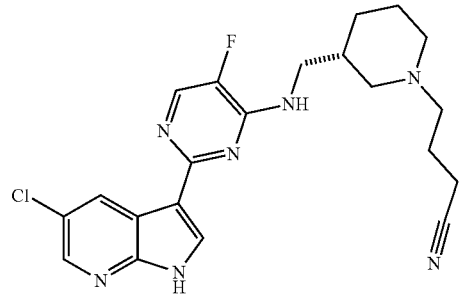

(S)-4-(3-((2-(5-chloro-1H-pyrrolo[2,3-b]pyridin-3-yl)-5-fluoropyrimidin-4-ylamino)methyl)piperidin-1-yl)butanenitrile (666)

LCMS RT=2.6 (M+1) 428.3, (M−1) 426.5.

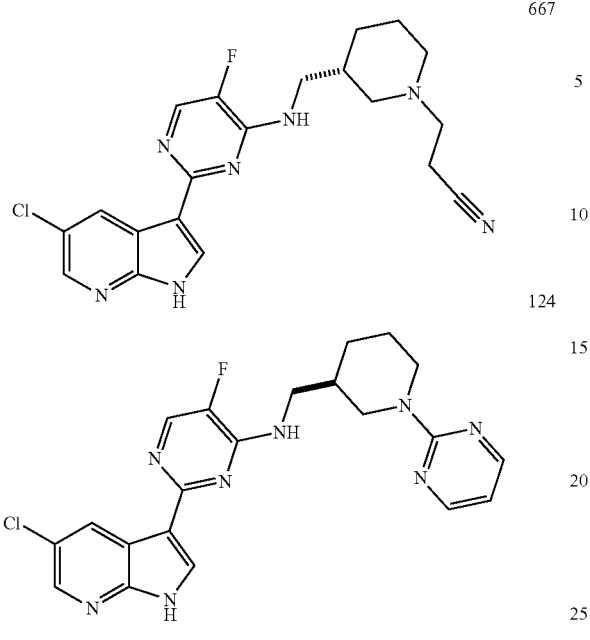

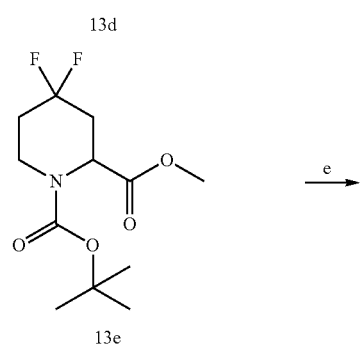
(S)-3-(3-((2-(5-chloro-1H-pyrrolo[2,3-b]pyridin-3-yl)-5-fluoropyrimidin-4-ylamino)methyl)piperidin-1-yl)propanenitrile (667)
LCMS RT=1.4 (M+1) 414.5.
(R)-2-(5-chloro-1H-pyrrolo[2,3-b]pyridin-3-yl)-5-fluoro-N-((1-(pyrimidin-2-yl)piperidin-3-yl)methyl)pyrimidin-4-amine (124)
LCMS RT=3.1 (M+1) 439.3 (M−H) 437.4.
General Scheme 13:
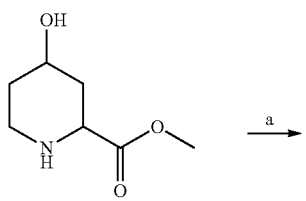
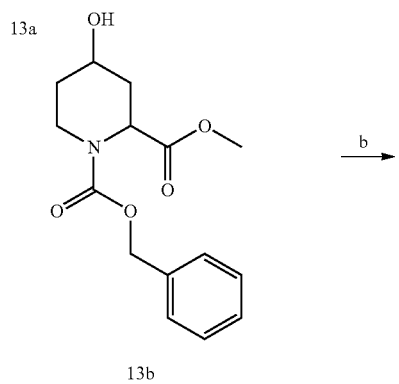
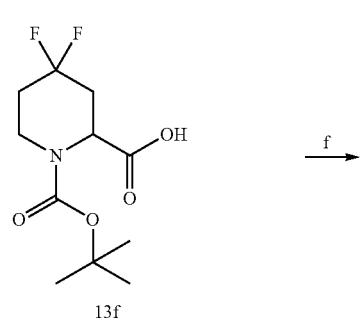
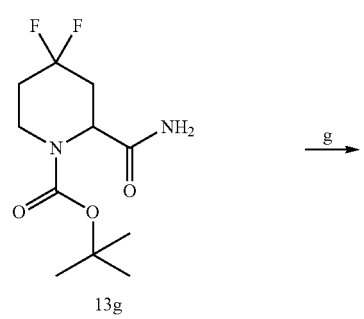

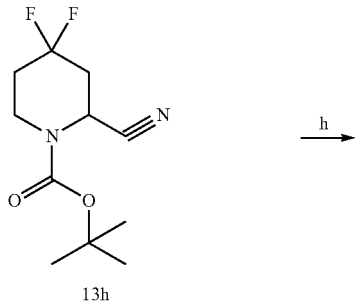

13h

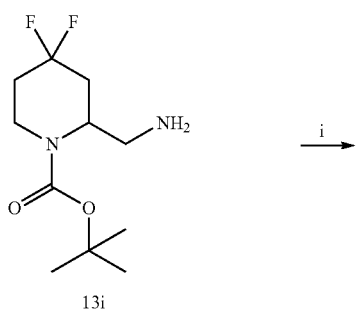

13i

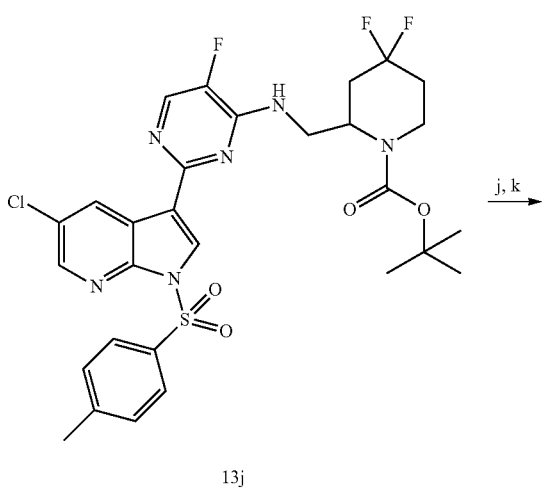

13j

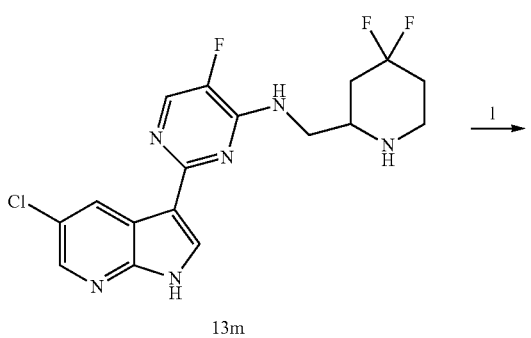

13m

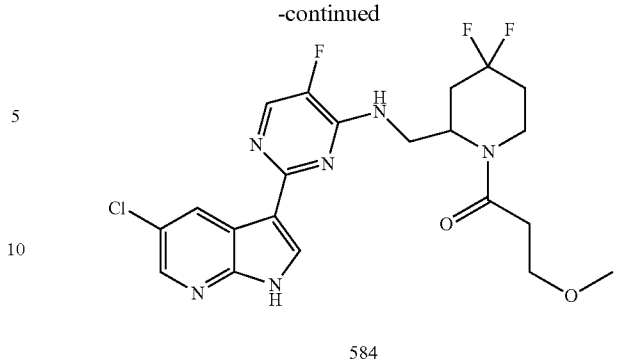

584

(a) Benzyl chloroformate, triethylamine, $CH_2Cl_2$; (b) dimethylsulfoxide, oxalyl chloride, triethylamine, $CH_2Cl_2$; (c) DAST, THF; (d) 10% Pd/C, MeOH, $H_2$, di-tert-butyl dicarbonate (e) LiOH, THF/MeOH/Water; (f) Pyridine, di-tert-butyl dicarbonate, $NH_4HCO_3$, 1,4-Dioxane; (g) triethylamine, TFAA, $CH_2Cl_2$; (h) Raney Ni, MeOH, $H_2$; (i) 5-chloro-3-(5-fluoro-4-(methylsulfinyl)pyrimidin-2-yl)-1-tosyl-1H-pyrrolo[2,3-b]pyridine, $^iPr_2NEt$, THF, microwave, 130° C. 15 min.; (j) NaOMe, MeOH (k) isoproponal/HCl, 45° C.; (l) 3-methoxy propanoyl chloride, $^iPr_2NEt$, $CH_2Cl_2$, DMF.

Formation of 1-benzyl 2-methyl 4-hydroxypiperidine-1,2-dicarboxylate (13b)

To a cold (5° C.) solution of methyl 4-hydroxypiperidine-2-carboxylate, 13a, (5.17 g, 32.48 mmol) and triethylamine (6.00 mL, 43.05 mmol) in $CH_2Cl_2$ (135 mL) was added dropwise benzyl chloroformate (6.20 mL, 43.43 mmol) over 10 min. The resulting solution was stirred at 5° C. for 1 hour and then allowed to warm to room temperature. The reaction mixture was diluted with water and the layers were separated. The aqueous was re-extracted with $CH_2Cl_2$ and the combined organics were dried over $MgSO_4$, filtered and evaporated to dryness. The crude was passed through a plug of silica gel, eluting with 30-80% EtOAc/Hexanes to afford the desired product, 13b.

$^1H$ NMR (300 MHz, $CDCl_3$) δ 7.36-7.33 (m, 5H), 5.17 (s, 2H), 4.89-4.78 (m, 1H), 4.18-4.09 (m, 1H), 3.96 (s, 1H), 3.76-3.70 (m, 3H), 3.53-3.41 (m, 2H), 2.44 (s, 1H), 1.96-1.91 (m, 1H) and 1.71 (s, 2H) ppm.

Formation of 1-benzyl 2-methyl 4-oxopiperidine-1,2-dicarboxylate (13c)

To a 500 ml flask, flamed dry under $N_2$ was added $CH_2Cl_2$ (65 mL) followed by oxalyl chloride (5.2 mL, 59.6 mmol). After cooling the reaction mixture to −78° C., dimethyl sulfoxide (8.4 mL, 118.4 mmol) was added, followed by 1-benzyl 2-methyl 4-hydroxypiperidine-1,2-dicarboxylate, 13b, (8.6 g, 29.2 mmol) in $CH_2Cl_2$ (65 mL). The reaction was allowed to stir at −78° C. for 45 min. To the mixture was added triethylamine (24.4 mL, 175.1 mmol) and the mixture was allowed to warm to room temperature. The reaction mixture was diluted with $CH_2Cl_2$ and 1N HCl. The layers were separated and the aqueous phase was re-extracted with $CH_2Cl_2$. The combined organic phases were washed with water, dried over $MgSO_4$, filtered and evaporated to dryness. The crude was purified by silica gel chromatography (30-50% EtOAc/hexanes) to give the desired product, 13c.

¹H NMR (300 MHz, CDCl₃) δ 7.37 (s, 5H), 5.24-5.18 (m, 3H), 5.02 (s, 1H), 4.12 (q, J=7.1 Hz, 1H), 3.74-3.65 (m, 3H), 2.79 (d, J=7.0 Hz, 2H) and 2.53 (s, 2H) ppm.

Formation of 1-benzyl 2-methyl 4,4-difluoropiperidine-1,2-dicarboxylate (13d)

To a cold (0° C.) solution of 1-benzyl 2-methyl 4-oxopiperidine-1,2-dicarboxylate, 13c, (7.4 g, 25.4 mmol) in THF (75 mL) was added (diethylamino)sulfur trifluoride (25.0 mL, 189.2 mmol). After 2 hours at 0° C., the reaction was quenched by the careful addition of water. The mixture was diluted with EtOAc and water. Solid NaHCO₃ was added to adjust the pH to neutral. The layers were separated and the organic was washed with water, brine, dried over MgSO₄, filtered and evaporated to dryness. The crude was passed through a plug of silica gel eluting with 15-20% EtOAc/hexanes to afford the desired product, 13d.

¹H NMR (300 MHz, CDCl₃) δ 7.37-7.31 (m, 5H), 5.30-5.06 (m, 3H), 4.45-4.22 (m, 1H), 3.76-3.52 (m, 3H), 3.45 (d, J=9.0 Hz, 1H), 2.76 (s, 1H) and 2.23-1.93 (m, 3H) ppm.

Formation of 1-tert-butyl 2-methyl 4,4-difluoropiperidine-1,2-dicarboxylate (13e)

To a Parr flask (1 L) was charged 10% palladium on carbon (0.57 g) and di-tert-butyl dicarbonate (4.47 g, 20.49 mmol). A solution of 1-benzyl 2-methyl-4,4-difluoropiperidine-1,2-dicarboxylate, 13d, (4.28 g, 13.66 mmol) in methanol (150 mL) was added and hydrogen was introduced via parr shaker (46 PSI). The reaction mixture was shaken over weekend at room temperature. The mixture was filtered through Celite and washed thoroughly with CH₂Cl₂. The filtrate was concentrated to dryness and redissolved in 10% EtOAc/hexanes. The crude was purified by silica gel chromatography (10-20% EtOAc/hexanes) to afford 5.1 g of a mixture of desired product, 13e, plus approximately 840 mg of contaminated product. The resulting crude mixture was used directly in next step without further purification.

¹H NMR (300 MHz, CDCl₃) δ 5.08 (s, 1H), 4.89 (s, 1H), 4.12 (q, J=7.2 Hz, 1H), 3.76 (s, H), 3.74 (s, 3H), 3.34 (s, 1H), 3.29 (t, J=7.2 Hz, 1H), 2.77 (s, 1H), 2.04 (m, 1H) and 1.53 (s, 9H) ppm.

Formation of 1-(tert-butoxycarbonyl)-4,4-difluoropiperidine-2-carboxylic acid (13f)

To a solution of 1-tert-butyl 2-methyl 4,4-difluoropiperidine-1,2-dicarboxylate, 13e, (4.6 g, 16.5 mmol) in THF (18 mL), methanol (18 mL) and H₂O (9 mL) was added lithium hydroxide (3.45 g, 82.22 mmol). The reaction mixture was stirred at room temperature for 1 hour. All volatiles were removed under reduced pressure. The residue was diluted with a slight amount of water and ether. The layers were separated and the organic phase was discarded. The aqueous phase was acidified to pH 3 with the addition of aqueous saturated KHSO₄ solution. The product was extracted with EtOAc. The organic phase was washed with water, dried over MgSO₄, filtered and evaporated to dryness. The resulting product was used without further purification.

¹H NMR (300 MHz, CDCl₃) δ 5.14 (s, 1H), 4.93 (s, 1H), 4.12 (q, J=7.1 Hz, 1H), 3.28 (d, J=6.3 Hz, 1H), 2.75 (d, J=8.7 Hz, 1H), 2.06 (d, J=8.5 Hz, 1H), 1.99-1.81 (m, 1H) and 1.47 (s, 9H) ppm.

Formation of tert-butyl 2-carbamoyl-4,4-difluoropiperidine-1-carboxylate (13 g)

To a solution of 1-tert-butoxycarbonyl-4,4-difluoro-piperidine-2-carboxylic acid, 13f, (1.67 g, 6.30 mmol) in 1,4-dioxane (12 mL) was added pyridine (0.35 mL, 4.33 mmol), followed by di-tert-butyl dicarbonate (1.78 g, 8.17 mmol) and ammonium bicarbonate (0.63 g, 7.86 mmol). The reaction mixture was stirred at room temperature overnight. The solvent was removed under reduced pressure and the residue was taken up in EtOAc. The organic phase was washed with water, aqueous saturated KHSO₄ solution, brine, dried over Na₂SO₄, filtered and evaporated to dryness. The crude residue was used without further purification.

Formation of tert-butyl 2-cyano-4,4-difluoropiperidine-1-carboxylate (13h)

To a solution of tert-butyl 2-carbamoyl-4,4-difluoro-piperidine-1-carboxylate, 13g, (1.72 g, 6.51 mmol) in CH₂Cl₂ (50 mL) was added was N,N-triethylamine (2.03 mL, 14.61 mmol) followed by the dropwise addition of (2,2,2-trifluoro-acetyl)-2,2,2-trifluoroacetate (1.02 mL, 7.32 mmol). After 15 minutes, the mixture was diluted with aqueous saturated NaHCO₃ solution and the layers were separated. The organic phase was washed with water, dried over Na₂SO₄, filtered and evaporated to dryness. The crude residue was passed through a plug of silica gel and eluted with 10-30% EtOAc/hexanes to afford the desired product, 13h.

¹H NMR (300 MHz, CDCl₃) δ 5.43 (s, 1H), 4.19 (s, 1H), 3.25 (s, 1H), 2.36 (m, 1H), 2.23-2.12 (m, 1H), 1.83 (s, 1H), 1.70 (s, 1H) and 1.53-1.46 (m, 9H) ppm.

Formation of tert-butyl 2-(aminomethyl)-4,4-difluoropiperidine-1-carboxylate (13i)

Raney nickel (0.36 mL, 5.40 mmol) was washed with MeOH (2×) and charged into a parr shaker. A solution of tert-butyl 2-cyano-4,4-difluoro-piperidine-1-carboxylate, 13h, (1.33 g, 5.40 mmol) in methanol (50 mL). The reaction mixture was subject to hydrogenation conditions overnight on the parr shaker (46PSI). The mixture was filtered through celite and washed thoroughly with CH₂Cl₂. All volatiles were removed at reduced pressure and the crude material was used without further purification.

Formation of tert-butyl 2-((2-(5-chloro-1-tosyl-1H-pyrrolo[2,3-b]pyridin-3-yl)-5-fluoropyrimidin-4-ylamino)methyl)-4,4-difluoropiperidine-1-carboxylate (13j)

To a solution of tert-butyl 2-(aminomethyl)-4,4-difluoro-piperidine-1-carboxylate, 13i, (0.10 g, 0.41 mmol) and 5-chloro-3-(5-fluoro-4-methylsulfinyl-pyrimidin-2-yl)-1-(p-tolylsulfonyl)pyrrolo[2,3-b]pyridine (0.18 g, 0.38 mmol) in THF (2 mL) was added ⁱPr₂NEt (0.20 mL, 1.15 mmol). The reaction mixture was heated in microwave at 130° C. for 15 minutes. The reaction was cooled to room temperature and the volatiles were removed under reduced pressure. The crude residue was purified via silica gel chromatography (0-100% EtOAc/hexanes) to afford the desired product, 13j.

LCMS (M−1) 649.52.

Formation of tert-butyl 2-((2-(5-chloro-1H-pyrrolo[2,3-b]pyridin-3-yl)-5-fluoropyrimidin-4-ylamino)methyl)-4,4-difluoropiperidine-1-carboxylate (13k)

To a solution of tert-butyl 2-[[[2-[5-chloro-1-(p-tolylsulfonyl)pyrrolo[2,3-b]pyridin-3-yl]-5-fluoro-pyrimidin-4-yl]

amino]methyl]-4,4-difluoro-piperidine-1-carboxylate, 13j, (0.23 g, 0.35 mmol) in methanol (4 mL) was added sodium methanolate (4 mL of 25% w/v, 18.51 mmol). The reaction mixture was allowed to stir at room temperature for 15 minutes. All volatiles were removed at reduced pressure and the residue was quenched with water. EtOAc was added and the layers were separated. The organic phase was washed with brine, dried (MgSO$_4$), filtered and evaporated to dryness. The crude residue was pure enough to be used without further purification.

LCMS (M+1) 497.44, (M−1) 495.52.

Formation of 2-(5-chloro-1H-pyrrolo[2,3-b]pyridin-3-yl)-N-((4,4-difluoropiperidin-2-yl)methyl)-5-fluoropyrimidin-4-amine (13m)

To a solution of tert-butyl 2-((2-(5-chloro-1H-pyrrolo[2,3-b]pyridin-3-yl)-5-fluoropyrimidin-4-ylamino)methyl)-4,4-difluoropiperidine-1-carboxylate, 13k, (0.09 g, 0.18 mmol) in 2-propanol (2 mL) was added propan-2-ol hydrochloride (2 mL of 6 M, 12.00 mmol). After stirring the reaction mixture at room temperature for 17 hours, an additional 1 mL of IPA/HCl was added and the reaction mixture was heated at 45° C. for 1 hour. All volatiles were removed at reduced pressure and the residue was used directly in the next step without further purification.

LCMS (M+1) 397.40, (M−1) 395.44.

Formation of 1-(2-((2-(5-chloro-1H-pyrrolo[2,3-b]pyridin-3-yl)-5-fluoropyrimidin-4-ylamino)methyl)-4,4-difluoropiperidin-1-yl)-3-methoxypropan-1-one (584)

To a solution of 2-(5-chloro-1H-pyrrolo[2,3-b]pyridin-3-yl)-N-[(4,4-difluoro-2-piperidyl)methyl]-5-fluoro-pyrimidin-4-amine, 13k, (0.086 g, 0.198 mmol) in CH$_2$Cl$_2$ (1 mL), DMF (0.5 mL) and $^i$Pr$_2$NEt (0.10 mL, 0.57 mmol) was added 3-methoxypropanoyl chloride (2.43 g, 0.20 mmol). The reaction mixture was stirred at room temperature for 17 hours. All volatiles were removed at reduced pressure and the residue was purified via silica gel chromatography to give a mixture enriched in desired product, 13, which was repurified via preparatory HPLC.

$^1$H NMR (300 MHz, d6-DMSO) δ 12.45 (m, 1H), 8.71 (d, J=8.5 Hz, 1H), 8.31 (m, 2H), 8.01 (m, 1H), 5.33 (s, 1H), 4.62-4.43 (m, 2H), 4.39-3.72 (m, 5H), 3.68 (s, 2H), 3.43-3.40 (m, 1H), 3.15 (s, 1H), 3.07 (s, 1H), 2.33 (s, 2H) and 2.08 (s, 2H) ppm: LCMS (M+1) 483.44, (M−1) 481.52.

Other analogs that may be prepared in the same manner as 584 are described below:

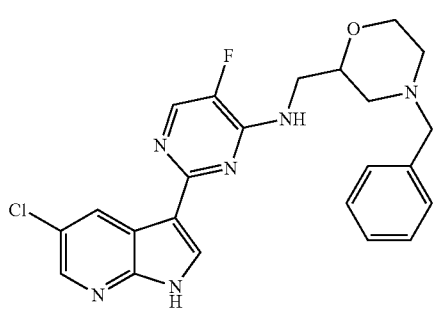

388

N-((4-benzylmorpholin-2-yl)methyl)-2-(5-chloro-1H-pyrrolo[2,3-b]pyridin-3-yl)-5-fluoropyrimidin-4-amine (388)

$^1$H NMR (300 MHz, CDCl$_3$) δ 9.14-9.09 (m, 1H), 8.81-8.71 (m, 1H), 8.29 (d, J=2.3 Hz, 1H), 8.07 (d, J=2.5 Hz, 1H), 7.34 (s, 5H), 5.58-5.41 (m, 1H), 3.92-3.43 (m, 4H), 2.83-2.72 (m, 2H), 2.38-2.28 (m, 2H) and 1.62 (m, 2H) ppm.

LCMS RT=1.8 (M+1) 453.4.

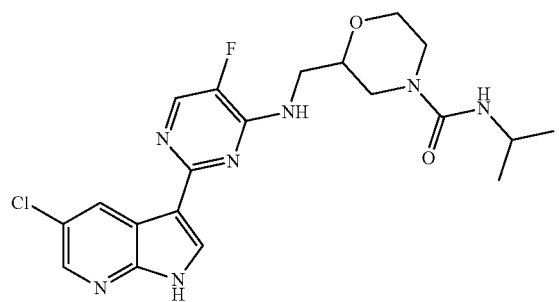

446

2-((2-(5-chloro-1H-pyrrolo[2,3-b]pyridin-3-yl)-5-fluoropyrimidin-4-ylamino)methyl)-N-isopropyl-morpholine-4-carboxamide (446)

LCMS RT=1.7 (M+1) 448.4

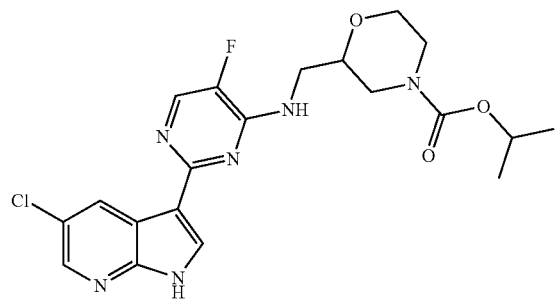

447

Isopropyl 2-((2-(5-chloro-1H-pyrrolo[2,3-b]pyridin-3-yl)-5-fluoropyrimidin-4-ylamino)methyl)morpholine-4-carboxylate (447)

LCMS RT=2.0 (M+1) 449.3

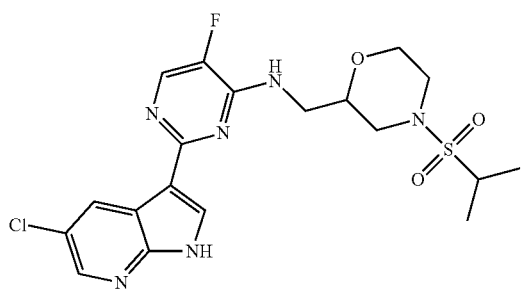

2-(5-chloro-1H-pyrrolo[2,3-b]pyridin-3-yl)-5-fluoro-
N-((4-(isopropylsulfonyl)morpholin-2-yl)methyl)
pyrimidin-4-amine (448)

LCMS RT=1.9 (M+1) 469.3

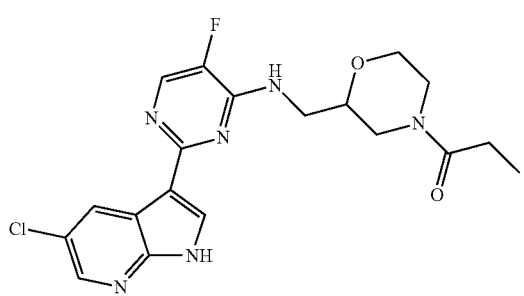

1-(2-((2-(5-chloro-1H-pyrrolo[2,3-b]pyridin-3-yl)-5-
fluoropyrimidin-4-ylamino)methyl)morpholino)pro-
pan-1-one (449)

LCMS RT=1.7 (M+1) 419.4

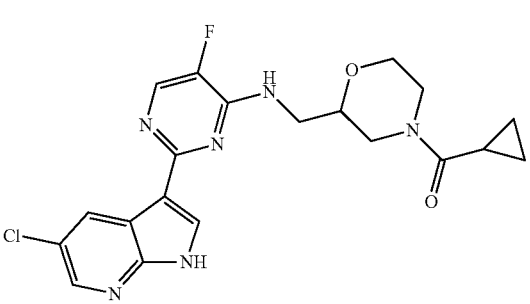

(2-((2-(5-chloro-1H-pyrrolo[2,3-b]pyridin-3-yl)-5-
fluoropyrimidin-4-ylamino)methyl)morpholino)(cy-
clopropyl)methanone (450)

LCMS RT=1.7 (M+1) 431.4

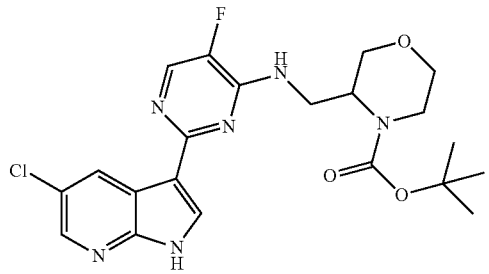

Tert-Butyl 3-((2-(5-chloro-1H-pyrrolo[2,3-b]pyridin-
3-yl)-5-fluoropyrimidin-4-ylamino)methyl)morpho-
line-4-carboxylate (515)

$^1$H NMR (300 MHz, CDCl$_3$) δ 10.38 (s, 1H), 8.81 (d, J=2.0 Hz, 1H), 8.49 (d, J=2.3 Hz, 1H), 8.38 (s, 1H), 8.08 (d, J=3.4 Hz, 1H), 6.11 (d, J=5.0 Hz, 1H), 4.44 (d, J=9.4 Hz, 1H), 4.02-3.62 (m, 6H), 3.55 (dd, J=2.4, 12.1 Hz, 1H), 3.35-3.27 (m, 1H) and 1.40-1.22 (m, 9H) ppm.
LCMS RT=2.5 (M+1) 463.5.

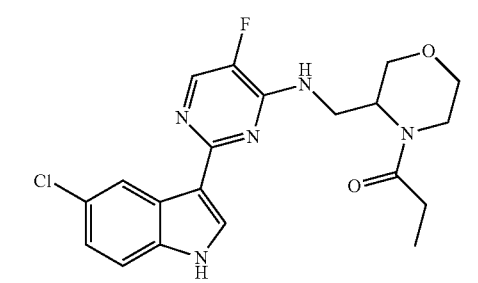

1-(3-((2-(5-chloro-1H-pyrrolo[2,3-b]pyridin-3-yl)-5-
fluoropyrimidin-4-ylamino)methyl)morpholino)pro-
pan-1-one (516)

LCMS RT=1.9 (M+1) 419.4

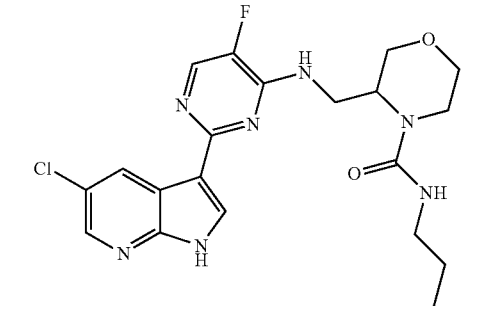

3-((2-(5-chloro-1H-pyrrolo[2,3-b]pyridin-3-yl)-5-
fluoropyrimidin-4-ylamino)methyl)-N-propylmor-
pholine-4-carboxamide (517)

$^1$H NMR (300 MHz, d6-DMSO) δ 12.54 (s, 1H), 8.76 (d, J=2.0 Hz, 1H), 8.46 (s, 1H), 8.32 (d, J=2.1 Hz, 1H), 8.26 (d,

J=3.9 Hz, 1H), 8.08 (d, J=7.5 Hz, 1H), 6.30 (s, 1H), 4.28 (s, 1H), 3.93-3.74 (m, 3H), 3.51-3.47 (m, 2H), 3.39-3.20 (m, 2H), 2.95 (dd, J=6.2, 13.1 Hz, 3H), 1.35-1.25 (m, 2H) and 0.76 (t, J=7.3 Hz, 3H) ppm.

LCMS RT=2.3 (M+1) 448.54.

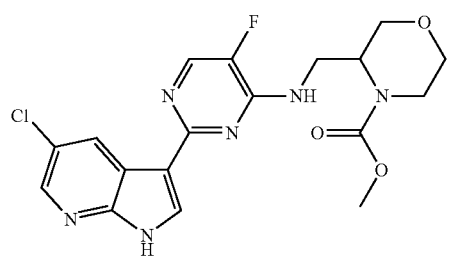

Methyl 3-((2-(5-chloro-1H-pyrrolo[2,3-b]pyridin-3-yl)-5-fluoropyrimidin-4-ylamino)methyl)morpholine-4-carboxylate (526)

LCMS RT=2.4 (M+1) 421.0.

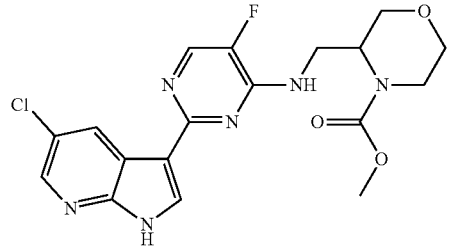

Ethyl 3-((2-(5-chloro-1H-pyrrolo[2,3-b]pyridin-3-yl)-5-fluoropyrimidin-4-ylamino)methyl)morpholine-4-carboxylate (527)

LCMS RT=2.5 (M+1) 435.1.

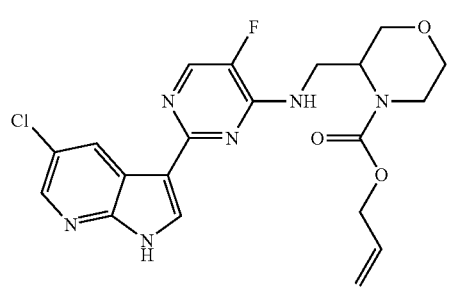

Allyl 3-((2-(5-chloro-1H-pyrrolo[2,3-b]pyridin-3-yl)-5-fluoropyrimidin-4-ylamino)methyl)morpholine-4-carboxylate (528)

LCMS RT=2.6 (M+1) 447.1.

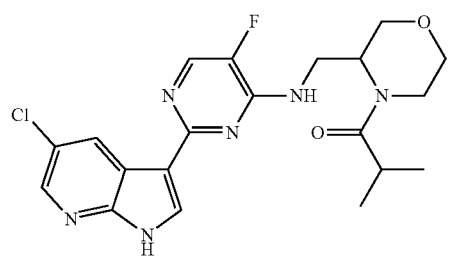

1-(3-((2-(5-chloro-1H-pyrrolo[2,3-b]pyridin-3-yl)-5-fluoropyrimidin-4-ylamino)methyl)morpholino)-2-methylpropan-1-one (529)

LCMS RT=2.5 (M+1) 433.1.

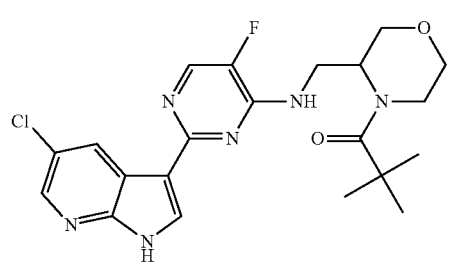

1-(3-((2-(5-chloro-1H-pyrrolo[2,3-b]pyridin-3-yl)-5-fluoropyrimidin-4-ylamino)methyl)morpholino)-2,2-dimethylpropan-1-one (530)

LCMS RT=1.9 (M+1) 447.1.

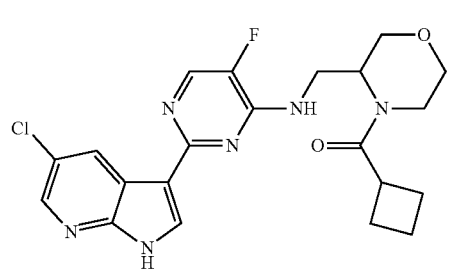

(3-((2-(5-chloro-1H-pyrrolo[2,3-b]pyridin-3-yl)-5-fluoropyrimidin-4-ylamino)methyl)morpholino)(cyclobutyl)methanone (531)

LCMS RT=2.6 (M+1) 445.1.

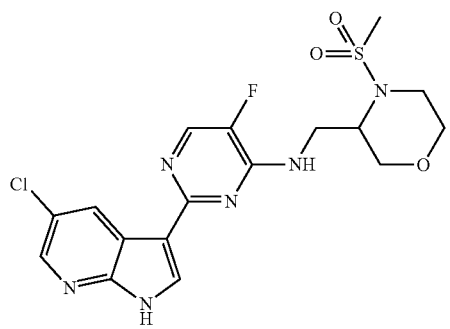

2-(5-chloro-1H-pyrrolo[2,3-b]pyridin-3-yl)-5-fluoro-N-((4-(methylsulfonyl)morpholin-3-yl)methyl)pyrimidin-4-amine (532)

LCMS RT=2.4 (M+1) 441.0.

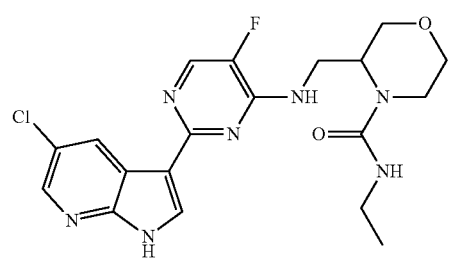

3-((2-(5-chloro-1H-pyrrolo[2,3-b]pyridin-3-yl)-5-fluoropyrimidin-4-ylamino)methyl)-N-ethylmorpholine-4-carboxamide (535)

LCMS RT=2.2 (M+1) 434.1.

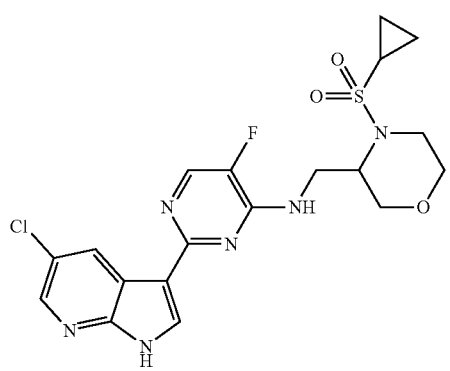

2-(5-chloro-1H-pyrrolo[2,3-b]pyridin-3-yl)-N-((4-(cyclopropylsulfonyl)morpholin-3-yl)methyl)-5-fluoropyrimidin-4-amine (533)

LCMS RT=2.4 (M+1) 467.0.

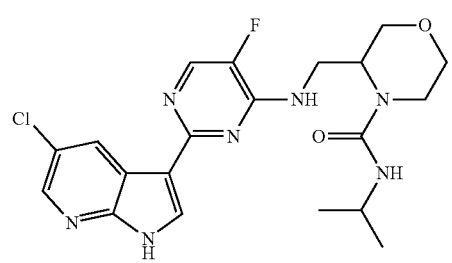

3-((2-(5-chloro-1H-pyrrolo[2,3-b]pyridin-3-yl)-5-fluoropyrimidin-4-ylamino)methyl)-N-isopropyl-morpholine-4-carboxamide (536)

LCMS RT=2.3 (M+1) 448.1.

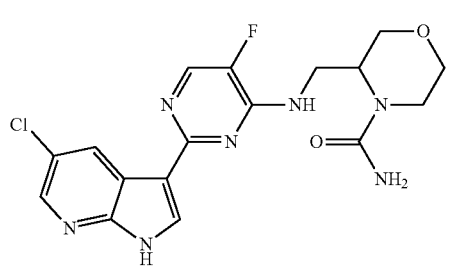

3-((2-(5-chloro-1H-pyrrolo[2,3-b]pyridin-3-yl)-5-fluoropyrimidin-4-ylamino)methyl)morpholine-4-carboxamide (534)

LCMS RT=2.0 (M+1) 406.0.

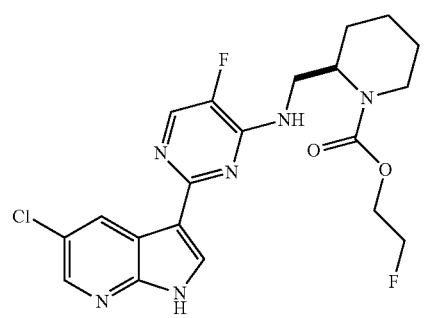

-continued

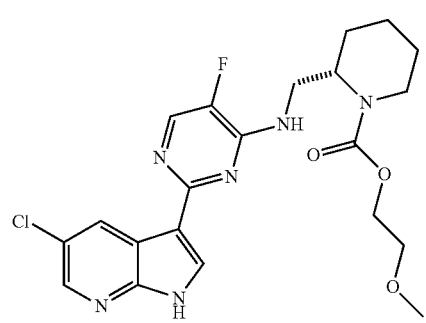

161

(R)-2-fluoroethyl 2-((2-(5-chloro-1H-pyrrolo[2,3-b]pyridin-3-yl)-5-fluoropyrimidin-4-ylamino)methyl)piperidine-1-carboxylate (180)

LCMS RT=2.1 (M+1) 451.4.

(S)-2-methoxyethyl 2-((2-(5-chloro-1H-pyrrolo[2,3-b]pyridin-3-yl)-5-fluoropyrimidin-4-ylamino)methyl)piperidine-1-carboxylate (161)

LCMS RT=2.8 (M+1) 463.4.

163

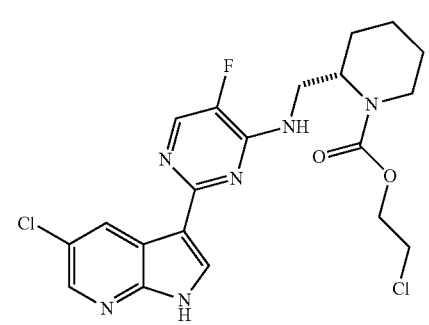

164

(S)-2-chloroethyl 2-((2-(5-chloro-1H-pyrrolo[2,3-b]pyridin-3-yl)-5-fluoropyrimidin-4-ylamino)methyl)piperidine-1-carboxylate (163)

LCMS RT=3.1 (M+1) 467.4.

(S)-prop-2-ynyl 2-((2-(5-chloro-1H-pyrrolo[2,3-b]pyridin-3-yl)-5-fluoropyrimidin-4-ylamino)methyl)piperidine-1-carboxylate (164)

LCMS RT=3.0 (M+1) 443.5.

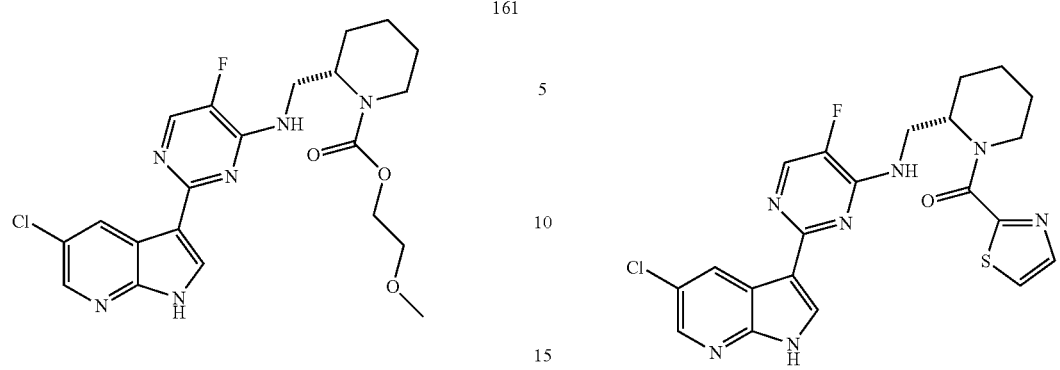

165

174

(S)-(2-((2-(5-chloro-1H-pyrrolo[2,3-b]pyridin-3-yl)-5-fluoropyrimidin-4-ylamino)methyl)piperidin-1-yl)(thiazol-2-yl)methanone (165)

LCMS RT=2.8 (M+1) 472.5.

(S)-(2-((2-(5-chloro-1H-pyrrolo[2,3-b]pyridin-3-yl)-5-fluoropyrimidin-4-ylamino)methyl)piperidin-1-yl)(3-methoxyphenyl)methanone (174)

LCMS RT=2.8 (M+1) 495.6.

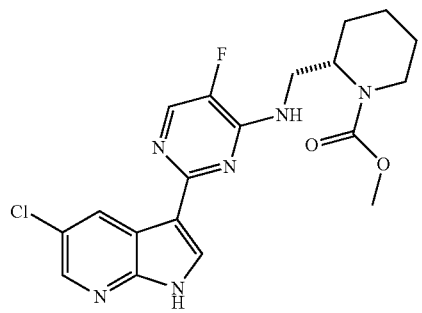

166

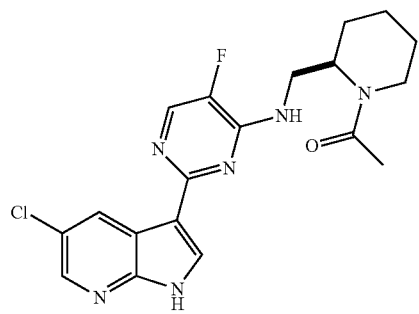

179

(S)-methyl 2-((2-(5-chloro-1H-pyrrolo[2,3-b]pyridin-3-yl)-5-fluoropyrimidin-4-ylamino)methyl)piperidine-1-carboxylate (166)

LCMS RT=2.9 (M+1) 419.5.

(R)-1-(2-((2-(5-chloro-1H-pyrrolo[2,3-b]pyridin-3-yl)-5-fluoropyrimidin-4-ylamino)methyl)piperidin-1-yl)ethanone (179)

LCMS RT=2.5 (M+1) 403.4.

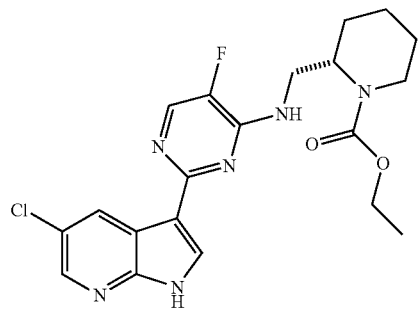

171

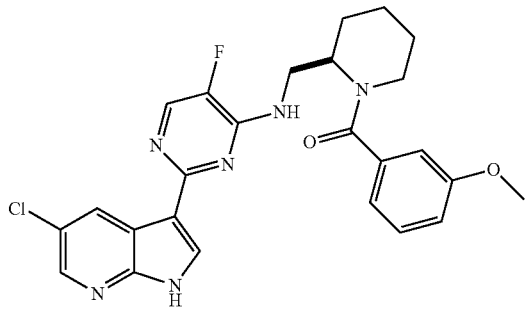

184

(S)-ethyl 2-((2-(5-chloro-1H-pyrrolo[2,3-b]pyridin-3-yl)-5-fluoropyrimidin-4-ylamino)methyl)piperidine-1-carboxylate (171)

LCMS RT=3.0 (M+1) 433.3.

(R)-(2-((2-(5-chloro-1H-pyrrolo[2,3-b]pyridin-3-yl)-5-fluoropyrimidin-4-ylamino)methyl)piperidin-1-yl)(3-methoxyphenyl)methanone (184)

LCMS RT=2.7 (M+1) 495.5.

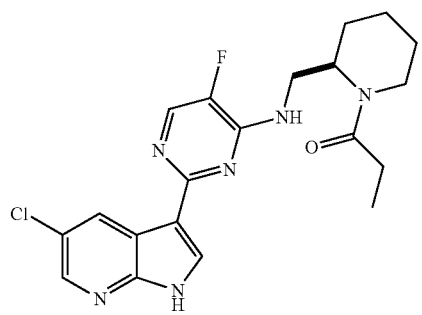

208

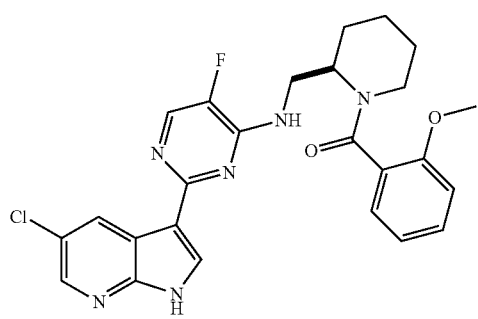

190

(R)-1-(2-((2-(5-chloro-1H-pyrrolo[2,3-b]pyridin-3-yl)-5-fluoropyrimidin-4-ylamino)methyl)piperidin-1-yl)propan-1-one (208)

LCMS RT=1.9 (M+1) 417.2.

(R)-(2-((2-(5-chloro-1H-pyrrolo[2,3-b]pyridin-3-yl)-5-fluoropyrimidin-4-ylamino)methyl)piperidin-1-yl)(2-methoxyphenyl)methanone (190)

LCMS RT=2.9 (M+1) 495.4.

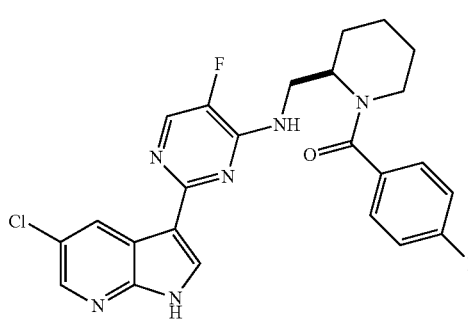

209

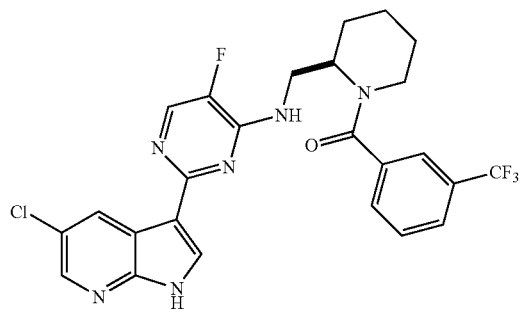

(R)-(2-((2-(5-chloro-1H-pyrrolo[2,3-b]pyridin-3-yl)-
5-fluoropyrimidin-4-ylamino)methyl)piperidin-1-yl)
(4-fluorophenyl)methanone (209)

LCMS RT=2.0 (M+1) 483.1.

(R)-(2-((2-(5-chloro-1H-pyrrolo[2,3-b]pyridin-3-yl)-
5-fluoropyrimidin-4-ylamino)methyl)piperidin-1-yl)
(3-(trifluoromethyl)phenyl)methanone (210)

LCMS RT=2.2 (M+1) 533.1.

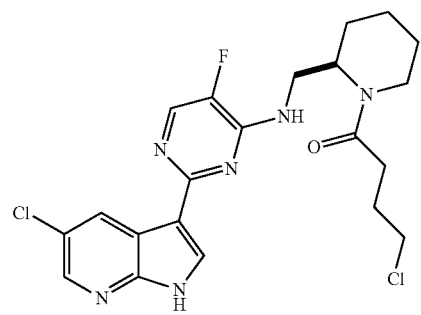

(R)-4-chloro-1-(2-((2-(5-chloro-1H-pyrrolo[2,3-b]
pyridin-3-yl)-5-fluoropyrimidin-4-ylamino)methyl)
piperidin-1-yl)butan-1-one (278)

LCMS RT=2.4 (M+1) 465.1.

(R)-1-(2-((2-(5-chloro-1H-pyrrolo[2,3-b]pyridin-3-
yl)-5-fluoropyrimidin-4-ylamino)methyl)piperidin-1-
yl)pent-4-en-1-one (279)

LCMS RT=2.1 (M+1) 443.2.

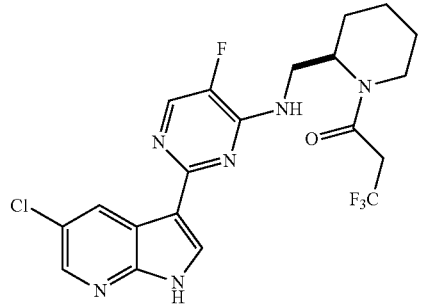

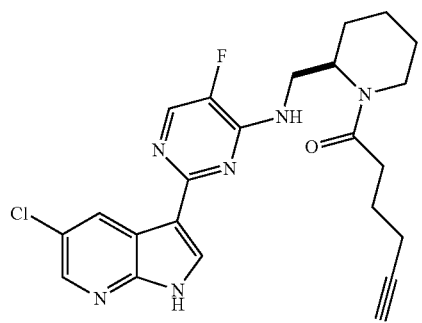

(R)-1-(2-((2-(5-chloro-1H-pyrrolo[2,3-b]pyridin-3-
yl)-5-fluoropyrimidin-4-ylamino)methyl)piperidin-1-
yl)-3,3,3-trifluoropropan-1-one (280)

LCMS RT=2.1 (M+1) 471.2.

(R)-1-(2-((2-(5-chloro-1H-pyrrolo[2,3-b]pyridin-3-
yl)-5-fluoropyrimidin-4-ylamino)methyl)piperidin-1-
yl)hex-5-yn-1-one (281)

LCMS (M+1) 454.2.

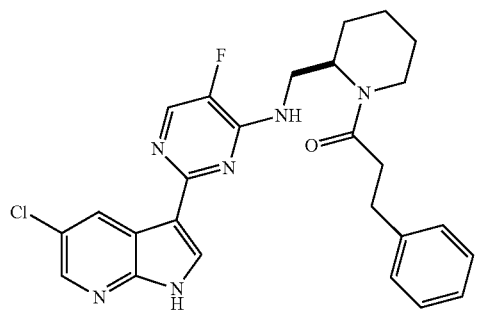

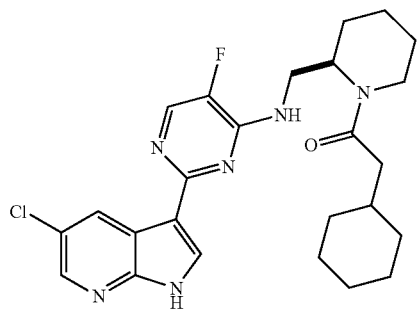

(R)-1-(2-((2-(5-chloro-1H-pyrrolo[2,3-b]pyridin-3-yl)-5-fluoropyrimidin-4-ylamino)methyl)piperidin-1-yl)-3-phenylpropan-1-one (293)

LCMS RT=3.1 (M+1) 493.2.

(R)-1-(2-((2-(5-chloro-1H-pyrrolo[2,3-b]pyridin-3-yl)-5-fluoropyrimidin-4-ylamino)methyl)piperidin-1-yl)-2-cyclohexylethanone (294)

LCMS RT=3.3 (M+1) 485.2.

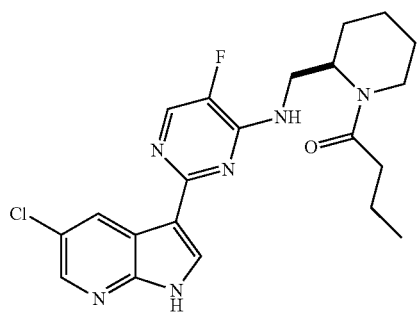

(R)-1-(2-((2-(5-chloro-1H-pyrrolo[2,3-b]pyridin-3-yl)-5-fluoropyrimidin-4-ylamino)methyl)piperidin-1-yl)butan-1-one (295)

LCMS RT=2.9 (M+1) 431.2.

(R)-1-(2-((2-(5-chloro-1H-pyrrolo[2,3-b]pyridin-3-yl)-5-fluoropyrimidin-4-ylamino)methyl)piperidin-1-yl)pentan-1-one (326)

LCMS RT=3.0 (M+1) 445.2.

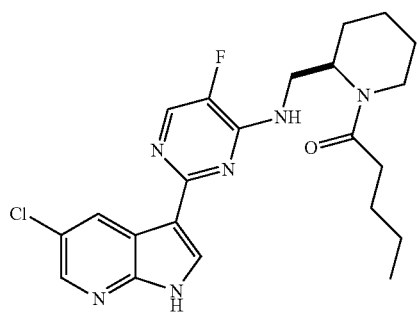

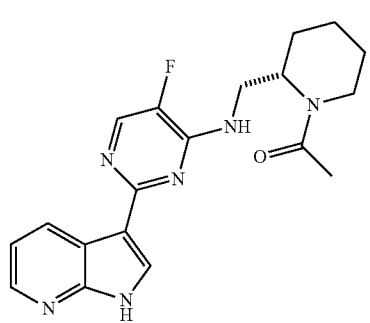

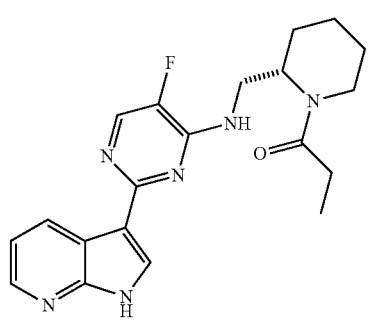

(S)-1-(2-((5-fluoro-2-(1H-pyrrolo[2,3-b]pyridin-3-yl)pyrimidin-4-ylamino)methyl)piperidin-1-yl)ethanone (256)

LCMS RT=2.2 (M+1) 369.3.

(S)-1-(2-((5-fluoro-2-(1H-pyrrolo[2,3-b]pyridin-3-yl)pyrimidin-4-ylamino)methyl)piperidin-1-yl)propan-1-one (257)

LCMS RT=2.3 (M+1) 383.3.

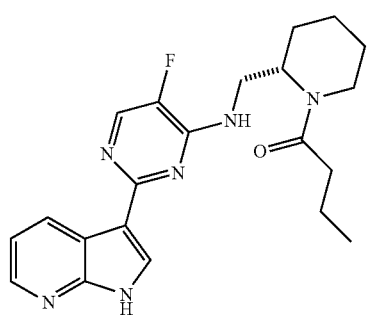

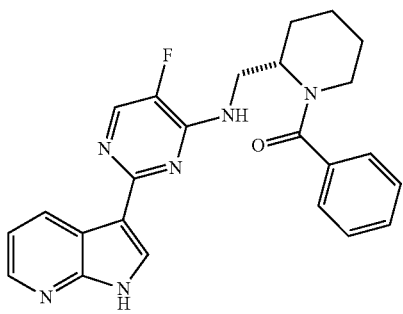

(S)-1-(2-((5-fluoro-2-(1H-pyrrolo[2,3-b]pyridin-3-yl)pyrimidin-4-ylamino)methyl)piperidin-1-yl)butan-1-one (258)

LCMS RT=2.5 (M+1) 397.3.

(S)-(2-((5-fluoro-2-(1H-pyrrolo[2,3-b]pyridin-3-yl)pyrimidin-4-ylamino)methyl)piperidin-1-yl)(phenyl)methanone (259)

LCMS RT=2.4 (M+1) 431.3.

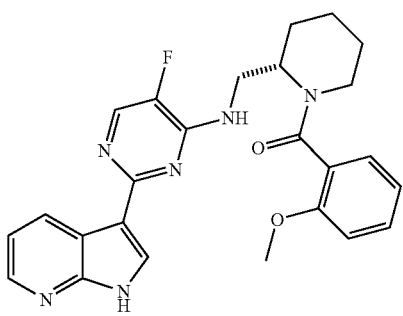

(S)-(2-((5-fluoro-2-(1H-pyrrolo[2,3-b]pyridin-3-yl)pyrimidin-4-ylamino)methyl)piperidin-1-yl)(2-methoxyphenyl)methanone (260)

LCMS RT=2.4 (M+1) 461.3.

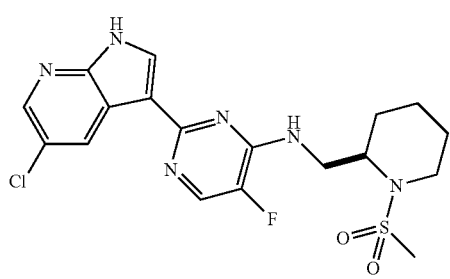

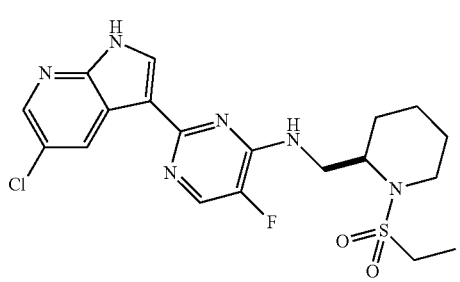

(R)-2-(5-chloro-1H-pyrrolo[2,3-b]pyridin-3-yl)-5-fluoro-N-((1-(methylsulfonyl)-piperidin-2-yl)methyl)pyrimidin-4-amine (381)

LCMS RT=2.7 min, (M+H) 439.3

(R)-2-(5-chloro-1H-pyrrolo[2,3-b]pyridin-3-yl)-5-fluoro-N-((1-(ethylsulfonyl)-piperidin-2-yl)methyl)pyrimidin-4-amine (382)

LCMS RT=2.9 min, (M+H) 453.3.

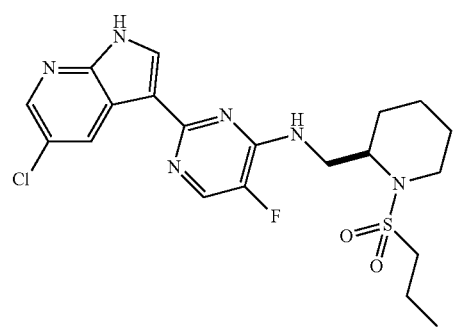

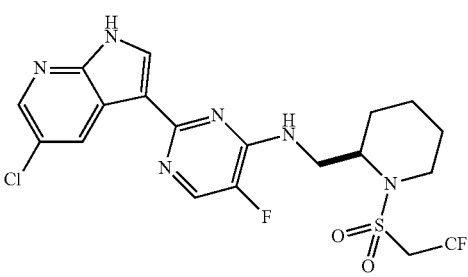

(R)-2-(5-chloro-1H-pyrrolo[2,3-b]pyridin-3-yl)-5-fluoro-N-((1-(propylsulfonyl)piperidin-2-yl)methyl)pyrimidin-4-amine (328)

LCMS RT=2.2 min, (M+H) 467.1.

(R)-2-(5-chloro-1H-pyrrolo[2,3-b]pyridin-3-yl)-5-fluoro-N-((1-(2,2,2-trifluoro-ethylsulfonyl)-piperidin-2-yl)methyl)pyrimidin-4-amine (383)

LCMS RT=3.0 min, (M+H) 507.3.

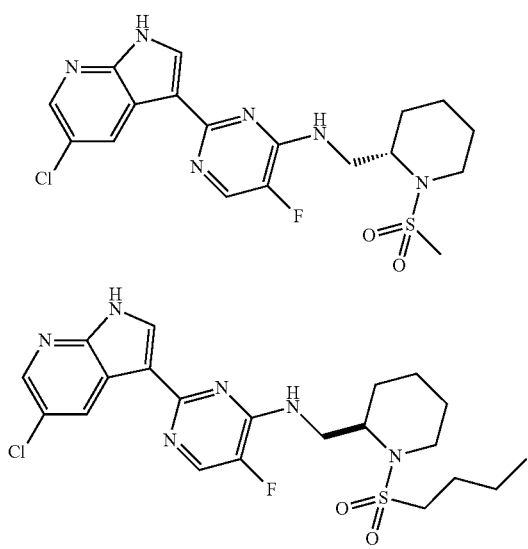

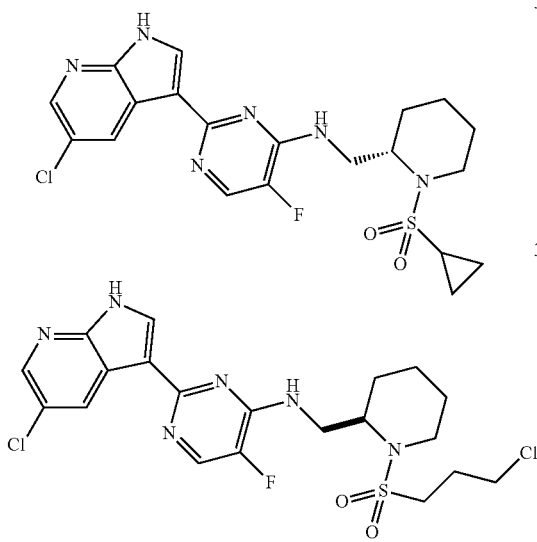

(S)-2-(5-chloro-1H-pyrrolo[2,3-b]pyridin-3-yl)-5-fluoro-N-((1-(methylsulfonyl)-piperidin-2-yl)methyl)pyrimidin-4-amine (384)

LCMS RT=2.7 min, (M+H) 439.3.

(R)—N-((1-(butylsulfonyl)piperidin-2-yl)methyl)-2-(5-chloro-1H-pyrrolo[2,3-b]pyridin-3-yl)-5-fluoropyrimidin-4-amine (329)

LCMS RT=2.3 min, (M+H) 481.2.

(S)-2-(5-chloro-1H-pyrrolo[2,3-b]pyridin-3-yl)-5-fluoro-N-((1-(cyclopropylsulfonyl)-piperidin-2-yl)methyl)pyrimidin-4-amine (386)

LCMS RT=2.9 min, (M+H) 465.3.

(R)-2-(5-chloro-1H-pyrrolo[2,3-b]pyridin-3-yl)-N-((1-(3-chloropropylsulfonyl)piperidin-2-yl)methyl)-5-fluoropyrimidin-4-amine (330)

LCMS RT=2.2 min, (M+H) 501.1.

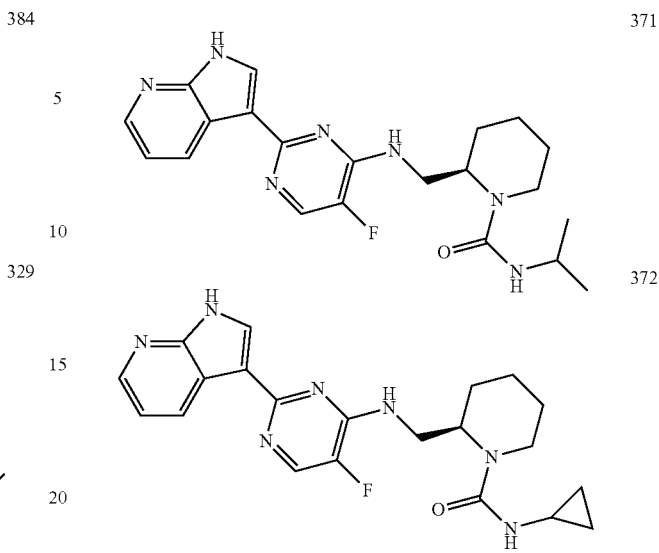

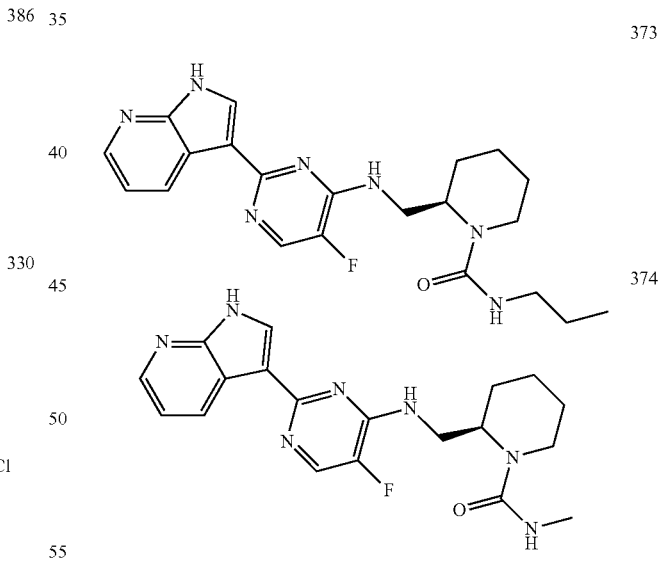

(R)-2-(5-fluoro-2-(1H-pyrrolo[2,3-b]pyridin-3-yl)pyrimidin-4-ylamino)methyl)-N-isopropylpiperidine-1-carboxamide (371)

LCMS RT=1.8 min, (M+H) 412.2.

(R)—N-cyclopropyl-2-((5-fluoro-2-(1H-pyrrolo[2,3-b]pyridin-3-yl)pyrimidin-4-ylamino)-methyl)piperidine-1-carboxamide (372)

LCMS RT=1.9 min, (M+H) 424.2.

(R)—N-ethyl-2-((5-fluoro-2-(1H-pyrrolo[2,3-b]pyridin-3-yl)pyrimidin-4-ylamino)-methyl)piperidine-1-carboxamide (373)

LCMS RT=1.7 min, (M+H) 398.2.

(R)-2-((5-fluoro-2-(1H-pyrrolo[2,3-b]pyridin-3-yl)pyrimidin-4-ylamino)methyl)-N-methylpiperidine-1-carboxamide (374)

LCMS RT=1.6 min, (M+H) 384.2.

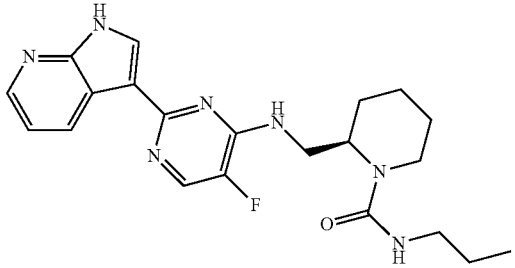

(R)-2-((5-fluoro-2-(1H-pyrrolo[2,3-b]pyridin-3-yl)pyrimidin-4-ylamino)methyl)-N-propylpiperidine-1-carboxamide (375)

LCMS RT=1.8 min, (M+H) 412.2.

General Scheme 14:

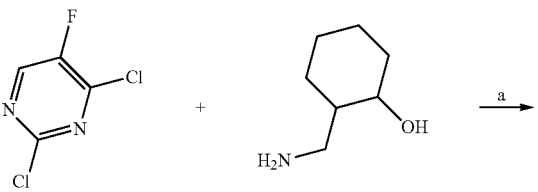

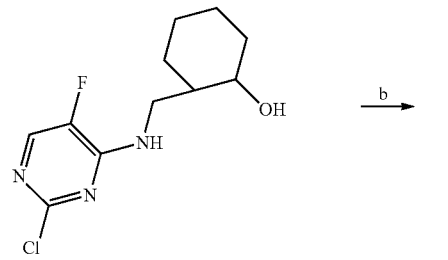

14a

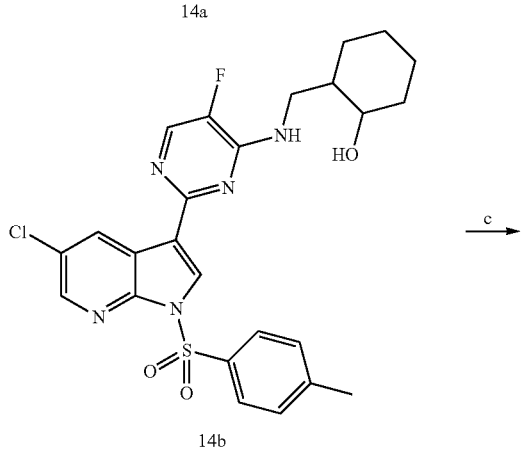

14b

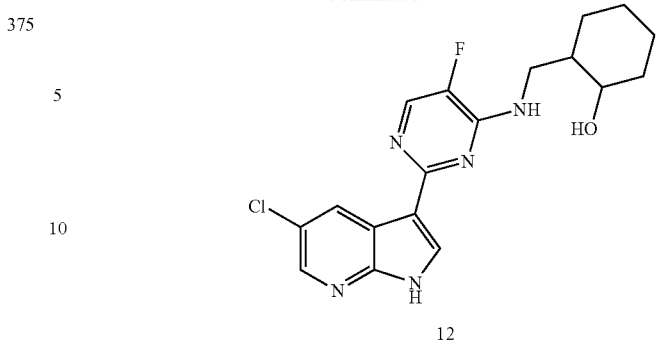

12

(a) $^i$Pr$_2$NEt, isopropanol, 80° C.; (b) 5-chloro-3-(4,4,5,5-tetramethyl-1,3,2-dioxaborolan-2-yl)-1-tosyl-1H-pyrrolo[2,3-b]pyridine, Pd(Ph$_3$P)$_4$, Na$_2$CO$_3$, DME, 130° C.; (c) HCl/dioxane, CH$_2$Cl$_2$; (d) propylisocyanate, pyridine, CH$_2$Cl$_2$.

Formation of 1-((2-chloro-5-fluoropyrimidin-4-ylamino)methyl)cyclohexanol (14a)

To a solution of 2-(aminomethyl)cyclohexanol hydrochloride (0.09 g, 0.54 mmol) and 2,4-dichloro-5-fluoro-pyrimidine (0.10 g, 0.60 mmol) in isopropanol (2 mL) was added $^i$Pr$_2$NEt (0.21 mL, 1.20 mmol). The reaction mixture was heated at 80° C. for 12 hours. The reaction mixture was concentrated under reduced pressure and the resulting residue was purified by silica gel chromatography (25%-75% EtOAc/hexanes) to afford desired product, 14a.
LCMS (M+1) 260.1, (M−1) 258.3.

Formation of 2-((2-(5-chloro-1-tosyl-1H-pyrrolo[2,3-b]pyridin-3-yl)-5-fluoropyrimidin-4-ylamino)methyl)cyclohexanol (14b)

To a degassed solution of 5-chloro-1-(p-tolylsulfonyl)-3-(4,4,5,5-tetramethyl-1,3,2-dioxaborolan-2-yl)pyrrolo[2,3-b]pyridine (0.15 g, 0.35 mmol), 1-((2-chloro-5-fluoropyrimidin-4-ylamino)methyl)cyclohexanol, 14a, (0.09 g, 0.35 mmol) and aqueous KOAc solution (1.04 mL of 1M solution, 1.04 mmol) in dimethylacetamide was added palladium triphenylphosphine (0.04 g, 0.03 mmol). The reaction mixture was heated at 140° C. in microwave for 15 min and then cooled to room temperature. The reaction mixture was filtered through celite, concentrated in vacuo, and the resulting crude residue was purified by by preparatory HPLC (0.1% TFA-H$_2$O/acetonitrile) to afford the desired product, 14b:
LCMS RT=2.6 (M+1) 530.3.

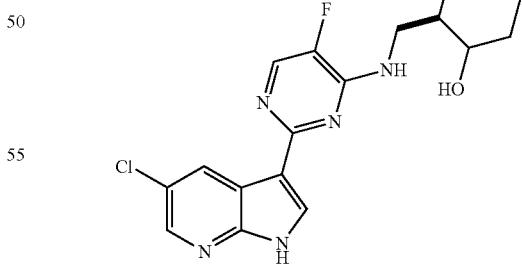

12

Formation of (2R)-2-((2-(5-chloro-1H-pyrrolo[2,3-b]pyridin-3-yl)-5-fluoropyrimidin-4-ylamino)methyl)cyclohexanol (12)

To a solution of 2-((2-(5-chloro-1-tosyl-1H-pyrrolo[2,3-b]pyridin-3-yl)-5-fluoropyrimidin-4-ylamino)methyl)cyclohexanol, 14b, (0.10 g, 0.19 mmol) in THF (3 mL) was added aqueous lithium hydroxide (1 mL of 1N solution). The reaction mixture was stirred at room temperature for 12 hours. The resulting residue was purified by preparatory HPLC (0.1% TFA-H₂O/acetonitrile) to afford the desired product, 12.

LCMS FIA RT=1.9 (M+1) 376.2.

General Scheme 14B:

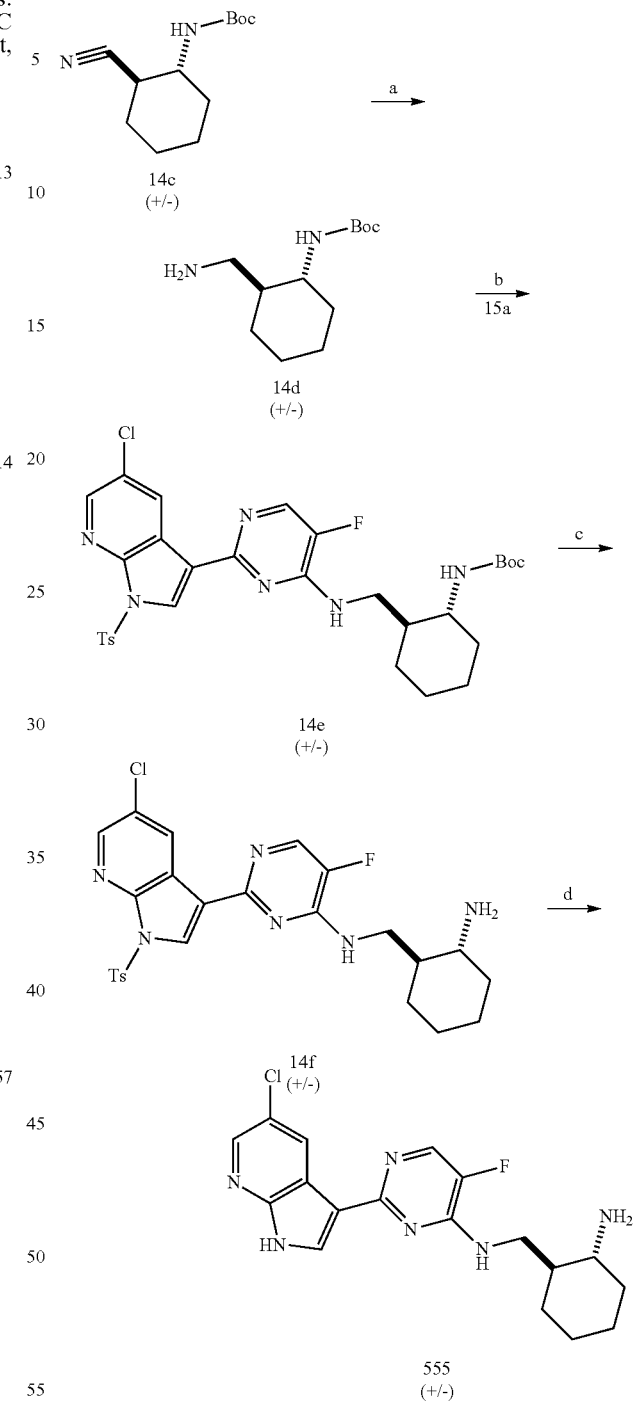

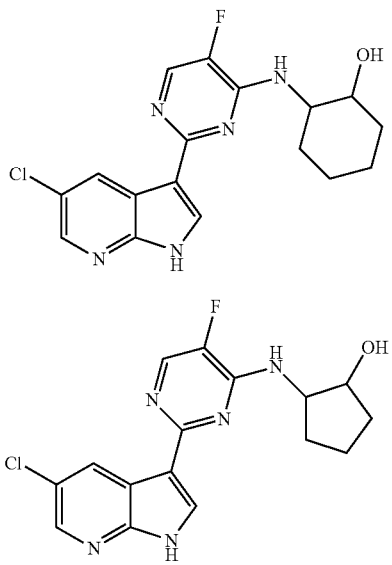

2-(2-(5-chloro-1H-pyrrolo[2,3-b]pyridin-3-yl)-5-fluoropyrimidin-4-ylamino)cyclohexanol (13)

LCMS FIA RT=1.8 (M+1) 362.2.

2-(2-(5-chloro-1H-pyrrolo[2,3-b]pyridin-3-yl)-5-fluoropyrimidin-4-ylamino)cyclopentanol (14)

LCMS FIA RT=1.0 (M+1) 348.3.

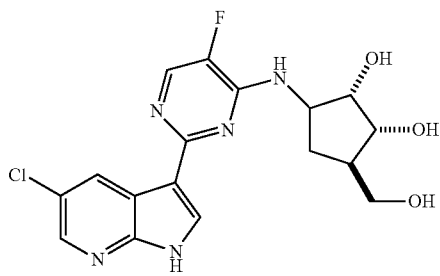

(1R,2S,3R,5R)-3-((2-(5-chloro-1H-pyrrolo[2,3-b]pyridin-3-yl)-5-fluoropyrimidin-4-ylamino)-5-(hydroxymethyl)cyclopentane-1,2-diol (657)

¹H NMR (300 MHz, DMSO) δ 12.41 (s, 1H), 8.80 (d, J=2.3 Hz, 1H), 8.28 (d, J=2.4 Hz, 1H), 8.25 (s, 1H), 8.17 (d, J=4.0 Hz, 1H), 7.64 (s, 1H), 4.80-4.50 (m, 3H), 4.47 (dd, J=7.5, 14.8 Hz, 1H), 3.89 (dd, J=5.3, 6.3 Hz, 1H), 3.77 (dd, J=5.1, 5.0 Hz, 1H), 3.50-3.37 (m, 2H), 2.36-2.24 (m, 1H), 2.04 (dd, J=8.3, 13.5 Hz, 1H), 1.99 (s, 1H), 1.27 (td, J=8.4, 4.4 Hz, 1H) and 1.21 (s, 1H) ppm.

LCMS RT=3.0 (M+1) 399.4.

(a) Raney-N₁, H₂ (50 PSI), EtOH; (b) 15a, THF, 70° C.; (c) TFA, CH₂Cl₂ (d) 1N LiOH, THF, 120° C.

Formation of tert-butyl trans-2-(aminomethyl)cyclohexylcarbamate (14d)

A solution of tert-butyl trans-2-cyanocyclohexylcarbamate and Raney-Ni in absolute EtOH was stirred under H₂ atmosphere (50 PSI) for 24 hours. Filtration and evaporation of the solvent followed by flash chromatography (SiO$_2$, O-20% MeOH—CH$_2$Cl$_2$, gradient elution) provided the target compound, 14d, as a racemic mixture of trans isomers (286 mg, 66% yield): FIA (M+H) 229.33.

Formation of tert-butyl trans-2-((2-(5-chloro-1-tosyl-1H-pyrrolo[2,3-b]pyridin-3-yl)-5-fluoro-pyrimidin-4-yl-amino)methyl)cyclohexylcarbamate (14e)

A mixture of 5-chloro-3-(5-fluoro-4-(methylsulfinyl)pyrimidin-2-yl)-1-tosyl-1H-pyrrolo[2,3-b]pyridine, 15a, (0.42 g, 0.90 mmol) and tert-butyl trans-2-(aminomethyl)cyclohexylcarbamate (0.24 g, 1.06 mmol) were heated in THF (10 mL) to 70° C. After 1.3 hours, the mixture was concentrated in vacuo. Flash chromatography (SiO$_2$, 0-60% EA/Hex, gradient elution) provided the desired intermediate, tert-butyl trans-2-((2-(5-chloro-1-tosyl-1H-pyrrolo[2,3-b]pyridin-3-yl)-5-fluoropyrimidin-4-ylamino)methyl)cyclohexylcarbamate, 14e, as a racemic mixture of trans isomers, which was taken into the next reaction without further purification (0.52 g, 92% yield).

Formation of N-((trans-2-aminocyclohexyl)methyl)-2-(5-chloro-1-tosyl-1H-pyrrolo[2,3-b]pyridin-3-yl)-5-fluoropyrimidin-4-amine (14f)

A solution of the tert-butyl trans-2-((2-(5-chloro-1-tosyl-1H-pyrrolo[2,3-b]pyridin-3-yl)-5-fluoropyrimidin-4-ylamino)methyl)cyclohexylcarbamate, 14e, (0.52 g) in CH$_2$Cl$_2$ (5 mL) was treated with TFA (2.5 mL) for 30 min. the solution was concentrated in vacuo and the resulting crude material was taken up in CH$_3$CN and concentrated in vacuo several times to remove excess TFA and to provide the desired amine, 14f, as racemic mixture of trans isomers, as the TFA salt, which was sufficiently pure for use in the next reaction.
LCMS RT=1.93 min, (M+H) 529.0

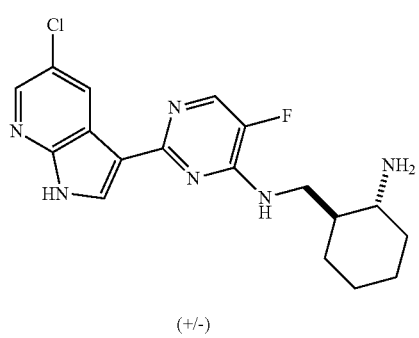

Formation of N-((trans-2-aminocyclohexyl)methyl)-2-(5-chloro-1H-pyrrolo[2,3-b]pyridin-3-yl)-5-fluoro-pyrimidin-4-amine (555)

A solution of N-((trans-2-aminocyclohexyl)methyl)-2-(5-chloro-1-tosyl-1H-pyrrolo[2,3-b]pyridin-3-yl)-5-fluoropyrimidin-4-amine, 14f, (0.050 g, 0.077 mmol) in THF was treated with LiOH (0.5 mL, 1.0M) at 60° C. After 5 min, at 120° C., the solution was diluted with EtOAc, and washed with brine, filtered and concentrated in vacuo. Preparative HPLC provided the desired compound, 555, as a racemic mixture of trans isomers (12 mg, 33% yield).
$^1$H NMR (300 MHz, MeOD) δ 8.75 (d, J=2.4 Hz, 1H), 8.31 (d, J=2.4 Hz, 1H), 8.29 (s, 1H), 8.24 (d, J=4.4 Hz, 1H), 3.96 (dd, J=5.8, 14.4 Hz, 1H), 3.73 (dd, J=4.3, 14.3 Hz, 1H), 3.08-3.00 (m, 1H), 2.05-1.87 (m, 3H), 1.80 (m, 3H) and 1.48-1.39 (m, 4H) ppm; LCMS RT=1.9 min, (M+H) 375.0.

General Scheme 14C:

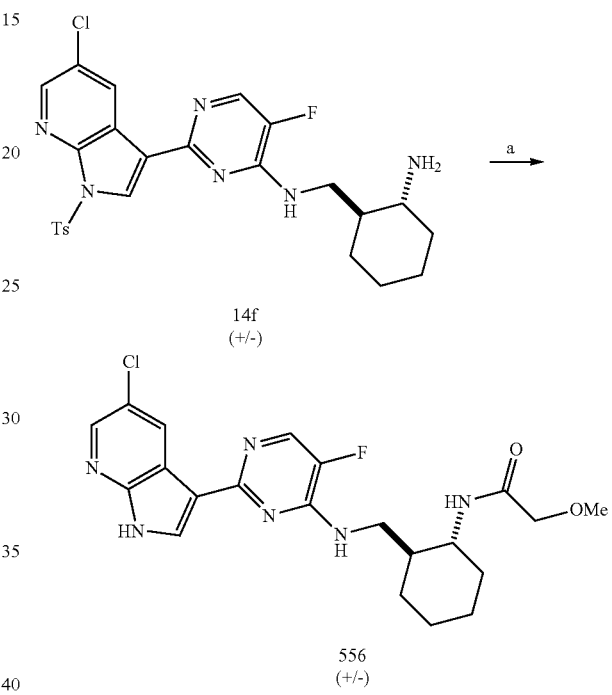

(a) i: RCOCl, DIEA, CH$_2$Cl$_2$ ii: 1N LiOH, THF, 120° C.

Formation of N-(trans-2-((2-(5-chloro-1H-pyrrolo[2,3-b]pyridin-3-yl)-5-fluoropyrimidin-4-ylamino)methyl)cyclohexyl)-2-methoxyethanamide (556)

To a cooled mixture of N-((trans-2-aminocyclohexyl)methyl)-2-(5-chloro-1-tosyl-1H-pyrrolo[2,3-b]pyridin-3-yl)-5-fluoropyrimidin-4-amine (0.060 g, 0.093 mmol) and $^i$Pr$_2$NEt (0.057 mL, 0.330 mmol) in CH$_2$Cl$_2$ (2 mL) at 0° C., was added 2-methoxyacetyl chloride (0.010 g, 0.098 mmol). After 5 min, the solution was allowed to warm to room temperature. After 3 hours, the mixture was concentrated in vacuo, taken up in THF (1 mL) and treated with LiOH (0.326 mL, 1.0 M solution) at 120° C. for 10 min. The resulting mixture was cooled to room temperature and partitioned and the aqueous layer extracted with EtOAc and the combined organics were concentrated in vacuo. Preparative HPLC provided the desired product, 556, as a racemic mixture of TFA salts (8.6 mg, 17% yield).
$^1$H NMR (300 MHz, MeOD) δ 8.74 (d, J=2.3 Hz, 1H), 8.42 (s, 1H), 8.38 (d, J=2.3 Hz, 1H), 8.27 (d, J=5.4 Hz, 1H), 3.85-3.81 (m, 2H), 3.75 (d, J=8.5 Hz, 2H), 3.26 (s, 3H), 1.97-1.77 (m, 5H) and 1.43-1.35 (m, 4H) ppm; LCMS RT=2.8 min, (M+H) 446.8.

The following analogs can be prepared in same manner as 556.

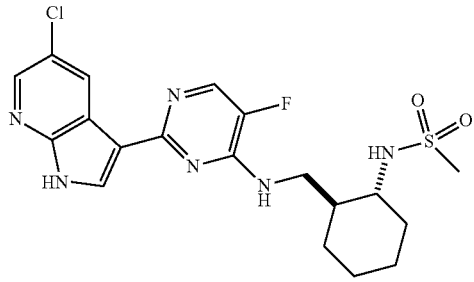

557

(+/-)

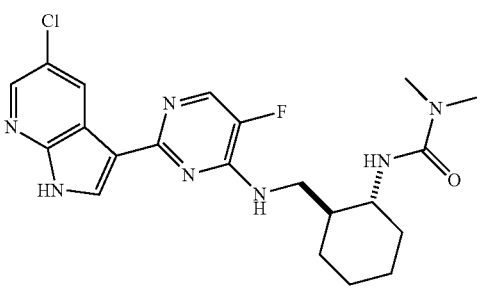

564

(+/-)

Formation of N-(trans-2-((2-(5-chloro-1H-pyrrolo[2,3-b]pyridin-3-yl)-5-fluoropyrimidin-4-ylamino)methyl)cyclohexyl)methanesulfonamide (557)

Sulfonamide 557 was prepared according to the procedure for compound 36 (Scheme 12B) using N-((trans-2-aminocyclohexyl)methyl)-2-(5-chloro-1-tosyl-1H-pyrrolo[2,3-b]pyridin-3-yl)-5-fluoropyrimidin-4-amine, 14f, and methane sulfonyl chloride, afforded desired product, 557, as a racemic mixture of trans isomers.

$^1$H NMR (300.0 MHz, MeOD) δ 8.78 (d, J=2.4 Hz, 1H), 8.45 (d, J=4.2 Hz, 1H), 8.37 (d, J=2.3 Hz, 1H), 8.26 (d, J=5.4 Hz, 1H), 4.12 (dd, J=4.5, 13.7 Hz, 1H), 3.89 (dd, J=7.1, 13.8 Hz, 1H), 3.26-3.16 (m, 1H), 3.00 (s, 3H), 2.18-1.90 (m, 2H), 1.79-1.74 (m, 2H) and 1.50-1.25 (m, 4H) ppm; LCMS RT=2.8 min, (M+H) 452.6.

Formation of 3-(trans-2-((2-(5-chloro-1H-pyrrolo[2,3-b]pyridin-3-yl)-5-fluoropyrimidin-4-ylamino)methyl)cyclohexyl)-1,1-dimethylurea (564)

Urea 564 was prepared according to the procedure for compound 20 (Scheme 12A) using N-((trans-2-aminocyclohexyl)methyl)-2-(5-chloro-1-tosyl-1H-pyrrolo[2,3-b]pyridin-3-yl)-5-fluoropyrimidin-4-amine, 14f, and dimethylcarbomoyl chloride, afforded desired product, 564, as a racemic mixture of trans isomers.

$^1$H NMR (300.0 MHz, MeOD) δ 8.78 (d, J=2.4 Hz, 1H), 8.45 (d, J=4.2 Hz, 1H), 8.37 (d, J=2.3 Hz, 1H), 8.26 (d, J=5.4 Hz, 1H), 4.12 (dd, J=4.5, 13.7 Hz, 1H), 3.89 (dd, J=7.1, 13.8 Hz, 1H), 3.26-3.16 (m, 1H), 3.00 (s, 3H), 2.18-1.90 (m, 2H), 1.79-1.74 (m, 2H) and 1.50-1.25 (m, 4H) ppm; LCMS RT=1.9 min, (M+H) 445.7.

General Scheme 15:

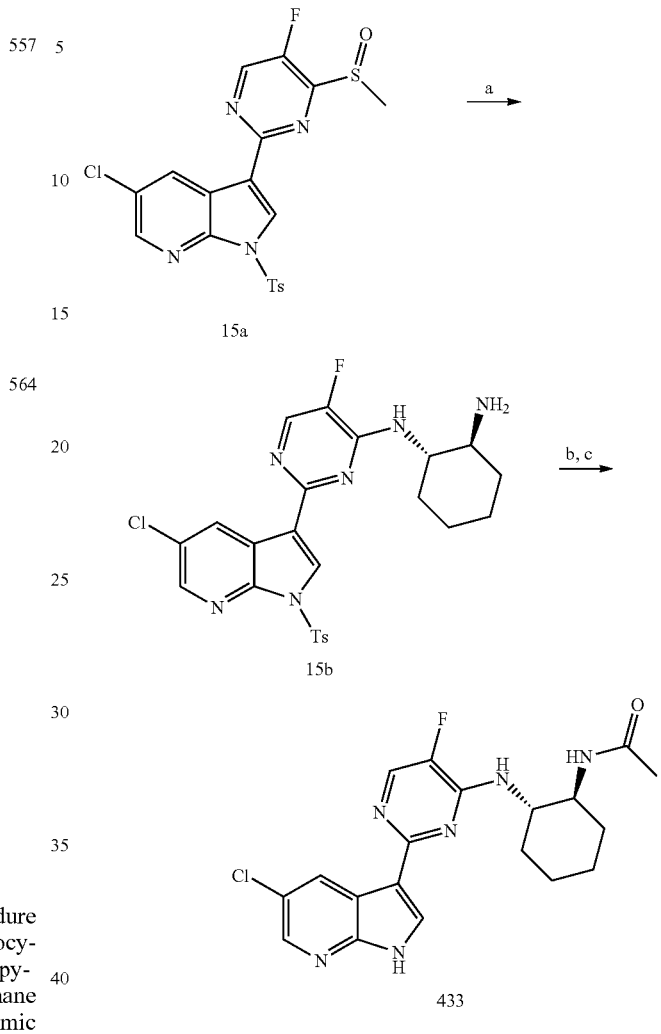

(a) (1S,2S)-cyclohexane-1,2-diamine, THF, 140° C.; (b) AcCl, $^i$Pr$_2$NEt, CH$_2$Cl$_2$; (c) 1M LiOH, DCE, 150° C., microwave 20 min.

Formation of (1S,2S)—N1-(2-(5-chloro-1-tosyl-1H-pyrrolo[2,3-b]pyridin-3-yl)-5-fluoropyrimidin-4-yl)cyclohexane-1,2-diamine (15b)

5-Chloro-3-(5-fluoro-4-methylsulfinyl-pyrimidin-2-yl)-1-(p-tolylsulfonyl)pyrrolo[2,3-b]pyridine, 15a, (0.25 g, 0.53 mmol) and (1S,2S)-cyclohexane-1,2-diamine (0.12 g, 1.08 mmol) were dissolved in THF (3.0 mL), and heated to 140° C. for 20 minutes in a sealed vial. The solvent was evaporated in vacuo and the residue was purified by silica gel chromatography (0%-15% MeOH/CH$_2$Cl$_2$) to provide product, 15b, as a white foamy solid (220 mg, 79% yield).

$^1$H NMR (300 MHz, CDCl$_3$) δ 8.85 (d, J=2.4 Hz, 1H), 8.52 (s, 1H), 8.40 (d, J=2.4 Hz, 1H), 8.13-8.09 (m, 3H), 7.31-7.28 (m, 2H), 5.14 (d, J=6.6 Hz, 1H), 3.96-3.85 (m, 1H), 2.69 (td, J=10.2, 4.7 Hz, 1H), 2.40 (s, 3H), 2.33 (d, J=5.6 Hz, 1H), 2.12-2.06 (m, 1H), 1.88-1.84 (m, 2H) and 1.60-1.21 (m, 4H) ppm; LCMS RT=2.33 (M+1) 515.2.

Formation of N-[(1s, 2S)-2-[[2-(5-chloro-1H-pyrrolo[2,3-b]pyridin-3-yl)-5-fluoro-pyrimidin-4-yl]amino]cyclohexyl]acetamide (433)

(1S,2S)—N-[2-[5-chloro-1-(p-tolylsulfonyl)pyrrolo[5,4-b]pyridin-3-yl]-5-fluoro-pyrimidin-4-yl]cyclohexane-1,2-diamine, 15b, (0.100 g, 0.194 mmol) was dissolved in dichloromethane (2 mL) and treated with $^i$Pr$_2$NEt (0.075 g, 0.101 mL, 0.583 mmol). Acetyl chloride (0.021 mL, 0.291 mmol) was added and the reaction was allowed to stir at room temperature for 30 minutes. The volatiles were evaporated under reduced pressure, and the residue was dissolved in dichloroethane (2 mL) and treated with LiOH (0.097 mL of 1 M solution, 0.971 mmol). The reaction mixture was heated in the microwave at 150° C. for 10 minutes. The reaction was diluted with EtOAc (5 mL) and water (5 mL) and the layers were separated. The aqueous layer was extracted with EtOAc (2×5 mL), and the combined organic extracts were dried over Na$_2$SO$_4$ and concentrated in vacuo to provide the crude product, which was purified by silica gel chromatography (0%-15% MeOH/CH$_2$Cl$_2$) to provide N-[(1S,2S)-2-[[2-(5-chloro-1H-pyrrolo[2,3-b]pyridin-3-yl)-5-fluoro-pyrimidin-4-yl]amino]cyclohexyl]acetamide, 433, (34 mg, 44% yield).

$^1$H NMR (300 MHz, d6-DMSO) δ 13.03 (s, 1H), 9.10 (s, 1H), 9.05 (s, 11-1), 8.67 (d, J=2.1 Hz, 1H), 8.48 (d, J=5.4 Hz, 1H), 8.43 (d, J=2.3 Hz, 1H), 7.97 (d, J=7.7 Hz, 1H), 4.15-4.07 (m, 1H), 3.93-3.87 (m, 1H), 2.20-2.15 (m, 1H), 1.99-1.92 (m, 1H), 1.85-1.79 (m, 2H), 1.74 (s, 3H) and 1.52-1.36 (m, 4H) ppm; LCMS RT=2.41 (M+1) 403.4.

General Scheme 16:

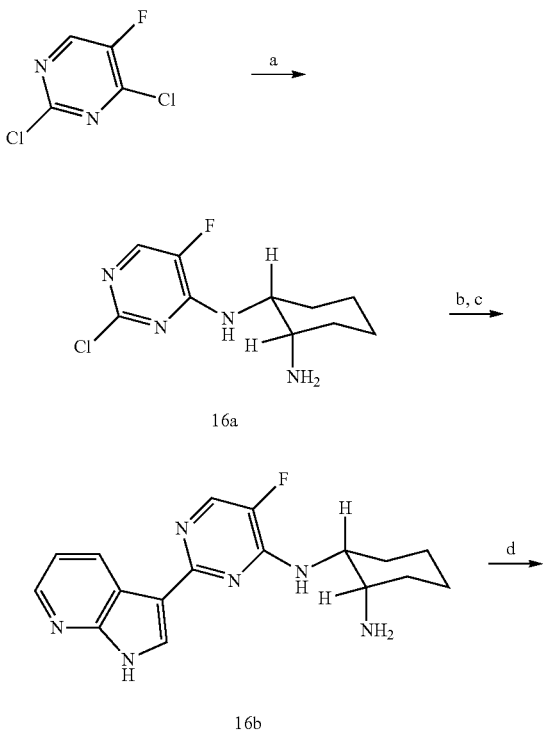

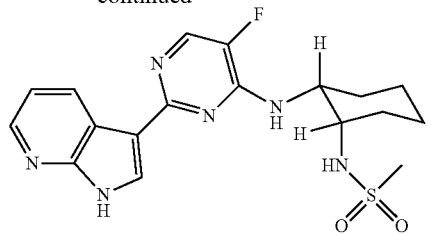

337

(a) cyclohexane-cis-1,2-diamine, isopropanol, $^i$Pr$_2$Net; (b) 3-(4,4,5,5-tetramethyl-1,3,2-dioxaborolan-2-yl)-1H-pyrrolo[2,3-b]pyridine, Pd(PPh$_3$)$_4$, Na$_2$CO$_3$, DME: DCE, 150° C., microwave; (c) 1M LiOH 150° C., microwave; (d) MeSO$_2$Cl, $^i$Pr$_2$NEt, DMF:DCM.

Formation of N1-(2-chloro-5-fluoropyrimidin-4-yl)cyclohexane-cis-1,2-diamine (16a)

2,4-Dichloro-5-fluoropyrimidine (0.50 g, 2.99 mmol) was dissolved in isopropanol (7 mL) and treated with $^i$Pr$_2$NEt (1.50 mL, 8.98 mmol). Cyclohexane-cis-1,2-diamine (0.46 g, 4.03 mmol) was added and the reaction was allowed to stir at room temperature overnight. The solvent was evaporated and the reaction mixture was diluted in EtOAc (15 mL) and washed with aqueous saturated NaHCO$_3$ solution. The aqueous layer was extracted with EtOAc (15 mL) and the combined organic layers were dried over Na$_2$SO$_4$ and concentrated in vacuo to provide the crude product. The resulting crude was purified by silica gel chromatography (5%-30% MeOH/CH$_2$Cl$_2$) to provide 16a (370 mg, 50% yield) as a white solid.

$^1$H NMR (300 MHz, CDCl$_3$) δ 7.83 (d, J=2.8 Hz, 1H), 6.16 (s, 1H), 4.08 (s, 1H), 3.13 (d, J=3.9 Hz, 1H) and 1.84-1.44 (m, 8H) ppm; LCMS RT=0.8 (M+1) 245.1.

Formation of N1-(5-fluoro-2-(1H-pyrrolo[2,3-b]pyridin-3-yl)pyrimidin-4-yl)cyclohexane-1,2-diamine (16b)

3-(4,4,5,5-Tetramethyl-1,3,2-dioxaborolan-2-yl)-1H-pyrrolo[2,3-b]pyridine (0.26 g, 0.65 mmol) was dissolved in DME (8 mL) and treated with N1-(2-chloro-5-fluoropyrimidin-4-yl)cyclohexane-cis-1,2-diamine, 16a, (0.16 g, 0.65 mmol). Pd(PPh$_3$)$_4$ (0.10 mg, 0.08 mmol) and 2M aqueous Na$_2$CO$_3$ (3.25 mL) were added and the suspension was heated in the microwave to 150° C. for 20 minutes. 1M aqueous LiOH (5 mL) was added, and the reaction was heated in the microwave to 150° C. for an additional 15 minutes. The organic solvent was evaporated under reduced pressure and the aqueous phase was extracted with CH$_2$Cl$_2$ (2×20 mL). The combined organic phases were dried over Na$_2$SO$_4$ and concentrated in vacuo. The resulting residue was purified by silica gel chromatography (0%-100% CH$_2$Cl$_2$/EtOAc) to provide product 16b (140 mg, 66% yield) as a brown foam.

$^1$H NMR (300 MHz, d6-DMSO) δ 12.14 (s, 1H), 8.66 (d, J=8.0 Hz, 1H), 8.29-8.22 (m, 3H), 7.81 (s, 2H), 7.28-7.19 (m, 2H), 4.55 (s, 1H), 3.74 (s, 1H) and 1.92-1.49 (m, 8H) ppm; LCMS RT=1.8 (M+1) 327.2.

Formation of N-[cis-2-[[5-fluoro-2-(1H-pyrrolo[2,3-b]pyridin-3-yl)pyrimidin-4-yl]amino]cyclohexyl]methanesulfonamide (337)

N1-(5-fluoro-2-(1H-pyrrolo[2,3-b]pyridin-3-yl)pyrimidin-4-yl)cyclohexane-1,2-diamine, 16b, (0.009 g, 0.027 mmol) was dissolved in an 8:2 mixture of CH₂Cl₂/DMF (1 mL) and treated with ⁱPr₂NEt (0.019 mL, 0.110 mmol) and methanesulfonyl chloride (0.006 mL, 0.083 mmol). The reaction was stirred at room temperature overnight, concentrated in vacuo and the residue was purified by HPLC with 10%-90% acetonitrile/water with 0.03% TFA to provide compound 337.

$^1$H NMR (300 MHz, d6-DMSO) δ 12.47 (s, 1H), 8.64 (d, J=7.8 Hz, 1H), 8.45-8.34 (m, 3H), 7.29 (dd, J=4.8, 7.8 Hz, 1H), 7.06 (d, J=7.5 Hz, 1H), 4.47-4.25 (m, 1H), 4.05-3.89 (m, 1H), 2.80 (s, 3H), 1.95-1.62 (m, 6H) and 1.49-1.24 (m, 2H) ppm.; LCMS RT=2.3 (M+1) 405.3.

The following compounds can be prepared in a manner similar to the one described in either Scheme 15 or Scheme 16:

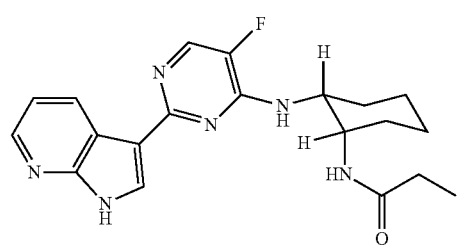

N-[cis-2-[[5-fluoro-2-(1H-pyrrolo[2,3-b]pyridin-3-yl)pyrimidin-4-yl]amino]-cyclohexyl]propanamide (341)

$^1$H NMR (300 MHz, d6-DMSO) δ 12.47 (s, 1H), 8.65 (d, J=8.1 Hz, 1H), 8.49-8.23 (m, 3H), 7.61 (d, J=7.8 Hz, 1H), 7.29 (dd, J=4.7, 8.0 Hz, 1H), 4.39 (d, J=19.5 Hz, 2H), 2.10 (q, J=7.6 Hz, 2H), 1.79-1.64 (m, 6H), 1.48 (d, J=6.4 Hz, 2H) and 0.91 (t, J=7.6 Hz, 3H) ppm; LCMS RT=2.3 (M+1) 383.4.

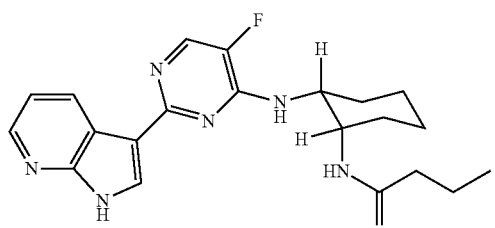

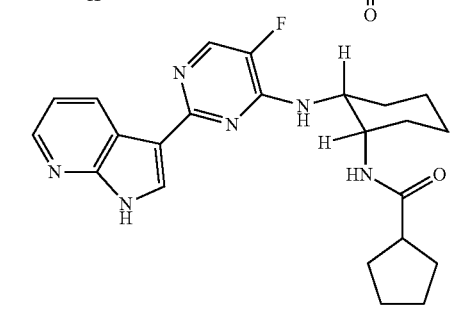

N-[cis-2-[[5-fluoro-2-(1H-pyrrolo[2,3-b]pyridin-3-yl)pyrimidin-4-yl]amino]cyclohexyl]butanamide (342)

LCMS RT=2.5 (M+1) 397.4.

N-[cis-2-[[5-fluoro-2-(1H-pyrrolo[2,3-b]pyridin-3-yl)pyrimidin-4-yl]amino]cyclohexyl]cyclopentanecarboxamide (343)

LCMS RT=2.7 (M+1) 423.4.

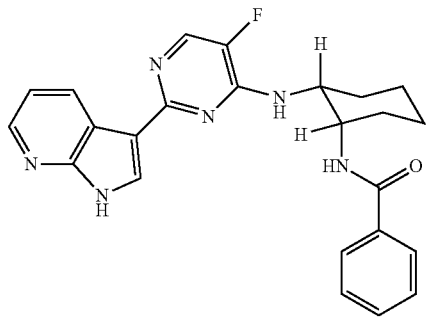

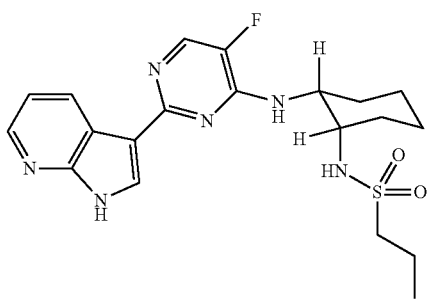

N-[cis-2-[[5-fluoro-2-(1H-pyrrolo[2,3-b]pyridin-3-yl)pyrimidin-4-yl]amino]cyclohexyl]benzamide (344)

LCMS RT=2.7 (M+1) 431.4.

N-[cis-2-[[5-fluoro-2-(1H-pyrrolo[2,3-b]pyridin-3-yl)pyrimidin-4-yl]amino]cyclohexyl]propane-1-sulfonamide (346)

$^1$H NMR (300 MHz, d6-DMSO) δ 12.41 (s, 1H), 8.65 (d, J=7.8 Hz, 1H), 8.38-8.33 (m, 3H), 7.28 (dd, J=4.7, 7.9 Hz, 1H), 7.06 (d, J=8.1 Hz, 1H), 4.36 (s, 1H), 3.88 (s, 1H), 2.83 (t, J=7.7 Hz, 2H), 1.85-1.70 (m, 6H), 1.59 (q, J=7.8 Hz, 2H), 1.47-1.24 (m, 2H) and 0.82 (t, J=7.4 Hz, 3H) ppm; LCMS RT=2.6 (M+1) 433.3.

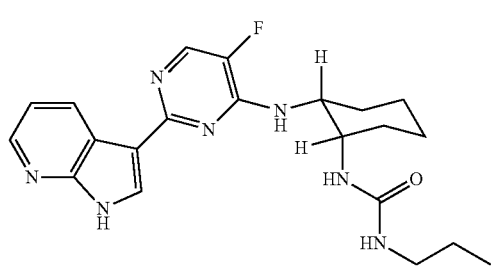

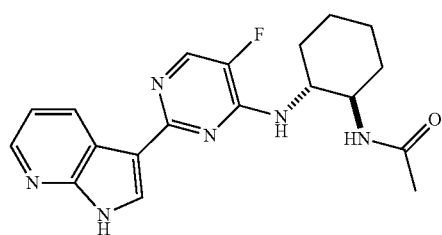

1-[cis-2-[[5-fluoro-2-(1H-pyrrolo[2,3-b]pyridin-3-yl)pyrimidin-4-yl]amino]cyclohexyl]-3-propyl-urea (347)

$^{1}$H NMR (300 MHz, d6-DMSO) δ 12.47 (s, 1H), 8.64 (d, J=7.8 Hz, 1H), 8.45-8.34 (m, 3H), 7.29 (dd, J=4.8, 7.8 Hz, 1H), 7.06 (d, J=7.5 Hz, 1H), 4.47-4.25 (m, 1H), 4.05-3.89 (m, 1H), 2.80 (s, 3H), 1.95-1.62 (m, 6H) and 1.49-1.24 (m, 2H) ppm; LCMS RT=2.4 (M+1) 412.4.

N-[(1R,2R)-2-[[5-fluoro-2-(1H-pyrrolo[2,3-b]pyridin-3-yl)pyrimidin-4-yl]amino]cyclohexyl]acetamide (348)

$^{1}$H NMR (300 MHz, d6-DMSO) δ 12.53 (s, 1H), 8.66 (d, J=7.6 Hz, 1H), 8.43 (s, 1H), 8.39-8.36 (m, 2H), 7.91 (d, J=7.9 Hz, 1H), 7.32 (dd, J=4.7, 7.9 Hz, 1H), 4.08-3.94 (m, 1H), 3.86 (d, J=8.4 Hz, 1H), 2.13 (d, J=24.3 Hz, 1H), 1.95 (d, J=10.2 Hz, 1H), 1.81-1.73 (m, 2H), 1.73 (s, 3H) and 1.43-1.14 (m, 4H) ppm; LCMS RT=2.2 (M+1) 369.4.

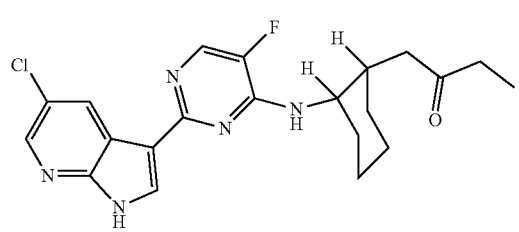

N-[trans-2-[[2-(5-chloro-1H-pyrrolo[2,3-b]pyridin-3-yl)-5-fluoro-pyrimidin-4-yl]amino]cyclohexyl]propanamide (349)

LCMS RT=2.7 (M+1) 417.3.

N-[(1R,2R)-2-[[2-(5-chloro-1H-pyrrolo[2,3-b]pyridin-3-yl)-5-fluoro-pyrimidin-4-yl]amino]cyclohexyl]cyclopentanecarboxamide (351)

LCMS RT=3.1 (M+1) 457.3.

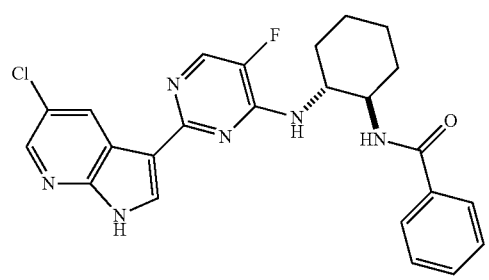

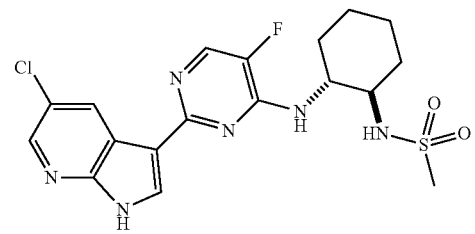

N-[(1R,2R)-2-[[2-(5-chloro-1H-pyrrolo[2,3-b]pyridin-3-yl)-5-fluoro-pyrimidin-4-yl]amino]cyclohexyl]benzamide (352)

LCMS RT=3.0 (M+1) 465.3.

N-[(1R,2R)-2-[[2-(5-chloro-1H-pyrrolo[2,3-b]pyridin-3-yl)-5-fluoro-pyrimidin-4-yl]amino]cyclohexyl]methanesulfonamide (353)

LCMS RT=2.7 (M+1) 439.4.

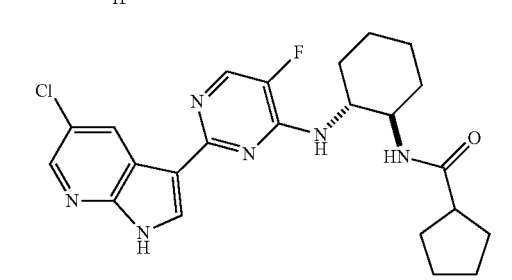

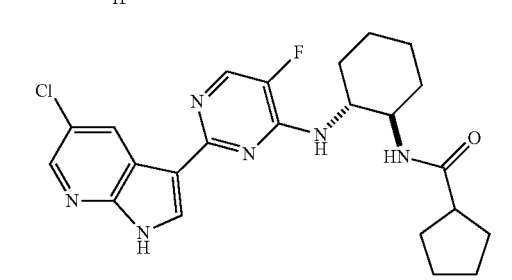

N-[(1R,2R)-2-[[2-(5-chloro-1H-pyrrolo[2,3-b]pyridin-3-yl)-5-fluoro-pyrimidin-4-yl]amino]cyclohexyl]propane-1-sulfonamide (354)

LCMS RT=3.0 (M+1) 467.3.

1-[(1R,2R)-2-[[2-(5-chloro-1H-pyrrolo[2,3-b]pyridin-3-yl)-5-fluoro-pyrimidin-4-yl]amino]cyclohexyl]-3-propyl-urea (355)

LCMS RT=2.8 (M+1) 446.3.

1H), 7.21 (d, J=8.3 Hz, 1H), 4.16 (d, J=9.3 Hz, 1H), 3.35 (d, J=9.8 Hz, 1H), 2.91 (d, J=8.9 Hz, 3H), 2.12-2.02 (m, 2H), 1.79-1.73 (m, 2H) and 1.64-1.15 (m, 4H) ppm; LCMS RT=2.4 (M+1) 405.3.

358

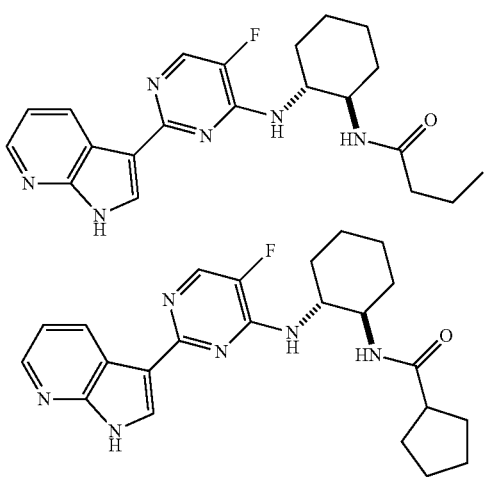

359

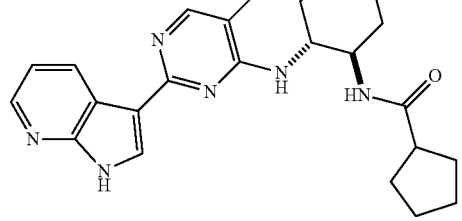

N-[(1R,2R)-2-[[5-fluoro-2-(1H-pyrrolo[2,3-b]pyridin-3-yl)pyrimidin-4-yl]amino]cyclohexyl]butanamide (358)

LCMS RT=2.5 (M+1) 397.4.

N-[(1R,2R)-2-[[5-fluoro-2-(1H-pyrrolo[2,3-b]pyridin-3-yl)pyrimidin-4-yl]amino]cyclohexyl]cyclopentanecarboxamide (359)

LCMS RT=2.7 (M+1) 423.4.

360

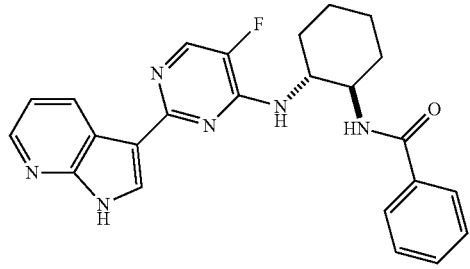

N-[(1R,2R)-2-[[5-fluoro-2-(1H-pyrrolo[2,3-b]pyridin-3-yl)pyrimidin-4-yl]amino]cyclohexyl]benzamide (360)

LCMS RT=2.63 (M+1) 431.4.

361

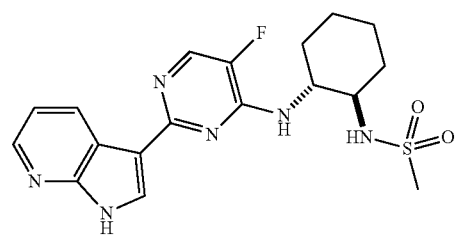

N-[(1R,2R)-2-[[5-fluoro-2-(1H-pyrrolo[2,3-b]pyridin-3-yl)pyrimidin-4-yl]amino]cyclohexyl]methanesulfonamide (361)

$^1$H NMR (300 MHz, d6-DMSO) δ 12.54 (s, 1H), 8.66 (d, J=8.0 Hz, 1H), 8.43-8.36 (m, 3H), 7.32 (dd, J=4.7, 7.9 Hz,

362

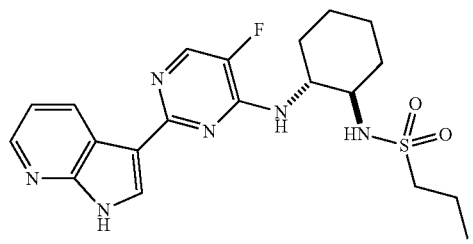

363

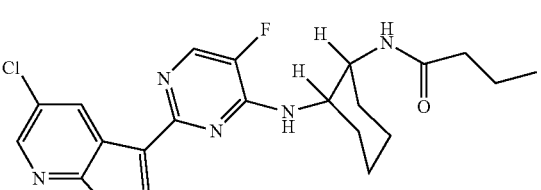

N-[(1R,2R)-2-[[5-fluoro-2-(1H-pyrrolo[2,3-b]pyridin-3-yl)pyrimidin-4-yl]amino]cyclohexyl]propane-1-sulfonamide (362)

$^1$H NMR (300 MHz, d6-DMSO) δ 12.43 (s, 1H), 8.68 (d, J=7.9 Hz, 1H), 8.38-8.33 (m, 3H), 7.29 (dd, J=4.7, 7.8 Hz, 1H), 7.17 (d, J=8.6 Hz, 1H), 4.14 (d, J=6.9 Hz, 1H), 3.33-3.26 (m, 1H), 3.07-2.89 (m, 2H), 2.07 (d, J=12.6 Hz, 2H), 1.76 (d, J=7.9 Hz, 2H), 1.61-1.33 (m, 6H) and 0.90 (t, J=7.4 Hz, 3H) ppm; LCMS RT=2.6 (M+1) 433.3.

N-[trans-2-[[2-(5-chloro-1H-pyrrolo[2,3-b]pyridin-3-yl)-5-fluoro-pyrimidin-4-yl]amino]cyclohexyl]butanamide (363)

LCMS RT=2.9 (M+1) 431.3.

364

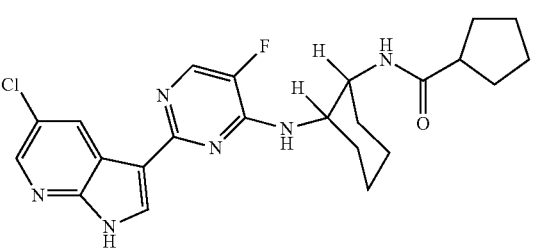

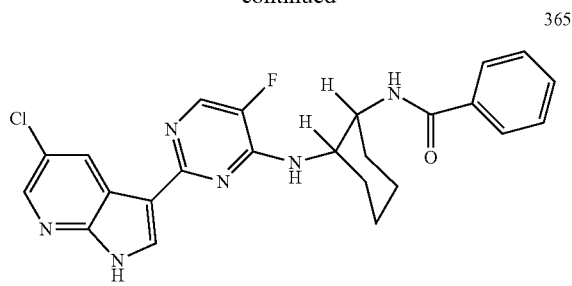

N-[(trans-2-[[2-(5-chloro-1H-pyrrolo[2,3-b]pyridin-3-yl)-5-fluoro-pyrimidin-4-yl]amino]cyclohexyl]cyclopentanecarboxamide (364)

LCMS RT=3.1 (M+1) 457.3.

N-[trans-2-[[2-(5-chloro-1H-pyrrolo[2,3-b]pyridin-3-yl)-5-fluoro-pyrimidin-4-yl]amino]cyclohexyl]benzamide (365)

LCMS RT=3.0 (M+1) 465.3.

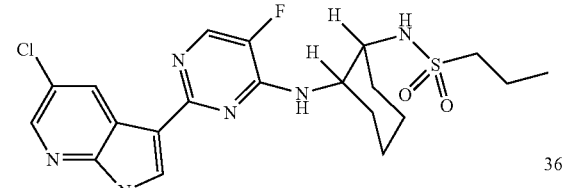

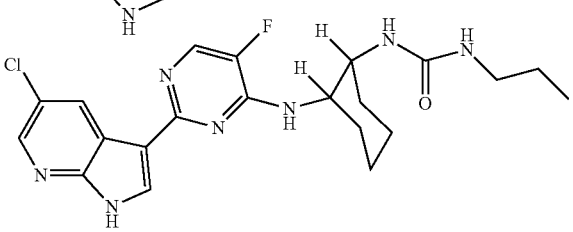

N-[trans-2-[[2-(5-chloro-1H-pyrrolo[2,3-b]pyridin-3-yl)-5-fluoro-pyrimidin-4-yl]amino]cyclohexyl]propane-1-sulfonamide (367)

LCMS RT=3.0 (M+1) 467.3.

1-[trans-2-[[2-(5-chloro-1H-pyrrolo[2,3-b]pyridin-3-yl)-5-fluoro-pyrimidin-4-yl]amino]cyclohexyl]-3-propyl-urea (368)

LCMS RT=2.8 (M+1) 446.3.

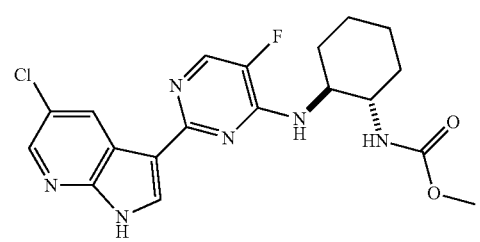

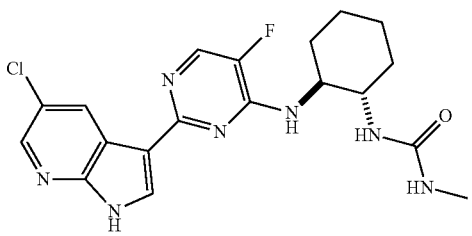

Methyl N-[(1S,2S)-2-[[2-(5-chloro-1H-pyrrolo[2,3-b]pyridin-3-yl)-5-fluoro-pyrimidin-4-yl]amino]cyclohexyl]carbamate (425)

$^1$H NMR (300 MHz, d6-DMSO) δ 13.02 (s, 1H), 9.10 (s, 2H), 8.67 (s, 1H), 8.44-8.40 (m, 2H), 7.26 (d, J=6.5 Hz, 1H), 4.19 (s, 1H), 3.66 (d, J=9.8 Hz, 1H), 3.48 (s, 3H), 2.13 (s, 1H), 2.02 (d, J=9.2 Hz, 1H), 1.78 (d, J=9.6 Hz, 2H) and 1.47-1.34 (m, 4H) ppm; LCMS RT=2.1 (M+1) 419.2.

1-[(1S,2S)-2-[[2-(5-chloro-1H-pyrrolo[2,3-b]pyridin-3-yl)-5-fluoro-pyrimidin-4-yl]amino]cyclohexyl]-3-methyl-urea (426)

$^1$H NMR (300 MHz, d6-DMSO) δ 12.56 (s, 1H), 8.70 (d, J=2.2 Hz, 1H), 8.35 (dd, J=2.4, 6.8 Hz, 2H), 8.28 (d, J=4.2 Hz, 1H), 5.99 (d, J=7.0 Hz, 1H), 5.80-5.63 (m, 1H), 3.91-3.87 (m, 1H), 3.66-3.45 (m, 1H), 2.54 (s, 3H), 2.30 (d, J=13.0 Hz, 1H), 2.04 (d, J=46.9 Hz, 1H), 1.78 (d, J=8.5 Hz, 2H) and 1.56-1.23 (m, 4H) ppm; LCMS RT=2.5 (M+1) 419.5.

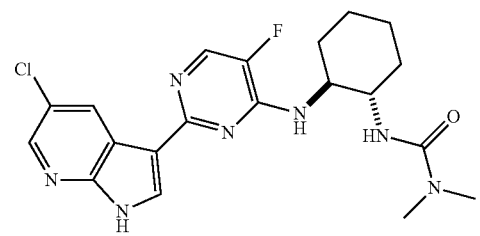

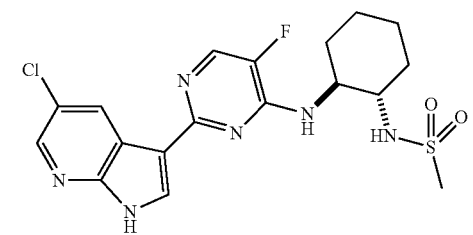

3-[(1S,2S)-2-[[2-(5-chloro-1H-pyrrolo[2,3-b]pyridin-3-yl)-5-fluoro-pyrimidin-4-yl]amino]cyclohexyl]-1,1-dimethyl-urea (427)

$^1$H NMR (300 MHz, d6-DMSO) δ 12.59 (s, 1H), 8.72 (d, J=2.3 Hz, 1H), 8.41 (d, J=2.7 Hz, 1H), 8.35 (d, J=2.3 Hz, 1H), 8.29 (d, J=4.4 Hz, 1H), 8.23 (s, 1H), 6.19 (d, J=7.8 Hz, 1H), 4.04-3.97 (m, 1H), 3.78-3.69 (m, 1H), 2.68 (s, 6H), 2.31 (d,

J=11.6 Hz, 1H), 1.95 (d, J=9.8 Hz, 1H), 1.79 (d, J=10.4 Hz, 2H) and 1.60-1.32 (m, 4H) ppm; LCMS RT=2.7 (M+1) 432.4.

N-[(1S,2S)-2-[[2-(5-chloro-1H-pyrrolo[2,3-b]pyridin-3-yl)-5-fluoro-pyrimidin-4-yl]amino]cyclohexyl] methanesulfonamide (428)

¹H NMR (300 MHz, d6-DMSO) δ 12.54 (s, 1H), 8.72 (d, J=2.3 Hz, 1H), 8.38-8.29 (m, 3H), 7.82 (s, 1H), 7.21 (d, J=8.3 Hz, 1H), 4.52 (brs, 1H), 4.12-4.05 (m, 1H), 2.92 (s, 3H), 2.09 (d, J=12.8 Hz, 2H), 1.78 (brs, 2H) and 1.49-1.39 (m, 4H) ppm; LCMS RT=2.7 (M+1) 439.4.

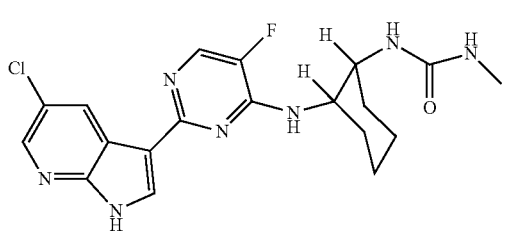

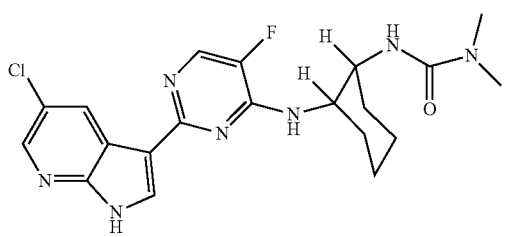

1-[cis-2-[[2-(5-chloro-1H-pyrrolo[2,3-b]pyridin-3-yl)-5-fluoro-pyrimidin-4-yl]amino]cyclohexyl]-3-methyl-urea (430)

¹H NMR (300 MHz, d6-DMSO) δ 12.61 (s, 1H), 8.68 (d, J=2.2 Hz, 1H), 8.39-8.31 (m, 4H), 6.12 (d, J=6.7 Hz, 1H), 5.91-5.83 (m, 1H), 4.29-4.13 (m, 1H), 4.02-3.91 (m, 1H), 2.55 (s, 3H), 1.93 (d, J=12.8 Hz, 1H) and 1.74-1.53 (m, 7H) ppm; LCMS RT=2.6 (M+1) 418.5.

3-[cis-2-[[2-(5-chloro-1H-pyrrolo[2,3-b]pyridin-3-yl)-5-fluoro-pyrimidin-4-yl]amino]cyclohexyl]-1,1-dimethyl-urea (431)

¹H NMR (300 MHz, d6-DMSO) δ 12.54 (s, 1H), 8.68 (d, J=2.3 Hz, 1H), 8.33-8.29 (m, 3H), 7.96 (s, 1H), 5.72 (d, J=6.9 Hz, 1H), 4.36 (s, 1H), 4.10 (s, 1H), 2.76 (s, 6H), 1.96-1.87 (m, 2H), 1.74-1.63 (m, 4H) and 1.55-1.45 (m, 2H) ppm; LCMS RT=2.8 (M+1) 432.4.

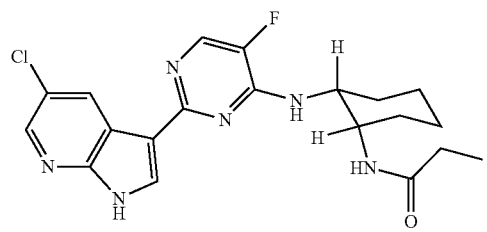

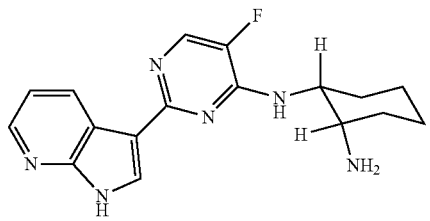

Methyl N-[cis-2-[[2-(5-chloro-1H-pyrrolo[2,3-b]pyridin-3-yl)-5-fluoro-pyrimidin-4-yl]amino]cyclohexyl]carbamate (432)

¹H NMR (300 MHz, d6-DMSO) δ 12.54 (s, 1H), 8.67 (d, J=2.2 Hz, 1H), 8.35-8.29 (m, 3H), 7.62 (s, 1H), 7.05 (d, J=7.2 Hz, 1H), 4.50-4.40 (m, 1H), 4.20-4.10 (m, 1H), 3.46 (s, 3H), 1.87 (d, J=10.9 Hz, 2H), 1.71-1.65 (m, 4H) and 1.43 (d, J=7.4 Hz, 2H) ppm; LCMS RT=2.9 (M+1) 419.4.

N-[5-fluoro-2-(1H-pyrrolo[5,4-b]pyridin-3-yl)pyrimidin-4-yl]cyclohexane-cis-1,2-diamine (206)

LCMS RT=1.9 (M+1) 327.2.

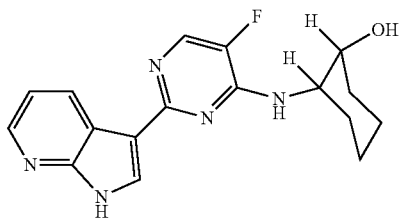

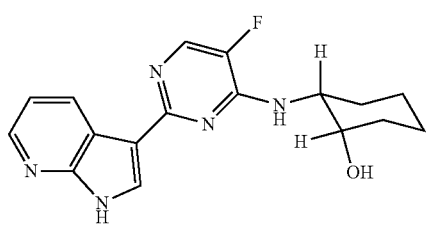

Trans-2-[[5-fluoro-2-(1H-pyrrolo[2,3-b]pyridin-3-yl)pyrimidin-4-yl]amino]cyclohexanol (207)

LCMS RT=2.2 (M+1) 328.2.

Cis-2-[[5-fluoro-2-(1H-pyrrolo[2,3-b]pyridin-3-yl)pyrimidin-4-yl]amino]cyclohexanol (277)

LCMS RT=1.6 (M+1) 328.2.

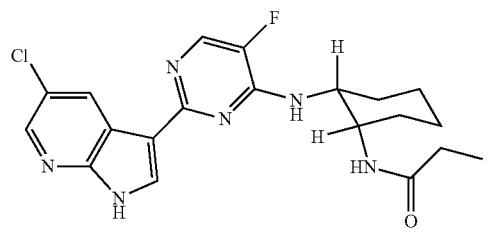
333

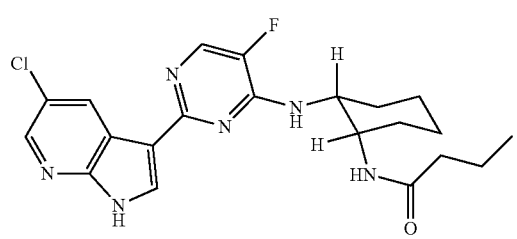
334

N-[cis-2-[[2-(5-chloro-1H-pyrrolo[2,3-b]pyridin-3-yl)-5-fluoro-pyrimidin-4-yl]amino]cyclohexyl]propanamide (333)

LCMS RT=2.7 (M+1) 417.4.

N-[cis-2-[[2-(5-chloro-1H-pyrrolo[2,3-b]pyridin-3-yl)-5-fluoro-pyrimidin-4-yl]amino]cyclohexyl]butanamide (334)

LCMS RT=2.9 (M+1) 431.4.

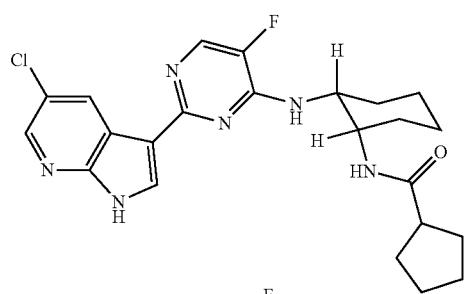
335

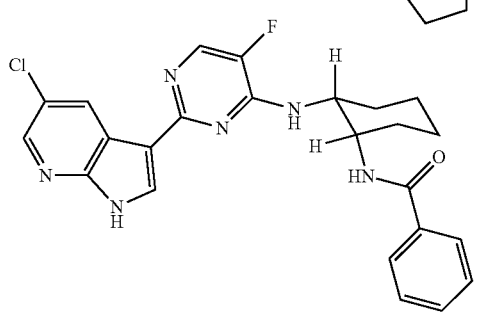
336

N-[cis-2-[[2-(5-chloro-1H-pyrrolo[2,3-b]pyridin-3-yl)-5-fluoro-pyrimidin-4-yl]amino]cyclohexyl]cyclopentanecarboxamide (335)

LCMS RT=3.1 (M+1) 457.3.

N-[cis-2-[[2-(5-chloro-1H-pyrrolo[2,3-b]pyridin-3-yl)-5-fluoro-pyrimidin-4-yl]amino]cyclohexyl]benzamide (336)

LCMS RT=3.0 (M+1) 465.4.

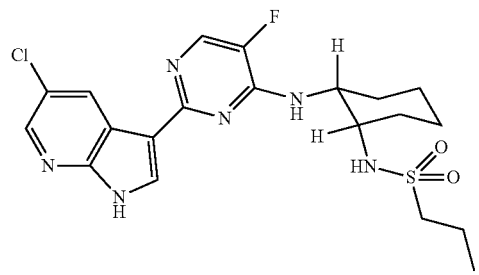
338

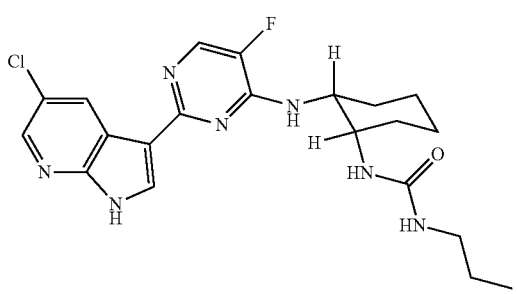
339

N-[cis-2-[[2-(5-chloro-1H-pyrrolo[2,3-b]pyridin-3-yl)-5-fluoro-pyrimidin-4-yl]amino]cyclohexyl]propane-1-sulfonamide (338)

LCMS RT=2.9 (M+1) 467.3.

1-[cis-2-[[2-(5-chloro-1H-pyrrolo[2,3-b]pyridin-3-yl)-5-fluoro-pyrimidin-4-yl]amino]cyclohexyl]-3-propyl-urea (339)

LCMS RT=2.9 (M+1) 446.3.

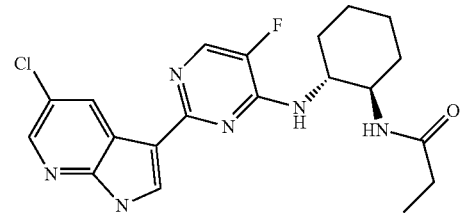
350

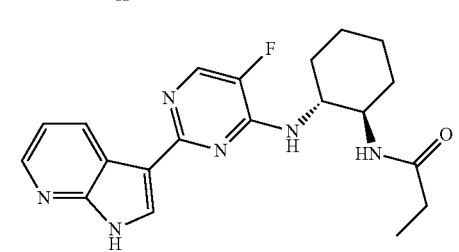
356

1-[trans-2-[[2-(5-chloro-1H-pyrrolo[2,3-b]pyridin-3-yl)-5-fluoro-pyrimidin-4-yl]amino]cyclohexyl]-3-propyl-urea (350)

LCMS RT=2.6 (M+1) 403.3.

N-[(1R,2R)-2-[[5-fluoro-2-(1H-pyrrolo[2,3-b]pyridin-3-yl)pyrimidin-4-yl]amino]cyclohexyl]propanamide (356)

LCMS RT=2.3 (M+1) 383.4.

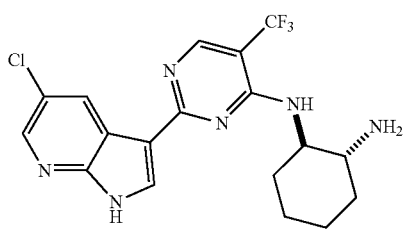

(1R,2R)—N1-(2-(5-chloro-1H-pyrrolo[2,3-b]pyridin-3-yl)-5-(trifluoromethyl)pyrimidin-4-yl)cyclohexane-1,2-diamine (31)

LCMS RT=2.2 (M+1) 411.2.

N1-(5-fluoro-2-(1H-pyrrolo[2,3-b]pyridin-3-yl)pyrimidin-4-yl)cyclohexane-1,2-diamine (4)

LCMS RT=2.2 (M+1) 327.2.

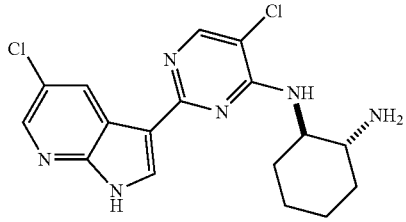

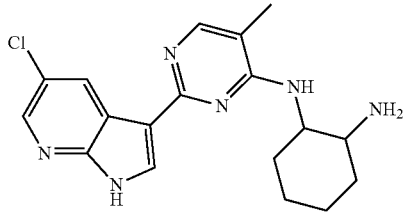

(1R,2R)—N1-(5-chloro-2-(5-chloro-1H-pyrrolo[2,3-b]pyridin-3-yl)pyrimidin-4-yl)cyclohexane-1,2-diamine (115)

LCMS RT=1.3 (M+1) 377.2.

N1-(2-(5-chloro-1H-pyrrolo[2,3-b]pyridin-3-yl)-5-methylpyrimidin-4-yl)cyclohexane-1,2-diamine (116)

LCMS RT=3.3 (M+1) 357.2.

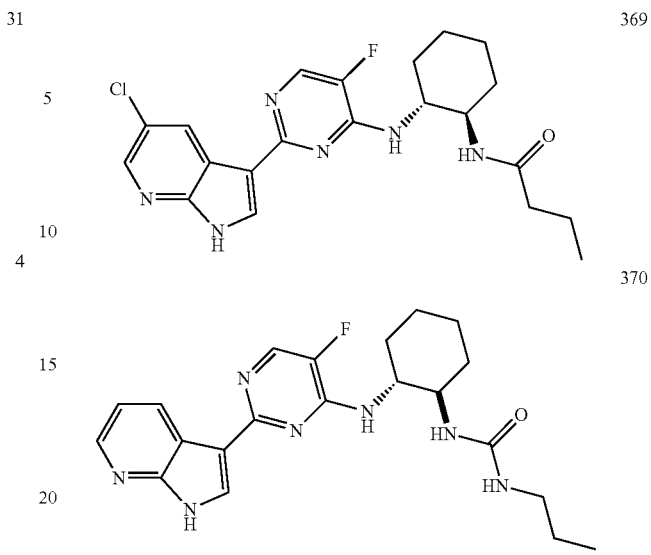

N-[(1R,2R)-2-[[2-(5-chloro-1H-pyrrolo[2,3-b]pyridin-3-yl)-5-fluoro-pyrimidin-4-yl]amino]cyclohexyl]butanamide (369)

LCMS RT=2.9 (M+1) 431.3.

1-[(1R,2R)-2-[[5-fluoro-2-(1H-pyrrolo[2,3-b]pyridin-3-yl)pyrimidin-4-yl]amino]cyclohexyl]-3-propyl-urea (370)

LCMS RT=2.4 (M+1) 412.4.

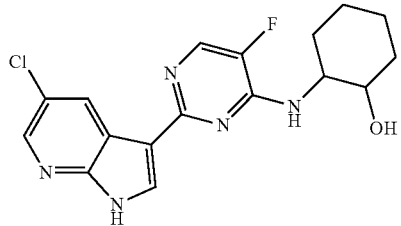

2-(5-chloro-1H-pyrrolo[2,3-b]pyridin-3-yl)-5-fluoro-N-(2-methoxycyclohexyl)-pyrimidin-4-amine (412)

LCMS RT=3.5 (M+1) 376.4.

General Scheme 18:

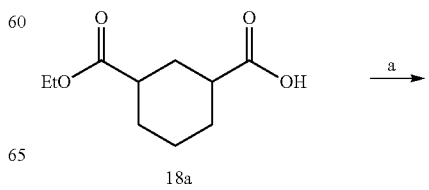

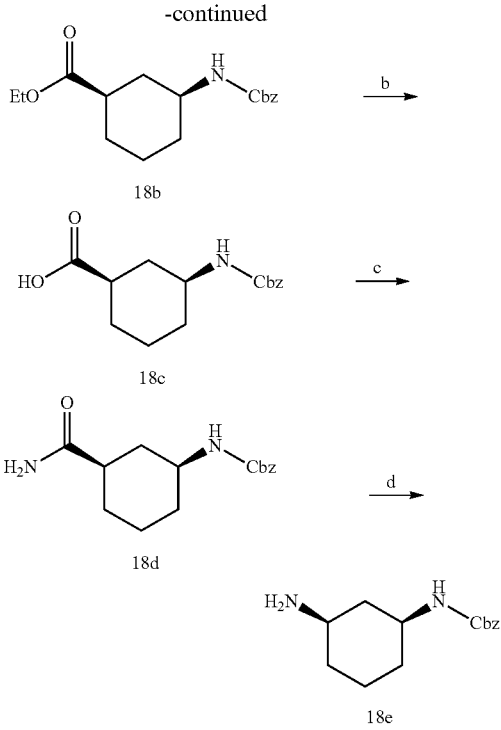

(a) i. DPPA, Et₃N, toluene, 110° C.; ii BnOH, 85° C.; (b) LiOH, THF:H₂O; (c) Boc₂O, pyridine, NH₄HCO₃, dioxane; (d) BTIB, CH₃CN:H₂O.

Formation of (1S,3R)-3-(ethoxycarbonyl)cyclohexanecarboxylic acid (18a)

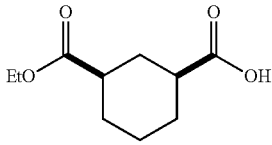 [SMILES: CCOC(=O)[C@@H]1CCC[C@H](C(=O)O)C1]

(1S,3R)-3-(ethoxycarbonyl)cyclohexanecarboxylic acid can be prepared following the literature procedures described in: Barnett, C. J., Gu, R. L., Kobierski, M. E., WO-2002024705, Stereoselective process for preparing cyclohexyl amine derivatives.

Formation of ethyl (1R,3S)-3-benzyloxycarbonylaminocyclohexanecarboxylate (18b)

(1S,3R)-3-(Ethoxycarbonyl)cyclohexanecarboxylic acid, 18a, (10.0 g, 49.9 mmol) was dissolved in toluene (100 mL) and treated with triethylamine (7.6 mL, 54.9 mmol) and DPPA (12.2 mL, 54.9 mmol). The resulting solution was heated to 110° C. and stirred for 1 hour. After cooling to 70° C., benzyl alcohol (7.7 mL, 74.9 mmol) was added, and the mixture was heated to 85° C. overnight. The resulting solution was cooled to room temperature, poured into EtOAc (150 mL) and water (150 mL) and the layers were separated. The aqueous layer was extracted with EtOAc (2×75 mL) and the combined organic extracts were washed with water (100 mL) and brine (100 mL), dried over Na₂SO₄ and concentrated in vacuo. The crude material was purified by silica gel chromatography (0%-50% EtOAc/hexanes) to provide 18b (15.3 g, containing ~25% benzyl alcohol), which was used for the next step without further purification.

Formation of (1R,3S)-3-benzyloxycarbonylaminocyclohexanecarboxylic acid (18c)

Ethyl (1R,3S)-3-benzyloxycarbonylaminocyclohexanecarboxylate, 18b, (36 g, 117.9 mmol) was dissolved in THF (144.0 mL) and treated with a solution of LiOH (5.647 g, 235.8 mmol) in water (216.0 mL). After stirring overnight, the reaction mixture was diluted with water (100 mL), washed with methyl tert-butyl ether (150 mL) and brought to pH 3 by addition of 3N HCl. The acidic solution was extracted with EtOAc (3×100 mL), and the combined organic layers were washed with water and brine, dried on Na₂SO₄ and concentrated in vacuo.

The crude product was triturated with methyl tert-butyl ether (30 mL) and filtered to provide a first crop of crystals. The filtrate was treated with heptane (20 mL), concentrated to 30 mL and allowed to stand at room temperature for 3 hours to provide a second crop of crystals that were collected by filtration for a total of 14.4 g (44% yield) 18c.

¹H NMR (300 MHz, CDCl₃) δ 7.38-7.33 (m, 5H), 5.11 (s, 2H), 4.68 (s, 1H), 3.55 (s, 1H), 2.44 (d, J=11.0 Hz, 1H), 2.32 (d, J=11.7 Hz, 1H), 2.03-1.86 (m, 3H) and 1.48-0.88 (m, 4H) ppm.

Formation of benzyl N-[(1S,3R)-3-carbamoylcyclohexyl]carbamate (18d)

To a solution of (1R,3S)-3-Benzyloxycarbonylaminocyclohexanecarboxylic acid, 18c, (10.0 g, 36.1 mmol) in 1,4-dioxane (300 mL) was added pyridine (2.9 mL, 36.1 mmol), followed by di-tert-butyl dicarbonate (10.7 mL, 46.9 mmol) and ammonium bicarbonate (10.1 g, 126.2 mmol). After 3 hours, another portion of di-tert-butyl dicarbonate (1.5 g, 6.8 mmol) and ammonium bicarbonate (1.5 g, 6.8 mmol) was added and stirring was continued overnight. The reaction was quenched by addition of 2N HCl (400 mL) and stirred for 1 hour. The resulting suspension was filtered under reduced pressure, washed with 2N HCl (50 mL), water (8×50 mL) and hexanes (3×50 mL) and vacuum dried to provide benzyl N-[(1S,3R)-3-carbamoylcyclohexyl]carbamate, 18d, (9.1 g, 91%) as a white solid.

¹H NMR (300 MHz, CDCl₃) δ 7.40-7.24 (m, 5H), 5.08 (s, 2H), 3.58-3.44 (m, 1H), 2.38-2.21 (m, 1H), 2.17 (d, J=12.7, 1H), 2.05-1.78 (m, 8H), 1.54-0.97 (m, 5H).

Formation of benzyl N-[(1S,3R)-3-aminocyclohexyl]carbamate (18e)

Benzyl N-[(1S,3R)-3-carbamoylcyclohexyl]carbamate, 18d, (9.1 g, 32.9 mmol) was suspended in a mixture of acetonitrile (100 mL) and water (100 mL) and treated with bis(trifluoroacetoxy)iodobenzene (15.5 g, 36.1 mmol). The suspension was allowed to stir at room temperature overnight and was then quenched with 1N HCl (100 mL). After evaporation of the acetonitrile, the acidic aqueous solution was washed with EtOAc (2×150 mL). The pH was adjusted to basic by addition of solid KOH and the resulting emulsion was extracted with EtOAc (3×200 mL). The combined organic layers were dried over Na₂SO₄ and concentrated in vacuo to provide product 18e (6.2 g, 75% yield).

¹H NMR (300 MHz, CDCl₃) δ 7.31-7.45 (m, 5H), 5.11 (s, 2H), 4.90 (br. s., 1H), 3.58 (br. s., 1H), 2.72-2.97 (m, 1H), 2.14

(d, J=11.90 Hz, 1H), 1.87-2.02 (m, 1H), 1.73-1.87 (m, 2H), 1.21-1.46 (m, 1H), 0.89-1.18 (m, 3H).

General Scheme 19:

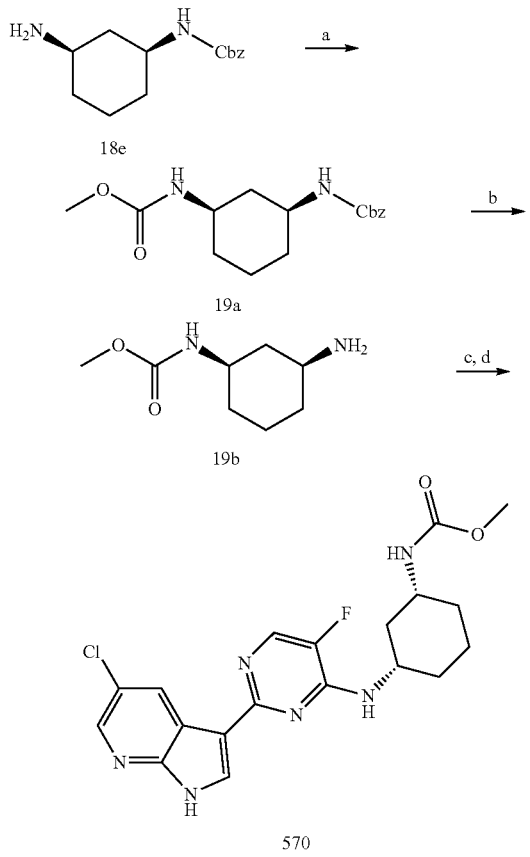

(a) MeOCOCl, Et$_3$N, THF; (b) H$_2$, Pd/C, EtOH; (c) 5-chloro-3-(5-fluoro-4-methylsulfinyl-pyrimidin-2-yl)-1-(p-tolylsulfonyl)pyrrolo[2,3-b]pyridine, THF, 130° C., microwave; (d) LiOH, 130° C., microwave.

Formation of methyl N-[(1R,3S)-3-benzyloxycarbonyl-aminocyclohexyl]carbamate (19a)

Benzyl N-[(1S,3R)-3-aminocyclohexyl]carbamate, 18e, (0.99 g, 3.99 mmol) was dissolved in THF (20 mL) and treated with methyl chloroformate (0.62 mL, 7.97 mmol), followed by triethylamine (1.67 mL, 11.96 mmol). After stirring for 1 hour at room temperature, the solvent was evaporated under reduced pressure and the residue was diluted into 1:3 mixture of CH$_2$Cl$_2$:EtOAc (130 mL) and washed with 1N HCl (50 mL) and 2N Na$_2$CO$_3$ (50 mL). The organic layer was dried over Na$_2$SO$_4$ and concentrated under reduced pressure to afford the desired product, 19a, as a white solid (1.09 g, 89% yield).

$^1$H NMR (300 MHz, CDCl$_3$) δ 7.21-7.37 (m, 5H), 5.02 (s, 2H), 4.26-4.62 (m, 1H), 3.58 (s, 3H), 3.34-3.54 (m, 2H), 2.24 (d, J=11.71 Hz, 1H), 1.82-2.03 (m, 2H), 1.72 (dt, J=3.14, 13.93 Hz, 1H), 1.23-1.44 (m, 1H), 0.79-1.02 (m, 3H).

Formation of methyl N-[(1R,3S)-3-aminocyclohexyl]carbamate (19b)

Methyl N-[(1R,3S)-3-benzyloxycarbonylaminocyclohexyl]carbamate, 19a, (1.09 g, 3.56 mmol) was dissolved in ethanol (100 mL) and treated with 10% Pd/C (0.38 g, 0.36 mmol). The flask was capped, degassed and fitted with a hydrogen balloon and allowed to stir overnight. The reaction mixture was filtered under nitrogen and concentrated in vacuo to provide the product, 19b, as a white solid.

$^1$H NMR (300 MHz, CDCl$_3$) δ 3.31-3.56 (m, 1H), 3.03 (s, 4H), 2.81 (t, J=10.67 Hz, 1H), 2.03-2.20 (m, 1H), 1.71-2.01 (m, 3H), 1.27-1.49 (m, 1H), 0.92-1.14 (m, 3H).

Formation of methyl N-[(1R,3S)-3-[[2-(5-chloro-1H-pyrrolo[2,3-b]pyridin-3-yl)-5-fluoro-pyrimidin-4-yl]amino]cyclohexyl]carbamate (570)

5-chloro-3-(5-fluoro-4-methylsulfinyl-pyrimidin-2-yl)-1-(p-tolylsulfonyl)-pyrrolo[2,3-b]pyridine, 19b, (2.04 g, 4.39 mmol) and methyl N-[(1R,3S)-3-amino-cyclohexyl]carbamate (0.60 g, 3.14 mmol) were suspended in THF (16 mL) and heated in the microwave to 130° C. for 20 minutes. Lithium hydroxide (15.67 mL of 1M solution, 15.67 mmol) was added, and the resulting mixture was heated in the microwave for 20 min at 130° C. The resulting solution was diluted with water (150 mL) and ethyl acetate (200 mL) and the layers were separated. The aqueous layer was extracted with EtOAc (100 mL) and t organic layers were combined, dried over Na$_2$SO$_4$ and concentrated in vacuo. The crude product was purified by silica gel chromatography (40-100% EtOAc/hexanes) followed by treatment of the pure fractions with 4N HCl in dioxane to provide the hydrochloride of compound, 570, as an off white solid.

$^1$H NMR (300 MHz, MeOD) δ 8.81 (d, J=2.1 Hz, 1H), 8.20 (d, J=2.3 Hz, 1H), 8.15 (s, 1H), 7.97 (d, J=4.1 Hz, 1H), 4.26-4.18 (m, 1H), 3.71-3.52 (m, 1H), 3.59 (s, 3H), 2.36 (d, J=10.5 Hz, 1H), 2.18 (d, J=10.7 Hz, 1H), 2.04-1.86 (m, 2H), 1.57 (s, 1H) and 1.43-1.15 (m, 3H) ppm; LCMS RT=2.0 (M+1) 419.4 (M−1) 417.3.

General Scheme 20:

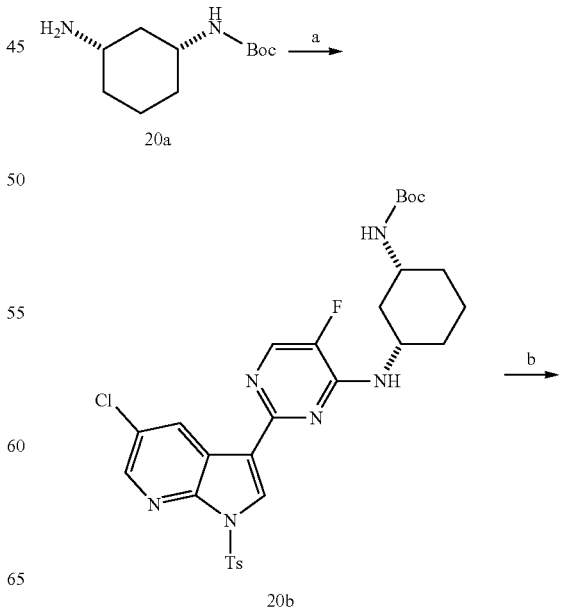

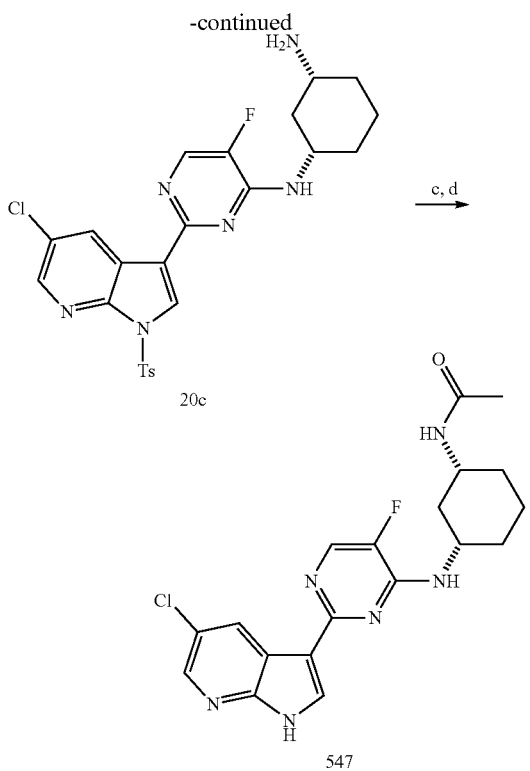

(a) 5-chloro-3-(5-fluoro-4-methylsulfinyl-pyrimidin-2-yl)-1-(p-tolylsulfonyl)pyrrolo[2,3-b]pyridine, THF; (b) CH₂Cl₂, trifluoroacetic acid; (c) acetyl chloride, Et₃N, THF; (d) LiOH, 130° C., microwave.

Formation of tert-butyl N-[(1R,3S)-3-[[2-[5-chloro-1-(p-tolylsulfonyl)pyrrolo[2,3-b]pyridin-3-yl]-5-fluoro-pyrimidin-4-yl]amino]cyclohexyl]carbamate (20b)

tert-Butyl N-[(1R,3S)-3-aminocyclohexyl]carbamate, 20a, (0.15 g, 0.70 mmol) and 5-chloro-3-(5-fluoro-4-methylsulfinyl-pyrimidin-2-yl)-1-(p-tolylsulfonyl)pyrrolo[2,3-b]pyridine, 1a, (0.49 g, 1.05 mmol) were dissolved in THF (30 mL) and allowed to stir at room temperature overnight. The solvent was evaporated under reduced pressure and the residue was purified by two rounds of silica gel chromatography—first with (0%-10% MeOH/CH₂Cl₂) second with (10%-50% EtOAc/hexanes) to provide tert-butyl N-[(1R,3S)-3-[[2-[5-chloro-1-(p-tolylsulfonyl)pyrrolo[2,3-b]pyridin-3-yl]-5-fluoro-pyrimidin-4-yl]amino]cyclohexyl]carbamate (20b) (330 mg, 38%).

¹H NMR (300 MHz, CDCl₃) δ 8.74 (d, J=2.4 Hz, 1H), 8.58 (s, 1H), 8.38 (d, J=2.4 Hz, 1H), 8.13 (s, 1H), 8.09 (t, J=3.3 Hz, 2H), 7.29 (d, J=8.1 Hz, 2H), 5.02 (d, J=7.1 Hz, 1H), 4.47 (d, J=7.7 Hz, 1H), 4.25-4.16 (m, 1H), 3.68 (d, J=2.0 Hz, 1H), 2.48 (d, J=11.7 Hz, 1H), 2.38 (s, 3H), 2.26 (d, J=12.8 Hz, 1H), 2.11 (d, J=11.9 Hz, 1H), 1.95-1.89 (m, 1H), 1.69-1.56 (m, 1H), 1.44 (s, 9H) and 1.28-1.11 (m, 3H) ppm.

Formation of (1R,3S)—N1-[2-[5-chloro-1-(p-tolylsulfonyl)pyrrolo[2,3-b]pyridin-3-yl]-5-fluoro-pyrimidin-4-yl]cyclohexane-1,3-diamine (20c)

tert-Butyl N-[(1S,3R)-3-[[2-[5-chloro-1-(p-tolylsulfonyl)pyrrolo[2,3-b]pyridin-3-yl]-5-fluoro-pyrimidin-4-yl]amino]cyclohexyl]carbamate, 20b, (0.33 g, 0.53 mmol) was dissolved in CH₂Cl₂ (10 mL) and treated with trifluoroacetic acid (2 mL). After stirring for 2 hours, the solvent was evaporated under reduced pressure and the resulting residue was passed through a polymer supported carbonate column to provide the free base of (1R,3S)—N1-[2-[5-chloro-1-(p-tolylsulfonyl)pyrrolo[2,3-b]pyridin-3-yl]-5-fluoro-pyrimidin-4-yl]cyclohexane-1,3-diamine, 20c, (0.25 g, 0.43 mmol, 81%).

¹H NMR (300 MHz, CDCl₃) δ 8.76 (dd, J=2.4, 6.3 Hz, 1H), 8.52-8.49 (m, 1H), 8.39 (d, J=2.4 Hz, 1H), 8.14-8.04 (m, 3H), 7.29 (d, J=7.5 Hz, 2H), 5.61 (s, 1H), 4.28-4.16 (m, 1H), 3.19-3.10 (m, 1H), 2.39 (s, 3H), 2.39-2.31 (m, 1H), 2.08-1.90 (m, 3H), 1.63-1.50 (m, 1H) and 1.40-1.17 (m, 3H) ppm.

Formation of N-[(1R,3S)-3-[[2-(5-chloro-1H-pyrrolo[2,3-b]pyridin-3-yl)-5-fluoro-pyrimidin-4-yl]amino]cyclohexyl]acetamide (547)

(1R,3S)—N1-[2-[5-chloro-1-(p-tolylsulfonyl)pyrrolo[2,3-b]pyridin-3-yl]-5-fluoro-pyrimidin-4-yl]cyclohexane-1,3-diamine, 20c, (0.050 g, 0.097 mmol) was dissolved in THF (1.0 mL) and treated with triethylamine (0.041 mL, 0.290 mmol) and acetyl chloride (0.013 mL, 0.190 mmol). After stirring overnight, the solvent was evaporated and the residue was taken into THF (1.0 mL) and treated with 1M LiOH (1.0 mL, 1.0 mmol). The reaction mixture was heated in the microwave to 130° C. for 10 minutes. The solvent was evaporated under reduced pressure, and the residue was purified by HPLC, using 5%-70% H₂O/acetonitrile with 0.1% TFA. The purified fractions were concentrated to dryness to provide the TFA salt of the product, which was dissolved in MeOH and passed through a polymer bound carbonate cartridge to provide the free base of product 547.

¹H NMR (300 MHz, MeOD) δ 8.81 (s, 1H), 8.20 (s, 1H), 8.15 (s, 1H), 7.99 (d, J=4.1, 1H), 4.23 (t, J=11.4, 1H), 3.90 (t, J=11.4, 1H), 2.35 (d, J=11.6, 1H), 2.20 (d, J=12.5, 1H), 2.00 (d, J=15.9, 2H), 1.92 (s, 3H), 1.67 (dd, J=26.3, 13.2, 1H), 1.53-1.06 (m, 3H) ppm LCMS RT=2.1 (M+1) 403.2.

The following compounds can be prepared by methods similar to those described in Scheme 19 and Scheme 20:

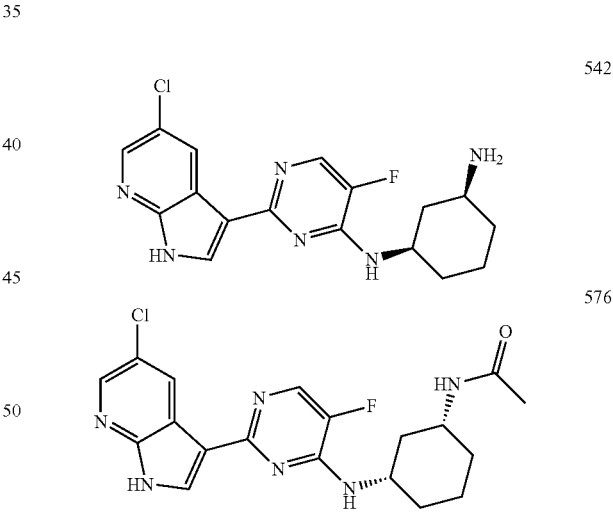

(1R,3S)—N1-[2-(5-chloro-1H-pyrrolo[2,3-b]pyridin-3-yl)-5-fluoro-pyrimidin-4-yl]cyclohexane-1,3-diamine (542)

LCMS RT=1.4 (M+1) 361.4.

N-[(1R,3S)-3-[[2-(5-chloro-1H-pyrrolo[2,3-b]pyridin-3-yl)-5-fluoro-pyrimidin-4-yl]amino]cyclohexyl]acetamide (576)

¹H NMR (300 MHz, MeOD) δ 8.81 (s, 1H), 8.20 (s, 1H), 8.15 (s, 1H), 7.99 (d, J=4.1, 1H), 4.23 (t, J=11.4, 1H), 3.90 (t, J=11.4, 1H), 2.35 (d, J=11.6, 1H), 2.20 (d, J=12.5, 1H), 2.00

(d, J=15.9, 2H), 1.92 (s, 3H), 1.67 (dd, J=26.3, 13.2, 1H), 1.53-1.06 (m, 3H) ppm; LCMS RT=1.8 (M+1) 403 (M−1) 401.4.

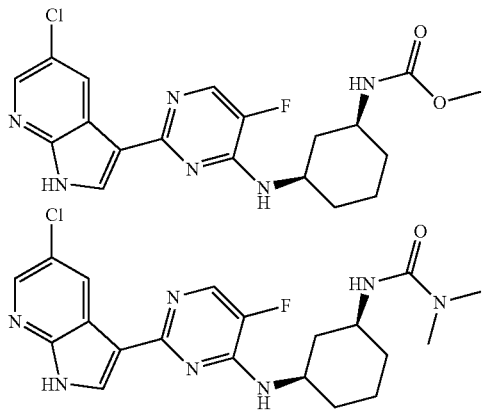

548

549

Methyl N-[(1S,3R)-3-[[2-(5-chloro-1H-pyrrolo[2,3-b]pyridin-3-yl)-5-fluoro-pyrimidin-4-yl]amino]cyclohexyl]carbamate (548)

LCMS RT=2.8 (M+1) 419.5.

3-[(1S,3R)-3-[[2-(5-chloro-1H-pyrrolo[2,3-b]pyridin-3-yl)-5-fluoro-pyrimidin-4-yl]amino]cyclohexyl]-1,1-dimethyl-urea (549)

LCMS RT=2.6 (M+1) 432.5.

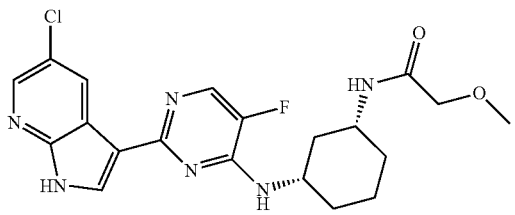

591

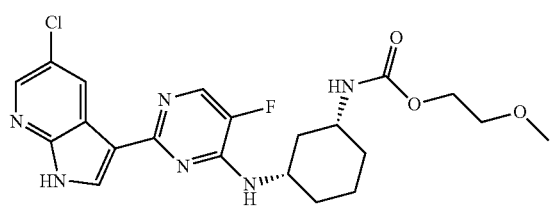

592

N-[(1R,3S)-3-[[2-(5-chloro-1H-pyrrolo[2,3-b]pyridin-3-yl)-5-fluoro-pyrimidin-4-yl]amino]cyclohexyl]-2-methoxy-acetamide (591)

¹H NMR (300 MHz, MeOD) δ 8.82 (d, J=2.4 Hz, 1H), 8.21 (d, J=2.3 Hz, 1H), 8.16 (s, 1H), 7.99 (d, J=4.1 Hz, 1H), 4.29-4.21 (m, 1H), 4.04-3.96 (m, 1H), 3.87 (s, 2H), 3.40 (s, 3H), 2.34 (d, J=11.6 Hz, 1H), 2.21 (d, J=12.5 Hz, 1H), 2.02-1.93 (m, 2H), 1.74-1.62 (m, 1H) and 1.54-1.28 (m, 3H) ppm. LCMS RT=2.6 (M+1) 433.4.

2-methoxyethyl N-[(1R,3S)-3-[[2-(5-chloro-1H-pyrrolo[2,3-b]pyridin-3-yl)-5-fluoro-pyrimidin-4-yl]amino]cyclohexyl]carbamate (592)

¹H NMR (300 MHz, MeOD) δ 8.84 (s, 1H), 8.21 (s, 1H), 8.16 (s, 1H), 7.99 (d, J=3.97 Hz, 1H), 4.18-4.34 (m, 1H), 4.14 (br. s., 2H), 3.49-3.74 (m, 3H), 3.3 (s, 3H) 2.38 (d, J=9.06 Hz, 1H), 2.19 (d, J=13.41 Hz, 1H), 1.84-2.11 (m, 2H), 1.51-1.78 (m, 1H), 1.12-1.47 (m, 3H) ppm.

LCMS RT=2.5 (M+1) 463.4.

General Scheme 21:

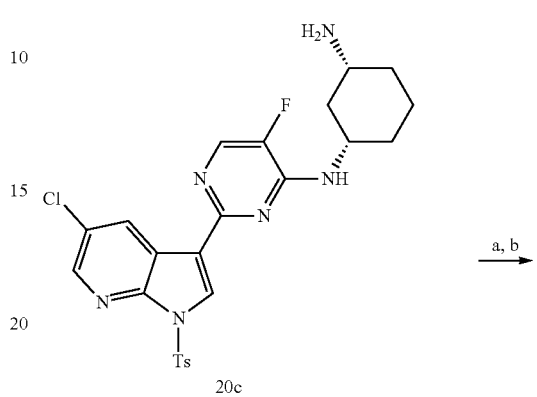

20c a, b

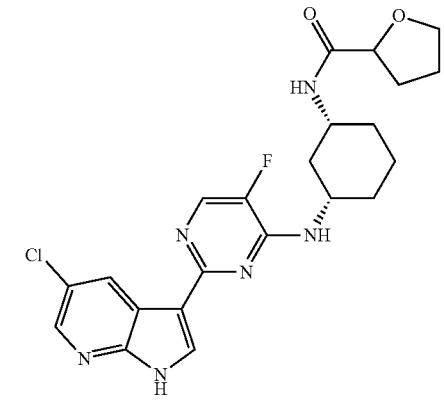

638

(a) tetrahydrofuran-2-carboxylic acid, EDC, HOBt, DIPEA, CH₂Cl₂, rt; (b) LiOH, 130° C., microwave.

Formation of N-[1R,3S)-3-[[2-(5-chloro-1H-pyrrolo[2,3-b]pyridin-3-yl)-5-fluoro-pyrimidin-4-yl]amino]cyclohexyl]tetrahydrofuran-2-carboxamide hydrochloride (638)

To a solution of (1S,3R)—N1-[2-[5-chloro-1-(p-tolylsulfonyl)pyrrolo[2,3-b]pyridin-3-yl]-5-fluoro-pyrimidin-4-yl]cyclohexane-1,3-diamine, 20c, (60 mg, 0.12 mmol) in CH₂Cl₂ (3 mL) was added tetrahydrofuran-2-carboxylic acid (20.3 mg, 0.17 mmol), EDC (26.8 mg, 0.14 mmol), HOBt (17.8 mg, 0.12 mmol) and DIPEA (60.2 mg, 0.47 mmol), and the reaction mixture was stirred at room temperature overnight. The solvent was evaporated under reduced pressure, and the residue was dissolved in THF (4 mL) and treated with 1M aqueous lithium hydroxide (3.0 mL, 3.0 mmol). The reaction mixture was heated in the microwave to 130° C. for 20 min. The solvent was evaporated under reduced pressure, and the residue was purified by HPLC, using 5-70% MeOH//

H₂O with 6 mM HCl over 15 minutes. The purified fractions were concentrated to provide the hydrochloride of N-[(1R,3S)-3-[[2-(5-chloro-1H-pyrrolo[2,3-1)]pyridin-3-yl)-5-fluoro-pyrimidin-4-yl]amino]cyclohexyl]tetrahydrofuran-2-carboxamide, 638.

¹H NMR (300 MHz, MeOD) δ 8.55 (d, J=1.0 Hz, 1H), 8.46-8.45 (m, 1H), 8.29-8.27 (m, 2H), 4.28 (d, J=6.1 Hz, 2H), 4.00-3.87 (m, 3H), 2.36-2.16 (m, 3H), 2.00-1.91 (m, 5H) and 1.75-1.41 (m, 4H) ppm.

LCMS RT=3.77 (M+1) 459.37, (M−1) 457.35.

The following compounds can be prepared by methods similar to those described in Scheme 19, Scheme 20 and Scheme 21:

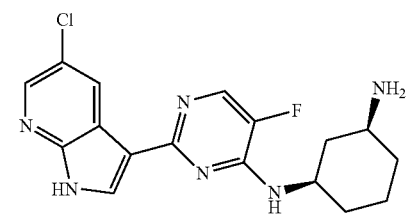

542

(1R,3S)—N1-[2-(5-chloro-1H-pyrrolo[2,3-b]pyridin-3-yl)-5-fluoro-pyrimidin-4-yl]cyclohexane-1,3-diamine (542)

LCMS RT=1.4 (M+1) 361.4.

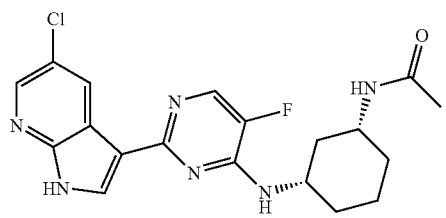

576

N-[(1R,3S)-3-[[2-(5-chloro-1H-pyrrolo[2,3-b]pyridin-3-yl)-5-fluoro-pyrimidin-4-yl]amino]cyclohexyl]acetamide (576)

¹H NMR (300 MHz, MeOD) δ 8.81 (s, 1H), 8.20 (s, 1H), 8.15 (s, 1H), 7.99 (d, J=4.1, 1H), 4.23 (t, J=11.4, 1H), 3.90 (t, J=11.4, 1H), 2.35 (d, J=11.6, 1H), 2.20 (d, J=12.5, 1H), 2.00 (d, J=15.9, 2H), 1.92 (s, 3H), 1.67 (dd, J=26.3, 13.2, 1H), 1.53-1.06 (m, 3H) ppm; LCMS RT=1.8 (M+1) 403 (M−1) 401.4.

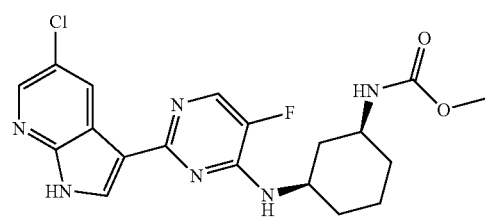

548

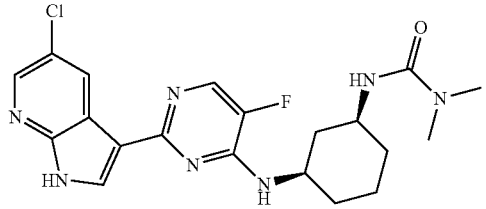

549

Methyl N-[(1S,3R)-3-[[2-(5-chloro-1H-pyrrolo[2,3-b]pyridin-3-yl)-5-fluoro-pyrimidin-4-yl]amino]cyclohexyl]carbamate (548)

LCMS RT=2.8 (M+1) 419.5.

3-[(1S,3R)-3-[[2-(5-chloro-1H-pyrrolo[2,3-b]pyridin-3-yl)-5-fluoro-pyrimidin-4-yl]amino]cyclohexyl]-1,1-dimethyl-urea (549)

LCMS RT=2.6 (M+1) 432.5.

591

592

N-[(1R,3S)-3-[[2-(5-chloro-1H-pyrrolo[2,3-b]pyridin-3-yl)-5-fluoro-pyrimidin-4-yl]amino]cyclohexyl]-2-methoxy-acetamide (591)

¹H NMR (300 MHz, MeOD) δ 8.82 (d, J=2.4 Hz, 1H), 8.21 (d, J=2.3 Hz, 1H), 8.16 (s, 1H), 7.99 (d, J=4.1 Hz, 1H), 4.29-4.21 (m, 1H), 4.04-3.96 (m, 1H), 3.87 (s, 2H), 3.40 (s, 3H), 2.34 (d, J=11.6 Hz, 1H), 2.21 (d, J=12.5 Hz, 1H), 2.02-1.93 (m, 2H), 1.74-1.62 (m, 1H) and 1.54-1.28 (m, 3H) ppm.

LCMS RT=2.6 (M+1) 433.4.

2-methoxyethyl N-[(1R,3S)-3-[[2-(5-chloro-1H-pyrrolo[2,3-b]pyridin-3-yl)-5-fluoro-pyrimidin-4-yl]amino]cyclohexyl]carbamate (592)

¹H NMR (300 MHz, MeOD) δ 8.84 (s, 1H), 8.21 (s, 1H), 8.16 (s, 1H), 7.99 (d, J=3.97 Hz, 1H), 4.18-4.34 (m, 1H), 4.14 (br. s., 2H), 3.49-3.74 (m, 3H), 3.3 (s, 3H) 2.38 (d, J=9.06 Hz, 1H), 2.19 (d, J=13.41 Hz, 1H), 1.84-2.11 (m, 2H), 1.51-1.78 (m, 1H), 1.12-1.47 (m, 3H) ppm.

LCMS RT=2.5 (M+1) 463.4.

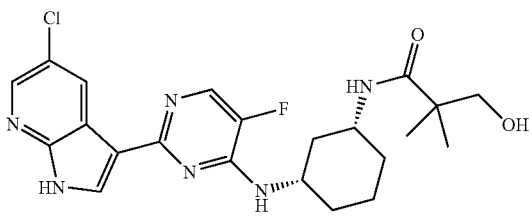

650

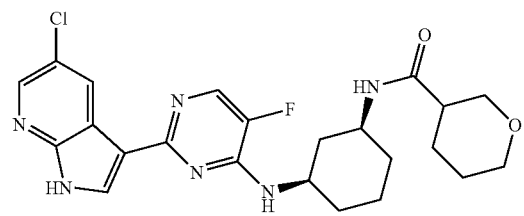

633

N-[(1R,3S)-3-[[2-(5-chloro-1H-pyrrolo[2,3-b]pyridin-3-yl)-5-fluoro-pyrimidin-4-yl]amino]cyclohexyl]-3-hydroxy-2,2-dimethyl-propanamide hydrochloride (650)

¹H NMR (300 MHz, MeOD) δ 8.56-8.54 (m, 2H), 8.34 (s, 1H), 8.30 (t, J=5.4 Hz, 1H), 4.29 (t, J=11.4 Hz, 1H), 3.93 (t, J=11.6 Hz, 1H), 3.54 (s, 2H), 2.34 (d, J=10.8 Hz, 1H), 2.18 (d, J=11.4 Hz, 1H), 2.01 (d, J=11.3 Hz, 2H), 1.73-1.37 (m, 4H) and 1.15 (s, 6H) ppm.
LCMS RT=3.79 (M+1) 461.38, (M−1) 459.4.

N-[(1R,3S)-3-[[2-(5-chloro-1H-pyrrolo[2,3-b]pyridin-3-yl)-5-fluoro-pyrimidin-4-yl]amino]cyclohexyl] tetrahydropyran-3-carboxamide hydrochloride (633)

¹H NMR (300 MHz, MeOD) δ 8.64 (d, J=2.2 Hz, 1H), 8.51 (s, 1H), 8.36 (d, J=2.2 Hz, 1H), 8.29 (d, J=5.5 Hz, 1H), 4.39 (t, J=11.9 Hz, 1H), 3.93-3.82 (m, 3H), 3.54-3.30 (m, 2H), 2.52-2.43 (m, 1H), 2.37-2.33 (m, 1H), 2.20 (d, J=11.6 Hz, 1H), 2.01 (d, J=11.3 Hz, 2H), 1.90-1.88 (m, 1H), 1.83-1.63 (m, 4H) and 1.59-1.26 (m, 3H) ppm.
LCMS RT=3.25 (M+1) 473.42, (M−1) 471.1.

634

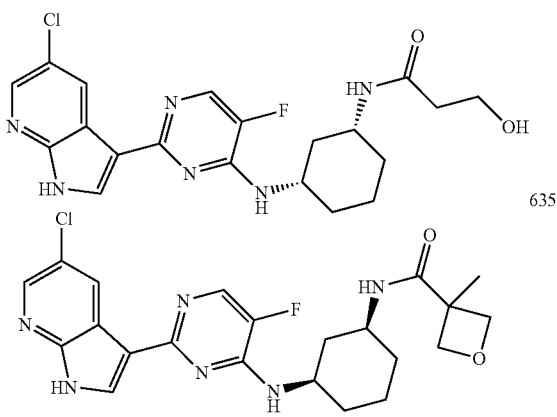

635

N-[(1R,3S)-3-[[2-(5-chloro-1H-pyrrolo[2,3-b]pyridin-3-yl)-5-fluoro-pyrimidin-4-yl]amino]cyclohexyl]-3-hydroxy-propanamide hydrochloride (634)

¹H NMR (300 MHz, MeOD) δ 8.61 (d, J=2.1 Hz, 1H), 8.53 (s, 1H), 8.35 (d, J=2.0 Hz, 1H), 8.29 (d, J=5.5 Hz, 1H), 4.37 (t, J=11.2 Hz, 1H), 3.95 (s, 1H), 3.80 (s, 2H), 2.42 (t, J=5.5 Hz, 3H), 2.20 (d, J=11.5 Hz, 1H), 2.03 (d, J=11.0 Hz, 2H) and 1.76-1.29 (m, 4H) ppm.
LCMS RT=3.47 (M+1) 433.21, (M−1) 431.3.

N-[(1R,3S)-3-[[2-(5-chloro-1H-pyrrolo[2,3-b]pyridin-3-yl)-5-fluoro-pyrimidin-4-yl]amino]cyclohexyl]-3-methyl-oxetane-3-carboxamide hydrochloride (635)

¹H NMR (300 MHz, MeOD) δ 8.48-8.45 (m, 2H), 8.29-8.23 (m, 2H), 4.84 (d, J=6.0 Hz, 1H), 4.38 (d, J=6.0 Hz, 1H), 4.26-4.23 (m, 1H), 3.96 (s, 1H), 3.77-3.62 (m, 2H), 2.36 (s, 1H), 2.18 (d, J=11.5 Hz, 1H), 2.02 (d, J=12.3 Hz, 2H), 1.70-1.25 (m, 4H) and 1.59 (s, 3H) ppm.
LCMS RT=3.12 (M+1) 459.38, (M−1) 457.4.

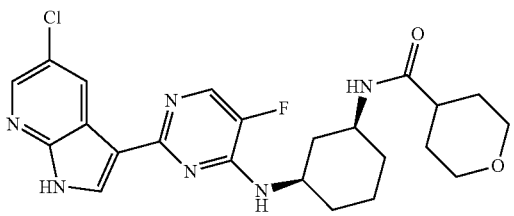

636

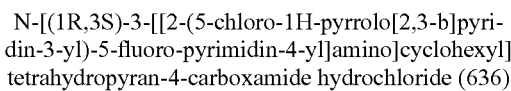

640

N-[(1R,3S)-3-[[2-(5-chloro-1H-pyrrolo[2,3-b]pyridin-3-yl)-5-fluoro-pyrimidin-4-yl]amino]cyclohexyl] tetrahydropyran-4-carboxamide hydrochloride (636)

¹H NMR (300 MHz, MeOD) δ 8.64 (d, J=2.3 Hz, 1H), 8.51 (s, 1H), 8.36 (d, J=2.3 Hz, 1H), 8.29 (d, J=5.6 Hz, 1H), 4.44-4.36 (m, 1H), 3.96-3.87 (m, 3H), 3.47-3.37 (m, 2H), 2.49-2.35 (m, 2H), 2.21 (d, J=12.4 Hz, 1H), 2.02 (d, J=11.9 Hz, 2H) and 1.83-1.23 (m, 8H) ppm. LCMS RT=3.12 (M+1) 473.4, (M−1) 471.4.

N-[(1R,3S)-3-[[2-(5-chloro-1H-pyrrolo[2,3-b]pyridin-3-yl)-5-fluoro-pyrimidin-4-yl]amino]cyclohexyl]-3-hydroxy-butanamide hydrochloride (640)

¹H NMR (300 MHz, MeOD) δ 8.69 (d, J=2.3 Hz, 1H), 8.51 (s, 1H), 8.37 (d, J=2.2 Hz, 1H), 8.29 (d, J=5.6 Hz, 1H), 4.43 (t, J=11.9 Hz, 1H), 4.14 (q, J=6.1 Hz, 1H), 3.94 (t, J=11.9 Hz, 1H), 2.40-2.19 (m, 4H), 2.03 (d, J=8.2 Hz, 2H), 1.78-1.69 (m, 1H), 1.59-1.44 (m, 3H) and 1.18 (d, J=6.1 Hz, 3H) ppm.
LCMS RT=3.37 (M+1) 447.41, (M−1) 445.1.

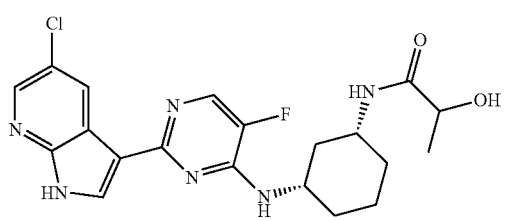

642

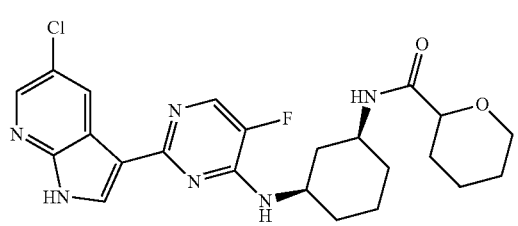

651

N-[(1R,3S)-3-[[2-(5-chloro-1H-pyrrolo[2,3-b]pyridin-3-yl)-5-fluoro-pyrimidin-4-yl]amino]cyclohexyl]-2-hydroxy-propanamide hydrochloride (642)

¹H NMR (300 MHz, MeOD) δ 8.68 (s, 1H), 8.56 (s, 1H), 8.39 (d, J=1.5 Hz, 1H), 8.31 (d, J=5.3 Hz, 1H), 4.47-4.40 (m, 1H), 4.15 (s, 1H), 3.98 (m, 1H), 2.41 (s, 1H), 2.23 (d, J=10.6 Hz, 1H), 2.04 (d, J=11.0 Hz, 2H) and 1.77-1.36 (m, 7H) ppm. LCMS RT=3.52 (M+1) 433.58, (M−1) 431.3.

N-[(1R,3S)-3-[[2-(5-chloro-1H-pyrrolo[2,3-b]pyridin-3-yl)-5-fluoro-pyrimidin-4-yl]amino]cyclohexyl]tetrahydropyran-2-carboxamide hydrochloride (651)

¹H NMR (300 MHz, MeOD) δ 8.56-8.51 (m, 2H), 8.33-8.29 (m, 2H), 4.30 (d, J=3.0 Hz, 1H), 3.98 (dd, J=11.5, 23.4 Hz, 2H), 3.83-3.79 (m, 1H), 3.55 (t, J=8.9 Hz, 1H), 2.35 (d, J=11.1 Hz, 1H), 2.19 (d, J=11.2 Hz, 1H), 2.03-1.90 (m, 4H) and 1.73-1.37 (m, 8H) ppm. LCMS RT=4.1 (M+1) 473.41, (M−1) 471.4.

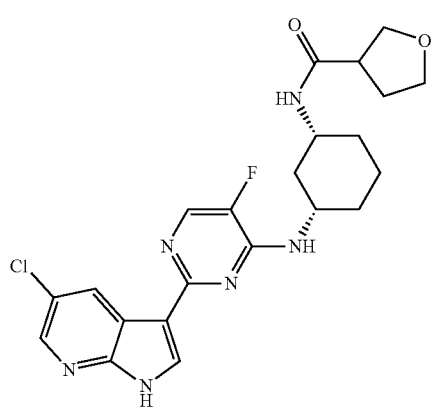

652

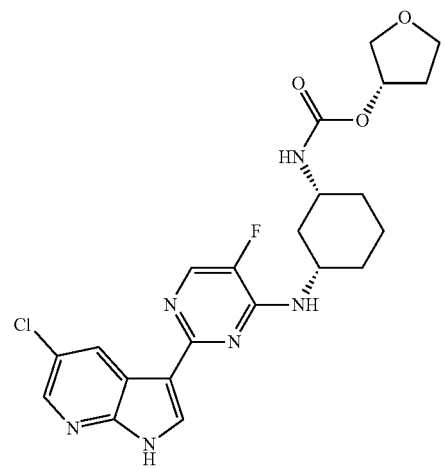

649

N-[(1R,3S)-3-[[2-(5-chloro-1H-pyrrolo[2,3-b]pyridin-3-yl)-5-fluoro-pyrimidin-4-yl]amino]cyclohexyl]tetrahydrofuran-3-carboxamide hydrochloride (652)

¹H NMR (300 MHz, MeOD) δ 8.72 (d, J=2.3 Hz, 1H), 8.56 (s, 1H), 8.42 (d, J=2.2 Hz, 1H), 8.34 (d, J=5.6 Hz, 1H), 4.51-4.43 (m, 1H), 4.02-3.88 (m, 3H), 3.86-3.78 (m, 2H), 3.07-3.02 (m, 1H), 2.42 (d, J=7.5 Hz, 1H), 2.25 (d, J=12.0 Hz, 1H), 2.19-2.06 (m, 4H) and 1.79-1.35 (m, 4H) ppm.

LCMS RT=3.9 (M+1) 459.41, (M−1) 457.4.

(S)-tetrahydrofuran-3-yl (1R,3S)-3-((2-(5-chloro-1H-pyrrolo[2,3-b]pyridin-3-yl)-5-fluoropyrimidin-4-ylamino)cyclohexylcarbamate (649)

LCMS RT=3.3 (M+1) 475.37, (M−1) 473.35.

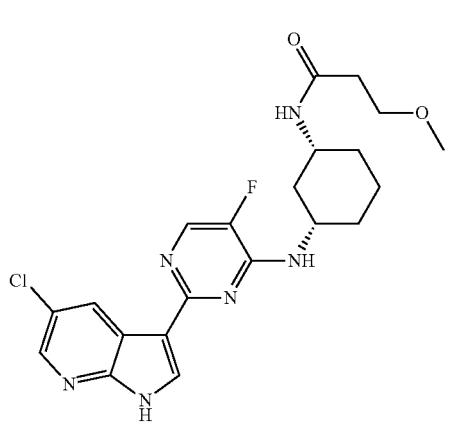

611

N-((1R,3S)-3-((2-(5-chloro-1H-pyrrolo[2,3-b]pyridin-3-yl)-5-fluoropyrimidin-4-ylamino)cyclohexyl)-3-methoxypropanamide (611)

LCMS RT=2.0 (M+1) 447.4, (M−1) 445.4.

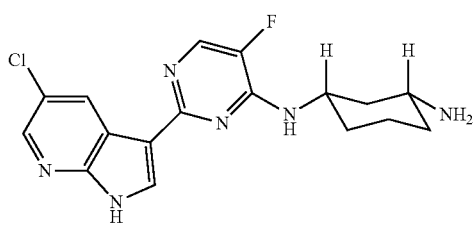

N-[2-(5-chloro-1H-pyrrolo[5,4-b]pyridin-3-yl)-5-
fluoro-pyrimidin-4-yl]cyclohexane-cis-1,3-diamine
(540)

LCMS RT=1.4 (M+1) 361.5.

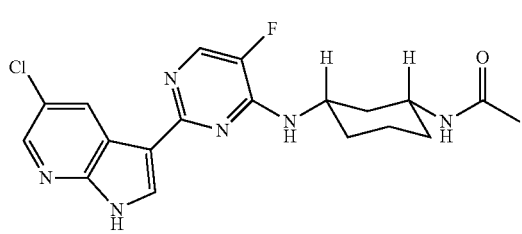

N-[cis-3-[[2-(5-chloro-1H-pyrrolo[2,3-b]pyridin-3-
yl)-5-fluoropyrimidin-4-yl]amino]cyclohexyl]aceta-
mide (452)

(prepared from cis/trans 1,3diamino cyclohexane; separated by HPLC from trans diastereomer)

LCMS RT=1.3 (M+1) 403.1 (M−1) 401.1.

N-[trans-3-[[2-(5-chloro-1H-pyrrolo[2,3-b]pyridin-3-
yl)-5-fluoro-pyrimidin-4-yl]amino]cyclohexyl]aceta-
mide acetamide (457)

(separated by HPLC from cis diastereomer)

LCMS RT=1.6 (M+1) 403.2 (M−1) 401.1.

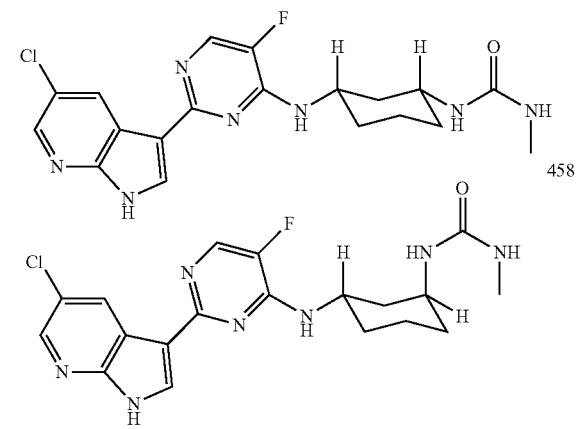

1-[cis-3-[[2-(5-chloro-1H-pyrrolo[2,3-b]pyridin-3-
yl)-5-fluoro-pyrimidin-4-yl]amino]cyclohexyl]-3-
methyl-urea (455)

(prepared from cis/trans 1,3diamino cyclohexane; separated by HPLC from trans diastereomer)

LCMS RT=1.7 (M+1) 416.2.

1-[trans-3-[[2-(5-chloro-1H-pyrrolo[2,3-b]pyridin-3-yl)-
5-fluoro-pyrimidin-4-yl]amino]cyclohexyl]-3-methyl-urea
(458)

(prepared from cis/trans 1,3-diamino cyclohexane; separated by HPLC from cis diastereomer)

LCMS RT=0.8 (M+1) 418.2 (M−1) 416.1.

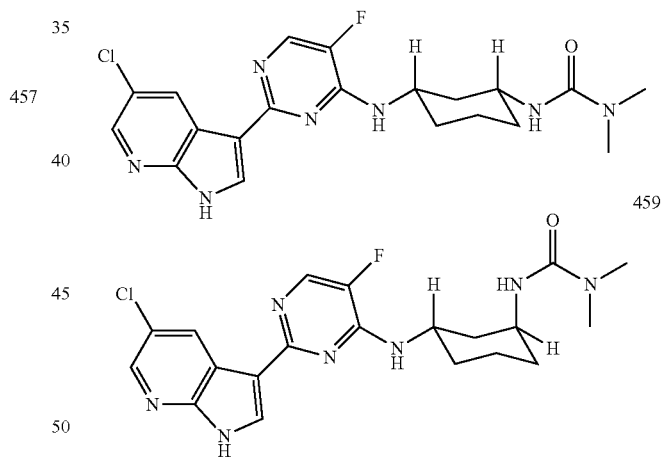

3-[cis-3-[[2-(5-chloro-1H-pyrrolo[2,3-b]pyridin-3-
yl)-5-fluoro-pyrimidin-4-yl]amino]cyclohexyl]-1,1-
dimethyl-urea (456)

(prepared from cis/trans 1,3diamino cyclohexane; separated by HPLC from trans diastereomer)

LCMS RT=1.5 (M+1) 432.2 (M−1) 430.2.

3-[trans-3-[[2-(5-chloro-1H-pyrrolo[2,3-b]pyridin-3-
yl)-5-fluoro-pyrimidin-4-yl]amino]cyclohexyl]-1,1-
dimethyl-urea (459)

(prepared from cis/trans 1,3diamino cyclohexane; separated by HPLC from cis diastereomer)

LCMS RT=1.5 (M+1) 432.2 (M−1) 430.2.

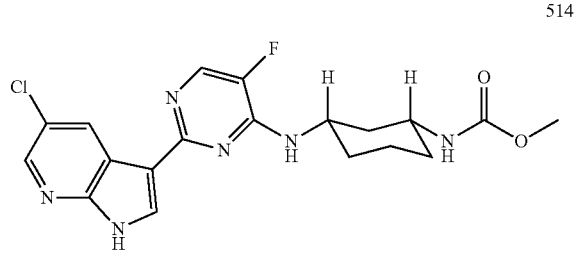

(+/-)

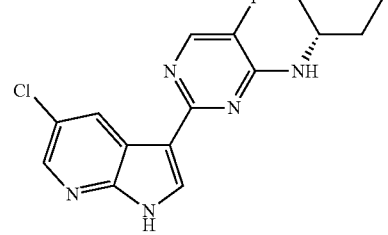

Methyl-cis-3-[[2-(5-chloro-1H-pyrrolo[2,3-b]pyridin-3-yl)-5-fluoro-pyrimidin-4-yl]amino]cyclohexyl-carbamate (514)

(racemic cis mixture—prepared from cis-1,3-diaminocyclohexane)
LCMS RT=1.3 (M+1) 418.8.

N-((1R,3S)-3-((2-(5-chloro-1H-pyrrolo[2,3-b]pyridin-3-yl)-5-fluoropyrimidin-4-ylamino)cyclohexyl)morpholine-4-carboxamide (647)

LCMS RT=3.6 (M+1) 474.4 (M−1) 472.5.

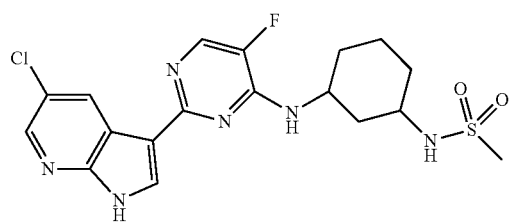

N-[3-[[2-(5-chloro-1H-pyrrolo[2,3-b]pyridin-3-yl)-5-fluoro-pyrimidin-4-yl]amino]cyclohexyl]methanesulfonamide (454)

LCMS RT=1.6 (M+1) 439.1 (M−1) 437.1.

(Tetrahydrofuran-3-yl)methyl (1R,3S)-3-((2-(5-chloro-1H-pyrrolo[2,3-b]pyridin-3-yl)-5-fluoropyrimidin-4-ylamino)cyclohexylcarbamate (648)

LCMS RT=3.7 (M+1) 489.38, (M−1) 487.49.

General Scheme 22:

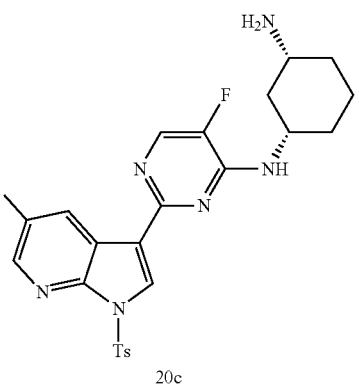

-continued

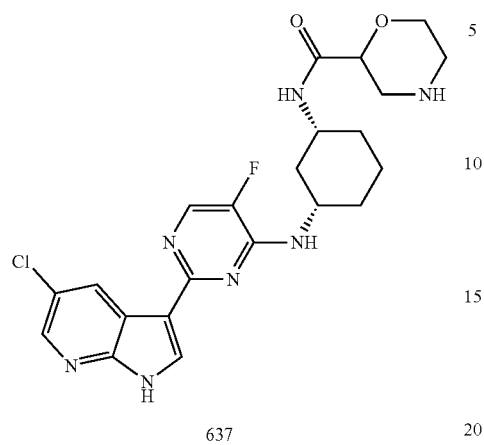

637

(a) 4-tert-butoxycarbonylmorpholine-2-carboxylic acid, EDC, HOBt, $^i$Pr$_2$NEt, CH$_2$Cl$_2$, rt (b) CH$_2$Cl$_2$, TFA (c) LiOH, 130° C., microwave Formation N-[(1R,3S)-3-[[2-(5-chloro-1H-pyrrolo[2,3-b]pyridin-3-yl)-5-fluoro-pyrimidin-4-yl]amino]cyclohexyl]morpholine-2-carboxamide bishydrochloride (637)

To a solution of (1S,3R)—N1-[2-[5-chloro-1-(p-tolylsulfonyl)pyrrolo[2,3-b]pyridin-3-yl]-5-fluoro-pyrimidin-4-yl]cyclohexane-1,3-diamine (0.06 g, 0.12 mmol) in CH$_2$Cl$_2$ (3 mL) was added 4-tert-butoxycarbonylmorpholine-2-carboxylic acid (40.4 mg, 0.17 mmol), EDC (0.03 g, 0.14 mmol), HOBt (0.02 g, 0.12 mmol) and $^i$Pr$_2$NEt (0.06 g, 0.47 mmol), and the reaction mixture was stirred at room temperature overnight. The solvent was evaporated under reduced pressure, and the residue was dissolved in CH$_2$Cl$_2$ (2 mL) and TFA (2 mL) and allowed to stir at room temperature for 2 hours. The resulting solution was concentrated in vacuo, dissolved in THF (4 mL) and treated with 1N aqueous lithium hydroxide (3.0 mL, 3.0 mmol). The reaction mixture was heated in the microwave to 130° C. for 20 min. The solvent was evaporated under reduced pressure, and the residue was purified by HPLC, using 5-70% MeOH/H$_2$O with 6 mM HCl over 15 minutes. The purified fractions were concentrated to provide the bis-hydrochloride of N-[(1R,3S)-3-[[2-(5-chloro-1H-pyrrolo[2, 3-1)]pyridin-3-yl)-5-fluoro-pyrimidin-4-yl]amino]cyclohexyl]morpholine-2-carboxamide.

$^1$H NMR (300 MHz, MeOD) δ 8.68 (s, 1H), 8.62 (s, 1H), 8.40 (s, 1H), 8.33 (d, J=4.7 Hz, 1H), 4.44-4.35 (m, 2H), 4.21 (d, J=12.2 Hz, 1H), 4.04-3.92 (m, 2H), 3.58 (d, J=12.3 Hz, 1H), 3.23-3.08 (m, 2H), 2.37 (d, J=8.1 Hz, 1H), 2.23 (d, J=11.1 Hz, 1H), 2.05 (d, J=9.7 Hz, 2H), 1.72 (m, 2H) and 1.59-1.44 (m, 2H) ppm; LCMS RT=2.4 (M+1) 474.43, (M−1) 472.4.

Other analogs that can be prepared in the same manner as 637 are described below:

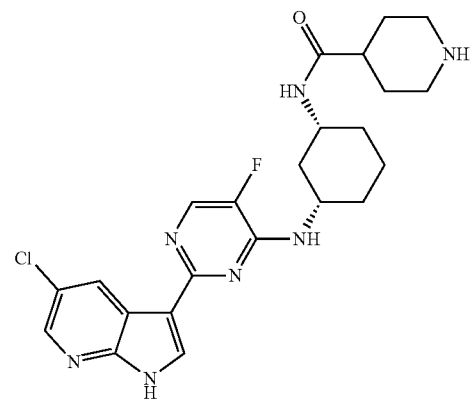

639

N-[(1R,3S)-3-[[2-(5-chloro-1H-pyrrolo[2,3-b]pyridin-3-yl)-5-fluoro-pyrimidin-4-yl]amino]cyclohexyl]piperidine-4-carboxamide bishydrochloride (639)

$^1$H NMR (300 MHz, MeOD) δ 8.66 (s, 1H), 8.60 (s, 1H), 8.38 (s, 1H), 8.31 (d, J=4.7 Hz, 1H), 4.43-4.36 (m, 1H), 3.98-3.91 (m, 1H), 3.43 (d, J=10.3 Hz, 2H), 3.03 (t, J=10.6 Hz, 2H), 2.60 (s, 1H), 2.38 (d, J=10.2 Hz, 1H), 2.21 (d, J=10.6 Hz, 1H), 2.07-1.92 (m, 6H) and 1.74-1.30 (m, 4H) ppm. LCMS RT=2.4 (M+1) 472.46, (M−1) 470.4.

General Scheme 23:

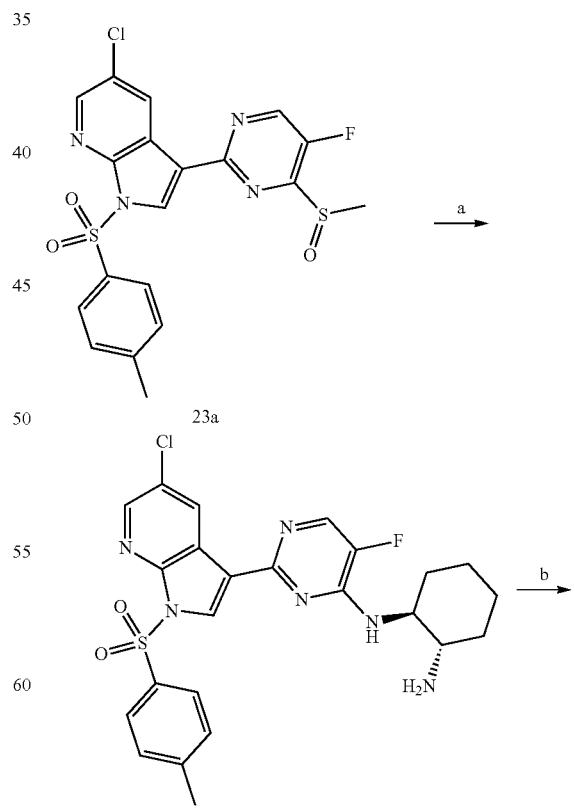

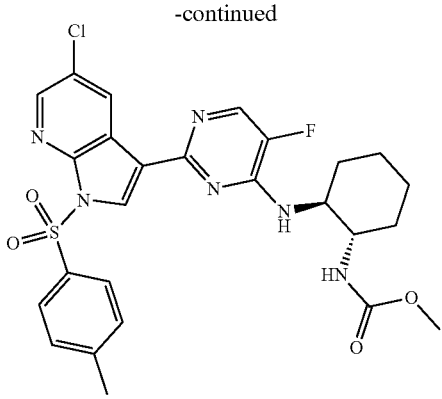

23c

↓ c

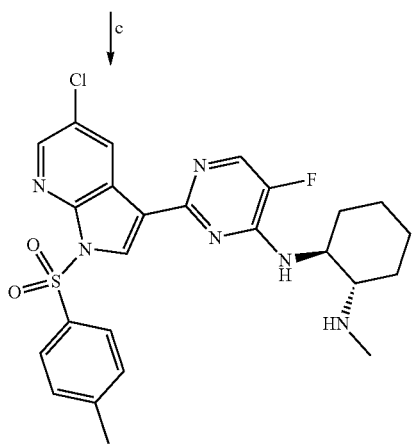

522

(a) (1S,2S)-cyclohexane-1,2-diamine, THF, 120° C. microwave (b) methyl-chloroformate, $^i$Pr$_2$NEt, CH$_2$Cl$_2$ (c) LiAlH$_4$, THF.

Formation of (1S,2S)—N1-(2-(5-chloro-1-tosyl-1H-pyrrolo[2,3-b]pyridin-3-yl)-5-fluoropyrimidin-4-yl)cyclohexane-1,2-diamine (23b)

A solution of 5-chloro-3-(5-fluoro-4-methylsulfinyl-pyrimidin-2-yl)-1-(p-tolylsulfonyl)pyrrolo[2,3-b]pyridine, 23a, (0.50 g, 1.08 mmol) in THF (4 mL) was treated with (1S,2S)-cyclohexane-1,2-diamine (0.27 g, 2.37 mmol) and $^i$Pr$_2$NEt (2.15 mmol) at 120° C. for 10 minutes. The mixture was concentrated in vacuo. The resulting residue was purified by silica gel chromatography (0-20% MeOH—CH$_2$Cl$_2$) to provide the desired intermediate as a white solid (410 mg).
LCMS RT=2.2 (M+1) 515.5.

Formation of methyl (1S,2S)-2-(2-(5-chloro-1-tosyl-1H-pyrrolo[2,3-b]pyridin-3-yl)-5-fluoro-pyrimidin-4-ylamino)cyclohexylcarbamate (23c)

To a mixture of (1S,2S)—N1-(2-(5-chloro-1-tosyl-1H-pyrrolo[2,3-b]pyridin-3-yl)-5-fluoropyrimidin-4-yl)cyclohexane-1,2-diamine, 23b, (0.18 g, 0.35 mmol) in dichloromethane (4 mL) at room temperature was added $^i$Pr$_2$NEt (0.12 mL, 0.70 mmol) followed by methyl chloroformate (0.03 mL, 0.37 mmol). After 35 minutes. the mixture was diluted with EtOAc, washed successively with aqueous saturated NH$_4$Cl and aqueous saturated NaHCO$_3$ and brine, dried over Na$_2$SO$_4$ filtered and concentrated in vacuo to provide the crude product sufficiently pure for use in the next reaction.
LCMS RT=4.1 (M+1) 573.4.

Formation of (1s, 2S)-M-(2-(5-chloro-1H-pyrrolo[2,3-b]pyridin-3-yl)-5-fluoropyrimidin-4-yl)-N2-methylcyclohexane-1,2-diamine (522)

To a stirred solution of methyl (1S,2S)-2-(2-(5-chloro-1-tosyl-1H-pyrrolo[2,3-b]pyridin-3-yl)-5-fluoropyrimidin-4-ylamino)cyclohexylcarbamate, 23c, (0.09 g, 0.16 mmol) in THF (3 mL) at room temperature was added LiAlH$_4$ (0.06 g, 1.66 mmol) and the mixture was stirred at room temperature for additional 2 hours. The reaction was quenched with 0.06 mL KOH (5% aq) followed by water (3×0.06 mL). Then, additional Et$_2$O (6 mL) was added and stirring was continued for 20 minutes. The milky white suspension was filtered and rinsed with EtOAc and the cake was rinsed with additional EtOAc. The combined organic phases were concentrated in vacuo and purified by preparative HPLC followed by preparative TLC to provide the desired product as the free base that was then converted to the HCl salt by treatment with HCl (4N in dioxane).
LCMS RT=1.7 (M+1) 375.5.
General Scheme 24:

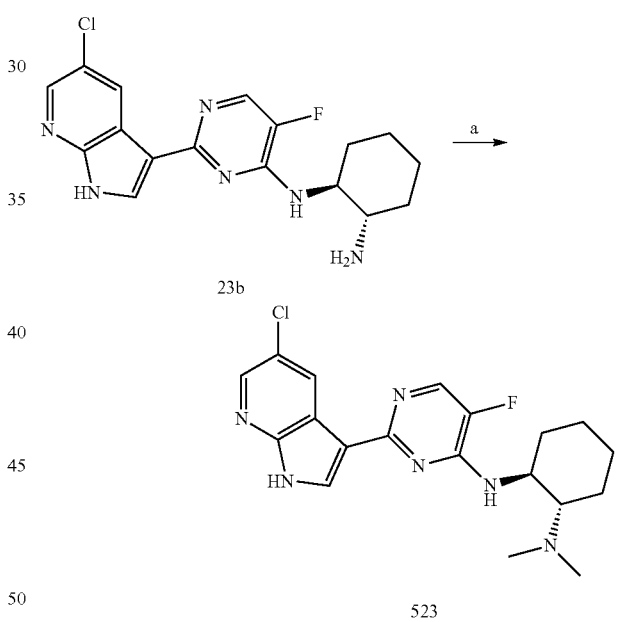

523

(a) NaCNBH$_3$, (CH$_2$O)$_n$, HOAc, CH$_3$CN.

Formation of (1S,2S)—N1-(2-(5-chloro-1H-pyrrolo[2,3-b]pyridin-3-yl)-5-fluoropyrimidin-4-yl)-N2,N2-dimethylcyclohexane-1,2-diamine (523)

To a mixture of (1S,2S)—N1-(2-(5-chloro-1H-pyrrolo[2,3-b]pyridin-3-yl)-5-fluoropyrimidin-4-yl)cyclohexane-1,2-diamine, 23b, (0.08 g, 0.22 mmol) in acetonitrile (1.6 mL) at room temperature was added formaldehyde (0.09 mL of 37% w/v, 1.11 mmol) followed by NaCNBH$_3$ (0.04 g, 0.56 mmol). A gelatinous mix formed and after 4 min the mixture became fluid again. After 4 hours, the reaction was quenched with 5 mL of 2N NaOH and the mixture was stirred overnight. The mixture was diluted with EtOAc and stirred until all solid dissolved. The layer was extracted with EtOAc several times, dried over Na₂SO₄, filtered and concentrated in vacuo. Silica gel chromatography (0-15% MeOH—CH₂Cl₂) followed by preparatory HPLC provided the desired product, which was converted to the corresponding HCl salt with HCl (4N in dioxane).

¹H NMR (300 MHz, MeOD) δ 8.65 (d, J=2.3 Hz, 1H), 8.54 (s, 1H), 8.43 (d, J=5.1 Hz, 1H), 8.40 (d, J=2.3 Hz, 1H), 4.82-4.72 (m, 1H), 3.66-3.53 (m, 1H), 2.96 (s, 3H), 2.77 (s, 3H), 2.33 (d, J=12.3 Hz, 2H), 2.10-1.97 (m, 2H) and 1.75-1.48 (m, 4H) ppm; LCMS RT=1.7 (M+1) 389.5.

to provide the free base of the desired product 1-[[(1R,3S)-3-[[2-(5-chloro-1H-pyrrolo[2, 3-1)]pyridin-3-yl)-5-fluoro-pyrimidin-4-yl]amino]cyclohexyl]amino]-3-methoxy-propan-2-ol, 610.

¹H NMR (300 MHz, MeOD) δ 8.85 (d, J=2.3 Hz, 1H), 8.22 (d, J=2.2 Hz, 1H), 8.15 (s, 1H), 7.98 (d, J=4.1 Hz, 1H), 4.20 (m, 1H), 3.82 (dd, J=3.9, 8.2 Hz, 1H), 3.55-3.45 (m, 1H), 3.30 (s, 3H), 3.23-3.07 (m, 1H), 2.86-2.77 (m, 2H), 2.68-2.59 (m, 1H), 2.44 (d, J=10.9 Hz, 1H), 2.15 (d, J=9.8 Hz, 1H), 2.07-1.94 (m, 2H), 1.65-1.56 (m, 1H) and 1.42-1.17 (m, 3H) ppm; LCMS RT=1.52 (M+1) 449.42.

General Scheme 25:

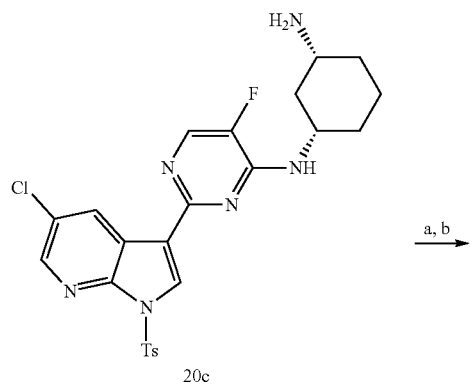

General Scheme 26:

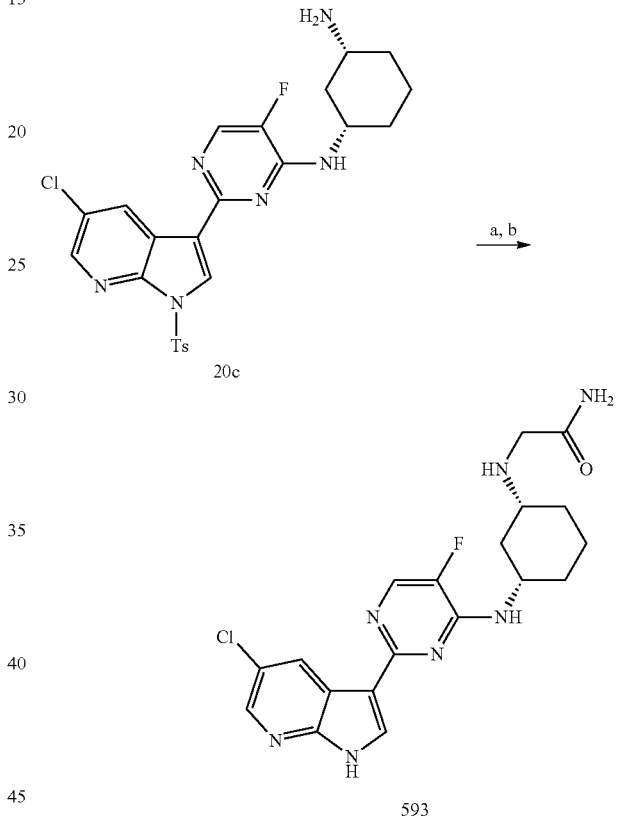

(a) 2-(methoxymethyl)oxirane, methanol, 130° C., microwave; (b) LiOH, 130° C., microwave.

(a) 2-bromoacetamide, Na₂CO₃, DMF, rt; (b) LiOH, 130° C., microwave.

Formation of 1-[[(1R,3S)-3-[[2-(5-chloro-1H-pyrrolo[2,3-b]pyridin-3-yl)-5-fluoro-pyrimidin-4-yl]amino]cyclohexyl]amino]-3-methoxy-propan-2-ol (610)

To a solution of (1S,3R)—N1-[2-[5-chloro-1-(p-tolylsulfonyl)pyrrolo[2,3-b]pyridin-3-yl]-5-fluoro-pyrimidin-4-yl]cyclohexane-1,3-diamine, 20c, (50 mg, 0.09 mmol) in methanol (2 mL) was added 2-(methoxymethyl)oxirane (9.4 mg, 0.11 mmol) and the reaction mixture was heated in the microwave to 140° C. for 10 min. 1M aqueous LiOH (1.0 mL, 1.0 mmol) was added, and the reaction mixture was heated in the microwave to 130° C. for 10 min. The solvent was evaporated under reduced pressure, and the residue was purified by HPLC, using 5-70% CH₃CN//H₂O with 0.1% TFA over 15 minutes. The purified fractions were concentrated, redissolved in MeOH and passed through a carbonate-PS column Formation of 2-[[1R,3S)-3-[2-(5-chloro-1H-pyrrolo[2,3-b]pyridin-3-yl)-5-fluoropyrimidin-4-yl]amino]cyclohexylamino]-acetamide (593)

To a solution of (1S,3R)—N1-[2-[5-chloro-1-(p-tolylsulfonyl)pyrrolo[2,3-b]pyridin-3-yl]-5-fluoro-pyrimidin-4-yl]cyclohexane-1,3-diamine, 20c, (0.050 g, 0.100 mmol) in DMF (2 mL) was added 2-bromoacetamide (0.015 g, 0.100 mmol) and Na₂CO₃ (0.021 g, 0.190 mmol). The reaction mixture was stirred at room temperature overnight 1M aqueous lithium hydroxide (2.0 mL, 2.0 mmol) was added, and the reaction mixture was heated in the microwave to 130° C. for 10 min. The solvent was evaporated under reduced pressure, and the residue was purified by HPLC, using 5-70% CH₃CN//H₂O with 0.1% TFA over 15 minutes. The purified fractions were concentrated, redissolved in MeOH and passed through a carbonate-PS column to provide the free base of the desired product 2-[[1R,3S)-3-[2-(5-chloro-1H-pyrrolo[2,3-b]pyridin-3-yl)-5-fluoropyrimidin-4-yl]amino]cyclohexylamino]-acetamide, 593.

¹H NMR (300 MHz, MeOD) δ 8.85 (d, J=2.3 Hz, 1H), 8.22 (d, J=2.2 Hz, 1H), 8.15 (s, 1H), 7.99 (d, J=4.1 Hz, 1H), 4.28-4.20 (m, 1H), 2.82-2.73 (m, 1H), 2.65 (s, 2H), 2.40 (d, J=10.2 Hz, 1H), 2.15 (d, J=8.5 Hz, 1H), 2.05-1.92 (m, 2H), 1.64-1.55 (m, 1H) and 1.44-1.12 (m, 3H) ppm; LCMS RT=1.47 (M+1) 418.21.

General Scheme 27:

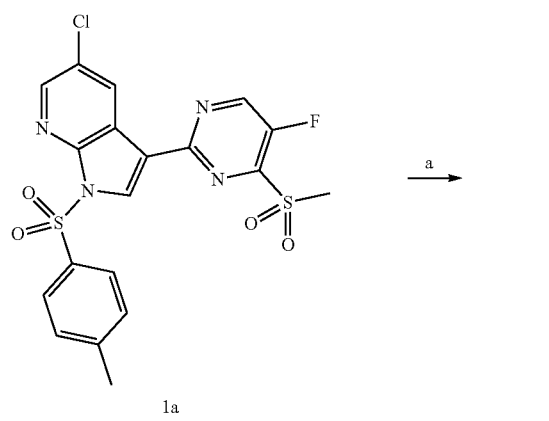

1a

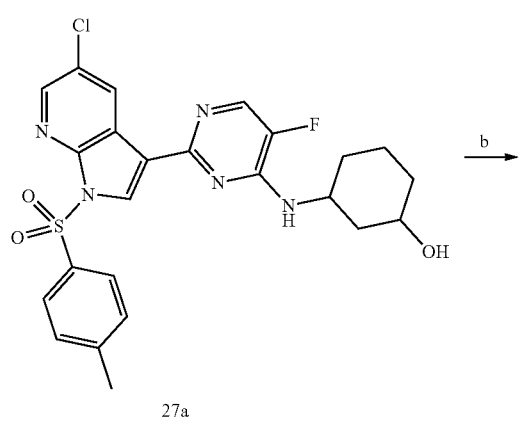

27a

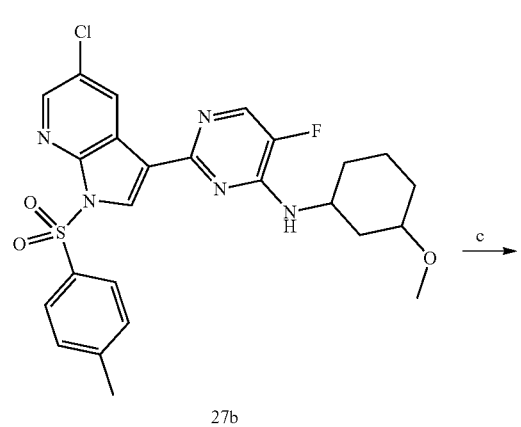

27b

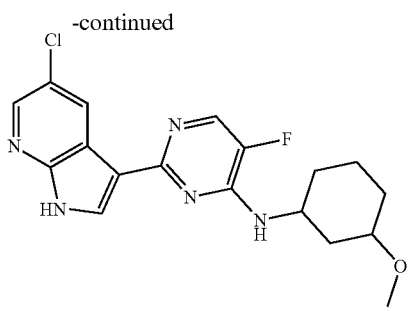

552

(a) 3-Aminocyclohexanol, ⁱPr₂NEt, THF, MW 130° C.; (b) Ag₂O, CaSO₄, CH₃I, r.t.; (c) sodium methoxide, THF.

Formation of (S)-3-((2-(5-chloro-1-tosyl-1H-pyrrolo[2,3-b]pyridin-3-yl)-5-fluoropyrimidin-4-ylamino)cyclohexanol (27a)

To a solution of 5-chloro-3-(5-fluoro-4-(methylsulfonyl)pyrimidin-2-yl)-1-tosyl-1H-pyrrolo[2,3-b]pyridine, 1a, (1.09 g, 2.34 mmol) and 3-aminocyclohexanol (0.32 g, 2.82 mmol) in THF was added DIEA (0.60 g, 4.69 mmol). The reaction mixture was heated at 130° C. in microwave for 10 min. The solvent was removed under reduced pressure and the resulting residue was purified by silica gel chromatography to afford 550 mg of the desired product, 27a.

¹H NMR (300 MHz, CDCl₃) δ 8.88 (s, 1H), 8.56 (s, 1H), 8.40 (d, J=2.4 Hz, 1H), 8.12-8.07 (m, 3H), 7.32-7.28 (m, 2H), 5.70 (m, 1H), 4.35 (m, 1H), 4.10 (m, 1H), 2.40 (s, 3H), 2.32 (d, J=12.3 Hz, 1H), 2.0-1.95 (m, 2H), 1.70-1.45 (m 4H).

Formation of 2-(5-chloro-1-tosyl-1H-pyrrolo[2,3-b]pyridin-3-yl)-5-fluoro-N-((1S)-3-methoxycyclohexyl)pyrimidin-4-amine (27b)

To a suspension of methyl iodide (0.20 g, 0.41 mmol) and 3-[[2-[5-chloro-1-(p-tolylsulfonyl)pyrrolo[2,3-b]pyridin-3-yl]-5-fluoro-pyrimidin-4-yl]amino]-cyclohexanol, 27a, (0.47 g, 2.04 mmol) was added silver oxide (0.578 g, 4.07 mmol and calcium sulfate (0.28 g, 2.04 (mmol). The reaction mixture was stirred at room temperature for 18 h. The mixture was filtered through celite and the resulting filtrate was concentrated in vacuo. The resulting crude mixture was purified by silica gel chromatography to afford 120 mg of the desired product, 27b.

¹H NMR (300 MHz, CDCl₃) δ 8.88 (s, 1H), 8.56 (s, 1H), 8.4 (d, J=2.4 Hz, 1H), 8.13-8.06 (m, 3H), 7.30 (d, J=8.7 Hz, 2H), 6.00 (s, 1H), 4.42-4.32 (m, 1H), 3.60-3.50 (m, 1H), 3.4 (s, 3H), 2.4 (s, 3H), 2.25 (dd, J=3.4, 9.7 Hz, 1H), 2.00-1.84 (m 3H), 1.75-1.60 (m, 3H), 1.60-1.50 (m, 1H).

Formation of 2-(5-chloro-1H-pyrrolo[2,3-b]pyridin-3-yl)-5-fluoro-N-((1S)-3-methoxycyclohexyl)pyrimidin-4-amine (552)

To a solution of 2-[5-chloro-1-(p-tolylsulfonyl)pyrrolo[2,3-b]pyridin-3-yl]-5-fluoro-N-(3-methoxycyclohexyl)pyrimidin-4-amine, 27b, (0.08 g, 0.15 mmol) in THF were added a few drops of NaOMe. The reaction mixture was stirred at room temperature for 20 min. To the reaction mixture was added ethyl acetate and brine. The organic phase was separated, dried (MgSO₄), filtered and concentrated in vacuo. The residue was dissolved in CH₃CN/H₂O and the mixture was purified by preparatory HPLC to afford 23 mg of the desired product, 552.

¹H NMR (300 MHz, CD₃OD) δ 8.70 (d, J=2.3 Hz, 1H), 8.45 (s, 1H), 8.35 (d, J=2.3 Hz, 1H), 8.25 (d, J=5.4 Hz, 1H), 4.35 (m, 1H), 3.52 (m, 1H), 3.4 (s, 3H), 2.53 (d, J=12.1 Hz, 1H), 2.18 (d, J=11.4 Hz, 2H), 2.05-1.95 (m, 1H), 1.65-1.4 (m, 3H), 1.38-1.25 (m, 1H); LCMS RT=2.22 min (M+1) 376.23

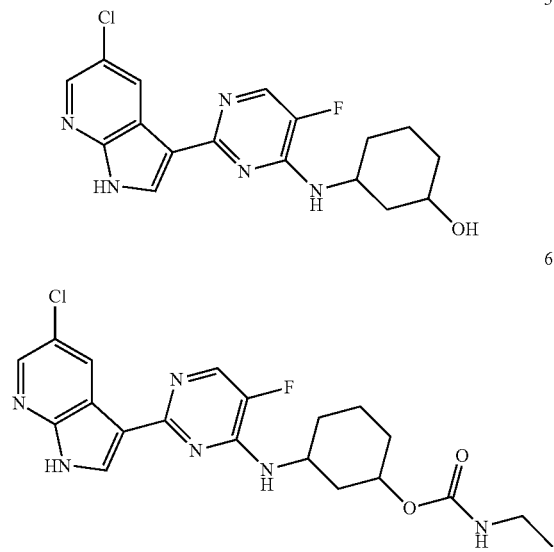

(3S)-3-((2-(5-chloro-1H-pyrrolo[2,3-b]pyridin-3-yl)-5-fluoropyrimidin-4-ylamino)cyclohexanol (524)

LCMS RT=2.0 (M+1) 362.48.

3-((2-(5-chloro-1H-pyrrolo[2,3-b]pyridin-3-yl)-5-fluoropyrimidin-4-ylamino)cyclohexyl ethylcarbamate (608)

LCMS RT=2.9 (M+1) 433.4.

General Scheme 28:

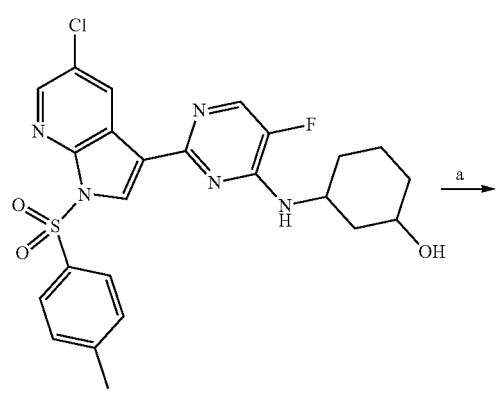

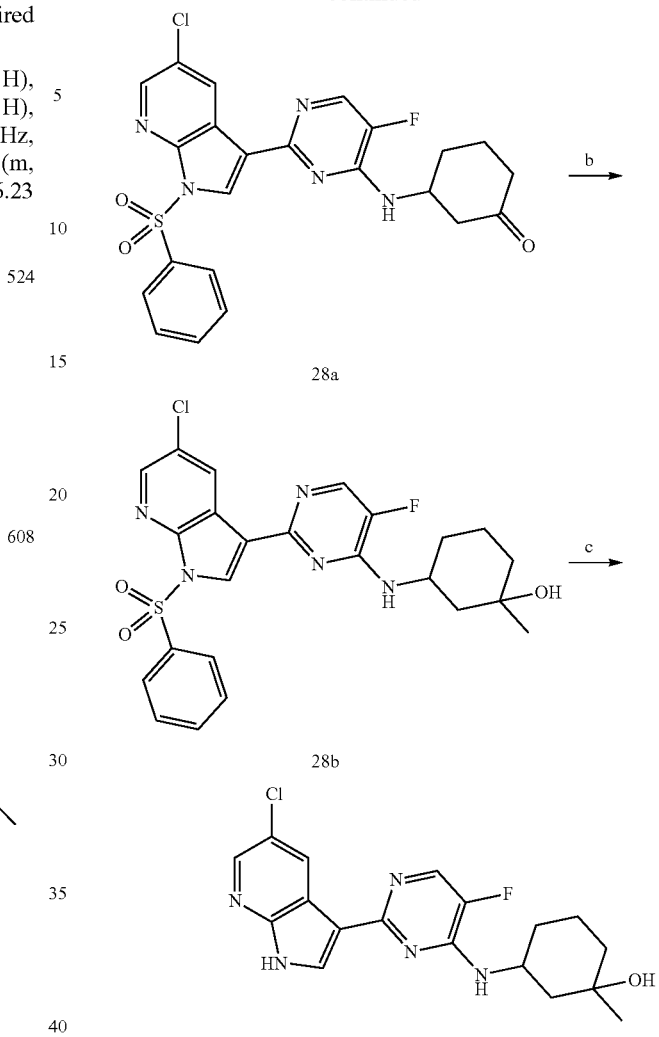

(a) Dess-Martin periodinane, CH₂Cl₂; (b) CH₃MgBr, THF; (c) sodium methoxide, THF.

Formation of 3-((2-(5-chloro-1-(phenylsulfonyl)-1H-pyrrolo[2,3-b]pyridin-3-yl)-5-fluoropyrimidin-4-ylamino)cyclohexanone(28a)

To a solution of 3-[[2-[5-chloro-1-(p-tolylsulfonyl)pyrrolo[2,3-b]pyridin-3-yl]-5-fluoro-pyrimidin-4-yl]amino]cyclohexanol, 27a, (0.54 g. 1.05 mmol) in 20 ml CH₂Cl₂ was added Dess-Martin periodinane (0.62 g, 1.47 mmol). The suspension was stirred at room temperature for 6 h. The reaction mixture was filtered through celite and the filtrate was concentrated in vacuo. The resulting residue was purified by silica gel chromatography (45% ethyl acetate/hexanes gradient) to afford 430 mg of the desired product.

¹H NMR (300 MHz, CDCl₃) δ 8.66 (d, J=2.4 Hz, 1H), 8.42 (s 1H), 8.31 (d, J=2.3 Hz, 1H), 8.05-8.02 (m, 3H), 7.24-7.19 (m, 2H), 2.99 (d, J=5.2 Hz, 1H), 4.56 (s, 1H), 2.85 (dd, J=4.7, 13.9 Hz, 1H), 2.50-2.40 (m, 3H), 2.40 (s, 3H), 1.95-1.80 (m, 2H), 1.70-1.50 (m, 2H).

Formation of 3-((2-(5-chloro-1-(phenylsulfonyl)-1H-pyrrolo[2,3-b]pyridin-3-yl)-5-fluoropyrimidin-4-ylamino)-1-methylcyclohexanol (28b)

To a cold (0° C.) solution of 3-[[2-[5-chloro-1-(p-tolylsulfonyl)pyrrolo[2,3-b]pyridin-3-yl]-5-fluoro-pyrimidin-4-yl]amino]cyclohexanone, 28a, (0.47 g, 0.92 mmol) in THF (5 mL) was added methylmagnesium bromide (3.30 ml of 1.4M solution, 4.58 mmol). The reaction mixture was stirred at 0° C. for 1 h. The reaction mixture was diluted with ethyl acetate and aqueous saturated NH$_4$Cl solution. The organic phase was separated, dried (MgSO$_4$), filtered and concentrated in vacuo. The products were purified by silica chromatography with DCM and methanol, two products were eluded with 95% DCM and 5% methanol no separation. The two diastereomers were taken on as a mixture without further purification.

LCMS (10-90% 3/5 min(grad/run) w/FA) indicated 2 peaks for the desired products. Peak 1: retention time=4.04 min (M+1: 530.42); peak 2: retention time=4.18 min (M+1: 530.45).

Formation of (3S)-3-((2-(5-chloro-1H-pyrrolo[2,3-b]pyridin-3-yl)-5-fluoropyrimidin-4-ylamino)-1-methylcyclohexanol (571 and 572)

To a solution of 3-((2-(5-chloro-1-(phenylsulfonyl)-1H-pyrrolo[2,3-b]pyridin-3-yl)-5-fluoropyrimidin-4-ylamino)-1-methylcyclohexanol, 28b, in THF was added a few drops of 25% sodium methoxide at room temperature. The reaction mixture was stirred at room temperature for 5 min. The reaction mixture was diluted with ethyl acetate and brine. The organic phase was separated, dried (MgSO$_4$), filtered and concentrated in vacuo. The product was purified by preparatory HPLC to afford two diastereomers.

Diastereomer 1-571.

$^1$H NMR (300 MHz, CD$_3$OD) δ 8.78 (d, J=2.2 Hz, 1H), 8.60 (s, 1H), 8.36 (s, 1H), 8.30 (dd, J=5.6, 9.9 Hz, 1H), 4.85 (m, 1H) 2.25-1.95 (m, 3H), 1.86-1.6 (m 4H), 1.40-1.3 (m 2H), 1.3 (s, 3H); LCMS RT 2.39 (M+1) 376.42.

Diastereomer 2-572.

$^1$H NMR (300 MHz, CD$_3$OD) 8.66 (d, J=2.1 Hz, 1H), 8.55 (d, J=2.7 Hz, 1H), 8.38 (s, 1H), 8.258 (dd, J=5.6, 9.5 Hz, 1H), 4.6 (s, 1H), 2.00-1.50 (m, 9H), 1.30 (s, 3H); LCMS RT 1.97 (M+1) 376.41.

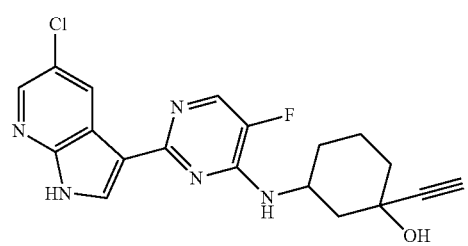

617, 618

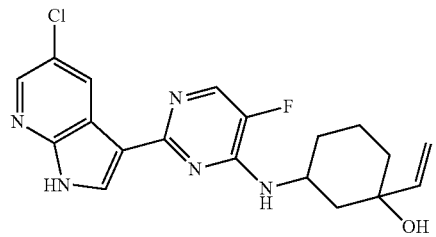

627, 628

3-((2-(5-chloro-1H-pyrrolo[2,3-b]pyridin-3-yl)-5-fluoropyrimidin-4-ylamino)-1-ethynylcyclohexanol (617 and 618)

Diastereomer 1-617: LCMS RT=3.6 (M+1) 386.4.
Diastereomer 2-618: LCMS RT=3.2 (M+1) 386.3.

3-((2-(5-chloro-1H-pyrrolo[2,3-b]pyridin-3-yl)-5-fluoropyrimidin-4-ylamino)-1-vinylcyclohexanol (627 and 628)

Diastereomer 1-627: LCMS RT=4.0 (M+1) 388.4.
Diastereomer 2-628: LCMS RT=3.7 (M+1) 388.4.

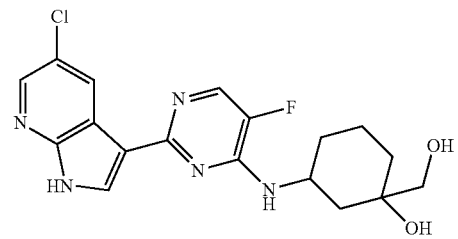

646

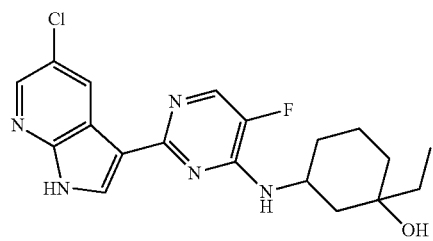

626

3-((2-(5-chloro-1H-pyrrolo[2,3-b]pyridin-3-yl)-5-fluoropyrimidin-4-ylamino)-1-(hydroxymethyl)cyclohexanol (646)

LCMS RT=3.4 (M+1) 392.4.

3-((2-(5-chloro-1H-pyrrolo[2,3-b]pyridin-3-yl)-5-fluoropyrimidin-4-ylamino)-1-ethylcyclohexanol (626)

LCMS RT=4.1 (M+1) 390.4.

General Scheme 29:

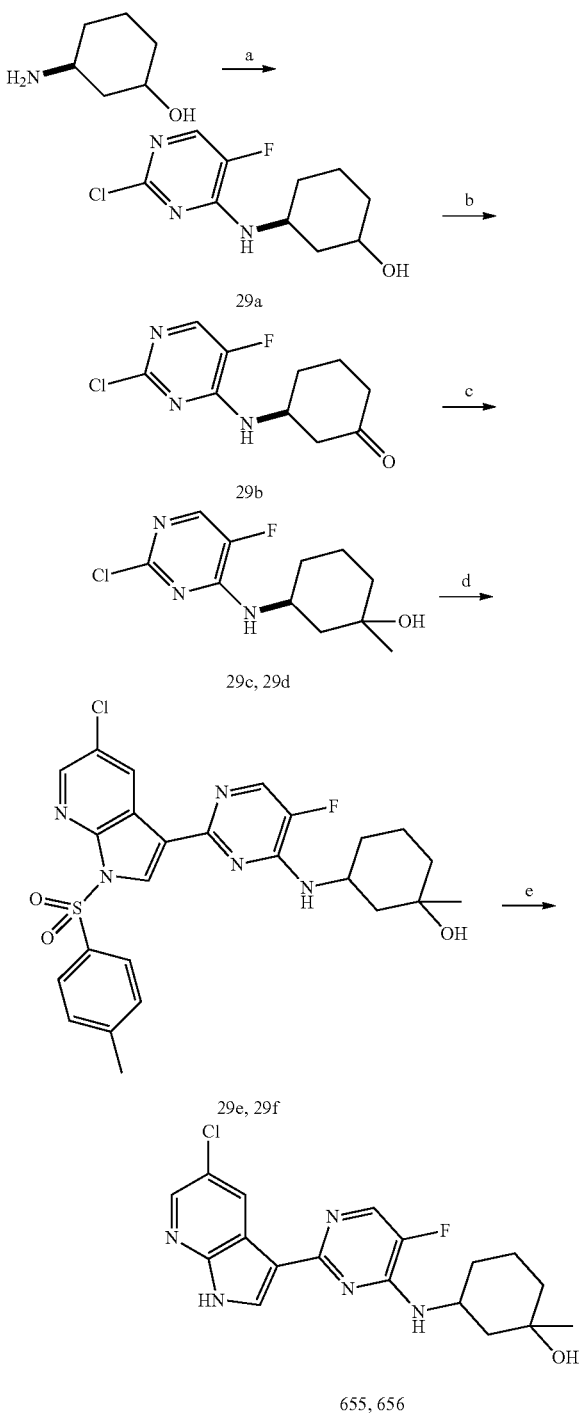

Formation of (3S)-3-(2-chloro-5-fluoropyrimidin-4-ylamino)cyclohexanol (29a)

The starting racemic alcohol, (3S)-3-aminocyclohexanol, was prepared following the procedure described by Bernardelli, P., Bladon, M., Lorthiois, E., Manage, A., Vergne, F. and Wrigglesworth, R., *Tetrahedron Asymmetry* 2004, 15, 1451-1455.

(3S)-3-(2-chloro-5-fluoropyrimidin-4-ylamino) cyclohexanol was prepared according to the procedure for compound 16a using (3S)-3-aminocyclohexanol, afforded desired product, 29a, as a solid.

Formation of (S)-3-(2-chloro-5-fluoropyrimidin-4-ylamino)cyclohexanone (29b)

To 700 ml DCM solution of 7.9 g (32.16 mmol) (3S)-3-[(2-chloro-5-fluoro-pyrimidin-4-yl)amino]cyclohexanol, 29a, (7.90 g, 32.16 mmol) in $CH_2Cl_2$ (700 mL) was added Dess-Martin reagent (17.73 g, 41.81 mmol). The reaction mixture was stirred at room temperature for 20 hours until TLC chromatography indicated reaction was complete. The reaction mixture was filtered through a pad of celite, and the resulting filtrate was washed with 200 mL of aqueous saturated $NaHCO_3$ solution and 200 mL brine. The organic phase was dried with $MgSO_4$, filtered and the solvent was removed under reduced pressure. The product was purified by silica gel chromatography (50% EtOAc/hexanes) to afford 7.3 g of the desired product, 29b (93% yield).
$^1$H NMR (300 MHz, $CD_3OD$) δ H NMR (300 MHz, $CDCl_3$) δ 7.96-7.93 (m, 1H), 7.28 (s, 1H), 5.12 (s, 1H), 4.57-4.48 (m, 1H), 2.87 (dd, J=4.8, 14.0 Hz, 1H), 2.51-2.23 (m, 4H), 2.12-2.02 (m, 1H); LCMS RT=2.97 (M+1) 244.26.

Formation of (3S)-3-(2-chloro-5-fluoropyrimidin-4-ylamino)-1-methylcyclohexanol (29c, 29d)

To a solution of (3S)-3-[(2-chloro-5-fluoro-pyrimidin-4-yl)amino]cyclohexanone (1.83 g, 7.49 mmol) in THF (100 mL) was added methylmagnesium bromide (21.4 ml of 1.4M solution, 29.96 mmol) at room temperature. The reaction mixture was stirred at room temperature for 5 minutes. To the reaction mixture was added aqueous saturated $NH_4Cl$ solution and EtOAc. The organic phase was washed with brine and dried with $MgSO_4$, filtered and concentrated in vacuo. The two spots were separated by silica gel chromatography (120 g silica gel column).
Fraction-1 (29c): $^1$H NMR (300 MHz, $CD_3OD$) δ 7.81 (d, J=2.8 Hz, 1H), 7.28 (d, J=0.5 Hz, H), 4.47 (q, J=3.8 Hz, 1H), 1.92-1.87 (m, 2H), 1.82-1.77 (m, 1H), 1.69 (dd, J=4.2, 14.0 Hz, 2H) and 1.56-1.48 (m, 4H) ppm; LCMS RT=3.43 (M+1) 260.3.
Fraction-2 (29d): $^1$H NMR (300 MHz, $CD_3OD$) δ 7.87 (d, J=2.8 Hz, H), 7.28 (s, H), 4.95 (d, J=5.0 Hz, 1H), 4.45-4.33 (m, 1H), 2.17 (s, H), 2.12-2.06 (m, 1H), 1.93-1.78 (m, 1H), 1.71 (dd, J=3.1, 5.6 Hz, 2H), 1.39-1.25 (m, 4H) and 1.19-1.05 (m, 1H) ppm; LCMS RT=3.10 (M+1) 260.29.

Formation of (3S)-3-((2-(5-chloro-1-tosyl-1H-pyrrolo[2,3-b]pyridin-3-yl)-5-fluoropyrimidin-4-ylamino)-1-methylcyclohexanol (29e, 29f)

Degassed a solution of 5-chloro-1-(p-tolylsulfonyl)-3-(4,4,5,5-tetramethyl-1,3,2-dioxaborolan-2-yl)pyrrolo[2,3-b]pyridine (1.46 g, 3.37 mmol), (3S)-3-[(2-chloro-5-fluoro-pyrimidin-4-yl)amino]-1-methyl-cyclohexanol, 29c, (0.72 g, 2.81 mmol) and $Na_2CO_3$ (4.21 mL of 2M solution, 8.433 mmol) in dimethoxyethane (15 mL) for 30 min with nitrogen. To the reaction mixture was added palladium tetrakis-triphenylphosphane (0.16 g, 0.14 mmol). The reaction mixture was heated at 130° C. in Q-tube apparatus for 45 minutes. The reaction mixture was filtered through a pad of 1 cm of silica gel and 2 cm celite. The product was purified by silica gel chromatography (hexanes/EtOAc) to afford the desired product, 29e (63% yield).

¹H NMR (300 MHz, CD₃OD) δ 8.81 (d, J=2.4 Hz, 1H), 8.50 (s, 1H), 8.38 (d, J=2.4 Hz, 1H), 8.10 (d, J=8.3 Hz, 2H), 8.04 (d, J=3.3 Hz, 1H), 7.29 (d, J=8.1 Hz, 2H), 6.85 (d, J=5.7 Hz, H), 4.58 (t, J=3.7 Hz, 1H), 2.39 (s, H), 1.98-1.93 (m, 2H), 1.86 (d, J=4.0 Hz, 2H), 1.72-1.56 (m, 5H), 1.36 (d, J=3.8 Hz, 3H) and 1.30-1.26 (m, 1H) ppm.

LCMS RT=4.62 (M+1) 530.4.

The diastereomer, 29f, was made according to the same procedure as 29e, substituting 29d as the starting material for the Suzuki coupling procedure.

¹H NMR (300 MHz, CD₃OD) δ 8.89 (d, J=2.4 Hz, 1H), 8.55 (s, 1H), 8.39 (d, J=2.4 Hz, 1H), 8.09 (t, J=8.4 Hz, 2H), 8.08 (s, 1H), 7.29 (d, J=8.2 Hz, 2H), 4.89 (d, J=6.6 Hz, 1H), 4.55 (m, 1H), 2.39 (s, 3H), 2.24 (t, J=1.8 Hz, 2H), 2.02-1.93 (m, 1H), 1.77 (t, J=3.3 Hz, 2H), 1.46-1.33 (m, 5H) and 1.29-1.15 (m, 1H) ppm.

LCMS RT=4.36 (M+1) 530.3.

Formation of (3S)-3-((2-(5-chloro-1-tosyl-1H-pyrrolo[2,3-b]pyridin-3-yl)-5-fluoropyrimidin-4-ylamino)-1-methylcyclohexanol (655, 656)

To a solution of (3S)-3-[[2-[5-chloro-1-(p-tolylsulfonyl)pyrrolo[2,3-b]pyridin-3-yl]-5-fluoro-pyrimidin-4-yl]amino]-1-methyl-cyclohexanol, 29f, (2.85 g, 5.38 mmol) in THF (200 mL) was added 1.5 ml 25% W/W sodium methoxide solution at room temperature. The reaction mixture was immediately injected into LC/MS. LC/MS indicated the reaction was complete. The reaction mixture was diluted with 200 ml EtOAc and the organic phase was washed twice with aqueous saturated NaHCO₃ and then twice with brine. The organic phase was dried with MgSO₄, filtered and concentrated in vacuo. The product was purified by silica gel chromatography (80 g silica, 5% MeOH/CH₂Cl₂) to afford 1.7 g of the desired product. The resulting product was dissolved in 70 ml THF, to it was added 1.8 ml 5M HCl/IPA. The resulting suspension was stirred for 1 hour at room temperature. The solvent was removed under reduced pressure to afford 1.7 g of the desired product, 655 as an HCl salt.

¹H NMR (300 MHz, CD₃OD) δ 9.54 (s, 1H), 8.86 (d, J=2.3 Hz, 1H), 8.31 (d, J=2.4 Hz, 1H), 8.15 (d, J=2.7 Hz, 1H), 8.04 (d, J=3.5 Hz, 1H), 7.28 (s, H), 6.66 (s, 1H), 4.62-4.59 (m, 1H), 1.96-1.88 (m, 4H), 1.81 (dd, J=4.5, 14.9 Hz, 1H) and 1.68-1.57 (m, 6H) ppm; LCMS RT=4.01 (M+1) 376.4.

The corresponding diastereomer, 656, can be prepared in the same fashion.

General Scheme 30:

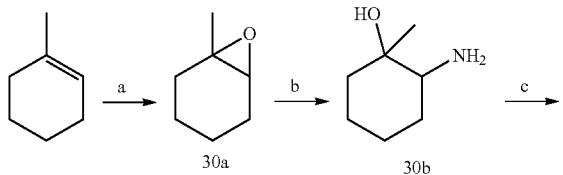

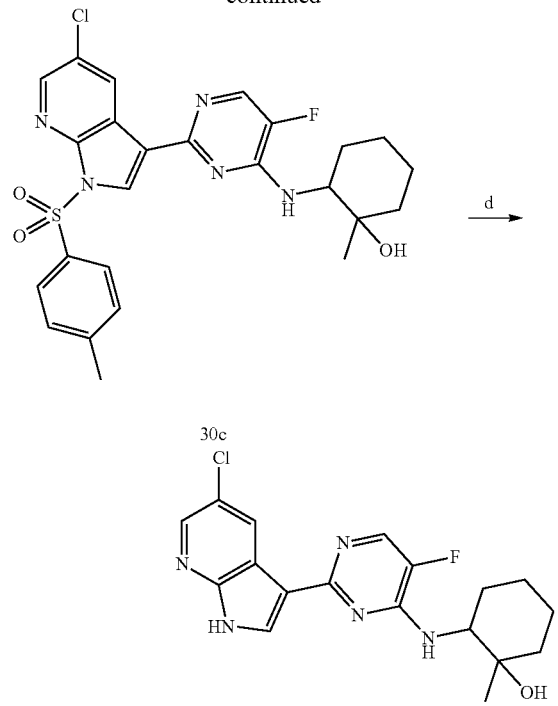

(a) mCPBA, CH₂Cl₂; (b) NH₄OH, water, 50° C., 72 h; (c) 5-chloro-3-(5-fluoro-4-(methylsulfinyl)pyrimidin-2-yl)-1-tosyl-1H-pyrrolo[2,3-b]pyridine, ᶦPr₂NEt, DMF, 90° C., 17 h; (d) 1N LiOH, THF, microwave, 120° C., 10 min.

Formation of 1-methyl-7-oxabicyclo[4.1.0]heptane (30a)

To a cold (0° C.) solution of 1-methylcyclohexene (3.0 g, 31.2 mmol) in CH₂Cl₂ (150 mL) was added mCPBA (8.4 g, 48.7 mmol). The reaction mixture was stirred at 0° C. for 1 h. The reaction mixture was diluted into aqueous saturated NaHCO₃ solution and extracted with ether. The organic phase was washed again with aqueous saturated NaHCO₃ solution, dried (MgSO₄), filtered and concentrated in vacuo to afford the desired product as an oil that was used without further purification.

Formation of 2-amino-1-methylcyclohexanol (30b)

To a solution of 1-methyl-7-oxabicyclo[4.1.0]heptane, 30a, (1.0 g, 7.1 mmol) in water was added ammonium hydroxide (6.0 mL, 154.1 mmol). The mixture was heated to 50° C. for 48 hours. The mixture was diluted with water, extracted with EtOAc and then twice with 20% MeOH/CHCl₃. The organic phases were dried (MgSO₄), filtered and concentrated in vacuo to provide the desired product, 30b, as an amorphous white solid.

¹H NMR (300.0 MHz, DMSO) δ 2.44 (dd, J=3.4, 10.8 Hz, 1H), 1.64-1.45 (m, 4H), 1.28-1.01 (m, 4H) and 0.97 (s, 3H) ppm.

Formation of 2-(2-(5-chloro-1-tosyl-1H-pyrrolo[2,3-b]pyridin-3-yl)-5-fluoropyrimidin-4-ylamino)-1-methylcyclohexanol (30c)

To a solution of 5-chloro-3-(5-fluoro-4-methylsulfinyl-pyrimidin-2-yl)-1-(p-tolylsulfonyl)pyrrolo[2,3-b]pyridine, 1a, (0.97 g, 2.09 mmol) and 2-amino-1-methylcyclohexanol, 30b, (0.40 g, 3.13 mmol) in DMF (10 mL) was added $^i$Pr$_2$NEt (0.73 mL, 4.17 mmol). The reaction mixture was heated at 90 C for 17 hours. The reaction mixture was cooled to room temperature and diluted into aqueous saturated NaCl solution. The aqueous phase was extracted twice with EtOAc. The organic phases were washed with twice with aqueous saturated NaCl solution, dried (MgSO$_4$), filtered and concentrated in vacuo. The crude residue was purified via silica gel chromatography (0-50% EtOAc/hexanes-loaded with CH$_2$Cl$_2$) to afford the desired product, 30c, as a white solid.

$^1$H NMR (300.0 MHz, DMSO) δ 9.00 (d, J=2.4 Hz, 1H), 8.49 (dd, J=2.4, 10.3 Hz, 1H), 8.42 (s, 1H), 8.23 (d, J=4.1 Hz, 1H), 8.10-8.01 (m, 2H), 7.52-7.43 (m, 2H), 7.21 (d, J=9.1 Hz, 1H), 4.52 (s, 1H), 4.28 (s, 1H), 2.35 (s, 3H), 1.78-1.50 (m, 6H), 1.34 (m, 2H) and 1.15 (s, 3H).

LCMS RT=4.1 (M+1) 530.6.

Formation of 2-(2-(5-chloro-1H-pyrrolo[2,3-b]pyridin-3-yl)-5-fluoropyrimidin-4-ylamino)-1-methylcyclohexanol (562 and 563)

To a solution of 2-[[2-[5-chloro-1-(p-tolylsulfonyl)pyrrolo[2,3-b]pyridin-3-yl]-5-fluoro-pyrimidin-4-yl]amino]-1-methyl-cyclohexanol, 30c, (0.41 g, 0.77 mmol) in THF was added 1M LiOH solution. The reaction mixture was heated in microwave at 120° C. for 5 minutes. The reaction mixture diluted with water, twice extracted with EtOAc and then twice with 10% MeOH/CH$_2$Cl$_2$. The combined organic phases were dried (MgSO$_4$), filtered and concentrated in vacuo. The crude residue was purified via silica gel chromatography (5-20% MeOH: CH$_2$Cl$_2$) to afford a white solid as a mixture of trans-enantiomers. The two trans-enantiomers were separated by chiral preparatory HPLC to afford 562 and 563.

Enantiomer 1-563: $^1$H NMR (300.0 MHz, DMSO) 812.32 (s, 1H), 8.86 (d, J=2.4 Hz, 1H), 8.28 (d, J=2.4 Hz, 1H), 8.20 (d, 1H), 8.15 (d, 1H), 6.92 (d, J=8.2 Hz, 1H), 4.56 (s, 1H), 4.31 (dd, J=5.9, 8.6 Hz, 1H), 1.89-1.35 (m, 8H) and 1.17 (s, 3H); LCMS RT=2.5 (M+1) 376.4.

General Scheme 31:

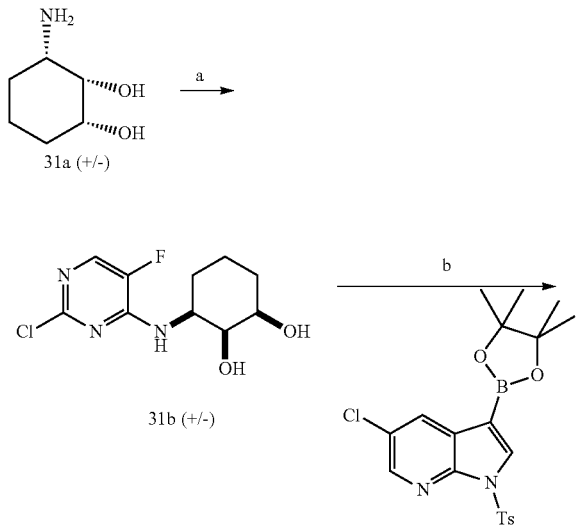

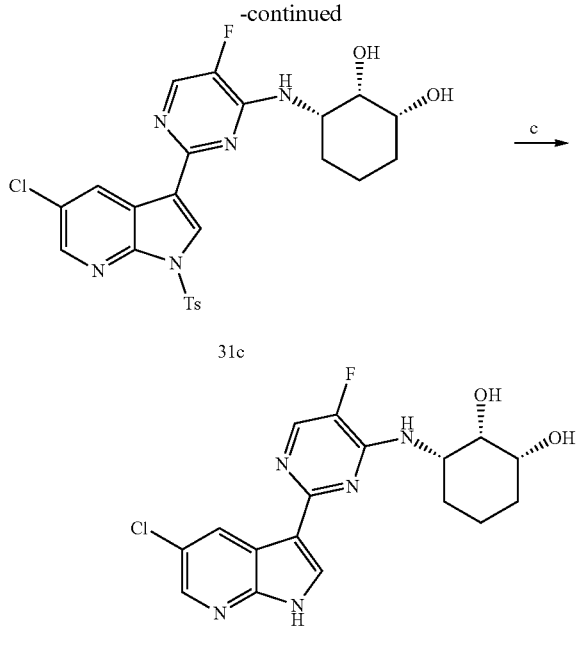

(a) 2,4-dichloro-5-fluoropyrimidine, acetonitrile/isopropanol, reflux 1.5 hrs; (b) 5-chloro-3-(4,4,5,5-tetramethyl-1,3,2-dioxaborolan-2-yl)-1-tosyl-1H-pyrrolo[2,3-b]pyridine, Pd(PPh$_3$)$_4$, 2M Na$_2$CO$_3$, acetonitrile, 120° C. microwave 15 min.; (c) TBAF, THF.

Formation of (1R,2S,3S)-3-(2-chloro-5-fluoropyrimidin-4-ylamino)cyclohexane-1,2-diol (31b)

The starting racemic diol, 31a, (1R,2S,3S)-3-aminocyclohexane-1,2-diol, was prepared following the procedure described in: Org. Bio. Chem. (2008) 6, 3751 and 3762, Davies, et. al. To a solution of racemic diol 31a (0.66 g, 5.00 mmol) in acetonitrile (5 mL) and isopropanol (5 mL) was added 2,4-dichloro-5-fluoro-pyrimidine (0.84 g, 5.03 mmol) and $^i$Pr$_2$NEt (3.25 g, 4.38 mL, 25.20 mmol). The reaction mixture was sealed and heated to 100° C. for 90 minutes and then concentrated to dryness. The crude was purified via silica gel chromatography (40%-100% EtOAc/Hex) to afford a racemate, which was further purified via chiral HPLC separation to give compound 31b (0.26 g) as a white solid.

$^1$H NMR (300 MHz, MeOH-d4) δ 7.80 (s, 1H), 4.60 (s, 6H), 4.10 (m, 1H), 3.80 (s, 1H), 3.60 (m, 1H), 3.20 (s, 1H), 3.15 (s, 2H), 1.50-1.70 (m, 5H), 1.20 (m, 1H) ppm.

LCMS RT=2.8 (M+1) 262.0, (M–1) 260.1.

Formation of (1R,2S,3S)-3-((2-(5-chloro-1-tosyl-1H-pyrrolo[2,3-b]pyridin-3-yl)-5-fluoropyrimidin-4-ylamino)cyclohexane-1,2-diol (31c)

To a deoxygenated solution of 5-chloro-1-(p-tolylsulfonyl)-3-(4,4,5,5-tetramethyl-1,3,2-dioxaborolan-2-yl)pyrrolo[2,3-b]pyridine (0.22 g, 0.51 mmol) and (1R,2S,3S)-3-(2-chloro-5-fluoropyrimidin-4-ylamino)cyclohexane-1,2-diol, 31b, (0.08 g, 0.24 mmol) in acetonitrile (6 ml) was added 2M sodium carbonate (0.45 mL of 2 M solution, 0.894 mmol) and Pd(PPh$_3$)$_4$ (34.5 mg, 0.030 mmol). The reaction was sealed and heated to 120° C. for 15 minutes in the microwave. The rxn was diluted with EtOAc and filtered thru florisil. The solution was concentrated to crude and purified via silica gel chromatography (DCM to 20% MeOH/DCM) to give compound 31c (0.11 g) as a pink solid.

LCMS RT=3.8 (M+1) 532.2, (M−1) 530.2.

Formation of (1R,2S,3S)-3-((2-(5-chloro-1H-pyrrolo[2,3-b]pyridin-3-yl)-5-fluoropyrimidin-4-ylamino)cyclohexane-1,2-diol (632)

To a solution of (1R,2S,3S)-3-((2-(5-chloro-1-tosyl-1H-pyrrolo[2,3-b]pyridin-3-yl)-5-fluoropyrimidin-4-ylamino)cyclohexane-1,2-diol, 31c, (0.11 g, 0.21 mmol) in THF was added TBAF (0.23 g, 0.84 mmol). The reaction was aged at room temperature 1 hour, quenched with 1N HCl (1 ml), and purified via reverse phase chromatography (5-70% MeCN/H$_2$O with 0.1% TFA). The product was desalted on an SPE bicarbonate cartridge, concentrated to dryness, and then triturated from MeOH to provide 18 mg of compound 632.

$^1$H NMR (300 MHz, MeOH-d4) δ 8.42 (s, 1H), 7.90 (s, 1H), 7.82 (s, 1H), 7.70 (s, 1H), 4.15 (m, 1H), 3.95 (m, 1H), 3.70 (m, 1H), 1.75 (m, 5H), 1.50 (m, 1H) ppm.

LCMS RT=3.0 (M+1) 378.2, (M−1) 376.0.

General Scheme 32:

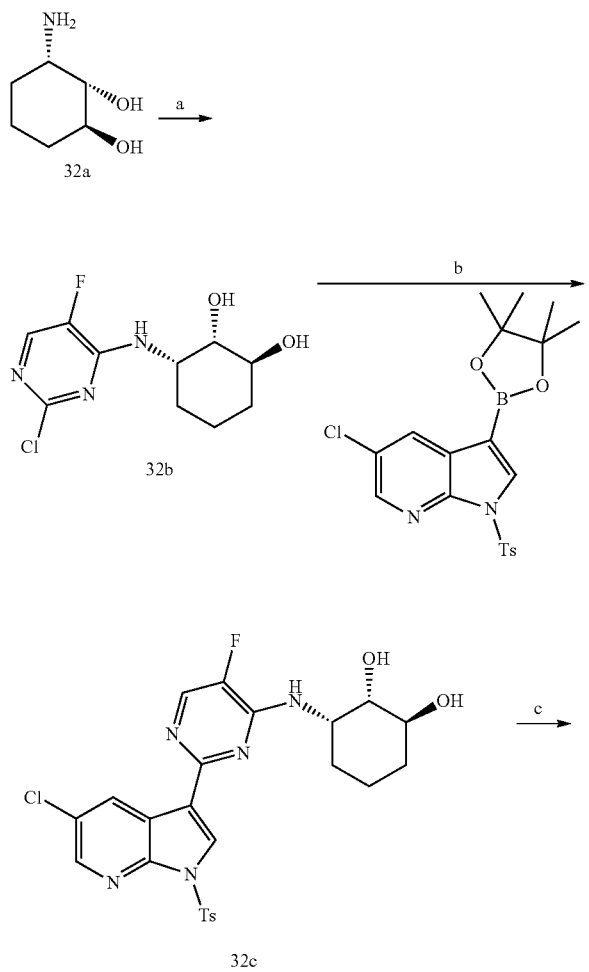

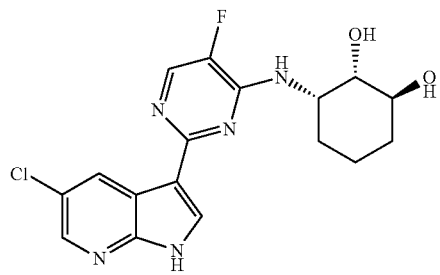

615

(a) 2,4-dichloro-5-fluoropyrimidine, acetonitrile, isopropanol, reflux 1.5 hours; (b) 5-chloro-3-(4,4,5,5-tetramethyl-1,3,2-dioxaborolan-2-yl)-1-tosyl-1H-pyrrolo[2,3-b]pyridine, Pd(PPh$_3$)$_4$, 2M Na$_2$CO$_3$, acetonitrile, 120° C. microwave, 15 min.; (c) TBAF, THF.

Formation of (1S,2S,3S)-3-(2-chloro-5-fluoropyrimidin-4-ylamino) cyclohexane-1,2-diol (32b)

The starting racemic diol, 32a, (1S,2S,3S)-3-aminocyclohexane-1,2-diol, was prepared following the procedure described in: Org. Bio. Chem. (2008) 6, 3751 and 3762, Davies, et. al.

According to the method for compound 632, except use the racemate of diol 32a (0.07 g, 0.53 mmol), to give compound 32b (0.03 g, 0.11 mmol) as a white solid.

$^1$H NMR (300 MHz, MeOH-d4) δ 7.90 (s, 1H), 4.45 (m, 1H), 3.80 (s, 1H), 3.62 (s, 1H), 1.40-1.80 (m, 6H), 0.85 (m, 1H) ppm.

LCMS RT=2.7 (M+1) 262.0.

Formation of (1S,2S,3S)-3-((2-(5-chloro-1-tosyl-1H-pyrrolo[2,3-b]pyridin-3-yl)-5-fluoropyrimidin-4-ylamino)cyclohexane-1,2-diol (32c)

According to the method for compound 31c, except use compound 32b (0.03 g, 0.11 mmol), to give compound 32c (0.06 g, 0.11 mmol).

LCMS RT=3.9 (M+1) 532.2, (M−1) 530.3.

Formation of (1S,2S,3S)-3-((2-(5-chloro-1H-pyrrolo[2,3-b]pyridin-3-yl)-5-fluoropyrimidin-4-ylamino)cyclohexane-1,2-diol (615)

According to the method for compound 624, except use compound 32c (0.06 g, 0.11 mmol) to give compound 615 (0.015 g, 0.035 mmol) as a white solid.

$^1$H NMR (300 MHz, MeOH-d4) δ 8.83 (s, 1H), 8.51 (s, 1H), 8.40 (s, 1H), 8.30 (s, 1H), 4.00 (bs, 2H), 0.60-0.90 (m, 4H), 0.50 (m, 2H) ppm.

LCMS RT=3.7 (M+1) 378.3, (M−1) 376.3.

General Scheme 33:

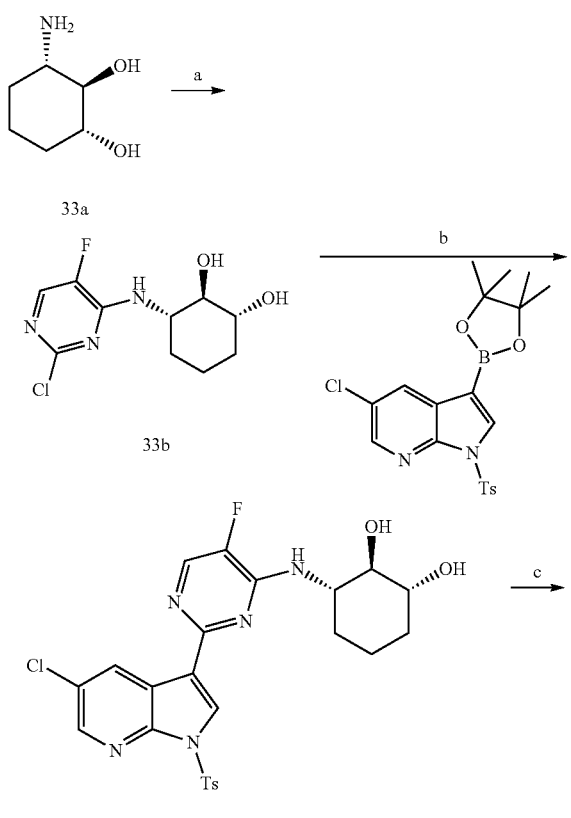

(a) 2,4-dichloro-5-fluoropyrimidine, acetonitrile, isopropanol, reflux 1.5 hours; (b) 5-chloro-3-(4,4,5,5-tetramethyl-1,3,2-dioxaborolan-2-yl)-1-tosyl-1H-pyrrolo[2,3-b]pyridine, Pd(PPh₃)₄, 2M Na₂CO₃, acetonitrile, 120° C. microwave, 15 min.; (c) TBAF, THF.

Formation of (1R,2R,3S)-3-(2-chloro-5-fluoropyrimidin-4-ylamino) cyclohexane-1,2-diol (33b)

The starting racemic diol, 33a, (1R,2R,3S)-3-aminocyclohexane-1,2-diol, was prepared following the procedure described in: Org. Lett. (2009) 6, 1333, Davies, et. al. According to the method for compound 632, except use the racemate of diol 33a (0.13 g, 1.01 mmol) to give compound 33b (0.14 g, 0.53 mmol) as a white solid.

$^1$H NMR (300 MHz, MeOH-d4) δ 7.90 (s, 1H), 4.05 (m, 2H), 3.70-3.80 (m, 0.6H), 1.95 (bs, 2.5H), 1.70 (m, 1.6H), 1.30-1.60 (m, 5.4H) ppm; $^{13}$C-APT NMR (300 MHz, MeOH-d4) δ 148.6, 145.2, 140.0, 139.8, 78.9, 75.2, 55.4, 49.15 (m, MeOH-d4), 33.9, 31.9, 22.4 ppm.

LCMS RT=2.4 (M+1) 262.0, (M−1) 260.1.

Formation of (1R,2R,3S)-3-((2-(5-chloro-1-tosyl-1H-pyrrolo[2,3-b]pyridin-3-yl)-5-fluoropyrimidin-4-ylamino)cyclohexane-1,2-diol (33c)

According to the method for compound 31c, except use compound 33b (0.07 g, 0.26 mmol) to give compound 33c (0.008 g, 0.015 mmol). DME was used as solvent, not acetonitrile. LCMS RT=4.2 (M+1) 532.3, (M−1) 530.3.

Formation of (1R,2R,3S)-3-((2-(5-chloro-1H-pyrrolo[2,3-b]pyridin-3-yl)-5-fluoropyrimidin-4-ylamino) cyclohexane-1,2-diol (625)

According to the method for compound 624, except use compound 33c (0.008 g, 0.015 mmol to give compound 625 (0.005 g, 0.012 mmol).

$^1$H NMR (300 MHz, MeOH-d4) δ 8.80 (s, 1H), 8.48 (s, 1H), 8.40 (s, 1H), 8.20 (s, 1H), 4.5 (m, 1H), 3.55 (m, 2H), 2.12 (m, 2H), 1.95 (m, 1H), 1.61 (m, 2H), 1.58 (m, 1H) ppm.

LCMS RT=2.4 (M+1) 378.2, (M−1) 376.2.

The following compounds, 631, 616 and 624, are enantiomers of 632, 615 and 625 and can be prepared by isolation from chiral preparatory HPLC chromatography from their respective enantiomeric mixtures.

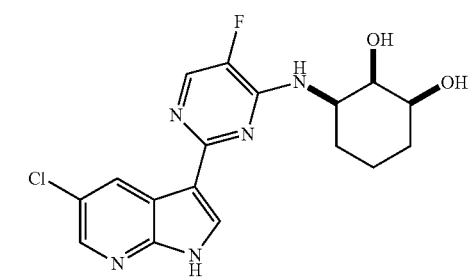

631

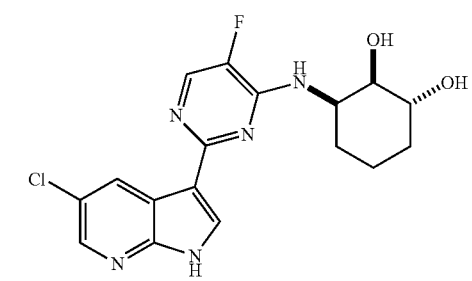

616

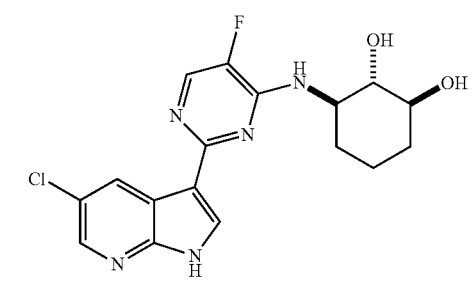

624

General scheme 35:

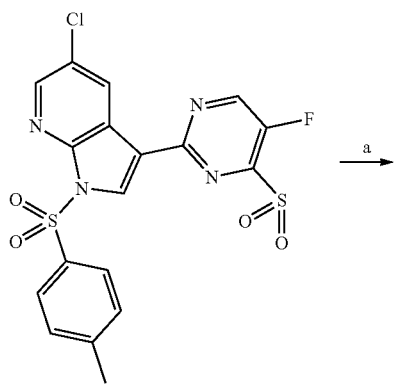

1a

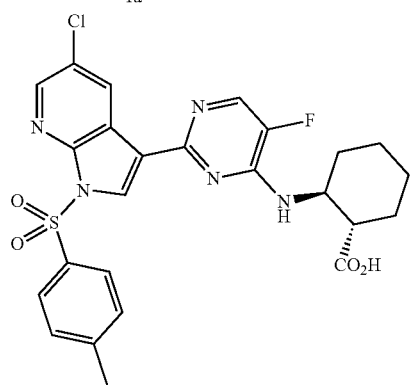

35a

553

(a) (1S,2S)-2-aminocyclohexanecarboxylic acid, $^{i}Pr_2NEt$, $Na_2CO_3$, THF—$CH_3CN$ (3:1), 135° C. microwave; (b) 1N LiOH, THF, microwave, 120° C.; (c) 4NHCl-dioxane, EtOH, 70° C.

Formation of (1s, 2S)-2-(2-(5-chloro-1H-pyrrolo[2,3-b]pyridin-3-yl)-5-fluoropyrimidin-4-ylamino)cyclohexanecarboxylic acid (553)

A mixture of 5-chloro-3-(5-fluoro-4-methylsulfonyl-pyrimidin-2-yl)-1-(p-tolylsulfonyl)pyrrolo[2,3-b]pyridine, 1a, (0.49 g, 1.05 mmol), (1S,2S)-2-amino-cyclohexanecarboxylic acid (0.30 g, 2.10 mmol), freshly ground $Na_2CO_3$ (0.22 g, 2.10 mmol), and $^{i}Pr_2NEt$ (0.37 mL, 2.10 mmol) in THF (10 mL) and $CH_3CN$ (2 mL) were heated in a sealed vessel to 130° C. for 30 minutes under microwave irradiation. The mixture was cooled to room temperature. A solution of 1N LiOH (3.1 mL, 3.1 mmol) was added and the mixture was stirred at 120° C. for 10 minutes under microwave irradiation. The mixture was acidified with 1N HCl until pH 2 under vigorous stirring. The newly formed solid was collected by vacuum filtration. The solid was washed with small amounts of water and EtOAc. The solid was dried in vacuo to provide the desired product.

$^1$H NMR (300 MHz, MeOD) δ 8.89 (d, J=2.4 Hz, 1H), 8.44 (s, 1H), 8.38 (d, J=2.3 Hz, 1H), 8.29 (d, J=5.6 Hz, 1H), 4.75 (m, 1H), 2.75-2.66 (m, 1H), 2.25-2.16 (m, 2H), 1.99-1.89 (m, 2H), 1.71-1.29 (m, 4H) ppm; LCMS RT=2.0 min, (M+H) 390.4.

Other analogs that can be prepared in the same manner as 553 are described below:

541

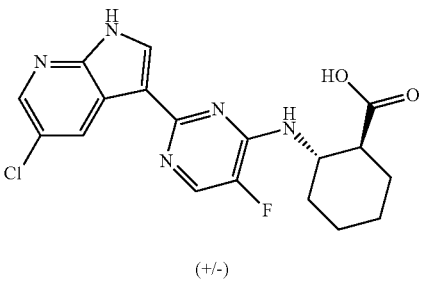

(+/-)

Trans-2-(2-(5-chloro-1H-pyrrolo[2,3-b]pyridin-3-yl)-5-fluoropyrimidin-4-ylamino)cyclohexanecarboxylic acid (541)

LCMS RT=2.4 min, (M+H) 390.5.

554

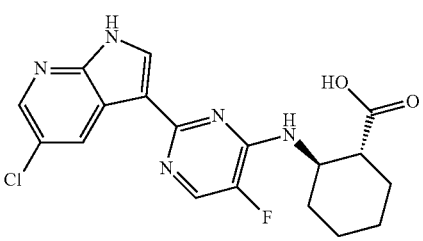

(+/-)

559

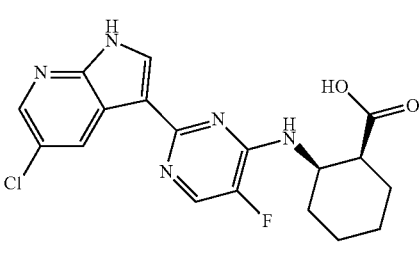

(+/-)

(1R,2R)-2-(2-(5-chloro-1H-pyrrolo[2,3-b]pyridin-3-yl)-5-fluoropyrimidin-4-ylamino)cyclohexanecarboxylic acid (554)

$^1$H NMR (300 MHz, MeOD) δ 8.89 (d, J=2.4 Hz, 1H), 8.44 (s, 1H), 8.38 (d, J=2.4 Hz, 1H), 8.29 (d, J=5.6 Hz, 1H), 4.77

(m, 1H), 2.75-2.66 (m, 1H), 2.24-2.17 (m, 2H), 1.94-1.89 (m, 2H) and 1.74-1.36 (m, 4H) ppm.

LCMS RT=2.3 min, (M+H) 390.4.

Cis-2-(2-(5-chloro-1H-pyrrolo[2,3-b]pyridin-3-yl)-5-fluoropyrimidin-4-ylamino)cyclohexanecarboxylic acid (559)

$^1$H NMR (300 MHz, MeOD) δ 8.75 (d, J=2.4 Hz, 1H), 8.38-8.35 (m, 2H), 8.24 (d, J=5.1 Hz, 1H), 4.70-4.62 (m, 1H), 3.25-3.17 (m, 1H), 2.32 (m, 1H), 2.14-1.80 (m, 4H) and 1.68-1.54 (m, 3H) ppm.

LCMS RT=2.3 min, (M+H) 389.8.

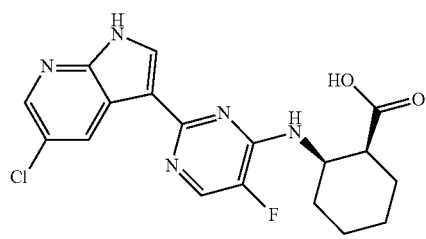

(1S,2R)-2-(2-(5-chloro-1H-pyrrolo[2,3-b]pyridin-3-yl)-5-fluoropyrimidin-4-ylamino)cyclohexanecarboxylic acid (579)

$^1$H NMR (300 MHz, d6-DMSO) δ 12.52 (s, 1H), 8.68 (d, J=2.3 Hz, 1H), 8.33 (d, J=2.5 Hz, 2H), 8.30 (d, J=4.4 Hz, 1H), 7.57 (s, 1H), 4.53 (m, 1H), 3.05 (m, 1H), 2.15-2.07 (m, 1H), 1.96 (m, 1H), 1.81-1.76 (m, 3H) and 1.51 (m, 3H) ppm.

LCMS RT=2.9 min, (M+H) 390.4.

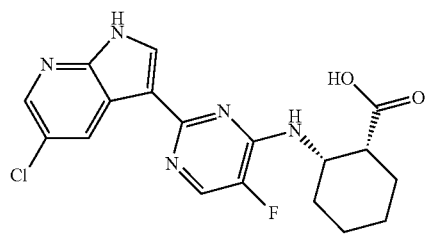

(1R,2S)-2-(2-(5-chloro-1H-pyrrolo[2,3-b]pyridin-3-yl)-5-fluoropyrimidin-4-ylamino)cyclohexanecarboxylic acid (578)

1H NMR (300 MHz, d6-DMSO) δ 12.51 (s, 1H), 8.68 (d, J=2.3 Hz, 1H), 8.33 (d, J=2.3 Hz, 2H), 8.29 (d, J=4.3 Hz, 1H), 7.55 (s, 1H), 4.53 (s, 1H), 3.05 (m, 1H), 2.13 (m, 1H), 1.96 (m, 1H), 1.79 (m, 3H) and 1.51 (m, 3H) ppm.

LCMS RT=2.8 min, (M+H) 390.4.

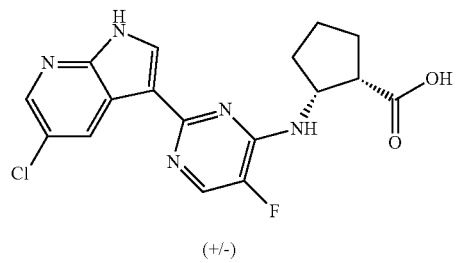

558

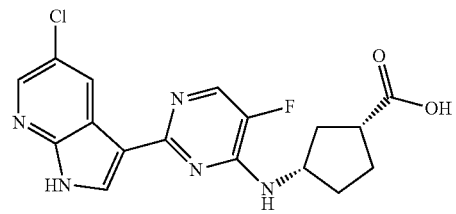

566
(+/-)

Cis-2-(2-(5-chloro-1H-pyrrolo[2,3-b]pyridin-3-yl)-5-fluoropyrimidin-4-ylamino)cyclopentanecarboxylic acid (558)

$^1$H NMR (300 MHz, MeOD) δ 8.78 (d, J=2.4 Hz, 1H), 8.38 (s, 1H), 8.33 (d, J=2.2 Hz, 1H), 8.25 (d, J=5.2 Hz, 1H), 4.98 (dd, J=7.2 Hz, 1H), 2.27-2.03 (m, 5H) and 1.86-1.76 (m, 1H) ppm.

LCMS RT=2.5 min, (M+H) 376.2.

(1R,3S)-3-((2-(5-chloro-1H-pyrrolo[2,3-b]pyridin-3-yl)-5-fluoropyrimidin-4-ylamino)cyclopentanecarboxylic acid (566)

$^1$H NMR (300 MHz, d6-DMSO) δ 12.42 (s, 1H), 8.72 (d, J=2.2 Hz, 1H), 8.29 (m, 2H), 8.22 (d, J=4.1 Hz, 1H), 7.87 (s, 1H), 4.56-4.49 (m, 1H), 2.87 (dd, J=8.4, 25.0 Hz, 1H), 2.87 (s, 1H), 2.42-2.33 (m, 1H), 2.15-2.04 (m, 1H), 2.00-1.85 (m, 3H) and 1.81-1.70 (m, 1H) ppm.

LCMS RT=2.3 min, (M+H) 376.4.

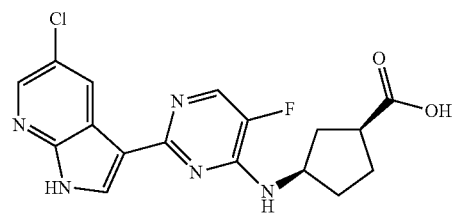

565

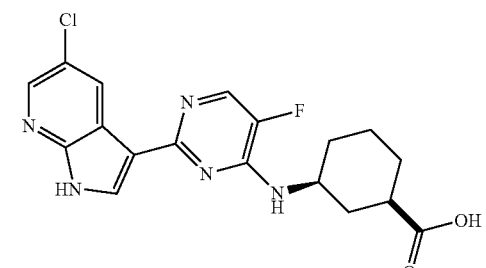

630

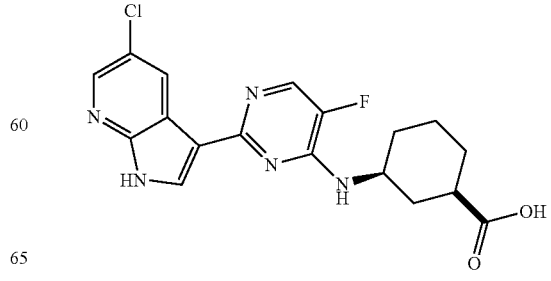

(1S,3R)-3-((2-(5-chloro-1H-pyrrolo[2,3-b]pyridin-3-yl)-5-fluoropyrimidin-4-ylamino)cyclopentanecarboxylic acid (565)

¹H NMR (300 MHz, d6-DMSO) δ 12.48 (s, 1H), 8.71 (d, J=2.3 Hz, 1H), 8.35-8.31 (m, 2H), 8.26 (d, J=4.3 Hz, 2H), 8.02 (s, 1H), 4.57-4.44 (m, 1H), 2.87 (qn, J=8.3 Hz, 1H), 2.39-2.32 (m, 1H), 2.15-2.05 (m, 1H), 2.00-1.86 (m, 3H) and 1.82-1.70 (m, 1H) ppm.
LCMS RT=2.4 min, (M+H) 376.4.

(1R,3S)-3-((2-(5-chloro-1H-pyrrolo[2,3-b]pyridin-3-yl)-5-fluoropyrimidin-4-ylamino)cyclohexanecarboxylic acid (630)

Compound 630 was prepared in same fashion from intermediate 18c, by removal of Cbz-protecting group and reaction with intermediate 1a, followed by removal of tosyl protecting group.
LCMS RT=3.2 min, (M+H) 390.4, (M−H) 388.1.

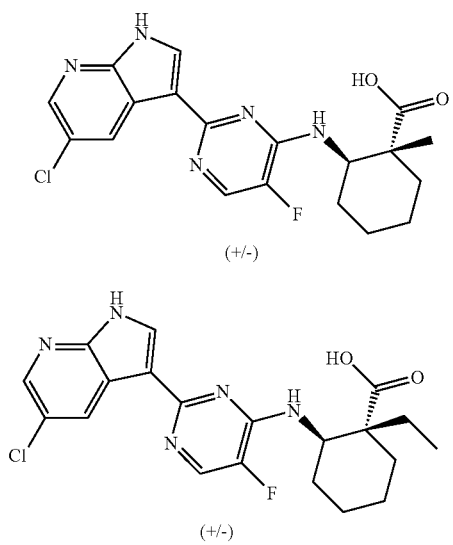

582

585, 586

Trans-2-(2-(5-chloro-1H-pyrrolo[2,3-b]pyridin-3-yl)-5-fluoropyrimidin-4-ylamino)-1-methylcyclohexanecarboxylic acid (582)

¹H NMR (300.0 MHz, d6-DMSO) δ 12.46 (s, 1H), 8.72 (d, J=2.4 Hz, 1H), 8.32-8.28 (m, 3H), 7.10 (d, J=7.1 Hz, 1H), 4.27-4.20 (m, 1H), 2.26 (d, J=10.1 Hz, 1H), 1.93 (m, 1H), 1.83 (m, 1H), 1.68-1.59 (m, 3H), 1.36 (m, 2H) and 1.24 (s, 3H) ppm.
LCMS RT=3.2 min, (M+H) 404.4.

Racemic trans-2-(2-(5-chloro-1H-pyrrolo[2,3-b]pyridin-3-yl)-5-fluoropyrimidin-4-ylamino)-1-ethylcyclohexanecarboxylic acid (586)

¹H NMR (300 MHz, MeOD) δ 8.93 (s, 1H), 8.85 (m, 2H), 8.93-8.87 (m, 1H), 8.31 (dd, J=4.5, 1.2 Hz, 2H), 8.31 (dd, J=4.5, 1.2 Hz, 2H), 8.30 (d, J=2.3 Hz, 1H), 8.19 (d, J=5.0 Hz, 1H), 5.26-5.20 (m, 1H), 3.37 (dd, J=3.3 Hz, 1.6, 2H), 3.33 (ddt, J=6.6, 3.3, 1.6 Hz, 118H), 2.11 (dd, J=8.0, 5.8 Hz, 2H), 1.80 (tdd, J=21.2, 18.9, 11.6 Hz, 8H), 1.63-1.54 (m, 3H), 0.86 (q, J=7.4 Hz, 4H) ppm.
LCMS RT=2.9 min, (M+H) 418.4.

Racemic cis-2-(2-(5-chloro-1H-pyrrolo[2,3-b]pyridin-3-yl)-5-fluoropyrimidin-4-ylamino)-1-ethylcyclohexanecarboxylic acid (585)

¹H NMR (300 MHz, MeOD) δ 8.80-8.76 (m, 1H), 8.37 (s, 1H), 8.35 (d, J=2.3 Hz, 1H), 8.27-8.23 (m, 1H), 4.49-4.42 (m, 1H), 2.43-2.34 (m, 1H), 2.09 (d, J=6.2 Hz, 1H), 1.98-1.36 (m, 12H), 0.94 (dd, J=11.3, 3.8 Hz, 3H) ppm.
LCMS RT=3.2 min, (M+H) 418.4.

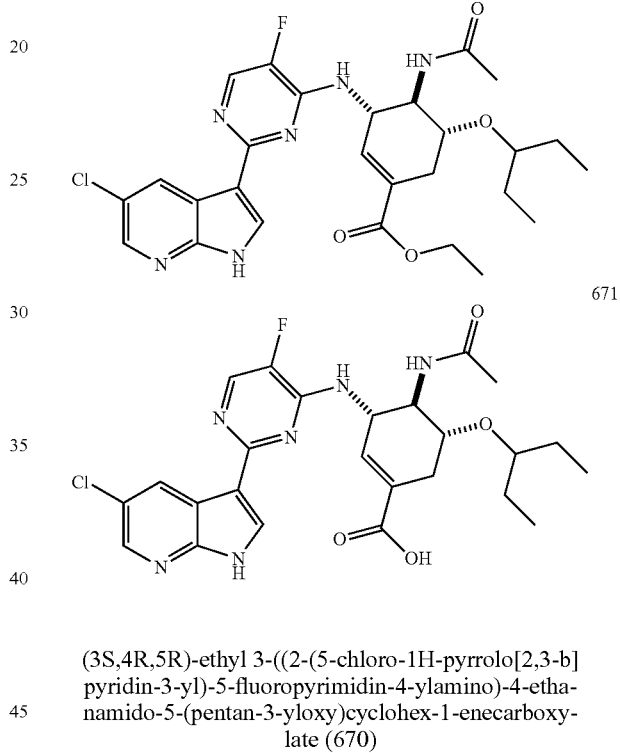

670

671

(3S,4R,5R)-ethyl 3-((2-(5-chloro-1H-pyrrolo[2,3-b]pyridin-3-yl)-5-fluoropyrimidin-4-ylamino)-4-ethanamido-5-(pentan-3-yloxy)cyclohex-1-enecarboxylate (670)

¹H NMR (300.0 MHz, MeOD) d 8.64 (d, J=2.3 Hz, 1H), 8.40 (s, 1H), 8.32 (d, J=2.3 Hz, 1H), 8.29 (d, J=5.0 Hz, 1H), 6.96 (m, 1H), 4.84-4.80 (m, 1H), 4.34 (m, 1H), 4.29-4.19 (m, 3H), 3.54-3.47 (m, 1H), 3.15-3.07 (m, 1H), 2.68-2.58 (m, 1H), 1.92 (s, 3H), 1.59-1.51 (m, 4H), 1.26 (t, J=7.1 Hz, 3H), 0.95 (t, J=7.4 Hz, 3H) and 0.89 (t, J=7.4 Hz, 3H) ppm
LCMS RT=3.6 (M+1) 559.4.

(3S,4R,5R)-3-((2-(5-chloro-1H-pyrrolo[2, 3-6]pyridin-3-yl)-5-fluoro pyrimidin-4-ylamino)-4-ethanamido-5-(pentan-3-yloxy)cyclohex-1-enecarboxylic acid (671)

¹H NMR (300.0 MHz, MeOD) d 8.66 (d, J=2.3 Hz, 1H), 8.39 (s, 1H), 8.32 (d, J=2.3 Hz, 1H), 8.29 (d, J=5.0 Hz, 1H), 6.97 (m, 1H), 4.82-4.79 (m, 1H), 4.34 (m, 1H), 4.25 (dd, J=7.6, 10.1 Hz, 1H), 3.54-3.47 (m, 2H), 3.11-3.04 (m, 1H), 2.65-2.57 (m, 1H), 1.91 (s, 3H), 1.59 (m, 4H), 0.95 (t, J=7.4 Hz, 3H) and 0.89 (t, J=7.4 Hz, 3H) ppm
LCMS RT=3.1 (M+1) 531.4.

General Scheme 36:

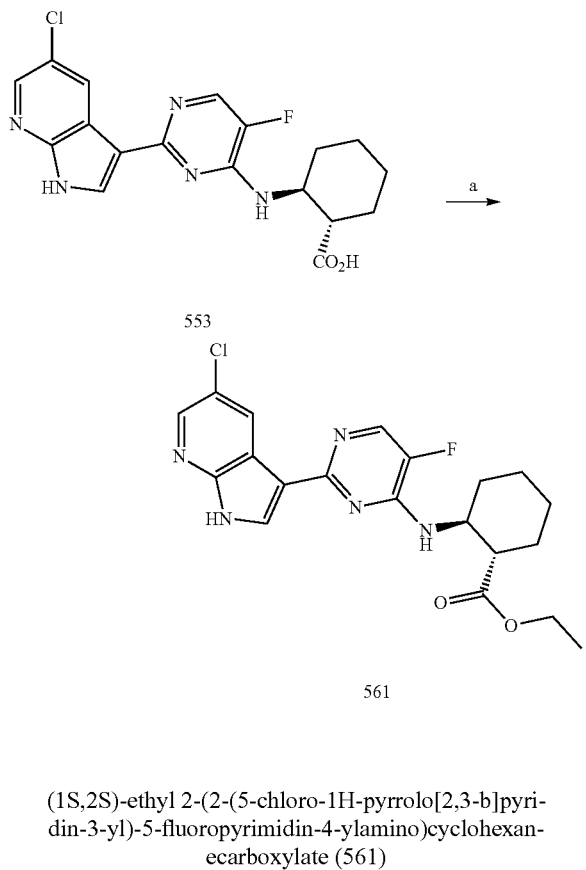

(1S,2S)-ethyl 2-(2-(5-chloro-1H-pyrrolo[2,3-b]pyridin-3-yl)-5-fluoropyrimidin-4-ylamino)cyclohexanecarboxylate (561)

To a mixed slurry of (1S, 2S)-2-[[2-(5-chloro-1H-pyrrolo[5,4-b]pyridin-3-yl)-5-fluoro-pyrimidin-4-yl]amino]cyclohexane-1-carboxylic acid, 553, (0.090 g, 0.231 mmol), in ethanol (1.5 mL) at room temperature was added HCl (0.577 mL of 4 M solution, 2.309 mmol). The solution was warmed to 50° C. After 6 hours, the mixture was basified with 1N NaOH, brine was added and the aqueous layer was and extracted repeatedly with EtOAc. The organic layer was dried over MgSO$_4$, and filtered through a short plug of silica gel and concentrated in vacuo to provide the desired product.

$^1$H NMR (300 MHz, MeOD) δ 8.95 (s, 1H), 8.19 (m, 2H), 7.99 (s, 1H), 4.61 (m, 1H), 3.93 (m, 2H), 2.61 (m, 1H), 2.17-2.05 (m, 2H), 1.89-1.32 (m, 7H) and 1.00 (m, 3H) ppm.

LCMS RT=2.7 min, (M+H) 418.4.

The following compounds can also be prepared in a manner similar to the one described in Scheme 36.

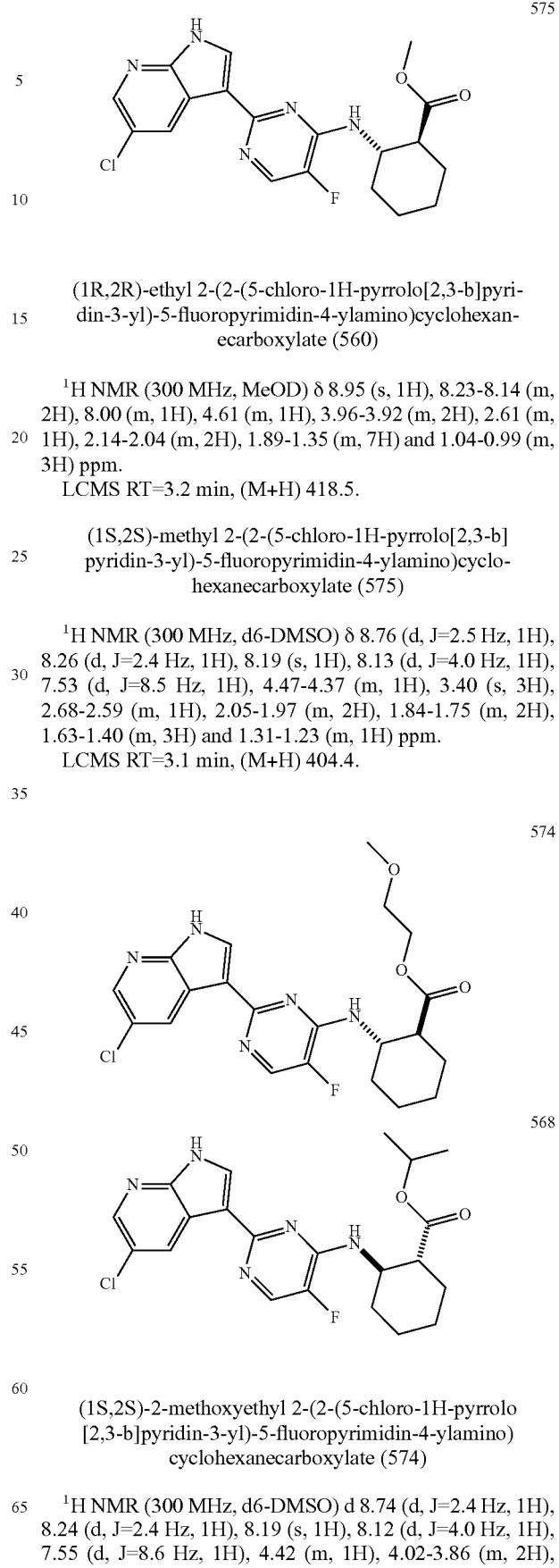

(1R,2R)-ethyl 2-(2-(5-chloro-1H-pyrrolo[2,3-b]pyridin-3-yl)-5-fluoropyrimidin-4-ylamino)cyclohexanecarboxylate (560)

$^1$H NMR (300 MHz, MeOD) δ 8.95 (s, 1H), 8.23-8.14 (m, 2H), 8.00 (m, 1H), 4.61 (m, 1H), 3.96-3.92 (m, 2H), 2.61 (m, 1H), 2.14-2.04 (m, 2H), 1.89-1.35 (m, 7H) and 1.04-0.99 (m, 3H) ppm.

LCMS RT=3.2 min, (M+H) 418.5.

(1S,2S)-methyl 2-(2-(5-chloro-1H-pyrrolo[2,3-b]pyridin-3-yl)-5-fluoropyrimidin-4-ylamino)cyclohexanecarboxylate (575)

$^1$H NMR (300 MHz, d6-DMSO) δ 8.76 (d, J=2.5 Hz, 1H), 8.26 (d, J=2.4 Hz, 1H), 8.19 (s, 1H), 8.13 (d, J=4.0 Hz, 1H), 7.53 (d, J=8.5 Hz, 1H), 4.47-4.37 (m, 1H), 3.40 (s, 3H), 2.68-2.59 (m, 1H), 2.05-1.97 (m, 2H), 1.84-1.75 (m, 2H), 1.63-1.40 (m, 3H) and 1.31-1.23 (m, 1H) ppm.

LCMS RT=3.1 min, (M+H) 404.4.

(1S,2S)-2-methoxyethyl 2-(2-(5-chloro-1H-pyrrolo[2,3-b]pyridin-3-yl)-5-fluoropyrimidin-4-ylamino)cyclohexanecarboxylate (574)

$^1$H NMR (300 MHz, d6-DMSO) δ 8.74 (d, J=2.4 Hz, 1H), 8.24 (d, J=2.4 Hz, 1H), 8.19 (s, 1H), 8.12 (d, J=4.0 Hz, 1H), 7.55 (d, J=8.6 Hz, 1H), 4.42 (m, 1H), 4.02-3.86 (m, 2H), 3.35-3.23 (m, 2H), 3.08 (s, 3H), 2.69-2.60 (m, 1H), 1.99 (m, 2H), 1.77 (m, 2H), 1.62-1.40 (m, 3H) and 1.27 (m, 1H) ppm. LCMS RT=3.0 min, (M+H) 448.4.

(1R,2R)-isopropyl 2-(2-(5-chloro-1H-pyrrolo[2,3-b]pyridin-3-yl)-5-fluoropyrimidin-4-ylamino)cyclohexanecarboxylate (568)

$^1$H NMR (300 MHz, d6-DMSO) δ 8.80 (d, J=2.5 Hz, 1H), 8.27 (d, J=2.4 Hz, 1H), 8.19 (s, 1H), 8.13 (d, J=4.0 Hz, 1H), 7.60 (d, J=8.6 Hz, 1H), 4.72 (qn, J=6.2 Hz, 1H), 4.55-4.48 (m, 1H), 2.61-2.54 (m, 1H), 1.96 (m, 2H), 1.77 (m, 2H), 1.63-1.41 (m, 3H), 1.30-1.23 (m, 1H) and 0.93 (d, J=6.2 Hz, 6H) ppm. LCMS RT=3.08 min, (M+H) 432.46.

569

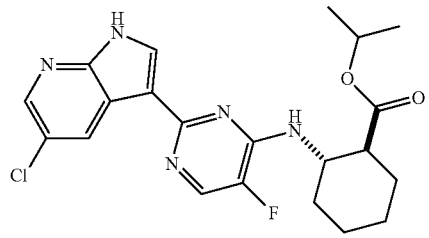

(1S,2S)-isopropyl 2-(2-(5-chloro-1H-pyrrolo[2,3-b]pyridin-3-yl)-5-fluoropyrimidin-4-ylamino)cyclohexanecarboxylate (569)

$^1$H NMR (300 MHz, d6-DMSO) δ 12.57 (s, 1H), 8.80 (d, J=2.4 Hz, 1H), 8.36-8.28 (m, 4H), 4.75 (td, J=12.5, 6.2 Hz, 1H), 4.52 (m, 1H), 2.65-2.56 (m, 1H), 2.00 (m, 2H), 1.83-1.76 (m, 2H), 1.57-1.42 (m, 3H), 1.32-1.24 (m, 1H) and 0.94 (d, J=6.2 Hz, 6H) ppm.
LCMS RT=2.7 min, (M+H) 432.5.

General Scheme 37:
Preparation of cis-2-amino-1-methylcyclohexanecarboxylic acid (37c)

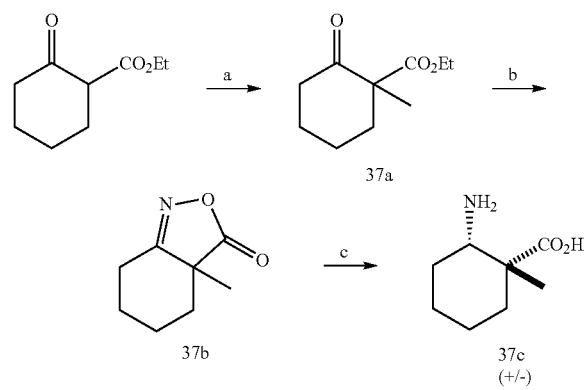

(a) NaH, iodomethane DMF; (b) NH$_2$OH—HCl, pyridine, EtOH; (c) Al (Hg), THF—H$_2$O (4:1).

Formation of ethyl 1-methyl-2-oxocyclohexanecarboxylate (37a)

The title compound was prepared following the procedure described in: Tetrahedron Letters (2005) 46, 681-685 and JCS, Perkin Trans 1 (2000) 3277-3289.

Sodium hydride (1.48 g, 37.14 mmol, 60% in oil) was rinsed twice with hexanes to remove oil and suspended in DMF (57 mL) at 0° C. Then, ethyl 2-oxocyclohexanecarboxylate (5.40 mL, 33.76 mmol) was added over 5 minutes. The mixture was stirred for 20 minutes and MeI (2.21 mL, 35.45 mmol) was added over 10 minutes. The mixture was warmed to room temperature and after 30 minutes, diluted with EtOAc (150 mL) and quenched with saturated NH$_4$Cl. The layers were separated and the aqueous layer was extracted twice more with EtOAc (2×100 mL). The organic layer was washed with brine (2×) dried over MgSO$_4$, filtered through silica gel and concentrated to provide the desired product (37a).

Formation of 3a-methyl-4,5,6,7-tetrahydrobenzo[c]isoxazol-3(3aH)-one (37b)

To a mixture of ethyl 1-methyl-2-oxo-cyclohexanecarboxylate, 37a, (2.05 g, 11.10 mmol) in EtOH (20 mL) was added hydroxylamine hydrochloride (0.97 g, 13.96 mmol) and pyridine (0.99 mL, 12.20 mmol). The mixture was heated to 65° C. overnight. The solution was concentrated in vacuo and the crude material was partitioned between water and EtOAc. The aqueous layer was extracted with EtOAc twice more. The combined organic phases were washed with brine, dried over MgSO$_4$, filtered and concentrated in vacuo. The resulting residue was purified via silica gel chromatography (0-35% EtOAc/hexanes) to afford the desired product, 37b.

$^1$H NMR (300 MHz, CDCl$_3$) δ 2.72-2.65 (m, 1H), 2.29 (td, J=13.3, 6.3 Hz, 1H), 2.18-2.09 (m, 1H), 2.07-2.03 (m, 1H), 1.84-1.79 (m, 1H), 1.76-1.56 (m, 2H), 1.54-1.42 (m, 1H) and 1.40 (s, 3H) ppm.

Formation of trans-2-amino-1-methylcyclohexanecarboxylic acid (37c)

To a solution of 3a-methyl-4,5,6,7-tetrahydro-2,1-benzoxazol-3-one, 37b, (0.075 g, 0.490 mmol) in THF—H$_2$O (2.5 mL of 4:1 mixture) at room temperature was added fresh Al(Hg) amalgam. Aluminum was amalgamated by dipping small strips of Aluminum foil in 2% HgCl$_2$ solution, rinsing with water and EtOH. After 1 hour, an additional 65 mg Al(Hg) was added and the mixture was allowed to stir overnight. The thick gray emulsion that formed was filtered through celite and rinsed with water and THF. The clear solution was concentrated in vacuo, stripped with methanol and THF to remove residual water and concentrated in vacuo to provide the desired product as a glassy solid as mixture of trans and cis isomers (~9:1) with the trans isomer as the predominant isomer. The product was sufficiently pure for use in the next reaction.

$^1$H NMR (300 MHz, MeOD) δ 2.91 (dd, J=3.9, 11.9 Hz, 1H), 2.25 (dd, J=1.9, 13.4 Hz, 1H), 1.89-1.85 (m, 1H), 1.78-1.53 (m, 3H), 1.47-1.32 (m, 2H), 1.21 (s, 3H) and 1.09-0.99 (m, 1H) ppm.

FIA (M+H) 158.1, (M−H) 156.2.

Formation of 2-amino-1-ethylcyclohexanecarboxylic acid

This compound was prepared by the methods described above as an inseparable mixture of cis and trans isomers (70:30) and was used without further purification.

General Scheme 38
Preparation of cis-2-amino-1-allkyl-cyclohexanecarboxylic acids:

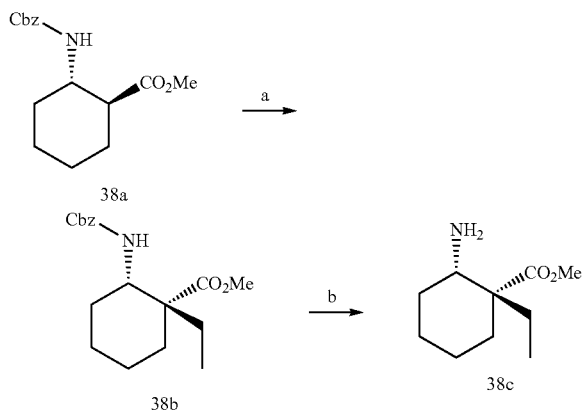

(a) LDA, iodoethane; THF; (b) H$_2$, Pd—C, MeOH.

An alternative scheme for the preparation cis-2-amino-1-alkyl-cyclohexanecarboxylic acid is exemplified above. The method is described in: (a) Nemoto, T.; Fukuyama, T.; Yamamoto, E.; Tamura, S.; Fukuda, T.; Matsumoto, T.; Akimoto, Y.; Hamada, Y. *Org. Lett.* 2007, 9 (5), 927-930. (b) Seebach, D.; Estermann, H. *Tetrahedron Lett.* 1987, 28 (27), 3103-3106.

(1R,2S)-methyl 2-(benzyloxycarbonylamino)-1-ethylcyclohexanecarboxylate (38b)

To a cold (−78° C.) solution of N-isopropylpropan-2-amine (0.77 mL, 5.49 mmol) in THF (7 mL) was added, dropwise, n-butyllithium (3.43 mL of 1.6 M solution, 5.49 mmol). The mixture was stirred at −78° C. for 10 minutes. Then a solution of methyl (1S,2S)-2-benzyloxycarbonylaminocyclohexanecarboxylate, 38a, (0.40 g, 1.37 mmol) in THF (2.5 mL) was added over a period of 3 minutes. After 15 minutes, the mixture was warmed slightly (−40° C.) for 15 minutes and recooled to −78° C. for a further 10 minutes. Then, iodoethane (0.86 g, 0.44 mL, 5.49 mmol) was added, dropwise over 3-5 minutes. The reaction mixture was maintained at −78° C. for 2 hours and allowed to warm to room temperature overnight. The reaction was quenched with 5 mL aqueous saturated NH$_4$Cl solution, extracted with EtOAc (3×), washed successively with 1N HCl and brine. The combined organic layers were dried over Na$_2$SO$_4$, filtered and concentrated in vacuo. Flash chromatography (SiO2, 0-20% EA/Hex slow gradient elution) provided 275 mg (63% yield) of the desired product (38b). NMR indicated a diastereomeric ratio greater than 10 to 1 (cis vs trans).

$^1$H NMR (300.0 MHz, MeOD) δ 7.35-7.28 (m, 5H), 6.62 (d, J=9.2 Hz, 1H), 5.07 (dd, J=12.5, 16.6 Hz, 2H), 3.67 (s, 3H), 3.59 (td, J=10.0, 4.6 Hz, 1H), 2.14 (m, 1H), 1.76-1.29 (m, 9H) and 0.83 (t, J=7.6 Hz, 3H) ppm.

(1R,2S)-methyl 2-amino-1-ethylcyclohexanecarboxylate (38c)

A solution of methyl (1R,2S)-2-benzyloxycarbonylamino-1-ethyl-cyclohexanecarboxylate, 38b, (0.27 g, 0.85 mmol) in MeOH (7.5 mL) was purged with nitrogen and a catalytic amount of Pd (5% Pd on carbon) was added. The solution was placed under H$_2$ atmosphere and stirred at room temperature. After 1 hour, the MeOH solution suspension was filtered through celite, and concentrated in vacuo to provide the desired product (138 mg, 88% yield). The material was diluted in acetonitrile and concentrated to remove residual methanol.

$^1$H NMR (300.0 MHz, MeOD) δ 3.69 (s, 3H), 2.71 (m, 1H), 2.07-2.01 (m, 1H), 1.82 (m, 2H), 1.71-1.27 (m, H), 1.64 (m, 2H), 1.56-1.27 (m, 5H) and 0.85 (t, J=7.5 Hz, 3H) ppm.

General Scheme 39
preparation of trans-2-amino-1-alkyl-cyclohexanecarboxylic acids:

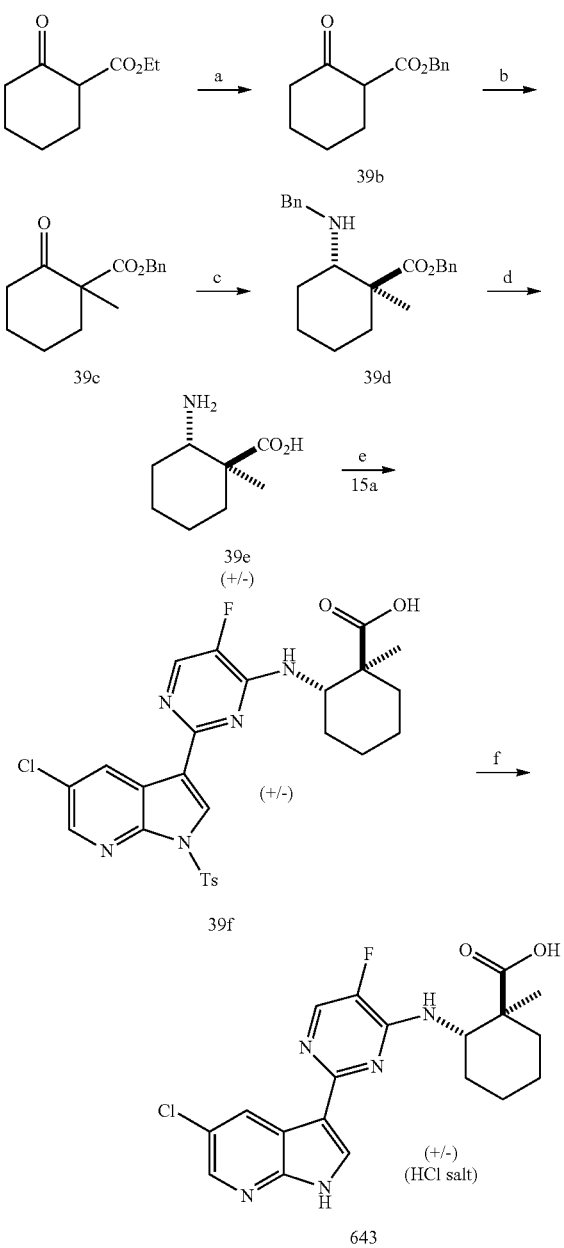

(a) Benzyl alcohol, toluene, 4 angstrom sieves, reflu; (b) NaH, MeI, DMF; (c) benzylamine, TiCl$_4$, CH$_2$Cl$_2$, then NaCNBH$_3$, MeOH, 0° C.; (d) H$_2$, Pd—C, MeOH; (e) 5-chloro-3-(5-fluoro-4-methylsulfinyl-pyrimidin-2-yl)-1-(p-tolylsulfonyl)pyrrolo[2,3-b]pyridine, Na$_2$CO$_3$, THF/CH$_3$CN, microwave irradiation 135° C.; (f) HCl, CH$_3$CN, dioxane, 80° C.

A general method for the synthesis of trans-2-amino-1-alkyl-cyclohexanecarboxylic acids is shown in the scheme above.

Benzyl 2-oxocyclohexanecarboxylate (39b)

This compound was prepared following literature procedures described in: Matsuo, J. et al. *Tetrahedon: Asymmetry* 2007, 18, 1906-1910.

Benzyl 1-methyl-2-oxocyclohexanecarboxylate (39c)

This compound was prepared following the literature procedures described in: (a) Hayashi, Y.; Shoji, M.; Kishida, S. *Tetrahedron Lett.* 2005, 46, 681-685. (Winfield, C. J.; Al-Mahrizy, Z.; Gravestock, M.; Bugg, T. D. H. *J. Chem. Soc., Perkin Trans.* 1, 2000, 3277.

Trans-Benzyl 2-(benzylamino)-1-methylcyclohexanecarboxylate (39d)-(racemic trans)

To a solution of benzyl 1-methyl-2-oxo-cyclohexanecarboxylate, 39c, (0.50 g, 2.03 mmol) and benzylamine (0.61 g, 0.63 mL, 5.75 mmol) in dichloromethane (10.0 mL), was added $TiCl_4$ (1.93 mL of 1 M solution, 1.93 mmol) dropwise, at room temperature. The mixture was stirred for 2 hours. The mixture was cooled to 0° C. and a solution of $NaBH_3CN$ (0.21 g, 3.34 mmol) in MeOH was added dropwise over a period of 3 minutes. After 15 min, the solution was warmed to RT and stirred for an additional 45 min. Then, the mixture was diluted with EtOAc, quenched with 10 mL 1M NaOH. The mixture was partitioned with $Et_2O$ and the aqueous layer was extracted several times with $Et_2O$ (2x) and EtOAc (1x). The combined organic phases were dried over $MgSO_4$, filtered and concentrated in vacuo. Flash chromatography ($SiO_2$, 0-50% EtOAc-Hexanes gradient elution) and isolation of the major component provided the desired product (320 mg) as a single racemic trans isomer.

$^1$H NMR (300.0 MHz, MeOD) δ 7.34-7.16 (m, 10H), 5.07 (dd, J=12.4, 31.2 Hz, 2H), 3.78 (d, J=13.0 Hz, 1H), 3.57 (d, J=13.0 Hz, 1H), 2.96 (m, 1H), 1.86 (m, 1H), 1.74-1.57 (m, 3H), 1.52-1.25 (m, 4H) and 1.20 (s, 3H) ppm.

Trans-2-Amino-1-methylcyclohexanecarboxylic acid (39e)

To a solution of racemic trans-benzyl (1S,2S)-2-(benzylamino)-1-ethyl-cyclohexanecarboxylate, 39d, (0.32 g, 0.91 mmol) in MeOH (12.8 mL), was added Pd (5% Pd on carbon, 0.07 g). The solution was degassed and placed under 50 PSI $H_2$ (Parr shaker) overnight. The mixture was filtered through celite and the filtrate was rinsed with MeOH. Concentration of the mother liquor followed by acetonitrile azeotrope (2x) to remove residual MeOH provided the desired product (162 mg).

$^1$H NMR (300.0 MHz, MeOD) δ 3.22 (m, 1H), 1.93 (m, 1H), 1.77 (m, 2H), 1.57-1.23 (m, 5H) and 1.17 (s, 3H) ppm.

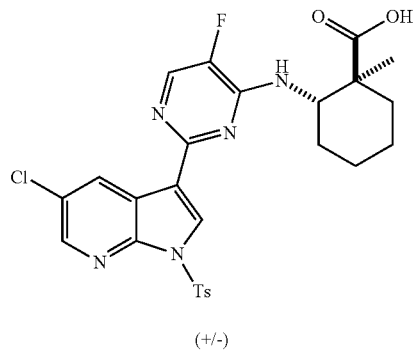

Trans-2-[[2-[5-chloro-1-(p-tolylsulfonyl)pyrrolo[2,3-b]pyridin-3-yl]-5-fluoro-pyrimidin-4-yl]amino]-1-methyl-cyclohexanecarboxylic acid (39f)

To a vessel charged with 5-chloro-3-(5-fluoro-4-methylsulfinyl-pyrimidin-2-yl)-1-(p-tolylsulfonyl)pyrrolo[2,3-b]pyridine, 15a, (0.27 g, 0.58 mmol) and trans-2-amino-1-methyl-cyclohexanecarboxylic acid, 39e, (0.08 g, 0.47 mmol) and freshly ground $Na_2CO_3$ (0.19 g, 1.75 mmol) was added anhydrous THF (4.5 mL) and $CH_3CN$ (0.9 mL). The vessel was sealed and heated to 135° C. for 35 min (microwave irradiation). LC-MS indicated complete consumption of starting material. Next, the reaction mixture was slowly poured into a vigorously stirred solution of 1N HCl (13.5 mL). The pH of the final solution was 1-2. The mixture was extracted with EtOAc (3x), dried over $Na_2SO_4$ and filtered through Celite and concentrated in vacuo. Flash chromatography ($SiO_2$, 0-10% MeOH-dichloromethane, gradient elution) provided a sticky yellow foam, which was suspended in acetonitrile. Sonication followed by evaporation of the solvent provided white amorphous solid (240 mg, 74% yield) as a racemic mixture of trans stereoisomers.

$^1$H NMR (300.0 MHz, MeOD) δ 9.02 (d, J=2.4 Hz, 1H), 8.52 (s, 1H), 8.33 (d, J=2.4 Hz, 1H), 8.09-8.05 (m, 3H), 7.38 (d, J=8.1 Hz, 2H), 5.04 (dd, J=3.6, 9.5 Hz, 1H), 2.38 (s, 3H), 2.09 (m, 1H), 1.83-1.59 (m, 7H), 1.29 (s, 3H) and 1.23 (m, 1H) ppm.

LCMS RT=4.00 min, (M+H) 558.34.

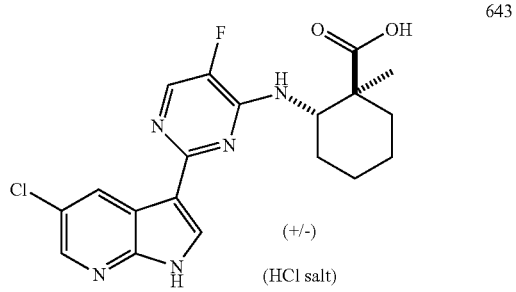 [SMILES: C[C@]1(C(=O)O)CCCC[C@@H]1Nc1nc(-c2c[nH]c3ncc(Cl)cc23)ncc1F]

Trans-2-[[2-(5-chloro-1H-pyrrolo[2,3-b]pyridin-3-yl)-5-fluoro-pyrimidin-4-yl]amino]-1-methyl-cyclohexanecarboxylic acid (643)

To a slurry of racemic trans-2-[[2-[5-chloro-1-(p-tolylsulfonyl)pyrrolo[2,3-b]pyridin-3-yl]-5-fluoro-pyrimidin-4-yl]

amino]-1-methyl-cyclohexanecarboxylic acid, 39f, (0.047 g, 0.084 mmol) in CH$_3$CN (2.35 mL) was added HCl (1.26 mL of 4 M solution, 5.05 mmol) in dioxane. The suspension became a clear solution. The vial was sealed and heated to 80° C. for 2 hours during which time a thick slurry formed. The slurry was allowed to cool to room temperature overnight. Additional CH$_3$CN was added and the mixture was centrifuged. The organic layer was discarded and the solid was triturated with CH$_3$CN three times more to provide an amorphous white solid as racemic mixture of trans stereoisomers.

$^1$H NMR (300.0 MHz, MeOD) δ 8.98 (d, J=2.3 Hz, 1H), 8.45 (s, 1H), 8.38 (d, J=2.3 Hz, 1H), 8.30 (d, J=5.7 Hz, 1H), 5.26-5.22 (m, 1H), 2.17-2.10 (m, 1H), 1.87-1.82 (m, 4H), 1.68-1.59 (m, 3H) and 1.36 (s, 3H) ppm.

LCMS RT=3.30 min, (M+H) 404.36.

General scheme 40:

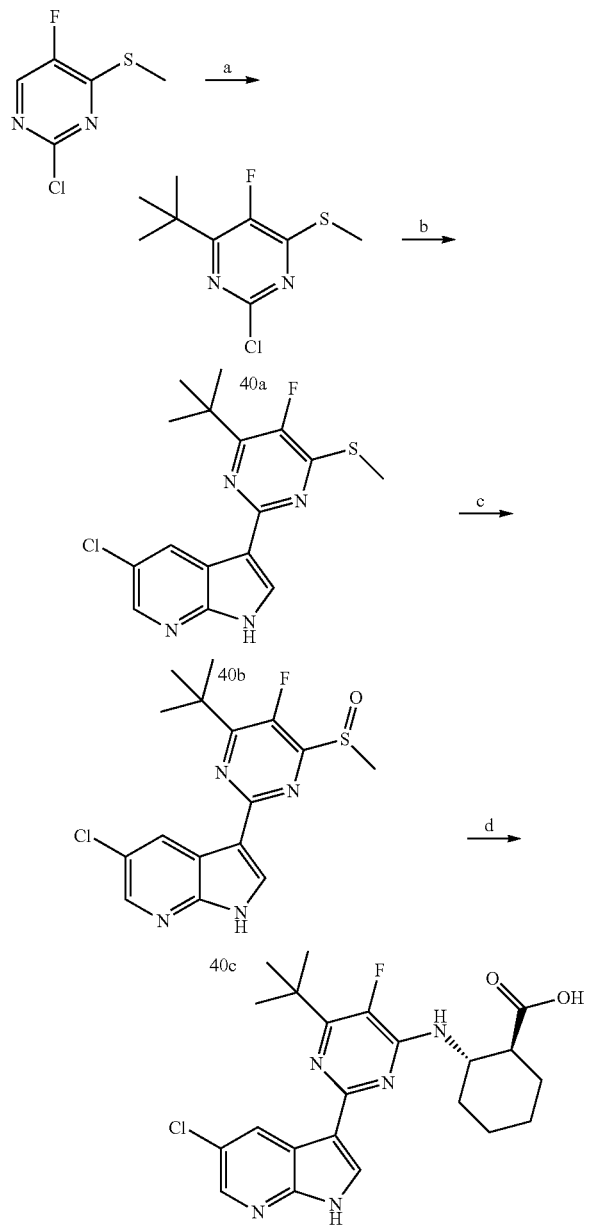

(a) tert-butylmagnesium chloride; I$_2$, Et$_3$N, THF, DME; (b) 5-chloro-1-(p-tolylsulfonyl)-3-(4,4,5,5-tetramethyl-1,3,2-dioxaborolan-2-yl)pyrrolo[2,3-b]pyridine, DME/H$_2$O, Na$_2$CO$_3$, tetrakis triphenylphosphinepalladium(0), 130° C., microwave; (c) mCPBA, CH$_2$Cl$_2$; (d) (1S,2S)-2-aminocyclohexanecarboxylic acid, Na$_2$CO$_3$, THF—CH$_3$CN (3:1), 150° C. microwave.

Formation of 4-tert-butyl-2-chloro-5-fluoro-6-(methylthio)pyrimidine (40a)

To a cold (0° C.) solution of tert-butylmagnesium chloride (7.5 mL, 1M solution in THF, 7.5 mmol) in THF (15 mL) was added slowly a solution of 2-chloro-5-fluoro-4-(methylthio) pyrimidine (0.9 g, 5.0 mmol) in 1,2-dimethoxyethane (5 mL). The reaction mixture was stirred at 15° C. for 1 hour, then cooled to 0° C. and triethylamine (0.7 mL, 5.0 mmol) was added, followed by the addition of a solution of iodine (1.3 g, 5.0 mmol) in tetrahydrofuran (3 mL). Water (10 mL) was added to quench the reaction and pH was adjusted to 1 using 6N hydrochloric acid. The aqueous phase was extracted twice with ethyl acetate (2×15 mL). The combined organic phases were washed with aqueous sodium thiosulfate and then brine, dried over MgSO$_4$, filtered and concentrated in vacuo to give a brown solid which was used without further purification.

$^1$H NMR (300.0 MHz, CDCl$_3$) δ 2.52 (s, 3H), 1.30 (s, 9H) ppm.

LCMS (M+1) 233.0.

Formation of 3-(tert-butyl-5-fluoro-6-(methylthio)pyrimidin-2-yl)-5-chloro-1H-pyrrolo[2,3-b]pyridine (40b)

To a degassed solution of 5-chloro-1-(p-tolylsulfonyl)-3-(4,4,5,5-tetramethyl-1,3,2-dioxaborolan-2-yl)pyrrolo[2,3-b] pyridine (0.22 g, 0.50 mmol), 4-tert-butyl-2-chloro-5-fluoro-6-thiomethoxypyrimidine, 40a, (0.12 g, 0.50 mmol) in 1,2-dimethoxyethane (3 mL) and aqueous Na$_2$CO$_3$ (0.75 mL of 2 M solution, 1.5 mmol) was added tetrakis(triphenylphosphine)palladium(0) (0.03 g, 0.03 mmol). The reaction mixture was degassed for an additional 15 minutes. The mixture was heated in a microwave at 150° C. for 20 minutes. Ethyl acetate (15 mL) was added. The organic layer was separated and washed with brine, dried over MgSO$_4$, filtered and concentrated in vacuo. The resulting crude residue was purified by silica gel chromatography (0%-100% EtOAc/hexanes) to afford the desired product, 40b (47 mg).

$^1$H NMR (300 MHz, CDCl$_3$) δ 10.82 (br, 1H), 8.81 (d, J=2.2 Hz, 1H), 8.27 (d, J=2.3 Hz, 1H), 8.20 (dd, J=7.2, 2.2 Hz, 1H), 7.18 (s, 1H), 2.63 (s, 3H), 1.41 (s, 9H) ppm.

LCMS (M+1) 352.3.

Formation of 3-(tert-butyl-5-fluoro-6-(methylsulfinyl)pyrimidin-2-yl)-5-chloro-1H-pyrrolo[2,3-b]pyridine (40c)

To the solution of 3-(tert-butyl-5-fluoro-6-(methylthio)pyrimidin-2-yl)-5-chloro-1H-pyrrolo[2,3-b]pyridine, 40b, (0.05 g, 0.11 mmol) in CH$_2$Cl$_2$ (3.4 mL) was added mCPBA (0.02 g, 0.11 mmol). The reaction mixture was stirred for 1 h. The reaction mixture was diluted with CH$_2$Cl$_2$ (10 mL) and saturated NaHCO$_3$ solution (5 mL). The aqueous layer was extracted with CH$_2$Cl$_2$ (10 mL). The combined organic phases were washed again with aqueous saturated NaHCO$_3$ solution, dried over Na$_2$SO$_4$, filtered and concentrated in vacuo to afford the desired product that was used without further purification.

¹H NMR (300 MHz, CDCl₃) δ 10.93 (br, 1H), 8.79 (d, J=2.2 Hz, 1H), 8.34 (s, 1H), 8.25 (d, J=2.2 Hz, 1H), 7.19 (s, 1H), 2.98 (s, 3H), 1.47 (s, 9H) ppm.

LCMS (M+1) 368.3.

Formation of (1S,2S)-2-(6-tert-butyl-2-(5-chloro-1H-pyrrolo[2,3-b]pyridin-3-yl)-5-fluoropyrimidin-4-ylamino)cyclohexanecarboxylic acid (629)

A mixture of 3-(tert-butyl-5-fluoro-6-(methylsulfinyl)pyrimidin-2-yl)-5-chloro-1H-pyrrolo[2,3-b]pyridine, 40c, (0.05 g, 0.14 mmol), (1S,2S)-2-amino-cyclohexanecarboxylic acid (0.04 g, 0.27 mmol), freshly ground Na₂CO₃ (0.04 g, 0.41 mmol), and ⁱPr₂NEt (0.37 mL, 0.27 mmol) in THF (1 mL) and CH₃CN (0.5 mL) was heated in a sealed vessel to 140° C. for 30 minutes under microwave irradiation. The mixture was cooled to room temperature. A solution of 1N HCl (0.5 mL, 0.5 mmol) was added and the mixture was concentrated to give a yellow solid, which was purified by reverse phase HPLC (0%-50% methanol in water) to afford the desired product, 629, as off-white solid.

¹H NMR (300 MHz, DMSO) δ 12.26 (s, 1H), 8.79 (d, J=2.4 Hz, 1H), 8.28 (d, J=2.4 Hz, 1H), 8.13 (d, J=2.7 Hz, 1H), 7.25 (d, J=8.3 Hz, 1H), 4.34 (m, 1H), 2.62 (m, 1H), 2.05 (m, 2H), 1.75 (m, 2H), 1.57 (m, 2H), 1.39 (s, 9H) and 1.26-1.17 (m, 2H) ppm.

LCMS (M+1) 446.23.

General Scheme 41:

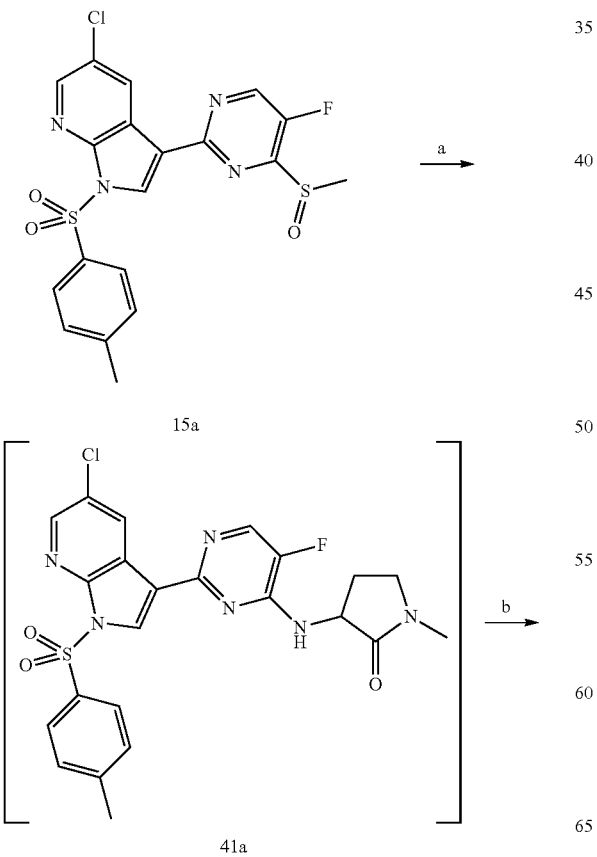

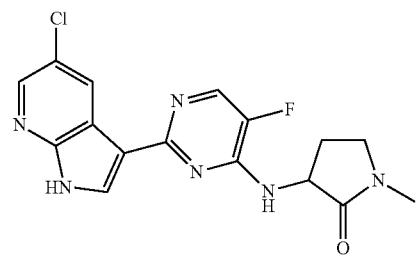

379

(a) 3-amino-1-methylpyrrolidin-2-one, DMA, 140° C. microwave; (b) i: LiOH, THF, microwave, 120° C., or ii: NaOMe, MeOH.

Formation of 3-((2-(5-chloro-1H-pyrrolo[2,3-b]pyridin-3-yl)-5-fluoropyrimidin-4-ylamino)-1-methylpyrrolidin-2-one (379)

A solution of 5-chloro-3-(5-fluoro-4-methylsulfinyl-pyrimidin-2-yl)-1-(p-tolylsulfonyl)pyrrolo[2,3-b]pyridine, 15a, (0.060 g, 0.129 mmol) in DMA (0.5 mL) was treated with 3-amino-1-methylpyrrolidin-2-one (0.030 g, 0.258 mmol) and the reaction was heated at 140° C. for 20 minutes. The reaction mixture was cooled to room temperature and then treated with 0.5 mL of 25% NaOMe in MeOH and heated at 50° C. for 15 min. The mixture was then partitioned between aqueous saturated Na₂CO₃ solution and EtOAc. The aqueous layer was extracted with EtOAc twice more and the combined organic phases were concentrated in vacuo. The crude material was purified by preparative HPLC. The isolated product was filtered through basic resin to remove residual TFA and provide the desired product.

¹H NMR (300 MHz, MeOD) δ 8.72 (d, J=2.3 Hz, 1H), 8.21 (d, J=2.4 Hz, 1H), 8.11-8.07 (m, 2H), 4.94 (t, J=9.3 Hz, 1H), 3.64-3.51 (m, 2H), 2.97 (s, 3H), 2.68-2.54 (m, 1H) and 2.37-2.23 (m, 1H) ppm.

LCMS RT=2.3 min, (M+H) 361.3.

The following compounds can also be prepared in a manner similar to the one described in Scheme 41.

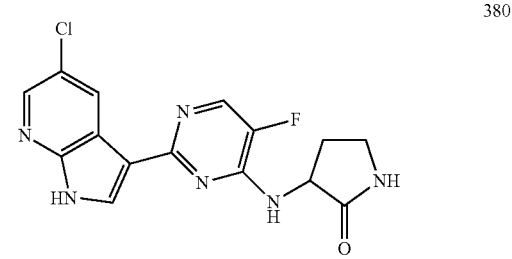

380

-continued

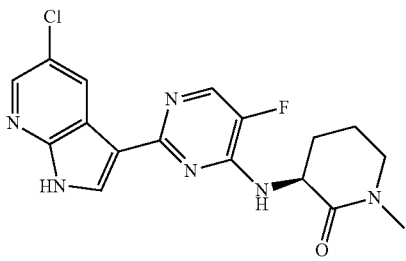

397

3-((2-(5-chloro-1H-pyrrolo[2,3-b]pyridin-3-yl)-5-fluoropyrimidin-4-ylamino)pyrrolidin-2-one (380)

¹H NMR (300 MHz, MeOD) δ 8.79 (d, J=2.4 Hz, 1H), 8.20 (d, J=2.4 Hz, 1H), 8.13 (s, 1H), 8.07 (d, J=3.9 Hz, 1H), 4.91 (dd, J=8.7, 10.6 Hz, 1H), 3.61-3.46 (m, 2H), 2.68-2.58 (m, 2H) and 2.48-2.31 (m, 1H) ppm.
LCMS RT=2.3 min, (M+H) 347.3.

(S)-3-((2-(5-chloro-1H-pyrrolo[2,3-b]pyridin-3-yl)-5-fluoropyrimidin-4-ylamino)-1-methylpiperidin-2-one (397)

¹H NMR (300.0 MHz, DMSO) δ 8.65 (d, J=2.5 Hz, 1H), 8.27 (d, J=2.4 Hz, 1H), 8.20-8.19 (m, 2H), 7.63 (d, J=7.8 Hz, 1H), 4.78-4.74 (m, 1H), 3.41 (t, J=5.4 Hz, 2H), 3.17 (MeOH), 2.89 (s, 3H), 2.50 (DMSO), 2.18-2.15 (m, 1H) and 1.99 (d, J=7.4 Hz, 2H) ppm.
LCMS RT=2.2 min, (M+H) 375.4.

416

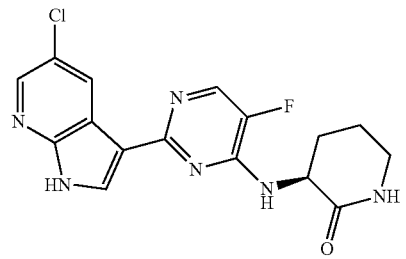

417

(S)-3-((2-(5-chloro-1H-pyrrolo[2,3-b]pyridin-3-yl)-5-fluoropyrimidin-4-ylamino)piperidin-2-one (416)

LCMS RT=1.6 min, (M+H) 361.3.

(S)-3-((2-(5-chloro-1H-pyrrolo[2,3-b]pyridin-3-yl)-5-fluoropyrimidin-4-ylamino)azepan-2-one (417)

¹H NMR (300 MHz, DMSO) δ 12.33 (s, 1H), 8.74 (d, J=2.3 Hz, 1H), 8.28 (d, J=2.4 Hz, 1H), 8.21 (t, J=3.7 Hz, 2H), 8.02-7.98 (m, 1H), 7.21 (d, J=5.8 Hz, 1H), 4.86 (dd, J=6.3, 10.5 Hz, 1H), 3.51-3.41 (m, 1H), 3.25-3.16 (m, 1H), 2.13-1.85 (m, 4H), 1.66-1.52 (m, 1H) and 1.40-1.20 (m, 1H) ppm.
LCMS RT=1.7 min, (M+H) 375.4.

460

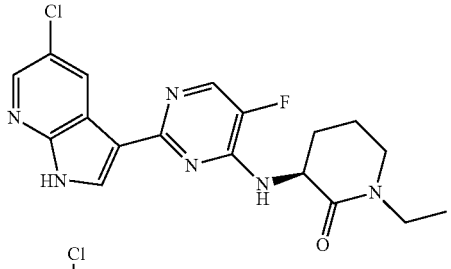

461

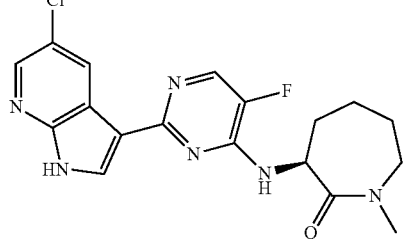

(S)-3-((2-(5-chloro-1H-pyrrolo[2,3-b]pyridin-3-yl)-5-fluoropyrimidin-4-ylamino)-1-ethylpiperidin-2-one (460)

LCMS RT=2.0 min, (M+H) 389.1.

(S)-3-((2-(5-chloro-1H-pyrrolo[2,3-b]pyridin-3-yl)-5-fluoropyrimidin-4-ylamino)-1-methylazepan-2-one (461)

LCMS RT=2.0 min, (M+H) 389.1.

462

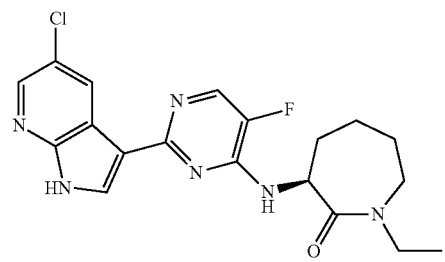

503

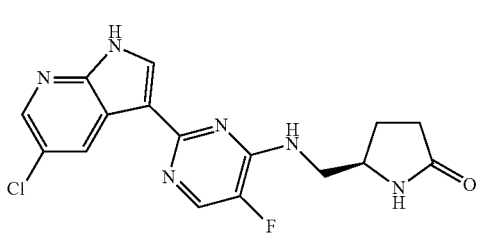

(S)-3-((2-(5-chloro-1H-pyrrolo[2,3-b]pyridin-3-yl)-5-fluoropyrimidin-4-ylamino)-1-ethylazepan-2-one (462)

¹H NMR (300 MHz, d6-DMSO) δ 12.35 (s, 1H), 8.68 (d, J=1.7 Hz, 1H), 8.27 (d, J=2.0 Hz, 1H), 8.21 (m, 2H), 7.28 (d,

J=6.0 Hz, 1H), 4.98 (dd, J=6.9, 10.7 Hz, 1H), 3.88-3.79 (m, 1H), 3.84 (dd, J=11.4, 15.5 Hz, 1H), 3.49-3.17 (m, 5H), 2.08 (d, J=13.1 Hz, 1H), 1.95-1.88 (m, 3H), 1.65-1.58 (m, 1H), 1.42 (m, 1H) and 1.04 (t, J=7.0 Hz, 3H) ppm.

LCMS RT=3.3 min, (M+H) 403.4.

(R)-5-(2-(5-chloro-1H-pyrrolo[2,3-b]pyridin-3-yl)-5-fluoropyrimidin-4-ylamino)methyl)pyrrolidin-2-one (503)

LCMS RT=2.2 min, (M+H) 361.2.

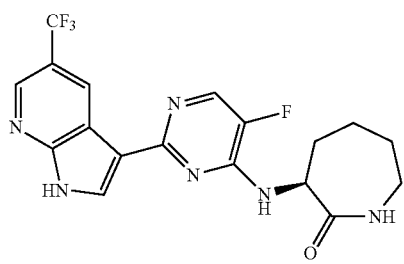

(S)-3-(5-fluoro-2-(5-(trifluoromethyl)-1H-pyrrolo[2,3-b]pyridin-3-yl)pyrimidin-4-ylamino)azepan-2-one (502)

LCMS RT=2.3 min, (M+H) 409.

(S)-6-(2-(5-chloro-1H-pyrrolo[2,3-b]pyridin-3-yl)-5-fluoropyrimidin-4-ylamino)-4-(4-methoxybenzyl)-1,4-oxazepan-2-one (505)

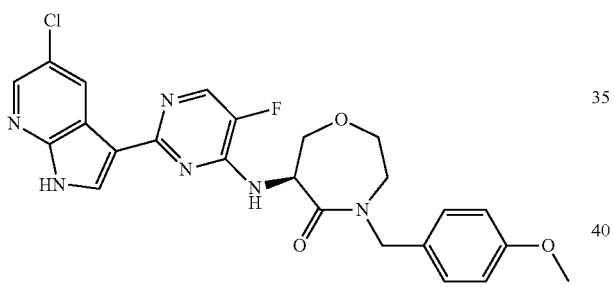

LCMS RT=3.1 min, (M+H) 497.7.

The starting amine for this compound was prepared following established procedures as described in: Blizzard, Timothy A.; Chen, Helen Y.; Wu, Jane Yang; Kim, Seongkon; Ha, Sookhee; Mortko, Christopher J.; Variankaval, Narayan; Chiu, Anna. 7-Oxo-2,6-Diazabicyclo[3.2.0]heptane-6-sulfonic acid derivatives as b-lactamase inhibitors and their preparation, pharmaceutical compositions and use in the treatment of bacterial infections. PCT Int. Appl. (2008), 101 pp. WO2008039420.

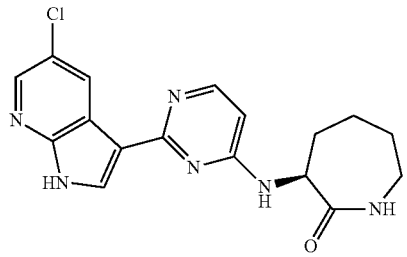

(S)-3-((2-(5-chloro-1H-pyrrolo[2,3-b]pyridin-3-yl)pyrimidin-4-ylamino)azepan-2-one (500)

LCMS RT=1.6 min, (M+H) 357.6.

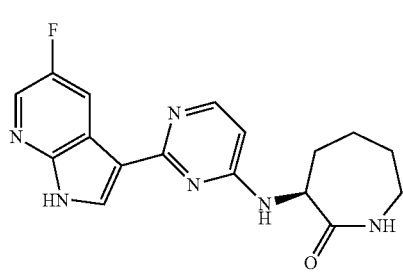

(S)-3-((2-(5-fluoro-1H-pyrrolo[2,3-b]pyridin-3-yl)pyrimidin-4-ylamino)azepan-2-one (501)

LCMS RT=1.6 min, (M+H) 341.4.

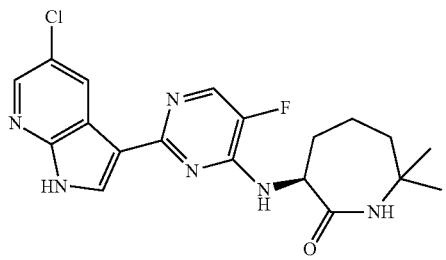

3-((2-(5-chloro-1H-pyrrolo[2,3-b]pyridin-3-yl)-5-fluoropyrimidin-4-ylamino)-7,7-dimethylazepan-2-one (504)

LCMS RT=3.2 min, (M+H) 403.6.

The amine for this compound was prepared following procedures as described in: J.

A. Robl, E. Sieber-McMaster, R. Sulsky Synthetic routes for the generation of 7,7-dialkyl-2-azepinones. *Tetrahedron Letters* (1996), 37(50), 8985-8988

General Scheme 42:

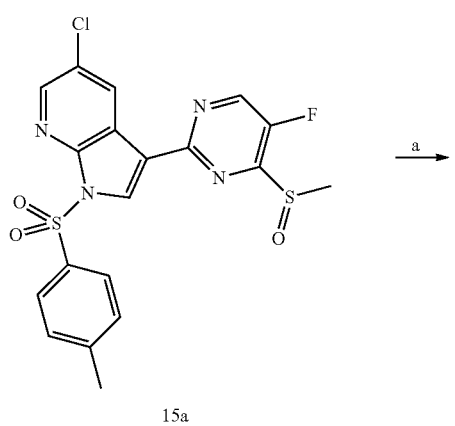

15a

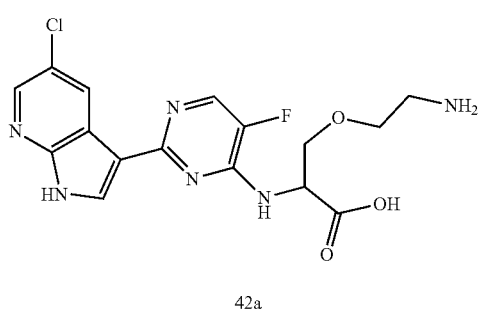

42a

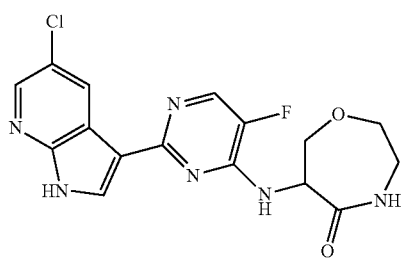

513

(a) 3-amino-1-methylpyrrolidin-2-one, DMA, 140° C. microwave; (b) LiOH, THF, microwave, 120° C. (c) EDCI, HOAt, $^iPr_2NEt$, DCM-DMF (2:1).

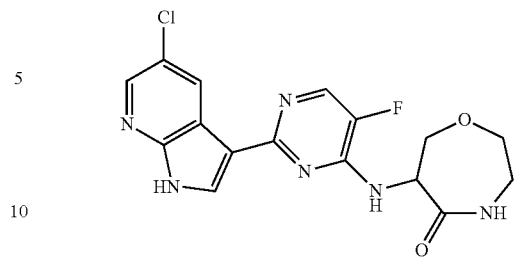

6-(2-(5-chloro-1H-pyrrolo[2,3-b]pyridin-3-yl)-5-fluoropyrimidin-4-ylamino)-1,4-oxazepan-5-one (513)

A mixture of 5-chloro-3-(5-fluoro-4-methylsulfinyl-pyrimidin-2-yl)-1-(p-tolylsulfonyl)pyrrolo[2,3-b]pyridine, 15a, (0.17 g, 0.36 mmol) and (6S)-6-amino-1,4-oxazepan-5-one (0.06 g, 0.43 mmol) in DMF (2 mL) with $^iPr_2NEt$ (0.10 mL, 0.57 mmol) was heated to 90° C. After 1 hour, the temperature was raised to 100° C. After 24 hours, the mixture was heated to 140° C. for 15 min (microwave). The mixture was partitioned between water and EtOAc and the aqueous layer was extracted with EtOAc twice more. The combined organic phases were dried organic over $Na_2SO_4$, filtered and concentrated in vacuo.

The resulting crude material (0.16 g) was treated with LiOH (1N solution, 1 mL) in THF (3 mL) overnight. LC-MS indicates hydrolysis of amide along with detosylation. The mixture was concentrated in vacuo and purified by preparative HPLC to provide semi pure product (23 mg). This material was subjected to cyclization conditions without further purification.

To a flask was charged with the crude material (0.020 g, 0.051 mmol), EDCI (0.010 g, 0.056 mmol) and HOAt (0.002 g, 0.015 mmol) and DCM (1 mL) was added $^iPr_2NEt$ (0.018 mL, 0.100 mmol) and DMF (0.5 mL). After 1 hour, additional EDCI was added (0.7 eq). After 3.5 hour, the reaction was complete and the mixture was concentrated in vacuo. Purification by preparative HPLC followed by removal of TFA salt by filtration through basic resin provided the desired product: LCMS RT=1.9 min, (M+H) 377.5.

The starting amine for this compound was prepared following the established procedures as described in: J. A. Robl, E. Sieber-McMaster, R. Sulsky Synthetic routes for the generation of 7,7-dialkyl-2-azepinones. Tetrahedron Letters (1996), 37(50), 8985-8988.

General Scheme 43:
The following are general procedures for conversion of the cyclohexane carboxylic acids, 553 or 35a, to carboxamides of type 43a:

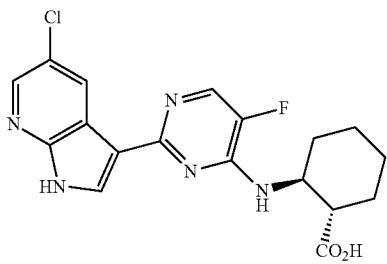

553 a or b

367

-continued

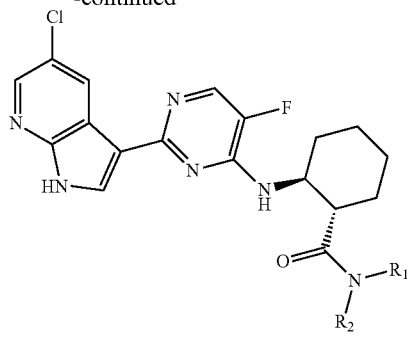

43a

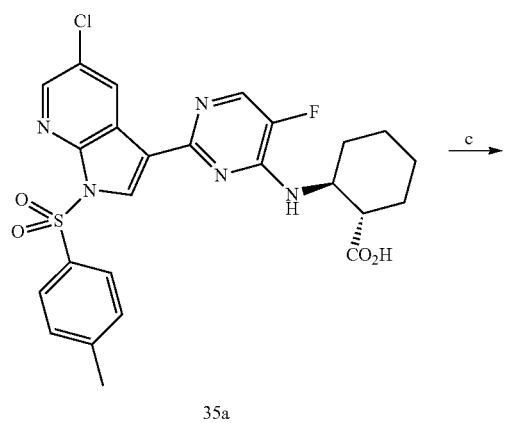

35a

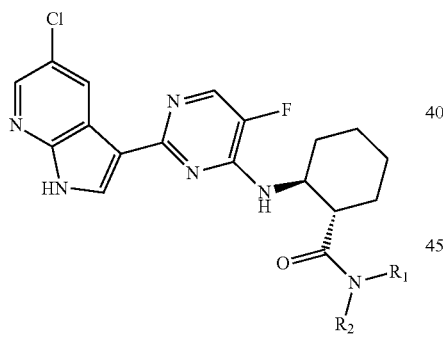

43a (a) Amine, HATU, DMF; (b) BOC$_2$O, NH$_4$CO$_3$H, pyridine, DMF; (c) i: Amine, HATU, DMF; then ii: 1N LiOH.

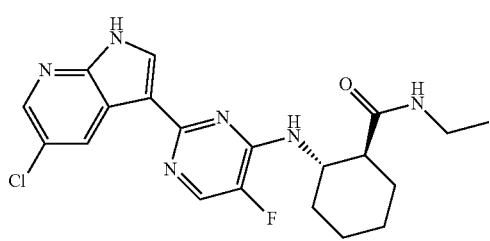

521

368

Formation of (1S,2S)-2-(2-(5-chloro-1H-pyrrolo[2,3-b]pyridin-3-yl)-5-fluoropyrimidin-4-ylamino)-N-ethylcyclohexanecarboxamide (521)

To a mixture of (1S,2S)-2-[[2-(5-chloro-1H-pyrrolo[5,4-b]pyridin-3-yl)-5-fluoro-pyrimidin-4-yl]amino]cyclohexane-1-carboxylic acid, 553, (0.049 g, 0.126 mmol) and HATU (0.056 g, 0.147 mmol) in DMF (1.0 mL) at room temperature was added ethylamine (0.189 mL of 2 M solution, 0.377 mmol). The mixture was stirred at room temperature until all starting material had been converted as judged by HPLC. After 45 minutes, the mixture was partitioned between aqueous K$_2$CO$_3$ and EtOAc and the organic layer was separated and dried over Na$_2$SO$_4$ and concentrated in vacuo. Preparative HPLC provide the desired product as the TFA salt, which was converted to the parent compound by elution through a basic PSA cartridge with MeOH followed by concentration in vacuo. (14 mg, 30% yield).

$^1$H NMR (300 MHz, MeOD) δ 8.93 (d, J=2.4 Hz, 1H), 8.22 (d, J=2.3 Hz, 1H), 8.18 (s, 1H), 7.99 (d, J=4.0 Hz, 1H), 4.53 (ddd, J=7.1, 11.1 Hz, 1H), 3.15-3.02 (m, 2H), 2.43-2.34 (m, 1H), 2.30-2.26 (m, 1H), 1.97-1.82 (m, 3H), 1.77-1.65 (m, 2H), 1.47-1.35 (m, 2H) and 0.97 (t, J=7.3 Hz, 3H) ppm.

LCMS RT=2.0 min, (M+H) 417.5.

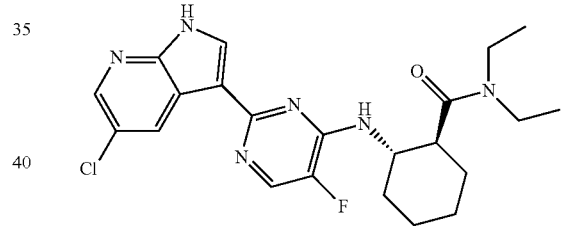

520

(1S,2S)-2-(2-(5-chloro-1H-pyrrolo[2,3-b]pyridin-3-yl)-5-fluoropyrimidin-4-ylamino)-N,N-diethylcyclohexanecarboxamide LCMS RT=2.26 min, (M+H) 445.58.

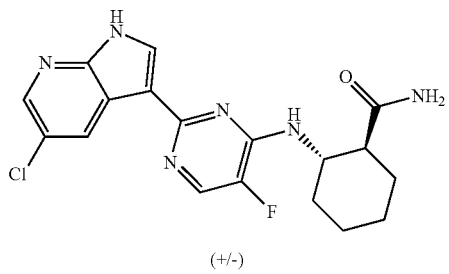

544

(+/−)

-continued

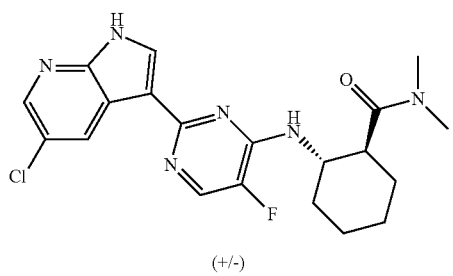

543

(+/-)

Formation of cis-2-(2-(5-chloro-1H-pyrrolo[2,3-b]pyridin-3-yl)-5-fluoropyrimidin-4-ylamino)cyclohexanecarboxamide (544) and Cis-2-(2-(5-chloro-1H-pyrrolo[2,3-b]pyridin-3-yl)-5-fluoropyrimidin-4-ylamino)-N,N-dimethylcyclohexanecarboxamide (543)

To a mixture of cis-2-[[2-(5-chloro-1H-pyrrolo[2, 3-1)]pyridin-3-yl)-5-fluoropyrimidin-4-yl]amino]cyclohexanecarboxylic acid, 554, (0.30 g, 0.77 mmol) in DMF (5 mL) at room temperature was added pyridine (0.61 g, 0.62 mL, 7.70 mmol) followed by di-tert-butyl dicarbonate (0.50 g, 2.31 mmol), and $NH_4CO_3H$ (0.33 g, 4.22 mmol). The mixture was stirred overnight at room temperature. LC-MS indicated the presence of the desired primary amide as well as the N,N-dimethylamide product. A 1 mL aliquot of the reaction solution was acidified with HOAc and diluted with DMSO. Preparative HPLC chromatography provided small amounts both products.

Primary amide, 544, racemic mixture—(8.6 mg): LCMS RT=1.94 min, (M+H) 389.42.

Dimethylamide, 543, racemic mixture—(3.7 mg): LCMS RT=2.52 min, (M+H) 417.44.

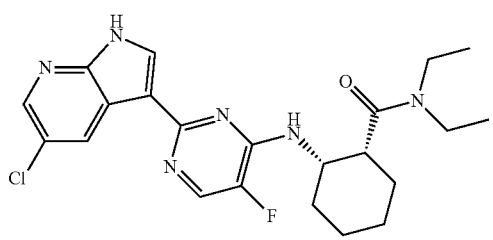

518

Formation of (1R,2S)-2-(2-(5-chloro-1H-pyrrolo[2,3-b]pyridin-3-yl)-5-fluoropyrimidin-4-ylamino)-N,N-diethylcyclohexanecarboxamide (518)

To a mixture of (1R,2S)-2-[[2-[5-chloro-1-(p-tolylsulfonyl)pyrrolo[5,4-b]pyridin-3-yl]-5-fluoro-pyrimidin-4-yl]amino]cyclohexane-1-carboxylic acid (0.050 g, 0.092 mmol), and HATU (0.045 g, 0.120 mmol) in DMF (1 mL) at room temperature was added N,N-diethylamine (0.138 mL of 2 M solution, 0.280 mmol). When the reaction appeared complete as judged by HPLC, LiOH (0.4 mL of 1 M solution, 0.4 mmol) in water was added. After 6 hours, LiOH (0.4 mL of 1 M, 0.4 mmol) was added again and the mixture was stirred overnight. The mixture was quenched with aqueous saturated $NH_4Cl$ solution. Aqueous $K_2CO_3$ was added and the mixture was extracted with EtOAc (3×), The combined organic phases were washed with aqueous saturated $NH_4Cl$ solution, filtered and concentrated in vacuo. Preparative HPLC provided the desired product as the TFA salt which was converted to the HCl salt by treatment with HCl in MeOH followed by evaporation of the solvents (12.9 mg, 28% yield).

$^1$H NMR (300 MHz, MeOD) δ 8.67 (d, J=2.3 Hz, 1H), 8.53 (s, 1H), 8.41 (d, J=2.3 Hz, 1H), 8.35 (d, J=5.5 Hz, 1H), 4.75-4.73 (m, 1H), 3.74-3.58 (m, 1H), 3.42 (m, 2H), 3.29-3.22 (m, 2H), 2.57 (m, 1H), 2.09-2.03 (m, 1H), 1.96-1.76 (m, 4H), 1.06 (t, J=7.1 Hz, 3H) and 0.94 (t, J=7.1 Hz, 3H) ppm.

LCMS RT=3.3 min, (M+H) 445.6.

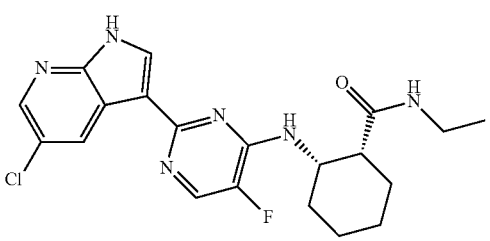

519

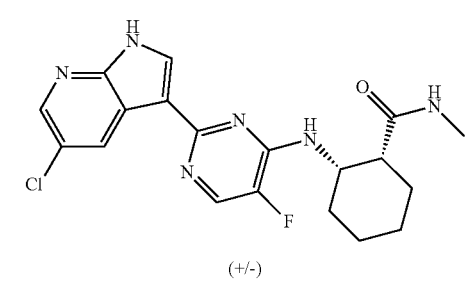

539

(+/-)

(1R,2S)-2-(2-(5-chloro-1H-pyrrolo[2,3-b]pyridin-3-yl)-5-fluoropyrimidin-4-ylamino)-N-ethylcyclohexanecarboxamide (519)

LCMS RT=2.95 min, (M+H) 417.5.

Cis-2-(2-(5-chloro-1H-pyrrolo[2,3-b]pyridin-3-yl)-5-fluoropyrimidin-4-ylamino)-N-methylcyclohexanecarboxamide (539)—racemic mixture LCMS RT=2.13 min, (M+H) 403.44.

General Scheme 44

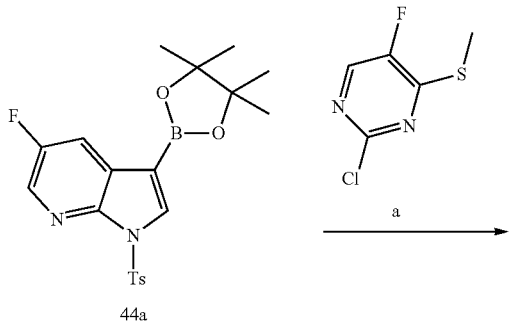

44a

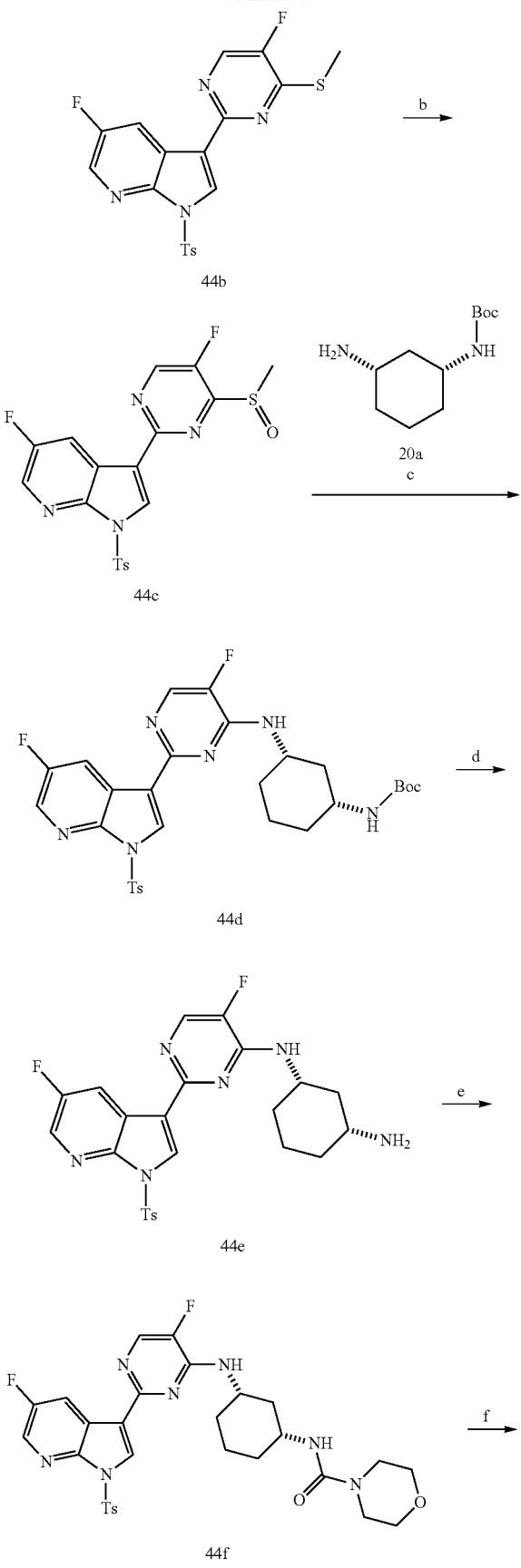
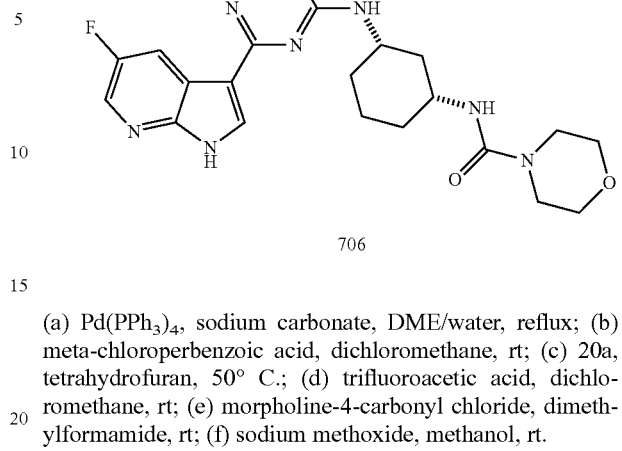

(a) Pd(PPh₃)₄, sodium carbonate, DME/water, reflux; (b) meta-chloroperbenzoic acid, dichloromethane, rt; (c) 20a, tetrahydrofuran, 50° C.; (d) trifluoroacetic acid, dichloromethane, rt; (e) morpholine-4-carbonyl chloride, dimethylformamide, rt; (f) sodium methoxide, methanol, rt.

Formation of 5-fluoro-3-[5-fluoro-4-(methylthio)pyrimidin-2-yl]-1-tosyl-1H-pyrrolo[2,3-b]pyridine (44b)

2-Chloro-5-fluoro-4-methylsulfanyl-pyrimidine (34.1 g, 191.0 mmol), 5-fluoro-1-(p-tolylsulfonyl)-3-(4,4,5,5-tetramethyl-1,3,2-dioxaborolan-2-yl)pyrrolo[2,3-b]pyridine, 44a, (53.0 g, 127.3 mmol) and Na₂CO₃ (40.5 g, 381.9 mmol) were dissolved in a mixture of DME (795 mL) and water (159 mL). The mixture was purged with nitrogen for 20 minutes and treated with Pd(PPh₃)₄ (7.4 g, 6.6 mmol). After purging with nitrogen for another 20 minutes, the reaction was heated to reflux overnight, cooled to room temperature and diluted with water (600 mL). The resulting suspension was stirred at room temperature for 30 minutes and the precipitate was then collected by filtration, washed with water and acetonitrile and dried at 50° C. to afford 48.2 g of 5-fluoro-3-[5-fluoro-4-(methylthio)pyrimidin-2-yl]-1-tosyl-1H-pyrrolo[2,3-b]pyridine as a white solid.

¹H NMR (300 MHz, DMSO-d6) δ 8.70-8.58 (m, 2H), 8.54-8.41 (m, 2H), 8.09 (d, J=8.4 Hz, 2H), 7.45 (d, J=8.2 Hz, 2H), 2.76 (s, 3H), 2.36 (s, 3H).

Formation of 5-fluoro-3-[5-fluoro-4-(methylsulfinyl)pyrimidin-2-yl]-1-tosyl-1H-pyrrolo[2,3-b]pyridine (44c)

5-fluoro-3-[5-fluoro-4-(methylthio)pyrimidin-2-yl]-1-tosyl-1H-pyrrolo[2,3-b]pyridine, 44b, (48.2 g, 111.5 mmol) was dissolved in dichloromethane (2.3 L) and treated portionwise with m-CPBA (27.5 g, 122.6 mmol) while keeping the temperature below 20° C. After addition was complete, the reaction was stirred at room temperature for 2 hours, then treated with another portion of m-CPBA (1.9 g) and stirred for another hour. The reaction mixture was washed with 12% aqueous K₂CO₃ (2×1.0 L) and the organic layer was dried on Na₂SO₄ and concentrated in vacuo to provide 50 g of 5-fluoro-3-[5-fluoro-4-(methylsulfinyl)pyrimidin-2-yl]-1-tosyl-1H-pyrrolo[2,3-b]pyridine as a yellow solid.

¹H NMR (300 MHz, DMSO-d6) δ 9.11 (d, J=1.5 Hz, 1H), 8.69 (s, 1H), 8.65 (dd, J=9.0, 2.9 Hz, 1H), 8.52 (dd, J=2.8, 1.2 Hz, 1H), 8.11 (d, J=8.4 Hz, 2H), 7.46 (d, J=8.3 Hz, 2H), 3.05 (s, 3H), 2.36 (s, 3H).

Formation of tert-butyl N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]carbamate (44d)

5-fluoro-3-(5-fluoro-4-methylsulfinyl-pyrimidin-2-yl)-1-(p-tolylsulfonyl)pyrrolo[2,3-b]pyridine, 44c, (5.9 g, 10.5 mmol) and tert-butyl N-[(1R,3S)-3-aminocyclohexyl]carbamate (3 g, 12.60 mmol) were dissolved in THF (100 mL). The reaction mixture was heated to 50° C. for 6 hours, then cooled to room temperature. Celite was added and the solvent was removed under reduced pressure. The Celite-supported residue was purified by silica gel chromatography (20-80% EtOAc/hexanes gradient to provide 3.7 g of tert-butyl N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]carbamate.

$^1$H NMR (300 MHz, CDCl$_3$) δ 8.51 (s, 1H), 8.46-8.41 (m, 1H), 8.29 (d, J=1.6 Hz, 1H), 8.11 (s, 1H), 8.08 (s, 1H), 8.06 (d, J=3.2 Hz, 1H), 7.27 (d, J=8.4 Hz, 2H), 4.91 (d, J=8.0 Hz, 1H), 4.41 (s, 1H), 4.29-4.01 (m, 1H), 3.64 (s, 1H), 2.47 (d, J=11.5 Hz, 1H), 2.36 (s, 3H), 2.24 (d, J=13.1 Hz, 1H), 2.08 (d, J=10.9 Hz, 1H), 1.91 (d, J=13.8 Hz, 1H), 1.43 (s, 9H), 1.30-1.03 (m, 4H).

Formation of (1S,3R)—N1-[5-fluoro-2-[5-fluoro-1-(p-tolylsulfonyl)pyrrolo[2,3-b]pyridin-3-yl]pyrimidin-4-yl]cyclohexane-1,3-diamine (44e)

tert-Butyl N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]carbamate, 44d, (3.7 g, 6.2 mmol) was dissolved in dichloromethane (105 mL) and treated with trifluoroacetic acid (31 mL). After 5 minutes, the volatiles were evaporated under reduced pressure, and the resulting residue was treated with 1N NaOH (75 mL). The resulting precipitate was collected by filtration, washed with water (3×30 mL) and vacuum dried to provide 2.7 g of (1s, 3R)—N1-[5-fluoro-2-[5-fluoro-1-(p-tolylsulfonyl)pyrrolo[2,3-b]pyridin-3-yl]pyrimidin-4-yl]cyclohexane-1,3-diamine as a white solid.

$^1$H NMR (300 MHz, MeOD) d 8.56 (dd, J=8.0, 3.9 Hz, 2H), 8.35-8.26 (m, 1H), 8.12 (dd, J=10.3, 6.1 Hz, 3H), 7.43 (d, J=8.4 Hz, 2H), 4.36-4.21 (m, 1H), 3.28-3.13 (m, 1H), 2.48 (d, J=12.3 Hz, 1H), 2.46 (s, 3H), 2.25-1.97 (m, J=17.3, 10.6, 4.1 Hz, 4H), 1.76-1.28 (m, 3H).

Formation of N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]morpholine-4-carboxamide (44f)

(1S,3R)—N1-[5-fluoro-2-[5-fluoro-1-(p-tolylsulfonyl)pyrrolo[2,3-b]pyridin-3-yl]pyrimidin-4-yl]cyclohexane-1,3-diamine, 44e, (2.3 g, 4.6 mmol) was dissolved in DMF (50 mL) and treated with morpholine-4-carbonyl chloride (2.1 g, 13.8 mmol) and DIPEA (4.2 g, 5.6 mL, 32.3 mmol). After one hour, the resulting solution was diluted with water (400 mL) and stirred for an additional two hours. The resulting precipitate was collected by filtration, washed with water (3×50 mL) and dried to provide the crude product. This material was purified by flash chromatography on a 40 g column using EtOAc/DCM 20-100%, to provide 2.0 g of N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]morpholine-4-carboxamide as a white solid.

$^1$H NMR (300 MHz, DMSO-d6) δ 8.53-8.43 (m, J=11.9, 2.7 Hz, 3H), 8.22 (d, J=3.9 Hz, 1H), 8.07 (d, J=8.4 Hz, 2H), 7.44 (d, J=8.3 Hz, 2H), 6.32 (d, J=7.5 Hz, 1H), 4.05 (s, J=19.4 Hz, 1H), 3.62 (s, 1H), 3.58-3.45 (m, 4H), 3.27-3.18 (m, 4H), 2.36 (s, 3H), 2.12 (d, J=11.7 Hz, 1H), 1.99 (d, J=9.5 Hz, 1H), 1.83 (d, J=10.3 Hz, 2H), 1.53-1.11 (m, J=32.3, 22.8, 10.9 Hz, 4H).

Formation of N-[(1R,3S)-3-[[5-fluoro-2-(5-fluoro-1H-pyrrolo[2,3-b]pyridin-3-yl)pyrimidin-4-yl]amino]cyclohexyl]morpholine-4-carboxamide (706)

N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]morpholine-4-carboxamide, 44f, (2.0 g, 3.2 mmol) was suspended in methanol (50 mL) and treated with 25% sodium methoxide in methanol (19.9 mL, 92.3 mmol). After stirring for 1 hour, the solvent was evaporated under reduced pressure, and the residue was partitioned between water (100 mL) and ethyl acetate (100 mL). The organic layer was collected, dried on Na$_2$SO$_4$ and concentrated to provide the crude product as a yellow solid. This material was purified by silica gel chromatography on a 40 g column, using DCM/MeOH 1-6%. The purified fractions were treated with 2N HCl in ether and concentrated to provide 1.5 g of N-[(1R,3S)-3-[[5-fluoro-2-(5-fluoro-1H-pyrrolo[2,3-b]pyridin-3-yl)pyrimidin-4-yl]amino]cyclohexyl]-morpholine-4-carboxamide as a white solid.

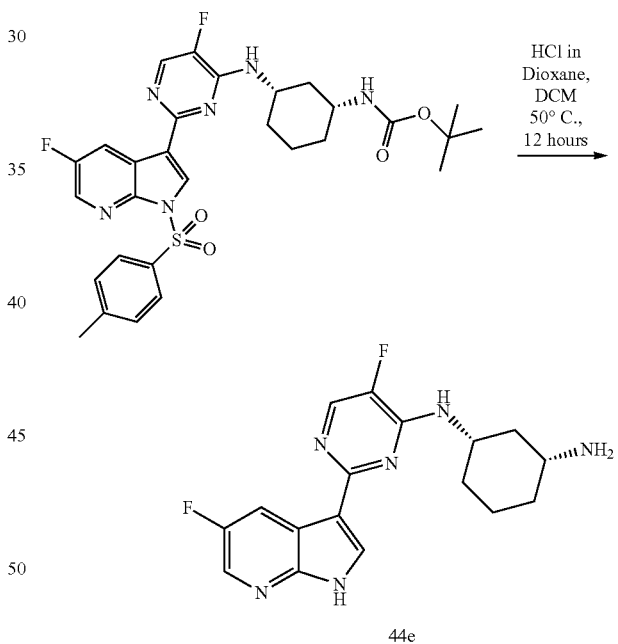

44e

Formation of (1S,3R)—N1-(2-fluoro-5-(5-fluoro-1H-pyrrolo[2,3-b]pyridin-3-yl)phenyl)cyclohexane-1,3-diamine (44e)

To a solution of tert-butyl (1R,3S)-3-(2-fluoro-5-(5-fluoro-1-tosyl-1H-pyrrolo-[2,3-b]pyridin-3-yl)phenylamino)cyclohexylcarbamate, 44d, (0.65 g, 1.09 mmol) in methylene chloride (22 mL) was added hydrogen chloride (2.71 mL of 4M solution in 1,4-dioxane, 10.86 mmol). The reaction was heated to 50° C. and stirred for 6 hours. The mixture was cooled to room temperature and concentrated in vacuo, producing a yellow solid. The crude residue was purified via

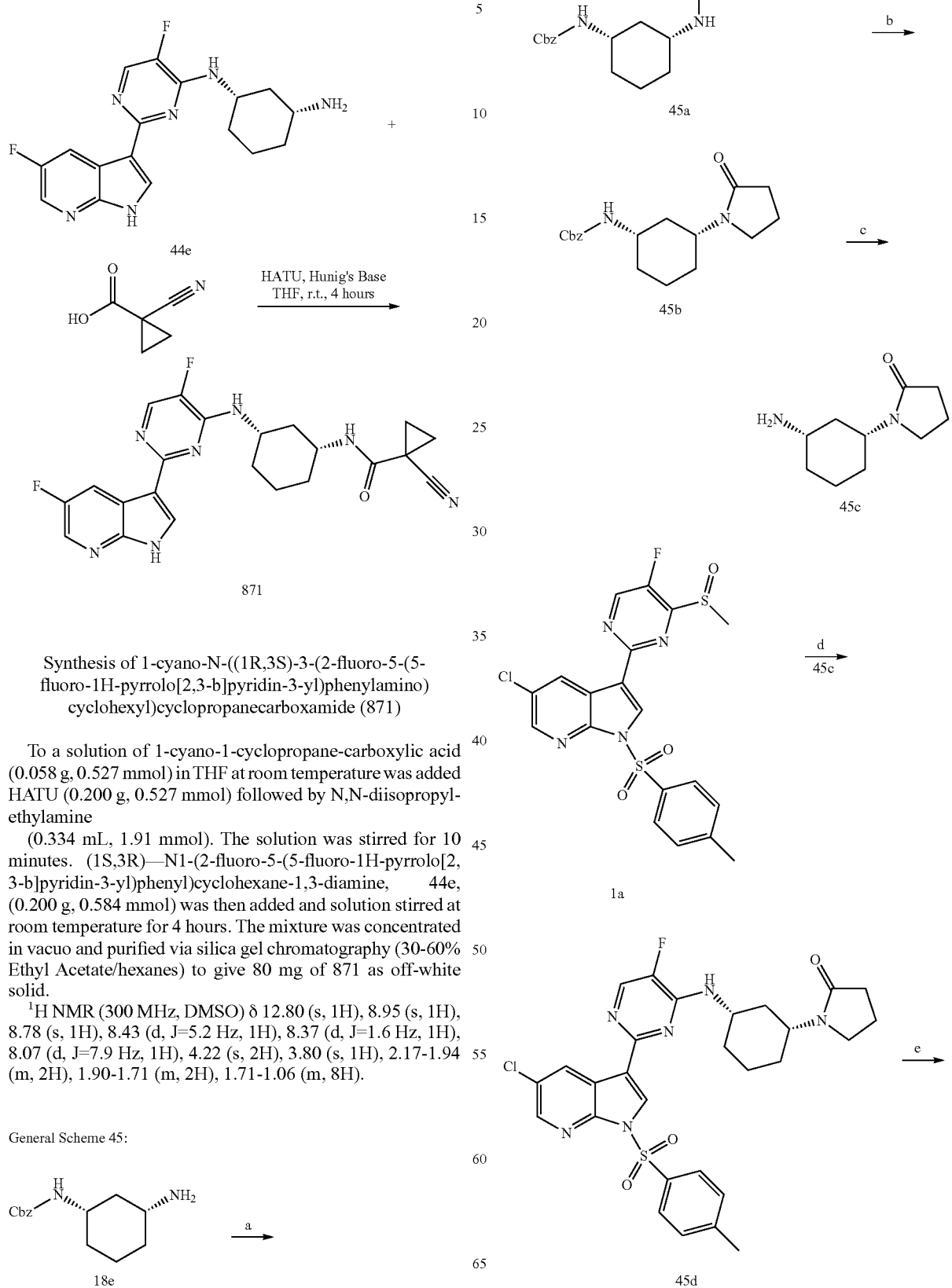

Synthesis of 1-cyano-N-((1R,3S)-3-(2-fluoro-5-(5-fluoro-1H-pyrrolo[2,3-b]pyridin-3-yl)phenylamino)cyclohexyl)cyclopropanecarboxamide (871)

To a solution of 1-cyano-1-cyclopropane-carboxylic acid (0.058 g, 0.527 mmol) in THF at room temperature was added HATU (0.200 g, 0.527 mmol) followed by N,N-diisopropylethylamine
(0.334 mL, 1.91 mmol). The solution was stirred for 10 minutes. (1S,3R)—N1-(2-fluoro-5-(5-fluoro-1H-pyrrolo[2,3-b]pyridin-3-yl)phenyl)cyclohexane-1,3-diamine, 44e, (0.200 g, 0.584 mmol) was then added and solution stirred at room temperature for 4 hours. The mixture was concentrated in vacuo and purified via silica gel chromatography (30-60% Ethyl Acetate/hexanes) to give 80 mg of 871 as off-white solid.

$^{1}$H NMR (300 MHz, DMSO) δ 12.80 (s, 1H), 8.95 (s, 1H), 8.78 (s, 1H), 8.43 (d, J=5.2 Hz, 1H), 8.37 (d, J=1.6 Hz, 1H), 8.07 (d, J=7.9 Hz, 1H), 4.22 (s, 2H), 3.80 (s, 1H), 2.17-1.94 (m, 2H), 1.90-1.71 (m, 2H), 1.71-1.06 (m, 8H).

General Scheme 45:

-continued

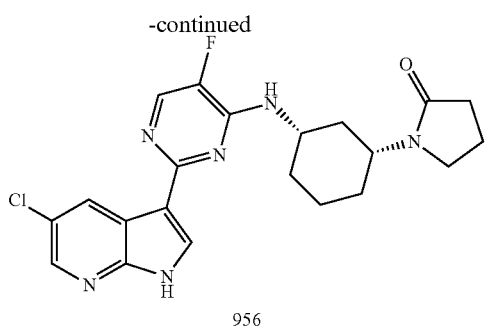

956

(a) 4-chlorobutanoyl chloride, Et₃N, CH₂Cl₂; (b) KOtBu, THF; (c) H₂, Pd—C, MeOH; (d) 45c, Na₂CO₃, THF—CH₃CN, 135° C.; (e) 4M HCl, dioxane-CH₃CN.

Formation of benzyl (1S,3R)-3-(4-chlorobutanamido)cyclohexylcarbamate (45a)

To a stirred slurry of benzyl N-[(1S,3R)-3-aminocyclohexyl]carbamate, 18e, (0.97 g, 3.41 mmol) in CH₂Cl₂ (34 mL), was added Et₃N (1.00 mL, 7.15 mmol), followed by 4-chlorobutanoyl chloride (0.40 mL, 3.58 mmol). After stirring at room temperature, the mixture was diluted with CH₂Cl₂, washed with 1N HCl (2×), 1N NaOH (2×), and brine. The organic layer was dried over Na₂SO₄, filtered and concentrated in vacuo to give 1.07 g of the desired product.

¹H NMR (300 MHz, MeOD) δ 7.33-7.26 (m, 5H), 5.04 (s, 2H), 3.73-3.65 (m, 1H), 3.56 (t, J=6.5 Hz, 2H), 3.44 (dq, J=3.9, 15.6 Hz, 1H), 2.33-2.28 (m, 2H), 2.11-1.97 (m, 3H), 1.90-1.75 (m, 3H), 1.45-1.28 (m, 1H) and 1.18-1.02 (m, 3H) ppm.

Formation of benzyl (1S,3R)-3-(2-oxopyrrolidin-1-yl)cyclohexylcarbamate (45b)

To a slurry of benzyl (1S,3R)-3-(4-chlorobutanamido)cyclohexylcarbamate, 45a, (0.21 g, 0.58 mmol) in THF (8.2 mL) was added potassium tert-butoxide (0.08 g, 0.69 mmol) at room temperature. After stirring at room temperature for 25 h, the mixture was quenched with aqueous saturated NH₄Cl and extracted with Et₂O (3×). The combined organic layers were washed with brine, dried over Na₂SO₄, filtered and concentrated in vacuo. Flash chromatography (SiO₂, 0-100% EtOAc-hexanes, gradient) provided a single fraction consisting of desired product and a small amount of starting material (168 mg). This material was immediately subjected to deprotection conditions.

¹H NMR (300 MHz, MeOD) δ 7.33-7.27 (m, 5H), 5.04 (s, 2H), 3.95-3.88 (m, 1H), 3.58-3.38 (m, 3H), 2.38-2.28 (m, 2H), 2.11-1.76 (m, 6H), 1.63 (d, J=2.7 Hz, 1H), 1.46-1.34 (m, 3H) and 1.21-1.06 (m, 2H) ppm.

Formation of 1-((1R,3S)-3-aminocyclohexyl)pyrrolidin-2-one (45c)

A degassed solution of benzyl (1S,3R)-3-(2-oxopyrrolidin-1-yl)cyclohexylcarbamate, 45b, (0.165 g, 0.522 mmol) and Pd on C (10% wet, Degussa, 0.050 g, 0.024 mmol) in MeOH (15 mL) was placed under H₂ atm (balloon). After 105 min, TLC (10% MeOH-DCM) indicated complete consumption of starting material. H₂ was removed and the solution filtered and concentrated in vacuo. The crude product was azeotroped with CH₃CN (2×) to remove any residual MeOH and provided the desired product (96 mg): FIA (M+H⁺) 183.27

Formation of 1-((1R,3S)-3-((2-(5-chloro-1-tosyl-1H-pyrrolo[2,3-b]pyridin-3-yl)-5-fluoropyrimidin-4-ylamino)cyclohexyl)pyrrolidin-2-one (45d)

A mixture of 5-chloro-3-(5-fluoro-4-methylsulfinyl-pyrimidin-2-yl)-1-(p-tolylsulfonyl)-pyrrolo[2,3-b]pyridine, 1a, (0.14 g, 0.29 mmol) and 1-((1R,3S)-3-aminocyclohexyl)pyrrolidin-2-one, 45c, (0.10 g, 0.53 mmol) and Na₂CO₃ (0.09 g, 0.88 mmol) freshly ground, in THF (2.25 mL) and CH₃CN (0.45 mL) and heat to 135° C. for 30 min. The mixture was slowly poured into 15 mL 1M HCl and extracted with EtOAc (5×). The combined organic layers were washed with brine, dried over Na₂SO₄ and filtered and concentrated in vacuo. Flash chromatography (SiO₂, 0-20% MeOH—CH₂Cl₂ gradient) provided the final product as a sticky residue. Trituration with CH₃CN provided an off white powder (105 mg) which was impure, but which was taken directly to the final deprotection step.

LC/MS R_t=3.90 min, (M+H) 589.49.

Formation of 1-((1R,3S)-3-((2-(5-chloro-1H-pyrrolo[2,3-b]pyridin-3-yl)-5-fluoro-pyrimidin-4-ylamino)cyclohexyl)pyrrolidin-2-one (956)

A mixture of partially purified 1-((1R,3S)-3-((2-(5-chloro-1-tosyl-1H-pyrrolo[2,3-b]pyridin-3-yl)-5-fluoropyrimidin-4-ylamino)cyclohexyl)pyrrolidin-2-one, 45d, (0.105 g, 0.180 mmol) in CH₃CN (5 mL) was treated with HCl (2 mL of 4 M, 8.00 mmol) in dioxane at 70° C. After 2H, the mixture was cooled to room temperature. Then CH₃CN was added and the solid that precipitated was triturated with more CH₃CN (3×). Preparative HPLC provided the desired product as the HCl salt (35 mg).

¹H NMR (300 MHz, MeOD) δ 8.72 (d, J=2.2 Hz, 1H), 8.49 (s, 1H), 8.39 (d, J=2.1 Hz, 1H), 8.29 (d, J=5.5 Hz, 1H), 4.54-4.47 (m, 1H), 4.13 (t, J=11.8 Hz, 1H), 3.57-3.45 (m, 2H), 2.42-2.36 (m, 2H), 2.25 (m, 1H), 2.15-2.00 (m, 4H), 1.90-1.59 (m, 4H) and 1.53-1.43 (m, 1H) ppm; LC/MS RT=3.15 min, (M+H) 429.53.

General Scheme 46:

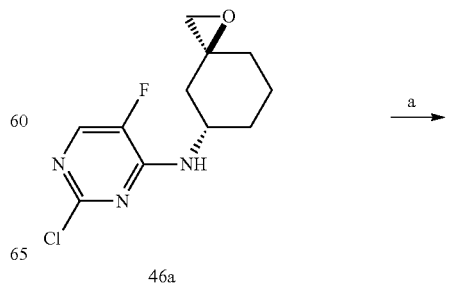

46a

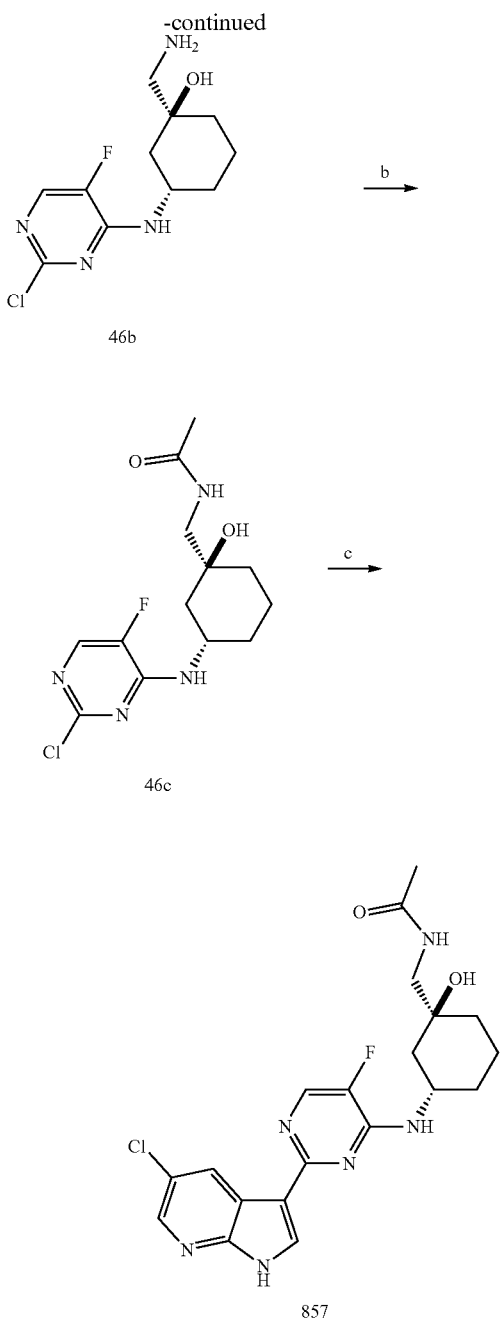

residue, (1S,3S)-1-(aminomethyl)-3-(2-chloro-5-fluoro-pyrimidin-4-ylamino)cyclohexanol, was taken into the next step without further purification.

Formation of N-{[(1S,3S)-3-(2-chloro-5-fluoropyrimidin-4-ylamino)-1-hydroxycyclohexyl]methyl}acetamide (46c)

(1S,3S)-1-(aminomethyl)-3-(2-chloro-5-fluoropyrimidin-4-ylamino)cyclohexanol, 46b, (0.19 g, 0.69 mmol) was dissolved in dichloromethane (15 mL) and treated with DIPEA (1.20 mL, 6.91 mmol) and acetyl chloride (0.10 mL, 1.38 mmol). After 5 minutes, the reaction mixture was diluted into 1N HCl (30 mL), and the aqueous layer was brought to a basic pH by addition of 1N NaOH. The resulting suspension was extracted with dichloromethane (50 mL). The organic layer was dried on $Na_2SO_4$ and concentrated in vacuo to provide the crude product, which was purified by silica gel chromatography (20-100% EtOAc/hexanes gradient) to afford 195 mg of N-{[(1S,3S)-3-(2-chloro-5-fluoropyrimidin-4-ylamino)-1-hydroxycyclo-hexyl]methyl}acetamide as a white foamy solid. LCMS RT=2.82 (M+1) 317.33.

Formation of N-{[(1S, 3S)-3-((2-(5-chloro-1H-pyrrolo[2,3-b]pyridin-3-yl)-5-fluoropyrimidin-4-ylamino)-1-hydroxycyclohexyl]methyl}acetamide (857)

N-{[(1S,3S)-3-(2-chloro-5-fluoropyrimidin-4-ylamino)-1-hydroxycyclohexy]-methyl}-acetamide, 46c, (0.2 g, 0.6 mmol) was dissolved in acetonitrile (6 mL) and treated with 5-chloro-1-(p-tolylsulfonyl)-3-(4,4,5,5-tetramethyl-1,3,2-dioxaborolan-2-yl)pyrrolo[2,3-b]pyridine (0.5 g, 1.2 mmol) followed by $Pd(PPh_3)_4$ (0.07 g, 0.06 mmol). Aqueous 2M sodium carbonate (3.0 mL, 6.1 mmol) was added, and the vial was sealed and heated in the microwave to 130° C. for 30 min. The organic layer was collected and concentrated in vacuo to provide the crude product, which was dissolved in DMSO and purified by HPLC using 5-70% MeOH/$H_2O$ with 6 mM HCl over 15 minutes to provide after concentration 75 mg of N-{[(1S,3S)-3-((2-(5-chloro-1H-pyrrolo[2,3-b]pyridin-3-yl)-5-fluoropyrimidin-4-ylamino)-1-hydroxycyclohexyl]methyl}acetamide hydrochloride as an off-white crystalline solid.

$^1$H NMR (300 MHz, DMSO-d6) δ 13.02 (s, 1H), 9.22 (s, 1H), 9.03 (d, J=2.4 Hz, 1H), 8.71 (d, J=2.1 Hz, 1H), 8.46 (d, J=5.5 Hz, 1H), 8.41 (d, J=2.1 Hz, 1H), 7.81 (t, J=5.8 Hz, 1H), 4.64 (d, J=8.0 Hz, 1H), 3.16-2.99 (m, 2H), 2.09-1.73 (m, 3H), 1.85 (s, 3H), 1.73-1.42 (m, 3H), 1.28 (dd, J=27.5, 10.6 Hz, 2H).; LCMS RT=3.47 (M+1) 433.37

(a) 30% ammonium hydroxide, water, 50° C.; (b) Acetyl chloride, diisopropylethylamine, dichloromethane, rt; (c) 5-chloro-3-(4,4,5,5-tetramethyl-1,3,2-dioxaborolan-2-yl)-1-tosyl-1H-pyrrolo[2,3-b]pyridine, $Pd(PPh_3)_4$, 2M sodium carbonate, acetonitrile, 130° C., microwave.

Formation of (1S,3S)-1-(aminomethyl)-3-(2-chloro-5-fluoropyrimidin-4-ylamino)cyclohexanol (46b)

2-Chloro-5-fluoro-N-[(3S,5S)-1-oxaspiro[2.5]octan-5-yl]pyrimidin-4-amine, 46a, (0.19 g, 0.73 mmol) was dissolved in water (75 mL) and treated with 30% ammonium hydroxide (10 mL, 86.0 mmol). The suspension was heated to 50° C. for 5 hrs then allowed to stir at room temperature overnight. The volatiles were evaporated under reduced pressure, and the General Scheme 47:

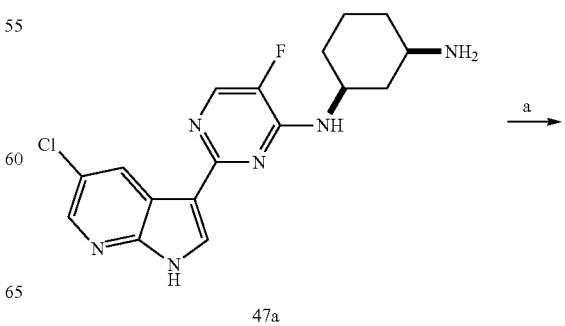

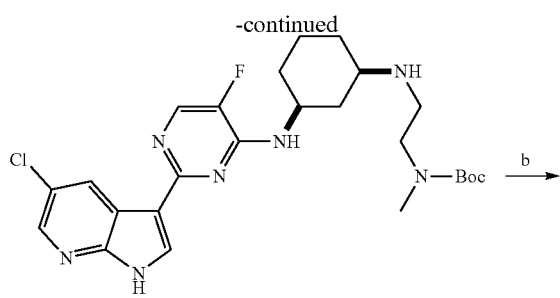

47b

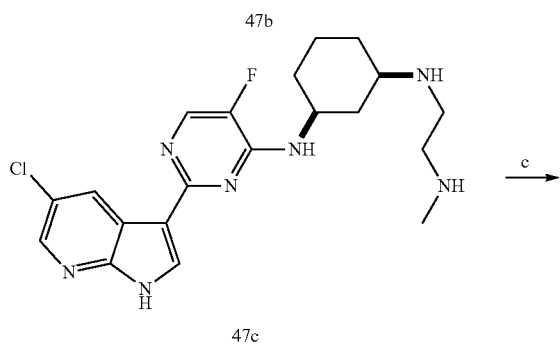

47c

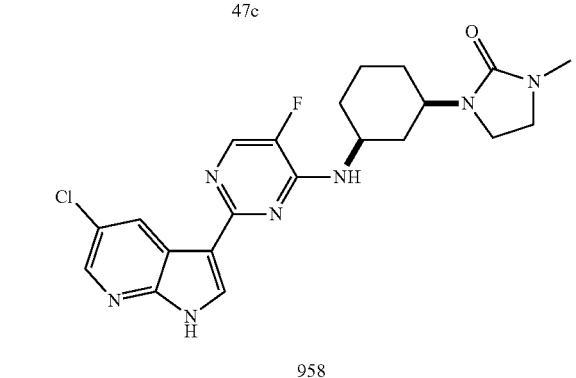

958

(a) tert-butyl N-methyl-N-(2-oxoethyl)carbamate, diisopropylethylamine, THF/EtOH, 70° C.;
(b) HCl/dioxane, THF/MeOH (c) bis(4-nitrophenyl) carbonate, diisopropylethylamine, DMF.

Formation of tert-butyl 2-((1R,3S)-3-((2-(5-chloro-1H-pyrrolo[2,3-b]pyridin-3-yl)-5-fluoropyrimidin-4-ylamino)cyclohexyl-amino)ethyl(methyl)carbamate (47b)

In a flask containing (1S,3R)—N1-(2-(5-chloro-1H-pyrrolo[2,3-b]pyridin-3-yl)-5-fluoropyrimidin-4-yl)cyclohexane-1,3-diamine, 47a, (0.14 g, 0.39 mmol) in THF/EtOH was added tert-butyl N-methyl-N-(2-oxoethyl)carbamate (0.10 g, 0.58 mmol) and diisopropylethylamine (0.13 mL, 0.77 mmol). The solution was heated at 70° C. for 30 min. Sodium triacetoxyborohydride (0.08 g, 0.39 mmol) was added. The solution was stirred at room temperature for 12 hrs. The solution was filtered and the solvent evaporated under reduced pressure. The resulting residue was purified by HPLC using 5-70% MeOH/H₂O with 6 mM HCl to provide the desired product.

Formation of (1S,3R)—N1-(2-(5-chloro-1H-pyrrolo[2,3-b]pyridin-3-yl)-5-fluoropyrimidin-4-yl)-N3-((2-(methylamino)ethyl)cyclohexane-1,3-diamine (47c)

In a flask containing tert-butyl 2-((1R,3S)-3-((2-(5-chloro-1H-pyrrolo[2,3-b]pyridin-3-yl)-5-fluoropyrimidin-4-ylamino)cyclohexylamino)ethyl(methyl)carbamate, 47b, (0.02 g, 0.04 mmol) in dichloromethane/MeOH mixture was added HCl in Dioxane (3.86 mL of 4 M solution, 15.44 mmol). The solution was stirred at room temperature for 12 hrs. The solvent was evaporated under reduced pressure and used without further purification.

Formation of 1-((1R,3S)-3-((2-(5-chloro-1H-pyrrolo[2,3-b]pyridin-3-yl)-5-fluoropyrimidin-4-ylamino)cyclohexyl)-3-methylimidazolidin-2-one (958)

In a flask containing (1St, 3R)—N1-(2-(5-chloro-1H-pyrrolo[2,3-b]pyridin-3-yl)-5-fluoropyrimidin-4-yl)-N3-((2-(methylamino)ethyl)cyclohexane-1,3-diamine, 47c, (0.020 g, 0.048 mmol) in DMF was added diisopropylethylamine (0.025 mL, 0.144 mmol) and bis(4-nitrophenyl) carbonate (0.016 g, 0.053 mmol). The reaction mixture was stirred at room temperature for 3 hrs. The resulting residue was purified by HPLC using 5-70% MeOH/H₂O with 6 mM HCl to provide the desired product.

General Scheme 48:

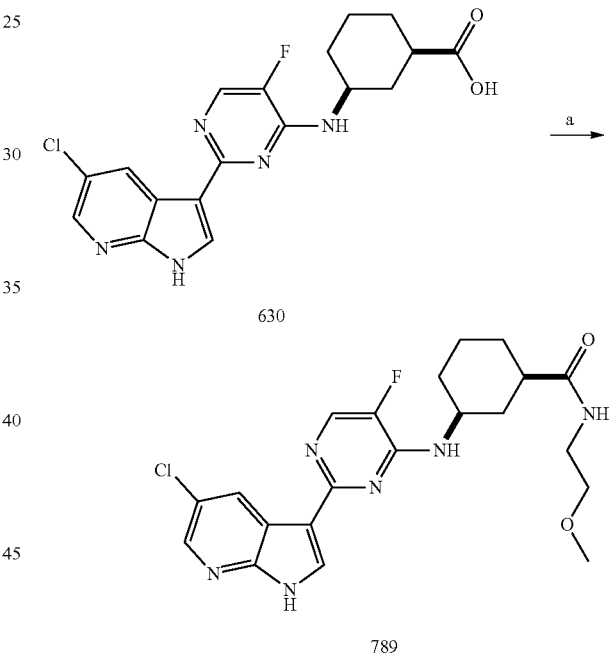

(a) 2-Methoxyethanamine, HATU, DIEA, CH₃CN, DMF.

Formation of (1R,3S)-3-((2-(5-chloro-1H-pyrrolo[2,3-b]pyridin-3-yl)-5-fluoropyrimidin-4-ylamino)-N-(2-methoxyethyl)cyclohexanecarboxamide (789)

(1R,3S)-3-[[2-(5-chloro-1H-pyrrolo[2,3-b]pyridin-3-yl)-5-fluoro-pyrimidin-4-yl]amino]cyclohexanecarboxylic acid (HCl salt) (0.05 g, 0.12 mmol), HATU (0.09 g, 0.24 mmol), diisopropylethylamine (0.06 g, 0.47 mmol) and 2-methoxyethanamine (0.04 g, 0.47 mmol) were stirred together in 1 ml each of DMF and CH₃CN at room temperature overnight. All volatiles were removed with a stream of nitrogen and heat. The residue was dissolved in methanol and purification with phase preparatory HPLC with 10-90% MeOH/water (HCl modifier) gave the desired product as the HCl salt.

General Scheme 49:

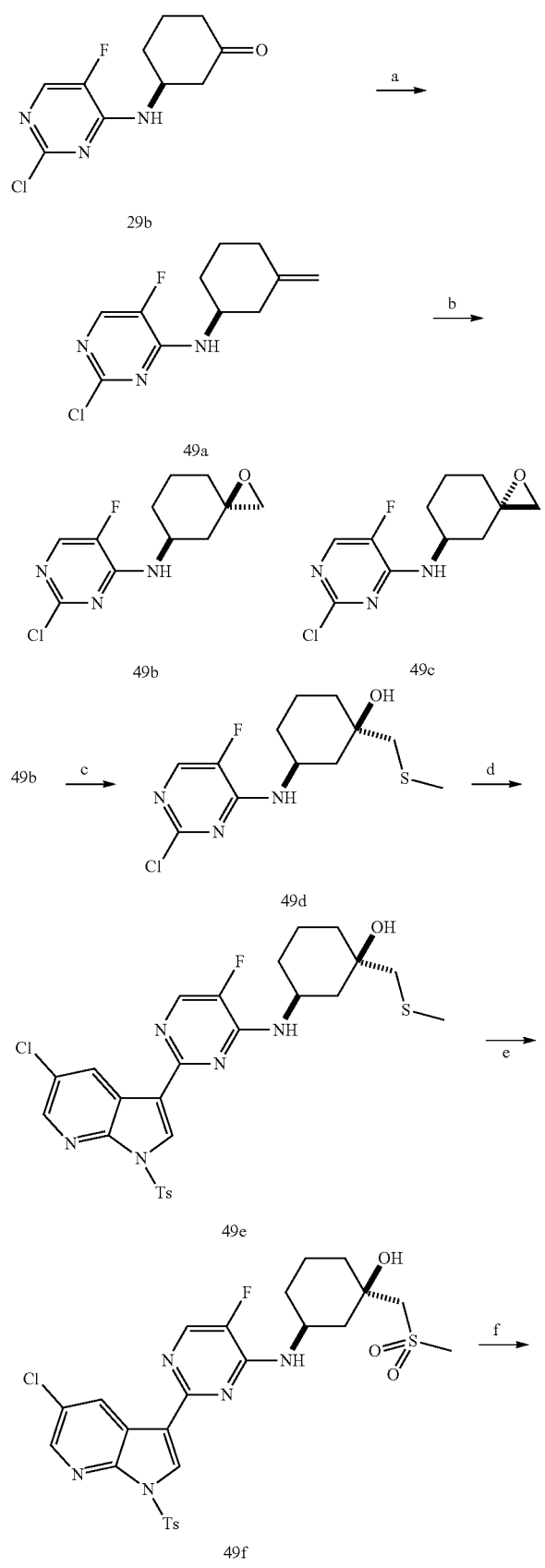

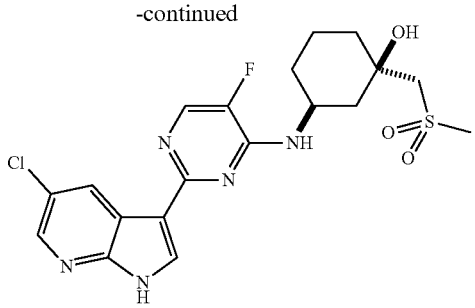

(a) methyl(triphenyl)phosphonium bromide, (bis(trimethylsilyl)amino)lithium, THF; (b) 3-chloroperoxybenzoic acid, MeOH, H₂O; (c) methylsulfanylsodium, THF; (d) 5-chloro-1-(p-tolylsulfonyl)-3-(4,4,5,5-tetramethyl-1,3,2-dioxaborolan-2-yl)pyrrolo[2,3-b]pyridine, Na₂CO₃, tetrakis triphenylphosphinepalladium(0), CH₃CN; (e) 3-chloroperoxybenzoic acid, CH₂Cl₂; (f) NaOMe, MeOH.

Formation of (S)-2-chloro-5-fluoro-N-(3-methylenecyclohexyl)pyrimidin-4-amine (49a)

To a suspension of methyl(triphenyl)phosphonium bromide (0.86 g, 2.40 mmol) in THF (100 mL) in a flamed dry flask was added (bis(trimethylsilyl)amino)lithium (2.40 mL of 1 M solution, 2.40 mmol) at room temperature. The reaction mixture was allowed to stir at room temperature for 1 hr. A solution of (S)-3-(2-chloro-5-fluoropyrimidin-4-ylamino)cyclohexanone, 29b, (0.48 g, 2.00 mmol) in 20 mL of THF was added. The reaction was allowed to stir at room temperature for 2 hrs. The mixture was quenched by pouring into brine and the aqueous phase was extracted with EtOAc. The layers were separated and the organic was dried over MgSO₄, filtered and evaporated to dryness. The crude residue was purified via silica gel chromatography (0-100% EtOAc/hexanes gradient) to afford 270 mg of the desired product: LCMS RT: 3.83 min, (M+1): 242.2.

Formation of 2-chloro-5-fluoro-N-((3R,5S)-1-oxaspiro[2.5]octan-5-yl)pyrimidin-4-amine (49b, 49c)

3-chloroperoxybenzoic acid (0.40 g, 1.79 mmol) was added to a solution of (S)-2-chloro-5-fluoro-N-(3-methylenecyclohexyl)pyrimidin-4-amine, 49a, (0.27 g, 1.12 mmol) in water (0.6 mL) and MeOH (1.5 mL) at room temperature. The reaction mixture was allowed to stir at room temperature for 1 hr. The mixture was diluted with EtOAc and washed with aqueous saturated NaHCO₃ solution. The organic phase was dried (MgSO₄), filtered and evaporated to dryness. The crude residue was purified via silica gel chromatography (0-100% EtOAc/hexanes gradient) which yielded both diastereomers, 49b and 49c. The isolated upper (less polar) spot, 49b, was carried forward: LCMS RT=3.21 (M+1) 258.2.

Formation of (1R,3S)-3-(2-chloro-5-fluoropyrimidin-4-ylamino)-1-(methyl-thiomethyl)cyclohexanol (49d)

2-chloro-5-fluoro-N-((3R,5S)-1-oxaspiro[2.5]octan-5-yl)pyrimidin-4-amine, 49b, (0.10 g, 0.38 mmol) was dissolved in THF (2 mL). Methylsulfanylsodium (0.08 g, 1.15 mmol) was added to the reaction and the mixture was allowed to stir at room temperature for 3 hrs. An additional 36 mg portion of methylsulfanylsodium in THF (2 mL) was added and the reaction mixture was stirred overnight at room temperature. After LCMS showed starting material was still present, the reaction was warmed to 50° C. and stirred for 1 hr. The reaction was quenched with water and diluted with EtOAc. The layers were separated and the organic phase was washed with brine, dried (MgSO$_4$), filtered and evaporated to dryness. The crude residue was purified via silica gel chromatography (0-100% Etoac/hexanes gradient). The product (contaminated with small amount of staring material) was carried on to the next step without further purification. LCMS RT=3.56 (M+1) 306.2.

Formation of (1R,3S)-3-((2-(5-chloro-1-tosyl-1H-pyrrolo[2,3-b]pyridin-3-yl)-5-fluoropyrimidin-4-ylamino)-1-(methylthiomethyl)cyclohexanol (49e)

To a solution of (1R,3S)-3-(2-chloro-5-fluoropyrimidin-4-ylamino)-1-(methylthiomethyl)cyclohexanol, 49d, (0.09 g, 0.28 mmol) in CH$_3$CN (4 mL) was added 5-chloro-1-(p-tolylsulfonyl)-3-(4,4,5,5-tetramethyl-1,3,2-dioxaborolan-2-yl)pyrrolo[2,3-b]pyridine (0.14 g, 0.33 mmol) followed by aqueous Na$_2$CO$_3$ (0.42 mL of 2 M solution, 0.83 mmol). The reaction was degassed with nitrogen for 15 min and tetrakis triphenylphosphinepalladium(0) (0.02 g, 0.01 mmol) was added. The reaction was heated to 140° C. via microwave irradiation for 20 minutes. The mixture was cooled to room temperature and was diluted with water/EtOAc. The layers were separated and the organic phase was washed with brine, dried over MgSO$_4$, filtered and evaporated to dryness. The crude residue was purified via silica gel chromatography (0-100% EtOAc/hexanes gradient).

1H NMR (300 MHz, DMSO) δ 8.76 (d, J=1.8 Hz, 1H), 8.47 (d, J=8.1 Hz, 1H), 8.30 (t, J=26.7 Hz, 1H), 8.05 (d, J=8.1 Hz, 2H), 7.95-7.45 (m, 2H), 7.43 (s, 1H), 4.81 (s, 1H), 4.32-3.84 (m, 1H), 2.70 (d, J=19.5 Hz, 2H), 2.36 (s, 2H), 2.14 (s, 1H), 2.13 (s, 1H), 2.14-1.94 (m, 2H), 2.14-1.59 (m, 6H), 1.48-0.83 (m, 3H).

Formation of (1R,3S)-3-((2-(5-chloro-1-tosyl-1H-pyrrolo[2,3-b]pyridin-3-yl)-5-fluoropyrimidin-4-ylamino)-1-(methylsulfonylmethyl)cyclohexanol (49f)

To a cold (0° C.) solution of (1R,3S)-3-((2-(5-chloro-1-tosyl-1H-pyrrolo[2,3-b]pyridin-3-yl)-5-fluoropyrimidin-4-ylamino)-1-(methylthiomethyl)cyclohexanol, 49e, (0.044 g, 0.077 mmol) in CH$_2$Cl$_2$ (2 mL) was added 3-chloroperoxybenzoic acid (0.034 g, 0.155 mmol). After stirring for 1 hour at 0° C., the mixture was diluted with water and CH$_2$Cl$_2$. The layers were separated and the organic was washed with aqueous saturated NaHCO$_3$ soln., dried over MgSO$_4$, filtered and evaporated to dryness. The crude residue was purified via silica gel chromatography (0-100% EtOAc/hexanes gradient). LCMS RT=4.20 (M+1) 608.3.

Formation of (1R,3S)-3-((2-(5-chloro-1H-pyrrolo[2,3-b]pyridin-3-yl)-5-fluoropyrimidin-4-ylamino)-1-(methylsulfonylmethyl)cyclohexanol (886)

To a solution of (1R,3S)-3-((2-(5-chloro-1-tosyl-1H-pyrrolo[2, 3-1)]pyridin-3-yl)-5-fluoropyrimidin-4-ylamino)-1-(methylsulfonylmethyl)cyclohexanol, 49f, (0.045 g, 0.074 mmol) in MeOH (2 mL) was added NaOMe (2 mL of 25% w/v, 9.255 mmol). The reaction mixture was allowed to stir at room temperature for 5 minutes, after which the mixture was quenched with the addition of aqueous saturated NH$_4$Cl solution and then diluted with EtOAc. The layers were separated and the organic was washed with brine, dried over MgSO$_4$, filtered and evaporated to dryness. The crude residue was purified via silica gel chromatography (0-10% MeOH/CH$_2$Cl$_2$ gradient).

General Scheme 50:

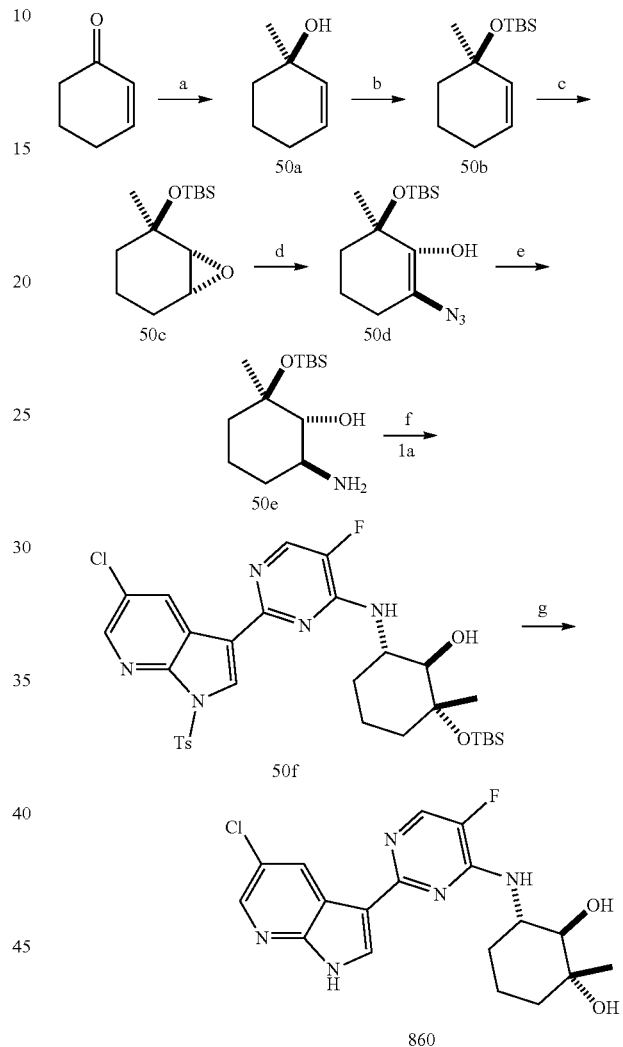

(a) AlMe$_3$, [Rh$_2$(cod)$_2$Cl$_2$], (S)-BINAP, THF, 0° C.; (b) TBSCl, imidazole, DMAP, DMF; (c) 3-chloroperoxybenzoic acid, CH$_2$Cl$_2$; (d) sodium azide, NH$_4$Cl, MeOH, H$_2$Ol; (e) H$_2$, Pd—C (10%), EtOAc; (f) 5-chloro-3-(5-fluoro-4-(methylsulfinyl)pyrimidin-2-yl)-1-tosyl-1H-pyrrolo[2,3-b]pyridine, $^i$Pr$_2$NEt, microwave, 70° C.; (g) TBAF, THF Formation of (R)-1-methylcyclohex-2-enol (50a)

In a 1000 mL flamed-dried round bottom flask, a mixture of (S)-BINAP (6.2 g, 10.0 mmol) and Rh$_2$(cod)$_2$Cl$_2$ (2.1 g, 4.2 mmol) in anhydrous THF (350 mL), was stirred under nitrogen for 30 minutes at room temperature. The homogeneous red reaction mixture was then cooled to 0° C. and cyclohex-2-en-1-one (16.0 g, 166.4 mmol) was added followed by dropwise addition of neat trimethylaluminium (12.4 g, 16.5 mL, 166.4 mmol). The mixture was allowed to warm to room temperature for 30 min and then stirred for 1 hour. The reaction was monitored by NMR and a worked up aliquot indicated complete conversion to tertiary alcohol.

When the reaction was complete, its temperature was lowered to 0° C. and quenched carefully with aqueous saturated NH$_4$Cl solution (500 mL). The layers were separated and the aqueous phase was further washed with ether (5×100 mL) and the combined organics were dried (MgSO$_4$) filtered over a celite pad and concentrated in vacuo to a yellow-brownish crude oil. Vacuum distillation (38° C. at 0.5-1 mm Hg), provided 13.9 g (72%) of light amber color oil.

Formation of (R)-tert-butyldimethyl(1-methylcyclohex-2-enyloxy)silane (50b)

To a solution of (R)-1-methylcyclohex-2-enol, 50a, (1.00 g, 8.91 mmol) in 20 dry DMF at room temperature was added 4H-imidazole (1.82 g, 26.74 mmol), tert-butyldimethylchlorosilane (2.02 g, 13.33 mmol) and a catalytic amount of 4-dimethylaminopyridine (0.11 g, 0.89 mmol). The resulting mixture was stirred at room temperature overnight. It was then diluted with ether, washed consecutively with water, citric acid and water. The organic phase was dried with MgSO$_4$, filtered and concentrated in vacuo. The colorless crude oil 1.98 g was used directly in the next step without further purification.

Formation of tert-butyldimethyl((1R,2R,6R)-2-methyl-7-oxabicyclo[4.1.0]heptan-2-yloxy)silane (50c)

3-chlorobenzenecarboperoxoic acid (2.47 g, 11.00 mmol) was added in one portion to a stirred solution of (R)-tert-butyldimethyl(1-methylcyclohex-2-enyloxy)silane, 50b, (1.98 g, 8.87 mmol) and sodium hydrogen carbonate in 30 mL of dry dichloromethane at room temperature under nitrogen. The resulting mixture was stirred for 20 hours. Then, 25% sodium sulfite solution (30 mL) was added and the resulting biphasic mixture was stirred for 15 minutes. The 2 layers were separated and the aqueous layer was extracted with dichloromethane (2×20 mL). The combined organic phases were washed with aqueous saturated NaHCO$_3$, dried (Na$_2$SO$_4$) and concentrated in vacuo. The crude residue was purified by silica gel chromatography (0-10% EtOAc-hexanes gradient) to provide 647 mg of compound 50c.

Formation of (1R,2R,3S)-3-azido-1-(tert-butyldimethylsilyloxy)-1-methylcyclo-hexan-2-ol (50d)

To a stirred solution of tert-butyl-dimethyl-[[(1R,5R,6R)-5-methyl-7-oxabicyclo[4.1.0]heptan-5-yl]oxy]silane, 50c, (0.05 g, 2.15 mmol) in methanol (5 mL) and H$_2$O(0.6 mL) was added NH$_4$Cl (0.23 g, 0.15 mL, 4.30 mmol), followed by portion wise addition of sodium azide (0.42 g, 1.26 mL, 6.45 mmol). The resulting reaction mixture was warmed to 60° C., stirred for 12 h, at which point TLC-analysis revealed traces of the starting material. The reaction mixture was cooled to ambient temperature, quenched with H$_2$O (2 mL), concentrated under reduced pressure to remove methanol, extracted with ethyl acetate (3×15 mL), washed with brine (10 mL), dried over MgSO$_4$, filter and concentrated under reduced pressure. The crude product was purified by silica gel chromatography (2.5-10% ethyl ether in hexanes gradient) to afford 254 mg of (1R,2S,6R)-2-azido-6-[tert-butyl(dimethyl)silyl]oxy-cyclohexanol, 50d, as a clear oil.

Formation of (1R,2R,3S)-3-amino-1-(tert-butyldimethylsilyloxy)-1-methylcyclohexan-2-ol (50e)

A solution of azide, 50d, (0.25 g; 0.89 mmol) in 20 mL of ethyl acetate was hydrogenated with Degussa palladium (20 mole %) under 1 atmosphere of hydrogen overnight. The reaction mixture was filtered over celite and the celite was eluted with 2×10 mL of EtOAc. The filtrate was concentrated in vacuo to afford 230 mg of an oil that was used directly for the next step without further purification.

Formation of (1R,2R,6S)-2-(tert-butyldimethylsilyloxy)-6-(2-(5-chloro-1-tosyl-1H-pyrrolo[2,3-b]pyridin-3-yl)-5-fluoropyrimidin-4-ylamino)-2-methylcyclohexanol (50f)

To a stirred suspension of (1R,2R,6S)-6-amino-2-[tert-butyl(dimethyl)silyl]oxy-2-methyl-cyclohexanol, 50e, (0.16 g, 0.62 mmol) in THF (8 mL) in a microwave sealed tube vessel was added 5-chloro-3-(5-fluoro-4-(methylsulfinyl)pyrimidin-2-yl)-1-tosyl-1H-pyrrolo[2,3-b]pyridine, 1a, (0.29 g, 0.63 mmol) followed by N-ethyl-N-isopropyl-propan-2-amine (0.13 mL, 0.74 mmol). The resulting reaction mixture was capped and warmed to 70° C., stirred for 14 h. The reaction mixture was cooled to ambient temperature, added water (2 mL), concentrated under reduced pressure to remove THF. The crude product was diluted with ethyl acetate (25 mL), insoluble material (sulfone 1a) was removed by filtration. The organic layer was separated, washed with brine (2×5 mL), dried over Na$_2$SO$_4$, filter and concentrated under reduced pressure. The crude product was purified by silica-gel plug using 10-30% ethyl acetate in hexanes as eluant to afford 350 mg of (1R,2R,6S)-2-[tert-butyl(dimethyl)silyl] oxy-6-[[2-methyl [5-chloro-1-(p-tolylsulfonyl)-pyrrolo[2,3-b]pyridin-3-yl]-5-fluoro-pyridin-4-yl]amino]cyclohexanol (500.

Formation of (1R,2R,3S)-3-((2-(5-chloro-1H-pyrrolo[2,3-b]pyridin-3-yl)-5-fluoro-pyrimidin-4-ylamino)-1-methylcyclohexane-1,2-diol (860)

To a stirred solution of (1R,2R,6S)-2-[tert-butyl(dimethyl) silyl]oxy-6-[[2-methyl[5-chloro-1-(p-tolylsulfonyl)-pyrrolo [2,3-b]pyridin-3-yl]-5-fluoro-pyridin-4-yl]amino]cyclohexanol, 50f, (0.11 g; 0.16 mmol) in THF (2 mL) at room temperature, was added tetrabutylammonium fluoride (1.5 equiv) and the reaction mixture stirred for 1.5 h, at which point HPLC-analysis revealed no starting material but the de-tosylated product was observed with minor desilylation. An additional equivalent of TBAF was added and the reaction mixture was stirred at room temperature overnight. The reaction mixture was suspended in ethyl acetate (10 mL), washed with H$_2$O (2×4 mL), aqueous saturated NH$_4$Cl solution (2 mL) and brine (2 mL). The organic phase was dried (Na$_2$SO$_4$) and concentrated in vacuo to provide 139 mg of crude. The crude residue was purified by reverse phase HPLC (5-95% MeOH/water w/HCl buffer over 15 minutes). to afford 15 mg of desired product, 860. LCMS M+1=392.34

General Scheme 51:

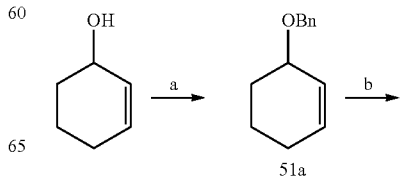

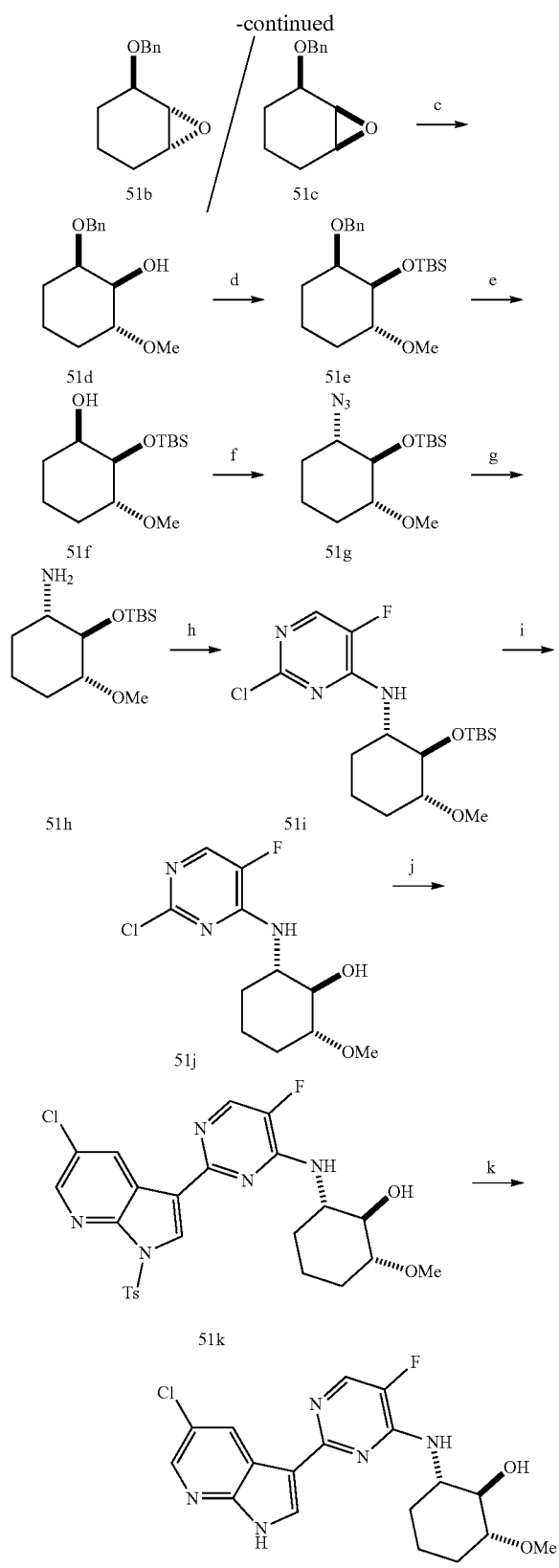

DMAP, DMF; (e) H₂, Pd—C (10%), EtOAc; triphenylphosphine, diisopropylazadicarboxylate, diphenylphosphoryl azide, THF; (g) H₂, Pd—C (10%), EtOAc; (h) 2,4-dichloro-5-fluoropyrimidine, K₂CO₃, CH₃CN/IPA; (i) TsOH, MeOH; (j) 5-chloro-3-(4,4,5,5-tetramethyl-1,3,2-dioxaborolan-2-yl)-1-tosyl-1H-pyrrolo[2,3-b]pyridine, aq Na₂CO₃, CH₃CN, microwave, 120° C.; (k) LiOH, H₂O/THF, microwave, 120° C.

Formation of ((cyclohex-2-enyloxy)methyl)benzene (51a)

A solution of cyclohex-2-en-1-ol (10.0 g, 101.9 mmol) in anhydrous THF (100 mL) was added to a stirred suspension containing sodium hydride (8.0 g, 199.7 mmol) (60% dispersion in oil) and benzyl bromide in anhydrous THF (250 mL) maintained at 50° C. The resulting solution was stirred at 55-60° C. for 18 h. After cooling to ambient temperature, water was added to quench the reaction and the mixture was diluted with ether (500 mL). The organic phase was separated, dried (Na₂SO₄), filtered and concentrated in vacuo to an oil that was subjected to a short silica plug filtration to provide 16.1 g of desired product 51a that was used directly in the next step without further purification.

Formation of racemic cis and trans-1-benzyloxy)-7-oxabicyclo[4.1.0]heptane (51b and 51c)

A solution of benzyl ether 51a (16.10 g, 0.89 mol) in 500 mL of CH₂Cl₂ at 0° C. was treated with 77% m-CPBA (21.08 g; 0.09 mol) portionwise. The reaction mixture was stirred at 0° C. for 2 h then at room temperature for 12 h. When the reaction is complete, it was quenched with sodium thiosulfate (100 mL) and the organic phase was further washed with another 100 mL of sodium thiosulfate, followed by aqueous NaHCO₃ solution, 5% NaOH (200 mL) and finally water. The organic phase was dried (Na₂SO₄) and concentrated in vacuo to afford an oil that was purified by silica gel chromatography (5% to 20% Et₂O/hexanes) to afford 11.44 g of trans-epoxide 51b and 3.95 g of cis-epoxide 51c were isolated (66:34 ratio).

Formation of racemic 1-benzyloxy-3-methoxycyclohexan-2-ol (51d)

A solution of cis-1-benzyloxy)-7-oxabicyclo[4.1.0]heptane, 51c, (2.0 g; 9.8 mmol) in 0.2N sulfuric acid (9.8 mmol) in 30 mL of anhydrous methanol was stirred at room temperature for 30 minutes. The reaction was diluted with water and extracted with ether. The organic phase was dried (Na₂SO₄) and concentrated in vacuo to afford 2.31 g of an oil that was used directly in the next step without further purification.

Formation of racemic [1-benzyloxy-3-methoxy-2-cyclohexanoxy]tert-butyl-dimethylsilane (51e)

To a solution of 1-benzyloxy-3-methoxy-cyclohexan-2-ol, 51d, (2.31 g, 9.78 mmol), tert-butyl-chlorodimethyl-silane (2.21 g, 2.73 mL, 14.66 mmol) in 20 dry DMF at room temperature was added 4H-imidazole (1.997 g, 29.33 mmol) and a catalytic amount of 4-dimethylaminopyridine (0.12 g, 0.98 mmol). The resulting mixture was stirred at room temperature overnight. It was then diluted with ether, washed with water, aqueous saturated citric acid solution and water again. The organic phase was dried with MgSO₄, filtered and (a) NaH, BnBr, THF, 60° C.; (b) 3-chloroperoxybenzoic acid, CH₂Cl₂, 0° C.; (c) H₂SO₄, MeOH; (d) TBSCl, imidazole, concentrated in vacuo. The colorless crude oil was used directly in the next step without further purification.

Formation of racemic [1-Hydroxy-3-methoxy-2-cyclohexanoxy]tert-butyl-dimethylsilane (51f)

A solution of racemic [1-benzyloxy-3-methoxy-2-cyclohexanoxy]tert-butyl-dimethylsilane, 51e, (3.4 g, 9.7 mmol) was dissolved in ethyl acetate (50 mL) and hydrogenated under 45 PSI of hydrogen with Pd—C 10% for 1 h. The reaction mixture was filtered over a nylon/fiberglass filter to provide, after concentration in vacuo 2.72 g of desired product 51f. This material was used directly in the next step without further purification.

Formation of racemic [1-Azido-3-methoxy-2-cyclohexanoxy]tert-butyl-dimethylsilane (51g)

To a solution of racemic [1-Hydroxy-3-methoxy-2-cyclohexanoxy]tert-butyl-dimethylsilane, 51f, (2.5 g; 9.6 mmol) in 60 mL of dry THF at room temperature was added, triphenylphosphine (5.0 g; 19.2 mmol), DIAD (3.9 g; 19.2 mmol) and diphenylphosphoryl azide (5.3 g; 19.2 mmol) and the reaction mixture was stirred at room temperature for 60 h. The solvent was concentrated in vacuo and the resultant oil was purified by silica gel chromatography (10% Et$_2$O-Hexane to ether gradient) to afford 2.57 g of the desired product 51g.

Formation of racemic [1-Amino-3-methoxy-2-cyclohexanoxy]tert-butyl-dimethylsilane (51h)

A solution of racemic [1-Azido-3-methoxy-2-cyclohexanoxy]tert-butyl-dimethylsilane, 51g, (2.57 g; 6.3 mmol) in 20 mL of ethyl acetate was hydrogenated with Pd—C 10% (5 mole %; Degussa) at 45 PSI in a Parr hydrogenation apparatus for 1 h. The reaction mixture was filtered over a nylon and glass fiber filter and concentrated in vacuo to provide 2.32 g of the desired product 51h as a white solid.

Formation of racemic N-((1-2-(tert-butyldimethylsilyloxy)-3-methoxycyclohexyl)-2-chloro-5-fluoropyrimidin-4-amine (51i)

In a flask was placed racemic [1-Amino-3-methoxy-2-cyclohexanoxy]tert-butyl-dimethylsilane, 51h, (2.32 g; 6.26 mmol). To this was added MeCN and IPA (1.5:1 v/v) to a total volume of 125 mL. To the solution was added dipotassium carbonate (4.32 g, 31.30 mmol) and the mixture was allowed to stir 30 minutes at room temperature (to remove any water that might be present). To this mixture was added 2,4-dichloro-5-fluoro-pyrimidine (3.14 g, 18.78 mmol) and the mixture was stirred at room temperature for 60 h. The reaction was filtered thru celite and concentrated in vacuo. The crude residue was purified by silica gel chromatography (20-100% Ether/hexanes gradient) to afford 2.27 g pure racemate compound 51i.

Formation of (1R,2S,6R)-2-(2-chloro-5-fluoropyrimidin-4-ylamino)-6-methoxy-cyclohexanol (51j)

To a solution of compound racemic N-((1-2-(tert-butyldimethylsilyloxy)-3-methoxycyclohexyl)-2-chloro-5-fluoropyrimidin-4-amine, 51i, (1.96 g, 5.03 mmol) in 30 mL of MeOH was added p-TsOH (1.73 g; 10.06 mmol). The reaction mixture was stirred at room temperature for 3 h and then was concentrated to dryness. The residue was dissolved in EtOAc (125 mL) and washed with aqueous potassium carbonate 1M (2×50 mL), then brine. The organic phase was dried (Na$_2$SO$_4$), filtered and concentrated in vacuo to give, after SFC enantiomers separation (50% EtOH-50% CO$_2$; 10 mL/min; 100 bar) 635 mg of chiral alcohol 51j as a white solid.

Formation of (1R,2S,6R)-2-(2-(5-chloro-1-tosyl-1H-pyrrolo[2,3-b]pyridin-3-yl)-5-fluoropyrimidin-4-ylamino)-6-methoxycyclohexanol (51k)

In a microwave tube was placed 5-chloro-1-(p-tolylsulfonyl)-3-(4,4,5,5-tetramethyl-1,3,2-dioxaborolan-2-yl)pyrrolo[2,3-b]pyridine (0.10 g, 0.23 mmol). To this was added acetonitrile (0.61 mL) and the solution was deoxygenated with nitrogen. To the reaction was added (1R,2S,6R)-2-(2-chloro-5-fluoropyrimidin-4-ylamino)-6-methoxy-cyclohexanol, 51j, (0.04 g, 0.14 mmol) and palladium catalyst (24 mg), and then aqueous sodium carbonate (0.21 mL of 2 M solution, 0.41 mmol). The reaction was sealed and heated to 120° C. in the microwave reactor for 15 min. The reaction was diluted with ethyl acetate (40 mL), filtered thru florisil, and concentrated in vacuo to give crude as a green solid. This was purified by silica gel chromatography (20-75% EtOAc/hexanes gradient). Used resulting product directly in the next step.

LCMS (M+1)=546.35.

Formation of (1R,2S,6R)-2-(2-(5-chloro-1H-pyrrolo[2,3-b]pyridin-3-yl)-5-fluoropyrimidin-4-ylamino)-6-methoxycyclohexanol (831)

In a microwave vial was placed azaindole 51k (0.050 g; 0.092 mmol). To this was added 3 mL of THF and 0.9 mL of 0.8 M LiOH. The vial was sealed and heated to 120° C. for 15 minutes in the microwave. When the reaction is complete, it was neutralized with 9 equivalents of 1N HCl (0.704 mL), then aqueous saturated NaHCO$_3$ solution was added and the organic phase was separated and loaded onto silica gel for purification and eluted w/2% MeOH to 12% gradient over 10 minutes (4 g column) to provide 34.5 mg (91%) desired product 831.

General Scheme 52:

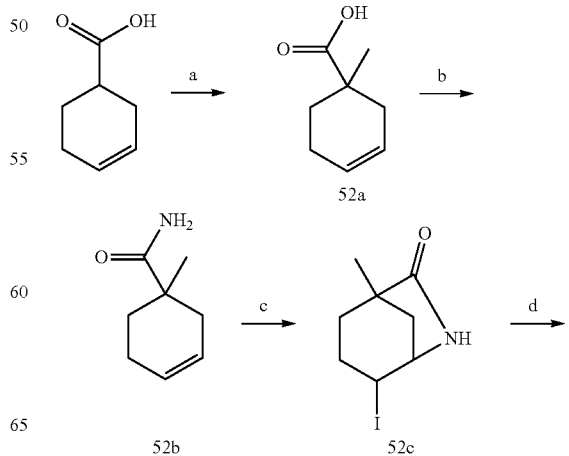

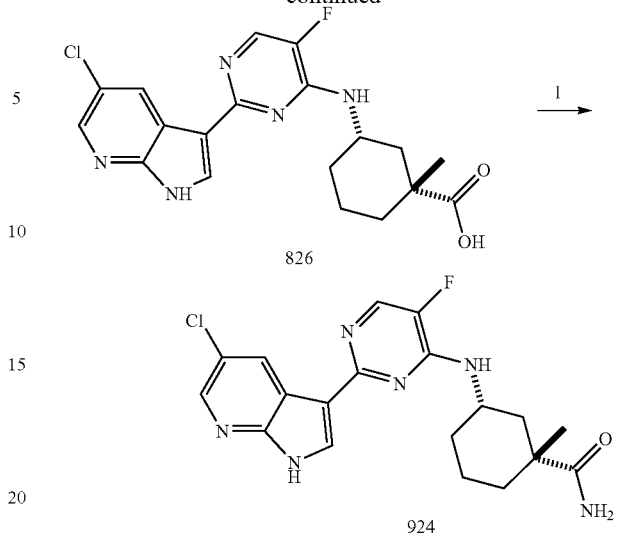

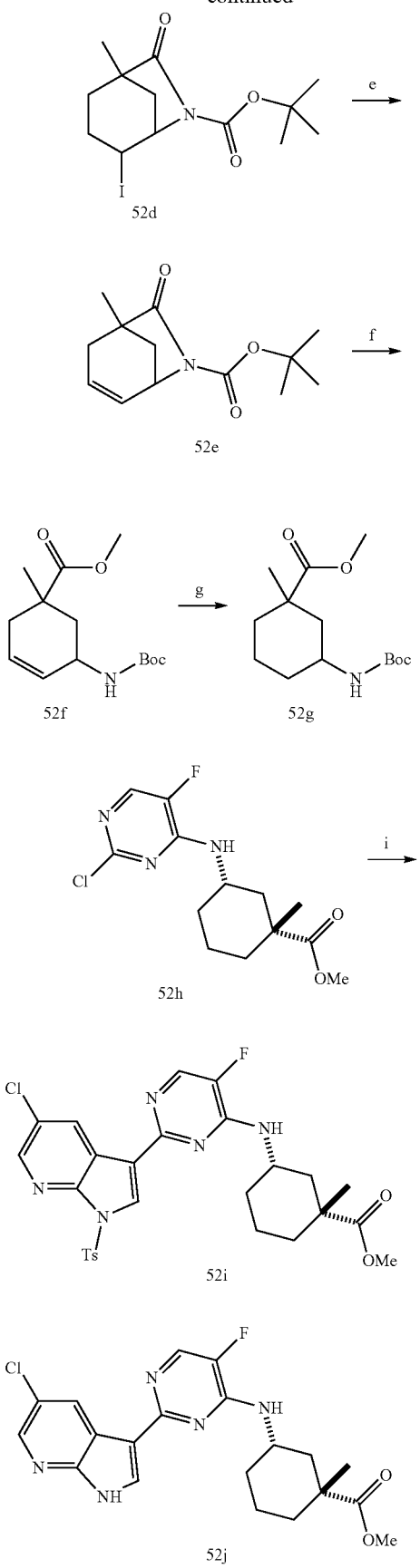

(a) LDA, iodomethane, THF, −78° C.; (b) SOCl$_2$, DMF, CH$_2$Cl$_2$, reflux, then NH$_4$OH; (c) TMSOTf, iodine, Et$_3$N, pentane, CH$_2$Cl$_2$; (d) Boc$_2$O, DMAP, CH$_2$Cl$_2$; (e) 1,8-Diazabicyclo[5.4.0]undec-7-ene, toluene, reflux; (f) Cs$_2$CO$_3$, MeOH; (g) H$_2$, Pd—C (5%), MeOH, 2 days; (h) HCl, MeOH; 2,4-dichloro-5-fluoropyrimidine, $^i$Pr$_2$NEt, DMF; SFC chiral separation; (i) 5-chloro-3-(4,4,5,5-tetramethyl-1,3,2-dioxaborolan-2-yl)-1-tosyl-1H-pyrrolo[2,3-b]pyridine, Pd(Ph$_3$P)$_4$, Na$_2$CO$_3$, THF/H$_2$O, reflux; (j) NaH, MeOH; (k) LiOH, H$_2$O/MeOH; (l) benzotriazol-1-yl-[bis(dimethylamino)methylene]oxonium hexafluorophosphate, $^i$Pr$_2$Net, THF, NH$_4$Cl.

Formation of 1-methylcyclohex-3-ene-1-carboxylic acid (52a)

N-isopropylpropan-2-amine (50.1 g, 69.5 mL, 495.5 mmol) was dissolved in 50 mL of THF. To the solution was added n-butyllithium (174.4 mL of 2.5 M solution in hexanes, 436.0 mmol) at −78° C. The resulting solution was stirred for 30 minutes at −78° C. To the reaction was then added cyclohex-3-ene-1-carboxylic acid (25.0 g, 198.2 mmol) and the reaction was allowed to warm to 60° C. for 2 hrs. The reaction was cooled to room temp and iodomethane (29.5 g, 13.0 mL, 208.1 mmol) was added and the reaction was allowed to stir overnight and then quenched with 1 N HCl until the pH<4. The crude product was extracted into CH$_2$Cl$_2$ and water. The organic phase was concentrated in vacuo to a yellow oil (27 g) and used without further purification.
MS/RT: 141.09 (M+H)/1.65

Formation of 1-methylcyclohex-3-ene-1-carboxamide (52b)

To a solution of 1-methylcyclohex-3-ene-1-carboxylic acid, 52a, (54.0 g, 385.2 mmol) dissolved in CH$_2$Cl$_2$ (200 mL) was added thionyl chloride (56.2 mL, 770.4 mmol) and 1 mL of DMF. The reaction was warmed to reflux for 3 hrs, then cooled and concentrated in vacuo. The residue was redissolved in 200 mL of CH$_2$Cl$_2$. To the reaction was added ammonium hydroxide (148.2 mL of 13 M solution, 1.9 mol) slowly. The reaction was stirred overnight. The reaction was extracted into CH$_2$Cl$_2$ and water. The organic phase was concentrated in vacuo and purified via flash silica gel chromatography (EtOAc), yielding 25 g of 1-methylcyclohex-3-ene-1-carboxamide.
MS/RT: 139.96 (M+H)/2.66

Formation of 4-iodo-1-methyl-6-azabicyclo[3.2.1]octan-7-one (52c)

A solution of 1-methylcyclohex-3-ene-1-carboxamide, 52b, (5.0 g, 35.9 mmol) dissolved in 100 mL of pentane and $CH_2Cl_2$ was cooled to 0° C. and treated with triethylamine (11.0 mL, 79.0 mmol) and trimethylsilyl-triflate (14.3 mL, 79.0 mmol) sequentially. The resulting mixture was stirred for 1 hour at room temperature. The lower layer was removed via pipette. The upper pentane layer was concentrated in vacuo and the resulting residue was dissolved in THF (100 mL). To the stirred reaction was added iodine (20.1 g, 79.02 mmol) and the reaction was allowed to stir overnight at room temperature. After quenching with $Na_2SO_3$ and $NaHCO_3$, the reaction was partitioned between $CH_2Cl_2$ and water. The organic layers were combined, dried over $Na_2SO_4$, concentrated in vacuo to a dark yellow oil (9.5 g) that was used without further purification.
MS/RT: 266.06 (M+H)/2.39

Formation of tert butyl 4-iodo-1-methyl-7-oxo-6-azabicyclo[3.2.1]octane-6-carboxylate (52d)

To a solution of 4-iodo-1-methyl-6-azabicyclo[3.2.1]octan-7-one, 52c, (9.5 g, 35.8 mmol) in $CH_2Cl_2$ (100 mL) was added DMAP (0.2 g, 1.8 mmol), triethylamine (15.0 mL, 107.5 mmol) and tert-butoxycarbonyl tert-butyl carbonate (7.8 g, 35.8 mmol). The reaction was stirred overnight at room temperature. The product was extracted into $CH_2Cl_2$ and water. The organic layer was concentrated in vacuo and the residue was purified via silica gel chromatography (4:1 Hexanes:EtOAc), yielding 7.6 g.
MS/RT: 366.06 (M+H)/3.95

Formation of tert butyl 4-iodo-1-methyl-7-oxo-6-azabicyclo[3.2.1]oct-3-ene-6-carboxylate (52e)

To a solution of tert-butyl 4-iodo-1-methyl-7-oxo-6-azabicyclo[3.2.1]octane-6-carboxylate, 52d, (7.6 g, 20.8 mmol) in 100 mL of toluene was added 1,8-diazabicyclo[5.4.0]undec-7-ene (6.2 mL, 41.6 mmol). The reaction was warmed to reflux and stirred overnight. The reaction was concentrated in vacuo and the resulting residue was purified by silica gel chromatography (4:1 Hexanes:EtOAc), yielding 4.9 g of the desired product, 52e.
MS/RT: 238.14 (M+H)/3.33

Formation of methyl 5-(tert-butoxycarbonylamino)-1-methylcyclohex-3-enecarboxylate (52l)

To a solution of tert-butyl 1-methyl-7-oxo-6-azabicyclo[3.2.1]oct-3-ene-6-carboxylate, 52e, (4.93 g, 20.78 mmol) in MeOH (100 mL) was added cesium carbonate (13.54 g, 41.56 mmol). The reaction was stirred overnight and then concentrated in vacuo. The cesium salts were precipitated with $Et_2O$ and filtered. The ether filtrate was evaporated to give 5.5 g of a yellow oil that was used without further purification.
MS/RT: 270.17 (M+H)/3.64

Formation of methyl 5-(tert-butoxycarbonylamino)-1-methylcyclohexanecarboxylate (52g)

Methyl 5-(tert-butoxycarbonylamino)-1-methylcyclohex-3-enecarboxylate, 52f, (5.59 g, 20.75 mmol) was dissolved in 100 mL of MeOH. To the stirred solution was added 5% palladium on carbon (1.11 g, 10.38 mmol) and the reaction was stirred under a hydrogen balloon for 2 days. The reaction was filtered through celite, and the filtrate was concentrated in vacuo and used without further purification.
MS/RT: 272.24 (M+H)/3.62

Isolation of (1R,3S)-methyl 3-(2-chloro-5-fluoropyrimidin-4-ylamino)-1-methyl-cyclohexanecarboxylate (52h)

A stirred solution of methyl 5-(tert-butoxycarbonylamino)-1-methylcyclohexanecarboxylate, 52g, (5.63 g, 20.75 mmol) in MeOH (20 mL) was treated with HCl gas for 10 minutes. The resulting solution was stirred at room temperature for 1 hour, then concentrated to dryness and redissolved in THF (50 mL). To the reaction mixture was added $^iPr_2NEt$ (10.84 mL, 62.25 mmol) and 2,4-dichloro-5-fluoro-pyrimidine (5.20 g, 31.12 mmol) sequentially. The reaction was stirred at reflux overnight, concentrated in vacuo and resulting residue was purified by silica gel chromatography (1:1 Hexane:EtOAc), yielding 2.2 g of the racemic product as a yellow oil. 300 mg of the racemic methyl 3-(2-chloro-5-fluoropyrimidin-4-ylamino)-1-methylcyclohexanecarboxylate was submitted for SFC chiral separation, yielding 100 mg of the desired product, 52h, as a yellow oil.
MS/RT: 302.16 (M+H)/3.68

Formation of (1R,3S)-methyl 3-((2-(5-chloro-1-tosyl-1H-pyrrolo[2,3-b]pyridin-3-yl)-5-fluoropyrimidin-4-ylamino)-1-methylcyclohexanecarboxylate (52i)

In a 25 mL round-bottomed flask were combined (1R,3S)-methyl 3-(2-chloro-5-fluoropyrimidin-4-ylamino)-1-methylcyclohexanecarboxylate, 52h, (0.061 g, 0.202 mmol), 5-chloro-1-(p-tolylsulfonyl)-3-(4,4,5,5-tetramethyl-1,3,2-dioxaborolan-2-yl)pyrrolo[2,3-b]pyridine (0.096 g, 0.222 mmol), disodium carbonate (0.064 g, 0.607 mmol) in 5 mL of THF and 1 ml of water. The reaction mixture was degassed via a stream of nitrogen. To the reaction was added tetrakis triphenyl phosphine palladium (O) (0.021 g, 0.202 mmol) and the reaction was stirred at reflux overnight. The reaction was concentrated in vacuo and purified by silica gel chromatography (4:1 Hexanes:EtOAc), yielding 85 mg of desired product, 52i.
MS/RT: 572.33 (M+H)/6.27

Formation of (1R,3S)-methyl 3-((2-(5-chloro-1H-pyrrolo[2,3-b]pyridin-3-yl)-5-fluoropyrimidin-4-ylamino)-1-methylcyclohexanecarboxylate (52j)

To a stirred solution of (1R,3S)-methyl 3-((2-(5-chloro-1-tosyl-1H-pyrrolo[2,3-b]pyridin-3-yl)-5-fluoropyrimidin-4-ylamino)-1-methylcyclohexanecarboxylate, 52i, (0.085 g, 0.149 mmol) in 10 mL of MeOH was added NaH (0.004 g, 0.178 mmol) at room temperature. The resulting suspension was stirred for 2 hrs, quenched with solid $NH_4Cl$. The mixture was concentrated in vacuo and purified via silica gel chromatography (3:1 Hexane:EtOAc), yielding 55 mg of the desired product, 52j.
MS/RT: 418.32 (M+H)/3.30

(1R,3S)-3-((2-(5-chloro-1H-pyrrolo[2,3-b]pyridin-3-yl)-5-fluoropyrimidin-4-ylamino)-1-methylcyclohexanecarboxylic acid (826)

To a solution of (1R,3S)-methyl 3-((2-(5-chloro-1H-pyrrolo[2,3-b]pyridin-3-yl)-5-fluoropyrimidin-4-ylamino)-1- methylcyclohexanecarboxylate, 52j, (0.035 g, 0.083 mmol) dissolved in MeOH (5 mL) and water (1 mL) was added LiOH (0.004 g, 0.168 mmol). The reaction was allowed to stir for 2 days at room temperature and then concentrated to dryness. The residue was washed with ethanol. The combined ethanol washings were concentrated in vacuo, yielding 30 mg of desired product as an off white solid.

$^1$H NMR: (300 MHz, DMSO) δ 12.34 (s, H), 8.74 (d, J=2.3 Hz, H), 8.33 (d, J=2.3 Hz, H), 8.28 (d, J=1.6 Hz, H), 8.17-8.12 (m, H), 4.34 (s, H), 4.29 (s, H), 3.89 (s, H), 3.55 (d, J=6.3 Hz, H), 3.32 (s, H), 2.50 (s, H), 2.29 (s, H), 1.95-1.90 (m, H), 1.82 (d, J=6.6 Hz, H), 1.76 (s, 3H), 1.67 (s, H), 1.55 (s, H), 1.44-1.42 (m, H), 1.31 (s, H), 1.23 (s, H), 1.17 (s, H), 1.07 (s, H), 0.84 (d, J=6.9 Hz, H) and −0.00 (d, J=1.0 Hz, H) ppm; MS/RT: 404.24 (M+H)/3.39.

Formation of (1R,3S)-3-[[2-(5-chloro-1H-pyrrolo[2,3-b]pyridin-3-yl)-5-fluoro-pyrimidin-4-yl]amino]-1-methyl-cyclohexanecarboxamide (924)

(1R,3S)-3-[[2-(5-chloro-1H-pyrrolo[2,3-b]pyridin-3-yl)-5-fluoro-pyrimidin-4-yl]amino]-1-methyl-cyclohexanecarboxylic acid, 826, (0.050 g, 0.108 mmol), benzotriazol-1-yl-[bis(dimethylamino)methylene]oxonium hexafluorophosphate (0.081 g, 0.216 mmol) and N-ethyl-N-isopropyl-propan-2-amine (0.075 mL, 0.432 mmol) were combined in 5 mL of THF. To the reaction was then added ammonia hydrochloride (0.002 g, 0.032 mmol) and the reaction was allowed to stir overnight at room temperature. After concentration under reduced pressure, the mixture was purified by reverse phase HPLC chromatography, yielding 3.3 mg of desired product.

$^1$H NMR (300 MHz, MeOD) δ 8.85 (d, J=2.4 Hz, H), 8.22 (d, J=2.3 Hz, H), 8.16 (s, H), 7.99 (d, J=4.1 Hz, H), 7.86 (s, H), 3.48 (d, J=7.0 Hz, H), 2.80 (s, H), 2.15 (s, H), 2.0 (s, H), 1.86 (qn, J=3.3 Hz, H), 1.80 (s, 3H), 1.74 (m, 2H), 1.44 (s, 6H); LC/MS: 403.34 (M+H), RT=1.77.

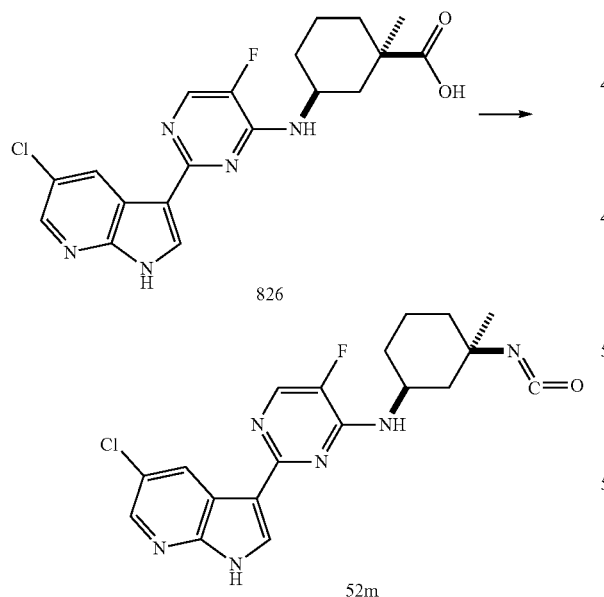

Formation of 2-(5-chloro-1H-pyrrolo[2,3-b]pyridin-3-yl)-5-fluoro-N-((1S,3R)-3-isocyanato-3-methylcyclohexyl)pyrimidin-4-amine (52m)

To a solution of (1R,3S)-3-[[2-(5-chloro-1H-pyrrolo[2,3-b]pyridin-3-yl)-5-fluoro-pyrimidin-4-yl]amino]-1-methyl-cyclohexanecarboxylic acid, 826, (0.100 g, 0.216 mmol) and (azido(phenoxy)phosphoryl)oxybenzene (0.093 mL, 0.432 mmol) in 10 mL of toluene was added 1 mL of N-ethyl-N-isopropyl-propan-2-amine. The reaction was warmed to reflux overnight. The mixture was concentrated to dryness and the residue was purified by silica gel chromatography (EtOAc), yielding 40 mg of desired product as a white foam.

MS/RT: 401.23 (M+H)/3.89

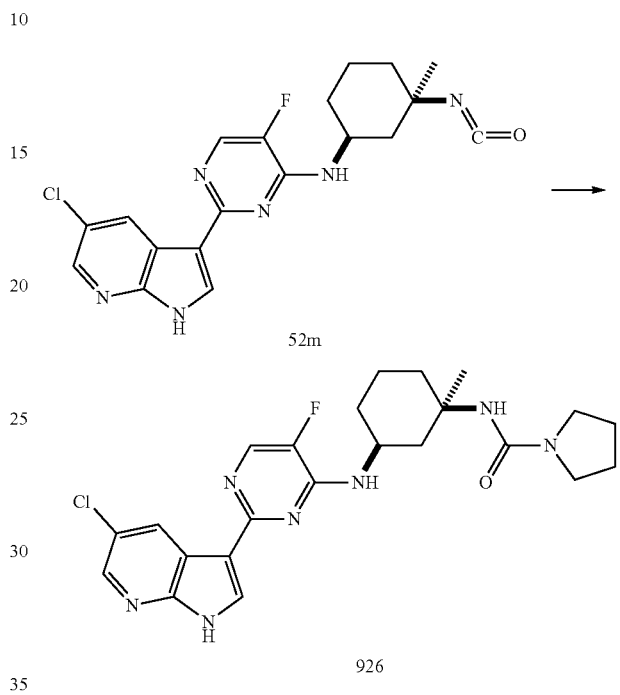

Formation of N-((1R,3S)-3-((2-(5-chloro-1H-pyrrolo[2,3-b]pyridin-3-yl)-5-fluoropyrimidin-4-ylamino)-1-methylcyclohexyl)pyrrolidine-1-carboxamide (926)

A solution of 2-(5-chloro-1H-pyrrolo[2,3-b]pyridin-3-yl)-5-fluoro-N-((1S,3R)-3-isocyanato-3-methylcyclohexyl)pyrimidin-4-amine, 52m, (0.035 g, 0.087 mmol) in 3 mL of NMP with 0.5 mL of pyrrolidine was warmed to 200° C. in a microwave for 30 minutes. The reaction was then concentrated in vacuo and purified by reverse phase HPLC chromatography, yielding 8.7 mg of desired product as a tan solid.

$^1$H NMR: (300.0 MHz, MeOD) δ 8.76 (d, J=2.4 Hz, H), 8.44-8.38 (m, 2H), 8.27 (d, J=5.6 Hz, H), 4.87 (d, J=5.1 Hz, H), 4.64-4.56 (m, 4H), 3.38-3.19 (m, 2H), 2.65 (s, 2H), 2.46 (m, H), 2.42 (s, 3H), 2.16 (s, H), 2.07 (t, J=12.0 Hz, H), 2.00 (s, H), 1.88 (q, J=6.6 Hz, H), 1.88 (s, H), 1.70 (s, H) and 1.61 (d, J=12.8 Hz, H) ppm; MS/RT: 472.38.

General Scheme 53

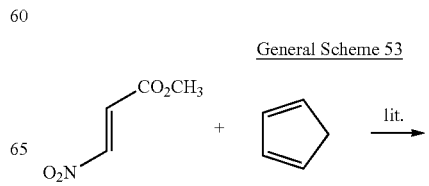

399
-continued

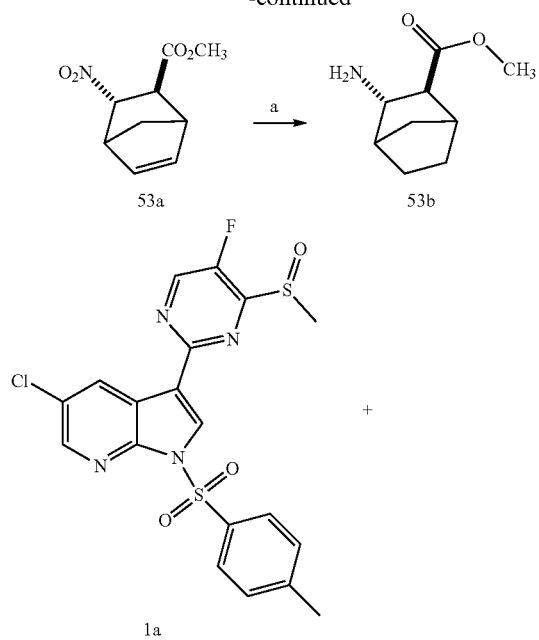

400
-continued

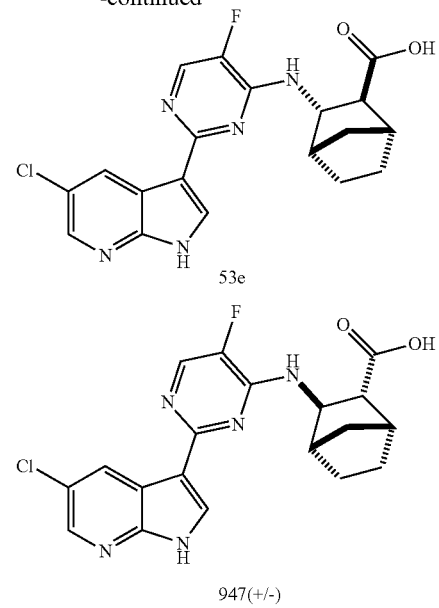

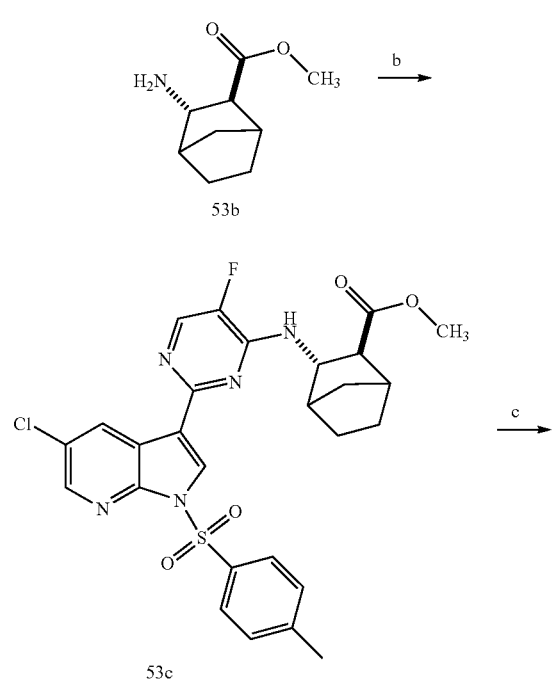

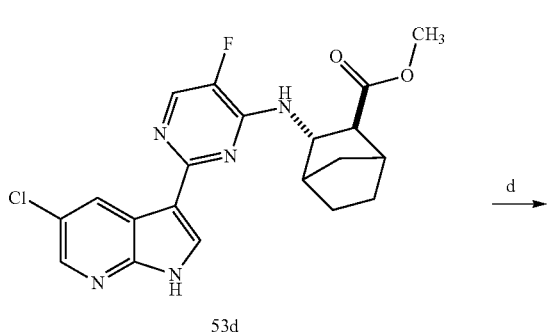

(a) H₂, Pd—C, MeOH; (b) Na₂CO₃, THF—CH₃CN, 135° C.; (c) NaOMe, MeOH, DCM; (d) NaOH, MeOH, THF.

Formation of (+/−)-2,3-Trans-methyl 3-nitrobicyclo[2.2.1]hept-5-ene-2-carboxylate (53a)

This compound was prepared as a mixture of trans isomers (endo:exo=84:16) following literature procedures described in: Chang, Linda L.; Truong, Quang; Doss, George A.; MacCoss, Malcolm; Lyons, Kathryn; McCauley, Ermengilda; Mumford, Richard; Forrest, Gail; Vincent, Stella; Schmidt, John A.; Hagmann, William K. Bioorg. Med. Chem. Lett. 2007, 17(3), 597-601.

Formation of (+/−)-2,3-Trans-methyl 3-aminobicyclo[2.2.1]heptane-2-carboxylate (53b)

A mixture of (+/−)-2,3-trans-methyl 3-nitrobicyclo[2.2.1]hept-5-ene-2-carboxylate, 53a, (0.32 g, 1.62 mmol) and Pd—C (10%) in MeOH was purged and placed under H₂ atm (50 PSI) and shaken overnight. The mixture was filtered through celite, concentrated in vacuo and azeotroped twice with CH₃CN to remove traces of MeOH.

¹H NMR of the crude mixture indicated the presence of both the endo and exo products (84:16=endo:exo) which were taken directly into the next reaction without further purification.

Formation of (+0-2,3-Trans-methyl 3-((2-(5-chloro-1-tosyl-1H-pyrrolo[2,3-b]pyridin-3-yl)-5-fluoropyrimidin-4-ylamino)bicyclo[2.2.1]heptane-2-carboxylate (53c)

A mixture of 5-chloro-3-(5-fluoro-4-(methylsulfinyl)pyrimidin-2-yl)-1-tosyl-1H-pyrrolo[2,3-b]pyridine, 1a, (0.46 g, 1.00 mmol) and (+/−)-trans-methyl 3-aminobicyclo[2.2.1]heptane-2-carboxylate, 53b, (0.27 g, 1.60 mmol) (84:16=endo:exo) and freshly ground Na₂CO₃ (0.32 g, 2.99 mmol in THF (3.7 mL) and CH₃CN (1.2 mL) was heated to 120° C. for 20 min in microwave. The reaction mixture was filtered and the solid was rinsed with Et₂O and THF. The organic layer was concentrated in vacuo to provide crude product which was purified by silica gel chromatography (0-40% EtOAc/hexanes, gradient) to provide the desired product (352 mg) as an inseparable mixture of trans-endo and trans-exo isomers (endo:exo=85:15) as indicated by NMR.

LC/MS $R_t$=6.13 min, (M+H) 570.34.

(+/−)-2,3-trans-endo-methyl 3-((2-(5-chloro-1H-pyrrolo[2,3-b]pyridin-3-yl)-5-fluoropyrimidin-4-ylamino)bicyclo[2.2.1]heptane-2-carboxylate (53d) and (+/−)-2,3-trans-exo-methyl 3-((2-(5-chloro-1H-pyrrolo[2,3-b]pyridin-3-yl)-5-fluoropyrimidin-4-ylamino)bicyclo[2.2.1]heptane-2-carboxylate (53d)

To a solution of trans-endo- and trans-exo-methyl 3-((2-(5-chloro-1-tosyl-1H-pyrrolo[2,3-b]pyridin-3-yl)-5-fluoro-pyrimidin-4-ylamino)bicyclo[2.2.1]heptane-2-carboxylate, 53c, (0.18 g, 0.31 mmol) in MeOH (3 mL) and CH$_2$Cl$_2$ (1 mL) was added NaOMe (3 mL of 25% w/v, 13.88 mmol). After 90 sec, NH$_4$Cl solution (5 mL) was added to quench the reaction. The mixture was partitioned between aqueous NH$_4$Cl (half saturated) and EtOAc. The aqueous layer was extracted again and the combined organic layers were washed with brine, dried over Na$_2$SO$_4$, filtered and concentrated in vacuo. Flash chromatography (SiO$_2$, O-15% MeOH-DCM, gradient) gave the desired products as a mixture. (white solid): 112 mg $^1$H NMR indicated desired product existed as a mixture of endo and exo isomers (endo:exo=84:16) which was taken forward into the hydrolysis step.

(+/−)-2,3-Trans-exo-methyl 3-((2-(5-chloro-1H-pyrrolo[2,3-b]pyridin-3-yl)-5-fluoropyrimidin-4-ylamino)bicyclo[2.2.1]heptane-2-carboxylate (53d)

minor isomer (exo): LC/MS (method: ml 17) $R_t$=3.17 min, (M+H) 416.27.

(+/−)-2,3-Trans-endo-methyl 3-((2-(5-chloro-1H-pyrrolo[2,3-b]pyridin-3-yl)-5-fluoropyrimidin-4-ylamino)bicyclo[2.2.1]heptane-2-carboxylate (53d)

major isomer (endo): LC/MS (method: ml 17) $R_t$=3.49 min, (M+H) 416.27.

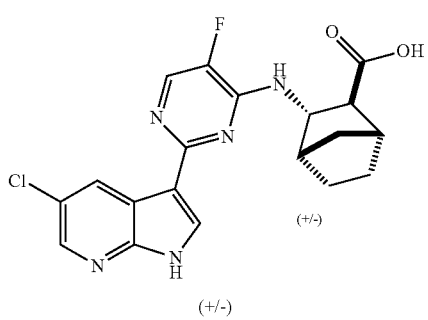

946

(+/-)

and

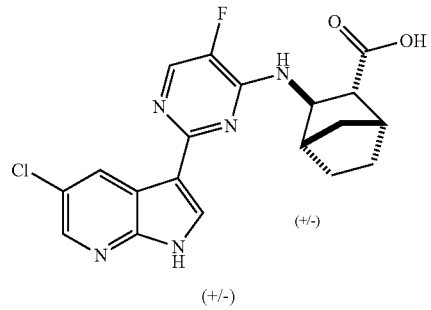

947

(+/-)

and

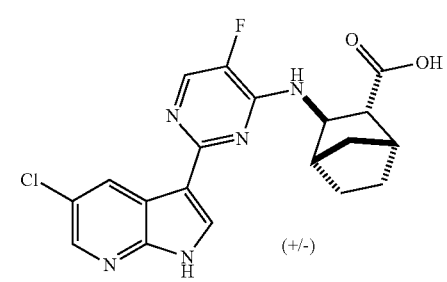

947(+/-)

(946) (+/−)-2,3-trans-endo-3-((2-(5-chloro-1H-pyrrolo[2,3-b]pyridin-3-yl)-5-fluoropyrimidin-4-ylamino)bicyclo[2.2.1]heptane-2-carboxylic acid and (947) (+/−)-2,3-trans-exo-3-((2-(5-chloro-1H-pyrrolo[2,3-b]pyridin-3-yl)-5-fluoropyrimidin-4-ylamino)bicyclo[2.2.1]heptane-2-carboxylic acid To a stirred solution of starting methyl esters, 53d, (0.076 g, 0.183 mmol) (84:16=endo:exo) in THF (0.60 mL) and MeOH (0.10 mL), was added NaOH (0.10 mL of 2 M, 0.201 mmol). The reaction progress was monitored by TLC. After 30 min, additional NaOH (0.18 mL of 2 M solution, 0.37 mmol) and MeOH (0.18 mL) was added. The mixture was stirred at room temperature for a further 16 hours. The mixture was neutralized with HCl (1M) and concentrated in vacuo. Purification by preparative HPLC provided 52 mg of the major isomer (946) and 11 mg of the minor isomer (947) as the hydrochloric acid salts.

(946) major (endo) isomer: $^1$H NMR (300 MHz, MeOD) δ 8.82 (d, J=2.2 Hz, 1H), 8.48 (s, 1H), 8.39 (d, J=2.2 Hz, 1H), 8.31 (d, J=5.6 Hz, 1H), 5.11 (m, 1H), 2.85 (br s, 1H), 2.68 (br s, 1H), 2.62 (d, J=4.8 Hz, 1H), 1.92 (d, J=10.1 Hz, 1H) and 1.77-1.51 (m, 5H) ppm; LC/MS $R_t$=3.51, (M+H) 402.32.

(947) minor (exo) isomer: $^1$H NMR (300 MHz, MeOD) δ 8.87 (d, J=2.1 Hz, 1H), 8.48 (s, 1H), 8.39 (d, J=1.9 Hz, 1H), 8.30 (d, J=5.7 Hz, 1H), 4.73 (d, J=3.3 Hz, 1H), 3.12 (m, 1H), 2.76 (br s, 1H), 2.56 (d, J=4.2 Hz, 1H), 1.86 (d, J=9.5 Hz, 2H), 1.79-1.49 (complex m, 2H) and 1.51 (embedded d, J=10.4 Hz, 2H) ppm; LC/MS R$_{t=3.42}$, (M+H) 402.32.

(1184) (2S,3S)-3-((2-(5-chloro-1H-pyrrolo[2,3-b]pyridin-3-yl)-5-fluoropyrimidin-4-yl)amino)bicyclo[2.2.2]octane-2-carboxylic acid

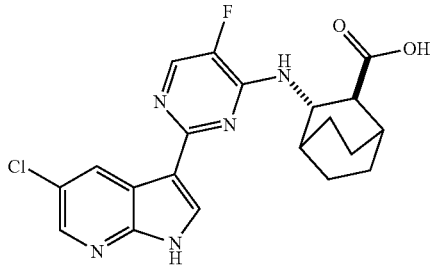

1184

Compound 1184 was made in a similar fashion as described above for compounds 946 and 947.

(1070) (2S,3S)-3-((2-(5-fluoro-1H-pyrrolo[2,3-b]pyridin-3-yl)-5-fluoropyrimidin-4-yl)amino)bicyclo[2.2.2]octane-2-carboxylic acid

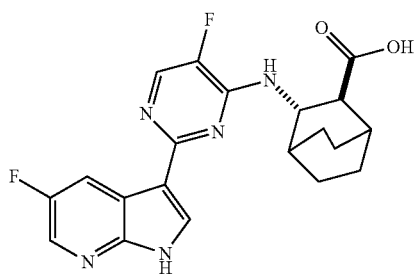

1070

Compound 1070 was made in a similar fashion as described above for compounds 946 and 947.

General Scheme 54:

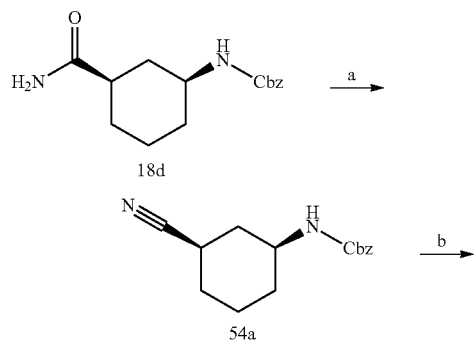

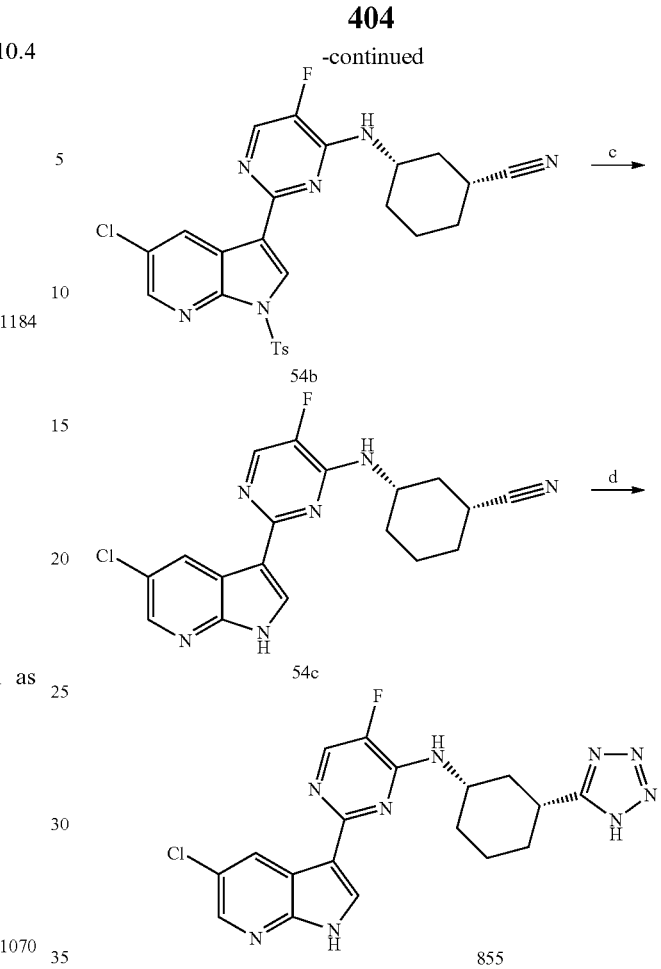

(a) Cyanogen chloride, DMF, 0° C.; (b) Pd(OH)$_2$/Carbon, H$_2$; 5-chloro-3-(5-fluoro-4-(methylsulfinyl)pyrimidin-2-yl)-1-tosyl-1H-pyrrolo[2,3-b]pyridine, $^i$Pr$_2$NEt/THF 45° C.; (c) Na/MeOH; (d) (n-Bu)$_2$SnO, TMSN$_3$, toluene, 110° C.

Formation of benzyl (1S,3R)-3-cyanocyclohexylcarbamate (54a)

A suspension of benzyl N-[(1S,3R)-3-carbamoylcyclohexyl]carbamate, 18d, (0.69 g, 2.50 mmol) in DMF (10 mL) at 0° C. was treated with 2,4,6-trichloro-1,3,5-triazine (0.61 g, 3.29 mmol) and allowed to stir while slowly warming to room temperature. After 20 minutes, the solution became gold in color. After 1 hour a precipitate had formed. Stirred for an additional 3 hours then quenched with ice water (100 mL) and extracted with CH$_2$Cl$_2$ (2×125 mL) then washed with 1N HCl (100 mL). The organic layer was concentrated in vacuo to afford an 730 mg of a residue that was purified using a pad of silica gel (45 mL) using 30% EtOAc/hexanes as eluent to afford 621 mg of a white solid after vacuum drying.

$^1$H NMR (300 MHz, CDCl$_3$) δ 7.45-7.30 (m, 5H), 5.09 (s, 2H), 4.67 (s, 1H), 3.49 (s, 1H), 2.66-2.32 (m, 2H), 2.16-1.79 (m, 3H), 1.52-1.03 (m, 4H).

Preparation of (1R,3S)-3-((2-(5-chloro-1-tosyl-1H-pyrrolo[2,3-b]pyridin-3-yl)-5-fluoropyrimidin-4-ylamino)cyclohexanecarbonitrile (54b)

Benzyl N-[(1S,3R)-3-cyanocyclohexyl]carbamate (0.26 g, 1.02 mmol) was dissolved in THF (15 mL) and treated with 0.13 g of 20% Pearlman's catalyst (50% wet by weight). The suspension was degassed with hydrogen for 2 min then placed under static hydrogen atmosphere. After 135 min, TLC showed no remaining starting material. The suspension was filtered through celite, washed with THF and degassed with nitrogen followed by the addition of $^i$Pr$_2$NEt (0.21 mL, 1.23 mmol) and 5-chloro-3-(5-fluoro-4-(methylsulfinyl)pyrimidin-2-yl)-1-tosyl-1H-pyrrolo[2,3-b]pyridine, 1a, (0.48 g, 1.02 mmol). The mixture was allowed to stir overnight at 45° C. then concentrated to dryness, absorbed on silica-gel and purified by silica gel chromatography using 0-60% EtOAc/hexanes gradient to afford 293 mg of a white solid.

$^1$H NMR (300 MHz, CDCl$_3$) δ 8.74 (d, J=2.4 Hz, 1H), 8.49 (s, 1H), 8.39 (d, J=2.4 Hz, 1H), 8.15-8.05 (m, 3H), 7.37-7.23 (m, 2H), 5.01 (d, J=6.2 Hz, 1H), 4.13 (s, 1H), 2.75 (d, J=23.0 Hz, 1H), 2.58 (s, 1H), 2.38 (s, 3H), 2.20 (d, J=9.1 Hz, 2H), 2.03 (d, J=7.8 Hz, 1H), 1.78-1.43 (m, 4H), 1.26 (s, 1H).

Preparation of (1R,3S)-3-((2-(5-chloro-1H-pyrrolo[2,3-b]pyridin-3-yl)-5-fluoropyrimidin-4-ylamino)cyclohexanecarbonitrile (54c)

(1R,3S)-3-[[2-[5-chloro-1-(p-tolylsulfonyl)pyrrolo[2,3-b]pyridin-3-yl]-5-fluoro-pyrimidin-4-yl]amino]cyclohexanecarbonitrile, 54b, (0.29 g, 0.55 mmol) was suspended in MeOH (15 mL) and sodium metal added and the mixture heated at 45° C. The sodium dissolved in advance of the compound. The mixture was allowed to stir until complete by TLC and LCMS. Concentrated to reduced volume then quenched with 1:1 aqueous saturated NH$_4$Cl:water mixture (1 ml) then concentrated to dryness. The residue was diluted with EtOAc and washed with water and brine. The organic layer was concentrated in vacuo to give 0.3 g of a yellow solid that was adsorbed on silica-gel and purified using 40 g isco column with the following gradient using 20% MeOH:DCM as the eluent: 0-25%/6 min hold 4 min; 25-50%/4 min hold 9 min to give 146 mg of a white solid. LCMS (10-90% MeOH:water with formic acid).LCMS RT 4.01 ES+371, ES-369.

Preparation of (1R,3S)-3-((2-(5-chloro-1H-pyrrolo[2,3-b]pyridin-3-yl)-5-fluoropyrimidin-4-ylamino)cyclohexanecarboxamide (847)

A sample of (1R,3S)-3-((2-(5-chloro-1H-pyrrolo[2,3-b]pyridin-3-yl)-5-fluoropyrimidin-4-ylamino)cyclohexanecarbonitrile was treated with 4N HCl/dioxane and heated at 78° C. overnight. Concentrated to dryness then quenched with aqueous saturated sodium bicarbonate and CH$_2$Cl$_2$ were added to give a slurry. Filtered and extracted with CH$_2$Cl$_2$. The organic phase was dried over Na$_2$SO$_4$ and concentrated in vacuo to give 189 mg of an orange residue that was purified by silica gel chromatography (0-10% MeOH:CH$_2$Cl$_2$ gradient) to afford 9.9 mg of a solid: LCMS (10-90% MeOH:water with formic acid): RT 3.79 min ES+389.

Preparation of N-((1S,3R)-3-(1H-tetrazol-5-yl)cyclohexyl)-2-(5-chloro-1H-pyrrolo[2,3-b]pyridin-3-yl)-5-fluoropyrimidin-4-amine (855)

A suspension of dibutyl(oxo)tin (0.016 g, 0.064 mmol) and (1R,3S)-3-[[2-(5-chloro-1H-pyrrolo[2,3-b]pyridin-3-yl)-5-fluoro-pyrimidin-4-yl]amino]cyclohexane-carbonitrile (54c) (0.043 g, 0.107 mmol) in toluene (3 mL) was treated with azido(trimethyl)silane (0.200 mL, 1.507 mmol). The mixture was heated in a sealed tube at 120° C. overnight. The mixture was absorbed onto silica-gel and purified by silica gel chromatography (25-50% gradient of 20% MeOH:DCM containing 0.5% AcOH modifier). The combined fractions were concentrated to dryness to give a residue that was triturated with ether then dried under vacuum at 45° C. to afford 44 mg of a yellow solid.

$^1$H NMR (300 MHz, DMSO) δ 12.33 (s, 1H), 8.74 (d, J=2.4 Hz, 1H), 8.41-8.04 (m, 3H), 7.62 (d, J=7.4 Hz, 1H), 4.30 (s, 1H), 3.54-3.06 (m, 3H), 2.67-2.31 (m, 1H), 2.23-1.33 (m, 6H).

General Scheme 55:

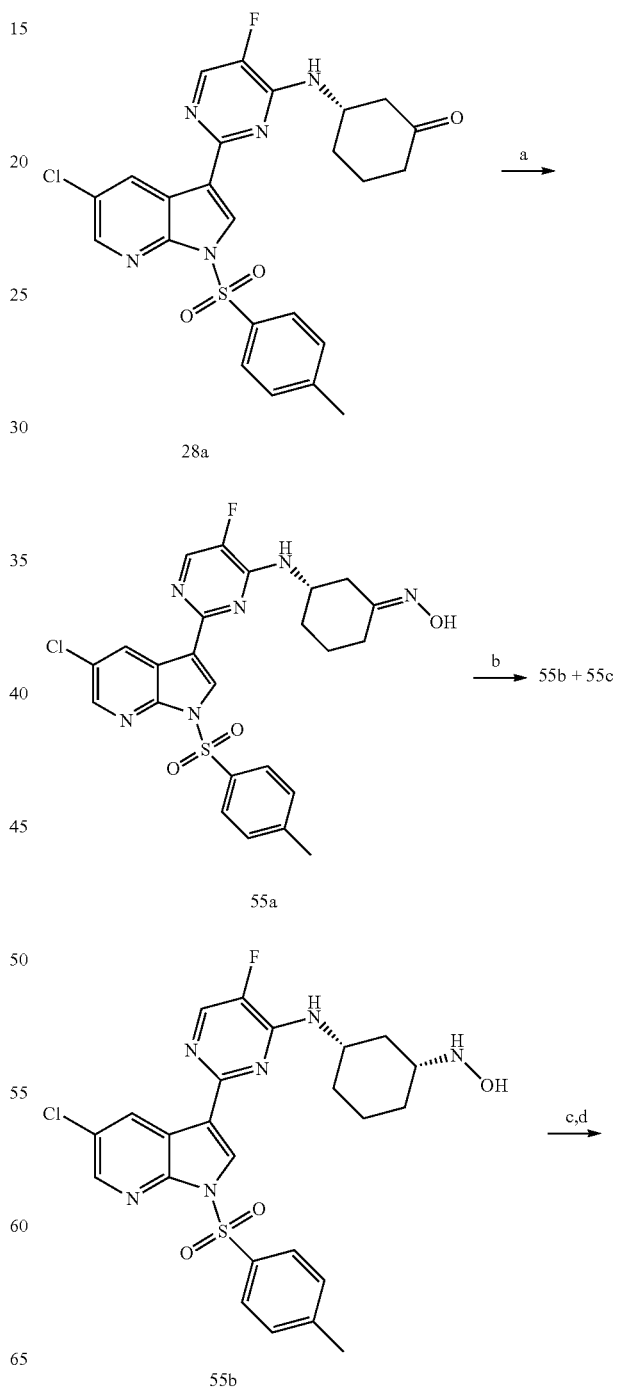

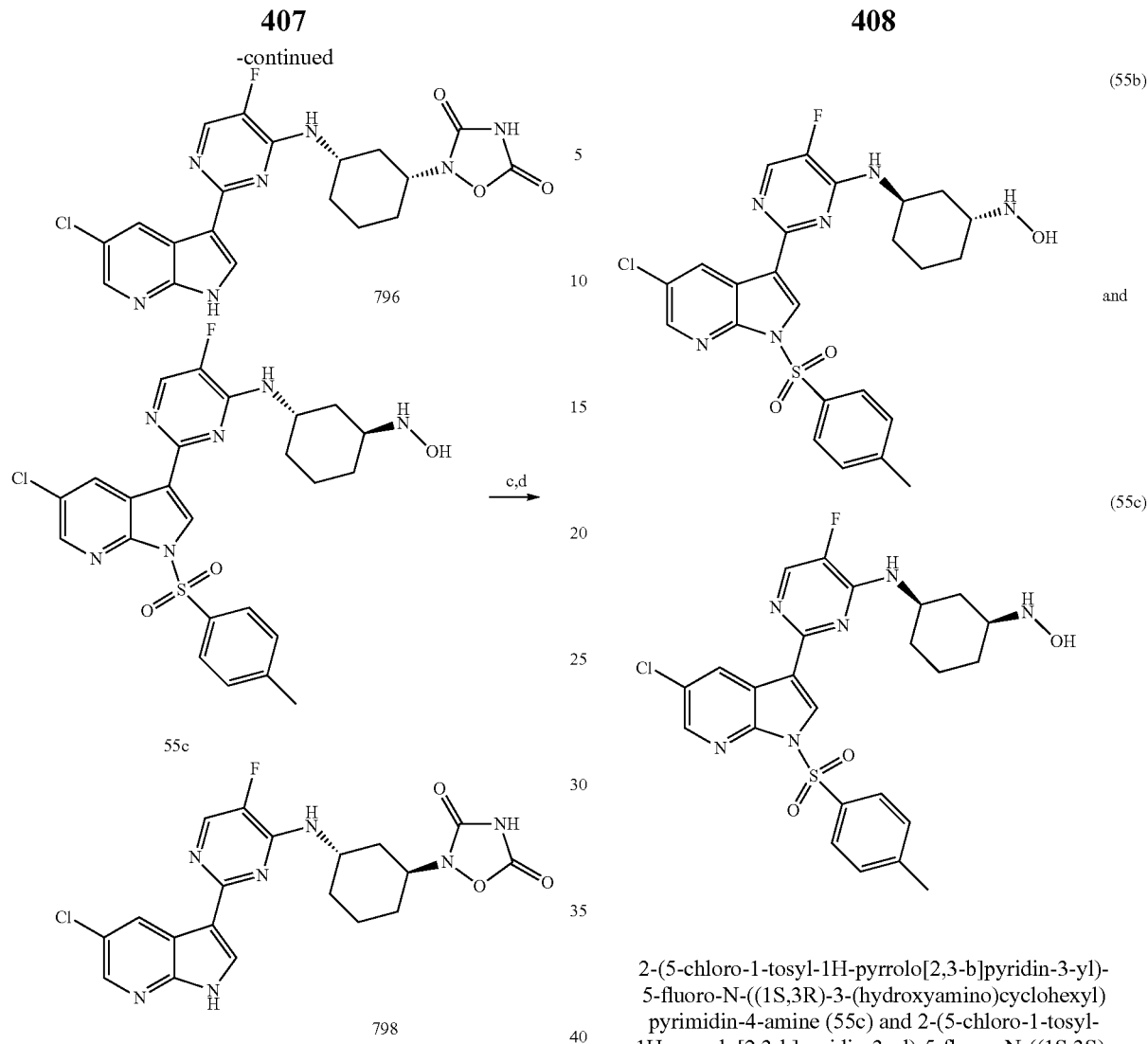

(a) hydroxylamine-HCl, EtOH; (b) 5-ethyl-2-methyl-pyridinium borane, HCl, MeOH; (c) N-(oxomethylene)carbamoyl chloride, THF; (d) NaOMe, MeOH.

Formation of (S)-3-((2-(5-chloro-1-tosyl-1H-pyrrolo[2,3-b]pyridin-3-yl)-5-fluoro-pyrimidin-4-ylamino)cyclohexanone oxime (55a)

To solution of (3S)-3-[[2-[5-chloro-1-(p-tolylsulfonyl)pyrrolo[2,3-b]pyridin-3-yl]-5-fluoro-pyrimidin-4-yl]amino]cyclohexanone (0.41 g, 0.81 mmol) in EtOH (8.2 mL) was added hydroxylamine hydrochloride (0.11 g, 1.61 mmol). The reaction mixture was stirred at room temperature overnight. Then the mixture was warmed to 70° C. for 15 min. The reaction mixture was concentrated in vacuo, suspended in EtOAc-DCM, washed with half saturated brine (2×) and filtered through a SiO$_2$ plug. The resulting residue was azeotroped with CH$_3$CN (2×) to provide an off white powder which was used without further purification.

$^1$H NMR (300 MHz, MeOD) δ 8.78 (d, J=2.4 Hz, 1H), 8.51 (d, J=10.8 Hz, 1H), 8.32 (d, J=2.3 Hz, 1H), 8.10-8.04 (m, 3H), 7.38 (d, J=8.2 Hz, 2H), 4.29-4.15 (m, 1H), 3.79-3.74 (m, 0.6H), 2.41 (m, 1H), 2.38 (s, 3H), 2.30-2.16 (m, 2H), 2.06-1.84 (m, 4H) and 1.66-1.59 (m, 2H) ppm; LC/MS (method: m120) R$_t$=3.90 min, (M+H) 529.44.

2-(5-chloro-1-tosyl-1H-pyrrolo[2,3-b]pyridin-3-yl)-5-fluoro-N-((1S,3R)-3-(hydroxyamino)cyclohexyl)pyrimidin-4-amine (55c) and 2-(5-chloro-1-tosyl-1H-pyrrolo[2,3-b]pyridin-3-yl)-5-fluoro-N-((1S,3S)-3-(hydroxyamino)cyclohexyl)pyrimidin-4-amine (55b)

To a stirred solution of (S)-3-((2-(5-chloro-1-tosyl-1H-pyrrolo[2,3-b]pyridin-3-yl)-5-fluoropyrimidin-4-ylamino)cyclohexanone oxime (0.20 g, 0.38 mmol) and HCl (0.19 mL of 6 M, 1.134 mmol) in MeOH (10 mL) was added (5-ethyl-2-methyl-pyridinium borane (0.12 mL, 0.76 mmol) at room temperature. After 30 min, the reaction was quenched with NaHCO$_3$. The mixture was extracted successively with Et$_2$O, EtOAc, CH$_2$Cl$_2$ and EtOAc. Each organic portion was washed with brine and the combined organic layers were dried over Na$_2$SO$_4$, filtered and concentrated in vacuo. Flash chromatography (SiO$_2$, 20-100% EtOAc-hexanes) provided the cis-4 (74 mg) and trans-3 (64 mg) isomers.

2-(5-chloro-1-tosyl-1H-pyrrolo[2,3-b]pyridin-3-yl)-5-fluoro-N41S,3S)-3-(hydroxyamino)cyclohexyl)pyrimidin-4-amine (stereoisomer-3)

$^1$H NMR (300 MHz, MeOD) δ 8.83 (d, J=2.4 Hz, 1H), 8.50 (s, 1H), 8.33 (d, J=2.4 Hz, 1H), 8.07-8.04 (m, 1H), 7.37 (d, J=8.4 Hz, 1H), 4.24-4.17 (m, 1H), 3.07-3.00 (m, 1H), 2.34 (m, 1H), 2.14-2.08 (m, 1H), 1.93 (t, J=3.5 Hz, 2H), 1.66-1.53 (m, 1H) and 1.44-1.12 (m, 3H) ppm; LC/MS RT=3.64 min, (M+H) 531.47.

2-(5-chloro-1-tosyl-1H-pyrrolo[2,3-b]pyridin-3-yl)-5-fluoro-N-((1S,3R)-3-(hydroxyamino)cyclohexyl)pyrimidin-4-amine (stereoisomer-4)

$^1$H NMR (300 MHz, MeOD) δ 8.84 (d, J=2.4 Hz, 1H), 8.53 (s, 1H), 8.32 (d, J=2.4 Hz, 1H), 8.07-8.04 (m, 1H), 7.37 (d, J=8.2 Hz, 1H), 4.58-4.54 (m, 1H), 3.26-3.23 (m, 1H), 2.38 (s, 3H), 1.98-1.83 (m, 4H) and 1.69-1.60 (m, 4H) ppm; LC/MS RT=3.67 min, (M+H) 531.47.

2-((1R,3S)-3-((2-(5-chloro-1H-pyrrolo[2,3-b]pyridin-3-yl)-5-fluoropyrimidin-4-yl-amino)cyclohexyl)-1,2,4-oxadiazolidine-3,5-dione (796)

To a solution of 2-(5-chloro-1-tosyl-1H-pyrrolo[2,3-b]pyridin-3-yl)-5-fluoro-N-((1S,3R)-3-(hydroxyamino)cyclohexyl)pyrimidin-4-amine, 55b, (0.072 g, 0.136 mmol) in THF (2 mL) at 0° C. was added N-(oxomethylene)carbamoyl chloride (0.014 mL, 0.176 mmol). A white solid formed immediately. The slurry was shaken and sonicated to make an even suspension/slurry. Then, CH$_2$Cl$_2$ (1 mL)) was added to help solvate the slurry. After 135 min, the mixture was treated with NaOMe (2 mL, 25% w/v). After 2 min, the mixture was quenched with saturated NH$_4$Cl and acidified with 1M HCl. The mixture was extracted with EtOAc (3×) and the combined organic layers were dried over Na$_2$SO$_4$, filtered and concentrated in vacuo. Preparative HPLC provided the desired product (25 mg).

$^1$H NMR (300 MHz, MeOD) δ 8.73 (s, 1H), 8.52 (s, 1H), 8.38 (s, 1H), 8.31 (br s, 1H), 4.34 (m, 1H), 2.60-2.56 (m, 1H), 2.27 (m, 1H), 2.08 (m, 3H) and 1.89-1.78 (m, 3H) ppm; LC/MS RT=3.12 min, (M+H) 446.45.

2-((1S,3S)-3-((2-(5-chloro-1H-pyrrolo[2,3-b]pyridin-3-yl)-5-fluoropyrimidin-4-ylamino)cyclohexyl)-1,2,4-oxadiazolidine-3,5-dione (798)

$^1$H NMR (300 MHz, MeOD) δ 8.67 (s, 1H), 8.56 (s, 1H), 8.38 (s, 1H), 8.31 (br s, 1H), 4.47 (m, 1H), 4.21 (m, 1H), 2.41 (m, 1H), 2.22 (m, 1H), 2.10-1.90 (m, 3H), 1.72 (m, 2H) and 1.50 (m, 1H) ppm; LC/MS RT=3.37 min, (M+H) 446.34.

General Scheme 56:

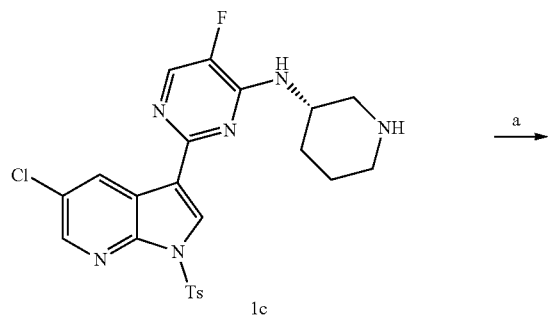

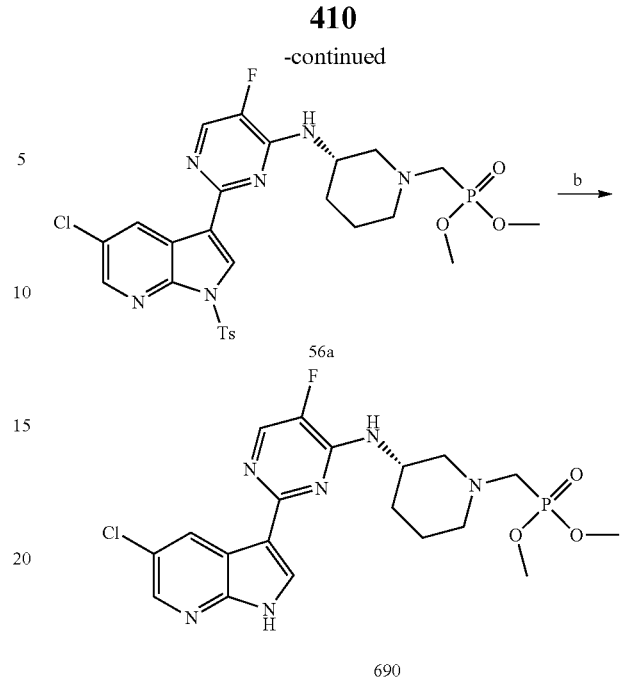

(a) paraformaldehyde, methoxyphosphonoyloxymethane, 4A sieves, toluene, 90° C.; (b) NaOMe, MeOH.

Formation of (S)-dimethyl (3-((2-(5-chloro-1-tosyl-1H-pyrrolo[2,3-b]pyridin-3-yl)-5-fluoropyrimidin-4-ylamino)piperidin-1-yl)methylphosphonate (56a)

To a solution of 2-[5-chloro-1-(p-tolylsulfonyl)pyrrolo[5,4-b]pyridin-3-yl]-5-fluoro-N-[(3S)-3-piperidyl]pyrimidin-4-amine, 1c, (2.00 g, 3.99 mmol) in dry toluene was added 4 angstrom molecular sieves and methoxyphosphonoyloxymethane (0.97 g, 0.81 mL, 8.78 mmol). While stirring under nitrogen, paraformaldehyde (0.90 g, 9.98 mmol) was added portionwise. The mixture was heated at 90° C. for 90 minutes. The reaction was cooled to room temperature, diluted with aqueous saturated NaHCO$_3$ solution, extracted twice with EtOAc. The combined organic phases were dried (MgSO$_4$), filtered and concentrated in vacuo. The resulting residue was purified by silica gel chromatography using 0-10% MeOH/CH$_2$Cl2 gradient to afford 2.0 g of desired product. LCMS RT=4.47 (M+H) 623.3.

Formation of (S)-dimethyl (3-((2-(5-chloro-1H-pyrrolo[2,3-b]pyridin-3-yl)-5-fluoropyrimidin-4-ylamino)piperidin-1-yl)methylphosphonate (690)

To a solution of 2-[5-chloro-1-(p-tolylsulfonyl)pyrrolo[2,3-b]pyridin-3-yl]-N-[(3S)-1-(dimethoxyphosphorylmethyl)-3-piperidyl]-5-fluoro-pyrimidin-4-amine, 56a, (1.00 g, 1.61 mmol) in MeOH (40 mL) was added sodium methanolate (20 mL of 25% w/v, 92.55 mmol) and the reaction mixture was stirred at room temperature for 30 minutes. All volatiles were removed at reduced pressure and the resulting residue was diluted with aqueous saturated NH$_4$Cl solution and extracted twice with CH$_2$Cl$_2$. The combined organic phases were dried (MgSO$_4$), filtered and concentrated in vacuo. The resulting residue was purified via silica gel chromatography using 0-10% MeOH:CH$_2$Cl$_2$ gradient to provide 270 mg of a white solid.

$^1$H NMR (300.0 MHz, DMSO) δ 12.33 (s, 1H), 8.70 (d, J=2.4 Hz, 1H), 8.28 (d, J=2.4 Hz, 1H), 8.20 (d, J=2.6 Hz, 1H), 8.17 (d, J=4.0 Hz, 1H), 7.35 (d, J=7.8 Hz, 1H), 4.27-4.17 (m, 1H), 3.67 (s, 3H), 3.64 (s, 3H), 3.21-3.16 (m, 1H), 2.96-2.90 (m, 3H), 2.33-2.20 (m, 2H), 1.99-1.94 (m, 1H), 1.80-1.60 (m, 2H) and 1.47-1.35 (m, 1H) ppm; LCMS RT=3.84 (M+1) 469.47.

General Scheme 57:

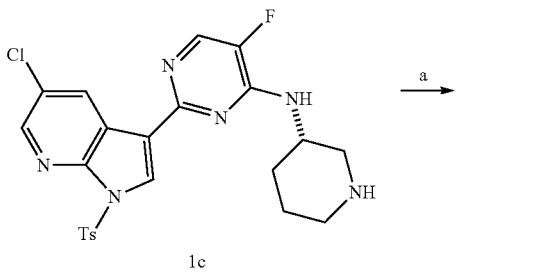

1c

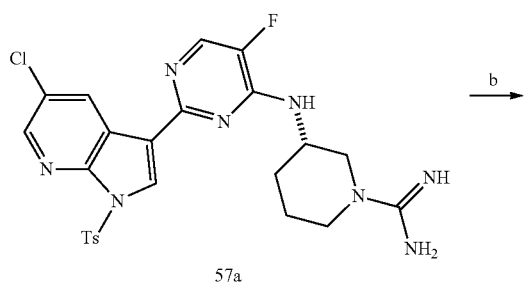

57a

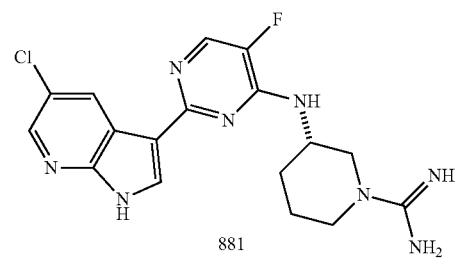

881

(a) pyrazole-1-carboxamidine hydrochloride, $^i$Pr$_2$NEt, 4A sieves, toluene, 90° C.; (b) NaOMe, MeOH.

Formation of ((S)-3-((2-(5-chloro-1-tosyl-1H-pyrrolo[2,3-b]pyridin-3-yl)-5-fluoro-pyrimidin-4-ylamino)piperidine-1-carboximidamide (57a)

To a solution of pyrazole-1-carboxamidine hydrochloride (0.12 g, 0.80 mmol) and 2-[5-chloro-1-(p-tolylsulfonyl)pyrrolo[2, 3-13]pyridin-3-yl]-5-fluoro-N-[(3S)-3-piperidyl]pyrimidin-4-amine, 1c, (0.40 g, 0.80 mmol) in DMF (0.9 mL) was added $^i$Pr$_2$NEt (0.14 mL, 0.80 mmol). The reaction mixture was stirred at room temperature for 4 hours. The mixture was diluted into water, filtered, washed with additional water, then ether. The filtrate was concentrated in vacuo. The resulting residue was purified by silica gel chromatography using 5-20% MeOH/CH$_2$Cl$_2$ gradient (product elutes with 20% MeOH) to afford 190 mg of the desired product.

$^1$H NMR (300 MHz, DMSO) δ 8.73 (d, J=2.2 Hz, 1H), 8.50-8.45 (m, 2H), 8.33 (d, J=3.7 Hz, 1H), 8.07 (d, J=8.2 Hz, 2H), 7.90 (d, J=7.0 Hz, 1H), 7.53-7.42 (m, J=9.0 Hz, 6H), 3.87 (d, J=13.6 Hz, 1H), 3.17 (d, J=5.2 Hz, 1H), 3.03 (q, J=10.9 Hz, 2H), 2.36 (s, 3H), 2.11 (d, J=9.9 Hz, 1H), 1.90 (d, J=12.6 Hz, 1H), 1.68 (dd, J=24.5, 13.9 Hz, 2H); LCMS RT=3.07 (M+1) 543.34.

Formation of (S)-3-((2-(5-chloro-1H-pyrrolo[2,3-b]pyridin-3-yl)-5-fluoropyrimidin-4-ylamino)piperidine-1-carboximidamide(881)

To a solution of (3S)-3-[[2-[5-chloro-1-(p-tolylsulfonyl)pyrrolo[2,3-b]pyridin-3-yl]-5-fluoro-pyrimidin-4-yl]amino]piperidine-1-carboxamidine, 57b, (0.18 g, 0.32 mmol) in MeOH (5 mL) was added sodium methanolate (3 mL of 25% w/v, 13.88 mmol) and the reaction was stirred at room temperature. After 5 min, the mixture was concentrated in vacuo to light yellow solid. The crude residue was purified via preparatory HPLC (MeOH/1% aqueous HCl) to afford the desired product.

$^1$H NMR (300 MHz, DMSO) δ 12.79 (s, 1H), 8.77 (s, 1H), 8.60 (d, J=2.3 Hz, 1H), 8.43 (d, J=4.8 Hz, 1H), 8.37 (d, J=2.3 Hz, 1H), 7.52 (s, 3H), 4.29 (s, 1H), 4.08 (d, J=12.6 Hz, 1H), 3.90 (d, J=13.7 Hz, 1H); 3.16-2.95 (m, 2H), 2.17 (d, J=9.7 Hz, 1H), 1.92 (d, J=8.5 Hz, 1H), 1.81-1.57 (m, 2H); LCMS RT=2.03 (M+1) 389.27.

General Scheme 58:

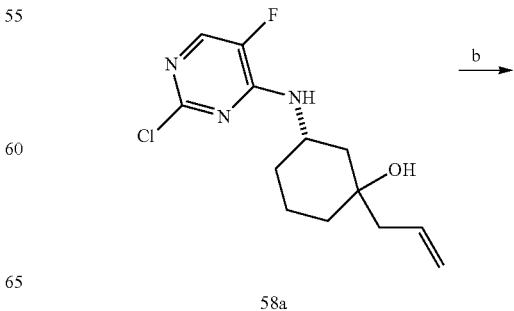

29b

58a

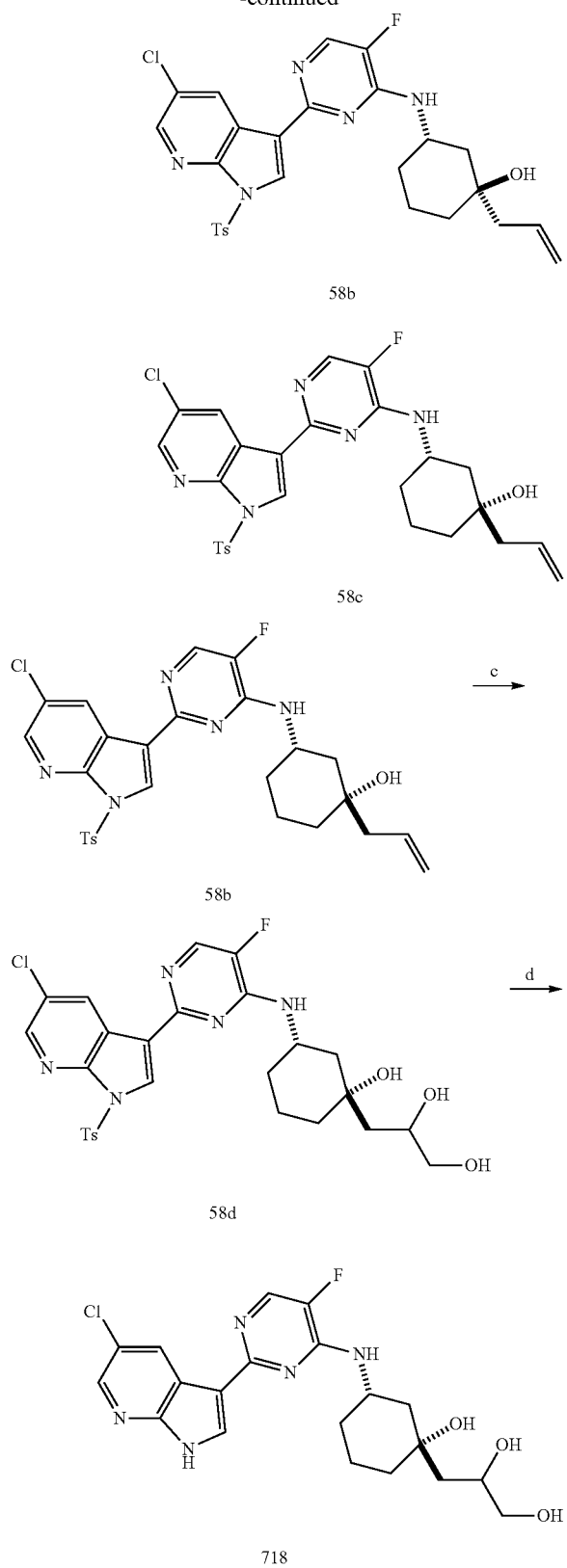

(a) 3-bromoprop-1-ene, Zn dust, DMF; (b) 5-chloro-3-(4,4,5,5-tetramethyl-1,3,2-dioxaborolan-2-yl)-1-tosyl-1H-pyrrolo[2,3-b]pyridine, Pd(Ph₃P)₄, Na₂CO₃, acetonitrile, water, 120° C., microwave; (c) OsO₄, pyridine, 4-methylmorpholine-N-oxide, tert-butanol, water, THF, 120° C.; (d) NaOMe, MeOH.

Formation of (3S)-1-allyl-3-(2-chloro-5-fluoropyrimidin-4-ylamino)cyclohexanol (58a)

To a solution of (3S)-3-[(2-chloro-5-fluoro-pyrimidin-4-yl)amino]cyclohexanone, 29b, (0.60 g, 2.46 mmol) and 3-bromoprop-1-ene (0.43 mL, 4.92 mmol) in DMF was added Zn dust (0.32 g, 4.92 mmol). The reaction was stirred at room temperature for 3 days. The mixture was diluted into aqueous saturated NH₄Cl solution, extracted twice with EtOAc. The combined organic phases were washed twice with brine, dried (MgSO₄), filtered and concentrated in vacuo. The crude residue was purified by silica gel chromatography using 0-50% EtOAc/hexanes gradient to afford 553 mg of desired product, 58a, as an oil. LC/MS-two peaks corresponding to two diastereomeric products: 286.4 (M+H), RT=3.41 and 3.78.

Formation of (1R,3S)-1-allyl-3-((2-(5-chloro-1-tosyl-1H-pyrrolo[2,3-b]pyridin-3-yl)-5-fluoropyrimidin-4-ylamino)cyclohexanol and (1R,3S)-1-allyl-3-((2-(5-chloro-1-tosyl-1H-pyrrolo[2,3-b]pyridin-3-yl)-5-fluoropyrimidin-4-ylamino)cyclohexanol (58b and 58c)

In a microwave tube was placed 5-chloro-1-(p-tolylsulfonyl)-3-(4,4,5,5-tetramethyl-1,3,2-dioxaborolan-2-yl)pyrrolo[2,3-b]pyridine (0.57 g, 1.32 mmol) and (3S)-1-allyl-3-[(2-chloro-5-fluoro-pyrimidin-4-yl)-amino]cyclohexanol, 58a, (0.32 g, 1.10 mmol) in acetonitrile (12 mL) and Na₂CO₃ (1.65 mL of 2 M aqueous solution, 3.31 mmol). The mixture was deoxygenated with nitrogen for 15 min. To the mixture was added tetrakis triphenyl phosphine palladium (O) (0.03 g, 0.02 mmol). The reaction was sealed and heated to 120° C. for 20 min. The mixture was diluted with brine, extracted twice with CH₂Cl₂. The combined organic phases were dried (MgSO₄), filtered and concentrated in vacuo. The resulting residue was purified via silica gel chromatography using a 10-60% EtOAc/hexanes gradient to afford two diastereomers:

Diastereomer 1 (more polar spot-58c): LCMS RT=4.45 min, (M+H)=556.48

Diastereomer 2 (less polar spot-58b): LCMS RT=4.48 min (M+H)=556.48

Formation of 3-((1R,3S)-3-((2-(5-chloro-1-tosyl-1H-pyrrolo[2,3-b]pyridin-3-yl)-5-fluoropyrimidin-4-ylamino)-1-hydroxycyclohexyl)propane-1,2-diol (58d)

To a solution of (3S)-1-allyl-3-[[2-[5-chloro-1-(p-tolylsulfonyl)pyrrolo[2,3-b]pyridin-3-yl]-5-fluoro-pyrimidin-4-yl]amino]cyclohexanol, 58c, (0.30 g, 0.54 mmol) in 2-methyl-2-propanol (9.23 mL), THF (3.69 mL) and water (1.85 mL) was added pyridine (0.09 mL, 1.08 mmol) and osmium tetroxide (0.27 mL of 2.5% w/v, 0.03 mmol) and 4-methylmorpholine N-oxide (0.07 mL, 0.65 mmol). The reaction mixture was heated to 80° C. for 20 hours. After cooling to room temperature, the mixture was diluted into aqueous saturated sodium bisulfite solution and extracted twice with 20% isopropanol/CH$_2$Cl$_2$. The combined organic phases were washed with more aqueous saturated sodium bisulfite solution, dried (MgSO$_4$), filtered and concentrated in vacuo. The crude residue was purified via silica gel chromatography using 5-10% MeOH/CH$_2$Cl$_2$ gradient to afford 175 mg of the desired product as a racemic mixture, 58d.

$^1$H NMR (d6-DMSO) δ 8.77 (t, J=2.6 Hz, 1H), 8.48 (d, J=2.4 Hz, 1H), 8.42 (d, J=6.0 Hz, 1H), 8.25-8.23 (m, 1H), 8.07 (d, J=7.4 Hz, 2H), 7.74 (dd, J=7.6, 13.5 Hz, 1H), 7.44 (d, J=8.3 Hz, 2H), 4.97 (d, J=12.8 Hz, 1H), 4.76-4.72 (m, 1H), 4.54-4.51 (m, 1H), 4.31 (m, 1H), 3.83 (m, 1H), 2.36 (s, 3H), 1.99-1.91 (m, 2H), 1.77-1.63 (m, 4H) and 1.57-1.46 (m, 4H) ppm; LCMS RT=4.31 (M+H) 590.5.

Formation of 3-((1R,3S)-3-((2-(5-chloro-1H-pyrrolo[2,3-b]pyridin-3-yl)-5-fluoropyrimidin-4-ylamino)-1-hydroxycyclohexyl)propane-1,2-diol (718)

To a solution of 3-((1R,3S)-3-((2-(5-chloro-1-tosyl-1H-pyrrolo[2,3-b]pyridin-3-yl)-5-fluoropyrimidin-4-ylamino)-1-hydroxycyclohexyl)propane-1,2-diol, 58d, (0.11 g, 0.18 mmol) in MeOH (5 mL) was added sodium methanolate (2 mL of 25% w/v solution, 9.26 mmol) and the reaction mixture was stirred at room temperature. After 20 min, the reaction mixture was diluted with aqueous saturated NH$_4$Cl solution and extracted twice with 20% IPA/CH$_2$Cl$_2$. The combined organic phases were dried (MgSO$_4$), filtered and concentrated in vacuo. Purification via silica gel chromatography using 5-20% MeOH: CH$_2$Cl$_2$ gradient to afford 56 mg of a white solid.

$^1$H NMR (300 MHz, d6-DMSO) δ 12.29 (s, 1H), 8.71 (t, J=2.3 Hz, 1H), 8.27 (d, J=2.4 Hz, 1H), 8.19 (dd, J=2.8, 4.5 Hz, 1H), 8.15 (t, J=3.7 Hz, 1H), 7.52 (t, J=7.7 Hz, 1H), 4.97 (d, J=16.0 Hz, 1H), 4.77 (dd, J=3.8, 10.5 Hz, 1H), 4.54 (t, J=5.6 Hz, 1H), 4.32 (m, 1H), 3.86 (m, 1H), 2.00-1.97 (m, 2H), 1.82-1.63 (m, 4H) and 1.59-1.45 (m, 4H) ppm; LCMS RT=3.71 (M+1) 436.48.

General Scheme 59:

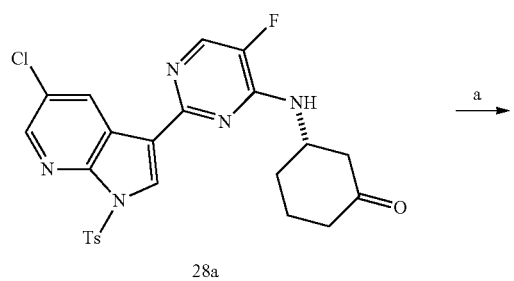

28a

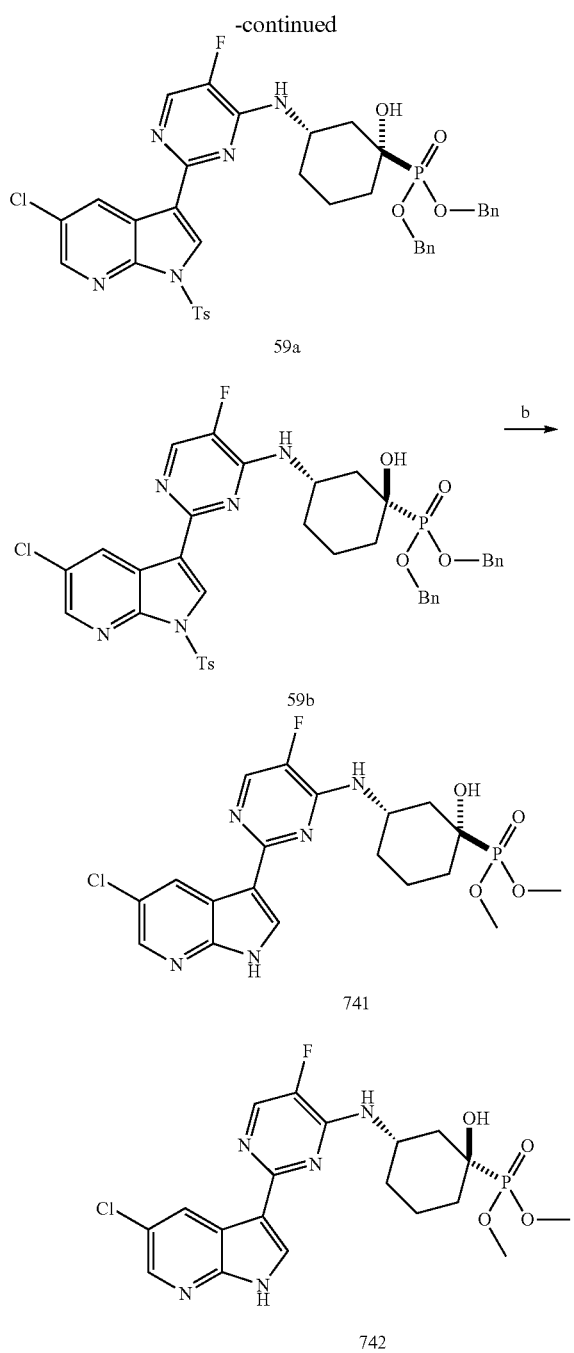

59a

59b

741

742

(a) benzyloxyphosphonoyloxymethylbenzene, triethylamine, 95° C., microwave; (b) NaOMe, MeOH.

Formation of dibenzyl (1S,3S)-3-((2-(5-chloro-1-tosyl-1H-pyrrolo[2,3-b]pyridin-3-yl)-5-fluoropyrimidin-4-ylamino)-1-hydroxycyclohexylphosphonate and dibenzyl (1R,3S)-3-((2-(5-chloro-1-tosyl-1H-pyrrolo[2,3-b]pyridin-3-yl)-5-fluoropyrimidin-4-ylamino)-1-hydroxycyclohexylphosphonate (59a and 59b)

To a solution of (3S)-3-[[2-[5-chloro-1-(p-tolylsulfonyl)pyrrolo[2,3-b]pyridin-3-yl]-5-fluoro-pyrimidin-4-yl]amino]cyclohexanone, 28a, (0.40 g, 0.78 mmol) in benzyloxyphosphonoyloxymethylbenzene (2.58 mL, 11.67 mmol) was added triethylamine (0.22 mL, 1.56 mmol). The reaction mixture was heated to 95° C. for 15 hours. The mixture was diluted with aqueous saturated NaHCO₃ solution, extracted with EtOAc, washed again with aqueous saturated NaHCO₃ solution. The organic phase was dried (MgSO₄), filtered and concentrated in vacuo to white solid. The crude product was purified via silica gel chromatography using 0-10% MeOH/CH₂Cl₂ gradient to afford 518 mg of a mixture of diastereomers, which contains somebenzyloxyphosphonoylmethylbenzene. The mixture was used without further purification in the next step. LCMS RT=4.6 (M+H) 776.32.

Formation of dimethyl (1S, 3S)-3-((2-(5-chloro-1H-pyrrolo[2,3-b]pyridin-3-yl)-5-fluoropyrimidin-4-ylamino)-1-hydroxycyclohexylphosphonate and dimethyl (1R,3S)-3-((2-(5-chloro-1H-pyrrolo[2,3-b]pyridin-3-yl)-5-fluoropyrimidin-4-ylamino)-1-hydroxycyclohexylphosphonate (741, 742)

To a solution of (1R,3S)-3-[[2-[5-chloro-1-(p-tolylsulfonyl)pyrrolo[2,3-b]pyridin-3-yl]-5-fluoro-pyrimidin-4-yl]amino]-1-dibenzyloxyphosphoryl-cyclohexanol and (1S, 3S)-3-[[2-[5-chloro-1-(p-tolylsulfonyl)pyrrolo[2,3-b]pyridin-3-yl]-5-fluoro-pyrimidin-4-yl]amino]-1-dibenzyloxy in MeOH was added sodium methanolate and the reaction was stirred at room temperature. After 15 min, the reaction mixture was diluted with aqueous saturated NH₄Cl solution and extracted twice with 20% IPA/CH₂Cl₂. The combined organic phases were dried (MgSO₄), filtered and concentrated in vacuo. The resulting residue was purified via silica gel chromatography using 0-5% MeOH:CH₂Cl₂ to elute impurity, 5%-10% to elute bottom two spots.

Diastereomer 1 [741]: ¹H NMR (300 MHz, DMSO) δ 12.32 (s, 1H), 8.70 (d, J=2.4 Hz, 1H), 8.27 (d, J=2.4 Hz, 1H), 8.26 (d, J=2.8 Hz, 1H), 8.18 (d, J=3.9 Hz, 1H), 7.34 (d, J=7.1 Hz, 1H), 5.77 (d, J=2.9 Hz, 1H), 4.60 (s, 1H), 3.73 (dd, J=10.1, 6.3 Hz, 6H), 2.30-2.15 (m, 1H), 2.04-1.86 (m, 1H), 1.85-1.50 (m, 6H); LCMS RT=3.82 (M+1) 470.5.

Diastereomer 2 [742]: ¹H NMR (300 MHz, DMSO) δ 12.30 (s, 1H), 8.75 (d, J=2.4 Hz, 1H), 8.27 (d, J=2.4 Hz, 1H), 8.18 (d, J=2.8 Hz, 1H), 8.14 (d, J=4.0 Hz, 1H), 7.44 (d, J=7.7 Hz, 1H), 5.38 (s, 1H), 4.55-4.36 (m, 1H), 3.71 (d, J=3.1 Hz, 3H), 3.68 (d, J=3.2 Hz, 3H), 2.16-2.01 (m, 2H), 2.00-1.72 (m, 3H), 1.71-1.41 (m, 2H), 1.39-1.18 (m, 1H); LCMS RT=3.70 (M+1) 470.5.

General Scheme 60:

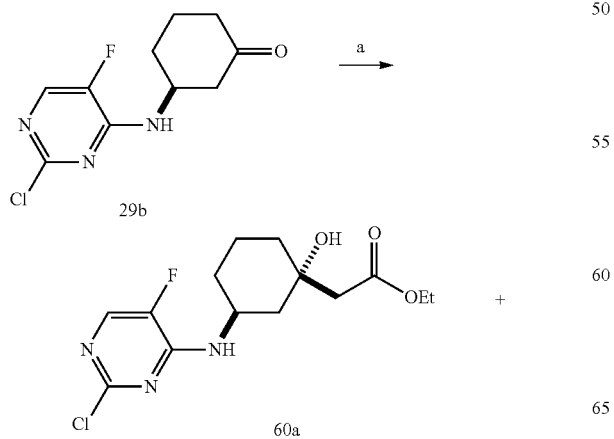

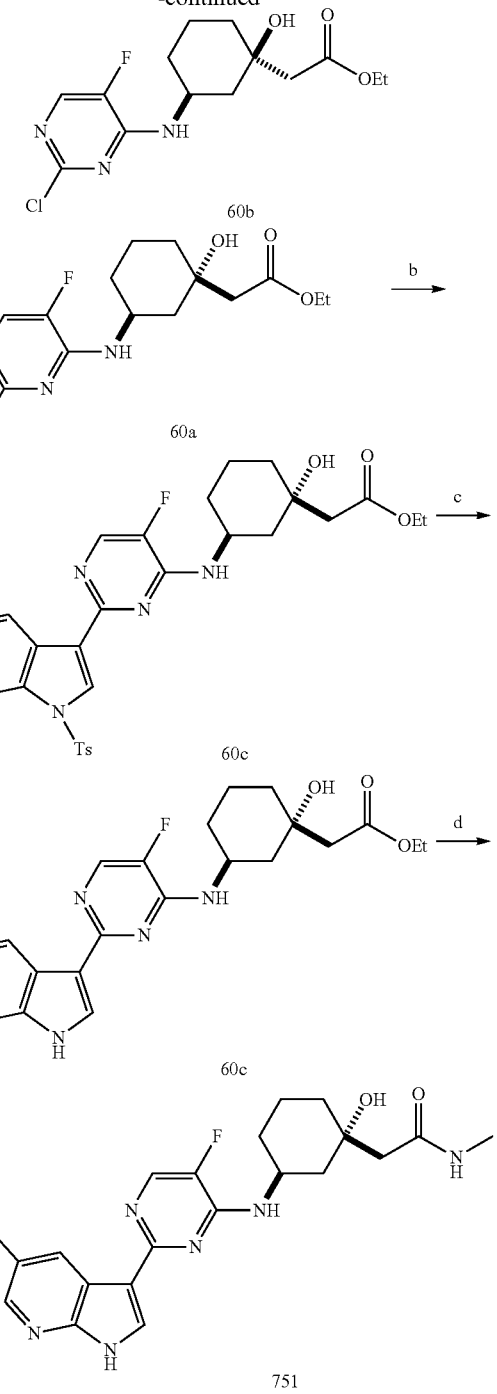

Formation of Ethyl 2-((1R,3S)-3-(2-chloro-5-fluoro-pyrimidin-4-ylamino)-1-hydroxy-cyclohexyl)ethanoate (60a)

Zinc dust (1.61 g, 24.62 mmol) was heated with a heat gun under N₂. THF (8.0 mL) was added, then a solution of chloro(trimethyl)silane (0.63 mL, 4.93 mmol) in THF (8.0 mL) was added and stirred for 15 min at room temperature then heated to reflux. After cooling to room temperature, a solution of ethyl 2-bromoacetate (2.73 mL, 24.62 mmol) in THF (6.0 mL) was added slowly to the zinc mixture. Then, a solution of (3S)-3-[(2-chloro-5-fluoro-pyrimidin-4-yl)amino]cyclohexanone, 29b, (2.00 g, 8.21 mmol) in THF (6.0 mL) was added. The mixture was refluxed for 2 hours then concentrated in vacuo. EtOAc and aqueous saturated NaHCO₃ solution were added and the product was extracted with additional EtOAc (3×), dried (Na₂SO₄) and concentrated in vacuo. Purification by silica gel chromatography (Hexanes:EtOAc) separated 2 products. The first peak was 60a (2.05 g, 6.18 mmol, 75%). LCMS+: 332.20 at 3.57 min (10-90% MeOH, 3/5 grad/run, Formic Acid).

Formation of Ethyl 2-((1R,3S)-3-((2-(5-chloro-1-tosyl-1H-pyrrolo[2,3-b]pyridin-3-yl)-5-fluoropyrimidin-4-ylamino)-1-hydroxycyclohexyl)ethanoate (60c)

To a solution of 5-chloro-1-(p-tolylsulfonyl)-3-(4,4,5,5-tetramethyl-1,3,2-dioxaborolan-2-yl)pyrrolo[2,3-b]pyridine (0.31 g, 0.72 mmol) in acetonitrile (6.0 mL) was added ethyl 2-((1R,3S)-3-(2-chloro-5-fluoropyrimidin-4-ylamino)-1-hydroxy-cyclohexyl)ethanoate, 60a, (0.20 g, 0.60 mmol) and degassed under N₂. Na₂CO₃ (0.90 mL of 2 M, 1.81 mmol) was added followed by Pd(PPh₃)₄ (0.10 g, 0.09 mmol). The reaction was sealed and microwaved at 120° C. for 30 min. The material was concentrated under reduced pressure then diluted in EtOAc and aqueous saturated NaHCO₃, then extracted with additional EtOAc (3×), dried (Na₂SO₄) and concentrated in vacuo. The material was diluted in DCM and silica gel chromatography (Hexanes:EtOAc) gave 217 mg of product 60c. LC MS+: 602.49 at 4.62 min (10-90% MeOH, 3/5 grad/run, Formic Acid).

Formation of 2-((1R,3S)-3-((2-(5-chloro-1H-pyrrolo[2,3-b]pyridin-3-yl)-5-fluoro-pyrimidin-4-ylamino)-1-hydroxycyclohexyl)ethanoic acid (60d)

To a solution of ethyl 2-((1R,3S)-3-((2-(5-chloro-1-tosyl-1H-pyrrolo[2,3-b]pyridin-3-yl)-5-fluoropyrimidin-4-ylamino)-1-hydroxycyclohexyl)ethanoate, 60c, (0.14 g, 0.22 mmol) in THF (5.0 mL) was added LiOH (1.12 mL of 1 M aqueous solution, 1.12 mmol). The reaction was microwaved at 130° C. for 30 min, neutralized with HCl (0.56 mL of 2 M, 1.12 mmol) and concentrated under reduced pressure, diluted in toluene and concentrated (2×) to give 60d which was used without further purification. LC MS+: 420.30 at 3.05 min (10-90% MeOH, 3/5 grad/run, Formic Acid).

Formation of 2-((1R,3S)-3-((2-(5-chloro-1H-pyrrolo[2,3-b]pyridin-3-yl)-5-fluoro-pyrimidin-4-ylamino)-1-hydroxycyclohexyl)-N-methylethanamide (751)

To a solution of 2-((1R,3S)-3-((2-(5-chloro-1H-pyrrolo[2,3-b]pyridin-3-yl)-5-fluoropyrimidin-4-ylamino)-1-hydroxy-cyclohexyl)ethanoic acid, 60d, (0.032 g, 0.076 mmol) in MeCN (1.6 mL) and DMF (1.6 mL) was added HATU (0.058 g, 0.152 mmol), Methanamine (0.154 mL of 2 M solution, 0.305 mmol) and ᶦPr₂NEt (0.053 mL, 0.305 mmol). The reaction was heated to 60° C. overnight then concentrated in vacuo. The resulting residue was purified by reverse phase HPLC (Water/HCl:MeOH). Pure fractions were combined and concentrated in vacuo to give 29 mg of 751 as the HCl salt.

General Scheme 61:

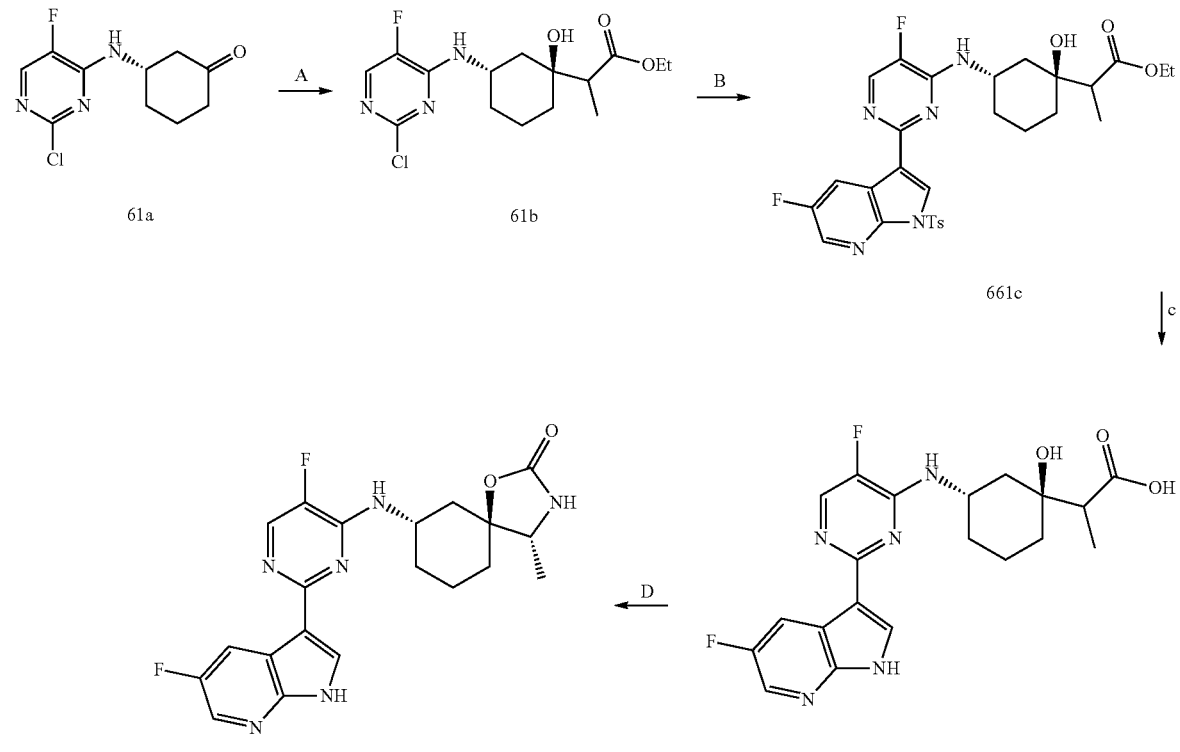

Formation of Ethyl 2-((1S,3S)-3-(2-chloro-5-fluoro-pyrimidin-4-ylamino)-1-hydroxycyclohexyl)propanoate (61b) (Step A)

Zinc dust (1.21 g, 18.47 mmol, 3 eq.) was heated with a heat gun under $N_2$. THF (6.0 mL) was added then a solution of chloro(trimethyl)silane (0.47 mL, 3.69 mmol) in THF (6.0 mL) was added and stirred for 15 min at room temperature then heated to reflux and cooled. A solution of ethyl 2-bromopropanoate (3.34 g, 18.47 mmol) and (3S)-3-[(2-chloro-5-fluoro-pyrimidin-4-yl)amino]cyclohexanone (61a) (1.50 g, 6.16 mmol) in THF (6.0 mL) was added to the zinc mixture slowly. This mixture was refluxed for 2 hours then concentrated in vacuo. EtOAc and aqueous saturated $NaHCO_3$ were added and the product was extracted with EtOAc (3×), dried ($Na_2SO_4$) and concentrated in vacuo. Purification by silica gel chromatography (Hexanes:EtOAc) separated 2 products. The first product eluted at 20-35% ethyl acetate and second product eluted at 35-40%. The fractions of the $2^{nd}$ product were concentrated in vacuo to give 760 mg of 61b. LCMS+: 346.23 at 3.35 min (10-90% MeOH, 3/5 grad/run, Formic Acid).

Formation of Ethyl 2-((1S,3S)-3-(5-fluoro-2-(5-fluoro-1-tosyl-1H-pyrrolo[2,3-b]pyridin-3-yl)pyrimidin-4-ylamino)-1-hydroxycyclohexyl)propanoate (61c)

To a solution of 5-fluoro-1-(p-tolylsulfonyl)-3-(4,4,5,5-tetramethyl-1,3,2-dioxaborolan-2-yl)pyrrolo[2,3-b]pyridine (0.21 g, 0.38 mmol) in acetonitrile (3.6 mL) was added ethyl 2-((1S,3S)-3-(2-chloro-5-fluoropyrimidin-4-ylamino)-1-hydroxy-cyclohexyl)propanoate (61b) (0.12 g, 0.35 mmol) and degassed under $N_2$. $Na_2CO_3$ (0.52 mL of 2 M aqueous solution, 1.041 mmol) was added followed by $Pd(PPh_3)_4$ (0.06 g, 0.052 mmol). The reaction was sealed and heated in a microwave at 120° C. for 30 min. The material was concentrated under reduced pressure and then diluted in EtOAc and aqueous saturated $NaHCO_3$, then extracted with additional EtOAc (3×). The combined organic phases were dried ($Na_2SO_4$) and concentrated in vacuo. The material was diluted in $CH_2Cl_2$ and silica gel chromatography (Hexanes:EtOAc) gave product 200 mg of 61c. LCMS+: 600.35 at 4.22 min (10-90% MeOH, 3/5 grad/run, Formic Acid).

Formation of 2-((1S,3S)-3-(5-fluoro-2-(5-fluoro-1H-pyrrolo[2,3-b]pyridin-3-yl)pyrimidin-4-ylamino)-1-hydroxycyclohexyl)propanoic acid (61d)

To a solution of ethyl 2-((1S,3S)-3-(5-fluoro-2-(5-fluoro-1-tosyl-1H-pyrrolo[2,3-b]pyridin-3-yl)pyrimidin-4-ylamino)-1-hydroxycyclohexyl)propanoate (61c) (0.20 g, 0.33 mmol) in THF (3 mL) was added LiOH (3 mL of 1 M aqueous solution, 3.0 mmol). The reaction was allowed to stir over 2 days at room temperature then neutralized with HCl (1.5 mL of 2M, 3.0 mmol) and concentrated to dryness, diluted in toluene and concentrated again (2×) to give 61d which was used without further purification. LCMS+: 418.32 at 2.62 min (10-90% MeOH, 3/5 grad/run, Formic Acid).

Formation of (4R,5S,7S)-7-(5-fluoro-2-(5-fluoro-1H-pyrrolo[2,3-b]pyridin-3-yl)pyrimidin-4-ylamino)-4-methyl-1-oxa-3-azaspiro[4.5]decan-2-one (967)

To a solution of 2-[(1S,3S)-3-[[5-fluoro-2-(5-fluoro-1H-pyrrolo[2,3-b]pyridin-3-yl)pyrimidin-4-yl]amino]-1-hydroxy-cyclohexyl]propanoic acid (61d) (0.095 g, 0.228 mmol) in toluene (5 mL) and triethylamine (0.048 mL, 0.341 mmol) was added (azido(phenoxy)phosphoryl)oxybenzene (0.059 mL, 0.273 mmol). The reaction was heated to 120° C. in a sealed tube overnight. The reaction was concentrated in vacuo and purified by reverse phase HPLC (Water/HCl: MeOH) to separate the diastereomers. To remove a trace amount of leftover starting material, the first peak was diluted in MeOH (1 mL) and passed through a PL-HCO₃ MP SPE cartridge to obtain the free base. This material was then salted (HCl in water) and concentrated in vacuo to give 16 mg of 967 as the HCl salt.

General Scheme 62:

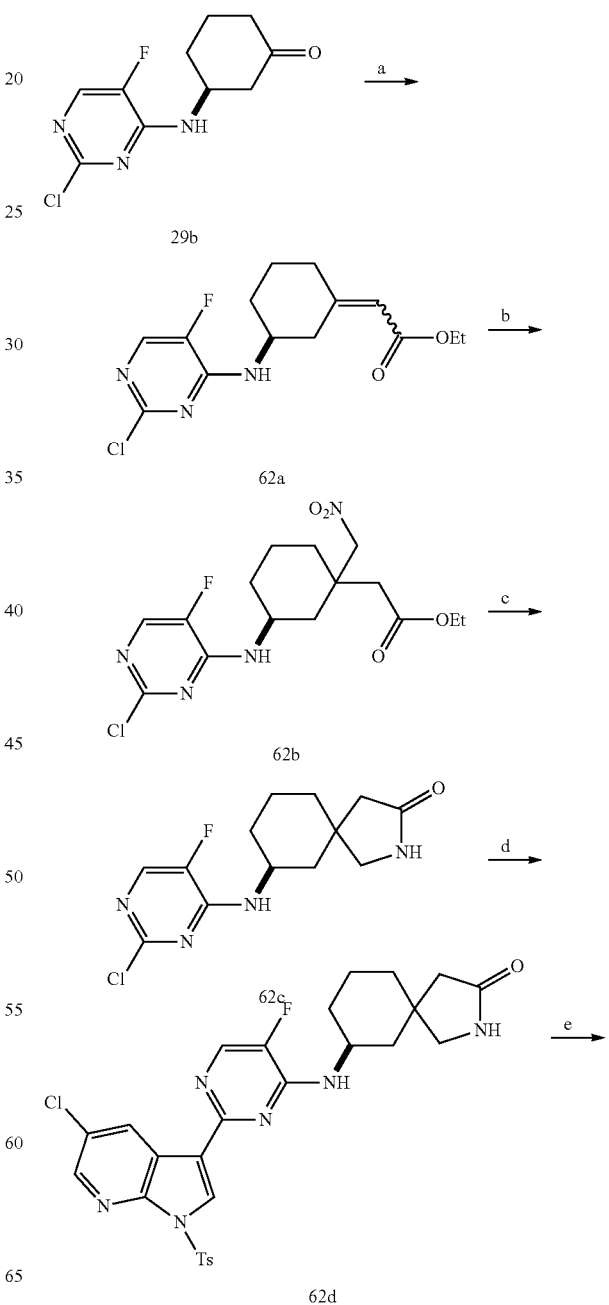

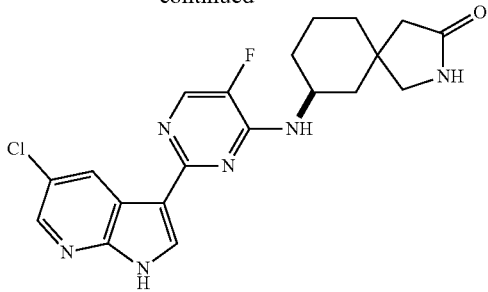

969

Formation of (S)-ethyl 2-(3-(2-chloro-5-fluoropyrimidin-4-ylamino)cyclohexylidene)ethanoate (62a)

To a solution of (3S)-3-[(2-chloro-5-fluoro-pyrimidin-4-yl)amino]cyclohexanone (29b) (2.00 g, 8.21 mmol) in toluene (40 mL) was added ethyl 2-triphenylphosphoranylideneacetate (4.29 g, 12.31 mmol). The reaction was refluxed overnight then concentrated in vacuo and purified by silica gel chromatography (Hexanes:EtOAc). The desired product eluted at 15% ethyl acetate. Clean fractions were combined and concentrated to give 2.57 g of 62a. LCMS+: 314.18 at 3.75 min (10-90% MeOH, 3/5 grad/run, Formic Acid).

Formation of Ethyl 2-((3S)-3-(2-chloro-5-fluoropyrimidin-4-ylamino)-1-(nitromethyl)cyclohexyl)ethanoate (62b)

To a solution of (5)-ethyl 2-(3-(2-chloro-5-fluoropyrimidin-4-ylamino)cyclohexylidene)ethanoate, 62a, (2.58 g, 8.22 mmol) in nitromethane (44.53 mL, 822.3 mmol) was added 1,1,3,3-tetramethylguanidine (1.55 mL, 12.33 mmol). The reaction was refluxed overnight then concentrated in vacuo and purified by silica gel chromatography (Hexanes:EtOAc) then a second chromatography (CH$_2$Cl$_2$:20% MeOH in CH$_2$Cl$_2$). Fractions containing pure product were combined and concentrated to give 1.8 g of 62b
LCMS+: 375.32 at 3.64 min (10-90% MeOH, 3/5 grad/run, Formic Acid).

Formation of (7S)-7-(2-chloro-5-fluoropyrimidin-4-ylamino)-2-azaspiro[4.5]decan-3-one (62c)

To a solution of ethyl 2-((3S)-3-(2-chloro-5-fluoropyrimidin-4-ylamino)-1-(nitromethyl)cyclohexyl)ethanoate, 62b, (1.60 g, 4.27 mmol) in MeOH (20 mL) was added Raney Nickel (0.03 g, 0.43 mmol). The reaction was shaken on a Parr apparatus at 40 psi of H$_2$ overnight. The reaction was filtered, concentrated in vacuo and purified by silica gel chromatography (CH$_2$Cl$_2$:20% MeOH in CH$_2$Cl$_2$) to give 155 mg of 62c. LCMS+: 299.13 at 2.87 min (10-90% MeOH, 3/5 grad/run, Formic Acid).

Formation of (7S)-7-(2-(5-chloro-1-tosyl-1H-pyrrolo[2,3-b]pyridin-3-yl)-5-fluoropyrimidin-4-ylamino)-2-azaspiro[4.5]decan-3-one (62d)

To a solution of 5-chloro-1-(p-tolylsulfonyl)-3-(4,4,5,5-tetramethyl-1,3,2-dioxaborolan-2-yl)pyrrolo[2,3-b]pyridine (0.083 g, 0.195 mmol) in acetonitrile (1.6 mL) was added (7S)-7-(2-chloro-5-fluoropyrimidin-4-ylamino)-2-azaspiro[4.5]decan-3-one (62c) (0.053 g, 0.177 mmol) and degassed under N$_2$. Aqueous Na$_2$CO$_3$ (0.266 mL of 2 M solution, 0.5320 mmol) was added followed by Pd(PPh$_3$)$_4$ (0.031 g, 0.027 mmol). The reaction was sealed and heated in a microwave at 120° C. for 30 min then concentrated in vacuo. The material was diluted in CH$_2$Cl$_2$ and silica gel chromatography using a gradient of Hexanes:EtOAc then 20% MeOH in CH$_2$Cl$_2$. Pure fractions were combined and concentrated to give 91 mg of 62d. LCMS+: 569.26 at 4.20 min (10-90% MeOH, 3/5 grad/run, Formic Acid).

Formation of (7S)-7-(2-(5-chloro-1H-pyrrolo[2,3-b]pyridin-3-yl)-5-fluoropyrimidin-4-ylamino)-2-azaspiro[4.5]decan-3-one (969)

To a solution of (7S)-7-(2-chloro-5-fluoropyrimidin-4-ylamino)-2-azaspiro[4.5]decan-3-one, 62d, (0.091 g, 0.159 mmol) in MeOH (2 mL) was added NaOMe (2 mL of 25% w/v, 9.255 mmol). The reaction was stirred for 0.5 hours then concentrated in vacuo. The material was purified by reverse phase HPLC (Water/HCl:MeOH) to give a mixture of diastereomers. The fractions containing pure product were combined and concentrated to give 50 mg of the HCl salt of 969.

General Scheme 63:

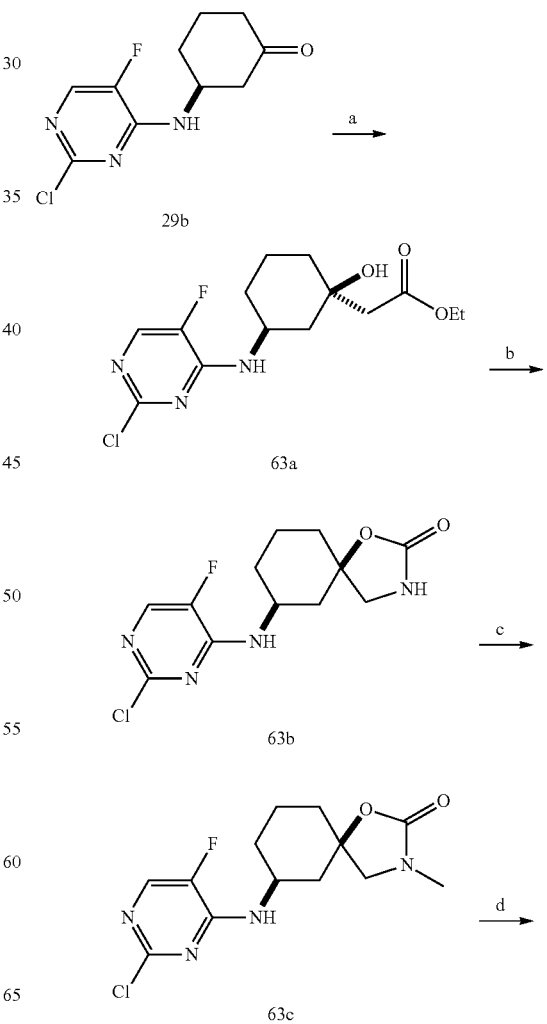

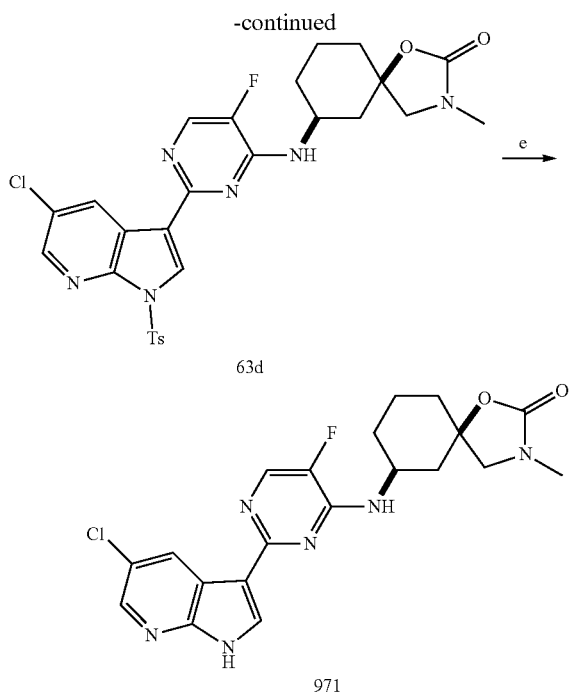

Formation of ethyl 2-((1S,3S)-3-(2-chloro-5-fluoro-pyrimidin-4-ylamino)-1-hydroxycyclohexyl)ethanoate (63a)

Zinc dust (1.61 g, 24.62 mmol) was heated with a heat gun under $N_2$. THF (8.0 mL) was added, then a solution of chloro (trimethyl)silane (0.63 mL, 4.93 mmol) in THF (8.0 mL) was added and stirred for 15 min at room temperature then heated to reflux and cooled. A solution of ethyl 2-bromoacetate (2.73 mL, 24.62 mmol) in THF (6.0 mL) was added slowly to the zinc mixture, then a solution of (3S)-3-[(2-chloro-5-fluoro-pyrimidin-4-yl)amino]cyclohexanone, 29b, (2.00 g, 8.21 mmol) in THF (6.0 mL) was added. The mixture was refluxed for 2 hours then concentrated in vacuo. EtOAc and aqueous saturated $NaHCO_3$ solution were added and the product was extracted with additional EtOAc (3×), dried ($Na_2SO_4$) and concentrated in vacuo. Purification by silica gel chromatography (Hexanes:EtOAc) separated 2 products. Fractions containing the second (minor) peak were combined and concentrated to give 470 mg of 63a. LCMS+: 332.13 at 3.2 min (10-90% MeOH, 3/5 grad/run, Formic Acid).

Formation of (5S,7S)-7-(2-chloro-5-fluoropyrimidin-4-ylamino)-1-oxa-3-azaspiro[4.5]decan-2-one (63b)

To a solution of ethyl 2-((1S,3S)-3-(2-chloro-5-fluoropyrimidin-4-ylamino)-1-hydroxycyclohexyl)ethanoate, 63a, (0.40 g, 1.20 mmol) in dry MeOH (6 mL) was added hydrazine (0.75 mL, 23.4 mmol). The reaction was stirred overnight at room temperature then concentrated under a stream of $N_2$. The reaction was diluted with HCl (20 mL of a 1M solution, 20 mmol) until acidic and cooled to 0°-5° C. Then $NaNO_2$ (1.44 mL of a 1M solution, 1.44 mmol) was added slowly. 1:1 Benzene:$CHCl_3$ (20 mL) was added and the mixture was stirred. The organic layer was separated and added slowly to refluxing benzene. This was refluxed for 0.5 h then concentrated. Silica gel chromatography ($CH_2Cl_2$:20% MeOH in $CH_2Cl_2$) gave 92 mg of pure product 63b. LCMS+: 301.15 at 2.76 min (10-90% MeOH, 3/5 grad/run, Formic Acid).

Formation of (5S,7S)-7-(2-chloro-5-fluoropyrimidin-4-ylamino)-3-methyl-1-oxa-3-azaspiro[4.5]decan-2-one (63c)

A solution of (5S,9S)-9-[(2-chloro-5-fluoro-pyrimidin-4-yl)amino]-1-oxa-3-azaspiro[4.5]decan-2-one, 63b, (0.049 g, 0.163 mmol) in DMF (8.2 mL) was cooled to 0° C. NaH (0.010 mg, 0.244 mmol) was added followed by MeI (0.011 mL, 0.179 mmol). The reaction was allowed to warm to room temperature overnight. The reaction was quenched with water and concentrated in vacuo. Aqueous saturated $NaHCO_3$ solution was added and the product was extracted with EtOAc (3×), washed with brine, dried ($Na_2SO_4$) and concentrated in vacuo. The material was purified using silica gel chromatography ($CH_2Cl_2$:20% MeOH in $CH_2Cl_2$) to give 63b. LCMS+: 315.19 at 2.83 min (10-90% MeOH, 3/5 grad/run, Formic Acid).

Formation of (5S,7S)-7-(2-(5-chloro-1-tosyl-1H-pyrrolo[2,3-b]pyridin-3-yl)-5-fluoropyrimidin-4-ylamino)-3-methyl-1-oxa-3-azaspiro[4.5]decan-2-one (63d)

To a solution of 5-chloro-1-(p-tolylsulfonyl)-3-(4,4,5,5-tetramethyl-1,3,2-dioxaborolan-2-yl)pyrrolo[2,3-b]pyridine (0.031 g, 0.0724 mmol) in acetonitrile (0.570 mL) was added (5S,7S)-7-(2-chloro-5-fluoropyrimidin-4-ylamino)-3-methyl-1-oxa-3-azaspiro[4.5]decan-2-one, 63c, (0.019 g, 0.060 mmol) and degassed under $N_2$. $Na_2CO_3$ (0.091 mL of 2 M, 0.1810 mmol) was added followed by $Pd(PPh_3)_4$ (0.010 g, 0.009 mmol). The reaction was sealed and heated in a microwave at 120° C. for 30 min. The mixture was then concentrated in vacuo. The material was diluted in $CH_2Cl_2$ and silica gel chromatography (Hexanes:EtOAc then 20% MeOH in $CH_2Cl_2$) gave product 63d. LCMS+: 585.25 at 4.17 min (10-90% MeOH, 3/5 grad/run, Formic Acid).

(5S,7S)-7-(2-(5-chloro-1H-pyrrolo[2,3-b]pyridin-3-yl)-5-fluoropyrimidin-4-ylamino)-3-methyl-1-oxa-3-azaspiro[4.5]decan-2-one (971)

To a solution of (5S,7S)-7-(2-(5-chloro-1-tosyl-1H-pyrrolo[2,3-b]pyridin-3-yl)-5-fluoropyrimidin-4-ylamino)-3-methyl-1-oxa-3-azaspiro[4.5]decan-2-one, 63d, (0.035 g, 0.060 mmol) in MeOH (2 mL) was added NaOMe (2 mL of 25% w/v, 9.255 mmol). The mixture was stirred for 30 min then concentrated in vacuo and purified by reverse phase HPLC (Water/HCl:MeOH). Pure fractions were combined and concentrated in vacuo to afford product 971 as the HCl salt.

General Scheme 64:

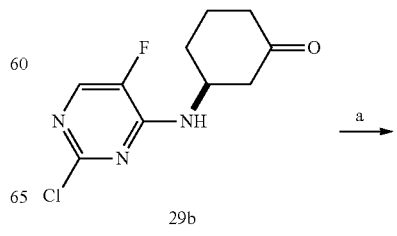

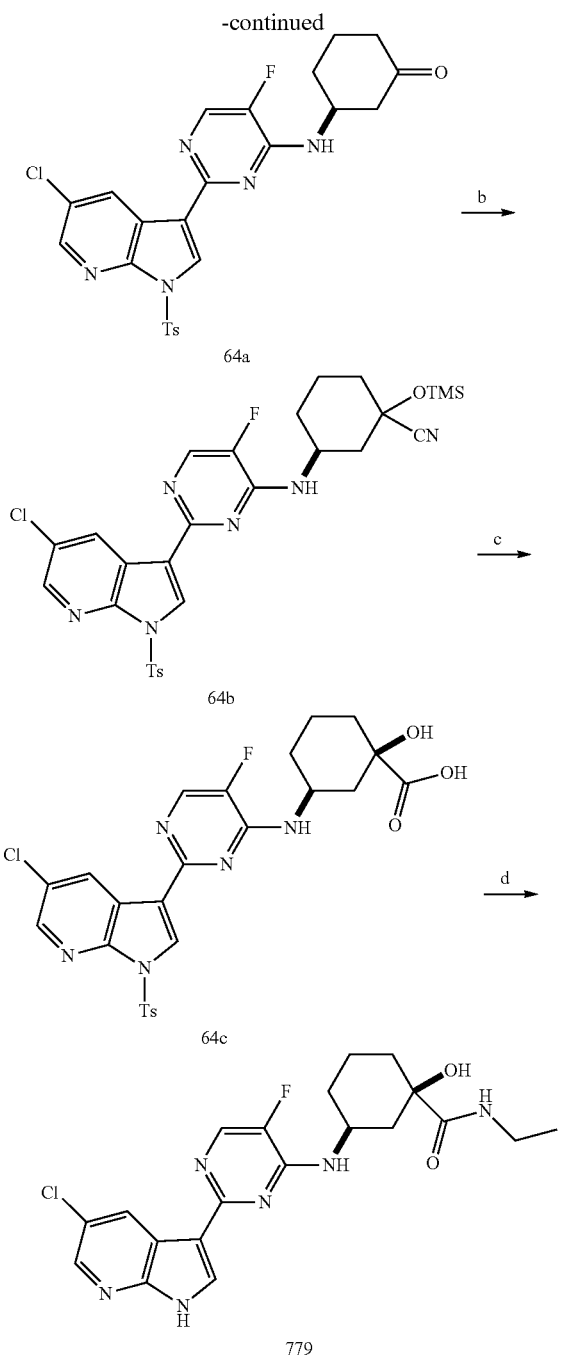

was diluted with ethyl acetate (40 mL), filtered through Celite. The filtrate was washed with brine, dried (MgSO$_4$), filtered and concentrated in vacuo. Purification via silica gel chromatography using 10-80% EtOAc/hexanes gradient afforded (3S)-3-[[2-[5-chloro-1-(p-tolylsulfonyl)pyrrolo[2,3-b]pyridin-3-yl]-5-fluoro-pyrimidin-4-yl]amino]cyclohexanone, 64a.

Formation of (3S)-3-[[2-[5-chloro-1-(p-tolylsulfonyl)pyrrolo[2,3-b]pyridin-3-yl]-5-fluoro-pyrimidin-4-yl]amino]-1-trimethylsilyloxy-cyclohexanecarbonitrile (64b)

To a solution of (3S)-3-[[2-[5-chloro-1-(p-tolylsulfonyl)pyrrolo[2,3-b]pyridin-3-yl]-5-fluoro-pyrimidin-4-yl]amino]cyclohexanone, 64a, (0.58 g, 1.13 mmol) in CH$_2$Cl$_2$ (20 mL) was added diiodozinc (0.36 g, 1.13 mmol) and trimethylsilylformonitrile (0.30 mL, 2.26 mmol) at room temperature. The reaction was refluxed overnight. The mixture was purified by silica gel chromatography to afford 600 mg of (3S)-3-[[2-[5-chloro-1-(p-tolylsulfonyl)pyrrolo[2,3-b]pyridin-3-yl]-5-fluoro-pyrimidin-4-yl]amino]-1-trimethyl-silyloxy-cyclohexanecarbonitrile, 64b.

Formation of (1S,3S)-3-[[2-(5-chloro-1H-pyrrolo[2,3-b]pyridin-3-yl)-5-fluoro-pyrimidin-4-yl]amino]-1-hydroxy-cyclohexanecarboxylic acid (64c)

(3S)-3-[[2-[5-chloro-1-(p-tolylsulfonyl)pyrrolo[2,3-b]pyridin-3-yl]-5-fluoro-pyrimidin-4-yl]amino]-1-trimethylsilyloxy-cyclohexanecarbonitrile, 64b, (0.57 g, 0.93 mmol) was heated in HCl (20 mL of 12 M solution, 240.0 mmol) at 80° C. in a sealed tube overnight. The solvent was evaporated and the crude product was purified by preparatory HPLC to provide 200 mg of (1S,3S)-3-[[2-(5-chloro-1H-pyrrolo[2,3-b]pyridin-3-yl)-5-fluoro-pyrimidin-4-yl]amino]-1-hydroxy-cyclohexanecarboxylic acid, 64c.

$^1$H NMR (300 MHz, MeOD) δ 8.70 (d, J=2.2 Hz, 1H), 8.47 (s, 1H), 8.37 (d, J=2.2 Hz, 1H), 8.28 (d, J=5.5 Hz, 1H), 5.37-4.57 (m, 49H), 3.38-3.26 (m, 26H), 2.42 (dd, J=13.3, 4.2 Hz, 2H), 2.15 (d, J=10.4 Hz, 1H), 2.07-1.87 (m, 3H), 1.77 (dd, J=18.1, 8.6 Hz, 3H); LCMS: 406.35 (M+1).

Formation of (1S,3S)-3-[[2-(5-chloro-1H-pyrrolo[2,3-b]pyridin-3-yl)-5-fluoro-pyrimidin-4-yl]amino]-N-ethyl-1-hydroxy-cyclohexanecarboxamide (779)

(1S,3S)-3-[[2-(5-chloro-1H-pyrrolo[2,3-b]pyridin-3-yl)-5-fluoro-pyrimidin-4-yl]amino]-1-hydroxy-cyclohexanecarboxylic acid, 64c, (0.040 g, 0.090 mmol) was dissolved in DMF (3 mL), then $^i$Pr$_2$NEt (0.047 mL, 0.271 mmol) and ethanamine (0.135 mL of 2 M solution, 0.271 mmol) was added, followed by HATU (0.080 g, 0.210 mmol). The reaction was stirred at room temperature for another 2 hours. The solution was evaporated and the product was purified by Preparatory HPLC to afford 10 mg of (1S,3S)-3-[[2-(5-chloro-1H-pyrrolo[2,3-b]pyridin-3-yl)-5-fluoro-pyrimidin-4-yl]amino]-N-ethyl-1-hydroxy-cyclohexanecarboxamide, 779.

$^1$H NMR (300 MHz, MeOD) d 8.72 (d, J=2.2 Hz, 2H), 8.48 (s, 2H), 8.34 (dd, J=23.7, 3.9 Hz, 3H), 4.99 (d, J=5.4 Hz, 3H), 4.88 (s, 1H), 4.85-4.67 (m, 32H), 3.44-2.95 (m, 4H), 2.29 (dd, J=13.5, 4.1 Hz, 3H), 2.11 (d, J=9.5 Hz, 2H), 2.04-1.80 (m, 7H), 1.76 (s, 3H), 1.13 (t, J=7.2 Hz, 4H); LCMS: 433.42 (M+1).

Formation of (3S)-3-[[2-[5-chloro-1-(p-tolylsulfonyl)pyrrolo[2,3-b]pyridin-3-yl]-5-fluoro-pyrimidin-4-yl]amino]cyclohexanone (64a)

A microwave tube was placed 5-chloro-1-(p-tolylsulfonyl)-3-(4,4,5,5-tetramethyl-1,3,2-dioxaborolan-2-yl)pyrrolo[2,3-b]pyridine (2.13 g, 4.93 mmol) and (3S)-3-[(2-chloro-5-fluoro-pyrimidin-4-yl)amino]cyclohexanone in DME (22.2 mL) and aqueous Na$_2$CO$_3$ (5.13 mL of 2 M solution, 10.26 mmol) solution. The mixture was deoxygenated with nitrogen for 20 min. To the reaction mixture was added tetrakis triphenylphosphane palladium (0.47 g, 0.41 mmol). The reaction was sealed and heated to 120° C. for 30 min. The reaction General Scheme 65:

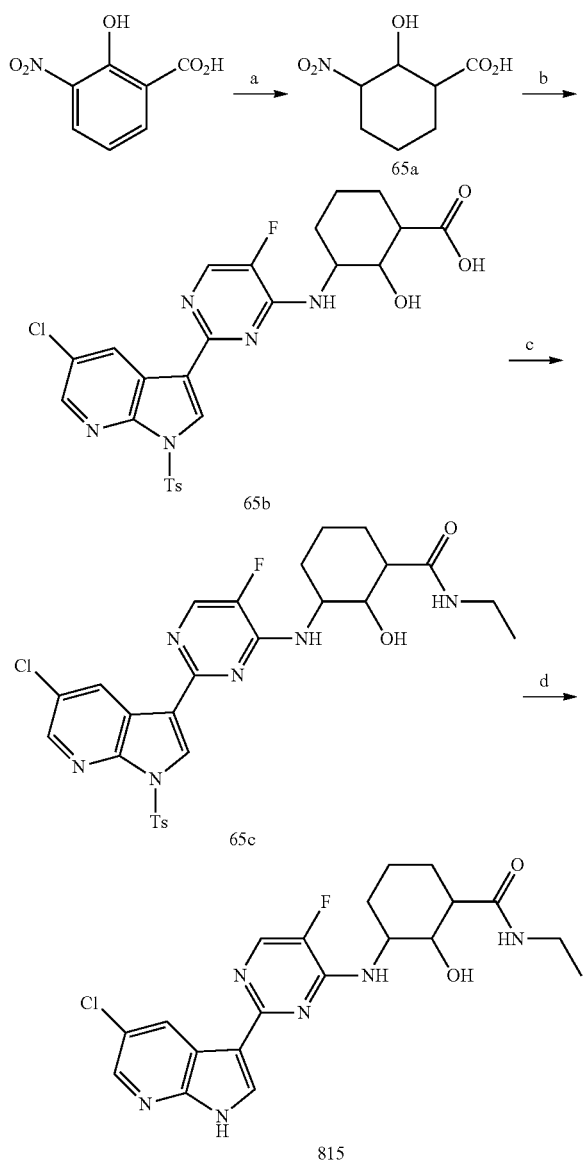

mmol), 3-amino-2-hydroxy-cyclohexanecarboxylic acid (0.19 g, 0.97 mmol), $^i$Pr$_2$NEt (0.45 mL, 2.58 mmol) in DMF (23.2 mL) solution was heated in microwave at 130° C. for 10 min. The solvent of the reaction mixture was removed under reduced pressure and the residue was purified by preparatory HPLC to give 240 mg of 3-[[2-[5-chloro-1-(p-tolylsulfonyl)pyrrolo[2,3-b]pyridin-3-yl]-5-fluoro-pyrimidin-4-yl]amino]-2-hydroxy-cyclohexanecarboxylic acid, 65b, as a mixture of stereoisomers.

Formation of 3-[[2-[5-chloro-1-(p-tolylsulfonyl)pyrrolo[2,3-b]pyridin-3-yl]-5-fluoro-pyrimidin-4-yl]amino]-N-ethyl-2-hydroxy-cyclohexanecarboxamide (65c)

3-[[2-[5-chloro-1-(p-tolylsulfonyl)pyrrolo[2,3-b]pyridin-3-yl]-5-fluoro-pyrimidin-4-yl]amino]-2-hydroxy-cyclohexanecarboxylic acid, 65b, (0.100 g, 0.179 mmol) was dissolved in DMF (2 mL) and $^i$Pr$_2$NEt (0.124 mL, 0.714 mmol) and ethanamine hydrochloride (0.029 g, 0.357 mmol) was added at room temperature. Then HATU (0.081 g, 0.214 mmol) was added to the solution at room temperature. After 30 min, EtOAc was added and the mixture was washed with 1 N HCl, aqueous saturated NH$_4$Cl solution, and brine. The organic phase was dried over Na$_2$SO$_4$, filtered and concentrated in vacuo. The crude product was used in the next step without further purification.

Formation of 3-[[2-(5-chloro-1H-pyrrolo[2,3-b]pyridin-3-yl)-5-fluoro-pyrimidin-4-yl]amino]-N-ethyl-2-hydroxy-cyclohexanecarboxamide (815)

3-[[2-[5-chloro-1-(p-tolylsulfonyl)pyrrolo[2,3-b]pyridin-3-yl]-5-fluoro-pyrimidin-4-yl]amino]-N-ethyl-2-hydroxy-cyclohexanecarboxamide, 65c, was treated with NaOMe in MeOH. The product was purified by preparatory HPLC to provide 3-[[2-(5-chloro-1H-pyrrolo[2,3-b]pyridin-3-yl)-5-fluoro-pyrimidin-4-yl]amino]-N-ethyl-2-hydroxy-cyclohexanecarboxamide as a mixture of stereoisomers. LCMS: 433.35 (M+1).

Formation of 3-amino-2-hydroxy-cyclohexanecarboxylic acid (65a)

2-Hydroxy-3-nitro-benzoic acid (5.0 g, 27.3 mmol) was mixed with HCl (125 mL of 0.5 M, 62.5 mmol) and dioxoplatinum (1.0 g, 4.4 mmol) in a hydrogenation bottle. The mixture was placed on a Parr shaker (50 psi H$_2$) for 24 hours. The catalyst was filtered and washed with hot H$_2$O. The filtrate was evaporated to provide 3-amino-2-hydroxy-cyclohexanecarboxylic acid as a mixture of stereoisomers which was utilized to the next step without further purification.

Formation of 3-[[2-[5-chloro-1-(p-tolylsulfonyl)pyrrolo[2,3-b]pyridin-3-yl]-5-fluoro-pyrimidin-4-yl]amino]-2-hydroxy-cyclohexanecarboxylic acid (65b)

5-chloro-3-(5-fluoro-4-methylsulfinyl-pyrimidin-2-yl)-1-(p-tolylsulfonyl)-pyrrolo[2,3-b]pyridine, 65a, (0.30 g, 0.64

General Scheme 66:

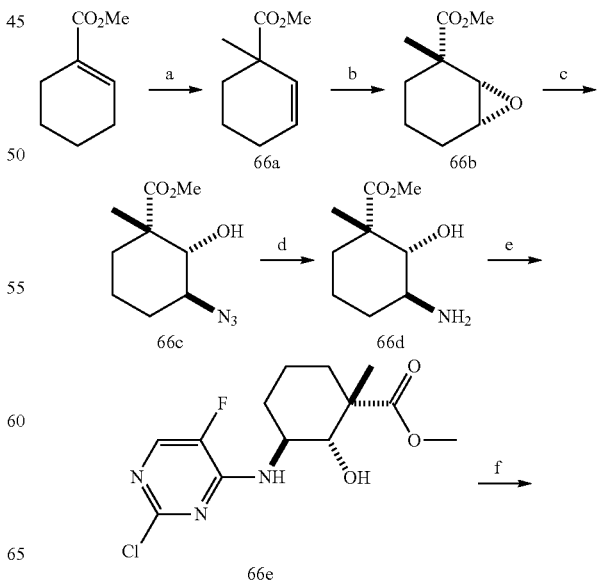

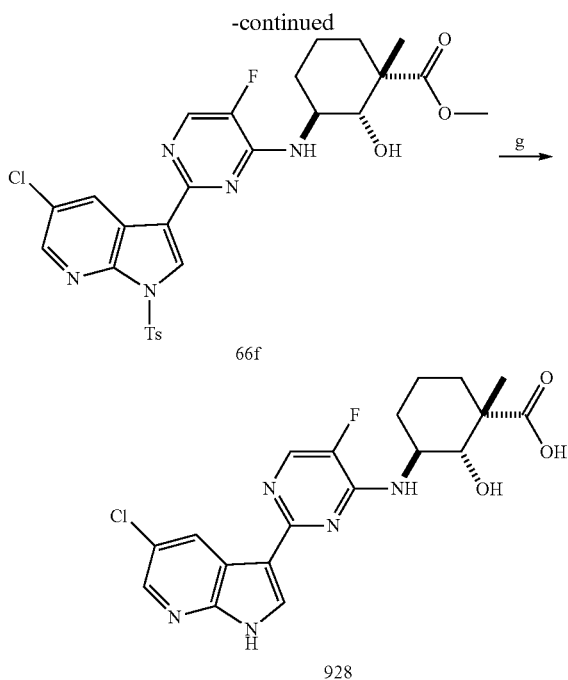

66f

928

Formation of Methyl-1-methylcyclohex-2-ene-1-carboxylate (66a)

To a cold (0° C.) solution of freshly distilled N-isopropylpropan-2-amine (4.20 mL, 29.96 mmol) in THF (150 mL) under argon was added dropwise nBuLi (12.65 mL of 2.2 M solution, 27.82 mmol). After 15 min the solution was cooled to −78° C. and dry HMPA (4.84 mL, 27.82 mmol) was added. The mixture was stirred for 30 min at −78° C. and methyl cyclohexene-1-carboxylate (3.00 g, 21.40 mmol) was then added. After stirring an additional 10 min, methyl iodide (2.00 mL, 32.10 mmol) was added. The solution was then allowed to warm to −5° C. over 2 h. An aqueous saturated solution of $NH_4Cl$ was poured into the orange mixture. After dilution with hexanes and washing with brine, the organic layer was dried over $Na_2SO_4$ and carefully evaporated to 3.3 g of generate methyl 1-methylcyclohex-2-ene-1-carboxylate, 66a, which was used without further purification.

$^1$H NMR (300 MHz, CDCl$_3$) δ 5.77 (dt, J=10.1, 3.5 Hz, 1H), 5.66 (s, 1H), 3.71-3.58 (m, 3H), 2.16 (ddd, J=12.9, 7.0, 3.4 Hz, 1H), 2.03-1.88 (m, 2H), 1.72-1.53 (m, 2H), 1.49-1.37 (m, 1H), 1.32-1.14 (m, 3H).

Formation of racemic cis-methyl 5-methyl-7-oxabicyclo[4.1.0]heptane-5-carboxylate (66b)

Methyl 1-methylcyclohex-2-ene-1-carboxylate, 66a, (3.30 g, 21.40 mmol) was treated with 3-chloroperoxybenzoic acid (7.39 g, 42.80 mmol) in CH$_2$Cl$_2$ (75 mL) at room temperature for 2 hours. The solution was clear but white precipitate was observed after 1 hour. The resulting white solid was filtered and washed with hexanes, and the filtration was diluted with EtOAc and washed with aqueous saturated NaHCO$_3$ solution followed by brine. The organic phase was then dried over Na$_2$SO$_4$, concentrated in vacuo and the crude residue was purified by silica gel chromatography (Hexanes/Ethyl acetate 100/0 to 10/1 gradient) to provide two products. The less polar spot is a colorless oil, which is assigned by $^1$H NMR to be cis-methyl 5-methyl-7-oxabicyclo[4.1.0]heptane-5-carboxylate (1.2 g) and the second fraction is a white solid, which is trans-methyl-5-methyl-7-oxabicyclo[4.1.0]heptane-5-carboxylate (2.2 g).

Racemic cis-isomer (66b): $^1$H NMR (300 MHz, CDCl$_3$) δ 3.67 (d, J=4.3 Hz, 3H), 3.23-3.12 (m, 1H), 3.08 (d, J=3.8 Hz, 1H), 2.02-1.78 (m, 2H), 1.68 (dtd, J=9.7, 6.8, 3.2 Hz, 1H), 1.49-1.27 (m, 2H), 1.25-1.15 (m, 3H), 1.06 (ddd, J=9.1, 7.4, 3.2 Hz, 1H).

Formation of racemic methyl-3-azido-2-hydroxy-1-methyl-cyclohexanecarboxylate (66c)

Racemic cis-methyl-5-methyl-7-oxabicyclo[4.1.0]heptane-5-carboxylate, 66b, (2.2 g, 12.93 mmol) was added to a flask containing MeOH (90 mL) and H$_2$O (10 mL) under nitrogen atmosphere. NH$_4$Cl (1.38 g, 0.90 mL, 25.86 mmol) and NaN$_3$ (2.52 g, 38.79 mmol) were then added to the reaction mixture. The mixture was heated to reflux for 16 hours. The solvent was evaporated under reduced pressure and the oil was taken up in H$_2$O and extracted with EtOAc. The combined organic phases were washed with brine and dried over Na$_2$SO$_4$. The crude product was purified by silica gel chromatography to afford 900 mg of racemic methyl-3-azido-2-hydroxy-1-methyl-cyclohexanecarboxylate.

$^1$H NMR (300 MHz, CDCl$_3$) δ 3.74 (d, J=3.1 Hz, 3H), 3.64-3.43 (m, 2H), 3.25-3.05 (m, 1H), 2.25-2.09 (m, 1H), 2.00 (ddd, J=9.7, 4.8, 2.9 Hz, 1H), 1.73-1.50 (m, 1H), 1.40 (d, J=6.3 Hz, 3H), 1.32-1.03 (m, 3H).

Formation of racemic methyl-3-amino-2-hydroxy-1-methyl-cyclohexanecarboxylate (66d)

A solution of racemic methyl-3-azido-2-hydroxy-1-methyl-cyclohexane-carboxylate, 66c, (0.90 g, 4.22 mmol) in a mixture of MeOH (50 mL) and AcOH (10 mL) was stirred under a hydrogen atmosphere (balloon) with the presence of palladium (0.50 g, 0.47 mmol) overnight at room temperature. The mixture was filtered through a celite bed and washed with MeOH. The combined filtrates were evaporated to provide methyl-3-amino-2-hydroxy-1-methyl-cyclohexanecarboxylate as a oil. Et$_2$O was added and the resulted acetic acid salt was stirred for 0.5 hour and was then filtered to give 1.0 g of racemic methyl-3-amino-2-hydroxy-1-methyl-cyclohexanecarboxylate acetic acid salt as a white solid.

Formation of racemic Methyl-3-[(2-chloro-5-fluoro-pyrimidin-4-yl)amino]-2-hydroxy-1-methyl-cyclohexanecarboxylate (66e)

To a solution of 2,4-dichloro-5-fluoro-pyrimidine (0.43 g, 2.58 mmol) and racemic methyl-3-amino-2-hydroxy-1-methyl-cyclohexanecarboxylate acetic acid salt, 66d, (0.58 g, 2.35 mmol) in THF (10 mL) and MeOH (8 mL) at room temperature was added $^i$Pr$_2$NEt (1.23 mL, 7.04 mmol). After stirring the reaction overnight at room temperature, the solvent was evaporated under reduced pressure and the crude residue was purified by silica gel chromatography (Hexanes/EtOAc 100/0 to 0/100, Rf=0.7 in Hexanes/EtOAc 2/1) to provide 650 mg of racemic methyl-3-[(2-chloro-5-fluoro-pyrimidin-4-yl)amino]-2-hydroxy-1-methyl-cyclohexanecarboxylate, 66e, as a white solid. LCMS: 318.16 (M+1).

Formation of racemic Methyl-3-[[2-[5-chloro-1-(p-tolylsulfonyl)pyrrolo[2,3-b]pyridin-3-yl]-5-fluoro-pyrimidin-4-yl]amino]-2-hydroxy-1-methyl-cyclohexanecarboxylate (66f)

To a solution of racemic methyl-3-[(2-chloro-5-fluoro-pyrimidin-4-yl)amino]-2-hydroxy-1-methyl-cyclohexanecarboxylate, 66e, (0.65 g, 2.05 mmol) and 5-chloro-1-(p-tolyl-sulfonyl)-3-(4,4,5,5-tetramethyl-1,3,2-dioxaborolan-2-yl)pyrrolo[2,3-b]pyridine (1.32 g, 3.05 mmol) in THF (20 mL) was added aqueous Na$_2$CO$_3$ (3.52 mL of 2 M solution, 7.04 mmol). The solution was degassed with N$_2$ for 20 minutes. Tetrakis triphenylphosphane palladium (O) (0.14 g, 0.12 mmol) was added and the mixture was refluxed overnight. LCMS showed good conversion, but some starting materials remained. More degassed 2 N Na$_2$CO$_3$ was added followed by another portion of Tetrakis triphenylphosphane palladium (0.14 g, 0.12 mmol). The reaction was refluxed for another 4 hours. The mixture was cooled to room temperature, extracted with EtOAc. The organic phase was washed by brine and dried over Na$_2$SO$_4$. After evaporation of solvent the crude mixture was purified by silica gel chromatography (Hexanes/EtOAc 100/0 to 0/100) to provide 1.0 g of racemic methyl-3-[[2-[5-chloro-1-(p-tolylsulfonyl)pyrrolo[2,3-b]pyridin-3-yl]-5-fluoro-pyrimidin-4-yl]amino]-2-hydroxy-1-methyl-cyclohexanecarboxylate, 66f. LCMS: 588.26 (M+1).

Formation of (1S,2S,3S)-3-[[2-(5-chloro-1H-pyrrolo[2,3-b]pyridin-3-yl)-5-fluoro-pyrimidin-4-yl]amino]-2-hydroxy-1-methyl-cyclohexanecarboxylic acid (928)

Racemic methyl-3-[[2-[5-chloro-1-(p-tolylsulfonyl)pyrrolo[2,3-b]pyridin-3-yl]-5-fluoro-pyrimidin-4-yl]amino]-2-hydroxy-1-methyl-cyclohexanecarboxylate, 66f, (0.100 g, 0.170 mmol) was dissolved in MeOH (1 mL) and THF (1 mL) and treated with aqueous LiOH (0.24 mL of 1 M solution, 0.24 mmol) and the reaction was heated to reflux overnight. The reaction was cooled to room temperature and the resulting material directly purified by preparatory HPLC to afford 20 mg of racemic 3-[[2-(5-chloro-1H-pyrrolo[2,3-b]pyridin-3-yl)-5-fluoro-pyrimidin-4-yl]amino]-2-hydroxy-1-methyl-cyclohexanecarboxylic acid. The enantiomers of the racemic material were separated by chiral SFC purification to afford 6 mg of (1R,2R,3R)-3-[[2-(5-chloro-1H-pyrrolo[2,3-b]pyridin-3-yl)-5-fluoro-pyrimidin-4-yl]amino]-2-hydroxy-1-methyl-cyclohexanecarboxylic acid and 6 mg of (1S,2S,3S)-3-[[2-(5-chloro-1H-pyrrolo[2,3-b]pyridin-3-yl)-5-fluoro-pyrimidin-4-yl]amino]-2-hydroxy-1-methyl-cyclohexanecarboxylic acid. LCMS: 420.36 (M+1).

General Scheme 67:

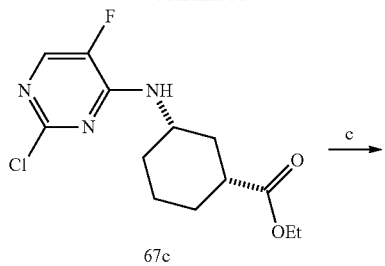
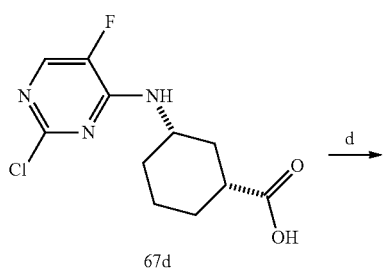
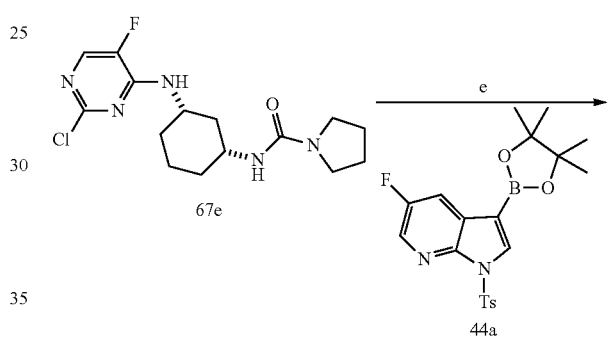
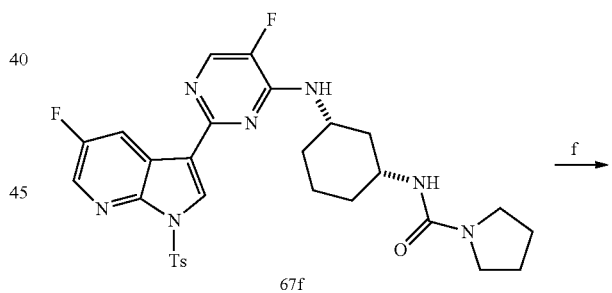
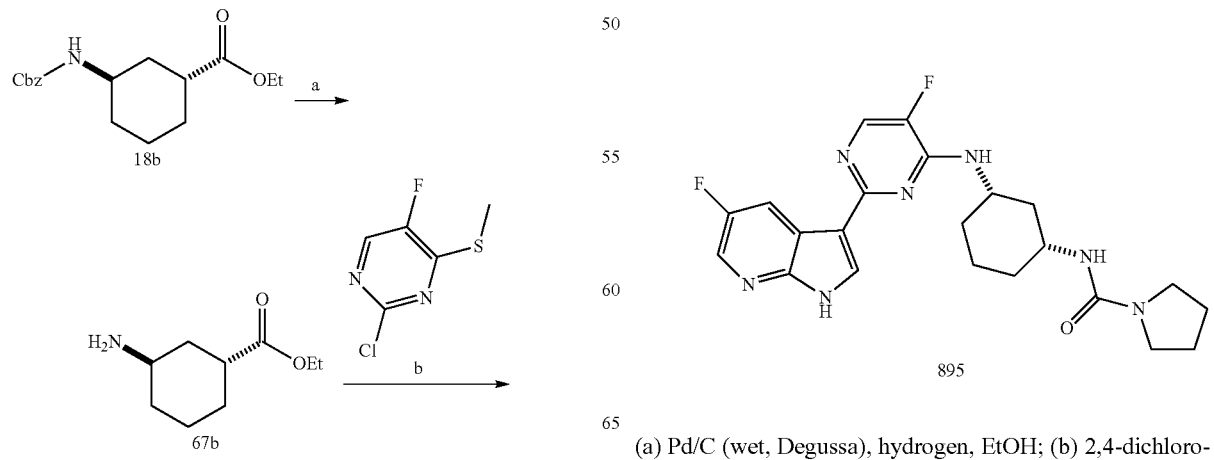

(a) Pd/C (wet, Degussa), hydrogen, EtOH; (b) 2,4-dichloro-5-fluoropyrimidine, $^i$Pr$_2$NEt, THF, reflux; (c) LiOH, THF/ water, 50° C.; (d) DPPA, Et₃N, THF, 85° C.; (e) 5-fluoro-3-(4,4,5,5-tetramethyl-1,3,2-dioxaborolan-2-yl)-1-tosyl-1H-pyrrolo[2,3-b]pyridine, XPhos, Pd₂(dba)₃, K₃PO₄, 2-methyl THF, water, 125° C.; (f)

Formation (1R,3S)-ethyl 3-aminocyclohexanecarboxylate (67b)

To a solution of (1R,3S)-ethyl 3-(benzyloxycarbonylamino)cyclohexane-carboxylate, 18b, (14.0 g, 45.9 mmol) in ethanol (3 mL) was added Pd/C (wet, Degussa (2.4 g, 2.3 mmol). The mixture was evacuated and then stirred under atmosphere of nitrogen at room temperature overnight. The reaction mixture was filtered through a pad of celite and the resulting filtrate concentrated in vacuo to provide an oil that was used without further purification.

Formation (1R,3S)-ethyl 3-(2-chloro-5-fluoropyrimidin-4-ylamino)cyclohexane-carboxylate (67c)

To a solution of (1R,3S)-ethyl 3-aminocyclohexanecarboxylate, 67b, (5.1 g, 24.1 mmol) and 2,4-dichloro-5,-fluoropyrimidine (6.0 g, 36.0 mmol) in THF (60 mL) was added diisopropylethylamine (9.6 mL, 55.4 mmol). The mixture was heated to reflux overnight. The reaction was cooled to room temperature and concentrated in vacuo. The residue was diluted with water and extracted twice with ethyl acetate. The combined organic phases were dried (MgSO₄), filtered and concentrated in vacuo. The residue was purified by silica gel chromatography (0-40% EtOAc/hexanes gradient) to provide 6.7 g of (1R,3S)-ethyl 3-(2-chloro-5-fluoropyrimidin-4-ylamino)cyclohexane-carboxylate as a white solid: LCMS RT=3.1 (M+H) 302.2.

Formation (1R,3S)-3-(2-chloro-5-fluoropyrimidin-4-ylamino)cyclohexanecarboxylic acid (67d)

To a solution of (1R,3S)-ethyl 3-(2-chloro-5-fluoropyrimidin-4-ylamino)cyclohexane-carboxylate, 67c, (20.0 g, 66.3 mmol) in THF (150 mL) was added added a solution of LiOH hydrate (8.3 g, 198.8 mmol) in 100 ml water. The reaction mixture was stirred at 50° C. overnight, To the reaction mixture was added HCl (16.6 mL of 12 M solution, 198.8 mmol) and EtOAc. The organic phase was washed with brine and dried over MgSO₄ and the solvent was removed under reduced pressure to afford 17.5 g of product that was used without further purification: ¹H NMR (300 MHz, CDCl₃) δ 7.91 (d, J=2.7 Hz, 2H), 5.24 (d, J=7.3 Hz, 2H), 4.19-4.03 (m, 3H), 3.84-3.68 (m, 3H), 2.59 (ddd, J=11.5, 8.2, 3.6 Hz, 2H), 2.38 (d, J=12.4 Hz, 2H), 2.08 (d, J=9.6 Hz, 6H), 1.99-1.76 (m, 5H), 1.63-1.34 (m, 6H), 1.32-1.15 (m, 4H).

Formation N-((1R,3S)-3-(2-chloro-5-fluoropyrimidin-4-ylamino)cyclohexyl)-pyrrolidine-1-carboxamide (67e)

A solution of (1R,3S)-3-(2-chloro-5-fluoropyrimidin-4-ylamino)cyclohexane-carboxylic acid, 67d, (8.2 g, 30.0 mmol), (azido(phenoxy)phosphoryl)oxybenzene (9.7 mL, 45.0 mmol) and triethylamine (5.8 mL, 42.0 mmol) in THF (200 mL) was degassed under nitrogen for 15 minutes. The reaction mixture was heated at 85° C. for 30 minutes until LC/MS indicated complete consumption of carboxylic acid, 67d. To the reaction mixture was added pyrrolidine (7.5 mL, 90.0 mmol) and the reaction was heated at 85° C. for an additional 15 min. The mixture was diluted into brine and extracted with EtOAc. The organic phase was separated, dried over MgSO₄. The product was isolated (6.25 g) by filtration after partial removal of solvent in vacuo.

¹H NMR (300 MHz, CDCl₃) δ 7.87 (d, J=2.8 Hz, 2H), 5.04 (d, J=8.1 Hz, 2H), 4.09 (ddd, J=26.9, 13.4, 5.6 Hz, 4H), 3.91-3.71 (m, 2H), 3.32 (t, J=6.5 Hz, 7H), 2.45 (d, J=11.5 Hz, 2H), 2.08 (dd, J=22.1, 12.0 Hz, 4H), 1.96-1.82 (m, 9H), 1.54 (dd, J=18.6, 8.5 Hz, 2H), 1.22-1.01 (m, 6H).

Formation N-((1R,3S)-3-(5-fluoro-2-(5-fluoro-1-tosyl-1H-pyrrolo[2,3-b]pyridin-3-yl)pyrimidin-4-ylamino)cyclohexyl)pyrrolidine-1-carboxamide (67f)

A solution of N-((1R,3S)-3-(2-chloro-5-fluoropyrimidin-4-ylamino)cyclohexyl)-pyrrolidine-1-carboxamide, 67e, (6.8 g, 20.0 mmol), 5-fluoro-1-(p-tolylsulfonyl)-3-(4,4,5,5-tetramethyl-1,3,2-dioxaborolan-2-yl)pyrrolo[2,3-b]pyridine, 44a, (12.5 g, 30.0 mmol) and K₃PO₄ (17.0 g, 80.0 mmol) in 2-methyl THF (180 mL) and water (20 mL) was degassed under nitrogen for 30 min. To the mixture was added dicyclohexyl-[2-(2,4,6-triisopropylphenyl)phenyl]phosphane (XPhos) (1.1 g, 2.4 mmol) and Pd₂(dba)₃ (0.5 g, 0.5 mmol). The reaction mixture was heated in a pressure bottle at 125° C. for 2.5 hr. The reaction mixture was filtered through celite, the solvent was removed under reduced pressure. The resulting residue was purified by silica gel chromatography (8% MeOH/CH₂Cl₂) to afford 11.5 g of the desired product.

¹H NMR (300 MHz, CDCl₃) δ 8.54 (s, 1H), 8.49 (dd, J=9.0, 2.8 Hz, 1H), 8.32 (d, J=2.1 Hz, 1H), 8.13 (d, J=8.3 Hz, 2H), 8.07 (d, J=3.2 Hz, 1H), 7.30 (d, J=8.5 Hz, 2H), 4.98 (d, J=6.3 Hz, 1H), 4.37-4.16 (m, 1H), 4.08 (d, J=7.3 Hz, 1H), 3.99-3.80 (m, 1H), 3.33 (t, J=6.5 Hz, 4H), 2.52 (d, J=11.6 Hz, 1H), 2.39 (s, 3H), 2.29 (d, J=11.3 Hz, 1H), 2.12 (d, J=11.1 Hz, 1H), 1.99-1.81 (m, 5H), 1.70-1.55 (m, 1H), 1.22-1.08 (m, 2H).

Formation N-((1R,3S)-3-(5-fluoro-2-(5-fluoro-1H-pyrrolo[2,3-b]pyridin-3-yl)-pyrimidin-4-ylamino)cyclohexyl)pyrrolidine-1-carboxamide (895)

A solution of N-((1R,3S)-3-(5-fluoro-2-(5-fluoro-1-tosyl-1H-pyrrolo[2,3-b]pyridin-3-yl)pyrimidin-4-ylamino)cyclohexyl)pyrrolidine-1-carboxamide, 67f, (11.5 g, 19.3 mmol) in THF (150 mL) was added sodium methoxide (4.173 g, 19.31 mmol). After stirring the reaction mixture for 2 minutes, the mixture was poured into an aqueous saturated solution of NaHCO₃. The organic phase was washed with brine, dried over MgSO₄ and the solvent was removed under reduced pressure. The resulting residue was purified by silica gel chromatography (10% MeOH/CH₂Cl₂) to afford 6.5 g of the desired product. The product was converted to an HCl salt by dissolving in MeOH (100 mL) and adding 2.4 mL of 12M HCl solution at room temperature. The solution was stirred at for 1 hour and the HCl salt precipitated out and filtered to provide 7.05 g of the HCl salt.

¹H NMR (300 MHz, DMSO) δ 9.36 (s, 2H), 9.05 (d, J=3.0 Hz, 2H), 8.49 (d, J=5.6 Hz, 2H), 8.41 (dd, J=2.6, 1.4 Hz, 2H), 8.31 (d, J=9.5 Hz, 2H), 5.92 (s, 3H), 4.24 (s, 3H), 3.64 (s, 2H), 3.18 (t, J=6.6 Hz, 7H), 2.07 (dt, J=22.7, 11.5 Hz, 4H), 1.87 (t, J=12.6 Hz, 4H), 1.77 (dd, J=8.0, 5.3 Hz, 7H), 1.65-1.13 (m, 8H).

General Scheme 68:

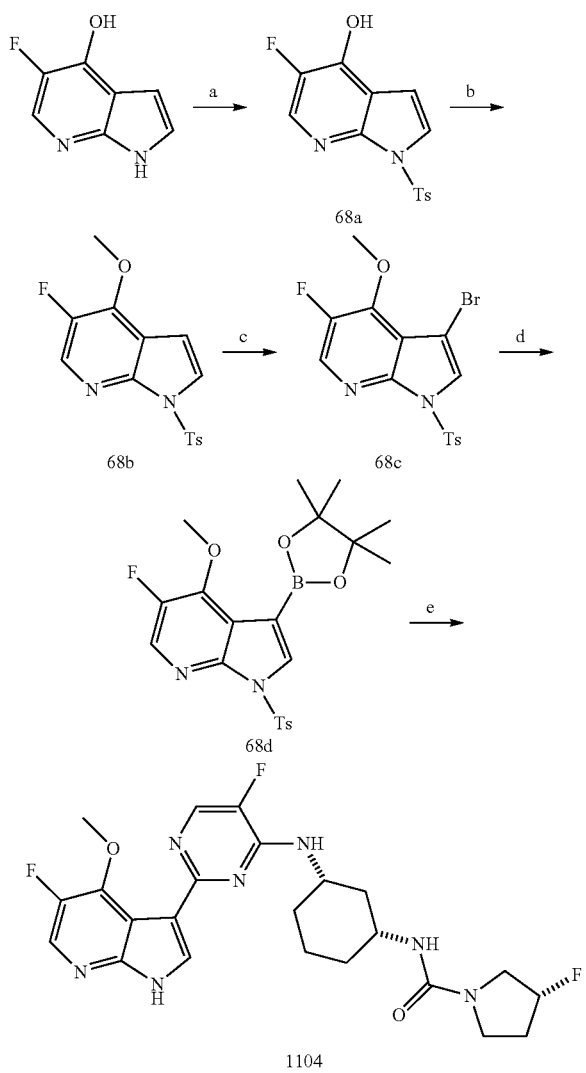

(a) TsCl, NaH, DMF, 45° C.; (b) methyl iodide, K₂CO₃, DMF; (c) bromine, CHCl₃, 0° C. to rt; (d) bis(pinacol)diborane, palladium (II) dichloro bis(tricyclohexylphosphane), KOAc, 2-methyl THF, 125° C.; (e) (R)—N-((1R,3S)-3-((2-chloro-5-fluoropyrimidin-4-yl)amino)cyclohexyl)-3-fluoropyrrolidine-1-carboxamide, XPhos, Pd₂(dba)₃, K₃PO₄, 2-methyl THF, water, 125° C.

Formation of 5-fluoro-1-tosyl-1H-pyrrolo[2,3-b]pyridin-4-ol (68a)

To a solution of 5-fluoro-1H-pyrrolo[2,3-b]pyridin-4-ol (1.2 g, 7.9 mmol) in 80 mL DMF at 0° C. was added toluenesulfonyl chloride (1.8 g, 9.5 mmol) followed by NaH (0.8 g, 19.7 mmol, 60% w/w). The reaction was slowly warmed to 45° C. after 3 hours and stirred for an additional 3 hours. The mixture was then concentrated in vacuo. The crude oil was dissolved in 100 mL EtOAc and washed with water (2×50 mL) and brine. The organic phase was dried over sodium sulfate and concentrated in vacuo. The resulting residue was purified via silica gel chromatography (10% EtOAc/Hexanes) to afford 1.5 g of the desired product.

Formation of 5-fluoro-4-methoxy-1-tosyl-1H-pyrrolo[2,3-b]pyridine (68b)

To a solution of 5-fluoro-1-tosyl-1H-pyrrolo[2,3-b]pyridin-4-ol, 68a, (0.70 g, 2.29 mmol) in DMF (25 mL) was added methyliodide (0.14 mL, 2.29 mmol) and K₂CO₃ (0.32 g, 2.29 mmol). The reaction mixture was stirred for 3 hours at ambient temperature. The reaction was diluted with deionized water and EtOAc. The organic phase was washed with brine, dried over sodium sulfate and concentrated in vacuo to afford 720 mg of the desired product that was used in next step without further purification.

Formation of 5-fluoro-4-methoxy-3-bromo-1-tosyl-1H-pyrrolo[2,3-b]pyridine (68c)

To a cold (0° C.) solution of 5-fluoro-4-methoxy-1-tosyl-1H-pyrrolo[2,3-b]pyridine, 68b, (0.79 g, 2.45 mmol) in chloroform (50 mL) was added bromine (0.13 mL, 2.45 mmol). The reaction mixture was stirred at 0° C. for 3 hours and then slowly warmed to ambient temperature. The mixture was diluted with deionized water and quenched with aqueous sodium bicarbonate. The aqueous phase was extracted with methylene chloride and dried over sodium sulfate. The resulting solid was purified via silica gel chromatography (15-30% EtOAc/Hexanes) to give 170 mg of the desired product.

Formation of 5-fluoro-4-methoxy-3-(4,4,5,5-tetramethyl-1,3,2-dioxaborolan-2-yl)-1-tosyl-1H-pyrrolo[2,3-b]pyridine (68d)

To a solution of 5-fluoro-4-methoxy-3-bromo-1-tosyl-1H-pyrrolo[2,3-b]pyridine, 68c, (0.17 g, 0.43 mmol) in 2-Me-THF (9 mL) in a microwave vial was added bis(pinacol) diborane (0.16 g, 0.64 mmol), followed by potassium acetate (0.23 g, 1.06 mmol) and palladium (II) dichloro bis(tricyclohexylphosphane) (0.02 g, 0.02 mmol). Reaction vial was sealed and irradiated with microwaves at 125° C. for 90 minutes. The mixture was filtered and purified via silica gel chromatography (10-30% EtOAc/Hexanes) to afford 100 mg of the desired product.

Formation of (R)-3-fluoro-N-((1R,3S)-3-((5-fluoro-2-(5-fluoro-4-methoxy-1H-pyrrolo[2,3-b]pyridin-3-yl)pyrimidin-4-yl)amino)cyclohexyl)pyrrolidine-1-carboxamide (1104)

To a solution of 5-fluoro-4-methoxy-3-(4,4,5,5-tetramethyl-1,3,2-dioxaborolan-2-yl)-1-tosyl-1H-pyrrolo[2,3-b] pyridine, 68d, (0.100 g, 0.220 mmol) in 2-Me-THF (2 mL) was added (R)—N-((1R,3S)-3-(2-chloro-5-fluoropyrimidin-4-yl)amino)cyclohexyl)-3-fluoropyrrolidine-1-carboxamide (0.060 g, 0.170 mmol). Potassium phosphate (0.130 g, 0.600 mmol) and deionized water (0.5 mL) were then added and solution was degassed under a flow of nitrogen for 10 minutes. 2-Dicyclohexylphosphino-2',4',6'-triisopropylbiphenyl (XPhos) (0.006 g, 0.012 mmol) and tris(dibenzylideneacetone)-dipalladium (O) (0.023 mg, 0.026 mmol) were then added and solution was again degassed under flow of nitrogen for 5 minutes. Vial was sealed and heated to 80° C. for 3 hours. Solution cooled to ambient temperature and was filtered and concentrated in vacuo. The crude oil was redissolved in anhydrous THF (5 mL) and a solution of 2N LiOH (2 mL) was added. The reaction mixture was heated to 80° C. for 2 hours. Solution was cooled to ambient temperature and concentrated in vacuo. Purification by preparative HPLC afforded 6 mg of the desired product.

General Scheme 69:

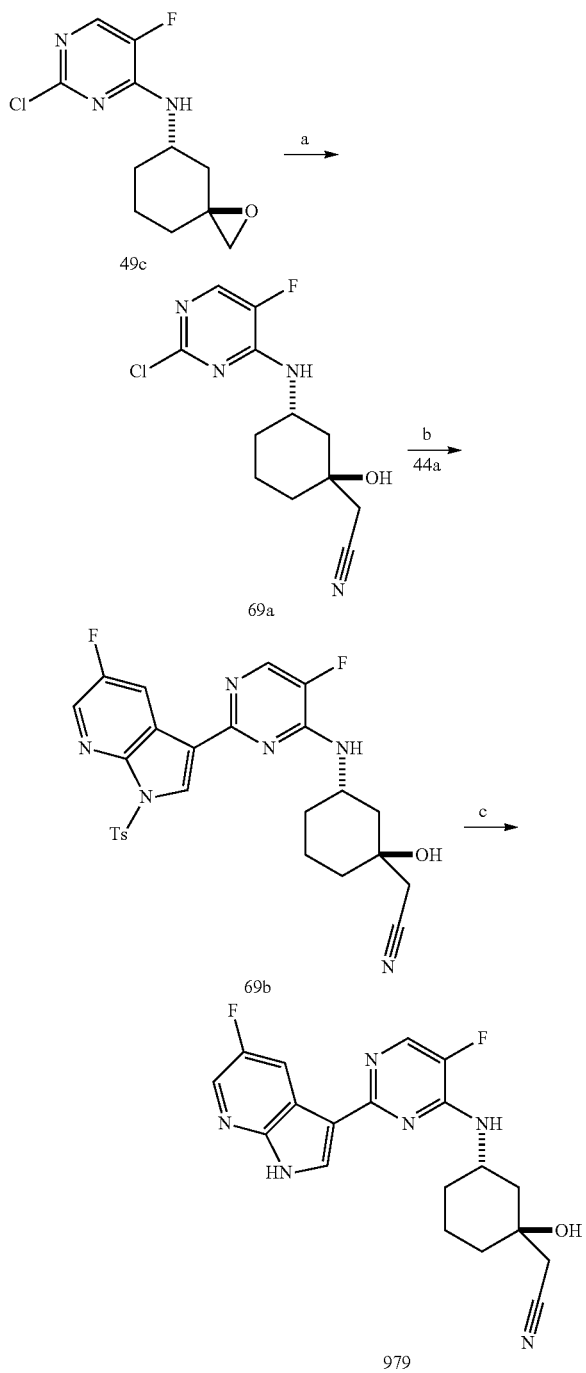

(a) NaCN, LiClO₄, CH₃CN; (b) 5-fluoro-1-(p-tolylsulfonyl)-3-(4,4,5,5-tetramethyl-1,3,2-dioxaborolan-2-yl)pyrrolo[2,3-b]pyridine, Na₂CO₃, Pd(PPh₃)₄, dimethoxyethane, 120° C.; (c) sodium methoxide, MeOH.

Formation of 2-((1S,3S)-3-(2-chloro-5-fluoropyrimidin-4-ylamino)-1-hydroxy-cyclohexyl)-ethanenitrile (69a)

A suspension of 2-chloro-5-fluoro-N-[(3S)-1-oxaspiro[2.5]octan-7-yl]pyrimidin-4-amine, 49c, (0.50 g, 1.94 mmol), NaCN (0.11 g, 2.33 mmol) and lithium perchlorate (0.25 g, 2.33 mmol) in CH₃CN was heated at 100° C. in a pressure tube for 3 h. The mixture was diluted into EtOAc and the organic phase was washed with aqueous saturated NaHCO₃ solution, dried with MgSO₄, filtered and the solvent was removed under reduced pressure. The resulting residue was purified by silica gel chromatography (EtOAc/hexanes) afforded the desired product: ¹H NMR (300.0 MHz, CDCl₃) δ 7.78 (d, J=2.7 Hz, 1H), 4.85 (d, J=6.6 Hz, 1H), 4.28 (qn, J=4.0 Hz, 1H), 2.45 (s, 2H), 2.16 (d, J=13.0 Hz, 1H), 2.05 (d, J=11.7 Hz, 1H), 1.80-1.71 (m, 3H), 1.46-1.28 (m, 2H) and 1.17-1.06 (m, 1H) ppm; LCMS RT=2.15 (M+H) 285.34.

Formation of 2-((1S,3S)-3-(5-fluoro-2-(5-fluoro-1-tosyl-1H-pyrrolo[2,3-b]pyridin-3-yl)pyrimidin-4-ylamino)-1-hydroxycyclohexyl)ethanenitrile (69b)

A solution of 5-fluoro-1-(p-tolylsulfonyl)-3-(4,4,5,5-tetramethyl-1,3,2-dioxaborolan-2-yl)pyrrolo[2,3-b]pyridine, 44a, (0.23 g, 0.55 mmol), 2-((1S,3S)-3-(2-chloro-5-fluoropyrimidin-4-ylamino)-1-hydroxycyclohexyl)-ethanenitrile, 69a, (0.14 g, 0.50 mmol) and Na₂CO₃ (0.75 mL of 2M solution, 1.50 mmol) in dimethoxyethane (15 mL) was degassed with nitrogen for 30 min. To the reaction mixture was added palladium; triphenylphosphane (0.03 g, 0.03 mmol) and continued to degas the solution for 15 min. The reaction mixture was heated at 120° C. in a pressure tube for 45 min. The reaction mixture was filtered through celite and the filtrate was removed under reduced pressure. The resulting residue was purified by silica gel chromatography (40% EtOAc/Hexanes) to afford 150 mg of desired product: LCMS RT=3.55 (M+H) 539.42.

Formation of 2-((1S,3S)-3-(5-fluoro-2-(5-fluoro-1H-pyrrolo[2,3-b]pyridin-3-yl)pyrimidin-4-ylamino)-1-hydroxycyclohexyl)ethanenitrile (979)

To a solution of 2-((1S,3S)-3-(5-fluoro-2-(5-fluoro-1-tosyl-1H-pyrrolo[2,3-b]pyridin-3-yl)pyrimidin-4-ylamino)-1-hydroxycyclohexyl)ethanenitrile, 69b, (0.14 g, 0.26 mmol) in methanol (10 mL) was added sodium methoxide (0.06 g, 0.26 mmol). After stirring at room temperature for 2 minutes, the reaction mixture was diluted into EtOAc and brine. The separated organic phase was dried over MgSO₄, filtered, and concentrated in vacuo. The resulting residue was purified by silica gel chromatography (10% MeOH/CH₂Cl₂) to afford 46 mg of desired product: ¹H NMR (300.0 MHz, MeOD) δ 8.65 (dd, J=2.8, 9.6 Hz, 1H), 8.19 (s, 1H), 8.14 (dd, J=2.0, 2.5 Hz, 1H), 7.98 (d, J=4.1 Hz, 1H), 4.66 (dd, J=8.0, 15.8 Hz, 1H), 2.64 (s, 2H), 2.20 (d, J=12.6 Hz, 2H), 2.01 (dd, J=3.4, 9.8 Hz, 2H), 1.84-1.75 (m, 1H), 1.63-1.47 (m, 2H), 1.33 (dd, J=3.6, 12.4 Hz, 1H) ppm; LCMS RT=2.31 (M+H) 385.45.

General Scheme 70:

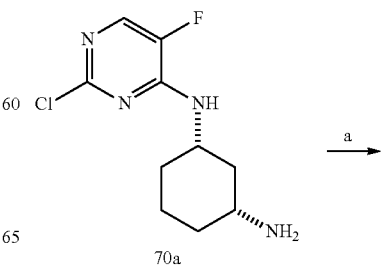

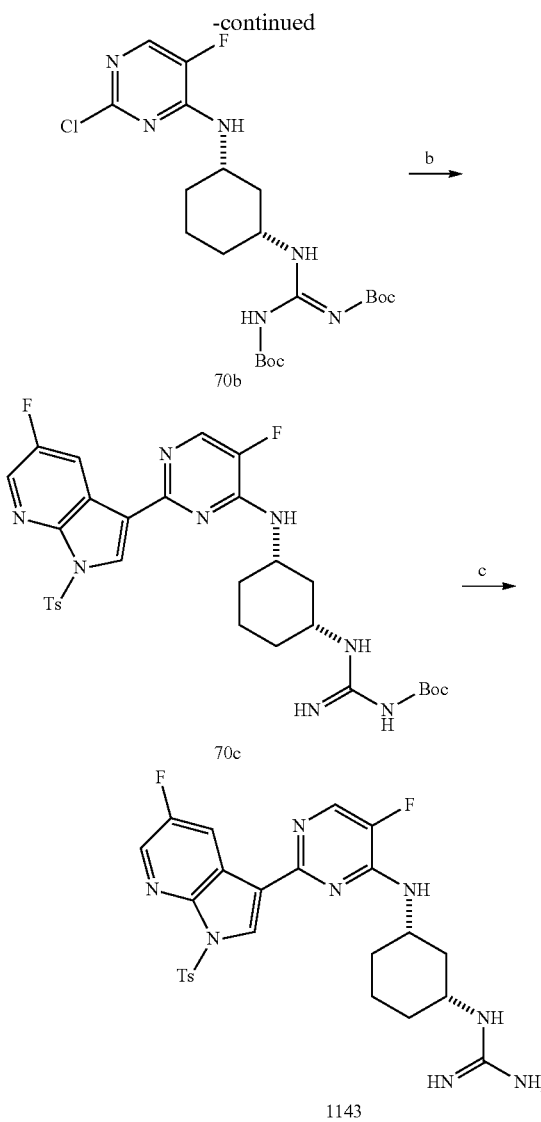

(a) tert-butyl N-(N-tert-butoxycarbonyl-C-pyrazol-1-yl-carbonimidoyl)carbamate, $CH_2Cl_2$; (b) 5-fluoro-1-(p-tolylsulfonyl)-3-(4,4,5,5-tetramethyl-1,3,2-dioxaborolan-2-yl)pyrrolo[2,3-b]pyridine, $Na_2CO_3$, $Pd(PPh_3)_4$, dimethoxyethane, 120° C.; (c) sodium methoxide, THF, MeOH.

Formation of tert-butyl (tert-butoxycarbonylamino) ((1R,3S)-3-(2-chloro-5-fluoropyrimidin-4-ylamino)cyclohexylamino)methylenecarbamate (70b)

To a solution of (1S,3R)—N1-(2-chloro-5-fluoro-pyrimidin-4-yl)cyclohexane-1,3-diamine, 70a, (0.122 g, 0.500 mmol) in $CH_2Cl_2$ (10 mL) was added tert-butyl N—(N-tert-butoxycarbonyl-C-pyrazol-1-yl-carbonimidoyl)carbamate (0.155 g, 0.500 mmol). The reaction mixture was stirred at room temperature for 2 days. The reaction mixture was concentrated in vacuo and used without further purification: $^1$H NMR (300 MHz, $CDCl_3$) δ 11.51 (s, 3H), 8.29 (d, J=8.3 Hz, 3H), 7.88 (d, J=2.8 Hz, 3H), 5.01 (d, J=7.4 Hz, 3H), 4.28-4.18 (m, 4H), 2.48 (d, J=11.7 Hz, 3H), 2.12 (d, J=9.4 Hz, 3H), 1.87 (dd, J=10.3, 3.5 Hz, 3H), 1.52 (s, 24H), 1.50 (s, 25H), 1.24-1.10 (m, 8H); LCMS RT=3.97 (M+H) 487.12.

Formation of tert-butyl N—[N-[(1R,3S)-3-[[5-fluoro-2-[5-fluoro-1-(p-tolylsulfonyl)-pyrrolo[2,3-b]pyridin-3-yl]pyrimidin-4-yl]amino]cyclohexyl]carbamimidoyl]-carbamate (70c)

Degassed a solution of (Z)-tert-butyl (tert-butoxycarbonylamino) ((1R,3S)-3-(2-chloro-5-fluoropyrimidin-4-ylamino)cyclohexylamino) methylenecarbamate, 70b, (0.200 g, 0.411 mmol), 5-fluoro-1-(p-tolylsulfonyl)-3-(4,4,5,5-tetramethyl-1,3,2-dioxaborolan-2-yl)pyrrolo[2,3-b]pyridine, 44a, (0.205 g, 0.493 mmol) and $Na_2CO_3$ (0.616 mL of 2M solution, 1.232 mmol) in dimethoxyethane (15 mL) for 30 min. To the mixture was added palladium triphenylphosphane (0.023 g, 0.021 mmol) and the reaction mixture was heated in a pressure tube at 120° C. for 45 min. The reaction mixture was filtered through a pad of celite and the filtrate concentrated in vacuo. Attempted purification of the resulting residue by silica gel chromatography (10% MeOH/$CH_2Cl_2$) yielded a mixture containing mostly desired product that was used without further purification: LCMS RT=2.30 (M+H) 641.02.

Formation of 1-((1R,3S)-3-(5-fluoro-2-(5-fluoro-1H-pyrrolo[2,3-b]pyridin-3-yl)pyrimidin-4-ylamino)cyclohexyl)guanidine (1143)

To a solution of tert-butyl N—[N-[(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]carbamimidoyl]carbamate, 70c, (0.100 g, 0.156 mmol) in THF (20 mL) was added sodium methoxide (0.033 g, 0.156 mmol) at room temperature. After 1 minute, the reaction mixture was diluted into EtOAc and aqueous saturated $NaHCO_3$ solution. The organic phase was dried over $MgSO_4$, filtered and the solvent was removed under reduced pressure. The resulting residue was purified by silica gel chromatography to afford 95 mg of the desired product. To 10 ml MeOH solution of the product was added hydrochloride/IPA (0.031 mL of 5 M solution, 0.156 mmol). The reaction mixture was stirred at room temperature for 1 hour after which the solvent was removed under reduced pressure to afford the product, as hydrochloride salt: $^1$H NMR (300 MHz, MeOD) δ 8.63 (s, 1H), 8.40 (dd, J=9.1, 2.7 Hz, 1H), 8.36 (s, 1H), 8.32 (d, J=5.5 Hz, 1H), 4.46 (d, J=11.7 Hz, 1H), 3.78-3.53 (m, 1H), 2.41 (d, J=11.7 Hz, 1H), 2.28 (d, J=12.0 Hz, 1H), 2.18-1.98 (m, 2H), 1.69 (dd, J=23.6, 11.8 Hz, 2H), 1.56-1.28 (m, 2H); LCMS RT=1.45 (M+H) 387.06.

General Scheme 71:

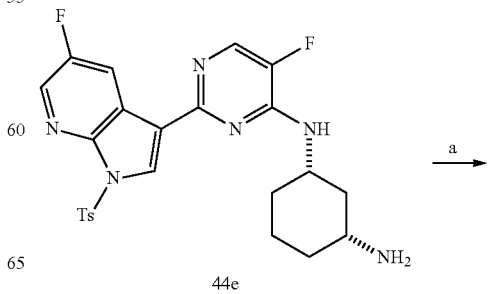

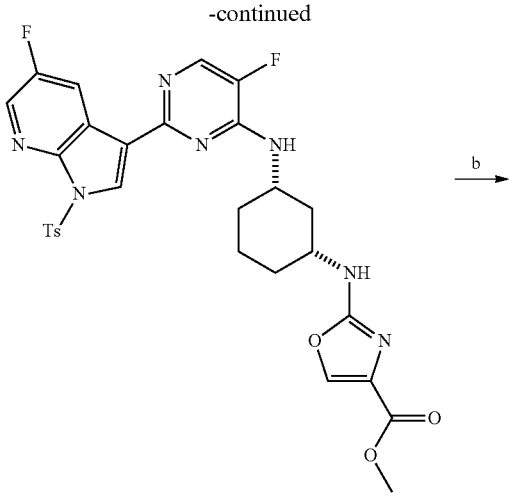

71a

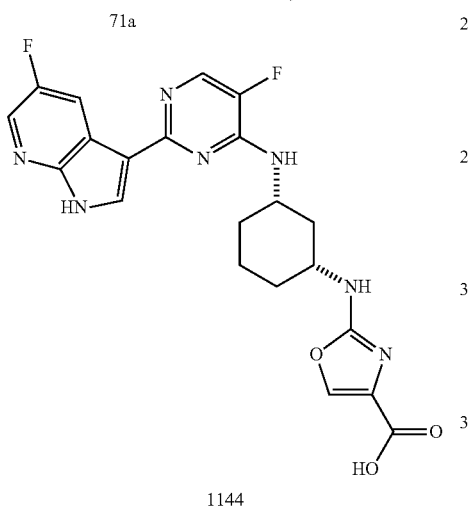

1144

(a) DBU, methyl 2-chlorooxazole-4-carboxylate, DMF, 75° C.; (b) LiOH, THF.

Formation of methyl 2-((1R,3S)-3-(5-fluoro-2-(5-fluoro-1-tosyl-1H-pyrrolo[2,3-b]pyridin-3-yl)pyrimidin-4-ylamino)cyclohexylamino)oxazole-4-carboxylate (71a)

To a solution of (1S,3R)—N1-[5-fluoro-2-[5-fluoro-1-(p-tolylsulfonyl)pyrrolo[2,3-b]pyridin-3-yl]pyrimidin-4-yl]cyclohexane-1,3-diamine, 44e, (0.089 g, 0.178 mmol) in DMF (1.5 mL) was added methyl 2-chlorooxazole-4-carboxylate (0.031 g, 0.195 mmol), followed by DBU (0.029 mL, 0.195 mmol). The reaction mixture was allowed to stir at room temperature overnight. The reaction was warmed to 75° C. and allowed to stir for 3 hours. Added an additional 16 mg of the chlorooxazole ester and the reaction was heated at 75° C. overnight. The mixture was diluted into water and EtOAc. The layers were separated and the organic phase was washed with brine, dried over MgSO$_4$, filtered and evaporated to dryness. The crude residue was purified by silica gel chromatography (0-20% MeOH/CH$_2$Cl$_2$) to afford 28 mg of desired product: LCMS RT=3.73 (M+1) 624.12.

Formation of 2-((1R,3S)-3-(5-fluoro-2-(5-fluoro-1H-pyrrolo[2,3-b]pyridin-3-yl)pyrimidin-4-ylamino)cyclohexylamino)oxazole-4-carboxylic acid (1144)

To a solution of methyl 2-[[(1R,3S)-3-[[5-fluoro-2-[5-fluoro-1-(p-tolylsulfonyl)-pyrrolo[2,3-b]pyridin-3-yl]pyrimidin-4-yl]amino]cyclohexyl]amino]oxazole-4-carboxylate, 71a, (0.028 g, 0.045 mmol) in THF (1 mL) was added LiOH (1 mL of 1 M solution, 1.000 mmol) and the reaction mixture was warmed to 130° C. via microwave irradiation. After heating and stirring for 20 minutes, the mixture was cooled to room temperature. All volatiles were removed under a stream of nitrogen and heat. The crude residue was suspended in MeOH and a few drops of trifluoroacetic acid were added to protonate molecule (solution occurs). The mixture was filtered and purified by reverse phase HPLC (5-95% CH$_3$CN/H$_2$O) to afford 5 mg of the desired product as a TFA salt: $^1$H NMR (300 MHz, MeOD) δ 8.83 (s, 1H), 8.67-8.09 (m, 4H), 2.67 (s, 3H), 2.18 (m, 5H), 1.34 (d, J=29.6 Hz, 3H); LCMS RT=1.78 (M+1) 456.07.

General Scheme 72:

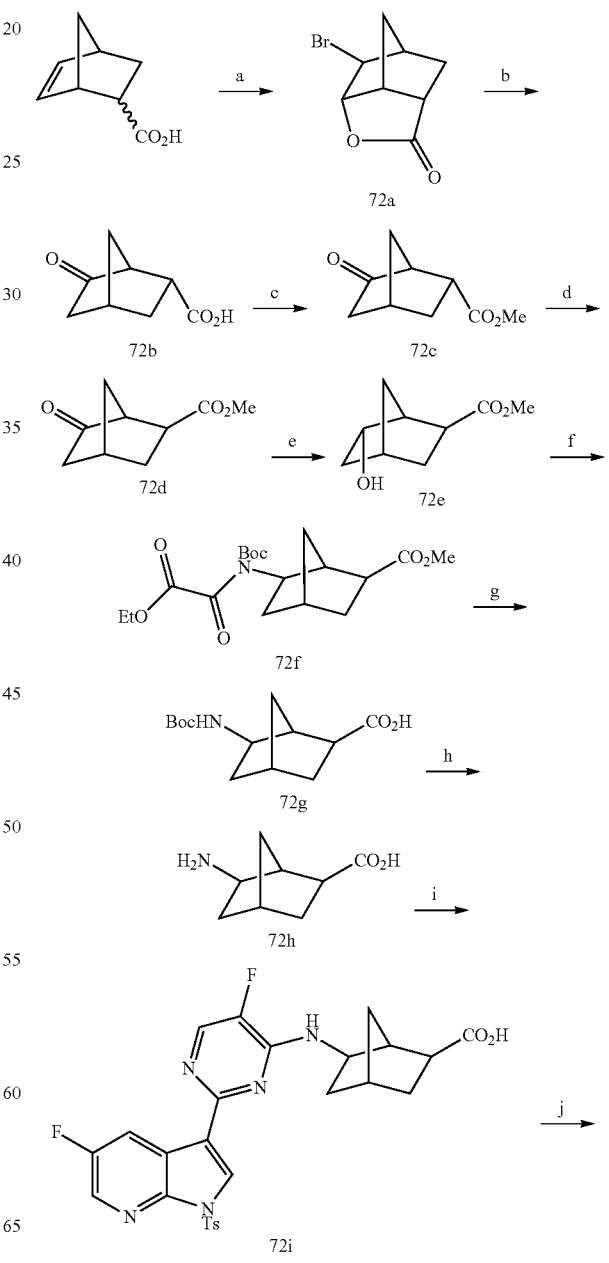

-continued

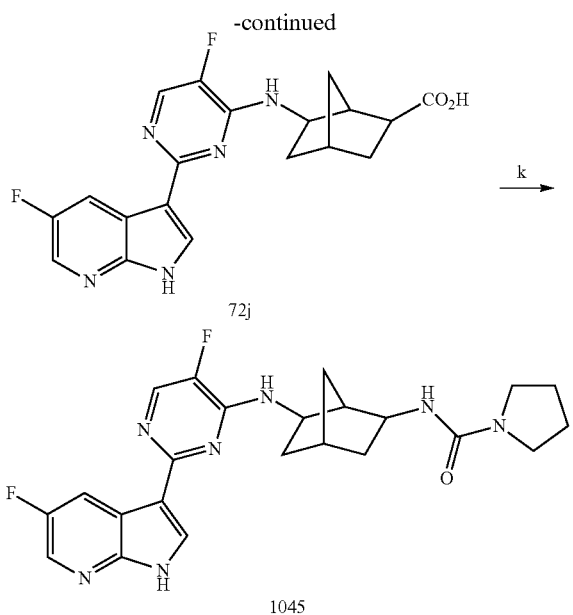

(a) NaHCO$_3$, Br$_2$, H$_2$O; (b) NaOH; (c) TMSCl, MeOH; (d) sodium methoxide, MeOH, 150° C.; (e) sodium borohydride, MeOH; (f) ethyl 2-(tert-butoxycarbonylamino)-2-oxo-acetate, DEAD, PPh$_3$, 85° C.; (g) NaOH, MeOH; (h) trifluoroacetic acid, CH$_2$Cl$_2$, 1N HCl/ether; (i) 5-fluoro-3-(5-fluoro-4-(methylsulfinyl)pyrimidin-2-yl)-1-tosyl-1H-pyrrolo[2,3-b]pyridine, $^i$Pr$_2$NEt, THF; (j) lithium hydroxide, THF; (k) DPPA, Et$_3$N, pyrrolidine.

Formation of 6-bromohexahydro-2H-3,5-methanocyclopenta[b]furan-2-one (72a)

To a solution of bicyclo[2.2.1]hept-5-ene-3-carboxylic acid (25.0 mL, 204.3 mmol) in NaHCO$_3$ (51.5 g, 612.9 mmol) in water was added bromine (32.7 g, 204.3 mmol) dropwise at 0° C. The solution was stirred for 1 hour and extracted with ether, and the organic phase was washed successively with 1 N Na$_2$S$_2$O$_3$ solution and brine, and the organic phase was then dried (Na$_2$SO$_4$), filtered and concentrated in vacuo to afford 30 g of crude product that was used without further purification.

Formation of 6-oxonorbornane-2-carboxylic acid (72b)

6-bromohexahydro-2H-3,5-methanocyclopenta[b]furan-2-one, 72a, (28.0 g, 129.0 mmol) was treated with NaOH (258.0 mL of 2 M solution, 516.0 mmol) in H$_2$O (350 mL) for 2 hour at room temperature. The reaction mixture was acidified with conc. HCl, extracted with Et$_2$O. The organic phase was dried (Na$_2$SO$_4$), filtered and concentrated in vacuo. The resulting residue was purified by silica gel chromatography (0-20% MeOH/CH$_2$Cl$_2$ gradient) to provide 16 g of 6-oxonorbornane-2-carboxylic acid.

Formation of Endo methyl 6-oxonorbornane-2-carboxylate (72c)

A solution of 6-oxonorbornane-2-carboxylic acid, 72b, (16.0 g, 103.8 mmol) in methanol (350.0 mL) was treated with TMSCl (42.04 g, 49.11 mL, 387.0 mmol). The reaction mixture was stirred at room temperature overnight. Solvent was evaporated under reduced pressure and the crude product was purified by silica gel chromatography (10% EtOAc/hexanes) to provide 12 g of Endo methyl 6-oxonorbornane-2-carboxylate.

Formation of Exo methyl 6-oxonorbornane-2-carboxylate (72d)

Endo methyl 6-oxonorbornane-2-carboxylate, 72c, (3.5 g, 20.8 mmol) was heated in a sealed tube in sodium methoxide (2.1 mL of 2 M solution in methanol, 4.2 mmol) at 150° C. for 17 hours. The solvent was evaporated and the crude product was purified by silica gel chromatography (0-16% EtOAc/hexanes gradient) to afford 3.3 g of starting endo methyl 6-oxonorbornane-2-carboxylate as the first fraction (PMA staining) and 4.0 g of the desired exo product as the second spot. The recovered starting material was treated with the same conditions again to generate another 1.0 g desired exo-product.

Formation of methyl 6-hydroxynorbornane-2-carboxylate (72e)

To a solution of exo methyl 6-oxonorbornane-2-carboxylate, 72d, (4.7 g, 27.9 mmol) in MeOH (50 mL) was added sodium borohydride (1.6 g, 41.9 mmol) in five portions at 0° C. TLC showed completed conversion after 2 hours. Aqueous saturated NH$_4$Cl solution was added to quench the reaction. The MeOH was evaporated under reduced pressure and then the aqueous phase was extracted with EtOAc. The combined organic phases were washed with brine, dried over Na$_2$SO$_4$, filtered and concentrated in vacuo. The resulting residue was purified by silica gel chromatography (0-100% EtOAc/hexanes, Rf=0.5 in 50% EtOAc/hexanes) to afford 3.96 g of the desired product: $^1$H NMR (300 MHz, CDCl$_3$) δ 4.23-4.06 (m, 1H), 3.56 (s, 3H), 3.37 (s, 1H), 3.03 (dd, J=8.9, 5.5 Hz, 1H), 2.41 (d, J=3.9 Hz, 1H), 2.13 (s, 1H), 1.93-1.69 (m, 2H), 1.63-1.42 (m, 1H), 1.34 (ddt, J=10.3, 3.2, 1.6 Hz, 1H), 1.20 (dd, J=10.4, 0.7 Hz, 1H), 0.77 (dt, J=12.6, 3.4 Hz, 1H).

Formation of methyl 6-(N-(tert-butoxycarbonyl)-2-ethoxy-2-oxoacetamido)bicyclo[2.2.1]heptane-2-carboxylate (72l)

To a cold (0° C.) solution of methyl 6-hydroxynorbornane-2-carboxylate, 72e, (3.2 g, 18.8 mmol) in THF (150 mL) was added ethyl 2-(tert-butoxycarbonylamino)-2-oxo-acetate (4.9 g, 22.6 mmol) and triphenylphosphine (5.9 g, 22.6 mmol) followed by dropwise addition of diisopropyl azodicarboxylate (4.5 g, 22.6 mmol). The reaction was then heated to 85° C. and maintained at that temperature for 2 days. The solvent was evaporated under reduced pressure and the crude product was purified by silica gel chromatography (0-100% EtOAc/hexanes gradient) to provide 6 g of methyl 6-(N-(tert-butoxycarbonyl)-2-ethoxy-2-oxoacetamido)bicyclo[2.2.1]heptane-2-carboxylate: LCMS 392.34 (M+Na$^+$); $^1$H NMR (300 MHz, CDCl$_3$) δ 4.26 (q, J=7.2 Hz, 2H), 4.08 (dt, J=14.3, 7.2 Hz, 1H), 3.62 (d, J=2.1 Hz, 3H), 2.72 (s, 1H), 2.42-2.26 (m, 2H), 2.08-1.80 (m, 2H), 1.80-1.51 (m, 3H), 1.45 (s, 9H), 1.38-1.25 (m, 3H).

Formation of 6-(tert-butoxycarbonylamino)norbornane-2-carboxylic acid (72 g)

To a solution of methyl 6-[tert-butoxycarbonyl-(2-ethoxy-2-oxo-acetyl)amino]norbornane-2-carboxylate, 72f, (0.80 g, 2.17 mmol) in methanol (20 mL) was added NaOH (4.33 mL of 2N solution, 8.66 mmol) at room temperature. The reaction mixture was stirred overnight. The mixture was diluted into 0.5 N HCl in ice, and extracted twice with EtOAc. The combined organic phases were dried (Na$_2$SO$_4$), filtered and concentrated in vacuo to afford 600 mg of desired product that was used without further purification.

Formation of 6-aminobicyclo[2.2.1]heptane-2-carboxylic acid (72h)

A solution of 6-(tert-butoxycarbonylamino)norbornane-2-carboxylic acid, 72g, in dichloromethane (5 mL) was treated with trifluoroacetic acid (5 mL) for 1 hour at room temperature. The solvent was evaporated under reduced pressure and the resulting product was dissolved in 2 mL TFA and added to a stirring 1N HCl in Et$_2$O solution. After stirring the mixture for 0.5 hour, the resulting precipitate was filtered and washed with dry Et$_2$O to give 6-aminobicyclo[2.2.1]heptane-2-carboxylic acid.

Formation of 6-(5-fluoro-2-(5-fluoro-1H-pyrrolo[2,3-b]pyridin-3-yl)pyrimidin-4-ylamino)bicyclo[2.2.1]heptane-2-carboxylic acid (72j)

To a solution of 5-fluoro-3-(5-fluoro-4-methylsulfinyl-pyrimidin-2-yl)-1-(p-tolylsulfonyl)pyrrolo[2,3-b]pyridine (0.187 g, 0.417 mmol) and 6-aminobicyclo-[2.2.1]heptane-2-carboxylic acid, 72h, (0.080 g, 0.417 mmol) in THF (3 mL) was added diisopropylethylamine (0.291 mL, 1.670 mmol). The reaction mixture was heated at 80° C. overnight. Aqueous LiOH (3 mL of 2M solution, 6.000 mmol) was added and the mixture was heated for another 7 hours. The mixture was diluted with MeOH, neutralized with trifluoroacetic acid, filtered and the resulting filtrate was purified by preparatory HPLC chromatography to afford 50 mg of desired product.

Formation of N-[6-[[5-fluoro-2-(5-fluoro-1H-pyrrolo[2,3-b]pyridin-3-yl)pyrimidin-4-yl]amino]norbornan-2-yl]pyrrolidine-1-carboxamide (1045)

To a solution of 6-[[5-fluoro-2-(5-fluoro-1H-pyrrolo[2,3-b]pyridin-3-yl)pyrimidin-4-yl]amino]norbornane-2-carboxylic acid, 72j, (0.030 g, 0.078 mmol) in THF (0.375 mL) was added triethylamine (0.032 mL, 0.234 mmol) and (azido(phenoxy)phosphoryl)oxybenzene (0.018 mL, 0.085 mmol). The reaction mixture was heated to 95° C. for 2.5 hours, cooled down to 5° C., and treated with pyrrolidine (0.010 mL, 0.117 mmol). The reaction was stirred for 3 days at room temperature. The reaction mixture was injected directly into a preparatory HPLC system for purification to provide the product as a racemic mixture. The single enantiomers were obtained by separation using SFC chiral purification to afford 5.7 mg of the desired product as well as 1.4 mg of the enantiomer.

General Scheme 73:

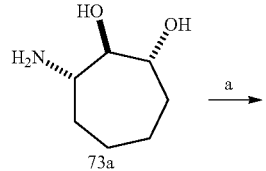

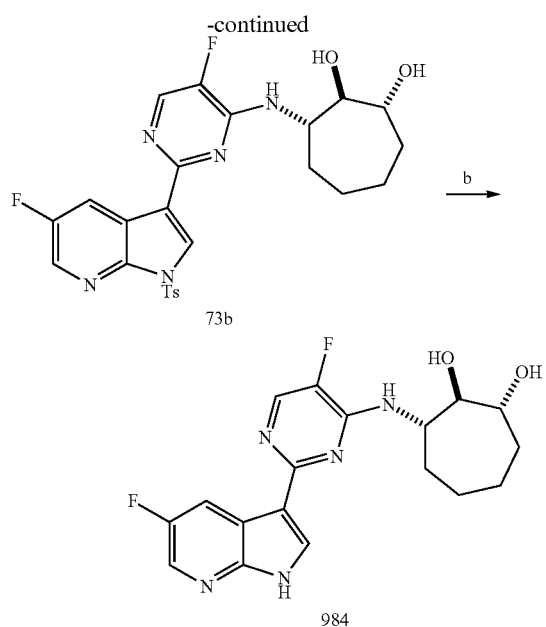

(a) $^i$Pr$_2$NEt, THF, reflux (b) 1N LiOH, THF/H$_2$O, 130° C., microwave.

Formation of (1R,2R,3S)-3-((5-fluoro-2-(5-fluoro-1-tosyl-1H-pyrrolo[2,3-b]pyridin-3-yl)pyrimidin-4-yl)amino)cycloheptane-1,2-diol (73b)

Aminodiol, 73a, was synthesized by following the literature procedure (JOC 2009, 74, 6735). Aminodiol (0.040 mg), diisopropylethylamine (0.054 mL, 0.310 mmol) and 5-fluoro-3-(5-fluoro-4-methylsulfinyl-pyrimidin-2-yl)-1-(p-tolylsulfonyl)pyrrolo[2,3-b]pyridine (0.139 g, 0.310 mmol) in THF was refluxed overnight. The solution was concentrated in vacuo and purified by silica gel chromatography (0-100% EtOAc/CH$_2$Cl$_2$) to give 43 mg of desired product as a white solid: $^1$H NMR (300 MHz, CDCl$_3$) δ 8.40 (q, J=2.8 Hz, 2H), 8.22 (d, J=1.8 Hz, 1H), 8.08-7.94 (m, 3H), 7.20 (d, J=10.1 Hz, 3H), 5.26 (d, J=4.9 Hz, 1H), 4.21-3.99 (m, 1H), 3.84 (s, 1H), 3.75-3.57 (m, 1H), 3.43 (t, J=8.7 Hz, 1H), 2.73 (s, 1H), 2.30 (s, 3H), 2.11-1.85 (m, 2H), 1.84-1.36 (m, 8H), 1.18 (s, 2H), 0.79 (dd, J=15.0, 6.8 Hz, 2H). LCMS (+H): M/Z=530.29

Formation of (1R,2R,3.9-3-((5-fluoro-2-(5-fluoro-1H-pyrrolo[2,3-b]pyridin-3-yl)pyrimidin-4-yl)amino)cycloheptane-1,2-diol (984)

LiOH (0.5 mL of 1N solution, 0.5 mmoL) was added to (1R,2R,3S)-3-((5-fluoro-2-(5-fluoro-1-tosyl-1H-pyrrolo[2,3-b]pyridin-3-yl)pyrimidin-4-yl)amino)cycloheptane-1,2-diol, 73a, in THF (3 mL). The reaction mixture was heated in microwave at 130° C. for 40 minutes. HCl (0.5 mL of 1.25 N solution in MeOH) and MeOH was added to the mixture. The solution was purified by preparative HPLC (MeCN/H$_2$O 10-70%) to give desired product as TFA salt. Neutralization and re-acidification with hydrogen chloride (1N in MeOH) afforded the desired product (28 mg) as a white solid (HCl salt): $^1$H NMR (300 MHz, MeOD) δ 8.52 (s, 1H), 8.48 (d, J=2.8 Hz, 1H), 8.34 (s, 1H), 8.28 (d, J=5.6 Hz, 1H), 4.62-4.35 (m, 1H), 3.65 (m, 2H), 2.11-1.43 (m, 8H); $^{19}$F NMR (282 MHz, MeOD) δ–137.38--137.51 (m, 1H), –156.06 (d, J=5.6 Hz, 1H); LCMS (+H): M/Z=376.28.

General Scheme 74:

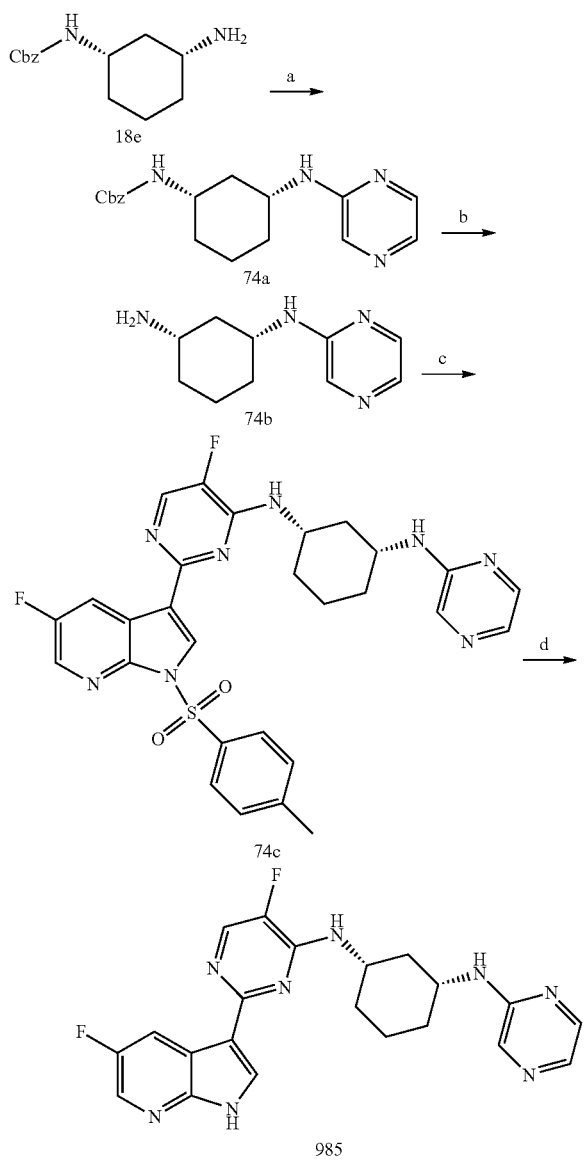

(a) CuI, 2-(2-methylpropanoyl)cyclohexanone, DMF; (b) H₂, Pd/C, MeOH; (c) 5-fluoro-3-(5-fluoro-4-methylsulfinyl-pyrimidin-2-yl)-1-(p-tolylsulfonyl)pyrrolo[2,3-b]pyridine; (d) 1N LiOH, THF/H₂O, 130° C. microwave.

Formation of benzyl ((1S,3R)-3-(pyrazin-2-ylamino)cyclohexyl)carbamate (74a)

A suspension of CuI (0.006 g, 0.030 mmol), benzyl N-[(1S,3R)-3-aminocyclo-hexyl]carbamate, 18e, (0.075 g, 0.302 mmol) and cesium carbonate (0.197 g, 0.604 mmol) in DMF was evacuated and refilled with nitrogen multiple times. 2-iodopyrazine (0.036 mL, 0.362 mmol) and 2-(2-methylpropanoyl)cyclohexanone (0.020 mL g, 0.121 mmol) were then added and the reaction was stirred at room temperature overnight. The reaction was diluted into ethyl acetate and aqueous saturated sodium bicarbonate. The organic phase was separated, dried (MgSO₄), filtered and concentrated in vacuo. The crude residue was purified by silica gel chromatography (0-10% MeOH/CH₂Cl₂) to afford 40 mg of the desired product as yellow solid.

Formation of (1R,3S)—N1-(pyrazin-2-yl)cyclohexane-1,3-diamine (74b)

To a solution of benzyl N-[(1S,3R)-3-(pyrazin-2-ylamino)cyclohexyl]carbamate, 74a, (0.040 g, 0.123 mmol) in methanol (10 mL) was added 10% Pd/C (0.043 g, 0.040 mmol) and the resulting suspension was stirred under an atmosphere of hydrogen for three hours until LCMS indicated completion of the reaction. The solution was filtered through a bed of celite and concentrated in vacuo to give a yellow solid, which was used without further purification.

Formation of (1S,3R)—N1-(5-fluoro-2-(5-fluoro-1-tosyl-1H-pyrrolo[2,3-b]pyridin-3-yl)pyrimidin-4-yl)-N3-(pyrazin-2-yl)cyclohexane-1,3-diamine (74c)

A solution of (1R,3S)—N1-pyrazin-2-ylcyclohexane-1,3-diamine 74b, diisopropylethylamine (0.30 mmol) and 5-chloro-3-(5-fluoro-4-methylsulfinyl-pyrimidin-2-yl)-1-(p-tolylsulfonyl)-pyrrolo[2,3-b]pyridine (0.06 g, 0.13 mmol) in THF (3 mL) was refluxed overnight. The mixture was then concentrated in vacuo and the resulting residue was purified by silica gel chromatography (0-20% MeOH/CH₂Cl₂ gradient) to afford 39 mg of desired product: $^1$H NMR (300 MHz, CDCl₃) δ 8.91-8.72 (m, 1H), 8.50 (d, J=11.8 Hz, 1H), 8.38 (t, J=7.5 Hz, 1H), 8.06 (dd, J=14.8, 5.9 Hz, 3H), 7.88 (d, J=1.4 Hz, 1H), 7.82 (s, 1H), 7.62 (t, J=6.8 Hz, 1H), 7.33 (dd, J=16.6, 7.1 Hz, 3H), 5.91 (s, 1H), 4.27 (s, 1H), 3.98 (t, J=11.3 Hz, 1H), 2.59 (d, J=12.0 Hz, 1H), 2.39 (s, 3H), 2.34-2.09 (m, 2H), 1.99 (d, J=14.0 Hz, 1H), 1.72 (dd, J=26.6, 13.1 Hz, 1H), 1.48-1.08 (m, 4H).

LCMS (+H): M/Z=593.25

Formation of (1S,3R)—N1-(5-fluoro-2-(5-fluoro-1H-pyrrolo[2,3-b]pyridin-3-yl)pyrimidin-4-yl)-N3-(pyrazin-2-yl)cyclohexane-1,3-diamine (985)

LiOH (0.3 mL of 1N solution, 0.3 mmoL) was added to a solution of (1S,3R)—N1-(5-fluoro-2-(5-fluoro-1-tosyl-1H-pyrrolo[2,3-b]pyridin-3-yl)pyrimidin-4-yl)-N3-(pyrazin-2-yl)cyclohexane-1,3-diamine, 74c, (35 mg) in THF (3 mL) and the reaction was heated in the microwave at 130° C. for 40 minutes. A solution of HCl (0.5 mL of a 1.25N in MeOH) was added and the resulting solution was purified by Gilson HPLC (MeCN/H₂O 10-70% in 8 mins) to give pure TFA salt product. Neutralization and re-acidification with hydrogen chloride (1.25N in MeOH) afforded 23 mg of the HCl salt of the desired product as a light yellow solid: $^1$H NMR (300 MHz, MeOD) δ 8.76 (d, J=2.4 Hz, 1H), 8.63 (s, 1H), 8.41 (d, J=2.3 Hz, 1H), 8.36 (d, J=5.7 Hz, 1H), 8.16 (s, 1H), 7.96 (s, 1H), 7.76 (s, 1H), 4.51 (m, J=11.8 Hz, 1H), 4.16-3.92 (m, 1H), 2.35-2.14 (m, 2H), 2.09 (m, J=13.8 Hz, 1H), 1.63 (d, J=11.8 Hz, 4H); $^{19}$F NMR (282 MHz, MeOD) 5-155.25 (s, 1H); LCMS (+H): M/Z=439.24.

General Scheme 75:

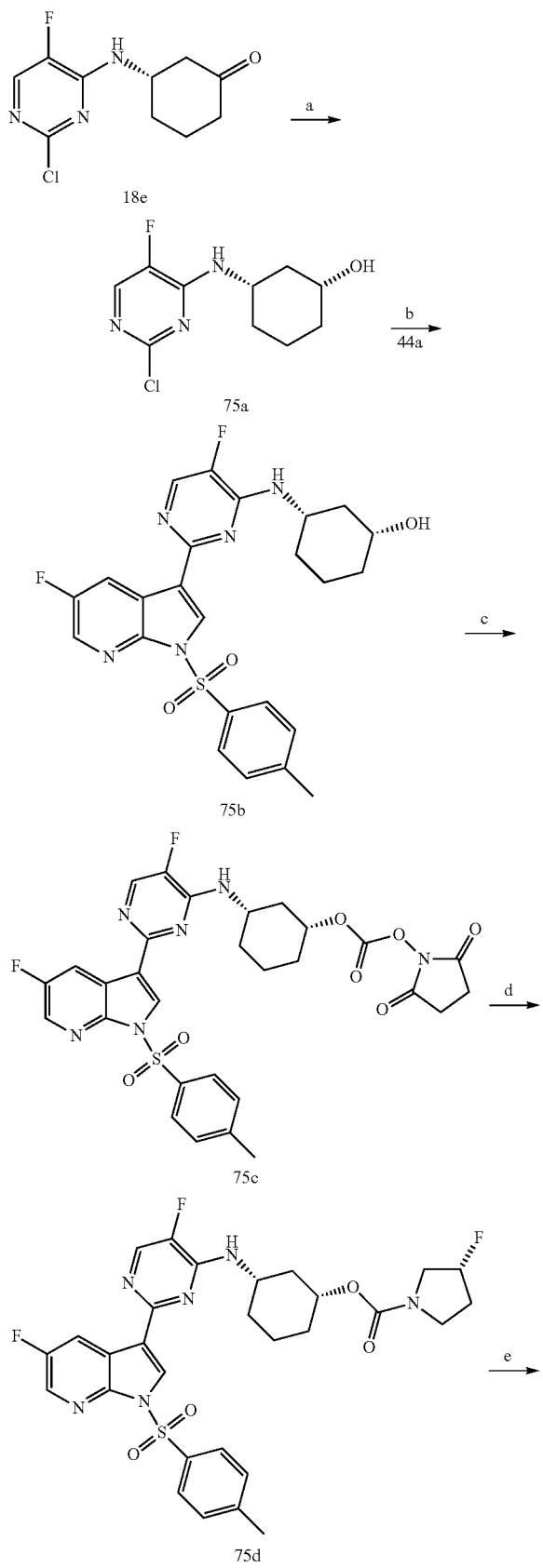

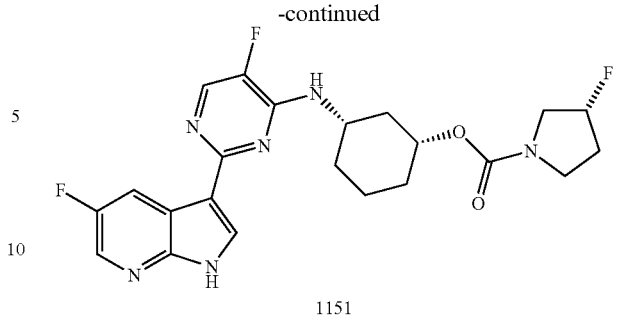

1151

(a) NaBH₄, MeOH; (b) 5-fluoro-3-(4,4,5,5-tetramethyl-1,3,2-dioxaborolan-2-yl)-1-tosyl-1H-pyrrolo[2,3-b]pyridine, 2-Me-THF, water, K₃PO₄, Pd(PPh₃)₄, XPhos, Tris(dibenzylideneacetone)dipalladium, reflux; (c) bis(2,5-dioxopyrrolidin-1-yl) carbonate, ⁱPr₂NEt, CH₃CN; (d) (3R)-3-fluoropyrrolidine, ⁱPr₂NEt, CH₃CN (e) 2N LiOH, THF.

Formation of (1R,3S)-3-((2-chloro-5-fluoropyrimidin-4-yl)amino)cyclohexanol (75a)

Mixed (3S)-3-[(2-chloro-5-fluoro-pyrimidin-4-yl)amino]cyclohexanone, 18e, (1.05 g, 4.31 mmol) in MeOH (20 mL) and dichloromethane (10 mL) and cooled to −78° C. using an external dry-ice/acetone bath and monitored with an internal thermometer. After 30 minutes, NaBH₄ (0.16 g, 4.31 mmol) was added in one portion and continued to stir. (slight exotherm) and then cooled back down to −78° C. The reaction was monitored by HPLC for consumption of starting material as it was allowed to warm to room temperature overnight. The reaction was diluted with brine and EtOAc. The organic phase was dried (MgSO₄), filtered and concentrated in vacuo. The resulting residue was purified by silica gel chromatography to afford 1.0 g of a colorless foamy solid: LCMS method m201: 10-90 CH₃CN/H₂O, formic acid modifier, 5 minutes, (C18); RT=2.08 min, MH⁺=246.21.

Formation of (1R,3S)-3-(5-fluoro-2-(5-fluoro-1-tosyl-1H-pyrrolo[2,3-b]pyridin-3-yl)pyrimidin-4-yl)amino)cyclohexanol (75b)

K₃PO₄ (2.59 g, 12.21 mmol) in water (6 mL) and 2-Me-THF (20 mL) was purged with a flow of nitrogen for 30 min. Added (1R,3S)-3-[(2-chloro-5-fluoro-pyrimidin-4-yl)amino]cyclohexanol, 75a, (1.00 g, 4.07 mmol) and 5-fluoro-3-(4,4,5,5-tetramethyl-1,3,2-dioxaborolan-2-yl)-1-tosyl-1H-pyrrolo[2,3-b]pyridine, 44a, (2.03 g, 4.88 mmol) and then purged with nitrogen for another 15 min. The reaction was then heated to 70° C. and then charged with Tris(dibenzylideneacetone)dipalladium (0.07 g, 0.08 mmol) and X-Phos (0.14 g, 0.28 mmol) under nitrogen. (Note Color changed from purple to hunter green). The reaction was heated to reflux for 1 h and 20 min. The reaction was cooled slowly to room temperature overnight. The mixture was treated with 100 mL of brine and 100 mL of ethyl acetate and separated the two layers. The aqueous phase was extracted again with EtOAc (50 mL). Combined organic layers and passed through a plug of fluoracil, dried over Na₂SO₄, decanted and removed the solvent by rotoevaporation to give crude product which was then purified by silica gel chromatography (25-50% EtOAc/Hexanes) to afford the desired product.

Formation of 2,5-dioxopyrrolidin-1-yl (1S,3R)-3-((5-fluoro-2-(5-fluoro-1-tosyl-1H-pyrrolo[2,3-b]pyridin-3-yl)pyrimidin-4-yl)amino)cyclohexyl) carbonate (75c)

To a solution of (1R,3S)-3-((5-fluoro-2-(5-fluoro-1-tosyl-1H-pyrrolo[2,3-b]pyridin-3-yl)-pyrimidin-4-yl)amino)cyclohexanol, 75b, (0.50 g, 1.00 mmol) and N,N-diisopropylethylamine (1.40 mL, 10.01 mmol) was added bis(2,5-dioxopyrrolidin-1-yl) carbonate (1.28 g, 5.01 mmol) in $CH_3CN$ (4 mL) and stirred at room temperature overnight. Used reaction mixture as is in next reaction. Using LCMS method m201:10-90 $CH_3CN/H_2O$, formic acid modifier, 5 minutes, (C18); RT=3.73 min, $MH^+$=641.43 (strong).

Formation of (R)-(1S,3R)-3-(5-fluoro-2-(5-fluoro-1-tosyl-1H-pyrrolo[2,3-b]pyridin-3-yl)pyrimidin-4-yl)amino)cyclohexyl 3-fluoropyrrolidine-1-carboxylate (75d)

To (2,5-dioxopyrrolidin-1-yl) [(1R,3S)-3-[[5-fluoro-2-[5-fluoro-1-(p-tolylsulfonyl)pyrrolo[2,3-b]pyridin-3-yl]pyrimidin-4-yl]amino]cyclohexyl]carbonate, 75c, (0.125 g, 0.195 mmol) already in acetonitrile was added (3R)-3-fluoropyrrolidine (0.445 g, 4.991 mmol) and the reaction mixture was stirred at room temperature for 20 hours; The reaction was monitored by HPLC until no more starting material was remaining. The reaction mixture was concentrated in vacuo and was carried on into the next reaction without further purification.

Formation of (S)-(1S,3R)-3-((5-fluoro-2-(5-fluoro-1H-pyrrolo[2,3-b]pyridin-3-yl)-pyrimidin-4-yl)amino)cyclohexyl 3-fluoropyrrolidine-1-carboxylate (1151)

To a solution of crude (R)-(1S,3R)-3-((5-fluoro-2-(5-fluoro-1-tosyl-1H-pyrrolo[2,3-b]pyridin-3-yl)pyrimidin-4-yl)amino)cyclohexyl 3-fluoropyrrolidine-1-carboxylate, 75d, (0.119 g, 0.019 mmol) in THF (2 mL) was added 5 mL 2N LiOH (10 mmol). The reaction mixture was heated at 50° C. for 2 hours. The mixture was diluted into aqueous saturated ammonium chloride (2 mL), and extracted with EtOAc (2×10 mL), dried over sodium sulfate, filtered and concentrated in vacuo. The resulting residue was purified on the semi-prep HPLC, 10-70% $CH_3CN/H_2O$; Three runs; homogeneous fractions were combined and the solvent removed under a stream of nitrogen and then removed residual solvent on roto-evaporator to afford 74 mg of the desired product: LCMS RT=2.15 min (M+H) 461.51.

General Scheme 76:

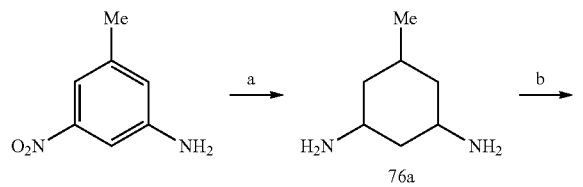

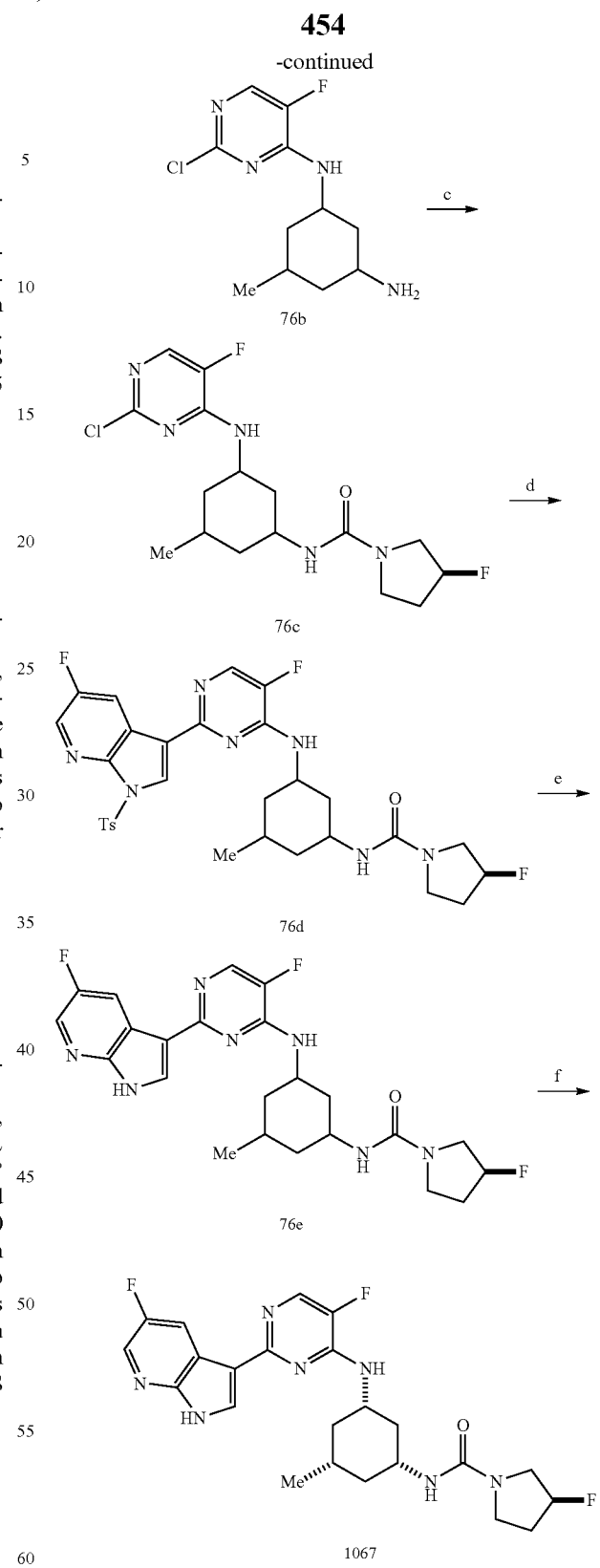

(a) $Rh/Al_2O_3$, $H_2O$, 100° C., 105 atm $H_2$, 19 hrs; (b) 2,4-dichloro-5-fluoropyrimidine, IPA, MeCN, room temperature; (c) CDI, $^iPr_2NEt$, (S)-3-fluoropyrrolidine, THF, RT, 2 days; (d) 5-fluoro-3-(4,4,5,5-tetramethyl-1,3,2-dioxaborolan-2-yl)-1-tosyl-1H-pyrrolo[2,3-b]pyridine, MeTHF, K$_3$PO$_4$, X-Phos, Pd$_2$ dba$_3$, H2O, microwave, 120° C., 20 minutes; (e) 25% NaOMe in MeOH, RT, 30 min; (f) SFC separation.

Formation of 5-methylcyclohexane-1,3-diamine (76a)

The 3-methyl-5-nitroaniline (10.0 g, 65.7 mmol) was added to water (146 ml) and treated with 6N HCl (22.5 ml, 135.0 mmol) and 5% Rhodium on Alumina (1.9 g, 0.9 mmol). The mixture was charged to 105 atm of Hydrogen and heated to 100° C. for 19 hours. The reaction was cooled and filtered through celite and concentrated to dryness to give 5-methyl-cyclohexane-1,3-diamine dihydrochloride (12.9 g, 64.5 mmol) as a racemic mixture. The salt (6.5 g, 32.5 mmol) was dissolved in isopropyl alcohol (100 ml) and acetonitrile (100 ml) and treated with potassium carbonate (25.2 g, 182.0 mmol). The mixture was stirred at room temperature overnight, filtered thru celite, and concentrated in vacuo to afford 2.2 g of 5-methylcyclohexane-1,3-diamine as a racemic brown oil: LCMS RT=0.41 (M+1) 128.9.

Formation of N$^1$-(2-chloro-5-fluoropyrimidin-4-yl)-5-methylcyclohexane-1,3-diamine (76b)

To a solution of 5-methylcyclohexane-1,3-diamine, 76a, (2.2 g, 17.2 mmol) in isopropyl alcohol (40 ml) and acetonitrile (40 ml) was added 2,4-dichloro-5-fluoropyrimidine (1.4 g, 8.6 mmol). The mixture was stirred at room temperature overnight, concentrated to dryness, and purified on silica gel eluted with 1-20% methanol/dichloromethane, to give 0.6 g of racemic N$^1$-(2-chloro-5-fluoropyrimidin-4-yl)-5-methyl-cyclohexane-1,3-diamine: $^1$H NMR (300 MHz, MeOD) δ 7.85 (d, J=3.5 Hz, 1H), 4.07 (ddd, J=11.9, 7.9, 4.1 Hz, 1H), 3.54 (qd, J=11.3, 4.2 Hz, 1H), 2.82 (tt, J=11.4, 3.7 Hz, 1H), 2.16 (dd, J=15.0, 13.0 Hz, 1H), 1.89 (t, J=13.4 Hz, 2H), 1.50 (dd, J=76.0, 21.9 Hz, 2H), 1.10 (dt, J=17.9, 9.0 Hz, 1H), 0.99 (dd, J=8.5, 5.0 Hz, 3H), 0.81 (ddd, J=23.8, 12.0, 8.2 Hz, 1H); LCMS RT=1.24 (M+1) 259.1.

Formation of (3S)—N-(3-((2-chloro-5-fluoropyrimidin-4-yl)amino)-5-methylcyclohexyl)-3-fluoropyrrolidine-1-carboxamide (76c)

To a solution of N$^1$-(2-chloro-5-fluoropyrimidin-4-yl)-5-methylcyclohexane-1,3-diamine, 76b, (0.14 g. 0.54 mmol) in THF (2.5 ml) was added carbonyldiimidazole (0.10 g, 0.60 mmol) and $^i$Pr$_2$NEt (0.28 mL, 1.62 mmol). The reaction was aged 2 hours at room temp, and treated with (S)-3-fluoropyrrolidine hydrochloride (0.07 g, 0.54 mmol). The reaction was stirred at room temperature for 2 days and then concentrated to dryness to afford 202 mg of (3S)—N-(3-((2-chloro-5-fluoropyrimidin-4-yl)amino)-5-methylcyclohexyl)-3-fluoropyrrolidine-1-carboxamide which was used without purification: LCMS RT=2.46 (M+1) 374.2, (M−1) 372.

Formation of (3S)-3-fluoro-N-(3-((5-fluoro-2-(5-fluoro-1-tosyl-1H-pyrrolo[2,3-b]pyridin-3-yl)pyrimidin-4-yl)amino)-5-methylcyclohexyl)pyrrolidine-1-carboxamide (76d)

To a solution of (3S) —N-(3-((2-chloro-5-fluoropyrimidin-4-yl)amino)-5-methyl-cyclohexyl)-3-fluoropyrrolidine-1-carboxamide, XXc, (0.101 g, 0.270 mmol) in 2-methyltetrahydrofuran (4 ml) was added potassium phosphate (0.090 g, 0.950 mmol) in water (1.2 ml), x-phos (0.027 g, 0.057 mmol), and Pd$_2$ dba$_3$ (0.015 g, 0.016 mmol). The reaction was heated in a microwave at 120° C., for 20 minutes, and the organic phase was filtered thru a pad of florisil and the filtrate concentrated in vacuo. The crude was purified on silica gel eluted with EtOAc to afford 127 mg of racemic (3S)-3-fluoro-N-(3-((5-fluoro-2-(5-fluoro-1-tosyl-1H-pyrrolo[2,3-b]pyridin-3-yl)pyrimidin-4-yl)amino)-5-methylcyclohexyl)pyrrolidine-1-carboxamide: LCMS RT=3.58 (M+1) 628.3, (M−1) 626.

Formation of (S)-3-fluoro-N-((1R,3S,5R)-3-((5-fluoro-2-(5-fluoro-1H-pyrrolo[2,3-b]pyridin-3-yl)pyrimidin-4-yl)amino)-5-methylcyclohexyl)pyrrolidine-1-carboxamide (76e)

To a solution of (3S)-3-fluoro-N-(3-((5-fluoro-2-(5-fluoro-1-tosyl-1H-pyrrolo[2,3-b]pyridin-3-yl)pyrimidin-4-yl)amino)-5-methylcyclohexyl)pyrrolidine-1-carboxamide, 76d, (0.090 g, 0.143 mmol) in MeOH (2.5 ml) was added 25% sodium methoxide in methanol (2 ml). The reaction was stirred at room temperature for 30 minutes and quenched with aqueous saturated NH$_4$Cl. The methanol was removed in-vacuo and the residue was extracted with EtOAc and water. The organics were dried over sodium sulfate and concentrated to dryness. The resulting crude racemate was purified by SFC separation on a chiral column. The second peak was concentrated in vacuo to afford 32 mg of enantiomerically pure (S)-3-fluoro-N-((1R,3S,5R)-3-((5-fluoro-2-(5-fluoro-1H-pyrrolo[2,3-b]pyridin-3-yl)pyrimidin-4-yl)amino)-5-methylcyclohexyl)pyrrolidine-1-carboxamide as a white solid: LCMS RT=1.89 (M+1) 474.2, (M−1) 472.4; SFC RT=3.2 min., 15% MeOH @ 5 mL/min on an ODH (4.6* 100), 100 bar, 35 C, 220 nm; $^1$H NMR (300 MHz, DMSO) δ 12.26 (s, 1H), 8.41 (dd, J=9.9, 2.8 Hz, 1H), 8.32-8.18 (m, 2H), 8.14 (d, J=4.0 Hz, 1H), 7.53 (d, J=7.6 Hz, 1H), 6.02 (d, J=7.9 Hz, 1H), 5.28 (d, J=53.6 Hz, 1H), 4.35-4.00 (m, 1H), 3.81-3.09 (m, 12H), 2.24-1.77 (m, J=41.2, 26.1, 10.6 Hz, 4H), 1.74-1.51 (m, 1H), 1.51-1.22 (m, 1H), 1.14-0.70 (m, 4H).

General Scheme 77:

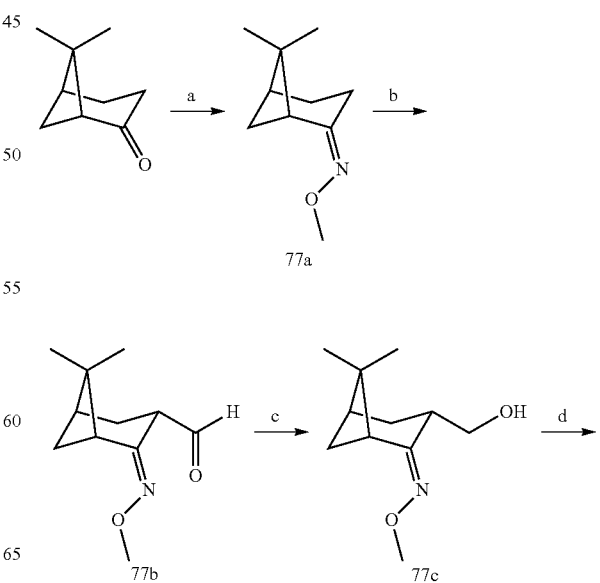

-continued

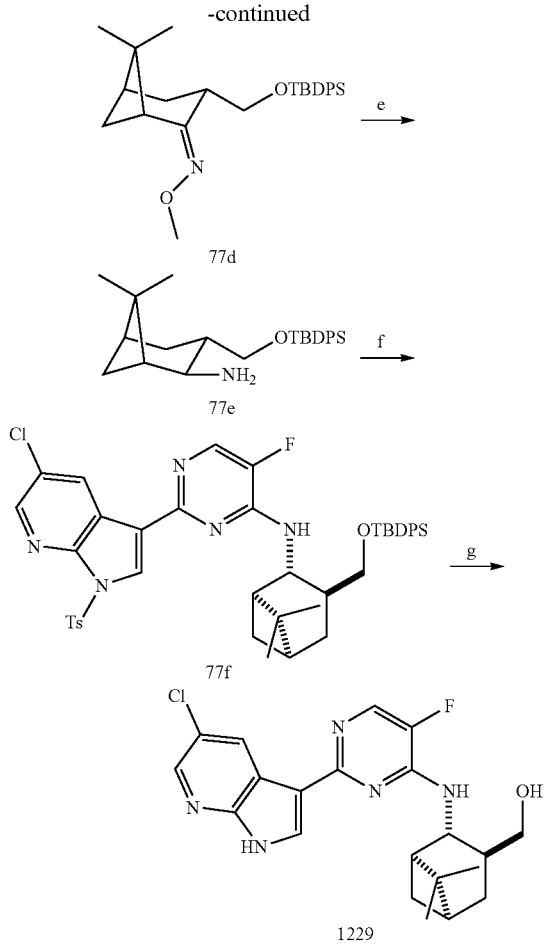

a) (R)-nopinone, O-methylhydroxylamine hydrochloride, pyridine, EtOH; (b) nBuLi, THF, −78° C., ethylformate; (c) NaBH₄, MeOH; (d) TBDPSCl, imidazole, DMF; (e) BH₃-THF, THF, 75° C.; (f) 5-chloro-3-(5-fluoro-4-(methylsulfinyl)pyrimidin-2-yl)-1-tosyl-1H-pyrrolo[2,3-b]pyridine, $^i$Pr₂NEt, 75° C.; (g) HCl, dioxane.

Formation of (1R,5S)-6,6-dimethylbicyclo[3.1.1]heptan-2-one O-methyl oxime (77a)

To a solution of (1S,5R)-6,6-dimethylnorpinan-2-one (3.09 g, 22.35 mmol) in ethanol (70 mL) was added O-methylhydroxylamine hydrochloride (2.05 g, 24.59 mmol) and pyridine (1.29 mL, 15.92 mmol). Heated reaction mixture to 80° C. for 4 hours. Removed solvent under reduced pressure. Diluted residue with 1N HCl and extracted twice with ether. The combined organic phases were washed with aqueous saturated NaHCO₃, dried (MgSO₄), filtered, concentrated in vacuo to afford 3.36 g of a colorless oil (mixture of oxime isomers) that was used without further purification.

Formation of (1R,3S,5R)-2-(methoxyimino)-6,6-dimethylbicyclo[3.1.1]heptane-3-carbaldehyde (77b)

To a cold (−78° C.) solution of (1R,5S)-6,6-dimethylbicyclo[3.1.1]heptan-2-one O-methyl oxime, 77a, (1.27 g, 7.59 mmol) in THF (33 mL) was added dropwise a solution of n-butyllithium (3.34 mL of 2.5 M solution in hexanes, 8.35 mmol). After stirring the mixture 20 min at −78° C. ethyl formate (0.61 mL, 7.59 mmol) was added dropwise. The reaction mixture was stirred at −78° C. for 3 hours and then quenched by pouring into aqueous saturated NaHCO₃ solution. The mixture was extracted with EtOAc. The organic phase was dried (MgSO₄), filtered and concentrated in vacuo. The resulting residue was purified via silica gel chromatography (0-20% EtOAc/Hexanes gradient) to afford 810 mg yellow oil: LCMS RT=3.54 (M+H) 196.28.

Formation of (1R,3S,5R)-3-(hydroxymethyl)-6,6-dimethylbicyclo[3.1.1]heptan-2-one O-methyl oxime (77c)

To a solution of (1R,3S,5R)-2-(methoxyimino)-6,6-dimethylbicyclo[3.1.1]heptane-3-carbaldehyde, 77b, (0.70 g, 3.58 mmol) in methanol (15 mL) was added sodium borohydride (0.16 g, 4.30 mmol). After stirring at room temperature for 30 minutes, the reaction was diluted into aqueous saturated NaHCO₃ solution and extracted with EtOAc. The organic phase was dried (MgSO₄), filtered and concentrated in vacuo. The resulting residue was purified via silica gel chromatography (0-50% EtOAc/Hexanes gradient) to afford 330 mg of the desired alcohol as mixture of oxime isomers.

Formation of (1R,3S,5R)-3-(((tert-butyldiphenylsilyl)oxy)methyl)-6,6-dimethyl-bicyclo[3.1.1]heptan-2-one O-methyl oxime (77d)

To a solution of (1R,3S,5R)-3-(hydroxymethyl)-6,6-dimethylbicyclo[3.1.1]-heptan-2-one O-methyl oxime, 77c, (0.32 g, 1.60 mmol) in DMF (6 mL) was added tert-butylchlorodiphenylsilane (0.55 g, 2.00 mmol) and imidazole (0.22 g, 3.20 mmol). The reaction mixture was stirred at room temperature for 18 hours. The reaction was diluted into aqueous saturated NH₄Cl solution and extracted twice with EtOAc. The combined organic phases were washed twice with brine, dried (MgSO₄), filtered and concentrated in vacuo. The resulting residue was purified via silica gel chromatography (0-15% EtOAc/Hexanes gradient) to afford 200 mg of one oxime isomer and 197 mg of second oxime isomer.

Formation of (1R,3S,5R)-3-(((tert-butyldiphenylsilyl)oxy)methyl)-6,6-dimethyl-bicyclo[3.1.1]heptan-2-amine (77e)

To a solution of (1R,3S,5R)-3-(((tert-butyldiphenylsilyl)oxy)methyl)-6,6-dimethyl-bicyclo[3.1.1]heptan-2-one O-methyl oxime, 77d, (0.20 g, 0.46 mmol) in THF (3 mL) was added borane-THF (1.38 mL of 1 M solution, 1.38 mmol). The reaction was heated to 75° C. for 18 hours. The mixture was diluted into 1N NaOH (50 mL) and extracted twice with EtOAc. The combined organic phases were dried (MgSO₄), filtered and concentrated in vacuo to afford 178 mg of a colorless oil that was used without further purification: LCMS RT=2.53 (M+H) 408.54.

Formation of N-((1R,2S,3S,5R)-3-(((tert-butyldiphenylsilyl)oxy)methyl)-6,6-dimethylbicyclo[3.1.1]heptan-2-yl)-2-(5-chloro-1-tosyl-1H-pyrrolo[2,3-b]pyridin-3-yl)-5-fluoropyrimidin-4-amine (77f)

To a solution of (1R,3S,5R)-3-(((tert-butyldiphenylsilyl)oxy)methyl)-6,6-dimethyl-bicyclo[3.1.1]heptan-2-amine, 77e, (0.20 g, 0.46 mmol) and 5-chloro-3-(5-fluoro-4-(methylsulfinyl)pyrimidin-2-yl)-1-tosyl-1H-pyrrolo[2,3-b]pyridine (0.14 g, 0.30 mmol) in DMF (1.5 mL) was added diisopropylethylamine (0.11 mL, 0.61 mmol). The reaction was heated to 75° C. for 18 hours. The mixture was diluted into aqueous saturated $NH_4Cl$ solution and extracted twice with EtOAc. The combined organic phases were washed twice with brine, dried ($MgSO_4$), filtered and concentrated in vacuo. The crude residue was purified via silica gel chromatography (0-5% MeOH/$CH_2Cl_2$ gradient) to afford 78 mg of the desired product.

Formation of ((1R,2S,3S,5R)-2-((2-(5-chloro-1H-pyrrolo[2,3-b]pyridin-3-yl)-5-fluoropyrimidin-4-yl)amino)-6,6-dimethylbicyclo[3.1.1]heptan-3-yl)methanol (1229)

To a solution of N-((1R,2S,3S,5R)-3-(((tert-butyldiphenylsilyl)oxy)methyl)-6,6-dimethylbicyclo[3.1.1]heptan-2-yl)-2-(5-chloro-1-tosyl-1H-pyrrolo[2,3-b]pyridin-3-yl)-5-fluoropyrimidin-4-amine, 77f, (0.037 g, 0.046 mmol) in acetonitrile (1.1 mL) was added HCl (0.221 mL of a 4 M solution in dioxane, 0.883 mmol). The mixture was heated to 70° C. for 18 h, during which a precipitate formed. The reaction was concentrated in vacuo and triturated three times with $CH_3CN$ to afford 4 mg of the desired product as a white solid: $^1H$ NMR (300.0 MHz, MeOD) δ 8.72-8.64 (m, 1H), 8.39 (s, 1H), 8.32 (d, J=2.3 Hz, 1H), 8.21 (d, J=5.2 Hz, 1H), 4.71 (d, J=6.3 Hz, 1H), 3.67-3.57 (m, 2H), 2.33-2.26 (m, 1H), 2.10 (m, 1H), 1.78-1.70 (m, 1H), 1.28-1.25 (m, 7H) and 1.19 (s, 3H) ppm; LCMS RT=3.13 (M+H) 416.42.

Influenza Antiviral Assay

Antiviral assays were performed using two cell-based methods:

A 384-well microtiter plate modification of the standard cytopathic effect (CPE) assay method was developed, similar to that of Noah, et al. (Antiviral Res. 73:50-60, 2006). Briefly, MDCK cells were incubated with test compounds and influenza A virus (A/PR/8/34), at a low multiplicity of infection (approximate MOI=0.005), for 72 hours at 37° C., and cell viability was measured using ATP detection (CellTiter Glo, Promega Inc.). Control wells containing cells and virus show cell death while wells containing cells, virus, and active antiviral compounds show cell survival (cell protection). Different concentrations of test compounds were evaluated, in quadruplicate, for example, over a range from approximately 20 µM to 1 nM. Dose-response curves were prepared using standard 4-parameter curve fitting methods, and the concentration of test compound resulting in 50% cell protection, or cell survival equivalent to 50% of the uninfected wells, was reported as the $IC_{50}$.

A second cell-based antiviral assay was developed that depends on the multiplication of virus-specific RNA molecules in the infected cells, with RNA levels being directly measured using the branched-chain DNA (bDNA), hybridization method (Wagaman et al, J. Virol Meth, 105:105-114, 2002). In this assay, cells are initially infected in wells of a 96-well microtiter plate, the virus is allowed to replicate in the infected cells and spread to additional rounds of cells, then the cells are lysed and viral RNA content is measured. This assay is stopped earlier that the CPE assay, usually after 18-36 hours, while all the target cells are still viable. Viral RNA is quantitated by hybridization of well lysates to specific oligonucleotide probes fixed to wells of an assay plate, then amplification of the signal by hybridization with additional probes linked to a reporter enzyme, according to the kit manufacturer's instructions (Quantigene 1.0, Panomics, Inc.). Minusstrand viral RNA is measured using probes designed for the consensus type A hemagglutination gene. Control wells containing cells and virus were used to define the 100% viral replication level, and dose-response curves for antiviral test compounds were analyzed using 4-parameter curve fitting methods. The concentration of test compound resulting in viral RNA levels equal to that of 50% of the control wells were reported as $EC_{50}$.

Virus and Cell culture methods: Madin-Darby Canine Kidney cells (CCL-34 American Type Culture Collection) were maintained in Dulbecco's Modified Eagle Medium (DMEM) supplemented with 2 mM L-glutamine, 1,000 U/ml penicillin, 1,000 ug/ml streptomycin, 10 mM HEPES, and 10% fetal bovine medium. For the CPE assay, the day before the assay, cells were suspended by trypsinization and 10,000cells per well were distributed to wells of a 384 well plate in 50 µl. On the day of the assay, adherent cells were washed with three changes of DMEM containing 1 ug/ml TPCK-treated trypsin, without fetal bovine serum. Assays were initiated with the addition of 30 $TCID_{50}$ of virus and test compound, in medium containing 1 m/ml TPCK-treated trypsin, in a final volume of 50 µl. Plates were incubated for 72 hours at 37° C. in a humidified, 5% $CO_2$ atmosphere. Alternatively, cells were grown in DMEM+fetal bovine serum as above, but on the day of the assay they were trypsinized, washed 2 times and suspended in serum-free EX-Cell MDCK cell medium (SAFC Biosciences, Lenexa, Kans.) and plated into wells at 20,000 cells per well. These wells were then used for assay after 5 hours of incubation, without the need for washing.

Influenza virus, strain A/PR/8/34 (tissue culture adapted) was obtained from ATCC (VR-1469). Low-passage virus stocks were prepared in MDCK cells using standard methods (WHO Manual on Animal Influenza Diagnosis and Surveillance, 2002), and $TCID_{50}$ measurements were performed by testing serial dilutions on MDCK cells in the 384-well CPE assay format, above, and calculating results using the Karber method.

Mean $IC_{50}$ values (mean all) for certain specific compounds are summarized in Tables 1-5:
A: $IC_{50}$ (mean all)<5 µM;
B 5 µM≤$C_{50}$ (mean all)≤20 µM;
C $IC_{50}$ (mean all)>10 µM;
D $IC_{50}$ (mean all)>20 µM;
E $IC_{50}$ (mean all)>3.3 µM.

Mean $EC_{50}$ values (mean all) for certain compounds are also summarized in Tables 1-5:
A: $EC_{50}$ (mean all)≤5 µM;
B 5 µM≤$EC_{50}$ (mean all)≤10 µM;
C $EC_{50}$ (mean all)>3.3 µM;
D $EC_{50}$ (mean all)>10 µM.

As can be seen in Tables 1-5, a lot of compounds of the invention showed positive effect on the survival of the A/PR/8/34 infected cells, and inhibitory effect on the replication of A/PR/8/34 influenza virus. Exemplary $IC_{50}$ and $EC_{50}$ values are as follows: Compound 428 had 0.03 µM of $IC_{50}$; Compound 895 had 0.0008 µM of $IC_{50}$ and 0.001 µM of $EC_{50}$; Compound 833 had 5.6 µM of $IC_{50}$ and 3.5 µM of $EC_{50}$.

TABLE 1

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 1 | | A | 411.38 | 2.69 | H NMR (300.0 MHz, DMSO) d 12.32 (s, 1H), 8.71 (d, J = 2.4 Hz, 1H), 8.28 (d, J = 2.4 Hz, 1H), 8.18-8.16 (m, 2H), 7.37 (d, J = 7.6 Hz, 1H), 6.33 (t, J= 4.4 Hz, 0.25H), 6.15 (t, J = 4.3 Hz, 0.5H), 5.96 (t, J = 4.3 Hz, 0.25H), 4.22 (d, J = 7.6 Hz, 1H), 3.13 (d, J = 11.2 Hz, 1H), 2.88 (m, 1H), 2.81 (ddd, J = 15.5, 4.2, 4.2 Hz, 2H), 2.30-2.20 (m, 2H), 1.98 (m, 1H), 1.72-1.61 (m, 2H) and 1.49-1.36 (m, 1H) ppm |
| 2 | | | 475 | 3.58 | 1H NMR (CD3OD): 1.1-1.3 (3H, m), 1.40-1.50 (3H, m), 1.55-2.10 (4H, m), 2.40-2.45 (1H, m), 3.3-3.5 (2H, m), 3.75-4.10 (4H, m). 5.4-5.5 (1H, m), 8.05-8.20 (3H, m), 8.70-8.80 (1H, m) |
| 3 | | | 446.14 | 2.96 | 1H NMR (DMSO): 1.39 (4H, m), 1.542 (1H, m), 1.74 (2H, m), 2.33 (1H, m), 2.61 (1H, m), 2.88 (1H, m), 4.18 (1H, m), 4.37 (1H, m), 5.21 (1H, m), 6.84 (2H, d), 7.33 (2H, d), 7.60 (2H, m), 8.23 (3H, m), 8.63 (1H, d), 12.33 (1H, s) |
| 4 | | D | 327 | 1.2 | 500 MHz, MeOD-d4: 8.83 (dd, 1H), 8.45 (s, 1H), 8.42 (dd, 1H), 8.32 (d, 1H), 7.65 (d, 2H), 7.42 (dd, 1H), 7.18 (d, 2H), 4.55 (m, 1H), 3.4 (m, 1H), 2.3 (s, 3H), 2.2 (m, 2H), 1.95 (m, 2H), 1.5 (m, 4H) |
| 5 | | | 385.3 | 1.74 | |
| 6 | | | 401.3 | 1.68 | |
| 7 | | D | 371.1 | 1.63 | |
| 8 | | | 421.1 | 1.82 | H NMR (500 MHz, DMSO-d6) 12.98 (s, 1H), 9.24 (s, 1H), 8.80 (s, 1H), 8.60 (s, 1H), 8.38 (d, J = 1.9 Hz, 1H), 8.21 (d, J = 7.0 Hz, 1H), 6.65 (d, J = 6.7 Hz, 1H), 3.81-3.43 (m, 4H), 2.36 (t, J = 1.8 Hz, 1H), 2.19 (d, J = 10.1 Hz, 1H), 1.62 (s, 6H), 0.00 (TMS) |
| 9 | | | 403.1 | 1.69 | H NMR (500 MHz, DMSO-d6) 13.01 (s, 1H), 9.40 (s, 1H), 8.85 (d, J = 6.9 Hz, 1H), 8.63 (s, 1H), 8.38 (d, J = 2.1 Hz, 1H), 8.18 (d, J = 7.0 Hz, 1H), 6.66 (s, 1H), 5.29-5.05 (m, 1H), 3.86-3.16 (m, 4H), 1.65 (d, J = 10.6 Hz, 2H), 1.60 (s, 6H), 0.00 (TMS) |
| 10 | | | 403.1 | 1.74 | H NMR (500 MHz, DMSO-d6) 12.99 (d, J = 6.1 Hz, 1H), 9.39 (s, 1H), 8.84 (s, 1H), 8.62 (s, 1H), 8.38 (s, 1H), 8.18 (d, J = 7.0 Hz, 1H), 6.65 (s, 1H), 5.29-5.05 (m, 1H), 3.87-3.15 (m, 4H), 1.64 (d, J = 10.8 Hz, 2H), 1.59 (s, 6H), 0.00 (TMS) |
| 11 | A | A | 362.2 | 1.8 | |
| 12 | D | | 376.2 | 1.9 | |
| 13 | A | | 362.2 | 1.8 | |
| 14 | B | A | | | (400 MHz, DMSO-d6): 12.80 (s, exchanged with D2O, 1H), 8.82 (d, J = 2.4 Hz, 1H), 8.28 (d, J = 2.4 Hz, 1H), 8.22 (d, J = 2.8 Hz, 1H), 8.14 (d, J = 4.0 Hz, 1H), 7.46 (br. d, J = 6.4 Hz, exchanged with D2O, 1H), 4.82 (d, J = 3.6 Hz, 1H), 4.27 (quintet, J = 6.4 Hz, 1H), 4.14 (quintet, J = 5.6 Hz, 1H), 2.20-2.10 (m, 1H), 1.94-1.77 (m, 1H), 1.77-1.70 (m, 2H), 1.65-1.50 (m, 2H). |
| 15 | B | A | 461.3 | 2.68 | H NMR (300 MHz, DMSO-d6) 12.32 (s, 1H), 8.72 (d, J = 2.5 Hz, 1H), 8.28 (d, J = 2.4 Hz, 1H), 8.19-8.15 (m, 1H), 7.75 (d, J = 5.3 Hz, 1H), 3.89 (s, 1H), 3.69 (s, 1H), 3.53-3.45 (m, 2H), 3.45 (s, 1H), 2.89-2.49 (m, 2H), 1.90-1.68 (m, 3H), 1.28 (m, 2H), 1.28 (s, 9H) |
| 16 | D | A | 461.3 | 2.63 | H NMR (300 MHz, DMSO-d6) 12.31 (s, 1H), 8.71 (d, J = 2.5 Hz, 1H), 8.27 (d, J = 2.4 Hz, 1H), 8.20-8.15 (m, 2H), 7.74 (d, J = 5.9 Hz, 1H), 3.88 (d, J = 3.8 Hz, 2H), 3.71 (d, J = 11.3 Hz, 1H), 3.53-3.35 (m, 3H), 2.86 (t, J = 10.4 Hz, 1H), 1.90 (s, 2H), 1.68 (s, 9.1 Hz, 1H), 1.41 (s, 2H), 1.28 (s, 9H), |
| 17 | B | A | 445.3 | 3.1 | |
| 18 | B | A | 443.3 | 2.9 | |
| 19 | D | | 503.4 | 2.8 | |
| 20 | B | | 460.4 | 3 | |
| 21 | A | A | 451.3 | 2.9 | |
| 22 | A | A | 486.3 | 2.9 | |
| 23 | A | A | 419.3 | 2.8 | |
| 24 | D | | 463.2 | 2.8 | |
| 25 | A | A | 490.3 | 2.6 | |
| 26 | A | A | 476.3 | 2.5 | |
| 27 | A | A | 446.4 | 2.7 | |
| 28 | D | A | 461.4 | 3.3 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 29 | B | | 418.3 | 2.4 | |
| 30 | B | A | 457.3 | 3.1 | |
| 31 | A | A | 411.2 | 2.22 | (400 MHz, DMSO-d6): 12.73 (s, exchanged with D2O, 1H), 8.85 (s, 1H), 8.65 (d, J = 5.6 Hz, 1H), 8.37 (d, J = 6.8 Hz, 1H), 8.03-7.89 (m, 4H, addition of D2O changed to d, J = 7.6 Hz, 1H), 4.03-3.98 (m, 1H), 3.60-3.50 (m, 1H), 2.18-1.95 (m, 2H), 1.77-1.23 (m, 6H). |
| 32 | A | A | 417.4 | 2.6 | |
| 33 | A | A | 433.3 | 3 | |
| 34 | A | | 431.4 | 2.8 | |
| 35 | D | | 447.4 | 3.2 | |
| 36 | A | A | 439.3 | 2.7 | |
| 37 | A | A | 403.3 | 2.4 | |
| 38 | A | A | 457.4 | 3.1 | |
| 39 | A | A | 444.4 | 2.6 | |
| 40 | D | | 481.3 | 2.5 | |
| 41 | A | A | 429.3 | 2.7 | |
| 42 | D | | 459.3 | 3.1 | |
| 43 | D | | 460.3 | 2.4 | |
| 44 | A | A | 471.3 | 2.8 | |
| 45 | A | A | 433.3 | 2.4 | |
| 46 | D | | 446.3 | 2.5 | |
| 47 | A | A | 480.3 | 2.4 | |
| 48 | D | | 471.3 | 2.4 | |
| 49 | A | A | 429.3 | 2.7 | |
| 50 | D | | 469.3 | 2.3 | |
| 51 | A | A | 472.9 | 1.7 | |
| 52 | A | A | 441.3 | 1.9 | |
| 53 | B | | 475.3 | 1.8 | |
| 54 | B | | 477.3 | 1.7 | |
| 55 | A | A | 501.3 | 2.5 | |
| 56 | A | A | 479.3 | 2.9 | |
| 57 | A | A | 443.3 | 2.8 | |
| 58 | A | | 483.3 | 2.9 | |
| 59 | A | A | 429.3 | 2.7 | |
| 60 | A | A | 527 | 3.2 | |
| 61 | A | A | 465.3 | 2.8 | |
| 62 | A | A | 531.3 | 3.1 | |
| 63 | D | | 539.3 | 3.2 | |
| 64 | B | A | 519.3 | 3.1 | |
| 65 | A | A | 519.2 | 3.1 | |
| 66 | A | A | 515.3 | 3.2 | |
| 67 | A | A | 579.2 | 3.3 | |
| 68 | B | A | 481.4 | 3.2 | |
| 69 | A | A | 511.3 | 3.2 | |
| 70 | A | A | 515.3 | 3.3 | |
| 71 | B | | 495.3 | 3.4 | |
| 72 | B | | 549.3 | 3.5 | |
| 73 | B | | 499.3 | 3.3 | |
| 74 | A | A | 445.2 | 3.1 | |
| 75 | A | A | 498.3 | 3 | |
| 76 | A | A | 510.3 | 2.9 | |
| 77 | B | | 522.3 | 2.8 | |
| 78 | A | A | 494.3 | 3 | |
| 79 | B | | 548.3 | 3.3 | |
| 80 | A | A | 503.3 | 1.9 | |
| 81 | A | A | 529.3 | 2 | |
| 82 | D | | 511.3 | 1.6 | |
| 83 | D | | 473.4 | 1.6 | |
| 84 | A | A | 499.4 | 2 | |
| 85 | B | A | 501.3 | 2.1 | |
| 86 | A | A | 501.3 | 2.1 | |
| 87 | A | A | 501.3 | 2.1 | |
| 88 | A | A | 561.3 | 2 | |
| 89 | A | A | 507.2 | 2.1 | |
| 90 | A | A | 519.2 | 2.1 | |
| 91 | A | A | 505.3 | 1.8 | |
| 92 | A | A | 437.2 | 2.7 | |
| 93 | A | A | 451.2 | 2.9 | |
| 94 | A | A | 495.3 | 2.9 | |
| 95 | A | A | 471.3 | 3.2 | |
| 96 | B | | 535.2 | 2.9 | |
| 97 | A | A | 471.2 | 2.9 | |
| 98 | A | A | 497.3 | 2.9 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 99 | A | A | 457.3 | 3.1 | |
| 100 | A | A | 471.3 | 3.1 | |
| 101 | A | A | 467.2 | 2.5 | |
| 102 | A | A | 455.3 | 2.7 | |
| 103 | A | | 509.3 | 2.8 | |
| 104 | A | A | 485.3 | 2.8 | |
| 105 | A | A | 445.3 | 3 | |
| 106 | A | A | 509.3 | 3 | |
| 107 | A | A | 521.3 | 3.2 | |
| 108 | A | A | 501.3 | 2.8 | |
| 109 | A | A | 525.3 | 2.7 | |
| 110 | A | A | 461.3 | 2.5 | |
| 111 | A | A | 403.2 | 2.4 | |
| 112 | A | A | 494.3 | 3 | |
| 113 | A | A | 495.3 | 2.8 | |
| 114 | D | | 442.5 | 1.6 | |
| 115 | D | | 377.2 | 1.286 | (400 MHz, DMSO-d6): 12.99 (m, exchanged with D2O, 1H), 9.01 (m, exchanged with D2O, 1H), 8.67 (s, 1H), 8.48 (s, 1H), 8.41 (s, 1H), 8.32 (overlapped s, 1H), 8.29 (overlapped br.s, exchanged with D2O, 1H), 7.50-7.20 (m, exchanged with D2O, 1H), 4.47-4.40 (m, 1H), 3.53-3.45 (m, 1H), 2.19 (br. d, J = 10.0 Hz, 1H), 2.08 (br. d, J = 10.4 Hz, 1H), 1.84 (br. d, J = 10.4 Hz, 2H), 1.60-1.29 (m, 4H). |
| 116 | D | | 357.2 | 3.267 | (400 MHz, DMSO-d6): 2.70 (br. hump, exchanged with D2O, 1H), 8.72 (s, 1H), 8.36 (s, 1H), 8.20-8.06 (overlapped hump, exchanged with D2O, 1H, + a s for an impurity), 7.47 (d, J = 7.6 Hz, 1H), 7.35-7.0 (overlapped m, exchanged with D2O, 2H), 7.10 (overlapped d, J = 8.0 Hz, 1H), 4.39-4.35 (m, 1H), 3.16-3.10 (m, 1H), 2.28 (s, 3H), 2.18-1.35 (m, 8H). |
| 117 | A | A | 486.3 | 2.8 | |
| 118 | B | | 504.2 | 2.6 | |
| 119 | A | A | 445.4 | 3.1 | |
| 120 | A | A | 552.4 | 3.2 | |
| 121 | D | | 446.4 | 2.2 | |
| 122 | A | A | 443.3 | 2.9 | |
| 123 | B | A | 461.5 | 3.4 | |
| 124 | A | A | 439.3 | 3.1 | |
| 125 | A | A | 490.4 | 2.6 | |
| 126 | A | A | 451.3 | 2.9 | |
| 127 | A | A | 457.3 | 3.1 | |
| 128 | A | A | 460.4 | 3 | |
| 129 | A | A | 486.4 | 2.9 | |
| 130 | A | | 500.6 | 2 | |
| 131 | A | A | 462.7 | 1.6 | |
| 132 | D | | 449.7 | 2.2 | |
| 133 | D | | 405.3 | 2.3 | |
| 134 | B | | 457.3 | 3.1 | |
| 135 | D | | 433.4 | 2.5 | |
| 136 | D | | 469.3 | 3.2 | |
| 137 | D | | 465.4 | 3.1 | |
| 138 | D | | 459.3 | 2.8 | |
| 139 | D | | 465.3 | 3.2 | |
| 140 | D | | 459.3 | 2.9 | |
| 141 | D | | 433.5 | 1.4 | |
| 142 | A | A | 541.5 | 2.8 | |
| 143 | A | A | 479.4 | 2.9 | |
| 144 | D | A | 533.3 | 3 | |
| 145 | A | A | 507.3 | 2.9 | |
| 146 | A | A | 533.3 | 3 | |
| 147 | A | A | 533.3 | 3.2 | |
| 148 | A | A | 509.3 | 3 | |
| 149 | A | A | 509.4 | 3 | |
| 150 | B | | 557.3 | 3.2 | |
| 151 | A | A | 501.4 | 2.9 | |
| 152 | A | A | 501.2 | 2.9 | |
| 153 | A | A | 495.3 | 2.8 | |
| 154 | B | A | 525.4 | 2.8 | |
| 155 | A | A | 479.4 | 2.9 | |
| 156 | A | A | 499.4 | 3 | |
| 157 | A | A | 493.1 | 2 | |
| 158 | A | | 510 | 2 | |
| 159 | B | A | 418.3 | 2.3 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 160 | D | A | 451.4 | 2.1 | |
| 161 | D | A | 463.4 | 2.8 | |
| 162 | D | A | 480.3 | 2.8 | |
| 163 | B | A | 467.4 | 3.1 | |
| 164 | D | A | 443.5 | 3 | |
| 165 | D | | 472.5 | 2.8 | |
| 166 | B | A | 419.5 | 2.9 | |
| 167 | D | B | 444.4 | 2.7 | |
| 168 | B | A | 432.3 | 2.6 | |
| 169 | D | B | 490.5 | 2.7 | |
| 170 | D | A | 446.4 | 2.7 | |
| 171 | D | B | 433.3 | 3 | |
| 172 | D | | 495.5 | 3.2 | |
| 173 | A | A | 403.3 | 2.5 | |
| 174 | D | | 495.6 | 2.8 | |
| 175 | A | A | 418.5 | 2.4 | |
| 176 | D | A | 467.3 | 2.3 | |
| 177 | A | A | 444.4 | 2.7 | |
| 178 | A | A | 446.4 | 2.8 | |
| 179 | A | A | 403.4 | 2.5 | |
| 180 | A | A | 451.3 | 2.9 | |
| 181 | B | A | 443.4 | 3 | |
| 182 | A | A | 432.3 | 2.6 | |
| 183 | B | A | 433.3 | 3 | |
| 184 | D | | 495.5 | 2.7 | |
| 185 | A | A | 463.4 | 2.8 | |
| 186 | A | A | 472.4 | 2.8 | |
| 187 | A | A | 480.3 | 2.8 | NMR 1H (CDCl3): 8.7 (s, 1H), 8.6 (s, 1H), 8.3 (s, 1H), 8.1 (s, 1H), 4.7 (m, 1H), 4.2 (m, 1H), 1.3-3.7 (m, 15H). |
| 188 | A | A | 419.4 | 2.9 | |
| 189 | A | A | 490.5 | 2.7 | |
| 190 | B | | 495.4 | 3.1 | |
| 191 | A | A | 446.3 | 2.7 | |
| 192 | A | A | 460.4 | 2.9 | |
| 193 | B | A | 474.4 | 3.1 | |
| 194 | A | A | 431.2 | 2.9 | |
| 195 | B | | 513.2 | 2.5 | |
| 196 | A | A | 432.1 | 2.6 | |
| 197 | A | A | 446.2 | 2.7 | |
| 198 | A | A | 453.1 | 2.9 | |
| 199 | A | A | 439.1 | 2.8 | |
| 200 | A | A | 453.1 | 2.9 | |
| 201 | D | A | 481.1 | 2.6 | |
| 202 | A | A | 478.2 | 2.7 | |
| 203 | A | A | 458.2 | 2.8 | |
| 204 | A | A | 462.2 | 2.5 | |
| 205 | A | A | 476.2 | 2.6 | |
| 206 | A | | 327.2 | 1.85 | H NMR (300.0 MHz, DMSO) d 12.14 (s, 1H), 8.66 (d, J = 8.0 Hz, 1H), 8.29-8.22 (m, 3H), 7.81 (s, 2H), 7.28-7.19 (m, 2H), 4.55 (s, 1H), 3.74 (s, 1H) and 1.92-1.49 (m, 8H) ppm |
| 207 | A | A | 328.2 | 2.22 | |
| 208 | A | A | 417.2 | 1.9 | |
| 209 | A | A | 483.1 | 2 | |
| 210 | D | B | 533.1 | 2.2 | |
| 211 | B | | 369.3 | 2.27 | |
| 212 | A | | 383.3 | 2.42 | |
| 213 | D | | 417.3 | 2.45 | |
| 214 | D | | 447.3 | 2.35 | |
| 215 | D | | 384.3 | 2.27 | |
| 216 | D | | 355.3 | 2.08 | |
| 217 | B | | 355.3 | 1.93 | |
| 218 | A | A | 369.4 | 2.08 | |
| 219 | D | | 383.3 | 2.23 | |
| 220 | A | | 384.3 | 2.12 | |
| 221 | B | | 417.3 | 2.34 | |
| 222 | D | | 447.3 | 2.25 | |
| 223 | B | | 369.3 | 2.12 | |
| 224 | B | | 383.3 | 2.27 | |
| 225 | B | | 397.4 | 2.38 | |
| 226 | A | | 431.3 | 2.49 | |
| 227 | B | | 461.3 | 2.49 | |
| 228 | B | | 398.3 | 2.31 | |
| 229 | D | | 370.3 | 2.05 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 230 | D | | 384.3 | 2.23 | |
| 231 | D | | 398.3 | 2.35 | |
| 232 | B | | 432.3 | 2.6 | |
| 233 | B | A | 370.3 | 1.9 | |
| 234 | B | | 384.3 | 2.04 | |
| 235 | B | | 398.3 | 2.2 | |
| 236 | B | | 432.4 | 2.38 | |
| 237 | B | | 384.3 | 2.05 | |
| 238 | B | | 398.3 | 2.19 | |
| 239 | D | | 369.3 | 2.27 | |
| 240 | D | | 383.3 | 2.43 | |
| 241 | B | | 417.3 | 2.48 | |
| 242 | D | | 447.3 | 2.45 | |
| 243 | D | | 384.4 | 2.26 | |
| 244 | D | | 355.3 | 1.97 | |
| 245 | B | | 369.3 | 2.08 | |
| 246 | D | | 383.3 | 2.19 | |
| 247 | D | | 384.3 | 2.15 | |
| 248 | D | | 370.3 | 2.05 | |
| 249 | D | | 384.3 | 2.23 | |
| 250 | D | | 396.5 | 2.36 | |
| 251 | B | | 432.3 | 2.64 | |
| 252 | D | | 370.4 | 1.89 | |
| 253 | D | | 382.4 | 1.99 | |
| 254 | D | | 398.3 | 2.12 | |
| 255 | B | | 432.4 | 2.37 | |
| 256 | B | | 369.3 | 2.2 | |
| 257 | B | | 383.3 | 2.31 | |
| 258 | B | | 397.3 | 2.46 | |
| 259 | B | | 431.3 | 2.42 | |
| 260 | D | | 461.3 | 2.36 | |
| 261 | B | | 398.3 | 2.35 | |
| 262 | D | | 412.4 | 2.27 | |
| 263 | B | | 446.3 | 2.6 | |
| 264 | B | | 384.3 | 2.12 | |
| 265 | D | | 398.4 | 2.23 | |
| 266 | B | | 412.3 | 2.38 | |
| 267 | B | | 446.4 | 2.6 | |
| 268 | B | | 369.3 | 2.08 | |
| 269 | B | | 383.3 | 2.27 | |
| 270 | B | | 397.3 | 2.42 | |
| 271 | B | | 431.4 | 2.49 | |
| 272 | D | | 461.3 | 2.46 | |
| 273 | B | | 398.3 | 2.31 | |
| 274 | B | | 384.3 | 2.05 | |
| 275 | B | | 398.4 | 2.2 | |
| 276 | D | | 412.4 | 2.31 | |
| 277 | A | A | 328.2 | 1.56 | |
| 278 | D | | 465.1 | 2.4 | |
| 279 | A | A | 443.2 | 2.1 | |
| 280 | A | A | 471.2 | 2.1 | |
| 281 | A | A | 455.2 | 2.1 | |
| 282 | A | A | 486.1 | 2 | |
| 283 | B | | 578.2 | 2.4 | |
| 284 | A | A | 458.2 | 2 | |
| 285 | D | | 498.2 | 1.6 | |
| 286 | D | | 516.2 | 1.7 | |
| 287 | D | | 488.2 | 1.9 | |
| 288 | B | | 488.2 | 1.9 | |
| 289 | D | | 501.2 | 1.6 | |
| 290 | B | | 529.2 | 1.8 | |
| 291 | D | | 488.2 | 1.9 | |
| 292 | D | | 481.2 | 1.6 | |
| 293 | A | A | 493.2 | 3.1 | |
| 294 | D | | 485.2 | 3.3 | |
| 295 | A | A | 431.2 | 2.9 | |
| 296 | B | | | | (400 MHz, CDCl3): 8.85 (d, J = 2.0 Hz, 1H), 8.80 (br s, 1H), 8.29 (d, J = 2.4 Hz, 1H), 8.11 (d, J = 2.8 Hz, 1H), 8.07 (d, J = 3.2 Hz, 1H), 6.19 (br. hump, 1H), 5.16 (qunitet, J = 7.6 Hz, 1H), 3.78-3.50 (series of m, 4H), 2.16-1.91(series of m, 4H), 1.58 (d, J = 7.6 Hz, 3H) |
| 297 | B | | | | (400 MHz, CDCl3): 8.95 (br. hump, exchanged withy D2O, 1H), 8.83 (d, J = 2.0 Hz, 1H), 8.29 (d, J = 2.4 Hz, 1H), 8.11 (d, J = 2.4 Hz, addtion of |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | D2O changed to s, 1H), 8.07 (d, J = 3.2 Hz, 1H), 6.40 (br. d, J = 5.6 Hz, 1H), 5.16 (qunitet, J = 6.8 Hz, addition of D2O changed to q, J = 6.8 Hz, 1H), 3.07-3.50 (series of m, 4H), 1.70-1.60 (series of m, 6H), 1.55 (d, J = 6.4 Hz, 3H) |
| 298 | D | | | | (400 MHz, CDCl3): (400 MHz, CDCl3): 9.15 (br. hump, exchanged with D2O, 1H), 8.83 (d, J = 2.4 Hz, 1H), 8.30 (d, J = 2.4 Hz, 1H), 8.11 (d, J = 2.8 Hz, 1H), 8.07 (d, J = 3.2 Hz, 1H), 6.29 (d, J 6.4 Hz, exchanged with D2O, 1H), 5.30 (quintet, J = 6.8 Hz, addtion of D2O changed with q, J = 6.8 Hz, 1H), 3.90-3.80 (m, 4H), 2.60-2.40 (m, 4H), 2.33 (s, 3H), 1.57 (d, J = 7.2 Hz, 3H). |
| 299 | D | | | | (400 MHz, CDCl3): 9.15 (br. hump, exchanged with D2O, 1H), 8.83 (br. s , 1H), 8.30 (br. s, 1H), 8.11-8.07 (m, 2H), 6.99 (br. s, exchanged with D2O, 1H), 5.40-5.30 (m, 1H), 3.90-3.40 (m, 8H), 2.14 (s, 3H), 1.57 (d overlapped with moisture, J = 7.2 Hz, 3H). |
| 300 | B | | | | (400 MHz, CDCl3): 9.10 ( br. hump, exchanged with D2O, 1H), 8.83 (br. s, 1H), 8.30 (br. s, 1H), 8.11 (br. s, 1H), 8.09 (d, J = 1.2 Hz, 1H), 6.24 (br. d, J = 5.2 Hz, exchanged with D2O, 1H), 5.30 (quintet, J = 7.2 Hz, addtion of D2O changed with q, J = 6.8 Hz, 1H), 3.90-3.80 (m, 8H), 1.54 (overlaped d, J = 7.2 Hz, 3H). |
| 301 | B | | 460.4 | 1.712 | (400 MHz, DMSO-d6, 7): 8.69 (d, J = 2.4 Hz, 1H), 8.25 (d, J = 2.8 Hz, 1H), 8.19 (d, J = 3.6 Hz, 1H), 8.16 (br.s, 1H), 5.25-5.15 (m, 1H), 3.82-3.25 (m, 8H), 1.93 (br. s, 3H), 1.80-170 (m, 2H), 1.43 (d, J = 6.8 Hz, 3H). |
| 302 | B | | | | (400 MHz, DMSO-d6): 8.56 (d, J = 2.0 Hz, 1H), 8.31 (br. s, 1H), 8.13 (d, J = 1.6 Hz, 1H), 8.07 (d, J = 2.8 Hz, 1H), 5.17 (dq, J = 7.6, 6.8 Hz, 1H), 3.77-3.70 (m, 1H), 3.67-3.49 (m, 3H), 2.10-2.01 (m, 2H), 1.95-1.90 (m, 2H), 1.57 (d, J = 6.8 Hz, 3H). |
| 303 | D | | | | (400 MHz, DMSO-d6): 9.375 (br. hump, exchanged with D2O, 1H), 8.84 (d, J = 1.6 Hz, 1H), 8.31 (d, J = 2.0 Hz, 1H), 8.13 (d, J = 2.0 Hz, 1H), 8.07 (d, J = 3.2 Hz, 1H), 6.36 (br. d, J = 6.8 Hz, 1H), 5.33 (q, J = 6.8 Hz, 1H), 3.71-3.61 (m, 4H), 1.71-1.61 (m, 6H), 1.56 (d, J = 6.4 Hz, 3H). |
| 304 | D | | | | (400 MHz, DMSO-d6): 9.09 (s, exchanged with D2O, 1H), 8.83 (d, J = 2.0 Hz, 1H), 8.31 (br. s, 1H), 8.12 (d, J = 2.8 Hz, 1H), 8.08 (d, J = 3.6 Hz, 1H), 6.28 (d, J = 6.8 Hz, exchanged with D2O, 1H), 5.31 (dq J = 7.2, 6.8 Hz, 1H), 3.80-3.70 (m, 4H), 2.55-2.40 (m, 4H), 2.34 (s, 3H), 1.56 (d, J = 7.2 Hz, 3H). |
| 305 | A | A | 460.3 | 2.58 | |
| 306 | A | A | 453.2 | 2.5 | |
| 307 | D | | 462.3 | 2.418 | (400 MHz, CDCl3): 8.90 (br. s, exchanged with D2O, 1H), 8.80 (d, J = 2.0 Hz, 1H), 8.31 (d, J = 2.8 Hz, 1H), 8.10 (s, 1H), 8.08 (d, J = 3.6 Hz, 1H), 6.20 (br. s, exchanged with D2O, 1H), 5.40-5.35 (m, 1H), 3.74 (s, 3H), 3.90-3.40 (series of m, 8H), 1.58 (d, J = 7.6 Hz, 3H) |
| 308 | D | | | | (400 MHz, CDCl3): 9.11 (s, exchanged with D2O, 1H), 8.80 (s, 1H), 8.31 (s, 1H), 8.10-8.08 (m, 2H), 6.17 (br. s, exchanged with D2O, 1H), 5.40-5.35 (m, 1H), 3.90-3.40 (series of m, 8H), 2.14 (s,3H), 1.59 (overlapped d, J = 6.4 Hz, 3H) |
| 309 | B | | | | (400 MHz, DMSO-d6): 12.07 (s, exchanged with D2O, 1H), 8.69 (d, J = 2.4 Hz, 1H), 8.25 (d, J = 2.4 Hz, 1H), 8.18 (d, J = 3.6 Hz, 1H), 8.17 (overlapped br. s, 1H), 7.16 (br. s, 1H), 5.20-5.05 (m, 1H), 3.90-3.40 (series of m, 8H), 2.56 (overlapped s with DMSO-d6 signal, 3H), 1.43(br. s, 3H), 1.40-1.20 (m, 2H) |
| 310 | D | | | | (400 MHz, CDCl3): 9.28 (s, exchanged with D2O, 1H), 8.81 (d, J = 2.0 Hz, 1H), 8.29 (d, J = 2.0 Hz, 1H), 8.11 (d, J = 3.3 Hz, 1H), 8.10 (d, J = 2.4 Hz, 1H), 6.22 (br. d, J = 6.4 Hz, 1H), 5.32 (quiniet, 6.4 Hz, addition of D2O changed to q, J = 6.4 Hz, 1H), 3.74 (s, 3H), 3.68-3.49 (series of m, 8H), 1.57 (d, J = 6.4 Hz, 3H) |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 311 | D | | | | (400 MHz, CDCl3): 9.04 (s, exchanged with D2O, 1H), 8.81 (d, J = 2.0 Hz, 1H), 8.29 (br. d, J = 2.0 Hz, 1H), 8.11 (d, J = 2.4 Hz, 1H), 8.09 (d, J = 3.2 Hz, 1H) , 6.23 (br. d, J = 6.8 Hz, 1H), 5.31 (quiniet, J = 6.8 Hz, addition of D2O changed to q, J = 6.8 Hz, 1H), 3.68-3.49 (series of m, 8H), 1.57 (d, J = 6.8 Hz, 3H) |
| 312 | A | A | | | (400 MHz, CDCl3): 9.72 (s, exchanged with D2O, 1H), 8.83 (d, J = 2.4 Hz, 1H), 8.29 (d, J = 2.0 Hz, 1H), 8.13 (d, J = 2.0 Hz, 1H), 8.08 (d, J = 4.4 Hz, 1H), 6.07 (d, J = 7.6 Hz, exchanged with D2O, 1H), 4.95 (qunitet, J = 7.2 Hz, 1H), 4.68 (q, J = 7.6 Hz, 1H), 4.36 (d, J = 8.4 Hz, 1H), 4.18-4.07 (m, 2H), 2.40-2.30 (m, 2H), 1.54 (d, J = 7.2 Hz, 3H). |
| 313 | B | A | | | (400 MHz, DMSO-d6, 80oC): 12.07 (s, exchanged with D2O, 1H), 8.71 (d, J = 2.4 Hz, 1H), 8.26 (d, J = 2.0 Hz, 1H), 8.21 (d, J = 2.0 Hz, 1H), 8.17 (br. s, 1H), 7.14 (br. s, exchanged with D2O, 1H), 5.20-5.10 (m, 1H), 3.70-3.50 (m, 8H), 1.54 (d, J = 7.2 Hz, 3H), 1.95-1.80 (m, 2H) |
| 314 | B | B | | | (400 MHz, CDCl3): 9.80 (s, exchanged with D2O, 1H), 8.83 (d, J = 2.4 Hz, 1H), 8.30 (d, J = 2.0 Hz, 1H), 8.13 (d, J = 2.0 Hz, 1H), 8.08 (d, J = 4.4 Hz, 1H), 6.08 (d, J = 6.4 Hz, exchanged with D2O, 1H), 4.95 (qunitet, J = 7.2 Hz, 1H), 4.68 (q, J = 7.6 Hz, 1H), 4.36 (d, J = 8.0 Hz, 1H), 4.18-4.07 (m, 2H), 2.40-2.30 (m, 2H), 1.55 (d, J = 7.2 Hz, 3H). |
| 315 | B | D | | | (400 MHz, DMSO-d6, 80oC): 12.08 (s, exchanged with D2O, 1H), 8.69 (d, J = 2.4 Hz, 1H), 8.24 (d, J = 2.0 Hz, 1H), 8.18 (d, J = 2.0 Hz, 1H), 8.16 (br. s, 1H), 7.14 (br. d , J = 7.2 Hz, exchanged with D2O, 1H), 5.20-5.10 (m, 1H), 3.70-3.50 (m, 8H), 1.46 (d, J =7.2 Hz, 3H), 1.95-1.80 (m, 2H) |
| 316 | B | A | 453.3 | 2.48 | |
| 317 | B | A | 415.1 | 2.7 | |
| 318 | D | A | 431.1 | 2.9 | |
| 319 | D | A | 429.1 | 2.8 | |
| 320 | B | B | 433.1 | 2.5 | |
| 321 | B | A | 439.1 | 2.7 | |
| 322 | D | A | 453.1 | 2.9 | |
| 323 | D | A | 446.2 | 2.7 | |
| 324 | B | A | 432.2 | 2.6 | |
| 325 | B | A | 429.2 | 2.7 | |
| 326 | B | A | 445.2 | 3 | |
| 327 | A | A | 447.2 | 1.8 | |
| 328 | D | | 467.1 | 2.2 | |
| 329 | D | | 481.2 | 2.3 | |
| 330 | A | A | 501.1 | 2.2 | |
| 331 | A | A | 465.1 | 2.2 | 1H NMR (300.0 MHz, MeOD) d 8.83 (d, J = 2.3 Hz, 1H), 8.24 (s, 1H), 8.22 (d, J = 2.4 Hz, 1H), 8.01 (d, J = 3.9 Hz, 1H), 4.44 (m, 1H), 4.06 (dd, J = 9.2, 13.8 Hz, 1H), 3.77 (dd, J = 6.3, 13.8 Hz, 1H), 3.71 (m, 1H), 2.47 (m, 1H), 1.87-1.66 (m, 6H) and 1.00-0.92 (m, 4H) ppm |
| 332 | A | A | 431.2 | 2 | |
| 333 | B | | 417.4 | 2.7 | |
| 334 | B | | 431.4 | 2.85 | |
| 335 | D | | 457.3 | 3.14 | |
| 336 | D | | 465.4 | 3.03 | |
| 337 | B | A | 439.3 | 2.66 | |
| 338 | D | | 467.3 | 2.93 | |
| 339 | B | | 446.3 | 2.85 | |
| 340 | A | A | 403.3 | 2.6 | |
| 341 | D | | 383.4 | 2.3 | H NMR (300.0 MHz, DMSO) d 12.47 (s, 1H), 8.65 (d, J = 8.1 Hz, 1H), 8.49-8.23 (m, 3H), 7.61 (d, J = 7.8 Hz, 1H), 7.29 (dd, J = 4.7, 8.0 Hz, 1H), 4.39 (d, J = 19.5 Hz, 2H), 2.10 (q, J = 7.6 Hz, 2H), 1.79-1.64 (m, 6H), 1.48 (d, J = 6.4 Hz, 2H) and 0.91 (t, J = 7.6 Hz, 3H) ppm |
| 342 | D | | 397.4 | 2.48 | |
| 343 | D | | 423.4 | 2.71 | |
| 344 | D | | 431.4 | 2.67 | |
| 345 | D | | 405.3 | 2.3 | H NMR (300.0 MHz, DMSO) d 12.47 (s, 1H), 8.64 (d, J = 7.8 Hz, 1H), 8.45-8.34 (m, 3H), 7.29 (dd, J = 4.8, 7.8 Hz, 1H), 7.06 (d, J = 7.5 Hz, 1H), 4.47- |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 346 | D | | 433.3 | 2.56 | 4.25 (m, 1H), 4.05-3.89 (m, 1H), 2.80 (s, 3H), 1.95-1.62 (m, 6H) and 1.49-1.24 (m, 2H) ppm<br>H NMR (300.0 MHz, DMSO) d 12.41 (s, 1H), 8.65 (d, J = 7.8 Hz, 1H), 8.38-8.33 (m, 3H), 7.28 (dd, J = 4.7, 7.9 Hz, 1H), 7.06 (d, J = 8.1 Hz, 1H), 4.36 (s, 1H), 3.88 (s, 1H), 2.83 (t, J = 7.7 Hz, 2H), 1.85-1.70 (m, 6H), 1.59 (q, J = 7.8 Hz, 2H), 1.47-1.24 (m, 2H) and 0.82 (t, J = 7.4 Hz, 3H) |
| 347 | D | | 412.4 | 2.41 | H NMR (300.0 MHz, DMSO) d 12.47 (s, 1H), 8.64 (d, J = 7.8 Hz, 1H), 8.45-8.34 (m, 3H), 7.29 (dd, J = 4.8, 7.8 Hz, 1H), 7.06 (d, J = 7.5 Hz, 1H), 4.47-4.25 (m, 1H), 4.05-3.89 (m, 1H), 2.80 (s, 3H), 1.95-1.62 (m, 6H) and 1.49-1.24 (m, 2H) ppm |
| 348 | D | | 369.4 | 2.19 | H NMR (300.0 MHz, DMSO) d 12.53 (s, 1H), 8.66 (d, J = 7.6 Hz, 1H), 8.43 (s, 1H), 8.39-8.36 (m, 2H), 7.91 (d, J = 7.9 Hz, 1H), 7.32 (dd, J = 4.7, 7.9 Hz, 1H), 4.08-3.94 (m, 1H), 3.86 (d, J = 8.4 Hz, 1H), 2.13 (d, J = 24.3 Hz, 1H), 1.95 (d, J = 10.2 Hz, 1H), 1.81-1.73 (m, 2H), 1.73 (s, 3H) and 1.43-1.14 (m, 4H) ppm |
| 349 | D | | 417.3 | 2.74 | |
| 350 | B | | 417.3 | 2.74 | |
| 351 | D | | 457.3 | 3.11 | |
| 352 | D | | 465.3 | 3.03 | |
| 353 | D | | 439.4 | 2.74 | |
| 354 | D | | 467.3 | 3.04 | |
| 355 | D | | 446.3 | 2.81 | |
| 356 | D | | 383.4 | 2.33 | |
| 357 | D | | | | (400 MHz, CDCl3, 75oC): 12.07 (br. s exchanged with d2O, 1H), 8.69 (s, J= 2.4 Hz, 1H), 8.25 (s, J = 4.0 Hz, 1H), 8.19 (s, J = 4.0 Hz, 1H), 8.15 (br. s, 1H), 7.15 (br. s, exchanged with D2O, 1H), 5.20-5.10 (q, 1H), 3.62-3.55 (m, 8H), 3.03 (s, 3H), 1.76 (d, J = 2.4 Hz, 2H), 1.43-1.41 (d, J = 8.0 Hz, 3H). |
| 358 | D | | 397.4 | 2.45 | |
| 359 | D | | 423.4 | 2.67 | |
| 360 | D | | 431.4 | 2.63 | |
| 361 | D | | 405.3 | 2.37 | H NMR (300.0 MHz, DMSO) d 12.54 (s, 1H), 8.66 (d, J = 8.0 Hz, 1H), 8.43-8.36 (m, 3H), 7.32 (dd, J = 4.7, 7.9 Hz, 1H), 7.21 (d, J = 8.3 Hz, 1H), 4.16 (d, J = 9.3 Hz, 1H), 3.35 (d, J = 9.8 Hz, 1H), 2.91 (d, J = 8.9 Hz, 3H), 2.12-2.02 (m, 2H), 1.79-1.73 (m, 2H) and 1.64-1.15 (m, 4H) ppm |
| 362 | D | | 433.3 | 2.63 | H NMR (300.0 MHz, DMSO) d 12.43 (s, 1H), 8.68 (d, J = 7.9 Hz, 1H), 8.38-8.33 (m, 3H), 7.29 (dd, J = 4.7, 7.8 Hz, 1H), 7.17 (d, J = 8.6 Hz, 1H), 4.14 (d, J = 6.9 Hz, 1H), 3.33-3.26 (m, 1H), 3.07-2.89 (m, 2H), 2.07 (d, J = 12.6 Hz, 2H), 1.76 (d, J = 7.9 Hz, 2H), 1.61-1.33 (m, 6H) and 0.90 (t, J = 7.4 Hz, 3H) ppm |
| 363 | D | | 431.3 | 2.88 | |
| 364 | D | | 457.3 | 3.11 | |
| 365 | D | | 465.3 | 3.03 | |
| 366 | A | A | 439.2 | 2.74 | |
| 367 | B | | 467.3 | 2.99 | |
| 368 | D | | 446.3 | 2.81 | |
| 369 | D | | 431.3 | 2.85 | |
| 370 | D | | 412.4 | 2.41 | |
| 371 | D | | 412.2 | 1.78 | |
| 372 | B | B | 424.2 | 1.87 | |
| 373 | B | D | 398.2 | 1.69 | |
| 374 | D | | 384.2 | 1.61 | |
| 375 | B | B | 412.2 | 1.8 | |
| 376 | B | | 327.1 | 41.46 | |
| 377 | D | | 313.3 | 31.38 | |
| 378 | D | | | | (300 MHz, DMSO-d6): 12.35 (br. s, exchanged with D2O, 1H), 8.72 (d, J = 2.4 Hz, 1H), 8.29 (d, J = 2.1 Hz, 1H), 8.21 (s, 1H), 8.17 (d, J = 3.9 Hz, 1H), 7.80 (br. s, exchanged with D2O, 1H), 7.10 (s, exchanged with D2O, 1H), 2.27-2.11 (m, 2H), 1.96 (m, 2H), 1.55 (m, 2H), 1.40-1.18 (m, 3H). |
| 379 | B | A | 361.3 | 2.32 | 1H NMR (300.0 MHz, MeOD) d 8.72 (d, J = 2.3 Hz, 1H), 8.21 (d, J = 2.4 Hz, 1H), 8.11-8.07 (m, |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 2H), 4.94 (t, J = 9.3 Hz, 1H), 3.64-3.51 (m, 2H), 2.97 (s, 3H), 2.68-2.54 (m, 1H) and 2.37-2.23 (m, 1H) ppm |
| 380 | B | | 347.3 | 2.27 | 1H NMR (300.0 MHz, MeOD) d 8.79 (d, J = 2.4 Hz, 1H), 8.20 (d, J = 2.4 Hz, 1H), 8.13 (s, 1H), 8.07 (d, J = 3.9 Hz, 1H), 4.91 (dd, J = 8.7, 10.6 Hz, 1H), 3.61-3.46 (m, 2H), 2.68-2.58 (m, 2H) and 2.48-2.31 (m, 1H) ppm |
| 381 | A | A | 439.3 | 2.72 | |
| 382 | A | A | 453.3 | 2.86 | |
| 383 | A | A | 507.3 | 3.01 | |
| 384 | A | | 439.3 | 2.72 | |
| 385 | A | | 453.3 | 2.82 | |
| 386 | A | | 465.3 | 2.9 | |
| 387 | B | | 507.2 | 2.49 | |
| 388 | D | | 453.4 | 1.84 | |
| 389 | A | A | 425.3 | 1.8 | |
| 390 | A | A | 467.3 | 2.1 | |
| 391 | A | A | 451.3 | 1.9 | |
| 392 | A | A | 493.5 | 2.3 | |
| 393 | A | A | 439.3 | 1.8 | |
| 394 | A | A | 453.3 | 1.9 | |
| 395 | A | A | 429.3 | 1.9 | |
| 396 | A | A | 433.3 | 1.7 | |
| 397 | A | A | 375.36 | 2.21 | 1H NMR (300.0 MHz, DMSO) d 8.65 (d, J = 2.5 Hz, 1H), 8.27 (d, J = 2.4 Hz, 1H), 8.20-8.19 (m, 2H), 7.63 (d, J = 7.8 Hz, 1H), 4.78-4.74 (m, 1H), 3.41 (t, J = 5.4 Hz, 2H), 3.17 (MeOH), 2.89 (s, 3H), 2.50 (DMSO), 2.18-2.15 (m, 1H) and 1.99 (d, J = 7.4 Hz, 2H) ppm |
| 398 | A | A | 411 | 1.7 | |
| 399 | A | | 425 | 1.8 | |
| 400 | B | | 439 | 1.9 | |
| 401 | B | | 437 | 1.9 | |
| 402 | B | | 453 | 2.1 | |
| 403 | B | | 465 | 2.1 | |
| 404 | D | | 439 | 2 | |
| 405 | B | | 411 | 1.7 | |
| 406 | D | | 453 | 2.1 | |
| 407 | D | | 425 | 1.8 | |
| 408 | D | | 439 | 1.9 | |
| 409 | B | | 437 | 1.9 | |
| 410 | B | | 439 | 2 | |
| 411 | A | A | 361.4 | 1.94 | |
| 412 | A | A | 376.4 | 3.53 | |
| 413 | D | | 361.3 | 2.41 | |
| 414 | A | A | 361.3 | 2.46 | |
| 415 | D | | 387 | 1.5 | |
| 416 | A | | 361.3 | 1.56 | |
| 417 | A | A | 375.3 | 1.68 | 1H NMR (300.0 MHz, DMSO) d 12.33 (s, 1H), 8.74 (d, J = 2.3 Hz, 1H), 8.28 (d, J = 2.4 Hz, 1H), 8.21 (t, J = 3.7 Hz, 2H), 8.02-7.98 (m, 1H), 7.21 (d, J = 5.8 Hz, 1H), 4.86 (dd, J = 6.3, 10.5 Hz, 1H), 3.51-3.41 (m, 1H), 3.25-3.16 (m, 1H), 2.13-1.85 (m, 4H), 1.66-1.52 (m, 1H) and 1.40-1.20 (m, 1H) ppm |
| 418 | A | | 421.37 | 1.79 | 1H NMR (300.0 MHz, DMSO) d 13.11 (d, J = 9.6 Hz, 1H), 13.05 (s, H), 9.30 (s, 1H), 8.72 (d, 1H), 8.62 (d, 1H), 8.49 (s, 1H), 8.18 (d, 1H), 6.83 (s, H), 6.72 (d, 1H), 4.30 (m, 1H), 3.88 (m, 1H), 3.76 (m, 1H) 3.46 (m, 1H), 3.10-3.01 (m, 4H), 2.12 (m, 1H), 1.92 (m, 1H), 1.68-1.61 (m, 2H), 1.20 (t, 3H), and −0.00 (TMS) ppm |
| 419 | A | A | 449.39 | 2.08 | 1H NMR (300.0 MHz, DMSO) d 13.08 (s, 1H), 8.70 (d, 1H), 8.60 (d, 2H), 8.48 (s, 1H), 8.18-8.12 (m, 1H), 6.64 (d, 1H), 5.91 (s, H), 4.30 (m, 1H), 3.88 (m, 1H), 3.76 (m, 1H) 3.46 (m, 1H), 3.10-3.01 (m, 4H), 2.08 (m, 1H), 1.91 (m, 1H), 1.61 (dd, 4H), 1.47 (m, 2H), 0.86 (t, 3H), and −0.00 (TMS) |
| 420 | D | | 461 | 2.83 | |
| 421 | B | | 447 | 1.8 | |
| 422 | D | | 433 | 1.8 | |
| 423 | D | | 425 | 2 | |
| 424 | D | | 447 | 1.8 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 425 | A | A | 419.21 | 2.13 | H NMR (300.0 MHz, DMSO) d 13.02 (s, 1H), 9.10 (s, 2H), 8.67 (s, 1H), 8.44-8.40 (m, 2H), 7.26 (d, J = 6.5 Hz, 1H), 4.19 (s, 1H), 3.66 (d, J = 9.8 Hz, 1H), 3.48 (s, 3H), 2.13 (s, 1H), 2.02 (d, J = 9.2 Hz, 1H), 1.78 (d, J = 9.6 Hz, 2H) and 1.47-1.34 (m, 4H) ppm |
| 426 | A | A | 419.5 | 2.53 | H NMR (300.0 MHz, DMSO) d 12.56 (s, 1H), 8.70 (d, J = 2.2 Hz, 1H), 8.35 (dd, J = 2.4, 6.8 Hz, 2H), 8.28 (d, J = 4.2 Hz, 1H), 5.99 (d, J = 7.0 Hz, 1H), 5.80-5.63 (m, 1H), 3.91-3.87 (m, 1H), 3.66-3.45 (m, 1H), 2.54 (s, 3H), 2.30 (d, J = 13.0 Hz, 1H), 2.04 (d, J = 46.9 Hz, 1H), 1.78 (d, J = 8.5 Hz, 2H) and 1.56-1.23 (m, 4H) ppm |
| 427 | D | | 432.4 | 2.69 | H NMR (300.0 MHz, DMSO) d 12.59 (s, 1H), 8.72 (d, J = 2.3 Hz, 1H), 8.41 (d, J = 2.7 Hz, 1H), 8.35 (d, J = 2.3 Hz, 1H), 8.29 (d, J = 4.4 Hz, 1H), 8.23 (s, 1H), 6.19 (d, J = 7.8 Hz, 1H), 4.04-3.97 (m, 1H), 3.78-3.69 (m, 1H), 2.68 (s, 6H), 2.31 (d, J = 11.6 Hz, 1H), 1.95 (d, J = 9.8 Hz, 1H), 1.79 (d, J = 10.4 Hz, 2H) and 1.60-1.32 (m, 4H) ppm |
| 428 | A | A | 439.4 | 2.71 | H NMR (300.0 MHz, DMSO) d 12.54 (s, 1H), 8.72 (d, J = 2.3 Hz, 1H), 8.38-8.29 (m, 3H), 7.82 (s, 1H), 7.21 (d, J = 8.3 Hz, 1H), 4.52 (brs, 1H), 4.12-4.05 (m, 1H), 2.92 (s, 3H), 2.09 (d, J = 12.8 Hz, 2H), 1.78 (brs, 2H) and 1.49-1.39 (m, 4H) ppm |
| 429 | B | | 403.4 | 2.57 | |
| 430 | A | | 418.5 | 2.57 | H NMR (300.0 MHz, DMSO) d 12.61 (s, 1H), 8.68 (d, J = 2.2 Hz, 1H), 8.39-8.31 (m, 4H), 6.12 (d, J = 6.7 Hz, 1H), 5.91-5.83 (m, 1H), 4.29-4.13 (m, 1H), 4.02-3.91 (m, 1H), 2.55 (s, 3H), 1.93 (d, J = 12.8 Hz, 1H) and 1.74-1.53 (m, 7H) ppm |
| 431 | A | | 432.4 | 2.77 | H NMR (300.0 MHz, DMSO) d 12.54 (s, 1H), 8.68 (d, J = 2.3 Hz, 1H), 8.33-8.29 (m, 3H), 7.96 (s, 1H), 5.72 (d, J = 6.9 Hz, 1H), 4.36 (s, 1H), 4.10 (s, 1H), 2.76 (s, 6H), 1.96-1.87 (m, 2H), 1.74-1.63 (m, 4H) and 1.55-1.45 (m, 2H) ppm |
| 432 | D | | 419.4 | 2.85 | H NMR (300.0 MHz, DMSO) d 12.54 (s, 1H), 8.67 (d, J = 2.2 Hz, 1H), 8.35-8.29 (m, 3H), 7.62 (s, 1H), 7.05 (d, J = 7.2 Hz, 1H), 4.50-4.40 (m, 1H), 4.20-4.10 (m, 1H), 3.46 (s, 3H), 1.87 (d, J = 10.9 Hz, 2H), 1.71-1.65 (m, 4H) and 1.43 (d, J = 7.4 Hz, 2H) ppm |
| 433 | A | A | 403.4 | 2.41 | H NMR (300.0 MHz, DMSO) d 13.03 (s, 1H), 9.10 (s, 1H), 9.05 (s, 1H), 8.67 (d, J = 2.1 Hz, 1H), 8.48 (d, J = 5.4 Hz, 1H), 8.43 (d, J = 2.3 Hz, 1H), 7.97 (d, J = 7.7 Hz, 1H), 4.15-4.07 (m, 1H), 3.93-3.87 (m, 1H), 2.20-2.15 (m, 1H), 1.99-1.92 (m, 1H), 1.85-1.79 (m, 2H), 1.74 (s, 3H) and 1.52-1.36 (m, 4H) ppm |
| 434 | A | A | 389.4 | 1.6 | |
| 435 | A | A | 403.4 | 1.8 | |
| 436 | A | | 417.4 | 1.9 | |
| 437 | D | | 431.4 | 2 | |
| 438 | A | A | 418.4 | 1.7 | |
| 439 | A | A | 432.4 | 1.8 | |
| 440 | A | A | 405.4 | 1.8 | |
| 441 | B | | 419.4 | 1.9 | |
| 442 | B | | 433.4 | 2.1 | |
| 443 | A | A | 461.3 | 1.8 | |
| 444 | A | A | 445.4 | 1.7 | |
| 445 | A | | 429.4 | 1.9 | |
| 446 | D | | 448.4 | 1.7 | |
| 447 | D | | 449.3 | 2 | |
| 448 | D | | 469.3 | 1.9 | |
| 449 | B | | 419.4 | 1.7 | |
| 450 | B | | 431.4 | 1.7 | |
| 451 | B | | 415.4 | 1.8 | |
| 452 | A | A | 403.14 | 1.261975 | |
| 453 | A | A | 419 | 1.178428 | |
| 454 | A | A | 439.11 | 1.548667 | |
| 455 | A | A | 418.16 | 1.690093 | |
| 456 | A | A | 432.17 | 1.518183 | |
| 457 | A | A | 403.22 | 1.57 | |
| 458 | A | A | 418.16 | 0.76 | |
| 459 | A | A | 432.17 | 1.46 | |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 460 | A | A | 389.14 | 2.01 | |
| 461 | A | A | 389.14 | 2.05 | |
| 462 | B | A | 403.15 | 2.24 | 1H NMR (300.0 MHz, DMSO) d 12.35 (s, 1H), 8.68 (d, J = 1.7 Hz, 1H), 8.27 (d, J =2.0 Hz, 1H), 8.21 (m, 2H), 7.28 (d, J = 6.0 Hz, 1H), 4.98 (dd, J = 6.9, 10.7 Hz, 1H), 3.88-3.79 (m, 1H), 3.84 (dd, J = 11.4, 15.5 Hz, 1H), 3.49-3.17 (m, 5H), 2.08 (d, J = 13.1 Hz, 1H), 1.95-1.88 (m, 3H), 1.65-1.58 (m, 1H), 1.42 (m, 1H) and 1.04 (t, J = 7.0 Hz, 3H) ppm |
| 463 | D | A | 475.2 | 2.26 | DMSO d-6: 13.21 (s, 1H), 9.29 (d, 1H), 8.76 (d, 1H), 8.60 (s, 1H), 8.47 (s, 1H), 8.17 (d, 1H), 6.67 (d, 1H), 4.29 (m, 1H), 3.75 (m, 1H), 3.46 (m, 1H), 3.07-2.98 (m, 3H), 2.27-1.45 (m, 12H), 1.28-1.24 (m, 2H), −0.00 (s, H) ppm |
| 464 | A | A | 435.14 | 2.03 | DMSO d-6: 13.21 (s, 1H), 9.29 (d, 1H), 8.76 (d, 1H), 8.60 (s, 1H), 8.47 (s, 1H), 8.17 (d, 1H), 6.67 (d, 1H), 4.29 (m, 1H), 3.75 (m, 1H), 3.46 (m, 1H), 3.07-2.98 (m, 3H), 2.2-2.1 (m, 1H), 1.85-2.0 (m, 1H), 1.72-1.57 (m, 4H), 0.95 (t, 3H) |
| 465 | B | | 435.14 | 2 | DMSO d-6: 13.21 (s, 1H), 9.29 (d, 1H), 8.76 (d, 1H), 8.60 (s, 1H), 8.47 (s, 1H), 8.17 (d, 1H), 6.67 (d, 1H), 4.25 (m, 1H), 3.79 (m, 1H), 3.53 (m, 1H), 3.37 (m, 1H), 3.17 (m, 1H), 2.14 (m, 1H), 1.90 (m, 1H), 1.66-1.60 (m, 1H), 1.21 (d, 6H). |
| 466 | B | | 407.12 | 1.85 | DMSO d-6: 13.21 (s, 1H), 9.29 (d, 1H), 8.76 (d, 1H), 8.60 (s, 1H), 8.47 (s, 1H), 8.17 (d, 1H), 6.67 (d, 1H), 4.4 (m, 1H), 3.75 (d, 1H), 3.4 (m, 1H), 3.1 (m, 1H), 2.9 (s, H), 2.10-1.9 (m, 2H), 1.8-1.65 (m, 2H). |
| 467 | D | | 431.4 | 1.6 | |
| 468 | B | | 391.3 | 1.6 | |
| 469 | D | | 465.3 | 2.3 | |
| 470 | D | | 479.3 | 2.3 | |
| 471 | A | | 375.3 | 1.6 | |
| 472 | B | | 405.3 | 1.6 | |
| 473 | B | | 431.3 | 1.6 | |
| 474 | D | | 446.3 | 1.4 | |
| 475 | D | | 461.3 | 2.6 | |
| 476 | B | | 391.3 | 2.6 | |
| 477 | D | | 419.4 | 2 | |
| 478 | B | | 431.3 | 1.6 | |
| 479 | D | | 479.3 | 2.3 | |
| 480 | A | | 375.3 | 1.6 | |
| 481 | B | | 405.3 | 2.2 | |
| 482 | A | | 431.3 | 1.6 | |
| 483 | D | | 446.3 | 1.4 | |
| 484 | B | | 461.3 | 2.6 | |
| 485 | B | | 371.46 | 1.89 | 1H NMR (300.0 MHz, DMSO) d 13.09 (s, H), 9.3 (s, 1H), 8.74 (d, J = 2.8 Hz, 1H), 8.57 (d, 1H), 8.47 (s, 1H), 8.18-8.14 (m, 1H), 6.66-6.58 (m, 1H), 4.5 (d, 1H), 4.43-4.05 (m, 1H), 4.29 (s, H), 3.88 (d, 2H), 3.34-3.08 (m, 2H), 2.13 (s, 1H), 2.07 (s, 1H), 1.91 1.56 (m, 3H), 0.00 (TMS) |
| 486 | B | | 401.48 | 1.87 | |
| 487 | B | | 443.9 | 1.97 | |
| 488 | D | | 415.5 | 1.9 | |
| 489 | A | | 413.51 | 2.12 | |
| 490 | A | A | 385.43 | 1.7 | 1H NMR (300.0 MHz, DMSO) d 13.12 (s, 1H), 9.52 (s, 1H), 8.73 (d, 1H), 8.65 (d, 1H), 8.45 (d, 1H), 8.14 (d, 1H), 6.63 (d, 1H), 4.29 (d, 1H), 4.04 (d, 1H), 3.80-3.32 (m, 3H), 3.10-3.02 (m, 1H), 2.07 (s, 3H), 1.99 (m, 2H), 1.8-1.6 (m, 2H), 1.55-1.24 (m, 2H) and −0.00 (TMS) ppm |
| 491 | A | | 415.43 | 1.7 | |
| 492 | B | | 457.49 | 1.79 | |
| 493 | A | A | 429.46 | 1.74 | |
| 494 | B | | 427.52 | 1.92 | |
| 495 | B | | 401.48 | 1.83 | 1H NMR (300.0 MHz, DMSO) d 13.12 (s, 1H), 9.44 (d, 1H), 8.73 (d, 1H), 8.65 (d, 1H), 8.45 (d, 1H), 8.14 (d, J = 7.2 Hz, H), 6.80 (d, 1H), 6.63 (d, 1H), 3.9 (dd, 1H) 3.76 (dd, 1H), 3.60-3.50 (m, 3H), 3.47 −(s, 3H), 3.05-2.8 (m, 2H), 1.93 (m, 2H), 1.83 (d, 2H), 1.42-1.35 (m, 2H), and −0.00 (TMS) ppm |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 496 | B | | 439.3 | 1.8 | |
| 497 | A | A | 403.3 | 1.7 | |
| 498 | A | | 419.3 | 1.9 | |
| 499 | A | A | 432.5 | 1.8 | |
| 500 | A | A | 357.62 | 1.62 | 1H NMR (300.0 MHz, DMSO) d 13.02 (s, 1H), 8.73 (d, 1H), 8.66 (d, 1H), 8.42 (d, 1H), 8.16 (d, 1H), 8.06 (t, 1H), 6.83 (d, 1H), 5.05-4.99 (m, 1H), 3.52-3.42 (m, 1H), 3.36 (d, H), 3.28-3.24 (m, 1H), 2.50 (qn, J = 1.8 Hz, H), 2.00-1.80 (m, 4H), 1.77-1.64 (m, 1H), 1.34 (m, 1H), 1.28 (s, H), 1.06 (t, J = 7.0 Hz, H) and 0.00 (TMS) ppm |
| 501 | B | | 341.38 | 1.56 | 1H NMR (300.0 MHz, DMSO) d 12.96 (s, 1H), 8.66 (d, 1H), 8.46-8.41 (m, 2H), 8.16 (d, 1H), 8.05 (d, 1H), 6.80 (d, 1H), 5.00 (dd, 1H), 3.54-3.40 (m, 1H), 3.26-3.21 (m, 1H), 2.50 (qn, J = 1.8 Hz, H), 2.03-1,86 (m, 4H), 1.64 (t, 1H), 1.36 (t, 1H) and −0.00 (TMS) ppm |
| 502 | A | A | 409.3 | 2.6 | |
| 503 | A | | 361.2 | 2.17 | |
| 504 | B | A | 403.3 | 2.85 | |
| 505 | B | | 497.72 | 3.05 | |
| 506 | A | A | 418.5 | 2.09 | 1H NMR (300.0 MHz, DMSO) d 13.06 (s, 1H), 9.24 (s, 1H), 9.05 (d, J = 2.4 Hz, 1H), 8.66 (d, J = 2.3 Hz, 1H), 8.52-8.45 (m, 2H), 4.35 (d, J = 8.0 Hz, 1H), 3.81 (qn, J = 6.1 Hz, 1H), 3.59-3.39 (m, 2H), 3.18 (t, J = 11.6 Hz, 1H), 2.61 (d, J = 16 Hz, 3H) and 2.12-1.67 (m, 6H) ppm |
| 507 | A | A | 390.42 | 1.69 | |
| 508 | D | | 397.37 | 1.59 | |
| 509 | A | A | 404.45 | 1.67 | |
| 510 | D | | 343.39 | 0.65 | |
| 511 | D | | 343.42 | 1.29 | |
| 512 | D | B | 361.3 | 2.36 | |
| 513 | B | A | 377.46 | 1.89 | |
| 514 | A | A | 418.78 | 1.26 | 1H NMR (300.0 MHz, MeOD) d 8.83 (d, J = 2.3 Hz, 1H), 8.22 (d, J = 2.3 Hz, 1H), 8.16 (s, 1H), 7.99 (d, J = 4.1 Hz, 1H), 4.29-4.17 (m, 1H), 3.67-3.60 (m, 1H), 3.60 (s, 3H), 2.37 (m, 1H), 2.19 (m, 1H), 2.07-1.90 (m, 2H), 1.72-1.60 (m, 1H), 1.40-1.25 (m, 2H) and −0.00 (TMS) ppm |
| 515 | D | | 463.5 | 2.47 | 1H NMR (300.0 MHz, CDCl3) d 10.38 (s, 1H), 8.81 (d, J = 2.0 Hz, 1H), 8.49 (d, J = 2.3 Hz, 1H), 8.38 (s, 1H), 8.08 (d, J = 3.4 Hz, 1H), 7.26 (s, CDCl3), 6.11 (d, J = 5.0 Hz, 1H), 4.44 (d, J = 9.4 Hz, 1H), 4.02-3.62 (m, 6H), 3.55 (dd, J = 2.4, 12.1 Hz, 1H), 3.35-3.27 (m, 1H) and 1.40-1.22 (m, 9H) ppm |
| 516 | B | | 419.4 | 1.91 | |
| 517 | B | | 448.54 | 2.26 | 1H NMR (300.0 MHz, DMSO) d 12.54 (s, 1H), 8.76 (d, J = 2.0 Hz, 1H), 8.46 (s, 1H), 8.32 (d, J = 2.1 Hz, 1H), 8.26 (d, J = 3.9 Hz, 1H), 8.08 (d, J = 7.5 Hz, 1H), 6.30 (s, 1H), 4.28 (s, 1H), 3.93-3.74 (m, 3H), 3.51-3.47 (m, 2H), 3.39-3.20 (m, 2H), 2.95 (dd, J = 6.2, 13.1 Hz, 3H), 1.35-1.25 (m, 2H) and 0.76 (t, J = 7.3 Hz, 3H) ppm |
| 518 | D | | 445.6 | 3.3 | 1H NMR (300.0 MHz, MeOD) d 8.67 (d, J = 2.3 Hz, 1H), 8.53 (s, 1H), 8.41 (d, J = 2.3 Hz, 1H), 8.35 (d, J = 5.5 Hz, 1H), 4.75-4.73 (m, 1H), 3.74-3.58 (m, 1H), 3.42 (m, 2H), 3.29-3.22 (m, 2H), 2.57 (m, 1H), 2.09-2.03 (m, 1H), 1.96-1.76 (m, 4H), 1.06 (t, J = 7.1 Hz, 3H) and 0.94 (t, J = 7.1 Hz, 3H) ppm |
| 519 | B | | 417.49 | 2.95 | |
| 520 | D | | 445.58 | 2.26 | |
| 521 | B | | 417.53 | 2.34 | 1H NMR (300.0 MHz, MeOD) d 8.93 (d, J = 2.4 Hz, 1H), 8.22 (d, J = 2.3 Hz, 1H), 8.18 (s, 1H), 7.99 (d, J = 4.0 Hz, 1H), 4.53 (ddd, J = 7.1, 11.1 Hz, 1H), 3.15-3.02 (m, 2H), 2.43-2.34 (m, 1H), 2.30-2.26 (m, 1H), 1.97-1.82 (m, 3H), 1.77-1.65 (m, 2H), 1.47-1.35 (m, 2H) and 0.97 (t, J = 7.3 Hz, 3H) ppm |
| 522 | D | | 375.46 | 1.68 | |
| 523 | D | | 389.54 | 1.72 | 1H NMR (300.0 MHz, MeOD) d 8.65 (d, J = 2.3 Hz, 1H), 8.54 (s, 1H), 8.43 (d, J = 5.1 Hz, 1H), 8.40 (d, J = 2.3 Hz, 1H), 4.82-4.72 (m, 1H), 3.66-3.53 (m, 1H), 2.96 (s, 3H), 2.77 (s, 3H), 2.33 (d, J = 12.3 |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | Hz, 2H), 2.10-1.97 (m, 2H) and 1.75-1.48 (m, 4H) ppm |
| 524 | A | A | 362.48 | 1.95 | |
| 525 | A | A | 421.52 | 1.48 | 1H NMR (300.0 MHz, DMSO) d 12.31 (s, 1H), 8.72 (d, J = 2.4 Hz, 1H), 8.28 (d, J = 2.4 Hz, 1H), 8.20 (d, J = 2.0 Hz, 1H), 8.17 (d, J = 4.0 Hz, 1H), 7.33 (d, J = 7.6 Hz, 1H), 4.54 (m, 1H), 4.44 (s, 1H), 4.36 (m, 1H), 3.64 (s, 1H), 3.40 (m, 1H), 3.03 (t, J = 11.0 Hz, 1H), 2.77 (m, 1H), 2.47-2.25 (m, 2H), 2.22-2.12 (m, 2H), 1.99-1.90 (m, 1H), 1.70-1.60 (m, 2H) and 1.45 (m, 1H) ppm |
| 526 | B | A | 421 | 2.36 | |
| 527 | D | D | 435.1 | 2.49 | |
| 528 | B | D | 447.1 | 2.64 | |
| 529 | B | D | 433.1 | 2.45 | |
| 530 | D | B | 447.1 | 1.93 | |
| 531 | B | A | 445.1 | 2.56 | |
| 532 | B | A | 441 | 2.4 | |
| 533 | B | A | 467 | 2.4 | |
| 534 | B | A | 406 | 1.96 | |
| 535 | B | D | 434.1 | 2.17 | |
| 536 | B | D | 448.1 | 2.34 | |
| 537 | A | A | 435.54 | 1.56 | 1H NMR (300.0 MHz, DMSO) d 12.35 (s, 1H), 8.73 (d, J = 2.4 Hz, 1H), 8.29 (d, J = 2.4 Hz, 1H), 8.19-8.09 (m, 2H), 7.36 (d, J = 7.5 Hz, 1H), 4.53 (dd, J = 4.5, 8.0 Hz, 1H), 4.27 (s, 1H), 3.77-3.72 (m, 1H), 3.36-3.20 (m, 3H), 3.22 (s, 3H), 3.03-2.97 (m, 1H), 2.76 (d, J = 10.6 Hz, 1H), 2.44-2.14 (m, 2H), 2.08 (m, 2H), 1.99-1.94 (m, 1H), 1.71-1.63 (m, 2H), 1.44 (m, 1H) and 1.23-1.15 (m, 1H) ppm |
| 538 | A | A | 419.55 | 1.61 | 1H NMR (300.0 MHz, DMSO) d 12.53 (s, 1H), 10.32 (s, 1H), 8.69 (dd, J = 2.5, 5.2 Hz, 1H), 8.56 (d, J = 2.4 Hz, 1H), 8.31 (m, 2H), 7.97 (s, 1H), 4.76 (m, 1H), 3.92 (m, 2H), 3.84-3.55 (m, 2H), 3.40-2.80 (m, 3H), 2.14-1.90 (m, 3H), 1.80-1.74 (m, 2H), 1.65 (m, 1H), 1.43-1.23 (m, 2H) and 0.96-0.85 (m, 3H) ppm |
| 539 | B | A | 403.44 | 2.13 | |
| 540 | A | A | 361.5 | 1.43 | |
| 541 | A | A | 390.46 | 2.43 | |
| 542 | B | B | 361.37 | 1.42 | |
| 543 | A | A | 417.44 | 2.52 | |
| 544 | D | A | 389.42 | 1.94 | |
| 545 | | A | 376.46 | 375.13 | 1H NMR (300.0 MHz, DMSO) d 12.32 (s, 1H), 8.86 (d, J = 2.4 Hz, 1H), 8.28 (d, J = 2.4 Hz, 1H), 8.20 (d, 1H), 8.15 (d, 1H), 6.92 (d, J = 8.2 Hz, 1H), 4.56 (s, 1H), 4.31 (dd, J = 5.9, 8.6 Hz, 1H), 1.89-1.35 (m, 8H), 1.17 (s, 3H) and 0.00 (TMS) ppm |
| 546 | | A | 419.49 | 418.17 | 1H NMR (300.0 MHz, CDCl3) d 9.60 (s, H), 8.87 (d, J = 2.3 Hz, H), 8.33 (d, J = 2.3 Hz, H), 8.17 (d, J = 2.7 Hz, H), 8.09 (d, J = 3.3 Hz, H), 8.04 (s, H), 7.28 (s, H), 5.34 (d, J = 11.5 Hz, H), 4.45-4.42 (m, H), 3.09 (d, J = 11.3 Hz, H), 2.98 (s, H), 2.90 (d, J = 0.5 Hz, H), 2.72 (d, J = 12.9 Hz, H), 2.62 (d, J = 6.3 Hz, H), 2.40 (s, H), 1.94 (d, J = 11.6 Hz, H), 1.86-1.72 (m, H), 1.62 (s, H), 1.27 (s, H) and 1.22 (s, H) ppm |
| 547 | | A | 403.22 | 3.99 | 1H NMR (300 MHz, MeOD) d 8.81 (s, 1H), 8.20 (s, 1H), 8.15 (s, 1H), 7.99 (d, J = 4.1 Hz, 1H), 4.23 (t, J = 11.4 Hz, 1H), 3.90 (t, J = 11.4 Hz, 1H), 2.35 (d, J = 11.6, 1H), 2.20 (d, J = 12.5, 1H), 2.00 (d, J = 15.9, 2H), 1.92 (s, 3H), 1.67 (dd, J = 26.3, 13.2, 1H), 1.53-1.06 (m, 3H) ppm LCMS |
| 548 | | A | 419.46 | 2.82 | |
| 549 | | A | 432.5 | 2.6 | |
| 550 | | A | 449.48 | 448.18 | 1H NMR (300.0 MHz, DMSO) d 12.33 (s, 1H), 8.72 (d, J = 2.5 Hz, 1H), 8.28 (d, J = 2.4 Hz, 1H), 8.22-8.20 (m, 2H), 6.72-6.62 (m, 1H), 4.61 (dd, J = 4.2, 10.0 Hz, 1H), 4.54 (m, 1H), 3.75-3.71 (m, 1H), 3.34-3.22 (m, 1H), 3.22 (d, 3H), 2.88-2.42 (m, 4H), 2.41-2.25 (m, 4H), 1.93 (m, 1H), 1.56 (m, 2H), 0.90 (d, J = 6.7 Hz, 3H) and −0.00 (TMS) ppm |
| 551 | | A | 463.51 | 462.19 | 1H NMR (300.0 MHz, DMSO) d 12.32 (s, 1H), 8.72 (d, J = 2.4 Hz, 1H), 8.28 (d, J = 2.4 Hz, 1H), |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 8.19-8.16 (m, 2H), 7.32 (d, J = 8.0 Hz, 1H), 4.42-4.37 (m, 2H), 3.70 (s, 1H), 3.52-3.42 (m, 1H), 3.35-3.25 (m, 1H), 2.99 (m, 1H), 2.73 (m, 1H), 2.43-2.11 (m, 4H), 1.94 (m, 1H), 1.75-1.60 (m, 2H), 1.52-1.40 (M, 1H), 1.10-0.99 (m, 6H) and 0.00 (TMS) ppm |
| 552 | | A | 376.23 | 2.22 | CD3OD: 8.7 (d, 1H), 8.45 (s, 1H), 8.35 (d, 1H), 8.25 (d, 1H), 4.37 (t, 1H), 3.58-3.48 (m, 1H), 3.4 (s, 3H), 2.55 (dd, 1H), 2.23-2.1 (m, 2H), 2.05-1.95 (m, 1H), 1.7-1.4 (m, 3H), 1.35-1.25 (m, 1H), 0.00 (TMS) |
| 553 | A | A | 390.35 | 2.05 | 1H NMR (300.0 MHz, MeOD) d 8.89 (d, J = 2.4 Hz, 1H), 8.44 (s, 1H), 8.38 (d, J = 2.3 Hz, 1H), 8.29 (d, J = 5.6 Hz, 1H), 4.75 (m, 1H), 2.75-2.66 (m, 1H), 2.25-2.16 (m, 2H), 1.99-1.89 (m, 2H), 1.71-1.29 (m, 4H) and 1.37 (m, contaminant) ppm |
| 554 | C | B | 390.41 | 2.3 | 1H NMR (300.0 MHz, MeOD) d 8.89 (d, J = 2.4 Hz, 1H), 8.44 (s, 1H), 8.38 (d, J = 2.4 Hz, 1H), 8.29 (d, J = 5.6 Hz, 1H), 4.77 (m, 1H), 2.75-2.66 (m, 1H), 2.24-2.17 (m, 2H), 1.94-1.89 (m, 2H) and 1.74-1.36 (m, 4H) ppm |
| 555 | C | A | 375 | 1.93 | 1H NMR (300.0 MHz, MeOD) d 8.75 (d, J = 2.4 Hz, 1H), 8.31 (d, J = 2.4 Hz, 1H), 8.29 (s, 1H), 8.24 (d, J = 4.4 Hz, 1H), 3.96 (dd, J = 5.8, 14.4 Hz, 1H), 3.73 (dd, J = 4.3, 14.3 Hz, 1H), 3.08-3.00 (m, 1H), 2.05-1.87 (m, 3H), 1.80 (m, 3H) and 1.48-1.39 (m, 4H) ppm |
| 556 | C | A | 446.8 | 2.8 | 1H NMR (300.0 MHz, MeOD) d 8.74 (d, J = 2.3 Hz, 1H), 8.42 (s, 1H), 8.38 (d, J = 2.3 Hz, 1H), 8.27 (d, J = 5.4 Hz, 1H), 3.85-3.81 (m, 2H), 3.75 (d, J = 8.5 Hz, 2H), 3.26 (s, 3H), 1.97-1.77 (m, 5H) and 1.43-1.35 (m, 4H) ppm |
| 557 | | A | 452.6 | 2.8 | 1H NMR (300.0 MHz, MeOD) d 8.78 (d, J = 2.4 Hz, 1H), 8.45 (d, J = 4.2 Hz, 1H), 8.37 (d, J = 2.3 Hz, 1H), 8.26 (d, J = 5.4 Hz, 1H), 4.12 (dd, J = 4.5, 13.7 Hz, 1H), 3.89 (dd, J = 7.1, 13.8 Hz, 1H), 3.26-3.16 (m, 1H), 3.00 (s, 3H), 2.18-1.90 (m, 2H), 1.79-1.74 (m, 2H) and 1.50-1.25 (m, 4H) ppm |
| 558 | A | A | 376.2 | 2.49 | 1H NMR (300.0 MHz, MeOD) d 8.78 (d, J = 2.4 Hz, 1H), 8.38 (s, 1H), 8.33 (d, J = 2.2 Hz, 1H), 8.25 (d, J = 5.2 Hz, 1H), 4.98 (dd, J = 7.2 Hz, 1H), 2.27-2.03 (m, 5H) and 1.86-1.76 (m, 3H) ppm |
| 559 | A | A | 389.8 | 2.27 | 1H NMR (300.0 MHz, MeOD) d 8.75 (d, J = 2.4 Hz, 1H), 8.38-8.35 (m, 2H), 8.24 (d, J = 5.1 Hz, 1H), 4.70-4.62 (m, 1H), 3.25-3.17 (m, 1H), 2.32 (m, 1H), 2.14-1.80 (m, 4H) and 1.68-1.54 (m, 3H) ppm |
| 560 | C | D | 418.46 | 3.21 | H NMR (300.0 MHz, MeOD) d 8.95 (s, 1H), 8.23-8.14 (m, 2H), 8.00 (m, 1H), 4.61 (m, 1H), 3.96-3.92 (m, 2H), 2.61 (m, 1H), 2.14-2.04 (m, 2H), 1.89-1.35 (m, 7H) and 1.04-0.99 (m, 3H) ppm |
| 561 | B | A | 418.41 | 2.73 | H NMR (300.0 MHz, MeOD) d 8.95 (s, 1H), 8.19 (m, 2H), 7.99 (s, 1H), 4.61 (m, 1H), 3.93 (m, 2H), 2.61 (m, 1H), 2.17-2.05 (m, 2H), 1.89-1.32 (m, 2.73 7H) and 1.00 (m, 3H) ppm |
| 562 (enantiomer 1) | C | A | 376.43 | 8.62 | H NMR (300.0 MHz, DMSO) d 8.85 (d, J = 2.5 Hz, 1H), 8.28 (d, J = 2.4 Hz, 1H), 8.19 (s, 1H), 8.14 (d, J = 4.2 Hz, 1H), 6.88 (d, J = 8.7 Hz, 1H), 4.52 (s, 1H), 4.32-4.25 (m, 1H), 1.90-1.33 (m, 8H) and 1.15 (s, 3H) ppm |
| 563 (enantiomer 2) | A | A | 376.43 | 11.16 | H NMR (300.0 MHz, DMSO) d 12.31 (s, 1H), 8.86 (d, J = 2.4 Hz, 1H), 8.28 (d, J = 2.4 Hz, 1H), 8.19 (d, J = 2.4 Hz, 1H), 8.16 (d, J = 4.2 Hz, 1H), 6.89 (d, J = 9.6 Hz, 1H), 4.54 (s, 1H), 4.30 (t, J = 8.8 Hz, 1H), 1.86-1.25 (m, 8H) and 1.16 (s, 3H) ppm |
| 564 | C | A | 445.7 | 1.91 | |
| 565 | B | A | 376.39 | 2.43 | H NMR (300.0 MHz, DMSO) d 12.48 (s, 1H), 8.71 (d, J = 2.3 Hz, 1H), 8.35-8.31 (m, 2H), 8.26 (d, J = 4.3 Hz, 2H), 8.02 (s, 1H), 4.57-4.44 (m, 1H), 2.87 (qn, J = 8.3 Hz, 1H), 2.39-2.32 (m, 1H), 2.15-2.05 (m, 1H), 2.00-1.86 (m, 3H) and 1.82-1.70 (m, 1H) ppm |
| 566 | A | A | 376.4 | 2.34 | H NMR (300.0 MHz, DMSO) d 12.42 (s, 1H), 8.72 (d, J = 2.2 Hz, 1H), 8.29 (m, 2H), 8.22 (d, J = 4.1 Hz, 1H), 7.87 (s, 1H), 4.56-4.49 (m, 1H), 2.87 (dd, J = 8.4, 25.0 Hz, 1H), 2.87 (s, 1H), 2.42-2.33 (m, |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 1H), 2.15-2.04 (m, 1H), 2.00-1.85 (m, 3H) and 1.81-1.70 (m, 1H) ppm |
| 567 | A | A | 404.42 | 2.13 | H NMR (300.0 MHz, DMSO) d 12.29 (s, 1H), 8.72 (d, J = 2.4 Hz, 1H), 8.28 (d, J = 2.4 Hz, 1H), 8.21 (s, 1H), 8.17 (d, J = 4.0 Hz, 1H), 7.41 (d, J = 7.7 Hz, 1H), 7.29 (s, 1H), 7.10 (s, 1H), 4.35-4.29 (m, 1H), 2.98-2.75 (m, 1H), 2.92 (d, J = 6.8 Hz, 2H), 2.68 (d, J = 10.8 Hz, 1H), 2.29-2.19 (m, 2H), 1.96-1.92 (m, 1H), 1.80-1.65 (m, 2H) and 1.53-1.42 (m, 1H) ppm |
| 568 | C | D | 432.46 | 3.08 | H NMR (300.0 MHz, DMSO) d 8.80 (d, J = 2.5 Hz, 1H), 8.27 (d, J = 2.4 Hz, 1H), 8.19 (s, 1H), 8.13 (d, J = 4.0 Hz, 1H), 7.60 (d, J = 8.6 Hz, 1H), 4.72 (qn, J = 6.2 Hz, 1H), 4.55-4.48 (m, 1H), 2.61-2.54 (m, 1H), 1.96 (m, 2H), 1.77 (m, 2H), 1.63-1.41 (m, 3H), 1.30-1.23 (m, 1H) and 0.93 (d, J = 6.2 Hz, 6H) ppm |
| 569 | C | D | 432.48 | 2.69 | H NMR (300.0 MHz, DMSO) d 12.57 (s, 1H), 8.80 (d, J = 2.4 Hz, 1H), 8.36-8.28 (m, 4H), 4.75 (td, J = 12.5, 6.2 Hz, 1H), 4.52 (m, 1H), 2.65-2.56 (m, 1H), 2.00 (m, 2H), 1.83-1.76 (m, 2H), 1.57-1.42 (m, 3H), 1.32-1.24 (m, 1H) and 0.94 (d, J = 6.2 Hz, 6H) ppm |
| 570 | A | A | 419.42 | 2 | H NMR (300.0 MHz, MeOD) d 8.81 (d, J = 2.1 Hz, 1H), 8.20 (d, J = 2.3 Hz, 1H), 8.15 (s, 1H), 7.97 (d, J = 4.1 Hz, 1H), 4.26-4.18 (m, 1H), 3.71-3.52 (m, 1H), 3.59 (s, 3H), 2.36 (d, J = 10.5 Hz, 1H), 2.18 (d, J = 10.7 Hz, 1H), 2.04-1.86 (m, 2H), 1.57 (s, 1H) and 1.43-1.15 (m, 3H) ppm |
| 571 (diastereomer 1) | A | A | 376.41 | 1.97 | CD3OD: 8.69 (d, 1H), 8.55 (s, 1H), 8.38 (d, 1H), 8.33 (d, 1H), 4.62 (m, 1H), 2.0-1.6 (m, 8H), 1.35 (s, 3H) |
| 572 (diasteroemer 2) | A | A | 376.42 | 2.39 | CD3OD: 8.78 (d, 1H), 8.55 (s, 1H), 8.35 (s, 1H), 8.25 (d, 1H), 4.8 (m, 1H), 2.25-1.95 (m 2H), 1.80-1.60 (m, 4H), 1.45-1.3 (m, 2H), 1.3 (s, 3H) |
| 573 | | A | 419.42 | 1.87 | H NMR (300.0 MHz, DMSO) d 12.51 (s, 1H), 10.28-10.00 (m, 1H), 8.70 (s, 1H), 8.38 (s, 1H), 8.31 (d, J = 2.4 Hz, 1H), 8.30 (d, J = 4.2 Hz, 1H), 7.89-7.75 (m, 1H), 4.70-4.50 (m, 1H), 4.33-4.29 (m, 1H), 3.79-3.45 (m, 2H), 3.20-2.80 (m, 2H), 2.12-1.95 (m, 3H), 1.72-1.60 (m, 1H) and 1.52 (d, J = 5.5 Hz, 3H) ppm |
| 574 | | A | 448.41 | 2.99 | 1H NMR (300.0 MHz, DMSO) d 8.74 (d, J = 2.4 Hz, 1H), 8.24 (d, J = 2.4 Hz, 1H), 8.19 (s, 1H), 8.12 (d, J = 4.0 Hz, 1H), 7.55 (d, J = 8.6 Hz, 1H), 4.42 (m, 1H), 4.02-3.86 (m, 2H), 3.35-3.23 (m, 2H), 3.08 (s, 3H), 2.69-2.60 (m, 1H), 1.99 (m, 2H), 1.77 (m, 2H), 1.62-1.40 (m, 3H) and 1.27 (m, 1H) ppm |
| 575 | | A | 404.38 | 3.12 | 1H NMR (300.0 MHz, DMSO) d 8.76 (d, J = 2.5 Hz, 1H), 8.26 (d, J = 2.4 Hz, 1H), 8.19 (s, 1H), 8.13 (d, J = 4.0 Hz, 1H), 7.53 (d, J = 8.5 Hz, 1H), 4.47-4.37 (m, 1H), 3.40 (s, 3H), 2.68-2.59 (m, 1H), 2.05-1.97 (m, 2H), 1.84-1.75 (m, 2H), 1.63-1.40 (m, 3H) and 1.31-1.23 (m, 1H) ppm |
| 576 | | A | 403.4 | 1.78 | 1H NMR (300 MHz, MeOD) d 8.81 (s, 1H), 8.20 (s, 1H), 8.15 (s, 1H), 7.99 (d, J = 4.1 Hz, 1H), 4.23 (t, J = 11.4, 1H), 3.90 (t, J = 11.4, 1H), 2.35 (d, J = 11.6, 1H), 2.20 (d, J = 12.5, 1H), 2.00 (d, J = 15.9, 2H), 1.92 (s, 3H), 1.67 (dd, J = 26.3, 13.2, 1H), 1.53-1.06 (m, 3H). |
| 577 | | A | 405.4 | 1.95 | 1H NMR (300.0 MHz, DMSO) d 12.46 (s, 1H), 8.70 (d, J = 2.4 Hz, 1H), 8.36 (d, J = 2.3 Hz, 1H), 8.31 (d, J = 2.4 Hz, 1H), 8.29 (d, J = 3.9 Hz, 1H), 7.79 (d, J= 7.0 Hz, 1H), 4.70-4.50 (m, 1H), 4.21 (s, 2H), 3.80-3.70 (m, 1H), 3.55-3.47 (m, 1H), 3.20-2.90 (m, 2H), 2.10-1.95 (m, 3H) and 1.69-1.60 (m, 1H) ppm |
| 578 | A | A | 390.41 | 2.82 | 1H NMR (300.0 MHz, DMSO) d 12.51 (s, 1H), 8.68 (d, J = 2.3 Hz, 1H), 8.33 (d, J = 2.3 Hz, 2H), 8.29 (d, J = 4.3 Hz, 1H), 7.55 (s, 1H), 4.53 (s, 1H), 3.05 (m, 1H), 2.13 (m, 1H), 1.96 (m, 1H), 1.79 (m, 3H) and 1.51 (m, 3H) ppm |
| 579 | | A | 390.36 | 2.92 | 1H NMR (300.0 MHz, DMSO) d 12.52 (s, 1H), 8.68 (d, J = 2.3 Hz, 1H), 8.33 (d, J = 2.5 Hz, 2H), 8.30 (d, J = 4.4 Hz, 1H), 7.57 (s, 1H), 4.53 (m, 1H), |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 3.05 (m, 1H), 2.15-2.07 (m, 1H), 1.96 (m, 1H), 1.81-1.76 (m, 3H) and 1.51 (m, 3H) ppm |
| 580 | | A | 376.44 | 2.28 | 1H NMR (300.0 MHz, MeOD) d 8.88 (d, 1H), 8.45 (s, 1H), 8.39 (d, J1H), 8.26 (d, 1H), 4.53 (t, 1H), 3.95-3.88 (m, 1H), 2.03-1.81 (m, 7H), 1.69 (m, 1H), 0.0 (TMS), |
| 581 | | A | 390.42 | 3 | 1H NMR (300.0 MHz, MeOD) d 8.80 (d, 1H), 8.54 (s, 1H), 8.41 (s, 1H), 8.27 (s, 111), 4.43 (d, 1H), 2.17 - 1.75 (m, 8H), 1.74 (m,2H), 1.65 (s, 3H), 0.00 (TMS) |
| 582 | | A | 404.43 | 3.21 | 1H NMR (300.0 MHz, DMSO) d 12.46 (s, 1H), 8.72 (d, J= 2.4 Hz, 1H), 8.32-8.28 (m, 3H), 7.10 (d, J = 7.1 Hz, 1H), 4.27-4.20 (m, 1H), 2.26 (d, J = 10.1 Hz, 1H), 1.93 (m, 1H), 1.83 (m, 1H), 1.68-1.59 (m, 3H), 1.36 (m, 2H) and 1.24 (s, 3H) ppm |
| 583 | | A | 418.45 | 1.65 | 1H NMR (300.0 MHz, MeOD) d 8.72 (d, 1H), 8.6 (d, 1H), 8.3 (m, 2H), 4.1 (m, 1H), 3.9-3.8 (m, 1H), 3.75-3.50 (dd, 1H), 2.45-2.35 (m, 1H), 2.35-2.15 (m, 2H), 1.95-1.85 (m 1H), (1.65 (dd, 3H), 0.00 (TMS) ppm |
| 584 | | A | 483.44 | 2.52 | 1H NMR (300.0 MHz, DMSO) d 12.45 (m, 1H), 8.71 (d, J = 8.5 Hz, 1H), 8.31 (m, 2H), 8.01 (m, 1H), 5.33 (s, 1H), 4.62-4.43 (m, 2H), 4.39-3.72 (m, 5H), 3.68 (s, 2H), 3.43-3.40 (m, 1H), 3.15 (s, 1H), 3.07 (s, 1H), 2.33 (s, 2H) and 2.08 (s, 2H) ppm |
| 585 | | A | 418.41 | 3.21 | 1H NMR (300 MHz, MeOD) ? 8.80 ? 8.76 (m, 1H), 8.37 (s, 1H), 8.35 (d, J = 2.3, 1H), 8.27 ? 8.23 (m, 1H), 4.49 ? 4.42 (m, 1H), 2.43 ? 2.34 (m, 11-1), 2.09 (d, J = 6.2, 1H), 1.98 ? 1.36 (m, 12H), 0.94 (dd, J = 11.3, 3.8, 3H). |
| 586 | A | A | 418.38 | 2.95 | 1H NMR (300.0 MHz, MeOD) ? 8.93 ? 8.85 (m, 2H), 8.93 ? 8.87 (m, 1H), 8.31 (dd, J = 4.5, 1.2, 2H), 8.31 (dd, J = 4.5, 1.2, 2H), 8.30 (d, J = 2.3, 1H), 8.19 (d, J = 5.0, 1H), 5.26 ? 5.20 (m, 1H), 3.37 (dd, J = 3.3, 1.6, 2H), 3.33 (ddt, J = 6.6, 3.3, 1.6, 118H), 2.11 (dd, J = 8.0, 5.8, 2H), 1.80 (tdd, J = 21.2, 18.9, 11.6, 8H), 1.63 ? 1.54 (m, 3H), 0.86 (q, J = 7.4, 4H) |
| 587 | A | A | 421.4 | 1.56 | |
| 588 | A | A | 421.4 | 1.56 | |
| 589 | | A | 427.42 | 1.56 | H NMR (300.0 MHz, DMSO) d 12.32 (s, 1H), 11.99 (m, 1H), 8.70 (d, J = 2.3 Hz, 1H), 8.28 (d, J = 2.4 Hz, 1H), 8.16 (d, J = 4.0 Hz, 1H), 8.11 (d, J = 2.8 Hz, 1H), 7.32 (d, J = 7.3 Hz, 1H), 6.93 (s, 2H), 4.31 (s, 1H), 4.19 (m, 1H), 3.66 (d, J = 14.0 Hz, 1H), 3.55 (d, J = 14.0 Hz, 1H), 3.01 (m, 1H), 2.77 (m, 1H), 2.15-1.90 (m, 3H), 1.75-1.68 (m, 1H) and 1.49-1.37 (m, 1H) ppm |
| 590 | | C | 433.37 | 2.09 | H NMR (300.0 MHz, MeOD) d 8.81 (d, 1H), 8.19 (d, 2H), 7.98 (d, 1H), 4.48 (s, 1H), 2.92-2.86 (m, 1H), 2.80-2.56 (m, 3H), 1.94-1.83 (m, 3H), 1.72-1.65 (m, 1H), 1.25(d, 6H), 0.00 (s, H) ppm |
| 591 | A | A | 433.41 | 2.6 | H NMR (300.0 MHz, MeOD) d 8.82 (d, J = 2.4 Hz, 1H), 8.21 (d, J = 2.3 Hz, 1H), 8.16 (s, 1H), 7.99 (d, J = 4.1 Hz, 1H), 4.29-4.21 (m, 1H), 4.04-3.96 (m, 1H), 3.87 (s, 2H), 3.40 (s, 3H), 2.34 (d, J = 11.6 Hz, 1H), 2.21 (d, J = 12.5 Hz, 1H), 2.02-1.93 (m, 2H), 1.74-1.62 (m, 1H) and 1.54-1.28 (m, 3H) ppm |
| 592 | | A | 463.42 | 2.52 | 1H NMR (300 MHz, METHANOL-d4) Shift 8.84 (s, 1H), 8.21 (s, 1H), 8.16 (s, 1H), 7.99 (d, J = 3.97 Hz, 1H), 4.18-4.34 (m, 1H), 4.14 (br. s., 2H), 3.49-3.74 (m, 3H), 3.3 (s, 3H) 2.38 (d, J = 9.06 Hz, 1H), 2.19 (d, J = 13.41 Hz, 1H), 1.84-2.11 (m, 2H), 1.51-1.78 (m, 1H), 1.12-1.47 (m, 3H) |
| 593 | | A | 418.21 | 1.47 | H NMR (300.0 MHz, MeOD) d 8.85 (d, J = 2.3 Hz, 1H), 8.22 (d, J = 2.2 Hz, 1H), 8.15 (s, 1H), 7.99 (d, J = 4.1 Hz, 1H), 4.28-4.20 (m, 1H), 2.82-2.73 (m, 1H), 2.65 (s, 2H), 2.40 (d, J = 10.2 Hz, 1H), 2.15 (d, J = 8.5 Hz, 1H), 2.05-1.92 (m, 2H), 1.64-1.55 (m, 1H) and 1.44-1.12 (m, 3H) ppm |
| 594 | A | A | 427.37 | 1.61 | H NMR (300.0 MHz, DMSO) d 12.31 (s, 1H), 11.86-11.77 (m, 1H), 8.70 (d, J = 2.2 Hz, 1H), 8.28 (d, J = 2.4 Hz, 1H), 8.15 (d, J = 3.9 Hz, 1H), 8.10 (d, J = 2.5 Hz, 1H), 7.54 (s, 1H), 7.31 (d, J = 7.6 Hz, 1H), 6.87 (s, 1H), 4.19 (m, 1H), 3.57 (d, J = 13.8 Hz, 1H), 3.48 (d, J = 13.8 Hz, 1H), 3.04 (d, J = |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 8.3 Hz, 1H), 2.80 (d, J = 10.4 Hz, 1H), 2.10-1.90 (m, 3H), 1.72-1.62 (m, 2H) and 1.51-1.35 (m, 1H) ppm |
| 595 | A | A | 405.37 | 1.65 | H NMR (300.0 MHz, DMSO) d 12.32 (s, 1H), 8.71 (d, J = 2.4 Hz, 1H), 8.28 (d, J = 2.4 Hz, 1H), 8.18-8.15 (m, 2H), 7.32 (d, J = 7.1 Hz, 1H), 4.20 (d, J = 7.1 Hz, 1H), 3.46 (t, J = 5.8 Hz, 2H), 3.19 (s, 3H), 3.10-3.06 (m, 1H), 2.82-2.78 (m, 1H), 2.57-2.50 (m, 2H), 2.11-1.95 (m, 3H), 1.71-1.63 (m, 2H) and 1.48-1.35 (m, 1H) ppm |
| 596 | A | A | 402.34 | 2.99 | H NMR (300.0 MHz, MeOD) d 8.86 (d, J = 2.3 Hz, 1H), 8.38 (s, 1H), 8.35 (d, J = 2.3 Hz, 1H), 8.25 (d, J = 5.1 Hz, 1H), 4.59 (d, J = 8.1 Hz, 1H), 3.00 (d, J = 8.0 Hz, 1H), 2.62 (m, 1H), 2.55 (m, 1H), 2.11 (d, J = 10.4 Hz, 1H), 1.85-1.59 (m, 3H) and 1.51-1.36 (m, 2H) ppm |
| 597 | C | A | | | H NMR (300.0 MHz, MeOD) d 8.78 (d, J = 2.3 Hz, 1H), 8.37 (s, 1H), 8.34 (d, J = 2.3 Hz, 1H), 8.23 (d, J = 4.9 Hz, 1H), 4.71-4.67 (m, 1H), 3.25-3.22 (m, 1H), 2.94 (m, 1H), 2.77 (m, 1H), 1.86 (d, J = 11.0 Hz, 1H) and 1.70-1.58 (m, 5H) ppm |
| 598 | A | A | 432.41 | 1.83 | H NMR (300.0 MHz, MeOD) d 8.86 (d, J = 2.4 Hz, 1H), 8.22 (d, J = 2.3 Hz, 1H), 8.17 (s, 1H), 8.02-7.97 (m, 1H), 4.45 (m, 1H), 3.14 (d, J = 10.8 Hz, 1H), 2.75 (d, J = 10.3 Hz, 1H), 2.38-2.26 (m, 2H), 2.12-2.08 (m, 1H), 1.92-1.70 (m, 2H), 1.66-1.55 (m, 1H), 1.20 (d, J = 7.5 Hz, 6H), 0.00 (TMS) ppm |
| 599 | A | A | 446.46 | 2.28 | H NMR (300.0 MHz, MeOD) d 8.86 (d, J = 2.4 Hz, H), 8.23 (d, J = 2.3 Hz, H), 8.17 (s, H), 8.03 (d, J = 4.1 Hz, H), 4.46 (m, 1H), 3.05 (d, J = 12.8 Hz, 1H), 2.66 (s, 3H), 2.34 (dd, J = 11.3, 20.6 Hz, 2H), 2.08 (d, J = 12.3 Hz, 1H), 1.89-1.71 (m, 2H), 1.66-1.54 (m, 1H), 1.10 (d, J = 6.4 Hz, 6H), and −0.00 (TMS) ppm |
| 600 | A | A | 460.46 | 2.31 | H NMR (300.0 MHz, MeOD) d 8.81 (d, J = 2.4 Hz, H), 8.22 (d, J = 2.4 Hz, H), 8.14 (s, H), 8.02 (d, J = 4.0 Hz, H), 4.45-4.37 (m, 1H), 3.61 (s, H), 2.97 (d, J = 8.8 Hz, 1H), 2.80 (s, 3H), 2.80-2.75 (m, 1H), 2.39-2.32 (m, 2H), 2.32 (s, H), 2.15 (dd, J = 3.6, 12.7 Hz, 1H), 1.91-1.79 (m, 2H), 1.53-1.47 (m, 1H), 1.10 (d, J = 6.8 Hz, 6H), and −0.00 (TMS) ppm |
| 601 | A | A | 490.47 | 2 | H NMR (300.0 MHz, MeOD) 8.88 (d, J = 2.3 Hz, H), 8.23 (d, J = 2.3 Hz, H), 8.17 (s, H), 8.02 (d, J = 4.1 Hz, H), 4.47-4.41 (m, 1H), 3.38 (m, H), 3.32-3.23 (m, 4H), 3.24 (s, 3H), 3.12-3.07 (m, 1H), 2.73 (d, J = 10.8 Hz, 1H), 2.35-2.29 (m, 2H), 2.19-2.15 (m, 1H), 1.91-1.80 (m, 2H), 1.47-1.42 (m, 1H), 1.10 (d, J = 6.5 Hz, 6H), and −0.00 (s, H) ppm |
| 602 | A | A | 472.4 | 22.3 | H NMR (300.0 MHz, MeOD) d 8.82 (d, J = 2.4 Hz, 1H), 8.22 (d, J = 2.3 Hz, H), 8.15 (s, H), 8.01 (d, J = 4.0 Hz, H), 4.41 (m, 1H), 3.02 (d, J = 10.0 Hz, 1H), 2.59-2.47 (m, 2H), 2.40-2.30 (m, 2H), 2.09-2.01 (m, 1H), 1.89-1.85 (m, 1H), 1.78-1.66 (m, 1H), 1.61-1.55 (m, 1H), 1.10 (d, J = 6.6 Hz, 6H), 0.68-0.63 (m, 2H), 00.44-0.40 (m, 2H) and 0.00 (s, H) ppm |
| 603 | A | A | 434.2 | 1.54 | H NMR (300.0 MHz, DMSO) d 12.31 (s, 1H), 8.71 (d, J = 1.6 Hz, 1H), 8.28 (d, J = 1.5 Hz, 1H), 8.20-8.16 (m, 2H), 7.32 (s, 1H), 7.19-7.11 (m, 1H), 5.20 (s, 1H), 4.24 (s, 1H), 3.99 (s, 1H), 3.01 (d, J = 9.0 Hz, 1H), 2.70-2.64 (m, 2H), 2.36-2.27 (m, 3H), 1.94 (s, 1H), 1.71 (s, 2H) and 1.48 (s, 1H) ppm |
| 604 | A | A | 461.2 | 1.79 | H NMR (300.0 MHz, DMSO) d 8.68 (d, J = 2.2 Hz, 1H), 8.25 (d, J = 2.2 Hz, 1H), 8.19-8.14 (m, 2H), 7.33 (d, J = 7.5 Hz, 1H), 4.21 (t, J = 5.9 Hz, 2H), 4.00-3.96 (m, 1H), 3.54 (t, J = 7.6 Hz, 1H), 3.15 (d, J = 8.9 Hz, 1H), 3.03-2.91 (m, 1H), 2.78 (d, J = 10.5 Hz, 1H), 2.11-1.92 (m, 3H), 1.71 (s, 2H), 1.43-1.35 (m, 1H), 1.27 (s, 3H), 1.22 (s, 1H) and 1.14 (s, 3H) ppm |
| 605 | C | C | 391.07 | 1.425 | H NMR (300.0 MHz, DMSO) d 12.51 (s, 1H), 8.72-8.57 (m, 3H), 8.35-8.32 (m, 3H), 7.94 (d, J = 7.9 |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | Hz, 1H), 7.48 (d, J = 8.0 Hz, 1H), 7.11 (d, J = 7.9 Hz, 1H), 5.02 (m, 1H), 3.69 (m, 1H), 3.33-3.24 (m, 4H), 2.29 (s, 1H) and 2.12-2.06 (m, 2H) ppm |
| 606 | A | A | 432.15 | 1.62 | |
| 607 | C | C | 433.18 | 1.87 | H NMR (300.0 MHz, DMSO) d 12.48 (s, 1H), 8.68 (s, 1H), 8.32-8.29 (m, 3H), 7.68 (d, J = 2.5 Hz, 1H), 4.77-4.73 (m, 1H), 4.27-4.10 (m, 2H), 3.76-3.40 (m, 2H), 3.19-3.04 (m, 2H) and 2.15-1.83 (m, 6H) ppm. 2.05 and 2.03 (acetyl rotamers, two burried s, 3H) |
| 608 | A | A | 433.36 | 2.88 | H NMR (300.0 MHz, DMSO) d 9.03 (s, 1H), 8.65 (s, 1H), 8.48 (d, J = 5.1 Hz, 1H), 8.41 (s, 1H), 4.64 (s, 1H), 4.27 (s, 1H), 2.97 (m, 2H), 2.30 (d, J = 10.5 Hz, 1H), 2.06 (s, 2H), 1.91 (d, J = 11.2 Hz, 2H), 1.64-1.23 (m, 5H), 0.99 (t, J = 6.9 Hz, 3H), and 0.00 (TMS), ppm |
| 609 | A | A | 433.32 | 2.79 | H NMR (300.0 MHz, MeOD) d 8.68 (s, 1H), 8.64 (s, 1H), 8.37 (d, J = 1.8 Hz, 1H), 8.29 (d, J = 5.4 Hz, 1H), 5.15 (s, 1H), 4.71-4.63 (m, 1H), 3.33 (d, J = 11.6 Hz, 1H), 3.10 (m, 2H), 2.26 (m, 2H), 2.04 (m, 3H), 1.83 (m, 1H), 1.70-1.50 (m, 2H), 1.03 (m, 3H), and 0.00 (TMS) ppm |
| 610 | A | C | 449.42 | 1.52 | H NMR (300.0 MHz, MeOD) d 8.85 (d, J = 2.3 Hz, 1H), 8.22 (d, J = 2.2 Hz, 1H), 8.15 (s, 1H), 7.98 (d, J = 4.1 Hz, 1H), 4.20 (m, 1H), 3.82 (dd, J = 3.9, 8.2 Hz, 1H), 3.55-3.45 (m, 1H), 3.30 (s, 3H), 3.23-3.07 (m, 1H), 2.86-2.77 (m, 2H), 2.68-2.59 (m, 1H), 2.44 (d, J = 10.9 Hz, 1H), 2.15 (d, J = 9.8 Hz, 1H), 2.07-1.94 (m, 2H), 1.65-1.56 (m, 1H) and 1.42-1.17 (m, 3H) ppm |
| 611 | A | A | 447.4 | 1.95 | H NMR (300.0 MHz, MeOD) d 8.78 (d, J = 2.3 Hz, 1H), 8.19 (d, J = 2.2 Hz, 1H), 8.14 (s, 1H), 7.96 (d, J = 4.0 Hz, 1H), 4.25-4.18 (m, 1H), 3.96-3.88 (m, 1H), 3.61 (t, J = 6.2 Hz, 2H), 3.31 (s, 3H), 2.39 (t, J = 6.2 Hz, 2H), 2.37 (d, J = 17.1 Hz, 1H), 2.18 (d, J = 12.0 Hz, 1H), 2.03-1.91 (m, 2H), 1.67 (q, J = 13.4 Hz, 1H) and 1.45-1.22 (m, 3H) ppm |
| 612 | A | A | 418.37 | 4.59 | H NMR (300.0 MHz, MeOD) d 8.77 (s, 1H), 8.37 (d, J = 2.7 Hz, 2H), 8.26 (d, J = 4.7 Hz, 1H), 4.46 (m, 1H), 2.39 (m, 1H), 2.10 (m, 1H), 1.92-1.35 (m, 8H) and 0.93 (t, J = 7.7 Hz, 3H) ppm |
| 613 | A | A | 388.13 | 1.82 | |
| 614 | A | A | 459.35 | 3.06 | H NMR (300.0 MHz, DMSO) d 12.32 (s, 1H), 8.72 (s, 1H), 8.29 (s, 1H), 8.18 (s, 2H), 7.31 (d, J = 6.2 Hz, 1H), 6.10 (d, J = 5.3 Hz, 1H), 4.16 (s, 2H), 3.04 (s, 1H), 2.79 (d, J = 8.6 Hz, 1H), 2.59 (d, J = 9.9 Hz, 2H), 2.26 (t, J = 9.5 Hz, 2H), 1.94 (s, 1H), 1.72 (s, 2H) and 1.48 (s, 1H) ppm |
| 615 | A | A | 378.3 | 3.59 | |
| 616 | C | C | 378.3 | 3.74 | |
| 617 (diasteromer 1) | A | A | 386.35 | 3.58 | H NMR (300.0 MHz, DMSO) d 13.15 (s, H), 9.58 (s, 1H), 9.49 (d, J = 6.4 Hz, 111H), 9.23 (s, H), 8.59 (s, H), 8.52 (d, J =5.0 Hz, 1H), 8.42 (s, 111), 4.52 (s, 1H), 3.34 (s, 1H), 3.17 (s, 1H), 2.11 (s, 2H), 1.96-1.85 (m, 4H), 1.5-1.2 (m, 2H), and −0.00 (s, H) ppm |
| 618 (diasteromer 2) | A | A | 386.34 | 3.16 | H NMR (300.0 MHz, DMSO) d 13.13 (s, 1H), 9.45 (s, 1H), 9.28 (s, 1H), 8.66 (s, 1H), 8.51 (d, J = 5.1 Hz, 1H), 8.42 (s, 1H), 4.61 (s, 1H), 3.33 (s, 1H), 3.17 (s, 1H), 2.16 (d, J = 12.5 Hz, H), 2.06 (s, 1H), 2.02-1.78 (m, 4H), 1.66-1.60 (m, 2H), 1.46 (m, 1H), and 0.00 (s, H) ppm |
| 619 | A | A | 446.23 | 2.23 | H NMR (300.0 MHz, DMSO) d 12.30 (s, 1H), 8.71 (s, 1H), 8.28 (s, 1H), 8.17 (d, J = 6.9 Hz, 2H), 7.42 (s, 1H), 7.35 (d, J = 7.6 Hz, 1H), 4.73 (d, J = 7.4 Hz, 1H), 4.23 (s, 1H), 3.51 (d, J = 5.8 Hz, 1H), 3.17 (dd, J = 9.2, 17.9 Hz, 1H), 3.04 (d, J = 10.9 Hz, 2H), 2.89 (s, 1H), 2.63 (d, J = 5.6 Hz, 1H), 2.25 (d, J = 11.4 Hz, 1H), 2.18-2.07 (m, 2H), 1.70 (d, J = 11.3 Hz, 2H) and 1.43-1.35 (m, 1H) ppm |
| 620 | B | A | 400.41 | 1.92 | |
| 621 | A | A | 445.45 | 2.39 | |
| 622 | A | A | 431.42 | 2.46 | |
| 623 | A | A | 435.4 | 3.62 | H NMR (300.0 MHz, DMSO) d 12.32 (s, 1H), 8.69 (s, 1H), 8.35-8.25 (m, 1H), 8.27 (d, J = 2.4 Hz, |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 1H), 8.21 (d, J = 3.9 Hz, 1H), 7.51 (d, J = 6.7 Hz, 1H), 5.02-4.60 (m, 3H), 4.37-4.20 (m, 3H), 3.62-3.40 (m, 2H), 3.17-2.62 (m, 2H), 2.10 (s, 1H) and 1.85-1.60 (m, 3H) ppm |
| 624 | A | B | 378.15 | 2.49 | MeOH d4 8.8 (d, 1H); 8.2 (d, 1H); 8.1 (s, 1H); 7.9 (d, 1H); 4.2 (dd, 1H_); 3.6 (dt, 1H); 3.4 (dd, 1H); 2.2 (bd, 1H); 2.05 (bd, 1H); 1.8 (dr, 1H); 1.6 (m, 1H); 1.4 (m, 2H). |
| 625 | A | A | 378.34 | 2.42 | MeOH d4 8.8 (d, 1H); 8.2 (d, 1H); 8.1 (s, 1H); 7.9 (d, 1H); 4.2 (dd, 1H_); 3.6 (dt, 1H); 3.4 (dd, 1H); 2.2 (bd, 1H); 2.05 (bd, 1H); 1.8 (dr, 1H); 1.6 (m, 1H); 1.4 (m, 2H). |
| 626 | A | A | 390.39 | 4.05 | H NMR (300.0 MHz, CDCl3) d 8.87 (d, J = 2.3 Hz, 1H), 8.31 (d, J = 2.3 Hz,1H), 8.17 (d, J = 2.7 Hz, 1H), 8.03 (d, J = 3.5 Hz, 1H), 7.28 (CDCl3), 6.8 (s, 1H), 4.67 (m, 1H), 2.1-1.88 (m, 4H), 1.8-1.50 (m, 7H), 0.99 (t, J = 7.5 Hz, 3H) ppm |
| 627 (diasteromer 1) | A | A | 388.36 | 4.01 | H NMR (300.0 MHz, CDCl3) d 9.65 (s, 1H), 8.97 (s, 1H), 8.31 (d, J = 2.3 Hz, 1H), 8.15 (d, J = 2.7 Hz, 1H), 8.05 (d, J = 3.4 Hz, 1H), 7.28 (s, CDCl3), 6.75 (s, 1H), 6.06 (dd, J = 10.7, 17.3 Hz, 1H), 5.32 (d, J = 3.9 Hz, 1H), 5.18 (d, J = 10.8 Hz, 1H), 4.66 (qn, J = 4.0 Hz, 1H), 2.08-1.86 (m, 4H), 1.79-1.61 (m, 6H), 1pp |
| 628 (diasteromer 2) | A | A | 388.37 | 3.65 | H NMR (300.0 MHz, CDCl3) d 9.62 (s, 1H), 8.95 (s, 1H), 8.34 (3, 1H), 8.20 (s, 1H), 8.10 (s, 1H), 7.28 (s, CDCl3), 6.03 (dd, J = 10.7, 17.3 Hz, 1H), 5.39-5.30 (m, 1H), 5.10 (d, J = 10.7 Hz, 1H), 4.87-4.81 (m, 1H), 4.76-4.64 (m, 1H), 2.29-2.24 (m, 2H), 2.19-2.02 (m, 2H), 1.84-1.78 (m, 3H), 1.62-1.21 (m, 3H), ppm |
| 629 | A | A | 446.23 | 4.45 | |
| 630 | A | A | 390.36 | 3.95 | H NMR (300.0 MHz, MeOD) d 8.72 (s, 1H), 8.53 (s, 1H), 8.39 (s, 1H), 8.30 (s, 1H), 4.65-4.60 (m, 1H), 2.66 (t, J = 11.3 Hz, 1H), 2.46 (d, J = 10.2 Hz, 1H), 2.17-2.04 (m, 3H) and 1.57-1.44 (m, 4H) ppm |
| 631 | A | A | 378.15 | 3.1 | |
| 632 | A | A | 378.15 | 2.97 | |
| 633 | A | A | 473.42 | 3.25 | H NMR (300.0 MHz, MeOD) d 8.64 (d, J = 2.2 Hz, 1H), 8.51 (s, 1H), 8.36 (d, J = 2.2 Hz, 1H), 8.29 (d, J = 5.5 Hz, 1H), 4.39 (t, J = 11.9 Hz, 1H), 3.93-3.82 (m, 3H), 3.54-3.30 (m, 2H), 2.52-2.43 (m, 1H), 2.37-2.33 (m, 1H), 2.20 (d, J = 11.6 Hz, 1H), 2.01 (d, J = 11.3 Hz, 2H), 1.90-1.88 (m, 1H), 1.83-1.63 (m, 4H) and 1.59-1.26 (m, 3H) ppm |
| 634 | A | A | 433.21 | 3.47 | H NMR (300.0 MHz, MeOD) d 8.61 (d, J = 2.1 Hz, 1H), 8.53 (s, 1H), 8.35 (d, J = 2.0 Hz, 1H), 8.29 (d, J =5.5 Hz, 1H), 4.37 (t, J =11.2 Hz, 1H), 3.95 (s, 1H), 3.80 (s, 2H), 2.42 (t, J = 5.5 Hz, 3H), 2.20 (d, J = 11.5 Hz, 1H), 2.03 (d, J = 11.0 Hz, 2H) and 1.76 - 1.29 (m, 4H) ppm |
| 635 | A | A | 459.38 | 3.12 | H NMR (300.0 MHz, MeOD) d 8.48-8.45 (m, 2H), 8.29-8.23 (m, 2H), 4.84 (d, J = 6.0 Hz, 1H), 4.38 (d, J = 6.0 Hz, 1H), 4.26-4.23 (m, 1H), 3.96 (s, 1H), 3.77-3.62 (m, 2H), 2.36 (s, 1H), 2.18 (d, J = 11.5 Hz, 1H), 2.02 (d, J = 12.3 Hz, 2H), 1.70-1.25 (m, 4H) and 1.59 (s, 3H) ppm |
| 636 | A | A | 473.4 | 3.12 | H NMR (300.0 MHz, MeOD) d 8.64 (d, J = 2.3 Hz, 1H), 8.51 (s, 1H), 8.36 (d, J = 2.3 Hz, 1H), 8.29 (d, J = 5.6 Hz, 1H), 4.44-4.36 (m, 1H), 3.96-3.87 (m, 3H), 3.47 - 3.37 (m, 2H), 2.49 - 2.35 (m, 2H), 2.21 (d, J = 12.4 Hz, 1H), 2.02 (d, J = 11.9 Hz, 2H) and 1.83-1.23 (m, 8H) ppm |
| 637 | A | A | 474.43 | 2.39 | H NMR (300.0 MHz, MeOD) d 8.68 (s, 1H), 8.62 (s, 1H), 8.40 (s, 1H), 8.33 (d, J = 4.7 Hz, 1H), 4.44-4.35 (m, 2H), 4.21 (d, J = 12.2 Hz, 1H), 4.04-3.92 (m, 2H), 3.58 (d, J = 12.3 Hz, 1H), 3.23-3.08 (m, 2H), 2.37 (d, J = 8.1 Hz, 1H), 2.23 (d, J = 11.1 Hz, 1H), 2.05 (d, J = 9.7 Hz, 2H), 1.72 (m, 2H) and 1.59-1.44 (m, 2H) ppm |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| 638 | A | A | 459.37 | 3.77 | H NMR (300.0 MHz, MeOD) d 8.55 (d, J = 1.0 Hz, 1H), 8.46-8.45 (m, 1H), 8.29-8.27 (m, 2H), 4.28 (d, J = 6.1 Hz, 2H), 4.00-3.87 (m, 3H), 2.36-2.16 (m, 3H), 2.00-1.91 (m, 5H) and 1.75-1.41 (m, 4H) ppm |
| 639 | C | C | 472.46 | 2.39 | H NMR (300.0 MHz, MeOD) d 8.66 (s, 1H), 8.60 (s, 1H), 8.38 (s, 1H), 8.31 (d, J = 4.7 Hz, 1H), 4.43-4.36 (m, 1H), 3.98-3.91 (m, 1H), 3.43 (d, J = 10.3 Hz, 2H), 3.03 (t, J = 10.6 Hz, 2H), 2.60 (s, 1H), 2.38 (d, J = 10.2 Hz, 1H), 2.21 (d, J = 10.6 Hz, 1H), 2.07-1.92 (m, 6H) and 1.74-1.30 (m, 4H) ppm |
| 640 (diasteromer 1) | A | A | 447.41 | 3.37 | H NMR (300.0 MHz, MeOD) d 8.69 (d, J = 2.3 Hz, 1H), 8.51 (s, 1H), 8.37 (d, J = 2.2 Hz, 1H), 8.29 (d, J = 5.6 Hz, 1H), 4.43 (t, J = 11.9 Hz, 1H), 4.14 (q, J = 6.1 Hz, 1H), 3.94 (t, J = 11.9 Hz, 1H), 2.40-2.19 (m, 4H), 2.03 (d, J = 8.2 Hz, 2H), 1.78-1.69 (m, 1H), 1.59-1.44 (m, 3H) and 1.18 (d, J = 6.1 Hz, 3H) ppm |
| 641 (diasteromer 2) | A | A | 447.41 | 3.47 | H NMR (300.0 MHz, MeOD) d 8.69 (d, J = 2.3 Hz, 1H), 8.51 (s, 1H), 8.37 (d, J = 2.2 Hz, 1H), 8.29 (d, J = 5.6 Hz, 1H), 4.43 (t, J = 11.9 Hz, 1H), 4.14 (q, J = 6.1 Hz, 1H), 3.94 (t, J = 11.9 Hz, 1H), 2.40-2.19 (m, 4H), 2.03 (d, J = 8.2 Hz, 2H), 1.78-1.69 (m, 1H), 1.59-1.44 (m, 3H) and 1.18 (d, J = 6.1 Hz, 3H) ppm |
| 642 | A | A | 433.38 | 3.52 | H NMR (300.0 MHz, MeOD) d 8.68 (s, 1H), 8.56 (s, 1H), 8.39 (d, J = 1.5 Hz, 1H), 8.31 (d, J = 5.3 Hz, 1H), 4.47-4.40 (m, 1H), 4.15 (s, 1H), 3.98 (m, 1H), 2.41 (m, 1H), 2.23 (d, J = 10.6 Hz, 1H), 2.04 (d, J = 11.0 Hz, 2H) and 1.77-1.36 (m, 7H) ppm |
| 643 | A | A | 404.36 | 3.3 | H NMR (300.0 MHz, MeOD) d 8.98 (d, J = 2.3 Hz, 1H), 8.45 (s, 1H), 8.38 (d, J = 2.3 Hz, 1H), 8.30 (d, J = 5.7 Hz, 1H), 5.26-5.22 (m, 1H), 2.17-2.10 (m, 1H), 1.87-1.82 (m, 4H), 1.68-1.59 (m, 3H) and 1.36 (s, 3H) ppm |
| 644 | C | C | 418.4 | 3.37 | H NMR (300.0 MHz, MeOD) d 8.87 (d, J = 2.3 Hz, 1H), 8.45 (s, 1H), 8.38 (d, J = 2.3 Hz, 1H), 8.31 (d, J = 5.6 Hz, 1H), 5.26-5.23 (m, 1H), 2.14-2.09 (m, 1H), 1.96-1.72 (m, 6H), 1.59 (s, 3H) and 0.87 (t, J = 7.4 Hz, 3H) ppm |
| 645 | A | A | 418.41 | 3.37 | H NMR (300.0 MHz, MeOD) d 8.87 (d, J = 2.3 Hz, 1H), 8.46 (s, 1H), 8.37 (d, J = 2.3 Hz, 1H), 8.30 (d, J = 5.6 Hz, 1H), 5.25-5.23 (m, 1H), 2.17-2.09 (m, 1H), 1.98-1.74 (m, 6H), 1.58 (m, 3H) and 0.87 (t, J = 7.4 Hz, 3H) ppm |
| 646 | A | A | 392.35 | 3.35 | H NMR (300.0 MHz, DMSO) d 12.30 (s, 1H), 8.71 (d, J = 2.4 Hz, 1H), 8.28 (d, J = 2.4 Hz, 1H), 8.20-8.15 (m, 2H), 4.57-4.54 (m, 1H), 4.4-4.3 (s, 1H), 4.08-4.01 (m, 1H), 3.37-3.29 (m, 2H), 3.17 (d, J = 5.3 Hz, H), 2.50 (qn, J = 1.7 Hz DMSO), 1.99 (s, 1H), 1.91 (d, J = 3.6 Hz, H), 1.77-1.65 (m, 6H), 1.59 (d, J = 7.5 Hz, 1H). |
| 647 | A | A | 474.4 | 3.59 | H NMR (300.0 MHz, MeOD) d 8.56 (s, 1H), 8.50 (d, J = 2.2 Hz, 1H), 8.30 (t, J = 5.6 Hz, 1H), 8.31 (s, 1H), 4.26 (t, J = 11.2 Hz, 1H), 3.82 (t, J = 11.1 Hz, 1H), 3.65-3.61 (m, 4H), 3.39-3.36 (m, 4H), 2.36 (d, J = 10.0 Hz, 1H), 2.17 (d, J = 12.0 Hz, 1H), 2.02 (d, J = 10.2 Hz, 2H) and 1.70-1.32 (m, 4H) ppm |
| 648 | A | A | 489.38 | 3.67 | H NMR (300.0 MHz, MeOD) d 8.65 (s, 1H), 8.52 (d, J = 1.6 Hz, 1H), 8.37 (d, J = 2.0 Hz, 1H), 8.28 (dd, J = 2.9, 5.5 Hz, 1H), 4.39 (s, 1H), 4.06-3.54 (m, 7H), 2.55-2.38 (m, 2H), 2.19 (d, J = 10.7 Hz, 1H), 2.03-1.99 (m, 3H) and 1.69-1.24 (m, 5H) ppm |
| 649 | A | A | 475.37 | 3.32 | H NMR (300.0 MHz, MeOD) d 8.79 (d, J = 2.3 Hz, 1H), 8.51 (s, 1H), 8.44 (d, J = 2.2 Hz, 1H), 8.32 (d, J = 5.6 Hz, 1H), 5.22 (dd, J = 4.4, 6.0 Hz, 1H), 4.53-4.45 (m, 1H), 4.21-3.50 (m, 5H), 2.52-2.43 (m, 1H), 2.27-2.04 (m, 5H) and 1.72-1.27 (m, 4H) ppm |
| 650 | A | A | 461.38 | 3.79 | H NMR (300.0 MHz, MeOD) d 8.56-8.54 (m, 2H), 8.34 (s, 1H), 8.30 (t, J = 5.4 Hz, 1H), 4.29 (t, J = 11.4 Hz, 1H), 3.93 (t, J = 11.6 Hz, 1H), 3.54 (s, |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
| | | | | | 2H), 2.34 (d, J = 10.8 Hz, 1H), 2.18 (d, J = 11.4 Hz, 1H), 2.01 (d, J = 11.3 Hz, 2H), 1.73-1.37 (m, 4H) and 1.15 (s, 6H) ppm |
| 651 | A | A | 473.41 | 4.1 | H NMR (300.0 MHz, MeOD) d 8.56-8.51 (m, 2H), 8.33-8.29 (m, 2H), 4.30 (d, J = 3.0 Hz, 1H), 3.98 (dd, J = 11.5, 23.4 Hz, 2H), 3.83-3.79 (m, 1H), 3.55 (t, J = 8.9 Hz, 1H), 2.35 (d, J = 11.1 Hz, 1H), 2.19 (d, J = 11.2 Hz, 1H), 2.03-1.90 (m, 4H) and 1.73-1.37 (m, 8H) ppm |
| 652 | A | A | 459.41 | 3.86 | H NMR (300.0 MHz, MeOD) d 8.72 (d, J = 2.3 Hz, 1H), 8.56 (s, 1H), 8.42 (d, J = 2.2 Hz, 1H), 8.34 (d, J = 5.6 Hz, 1H), 4.51-4.43 (m, 1H), 4.02-3.88 (m, 3H), 3.86-3.78 (m, 2H), 3.07-3.02 (m, 1H), 2.42 (d, J = 7.5 Hz, 1H), 2.25 (d, J = 12.0 Hz, 1H), 2.19-2.06 (m, 4H) and 1.79-1.35 (m, 4H) ppm |
| 653 | A | A | 418.4 | 3.37 | H NMR (300.0 MHz, MeOD) d 8.87 (d, J = 2.0 Hz, 1H), 8.28 (s, 1H), 8.19 (d, J = 1.8 Hz, 1H), 8.01 (d, J = 3.7 Hz, 1H), 4.90 (m, 1H), 2.12 (m, 2H), 1.76-1.58 (m, 7H) and 0.86 (t, J = 7.3 Hz, 3H) ppm |
| 654 | B | B | 411.37 | 2.87 | |
| 655 (diasteromer 1) | A | A | 376.39 | 3.93 | H NMR (300.0 MHz, CDCl3) d 10.63 (s, 1H), 8.85-8.82 (m, 1H), 8.27 (dd, J = 2.4, 12.5 Hz, 1H), 8.17-8.14 (m, 1H), 8.03 (d, J = 3.4 Hz, 1H), 7.28 (s, H), 4.84 (d, J = 6.3 Hz, 1H), 4.58 (dq, J = 3.9, 15.7 Hz, 1H), 2.26 (d, J = 12.0 Hz, 2H), 2.09-1.95 (m, 2H), 1.84-1.75 (m, 3H), 1.47-1.32 (m, 5H) and 1.22 (td, J = 12.4, 5.2 Hz, 1H) ppm |
| 656 (diasteromer 2) | A | A | 376.38 | 4.01 | H NMR (300.0 MHz, CDCl3) d 9.54 (s, 1H), 8.86 (d, J = 2.3 Hz, 1H), 8.31 (d, J = 2.4 Hz, 1H), 8.15 (d, J = 2.7 Hz, 1H), 8.04 (d, J = 3.5 Hz, 1H), 7.28 (s, H), 6.66 (s, 1H), 4.62-4.59 (m, 1H), 1.96-1.88 (m, 4H), 1.81 (dd, J = 4.5, 14.9 Hz, 2H) and 1.68-1.57 (m, 5H) ppm |
| 657 | C | C | 394.41 | 2.97 | H NMR (300.0 MHz, DMSO) d 12.41 (s, 1H), 8.80 (d, J = 2.3 Hz, 1H), 8.28 (d, J = 2.4 Hz, 1H), 8.25 (s, 1H), 8.17 (d, J = 4.0 Hz, 1H), 7.64 (s, 1H), 4.80-4.50 (m, 3H), 4.47 (dd, J = 7.5, 14.8 Hz, 1H), 3.89 (dd, J = 5.3, 6.3 Hz, 1H), 3.77 (dd, J = 5.1, 5.0 Hz, 1H), 3.50-3.37 (m, 2H), 2.36-2.24 (m, 1H), 2.04 (dd, J = 8.3, 13.5 Hz, 1H), 1.99 (s, 1H), 1.27 (td, J = 8.4, 4.4 Hz, 1H) and 1.21 (s, 1H) ppm |
| 658 | A | A | 459.29 | 3.5 | |
| 659 | A | A | 445.21 | 3.41 | |
| 660 | A | A | 445.21 | 3.35 | |
| 661 | A | A | 395.17 | 2.13 | |
| 662 | A | A | | | H NMR (300.0 MHz, DMSO) d 12.26 (s, 1H), 8.42 (dd, J = 2.8, 9.8 Hz, 1H), 8.27 (q, J = 1.3 Hz, 1H), 8.21 (d, J = 2.7 Hz, 1H), 8.16 (d, J = 4.0 Hz, 1H), 7.35 (d, J = 7.4 Hz, 1H), 4.49 (m, 1H), 4.39 (d, J = 4.0 Hz, 1H), 4.24-4.21 (m, 1H), 3.64-3.61 (m, 1H), 3.05-3.02 (m, 1H), 2.77 (t, J = 9.7 Hz, 1H), 2.36 (ddd, J = 4.8, 12.7, 12.7 Hz, 2H), 2.18-2.12 (m, 2H), 1.95-1.91 (m, 1H), 1.76-1.72 (m, 1H) and 1.66-1.41 (m, 2H) ppm |
| 663 | A | A | 445.34 | 2.64 | |
| 664 | A | A | 431.26 | 2.48 | |
| 665 | A | A | 431.26 | 2.53 | |
| 666 | | D | 428.3 | 2.6 | |
| 667 | | D | 414.5 | 1.4 | |
| 668 | | A | 429.3 | 3.51 | H NMR (300.0 MHz, DMSO) d 12.32 (s, 1H), 8.71 (d, J = 2.4 Hz, 1H), 8.28 (d, J = 2.4 Hz, 1H), 8.18-8.16 (m, 2H), 7.38 (d, J = 7.7 Hz, 1H), 4.22-4.17 (m, 1H), 3.31-3.16 (m, 3H), 2.90 (m, 1H), 2.40 (t, J = 10.2 Hz, 2H), 2.00-1.95 (m, 1H), 1.77-1.60 (m, 2H) and 1.50-1.38 (m, 1H) ppm |
| 669 | A | A | 386.08 | 2.26 | H NMR (300.0 MHz, DMSO) d 12.31 (s, 1H), 8.69 (d, J = 2.4 Hz, 1H), 8.28 (d, J = 2.4 Hz, 1H), 8.19-8.17 (m, 2H), 7.47 (d, J = 7.7 Hz, 1H), 4.30-4.20 (m, 1H), 3.80 (s, 2H), 3.07-3.03 (m, 1H), 2.82-2.73 (m, 1H), 2.29-2.10 (m, 2H), 2.05-1.96 (m, 1H), 1.87-1.65 (m, 2H) and 1.49-1.40 (m, 1H) ppm |
| 670 | C | C | 559.42 | 3.573 | H NMR (300.0 MHz, MeOD) d 8.64 (d, J = 2.3 Hz, 1H), 8.40 (s, 1H), 8.32 (d, J = 2.3 Hz, 1H), 8.29 (d, J = 5.0 Hz, 1H), 6.96 (m, 1H), 4.84-4.80 (m, 1H), |

TABLE 1-continued

IC$_{50}$, EC$_{50}$, NMR and LCMS Data of Compounds of FIG. 3:

| Compound Nos. | IC$_{50}$ | EC$_{50}$ | LCMS_Plus | LCMS_RT | NMR |
|---|---|---|---|---|---|
|  |  |  |  |  | 4.34 (m, 1H), 4.29-4.19 (m, 3H), 3.54-3.47 (m, 1H), 3.15-3.07 (m, 1H), 2.68-2.58 (m, 1H), 1.92 (s, 3H), 1.59-1.51 (m, 4H), 1.26 (t, J = 7.1 Hz, 3H), 0.95 (t, J = 7.4 Hz, 3H) and 0.89 (t, J = 7.4 Hz, H) ppm |
| 671 | C | C | 531.4 | 3.143 | H NMR (300.0 MHz, MeOD) d 8.66 (d, J = 2.3 Hz, 1H), 8.39 (s, 1H), 8.32 (d, J = 2.3 Hz, 1H), 8.29 (d, J = 5.0 Hz, 1H), 6.97 (m, 1H), 4.82-4.79 (m, 1H), 4.34 (m, 1H), 4.25 (dd, J = 7.6, 10.1 Hz, 1H), 3.54-3.47 (m, 2H), 3.11-3.04 (m, 1H), 2.65-2.57 (m, 1H), 1.91 (s, 3H), 1.59 (m, 4H), 0.95 (t, J = 7.4 Hz, H) and 0.89 (t, J = 7.4 Hz, 3H) ppm |

TABLE 2

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 672 | A | A | 432.28 | 3.83 |  |
| 673 | A | A | 448.28 | 3.81 |  |
| 674 | A | A | 405.15 | 3.16 |  |
| 675 | C | C | 428.32 | 2.2 |  |
| 676 | A | A | 445.34 | 2.45 |  |
| 677 | A | A | 404.38 | 3.32 | H NMR (300.0 MHz, MeOD) d 8.93 (d, J = 2.4 Hz, 1H), 8.21-8.19 (m, 2 11), 7.97 (d, J = 4.0 Hz, 1H), 4.81 (dd, J = 2.8, 9.4 Hz, 1H), 2.24-2.16 (m, 1H), 2.11-2.05 (m, 1H), 1.74 (m, 2H), 1.63-1.52 (m, 4H) and 1.26 (s, 3H) ppm |
| 678 | A | A | 388.44 | 3.13 | H NMR (300.0 MHz, MeOD) d 8.67 (dd, J = 2.4, 9.1 Hz, 1H), 8.47 (s, 1H), 8.34-8.31 (m, 2H), 5.27-5.23 (m, 1H), 2.12-2.04 (m, 1H), 1.88-1.80 (m, 4H), 1.66-1.56 (m, 3H) and 1.35 (s, 3H) ppm |
| 679 | A | A | 471.06 | 3.28 |  |
| 680 | A | A | 471.19 | 3.31 |  |
| 681 | A | A | 447.5 | 3.65 | H NMR (300.0 MHz, MeOD) d 8.69 (d, J = 2.3 Hz, 1H), 8.49 (s, 1H), 8.36 (t, J = 2.2 Hz, 1H), 8.27 (d, J = 5.6 Hz, 1H), 4.42 (t, J = 3.8 Hz, 1H), 3.89 (t, J = 3.5 Hz, 1H), 2.33 (d, J = 6.0 Hz, 1H), 2.22 (d, J = 11.4 Hz, 1H), 2.00 (d, J = 11.8 Hz, 2H), 1.78-1.39 (m, 4H) and 1.34 (d, J = 8.3 Hz, 6H) ppm |
| 682 | A | A | 473.49 | 3.96 | H NMR (300.0 MHz, MeOD) d 8.68 (d, J = 1.7 Hz, 1H), 8.49 (d, J = 0.8 Hz, 1H), 8.36 (d, J = 2.3 Hz, 1H), 8.27 (d, J = 5.6 Hz, 1H), 4.47-4.38 (m, 1H), 3.94-3.87 (m, 3H), 2.33-2.19 (m, 3H), 2.04-1.88 (m, 3H), 1.90-1.73 (m, 2H), 1.73-1.41 (m, 4H) and 1.36 (d, J = 8.6 Hz, 3H) ppm |
| 683 | A | A | 417.49 | 3.85 | H NMR (300.0 MHz, MeOD) d 8.67 (d, J = 2.3 Hz, 1H), 8.51 (s, 1H), 8.37 (d, J = 2.3 Hz, 1H), 8.28 (d, J = 5.6 Hz, 1H), 4.46-4.36 (m, 1H), 3.95-3.87 (m, 1H), 2.35 (d, J = 11.7 Hz, 1H), 2.23-2.16 (m, 3H), 2.02 (d, J = 10.5 Hz, 2H), 1.77-1.64 (m, 1H), 1.58-1.43 (m, 2H), 1.40-1.23 (m, 1H) and 1.11 (t, J = 7.6 Hz, 3H) ppm |
| 684 | A | A | 429.49 | 3.86 | H NMR (300.0 MHz, MeOD) d 8.61 (d, J = 2.3 Hz, 1H), 8.51 (s, 1H), 8.35 (d, J = 2.3 Hz, 1H), 8.29 (d, J = 5.6 Hz, 1H), 4.42-4.32 (m, 1H), 3.96-3.88 (m, 1H), 2.35 (d, J = 11.7 Hz, 1H), 2.19 (d, J = 12.0 Hz, 1H), 2.04-2.00 (m, 2H), 1.72-1.27 (m, 5H) and 0.88-0.70 (m, 4H) ppm |
| 685 | A | A | 431.49 | 3.87 | H NMR (300.0 MHz, MeOD) d 8.60 (d, J = 2.3 Hz, 1H), 8.56-8.52 (m, 1H), 8.33 (dd, J = 2.3, 5.7 Hz, 1H), 8.28 (d, J = 5.6 Hz, 1H), 4.39-4.30 (m, 1H), 3.94-3.86 (m, 1H), 2.48-2.34 (m, 2H), 2.17 (d, J = 11.8 Hz, 1H), 1.99 (d, J = 11.8 Hz, 2H), 1.71-1.67(m, 1H), 1.62-1.27 (m, 3H) and 1.10 (d, J = 6.1 Hz, 6H) ppm |
| 686 | A | A | 443.49 | 3.99 | H NMR (300.0 MHz, MeOD) d 8.62 (d, J = 2.3 Hz, 1H), 8.51 (s, 1H), 8.35 (d, J = 2.3 Hz, 1H), 8.28 (d, J = 5.6 Hz, 1H), 4.43-4.32 (m, 1H), 4.00-3.92 (m, 1H), 2.31 (d, J = 11.8 Hz, 1H), 2.21 (d, J = 12.1 Hz, |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| | | | | | 1H), 2.04-1.97 (m, 2H), 1.76-1.58 (m, 2H), 1.53-1.33 (m, 2H), 1.32 (s, 3H), 1.18-1.03 (m, 2H) and 0.63-0.55 (m, 2H) ppm |
| 687 | A | C | 450.2 | 3.43 | |
| 688 | A | A | 475.41 | 4.65 | |
| 689 | A | A | 445.47 | 3.7 | H NMR (300.0 MHz, MeOD) d 8.69 (d, J = 2.3 Hz, 1H), 8.49 (s, 1H), 8.37 (d, J = 2.2 Hz, 1H), 8.27 (d, J = 5.6 Hz, 1H), 4.48-4.41 (m, 1H), 4.00-3.93 (m, 1H), 2.35 (d, J = 6.0 Hz, 1H), 2.22 (d, J = 11.3 Hz, 1H), 2.03 (d, J = 13.0 Hz, 2H), 1.74-1.35 (m, 4H), 1.18-1.14 (m, 2H) and 0.99-0.86 (m, 2H) ppm |
| 690 | A | A | 469.47 | 3.84 | H NMR (300.0 MHz, DMSO) d 12.33 (s, 1H), 8.70 (d, J = 2.4 Hz, 1H), 8.28 (d, J = 2.4 Hz, 1H), 8.20 (d, J = 2.6 Hz, 1H), 8.17 (d, J = 4.0 Hz, 1H), 7.35 (d, J = 7.8 Hz, 1H), 4.27-4.17 (m, 1H), 3.67 (s, 3H), 3.64 (s, 3H), 3.21-3.16 (m, 1H), 2.96-2.90 (m, 3H), 2.33-2.20 (m, 2H), 1.99-1.94 (m, 1H), 1.80-1.60 (m, 2H) and 1.47-1.35 (m, 1H) ppm |
| 691 | A | A | | | |
| 692 | A | A | 420.3 | 3.13 | |
| 693 | A | A | 448.32 | 3.51 | |
| 694 | A | A | 420.3 | 2.94 | |
| 695 | A | A | 448.32 | 3.3 | |
| 696 | A | A | 390.42 | 3.29 | 1H NMR (300 MHz, DMSO) d 12.55 (bs, 1H), 8.73 (d, J = 2.4 Hz, 1H), 8.26 (d, J = 2.4 Hz, 1H), 8.16 (s, 1H), 8.10 (d, J = 4.0 Hz, 1H), 7.94 (bs, 1H), 4.11 (bs, 1H), 2.26-2.02 (m, J = 10.7 Hz, 3H), 2.00-1.69 (m, J = 32.8, 20.4 Hz, 4H), 1.68-1.21 (m, 5H). |
| 697 | A | A | 447.49 | 3.91 | H NMR (300.0 MHz, MeOD) d 8.71 (s, 1H), 8.51 (s, 1H), 8.39 (s, 1H), 8.28 (d, J = 5.5 Hz, 1H), 4.46-4.38 (m, 1H), 3.69-3.61 (m, 1H), 2.37 (d, J = 11.7 Hz, 1H), 2.18 (d, J = 10.6 Hz, 1H), 2.07-1.98 (m, 2H), 1.74-1.62 (m, 1H), 1.57-1.39 (m, 2H), 1.39-1.25 (m, 1H) and 1.19 (d, J = 6.1 Hz, 6H) ppm |
| 698 | A | A | 447.48 | 3.6 | H NMR (300.0 MHz, MeOD) d 8.71 (s, 1H), 8.50 (s, 1H), 8.38 (d, J = 1.6 Hz, 1H), 8.28 (d, J = 5.3 Hz, 1H), 4.46-4.39 (m, 1H), 3.93 (t, J = 6.4 Hz, 2H), 3.62 (t, J = 11.5 Hz, 1H), 2.38 (d, J = 11.1 Hz, 1H), 2.18 (d, J = 11.0 Hz, 1H), 2.07-1.99 (m, 2H), 1.71-1.49 (m, 4H), 1.35-1.22 (m, 2H) and 0.93 (s, 3H) ppm |
| 699 | A | A | 461.51 | 4.18 | H NMR (300.0 MHz, MeOD) d 8.70 (s, 1H), 8.51 (s, 1H), 8.39 (s, 1H), 8.28 (d, J = 5.3 Hz, 1H), 4.46-4.39 (m, 1H), 3.77 (d, J = 6.5 Hz, 2H), 3.70-3.62 (m, 1H), 2.38 (d, J = 11.8 Hz, 1H), 2.18 (d, J = 10.6 Hz, 1H), 2.07-1.99 (m, 2H), 1.88-1.84 (m, 1H), 1.71-1.28 (m, 4H) and 0.91 (d, J = 4.5 Hz, 6H) ppm |
| 700 | A | A | 433.49 | 4 | H NMR (300.0 MHz, MeOD) d 8.70 (s, 1H), 8.50 (s, 1H), 8.38 (d, J = 1.9 Hz, 1H), 8.28 (d, J = 5.5 Hz, 1H), 4.46-4.38 (m, 1H), 4.01 (q, J = 7.0 Hz, 2H), 3.66 (t, J = 11.7 Hz, 1H), 2.38 (d, J = 11.3 Hz, 1H), 2.18 (d, J = 11.0 Hz, 1H), 2.07-1.99 (m, 2H), 1.75-1.62 (m, 1H), 1.57-1.39 (m, 2H) and 1.36-1.19 (m, 4H) ppm |
| 701 | A | A | 457.48 | 4.03 | H NMR (300.0 MHz, MeOD) d 8.69 (s, 1H), 8.49 (s, 1H), 8.37 (d, J = 1.6 Hz, 1H), 8.27 (d, J = 5.4 Hz, 1H), 4.55 (s, 2H), 4.37 (t, J = 11.6 Hz, 1H), 3.70-3.57 (m, 1H), 2.37 (d, J = 10.7 Hz, 1H), 2.17 (d, J = 11.2 Hz, 1H), 2.07-1.98 (m, 2H), 1.78 (s, 3H) and 1.70-1.22 (m, 4H) ppm |
| 702 | A | A | 443.46 | 3.84 | H NMR (300.0 MHz, MeOD) d 8.69 (s, 1H), 8.49 (s, 1H), 8.38 (s, 1H), 8.27 (d, J = 5.4 Hz, 1H), 4.61 (s, 1H), 4.41 (t, J = 11.7 Hz, 1H), 3.65-3.53 (m, 3H), 2.37 (d, J = 8.2 Hz, 1H), 2.17 (d, J = 10.9 Hz, 1H), 2.02 (t, J = 13.2 Hz, 2H) and 1.70-1.27 (m, 4H) ppm |
| 703 | A | A | 417.52 | 3.66 | H NMR (300.0 MHz, MeOD) d 8.54 (s, 1H), 8.39 (dd, J = 2.7, 9.1 Hz, 1H), 8.34 (s, 1H), 8.29 (d, J = 5.5 Hz, 1H), 4.49-4.41 (m, 1H), 4.04-3.97 (m, 1H), 3.88 (s, 2H), 3.41 (s, 3H), 2.35 (d, J = 11.8 Hz, 1H), 2.21 (d, J = 11.2 Hz, 1H), 2.02 (d, J = 11.7 Hz, 2H) and 1.73-1.36 (m, 4H) ppm |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 704 | A | A | 457.56 | 3.77 | H NMR (300.0 MHz, MeOD) d 8.51 (s, 1H), 8.39 (d, J = 9.1 Hz, 1H), 8.34 (s, 1H), 8.27 (d, J = 5.4 Hz, 1H), 4.41 (t, J = 11.3 Hz, 1H), 4.03 (d, J = 10.5 Hz, 1H), 3.91 (t, J = 11.3 Hz, 1H), 3.79-3.76 (m, 1H), 3.51 (d, J = 7.5 Hz, 1H), 2.31 (d, J = 11.2 Hz, 1H), 2.20 (d, J = 12.4 Hz, 1H), 2.00-1.89 (m, 4H) and 1.67-1.33 (m, 8H) ppm |
| 705 | A | A | 403.49 | 3.47 | H NMR (300.0 MHz, MeOD) d 8.54 (s, 1H), 8.40 (dd, J = 2.6, 9.1 Hz, 1H), 8.36 (s, 1H), 8.28 (d, J = 5.5 Hz, 1H), 4.43 (t, J = 11.7 Hz, 1H), 3.68-3.61 (m, 4H), 2.39 (d, J = 11.1 Hz, 1H), 2.19 (d, J = 11.2 Hz, 1H), 2.03-1.99 (m, 2H) and 1.65-1.25 (m, 4H) ppm |
| 706 | A | A | 458.53 | 3.42 | H NMR (300.0 MHz, MeOD) d 8.52 (s, 1H), 8.37 (dd, J = 2.7, 9.1 Hz, 1H), 8.34 (s, 1H), 8.27 (d, J = 5.6 Hz, 1H), 4.43 (t, J = 11.8 Hz, 1H), 3.81 (t, J = 11.6 Hz, 1H), 3.65-3.62 (m, 4H), 3.37-3.34 (m, 4H), 2.35 (d, J = 11.7 Hz, 1H), 2.22 (d, J = 11.8 Hz, 1H), 2.01 (d, J = 11.0 Hz, 2H) and 1.66-1.29 (m, 4H) ppm |
| 707 | | | | | |
| 708 | A | A | 432.5 | 3.49 | H NMR (300.0 MHz, MeOD) d 8.86 (d, J = 2.2 Hz, 1H), 8.47 (s, 1H), 8.38 (d, J = 2.2 Hz, 1H), 8.31 (d, J =5.6 Hz, 1H), 5.22-5.19 (m, 1H), 2.15-2.10 (m, 1H), 2.01-1.72 (m, 6H), 1.64-1.53 (m, 3H), 1.40-1.13 (m, 2H) and 0.90 (t, J = 7.2 Hz, 3H) ppm |
| 709 (enantiomer 1, see 710) | A | A | 390.46 | 4.11 | H NMR (300.0 MHz, CDCl3) d 9.89 (s, 1H), 8.86 (d, J = 2.1 Hz, 1H), 8.30 (s, 1H), 8.16 (d, J = 2.2 Hz, 1H), 8.02 (d, J = 3.4 Hz, 1H), 7.28 (s, H), 6.81 (d, J = 5.6 Hz, 1H), 4.65-4.61 (m, 1H), 2.04 (d, J = 12.8 Hz, 1H), 1.87-1.84 (m, 3H), 1.77-1.71 (m, 3H), 1.65-1.55 (m, 2H), 1.38-1.22 (m, 3H) and 0.92-0.85 (m, 3H) ppm |
| 710 (enantiomer 2, see 709) | A | A | 390.47 | 4.02 | H NMR (300.0 MHz, CDCl3) d 10.15 (s, 1H), 8.90 (d, J = 2.3 Hz, 1H), 8.29 (dd, J = 2.4, 7.3 Hz, 1H), 8.16 (d, J = 2.7 Hz, 1H), 8.05-8.02 (m, 1H), 7.30 (d, J = 11.4 Hz, H), 4.85 (d, J = 8.2 Hz, 1H), 4.68-4.55 (m, 1H), 2.30-2.24 (m, 2H), 2.10-1.95 (m, 1H), 1.81-1.72 (m, 5H), 1.66-1.49 (m, 2H), 1.45-1.16 (m, 3H) and 1.01-0.90 (m, 3H) ppm |
| 711 | C | C | 503.52 | 2.91 | 1H NMR (300 MHz, MeOD) d 8.94 (d, J = 2.2 Hz, 1H), 8.53 (s, 1H), 8.45-8.31 (m, 2H), 5.25 (d, J = 9.4 Hz, 1H), 4.15-3.95 (m, 2H), 3.84 (t, J = 10.8 Hz, 2H), 3.52 (t, J = 14.1 Hz, 3H), 3.26-3.03 (m, 3H), 2.66 (s, 2H), 2.40-2.13 (m, 3H), 2.02 (d, J = 32.7 Hz, 4H), 1.82-1.46 (m, 3H). |
| 712 | A | A | 402.47 | 3.98 | H NMR (300.0 MHz, DMSO) d 12.28 (s, 1H), 8.77 (d, J = 2.4 Hz, 1H), 8.27 (d, J = 2.4 Hz, 1H), 8.18 (s, 1H), 8.11 (d, J = 4.0 Hz, 1H), 7.34 (d, J = 7.7 Hz, 1H), 5.98-5.84 (m, 1H), 5.06 (s, 1H), 5.02 (d, J = 2.8 Hz, 1H), 4.52-4.42 (m, 1H), 4.20 (s, 1H), 2.19 (d, J = 7.3 Hz, 2H), 2.06 (d, J = 11.8 Hz, 1H), 1.95-1.77 (m, 2H), 1.57 (d, J = 12.0 Hz, 2H), 1.44 (t, J = 12.3 Hz, 1H) and 1.28-1.16 (m, 2H) ppm |
| 713 | A | A | 402.49 | 4.13 | H NMR (300.0 MHz, DMSO) d 12.31 (s, 1H), 8.72 (d, J = 2.4 Hz, 1H), 8.28 (d, J = 2.4 Hz, 1H), 8.19 (s, 1H), 8.14 (d, J = 4.0 Hz, 1H), 7.51 (d, J = 7.4 Hz, 1H), 6.00-5.86 (m, 1H), 5.09-5.03 (m, 2H), 4.67 (s, 1H), 4.36-4.33 (m, 1H), 2.33 (d, J = 7.0 Hz, 2H), 1.86-1.70 (m, 3H) and 1.65-1.35 (m, 5H) ppm |
| 714 | A | A | 435.34 | 3.3 | |
| 715 | A | A | 491.39 | 3.68 | |
| 716 | A | A | 477.37 | 3.75 | |
| 717 | A | A | 436.48 | 3.71 | H NMR (300.0 MHz, DMSO) d 12.28 (d, J = 2.0 Hz, 1H), 8.79 (dd, J = 2.4, 5.4 Hz, 1H), 8.26 (d, J = 2.4 Hz, 1H), 8.17 (d, J = 2.7 Hz, 1H), 8.12 (dd, J = 1.5, 4.0 Hz, 1H), 7.35 (d, J = 7.9 Hz, 1H), 4.73 (t, J = 3.9 Hz, 1H), 4.55-4.51 (m, 2H), 3.85-3.82 (m, 1H), 2.02-1.87 (m, 3H), 1.72-1.41 (m, 5H) and 1.31-1.19 (m, 2H) ppm |
| 718 | A | A | 436.49 | 3.6 | H NMR (300.0 MHz, DMSO) d 12.29 (s, 1H), 8.71 (t, J = 2.3 Hz, 1H), 8.27 (d, J = 2.4 Hz, 1H), 8.19 (dd, J = 2.8, 4.5 Hz, 1H), 8.15 (t, J = 3.7 Hz, 1H), 7.52 (t, J = 7.7 Hz, 1H), 4.97 (d, J = 16.0 Hz, 1H), |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| | | | | | 4.77 (dd, J = 3.8, 10.5 Hz, 1H), 4.54 (t, J = 5.6 Hz, 1H), 4.32 (m, 1H), 3.86 (m, 1H), 2.00-1.97 (m, 2H), 1.82-1.63 (m, 4H) and 1.59-1.45 (m, 4H) ppm |
| 719 | A | A | 443.5 | 4.07 | H NMR (300.0 MHz, DMSO) d 12.58 (s, 1H), 8.68 (d, J = 2.2 Hz, 1H), 8.36-8.23 (m, 4H), 7.81 (t, J = 5.5 Hz, 1H), 4.17 (d, J = 7.5 Hz, 1H), 2.94 (t, J = 6.0 Hz, 2H), 2.43-2.35 (m, 1H), 2.14-1.22 (m, 8H), 0.91-0.80 (m, 1H), 0.40-0.31 (m, 2H) and 0.20-0.10 (m, 2H) ppm |
| 720 | A | A | 459.5 | 3.99 | H NMR (300.0 MHz, DMSO) d 12.72 (s, 1H), 8.65 (s, 1H), 8.54 (s, 1H), 8.45 (d, J = 2.7 Hz, 1H), 8.39-8.37 (m, 2H), 4.42-4.08 (m, 3H), 4.02-3.88 (m, 2H), 3.64-3.57 (m, 1H), 3.18-3.12 (m, 3H) and 2.12-1.19 (m, 9H) ppm |
| 721 | A | A | 417.5 | 3.93 | H NMR (300.0 MHz, DMSO) d 12.31 (s, 1H), 8.72 (d, J = 2.4 Hz, 1H), 8.29 (d, J = 2.4 Hz, 1H), 8.19 (s, 1H), 8.14 (d, J = 4.0 Hz, 1H), 7.71 (s, 1H), 7.53 (d, 1H), 4.19-4.06 (m, 1H), 3.05 (dd, J = 5.6, 7.1 Hz, 2H), 2.33 (m, 1H), 2.13-1.20 (m, 8H) and 0.98 (t, 3H) ppm |
| 722 | A | A | 447.52 | 4.11 | H NMR (300.0 MHz, DMSO) d 13.14 (s, 1H), 9.50-9.45 (m, 1H), 9.26 (s, 1H), 8.58 (d, J = 5.1 Hz, 1H), 8.49 (d, J = 5.1 Hz, 1H), 8.40 (s, 1H), 8.01 (s, 1H), 5.60 (s, H), 5.50 (s, 1H), 4.39 (s, 1H), 2.94 (d, J = 7.3 Hz, 1H), 2.81 (qn, J = 6.3 Hz, 1H), 2.51 (s, H), 2.32 (d, J = 7.0 Hz, 2H), 2.08 (s, 2H), 1.87-1.64 (m, 4H), 1.17 (t, J = 7.2 Hz, 3H) and −0.00 (s, H) ppm |
| 723 | A | A | 445.5 | 4.03 | 1H NMR (300 MHz, MeOD) d 8.66 (d, J = 2.2 Hz, 1H), 8.51 (s, 1H), 8.37 (d, J = 2.2 Hz, 1H), 8.29 (d, J = 5.6 Hz, 1H), 4.51-4.28 (m, 1H), 4.01-3.80 (m, 1H), 2.40-2.15 (m, 2H), 2.11-1.86 (m, 2H), 1.84-1.26 (m, 4H), 1.18 (s, 9H) |
| 724 | A | A | 428.45 | 3.69 | 1H NMR (300 MHz, MeOD) d 8.69 (d, J = 1.9 Hz, 1H), 8.53 (s, 1H), 8.38 (d, J = 1.7 Hz, 1H), 8.29 (d, J = 5.3 Hz, 1H), 4.52-4.34 (m, 1H), 4.02-3.84 (m, J = 11.5 Hz, 1H), 3.52 (s, 2H), 2.40 (d, J = 12.0 Hz, 1H), 2.22 (d, J = 10.9 Hz, 1H), 2.14-1.97 (m, 2H), 1.81-1.23 (m, 4H). |
| 725 | A | A | 446.48 | 2.47 | 1H NMR (300 MHz, MeOD) d 8.73 (d, J = 1.6 Hz, 1H), 8.56 (s, 1H), 8.47 (s, 1H), 8.37 (t, J = 7.8 Hz, 1H), 8.31 (d, J = 5.2 Hz, 1H), 4.56-4.37 (m, 1H), 4.13-3.98 (m, 1H), 3.93 (s, 2H), 2.92 (d, J = 3.6 Hz, 6H), 2.43 (d, J = 12.4 Hz, 1H), 2.22 (d, J = 12.4 Hz, 1H), 2.07 (t, J = 13.1 Hz, 2H), 1.83-1.24 (m, 4H). |
| 726 | A | A | 443.53 | 3.92 | 1H NMR (300 MHz, MeOD) d 8.61 (d, J = 2.3 Hz, 1H), 8.53 (s, 1H), 8.35 (d, J = 2.2 Hz, 1H), 8.29 (d, J = 5.6 Hz, 1H), 4.47-4.24 (m, 1H), 4.01-3.77 (m, 1H), 3.14-2.98 (m, 1H), 2.41-1.01 (m, 14H). |
| 727 | A | A | 457.51 | 4.04 | 1H NMR (300 MHz, MeOD) d 8.68 (d, J = 2.3 Hz, 1H), 8.52 (s, 1H), 8.36 (d, J = 2.3 Hz, 1H), 8.28 (d, J = 5.6 Hz, 1H), 4.51-4.30 (m, 1H), 4.04-3.80 (m, 1H), 3.25-3.04 (m, 1H), 2.39 (d, J = 20.1 Hz, 1H), 2.22 (d, J = 12.3 Hz, 1H), 2.02 (d, J = 12.9 Hz, 2H), 1.94-1.24 (m, 4H), 1.12 (dd, J = 10.1, 3.0 Hz, 6H), 1.04-0.94 (m, J = 9.4, 4.3 Hz, 1H), 0.75-0.62 (m, 1H). |
| 728 | A | A | 459.56 | 4.17 | 1H NMR (300 MHz, MeOD) d 8.68 (d, J = 2.3 Hz, 1H), 8.49 (d, J = 22.9 Hz, 1H), 8.36 (t, J = 5.8 Hz, 1H), 8.28 (d, J = 5.6 Hz, 1H), 4.53-4.27 (m, J = 11.6, 8.2, 3.7 Hz, 1H), 4.02-3.83 (m, J = 15.7, 7.7 Hz, 1H), 2.37 (d, J = 12.0 Hz, 1H), 2.22 (d, J = 12.1 Hz, 1H), 2.06 (d, J = 14.0 Hz, 2H), 2.06 (s, 2H), 1.82-1.15 (m, 4H), 1.01 (s, 9H). |
| 729 | A | A | 486.54 | 2.78 | |
| 730 | A | A | 488.52 | 3.82 | |
| 731 | C | C | | | (400 MHz, DMSO-d6): 12.33 (br s, exchanged with D2O, 2H), 8.72 (d, J = 1.6 Hz , 1H), 8.27(d, J = 2.4 Hz, 1H), 8.20 (s, 1H), 8.13 (d, J = 3.6 Hz, 1H), 7.47(d, J = 7.2 Hz, exchanged with D2O, 1H), 4.04-4.02 (m, 1H), 2.17-2.00 (m, 5H), 1.63-1.39 (m, 4H). |
| 732 | A | A | | | (400 MHz, CDCl3): 12.33(s, 1H), 8.75(d, J = 2.4Hz, 1H), 8.28(d, J = 2.4Hz, 1H), 8.18(s, 1H), |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 733 | A | A | | | 8.12(d, J = 4Hz, 1H), 7.49(d, J = 8Hz, 1H), 4.3(t, J = 5.2Hz, 1H), 4.04-3.97(m, 1H), 3.48-3.43(m, 1H), 3.38-3.34(m, 2H), 2.09-2.0(m, 1H), 1.95-1.93(m, 1H), 1.81-1.25(m, 7H). (400 MHz, DMSO-d6): 12.33(br s, exchanged with D2O, 1H), 8.27(d, J = 2 Hz, 1H), 8.19(s, 1H), 8.11(d, J = 3.6 Hz, 1H), 7.39(d, J = 6.4 Hz, Exchanged with D2O, 1H), 4.05(br s, 1H), 2.39(s,1H), 2.14-2.12(m, 2H), 1.77-1.61(m, 6H). |
| 734 | A | A | 443.4 | 3.39 | 1H NMR (300 MHz, MeOD) d 8.71 (d, J = 2.3 Hz, 1H), 8.49 (s, 1H), 8.38 (d, J = 2.3 Hz, 1H), 8.29 (d, J = 5.6 Hz, 1H), 4.45 (s, 1H), 3.91 (s, 1H), 3.77-3.50 (m, 2H), 2.35 (d, J = 10.0 Hz, 1H), 2.22 (d, J = 11.9 Hz, 1H), 2.02 (d, J = 11.7 Hz, 2H), 1.71 (d, J = 14.0 Hz, 1H), 1.38 (tdd, J = 16.2, 11.9, 4.6 Hz, 6H), 1.08 (t, J = 5.5 Hz, 3H), 1.04-0.94 (m, 1H), 0.61-0.49 (m, 1H). |
| 735 | A | A | 529.46 | 4.62 | |
| 736 | A | A | 489.4 | 4.56 | |
| 737 | A | A | 485.44 | 4.57 | |
| 738 | A | A | 439.37 | 3.31 | 1H NMR (300 MHz, MeOD) d 8.60 (d, J = 37.9 Hz, 1H), 8.33 (d, J = 23.9 Hz, 1H), 7.64 (d, J = 8.1 Hz, 1H), 7.41 (d, J = 8.0 Hz, 1H), 6.00 (t, J = 54.0 Hz, 1H), 4.42 (s, 1H), 4.01 (s, 1H), 2.47-2.31 (m, 2H), 2.23 (d, J = 10.9 Hz, 1H), 2.12-1.97 (m, 2H), 1.77-1.17 (m, 5H), 0.95-0.83 (m, 1H). |
| 739 | A | C | 486.52 | 2.16 | 1H NMR (300 MHz, MeOD) d 8.65 (d, J = 45.0 Hz, 1H), 8.34 (d, J = 23.5 Hz, 1H), 7.70 (d, J = 7.7 Hz, 1H), 7.22 (d, J = 7.6 Hz, 1H), 4.45 (s, 1H), 4.01 (s, 1H), 3.72 (s, 1H), 3.45 (s, 1H), 3.10 (d, J = 11.3 Hz, 1H), 2.82 (d, J = 12.1 Hz, 3H), 2.36 (s, 1H), 2.28-1.25 (m, 16H). |
| 740 | A | | 447.53 | 3.98 | H NMR (300 MHz, MeCD) d 8.73(s, 1H), 8.45(s, 1H), 8.37(d, J = 2.1 Hz, 1H), 7.25(d, J = 5.5 Hz, 1H), 4.89-4.8 (m, 1H), 3.02-2.95(m, 2H), 2.86(d, J = 0.5 Hz, 1H), 2.65(d, J = 12.0 Hz, 1H), 2.46(d, J = 12.2 Hz, 1H), 2.03-1.98(m, 1H), 1.9-1.8(m, 1H), 1.78-1.68(m, 1H), 1.5-1.3(m, 2H), 0.95(t, J = 7.3 Hz, 3H) and 0.0(s, TMS) |
| 741 | A | | 470.46 | 3.82 | 1H NMR (300 MHz, DMSO) d 12.32 (s, 1H), 8.70 (d, J = 2.4 Hz, 1H), 8.27 (d, J = 2.4 Hz, 1H), 8.26 (d, J = 2.8 Hz, 1H), 8.18 (d, J = 3.9 Hz, 1H), 7.34 (d, J = 7.1 Hz, 1H), 5.77 (d, J = 2.9 Hz, 1H), 4.60 (s, 1H), 3.73 (dd, J = 10.1, 6.3 Hz, 6H), 2.30-2.15 (m, 1H), 2.04-1.86 (m, 1H), 1.85-1.50 (m, 6H). |
| 742 | A | | 470.49 | 3.7 | 1H NMR (300 MHz, DMSO) d 12.30 (s, 1H), 8.75 (d, J = 2.4 Hz, 1H), 8.27 (d, J = 2.4 Hz, 1H), 8.18 (d, J = 2.8 Hz, 1H), 8.14 (d, J = 4.0 Hz, 1H), 7.44 (d, J = 7.7 Hz, 1H), 5.38 (s, 1H), 4.55-4.36 (m, 1H), 3.71 (d, J = 3.1 Hz, 3H), 3.68 (d, J = 3.2 Hz, 3H), 2.16-2.01 (m, 2H), 2.00-1.72 (m, 3H), 1.71-1.41 (m, 2H), 1.39-1.18 (m, 1H). |
| 743 | A | A | 419.34 | 2.86 | |
| 744 | A | A | 419.34 | 2.61 | |
| 745 | A | A | 447.5 | 3.8 | 1H NMR (300 MHz, MeOD) d 8.70 (d, J = 18.1 Hz, 1H), 8.50 (s, 1H), 8.38 (d, J = 10.4 Hz, 1H), 8.30 (s, 1H), 4.54 (s, 2H), 4.19 (s, 2H), 3.42 (s, 3H), 2.95 (d, J = 15.2 Hz, 3H), 2.25 (d, J = 11.8 Hz, 1H), 2.09 (s, 2H), 1.98-1.39 (m, J = 62.5 Hz, 5H). |
| 746 (racemic mixture of diastereomer 1 with respect 1-OH of the cyclohexyl ring, see 755) | A | | 422.48 | 3.6 | |
| 747 | A | A | 448.48 | 3.42 | |
| 748 | A | | 448.5 | 3.51 | |
| 749 | A | A | 422.47 | 3.6 | |
| 750 | A | A | 447.36 | 3.07 | |
| 751 | A | A | 433.35 | 2.88 | |
| 752 | A | A | 447.36 | 2.78 | |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 753 | A | A | 454.4 | 3.32 | |
| 754 | A | C | 406.35 | 3.16 | 1H NMR (300 MHz, MeOD) d 8.70 (d, J = 2.2 Hz, 1H), 8.47 (s, 1H), 8.37 (d, J = 2.2 Hz, 1H), 8.28 (d, J = 5.5 Hz, 1H), 5.37-4.57 (m, 49H), 2.42 (dd, J = 13.3, 4.2 Hz, 2H), 2.15 (d, J = 10.4 Hz, 1H), 2.07-1.87 (m, 3H), 1.77 (dd, J = 18.1, 8.6 Hz, 3H). |
| 755 (racemic mixture of diastereomer 2 with respect 1-OH of the cyclohexyl ring, see 746) | A | C | 406.35 | 3.03 | |
| 756 | A | A | 472.45 | 2.24 | |
| 757 | A | A | 399.52 | 3.29 | 1H NMR (300 MHz, MeOD) d 9.00 (d, J = 7.7 Hz, 1H), 8.59 (s, 1H), 8.52 (d, J = 4.8 Hz, 1H), 8.33 (d, J = 5.3 Hz, 1H), 7.69 (d, J = 5.3 Hz, 1H), 4.54-4.32 (m, 1H), 4.18-3.99 (m, 1H), 3.88 (s, 2H), 3.40 (s, 3H), 2.44 (d, J = 11.6 Hz, 1H), 2.13 (d, J = 10.9 Hz, 1H), 1.97 (t, J = 13.6 Hz, 2H), 1.77-1.28 (m, 4H). |
| 758 | A | A | 427.4 | 3.26 | 1H NMR (300 MHz, MeOD) d 8.71 (dd, J = 14.6, 2.9 Hz, 1H), 8.49 (s, 1H), 8.38 (s, 1H), 8.29 (d, J = 5.6 Hz, 1H), 4.42 (t, J = 11.9 Hz, 1H), 3.95 (t, J = 11.6 Hz, 2H), 2.39 (d, J = 12.1 Hz, 1H), 2.27-2.12 (m, 1H), 2.03 (d, J = 10.0 Hz, 2H), 1.95 (s, 1H), 1.70 (d, J = 13.1 Hz, 1H), 1.61-1.18 (m, 8H). |
| 759 | A | A | 460.48 | 2.15 | 1H NMR (300 MHz, MeOD) d 8.72 (d, J = 1.8 Hz, 1H), 8.57-8.44 (m, 1H), 8.38 (d, J = 1.4 Hz, 1H), 8.29 (d, J = 5.0 Hz, 1H), 4.45 (s, 1H), 4.00 (s, 1H), 3.86 (d, J = 8.5 Hz, 1H), 2.97-2.80 (m, 7H), 2.47 (s, 1H), 2.22 (d, J = 11.5 Hz, 1H), 2.06 (d, J = 11.1 Hz, 2H), 1.84-1.19 (m, 9H). |
| 760 | A | A | | | (400 MHz, DMSO-d6): 12.35 (br s, 1H), 8.75 (d, J = 2.4 Hz, 1H), 8.29 (d, J = 2 Hz, 1H), 8.2-8.17 (m, 2H), 6.97 (d, J = 6.8 Hz, 1H), 4.6-4.54 (m,1H), 4.5(br s, 1H), 3.58-3.48(m, 2H), 2.57 (s, 1H), 2.33-2.227 (m, 2H), 1.76-1.69 (m, 2H), 1.61-1.59 (m, 1H), 1.43-1.32 (m, 2H) |
| 761 | A | A | | | (400 MHz, DMSO-d6): 12.35 (br s, 1H), 8.75 (d, J = 2.4 Hz, 1H), 8.29 (d, J = 2 Hz,1H), 8.2-8.17(m, 2H), 6.97(d, J = 6.8 Hz, 1H), 4.6-4.55 (m, 1H), 4.5 (br s, 1H), 3.58-3.5 (m, 2 H), 2.56 (s, 1H), 2.33-2.227 (m, 2H), 1.76-1.69 (m, 2H), 1.61-1.59 (m, 1H), 1.43-1.32 (m, 2H) |
| 762 | A | A | 406.35 | 3.23 | |
| 763 | A | A | 406.35 | 3.06 | 1H NMR (300 MHz, MeOD) d 8.70 (d, J = 2.2 Hz, 1H), 8.47 (s, 1H), 8.37 (d, J = 2.2 Hz, 1H), 8.28 (d, J = 5.5 Hz, 1H), 5.37-4.57 (m, 49H), 3.38-3.26 (m, 26H), 2.42 (dd, J = 13.3, 4.2 Hz, 2H), 2.15 (d, J = 10.4 Hz, 1H), 2.07-1.87 (m, 3H), 1.77 (dd, J = 18.1, 8.6 Hz, 3H). |
| 764 | A | A | 420.36 | 3.2 | 1H NMR (300 MHz, MeOD) d 8.70 (d, J = 2.3 Hz, 1H), 8.50 (s, 1H), 8.39 (d, J = 2.3 Hz, 1H), 8.30 (d, J = 5.5 Hz, 1H), 4.91-4.77 (m, 27H), 3.77 (s, 3H), 3.38-3.26 (m, 39H), 2.45 (dd, J = 13.2, 3.8 Hz, 2H), 2.20 (d, J = 9.8 Hz, 1H), 2.06 (s, 1H), 2.00-1.82 (m, 3H), 1.82-1.23 (m, 5H). |
| 765 | A | A | 453.38 | 3.34 | |
| 766 | A | A | 449.41 | 3.4 | |
| 767 | A | A | 487.42 | 3.56 | |
| 768 | A | A | 486.46 | 2.24 | |
| 769 | A | C | 415.5 | 2.75 | 1H NMR (300 MHz, MeOD) d 8.84 (s, 1H), 8.31 (s, 2H), 6.99 (s, 1H), 4.42 (s, 1H), 4.08 (s, 1H), 3.90 (s, 2H), 3.42 (s, 3H), 2.40 (s, J = 20.9 Hz, 1H), 2.26-1.85 (m, J = 27.0 Hz, 4H). |
| 770 | A | A | 469.44 | 3.22 | NMR 1H (MeOH-d4): 9.0 (s, 1H), 8.6 (m, 2H), 8.3 (m, 2H), 8.1 (s, 1H), 4.5 (m, 1H), 4.1 (m, 1H), 3.9 (s, 3H), 1.3-2.6 (m, 10H). |
| 771 | A | A | 472.45 | 2.21 | |
| 772 | A | A | 455.43 | 2.97 | |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 773 | A | A | 451.4 | 3.31 | NMR 1H (MeOH-d4): 8.7 (s, 1H), 8.5 (s, 1H), 8.3 (s, 1H), 8.2 (d, 1H), 4.7 (s, 1H), 4.15-4.5 (m, 4H), 3.7 (t, 1H), 2.4 (m, 1H), 2.2 (m, 1H), 2.0 (t, 2H), 1.2-1.8 (m, 4H). |
| 774 | A | C | 472.45 | 2.21 | NMR 1H (MeOH-d4): 8.7 (d, 2H), 8.3 (d, 2H), 4.4 (m, 1H), 3.6-4.0 (m, 3H), 3.3 (s, 3H), 2.9 (m, 3H), 2.0-2.5 (m, 6H), 1.2-1.8 (m, 4H). |
| 775 | A | A | 435.34 | 3.21 | 1H NMR (300 MHz, MeOD) d 7.40 (d, J = 2.1 Hz, 1H), 7.21 (s, 1H), 7.10 (d, J = 2.2 Hz, 1H), 7.03 (d, J = 5.6 Hz, 1H), 2.71 (dt, J = 13.2, 6.7 Hz, 1H), 2.55 (dt, J = 18.3, 9.2 Hz, 1H), 2.26 (s, 3H), 0.90-0.67 (m, 2H), 0.58 (d, J = 13.5 Hz, 1H), 0.53-0.37 (m, 2H), 0.37-0.18 (m, 1H). |
| 776 | A | A | 392.34 | 2.9 | 1H NMR (300 MHz, MeOD) d 7.40 (d, J = 2.1 Hz, 1H), 7.21 (s, 1H), 7.10 (d, J = 2.2 Hz, 1H), 7.03 (d, J = 5.6 Hz, 1H), 2.71 (dt, J = 13.2, 6.7 Hz, 1H), 2.55 (dt, J = 18.3, 9.2 Hz, 1H), 2.26 (s, 3H), 0.90-0.67 (m, 2H), 0.58 (d, J = 13.5 Hz, 1H), 0.53-0.37 (m, 2H), 0.37-0.18 (m, 1H). |
| 777 | C | C | 410.32 | 2.37 | |
| 778 | A | A | 507.53 | 3.54 | 1H NMR (300 MHz, DMSO) d 12.32 (s, 1H), 8.72 (dd, J = 4.9, 2.4 Hz, 1H), 8.28 (d, J = 2.4 Hz, 1H), 8.22-8.09 (m, 2H), 7.45 (dd, J = 16.1, 8.1 Hz, 1H), 6.85 (d, J = 11.9 Hz, 1H), 4.51-4.41 (m, 1H), 4.32-4.16 (m, 2H), 3.84-3.71 (m, 2H), 3.60 (s, 1H), 3.26 (d, J = 2.6 Hz, 3H), 2.70-2.56 (m, J = 22.6 Hz, 1H), 2.45 (s, 1H), 2.17-1.92 (m, 2H), 1.77-1.41 (m, 4H), 1.33-1.11 (m, 2H). |
| 779 | A | A | 433.42 | 3.22 | 1H NMR (300 MHz, MeOD) d 8.72 (d, J = 2.2 Hz, 2H), 8.48 (s, 2H), 8.34 (dd, J = 23.7, 3.9 Hz, 3H), 4.99 (d, J = 5.4 Hz, 3H), 4.88 (s, 1H), 4.85-4.67 (m, 32H), 3.44-2.95 (m, 44H), 2.29 (dd, J = 13.5, 4.1 Hz, 3H), 2.11 (d, J = 9.5 Hz, 2H), 2.04-1.80 (m, 7H), 1.76 (s, 3H), 1.13 (t, J = 7.2 Hz, 4H). |
| 780 | A | A | 487.36 | 3.57 | |
| 781 | A | A | 394.32 | 2.81 | |
| 782 | A | A | 424.5 | 3.96 | |
| 783 | A | A | 456.39 | 2.9 | |
| 784 | A | A | 473.41 | 3.29 | |
| 785 | A | A | 461.44 | 3.59 | |
| 786 | A | A | 419.34 | 3.01 | |
| 787 | A | A | 382.399 | 2.47 | (400 MHz, DMSO-d6): 12.36 (s, exchanged with D2O, 1H), 8.71 (d, J = 2.4 Hz, 1H), 8.29 (d, J = 1.6 Hz, 1H), 8.25 (s, 1H), 8.18 (d,J = 4Hz, 1H), 7.58 (d, J = 7.2 Hz, exchanged with D2O, 1H), 4.27 (br s, 1H), 2.15-2.06 (m, 6H), 1.75-1.69 (m, 2H). |
| 788 | A | A | 362.399 | 2.68 | (400 MHz, DMSO-d6): 12.34 (s, exchanged with D2O, 1H), 8.72 (d, J = 2.4 Hz, 1H),. 8.28 (d, J =2.4 Hz, 1H), 8.20 (d, J = 2.4 Hz, 1H), 8.13 (d, J =4.4 Hz, 1H), 7.5 (d, J = 6 Hz, exchanged with D2O, 1H), 4.42 (br s, exchanged with D2O, 1H), 4.04 (t, J = 3.6 Hz, 1H), 3.88 (s, 1H), 1.89-1.6 ( |
| 789 | A | A | | | H NMR (300.0 MHz, DMSO) d 12.90 (s, 1H), 8.96 (s, 1H), 8.84 (s, 1H), 8.64 (s, 1H), 8.42 (d, J = 5.1 Hz, 2H), 7.85 (t, J = 5.4 Hz, 1H), 4.22 (d, J = 7.8 Hz, 1H), 3.34-3.17 (m, 7H) and 2.09-1.26 (m, 9H) ppm |
| 790 | A | A | 406.49 | 3.87 | H NMR (300.0 MHz, CDCl3) d 14.46 (s, 1H), 8.81 (s, 1H), 8.22 (s, 1H), 8.12 (s, 1H), 7.96 (t, J = 1.6 Hz, 1H), 7.34 (d, J = 11.5 Hz, H), 4.59 (d, J = 3.1 Hz, 1H), 3.94 (s, 2H), 2.04-1.70 (m, 8H), 1.68 (m, 2H), and 0.00 (s, H) ppm |
| 791 | A | A | 434.38 | 3.26 | |
| 792 | A | A | 434.38 | 2.9 | |
| 793 | A | A | 406.5 | 3.69 | H NMR (300.0 MHz, CDCl3) d 9.47 (s, 1H), 8.93 (d, J = 2.3 Hz, 1H), 8.27 (d, J = 2.3 Hz, 1H), 8.16 (d, J = 2.7 Hz, 1H), 8.06 (d, J = 3.4 Hz, 1H), 7.28 (s, H), 4.85 (s, 1H), 4.75 (m, 1H), 4.01-3.97 (m, 2H), 3.07 (s, 1H), 2.50 (m, 2H), 2.30 (m, 1H), 2.10 (m, 1H), 1.89-1.79 (m, 4H), 1.36 (m, 3H) and 0.99 (s, 1H) ppm |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 794 | B | A | 449.48 | 3.9 | |
| 795 | A | A | 432.39 | 3.86 | 1H NMR (300 MHz, CDCl3) d 8.80 (1H, s), 8.25 (1H, s), 8.0 (1H, s), 7.95 (1H, s), 5.2 (1H, m), 4.25 (2H, q), 1.95-1.45 (8H, m), 1.25 (3H, s), 1.15 (3H, t) ppm. |
| 796 | A | A | 446.45 | 3.12 | H NMR (300.0 MHz, MeOD) d 8.73 (s, 1H), 8.52 (s, 1H), 8.38 (s, 1H), 8.31 (br s, 1H), 4.34 (m, 1H), 2.60-2.56 (m, 1H), 2.27 (m, 1H), 2.08 (m, 3H) and 1.89-1.78 (m, 3H) ppm |
| 797 | A | A | 450.5 | 3.86 | 1H NMR (300 MHz, DMSO) d 12.30 (s, 1H), 8.73 (t, J = 2.7 Hz, 1H), 8.28 (d, J = 2.4 Hz, 1H), 8.18 (d, J = 2.8 Hz, 1H), 8.14 (d, J = 3.9 Hz, 1H), 7.53 (d, J = 7.6 Hz, 1H), 5.29 (d, J = 5.0 Hz, 1H), 4.79-4.65 (m, 2H), 4.37 (s, 1H), 3.23-3.14 (m, 2H), 2.02 (dd, J = 40.1, 10.3 Hz, 1H), 1.91-1.64 (m, 7H), 1.59-1.44 (m, 3H), 1.19 (d, J = 10.6 Hz, 3H). |
| 798 | A | A | 446.34 | 3.37 | H NMR (300.0 MHz, MeOD) d 8.67 (s, 1H), 8.56 (s, 1H), 8.38 (s, 1H), 8.31 (br s, 1H), 4.47 (m, 1H), 4.21 (m, 1H), 2.41 (m, 1H), 222 (m, 1H), 2.10-1.90 (m, 3H), 1.72 (m, 2H) and 1.50 (m, 1H) ppm |
| 799 | A | A | 433.43 | 3.01 | |
| 800 | A | A | 433.42 | 2.66 | |
| 801 (racemic mixture of diastereomer 1, see 802) | A | A | 461.44 | 3.35 | |
| 802 (racemic mixture of diastereomer 2, see 801) | A | A | 461.44 | 2.81 | |
| 803 | A | A | 461.44 | 2.94 | |
| 804 | A | A | 404.3 | 3.45 | H NMR (300.0 MHz, MeOD) d 8.84 (s, H), 8.61 (s, H), 8.36 (s, H), 8.30 (d, J = 5.1 Hz, H), 5.57 (s, H), 3.5 (1 H, M), 1.97-1.3 (m, 8 H), 0.93 (s, 3H), ppm |
| 805 | A | A | 403.34 | 2.98 | H NMR (300.0 MHz, MeOD) d 8.85 (d, J = 2.4 Hz, H), 8.22 (d, J = 2.3 Hz, H), 8.16 (s, H), 7.99 (d, J = 4.1 Hz, H), 7.86 (s, H), 3.48 (d, J = 7.0 Hz, H), 2.80 (s, H), 2.15 (s, H), 2.0 (s, H), 1.86 (qn, J = 3.3 Hz, H), 1.80 (s, H), 1.74 (s, H), 1.44 (s, H). |
| 806 | A | A | 417.36 | 3.1 | H NMR (300.0 MHz, CDCl3) d 9.01 (d, J = 2.4 Hz, H), 8.77 (d, J = 2.4 Hz, H), 8.21 (d, J = 2.4 Hz, H), 8.06-7.96 (m, H), 3.44 (s, H), 3.42 (d, J = 4.0 Hz, H), 3.41 (t, J = 4.0 Hz, H), 2.19-1.66 (m, H), 1.97 (s, H) and 1.56 (s, H) ppm |
| 807 | A | A | 431.37 | 3.24 | |
| 808 | C | A | 392.34 | 2.9 | |
| 809 | A | A | 392.34 | 2.9 | 1H NMR (300 MHz, DMSO) d 13.10 (s, 1H), 9.20 (d, J = 2.7 Hz, 1H), 8.93-8.67 (m, 2H), 8.49 (d, J = 5.6 Hz, 1H), 8.39-8.30 (m, 0H), 4.78 (s, 1H), 3.54 (s, 1H), 3.17 (s, 2H), 2.51 (s, 4H), 2.02-1.63 (m, 3H), 1.46 (dd, J = 41.3, 11.6 Hz, 3H), 1.18 (s, 3H). |
| 810 | A | A | | | H NMR (300.0 MHz, DMSO) d 8.69 (d, J = 2.4 Hz, 1H), 8.21-8.18 (m, 2H), 8.10 (d, J = 4.0 Hz, 1H), 7.29 (d, J = 7.6 Hz, 1H), 6.83 (s, 1H), 5.84-5.70 (m, 1H), 5.07-5.00 (m, 2H), 4.27 (t, J = 4.0 Hz, 1H), 3.50 (d, J = 7.2 Hz, 3H), 2.39 (d, J = 8.3 Hz, 3H), 2.32-2.07 (m, 2H) and 1.82-1.08 (m, 5H) ppm |
| 811 | A | A | 447.36 | 3.18 | |
| 812 | A | A | 447.36 | 2.7 | |
| 813 | A | A | 447.36 | 2.79 | |
| 814 | A | A | | | H NMR (300.0 MHz, DMSO) d 12.92 (s, 1H), 9.02-8.88 (m, 2H), 8.64 (s, 1H), 8.41 (s, 2H), 4.29 (s, br 1H), 4.00-3.35 (m, 8H) and 2.17-1.27 (m, 10H) ppm |
| 815 | A | A | 433.35 | 2.92 | |
| 816 | A | A | 406.29 | 3.24 | |
| 817 | A | A | 439.3 | 1.48 | |
| 818 | A | A | 465.34 | 1.73 | |
| 819 | A | A | 505.3 | 1.47 | |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 820 | A | A | 493.3 | 2 | |
| 821 | A | A | | | (400 MHz, DMSO-d6): 12.34 (s, exchanged with D2O, 1H), 8.76(s, 1H), 8.28 (s,1H ), 8.19 (s, 1H), 8.14 (d, J = 4 Hz, 1H), 7.54 (d, J = 6.8 Hz, exchanged with D2O, 1H), 4.71-4.66 (m, 1H), 4.59(d, J = 3.2 Hz, exchanged with D2O, 1H), 4.27 (br s, 1H), 2.23-2.20(m, 1H), 1.98-1.57(m, 10H) |
| 822 | A | A | | | (400 MHz, DMSO-d6): 12.34 (s, exchanged with D2O, 1H), 8.73 (d, J = 1.6 Hz, 1H), 8.28d, J = 2 Hz, 1H), 8.21 (s, 1H), 8.15(d, J = 3.6 Hz, 1H), 7.49 (d, J = 7.2 Hz, exchanged with D2O, 1H), 4.75(d, J = 3.6 Hz, exchanged with D2O, 1H), 4.49-4.44 (m, 1H), 4.22-4.21 (m, 1H), 2.34-1.50 (m, 8H) |
| 823 | A | A | 448.39 | 3.67 | |
| 824 | A | A | 448.39 | 3.05 | |
| 825 | A | A | 404.3 | 3.38 | |
| 826 | A | A | 404.3 | 3.38 | H NMR (300.0 MHz, DMSO) d 12.34 (s, H), 8.74 (d, J = 2.3 Hz, H), 8.33 (d, J = 2.3 Hz, H), 8.28 (d, J = 1.6 Hz, H), 8.17-8.12 (m, H), 4.34 (s, H), 4.29 (s, H), 3.89 (s, H), 3.55 (d, J = 6.3 Hz, H), 3.32 (s, H), 2.50 (s, H), 2.29 (s, H), 1.95-1.90 (m, H), 1.82 (d, J = 6.6 Hz, H), 1.76 (s, H), 1.67 (s, H), 1.55 (s, H), 1.44-1.42 (m, H), 1.31 (s, H), 1.23 (s, H), 1.17 (s, H), 1.07 (s, H), 0.84 (d, J = 6.9 Hz, H) and −0.00 (d, J = 1.0 Hz, H) ppm |
| 827 | A | A | 404.37 | 2.72 | |
| 828 | A | A | 377.37 | 1.9 | |
| 829 | A | A | 470.4 | 2.95 | |
| 830 | A | B | 392.34 | 2.98 | MeOD d4: 8.8 (d, 1H); 8.5 (s, 1H); 8.4 (d, 1H); 8.3 (d, 1H); 4.5 (dd, 1H); 3.6 (dd, 1H); 3.3 (dd, 1H); 2.3 (m, 2H); 2.1 (m, 1H); 1.9 (m, 1H); 1.6 (app t, 2H); 1.3 (m, 1H). |
| 831 | A | A | 392.34 | 2.98 | MeOD d4: 8.8 (d, 1H); 8.5 (s, 1H); 8.4 (d,1H); 8.3 (d, 1H); 4.5 (dd,1H); 3.6 (dd, 1H); 3.3 (dd, 1H); 2.3 (m, 2H); 2.1 (m, 1H); 1.9 (m, 1H); 1.6 (app t, 2H); 1.3 (m, 1H). |
| 832 | A | A | 376.34 | 2.94 | MeOD d4: 8.8 (d, 1H); 8.65 (s, 1H); 8.45 (d, 1H); 8.35 (d, 1H); 4.2 (dd, 1H); 3.4 (dd, 1H); 2.2 (m, 2H); 2.0 (m, 1H); 1.6 (m, 4H); 1.2 (d, 3H). |
| 833 | B | A | 376.34 | 2.94 | MeOD d4: 8.8 (d, 1H); 8.65 (s, 1H); 8.45 (d, 1H); 8.35 (d, 1H); 4.2 (dd, 1H); 3.4 (dd, 1H); 2.2 (m, 2H); 2.0 (m, 1H); 1.6 (m, 4H); 1.2 (d, 3H). |
| 834 | A | A | 442.37 | 3.25 | H NMR (300.0 MHz, DMSO) d 12.32 (s, 1H), 8.70 (d, J = 2.4 Hz, 1H), 8.28 (d, J = 2.4 Hz, 1H), 8.19-8.18 (m, 2H), 7.31 (d, J = 7.1 Hz, 1H), 5.76 (s, 1H), 5.26 (t, J = 6.4 Hz, 1H), 4.58 (s, 1H), 3.87-3.74 (m, 2H), 2.50 (qn, J = 1.8 Hz, H), 2.01-1.80 (m, 3H), 1.74-1.50 (m, H) and −0.00 (TMS) ppm |
| 835 | A | A | 442.37 | 2.84 | H NMR (300.0 MHz, DMSO) d 12.30 (s, 1H), 8.76 (d, J = 2.2 Hz, 1H), 8.28 (d, J = 2.3 Hz, 1H), 8.19-8.13 (m, H), 7.44 (d, J = 7.6 Hz, H), 5.22-5.17 (m, 2H), 4.48-4.45 (m, 1H), 3.80 (td, J = 15.9, 7.4 Hz, H), 3.18 (d, J = 5.2 Hz, 2H), 2.51 (s, H), 2.09 (d, J = 11.4 Hz, 1H), 2.03 (s, 1H), 1.92-1.80 (m, 1H), 1.70 (t, J = 12.3 Hz, H), 1.70-1.60 (m, 3H), 1.42 (dd, J = 9.9, 12.9 Hz, 1H), 1.26 (dd, J = 11.5, 22.0 Hz, 1H) and −0.00 (s, H) ppm |
| 836 | A | A | 483.39 | 3.37 | |
| 837 | A | A | 483.39 | 2.93 | |
| 838 | A | C | 388.37 | 4.02 | |
| 839 | A | | 433.4 | 3.69 | 1H NMR (300 MHz, MeOD) d 8.83 (d, J = 2.1 Hz, 1H), 8.49 (s, 1H), 8.38 (d, J = 1.9 Hz, 1H), 8.26 (d, J = 5.6 Hz, 1H), 3.49-3.14 (m, 3H), 2.68 (s, 0H), 2.19 (d, J = 14.2 Hz, 1H), 2.09 (d, J = 13.0 Hz, 1H), 1.96 (s, 4H), 1.76 (s, 2H), 1.49 (d, J = 41.9 Hz, 3H). |
| 840 | A | | 438.32 | 3.68 | H NMR (300.0 MHz, DMSO) d 12.29 (s, 1H), 8.78 (dd, J = 2.4, 6.6 Hz, 1H), 8.27 (d, J = 2.4 Hz, 1H), 8.18 (d, J = 1.9 Hz, 1H), 8.13 (dd, J = 0.8, 4.0 Hz, 1H), 7.44 (d, J = 8.1 Hz, 1H), 4.83-4.78 (m, 1H), 4.52 (t, J = 3.6 Hz, 1H), 2.97-2.82 (m, 2H), 2.58 (d, J = 1.4 Hz, 3H), 2.19-1.81 (m, 3H), 1.72-1.57 (m, 2H), 1.54-1.32 (m, 1H) and 1.31-1.12 (m, 2H) ppm |
| 841 | A | A | 390.5 | 2.97 | (400 MHz, DMSO-d6): 12.8 (br.s, exchanged with D2O, 1H), 8.68 (br.s, 1H), 8.40-8.38 (m, 2H), 4.59- |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| | | | | | 4.57 (m, 1H), 2.36-2.11 (m, 4H), 2.11-2.06 (m, 1H), 1.92-1.79 (m, 2H), 1.46-1.44 (m, 2H). |
| 842 | A | | 454.37 | 3.47 | H NMR (300.0 MHz, DMSO) d 13.06 (s, 1H), 9.35 (d, J = 6.4 Hz, 1H), 9.10 (d, J = 2.5 Hz, 1H), 8.74 (s, 1H), 8.48 (d, J = 5.6 Hz, 1H), 8.41 (s, 1H), 4.67 (d, J = 7.7 Hz, 1H), 3.41-3.25 (m, 2H), 3.02 (s, 3H), 2.29 (d, J = 11.8 Hz, 1H) and 2.08-1.35 (m, 8H) ppm |
| 843 | A | A | 525.43 | 3.58 | |
| 844 | A | A | 525.43 | 3.09 | |
| 845 | A | | 449.41 | 3.36 | 1H NMR (300 MHz, MeOD) d 8.36 (s, 1H), 8.22 (s, 1H), 8.13 (s, 1H), 4.25 (br s, 1H), 4.14-3.79 (m, 3H), 3.44 (s, 3H), 2.38 (br s, 1H), 2.17 (br s, 1H), 2.09-1.92 (m, 2H), 1.79-1.29 (m, J = 62.8 Hz, 4H). |
| 846 | | A | 390.399 | 2.91 | (400 MHz, DMSO-d6): 12.61 (br.s, exchanged with D2O, 1H), 8.69 (s, 1H), 8.41-8.30 (m, 3H), 3.54-3.43 (m, 2H), 2.74-2.68 (m, 1H), 2.46-2.42 (1H), 2.15-2.08 (m, 2H), 1.82 (br.s, 3H), 1.57-1.47 (m, 2H). |
| 847 | | A | 389.35 | 3.79 | |
| 848 | | A | 376.399 | 2.79 | (400 MHz, DMSO-d6): 12.6 (br.s, exchanged with D2O, 1H), 8.70 (s, 1H), 8.40-8.30 (m, 3H), 4.65-4.60 (m, 1H), 3.01-2.93 (m, 1H), 2.28-1.95 (m, 4H), 1.86-1.72 (m, 2H). |
| 849 | | A | 390.399 | 2.89 | (400 MHz, DMSO-d6): 12.90 (br.s, exchanged with D2O, 1H), 9.20 (br.s, exchanged with D2O, 1H), 8.65 (s, 1H), 8.44 (d, J = 4.8 Hz, 1H), 8.39 (d, J = 2 Hz, 1H), 3.56-3.49 (m, 3H), 2.85-2.80 (m, 1H), 2.01-1.89 (m, 3H), 1.77-1.67 (m, 2H), 1.44-1.39 (m, 1H). |
| 850 | | A | | | (400 MHz, DMSO-d6): 12.32 (br s, exchanged with D2O, 1H), 8.75 (s, 1H), 8. 28 (s, 1H), 8.20 (s, 1H), 8.14 (d, J = 3.6 Hz, 1H), 7.6 (d, J = 6.4 Hz, exchanged with D2O, 1H), 4.58-4.53 (m, 1H), 2.27 (d, J = 7.2 Hz, 2H), 2.19-1.67 (m, 5H), 1.36-1.2 9 (m, 1H). |
| 851 | A | A | 483.39 | 3.6 | |
| 852 | A | A | 483.39 | 3.05 | |
| 853 | | A | 438.36 | 3.58 | H NMR (300.0 MHz, DMSO) d 12.29 (s, 1H), 8.78 (s, 1H), 8.26-8.18 (m, 3H), 7.44 (s, 1H), 5.05-4.30 (m, 2H), 3.08-2.74 (M, 1H) and 2.26-0.92 (m, 12H) ppm |
| 854 | A | A | 454.27 | 2.64 | H NMR (300.0 MHz, DMSO) d 12.30 (s, 1H), 8.79 (d, J = 2.3 Hz, 1H), 8.27 (d, J = 2.3 Hz, 1H), 8.19 (d, J = 2.7 Hz, 1H), 8.13 (d, J = 4.0 Hz, 1H), 7.47 (d, J = 7.7 Hz, 1H), 4.90 (s, 1H), 4.51 (t, J = 3.9 Hz, 1H), 3.01 (s, 3H), 2.24 (d, J = 12.3 Hz, 1H), 2.09-1.79 (m, 4H), 1.71-1.41 (m, 3H) and 1.36-1.05 (m, 2H) ppm |
| 855 | A | A | 414.35 | 3 | 1H NMR (300 MHz, DMSO) d 12.33 (s, 1H), 8.74 (d, J = 2.4 Hz, 1H), 8.41-8.04 (m, 3H), 7.62 (d, J = 7.4 Hz, 1H), 4.30 (s, 1H), 3.54-3.06 (m, 3H), 2.67 2.31 (m, 1H), 2.23-1.33 (m, 6H) |
| 856 | A | A | 424.34 | 3.63 | H NMR (300.0 MHz, CDCl3) d 8.85 (q, J = 2.3 Hz, H), 8.17 (dd, J = 2.3, 21.3 Hz, 2H), 8.00 (d, J = 3.5 Hz, 1H), 5.03 (s, H), 4.64-4.55 (m, 1H), 4.38 (dd, J = 4.0, 8.3 Hz, 1H), 4.01-3.88 (m, 2H), 2.45-1.90 (m, 4H), 1.51-1.25 (m, 3H) and 0.00 (s, H) ppm |
| 857 | A | A | 433.37 | 3.47 | 1H NMR (300 MHz, DMSO) d 13.02 (s, 1H), 9.22 (s, 1H), 9.03 (d, J = 2.4 Hz, 1H), 8.71 (d, J = 2.1 Hz, 1H), 8.46 (d, J = 5.5 Hz, 1H), 8.41 (d, J = 2.1 Hz, 1H), 7.81 (t, J= 5.8 Hz, 1H), 4.64 (d, J = 8.0 Hz, 1H), 3.16-2.99 (m, 2H), 2.09-1.73 (m, 3H), 1.85 (s, 3H), 1.73-1.42 (m, 3H), 1.28 (dd, J = 27.5, 10.6 Hz, 2H). |
| 858 | A | A | 490.36 | 2.78 | |
| 859 | A | A | 424.41 | 3.8 | H NMR (300.0 MHz, MeOD) d 8.73 (s, 1H), 8.17 (d, J = 1.8 Hz, 1H), 8.11 (d, J = 2.0 Hz, 1H), 7.96 (d, J = 3.7 Hz, 1H), 4.57 (s, 1H), 4.50 (d, 1H), 4.10-3.80 (m, 2H), 2.21-1.60 (m, 8H) and 0.00 (s, H) ppm |
| 860 | A | A | 392.34 | 2.82 | MeOD4: 8.75 (d, 1H); 8.5 (s, 1H); 8.4 (d, 1H); 8.25 (d, 1H); 7.7 (d, 1H); 7.2 (d, 1H); 4.5 (ddd, 1H); 3.65 (d, 1H); 2.35 (s, 1H); 2.1 (m, 1H); 1.85 (m, 2H); 1.6 (m, 3H); 1.35 (s, 3H). |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 861 | A | A | 362.33 | 2.43 | MeOD4 8.55 (dd, 1H); 8.2 (d, 2H); 8.0 (d, 1H); 7.7 (d, 1H); 7.2 (d, 1H); 4.2 (ddd, 1H); 3.6, (ddd, 1H); 3.4 (dd, 1H); 2.4 (s, 2H); 2.2 (m, 1H); 2.1 (m, 2H); 1.8 (m, 1H); 1.4 (m, 3H). |
| 862 | A | A | 442.44 | 3.77 | 1H NMR (300 MHz, DMSO) d 12.28 (s, 1H), 8.75 (d, J = 2.4 Hz, 1H), 8.27 (d, J = 2.4 Hz, 1H), 8.15 (s, 1H), 8.11 (d, J = 4.0 Hz, 1H), 7.69 (d, J = 2.2 Hz, 1H), 7.41 (d, J = 1.7 Hz, 1H), 7.38 (s, 1H), 6.22 (t, J = 2.0 Hz, 1H), 4.67 (s, 1H, OH), 4.49-4.38 (m, 1H), 4.10 (s, 2H), 2.05-1.80 (m, 2H), 1.72-1.55 (m, 2H), 1.52-1.40 (m, 2H), 1.35-1.14 (m, 2H). |
| 863 | A | A | 503.42 | 3.36 | |
| 864 | A | A | 503.42 | 3.46 | |
| 865 | A | A | 517.43 | 3.57 | |
| 866 | A | A | 416.33 | 2.75 | 1H NMR (300 MHz, MeOD) d 8.53 (s, 1H), 8.38-8.30 (m, 2H), 8.28 (d, J = 5.6 Hz, 1H), 4.40 (ddd, J = 11.9, 8.2, 3.9 Hz, 1H), 3.78 (ddd, J = 11.9, 8.2, 3.8 Hz, 1H), 2.89 (s, 6H), 2.33 (d, J = 11.6 Hz, 1H), 2.21 (d, J = 11.4 Hz, 1H), 2.05-1.96 (m, J = 6.8, 4.1 Hz, 3H), 1.67-1.33 (m, 4H). |
| 867 | A | A | 503.35 | 2.79 | |
| 868 | A | A | 503.35 | 2.93 | |
| 869 | A | A | 376.28 | 2.6 | 1H NMR (300 MHz, MeOD) d 8.65 (dd, J = 9.6, 2.8 Hz, 1H), 8.20 (s, 1H), 8.17-8.09 (m, 1H), 8.01 (d, J = 4.0 Hz, 1H), 4.53 (s, 1H), 3.60 (s, 2H), 1.89 (dd, J = 28.7, 12.9 Hz, 3H), 1.74-1.41 (m, 5H), 1.28 (s, 3H). |
| 870 | A | A | 457 | 2.84 | 1H NMR (300 MHz, DMSO) d 12.23 (s, 1H), 8.41 (dd, J = 9.9, 2.8 Hz, 1H), 8.24 (d, J = 13.1 Hz, 2H), 8.14 (d, J = 4.0 Hz, 1H), 7.79 (d, J = 7.6 Hz, 1H), 7.48 (d, J = 7.6 Hz, 1H), 4.12 (s, 1H), 3.76 (d, J = 11.2 Hz, 2H), 3.38-3.15 (m, 3H), 2.35 (dd, J = 12.6, 8.6 Hz, 1H), 2.04 (dd, J = 25.4, 9.8 Hz, 2H), 1.89-0.99 (m, 10H). |
| 871 | A | A | 438.34 | 2.89 | |
| 872 | A | A | 376.28 | 2.57 | |
| 873 | A | A | 486.46 | 2.98 | 1H NMR (300 MHz, MeOD) d 8.49 (s, 1H), 8.41 (dd, J = 9.0, 2.6 Hz, 1H), 8.35 (s, 1H), 8.28 (d, J = 5.6 Hz, 1H), 4.55-4.37 (m, 1H), 3.83 (d, J = 12.8 Hz, 2H), 3.59-3.43 (m, 2H), 2.50-2.28 (m, 3H), 2.22 (d, J = 10.6 Hz, 1H), 2.01 (d, J = 11.6 Hz, 2H), 1.74-1.25 (m, 5H), 1.15 (d, J = 6.2 Hz, 6H). |
| 874 | A | A | 486.46 | 2.9 | 1H NMR (300 MHz, MeOD) d 8.51 (s, 1H), 8.42 (d, J = 9.0 Hz, 1H), 8.35 (s, 1H), 8.28 (d, J = 5.3 Hz, 1H), 4.46 (s, 1H), 3.95-3.76 (m, J = 11.0 Hz, 2H), 3.76-3.61 (m, 2H), 3.61-3.51 (m, 1H), 3.50-3.39 (m, 2H), 2.43-2.28 (m, 1H), 2.22 (d, J = 12.0 Hz, 1H), 2.01 (d, J = 11.0 Hz, 2H), 1.53 (ddd, J = 44.1, 27.8, 15.6 Hz, 4H), 1.32-1.10 (m, 6H). |
| 875 | A | A | 401.3 | 3.01 | H NMR (300.0 MHz, DMSO) d 12.32 (s, 1H), 8.71 (d, J = 2.4 Hz, 1H), 8.29-8.26 (m, 2H), 8.17 (d, J = 3.9 Hz, 1H), 7.44 (d, J = 7.7 Hz, 1H), 4.31 (s, 1H), 2.85 (d, J = 5.9 Hz, 2H), 2.51 (t, J = 1.7 Hz, H), 2.08-1.98 (m, 1H), 1.77-1.64 (m, 4H), 1.50 (d, J = 6.3 Hz, 3H) and 0.00 (s, H) ppm |
| 876 | A | A | 489.34 | 2.99 | |
| 877 | A | A | 489.34 | 2.75 | |
| 878 | A | A | 374.21 | 1.64 | |
| 879 | A | A | 483.45 | 2.35 | |
| 880 | A | A | 427.4 | 2.97 | |
| 881 | C | C | 389.27 | 2.03 | 1H NMR (300 MHz, DMSO) d 12.79 (s, 1H), 8.77 (s, 1H), 8.60 (d, J = 2.3 Hz, 1H), 8.43 (d, J = 4.8 Hz, 1H), 8.37 (d, J = 2.3 Hz, 1H), 7.52 (s, 3H), 4.29 (s, 1H), 4.08 (d, J = 12.6 Hz, 1H), 3.90 (d, J = 13.7 Hz, 1H), 3.16-2.95 (m, 2H), 2.17 (d, J = 9.7 Hz, 2H), 1.92 (d, J = 8.5 Hz, 1H), 1.81-1.57 (m, 2H). |
| 882 | A | A | 401.3 | 2.73 | H NMR (300.0 MHz, MeOD) d 8.86 (d, J = 2.4 Hz, 1H), 8.19-8.16 (m, 2H), 7.97 (d, J = 4.0 Hz, 1H), 4.69-4.58 (m, 1H), 2.65 (s, 2H), 2.26-1.98 (m, 3H), 1.84 (d, 1H), 1.79-1.73 (m, 1H), 1.67-1.47 (m, 2H), 1.36-1.21 (m, 1H) and 0.00 (TMS) ppm |
| 883 | A | A | 457.38 | 3.55 | 1H NMR (300 MHz, DMSO) d 12.25 (s, 1H), 8.63-8.02 (m, 4H), 7.62 (dd, J = 62.6, 7.2 Hz, 2H), 3.90 (t, J = 60.4 Hz, 4H), 2.47-0.73 (m, 15H). |
| 884 | E | A | 471.39 | 3.74 | |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| 885 | A | A | 420.24 | 3.09 | |
| 886 | A | A | 454.26 | 3.62 | H NMR (300.0 MHz, DMSO) d 12.32 (s, 1H), 8.72 (d, J = 2.2 Hz, 1H), 8.28-8.24 (m, 2H), 8.17 (d, J = 3.8 Hz, 1H), 7.44 (d, J = 7.2 Hz, 1H), 5.34 (s, 1H), 4.32 (s, 1H), 3.41 (s, 2H), 3.04 (s, 3H), 2.22 (d, J = 11.7 Hz, 1H), 2.12-1.69 (m, 4H) and 1.52 (d, J = 8.7 Hz, 3H) ppm |
| 887 | A | C | 420.24 | 3.09 | |
| 888 (diastereomer 1, see 889) | A | A | 420.36 | 3.93 | H NMR (300.0 MHz, MeOD) d 8.81 (d, J = 2.4 Hz, 1H), 8.21 (d, J = 2.4 Hz, 1H), 8.13 (s, 1H), 7.97 (d, J = 4.0 Hz, 1H), 4.50 (s, 1H), 4.28-4.18 (m, 1H), 3.72 (dd, J = 4.2, 9.1 Hz, 2H), 2.02 (d, J = 6.3 Hz, 1H), 1.89-1.81 (m, 4H), 1.69-1.55 (m, 3H), 1.26-1.20 (m, 4H) and −0.00 (s, H) ppm |
| 889 (diastereomer 2, see 888) | A | A | 420.37 | 3.94 | H NMR (300.0 MHz, MeOD) d 8.79 (d, J = 2.4 Hz, 1H), 8.21 (d, J = 2.4 Hz, 1H), 8.12 (s, 1H), 7.99 (d, J = 4.0 Hz, 1H), 4.47 (dd, J = 3.6, 7.6 Hz, 1H), 4.25-4.17 (m, 1H), 2.10 (dd, J = 3.7, 13.4 Hz, 1H), 1.91-1.77 (m, 3H), 1.69-1.50 (m, 4H), 1.20 (d, J = 9.4 Hz, 2H) and −0.00 (TMS) ppm |
| 890 | A | A | 472.42 | 3.6 | |
| 891 | A | A | 456.4 | 3.82 | |
| 892 | A | A | 472.41 | 3.69 | |
| 893 | A | A | 486.42 | 3.6 | |
| 894 | A | A | 486.44 | 3.6 | |
| 895 | A | A | 442.42 | 3.7 | |
| 896 | A | A | 500.42 | 3.77 | |
| 897 | A | A | 458.42 | 3.48 | |
| 898 | A | A | 472.42 | 3.51 | |
| 899 | A | A | 401 | 3.6 | 1H NMR (300 MHz, DMSO) d 12.30 (s, 1H), 8.41 (dd, J = 9.8, 2.9 Hz, 1H), 8.24 (d, J = 9.7 Hz, 2H), 8.13 (d, J = 4.0 Hz, 1H), 7.71 (d, J = 7.6 Hz, 1H), 7.48 (d, J = 7.4 Hz, 1H), 4.15 (s, 1H), 3.73 (s, 1H), 2.22-1.91 (m, 4H), 1.82 (d, J = 11.1 Hz, 2H), 1.29 (ddd, J = 54.3, 34.3, 10.3 Hz, 4H), 0.97 (t, J = 7.6 Hz, 3H). |
| 900 | A | A | 413 | 3.56 | 1H NMR (300 MHz, DMSO) d 12.23 (s, 1H), 8.40 (dd, J = 9.9, 2.9 Hz, 1H), 8.25 (s, 1H), 8.22 (s, 1H), 8.13 (d, J = 4.0 Hz, 1H), 8.02 (d, J = 7.7 Hz, 1H), 7.48 (d, J = 7.5 Hz, 1H), 4.15 (s, 1H), 3.72 (s, 1H), 2.22-1.73 (m, 4H), 1.62-1.04 (m, 5H), 0.75-0.53 (m, 4H). |
| 901 | A | A | 442.37 | 2.97 | |
| 902 | A | A | 472.43 | 3.41 | |
| 903 | A | A | 472.48 | 3.65 | |
| 904 | A | A | 472.38 | 2.72 | |
| 905 | A | A | 472.38 | 2.61 | |
| 906 | A | A | 472.38 | 2.67 | |
| 907 | A | A | 486.4 | 2.88 | |
| 908 | A | A | 457.35 | 2.53 | |
| 909 | A | A | 499.38 | 2.62 | |
| 910 | A | A | 486.4 | 3.02 | |
| 911 | A | A | 506.29 | 2.57 | |
| 912 | A | A | 460.35 | 2.79 | |
| 913 | A | A | 456.39 | 2.98 | |
| 914 | A | A | 486.4 | 2.79 | |
| 915 | A | A | 456.39 | 2.98 | |
| 916 | A | A | 500.41 | 3.1 | |
| 917 | | A | 454.34 | 2.54 | |
| 918 | | A | 508.34 | 3.38 | |
| 919 | | A | 470.4 | 1.59 | |
| 920 | | A | 384.34 | 1.74 | |
| 921 | | A | 488.38 | 1.92 | |
| 922 | | A | 481.4 | 1.79 | H NMR (300.0 MHz, MeOD) d 8.44-8.41 (m, 2H), 8.32 (dd, J = 1.6, 2.7 Hz, 1H), 8.24 (d, J = 5.5 Hz, 1H), 4.42 (t, J = 11.8 Hz, 1H), 3.79 (t, J = 11.6 Hz, 1H), 3.65 (td, J = 10.2, 4.7 Hz, 2H), 3.54 (qn, J = 1.6 Hz, 1H), 2.97 (dt, J = 12.5, 4.2 Hz, 1H), 2.34 (d, J = 10.7 Hz, 1H), 2.21 (d, J = 12.1 Hz, 1H), 2.03-1.87 (m, 4H) and 1.79-1.23 (m, 7H) ppm |
| 923 | | A | 499.38 | 1.57 | H NMR (300.0 MHz, MeOD) d 8.53 (dd, J = 2.8, 9.6 Hz, 1H), 8.18-8.08 (m, 2H), 7.99 (d, J = 4.1 Hz, 1H), 4.25 (dt, J = 15.2, 4.8 Hz, 1H), 4.04 (d, 2H), 3.83-3.68 (m, 1H), 2.80 (dd, J = 2.5, 25.7 Hz, 2H), 2.46-2.35 (m, 2H), 2.21 (d, J = 10.7 Hz, 1H), |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| | | | | | 1.97 (s, 1H), 1.80-1.75 (m, 2H), 1.63-1.29 (m, 3H) and 1.22 (d, J = 4.8 Hz, 4H) ppm |
| 924 | | A | 403.34 | 1.77 | |
| 925 | | C | 398.35 | 1.75 | |
| 926 | | A | 472.38 | 2.08 | H NMR (300.0 MHz, MeOD) d 8.76 (d, J = 2.4 Hz, H), 8.44-8.38 (m, H), 8.27 (d, J = 5.6 Hz, H), 4.87 (d, J = 5.1 Hz, H), 4.64-4.56 (m, H), 3.38-3.19 (m, H), 2.65 (s, H), 2.46 (s, H), 2.42 (s, H), 2.16 (s, H), 2.07 (t, J = 12.0 Hz, H), 2.00 (s, H), 1.88 (q, J = 6.6 Hz, H), 1.88 (s, H), 1.70 (s, H) and 1.61 (d, J = 12.8 Hz, H) ppm |
| 927 | | C | 420.36 | 1.8 | |
| 928 | | A | 420.36 | 1.79 | |
| 929 | | | 431.19 | 1.82 | H NMR (300.0 MHz, MeOD) d 8.85 (d, J = 2.4 Hz, H), 8.22 (d, J = 2.3 Hz, H), 8.15 (s, H), 7.99 (d, J = 4.1 Hz, H), 7.70 (d, J = 8.0 Hz, H), 7.64 (s, H), 5.49 (s, H), 5.01 (s, H), 4.95 (s, H), 4.88 (s, H), 4.56-4.47 (m, H), 3.53 (d, J = 1.7 Hz, H), 3.35-3.17 (m, H), 3.07 (s, H), 2.66 (s, H), 2.36 (s, H), 2.13 (d, J = 9.6 Hz, H), 2.02-1.98 (m, H), 1.89 (s, H), 1.83-1.77 (m, H), 1.73-1.68 (m, H), 1.63 (s, H), 1.49-1.42 (m, H), 1.36 (s, H), 1.28 (s, H), 1.20-1.07 (m, H) and 0.01 (d, J = 3.3 Hz, H) ppm |
| 930 | | | 417.19 | 1.84 | H NMR (300.0 MHz, MeOD) d 8.86 (d, J = 2.4 Hz, H), 8.26-8.22 (m, H), 8.15 (s, H), 8.03-7.98 (m, H), 7.67 (s, H), 7.62 (s, H), 5.47 (d, J = 10.7 Hz, H), 5.09 (d, J = 6.6 Hz, H), 5.01 (s, H), 4.88 (s, H), 4.61 (s, H), 4.52 (dd, J = 7.1, 15.2 Hz, H), 4.52 (s, H), 3.72 (s, H), 3.66 (s, H), 3.60 (d, J = 7.1 Hz, H), 3.54-3.43 (m, H), 3.34 (s, H), 3.31 (qn, J = 1.6 Hz, H), 3.08 (t, J = 1.7 Hz, H), 2.76-2.71 (m, H), 2.13 (d, J = 12.7 Hz, H), 2.01 (d, J = 8.5 Hz, H), 1.83-1.76 (m, H), 1.72-1.67 (m, H), 1.63 (s, H), 1.42 (s, H), 1.37 (d, J = 6.5 Hz, H), 1.29-1.15 (m, H), 0.98 (s, H), 0.83 (s, H), 0.20 (s, H), 0.07 (s, H), 0.00 (TMS) and −0.20 (s, H) ppm |
| 931 | | | 494.39 | 2.04 | |
| 932 | A | A | 416.44 | 2.93 | |
| 933 | A | A | 453.4 | 1.5 | |
| 934 | A | A | 476.09 | 1.92 | |
| 935 | A | A | 478.08 | 1.89 | |
| 936 | A | A | 460.1 | 1.76 | |
| 937 | A | A | 474.6 | 2.02 | |
| 938 | A | A | 388.11 | 1.87 | |
| 939 | A | A | 392.41 | 2.42 | |
| 940 | | | 490.1 | 2.04 | |
| 941 | | | 472.13 | 1.79 | H NMR (300.0 MHz, MeOD) d 8.70 (d, J = 2.2 Hz, H), 8.51-8.43 (m, H), 8.33 (s, H), 8.10 (d, J = 5.6 Hz, H), 4.77 (s, H), 4.63-4.53 (m, H), 4.15 (d, J = 4.5 Hz, H), 3.98-3.90 (m, H), 3.84 (t, J = 5.0 Hz, H), 3.63-3.53 (m, H), 3.48-3.41 (m, H), 3.21 (s, H), 3.16 (s, H), 3.11 (s, H), 2.82 (s, H), 2.65 (s, H), 2.49 (d, J = 9.8 Hz, H), 2.13-1.90 (m, H), 1.86-1.72 (m, H), 1.67 (s, H), 1.62-1.51 (m, H), 1.33 (dd, J = 6.5, 17.5 Hz, H) and −0.00 (TMS) ppm |
| 942 | | | 466.2 | 1.66 | |
| 943 | | | 456.13 | 1.92 | H NMR (300.0 MHz, MeOD) d 12.44 (s, H), 8.49-8.46 (m, H), 8.33 (s, H), 8.23 (d, J = 5.6 Hz, H), 7.31-7.25 (m, H), 7.19 (d, J = 7.9 Hz, H), 7.12 (s, H), 7.07 (t, J = 7.2 Hz, H), 4.90 (d, J = 12.9 Hz, H), 4.81 (d, J = 6.3 Hz, H), 4.75 (s, H), 4.69 (s, H), 4.60 (t, J = 11.1 Hz, H), 4.58 (s, H), 4.23 (s, H), 4.06 (d, J = 8.5 Hz, H), 3.72 (s, H), 3.54 (s, H), 3.44-3.39 (m, H), 3.32-3.25 (m, H), 3.18 (t, J = 1.7 Hz, H), 3.15 (s, H), 3.08-3.07 (m, H), 2.98 (s, H), 2.65 (s, H), 2.47 (d, J = 12.5 Hz, H), 2.05 (q, J = 11.9 Hz, H), 2.00 (s, H), 1.91-1.83 (m, H), 1.73 (d, J = 9.7 Hz, H), 1.64 (s, H), 1.56 (d, J = 12.6 Hz, H), 1.45 (s, H), 1.37 (d, J = 6.9 Hz, H), 0.20 (s, H), 0.07 (s, H), 0.01-0.02 (m, H), −0.20 (s, H), −2.49 (s, H) and −2.71 (s, H) ppm |
| 944 | | | 482.1 | 1.93 | |
| 945 | A | A | 402.399 | 2.23 | (400 MHz, DMSO-d6): 12.35 (br s, exchanged with D2O, 1H), 9.18 (br s, exchanged with D2O, 1H), 8.75 (s, 1H), 8.28 (s, 1H), 8.19 (s, 1H), 8.15 (d, |

TABLE 2-continued

IC$_{50}$, EC$_{50}$, NMR and LCMS Data of Compounds of FIGS. 4 and 5:

| Compound Nos. | IC$_{50}$ | EC$_{50}$ | LCMS_Plus | LCMS_RT | NMR |
|---|---|---|---|---|---|
| | | | | | J = 3.2 Hz, 1H), 4.38 (br s, 1H), 3.01 (d, J = 10 Hz, 1H), 2.8 (s, 1H), 2.58 (s, 1H), 1.68 (d, J = 9.2 Hz, 1H), 1.56-1.22 (m, 5H) |
| 946 | A | A | 402.399 | 1.88 | (400 MHz, DMSO-d6): 12.15 (br s, exchanged with D2O, 3H), 8.77 (d, J = 2.4 Hz, 1H), 8.28 (d, J = 2 Hz, 1H), 8.20 (s, 1H), 8.17 (d, J = 4 Hz, 1H), 7.78 (d, J = 6 Hz, 1H), 4.66-4.65 (m, 1H), 2.7-2.65 (m, 2H), 1.72 (d, J = 9.6 Hz, 1H), 1.58-1.32 (m, 5H) |
| 947 | A | A | 402.32 | 3.42 | H NMR (300.0 MHz, MeOD) d 8.87 (d, J = 2.1 Hz, 1H), 8.48 (s, 1H), 8.39 (d, J = 1.9 Hz, 1H), 8.30 (d, J = 5.7 Hz, 1H), 4.73 (d, J = 3.3 Hz, 1H), 3.12 (m, 1H), 2.76 (br s, 1H), 2.56 (d, J = 4.2 Hz, 1H), 1.86 (d, J = 9.5 Hz, 2H), 1.79-1.49 (complex m, 2H) and 1.51 (embedded d, J = 10.4 Hz, 2H) ppm |
| 948 | A | A | 417.36 | 3.11 | |
| 949 | A | A | 417.29 | 2.99 | |
| 950 | | A | 430.41 | 3 | |
| 951 | A | A | 431.37 | 2.98 | NMR 1H (MeOH-d6): 8.7 (s, 1H), 8.5 (s, 1H), 8.35 (s, 1H), 8.3 (s, 1H), 4.5 (m, 1H), 4.3 (m, 2H), 3.9 (m, 1H), 3.7 (m, 2H), 2.2 (m, 2H), 1.3-2.1 (m, 6H). |
| 952 | A | A | 430.83 | 2.83 | |
| 953 | A | A | 430.43 | 3.17 | |
| 954 | A | A | 444.36 | 3.33 | |
| 955 | A | A | 458.37 | 3.58 | |
| 956 | A | A | 429.53 | 3.15 | H NMR (300.0 MHz, MeOD) d 8.72 (d, J = 2.2 Hz, 1H), 8.49 (s, 1H), 8.39 (d, J = 2.1 Hz, 1H), 8.29 (d, J = 5.5 Hz, 1H), 4.54-4.47 (m, 1H), 4.13 (t, J = 11.8 Hz, 1H), 3.57-3.45 (m, 2H), 2.42-2.36 (m, 2H), 2.25 (m, 1H), 2.15-2.00 (m, 4H), 1.90-1.59 (m, 4H) and 1.53-1.43 (m, 1H) ppm |
| 957 | A | A | 544.4 | 3.62 | |
| 958 | A | A | 444.4 | 3.21 | NMR 1H (MeOH-d4): conclusive with structure. |
| 959 | A | A | 431.37 | 3.21 | |
| 960 | A | A | 431.37 | 3.24 | |
| 961 | A | A | 431.37 | 3.05 | |
| 962 | A | A | 431.37 | 3.09 | |
| 963 | A | A | 445.38 | 3.39 | |
| 964 | A | A | 445.38 | 3.16 | |
| 965 | A | A | 415.37 | 2.9 | |
| 966 | A | A | 415.37 | 2.9 | |
| 967 | A | A | 415.37 | 2.64 | |
| 968 | A | A | 415.37 | 2.72 | |
| 969 | A | A | 415.31 | 2.94 | |
| 970 | A | A | 431.3 | 3.16 | |
| 971 | A | A | 431.3 | 3.01 | |
| 972 | A | A | 415.31 | 2.94 | |
| 973 | A | A | 415.31 | 2.95 | |
| 974 | A | A | 416.33 | 1.79 | |
| 975 | A | A | 415.37 | 1.82 | |
| 976 | A | A | 415.37 | 1.72 | |
| 977 | A | A | 399.53 | 2.17 | |

TABLE 3

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_Plus | LCMS_RT | NMR |
|---|---|---|---|---|---|
| 979 | A | A | 385.48 | 2.31 | H NMR (300.0 MHz, MeOD) d 8.65 (dd, J = 2.8, 9.6 Hz, 1H), 8.19 (s, 1H), 8.14 (dd, J = 2.0, 2.5 Hz, 1H), 7.98 (d, J = 4.1 Hz, 1H), 4.75-4.65 (m, 1H), 2.64 (s, 2H), 2.20 (d, J = 12.6 Hz, 2H), 2.01 (dd, J = 3.4, 9.8 Hz, 2H), 1.84-1.75 (m, 1H), 1.63-1.47 (m, 2H), 1.33 (dd, J = 3.6, 12.4 Hz, 1H) |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_Plus | LCMS_RT | NMR |
|---|---|---|---|---|---|
| | | | | | and 0.00 (TMS) ppm |
| 980 | A | A | 432.26 | 2.46 | DMSO d6: 12.5 (bs, 1H); 8.75 (d, 1H); 8.65 (d, 1H); 8.3 (m, 4H); 7.7 (m, 2H); 7.2 (bs, 1H); 4.5 (bs, 1H); 2.7 (s, 3H); 2.3 9dd, 1H); 2.0 (m, 2H); 1.8-1.2 (m, 8H); 0.8 (t, 3H). |
| 981 | A | A | 399.25 | 1.65 | 1H NMR (300 MHz, MeOD) d 8.52 (s, 1H), 8.46-8.23 (m, 3H), 4.51 (t, J = 11.9 Hz, 1H), 3.23 (s, 1H), 3.04 (d, J = 7.3 Hz, 3H), 2.44 (s, 2H), 2.25 (d, J = 11.9 Hz, 1H), 2.11 (d, J = 12.7 Hz, 1H), 2.01-1.80 (m, 2H), 1.72 (d, J = 12.4 Hz, 2H), 1.47 (s, 2H), 1.30 (t, J = 7.3 Hz, 5H). |
| 982 | A | A | 399.25 | 1.64 | 1H NMR (300 MHz, MeOD) d 8.52 (s, 1H), 8.30 (d, J = 5.6 Hz, 3H), 4.50 (t, J = 12.1 Hz, 1H), 3.48 (s, 2H), 3.35 (s, 2H), 3.04 (q, J = 7.3 Hz, 5H), 2.25 (d, J = 3.5 Hz, 4H), 2.02-1.82 (m, 2H), 1.70 (t, J = 12.5 Hz, 2H), 1.58-1.35 (m, 3H), 1.30 (t, J = 7.3 Hz, 8H). |
| 983 | A | A | 486.2 | 1.83 | |
| 984 | A | A | 376.28 | 1.58 | |
| 985 | A | A | 439.24 | 1.94 | |
| 986 | A | A | 458.24 | 1.66 | |
| 987 | A | A | 401.83 | 2.12 | |
| 988 | A | A | 401.9 | 1.99 | |
| 989 | B | A | 474.3 | 1.45 | NMR 1H (MeOH-d4): 8.3 (m, 2H), 8.1 (s, 1H), 4.4 (t, 1H), 3.8 (t, 1H), 3.6 (m, 4H), 3.4 (m, 4H), 2.3 (m, 1H), 2.2 (m, 1H), 2.0 (m, 2H), 1.3-1.7 (m, 4H). |
| 990 | A | A | 429.26 | 1.92 | |
| 991 | C | C | 429.26 | 1.96 | |
| 992 | A | A | 526.3 | 1.99 | in MeOH-d4 |
| 993 | A | A | 438.21 | 1.83 | |
| 994 | A | A | 512.3 | 1.83 | NMR 1H (MeOH-d4): 8.6 (d, 1H), 8.4 (s, 1H), 8.3 (d, 1H), 8.2 (m, 1H), 4.3 (t, 1H), 3.8 (t, 1H), 3.5-3.6 (m, 3H), 3.1 (m, 2H), 2.8 (t, 1H), 2.3 (m, 3H), 2.2 (m, 2H), 2.0 (m, 2H), 1.85 (m, 1H), 1.3-1.75 (m, 4H). |
| 995 | A | A | 470.5 | 2.04 | 1H NMR (300 MHz, DMSO) d 8.41 (dd, J = 9.8, 2.9 Hz, 1H), 8.33-8.04 (m, 2H), 7.49 (d, J = 7.4 Hz, 1H), 6.21 (d, J = 8.0 Hz, 1H), 4.61 (s, 3H), 4.11 (d, J = 7.9 Hz, 1H), 3.90 (s, 3H), 3.66-3.42 (m, 1H), 2.18-1.90 (m, 2H), 1.87-1.69 (m, 2H), 1.58-0.68 (m, 8H) |
| 996 | A | A | 470.49 | 2.23 | 1H NMR (300 MHz, DMSO) d 8.41 (dd, J = 9.8, 2.9 Hz, 1H), 8.32-8.04 (m, 2H), 7.49 (d, J = 7.6 Hz, 1H), 6.22 (d, J = 8.0 Hz, 1H), 4.61 (s, 3H), 4.09 (s, 1H), 3.90 (s, 3H), 3.66-3.41 (m, 1H), 2.17-1.89 (m, 2H), 1.78 (dd, J = 10.3, 7.1 Hz, 2H), 1.65-0.69 (m, 8H). |
| 997 | A | A | 526.3 | 2 | |
| 998 | C | C | 526.3 | 2 | |
| 999 | A | A | 508.28 | 2.09 | |
| 1000 | A | A | 476.22 | 1.86 | |
| 1001 | A | A | 467.27 | 1.94 | |
| 1002 | A | A | 481.28 | 2.2 | |
| 1003 | A | A | 526.39 | 2.29 | |
| 1004 | A | A | 543.41 | 1.45 | |
| 1005 | A | A | 541.49 | 1.57 | |
| 1006 | A | A | 526.39 | 2.25 | |
| 1007 | A | A | 526.39 | 2.25 | |
| 1008 | A | A | 429.45 | 2.64 | CDCl3: 9.6 (m, 1H); 8.5 (dd, 1H); 8.25 (m, 2H); 8.1 (d, 1H); 4.8 (appt, 1H); 4.5 (m, 1H); 3.4 (m, 1H); 2.8 (s, 3H); 2.6 (m, 1H); 2.25 (m, 1H); 1.9 (m, 3H); 1.5-1.0 (m, 5H) |
| 1009 | A | A | 443.7 | 2.81 | CDCl3: 9.4 (m, 1H); 8.6 (dd, 1H); 8.25 |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_ Plus | LCMS__ RT | NMR |
|---|---|---|---|---|---|
| | | | | | (bs, 2H); 8.1 (d, 1H); 4.8 (appt, 1H); 4.6 (m, 1H); 3.5 (m, 2H); 3.1 (m, 1H); 2.6 (m, 1H); 2.25 (m, 1H); 1.9 (m, 3H); 1.5-1.0 (m, 6H) |
| 1010 | A | A | 487.29 | 1.93 | CDCl3: 9.6 (m, 1H); 8.5 (dd, 1H); 8.25 (bs, 2H); 8.0 (d, 1H); 4.75 (app t, 1H); 4.5 (m, 1H); 4.25 (m, 1H); 3.6 (m, 1H); 3.55 (s, 3H); 3.5 (m, 2H); 2.7 (m, 1H); 2.26 (app t, 1H); 2.0 (m, 3H); 1.9 (m, 3H); 1.5-1.0 (m, 7H) |
| 1011 | A | A | 473.28 | 1.79 | |
| 1012 | A | C | 504.06 | 2.09 | |
| 1013 | A | A | 486.47 | 2.52 | 1H NMR (d6-DMSO) 12.10 (s, 1H), 8.48-8.45 (m, 1H), 8.40-8.32 (m, 3H), 6.12 (d, J = 7.8 Hz, 1H), 4.27-4.09 (m, 2H), 3.72-3.47 (m, 1H), 3.41-3.11 (m, 2H), 2.17-1.98 (m, 3H), 1.90-1.72 (m, 4H), 1.60-1.37 (m, 2H), 1.32-1.20 (m, 1H) |
| 1014 | A | A | 441.45 | 2.07 | 1H NMR (300 MHz, DMSO) d 12.26 (s, 1H), 8.53-8.01 (m, 3H), 7.89 (s, 1H), 7.60 (d, J = 7.4 Hz, 1H), 4.33-3.68 (m, 4H), 2.74 (s, 2H), 2.23 (d, J = 13.1 Hz, 1H), 2.08-1.73 (m, 3H), 1.70-1.08 (m, 3H). |
| 1015 | A | A | 527.47 | 1.38 | 1H NMR (300 MHz, DMSO) d 12.61 (s, 1H), 8.38 (ddd, J = 9.6, 8.6, 2.9 Hz, 4H), 6.17 (d, J = 7.5 Hz, 1H), 4.20 (d, J = 10.5 Hz, 1H), 3.91 (d, J = 30.8 Hz, 4H), 3.72-2.96 (m, 11H), 2.37-1.68 (m, 6H), 1.52-1.10 (m, 4H). |
| 1016 | A | A | 468.42 | 1.68 | 1H NMR (300 MHz, DMSO) d 12.67 (s, 1H), 9.15 (s, 1H), 8.49 (dd, J = 9.3, 3.8 Hz, 3H), 8.28 (d, J = 2.0 Hz, 1H), 6.41 (d, J = 7.5 Hz, 1H), 4.32 (s, 1H), 3.67 (s, 1H), 3.57-3.46 (m, 3H), 3.25-3.19 (m, 3H), 2.91-2.61 (m, 2H), 2.51 (dt, J = 3.6, 1.8 Hz, 4H), 2.23-1.81 (m, 4H), 1.54-1.37 (m, 2H), 1.32-1.23 (m, 3H). |
| 1017 | A | A | 429.26 | 1.84 | |
| 1018 | A | A | 429.26 | 1.83 | |
| 1019 | A | A | 500.41 | 1.78 | |
| 1020 | A | A | 514.42 | 1.91 | |
| 1021 | A | A | 514.42 | 1.85 | |
| 1022 | A | A | 460.48 | 1.76 | 1H NMR (300 MHz, DMSO) d 12.26 (s, 1H), 8.42 (dd, J = 9.8, 2.8 Hz, 1H), 8.29-8.20 (m, 2H), 8.14 (d, J = 4.0 Hz, 1H), 7.54 (d, J = 7.3 Hz, 1H), 6.04 (d, J = 7.9 Hz, 1H), 5.37 (s, 1H), 5.19 (s, 1H), 4.11 (d, J = 4.5 Hz, 1H), 3.63 (d, J = 7.6 Hz, 1H), 3.57-3.40 (m, 2H), 3.23 (ddd, J = 18.1, 10.3, 5.4 Hz, 2H), 2.17-2.01 (m, 3H), 1.90-1.74 (m, 2H), 1.52-1.20 (m, 4H). |
| 1023 | A | A | 499.45 | 2.15 | H NMR (300.0 MHz, MeOD) d 8.51 (dd, J = 2.8, 9.6 Hz, 1H), 8.18-8.15 (m, 2H), 7.99 (d, J = 4.1 Hz, 1H), 4.75 (s, H), 4.31-4.19 (m, H), 3.82-3.73 (m, 2H), 3.76 (dd, J = 3.6, 11.9 Hz, 1H), 3.54-3.45 (m, 1H), 2.68 (s, 3H), 2.36 (d, J = 11.8 Hz, 1H), 2.22-1.90 (m, 6H), 1.62 (s, H), 1.52-1.24 (m, 4H) and −0.00 (TMS) ppm |
| 1024 | A | A | 427.27 | 2.07 | |
| 1025 | A | A | 427.27 | 2.04 | |
| 1026 | A | A | 413.26 | 1.94 | |
| 1027 | B | A | 413.26 | 1.9 | |
| 1028 | A | A | 414.34 | 2.36 | 1H NMR (300 MHz, MeOD) d 8.56 (dd, J = 9.2, 2.8 Hz, 1H), 8.47 (s, 1H), 8.37-8.32(m, 1H), 8.30 (d, J = 5.6 Hz, 1H), 5.17 (d, J = 6.9 Hz, 1H), 3.69 (s, 3H), 2.96 (d, J = 6.8 Hz, 1H), 2.19-2.11 (m, 1H), 2.09-2.02 (m, 1H), 1.74 (complex m, 9H). |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_ Plus | LCMS_ RT | NMR |
|---|---|---|---|---|---|
| 1029 | A | A | 443.27 | 1.97 | CDCl3: 9.75 (bs,1H); 8.6 (dd, 1H); 8.25 (d, 1H); 8.23 (s, 1H); 8.15 (d, 1H); 4.8 (d, 1H); 4.6 (m, 1H); 3.5 (m, 3H); 3.1 (m, 1H); 2.75 (bd, 1H); 2.25 (bd, 1H); 2.0 (m, 2H); 1.4 (d, 3H); 1.25 (t, 3H). |
| 1030 | A | A | 443.27 | 1.99 | CDCl3: 9.75 (bs, 1H); 8.5 (dd, 1H); 8.25 (d, 1H); 8.23 (s, 1H); 8.0 (d, 1H); 4.8 (d, 1H); 4.5 (m, 1H); 3.5 (m, 2H); 3.4 (m, 1H); 2.5 (bd, 1H); 2.1 (bd, 1H); 1.7 (m, 3H); 1.4 (ddd, 1H); 1.2 (m, 6H). |
| 1031 | A | A | 416.46 | 1.69 | |
| 1032 | A | A | 510.52 | 2.1 | |
| 1033 | A | A | 479.39 | 2.08 | 1H NMR (300 MHz, DMSO) d 12.23 (s, 1H), 8.50-8.46 (m, 1H), 8.42 (dd, J = 9.8, 2.8 Hz, 1H), 8.26 (dd, J = 2.7, 1.5 Hz, 1H), 8.22 (d, J = 2.7 Hz, 1H), 8.14 (d, J = 4.0 Hz, 1H), 7.73 (td, J = 7.7, 1.8 Hz, 1H), 7.47 (d, J = 7.3 Hz, 1H), 7.31-7.15 (m, 2H), 6.32 (t, J = 5.8 Hz, 1H), 6.14 (d, J = 7.8 Hz, 1H), 4.29 (d, J = 5.8 Hz, 2H), 4.22-3.97 (m, 1H), 3.57 (d, J = 7.7 Hz, 1H), 2.21-2.10 (m, J = 11.0 Hz, 1H), 2.07-1.98 (m, 1H), 1.95-1.72 (m, 2H), 1.59-0.88 (m, 4H). |
| 1034 | A | A | 400.37 | 2.15 | 1H NMR (300 MHz, MeOD) d 8.58 (dd, J = 9.3, 2.8 Hz, 1H), 8.41 (s, 1H), 8.29 (dd, J = 2.7, 1.7 Hz, 1H), 8.22 (d, J = 5.3 Hz, 1H), 5.10 (d, J = 6.9 Hz, 1H), 2.89 (d, J = 7.0 Hz, 1H), 2.17 (br s, 1H), 2.03 (br s, 1H), 1.99-1.49 (m, 7H). |
| 1035 | A | A | 444.42 | 1.81 | |
| 1036 | A | A | 472.5 | 1.67 | NMR 1H (MeOH-d4): 8.4 (m, 2H), 8.25 (m, 2H), 4.4 (m, 1H), 3.8 (m, 2H), 3.6 (m, 2H), 3.4 (m, 2H), 2.35 (m, 1H), 2.2 (m, 1H), 2.0 (m, 2H), 1.8 (m, 2H), 1.15-1.46 (6H). |
| 1037 | C | C | 470.4 | 1.72 | |
| 1038 | A | A | 470.4 | 1.73 | |
| 1039 | A | A | 458.43 | 1.61 | H NMR (300.0 MHz, CDCl3) d 7.70 (s, H), 7.28 (s, H), 7.11 (s, H), 5.31 (s, H), 4.17-4.02 (m, H), 3.78 (s, H), 3.73 (q, J = 7.0 Hz, H), 3.49 (s, H), 2.97 (s, H), 2.90 (s, H), 2.65 (s, H), 2.03 (d, J = 11.7 Hz, H), 1.87 (s, H), 1.29-1.21 (m, H) and 0.93 (d, J = 6.7 Hz, H) ppm |
| 1040 | A | A | 428.43 | 1.67 | H NMR (300.0 MHz, CDCl3) d 10.54 (s, H), 8.53 (dd, J = 2.8, 9.4 Hz, H), 8.50 (s, H), 8.25-8.06 (m, H), 7.30 (d, J = 10.7 Hz, H), 5.96 (s, H), 5.32 (s, H), 4.95 (d, J = 8.0 Hz, H), 4.87 (d, J = 6.6 Hz, H), 4.27-4.11 (m, H), 4.02-3.92 (m, H), 3.77 (t, J = 6.2 Hz, H), 3.51 (s, H), 2.92 (s, H), 2.73-2.67 (m, H), 2.45-2.37 (m, H), 2.26 (d, J = 10.3 Hz, H), 2.18 (d, J = 3.9 Hz, H), 2.12 (s, H), 2.06-1.95 (m, H), 1.89 (s, H), 1.87 (q, J = 3.4 Hz, H), 1.73 (d, J = 8.6 Hz, H), 1.67 (s, H), 1.63-1.58 (m, H), 1.33-1.26 (m, H), 1.17 (t, J = 11.6 Hz, H), 0.94 (d, J = 6.6 Hz, H), 0.85-0.68 (m, H), 0.61 (t, J = 7.0 Hz, H), 0.62 (s, H) and 0.53 (d, J = 7.2 Hz, H) ppm |
| 1041 | A | A | 486.46 | 1.95 | 1H NMR (300 MHz, MeOD) d 8.42 (dd, J = 9.2, 2.8 Hz, 1H), 8.40 (d, J = 2.8 Hz, 1H), 8.34-8.29 (m, 1H), 8.26 (d, J = 5.5 Hz, 1H), 4.43 (dd, J = 14.0, 10.0 Hz, 1H), 3.99-3.90 (m, 1H), 3.75 (ddd, J = 15.3, 7.6, 3.6 Hz, 2H), 3.40 (d, J = 5.3 Hz, 3H), |

TABLE 3-continued

IC₅₀, EC₅₀, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_ Plus | LCMS__ RT | NMR |
|---|---|---|---|---|---|
| | | | | | 3.35 (s, 3H), 2.36 (d, J = 11.9 Hz, 1H), 2.22 (d, J = 12.9 Hz, 1H), 2.04-1.75 (m, 7H), 1.68-1.19 (m, 6H). |
| 1042 | A | C | 457.5 | 1.31 | |
| 1043 | A | A | | | |
| 1044 | A | A | 454.53 | 1.91 | |
| 1045 | A | A | 454.4 | 1.9 | |
| 1046 | C | C | 479.41 | 2.08 | 1H NMR (300 MHz, DMSO) d 12.23 (d, J = 2.3 Hz, 1H), 8.51-8.35 (m, J = 8.5, 4.9, 1.7 Hz, 3H), 8.32-8.19 (m, 2H), 8.14 (d, J = 4.0 Hz, 1H), 7.63 (dt, J = 7.8, 1.9 Hz, 1H), 7.47 (d, J = 7.5 Hz, 1H), 7.36-7.25 (m, 1H), 6.27 (t, J = 6.0 Hz, 1H), 6.00 (d, J = 7.9 Hz, 1H), 4.22 (d, J = 6.0 Hz, 2H), 4.17-3.98 (m, J = 10.5, 6.4 Hz, 1H), 3.67-3.44 (m, J = 7.8 Hz, 1H), 2.16 (d, J = 11.3 Hz, 1H), 2.03 (d, J = 11.7 Hz, 1H), 1.95-1.70 (m, J = 25.5, 11.7 Hz, 2H), 1.53-0.93 (m, J = 33.7, 28.1, 12.8 Hz, 4H). |
| 1047 | A | A | 501.5 | 1.65 | |
| 1048 | A | A | 396.41 | 2.17 | 1H NMR (300 MHz, MeOD) d 9.07 (d, J = 6.8 Hz, 1H), 8.56-8.50 (m, 2H), 8.37 (d, J = 5.6 Hz, 1H), 7.55 (dd, J = 8.1, 5.1 Hz, 1H), 5.21 (d, J = 6.8 Hz, 1H), 3.73 (s, 3H), 3.00 (d, J = 6.6 Hz, 1H), 2.21-2.15 (m, 1H), 2.10-2.05 (m, J = 5.8 Hz, 1H), 1.99-1.52 (m, 9H). |
| 1049 | A | A | 440.62 | 2 | 1H NMR (300 MHz, MeOD) d 9.08 (d, J = 7.2 Hz, 1H), 8.58 (s, 1H), 8.55 (dd, J = 5.3, 0.8 Hz, OH), 8.34 (d, J = 5.6 Hz, 1H), 7.74 (dd, J = 8.0, 5.4 Hz, 1H), 4.49-4.37 (m, 1H), 3.93-3.81 (m, 1H), 3.67-3.56 (m, 4H), 3.39-3.31 (m, 4H), 2.42 (d, J = 11.1 Hz, 1H), 2.17-2.05 (m, J = 11.4 Hz, 1H), 1.99 (burried m, 3H), 1.67-1.26 (m, 5H). |
| 1050 | A | A | 456.57 | 2.71 | 1H NMR (300 MHz, DMSO) d 12.23 (s, 1H), 8.42 (dd, J = 9.8, 2.8 Hz, 1H), 8.22 (ddd, J = 28.3, 14.1, 2.7 Hz, 3H), 7.49 (d, J = 7.7 Hz, 1H), 5.79 (d, J = 7.9 Hz, 1H), 4.20-4.00 (m, 1H), 3.61 (d, J = 8.0 Hz, 1H), 3.49-3.36 (m, 1H), 3.17 (d, J = 5.2 Hz, 1H), 2.84-2.65 (m, 1H), 2.22-1.72 (m, 5H), 1.48-1.10 (m, 5H), 0.98 (dd, J = 6.6, 1.8 Hz, 3H). |
| 1051 | A | A | 456.44 | 2.6 | 1H NMR (300 MHz, DMSO) d 12.23 (d, J = 2.3 Hz, 1H), 8.42 (dd, J = 9.9, 2.9 Hz, 1H), 8.22 (ddd, J = 28.6, 14.3, 2.8 Hz, 3H), 7.49 (d, J = 7.4 Hz, 1H), 5.79 (d, J = 7.9 Hz, 1H), 4.21-3.99 (m, 1H), 3.61 (d, J = 7.9 Hz, 1H), 3.40 (dd, J = 9.7, 7.3 Hz, 1H), 3.14 (dd, J = 17.0, 7.6 Hz, 1H), 2.71 (dd, J = 9.7, 8.0 Hz, 1H), 2.20-1.73 (m, 5H), 1.54-1.11 (m, 5H), 0.98 (d, J = 6.6 Hz, 3H). |
| 1052 | A | A | 456.67 | 2.75 | 1H NMR (300 MHz, DMSO) d 12.23 (d, J = 2.1 Hz, 1H), 8.42 (dd, J = 9.9, 2.9 Hz, 1H), 8.22 (ddd, J = 30.6, 15.3, 2.8 Hz, 3H), 7.49 (d, J= 7.5 Hz, 1H), 5.74 (d, J = 7.9 Hz, 1H), 4.07 (d, J = 5.2 Hz, 1H), 3.88 (dd, J = 8.7, 4.5 Hz, 1H), 3.69-3.50 (m, 1H), 3.27-3.24 (m, 1H), 3.17 (t, J = 3.7 Hz, 1H), 2.21-1.66 (m, 5H), 1.38 (dd, J = 41.1, 29.2 Hz, 5H), 1.04 (d, J = 6.2 Hz, 3H). |
| 1053 | A | A | 456.27 | 2.65 | 1H NMR (300 MHz, DMSO) d 12.23 (d, J = 2.1 Hz, 1H), 8.42 (dd, J = 9.9, 2.9 Hz, 1H), 8.22 (ddd, J = 27.2, 13.6, 2.8 Hz, 3H), 7.49 (d, J = 7.5 Hz, 1H), 5.75 (d, J = 8.0 Hz, 1H), 4.26-4.02 (m, 1H), 3.97-3.83 |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_ Plus | LCMS_ RT | NMR |
|---|---|---|---|---|---|
| | | | | | (m, 1H), 3.72-3.53 (m, 1H), 3.31 (s, 1H), 3.16 (s, 1H), 2.15-1.64 (m, 5H), 1.44 (s, 5H), 1.04 (d, J = 6.2 Hz, 3H). |
| 1054 | A | A | 472.42 | 2.34 | 1H NMR (300 MHz, DMSO) d 12.27 (s, 1H), 8.42 (dd, J = 9.9, 2.8 Hz, 1H), 8.27 (dd, J = 2.7, 1.4 Hz, 1H), 8.23 (d, J = 2.8 Hz, 1H), 8.14 (d, J = 4.0 Hz, 1H), 7.53 (d, J = 7.5 Hz, 1H), 7.29 (s, 1H), 6.70 (s, 1H), 5.91 (d, J = 8.0 Hz, 1H), 4.11 (s, 1H), 3.90 (d, J = 3.0 Hz, 1H), 3.62 (d, J = 8.1 Hz, 1H), 3.27 (d, J = 4.2 Hz, 2H), 2.11 (d, J = 10.4 Hz, 1H), 1.99 (s, 2H), 1.93-1.77 (m, 4H), 1.75 (s, 1H), 1.54-1.21 (m, 5H). |
| 1055 | A | A | 472.41 | 2.34 | |
| 1056 | A | A | 486.33 | 1.89 | |
| 1057 | A | C | 486.4 | 1.89 | |
| 1058 | A | A | 472.43 | 2.67 | 1H NMR (300 MHz, MeOD) d 8.46 (dd, J = 10.0, 2.8 Hz, 1H), 8.17-7.91 (m, 2H), 4.28-4.08 (m, 1H), 3.88-3.71 (m, 1H), 3.62 (d, J = 5.1 Hz, 3H), 3.46-3.32 (m, 4H), 2.87 (s, 3H), 2.32 (d, J = 11.9 Hz, 1H), 2.15 (d, J = 12.9 Hz, 1H), 2.03-1.85 (m, 2H), 1.67-1.20 (m, 4H). |
| 1059 | A | A | 495 | 2.03 | |
| 1060 | A | A | 508 | 1.42 | |
| 1061 | A | A | 474 | 1.89 | NMR 1H (MeOH-d4): 8.5 (s, 1H), 8.15-8.34 (m, 3H), 4.4 (m, 1H), 3.8 (m, 1H), 3.5 (m, 2H), 3.5 (m, 2H), 3.3 (m, 2H), 2.9 (s, 1H), 2.4 (m, 1H), 2.2 (m, 1H), 2.0 (m, 2H), 1.2-1.5 (m, 4H), 1.1 (t, 3H). |
| 1062 | A | A | 458 | 1.68 | |
| 1063 | A | A | 444 | 1.91 | |
| 1064 | A | A | 504.5 | 1.91 | H NMR (300.0 MHz, MeOD) d 8.44 (dd, J = 2.8, 9.6 Hz, H), 8.14 (t, J = 4.5 Hz, H), 8.13 (s, H), 7.98-7.94 (m, H), 7.70 (s, H), 7.06 (s, H), 6.28 (d, J = 7.3 Hz, H), 5.49 (s, H), 4.83 (s, H), 4.52 (s, H), 4.22-4.09 (m, H), 3.75 (dd, J = 3.8, 11.4 Hz, H), 3.69 (s, H), 3.57-3.30 (m, H), 3.26 (s, H), 3.10 (s, H), 2.99 (s, H), 2.87 (d, J = 8.6 Hz, H), 2.36-2.33 (m, H), 2.19 (d, J = 12.2 Hz, H), 2.03 (d, J = 10.6 Hz, H), 1.95-1.89 (m, H), 1.65 (s, H), 1.61-1.52 (m, H), 1.43-1.13 (m, H) and −0.00 (s, H) ppm |
| 1065 | A | A | 486 | 1.96 | |
| 1066 | A | A | 474 | 1.82 | |
| 1067 | A | A | 474 | 1.89 | in MeOH-4 |
| 1068 | A | A | 474 | 1.86 | in MeOH-d4 |
| 1069 | A | A | 484 | 1.99 | |
| 1070 | A | A | 400.39 | 2.15 | 1H NMR (300 MHz, MeOD) d 8.66 (dd, J = 9.6, 2.8 Hz, 1H), 8.19 (s, 2H), 7.98 (d, J = 4.1 Hz, 1H), 4.91 (d, J = 6.8 Hz, 1H), 2.75-2.63 (m, 1H), 2.18-1.41 (m, 10H). |
| 1071 | A | A | 400.56 | 2.15 | 1H NMR (300 MHz, MeOD) d 8.66 (dd, J = 9.6, 2.8 Hz, 1H), 8.19 (s, 2H), 4.90 (d, J = 6.9 Hz, 1H), 2.75-2.64 (m, 1H), 2.15-1.42 (m, 10H). |
| 1072 | A | A | 537 | 2.09 | 1H NMR (300 MHz, DMSO) d 12.55 (s, 1H), 8.40 (t, J = 3.1 Hz, 1H), 8.36 (d, J = 2.8 Hz, 1H), 8.33 (t, J = 3.7 Hz, 2H), 6.43 (d, J = 7.7 Hz, 1H), 4.19 (d, J = 7.2 Hz, 1H), 3.66 (d, J = 7.4 Hz, 1H), 3.48 (dd, J = 13.1, 5.9 Hz, 4H), 3.35-3.25 (m, 1H), 2.67 (d, J = 7.0 Hz, 2H), 2.21-1.80 (m, 6H), 1.56-1.22 (m, 4H). |
| 1073 | A | A | 490 | 1.99 | |
| 1074 | A | A | 490 | 2.01 | |
| 1075 | A | A | 458 | 2.04 | NMR 1H (MeOH-d4): 8.44 (s, 1H), 8.4 (d, 1H), 8.3 (m, 1H), 8.2 (d, 1H), 4.3-4.4 (m, |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_Plus | LCMS_RT | NMR |
|---|---|---|---|---|---|
| | | | | | 2H), 3.8 (m, 1H), 3.2 (q, 2H), 2.2-2.34 (m, 2H), 2.0 (m, 2H), 1.3-1.6 (m, 4H), 1.1 (m, 8H). |
| 1076 | A | A | 473 | 1.33 | NMR 1H (MeOH-d4): 8.5 (s, 1H), 8.4 (dd, 1H), 8.3 (m, 1H), 8.26 (d, 1H), 4.4-4.45 (m, 1H), 3.8 (m, 1H), 3.5-3.7 (m, 2H), 3.3 (m, 2H), 2.95 (m, 9H), 2.35 (m, 1H), 2.2 (m, 2H), 1.95 (m, 2H), 1.25-1.55 (m, 5H). |
| 1077 | A | A | 474.43 | 1.68 | H NMR (300.0 MHz, MeOD) d 8.47-8.25 (m, H), 7.98 (s, H), 4.95 (s, H), 4.89 (s, H), 4.82 (s, H), 4.49-4.40 (m, H), 4.21-4.10 (m, H), 4.01 (s, H), 3.92 (s, H), 3.54 (t, J = 1.7 Hz, H), 3.44-3.30 (m, H), 3.07 (t, J = 1.6 Hz, H), 2.99 (s, H), 2.87 (d, J = 6.6 Hz, H), 2.65 (s, H), 2.51 (q, J = 12.1 Hz, H), 2.36-2.31 (m, H), 2.24-2.04 (m, H), 1.99 (s, H), 1.81 (d, J = 11.6 Hz, H), 1.71-1.66 (m, H), 1.61-1.45 (m, H), 1.40-1.37 (m, H), 1.18-1.08 (m, H), 0.19 (s, H), −0.00 (TMS) and −0.20 (s, H) ppm |
| 1078 | A | A | 481 | 1.91 | NMR 1H (MeOH-d4): 8.5 (s, 1H), 8.17-8.33 (m, 3H), 4.4 (m, 1H), 3.75 (m, 1H), 3.6 (m, 2H), 2.7-2.9 (m, 3H), 2.4 (m, 1H), 2.2 (m, 1H), 2.05 (m, 2H), 1.2-1.7 (m, 4H), 0.9 (m, 2H), 0.75 (m, 2H). |
| 1079 | A | A | 472.37 | 2.11 | 1H NMR (300 MHz, DMSO) d 12.23 (s, 1H), 8.42 (dd, J = 9.9, 2.9 Hz, 1H), 8.30-8.19 (m, 2H), 8.13 (d, J = 4.0 Hz, 1H), 7.49 (d, J = 7.5 Hz, 1H), 5.77 (t, J = 6.3 Hz, 1H), 4.66 (s, 1H), 4.20-4.04 (m, 1H), 3.71-3.50 (m, J = 7.7 Hz, 1H), 3.30 (q, J = 5.3 Hz, 1H), 3.18 (dd, J = 7.8, 4.8 Hz, 2H), 3.04 (d, J = 10.5 Hz, 1H), 2.11 (d, J = 11.6 Hz, 1H), 2.00 (d, J = 9.5 Hz, 1H), 1.88-1.59 (m, 4H), 1.52-1.32 (m, 2H), 1.35-1.18 (m, 5H). |
| 1080 | A | A | 500 | 2.01 | NMR 1H (MeOH-d4): 8.5 (s, 1H), 8.26-8.33 (m, 3H), 4.36 (m, 1H), 4.05 (m, 1H), 3.9 (m, 1H), 3.75 (m, 2H), 3.3 (m, 2H), 3.2 (m, 2H), 2.4 (m, 1H), 2.2 (m, 2H), 1.8-2.0 (m, 5H), 1.2-1.6 (m, 5H), 1.1 (t, 3H). |
| 1081 | A | A | 512 | 1.84 | NMR 1H (MeOH-d4): 8.4 (s, 1H), 8.25-8.35 (m, 3H), 4.7 (s, 2H), 4.35 (m, 1H), 3.8 (m, 1H), 3.35 (q, 2H), 2.2-2.3 (m, 5H), 2.0 (m, 2H), 1.3-1.8 (m, 4H), 1.1 (t, 3H). |
| 1082 | B | A | 498.35 | 2.69 | 1H NMR (300 MHz, CDCl3) d 10.71 (s, 1H), 8.53 (d, J = 9.9 Hz, 1H), 8.20 (s, 1H), 8.11 (d, J = 2.9 Hz, 1H), 4.87 (d, J = 6.9 Hz, 1H), 4.29 (d, J = 6.9 Hz, 1H), 4.14 (m, 1H), 3.82 (m, 4H), 3.34 (m, 4H), 2.56 (s, 1H), 2.30 (m, 1H), 2.05 (m, 1H),, 1.91 (m 1H), 1.81-1.42 (m, 2H), 1.41-0.87 (m, 7H). |
| 1083 | A | A | 456.2 | 2.74 | 1H NMR (300 MHz, MeOD) d 8.33-8.21 (m, 2H), 8.11 (dd, J = 9.3, 2.3 Hz, 1H), 4.38 (m, 1H), 3.51(4 H), 3.72 (m, 1H), 2.85 (s, 3H), 2.30 (m, 1H), 2.10 (m, 1H), 2.02-1.88 (m, 6H), 1.57-1.30 (m, 4H). |
| 1084 | A | A | 486.46 | 1.76 | |
| 1085 | A | A | 458.5 | 2.05 | |
| 1086 | A | A | 444.61 | 1.87 | |
| 1087 | A | A | 458.56 | 2.04 | |
| 1088 | C | C | 482.46 | 2.87 | 1H NMR (300 MHz, MeOD) d 8.40 (d, J = 10.0 Hz, 1H), 8.01 (dd, J = 17.7, 2.5 Hz, 2H), 4.14 (s, 1H), 3.84-3.53 (m, 2H), 3.28 (s, 3H), 2.28 (d, J = 11.9 Hz, 1H), 2.11 (s, 1H), 2.05-1.76 (m, 6H), 1.61-1.00 (m, 9H). |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_Plus | LCMS_RT | NMR |
|---|---|---|---|---|---|
| 1089 | A | A | 424.69 | 1.77 | 1H NMR (300 MHz, MeOD) d 9.32-9.10 (m, 1H), 8.67 (s, 1H), 8.65-8.59 (m, 1H), 8.39 (d, J = 5.6 Hz, 1H), 7.87 (dd, J = 8.1, 5.6 Hz, 1H), 4.53-4.34 (m, 1H), 3.97-3.79 (m, 1H), 2.42 (d, J = 11.5 Hz, 1H), 2.11 (d, J = 10.5 Hz, 1H), 2.05-1.83 (m, 5H), 1.70-1.33 (m, 4H). |
| 1090 | A | A | 382.61 | 1.96 | 1H NMR (300 MHz, MeOD) d 9.00 (dd, J = 8.1, 1.5 Hz, 1H), 8.46 (dd, J = 5.0, 1.4 Hz, 1H), 8.32 (d, J = 5.6 Hz, 1H), 7.47 (dd, J = 8.1, 5.0 Hz, 1H), 5.21-5.10 (m, J = 6.8 Hz, 1H), 3.01-2.87 (m, J = 6.8 Hz, 1H), 2.23-2.12 (m, 1H), 2.06-1.98 (m, 1H), 1.98-1.47 (m, 7H). |
| 1091 | A | A | 472.25 | 1.77 | |
| 1092 | A | A | 472.25 | 1.77 | |
| 1093 | A | A | 488.19 | 1.9 | |
| 1094 | A | A | 488.19 | 1.9 | |
| 1095 | A | A | 514.41 | 2.33 | 1H NMR (300 MHz, DMSO) d 12.27 (s, 1H), 8.42 (dd, J = 9.8, 2.8 Hz, 1H), 8.29-8.25 (m, J = 1.4 Hz, 1H), 8.23 (d, J = 2.8 Hz, 1H), 8.14 (d, J = 4.0 Hz, 1H), 7.52 (d, J = 7.4 Hz, 1H), 6.23 (d, J = 7.7 Hz, 1H), 4.21-3.92 (m, 3H), 3.60 (s, 1H), 3.17 (d, J = 5.2 Hz, 2H), 2.11 (d, J = 12.4 Hz, 1H), 2.00 (d, J = 7.9 Hz, 1H), 1.81 (d, J = 10.7 Hz, 2H), 1.62 (d, J = 11.8 Hz, 2H), 1.52-1.17 (m, 6H), 1.02 (d, J = 9.4 Hz, 8H). |
| 1096 | A | A | 456.45 | 2.01 | |
| 1097 | A | A | 488 | 1.56 | |
| 1098 | A | A | 460.39 | 2.38 | 1H NMR (300 MHz, DMSO) d 12.27 (s, IH), 8.42 (dd, J = 9.9, 2.8 Hz, 1H), 8.29-8.01 (m, 3H), 7.50 (d, J = 7.1 Hz, 1H), 5.84 (d, J = 7.8 Hz, 1H), 5.60 (d, J = 8.2 Hz, 1H), 4.29-3.99 (m, 1H), 3.72 (dd, J = 12.8, 6.6 Hz, 1H), 3.52 (d, J = 8.1 Hz, IH), 3.25-3.05 (m, 4H), 2.19-1.68 (m, 3H), 1.52-1.11 (m, 3H), 1.00 (d, J = 6.7 Hz, 3H). |
| 1099 | A | A | 470.35 | 2.2 | 1H NMR (300 MHz, DMSO) d 12.26 (d, J = 2.4 Hz, 1H), 8.42 (dd, J = 9.8, 2.9 Hz, 1H), 8.23 (ddd, J = 30.4, 15.2, 2.7 Hz, 2H), 7.54 (d, J = 7.5 Hz, 1H), 6.14 (d, J = 8.0 Hz, 1H), 4.50 (d, J = 10.5 Hz, 2H), 4.25-3.95 (m, 1H), 3.62 (dd, J = 12.4, 6.7 Hz, 2H), 3.25-3.03 (m, 2H), 2.19-0.90 (m, 10H). |
| 1100 | | | 474 | 1.55 | |
| 1101 | A | A | 502.5 | 1.76 | |
| 1102 | A | A | 571.14 | 1.65 | 1H NMR (300 MHz, DMSO) d 12.26 (s, 1H), 8.42 (dd, J = 9.8, 2.9 Hz, 1H), 8.29-8.25 (m, J = 2.8, 1.5 Hz, 1H), 8.23 (s, 1H), 8.14 (d, J = 4.0 Hz, 1H), 7.54 (d, J = 7.7 Hz, 1H), 5.97 (d, J = 7.8 Hz, 1H), 4.20-4.08 (m, J = 5.2 Hz, 1H), 4.08-3.98 (m, 2H), 3.97-3.86 (m, J = 11.5, 8.4 Hz, 1H), 3.30-3.23 (m, 1H), 3.17 (d, J = 5.2 Hz, 1H), 3.07 (d, J = 5.4 Hz, 1H), 2.18-2.07 (m, J = 11.8 Hz, 1H), 2.06-1.93 (m, J = 10.5 Hz, 1H), 1.92-1.74 (m, 6H), 1.76-1.63 (m, 2H), 1.42 (dd, J = 23.4, 11.6 Hz, 2H), 1.35-1.15 (m, 3H), 0.81 (dd, J = 13.3, 6.8 Hz, 6H). |
| 1103 | A | A | 486 | 1.72 | 1H NMR (300 MHz, DMSO) d 8.36 (d, J = 8.1 Hz, 1H), 8.23 (d, J = 1.5 Hz, 1H), 8.20 (s, 1H), 8.11 (d, J = 3.8 Hz, 1H), 7.43 (s, 1H), 6.13 (d, J = 7.5 Hz, 1H), 5.76 (s, 1H), 4.13 (s, 2H), 3.24-2.98 (m, 4H), 2.27-2.20 (m, 1H), 2.01 (d, J = 11.5 Hz, 3H), |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_Plus | LCMS_RT | NMR |
|---|---|---|---|---|---|
| | | | | | 1.81 (d, J = 11.6 Hz, 2H), 1.63-0.93 (m, 11H). |
| 1104 | A | A | 490.43 | 1.59 | 1H NMR (300 MHz, d6-DMSO) ☐☐ 12.70 (s, 1H), 8.42 (s, 1H), 8.34 (s, 1H), 8.26 (d, J = 17.1 Hz, 1H), 6.02 (d, J = 7.2 Hz, 1H), 5.37 (s, 1H), 5.19 (s, 1H), 4.33 (s, 1H), 4.13 (s, 3H), 2.27 (s,1H), 2.10 (s, 3H), 1.77 (s, 5H), 1.48-1.14 (m, 6H) |
| 1105 | A | A | 474.4 | 1.5 | NMR 1H (MeOH-d4): 8.5 (s, 1H), 8.25-8.33 (m, 3H), 4.4 (m, 1H), 4.1 (d, 2H), 3.8 (m, 1H), 3.5 (dd, 2H), 2.3-2.4 (m, 2H), 2.0 (d, 2H), 1.3-1.6 (m, 4H). |
| 1106 | A | A | 502.43 | 2.35 | 1H NMR (300 MHz, DMSO d 12.26 (s, 1H), 8.42 (dd, J = 9.8, 2.8 Hz, 1H), 8.30-8.05 (m, 3H), 7.54 (d, J = 7.5 Hz, 1H), 5.96 (d, J = 7.8 Hz, 1H), 4.26-3.93 (m, 1H), 3.80 (s, 2H), 3.59 (s, 1H), 3.33-3.16 (m, 8H), 1.93 (dd, J = 67.2, 22.0 Hz, 4H), 1.60-0.89 (m, 5H). |
| 1107 | A | A | 502.02 | 2.38 | 1H NMR (300 MHz, DMSO d 12.26 (s, 1H), 8.42 (dd, J = 9.9, 2.8 Hz, 1H), 8.35-8.01 (m, 3H), 7.54 (d, J = 7.5 Hz, 1H), 5.96 (d, J = 7.8 Hz, 1H), 4.13 (s, 1H), 3.80 (s, 2H), 3.69-3.44 (m, 1H), 3.28 (d, J = 9.4 Hz, 7H), 2.04 (d, J = 32.3 Hz, 2H), 1.83 (d, J = 8.8 Hz, 2H), 1.33 (dt, J = 25.0, 12.2 Hz, 5H). |
| 1108 | A | A | 516.71 | 2.2 | 1H NMR (300 MHz, DMSO d 12.26 (s, 1H), 8.65-7.90 (m, 4H), 7.53 (d, J = 6.6 Hz, 1H), 6.29 (d, J = 6.9 Hz, 1H), 4.12 (s, 1H), 3.72-2.94 (m, 11H), 2.04 (d, J = 30.8 Hz, 2H), 1.72 (d, J = 44.2 Hz, 3H), 1.32 (d, J = 56.3 Hz, 5H). |
| 1109 | A | A | 516.41 | 2.39 | 1H NMR (300 MHz, DMSO d 12.27 (s, 1H), 8.27 (dd, J = 48.0, 38.1 Hz, 4H), 7.55 (s, 1H), 6.36 (s, 1H), 4.12 (s, 1H), 3.81-2.81 (m, 11H), 2.21-1.68 (m, 5H), 1.32 (d, J = 53.8 Hz, 6H). |
| 1110 | A | A | 458.5 | 2.02 | |
| 1111 | A | A | 472.51 | 1.72 | |
| 1112 | A | A | 472.45 | 1.73 | |
| 1113 | A | A | 472.45 | 1.73 | |
| 1114 | A | A | 487.48 | 1.64 | |
| 1115 | A | A | 521.5 | 1.5 | NMR 1H (MeOH-d4): 8.5 (s, 1H), 8.3-8.35 (m, 3H), 6.37-6.7 (tt, 1H), 4.4 (m, 1H), 3.8 (m, 1H), 3.5-3.75 (m, 5H), 2.18-2.4 (m, 2H), 2.0 (d, 2H), 1.3-1.7 (m, 4H). |
| 1116 | B | C | 445.45 | 1.64 | |
| 1117 | A | A | 501.56 | 2.16 | |
| 1118 | A | A | 486.5 | 1.68 | NMR 1H (MeOH-d4): 8.27-8.32 (m, 4H), 4.4 (m, 1H), 3.35 (m, 1H), 2.4-2.64 (m, 2H), 1.8-2.2 (m, 4H), 1.4-1.75 (m, 4H). |
| 1119 | A | A | 474.24 | 1.89 | |
| 1120 | A | A | 490.23 | 2.01 | |
| 1121 | A | A | 490.23 | 2.01 | |
| 1122 | A | A | 456.26 | 1.93 | |
| 1123 | A | A | 456.26 | 1.93 | |
| 1124 | A | A | 472.25 | 2.06 | |
| 1125 | A | A | 472.19 | 2.06 | |
| 1126 | A | A | 474.24 | 1.89 | |
| 1127 | A | A | 492.08 | 2.82 | 1H NMR (300 MHz, DMSO) d 12.25 (s, 1H), 8.41 (dd, J = 9.8, 2.7 Hz, 1H), 8.30-8.05 (m, 2H), 7.50 (s, 1H), 7.23 (td, J = 6.1, 2.9 Hz, 5H), 6.17 (d, J = 8.3 Hz, 1H), 5.80 (d, J = 7.9 Hz, 1H), 4.73 (s, 1H), 4.11 (d, J = 5.3 Hz, 1H), 3.50 (s, 1H), 2.21-1.66 (m, 4H), 1.28 (dd, J = 14.7, 9.7 Hz, 7H). |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_Plus | LCMS_RT | NMR |
|---|---|---|---|---|---|
| 1128 | A | A | 458.41 | 2.87 | 1H NMR (300 MHz, DMSO) d 12.26 (s, 1H), 8.42 (dd, J = 9.9, 2.9 Hz, 1H), 8.23 (ddd, J = 29.2, 15.1, 2.7 Hz, 3H), 7.53 (d, J = 7.4 Hz, 1H), 5.97 (d, J = 7.8 Hz, 1H), 4.11 (d, J = 5.2 Hz, 1H), 3.62 (d, J = 7.8 Hz, 1H), 3.15 (dd, J = 9.6, 6.3 Hz, 2H), 2.74 (s, 2H), 2.05 (dd, J = 27.0, 11.4 Hz, 2H), 1.81 (d, J = 11.2 Hz, 2H), 1.55-1.06 (m, 7H), 0.86 (t, J = 7.2 Hz, 3H). |
| 1129 | A | A | 444.41 | 2.59 | 1H NMR (300 MHz, DMSO) d 12.26 (d, J = 2.1 Hz, 1H), 8.42 (dd, J = 9.8, 2.8 Hz, 1H), 8.23 (ddd, J = 30.0, 15.0, 2.7 Hz, 3H), 7.53 (d, J = 7.5 Hz, 1H), 5.98 (d, J = 7.9 Hz, 1H), 4.35-3.94 (m, 1H), 3.63 (d, J = 8.8 Hz, 1H), 3.22-3.02 (m, 2H), 2.75 (s, 2H), 2.05 (dd, J = 26.7, 11.8 Hz, 2H), 1.81 (d, J = 10.5 Hz, 2H), 1.37 (ddd, J = 41.6, 24.7, 8.1 Hz, 6H), 0.79 (t, J = 7.4 Hz, 3H). |
| 1130 | A | A | 444.1 | 2.6 | |
| 1131 | A | A | 430.07 | 2.47 | 1H NMR (300 MHz, DMSO) d 12.26 (s, 1H), 8.42 (dd, J = 9.8, 2.9 Hz, 1H), 8.23 (ddd, J = 29.8, 15.3, 2.7 Hz, 2H), 7.53 (d, J = 7.5 Hz, 1H), 6.00 (d, J = 7.9 Hz, 1H), 4.11 (d, J = 5.2 Hz, 1H), 3.62 (d, J = 9.3 Hz, 1H), 3.25-3.06 (m, 2H), 2.74 (s, 2H), 2.05 (dd, J = 28.7, 11.2 Hz, 2H), 1.81 (d, J = 10.5 Hz, 1H), 1.55-1.09 (m, 4H), 0.96 (t, J = 7.0 Hz, 2H). |
| 1132 | A | A | 486.1 | 2.46 | 1H NMR (300 MHz, DMSO) d 12.26 (s, 1H), 8.42 (dd, J = 9.8, 2.8 Hz, 1H), 8.20 (dd, J = 32.6, 8.6 Hz, 2H), 7.53 (d, J = 7.7 Hz, 1H), 5.90 (d, J = 7.9 Hz, 1H), 4.28-3.92 (m, 2H), 3.62 (d, J = 7.1 Hz, 1H), 3.45-3.08 (m, 9H), 2.21-1.68 (m, 5H), 1.53-0.89 (m, 6H). |
| 1133 | A | A | 488.19 | 1.88 | 1H NMR (300 MHz, MeOD) d 8.36 (dd, J = 9.4, 2.6 Hz, 1H), 8.28 (m, 2H), 5.13 (s, 2H), 4.35 (m, 1H), 3.79 (s, 1H), 3.67-3.56 (m, 4H), 3.39-3.32 (m, 4H), 2.33 (m, 1H), 2.16 (m, 1H), 1.98 (m, 2H), 1.69-1.20 (m, 4H). |
| 1134 | A | A | 442 | 2.3 | NMR 1H (MeOH-d4): 8.5 (s, 1H), 8.3 (m, 3H), 4.4 (m, 1H), 3.6 (m, 4H), 2.6 (m, 1H), 1.5-2.3 (m, 12H). |
| 1135 | A | A | 484.42 | 2.32 | 1H NMR (300 MHz, DMSO) d 12.23 (s, 1H), 8.42 (dd, J = 9.8, 2.7 Hz, 1H), 8.33-8.06 (m, 3H), 7.49 (d, J = 7.7 Hz, 1H), 6.15 (d, J = 7.7 Hz, 1H), 4.24 (s, 3H), 3.55 (d, J = 12.5 Hz, 3H), 2.83 (d, J = 12.5 Hz, 2H), 1.99 (s, 2H), 1.72 (ddd, J = 33.2, 19.4, 9.2 Hz, 5H), 1.46-1.02 (m, 4H). |
| 1136 | A | A | 417.48 | 1.99 | |
| 1137 | A | A | 459.52 | 2 | |
| 1138 | A | A | 345.16 | 0.55 | 1H NMR (300 MHz, DMSO) d 12.40 (s, 1H), 8.56-8.13 (m, 2H), 7.89 (s, 2H), 4.37 (s, 6H), 3.21 (d, J = 22.3 Hz, 1H), 2.27 (s, 1H), 2.01 (s, 1H), 1.63-1.14 (m, 2H). |
| 1139 | A | A | 472.32 | 2.06 | 1H NMR (300 MHz, MeOD) d 8.55 (dd, J = 9.8, 2.7 Hz, 1H), 8.08 (m, 2H), 5.12 (m, 2H), 4.19 (m, 1H), 3.80 (m, 1H), 2.33 (m, 1H), 2.17 (m, 1H), 2.06-1.77 (m, 8H), 1.69-1.21 (m, 4H). |
| 1140 | A | A | 443.53 | 2.29 | 1H NMR (300 MHz, CDCl3) δ 9.91 (s, 1H), 8.51 (dd, J = 9.4, 2.8 Hz, 1H), 8.26 (dd, J = 2.6, 1.7 Hz, 1H), 8.22 (d, J = 2.8 Hz, 1H), 8.07 (d, J = 3.5 Hz, 1H), 5.42 (d, J = 6.2 Hz, 1H), 5.10-4.92 (m, J = 7.8, 3.9 Hz, 1H), 4.48-4.30 (m, 1H), 3.42 (q, J = 11.8, 6.1 Hz, 4H), 2.44 (dt, J = 12.9 |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_ Plus | LCMS_ RT | NMR |
|---|---|---|---|---|---|
| | | | | | Hz, 1H), 2.11-1.81 (m, 7H), 1.75-1.46 (m, 3H) |
| 1141 | A | A | 467.52 | 1.78 | |
| 1142 | A | A | 403.15 | 1.7 | H NMR (300.0 MHz, MeOD) d 8.67 (d, J = 2.3 Hz, 1H), 8.61 (s, 1H), 8.39 (d, J = 2.3 Hz, 1H), 8.32 (d, J = 5.5 Hz, 1H), 4.50-4.43 (m, 1H), 3.70-3.63 (m, 1H), 3.31 (qn, J = 1.6 Hz, H), 2.47-2.39 (m, 1H), 2.30 (d, J = 12.1 Hz, 1H), 2.15-2.08 (m, 2H), 1.70 (q, J = 11.9 Hz, 2H), 1.50-1.14 (m, 2H) and −0.00 (TMS) ppm |
| 1143 | A | A | 387.06 | 1.45 | |
| 1144 | A | A | 456.07 | 1.78 | 1H NMR (300 MHz, MeOD) d 8.83 (s, 1H), 8.67-8.09 (m, 4H), 2.67 (s, 3H), 2.18 (dd, J = 101.0, 49.9 Hz, 5H), 1.34 (d, J = 29.6 Hz, 3H). |
| 1145 | A | A | | | 1H NMR (300 MHz, DMSO) d 12.24 (d, J = 2.3 Hz, 1H), 8.43 (dd, J = 9.8, 2.9 Hz, 1H), 8.26 (dd, J = 2.7, 1.5 Hz, 1H), 8.16 (d, J = 3.8 Hz, 1H), 7.78 (s, 1H), 7.50 (d, J = 7.3 Hz, 1H), 4.58-4.18 (m, 1H), 3.42-3.32 (m, 1H), 2.11 (d, J = 13.1 Hz, 2H), 1.98-1.69 (m, 4H), 1.68-1.14 (m, 4H), 0.92 (t, J = 7.4 Hz, 3H). |
| 1146 | A | A | | | 1H NMR (300 MHz, DMSO) d 12.25 (d, J = 2.1 Hz, 1H), 8.43 (dd, J = 9.8, 2.9 Hz, 1H), 8.26 (dd, J = 2.8, 1.5 Hz, 1H), 8.21-8.10 (m, 2H), 7.80 (s, 1H), 7.48 (d, J = 7.4 Hz, 1H), 4.59-4.22 (m, 1H), 3.33-3.20 (m, 4H), 2.31-1.96 (m, 2H), 1.94-1.16 (m, 7H), 0.92 (t, J = 7.4 Hz, 3H). |
| 1147 | A | A | | | 1H NMR (300 MHz, DMSO) d 12.24 (s, 1H), 8.39 (dd, J = 9.8, 2.8 Hz, 1H), 8.32-8.26 (m, 1H), 8.20 (dd, J = 9.7, 3.2 Hz, 1H), 7.89 (s, 1H), 7.24 (t, J = 22.3 Hz, 1H), 4.37 (s, 1H), 3.47 (d, J = 7.8 Hz, 1H), 2.18 (d, J = 10.5 Hz, 1H), 2.03-1.14 (m, 9H), 0.96 (t, J = 7.3 Hz, 3H). |
| 1148 | A | A | | | 1H NMR (300 MHz, DMSO) d 12.30 (s, 1H), 8.39 (dd, J = 9.8, 2.9 Hz, 1H), 8.28 (dd, J = 2.7, 1.5 Hz, 1H), 8.18 (dd, J = 4.9, 3.0 Hz, 1H), 7.92 (s, 1H), 7.40 (d, J = 8.1 Hz, 1H), 4.32 (s, 1H), 3.40 (d, J = 8.5 Hz, 1H), 2.14 (d, J = 12.7 Hz, 1H), 1.97-1.17 (m, 9H), 1.10-0.80 (m, 3H). |
| 1149 | A | A | 445.51 | 2.37 | |
| 1150 | A | A | 457.47 | 2.47 | |
| 1151 | A | A | 461.51 | 2.15 | |
| 1152 | A | A | 493.5 | 2.39 | |
| 1153 | A | A | 443.21 | 1.99 | |
| 1154 | A | A | | | 1H NMR (300 MHz, MeOD) d 8.63-8.40 (m, 1H), 8.31-8.03 (m, 2H), 7.99 (dd, J = 3.9, 1.1 Hz, 1H), 4.49 (t, J = 11.5 Hz, 1H), 3.44-3.25 (m, 3H), 3.22-3.08 (m, 1H), 2.29 (dd, J = 40.0, 12.5 Hz, 2H), 2.13-1.16 (m, 8H), 1.00 (q, J = 7.0 Hz, 3H). |
| 1155 | A | A | 457.28 | 2.16 | |
| 1156 | A | A | 457.28 | 2.13 | |
| 1157 | A | A | 443.21 | 2.11 | |
| 1158 | A | A | 443.41 | 2.09 | 1H NMR (300 MHz, MeOD) d 8.63-8.40 (m, 1H), 8.23-8.12 (m, 2H), 8.04 (t, J = 4.4 Hz, 1H), 4.56 (dd, J = 7.7, 3.8 Hz, 1H), 3.64-3.47 (m, 1H), 2.28 (dd, J = 13.6, 4.0 Hz, 1H), 2.19-1.46 (m, 9H), 1.01-0.73 (m, 3H). |
| 1159 | A | A | 457.22 | 2.25 | |
| 1160 | A | A | 457.22 | 2.21 | |
| 1161 | A | A | 360.47 | 1.68 | |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_Plus | LCMS_RT | NMR |
| --- | --- | --- | --- | --- | --- |
| 1162 | A | A | 430.14 | 2.5 | 1H NMR (300 MHz, DMSO) d 12.32 (s, 1H), 8.78 (d, J = 2.3 Hz, 1H), 8.29 (d, J = 2.4 Hz, 1H), 8.17 (dd, J = 4.8, 3.4 Hz, 2H), 7.60 (d, J = 6.9 Hz, 1H), 4.74 (t, J = 6.4 Hz, 1H), 3.64 (d, J = 17.5 Hz, 3H), 2.95 (d, J = 6.9 Hz, 1H), 2.03-1.30 (m, 11H). |
| 1163 | C | C | 470.46 | 1.58 | |
| 1164 | A | A | 470.46 | 1.65 | |
| 1165 | A | A | 441.64 | 2.75 | 1H NMR (300 MHz, DMSO) d 12.27 (s, 1H), 8.70-8.02 (m, 3H), 7.63 (dd, J = 63.2, 7.4 Hz, 2H), 4.13 (s, 1H), 3.70 (s, 1H), 2.23-0.92 (m, 18H). |
| 1166 | A | A | 455.65 | 2.96 | 1H NMR (300 MHz, DMSO) d 12.27 (s, 1H), 8.62-7.97 (m, 3H), 7.59 (dd, J = 41.7, 7.6 Hz, 2H), 4.13 (s, 1H), 3.71 (s, 1H), 2.21-0.92 (m, 20H). |
| 1167 | C | C | 543.6 | 2.55 | |
| 1168 | A | C | 444.49 | 1.78 | |
| 1169 | A | A | 486.52 | 1.74 | |
| 1170 | A | A | 531.57 | 2.02 | |
| 1171 | C | A | 577.51 | 2.57 | |
| 1172 | A | A | 501.5 | 2.16 | |
| 1173 | A | A | 442.29 | 2.94 | 1H NMR (300 MHz, DMSO) d 12.33 (d, J = 2.4 Hz, 1H), 8.78 (dd, J = 19.9, 2.5 Hz, 1H), 8.29 (d, J = 2.4 Hz, 1H), 8.20 (d, J = 2.8 Hz, 1H), 8.13 (d, J = 4.1 Hz, 1H), 7.26 (d, J = 8.8 Hz, 1H), 4.47-4.21 (m, 2H), 2.12 (s, 2H), 1.76-1.33 (m, J = 25.6, 14.7 Hz, 11H), 1.19 (d, J = 9.9 Hz, 3H), 1.08 (d, J = 7.0 Hz, 1H). |
| 1174 | C | C | 583.52 | 1.77 | 1H NMR (300 MHz, MeOD) d 8.49 (d, J = 6.1 Hz, 1H), 8.42 (d, J = 2.6 Hz, OH), 8.39 (s, 1H), 8.35 (s, 1H), 8.29 (d, J = 5.6 Hz, 1H), 8.19 (d, J = 4.1 Hz, OH), 4.74-4.58 (m, 1H), 4.38 (dt, J = 42.8, 21.3 Hz, 2H), 3.84 (dd, J = 16.3, 6.7 Hz, 1H), 3.70-3.58 (m, 1H), 3.48 (s, 1H), 3.31 (dt, J = 3.2, 1.6 Hz, 6H), 3.02 (s, 1H), 2.61 (t, J = 11.7 Hz, 1H), 2.21 (d, J = 6.0 Hz, 3H), 2.11-1.86 (m, 5H), 1.86-1.27 (m, 7H), 0.92 (d, J = 6.1 Hz, 6H). |
| 1175 | A | A | 456.35 | 2.98 | 1H NMR (300 MHz, DMSO) d 12.33 (s, 1H), 8.83 (d, J = 2.4 Hz, 1H), 8.29 (d, J = 2.4 Hz, 1H), 8.19 (d, J = 2.8 Hz, 1H), 8.13 (d, J = 4.1 Hz, 1H), 7.18 (d, J = 9.2 Hz, 1H), 4.33 (s, 1H), 4.23-3.97 (m, J = 25.1, 15.2 Hz, 1H), 2.05 (bd s, J = 34.2 Hz, 2H), 1.91-1.31 (m, 14H), 0.83 (t, J = 7.0 Hz, 3H). |
| 1176 | A | A | 401.17 | 1.72 | |
| 1177 | A | A | 417.16 | 1.95 | 1H NMR (300 MHz, d6-DMSO) δ 12.39 (s, 1H), 8.74 (d, J = 2.4 Hz, 1H), 8.55 (s, 1H), 8.31 (d, J = 2.6 Hz, 1H), 8.27 (d, J = 2.4 Hz, 1H), 8.18 (d, J = 4.0 Hz, 1H), 7.44 (d, J = 7.2 Hz, 1H), 4.51-4.31 (m, 1H), 4.13-3.93 (m, 3H), 3.17 (d, J = 5.3 Hz, 1H), 2.11-1.89 (m, 1H), 1.88-1.49 (m, 2H), 1.48-1.13 (m, 2H) |
| 1178 | A | A | 430.22 | 2.5 | 1H NMR (300 MHz, DMSO) d 12.32 (s, 1H), 8.78 (d, J = 2.4 Hz, 1H), 8.29 (d, J = 2.4 Hz, 1H), 8.17 (dd, J = 4.9, 3.2 Hz, 2H), 7.60 (d, J = 6.9 Hz, 1H), 4.73 (t, J = 6.3 Hz, 1H), 4.07 (q, J = 5.3 Hz, 2H), 3.61 (s, 3H), 3.17 (d, J = 5.3 Hz, 4H), 2.95 (d, J = 6.7 Hz, 1H), 2.02-1.35 (m, 10H). |
| 1179 | A | A | | | 1H NMR (300 MHz, DMSO) d 12.32 (s, 1H), 8.78 (d, J = 2.4 Hz, 1H), 8.29 (d, J = 2.4 Hz, 1H), 8.24-8.11 (m, 2H), 7.60 (d, J = 6.9 Hz, 1H), 4.74 (t, J = 6.8 Hz, 1H), |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_Plus | LCMS_RT | NMR |
|---|---|---|---|---|---|
| | | | | | 4.07 (q, J = 5.3 Hz, 2H), 3.63 (s, 3H), 2.95 (d, J = 6.6 Hz, 1H), 2.06-1.33 (m, 10H). |
| 1180 | A | A | 467.46 | 1.8 | |
| 1181 | A | A | 459.09 | 2.26 | 1H NMR (300 MHz, CDCl3) d 8.24 (s, 1H), 8.02 (d, J = 3.6 Hz, 1H), 4.36 (d, J = 6.8 Hz, 1H), 3.91 (s, 2H), 3.74-3.64 (m, 3H), 3.49-3.30 (m, 3H), 2.68 (s, 1H), 2.23 (s, 1H), 2.09 (s, 1H), 1.91 (s, 1H), 1.58 (d, J = 13.4 Hz, 2H), 1.22 (dd, J = 21.2, 9.9 Hz, 3H). |
| 1182 | A | A | 486.65 | 2.05 | 1H NMR (300 MHz, DMSO) d 8.30-8.05 (m, 1H), 7.60 (dd, J = 7.3, 2.4 Hz, 1H), 7.31 (dd, J = 5.0, 2.1 Hz, 1H), 4.09 (m, 1H), 3.57 (m, 1H), 3.17 (m, 4H), 1.99 (m, 2H), 1.77 (m, Hz, 4H), 1.56-1.10 (m, 3H). |
| 1183 | A | A | 416.31 | 3.04 | 1H NMR (300 MHz, MeOD) d 8.94 (d, J = 2.3 Hz, 1H), 8.21 (d, J = 2.2 Hz, 1H), 8.16 (s, 1H), 8.00 (d, J = 4.1 Hz, 1H), 4.92 (d, J = 6.8 Hz, 1H), 2.76 (d, J = 6.8 Hz, 1H), 2.07 (d, J = 23.8 Hz, 2H), 1.89-1.46 (m, 7H). |
| 1184 | A | A | 416.13 | 2.26 | 1H NMR (300 MHz, MeOD) d 8.92 (d, 1H), 8.22 (d, J = 2.3 Hz, 1H), 8.19 (s, 1H), 8.02 (d, J = 4.2 Hz, 1H), 4.94 (d, J = 6.9 Hz, 1H), 2.78 (d, J = 6.7 Hz, 1H), 2.13-2.02 (m, 3H), 1.93-1.45 (m, 7H). |
| 1185 | A | A | 360.15 | 1.71 | |
| 1186 | A | A | 570.68 | 1.56 | |
| 1187 | A | A | 444.01 | 2.61 | 1H NMR (300 MHz, DMSO) d 12.74 (s, 1H), 8.76 (d, J = 2.3 Hz, 1H), 8.58 (s, 1H), 8.43-8.34 (m, 2H), 4.94-4.84 (m, 1H), 4.08 (ddd, J = 7.1, 2.3 Hz, 2H), 3.01 (d, J = 6.8 Hz, 1H), 2.05-1.99 (m, 1H), 1.98-1.84 (m, 2H), 1.65 (complex m, J = 79.2 Hz, 8H), 1.13 (t, J = 7.1 Hz, 3H). |
| 1188 | A | A | 396.24 | 1.97 | 1H NMR (300 MHz, MeOD) d 8.49 (ddd, J = 27.3, 9.7, 2.9 Hz, 1H), 8.25-8.08 (m, 2H), 8.01 (dd, J = 9.2, 4.1 Hz, 1H), 7.73 (dd, J = 23.6, 2.3 Hz, 1H), 7.56-7.43 (m, 1H), 6.28 (dt, J = 7.3, 2.4 Hz, 1H), 4.73-4.27 (m, 2H), 2.60-1.58 (m, 9H). |
| 1189 | C | A | 461 | 4.64 | (400 MHz, DMSO-d6): 12.01 (b s, exchanged with D2O; 1H), 8.73 (d, J = 2 Hz; 1H), 8.23 (d, J = 2 Hz; 1H), 8.10 (dd, J = 13.6, 4.4 Hz; 2H), 7.29 (bs, exchanged with D2O; 1H), 3.87-3.86 (m, 1H), 3.58-3.52 (m, 2H), 3.35-3.19 (m, 2H), 2.07-1.95 (m, 2H), 1.88-1.70 |
| 1190 | | | 474.2 | 2.03 | |
| 1191 | | | 476.15 | 2.34 | |
| 1192 | | | 432.11 | 2.27 | |
| 1193 | A | A | 500.22 | 2.04 | 1H NMR (300 MHz, MeOD) d 8.45 (dd, J = 9.6, 2.7 Hz, 1H), 8.36-8.18 (m, 2H), 5.17 (t, J = 7.1 Hz, 1H), 4.42 (m, 1H), 3.77 (m, 1H), 3.29 (m, 4H), 2.34-2.19 (m, 2H), 2.08-1.84 (m, 4H), 1.74-1.28 (m, 4H), 0.98 (t, J = 7.4 Hz, 3H). |
| 1194 | B | A | 500.28 | 2.23 | |
| 1195 | | | 563.24 | 2.47 | in DMSO-d6 and D20 exchange |
| 1196 | A | A | 388.43 | 1.84 | |
| 1197 | A | A | 415.18 | 1.96 | 1H NMR (300 MHz, MeOD) d 8.91 (d, J = 2.3 Hz, 1H), 8.44 (s, 1H), 8.38 (d, J = 2.3 Hz, 1H), 8.27 (d, J = 5.6 Hz, 1H), 5.30 (d, J = 6.9 Hz, 1H), 2.86 (d, J = 6.8 Hz, 1H), 2.12-2.03 (m, 2H), 1.98-1.64 (m, 6H), 1.63-1.52 (m, 2H). |
| 1198 | | | 486.27 | 1.99 | |
| 1199 | | | 486.43 | 2.14 | |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bDNA EC50 uM(Mean (All)) | LCMS_Plus | LCMS_RT | NMR |
|---|---|---|---|---|---|
| 1200 | | | 485.1 | 2.34 | |
| 1201 | | | 458.98 | 2.18 | |
| 1202 | | | 406.43 | 1.79 | 1H NMR (300 MHz, DMSO) d 12.08 (s, 1H), 8.73 (ddd, J = 7.9, 4.4, 1.5 Hz, 1H), 8.41-7.98 (m, 3H), 7.47 (dd, J = 41.7, 7.0 Hz, 1H), 7.19 (ddd, J = 14.2, 7.9, 4.7 Hz, 1H), 5.82-5.63 (m, 2H), 4.71 (d, J = 73.1 Hz, 1H), 4.31 (d, J = 11.2 Hz, 1H), 2.36-1.55 (m, 13H). |
| 1203 | | | 490.23 | 1.99 | 1H NMR (300 MHz, CDCl3) d 11.09 (s, 1H), 8.11 (s, 1H), 8.05 (m, 1H), 7.86 (d, J = 3.5 Hz, 1H), 5.32-4.78 (m, 4H), 4.14 (d, J = 8.0 Hz, 1H), 3.84 (s, 1H), 3.74-3.18 (m, 6H), 2.67 (d, J = 11.7 Hz, 1H), 2.33-1.75 (m, 7H), 1.48-1.27 (m, 2H), 1.26-0.95 (m, 4H). |
| 1204 | | | 457.06 | 2.04 | |
| 1205 | | | 417.16 | 1.77 | |
| 1206 | | | 429.58 | 1.94 | |
| 1207 | | | 431.5 | 1.94 | |
| 1208 | | | 429.5 | 1.85 | |
| 1209 | | | 456.42 | 1.88 | |
| 1210 | | | 472.47 | 1.75 | |
| 1211 | | | 486.42 | 1.88 | |
| 1212 | | | 396.44 | 1.94 | 1H NMR (300 MHz, DMSO) d 12.28 (s, 1H), 8.59-8.07 (m, 4H), 7.90-7.36 (m, 3H), 6.25 (dt, J = 16.0, 2.0 Hz, 1H), 4.79-4.15 (m, 2H), 2.36 (d, J = 8.8 Hz, 1H), 2.19-1.55 (m, 6H), 1.50-1.10 (m, 1H). |
| 1213 | | | 480.65 | 2.16 | |
| 1214 | | | 411.49 | 1.74 | |
| 1215 | | | 460.23 | 1.91 | |
| 1216 | | | 444.23 | 2.15 | |
| 1217 | | | 430.39 | 2.26 | 1H NMR (300 MHz, DMSO) d 12.38 (s, 1H), 8.75 (d, J = 2.4 Hz, 1H), 8.55 (s, 1H), 8.29 (d, J = 2.4 Hz, 1H), 8.25 (d, J = 3.8 Hz, 1H), 8.22-8.16 (m, J = 4.8 Hz, 2H), 7.47 (d, J = 31.1 Hz, 2H), 5.23 (t, J = 8.1 Hz, 1H), 4.11 (q, J = 5.1 Hz, 1H), 3.17 (d, J = 5.2 Hz, 2H), 1.09 (d, J = 6.0 Hz, 3H), 0.94 (d, J = 6.7 Hz, 3H). |
| 1218 | | | 406.18 | 1.8 | |
| 1219 | | | 406.44 | 1.79 | 1H NMR (300 MHz, DMSO) d 12.08 (s, 1H), 8.86-8.63 (m, 1H), 8.39-7.90 (m, 3H), 7.53 (d, J = 7.5 Hz, 1H), 7.21 (dd, J = 7.9, 4.7 Hz, 1H), 5.74 (s, 1H), 4.27 (d, J = 10.5 Hz, 2H), 2.89 (s, 1H), 2.79-2.66 (m, 1H), 2.15 (d, J = 48.2 Hz, 6H), 1.93-1.17 (m, 4H) |
| 1220 | | | 424.44 | 2.1 | 1H NMR (300 MHz, DMSO) d 12.27 (s, 1H), 8.45 (dd, J = 9.8, 2.8 Hz, 1H), 8.30-8.08 (m, 3H), 7.45 (d, J = 6.9 Hz, 1H), 4.86 (s, 1H), 4.59 (s, 1H), 2.35-1.94 (m, 7H), 1.81 (d, J = 5.5 Hz, 5H). |
| 1221 | | | 424.45 | 2.02 | |
| 1222 | | | 440.46 | 2.22 | |
| 1223 | | | 440.5 | 2.34 | 1H NMR (300 MHz, DMSO) d 12.35 (s, 1H), 8.74 (d, J = 2.4 Hz, 1H), 8.40-8.01 (m, 3H), 7.48 (d, J = 6.7 Hz, 1H), 4.84 (s, 1H), 4.59 (s, 1H), 2.35-1.56 (m, 13H). |
| 1224 | | | 461.19 | 2.46 | 1H NMR (300 MHz, DMSO) d 12.56 (s, 1H), 8.72 (t, J = 8.2 Hz, 1H), 8.54 (t, J = 5.7 Hz, 1H), 8.40 (t, J = 7.9 Hz, 1H), 8.33 (t, J = 3.4 Hz, 2H), 7.79 (d, J = 7.3 Hz, 1H), 4.66 (t, J = 8.0 Hz, 1H), 3.81 (qd, J = 17.5, 5.8 Hz, 2H), 1.78 (td, J = 28.9, 16.0 Hz, 6H), 1.18 (s, 5H). |
| 1225 | | | 517.24 | 2.99 | 1H NMR (300 MHz, DMSO) d 12.44 (s, 1H), 8.71 (d, J = 2.4 Hz, 1H), 8.58 (d, J = |

TABLE 3-continued

IC$_{50}$, EC$_{50}$, NMR and LCMS Data of Compounds of FIG. 6

| Comp. Nos. | Cell Flu, MDCK protection, ATP (All: IC50: uM)(Mean (All)) | Cell Influenza HA(−) 30 hr A/PR/8 bDNA:bD NA EC50 uM(Mean (All)) | LCMS_Plus | LCMS_RT | NMR |
|---|---|---|---|---|---|
| | | | | | 2.8 Hz, 1H), 8.28 (d, J = 2.4 Hz, 1H), 8.23 (d, J = 4.0 Hz, 1H), 8.20 (s, 1H), 7.55 (s, 1H), 4.72 (t, J = 8.4 Hz, 1H), 4.17 (d, J = 9.2 Hz, 1H), 1.90 (s, 2H), 1.68 (d, J = 21.4 Hz, 4H), 1.32-0.95 (m, 5H), 0.84 (s, 9H). |
| 1226 | | | 388.5 | 1.8 | |
| 1227 | | | 510.23 | 2.12 | |
| 1228 | | | 411.67 | 1.79 | MeOD4; 8.5 (dd, 1H); 8.26 (s, 1H); 8.25 (dd, 1H); 7.95 (d, 1H); 4.6 (app d, 1H), 4.25 (m, 1H); 4.25 (m, 1H); 3.3 (m, 4H); 2.75 (m, 2H); 2.5 (app d, 1H); 2.2 (m, 4H); 1.7 (m, 2H). |
| 1229 | | | 416.42 | 2.29 | H NMR (300.0 MHz, MeOD) d 8.72-8.64 (m, 1H), 8.39 (s, 1H), 8.32 (d, J = 2.3 Hz, 1H), 8.21 (d, J = 5.2 Hz, 1H), 4.71 (d, J = 6.3 Hz, 1H), 3.67-3.57 (m, 2H), 2.33-2.26 (m, 1H), 2.10 (m, 1H), 1.78-1.70 (m, 1H), 1.28-1.25 (m, 7H) and 1.19 (s, 3H) ppm |
| 1230 | A | A | 443.04 | 2.48 | 1H NMR (300 MHz, CDCl3) d 8.15 (d, J = 1.2 Hz, 1H), 8.08 (d, J = 6.3 Hz, 1H), 7.88 (d, J = 3.3 Hz, 1H), 3.80 (d, J = 11.2 Hz, 1H), 3.68 (s, 1H), 3.26 (d, J = 6.4 Hz, 4H), 2.56 (d, J = 11.8 Hz, 1H), 2.14 (d, J = 12.8 Hz, 1H), 1.99 (d, J = 10.3 Hz, 1H), 1.9 |
| 1231 | A | A | 422.5 | 1.68 | NMR 1H (MeOH-d4): 8.5 (dd, 1H), 8.15 (m, 2H), 8.0 (d, 1H), 4.2 (m, 1H), 3.75 (m, 1H), 2.3 (d, 1H), 2.2 (d, 1H), 1.9 (m, 2H), 1.2-1.6 (m, 4H). |
| 1232 | A | A | 450.5 | 1.8 | NMR 1H (MeOH-d4): 8.2 (m, 4H), 4.5 (m, 1H), 3.9 (m, 1H), 2.2 (m, 4H), 1.3-1.6 (m, 4H). |

TABLE 4

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| 1300 | D | | 334 | 1.8 | |
| 1301 | | | | | (400 MHz, CDCl3): 9.97 (br. s, exchanged with D2O, 1H), 8.95 (d, J = 2.0 Hz, 1H), 8.28 (s, 1H), 8.18 (s, 1H), 8.15 (d, J = 6.0 Hz, 1H), 6.21 (d, J = 4.8 Hz, 1H), 6.16 (br. s, exchanged with D2O, 1H), 3.45-3.35 (br. hump, 1H), 2.95-2.85 (br. hump, 1H), 2.6-2.4 (br. hump, 3H), 1.98-1.7 (m, 4H), 1.59 (s, 3H), 1.57 (s, 3H), 1.16 (d, J = 5.6 Hz, 3H) |
| 1302 | B | | | | (400 MHz, CDCl3): 9.95 (br. hump, exchanged with D2O, 1H), 8.95 (s, 1H), 8.28 (d, J = 1.6 Hz, 1H), 8.18 (s, 1H), 8.14 (d, J = 6.0 Hz, 1H), 6.19 (d, J = 6.0 Hz, 1H), 5.72 (s, exchanged with D2O, 1H), 3.6-3.4 (m, 4H), 2.90-2.80 (m, 2H), 2.1-2.05 (m, 2H), 1.52 (s, 6H) |
| 1303 | D | | 360 | 2.6 | 500 MHz, CDCl3: 10.8 (br ex, 1H), 9.12 (d, 1H), 8.75 (s, 1H), 8.45 (d, 1H), 8.35 (d, 1H), 7.5 (dd, 1H), 7.31 (d, 1H), |

TABLE 4-continued

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| 1304 | | | 360 | 2.6 | 7.29 (d, 1H), 7.24 (m, 2H), 6.3 (d, 1H) 5.62 (dt, 1H), 2.9 (m, 2H), 2.23 (dm, 2H), 2.0(m, 2H) 500 MHz, CDCl3: 10.8 (br ex, 1H), 9.12 (d, 1H), 8.75 (s, 1H), 8.45 (d, 1H), 8.35 (d, 1H), 7.5 (dd, 1H), 7.31 (d, 1H), 7.29 (d, 1H), 7.24 (m, 2H), 6.3 (d, 1H) 5.62 (dt, 1H), 2.9 (m, 2H), 2.23 (dm, 2H), 2.0 (m, 2H) |
| 1305 | | | 342 | 2.3 | |
| 1306 | | | 342 | 2.3 | 500 MHz MeOD-d4: 8.65 (d, 1H), 8.42 (s, 1H), 7.9 (d, 1H), 7.24 (dd, 2H), 7.13 (m, 4H), 6.5 (d, 1H), 5.65 (m, 1H), 2.8 (m, 3H), 2.2 (m, 1H), 2.08 (m, 1H) 1.9 (m, 3H) |
| 1307 | A | A | 380.2 | 3.52 | DMSO d6 12.2 (s, 1H); 8.7 (s, 1H); 8.3 (s, 1H); 8.15 (m, 2H); 7.0 (d, 1H); 5.4 (d, 1H); 4.8 (d, 1H); 4.4 (bs, 1H); 4.1 (bs, 1H); 1.9-1.6 (m, 6H) |
| 1308 | | | 370 | 2.1 | 500 MHz : MeOD-d4: 8.9 (d, 1H), 8.4 (s, 2H), 8.3 (d, 1H), 7.4 (m, 1H), 2.1 (m, 1H), 1.9 (m, 2H), 1.8 (m, 2H), 1.75 (m, 2H), 1.3 (m, 6H) |
| 1309 | | | 326 | 2.1 | |
| 1310 | | | 327 | 0.4 | 500 MHz, MeOD-d4: 8.75 (dd, 1H), 8.42 (s, 1H), 8.39 (dd, 1H), 8.25 (d, 1H), 7.69 (d, 2H), 7.35(dd, 1H), 7.2 (d, 2H), 4.36 (m, 1H), 3.40 (t, 1H), 3.2 (m, 1H), 2.3(m, 5H), 2.00 (qin, 1H), 1.7 (m, 4H) |
| 1311 | | | 328.3 | 2 | |
| 1312 | A | A | 328.3 | 2 | |
| 1313 | D | | 330.1 | 2.25 | (300 MHz, CDCl3) 10.68 (br s, 1H), 8.56 (dd, 1H), 8.25 (d, 1H), 8.04 (d, 1H), 4.95 (d, 1H), 4.14 (m, 1H), 2.20 (m, 2 H), 1.89-1.31 (m, 7H) |
| 1314 | D | | 362 | 2.3 | |
| 1315 | B | | 360.2 | 3.05 | (CDCl3, 300 MHz) 8.76 (d, 1H), 8.28 (d, 1H), 7.99 (d, 1H), 7.98 (s, 1H), 4.92 (d, 1H), 4.11 (m, 1H), 3.89 (s, 3H), 2.21 (m, 2H), 1.89-1.23 (m, 8H) |
| 1316 | D | | | | (400 MHz, CDCl3): 9.16 (s, exchanged with D2O, 1H), 9.07 (d , J = 2.0 Hz, 1H), 8.30 (d, J = 2.4 Hz, 1H), 8.17 (d, J = 2.4 Hz, addition of D2O changed to s, 1H), 8.07 (d, J = 3.6 Hz, 1H), 5.28 (S, exchanged with D2O, 1H), 2.98-2.95 (m, 1H), 1.05-1.00 (q, 2H), 0.75-0.71 (m, 2H). |
| 1317 | B | | | | (400 MHz, CDCl3): 8.98 (s, exchanged with D2O, 1H), 8.92 (s, 1H), 8.28 (br. s, 1H), 8.17 (br. s, 1H), 7.98 (s, 1H), 4.42 (d, J = 6.4 Hz, addition of D2O changed to s, 1H), 4.20-4.15 (m, 1H), 2.25 (b r. d, J = 11.2 Hz, 2H), 2.03 (s, 3H), 1.88 (br. d, J = 12.4 Hz, 2H), 1.78-1.75 (m, J = 13.2 Hz, 1H), 1.61-1.50 (m, 2H), 1.33-1.27 (m, 3H). |
| 1318 | A | A | 312.1 | 1.96 | H NMR (300 MHz, CDCl3) 10.72 (s, 1H), 8.85 (dd, J = 1.3, 7.9 Hz, 1H), 8.38 (d, J = 3.9 Hz, 1H), 8.25 (s, 1H), 8.05 (d, J = 3.5 Hz, 1H), 7.23 (dd, J = 4.8, 8.0 Hz, 1H), 4.97 (d, J = 6.5 Hz, 1H), 4.23-4.13 (m, 1H), 2.22-2.18 (m, 2H), 1.91-1.26 (m, 8H) |
| 1319 | B | | 327.1 | 1.5 | H NMR (300 MHz, d4 methanol) 8.24 (d, 1H), 7.99 (s, 1H), 17.92 (d, 1H), 7.88 (d, 1H), 4.15 (m, 1H), 2.15 (m, 2 H), 1.91-1.26 (m, 8H) |
| 1320 | D | | 360.2 | 2.3 | |
| 1321 | D | | 360.2 | 2.3 | |
| 1322 | D | | 374.2 | 2.4 | |
| 1323 | D | | 362.2 | 1.5 | |

TABLE 4-continued

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| 1324 | D | | 328.2 | 2.07 | H NMR (300 MHz, CDCl3) 10.84 (s, 1H), 8.91 (d, J = 2.2 Hz, 1H), 8.29-8.14 (m, 3 H), 6.13 (d, J = 5.9 Hz, 1H), 4.96 (s, 1H), 3.86 (s, 1H), 2.15-1.48 (m, 10H) |
| 1325 | D | | | | (400 MHz, DMSO-d6): 12.35 (br. s, exchanged with D2O, 1H), 8.76 (d, J = 2.4 Hz, 1H), 8.28 (d, J = 2.4 Hz, addition of D2O changed to s, 1H), 8.20 (d, J = 2.4 Hz, 1H), 8.16 (d, J = 3.6 Hz, 1H), 7.84 (br. d, J = 6.4 Hz, exchanged with D2O, 1H), 4.64 (sextet, J = 8.0 Hz, addition of D2O changed to quintet, J = 8.0 Hz, 1H), 2.49-2.19 (m, 2H) 2.17-2.10 (m, 2H), 1.80-1.72 (m, 2H). |
| 1326 | B | | | | (400 MHz, DMSO-d6): 12.31 (br. s, exchanged with D2O, 1H), 8.75 (br. d, J = 2.4 Hz, 1H), 8.27 (d, J = 2.4 Hz, 1H), 8.19 (d, J = 2.4 Hz, 1H), 8.13 (d, J = 3.6 Hz, 1H), 7.55-7.50 (m, exchanged with D2O, 1H), 4.47-4.40 (m, 1H), 2.06-2.0 (m, 2H), 1.80-1.50 (m, 6H). |
| 1327 | D | | | | (400 MHz, DMSO-d6): 12.87 (d, J = 2.4 Hz exchanged with D2O, 1H), 8.73 (d, J = 2.4 Hz 1H), 8.28 (d, J = 2.4 Hz, 1H), 8.16 (d, J = 4.0 Hz, 1H), 8.11 (d, J = 2.4 Hz, addition of D2O changed to s, 1H), 6.70 (s, 1H), 4.90 ( br. s, exchanged with d2O, 1H), 3.79 (s, 2H), 2.25-2.20 (m, 2H), 1.95-1.85 (m, 2H), 1.80-1.62 (m, 4H). |
| 1328 | A | A | | | (400 MHz, DMSO-d6) : 12.49 (s, exchanged with D2O, 1H), 10.1 (s, exchanged with D2O, 1H), 8.72 (br. s, 1H), 8.29 (br. s, 1H), 8.23-8.20 (m, 2H), 4.70-4.50 (m, 1H), 3.94 (br. s, 2H), 2.69 (s, 3H), 2.32 (s, 2H), 2.19-2.00 (m, 6H). |
| 1329 | D | | 361.2 | 1.4 | |
| 1330 | D | | 361.2 | 1.4 | |
| 1331 | D | | | | (400 MHz, DMSO-d6): 12.30 (s, exchanged with D2O, 1H), 8.66 (d, J = 2.4 Hz, 1H), 8.40 (s, exchanged with D2O, 1H), 8.27 (d, J = 2.4 Hz, 1H), 8.24 (d, J = 3.6 Hz, 1H), 8.03 (d, J = 2.8 Hz, 1H), 3.57 (s, 3H), 2.79-2.73 (m, 2H), 2.45-2.38 (m, 2H), 2.05-1.96 (m, 2H). |
| 1332 | D | | | | (400 MHz, DMSO-d6): 13.11 (s, exchanged with D2O, 1H), 9.22 (s, exchanged with D2O, 1H), 8.62 (d, J = 2.4 Hz, 1H), 8.43 (d, J = 2.0 Hz, 1H), 8.32 (s, exchanged with 2H), 8.07 (s, 1H), 4.20-4.17 (m, 1H), 3.15-3.10 (m, 1H), 2.16-2.10 (m, 7H), 1.70-1.59 (m, 4H). |
| 1333 | D | | 342 | 0.25 | (d4-methanol, 300 MHz) 8.88 (d, 1H), 8.63 (s, 1H), 8.48 (d, 1H), 8.36 (d, 1H), 3.89 (dd, 2H), 3.73-3.59 (m, 2H), 3.02 (dd, 2H), 2.44 (m, 1H), 2.02 (br dd, 2H), 1.80 (m, 1H), 1.59 (m, 1H) |
| 1334 | D | | 377.1 | 3.863 | (400 MHz, DMSO-d6 + D2O): 8.64 (d, J = 2.4 Hz, 1H), 8.51 (s, 1H), 8.39 (d, J = 2.4 Hz, 1H), 8.36 (s, 1H), 4.13-4.10 (m, 1H), 3.10-3.0 (m, 1H), 2.10 (br. d, J = 10 Hz, 4H), 1.66-1.42 (m, 4H). |
| 1335 | D | | 406.1 | 3.217 | (400 MHz, DMSO-d6): 12.39 (s, exchanged with D2O, 1H), 8.74 (d, J = 2.0 Hz, 1H), 8.34 (s, 1H), 8.27 (d, J = 2.4 Hz, 1H), 8.15 (d, J = 2.8 Hz, 1H), 6.60 (s, exchanged with D2O, 1H), 2.25 (d, J = 13.2 Hz, 2H), 1.95 (br. t, J = 11.6 Hz, 2H), 1.59-1.40 (m, 6H). |
| 1336 | D | | 396.1 | 5.16 | (400 MHz, DMSO-d6): 8.66 (d, J = 1.6 Hz, 1H), 8.40 (s, 1H), 8.38 (s, 1H), 8.26 (d, J = 2.0 Hz, 1H), 6.59 (d, J = 6.8 Hz, exchanged with |

TABLE 4-continued

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| | | | | | D2O, 1H), 4.27-4.20 (m, 1H), 1.95 (br. s, 2H), 1.81 (br. s, 2H), 1.68 (br. d, J = 11.2 Hz, 2H), 1.54-1.42 (m, 4H). |
| 1337 | A | A | 411.2 | 1.166 | (400 MHz, DMSO-d6 + D2O): 8.67 (d, J = 2.4 Hz, 1H), 8.50 (s, 1H), 8.36 (d, J = 2.4 Hz, 1H), 8.06 (s, 1H), 4.27-4.20 (br.s, 1H), 3.50-3.40 (m, 1H), 2.10-1.50 (m, 8H). |
| 1338 | D | | 376.2 | 2.13 | NMR 1H DMSO-d6: 12.6 (s, 1H), 8.9 (s, 1H), 8.4 (m, 3H), 8.0 (m, 1H), 4.8 (bs, 1H), 3.7 (s, 2H), 1.1-1.6 (m, 10H). |
| 1339 | D | | 386.25 | 2.85 | NMR 1H DMSO-d6: 12.7 (s, 1H), 8.7 (m, 1H), 8.4 (m, 4H), 7.6 (m, 2H), 5.5 (bs, 1H), 4.1 (m, 1H), 1.0-2.3 (m, 14H). |
| 1340 | A | A | 400.3 | 3.22 | |
| 1341 | B | | 355.4 | 3.1 | |
| 1342 | A | A | 428.2 | 2.84 | |
| 1343 | D | | 375.3 | 1.39 | (d4-methanol, 300 MHz) 8.83 (d, 1H), 8.44 and 8.29 (2s, 1H), 8.24 (d, 1H), 8.18 (s, 1H), 8.05 (d, 1H), 3.72 (dd, 1H), 3.51 (m, 2H), 2.84-2.64 (m, 3 H), 2.77 (s, 3 H), 2.44 (m, 1H), 2.15-1.99 (m, 2H), 1.79 (m, 1H), 1.36 (m, 1H) |
| 1344 | A | A | 413.3 | 2.9 | |
| 1345 | A | A | 361.2 | 1.5 | |
| 1346 | D | | 361.2 | 0.7 | |
| 1347 | B | | 358.1 | 2.1 | |
| 1348 | D | | 313.2 | 2.15 | |
| 1349 | D | | 313.2 | 2 | |
| 1350 | D | | 313.2 | 2.08 | |
| 1351 | B | | 327.2 | 2.15 | |
| 1352 | D | | 327.2 | 2.15 | |
| 1353 | A | A | 327.2 | 2.19 | |
| 1354 | B | B | 342.2 | 1.6 | |
| 1355 | D | | 313.6 | 1.04 | |
| 1356 | B | | 375.15 | 1.61 | |
| 1357 | A | | 347 | 1.3 | |
| 1358 | A | A | 363.3 | 1.3 | |
| 1359 | B | | 347.3 | 1.3 | |
| 1360 | D | | 367.3 | 1.4 | |
| 1361 | A | | 369.5 | 1.53 | |
| 1362 | C | C | 361.3 | 2.1 | |
| 1363 | A | A | 481.37 | 3.56 | H NMR (300.0 MHz, MeOD) d 8.77 (d, J = 2.3 Hz, 1H), 8.30 (s, 1H), 8.27 (d, J = 2.2 Hz, 1H), 8.22 (d, J = 4.4 Hz, 1H), 7.58-7.54 (m, 5H), 4.94-4.87 (m, 1H), 4.45 (dd, J = 13.1, 30.3 Hz, 2H), 3.78-3.54 (m, 2H), 3.47-3.37 (m, 1H), 2.46-2.40 (m, 1H) and 2.09 (m, 1H) ppm |
| 1364 | A | C | 348.11 | 3.46 | |
| 1365 | A | A | 362.33 | 3.29 | H NMR (300.0 MHz, MeOD) d 8.71 (d, J = 2.1Hz, 1H), 8.45 (s, 1H), 8.35 (d, J = 2.2 Hz, 1H), 8.29 (d, J = 5.5 Hz, 1H), 4.07 (s, 2H), 2.13 (qn, J = 1.5 Hz, H), 1.37-1.33 (m, 2H) and 1.17-1.11 (m, 2H) ppm |
| 1366 | A | A | 362.15 | 3.6 | Methanol d4 8.7 (d, 1H); 8.2 (d, 1H); 8.1 (s, 1H); 8.0 (d, 1H); 7.65 (m, 1H); 4.2 (m, 2H); 2.0-1.6 (m, 6H) |
| 1367 | A | A | | | 1H NMR (400 MHz, DMSO-d6): 12.30 (s, exchanged with D2O, 1H), 9.17 (d, J = 2.4 Hz, 1H), 8.26 (d, J = 2.4 Hz, 1H), 8.22 (d, J = 4 Hz, 1H), 8.17 (s, 1H), 7.32 (s, exchanged with D2O, 1H), 3.32 (s, 1H), 1 .77-1.61 (m, 8H), 1.30-1.28 (m, 2H) |
| 1368 | A | A | | | 1H NMR (400 MHz, DMSO-d6): 12.33 (s, exchanged with D2O, 1H), 8.74 (d, J = 2.4 Hz, 1H), 8.29 (d, J = 2.4 Hz, 1H), 8.17 (d, J = 4 Hz, 1H), 8.10 (d, J = 2 Hz, 1H), 6.74 (s, 1H, partially exchanged with D2O), 4.60 (s, exchanged |

TABLE 4-continued

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| | | | | | with D2O, 1H), 2.25 (br s, 2H), 2.12(br s, 5H), 1. |
| 1369 | A | A | | | 1H NMR (400 MHz, DMSO-d6): 12.33 (s, exchanged with D2O, 1H), 8.70 (s, 1H), 8.28 (s, 1H), 8.17 (d, J = 4.4 Hz, 1H), 6.99 (s, 1H), 4.3 (s, 1H), 2.20-1.75 (m, 13H), 1.55 (d, J = 12.8 Hz, 2H) |
| 1370 | A | A | 360.42 | 3.78 | H NMR (300.0 MHz, DMSO) d 12.35 (s, 1H), 8.66 (d, J = 2.4 Hz, 1H), 8.28 (d, J = 2.4 Hz, 1H), 8.23-8.20 (m, 2H), 7.75 (d, J = 7.5 Hz, 1H), 4.45 (d, J = 9.4 Hz, 1H), 2.65-2.62 (m, 2H), 2.50 (t, J = 1.8 Hz, H), 2.36 (dd, J = 12.2, 17.4 Hz, 1H), 2.26-2.20 (m, 3H), 2.07-2.04 (m, 1H), 1.84-1.74 (m, 2H) and -0.00 (s, H) ppm |
| 1371 | A | A | | | (400 MHz, DMSO-d6): 12.32 (s, 1H), 8.78 (br s, 1H), 8.28 (br s, 1H), 8.17 (br s, 1H), 8.13 (d, J = 3.6 Hz, 1H), 7.40 (d, J = 8 Hz, exchanged with D2O, 1H), 4.85 (br s, 1H), 2.31-2.25 (m, 1H), 1.87-1.82 (m, 1H), 1.68 (br s, 2H), 1.47 (br s, 1H), 1.29-1.16 (m, 5H), 0.89-0.81 (m, 1H). |
| 1372 | A | A | | | (400 MHz, DMSO-d6): 12.33 (s, 1H), 8.77 (d, J = 2 Hz, 1H), 8.27 (d, J = 2.4 Hz, 1H), 8.18 (d, J = 2 Hz, 1H), 8.13 (d, J = 4 Hz, 1H), 7.65 (d, J = 8.4 Hz, 1H), 4.85-4.77 (m, 1H), 2.64-2.60 (m, 1H), 2.36-2.34 (m, 1H), 2.22-2.19 (m, 1H), 1.97 (br s, 1H), 1.85-1.84 (m, 1H), 1.72-0.83 (m, 13H) |
| 1373 | A | A | | | (400 MHz, DMSO-d6): 12.51 (s, exchanged with D2O, 1H), 8.69 (s, 1H), 8.32 (d, J = 2 Hz, 1H), 8.29 (d, J = 3.6 Hz, 1H), 8.23 (s, 1H), 6.96 (s, exchanged with D2O, 1H), 3.03 (s, 2H), 2.47 (d, J = 12.8 Hz, 2H), 1.75-1.74 (m, 2H), 1.51 (br s, 5H), 1.35-1.33 (m, 1H). |
| 1374 | A | A | | | (400 MHz, DMSO-d6): 12.33 (s, 1H), 8.77 (d, J = 2 Hz, 1H), 8.27 (d, J = 2.4 Hz, 1H), 8.18 (d, J = 3.2 Hz, 1H), 8.13 (d, J = 4 Hz, 1H), 7.65 (d, J = 8.4 Hz, 1H), 4.83-4.79 (m, 1H), 2.64-2.19 (m, 3H), 1.97 (br s, 1H), 1.85-1.83 (m, 1H), 1.72 (dd, J1 = 11.6, 6.4 Hz, 1H), 1.28 (s, 9H), 1.1 (d, J = 7, 3H) |
| 1375 | B | C | 360.4 | 3.82 | H NMR (300.0 MHz, DMSO) d 12.53 (s, 1H), 8.63 (d, J = 2.4 Hz, 1H), 8.33 (dd, J = 2.7, 9.8 Hz, 1H), 8.32 (s, 1H), 8.21 (d, J = 3.2 Hz, 1H), 2.65 (d, J =10.3 Hz, 1H), 2.43-2.37 (m, 4H), 2.24 (t, J = 9.1Hz, 1H), 1.82 (t, J = 11.6 Hz, 2H) and -0.00 (s, H) ppm |
| 1376 | C | C | | | (400 MHz, DMSO-d6): 12.32 (s, exchanged with D2O, 1H), 8.76 (s, 1H), 8.29-8.11 (m, 3H), 6.64 (s, exchanged with D2O, 1H), 2.25-2.14 (m, 9H), 1.80-1.70 (m, 6H). |
| 1377 | C | C | | | (400 MHz, DMSO-d6): 12.35 (br s, 1H), 8.71 (d, J = 2.4 Hz, 1H), 8.29 (d, J = 2.4 Hz, 1H), 8.19-8.17 (m, 2H), 6.79 (d, J = 9.6 Hz, partially exchanged with D2O, 1H), 5.01-4.99 (m, 1H), 1.82-1.79 (m, 3H), 1.66-1.27 (m, 6H), 0.88 (s, 9H). |
| 1378 | A | A | | | 400 MHz, DMSO-d6): 12.32 (s, 1H), 8.74 (d, J = 2 Hz, 1H), 8.28 (d, J = 2 Hz, 1H), 8.18 (d , J = 2.8 Hz, 1H), 8.11(d, J = 3.6 Hz, 1H), 7.46 (d, J = 8.8 Hz, 1H), 4.19-4.16 (m, 1H), 1.99-1.91 (m, 2H), 1.78-1.48 (m, 5H), 1.15-1.07 (m, 2H), 0.91 (d, J = 6.8 Hz, 3H), 0.88 (d, J = 7.2 Hz, 3H), 0.71 (d, J = 6.8 Hz, 3H). |
| 1379 | A | A | 358.3 | 2.91 | (400 MHz, DMSO-d6): 12.33 (br s, 1H), 8.76 (d, J = 2 Hz, 1H), 8.28 (d, J = 2 Hz, 1H) , 8.18 (d, J = 2 Hz, 1H), 8.14 (d, J = 3.6 Hz, 1H), 7.6 (d, |

TABLE 4-continued

IC$_{50}$, EC$_{50}$, NMR and LCMS Data of Compounds of FIG. 7

| Comp. Nos | Cell Flu, MDCK protection, ATP (All: IC50: uM)(Mean (All)) | Cell Influenza HA(-) 30 hr A/PR/8 bDNA (All: EC50: uM)(Mean (All)) | LCMS_Plus | LCMS_RT | NMR |
|---|---|---|---|---|---|
| | | | | | J = 5.6 Hz, 1H) 4.37-4.36 (br m, 1H), 3.16 (d, J = 5.6 Hz, 1H), 2.69 (br s, 1H), 2.24 (br s, 1H), 1.99 (t, J = 12, 1H), 1.6-1.2 (m, 8H) |
| 1380 | A | C | 403.34 | 3.1 | |
| 1381 | A | C | 388.37 | 4.04 | |
| 1382 | A | A | 388.37 | 4.02 | |
| 1383 | | A | 371.34 | 3.99 | |
| 1384 | | C | 388.37 | 4.26 | |
| 1385 | A | A | 388.37 | 4.26 | |
| 1386 | C | C | 401.23 | 3.89 | |
| 1387 | | | 424.54 | 3.53 | 1H NMR (300 MHz, DMSO) d 12.30 (s, 1H), 8.68 (d, J = 2.4 Hz, 1H), 8.25 (d, J = 2.4 Hz, 1H), 8.32-8.09 (m, J = 19.6, 9.0 Hz, 2H), 7.62 (d, J = 7.1 Hz, 1H), 7.06 (d, J = 8.4 Hz, 1H), 6.77-6.59 (m, 2H), 4.57-4.33 (m, 1H), 3.71 (s, 3H), 3.21-2.77 (m, 4H), 2.29-2.11 (m, J = 14.7 Hz, 1H), 1.87-1.66 (m, J = 23.9, 12.0, 5.7 Hz, 1H). |

TABLE 5

Figure 8A:
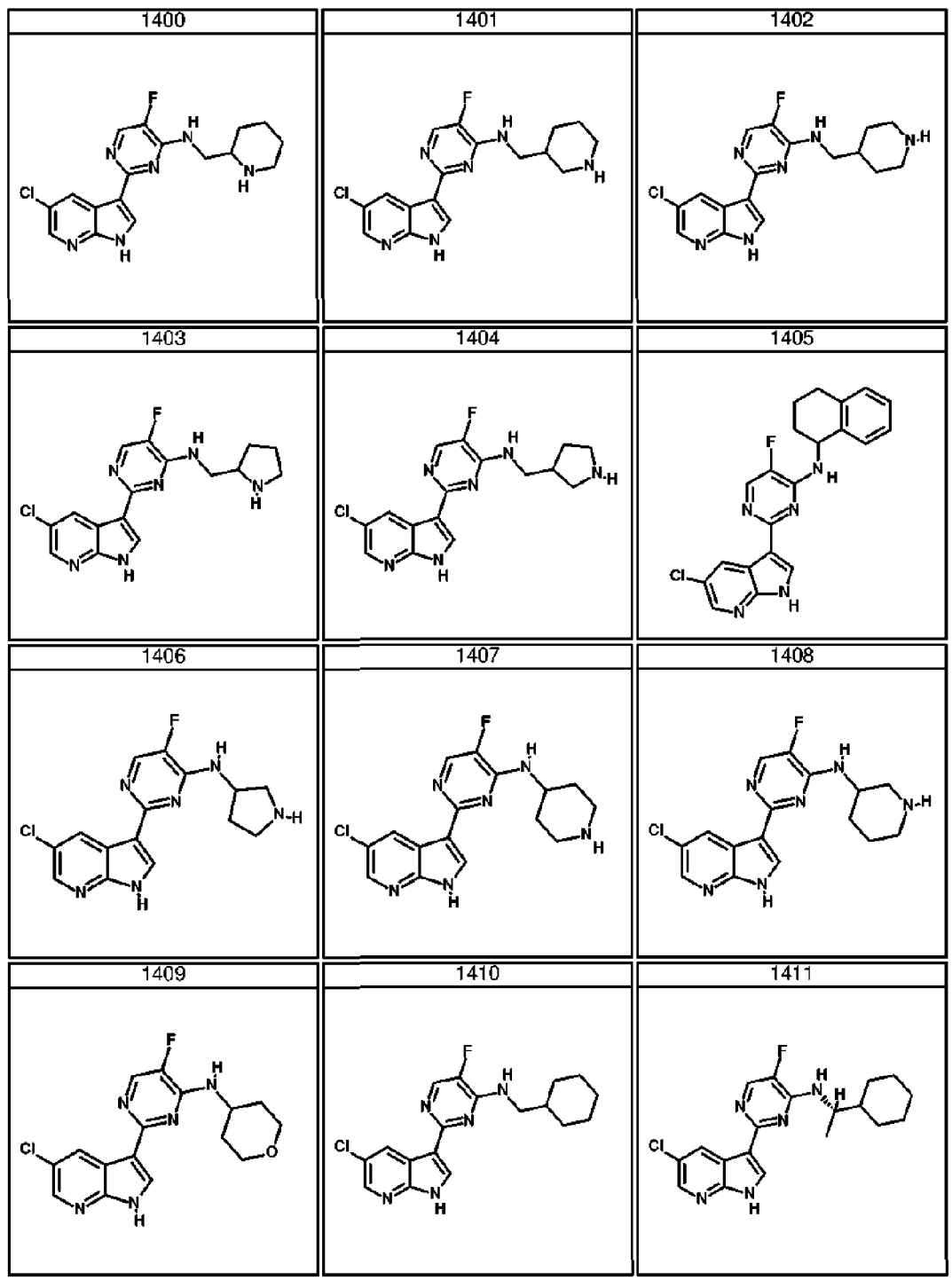
Figure 8B:
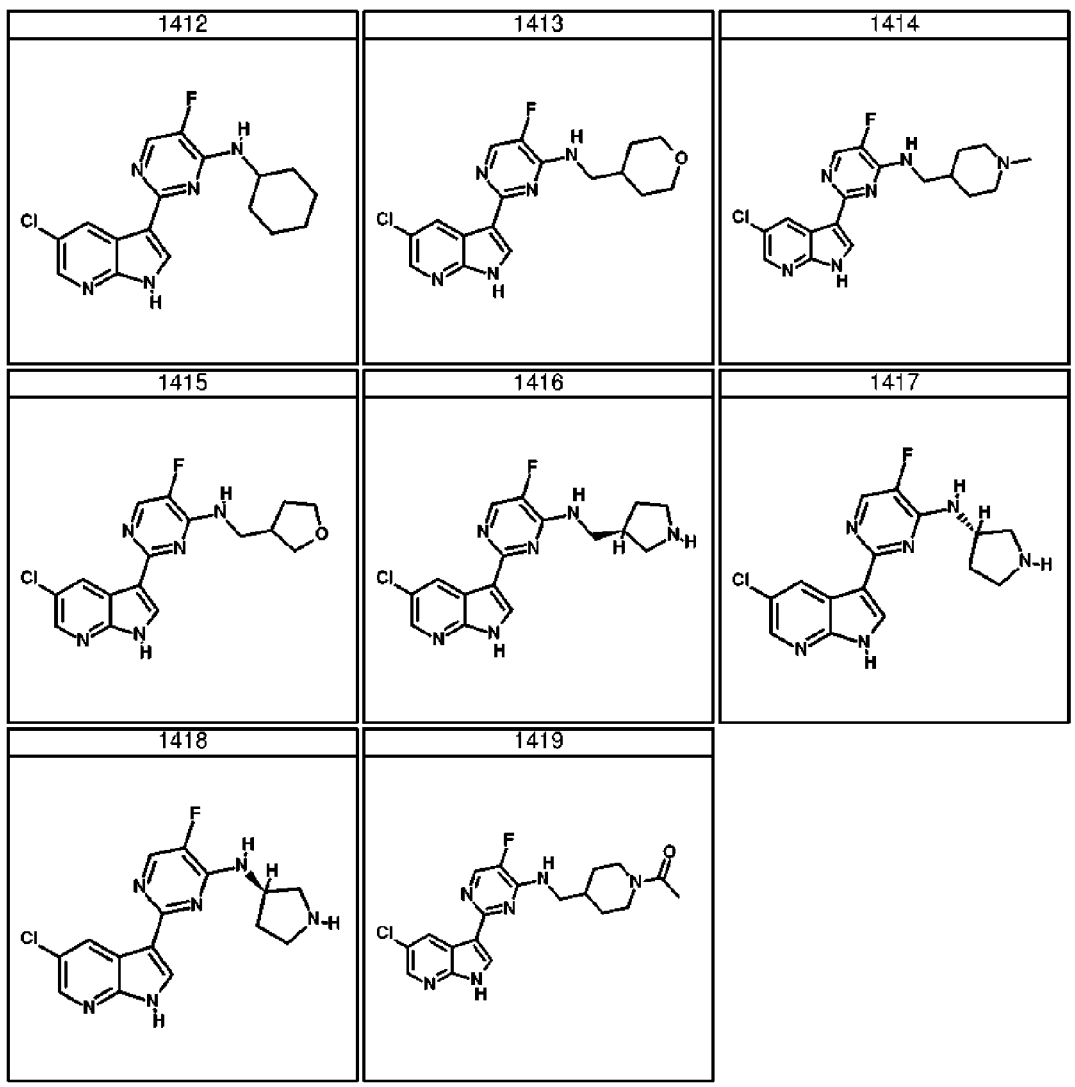

IC$_{50}$, EC$_{50}$, NMR and LCMS Data of Compounds of FIG. 8

| Nos | Cell Flu, MDCK protection, ATP (IC50: IC50: uM)(Mean (All)) | Cell Influenza HA(-) 30 hr A/PR/8 bDNA:bDNA EC50 uM(Mean (All)) | LCMS_Plus | LCMS_RT | NMR |
|---|---|---|---|---|---|
| 1400 | B | | 361.44 | 3.7 | 1H NMR (DMSO-d6): 1.53 (3H, m), 1.81 (2H, m), 1.98 (1H, m), 2.90 (1H, m), 3.31 (1H, m), 3.43 (1H, m), 3.58 (2H, m), 7.85 (1H, s), 8.30 (2H, d), 8.36 (1H, s), 8.68 (1H, d), 8.84 (1H, s), 12.52 (1H, s) |
| 1401 | B | | 361.44 | 3.59 | 1H NMR (DMSO-d6): 1.34 (1H, m), 1.60 (1H, m), 1.92 (2H, m), 2.20 (1H, m), 2.78 (2H, m), 3.24 (3H, m), 3.54 (1H, m), 7.99 (1H, s), 8.23 (1H, m), 8.30 (2H, d), 8.60 (1H, d), 8.70 (1H, s), 12.45 (1H, s) |
| 1402 | D | | 361.44 | 3.57 | 1H NMR (DMSO-d6): 1.41 (2H, m), 1.92 (2H, m), 2.08 (1H, m), 2.83 (2H, m), 3.29 (2H, m), 3.44 (2H, m), 7.97 (1H, s), 8.20 (1H, s), 8.25 (1H, s), 8.30 (1H, s), 8.48 (1H, d), 8.71 (1H, s), 12.43 (1H, s) |
| 1403 | B | | 347.4 | 3.67 | 1H NMR (DMSO-d6): 1.94 (1H, m), 1.96 (2H, m), 2.14 (2H, m), 3.20 (2H, m), 3.71 (2H, m), 3.83 (1H, m), 7.89 (1H, s), 8.30 (4H, m), 8.69 (1H, s), 8.91 (1H, s), 12.58 (1H, s) |
| 1404 | | | 347.4 | 3.54 | 1H NMR (DMSO-d6): 1.77 (1H, m), 2.12 (1H, m), 2.77 (1H, m), 3.00 (1H, m), 3.17 (1H, m), 3.34 (2H, m), 3.60 (2H, m), 7.98 (1H, s), 8.23 (1H, d), 8.31 (2H, m), 8.71 (3H, m), 12.53 (1H, s) |
| 1405 | D | | 394.45 | 5.28 | 1H NMR (DMSO-d6): 2.04 (4H, m), 2.84 (2H, m), 3.33 (1H, s), 5.61 (1H, m), 7.18 (3H, m), 7.27 (1H, d), 8.00 (1H, d), 8.21 (1H, t), 8.23 (1H, s), 8.26 (1H, s), 8.68 (1H, s), 12.34 (1H, s) |

TABLE 5-continued

IC$_{50}$, EC$_{50}$, NMR and LCMS Data of Compounds of FIG. 8

| Nos | Cell Flu, MDCK protection, ATP (IC50: IC50: uM)(Mean (All)) | Cell Influenza HA(-) 30 hr A/PR/8 bDNA:bDNA EC50 uM(Mean (All)) | LCMS_Plus | LCMS_RT | NMR |
|---|---|---|---|---|---|
| 1406 | | | 333 | 3.54 | 1H NMR (CD3OD): 2.40-2.50 (2H, m), 2.6-2.7 (2H, m), 3.50-3.60 (3H, m), 3.7-3.8 (1H, m), 5.2-5.3 (1H, m), 8.40 (1H, s), 8.50 (1H, m), 8.55 (1H, s), 8.75 (1H, s) |
| 1407 | | | 347 | 3.5 | 1H NMR (DMSO-d6): 1.80-1.90 (2H, m), 2.1-2.2 (2H, m), 3.05-3.15 (2H, m), 3.4-3.5 (2H, m), 4.30-4.40 (1H, m), 7.65-7.70 (1H, m), 8.30-8.35 (2H, m), 8.40-8.50 (1H, s), 8.60-8.70 (1H, s), 8.75-8.80 (1H, m), 12.0 (1H, s) |
| 1408 | A | | 347.47 | 3.68 | 1H NMR (DMSO-d6): 1.66 (1H, m), 1.85 (1H, m), 1.98 (1H, m), 2.11 (1H, m), 2.90 (2H, m), 3.32 (1H, m), 3.47 (1H, m), 4.46 (1H, m), 7.57 (1H, d), 8.31 (3H, m), 8.66 (3H, m), 12.47 (1H, s) |
| 1409 | D | | 348.44 | 4.42 | 1H NMR (DMSO-d6): 1.67 (2H, m), 1.96 (2H, d), 3.49 (2H, t), 3.96 (2H, d), 4.30 (1H, m), 7.62 (1H, d), 8.18 (1H, s), 8.22 (1H, s), 8.29 (1H, s), 8.72 (1H, s), 12.36 (1H, s) |
| 1410 | A | | 360.46 | 5.39 | 1H NMR (DMSO-d6): 1.17 (5H, m), 1.70 (6H, m), 2.67 (2H, d), 8.27 (1H, s), 8.42 (2H, s), 8.72 (1H, s), 12.57 (1H, s) |
| 1411 | | | 374.5 | 5.47 | 1H NMR (DMSO-d6): 1.15 (8H, m), 1.28 (2H, m), 1.72 (2H, m), 1.84 (2H, m), 4.23 (1H, m), 7.43 (1H, d), 8.12 (1H, s), 8.18 (1H, s), 8.27 (1H, s), 8.73 (1H, s), 12.32 (1H, s) |
| 1412 | A | | 346.43 | 5.25 | 1H NMR (DMSO-d6): 0.85 (1H, m), 1.48 (4H, m), 1.68 (1H, d), 1.81 (2H, m), 2.04 (2H, m), 4.03 (1H, m), 7.49 (1H, d), 8.13 (1H, s), 8.19 (1H, s), 8.29 (1H, s), 8.73 (1H, s), 12.21 (1H, s) |
| 1413 | | | 362 | 4.5 | (d6-DMSO, 400 MHz) 1.23-1.33 (2H, m), 1.72 (2H, d), 1.99-2.04 (1H, m), 3.27 (2H, t), 3.41 (2H, t), 3.85-3.89 (2H, m), 7.80 (1H, t), 8.14 (1H, d), 8.21 (1H, s), 8.28 (1H, d), 8.74 (1H, d), 12.35 (1H, brs) |
| 1414 | | | 375 | 3.95 | (d6-DMSO, 400 MHz) 1.14-1.24 (2H, m), 1.75-1.80 (5H, m), 2.11 (3H, m), 2.75 (2H, d), 3.40 (2H, t), 7.80 (1H, t), 8.13 (1H, d), 8.20 (1H, s), 8.28 (1H, d), 8.73 (1H, d), 12.35 (1H, s) |
| 1415 | D | | 348 | 3.27 | (d6-DMSO, 400 MHz) 1.66-1.74 (1H, m), 1.99-2.08 (1H, m), 2.67-2.74 (1H, m), 3.49-3.51 (2H, m), 3.58-3.67 (2H, m), 3.73 (1H, t), 3.79-3.84 (1H, m), 7.88 (1H, t), 8.16 (1H, d), 8.22 (1H, s), 8.29 (1H, d), 8.74 (1H, d), 12.36 (1H, brs) |
| 1416 | B | | 347.47 | 3.54 | 1H NMR (CDCl3/MeOD): 0.83 (2H, m), 1.94 (1H, m), 2.32 (1H, m), 3.00 (1H, m), 3.30 (1H, m), 3.36 (2H, m), 3.46 (1H, m), 3.60 (1H, m), 3.87 (1H, m), 8.15 (1H, s), 8.24 (1H, s), 8.29 (1H, s), 8.68 (1H, s) |
| 1417 | D | | 333.51 | 5 | 1H NMR (DMSO-d6): 2.15 (1H, m), 2.30 (2H, m), 3.35 (2H, m), 3.58 (1H, m), 4.77 (1H, m), 7.87 (1H, s), 8.29 (3H, m), 8.81 (1H, s), 8.94 (2H, br s), 12.45 (1H, s) |
| 1418 | D | | 333.4 | 5 | 1H NMR (DMSO-d6): 2.17 (1H, m), 2.34 (1H, m), 3.34 (3H, m), 3.58 (1H, m), 4.79 (1H, m), 7.87 (1H, d), 8.27 (3H, m), 8.68 (1H, s), 8.81 (2H, br s), 12.45 (1H, s) |
| 1419 | B | | 403.48 | 3.18 | 1H NMR (DMSO-d6): 0.82 (2H, m), 1.11 (1H, m), 1.22 (1H, m), 1.85 (2H, t), 1.98 (3H, s), 2.07 (1H, br s), 3.00 (1H, t), 3.51 (1H, s), 3.83 (1H, m), 4.40 (1H, d), 8.40 (1H, s), 8.44 (1H, d), 8.65 (1H, s), 8.88 (1H, s), 9.20 (1H, br s), 12.91 (1H, s) |

In Vivo Assay

For efficacy studies, Balb/c mice (4-5 weeks of age) were challenged with $5 \times 10^3$ $TCID_{50}$ in a total volume of 50 µl by intranasal by intranasal instillation (25 µl/nostril) under general anesthesia (Ketamine/Xylazine). Uninfected controls were challenged with tissue culture media (DMEM, 50 µl total volume). For the prophylaxis study (FIG. 1), the initial dose of Compound 514 (100 mg/kg) or vehicle only (0.5% Methylcellulose/0.5% Tween 80) were administered 2 hours prior to infection by oral gavage (10 mL/kg) and continued twice daily for 5 days. For the treatment study (FIG. 2), Compound 588 (200 mg/kg) or vehicle only (0.5% Methylcellulose/0.5% Tween 80) were administered by oral gavage 24 hours post infection and continued twice daily for 10 days. Animals were monitored for survival for 21 days and Kaplan Meier plots. As shown in FIGS. 1 and 2, Compound 514 and Compound 588 provided complete survival that was statistically significant from vehicle treated controls (P<0.0001).

TABLE 6

Influneza Therapeutic Mouse Model (Dosing @ 48 hours post infection with 30 mg/kg BID X 10 days)

| Compounds | Percent Survival | Percent Weight Loss (Day 8) |
| --- | --- | --- |
| 895 | 100 | 12.8 |
| 936 | 100 | 20.9 |
| 933 | 100 | 28.0 |
| 706 | 75 | 27.0 |
| 967 | 75 | 30.9 |
| 866 | 62.5 | 29.5 |
| 968 | 37.5 | 32.7 |

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of the formula

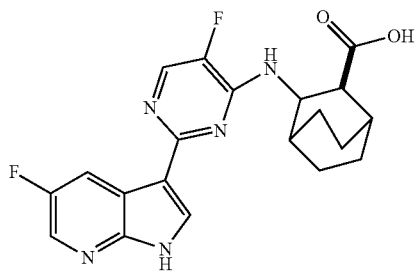 [SMILES: O=C(O)[C@H]1C2CCC(CC2)C1Nc1nc(-c2c[nH]c3ncc(F)cc23)ncc1F]

or a pharmaceutically acceptable salt thereof.

2. A pharmaceutical composition comprising the compound of claim 1 and a pharmaceutically acceptable carrier, adjuvant, or vehicle.

* * * * *